US007652020B2

(12) United States Patent
Guo et al.

(10) Patent No.: US 7,652,020 B2
(45) Date of Patent: Jan. 26, 2010

(54) COMPOUNDS FOR THE TREATMENT OF INFLAMMATORY DISORDERS

(75) Inventors: Zhuyan Guo, Scotch Plains, NJ (US); Peter Orth, New York, NY (US); Zhaoning Zhu, Plainsboro, NJ (US); Robert D. Mazzola, Stewartsville, NJ (US); Tin-Yau Chan, Edison, NJ (US); Henry A. Vaccaro, South Plainfield, NJ (US); Brian McKittrick, New Vernon, NJ (US); Joseph A. Kozlowski, Princeton, NJ (US); Brian J. Lavey, Basking Ridge, NJ (US); Guowei Zhou, Livingston, NJ (US); Sunil Paliwal, Monroe Township, NJ (US); Shing-Chun Wong, Union, NJ (US); Neng-Yang Shih, Warren, NJ (US); Pauline C. Ting, New Providence, NJ (US); Kristin E. Rosner, Watertown, MA (US); Gerald W. Shipps, Jr., Stoneham, MA (US); M. Arshad Siddiqui, Newton, MA (US); David B. Belanger, Cambridge, MA (US); Chaoyang Dai, Acton, MA (US); Dansu Li, Watertown, MA (US); Vinay M. Girijavallabhan, Woburn, MA (US); Janeta Popovici-Muller, Waltham, MA (US); Wensheng Yu, Edison, NJ (US); Lianyun Zhao, Dorchester, MA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 11/142,601

(22) Filed: Jun. 1, 2005

(65) Prior Publication Data
US 2006/0252778 A1 Nov. 9, 2006

Related U.S. Application Data

(60) Provisional application No. 60/576,153, filed on Jun. 2, 2004.

(51) Int. Cl.
| | | |
|---|---|---|
| A61K 31/519 | (2006.01) | |
| A61K 31/506 | (2006.01) | |
| A61K 31/4709 | (2006.01) | |
| A61K 31/43 | (2006.01) | |
| A61K 31/4245 | (2006.01) | |
| C07D 413/00 | (2006.01) | |
| C07D 241/36 | (2006.01) | |
| C07D 471/00 | (2006.01) | |
| C07D 295/00 | (2006.01) | |
| C07D 471/02 | (2006.01) | |
| C07D 401/00 | (2006.01) | |
| C07D 513/00 | (2006.01) | |
| C07D 277/22 | (2006.01) | |
| C07D 277/62 | (2006.01) | |
| C07D 263/30 | (2006.01) | |
| C07D 261/06 | (2006.01) | |
| C07D 235/00 | (2006.01) | |
| C07D 209/04 | (2006.01) | |
| C07D 207/00 | (2006.01) | |
| C07D 205/00 | (2006.01) | |
| C07D 409/00 | (2006.01) | |
| C07D 307/00 | (2006.01) | |

(52) U.S. Cl. ............ 514/265.1; 514/275; 514/300; 514/301; 514/303; 514/310; 514/343; 514/364; 514/365; 514/366; 514/406; 544/111; 544/343; 544/344; 544/350; 544/386; 544/405; 546/122; 546/192; 546/268.1; 548/153; 548/179; 548/203; 548/235; 548/247; 548/309.7; 548/364.1; 548/453; 548/491; 548/530; 548/953; 549/59; 549/471; 549/472

(58) Field of Classification Search ............ 548/470, 548/153, 179, 203, 235, 247, 309.7, 364.1, 548/453, 491, 530, 953; 514/265.1, 275, 514/300, 301, 303, 310, 343, 364, 365, 366, 514/406; 544/111, 343, 344, 350, 386, 405; 546/122, 192, 268.1; 549/59, 471, 472
See application file for complete search history.

(56) References Cited

U.S. PATENT DOCUMENTS 5,618,842 A 4/1997 Della Valle et al.

(Continued)

FOREIGN PATENT DOCUMENTS

FR 1 484 601 6/1967

(Continued)

OTHER PUBLICATIONS

Frankland, Edward Percy "CCLXIX—The Reaction Between Benzylamine and the Dibromosuccinic Acids" Journal of the Chemical Society 1914, vol. 105, pp. 2879-2887.*

(Continued)

*Primary Examiner*—Rei-Tsang Shiao
*Assistant Examiner*—Joseph R Kosack
(74) *Attorney, Agent, or Firm*—Krishna G. Banerjee; Jeremy McKnown

(57) ABSTRACT

This invention relates to compounds of the Formula (I):

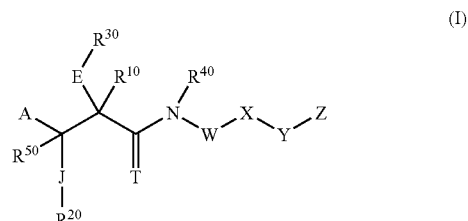

or a pharmaceutically acceptable salt, solvate or isomer thereof, which can be useful for the treatment of diseases or conditions mediated by MMPs, ADAMs, TACE, TNF-α or combinations thereof.

48 Claims, No Drawings

U.S. PATENT DOCUMENTS

| | | | |
|---|---|---|---|
| 6,344,457 | B1 | 2/2002 | Jeanpetit et al. |
| 6,495,565 | B2 | 12/2002 | Duan et al. |
| 6,534,491 | B2 | 3/2003 | Levin et al. |
| 6,677,355 | B1 | 1/2004 | Conrad et al. |
| 7,056,942 | B2 * | 6/2006 | Hildesheim et al. ......... 514/411 |
| 2006/0178366 | A1 * | 8/2006 | Siddiqui et al. .......... 514/237.5 |

FOREIGN PATENT DOCUMENTS

| | | |
|---|---|---|
| WO | WO 01/21661 | 3/2001 |
| WO | WO 03/076461 | 9/2001 |
| WO | WO 01/77075 | 10/2001 |

OTHER PUBLICATIONS

Lu et al. "Two New Asymmetric Epoxidation Catalysts, Unusual Stoichiometry and Inverse Enantiofacial Selection" Journal of Organic Chemistry, 1984, vol. 49, pp. 728-731.*

Frankland et al., CAS Accession No. 1907:2912.*

Einhorn et al. CAS Accession No. 1908:12246.*

C. Giordano et al., "First Asymmetric Synthesis of Enantiomerically Pure (1R,2S)-(-)-(1,2-Epoxypropyl)phosphonic Acid (Fosfomycin)", J. Organic Chemistry, 1989, pp. 1470-1473, vol. 54 No. 6.

L.D.-L. Lu et al., "Two New Asymmetric Epoxidation Catalysts. Unusual Stoichiometry and Inverse Enantiofacial Selection", J. Organic Chemistry, 1984, pp. 728-731, vol. 49, No. 4.

Ruo Wang et al., "A Search for Pyrophosphate Mimics for the Development of Substrates and Inhibitors of Glycosyltransferases", Bioorganic & Medicinal Chemistry, 1997, pp. 661-672, vol. 5, No. 4.

Abstract of: Koenig S et al., "Synthese Von N-Tert-Alkylglyoxysaeureamiden", Synthesis, Georg Thieme Verlag, Stuttgart, Dec. 1993, pp. 1233-1234.

Ping Xu et al., "Synthesis of a Peptidomimetic HCMV Protease Inhibitor Library", Synthesis, 2002, pp. 1017-1026, No. 8.

F. Massicot et al., "Solvent-Free Synthesis of Tartramides Under Microwave Activation", Synthesis, 2001, pp. 2441-2444, No. 16.

J. R. Coggins et al., "Use of Dimethyl Suberimidate and Novel Perodate-Cleavable Bis(imido esters) to Study the Quaternary Structure of the Pyruvate Dehydrogenase Multienzyme Complex of *Escherichia coli*" Biochemistry, 1976, pp. 2527-2533, vol. 15, No. 12.

J., D. D'Ianni et al., "Hydrogenation of Hydroxyamides", Journal of the American Chemical Society, 1939, pp. 1675-1681, vol. 61.

Gawronski J. et al., "Factors Affecting Conformation of (R,R)-Tartaric Acid Ester, Amide and Nitrile Derivatives. X-Ray Diffraction, Circular Dichroism, Nuclear Magnetic Resonance and Ab Initio Studies" Tetrahedron Elsevier Science Publishers, Apr. 1997, pp. 6113-6144, vol. 53, No. 17, Amsterdam, NL.

Abstract of: K. Rehse et al., "Antiaggregatorisch und anticoagulante Eigenschaften von Oligoaminen, 6. Mitt.: Oligohydroxyalkandiamine" Archiv der Pharmazie, 1987, pp. 1155-1161, vol. 320.

Allenmark S. et. al., "Chiral selectors based on C2-symmetric dicarboxylic acids" Tetrahedron: Asymmetry, Elsevier Science Publishers, Sep. 8, 2000, pp. 3527-3534, vol. 11, No. 17.

International Search Report for International application No. PCT/US2005/019131, mailed May 8, 2006, 8pgs.

* cited by examiner

COMPOUNDS FOR THE TREATMENT OF INFLAMMATORY DISORDERS

BACKGROUND OF THE INVENTION

1. Field of the Invention

This invention relates generally to tartaric acid functional compounds that can inhibit matrix metalloproteinases (MMPs), a disintegrin and metalloproteases (ADAMs) and/or tumor necrosis factor alpha—converting enzyme (TACE) and in so doing prevent the release of tumor necrosis factor alpha (TNF-α), pharmaceutical compositions comprising such compounds, and methods of treatment using such compounds.

2. Description

Osteo- and rheumatoid arthritis (OA and RA, respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. J. Bone Joint Surg. 52A (1970) 424-434). There are four classes of protein degradative enzymes in mammalian cells: serine, cysteine, aspartic and metalloproteases. The available evidence supports the belief that it is the metalloproteases that are responsible for the degradation of the extracellular matrix of articullar cartilage in OA and RA. Increased activities of collagenases and stromelysin have been found in OA cartilage and the activity correlates with severity of the lesion (Mankin et al. Arthritis Rheum. 21, 1978, 761-766, Woessner et al. Arthritis Rheum. 26, 1983, 63-68 and Ibid. 27, 1984, 305-312). In addition, aggrecanase (a newly identified metalloprotease) has been identified that provides the specific cleavage product of proteoglycan, found in RA and OA patients (Lohmander L. S. et al. Arthritis Rheum. 36, 1993, 1214-22).

Metalloproteases (MPs) have been implicated as the key enzymes in the destruction of mammalian cartilage and bone. It can be expected that the pathogenesis of such diseases can be modified in a beneficial manner by the administration of MP inhibitors (see Wahl et al. Ann. Rep. Med. Chem. 25, 175-184, AP, San Diego, 1990).

MMPs are a family of over 20 different enzymes that are involved in a variety of biological processes important in the uncontrolled breakdown of connective tissue, including proteoglycan and collagen, leading to resorption of the extracellular matrix. This is a feature of many pathological conditions, such as RA and OA, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as alpha-2-macroglobulins and TIMPs (tissue inhibitor of MPs), which form inactive complexes with the MMP's.

Tumor necrosis factor alpha (TNF-α) is a cell-associated cytokine that is processed from a 26 kDa precursor form to a 17 kd active form. See Black R. A. "Tumor necrosis factor-alpha converting enzyme" Int J Biochem Cell Biol. 2002 January;34(1):1-5 and Moss M L, White J M, Lambert M H, Andrews R C. "TACE and other ADAM proteases as targets for drug discovery" Drug Discov Today. 2001 Apr. 1;6(8): 417-426, each of which is incorporated by reference herein.

TNF-α has been shown to play a pivotal role in immune and inflammatory responses. Inappropriate or over-expression of TNF-α is a hallmark of a number of diseases, including RA, Crohn's disease, multiple sclerosis, psoriasis and sepsis. Inhibition of TNF-α production has been shown to be beneficial in many preclinical models of inflammatory disease, making inhibition of TNF-α production or signaling an appealing target for the development of novel anti-inflammatory drugs.

TNF-α is a primary mediator in humans and animals of inflammation, fever and acute phase responses, similar to those observed during acute infection and shock. Excess TNF-α has been shown to be lethal. Blocking the effects of TNF-α with specific antibodies can be beneficial in a variety of conditions, including autoimmune diseases such as RA (Feldman et al, Lancet, (1994) 344, 1105), non-insulin dependent diabetes mellitus (Lohmander L. S. et al., Arthritis Rheum. 36 (1993) 1214-22) and Crohn's disease (Macdonald T. et al., Clin. Exp. Immunol. 81 (1990) 301).

Compounds that inhibit the production of TNF-α are therefore of therapeutic importance for the treatment of inflammatory disorders. Recently it has been shown that metalloproteases, such as TACE, are capable of converting TNF-α from its inactive to active form (Gearing et al Nature, 1994, 370, 555). Since excessive TNF-α production has been noted in several disease conditions also characterized by MMP-mediated tissue degradation, compounds which inhibit both MMPs and TNF-α production may also have a particular advantage in diseases where both mechanisms are involved.

One approach to inhibiting the harmful effects of TNF-α is to inhibit the enzyme, TACE before it can process TNF-α to its soluble form. TACE is a member of the ADAM family of type I membrane proteins and mediates the ectodomain shedding of various membrane-anchored signaling and adhesion proteins. TACE has become increasingly important in the study of several diseases, including inflammatory disease, because of its role in cleaving TNF-α from its "stalk" sequence and thus releasing the soluble form of the TNF-α protein (Black R. A. Int J Biochem Cell Biol. 2002 34, 1-5).

There are several patents which disclose hydroxamate, carboxylate and/or lactam based MMP inhibitors.

U.S. Pat. No. 6,677,355 and U.S. Pat. No. 6,534,491 (B2), describe compounds that are hydroxamic acid derivatives and MMP inhibitors.

U.S. Pat. No. 6,495,565 discloses lactam derivatives that are potential inhibitors of matrix metalloproteases and/or TNF-α.

There is a need in the art for inhibitors of MMPs, ADAMs, TACE, and TNF-α, which can be useful as anti-inflammatory compounds and cartilage protecting therapeutics. The inhibition of TNF-α, TACE and or other MMPs can prevent the degradation of cartilage by these enzymes, thereby alleviating the pathological conditions of OA and RA as well as many other auto-immune diseases.

SUMMARY OF THE INVENTION

In its many embodiments, the present invention provides a novel class of compounds as inhibitors of TACE, the production of TNF-α, MMPs, ADAMs or any combination thereof, methods of preparing such compounds, pharmaceutical compositions comprising one or more such compounds, methods of preparing pharmaceutical formulations comprising one or more such compounds, and methods of treatment, prevention, inhibition or amelioration of one or more diseases associated with TACE, TNF-α, MMPs, ADAMs or any combination thereof using such compounds or pharmaceutical compositions.

In one embodiment, the present application discloses a compound, or pharmaceutically acceptable salts or solvates of said compound, said compound having the general structure shown in formula (I):

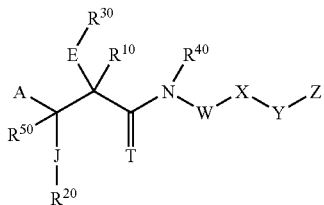

formula (I)

or a pharmaceutically acceptable salt or solvate thereof, wherein:

A is selected from the group consisting of:

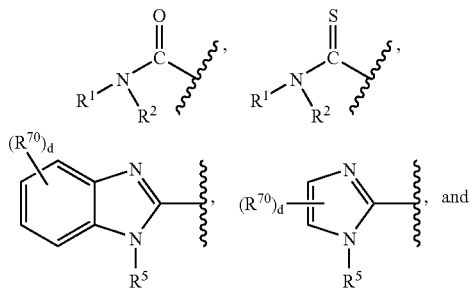

—$CO_2R^1$;

d is 0 to 4;

J is from the group consisting of: O, S, and $NR^5$;

E is selected from the group consisting of: O, S, and $NR^5$;

T is O or S;

$R^1$ and $R^2$ are the same or different, each being independently selected from the group consisting of H, alkyl, cycloalkyl, heterocyclyl, aryl, arylalkyl, heteroaralkyl, and heteroaryl; or alternatively $R^1$ and $R^2$, taken together with the N to which $R^1$ and $R^2$ are shown attached, represent a 4-8 membered heterocyclic ring having 1-3 heteroatoms including said N, said heterocyclic ring being optionally fused with aryl, heteroaryl, cycloalkyl, or heterocyclyl, wherein each of said alkyl, cycloalkyl, heterocyclyl, aryl, arylalkyl, heteroaralkyl, heteroaryl and 4-8 membered heterocyclic ring can be unsubstituted or optionally independently substituted with one or more moieties which can be the same or different, each moiety being independently selected from the group of $R^{70}$ moieties below;

$R^{10}$ is selected from the group consisting of H, alkyl, and fluoroalkyl;

$R^{20}$ is selected from the group consisting of H, alkyl, and fluoroalkyl;

$R^{30}$ is H or alkyl, or alternatively $R^{30}$ and $R^{40}$ taken together with the N to which $R^{40}$ is shown attached to in Formula I, are joined to form a 4-7 membered heterocylic ring, wherein said heterocylic ring is unsubstituted or optionally independently substituted with one or more moieties which can be the same or different, each moiety being independently selected from the group of $R^{70}$ moieties below;

$R^{40}$ is H or alkyl;

$R^{50}$ is H or alkyl;

W is —$(CR^{13}_2)_n$—, wherein n is 0 to 5 or a covalent bond, or alternatively two $R^{13}$ groups can fuse to form a 3-8 membered cycloalkyl, wherein said 3-8 membered cycloalkyl can be unsubstituted or optionally independently substituted with one or more moieties which can be the same or different, each moiety being independently selected from the group of $R^6$ moieties below;

X is absent or present, and if present X is selected from the group consisting of a covalent bond, alkyl, alkenyl, alkynyl, cycloalkyl, heterocyclyl, aryl, and heteroaryl, wherein said alkyl, alkenyl, alkynyl, cycloalkyl, heterocyclyl, aryl, and heteroaryl can be unsubstituted or optionally independently substituted with one or more moieties which can be the same or different, each moiety being independently selected from the group of $R^{70}$ moieties below;

Y is absent or present, and if present Y is selected from the group consisting of a covalent bond, —$[C(R^6)_2]_n$— wherein n is 1 to 2, —O—, —S—, —$NR^1$—, —$SO_v$— wherein v is 1 to 2, —$SO_n(CR^6_2)_p$— wherein n is 1 or 2 and p is 1 to 4, —$O(CR^6_2)_q$— or —$(CR^6_2)_qO$— wherein q is 1 to 4, —$N(R^7)S(O)_n$— or —$S(O)_nN(R^7)$— wherein n is 1 or 2, and —$N(R^7)C(O)$— or —$C(O)N(R^7)$—;

Z is selected from the group consisting of H, alkyl, alkenyl, alkynyl, cycloalkyl, heterocyclyl, aryl, and heteroaryl, said cycloalkyl, heterocyclyl, aryl, and heteroaryl being optionally fused with aryl, heterocyclyl, heteroaryl or cycloalky; wherein each of said alkyl, alkenyl, alkynyl, cycloalkyl, heterocyclyl, aryl, and heteroaryl can be unsubstituted or optionally independently substituted with one or more moieties which can be the same or different, each moiety being independently selected from the group of $R^{70}$ moieties below;

$R^5$ is selected from the group consisting of hydrogen, alkyl, and alkylaryl;

each $R^6$ is the same or different and is independently selected from the group consisting of hydrogen, halogen, —$SR^{15}$, —$S(O)_qR^{15}$ wherein q is 1 to 2, alkyl, cycloalkyl, heterocyclyl, alkoxyl, hydroxy, nitro, cyano, amino, alkenyl, alkynyl, arylalkyl, aminocarbonyl, alkylcarbonyl, and alkoxycarbonyl;

each $R^7$ is the same or different and is independently selected from the group consisting of hydrogen, alkyl, aryl, cycloalkyl, heteroaryl, heterocyclyl, alkenyl, alkynyl, arylalkyl, alkylcarbonyl, and alkoxycarbonyl, wherein each of the aryl, heteroaryl and heterocyclyl can be unsubstituted or optionally independently substituted with one or more moieties which can be the same or different, each moiety being independently selected from the group of $R^{70}$ moieties below;

$R^{13}$ is the same or different and is independently selected from the group consisting of hydrogen, halogen, —OH, —$OR^{14}$, alkyl, cycloalkyl, heterocyclyl, alkenyl, alkynyl, alkylaryl, alkylamino, and alkylcarbonyl;

$R^{14}$ is alkyl;

each $R^{70}$ is a substituent for H where indicated and is the same or different and is independently selected from the group consisting of alkyl, alkenyl, alkynyl, cycloalkyl, cycloalkenyl, heterocyclyl, aryl, arylalkyl, heteroaryl, heteroarylalkyl, halo, —CN, —$CF_3$, —$OCF_3$, —$OR^{15}$, —$C(O)R^{15}$, —$C(O)OR^{15}$, —$C(O)N(R^{15})(R^{16})$, —$SR^{15}$, —$S(O)_qN(R^{15})(R^{16})$ wherein q is 1 to 2, —$C(=NOR^{15})R^{16}$, —$N(R^{15})(R^{16})$, -alkyl-$N(R^{15})(R^{16})$, —$N(R^{15})C(O)R^{16}$, —$CH_2$—$N(R^{15})C(O)R^{16}$, —$N(R^{15})S(O)R^{16}$, —$N(R^{15})S(O)_2R^{16}$, —$CH_2$—N $(R^{15})S(O)_2R^{16}$, $-N(R^{17})S(O)_2N(R^{16})(R^{15})$, $-N(R^{17})S(O)N(R^{16})(R^{15})$, $-N(R^{17})C(O)N(R^{16})(R^{15})$, $-CH_2-N(R^{17})C(O)N(R^{16})(R^{15})$, $-N(R^{15})C(O)OR^{16}$, $-CH_2-N(R^{15})C(O)OR^{16}$, and $-S(O)_qR^{15}$ wherein q is 1 to 2; and wherein each of the alkyl, cycloalkyl, heterocyclyl, aryl, arylalkyl, heteroaryl, heteroarylalkyl, alkenyl and alkynyl are independently unsubstituted or substituted by 1 to 5 groups independently selected from the group consisting of alkyl, cycloalkyl, heterocyclyl, aryl, heteroaryl, halo, $-CF_3$, $-CN$, $-OR^{15}$, $-N(R^{15})(R^{16})$, $-C(O)OR^{15}$, $-C(O)N(R^{15})(R^{16})$, and $-N(R^{15})S(O)R^{16}$;

each $R^{15}$, $R^{16}$ and $R^{17}$ are independently selected from the group consisting of H, alkyl, cycloalkyl, heterocyclyl, aryl, and heteroaryl, or alternatively $R^{15}$ and $R^{16}$ taken together with the N to which they are shown attached, are joined to form a 4-8 membered heteroclic ring, wherein said 4-8 membered cycloalkyl can be unsubstituted or optionally independently substituted with one or more moieties which can be the same or different, each moiety being independently selected from the group of $R^{75}$ moieties below;

each $R^{75}$ is independently selected from the group consisting of alkyl, cycloalkyl, heterocyclyl, aryl, arylalkyl, heteroaryl, heteroarylalkyl, alkenyl and alkynyl, and wherein each of the alkyl, cycloalkyl, heterocyclyl, aryl, arylalkyl, heteroaryl, heteroarylalkyl, alkenyl and alkynyl are independently unsubstituted or substituted by 1 to 5 groups independently selected from the group consisting of alkyl, cycloalkyl, heterocyclyl, aryl, heteroaryl, halo, $-CF_3$, $-CN$, $-OR^{19}$, $-N(R^{19})_2$, $-C(O)OR^{19}$, $-C(O)N(R^{19})_2$, and $-N(R^{19})S(O)R^{19}$; and each $R^{19}$ is independently selected from the group consisting of H, alkyl, cycloalkyl, heterocyclyl, aryl, and heteroaryl.

The compounds of Formula I can be useful as inhibitors and may be useful in the treatment and prevention of diseases associated with TACE, TNF-α, MMPs, ADAMs or any combination thereof.

DETAILED DESCRIPTION OF THE INVENTION

In its several embodiments, the present invention provides a novel class of inhibitors of TACE, the production of TNF-α, MMPs, ADAMs or any combination thereof, pharmaceutical compositions containing one or more of the compounds, methods of preparing pharmaceutical formulations comprising one or more such compounds, and methods of treatment, prevention or amelioration of one or more of the symptoms of inflammation.

In one embodiment, the present invention provides compounds which are represented by structural Formula (I) above or a pharmaceutically acceptable salt, solvate or isomer thereof, wherein the various moieties are as described above.

In one embodiment, $R^1$ and $R^2$ are the same or different, each being independently selected from the group consisting of alkyl, cycloalkyl, heterocyclyl, aryl, arylalkyl, heteroaralkyl, and heteroaryl; or alternatively $R^1$ and $R^2$, taken together with the N to which $R^1$ and $R^2$ are shown attached, represent a 4-8 membered heterocyclic ring having 1-3 heteroatoms including said N, said heterocyclic ring being optionally fused with aryl, heteroaryl, cycloalkyl, or heterocyclyl, wherein each of said alkyl, cycloalkyl, heterocyclyl, aryl, arylalkyl, heteroaralkyl, heteroaryl and 4-8 membered heterocyclic ring can be unsubstituted or optionally independently substituted with one or more moieties which can be the same or different, each moiety being independently selected from the group of $R^{70}$.

In one embodiment, $R^1$ and $R^2$ are the same or different, each being independently selected from the group consisting of H, cycloalkyl, heterocyclyl, aryl, arylalkyl, heteroaralkyl, and heteroaryl; or alternatively $R^1$ and $R^2$, taken together with the N to which $R^1$ and $R^2$ are shown attached, represent a 4-8 membered heterocyclic ring having 1-3 heteroatoms including said N, said heterocyclic ring being optionally fused with aryl, heteroaryl, cycloalkyl, or heterocyclyl, wherein each of said alkyl, cycloalkyl, heterocyclyl, aryl, arylalkyl, heteroaralkyl, heteroaryl and 4-8 membered heterocyclic ring can be unsubstituted or optionally independently substituted with one or more moieties which can be the same or different, each moiety being independently selected from the group of $R^{70}$.

In one embodiment, A is selected from the group consisting of:

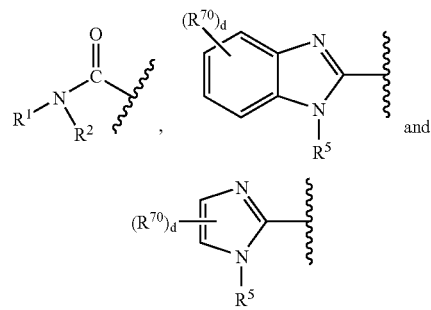

and wherein $R^1$ and $R^2$, taken together with the N to which $R^1$ and $R^2$ are shown attached, represent a 4-8 membered heterocyclic ring having 1-3 heteroatoms including said N, said heterocyclic ring being optionally substituted with $R^{70}$, or optionally fused with aryl, heteroaryl, cycloalkyl, or heterocyclyl, wherein said 4-8 membered heterocyclic ring can be unsubstituted or optionally independently substituted with one or more moieties which can be the same or different, each moiety being independently selected from the group of $R^{70}$ moieties.

In another embodiment, A is

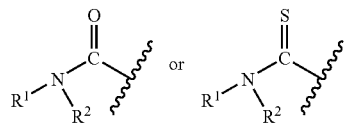

wherein $R^1$ and $R^2$ are the same or different, each being independently selected from the group consisting of H, alkyl, cycloalkyl, heterocyclyl, aryl, arylalkyl, heteroaralkyl, and heteroaryl; wherein said alkyl, cycloalkyl, heterocyclyl, aryl, arylalkyl, heteroaralkyl and heteroaryl can be unsubstituted or optionally independently substituted with one or more moieties which can be the same or different, each moiety being independently selected from the group of $R^{70}$ moieties.

In another embodiment, A is

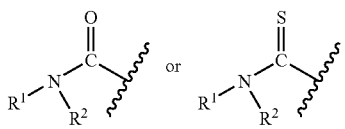

wherein $R^1$ and $R^2$ are the same or different, each being independently selected from the group consisting of alkyl, cycloalkyl, heterocyclyl, aryl, arylalkyl, heteroaralkyl, and heteroaryl; wherein said alkyl, cycloalkyl, heterocyclyl, aryl, arylalkyl, heteroaralkyl and heteroaryl can be unsubstituted or optionally independently substituted with one or more moieties which can be the same or different, each moiety being independently selected from the group of $R^{70}$ moieties.

In another embodiment, A is

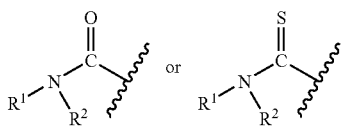

wherein $R^1$ and $R^2$ are the same or different, each being independently selected from the group consisting of H, cycloalkyl, heterocyclyl, aryl, arylalkyl, heteroaralkyl, and heteroaryl; wherein said alkyl, cycloalkyl, heterocyclyl, aryl, arylalkyl, heteroaralkyl and heteroaryl can be unsubstituted or optionally independently substituted with one or more moieties which can be the same or different, each moiety being independently selected from the group of $R^{70}$ moieties.

In another embodiment, A is

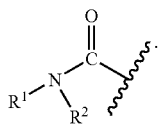

In another embodiment, A is

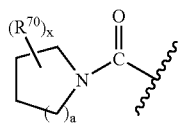

wherein a is 0 to 4 and x is 0 to 4.

In another embodiment, A is

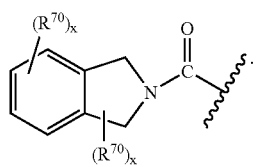

wherein each x idependently is 0 to 4.

In another embodiment, A is selected from the group consisting of:

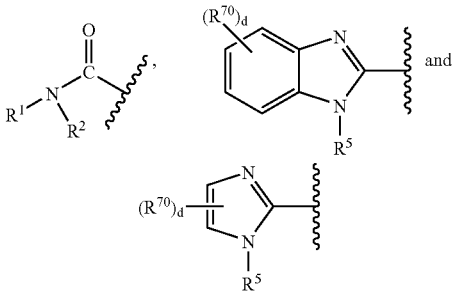

wherein $R^1$ and $R^2$, taken together with the N to which $R^1$ and $R^2$ are shown attached, represent a 3-8 membered heterocyclic ring having 1-3 heteroatoms including said N, said heterocyclic ring being optionally substituted with $R^{70}$, or optionally fused with aryl, heteroaryl, cycloalkyl, or heterocyclyl, wherein said 3-8 membered heterocyclic ring can be unsubstituted or optionally independently substituted with one or more moieties which can be the same or different, each moiety being independently selected from the group of $R^{70}$ moieties;

wherein a ring is formed from $-NR^1R^2$ and said ring is

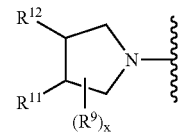

wherein
each $R^9$ is a substituent for H where indicated and can be the same or different, each being independently selected from the group consisting of —OH, —OR$^{14}$, —C(O)OR$^{15}$, —C(O)N(R$^{15}$)(R$^{16}$), alkyl, aryl, heteroaryl, alkenyl, alkynyl, cycloalkyl and heterocyclyl, wherein said alkyl, aryl, heteroaryl, alkenyl, alkynyl, cycloalkyl and heterocyclyl can be unsubstituted or optionally independently substituted with one or more moieties which can be the same or different, each moiety being independently selected from the group of $R^{70}$ moieties;

$R^{11}$ and $R^{12}$ taken together with the carbon to which each $R^{11}$ and $R^{12}$ are shown attached are fused heteroaryl or fused cycloalkyl, wherein said fused heteroaryl and fused cycloalkyl can be unsubstituted or optionally independently substituted with one or more moieties which can be the same or different, each moiety being independently selected from the group of $R^{70}$ moieties; and x is 0 to 4, and when x is greater than 1, each $R^9$ moiety can be the same or different, each moiety being independently selected from the group of $R^9$ moieties.

In another embodiment, A is selected from the group consisting of:

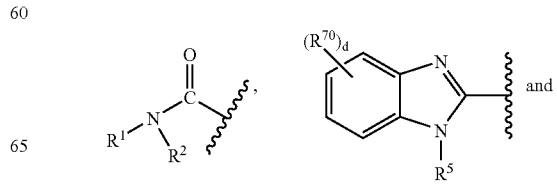

-continued

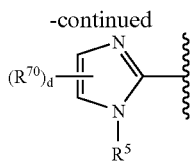

wherein $R^1$ and $R^2$, taken together with the N to which $R^1$ and $R^2$ are shown attached, represent a 3-8 membered heterocyclic ring having 1-3 heteroatoms including said N, said heterocyclic ring being optionally substituted with $R^{70}$, or optionally fused with aryl, heteroaryl, cycloalkyl, or heterocyclyl, wherein said 3-8 membered heterocyclic ring can be unsubstituted or optionally independently substituted with one or more moieties which can be the same or different, each moiety being independently selected from the group of $R^{70}$ moieties;

wherein a ring is formed from —$NR^1R^2$ and said ring is

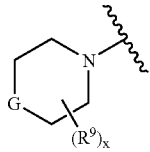

wherein
each $R^9$ is a substituent for H where indicated and can be the same or different, each being independently selected from the group consisting of —OH, —$OR^{14}$, —C(O)$OR^{15}$, —C(O)N($R^{15}$)($R^{16}$), alkyl, aryl, heteroaryl, alkenyl, alkynyl, cycloalkyl and heterocyclyl, wherein said alkyl, aryl, heteroaryl, alkenyl, alkynyl, cycloalkyl and heterocyclyl can be unsubstituted or optionally independently substituted with one or more moieties which can be the same or different, each moiety being independently selected from the group of $R^{70}$ moieties;
x is 0 to 4, and when x is greater than 1, each $R^9$ moiety can be the same or different, each moiety being independently selected from the group of $R^9$ moieties; and
G is selected from the group consisting of $CH_2$, $NR^7$, O, S, or $SO_2$.

In another embodiment, A is selected from the group consisting of:

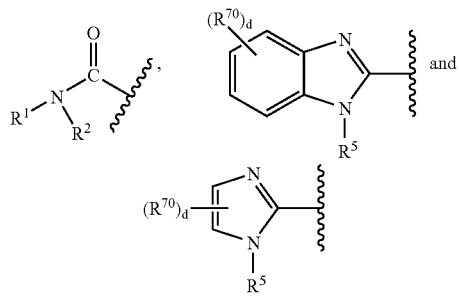

wherein $R^1$ and $R^2$, taken together with the N to which $R^1$ and $R^2$ are shown attached, represent a 3-8 membered heterocyclic ring having 1-3 heteroatoms including said N, said heterocyclic ring being optionally substituted with $R^{70}$, or optionally fused with aryl, heteroaryl, cycloalkyl, or heterocyclyl, wherein said 3-8 membered heterocyclic ring can be unsubstituted or optionally independently substituted with one or more moieties which can be the same or different, each moiety being independently selected from the group of $R^{70}$ moieties;

a ring is formed from —$NR^1R^2$ and said ring is selected from the group consisting of

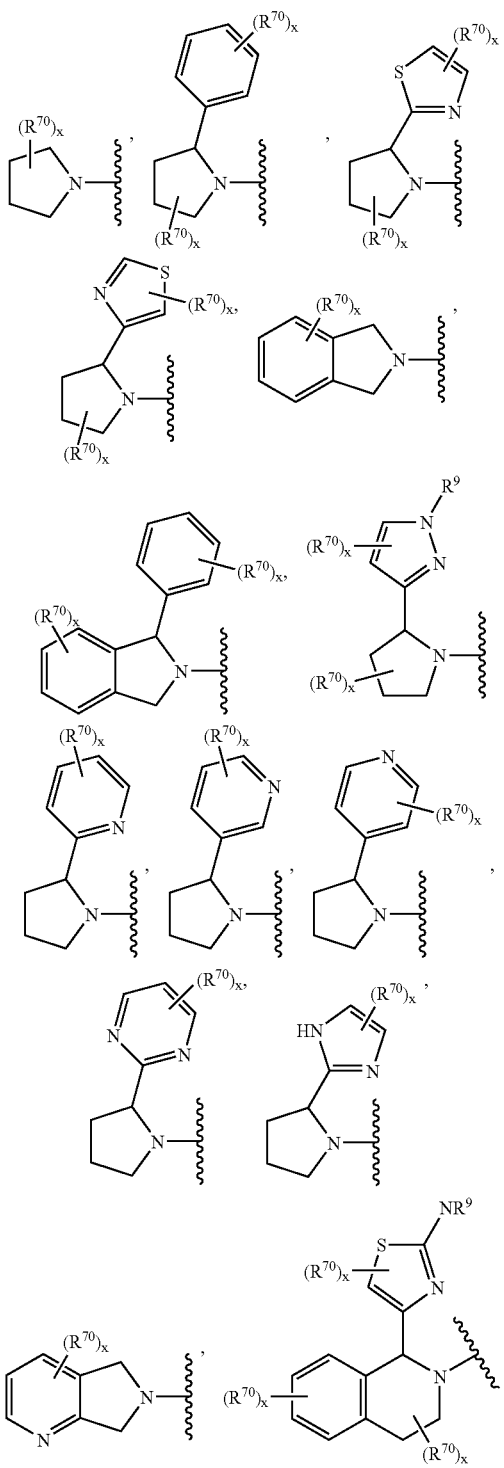

-continued

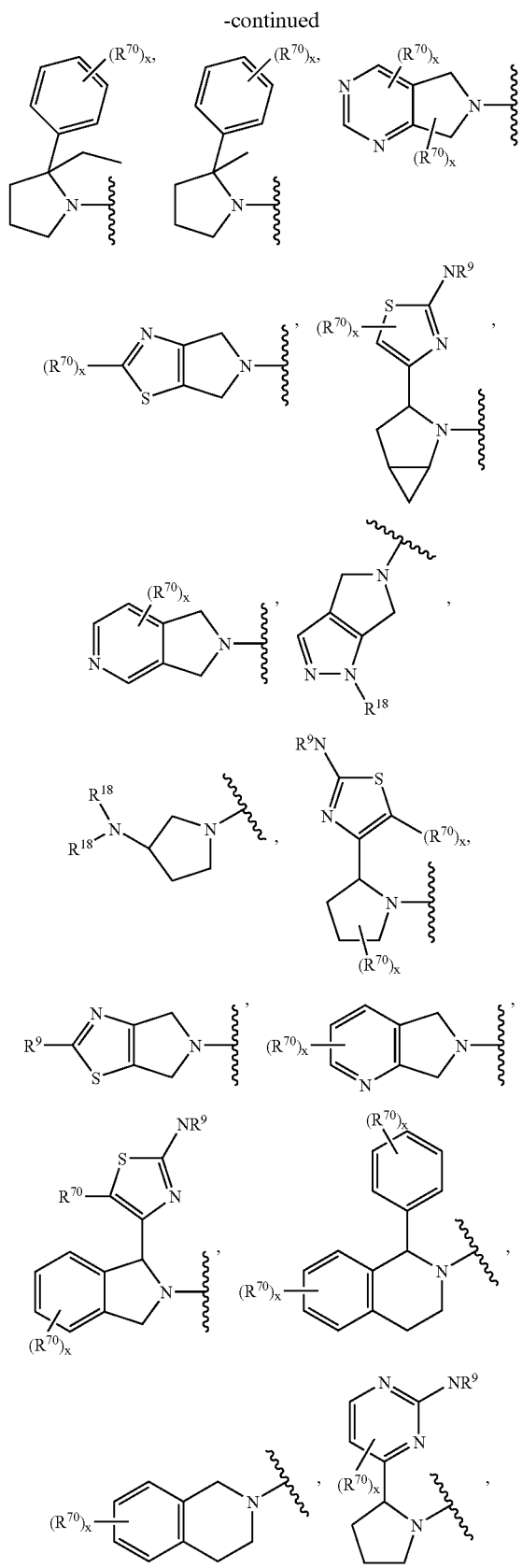

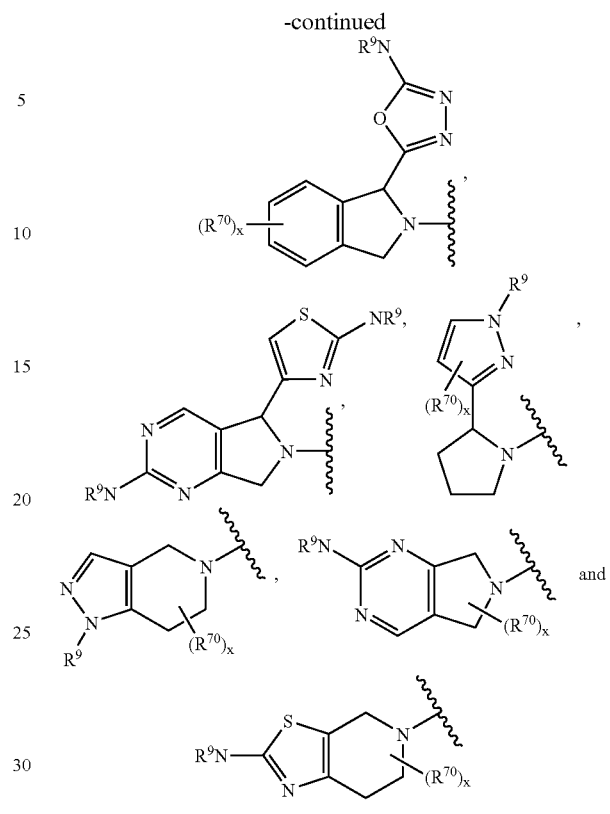

wherein
x is 0 to 4, and when x is greater than 1, each $R^{70}$ moiety can be the same or different, each moiety being independently selected from the group of $R^{70}$ moieties; and
each $R^{18}$ is the same or different and is independently H or alkyl.

In another embodiment, A is selected from the group consisting of:

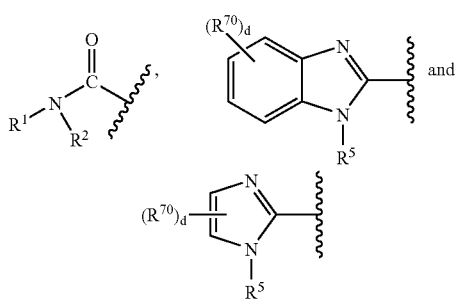

wherein $R^1$ and $R^2$, taken together with the N to which $R^1$ and $R^2$ are shown attached, represent a 3-8 membered heterocyclic ring having 1-3 heteroatoms including said N, said heterocyclic ring being optionally substituted with $R^{70}$, or optionally fused with aryl, heteroaryl, cycloalkyl, or heterocyclyl, wherein said 3-8 membered heterocyclic ring can be unsubstituted or optionally independently substituted with one or more moieties which can be the same or different, each moiety being independently selected from the group of $R^{70}$ moieties;
a ring is formed from —$NR^1R^2$ and said ring is selected from the group consisting of

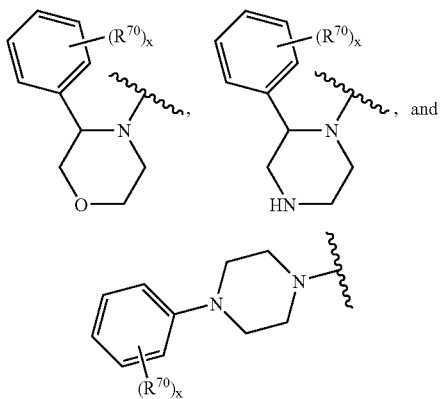

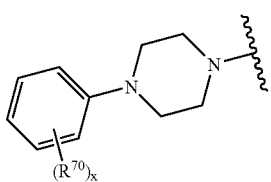

wherein x is 0 to 4, and when x is greater than 1, each $R^{70}$ moiety can be the same or different, each moiety being independently selected from the group of $R^{70}$ moieties.

In another embodiment, A is selected from the group consisting of:

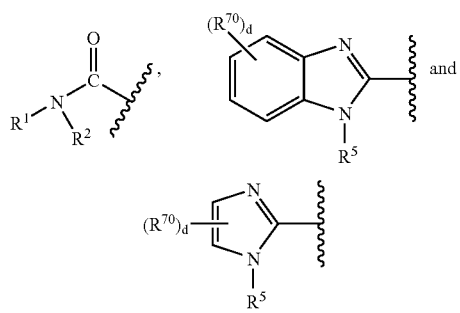

wherein $R^1$ and $R^2$, taken together with the N to which $R^1$ and $R^2$ are shown attached, represent a 3-8 membered heterocyclic ring having 1-3 heteroatoms including said N, said heterocyclic ring being optionally substituted with $R^{70}$, or optionally fused with aryl, heteroaryl, cycloalkyl, or heterocyclyl, wherein said 3-8 membered heterocyclic ring can be unsubstituted or optionally independently substituted with one or more moieties which can be the same or different, each moiety being independently selected from the group of $R^{70}$ moieties; a ring is formed from —$NR^1R^2$ and said ring is

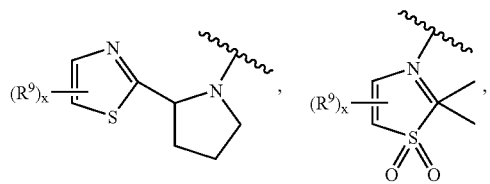

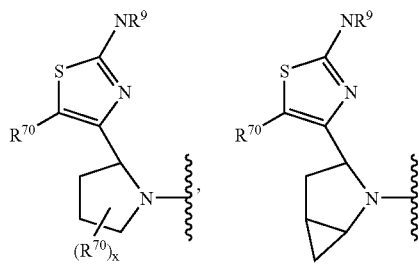

-continued

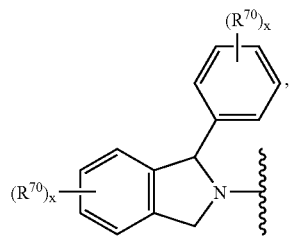

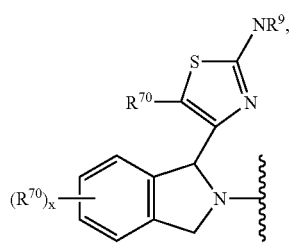

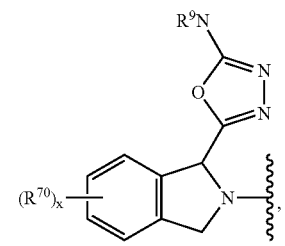

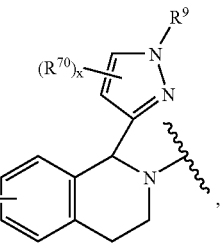

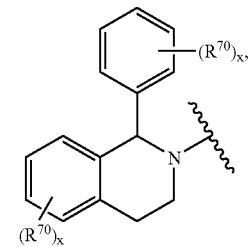

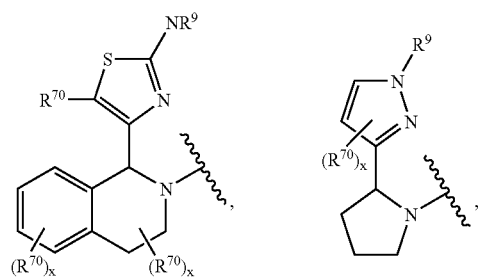

-continued

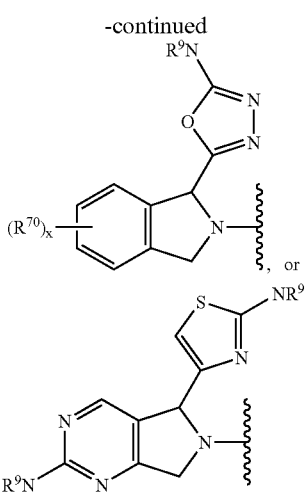

wherein
each R⁹ is a substituent for H where indicated and can be the same or different, each being independently selected from the group consisting of —OH, —OR$^{14}$, —C(O)OR$^{15}$, —C(O)N(R$^{15}$)(R$^{16}$), alkyl, aryl, heteroaryl, alkenyl, alkynyl, cycloalkyl and heterocyclyl, wherein said alkyl, aryl, heteroaryl, alkenyl, alkynyl, cycloalkyl and heterocyclyl can be unsubstituted or optionally independently substituted with one or more moieties which can be the same or different, each moiety being independently selected from the group of R$^{70}$ moieties; and x is 0 to 4, and when x is greater than 1, each R⁹ moiety can be the same or different, each moiety being independently selected from the group of R⁹ moieties.

In another embodiment, J is O.
In another embodiment, E is O.
In another embodiment, R$^{10}$ is H or alkyl.
In another embodiment, R$^{20}$, R$^{30}$, R$^{40}$, and R$^{50}$ are all the same and are H.
In another embodiment, R$^{6}$ is H or alkyl.
In another embodiment, R$^{6}$ is H.
In another embodiment, R$^{13}$ is H or alkyl.
In another embodiment, R$^{13}$ is H or —CH$_3$.
In another embodiment, A is selected from the group consisting of

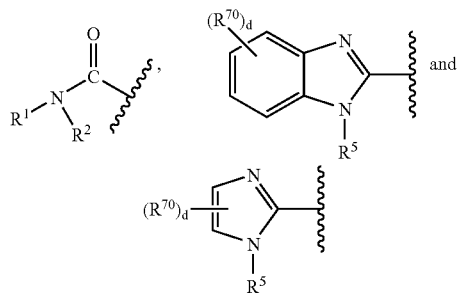

wherein R$^1$ and R$^2$, taken together with the N to which R$^1$ and R$^2$ are shown attached, represent a 4-6 membered heterocyclic ring having 1-3 heteroatoms including said N, said heterocyclic ring being optionally substituted with R$^{70}$, wherein R$^{70}$ is aryl.

In another embodiment, Y is a covalent bond or —[C(R$^6$)$_2$]$_n$— wherein n is 1 to 2, —CH$_2$—.

In another embodiment, Y is selected from the group consisting of a covalent bond, —CH$_2$—, —C(H)(OH)—, —C(O)— and —O—.

In another embodiment, Y is a covalent bond or —CH$_2$—.
In another embodiment, Y is a covalent bond.
In another embodiment, W is —(CR$^{13}{}_2$)$_n$—, in which n is 0-5.
In another embodiment, W is —(CR$^{13}{}_2$)$_n$—, in which n is 1-5 and each R$^{13}$ is H or alkyl.
In another embodiment, W is selected from the group consisting of —CH$_2$—, —C(H)(CH$_3$)—, —C(CH$_3$)$_2$— and —CH$_2$CH$_2$—.
In another embodiment, W is —CH$_2$—.
In another embodiment, W is —C(H)(CH$_3$)—.
In another embodiment, X is selected from the group consisting of alkyl, aryl, heterocyclyl and heteroaryl.
In another embodiment, X is aryl.
In another embodiment, X is heteroaryl.
In another embodiment, X is selected from the group consisting of phenyl, azetidinyl, pyrrolidinyl, piperidinyl, pyridinyl, thienyl, thiazolyl, oxazolyl, imidazolyl and pyrazolyl.
In another embodiment, X is selected from the group consisting of phenyl, pyridinyl and piperidinyl.
In another embodiment, X is selected from the group consisting of

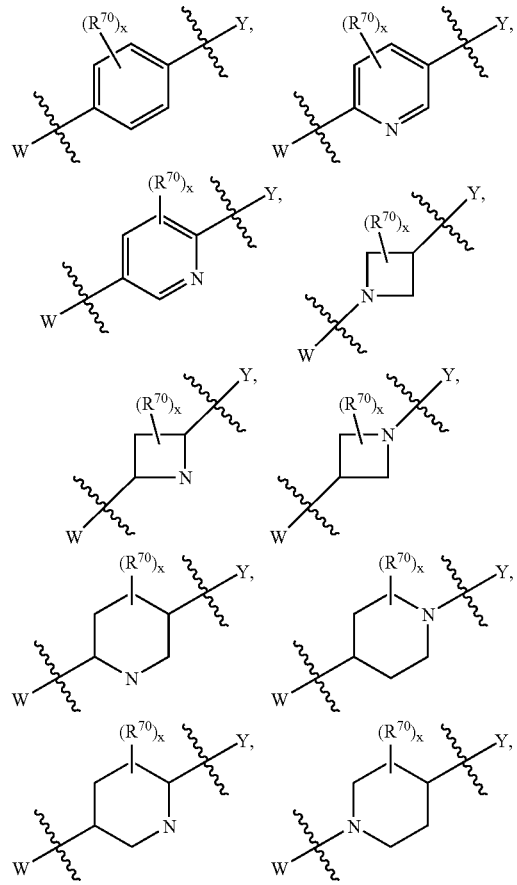

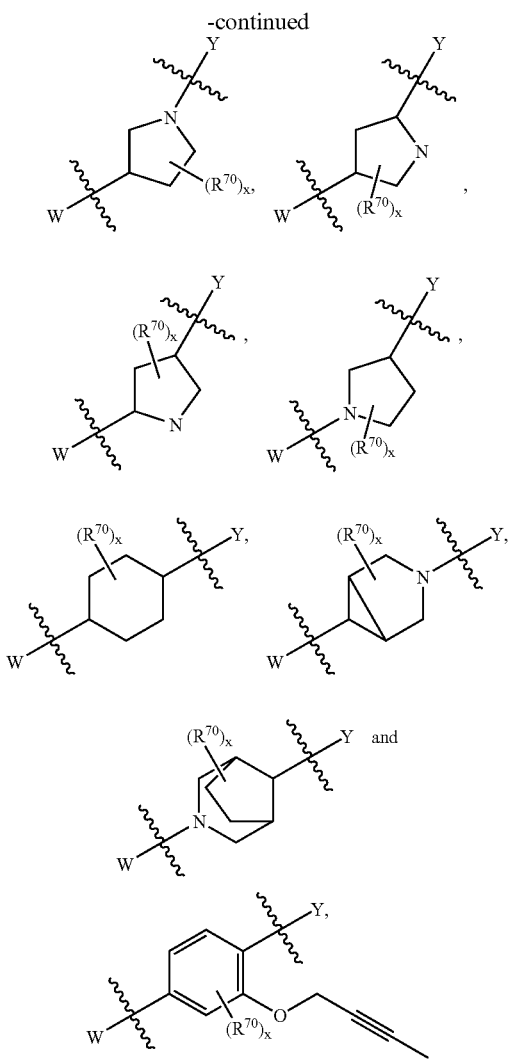

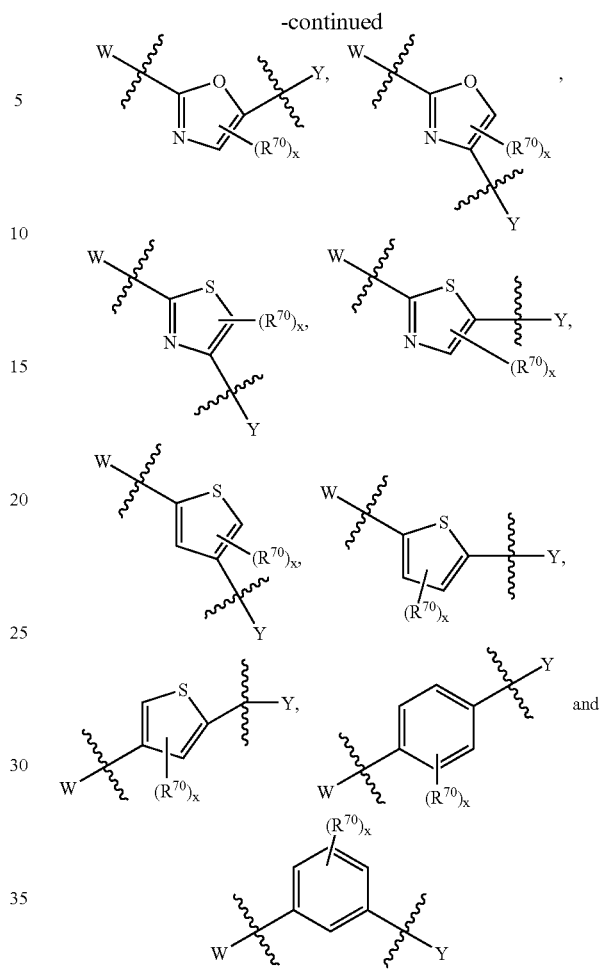

wherein
x is 0 to 4, and wherein x is greater than 1, each $R^{70}$ moiety can be the same or different, each moiety being independently selected from the group of $R^{70}$ moieties.

In the above shown moieties for X, X is the moiety enclosed by ⌊─⌋ and W and Y are shown only to indicate which end of the X is attached to W and which end to Y. Similar depictions occur throughout this application with similar connotations.

In another embodiment X is selected from the group consisting of

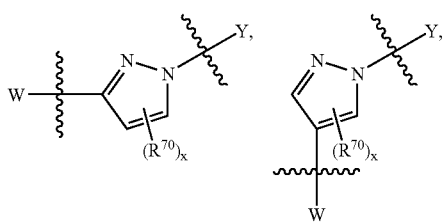

wherein x is 0 to 4, and when x is greater than 1, each $R^{70}$ moiety can be the same or different, each moiety being independently selected from the group of $R^{70}$ moieties.

In another embodiment, Z is selected from the group consisting of H, aryl and heteroaryl.

In another embodiment, Z is selected from the group consisting of H, phenyl, indolyl, benzimidazolyl, pyrazolyl, thienyl, pyridinyl, thiazolyl, thiadiazolyl, imidazolyl, pyrrolidinyl, pyrazinyl, triazolyl, tetrazolyl and tetrazinyl, wherein said phenyl, indolyl, benzimidazolyl, pyrazolyl, thienyl, pyridinyl, thiazolyl, thiadiazolyl, imidazolyl, pyrrolidinyl, pyrazinyl, triazolyl, tetrazolyl and tetrazinyl can be unsubstituted or optionally independently substituted with one or more moieties which can be the same or different, each moiety being independently selected from the group consisting of $R^{70}$ moieties.

In another embodiment, Z is selected from the group consisting of

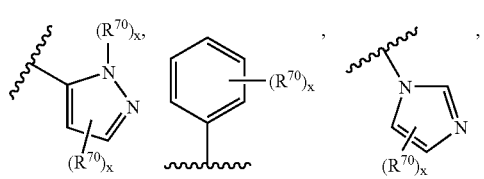

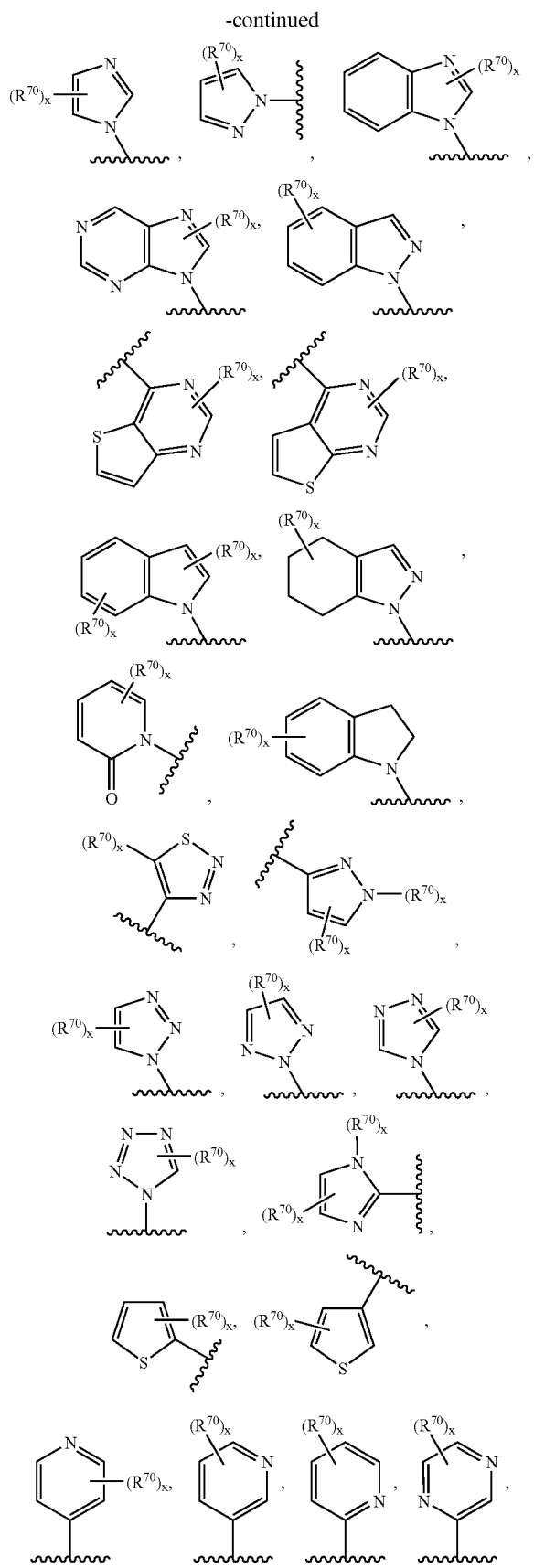

-continued

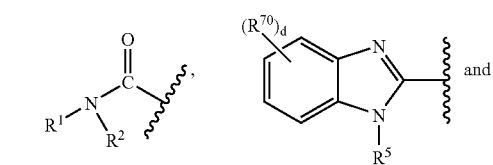

wherein x is 0 to 4, and when x is greater than 1, each $R^{70}$ moiety can be the same or different, each moiety being independently selected from the group of $R^{70}$ moieties.

In another embodiment, Z is phenyl.

In another embodiment, Z is a phenyl substituted with at least one substituent selected from the group consisting of cyano, alkoxy, halogen, alkyl, haloalkyl, hydroxy, aryl, heteroaryl, aryloxy, amino and tetrazole.

In another embodiment, Z is thienyl.

In another embodiment, Z is a thienyl substituted with at least one substituent selected from the group consisting of cyano, alkoxy, halogen, alkyl, haloalkyl, hydroxy, aryl, heteroaryl, aryloxy, amino and tetrazole.

In another embodiment, Z is pyrazolyl.

In another embodiment, Z is a pyrazolyl substituted with at least one substituent selected from the group consisting of cyano, alkoxy, halogen, alkyl, haloalkyl, hydroxy, aryl, heteroaryl, aryloxy, amino and tetrazole.

In another embodiment, Z is pyridinyl.

In another embodiment, Z is a pyridinyl substituted with at least one substituent selected from the group consisting of cyano, alkoxy, halogen, alkyl, haloalkyl, hydroxy, aryl, heteroaryl, aryloxy, amino and tetrazole.

In another embodiment, Z is imidazolyl.

In another embodiment, Z is an imidazolyl substituted with at least one substituent selected from the group consisting of cyano, alkoxy, halogen, alkyl, haloalkyl, hydroxy, aryl, heteroaryl, aryloxy, amino and tetrazole.

In another embodiment, A is selected from the group consisting of:

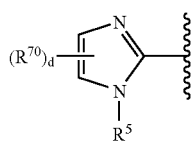

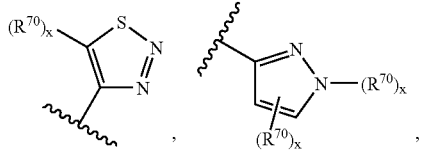

wherein $R^1$ and $R^2$, taken together with the N to which $R^1$ and $R^2$ are shown attached, represent a 4-8 membered heterocyclic ring having 1-3 heteroatoms including said N, said heterocyclic ring being optionally substituted with one or more $R^{70}$, or optionally fused with aryl, heteroaryl, cycloalkyl, or heterocyclyl, wherein said 4-8 membered heterocyclic ring can be unsubstituted or optionally independently substituted with one or more moieties which can be the same or different, each moiety being independently selected from the group of $R^{70}$ moieties; E, J and T are the same and are O; $R^{10}$ is H or alkyl; $R^{20}$, $R^{30}$, $R^{40}$, and $R^{50}$ are the same and are H; W is —$(CR^{13}_2)_n$—, wherein n is 0 to 5; X is selected from the group consisting of aryl, heteroaryl and heterocyclyl; Y is selected from the group consisting of a covalent bond, —[C$(R^6)_2]_n$— wherein n is 1 to 2, —O—, —S—, and —$NR^1$—; and Z is selected from the group consisting of

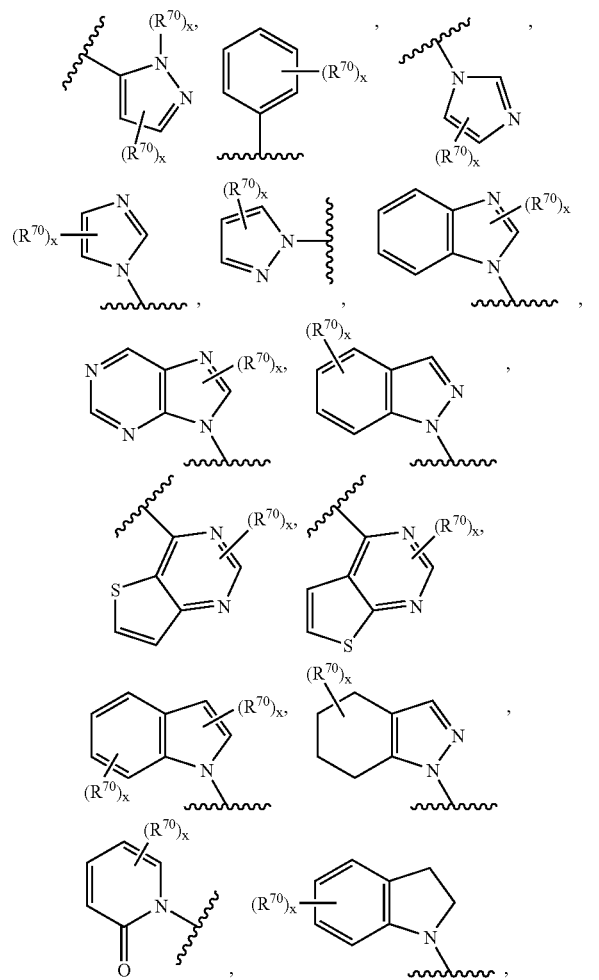

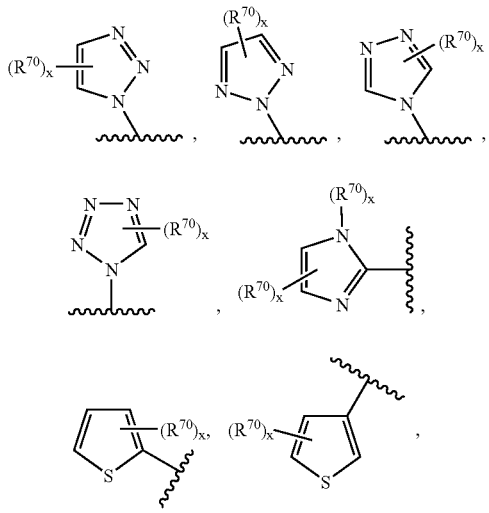

In another embodiment, A is:

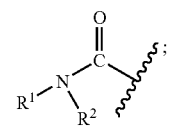

wherein;
the —NR¹R² of

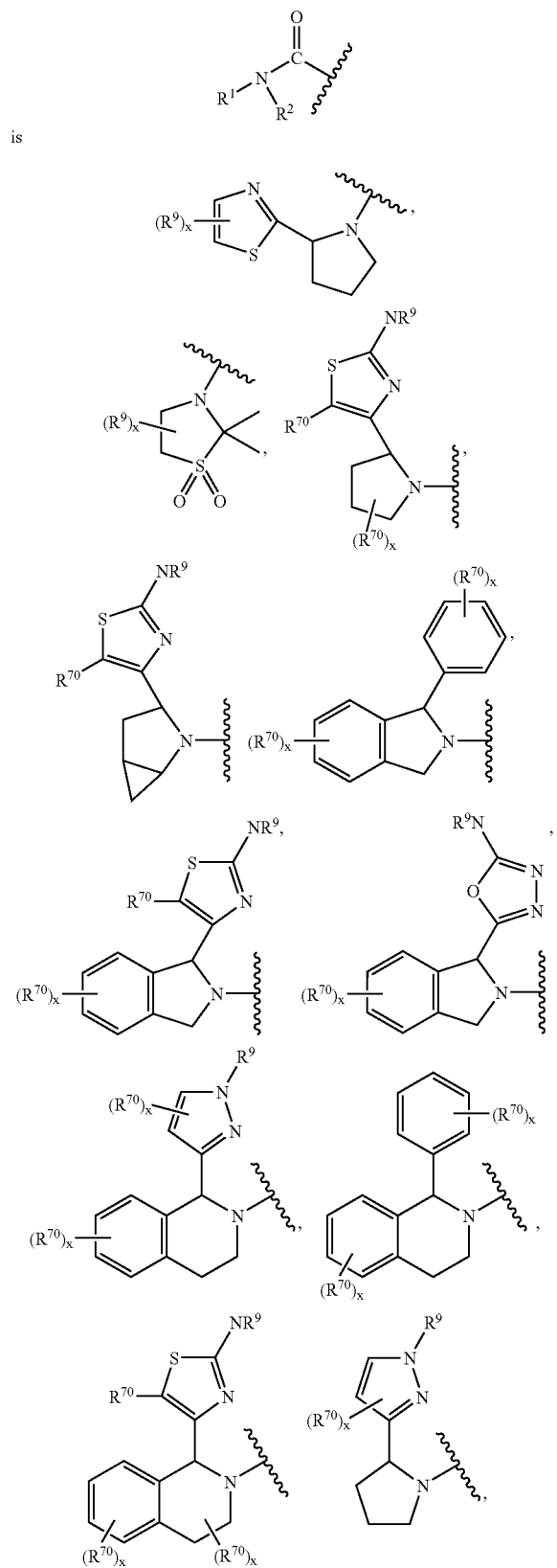

is

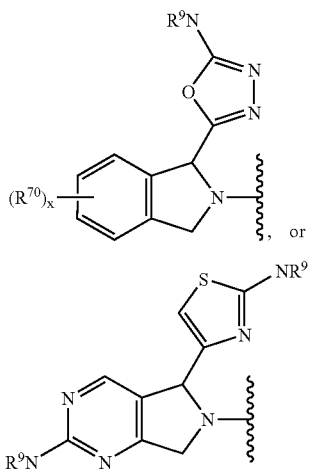

wherein
each $R^9$ is a substituent for H where indicated and can be the same or different, each being independently selected from the group consisting of —OH, —OR¹⁴, —C(O)OR¹⁵, —C(O)N(R¹⁵)(R¹⁶), alkyl, aryl, heteroaryl, alkenyl, alkynyl, cycloalkyl and heterocyclyl, wherein said alkyl, aryl, heteroaryl, alkenyl, alkynyl, cycloalkyl and heterocyclyl can be unsubstituted or optionally independently substituted with one or more moieties which can be the same or different, each moiety being independently selected from the group of $R^{70}$ moieties; and x is 0 to 4, and when x is greater than 1, each $R^9$ moiety can be the same or different, each moiety being independently selected from the group of $R^9$ moieties;

E, J and T are the same and are O; $R^{10}$ is H or alkyl; $R^{20}$, $R^{30}$, $R^{40}$, and $R^{50}$ are the same and are H; W is —(CR¹³₂)ₙ—, wherein n is 0 to 5; X is selected from the group consisting of aryl, heteroaryl and heterocyclyl; Y is selected from the group consisting of a covalent bond, —[C(R⁶)₂]ₙ— wherein n is 1 to 2, —O—, —S—, and —NR¹—; and Z is selected from the group consisting of

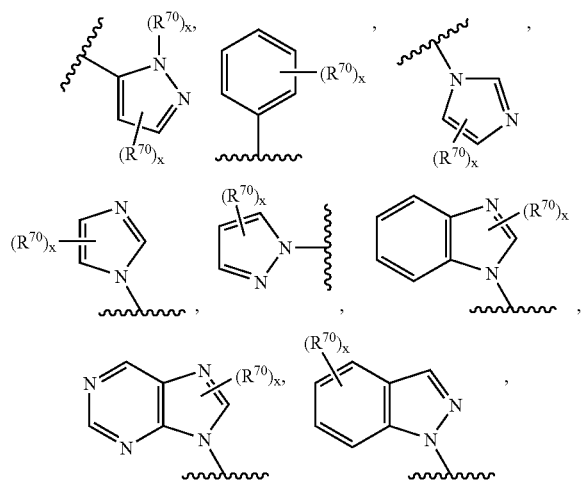

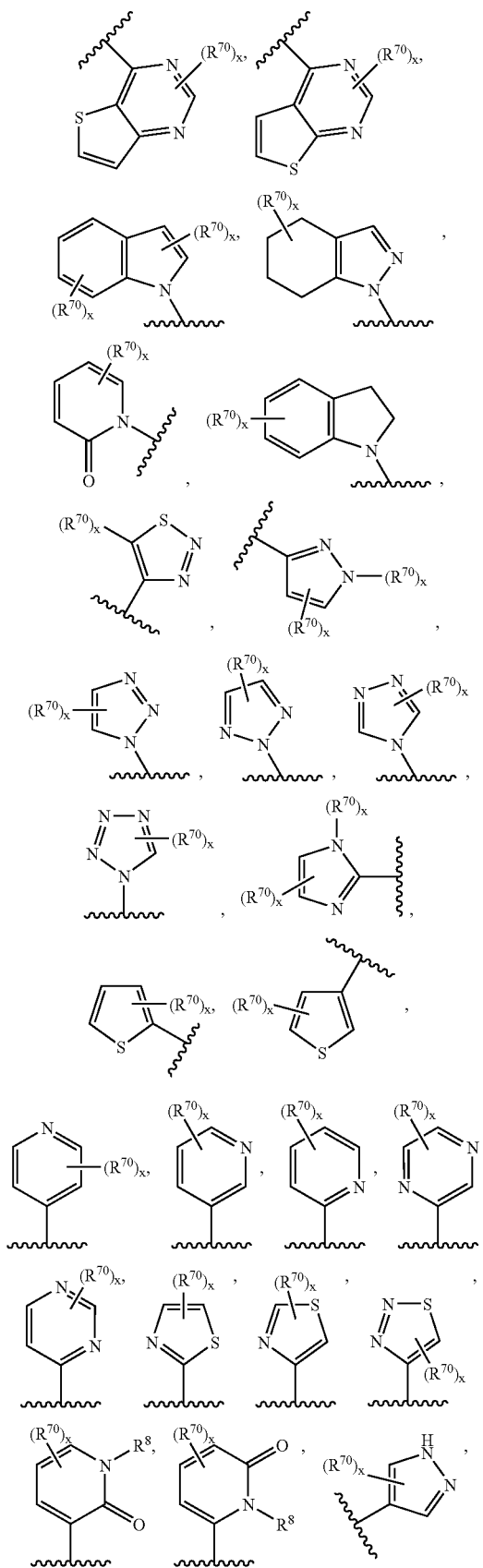

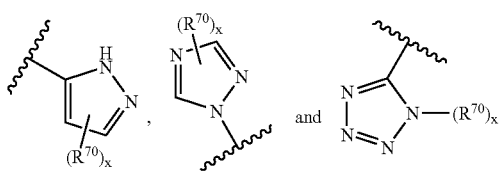

In another embodiment, A is:

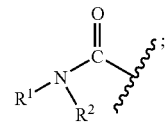

wherein $R^1$ and $R^2$, taken together with the N to which $R^1$ and $R^2$ are shown attached, represent a 4-8 membered heterocyclic ring having 1-3 heteroatoms including said N, said heterocyclic ring being optionally substituted with one or more $R^{70}$, or optionally fused with aryl, heteroaryl, cycloalkyl, or heterocyclyl, wherein said 4-8 membered heterocyclic ring can be unsubstituted or optionally independently substituted with one or more moieties which can be the same or different, each moiety being independently selected from the group of $R^{70}$ moieties; E, J and T are the same and are O; $R^{10}$ is H or alkyl;

$R^{20}$, $R^{30}$, $R^{40}$, and $R^{50}$ are the same and are H; W is $-(CR^{13}_2)_n-$, wherein n is 0 to 5; X is selected from the group consisting of aryl, heteroaryl and heterocyclyl; Y is selected from the group consisting of a covalent bond, $-[C(R^6)_2]_n-$ wherein n is 1 to 2, $-O-$, $-S-$, and $-NR^1-$; and Z is selected from the group consisting of

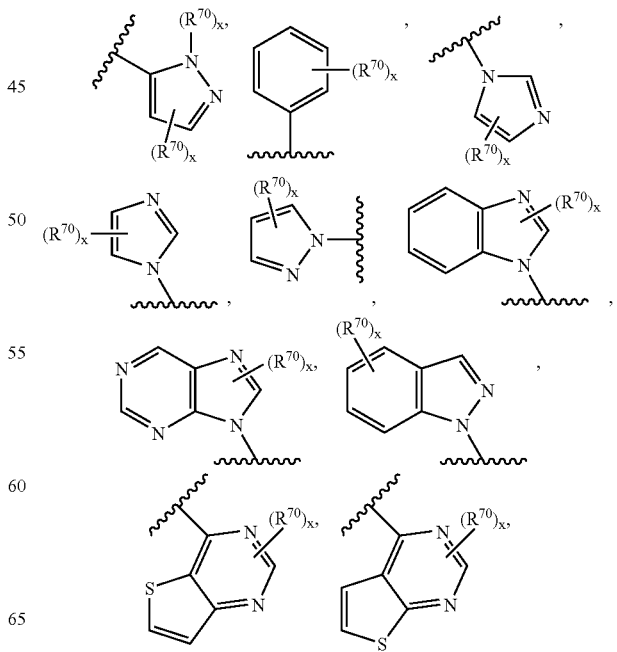

-continued

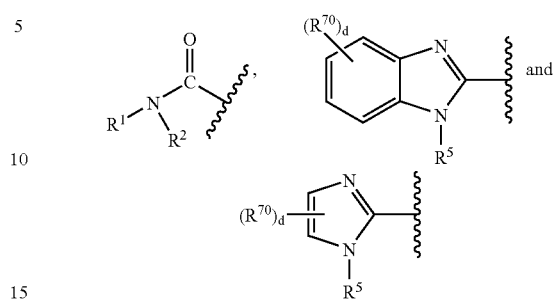

In another embodiment, A is selected from the group consisting of:

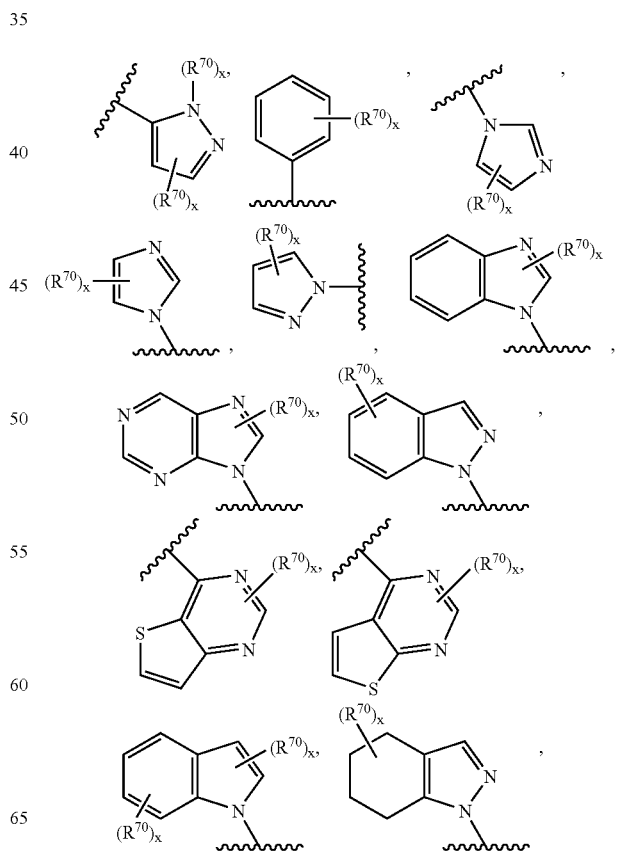

wherein $R^1$ and $R^2$, taken together with the N to which $R^1$ and $R^2$ are shown attached, represent a 3-8 membered heterocyclic ring having 1-3 heteroatoms including said N, said heterocyclic ring being optionally substituted with one or more $R^{70}$, or optionally fused with aryl, heteroaryl, cycloalkyl, or heterocyclyl, wherein said 3-8 membered heterocyclic ring can be unsubstituted or optionally independently substituted with one or more moieties which can be the same or different, each moiety being independently selected from the group of $R^{70}$ moieties;

wherein E, J and T are the same and are O; $R^{10}$ is H or alkyl; $R^{20}$, $R^{30}$, $R^{40}$, and $R^{50}$ are the same and are H; W is $-(CR^6{}_2)_n-$, wherein n is 0 to 5; X is selected from the group consisting of phenyl, piperidinyl, pyridinyl, thienyl, thiazolyl, oxazolyl and pyrazolyl; Y is $-[C(R^6)_2]_n-$ wherein n is 1 to 2; and Z is selected from the group consisting of -continued

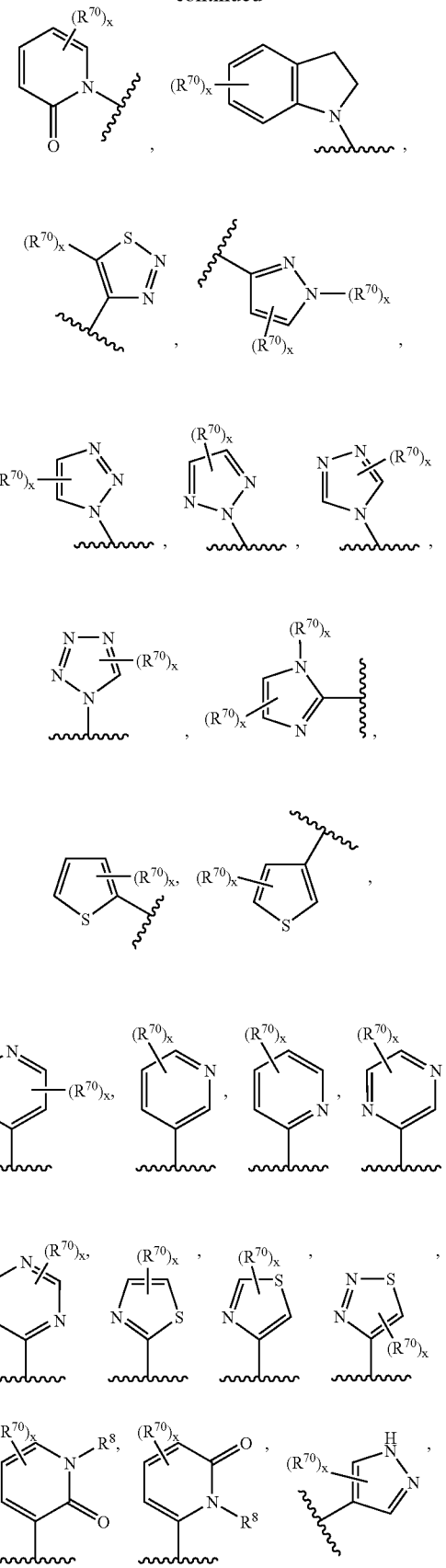

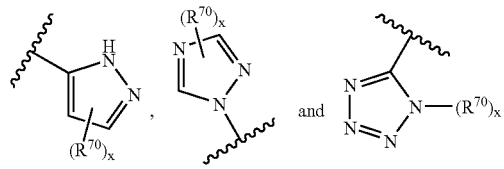

In another embodiment, A is:

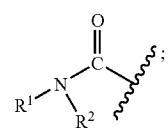

wherein $R^1$ and $R^2$, taken together with the N to which $R^1$ and $R^2$ are shown attached, represent a 3-8 membered heterocyclic ring having 1-3 heteroatoms including said N, said heterocyclic ring being optionally substituted with one or more $R^{70}$, or optionally fused with aryl, heteroaryl, cycloalkyl, or heterocyclyl, wherein said 3-8 membered heterocyclic ring can be unsubstituted or optionally independently substituted with one or more moieties which can be the same or different, each moiety being independently selected from the group of $R^{70}$ moieties;

wherein E, J and T are the same and are O; $R^{10}$ is H or alkyl; $R^{20}$, $R^{30}$, $R^{40}$, and $R^{50}$ are the same and are H; W is $-(CR^6_2)_n-$, wherein n is 0 to 5; X is selected from the group consisting of phenyl, piperidinyl, pyridinyl, thienyl, thiazolyl, oxazolyl and pyrazolyl; Y is $-[C(R^6)_2]_n-$ wherein n is 1 to 2; and Z is selected from the group consisting of

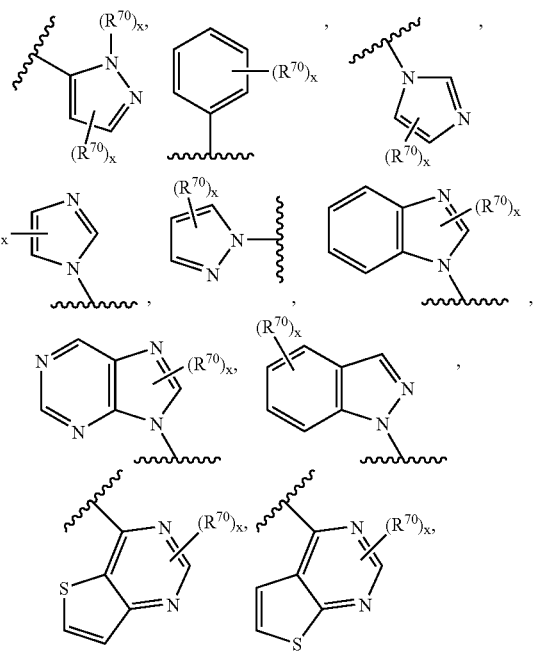

-continued

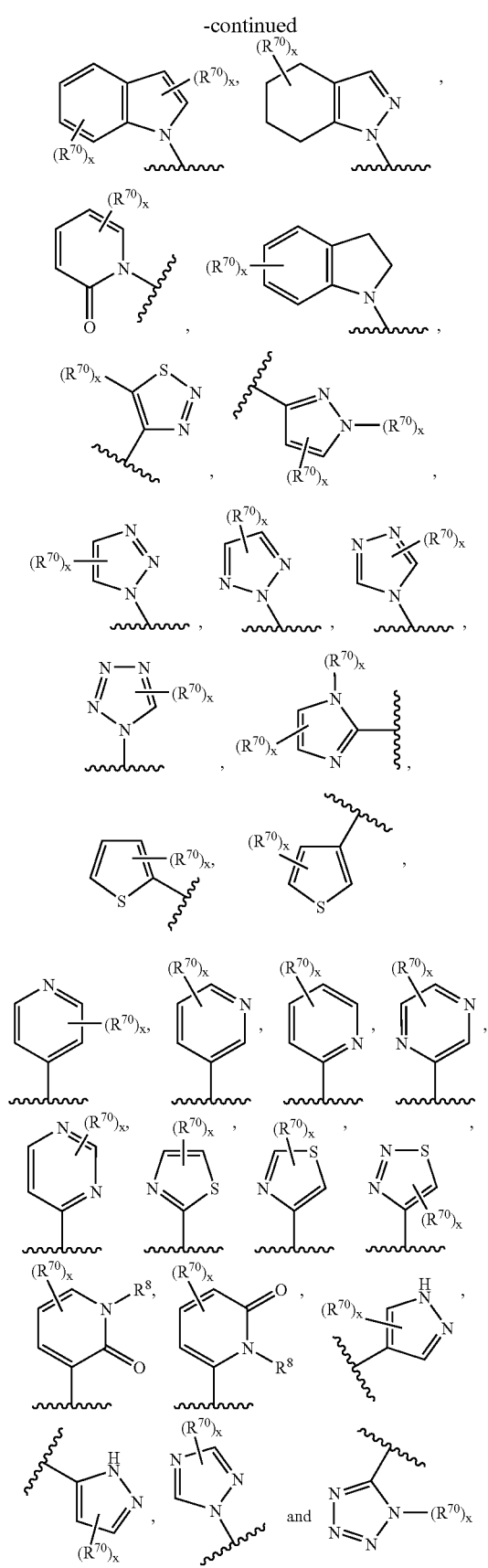

In another embodiment, A is selected from the group consisting of:

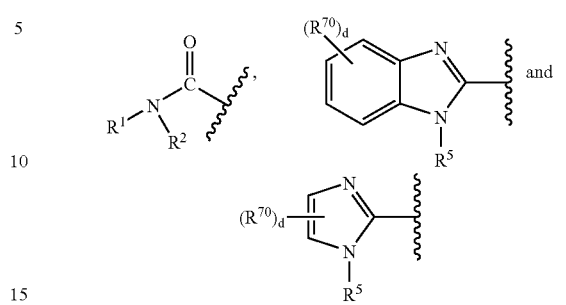

wherein $R^1$ and $R^2$, taken together with the N to which $R^1$ and $R^2$ are shown attached, represent a 3-8 members heterocyclic ring having 1-3 heteroatoms including said N, said heterocyclic ring being optionally substituted with one or more $R^{70}$, or optionally fused with aryl, heteroaryl, cycloalkyl, or heterocyclyl, wherein said 3-8 membered heterocyclic ring can be unsubstituted or optionally independently substituted with one or more moieties which can be the same or different, each moiety being independently selected from the group of $R^{70}$ moieties;

E, J and T are the same and are O; $R^{10}$ is H or alkyl; $R^{20}$, $R^{30}$, $R^{40}$, and $R^{50}$ are the same and are H; W is —$(CR^6_2)_n$—, wherein n is 0 to 5; X is selected from the group consisting of phenyl, piperidinyl, pyridinyl, thienyl, thiazolyl, oxazolyl and pyrazolyl; Y is selected from the group consisting of O—, —S—, and —$NR^1$—; and Z is selected from the group consisting of

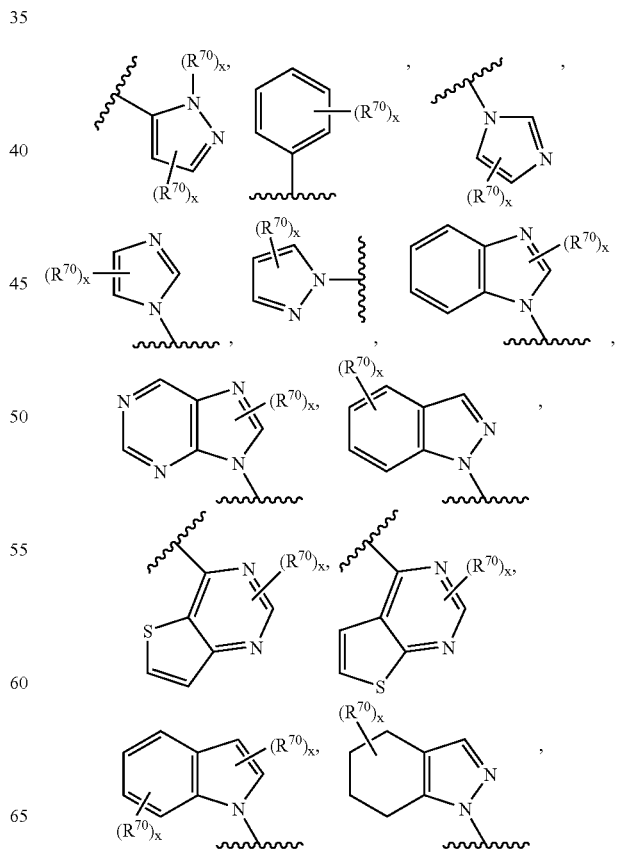

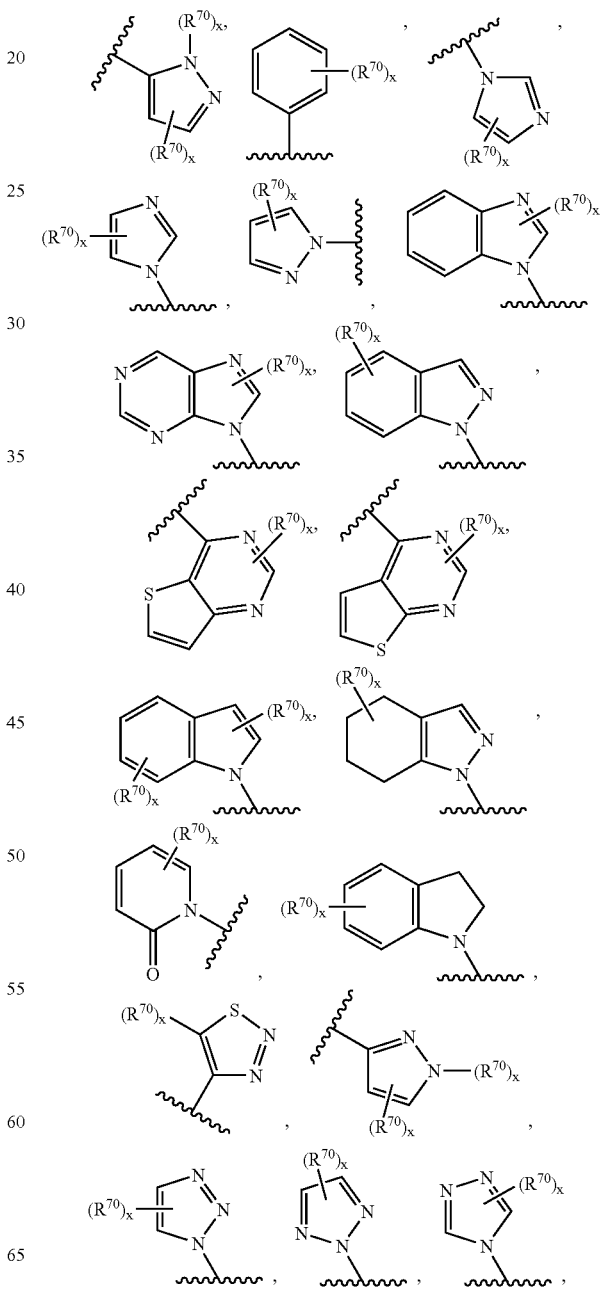

heterocyclic ring being optionally substituted with one or more R⁷⁰, or optionally fused with aryl, heteroaryl, cycloalkyl, or heterocyclyl, wherein said 3-8 membered heterocyclic ring can be unsubstituted or optionally independently substituted with one or more moieties which can be the same or different, each moiety being independently selected from the group of $R^{70}$ moieties;

wherein E, J and T are the same and are O; $R^{10}$ is H or alkyl; $R^{20}$, $R^{30}$, $R^{40}$, and $R^{50}$ are the same and are H; W is $-(CR^{6}_{2})_{n}-$, wherein n is 0 to 5; X is selected from the group consisting of phenyl, piperidinyl, pyridinyl, thienyl, thiazolyl, oxazolyl and pyrazolyl; Y is selected from the group consisting of O—, —S—, and —NR¹—; and Z is selected from the group consisting of In another embodiment, A is

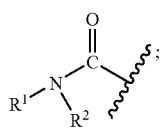

wherein R¹ and R² , taken together with the N to which R¹ and R² are shown attached, represent a 3-8 membered heterocyclic ring having 1-3 heteroatoms including said N, said -continued

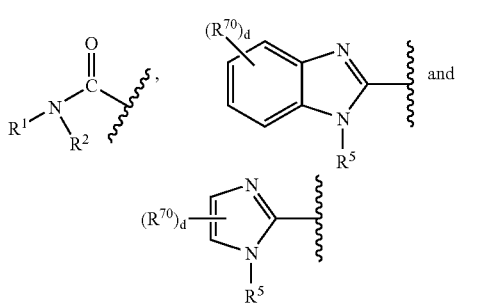

In another embodiment, A is selected from the group consisting of:

wherein R[1] and R[2], taken together with the N to which R[1] and R[2] are shown attached, represent a 3-8 membered heterocyclic ring having 1-3 heteroatoms including said N, said heterocyclic ring being optionally substituted with one or more R[70], or optionally fused with aryl, heteroaryl, cycloalkyl, or heterocyclyl, wherein said 3-8 membered heterocyclic ring can be unsubstituted or optionally independently substituted with one or more moieties which can be the same or different, each moiety being independently selected from the group of R[70] moieties;

wherein E, J and T are the same and are O; R[10] is H or alkyl; R[20], R[30], R[40], and R[50] are the same and are H; W is —(CR[13]$_2$)$_n$— wherein n is 1 or 2; X is selected from the group consisting of phenyl, piperidinyl, pyridinyl, thienyl, thiazolyl, oxazolyl and pyrazolyl; Y is a covalent bond and Z is selected from the group consisting of

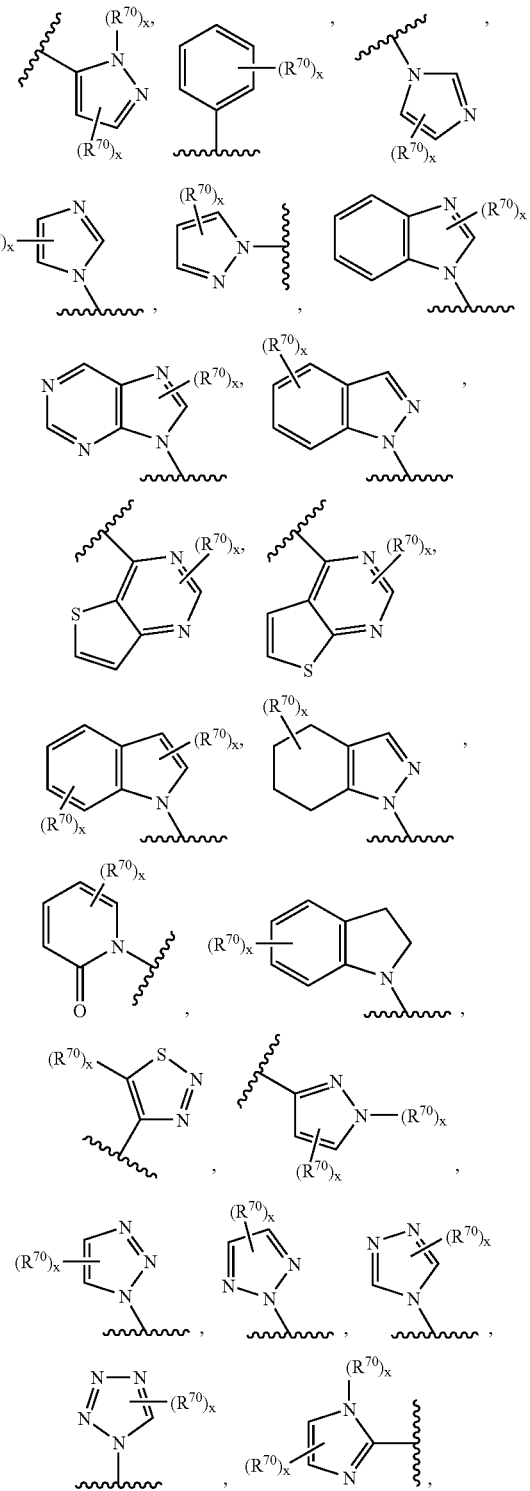

-continued

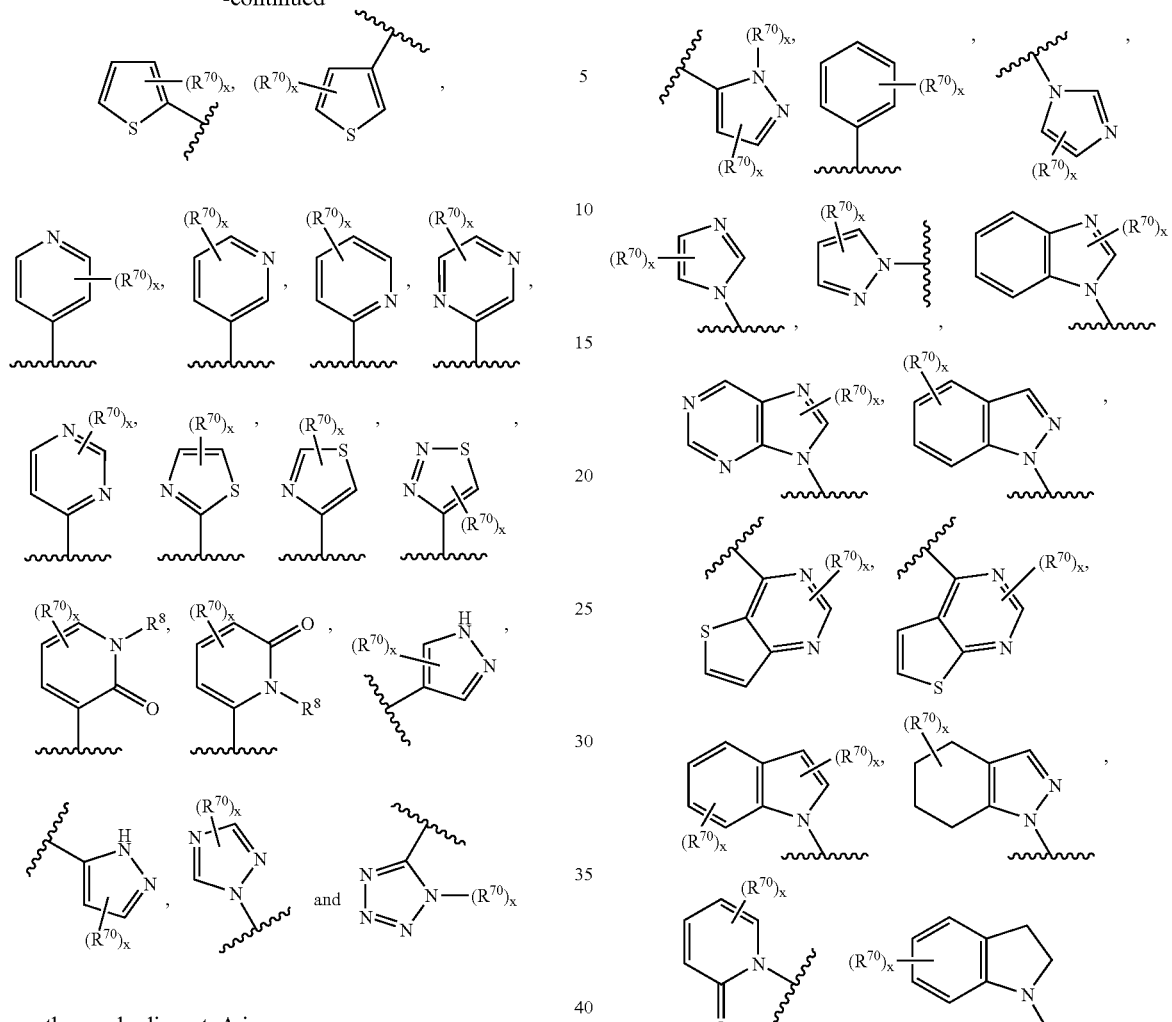

In another embodiment, A is

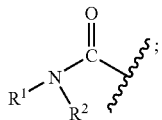

wherein $R^1$ and $R^2$, taken together with the N to which $R^1$ and $R^2$ are shown attached, represent a 3-8 membered heterocyclic ring having 1-3 heteroatoms including said N, said heterocyclic ring being optionally substituted with one or more $R^{70}$, or optionally fused with aryl, heteroaryl, cycloalkyl, or heterocyclyl, wherein said 3-8 membered heterocyclic ring can be unsubstituted or optionally independently substituted with one or more moieties which can be the same or different, each moiety being independently selected from the group of $R^{70}$ moieties; wherein E, J and T are the same and are O; $R^{10}$ is H or alkyl; $R^{20}$, $R^{30}$, $R^{40}$, and $R^{50}$ are the same and are H; W is —$(CR^{13}_2)_n$, wherein n is 1 or 2; X is selected from the group consisting of phenyl, piperidinyl, pyridinyl, thienyl, thiazolyl, oxazolyl and pyrazolyl; Y is a covalent bond and Z is selected from the group consisting of -continued

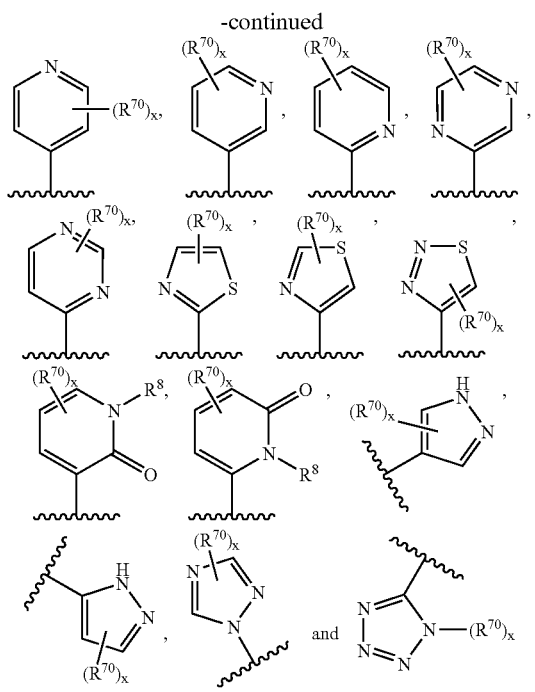
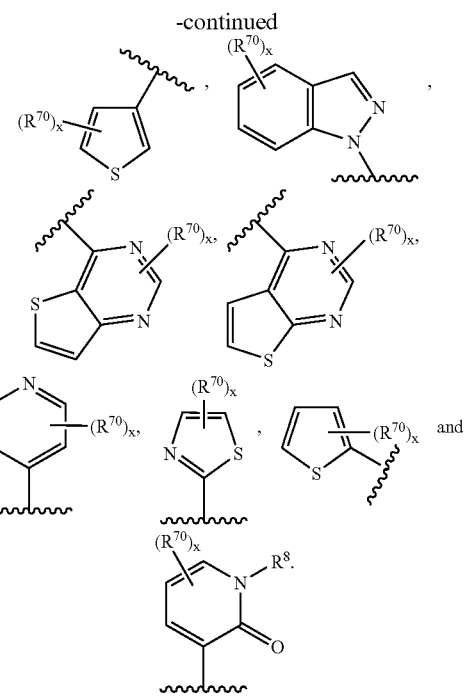

In another embodiment, X is selected from the group consisting of phenyl, piperidinyl, pyridinyl, thienyl, thiazolyl, oxazolyl, and pyrazolyl.

In another embodiment, X is selected from the group consisting of phenyl, piperidinyl, thienyl, and pyridinyl and Y is selected from the group consisting of a covalent bond, —[C(R$^6$)$_2$]$_n$— wherein n is 1 to 2 and —O—.

In another embodiment, X is phenyl and Y is selected from the group consisting of a covalent bond, —CH$_2$— and —O—.

In another embodiment, X is piperidinyl, Y is a covalent bond, and Z is aryl or heteroaryl having two substituents which can be the same or different, each moiety being independently selected from the group consisting of cyano, alkoxy, halogen, alkyl, haloalkyl, hydroxy, aryl, heteroaryl, aryloxy and amino.

In another embodiment, W is selected from the group consisting of —CH$_2$—, —C(H)CH$_3$—, —C(CH$_3$)$_2$— and Y is a covalent bond.

In another embodiment, W is —CH$_2$— and Y is —CH$_2$—.

In another embodiment, Z is selected from the group consisting of

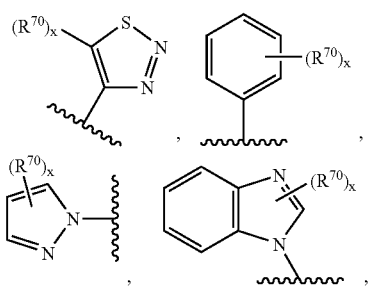

Another embodiment of the invention discloses the compounds shown in Table 1 below.

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl. The term "Fluoroalkyl" means an alkyl group in which alkyl is as previously described wherein one or more hydrogens are replaced with fluorine atoms.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

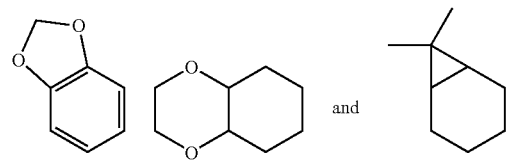

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

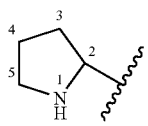

there is no —OH attached directly to carbons marked 2 and 5.

It should also be noted that tautomeric forms such as, for example, the moieties:

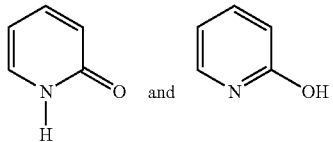

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula I or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the CDK(s) and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

Polymorphic forms of the compounds of Formula I, and of the salts, solvates and prodrugs of the compounds of Formula I, are intended to be included in the present invention.

The compounds according to the invention have pharmacological properties; in particular, the compounds of Formula I can be inhibitors of TACE, TNF-α, ADAM and/or MMP activity.

In one aspect, the invention provides a pharmaceutical composition comprising as an active ingredient at least one compound of formula 1.

In another aspect, the invention provides a pharmaceutical composition of formula 1 additionally comprising at least one pharmaceutically acceptable carrier.

In another aspect, the invention provides a method of treating disorders associated with TACE, TNF-α, MMPs, ADAMs or any combination thereof or any combination thereof, said method comprising administering to a patient in need of such treatment a pharmaceutical composition which comprises therapeutically effective amounts of at least one compound of formula 1.

In another aspect, the invention provides a use of a compound of formula 1 for the manufacture of a medicament to treat disorders associated with TACE, TNF-α, MMPs, ADAMs or any combination thereof.

The compounds of Formula I can have anti-inflammatory activity and/or immunomodulatory activity and can be useful in the treatment of diseases including but not limited to septic shock, haemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitis, OA and RA, ankylosing spondylitis, psoriatic arthritis, adult Still's disease, ureitis, Wegener's granulomatosis, Behcehe disease, Sjogren's syndrome, sarcoidosis, polymyositis, dermatomyositis, multiple sclerosis, sciatica, complex regional pain syndrome, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, reversible airway obstruction, adult respiratory distress syndrome, asthma, chronic obstructive pulmonary disease (COPD) and/or bronchitis. It is contemplated that a compound of this invention may be useful in treating one or more of the diseases listed.

In another aspect, the invention provides a method of preparing a pharmaceutical composition for treating the disorders associated with TACE, TNF-α, MMPs, ADAMs or any combination thereof, said method comprising bringing into intimate contact at least one compound of formula 1 and at least one pharmaceutically acceptable carrier.

In another aspect, the invention provides a compound of formula (I) exhibiting TACE, TNF-α, MMPs, ADAMs or any combination thereof inhibitory activity, including enantiomers, stereoisomers and tautomers of said compound, and pharmaceutically acceptable salts or solvates of said compound, said compound being selected from the compounds of structures listed below:

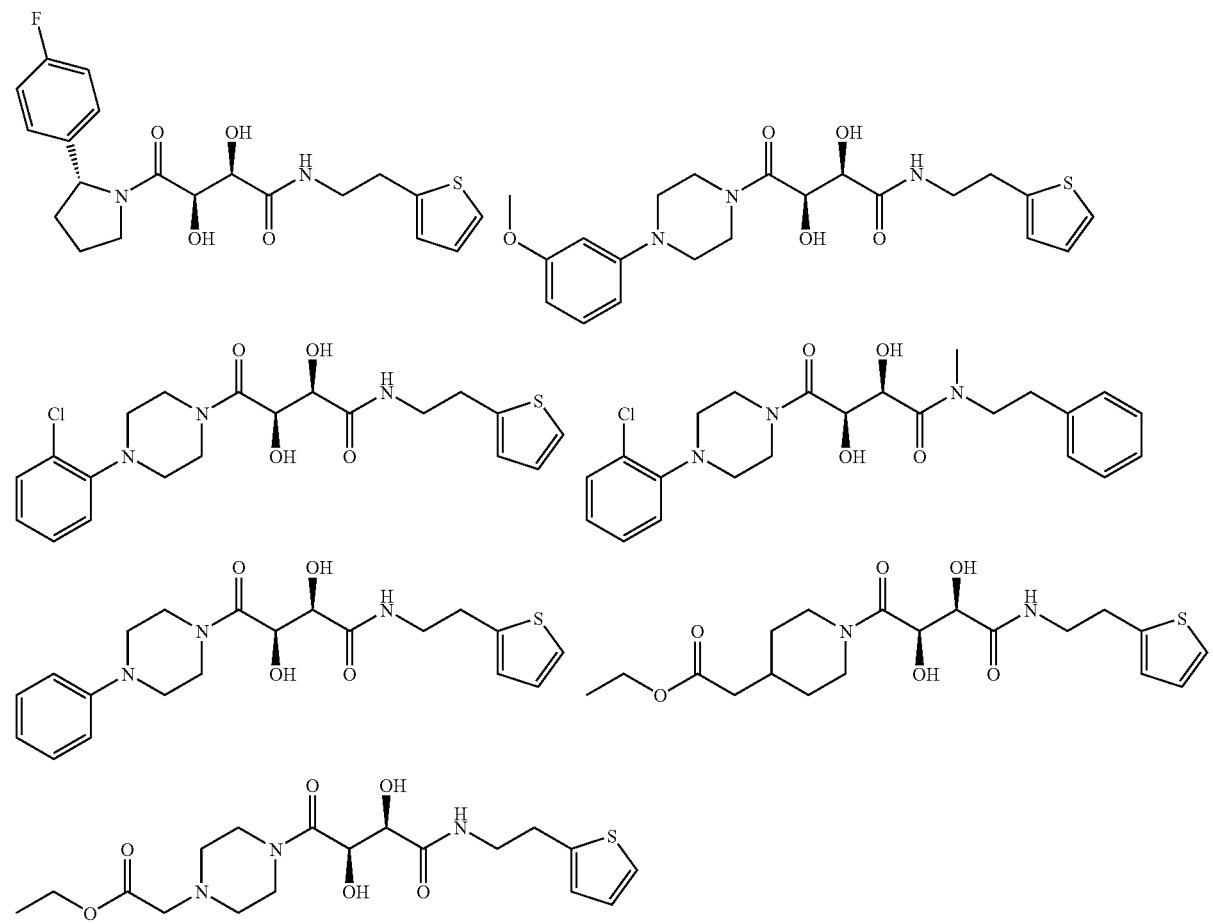

-continued
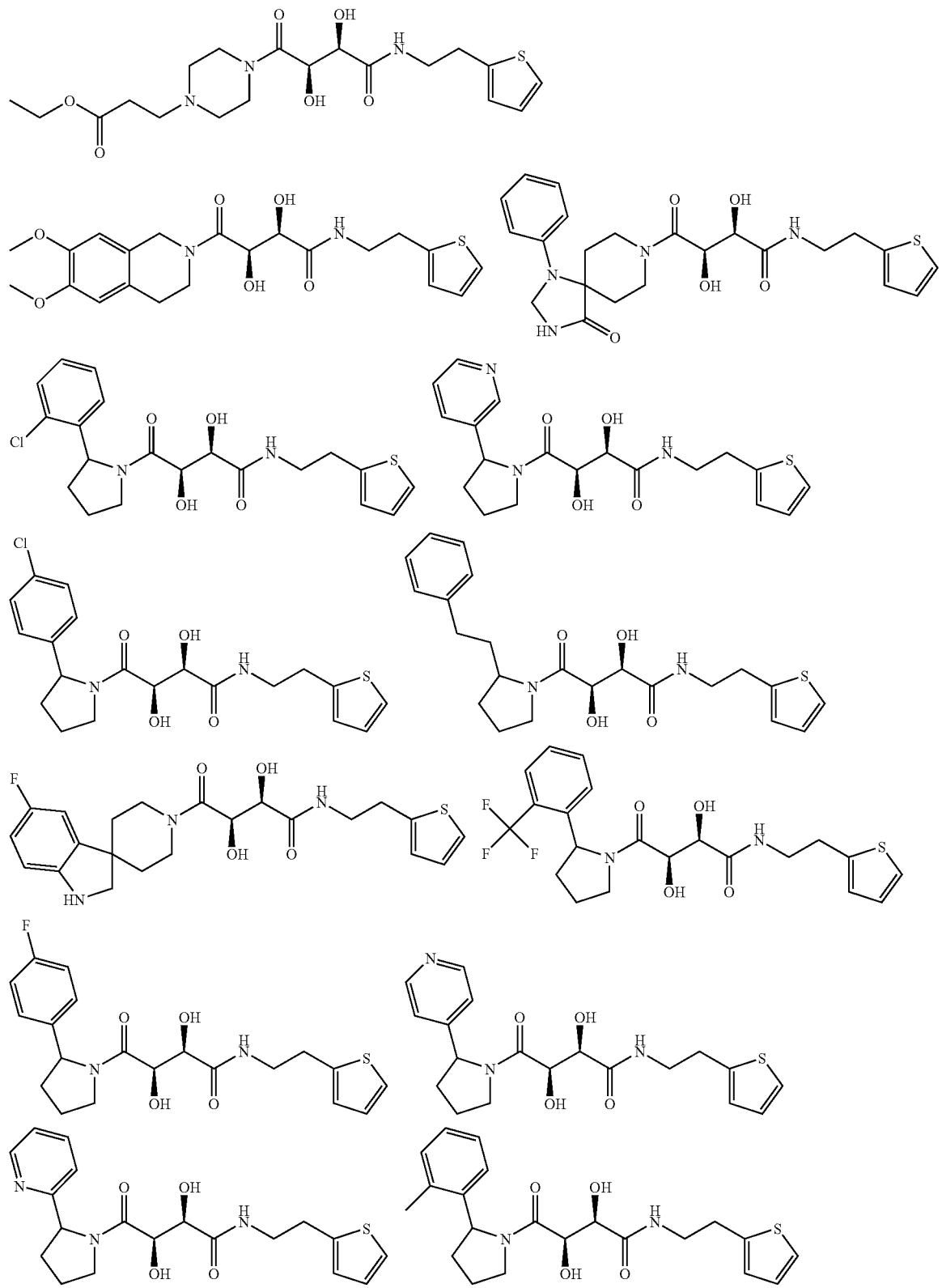

-continued
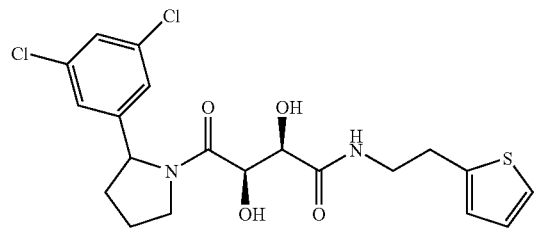
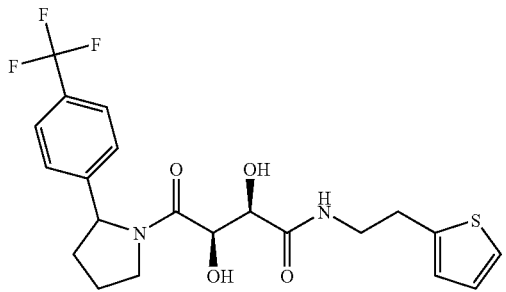
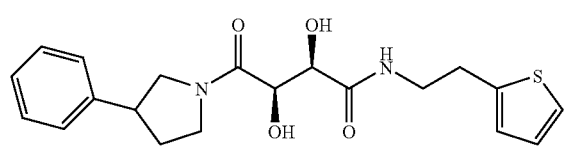
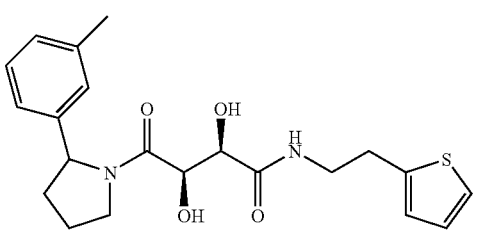
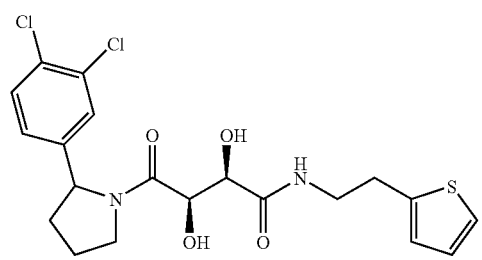
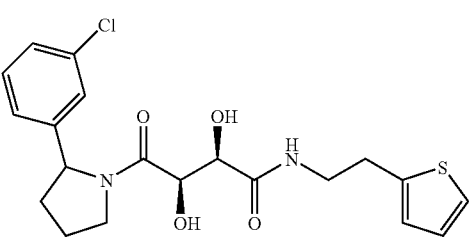
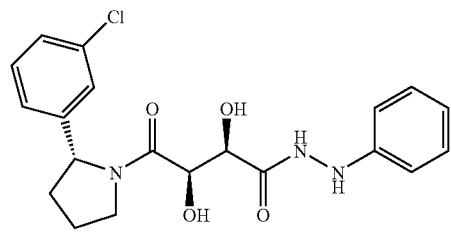
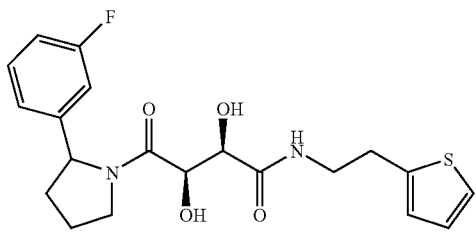
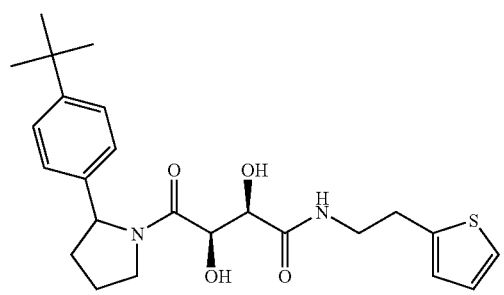
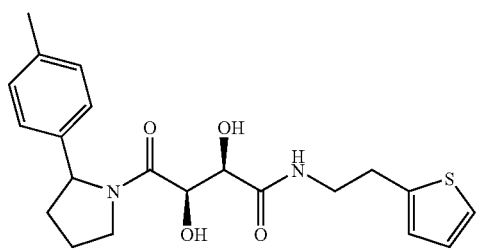
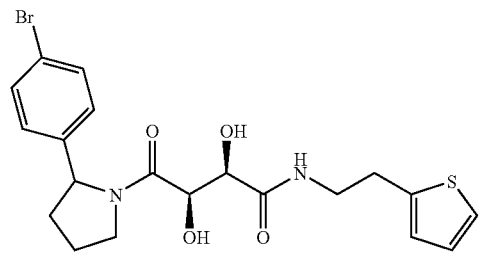
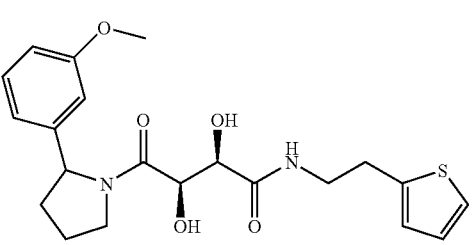

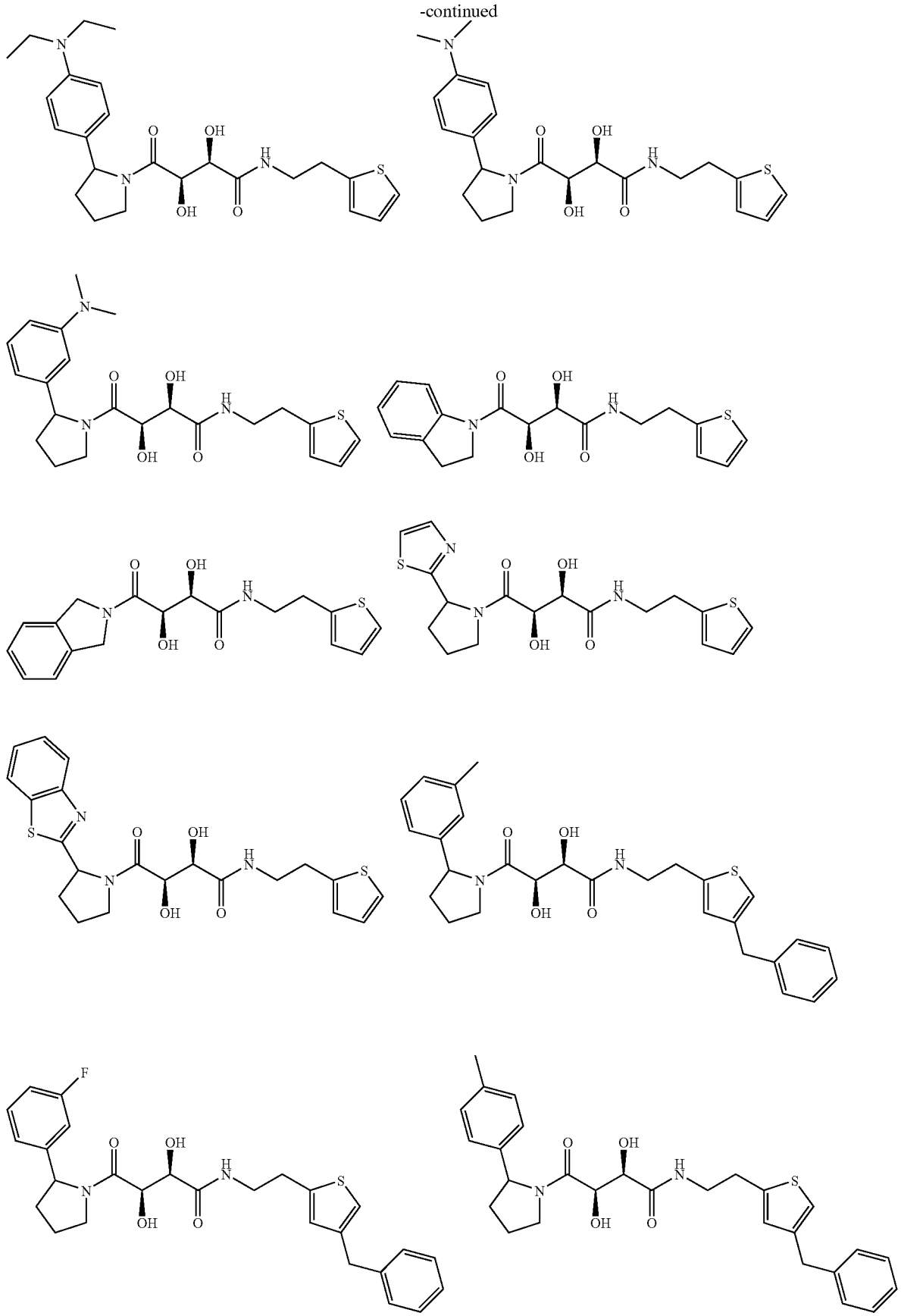

-continued
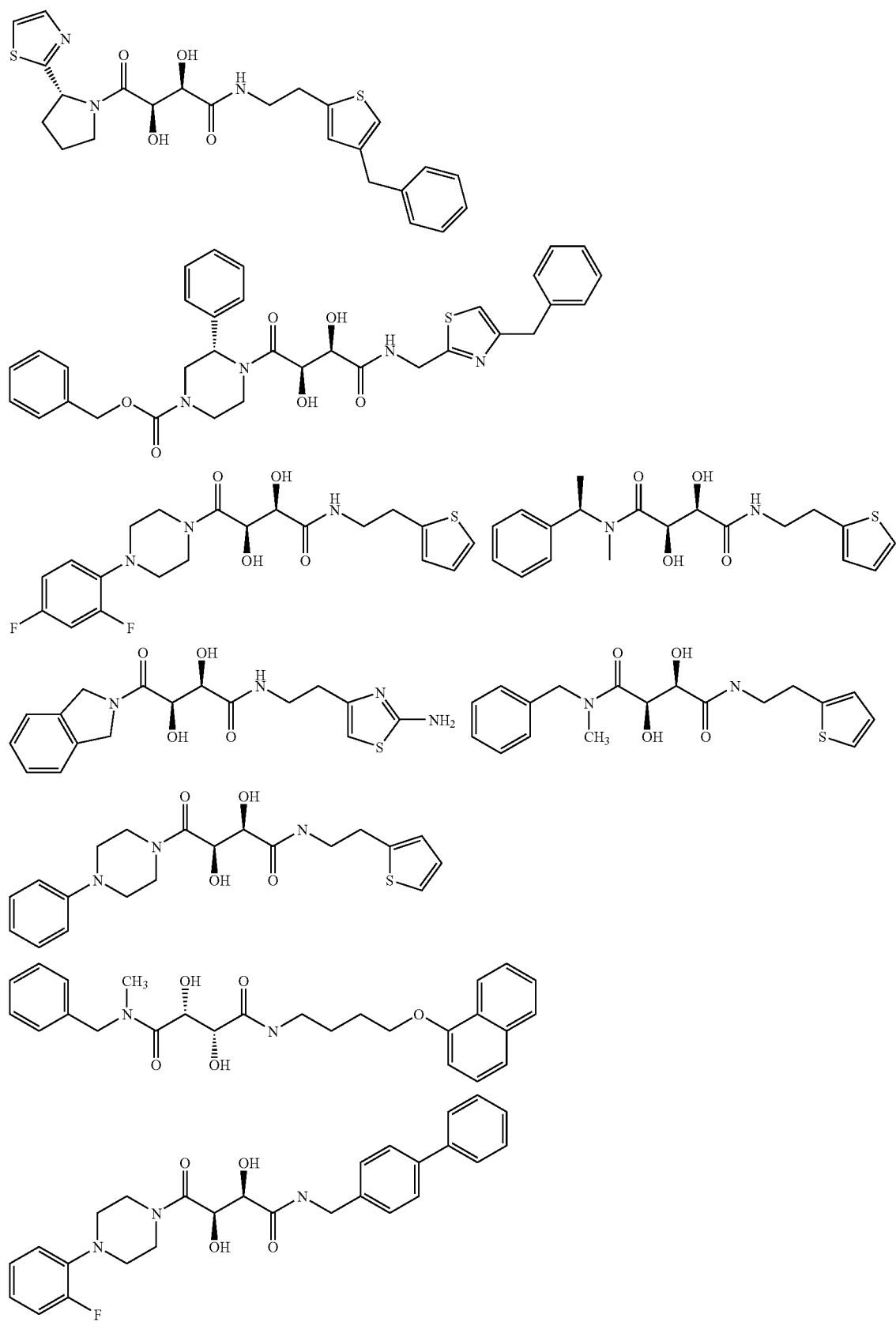

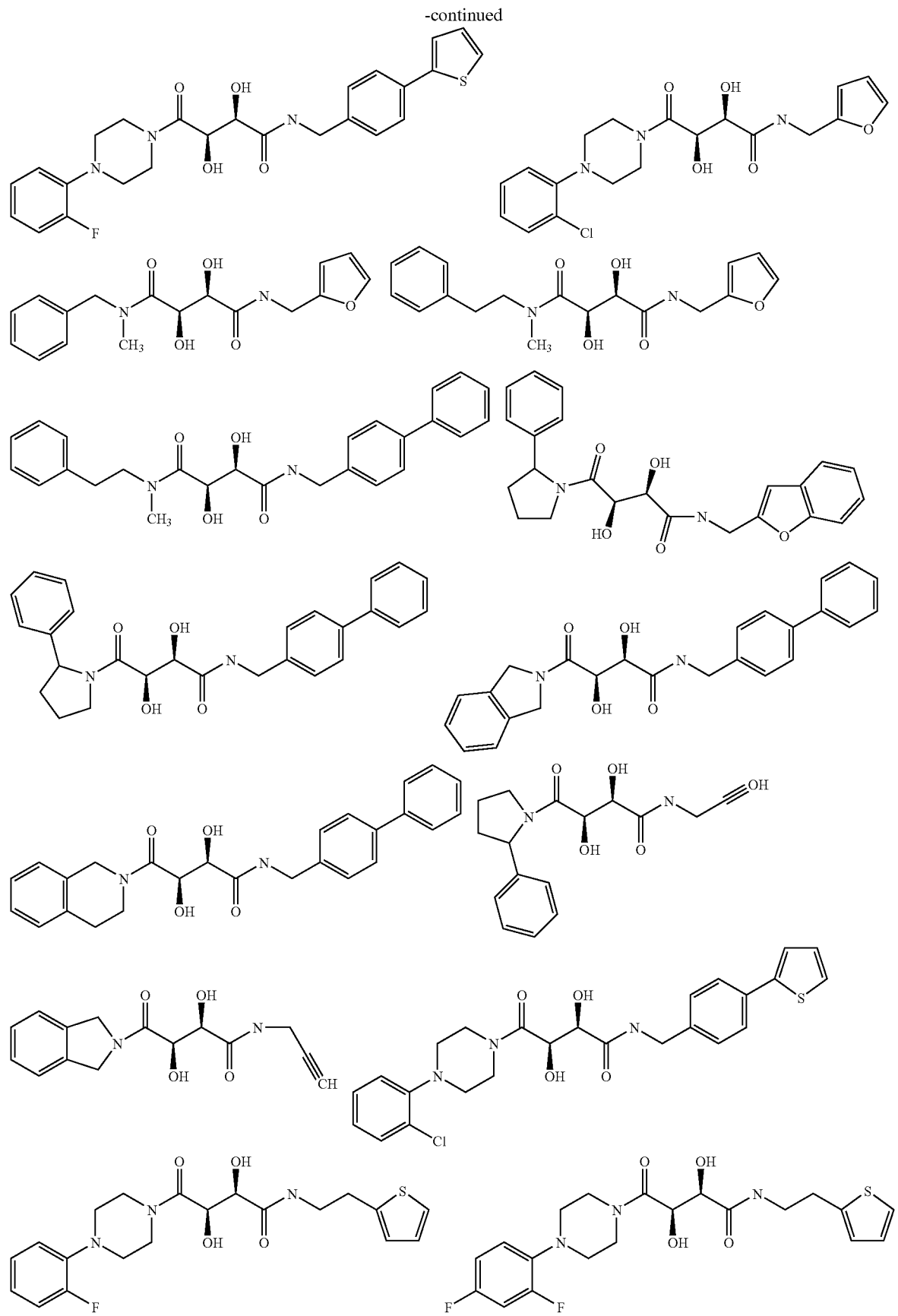

-continued
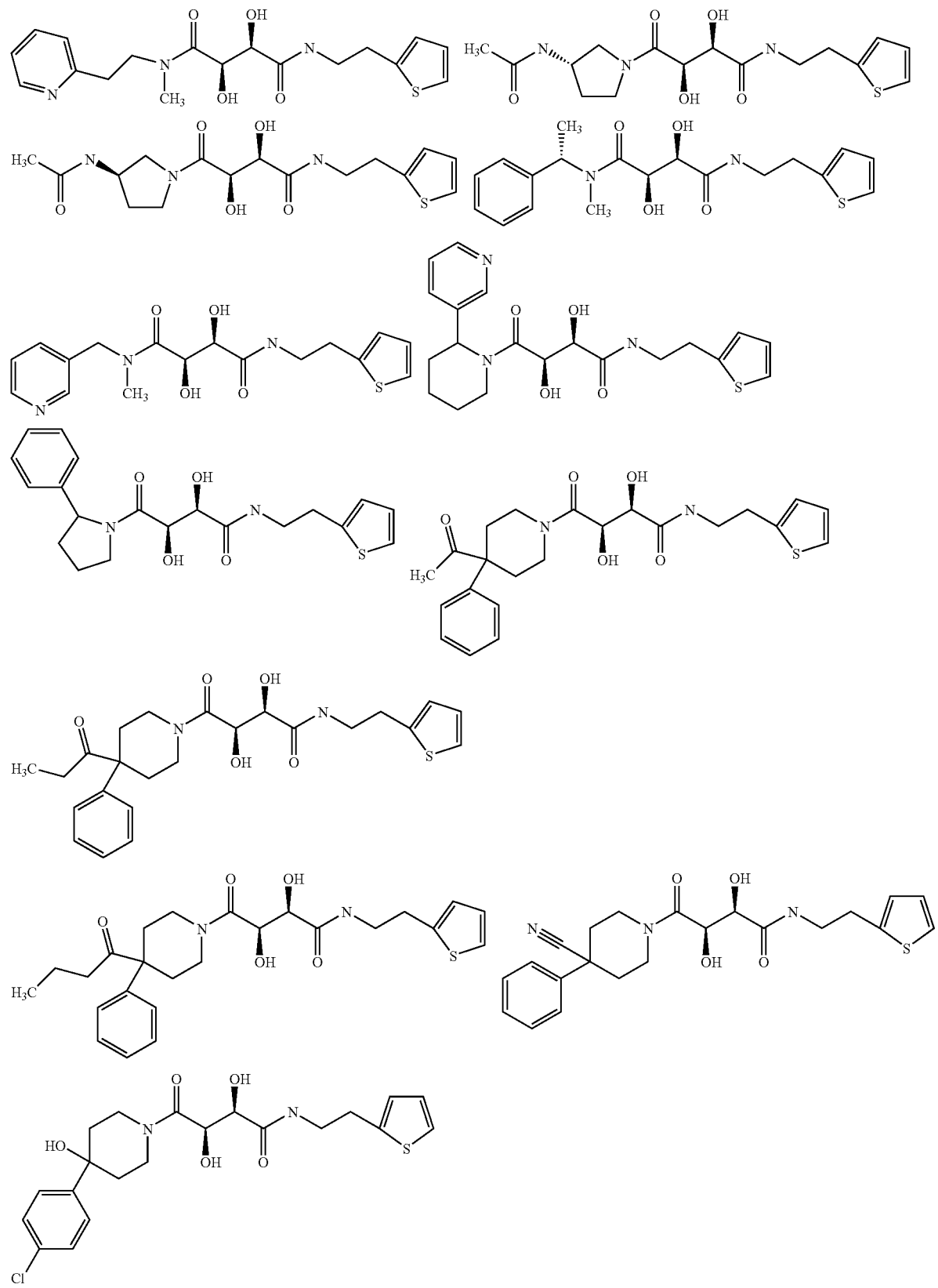

-continued
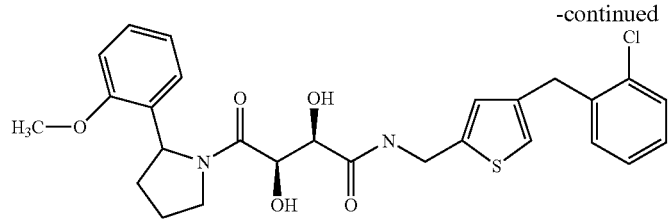
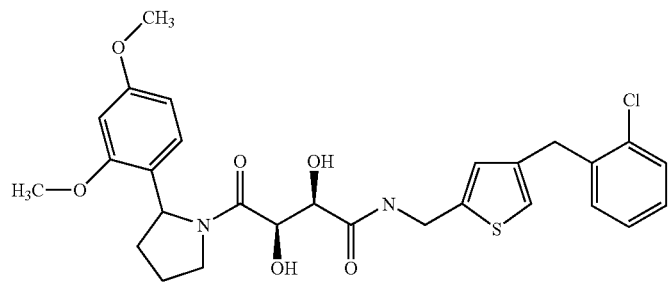
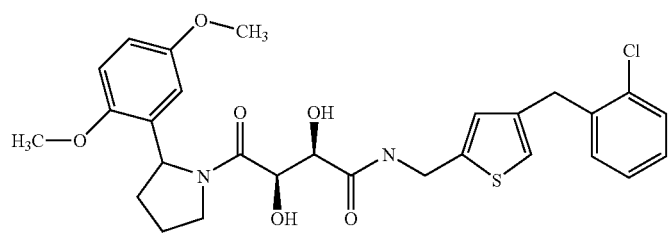
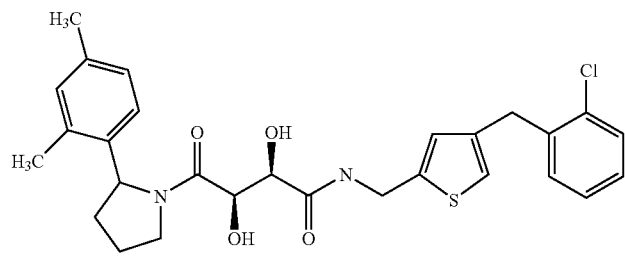
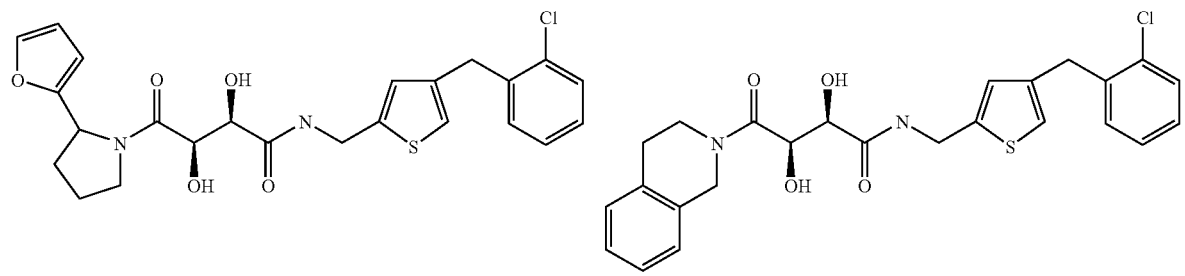
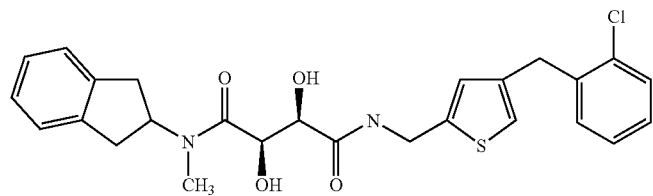

-continued
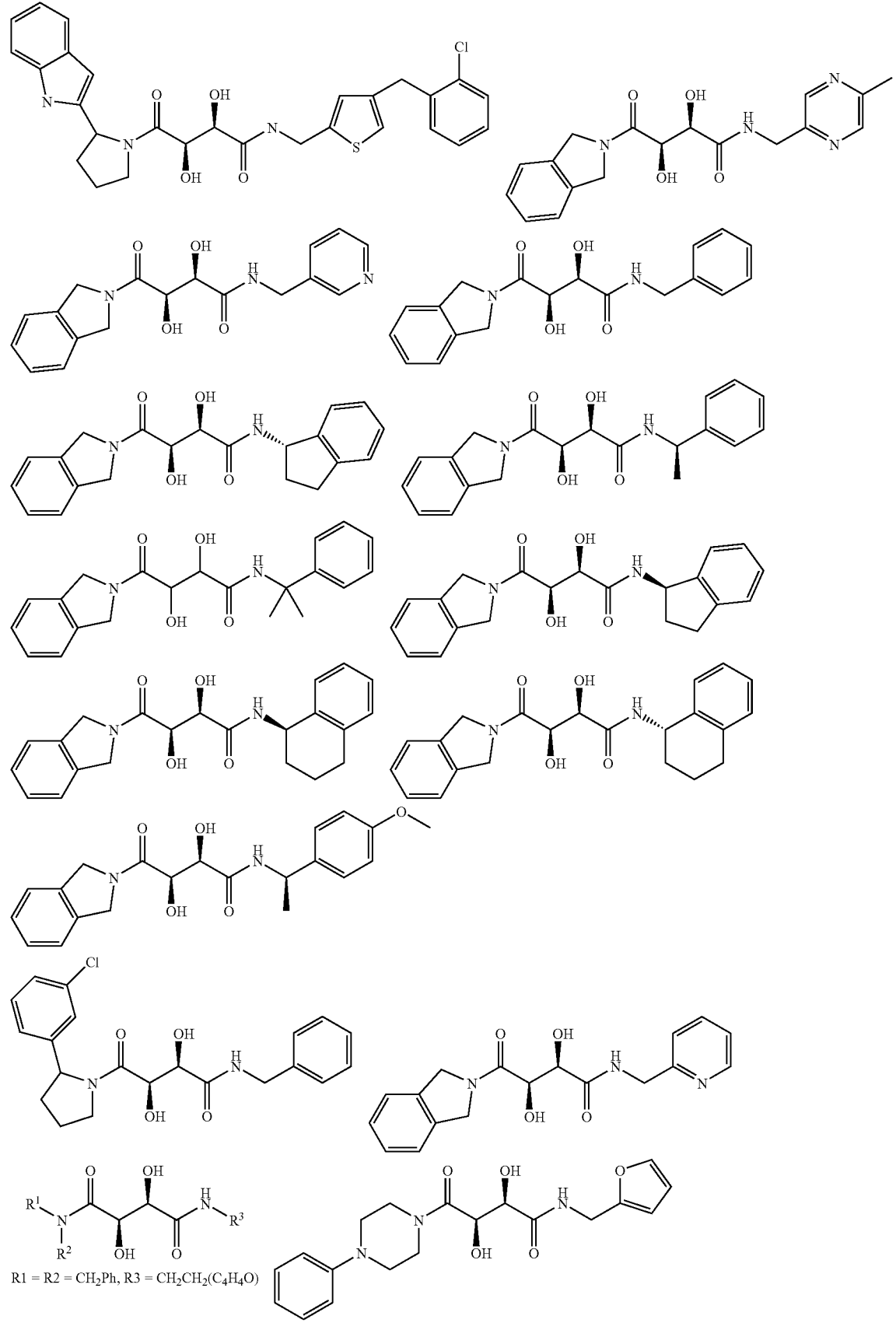

-continued
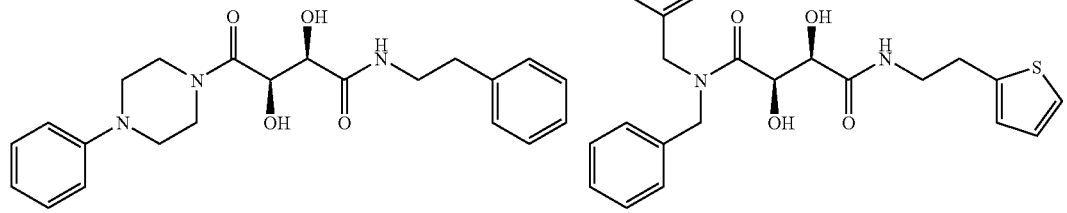
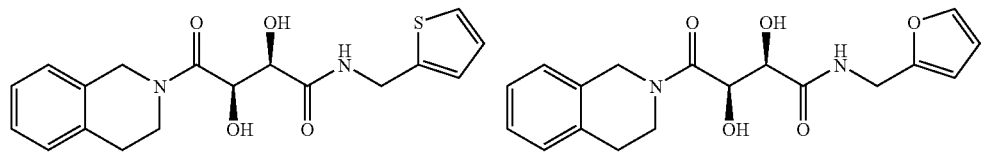
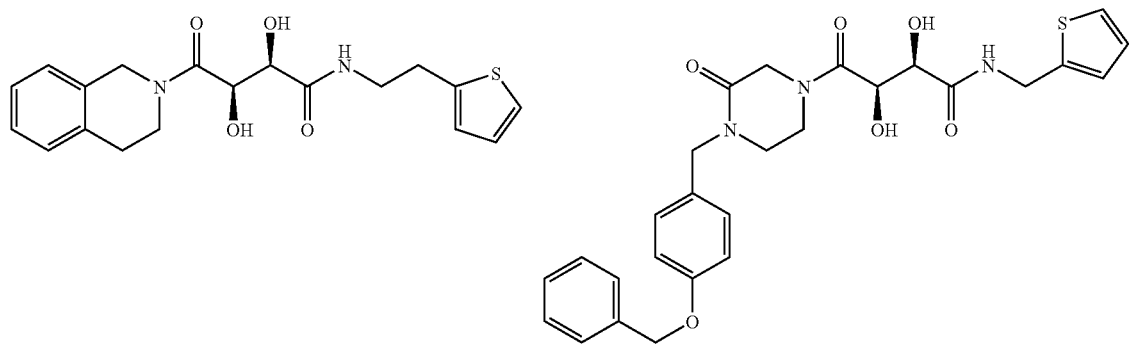
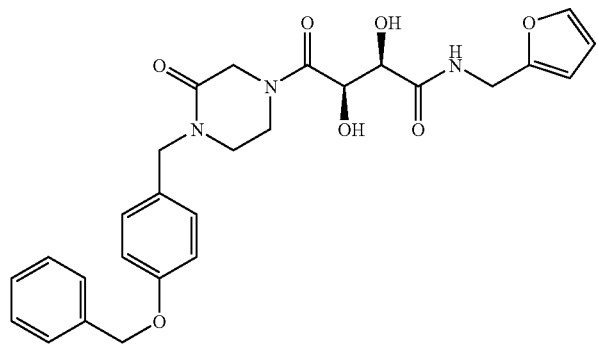
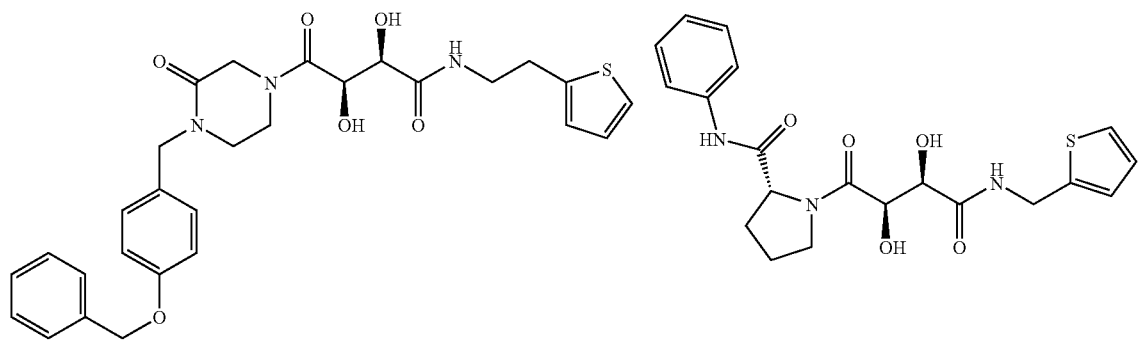

-continued
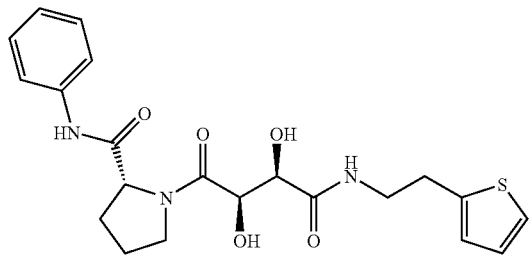 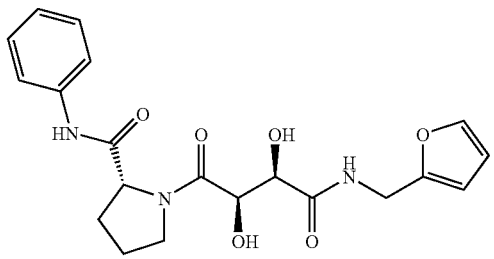
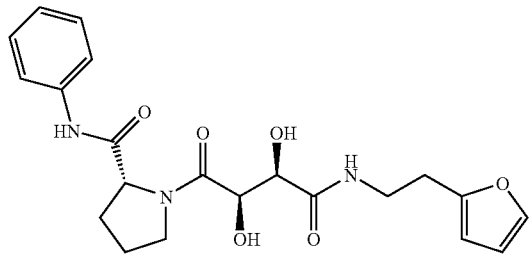 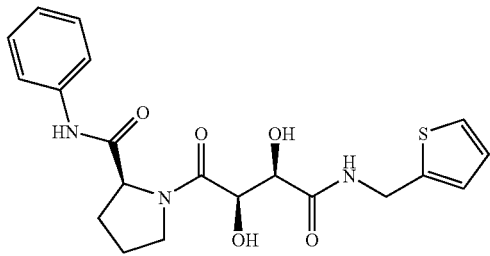
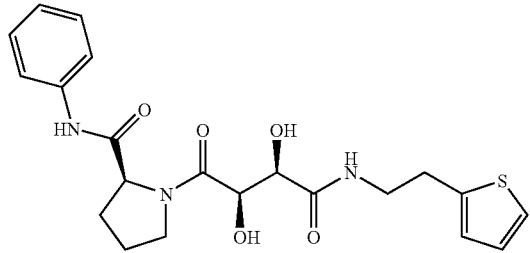 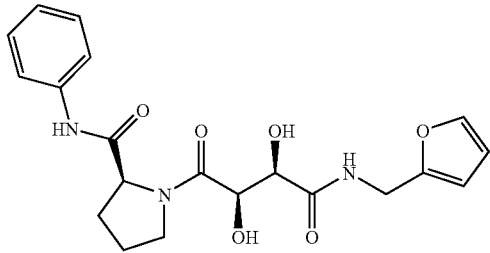
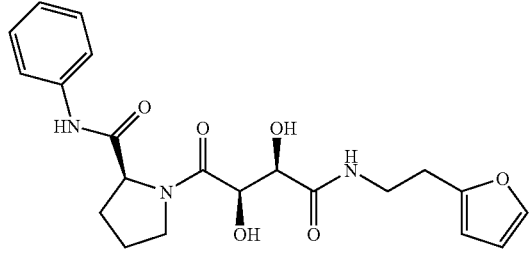 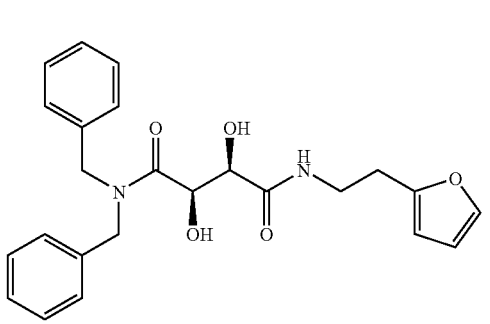
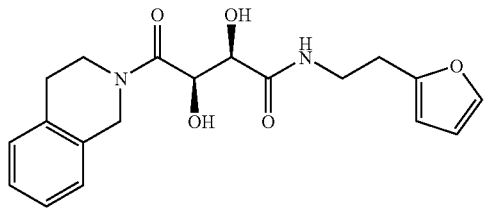 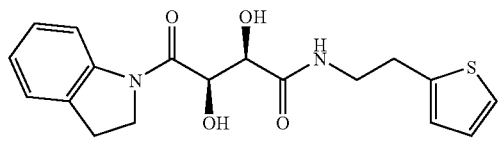
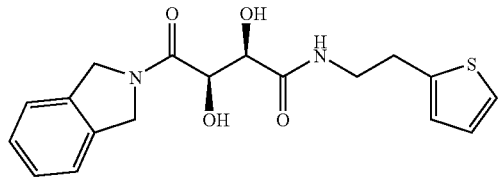 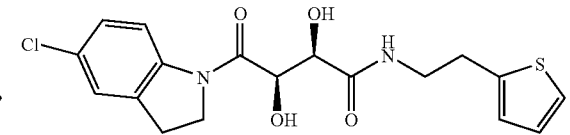
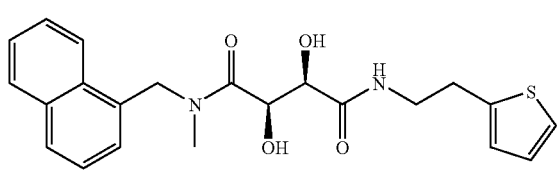 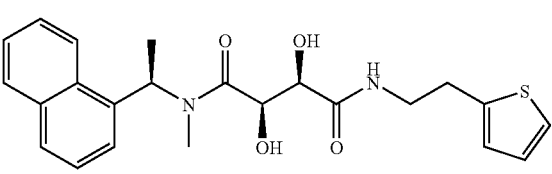

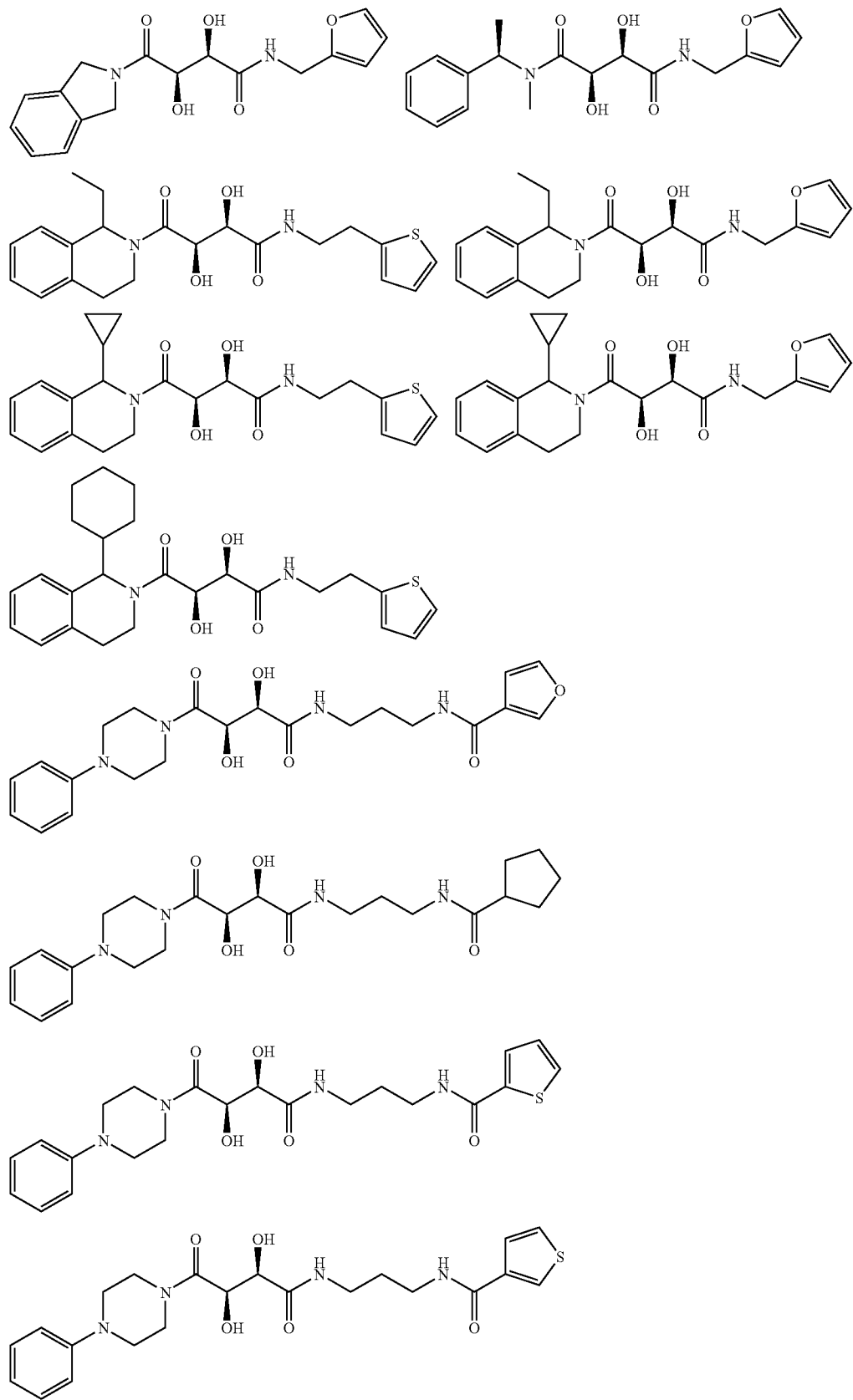

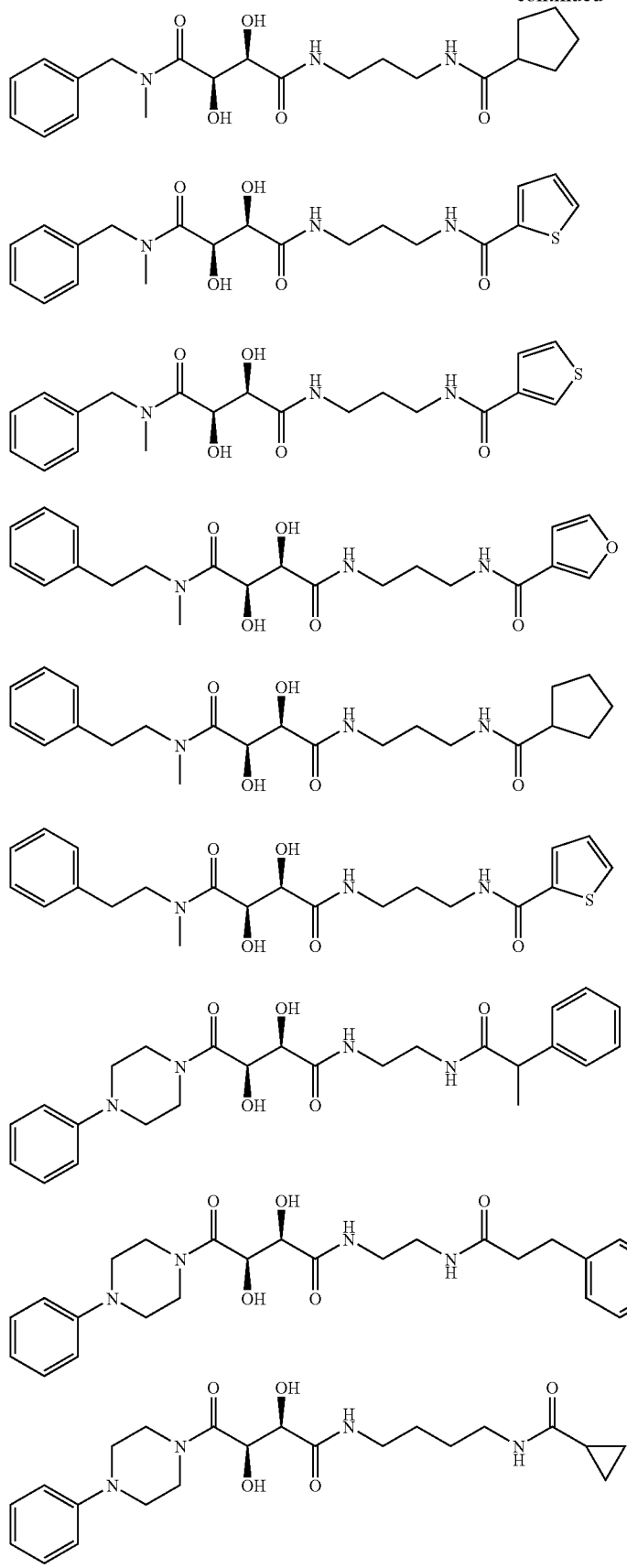

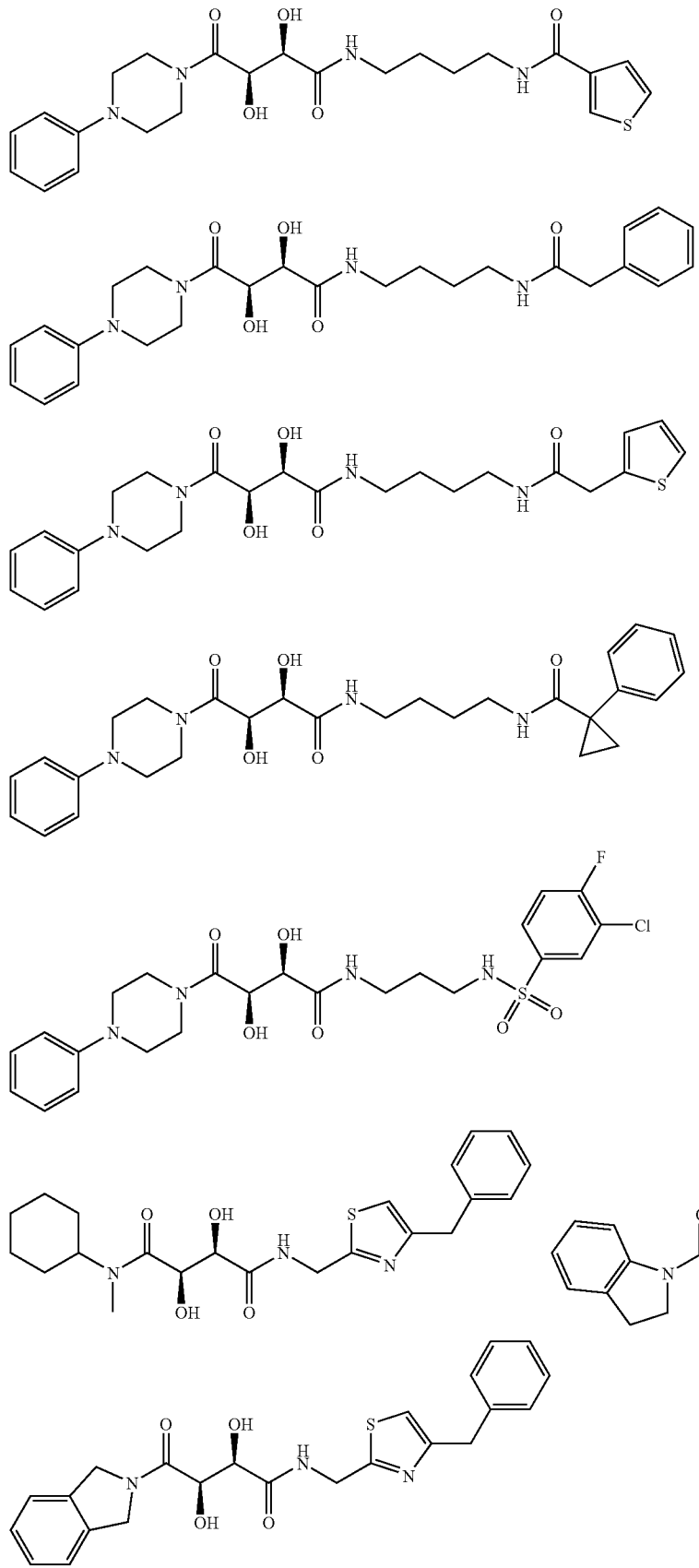

-continued
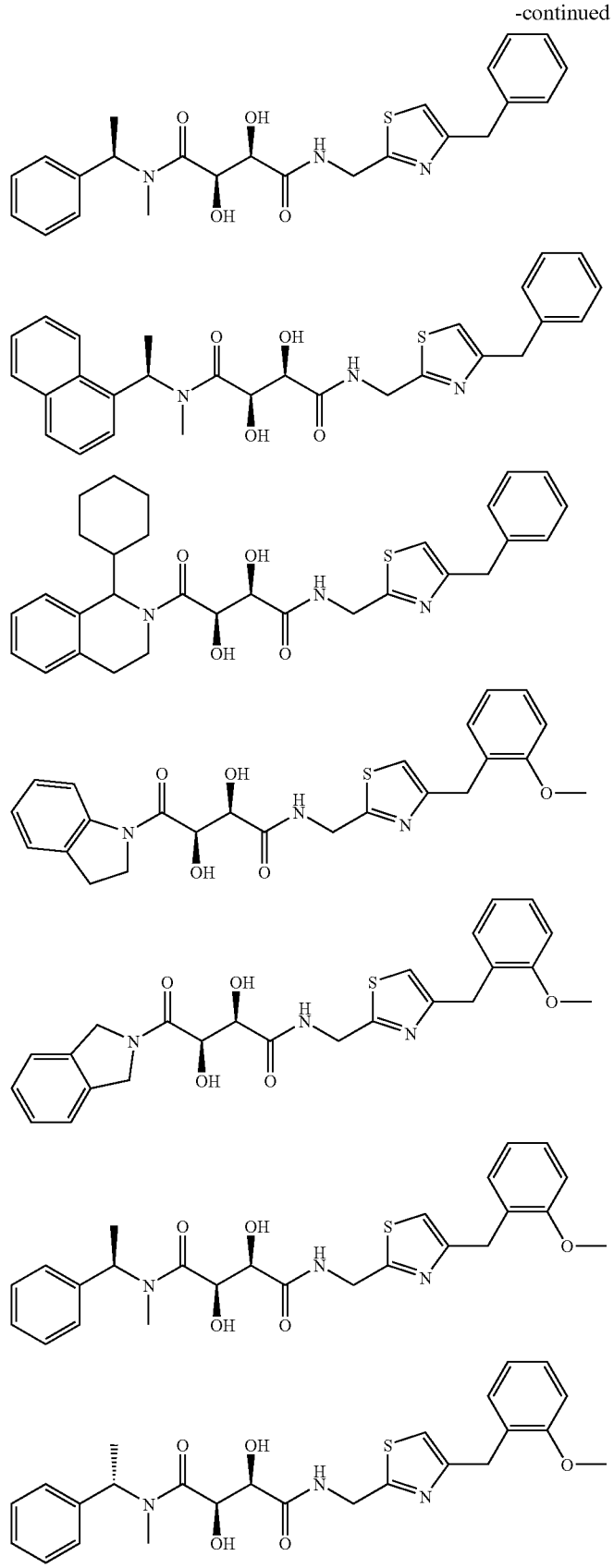

-continued
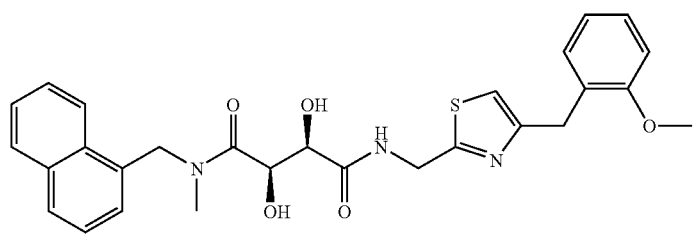
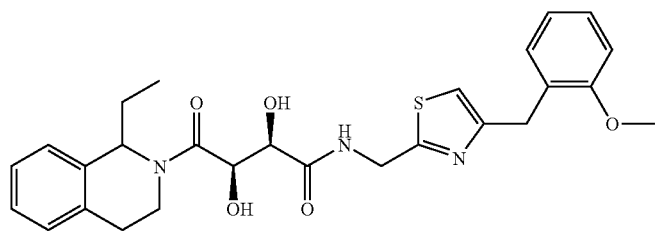
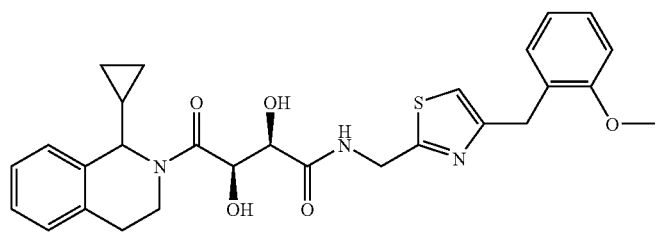
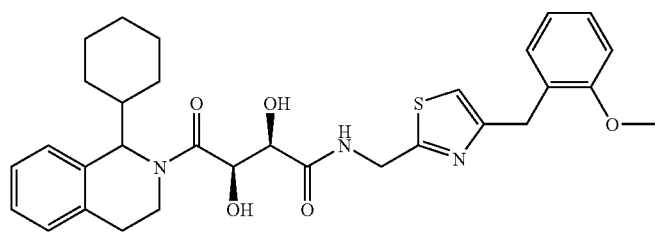
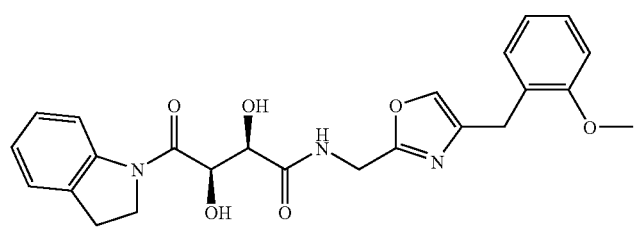
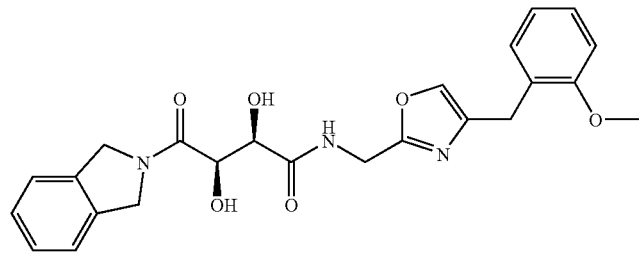

-continued
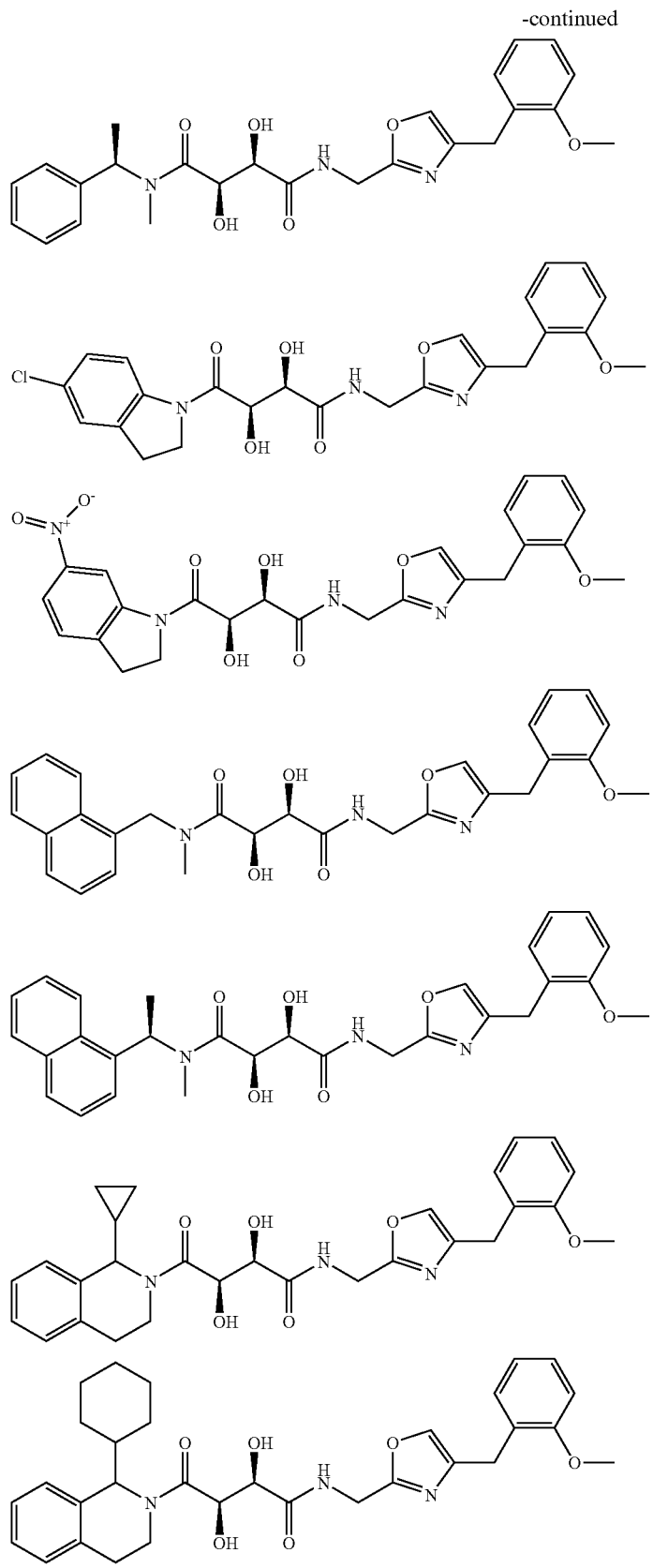

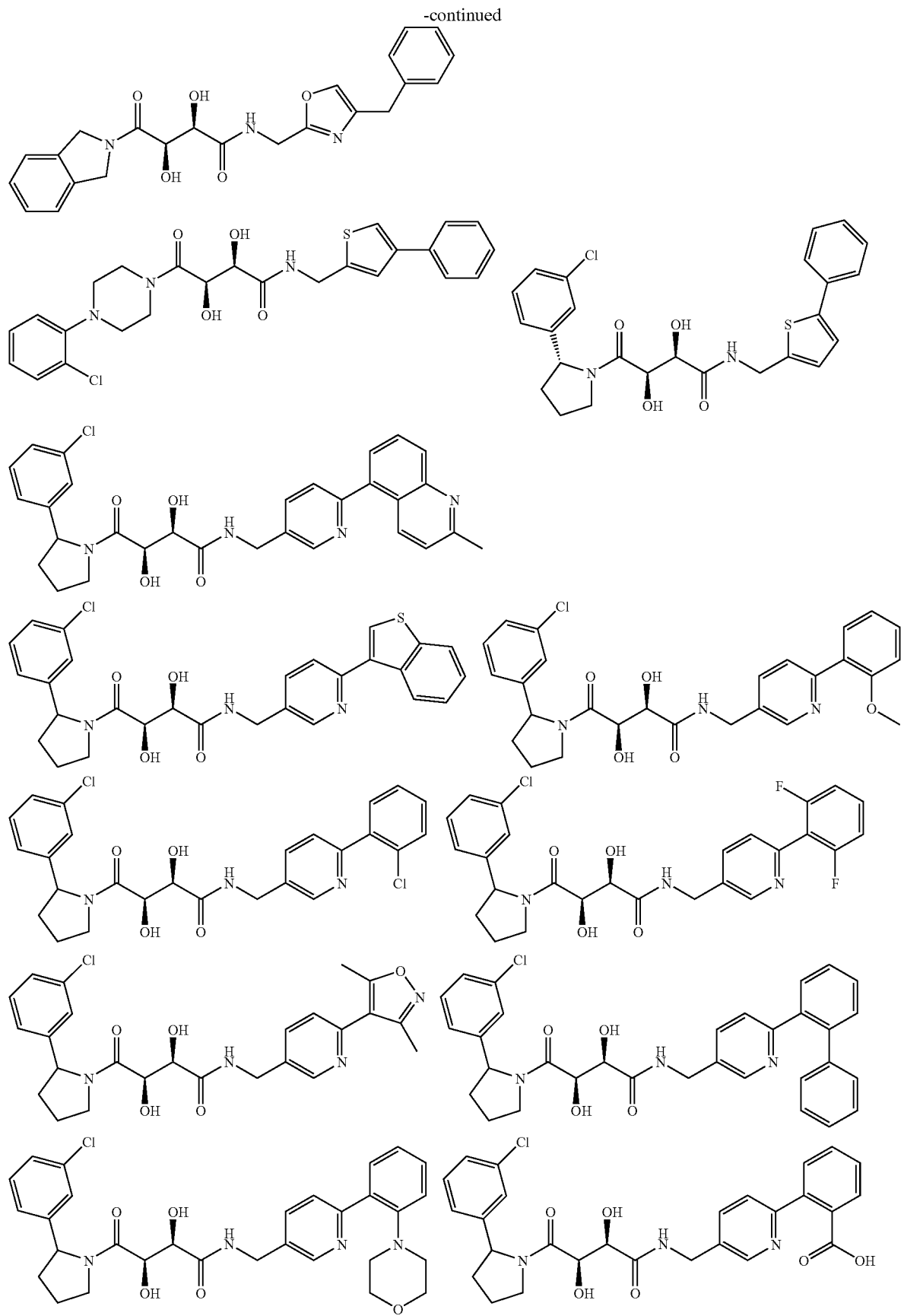

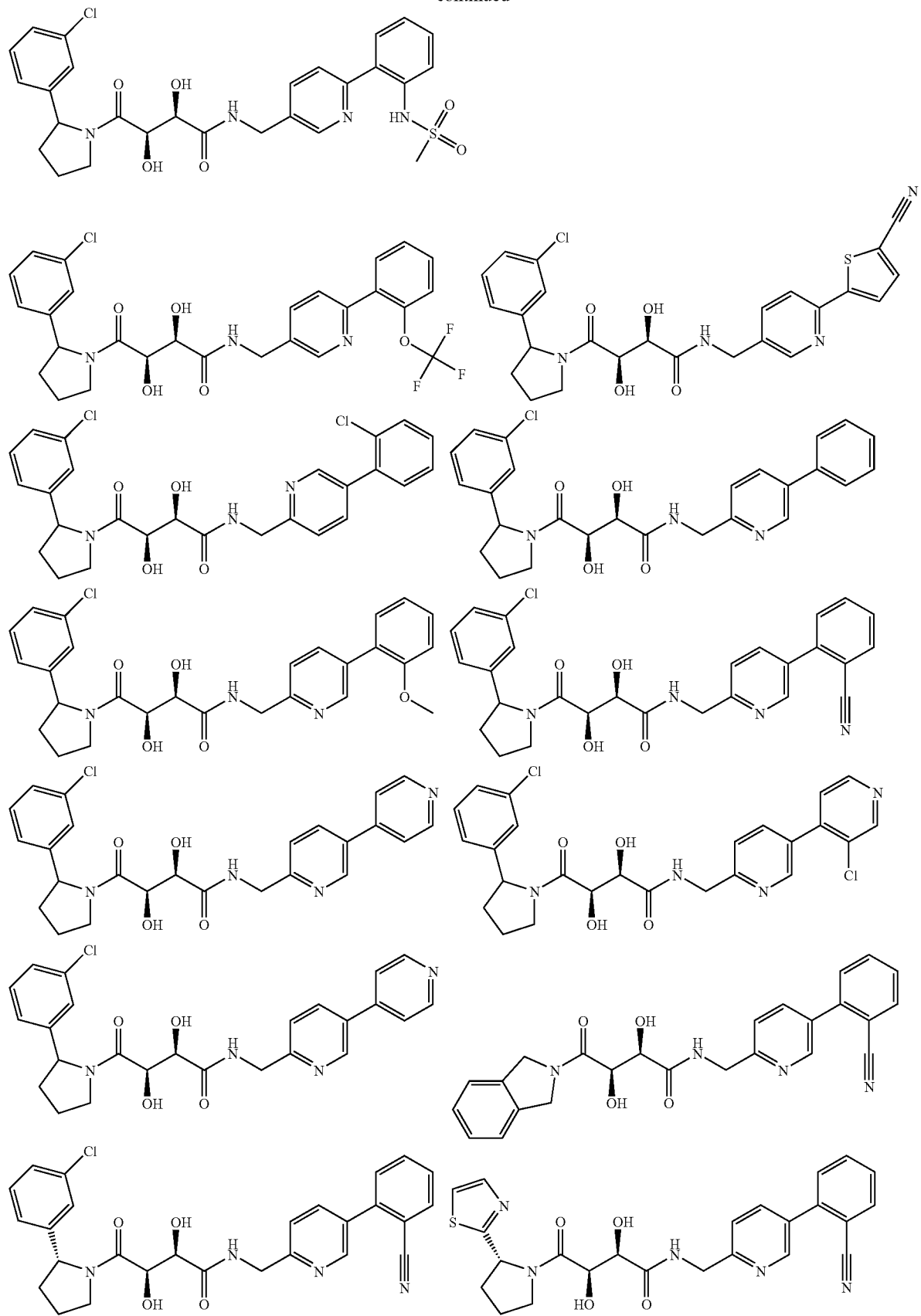

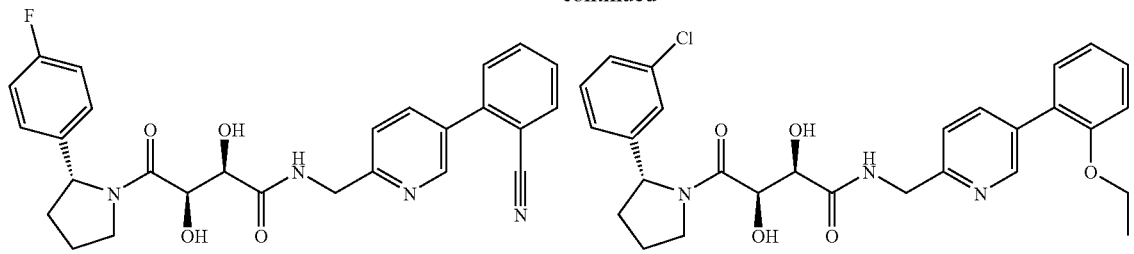
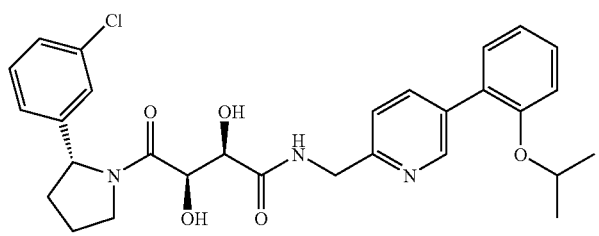
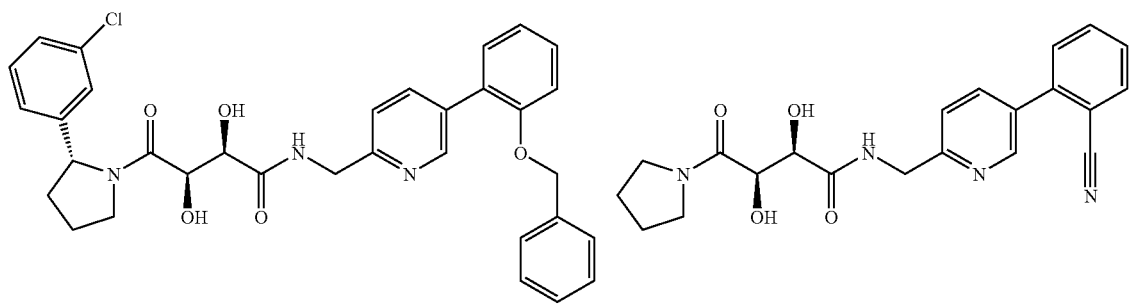
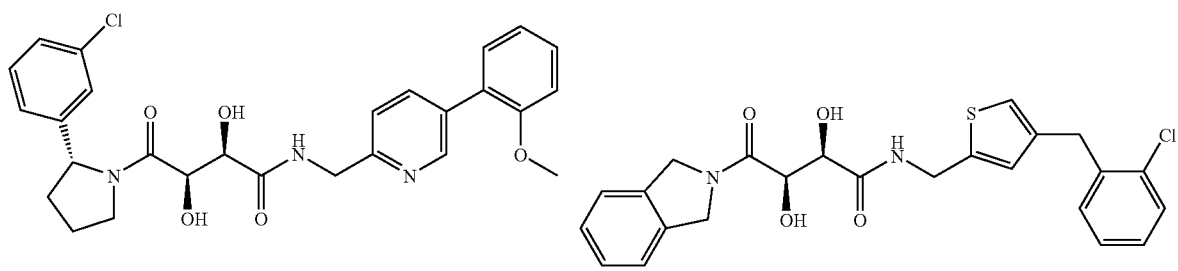
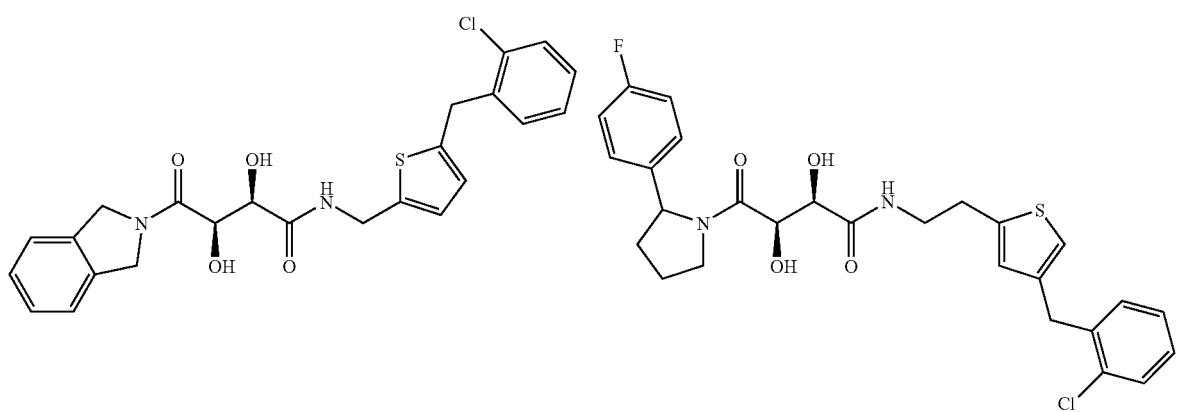

-continued
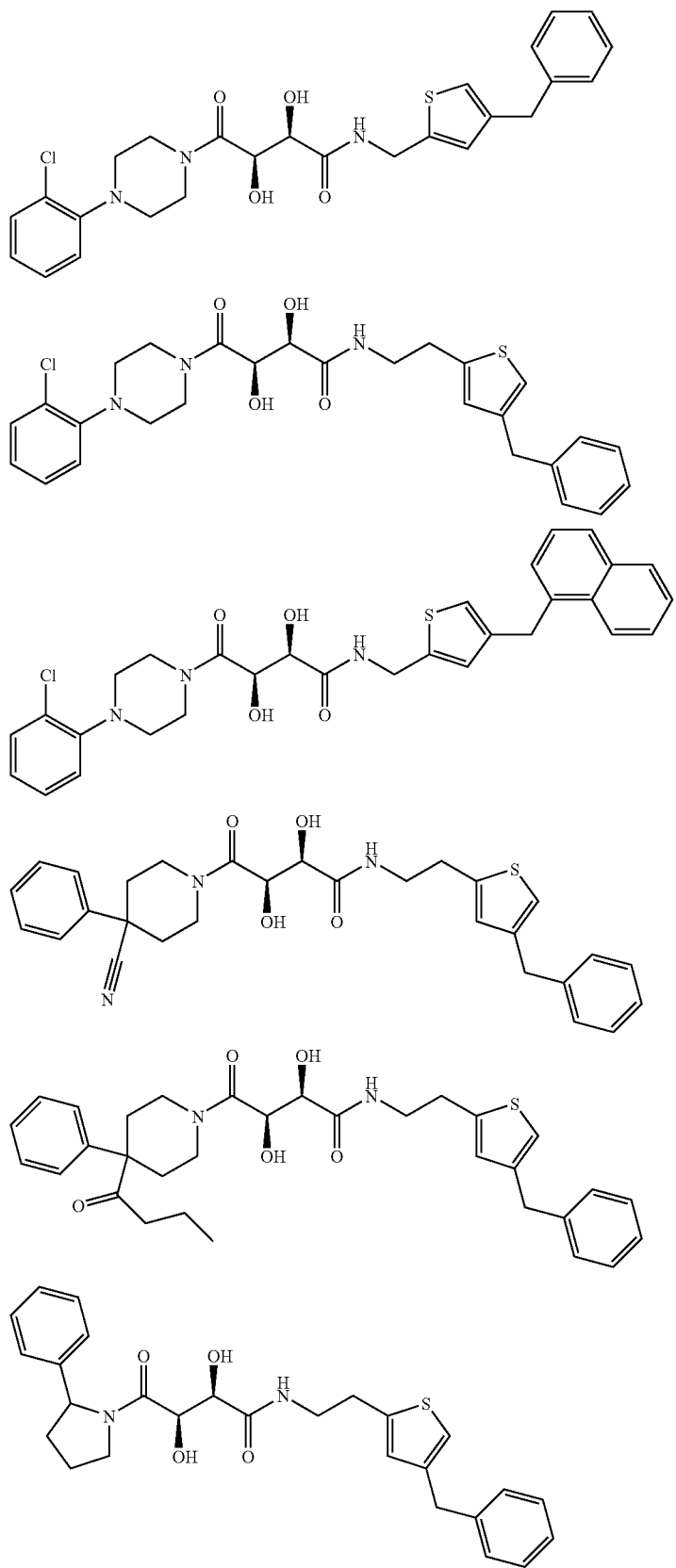

-continued
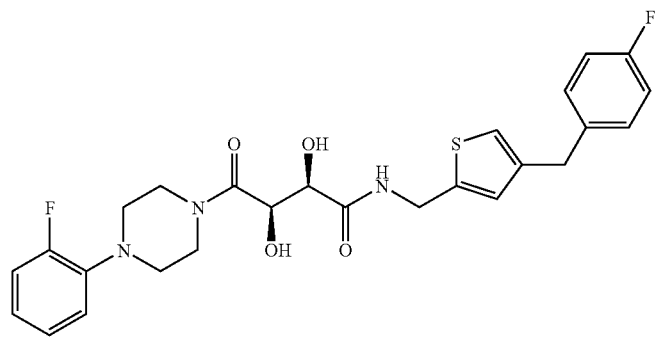
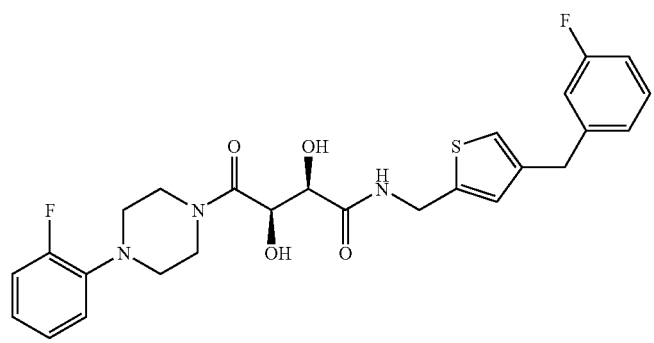
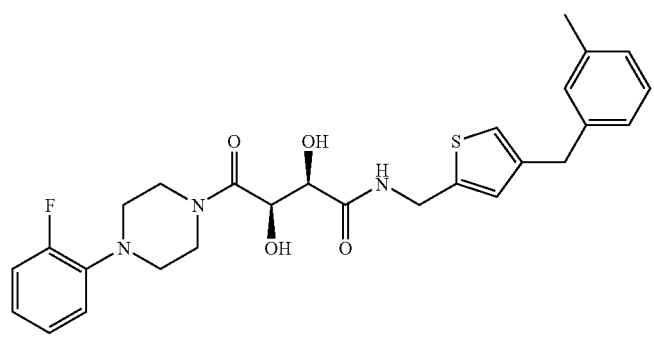
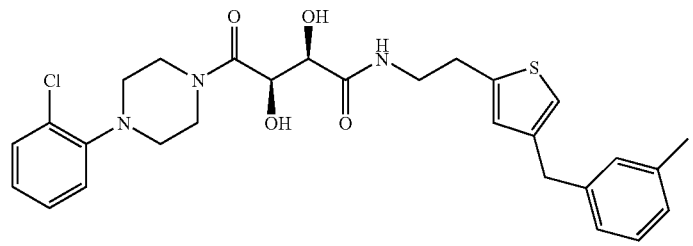
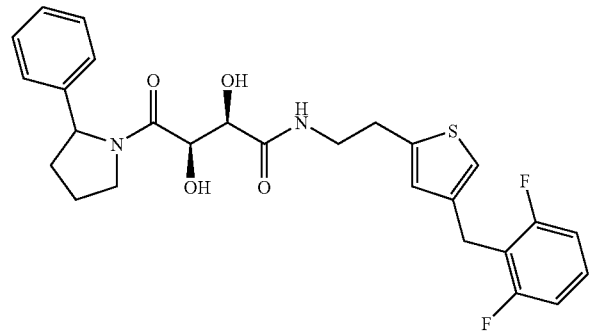

-continued
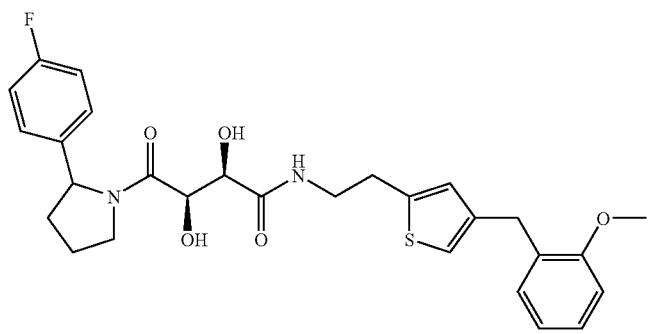
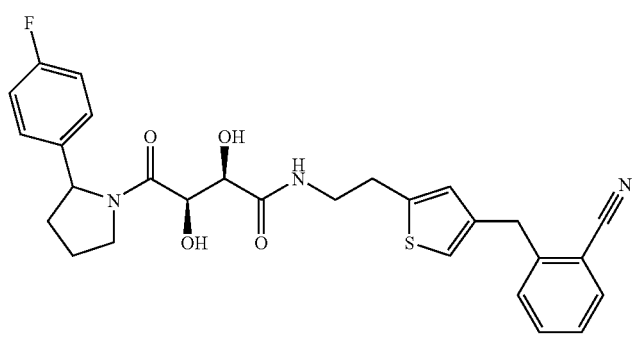
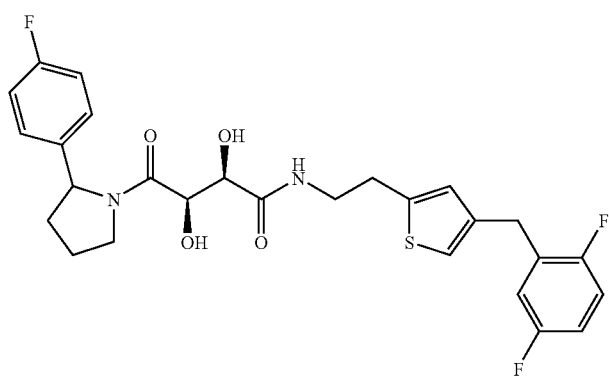
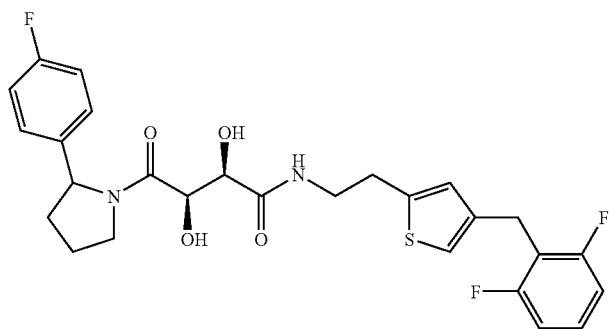

-continued
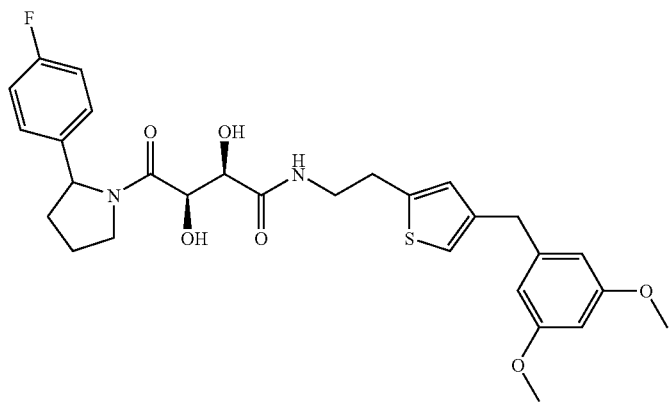
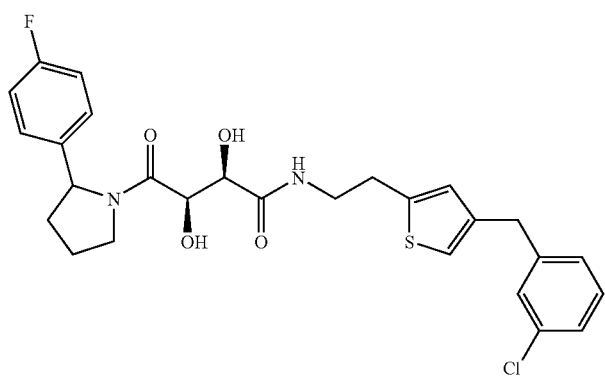
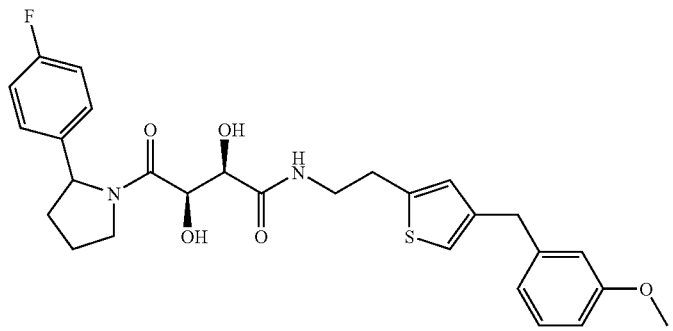
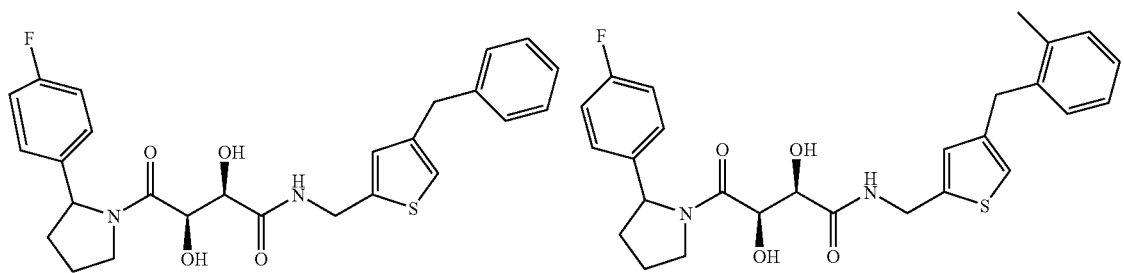
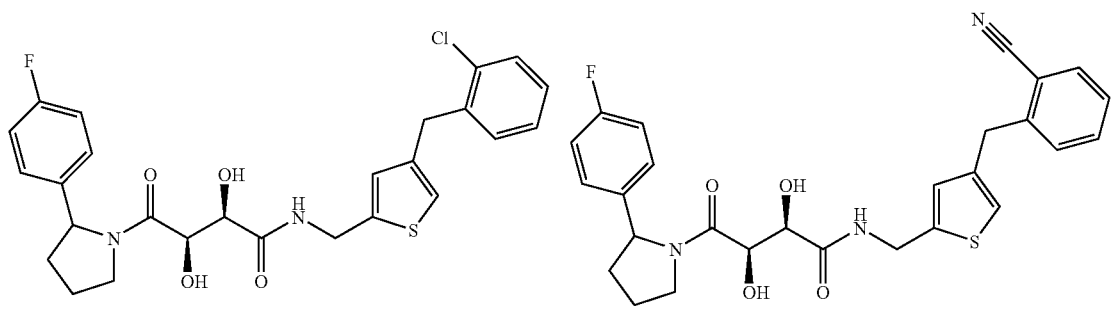

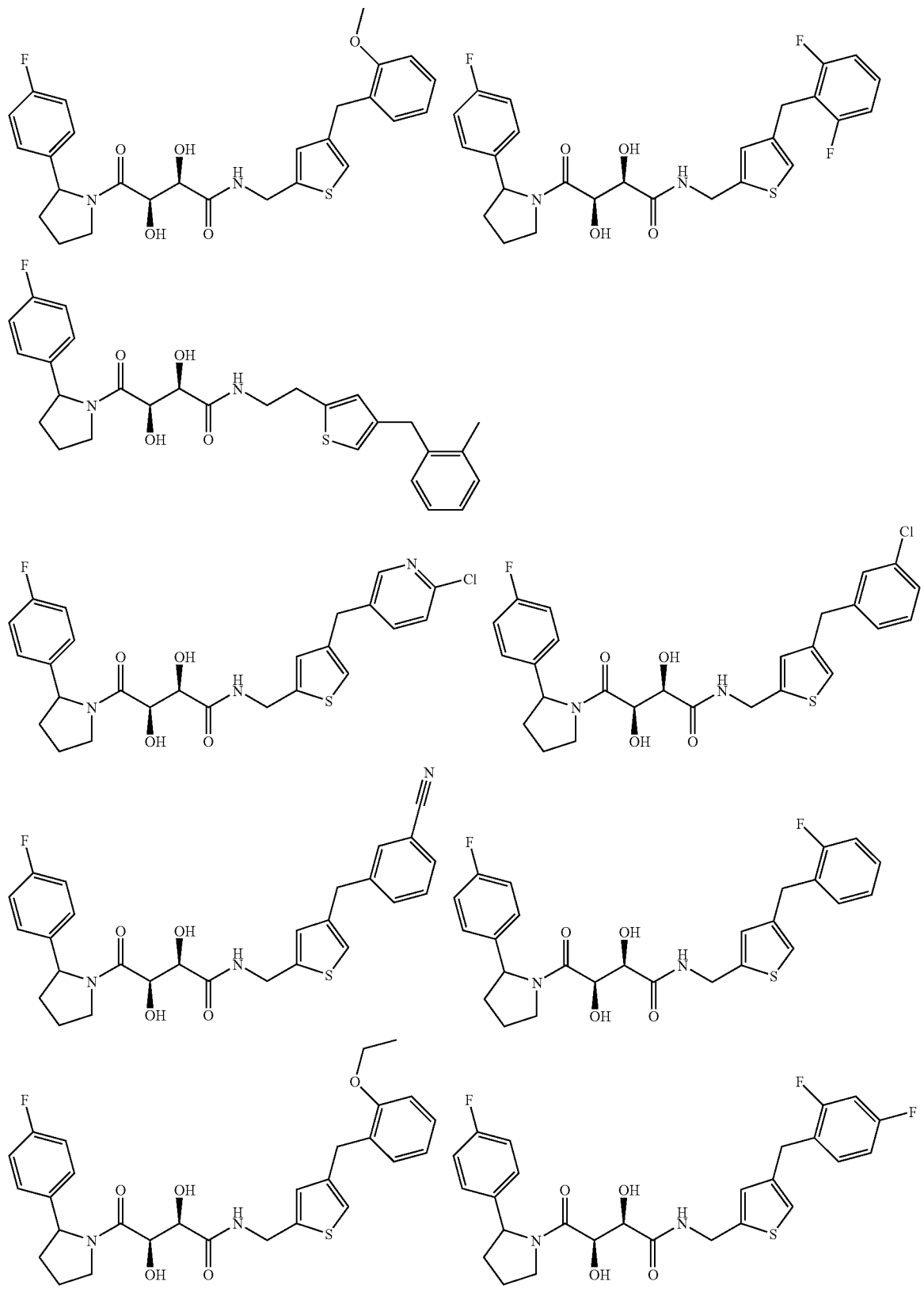

-continued
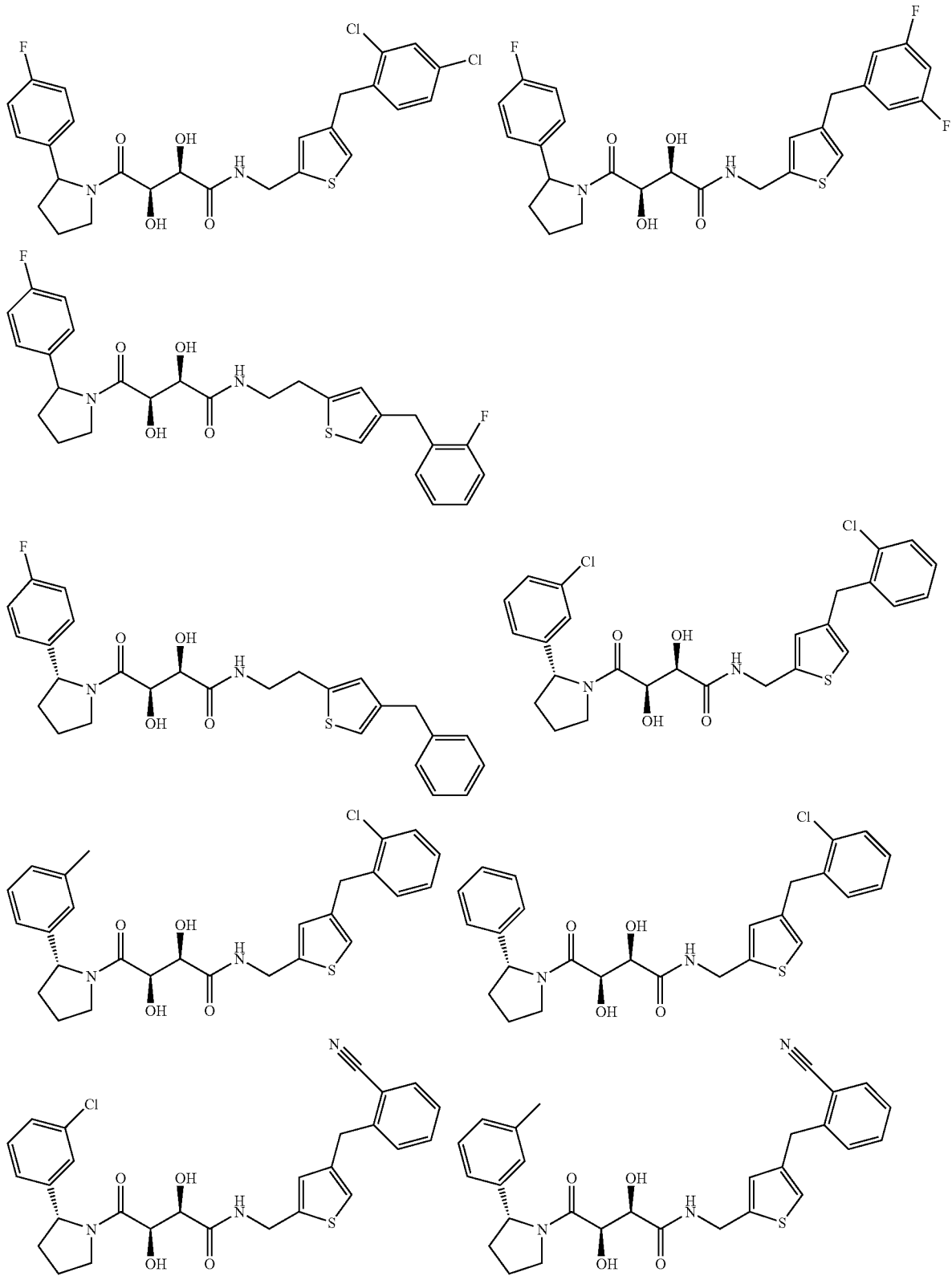

-continued
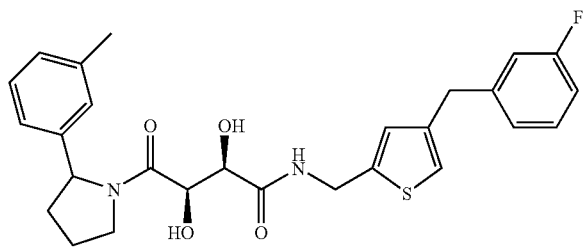
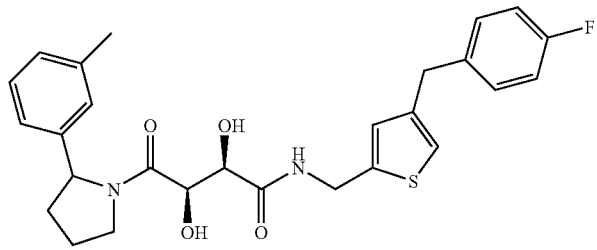
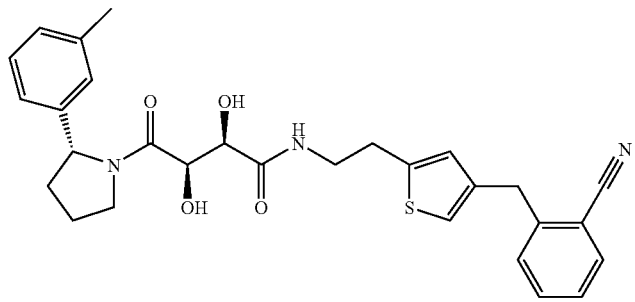
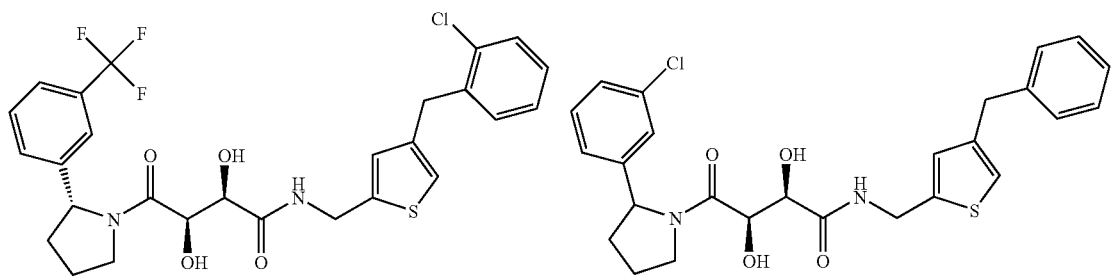
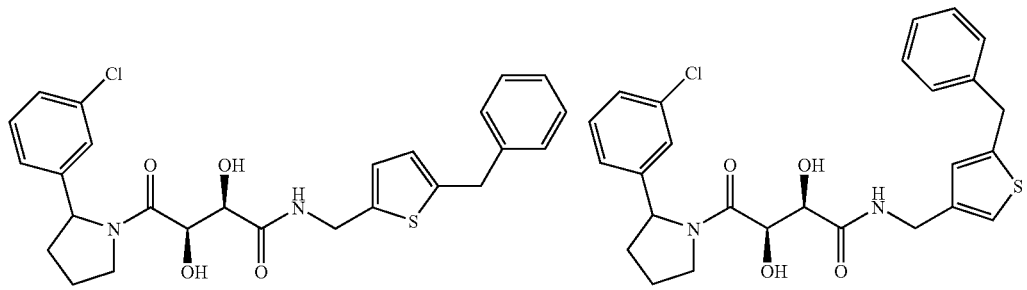
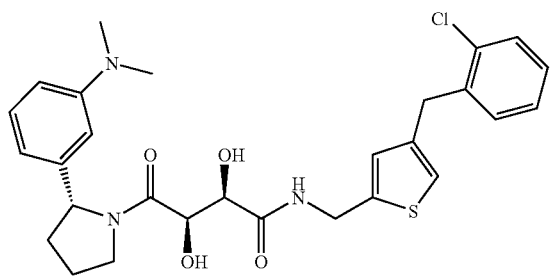

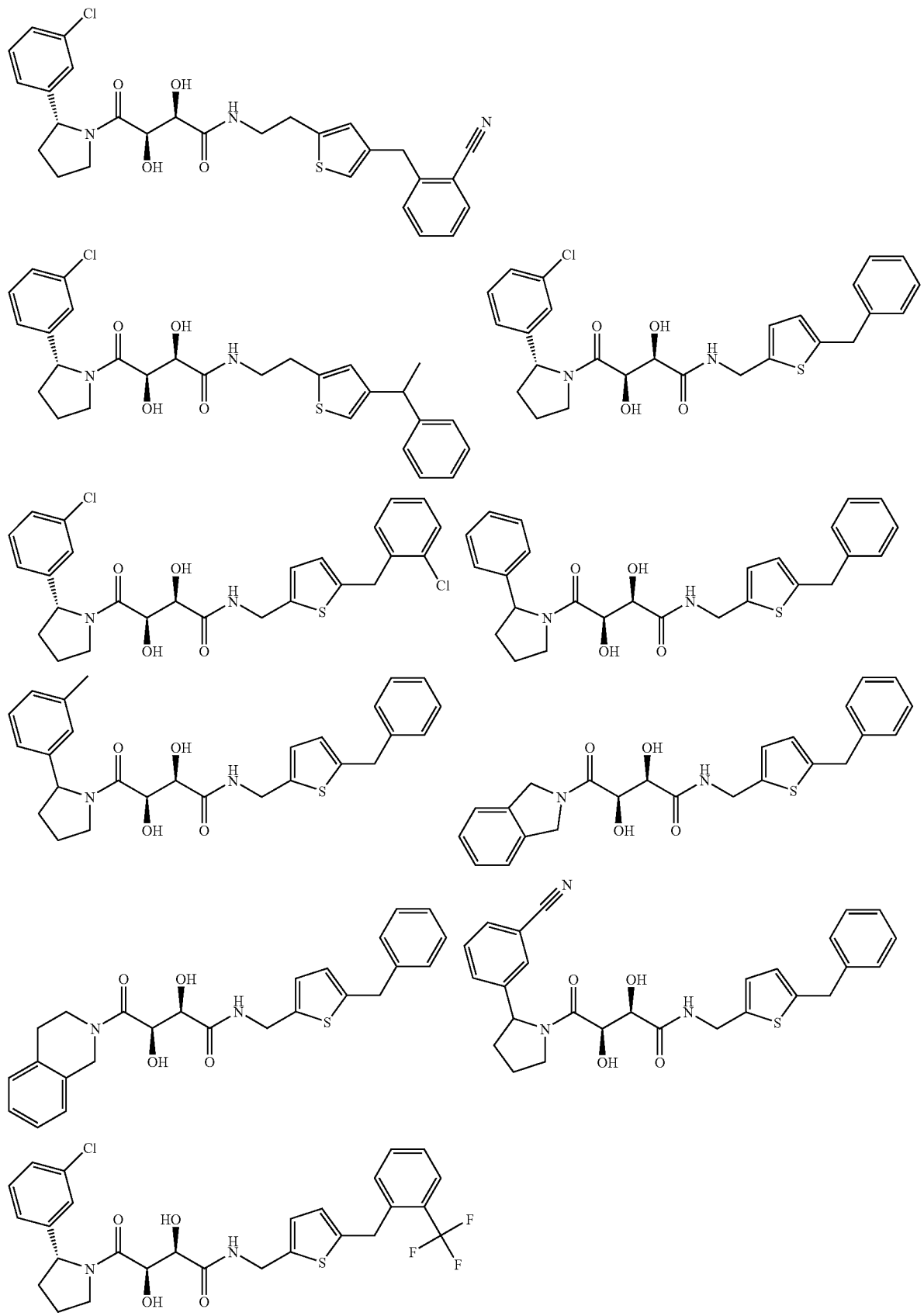

-continued
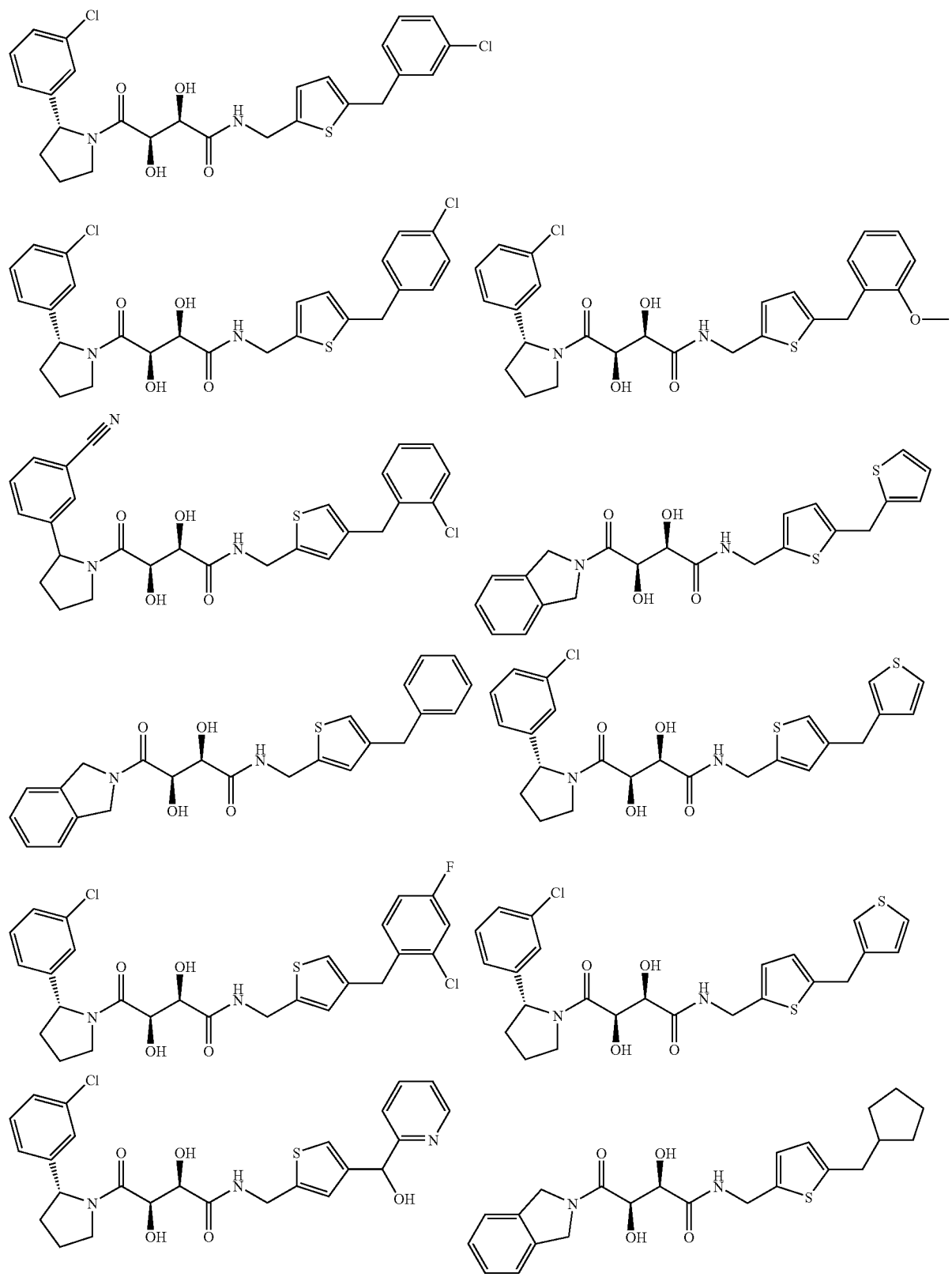

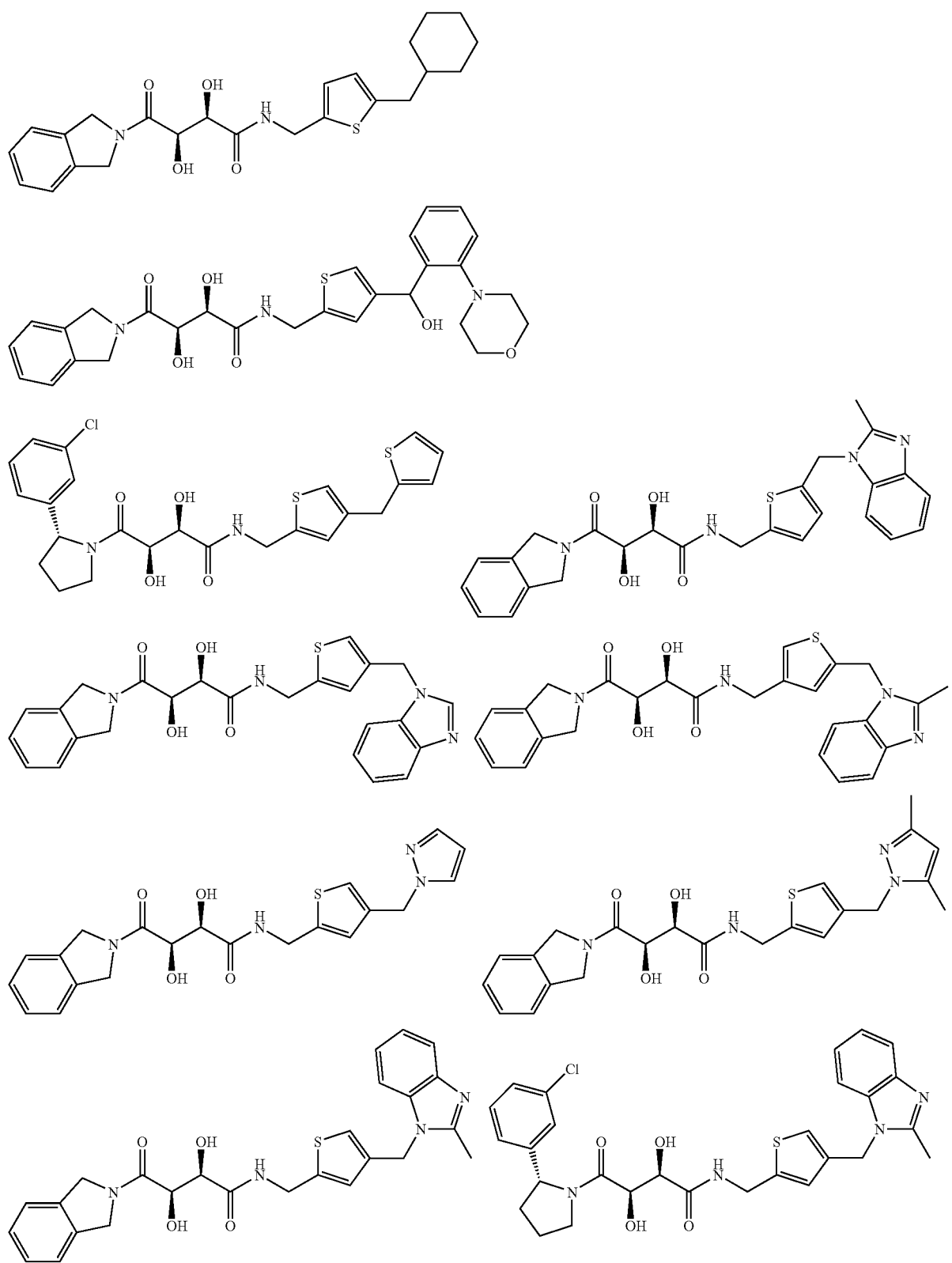

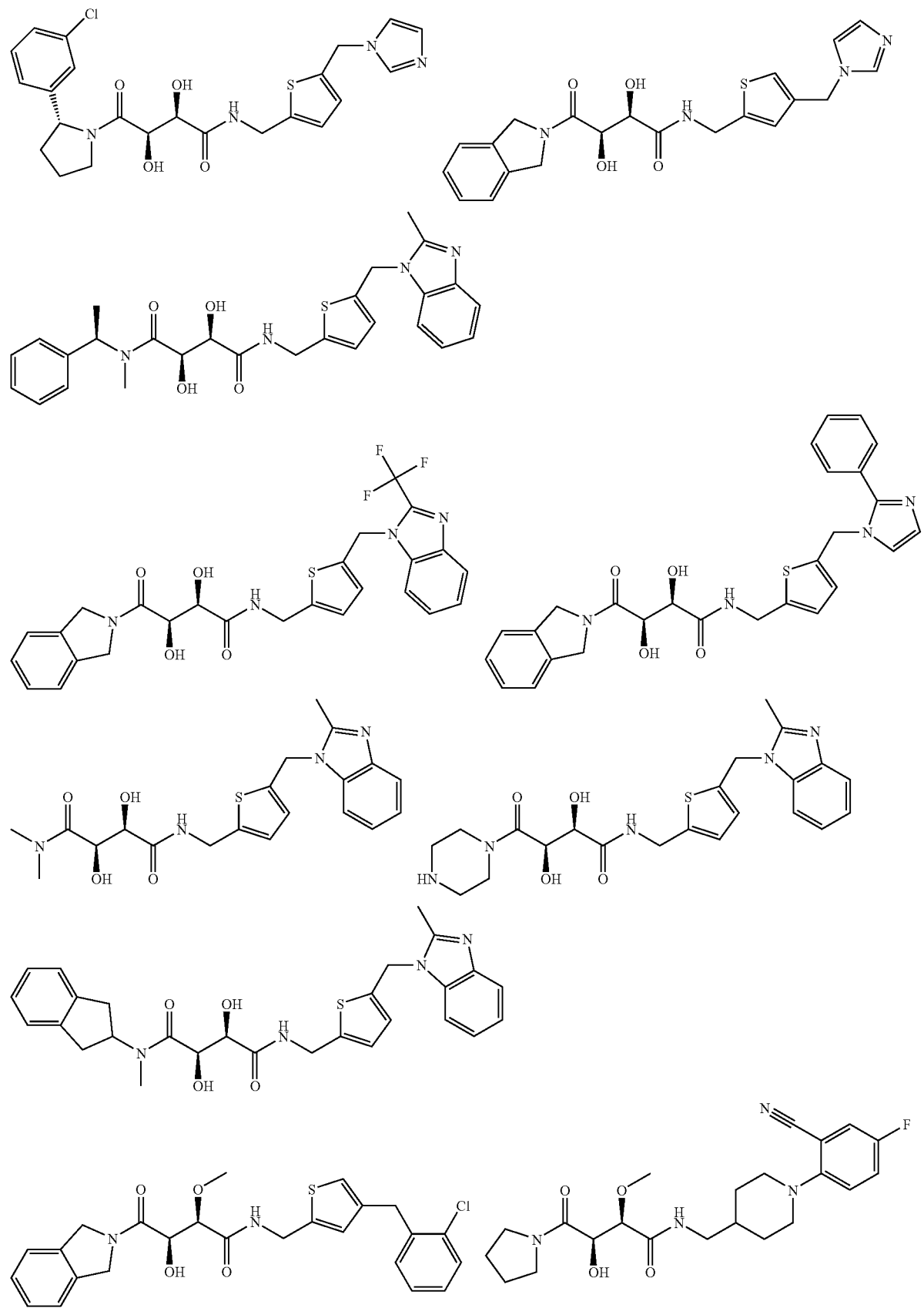

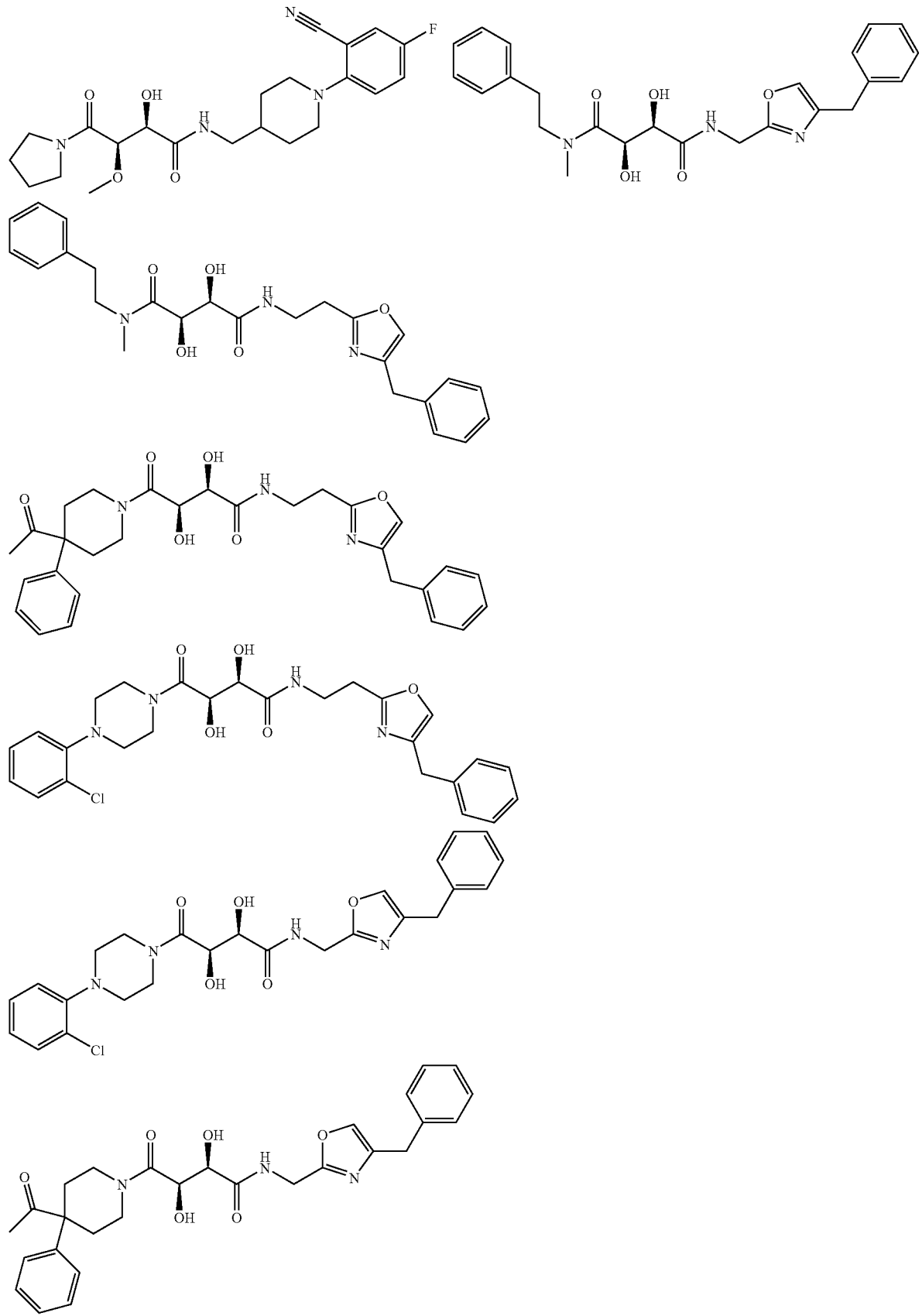

-continued
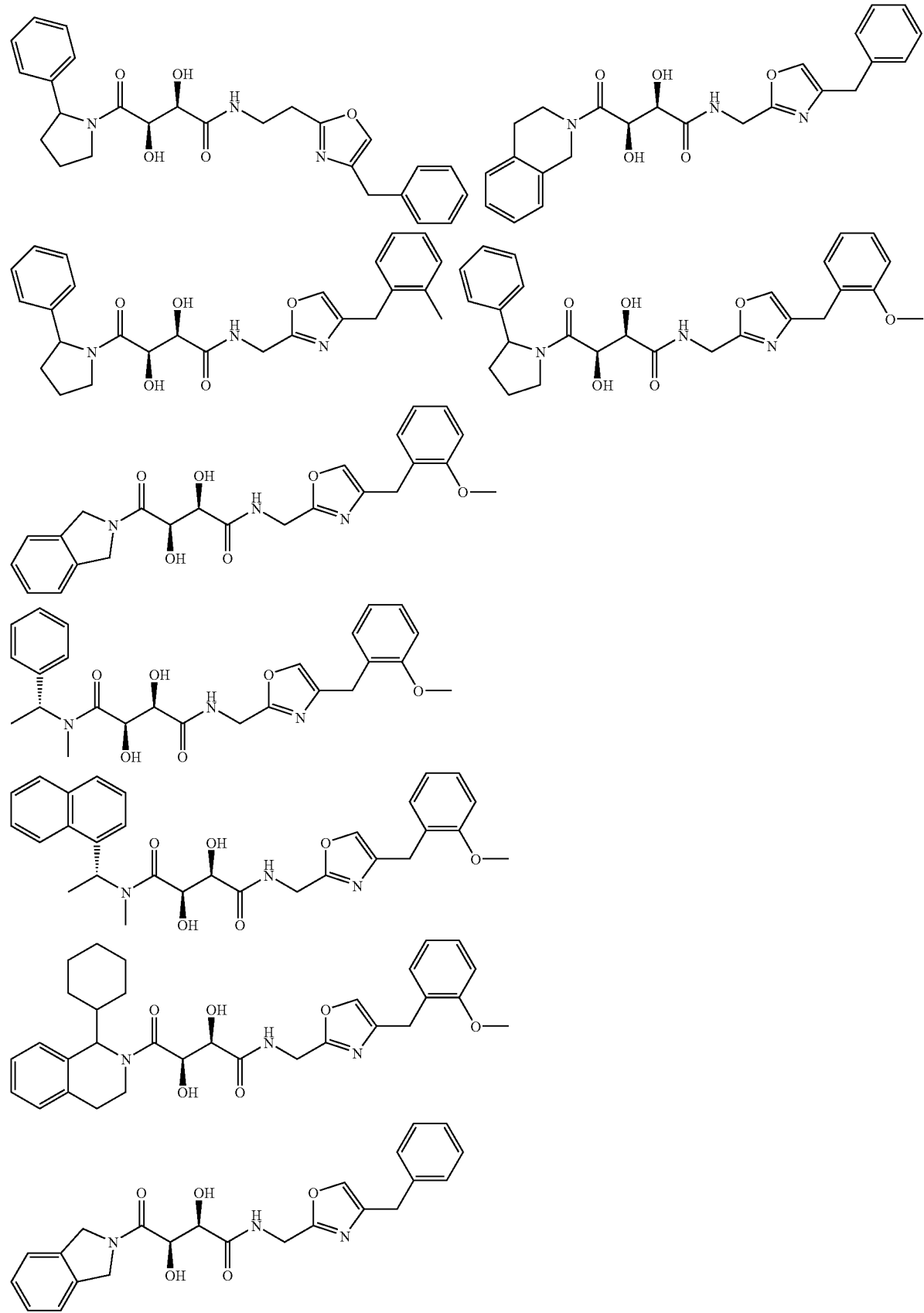

-continued
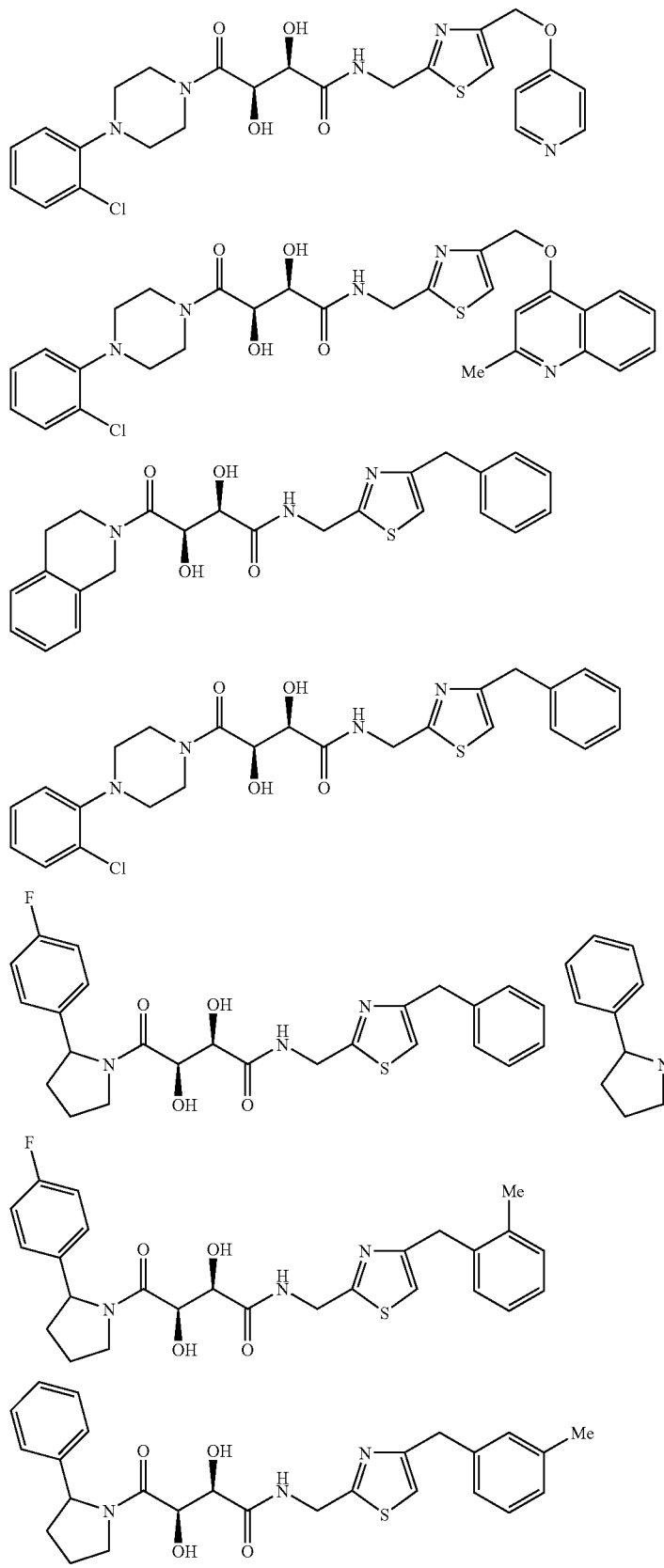

-continued
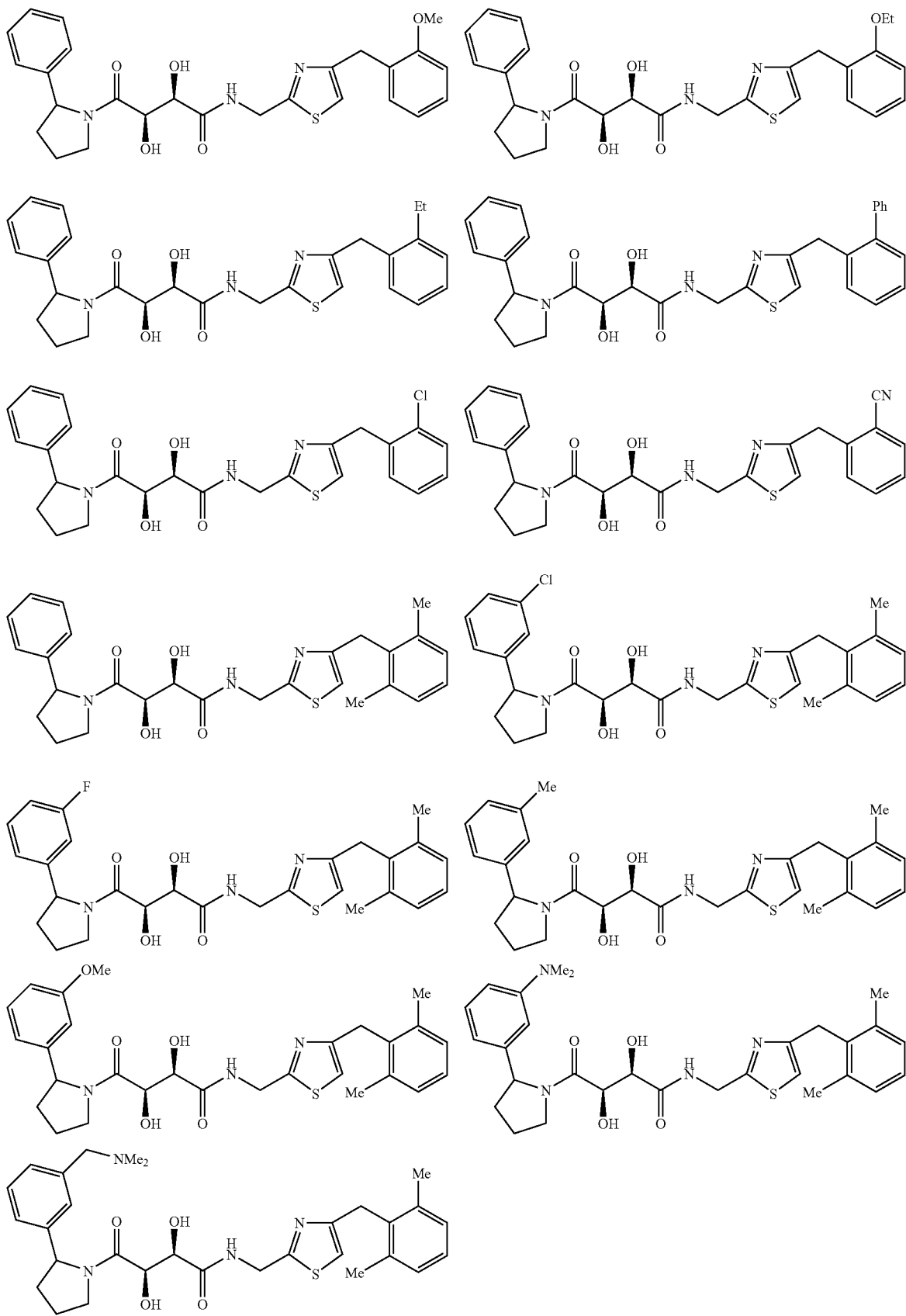

-continued
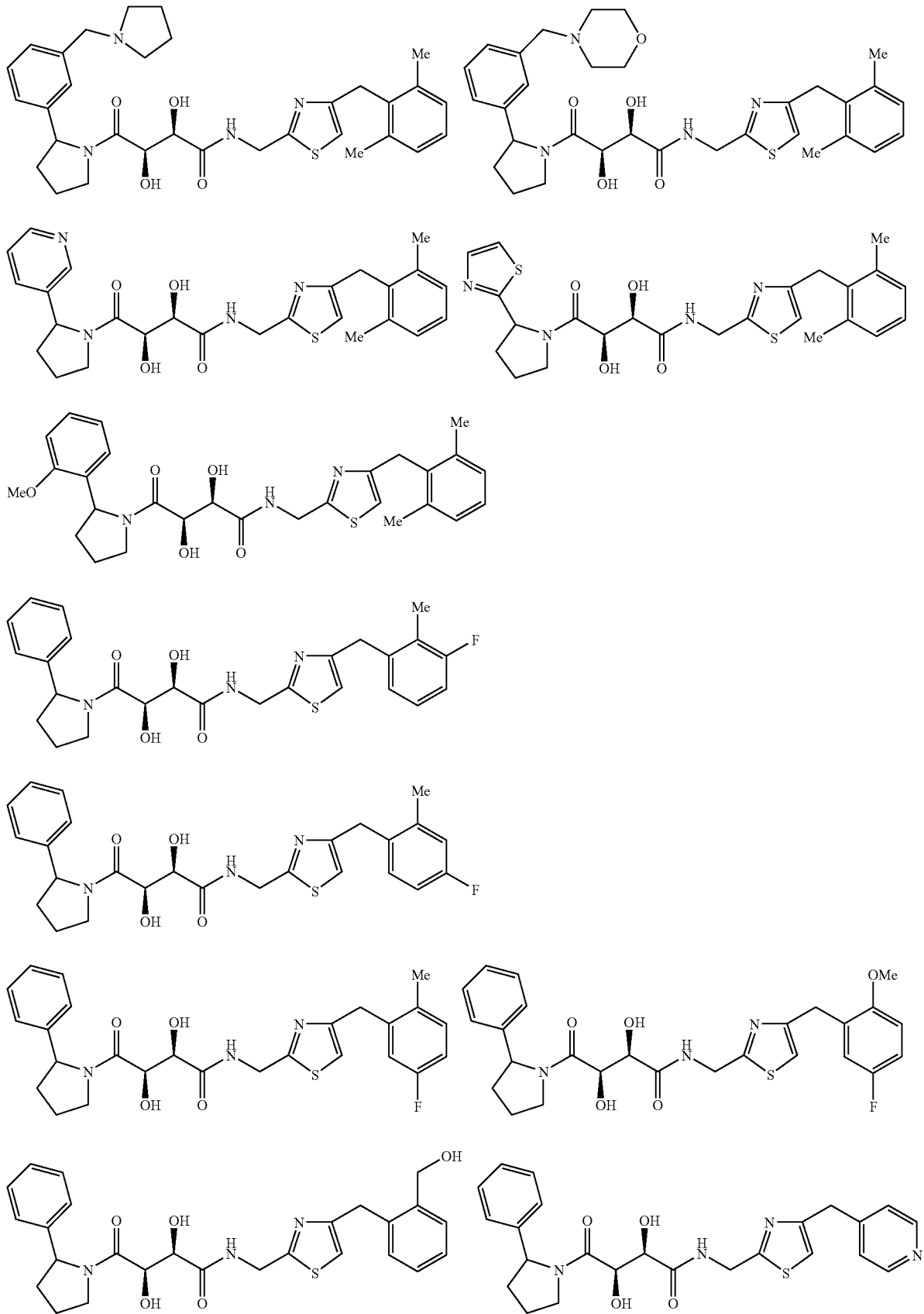

-continued
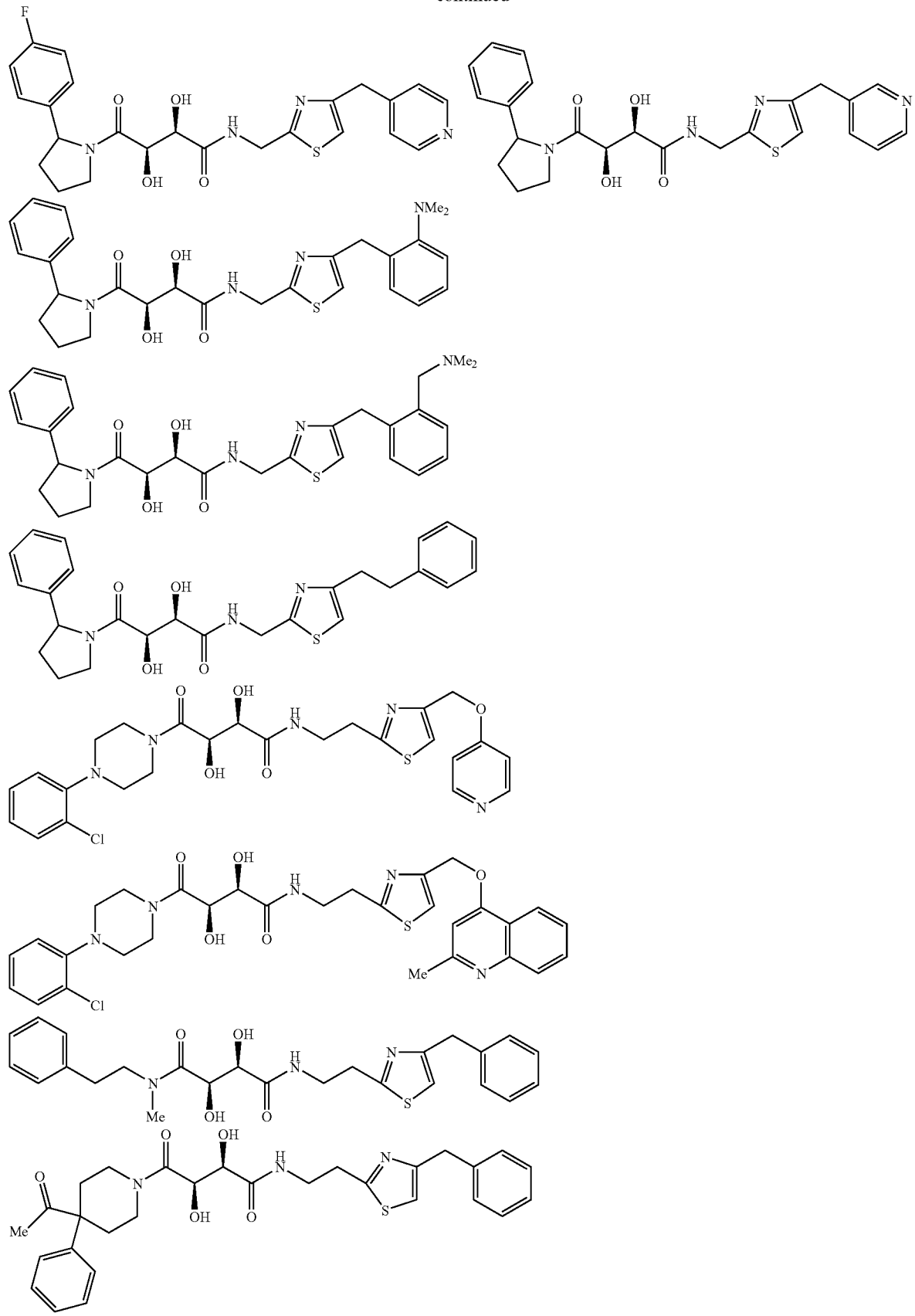

-continued
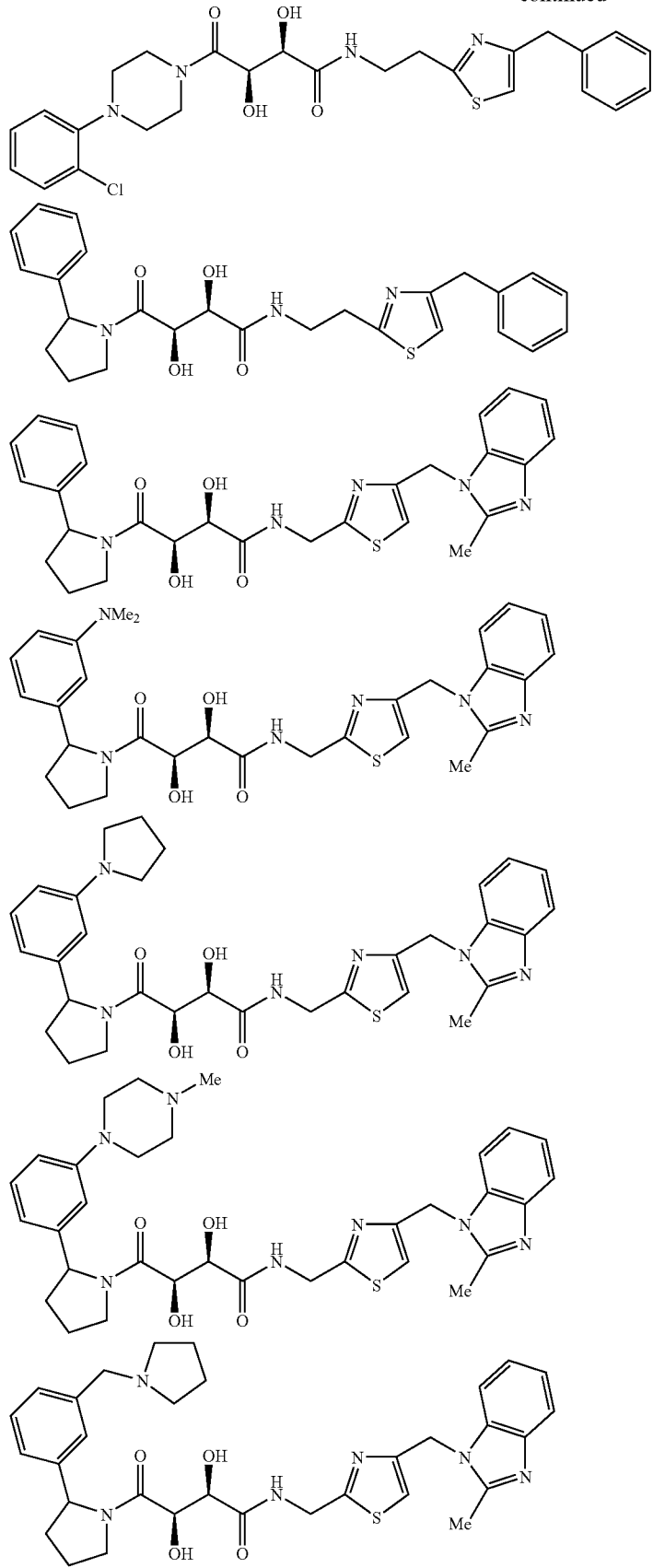

-continued
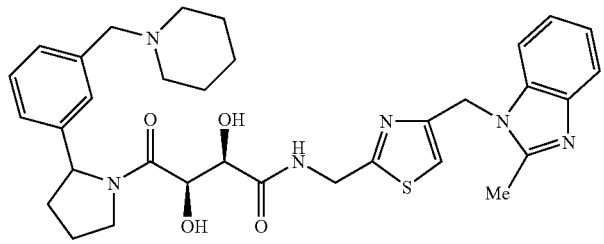
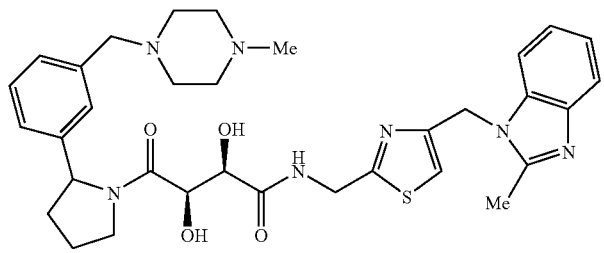
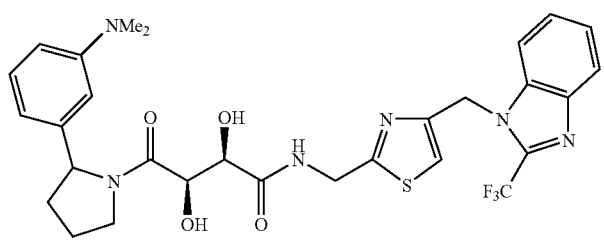
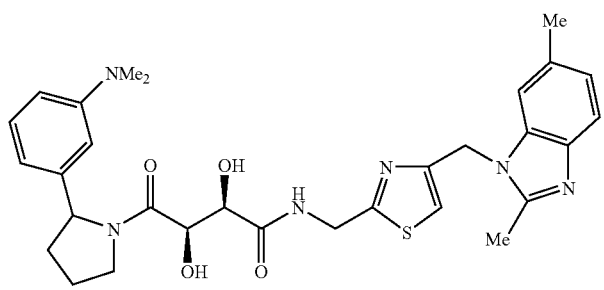
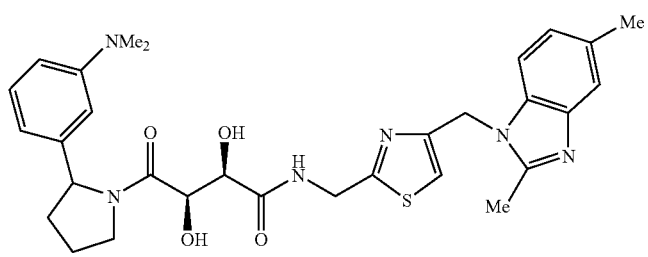
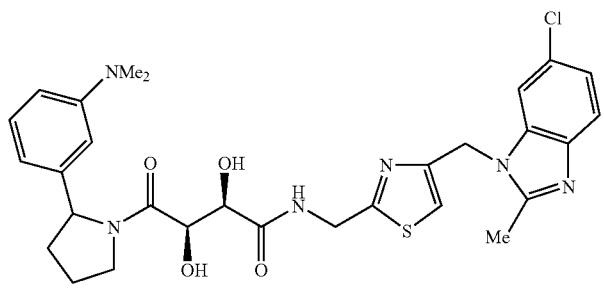

-continued
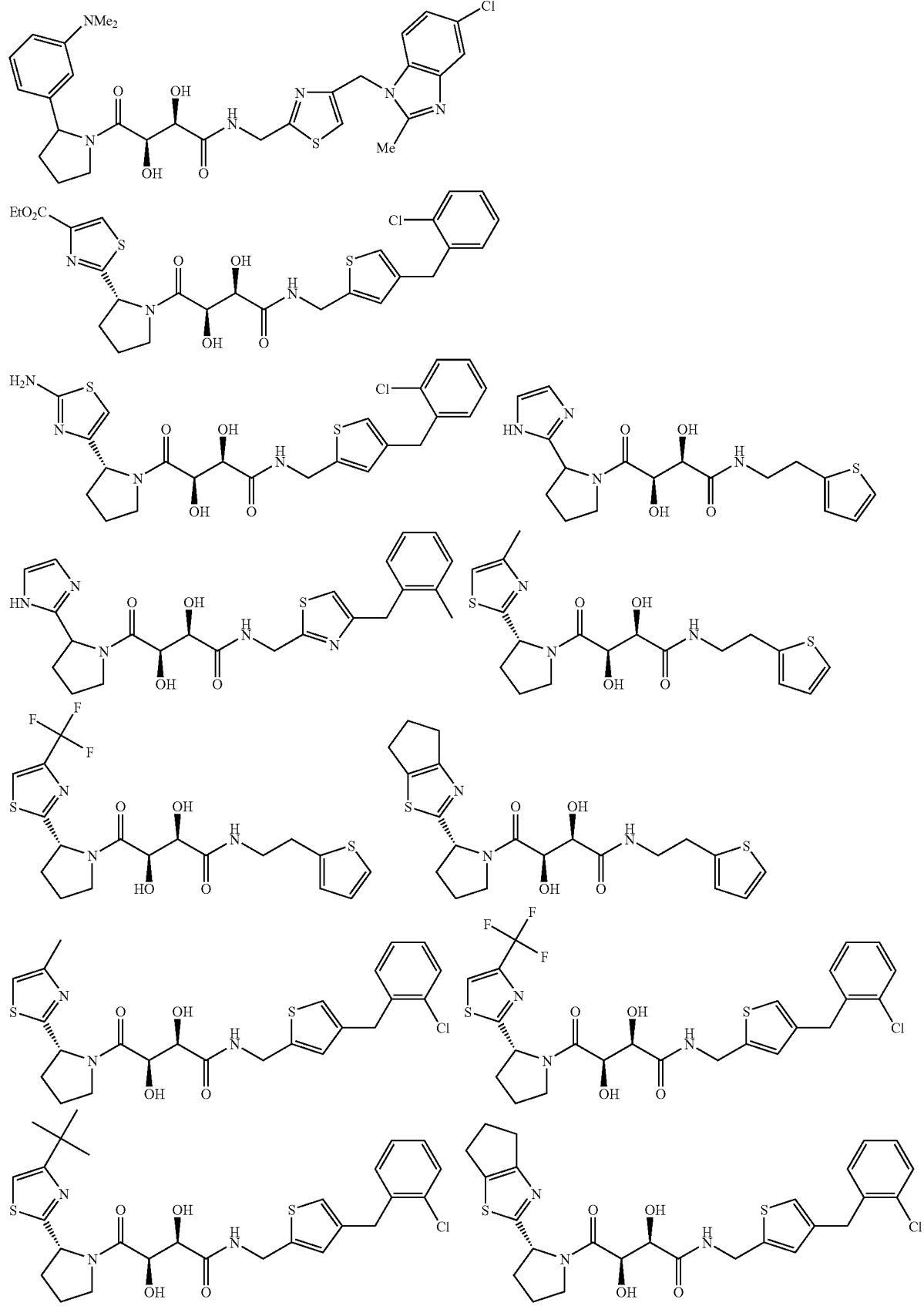

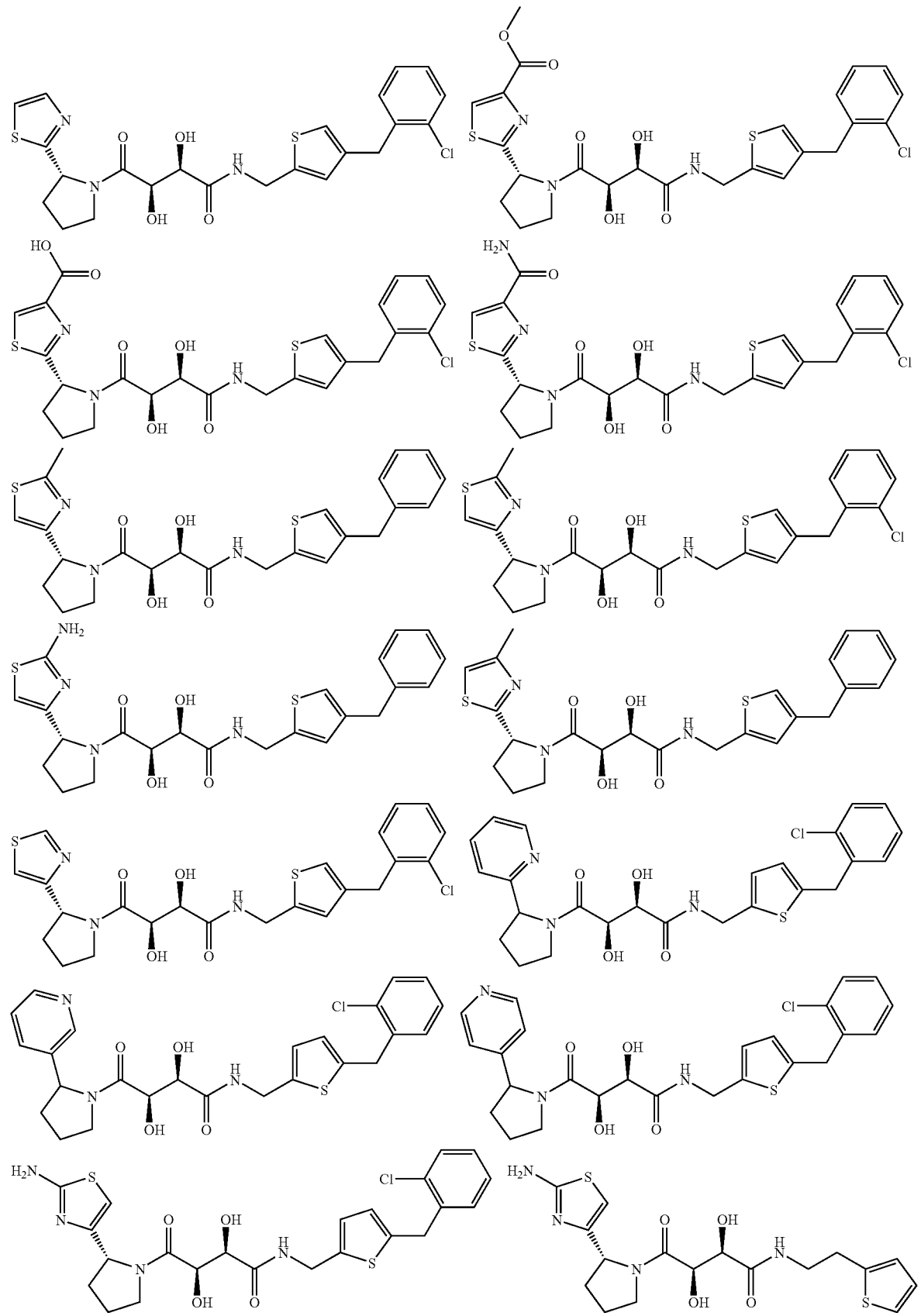

-continued
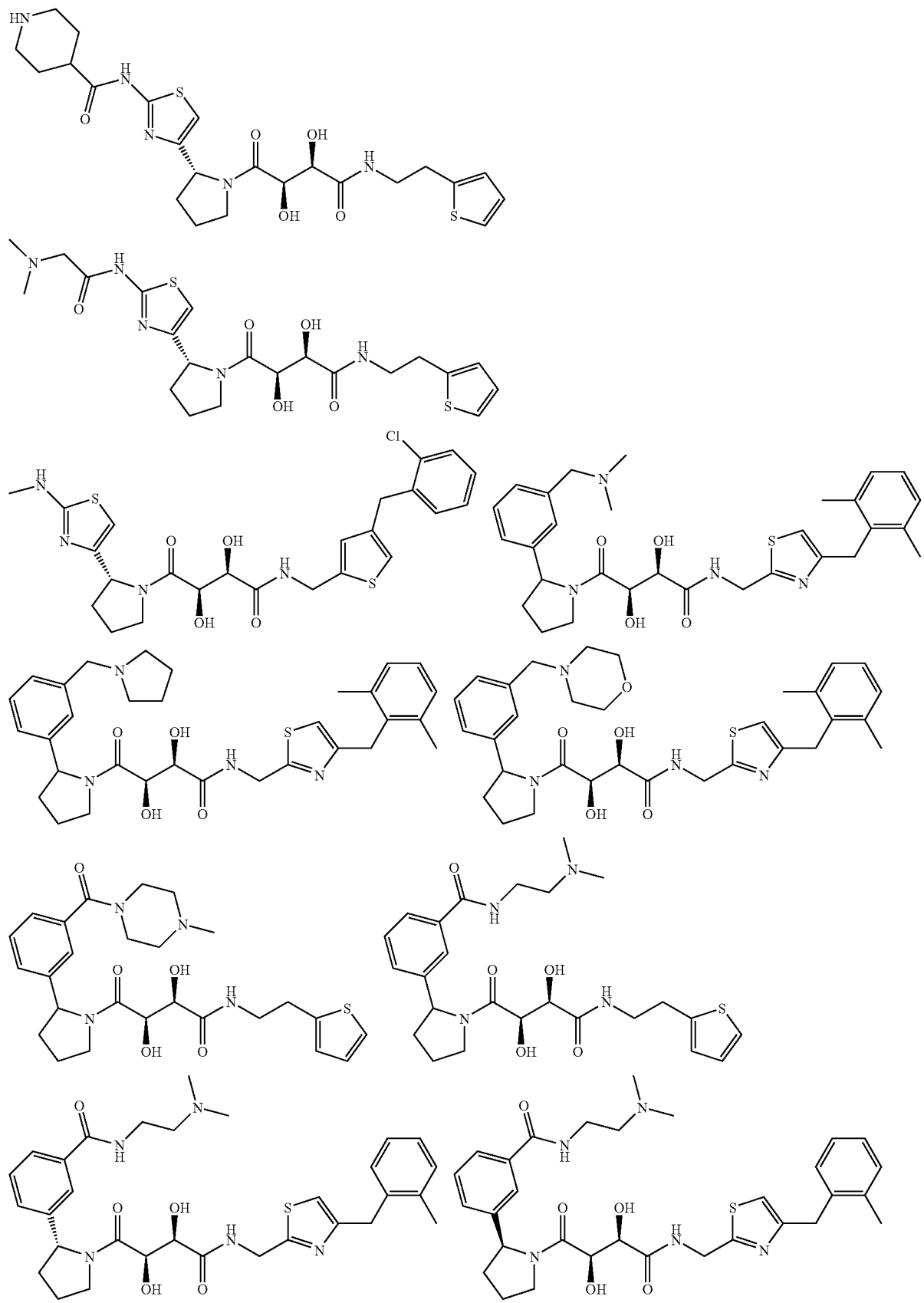

-continued
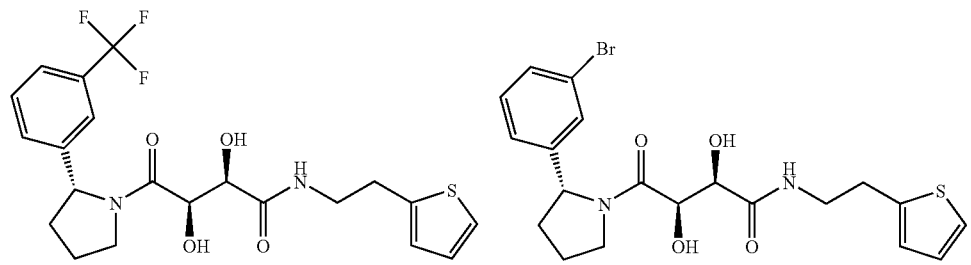
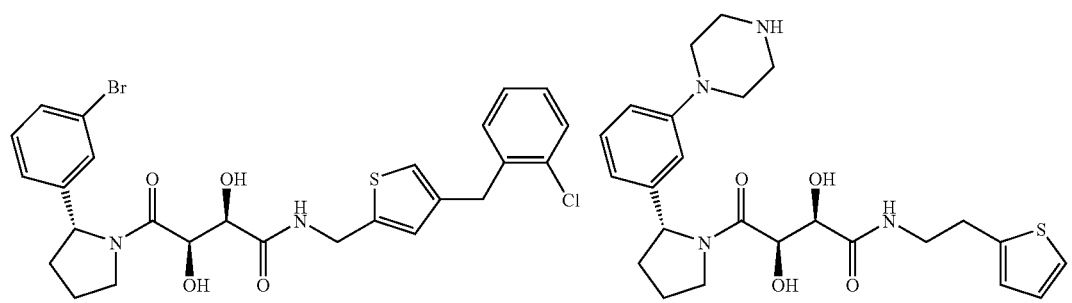
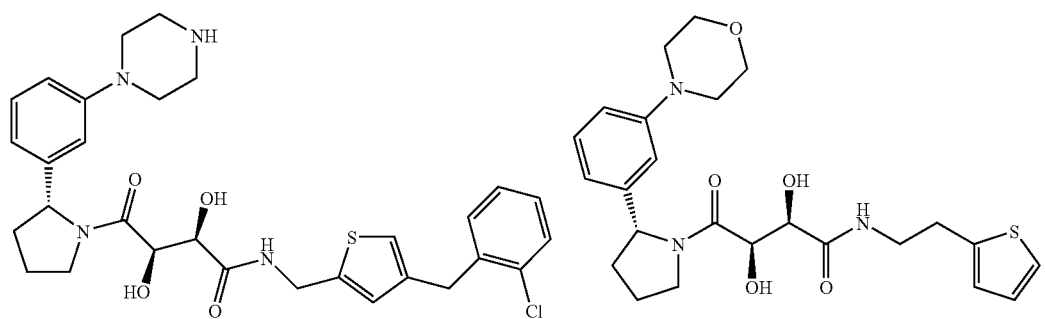
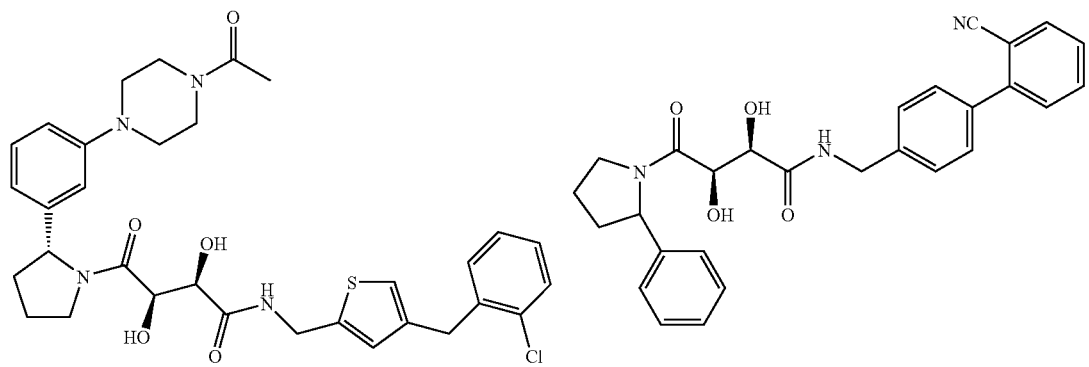

-continued
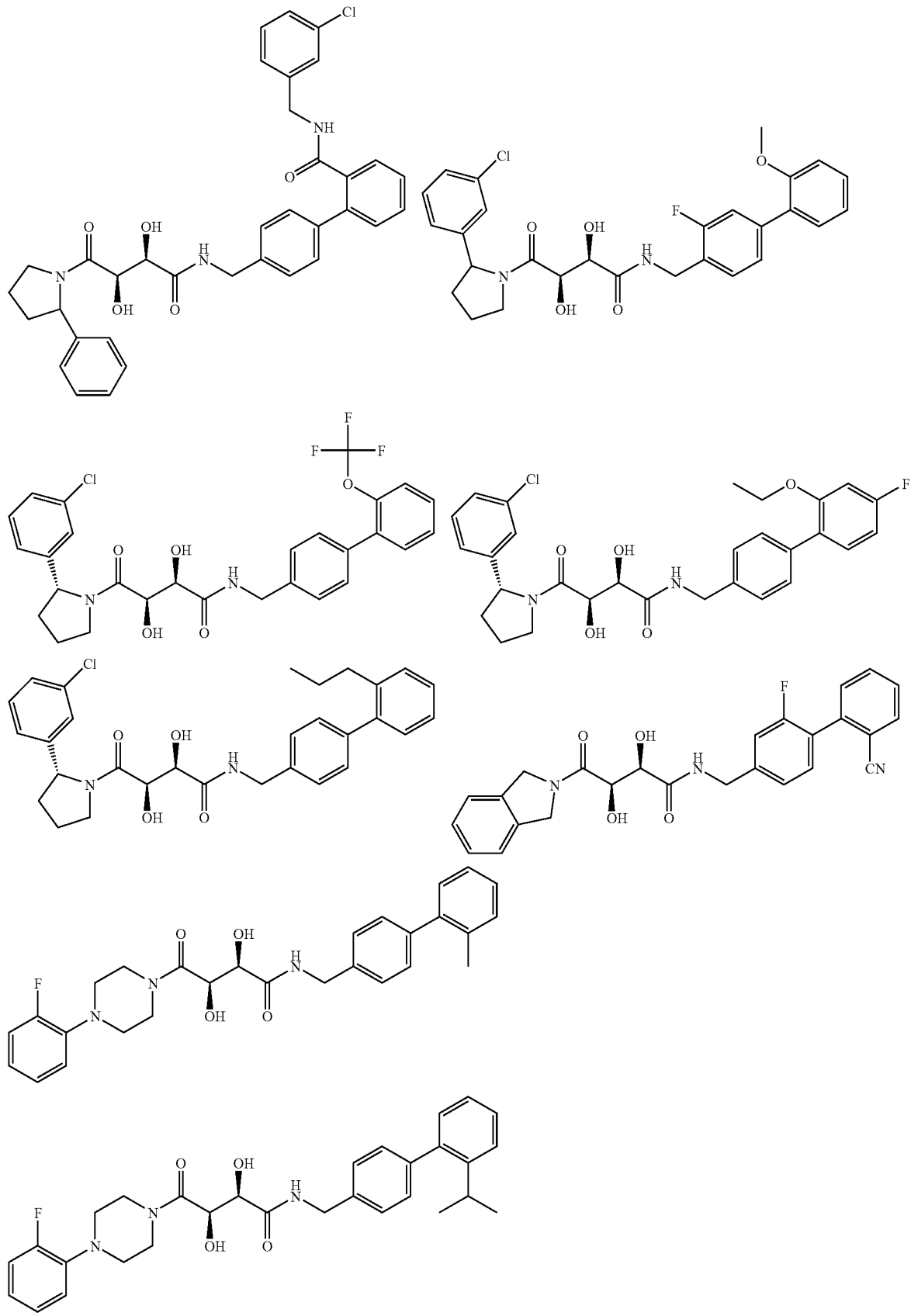

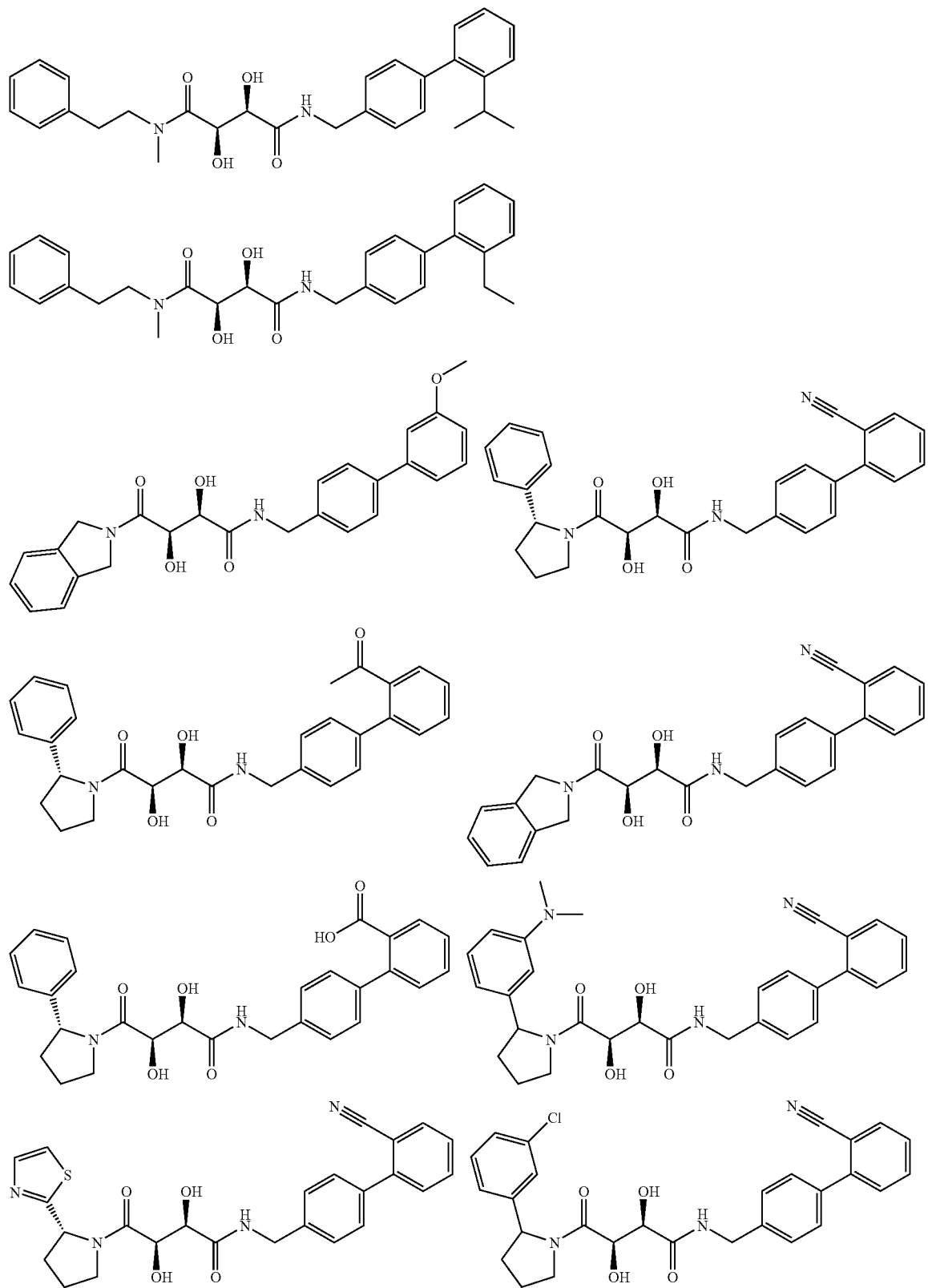

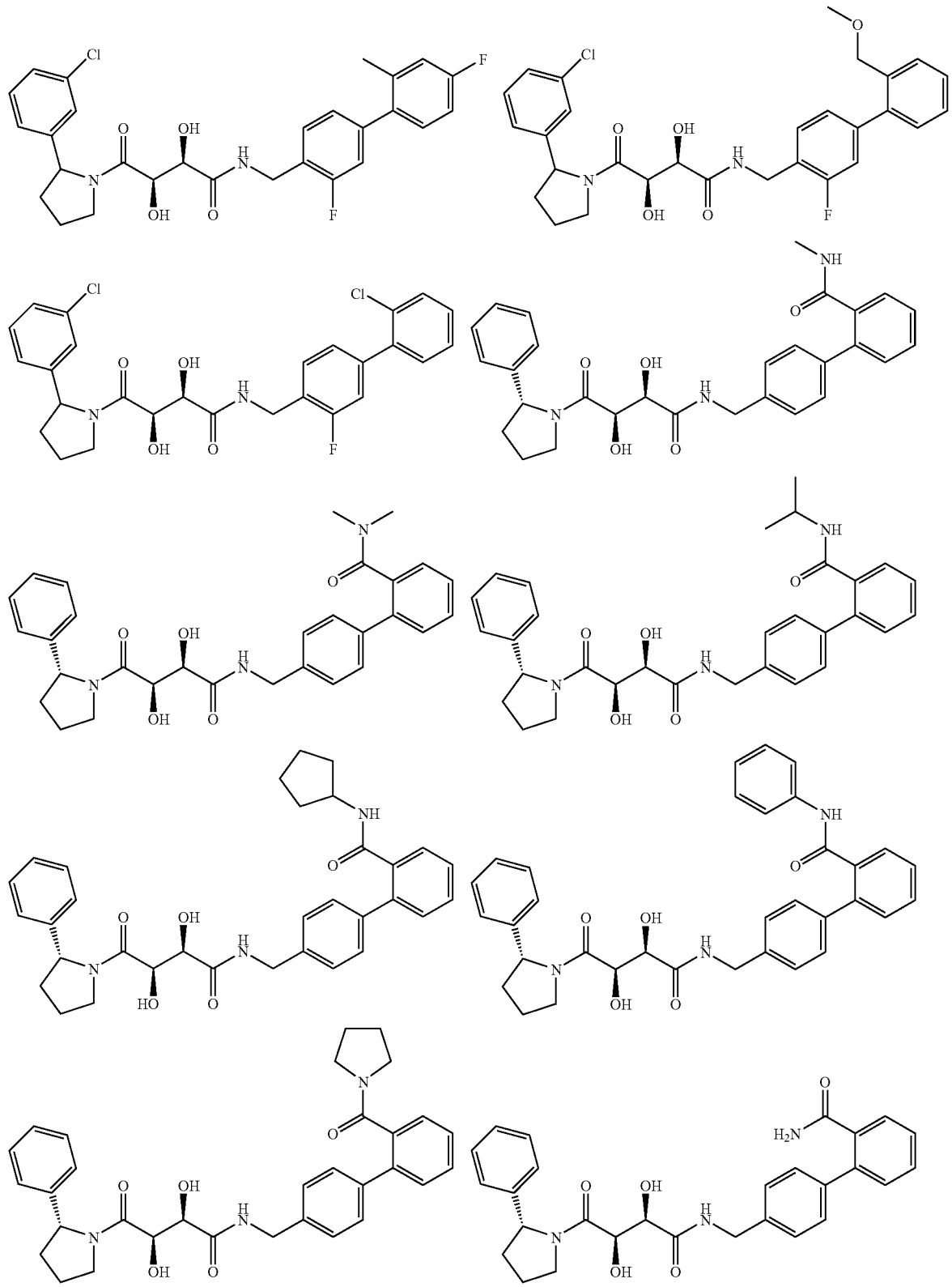

-continued
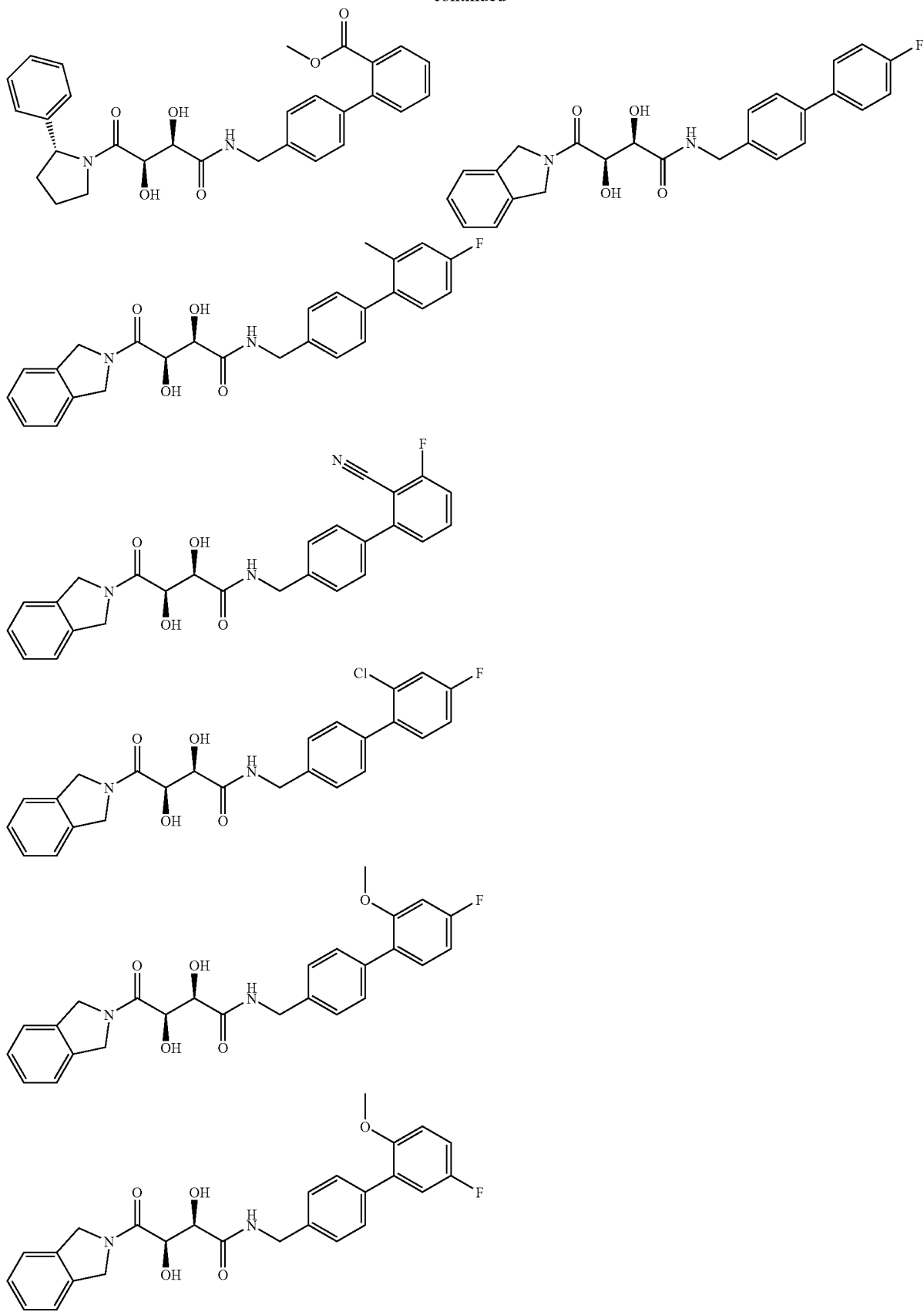

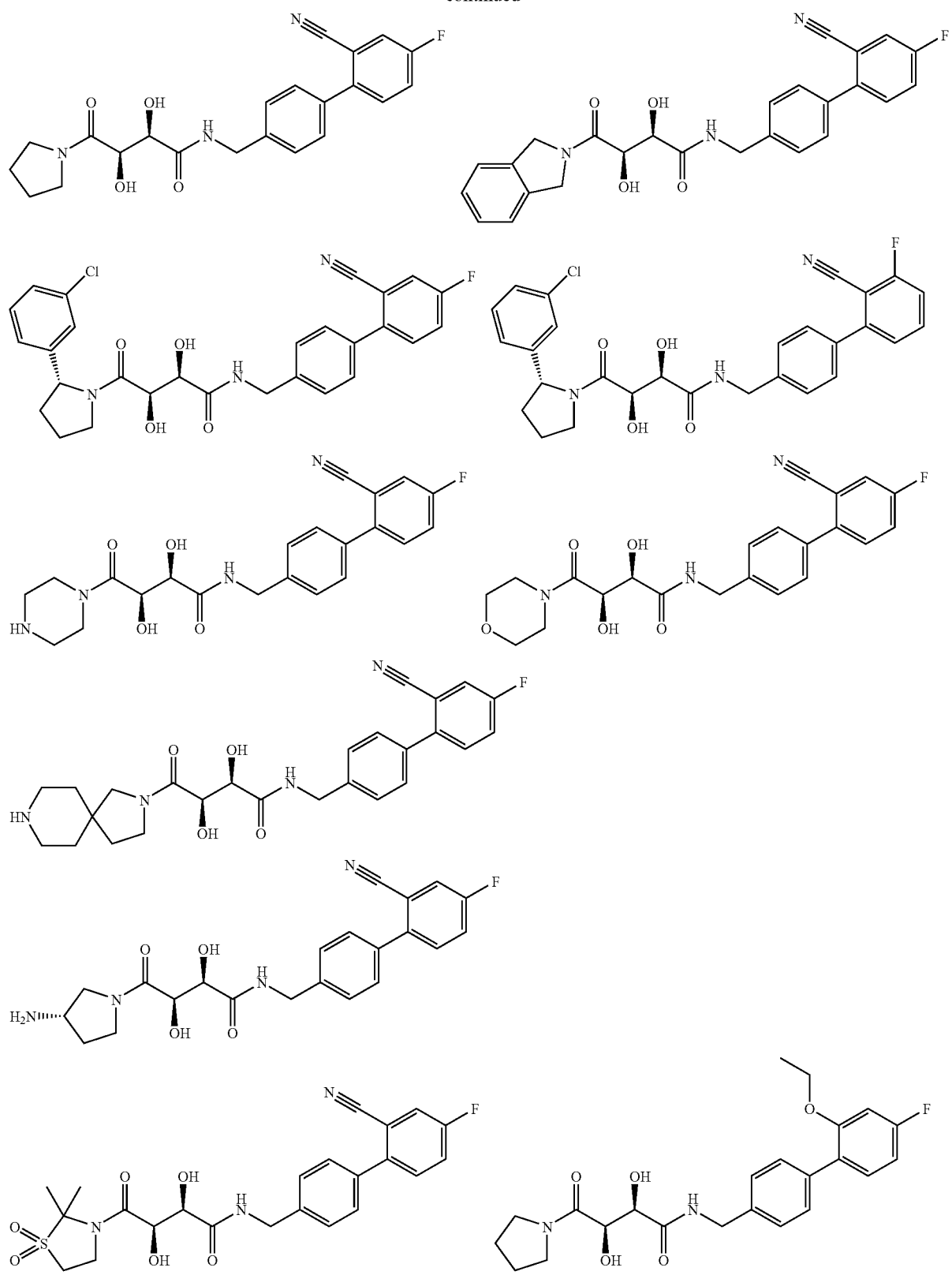

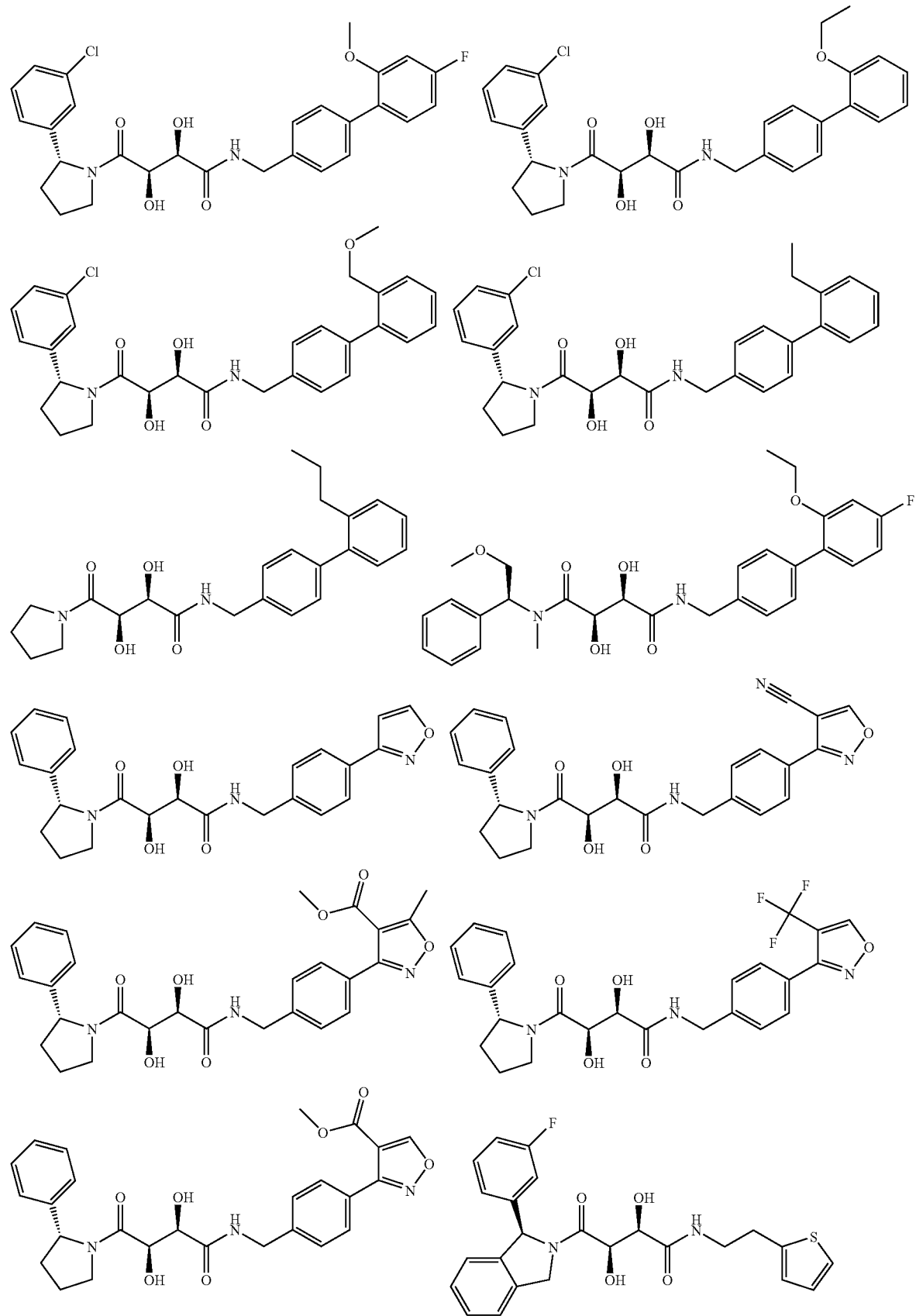

-continued
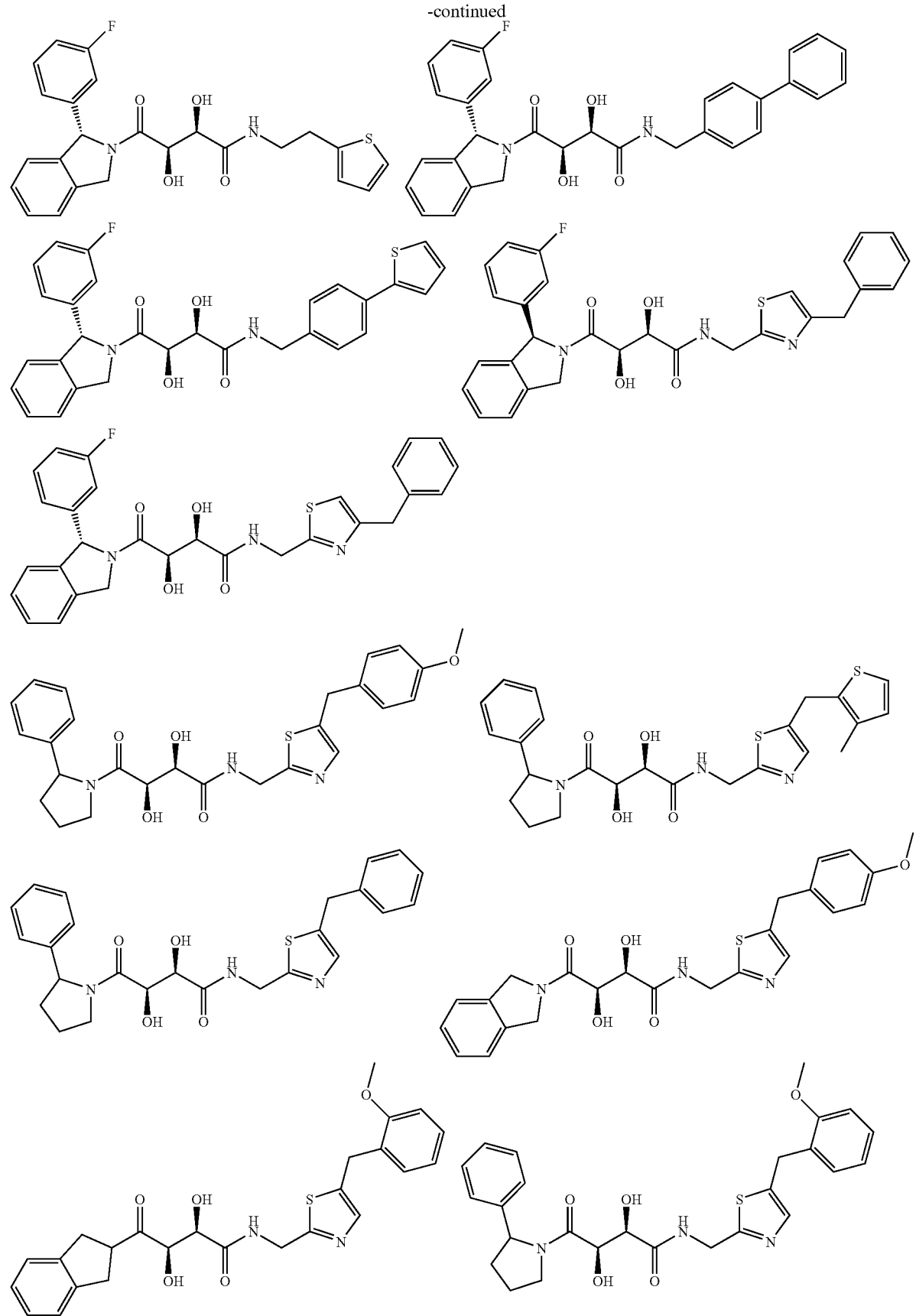

-continued
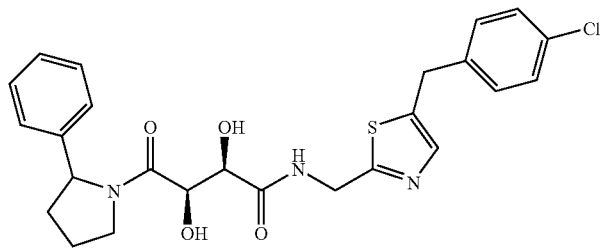
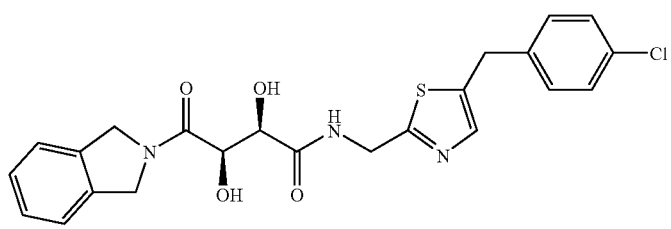
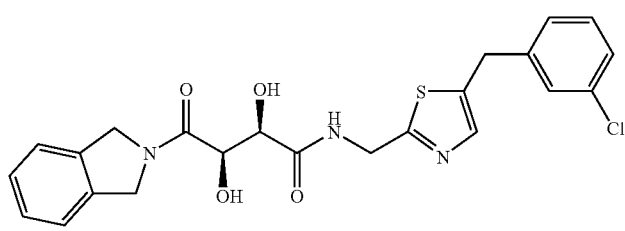
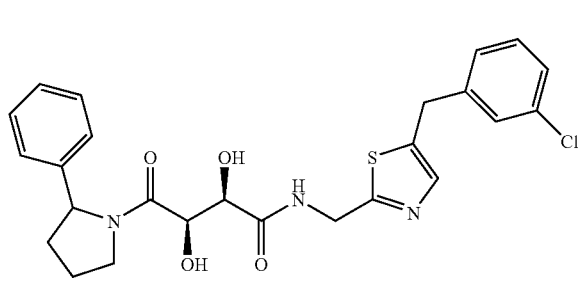
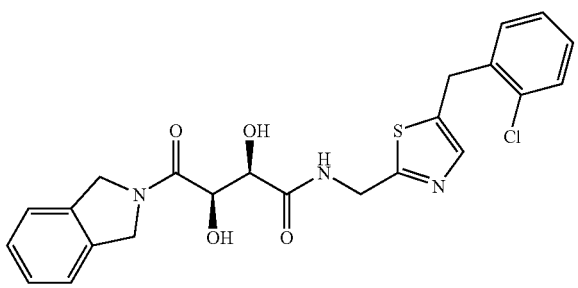
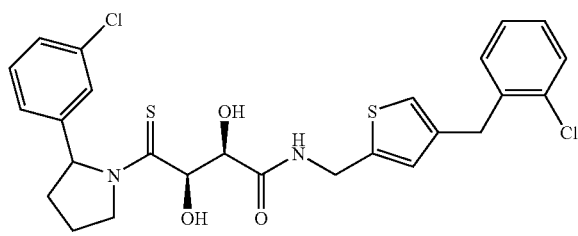
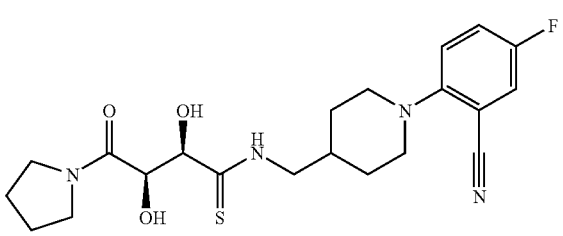
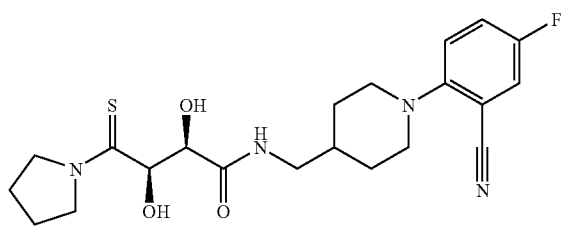
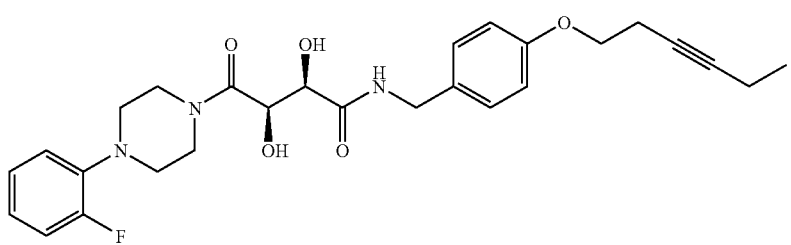

-continued
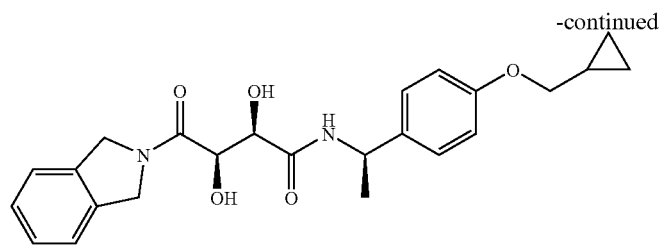
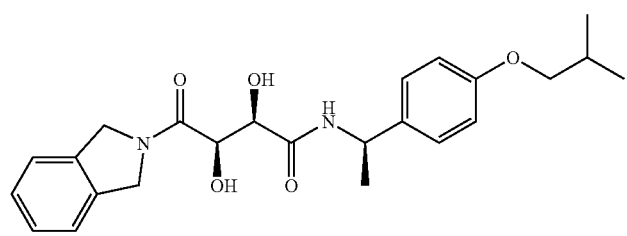
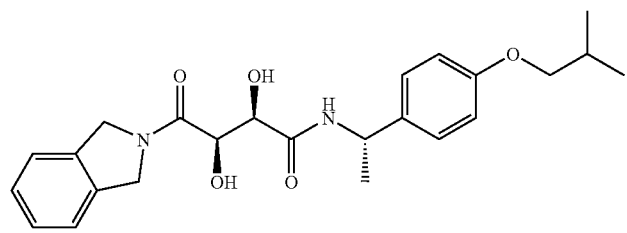
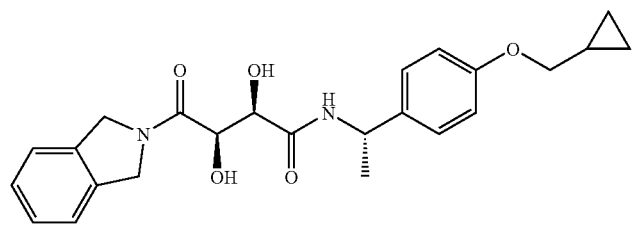
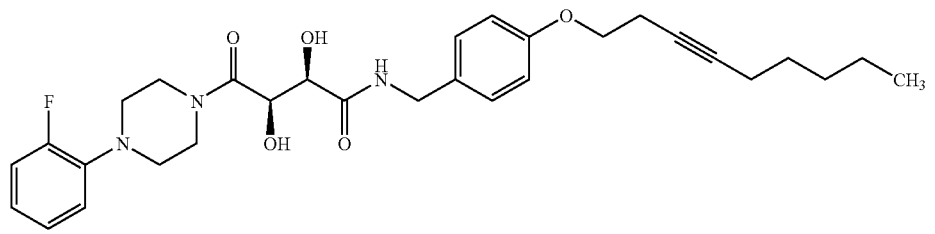
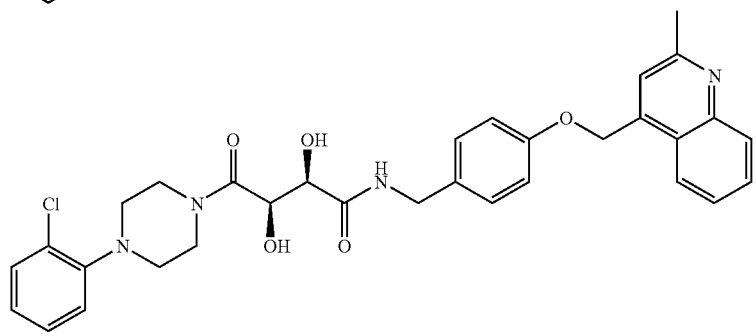

-continued
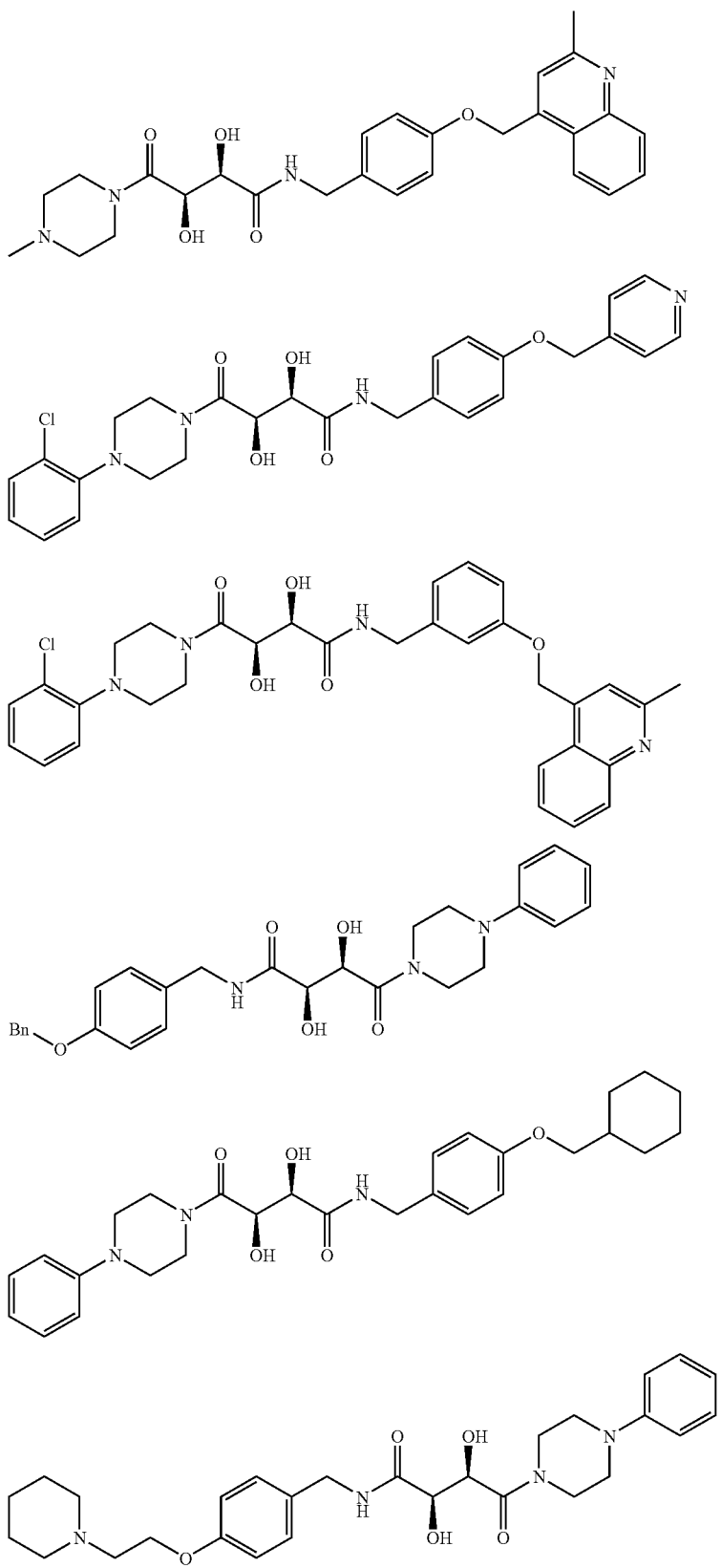

-continued
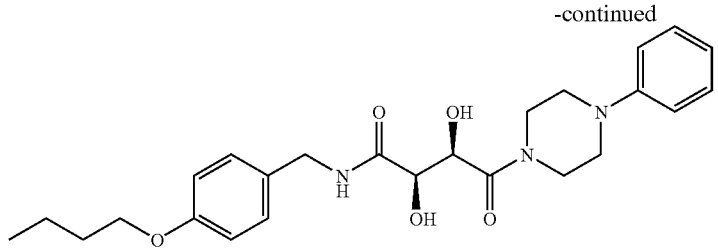
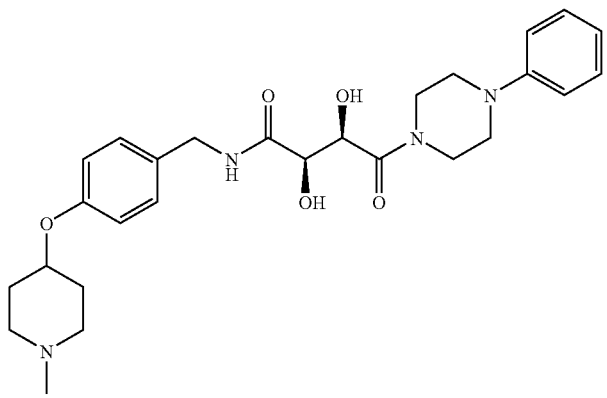
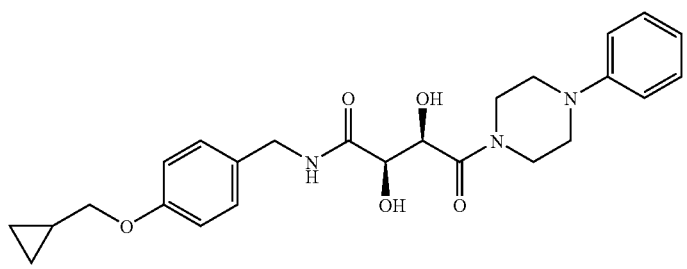
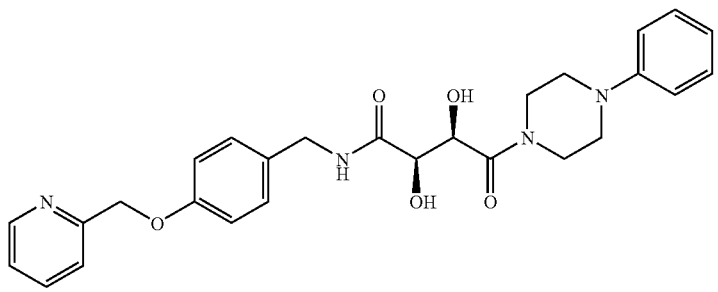
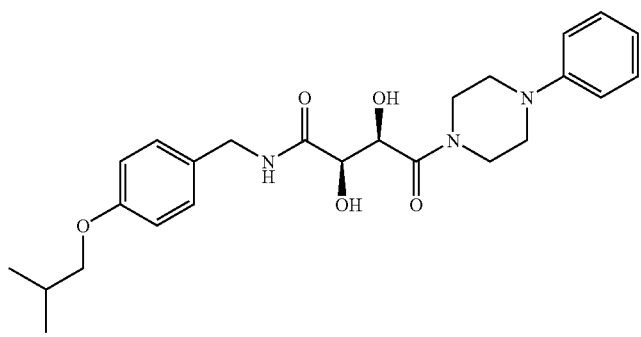

-continued
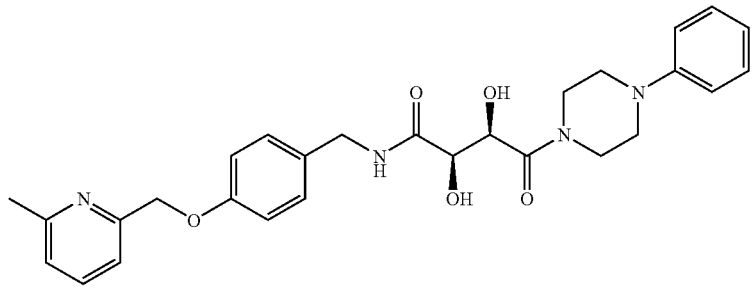
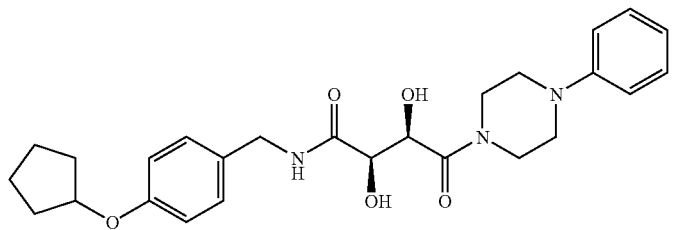
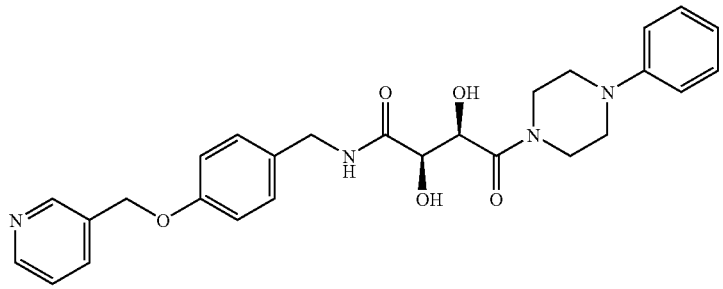
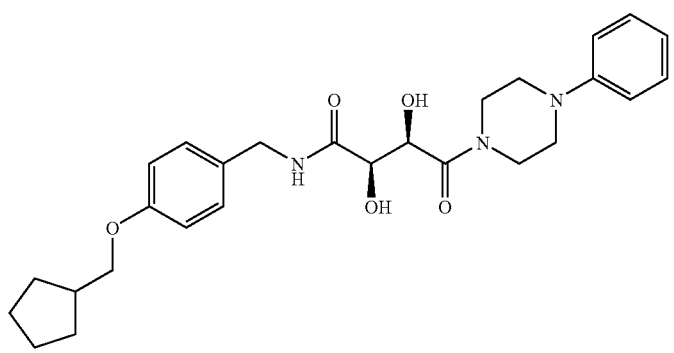
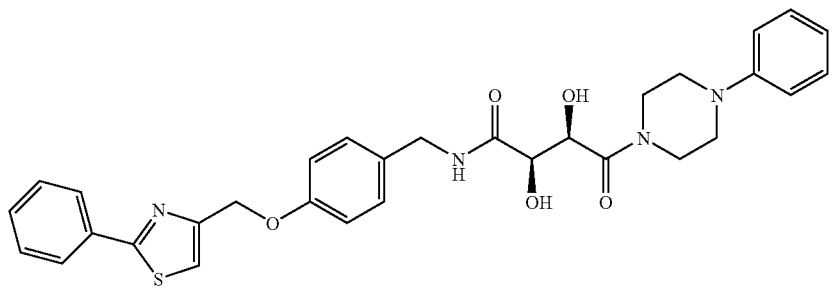
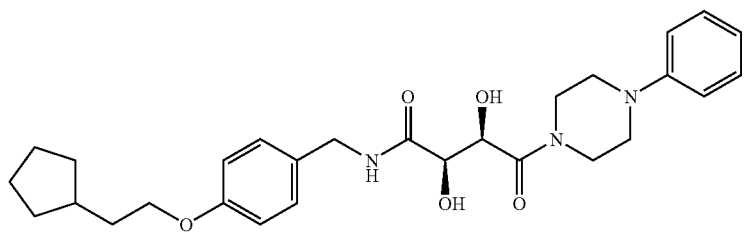

-continued
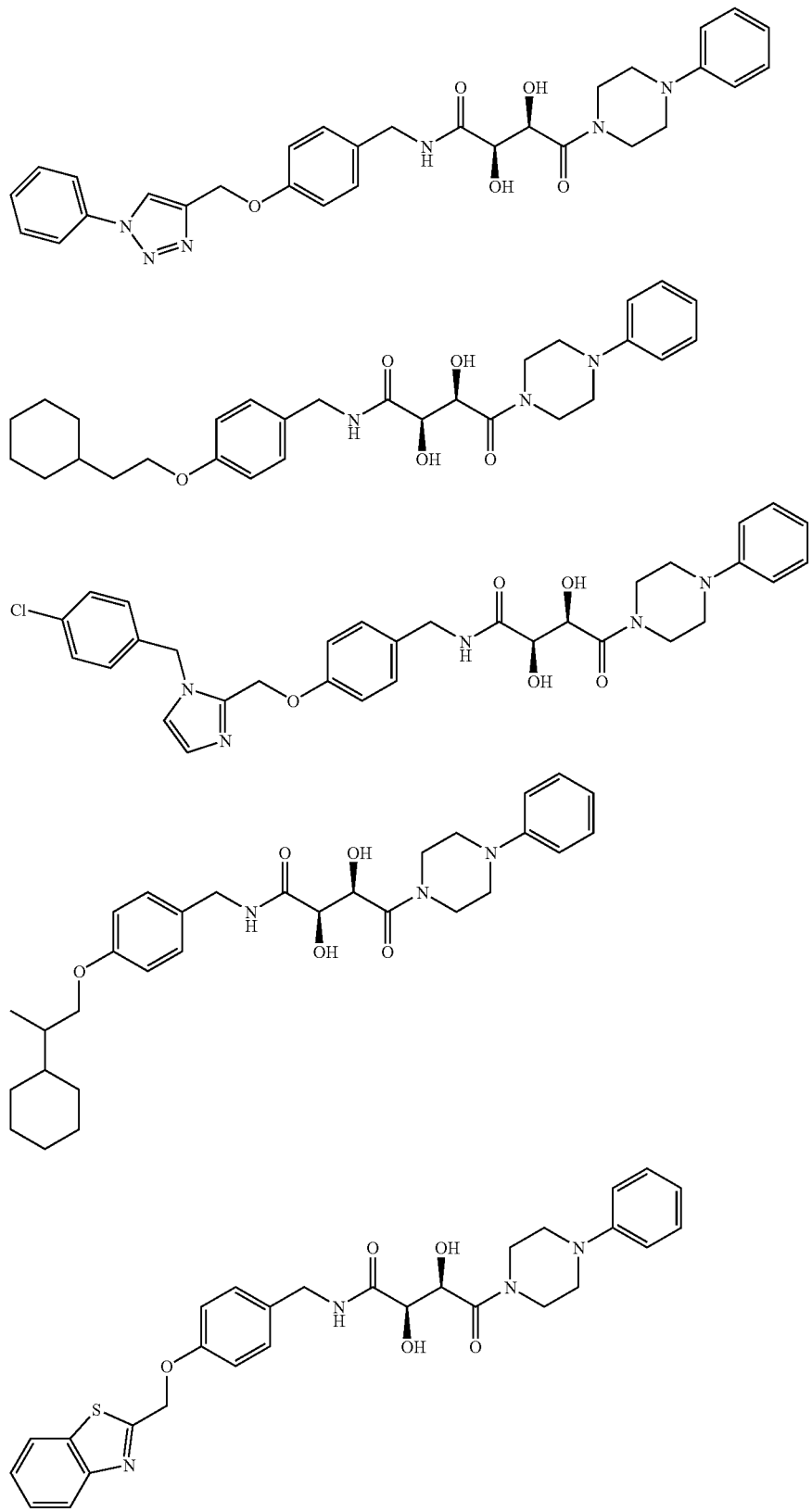

-continued
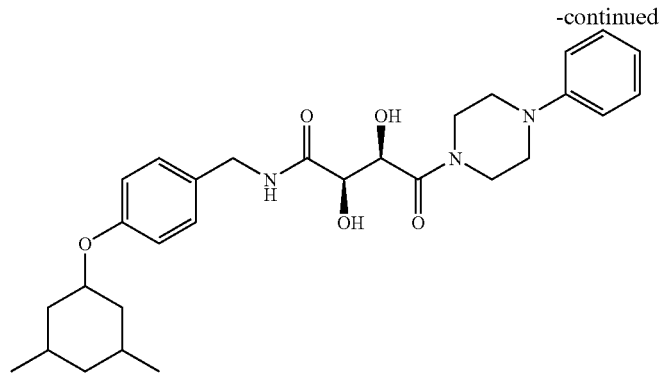
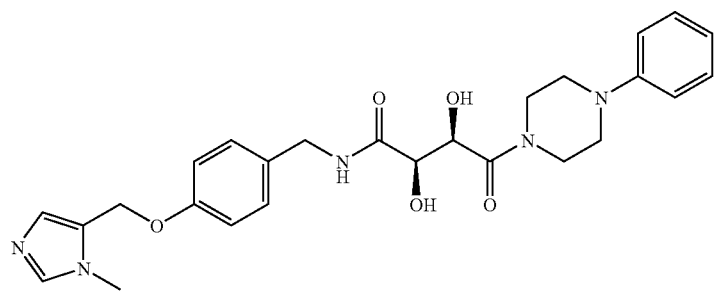
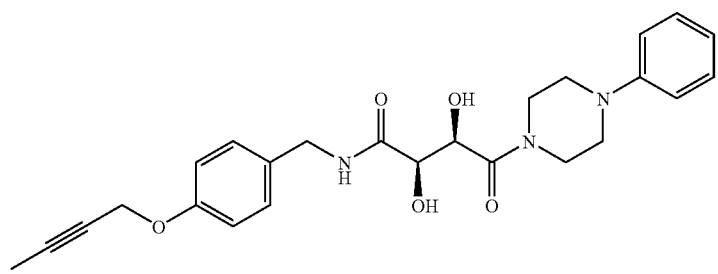
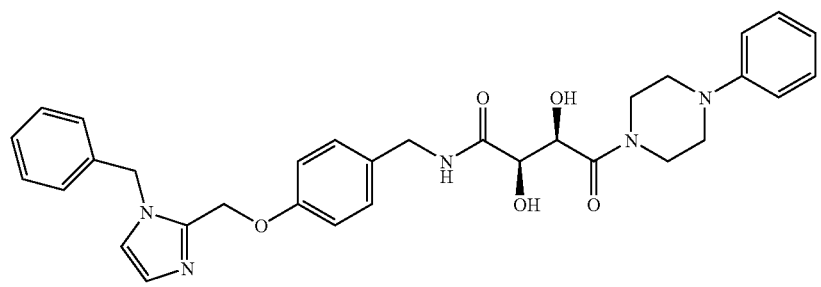
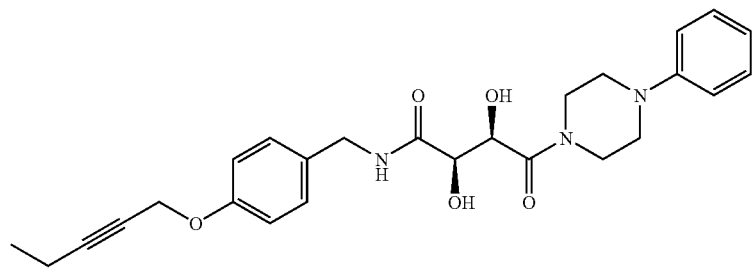

-continued
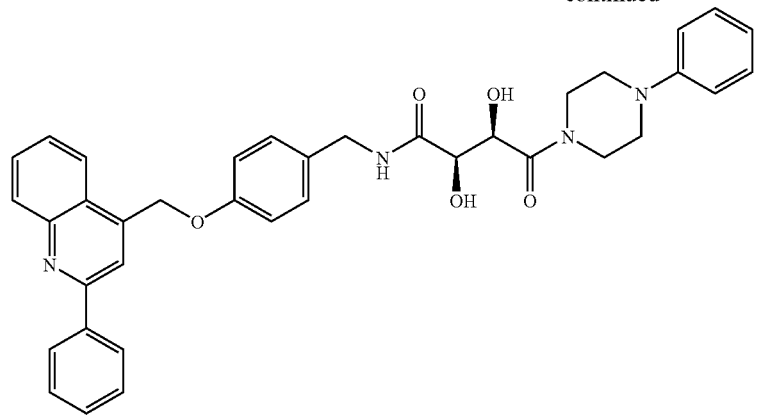
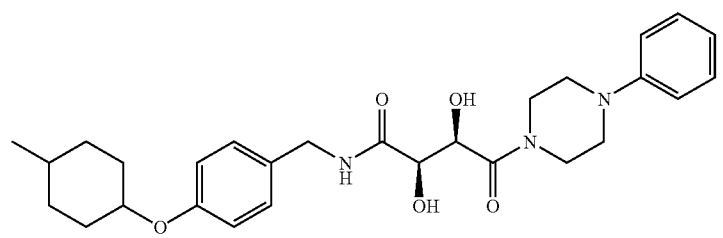
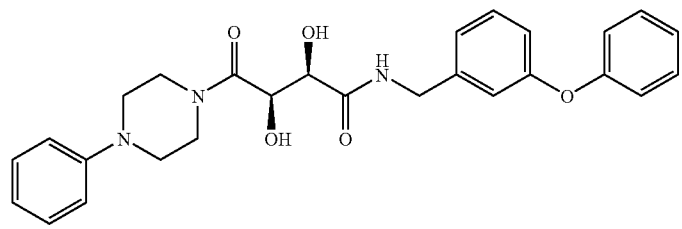
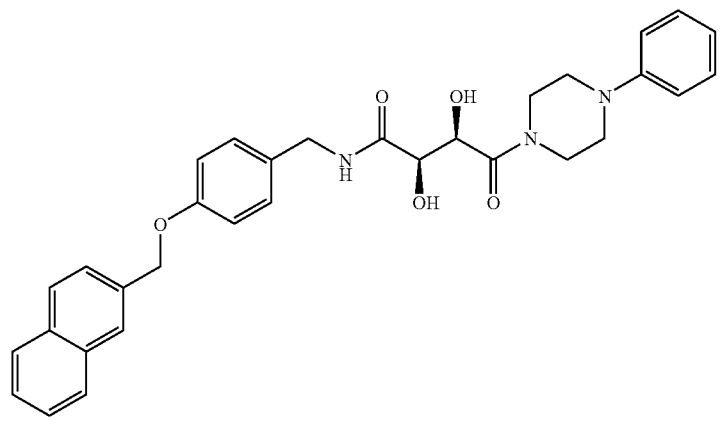
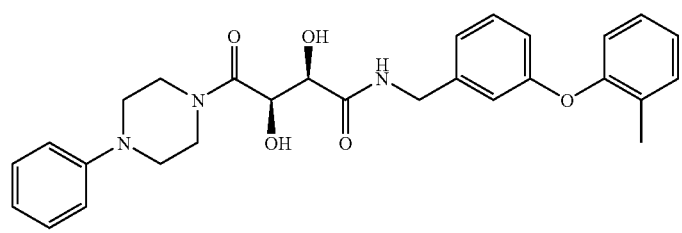

-continued
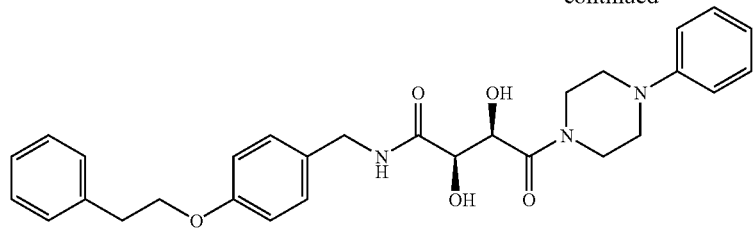
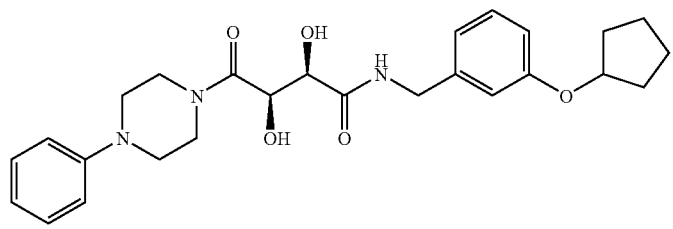
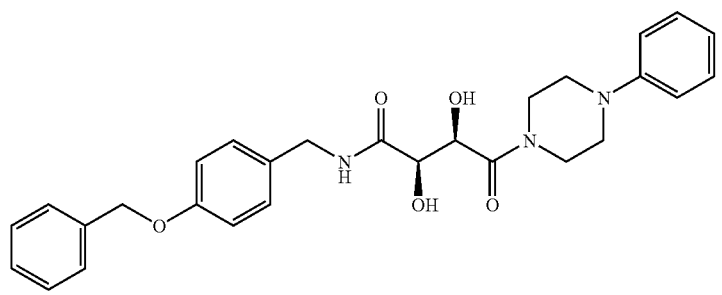
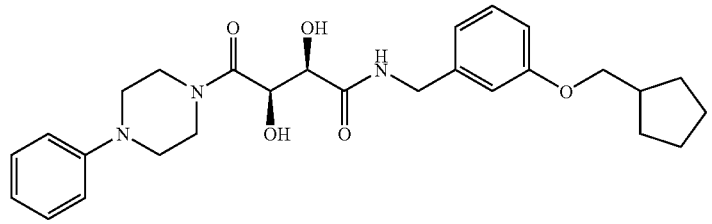
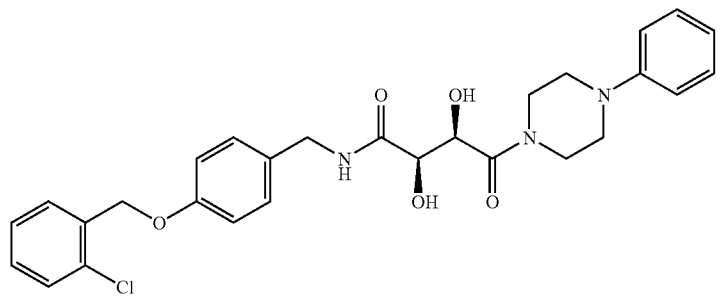
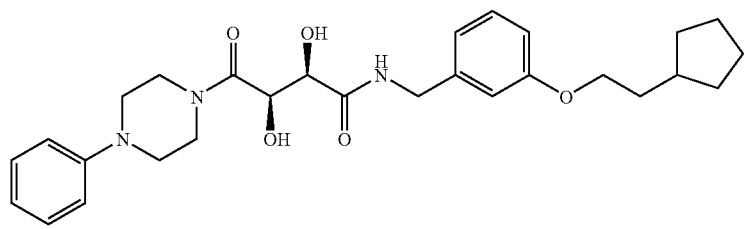

-continued
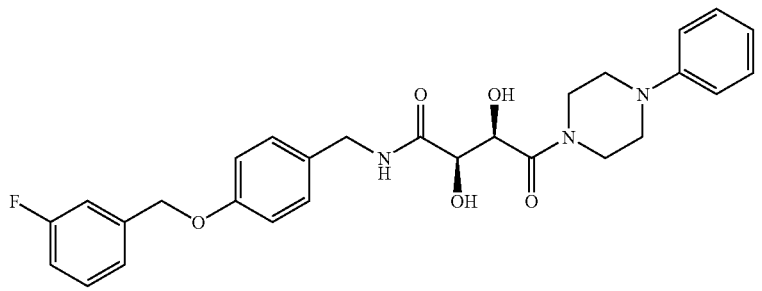
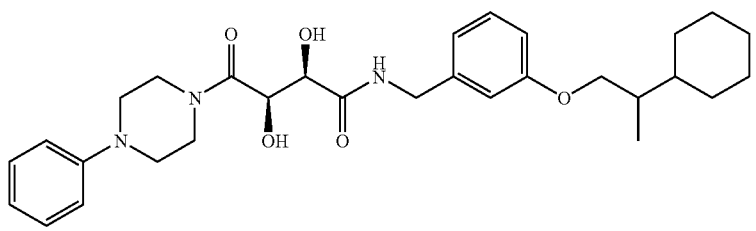
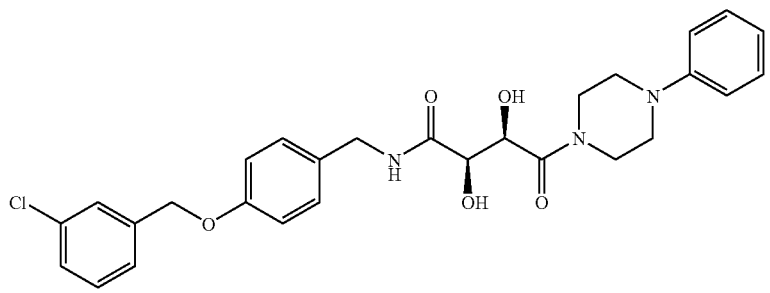
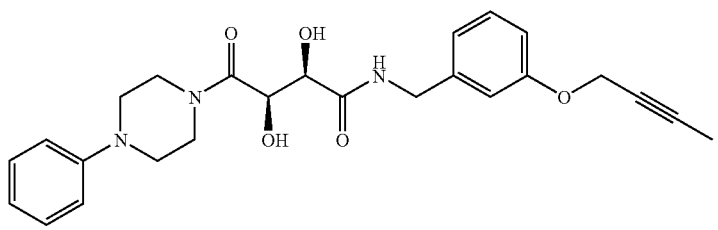
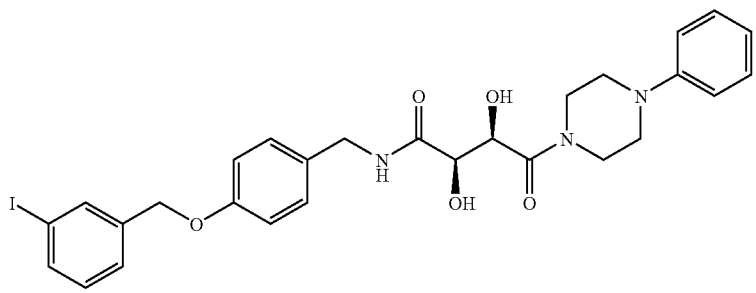
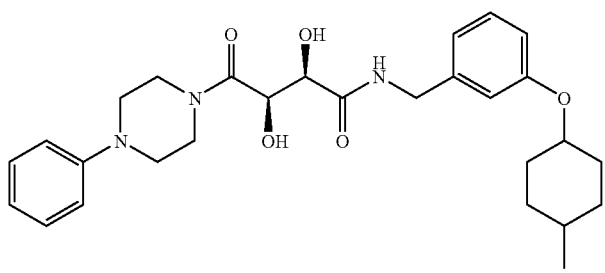

-continued
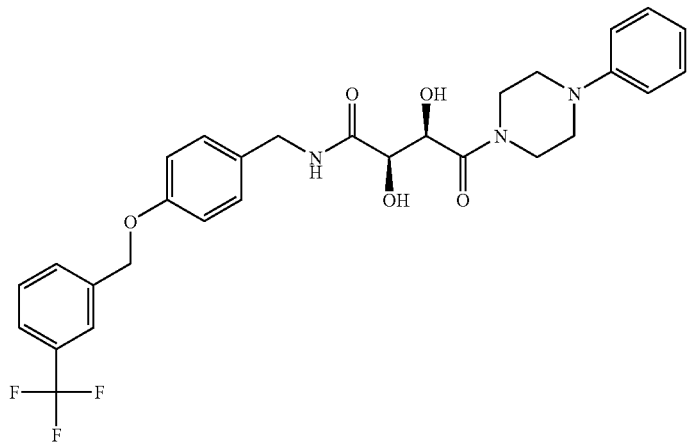
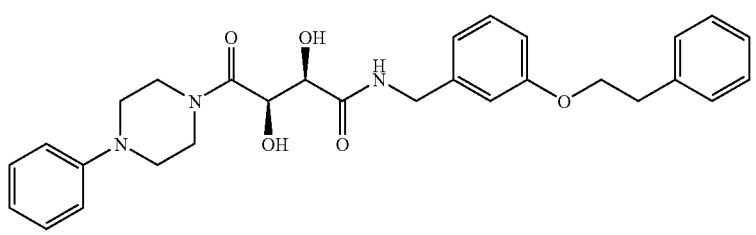
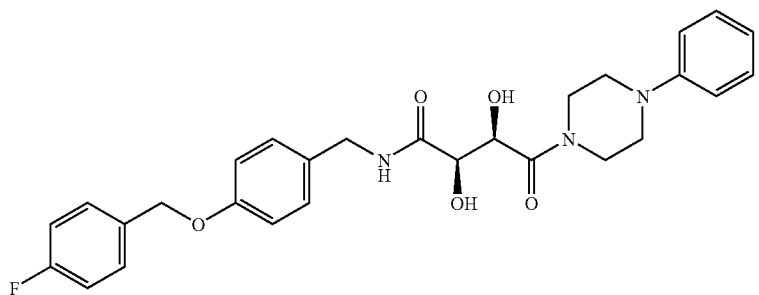
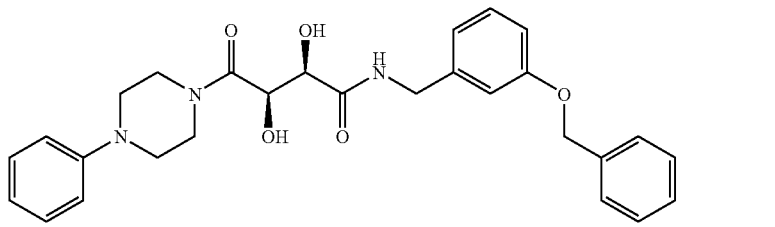
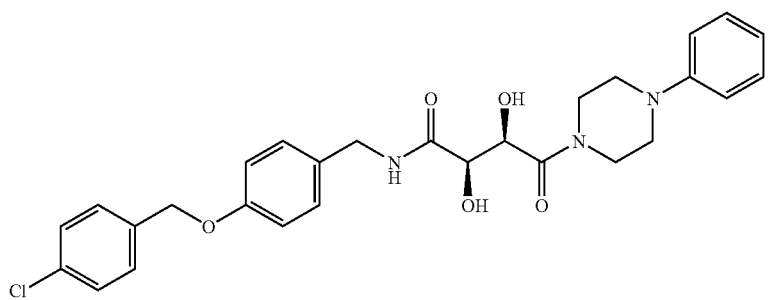

-continued
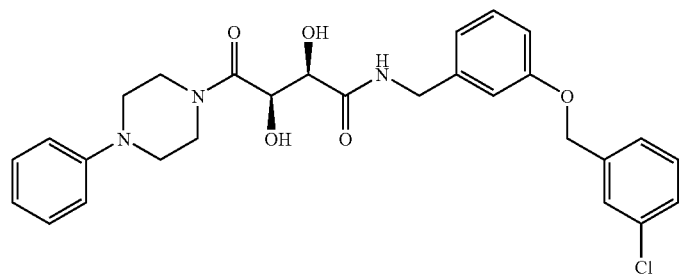
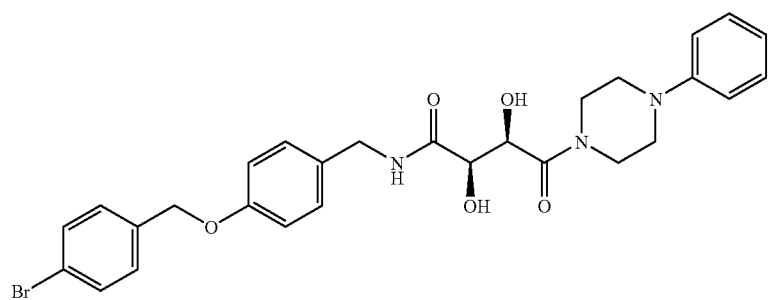
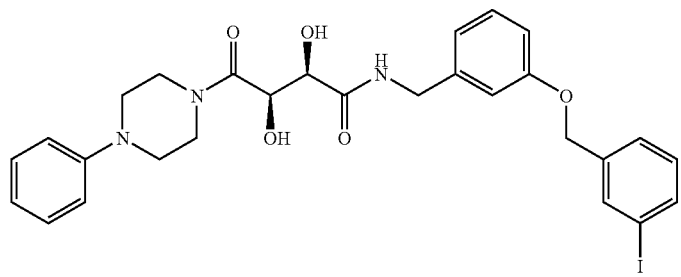
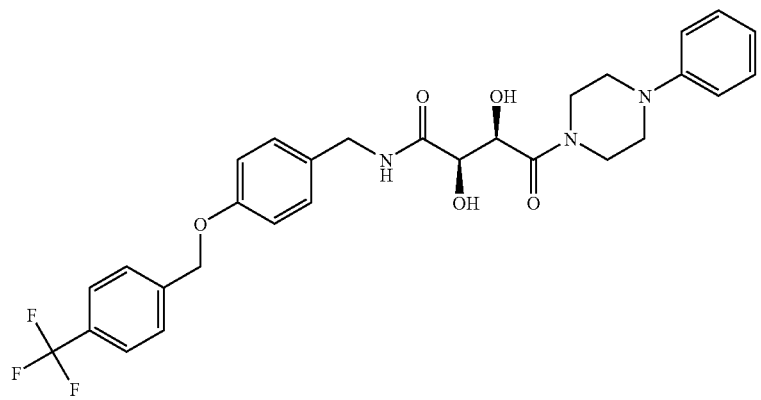
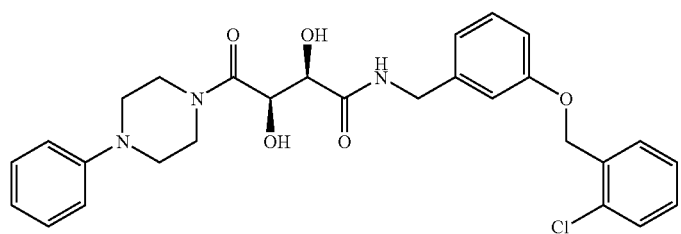

-continued
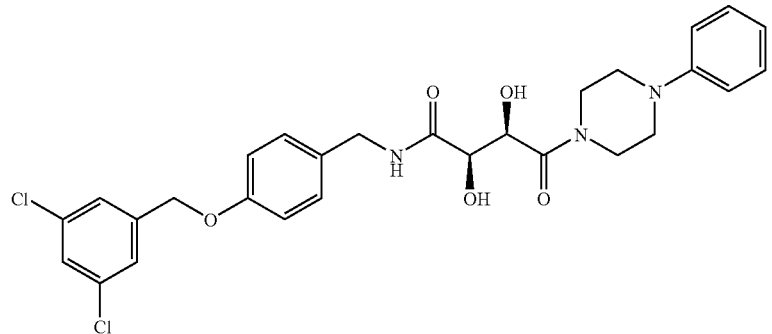
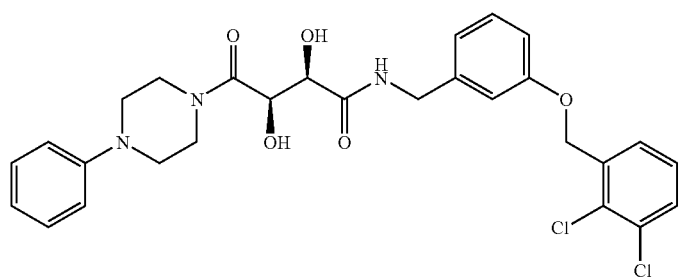
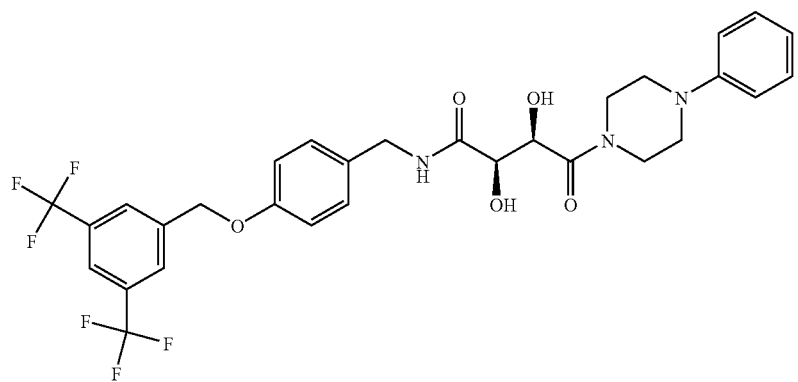
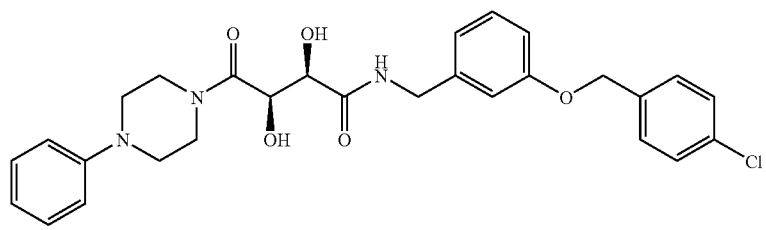
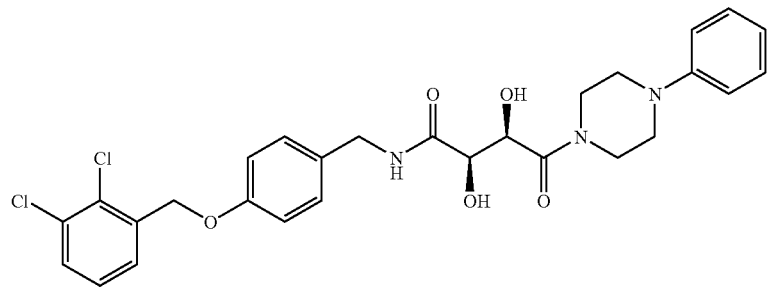

-continued
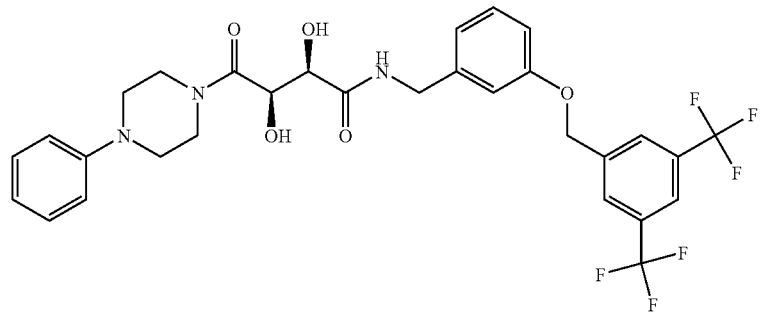
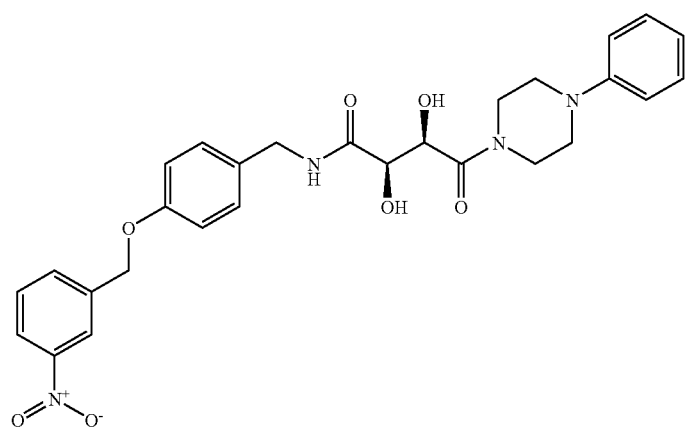
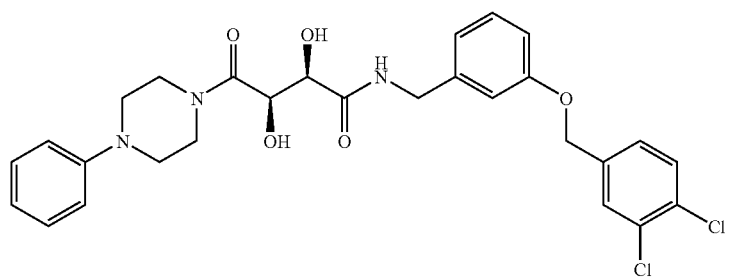
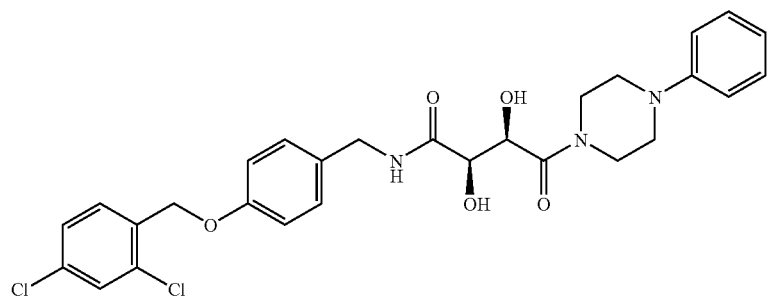
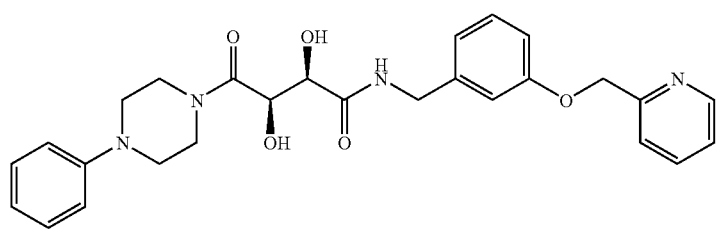

-continued
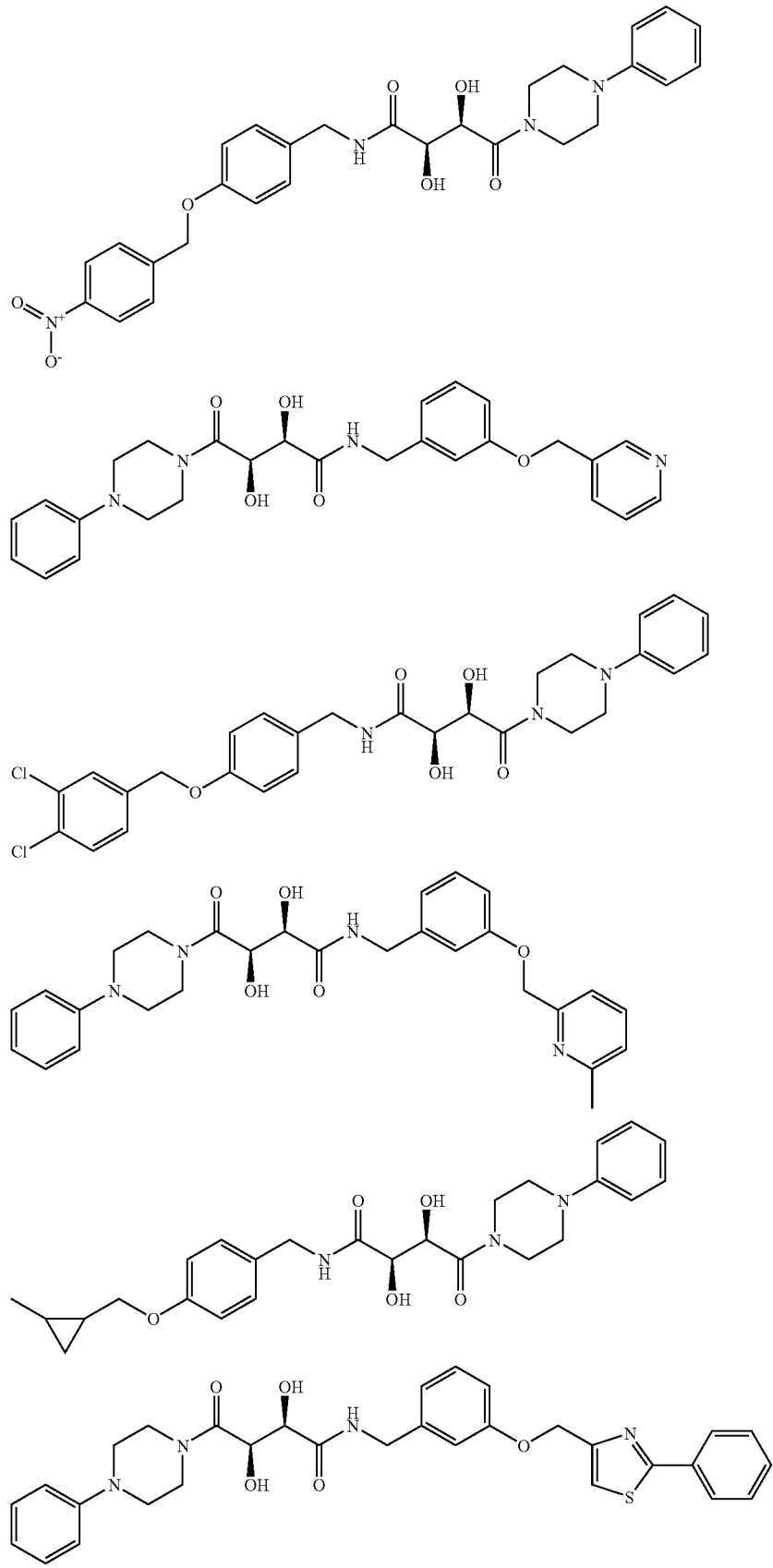

-continued
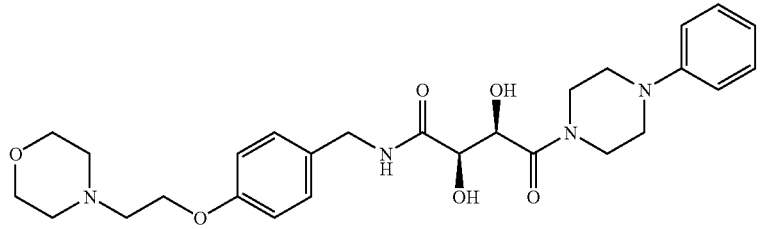
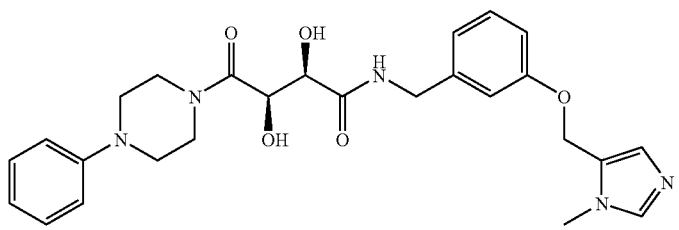
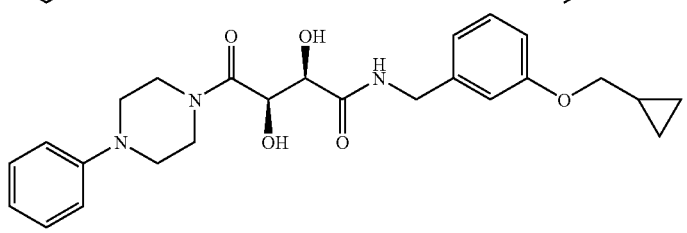
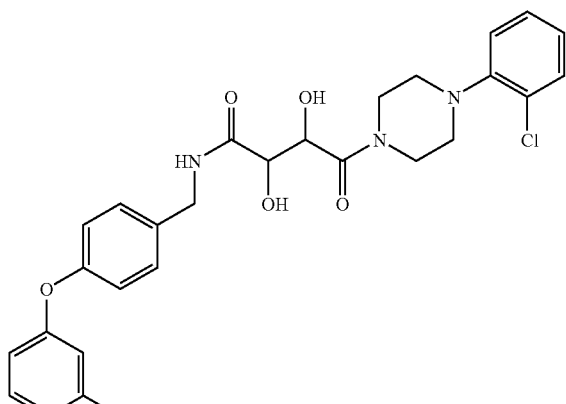
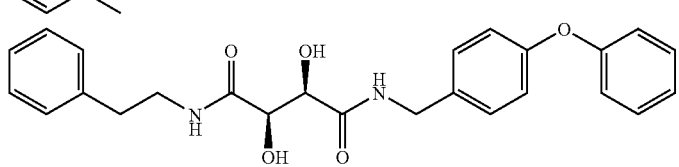
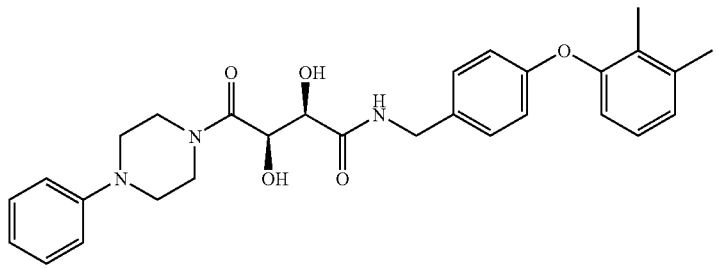

-continued
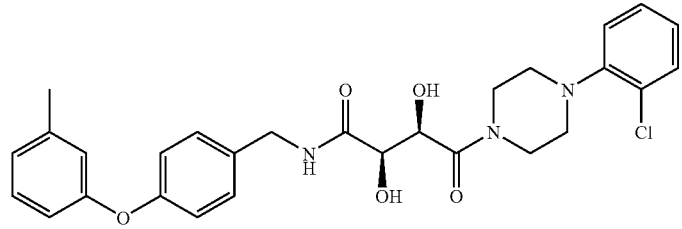
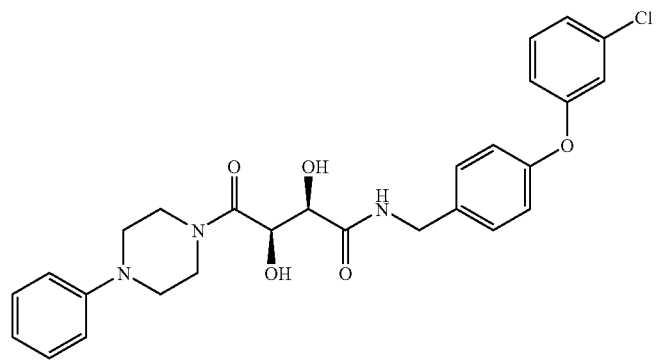
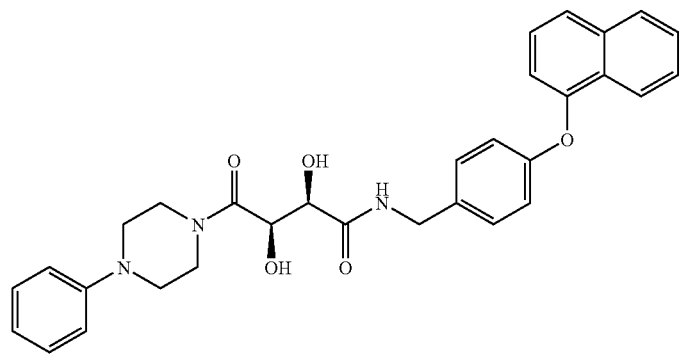
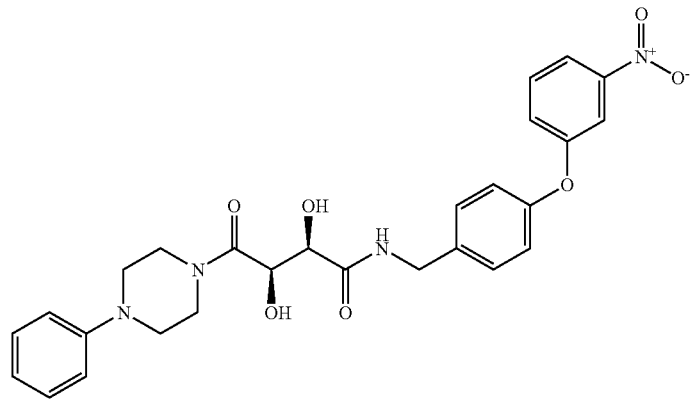
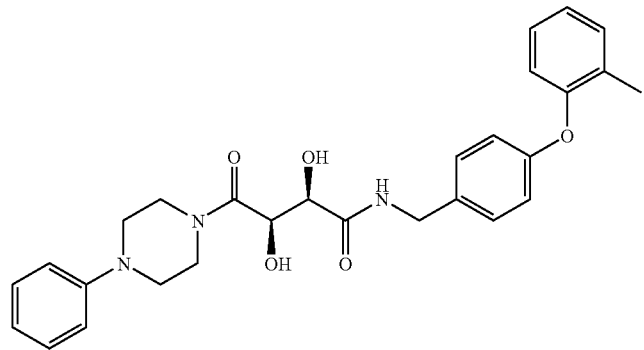

-continued
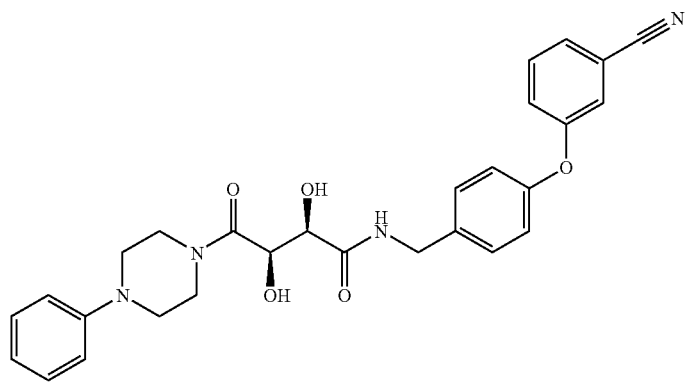
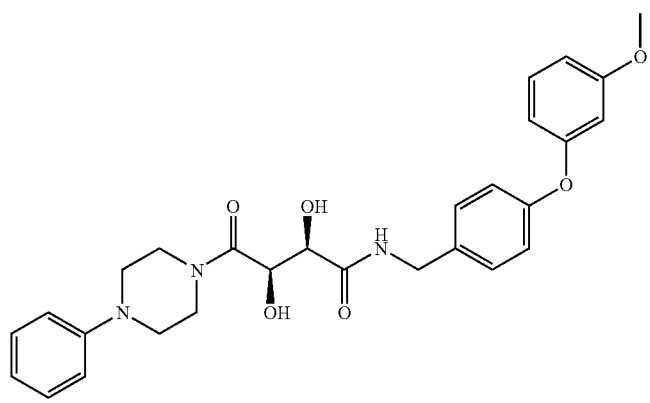
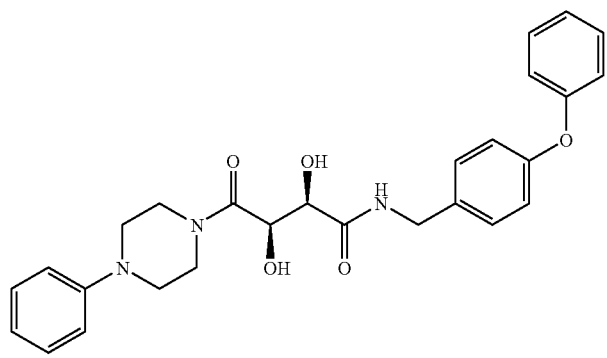
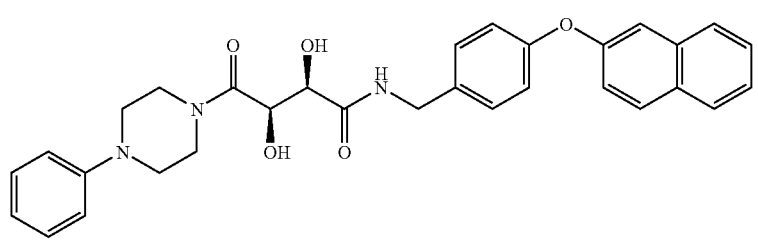

-continued
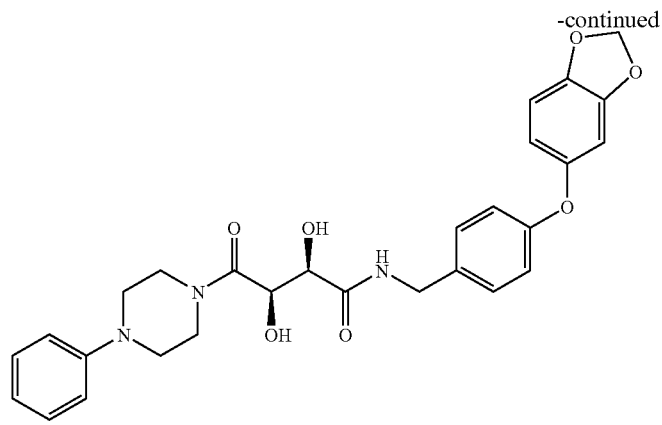
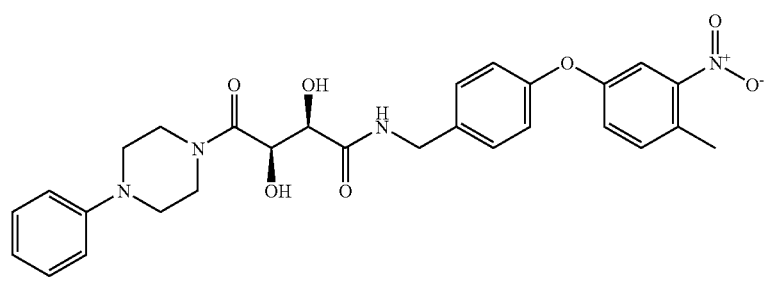
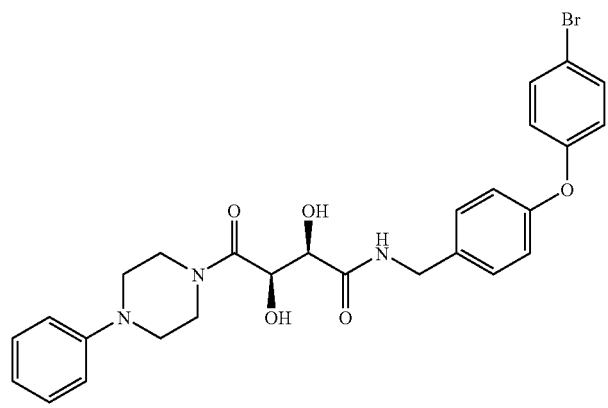
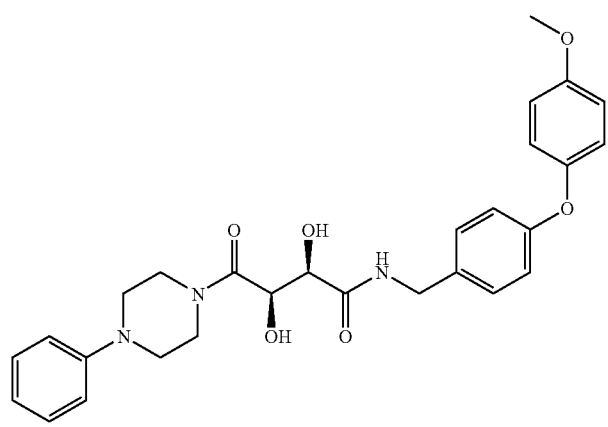

-continued
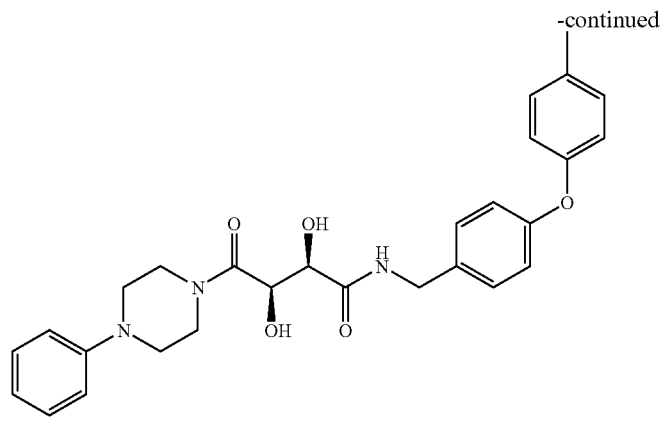
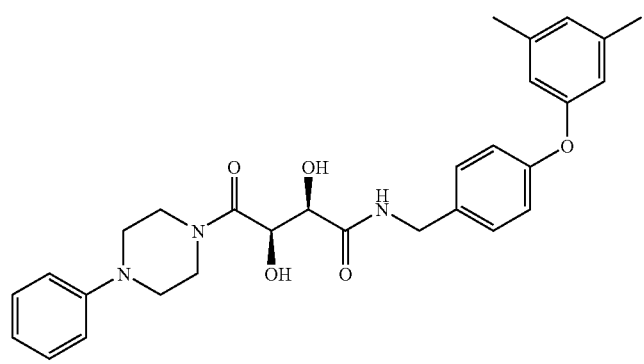
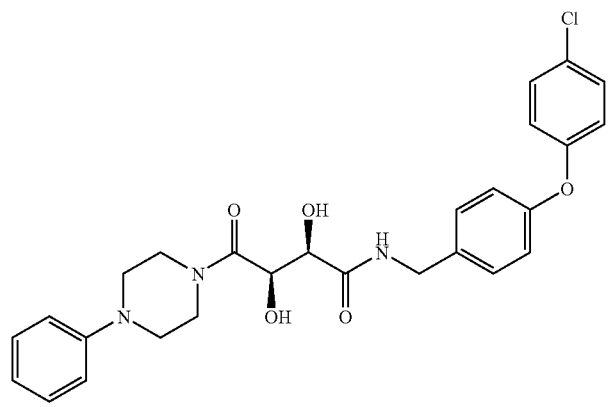
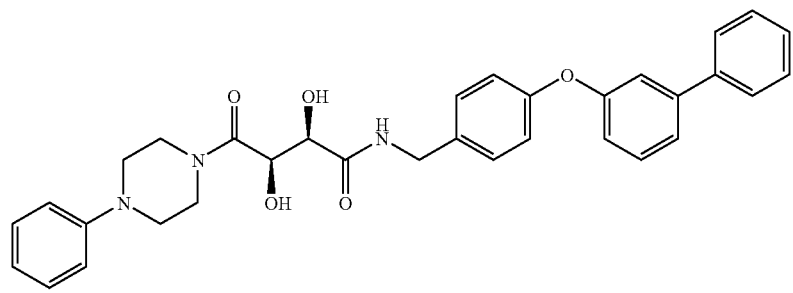

-continued
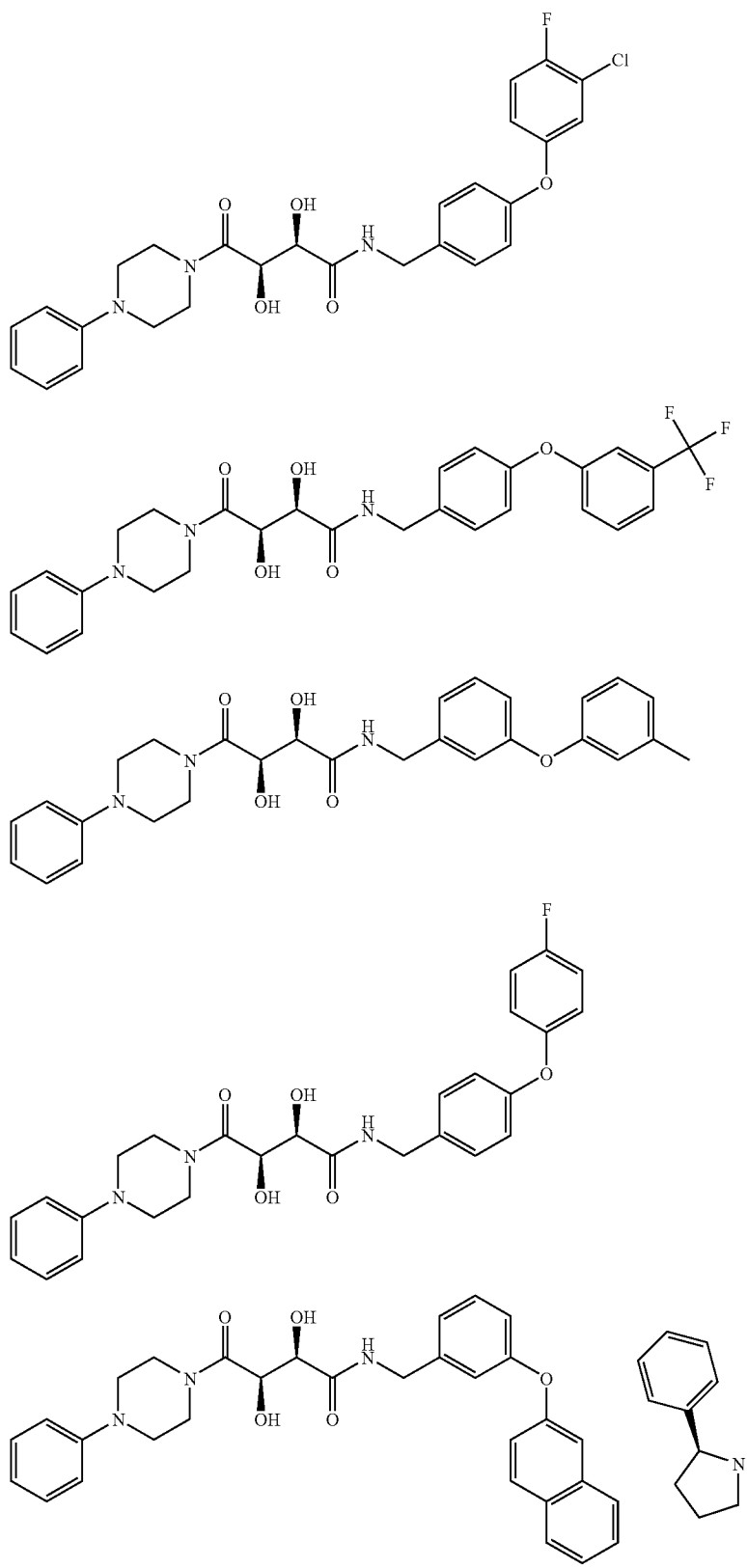

-continued
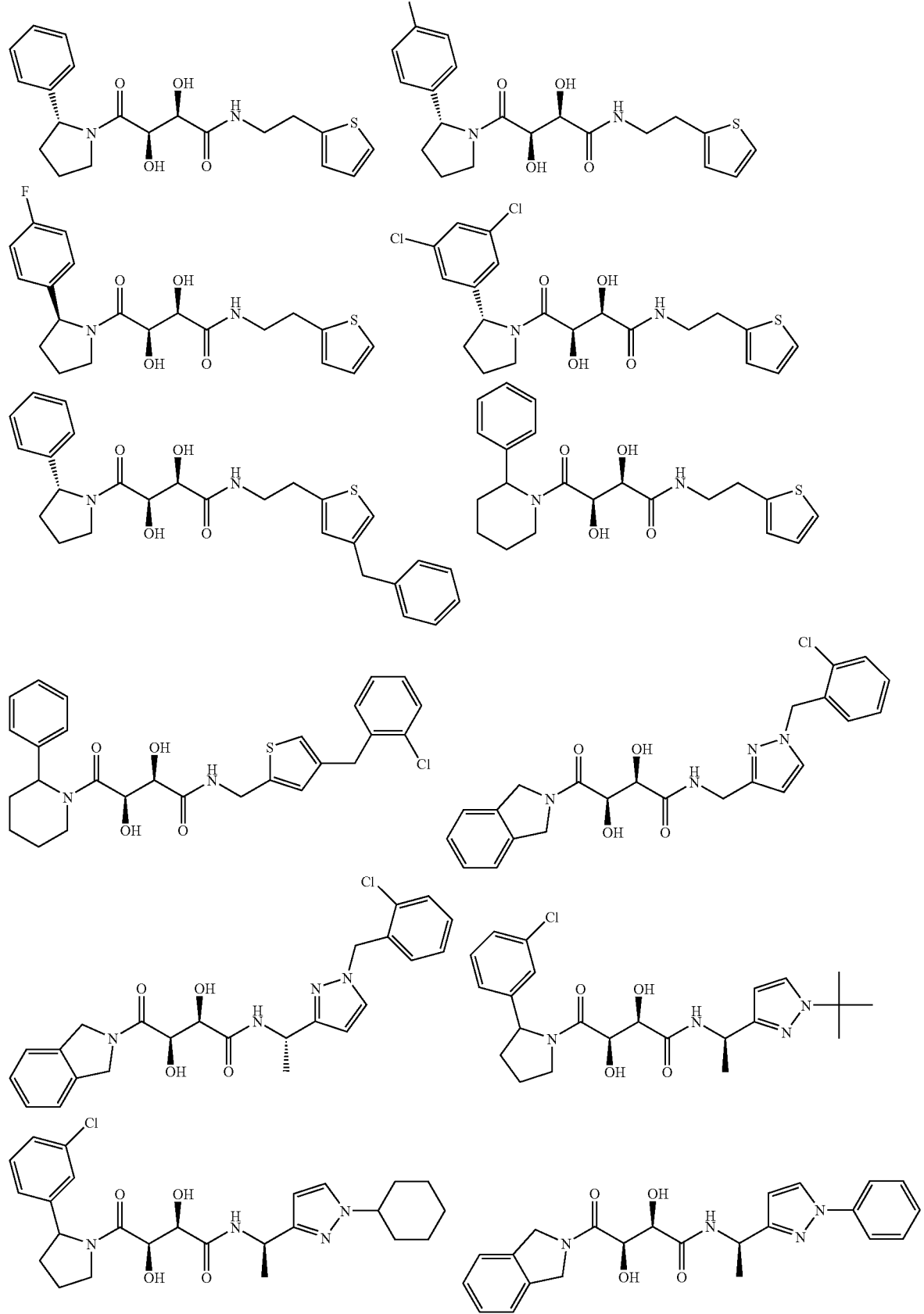

-continued
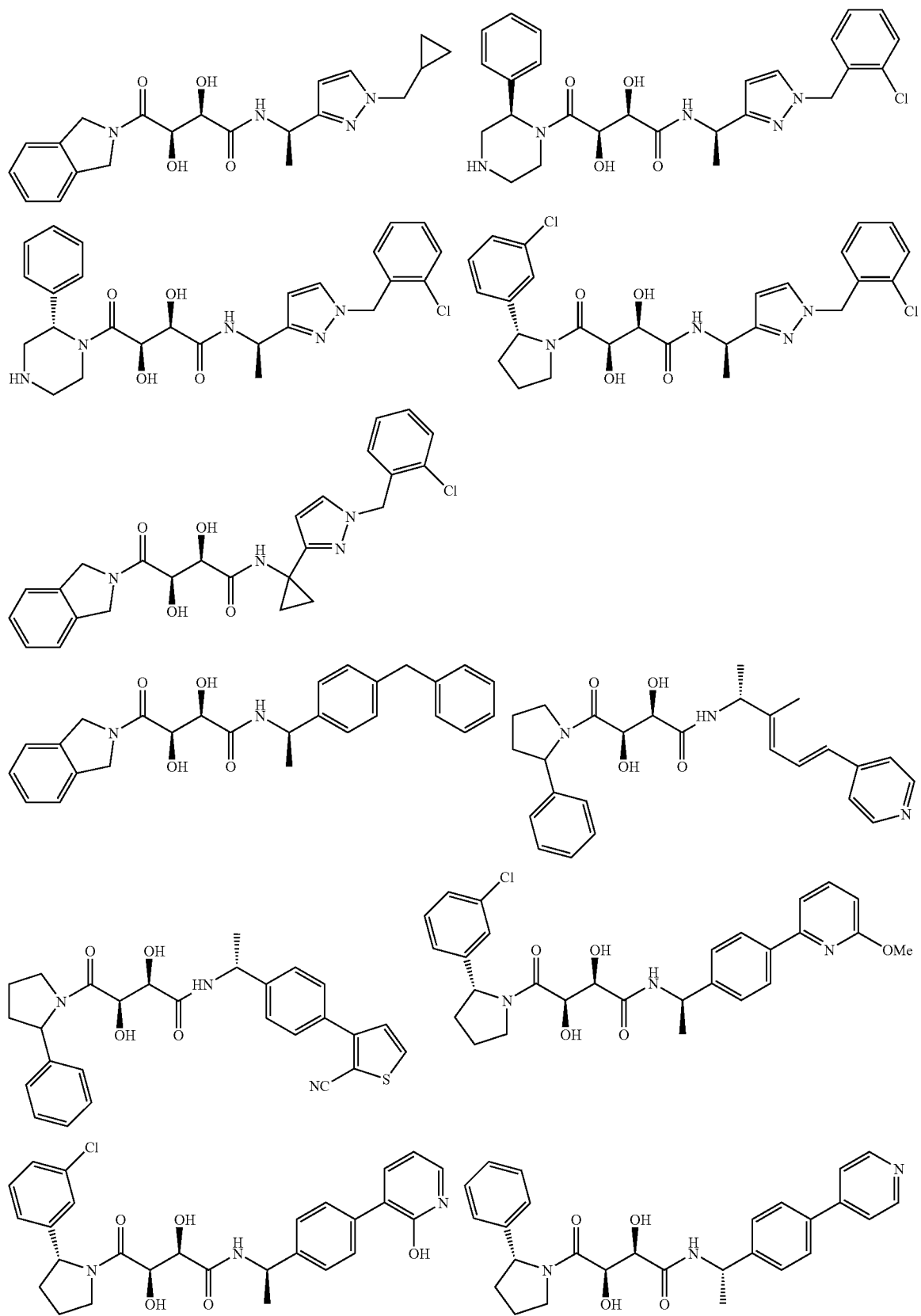

193 194
-continued
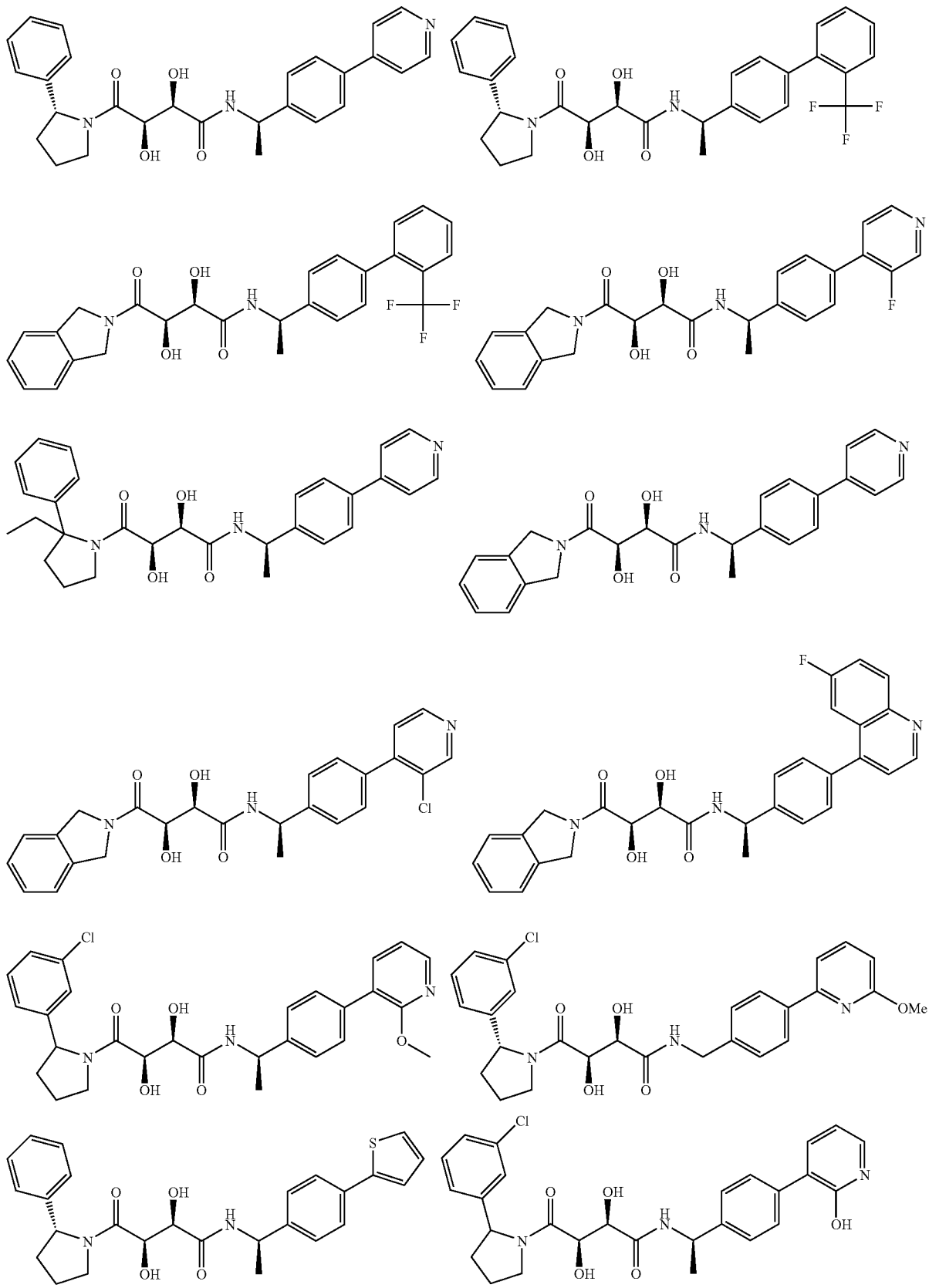

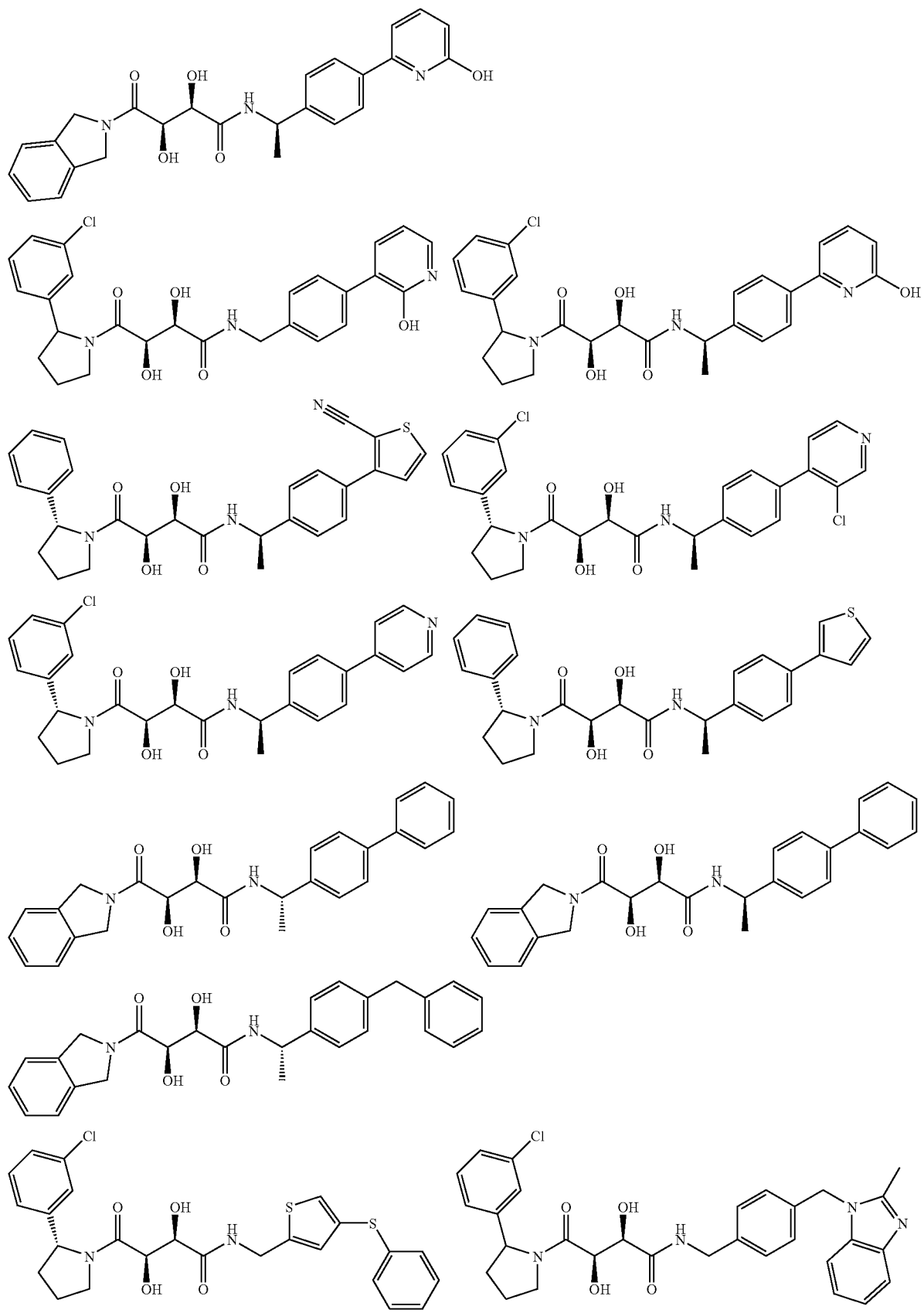

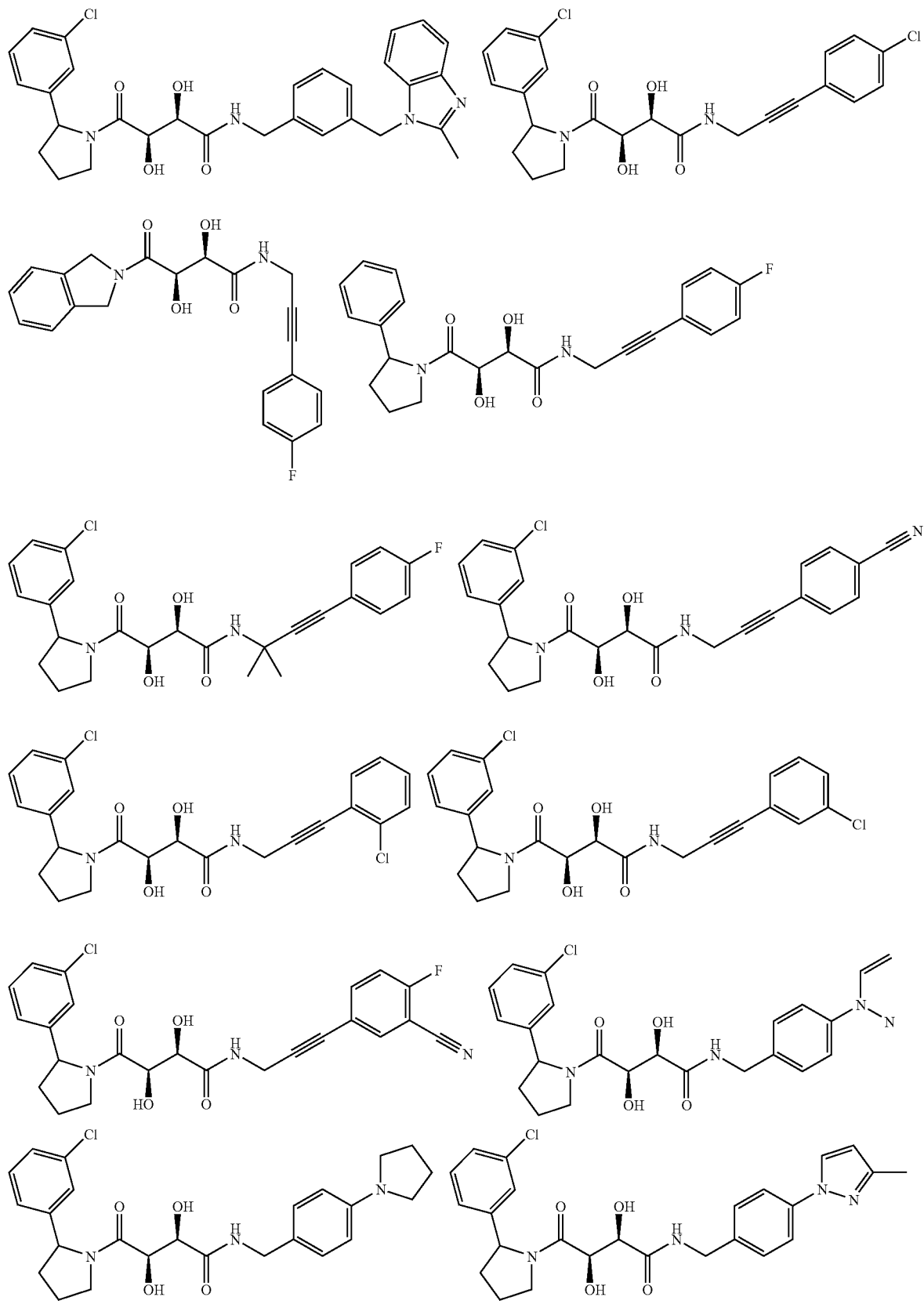

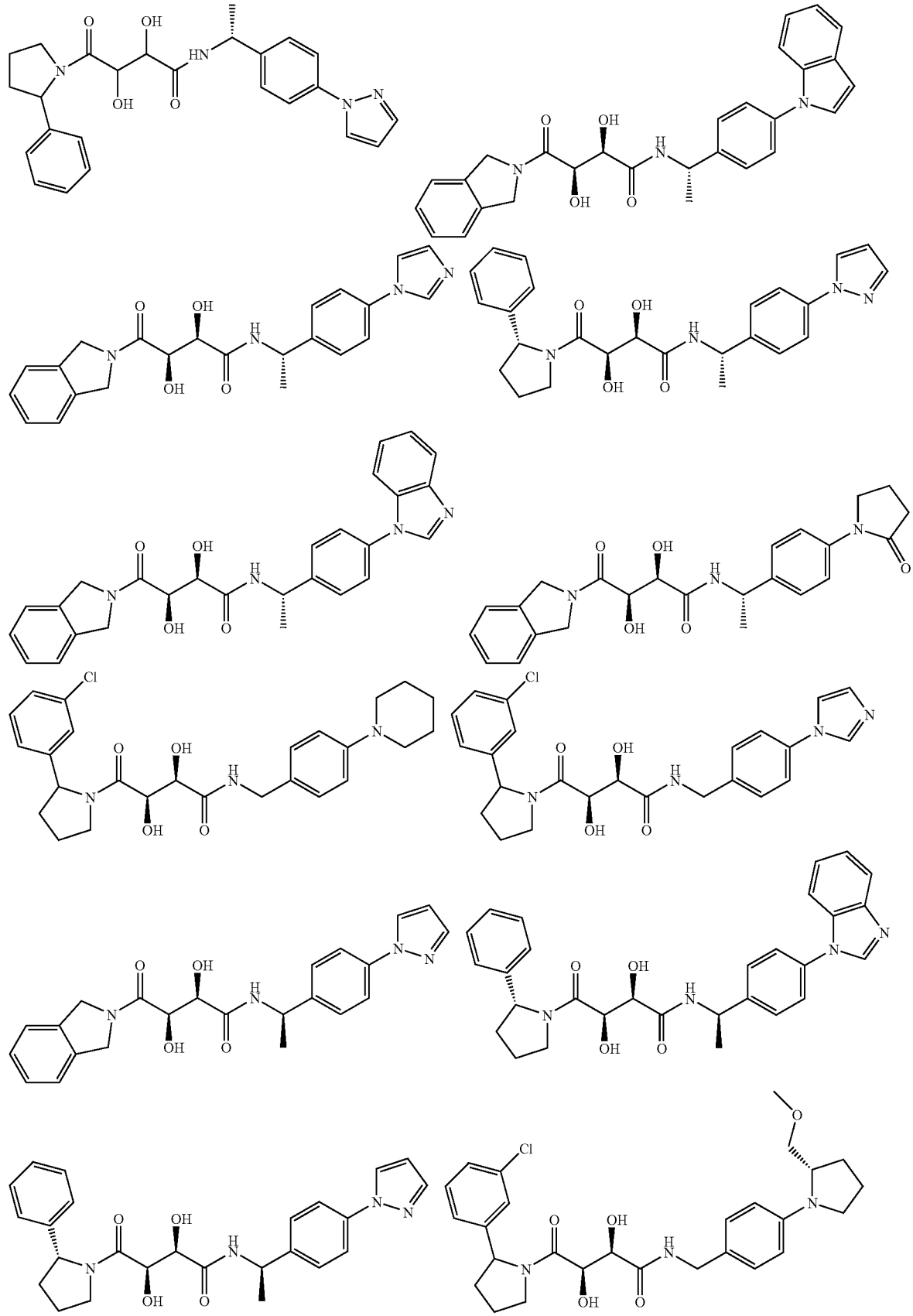

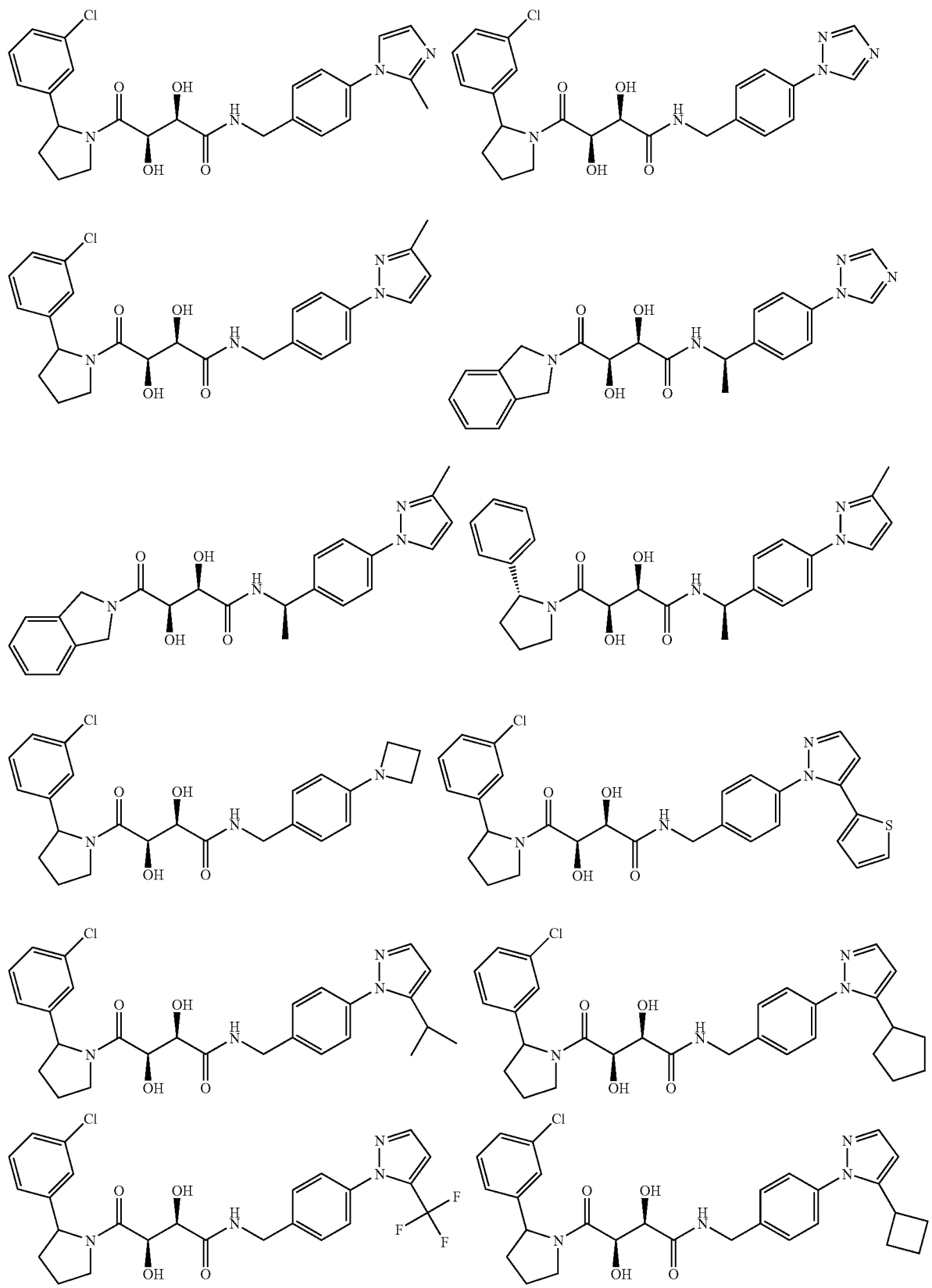

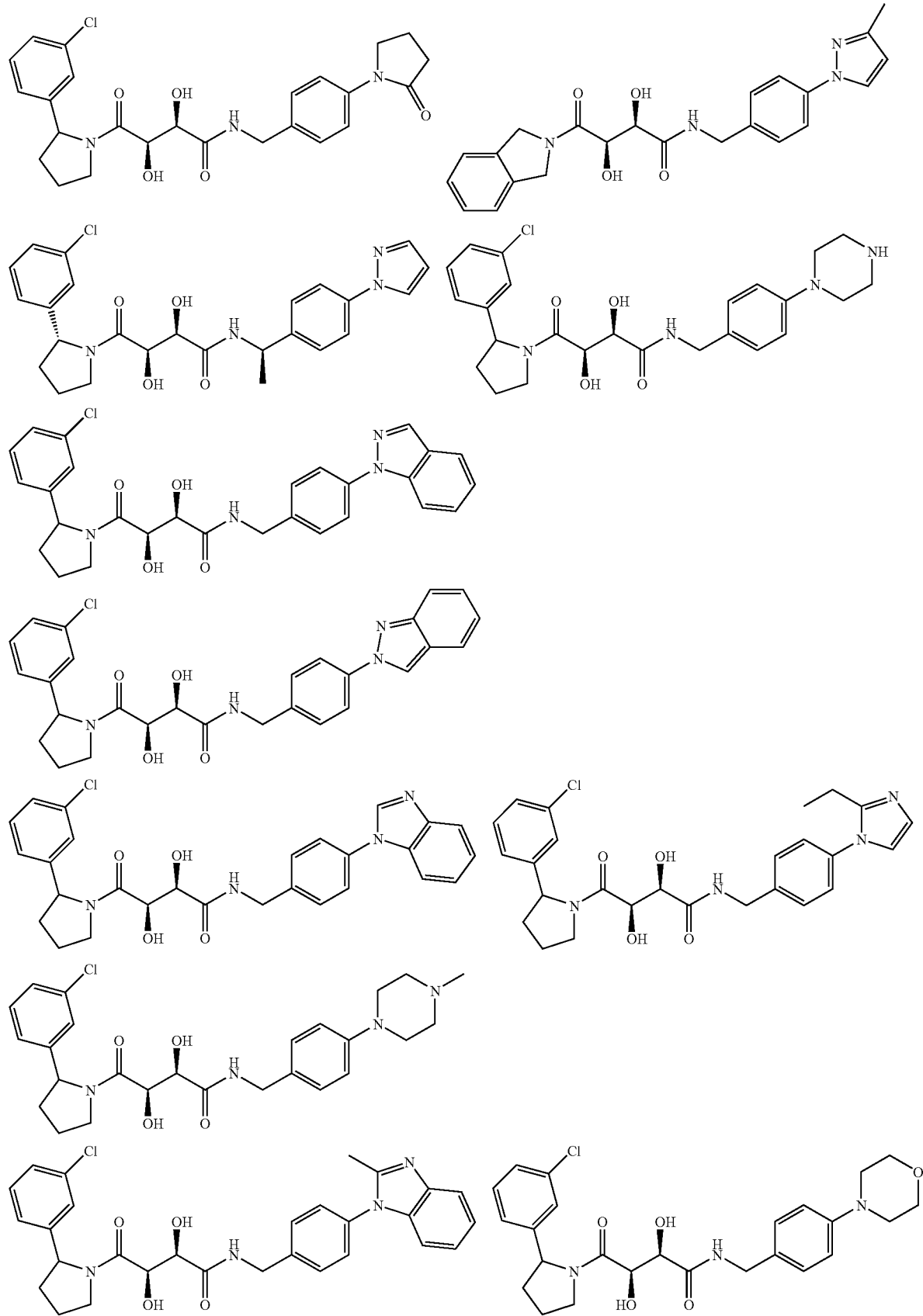

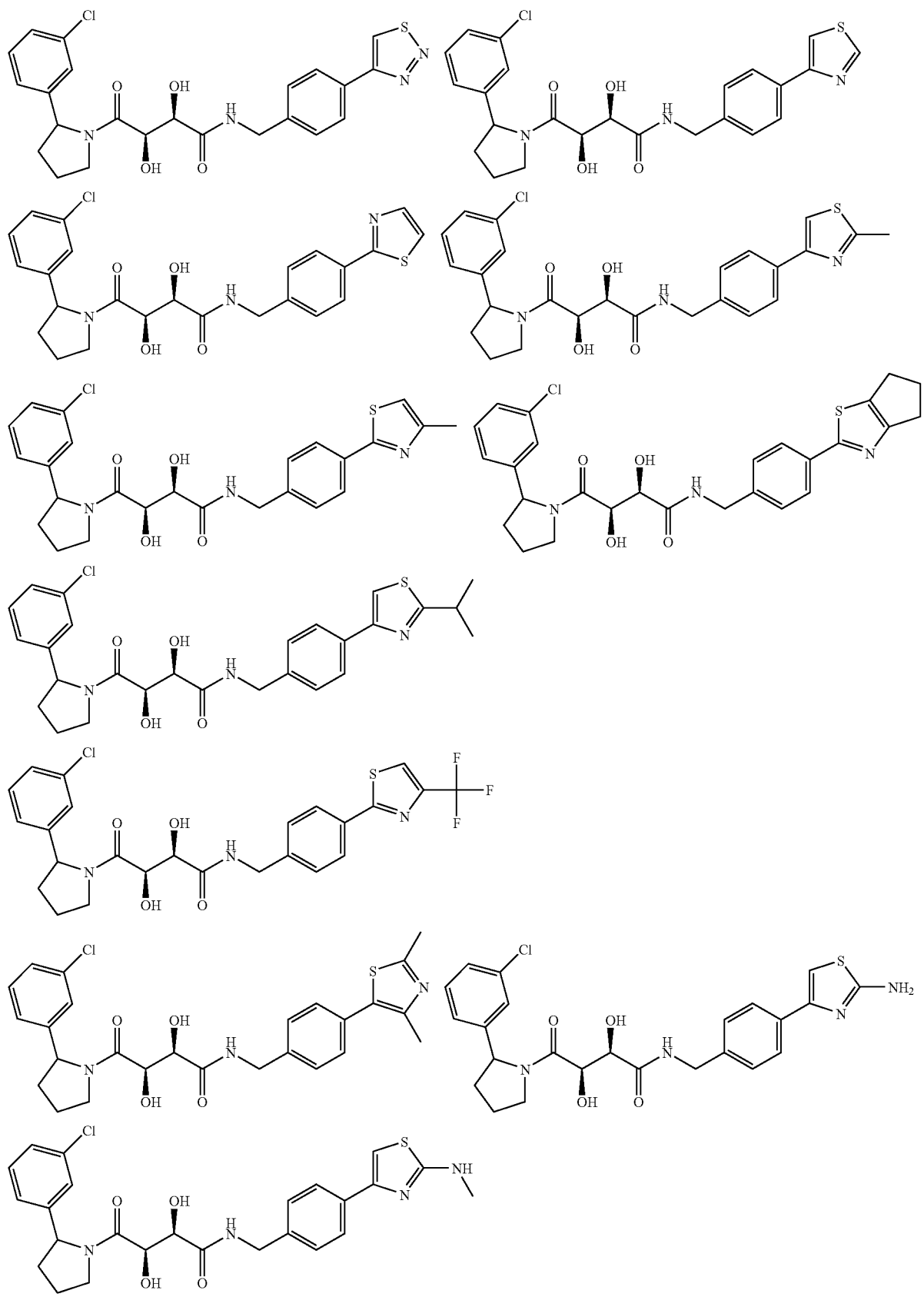

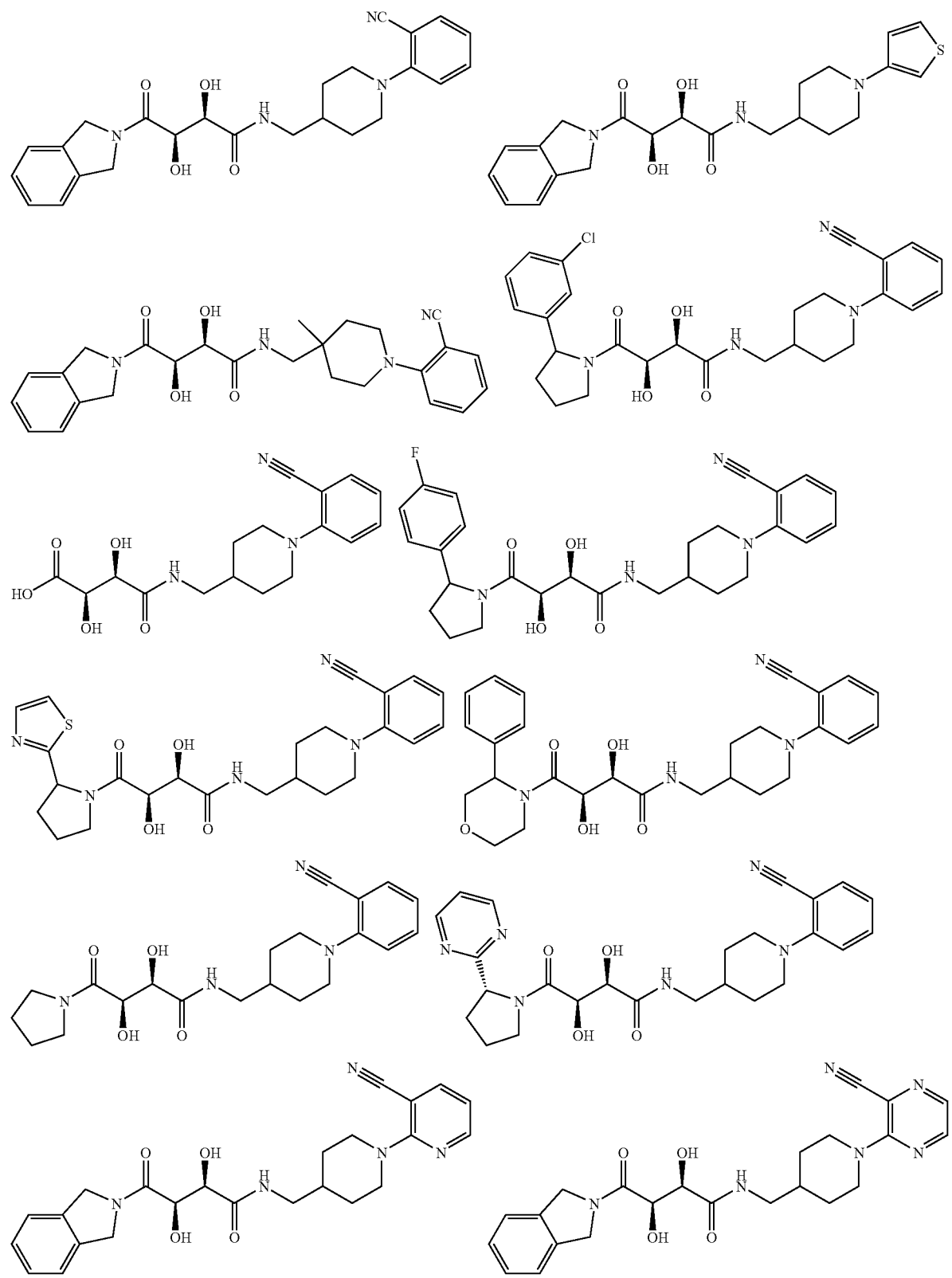
-continued

-continued
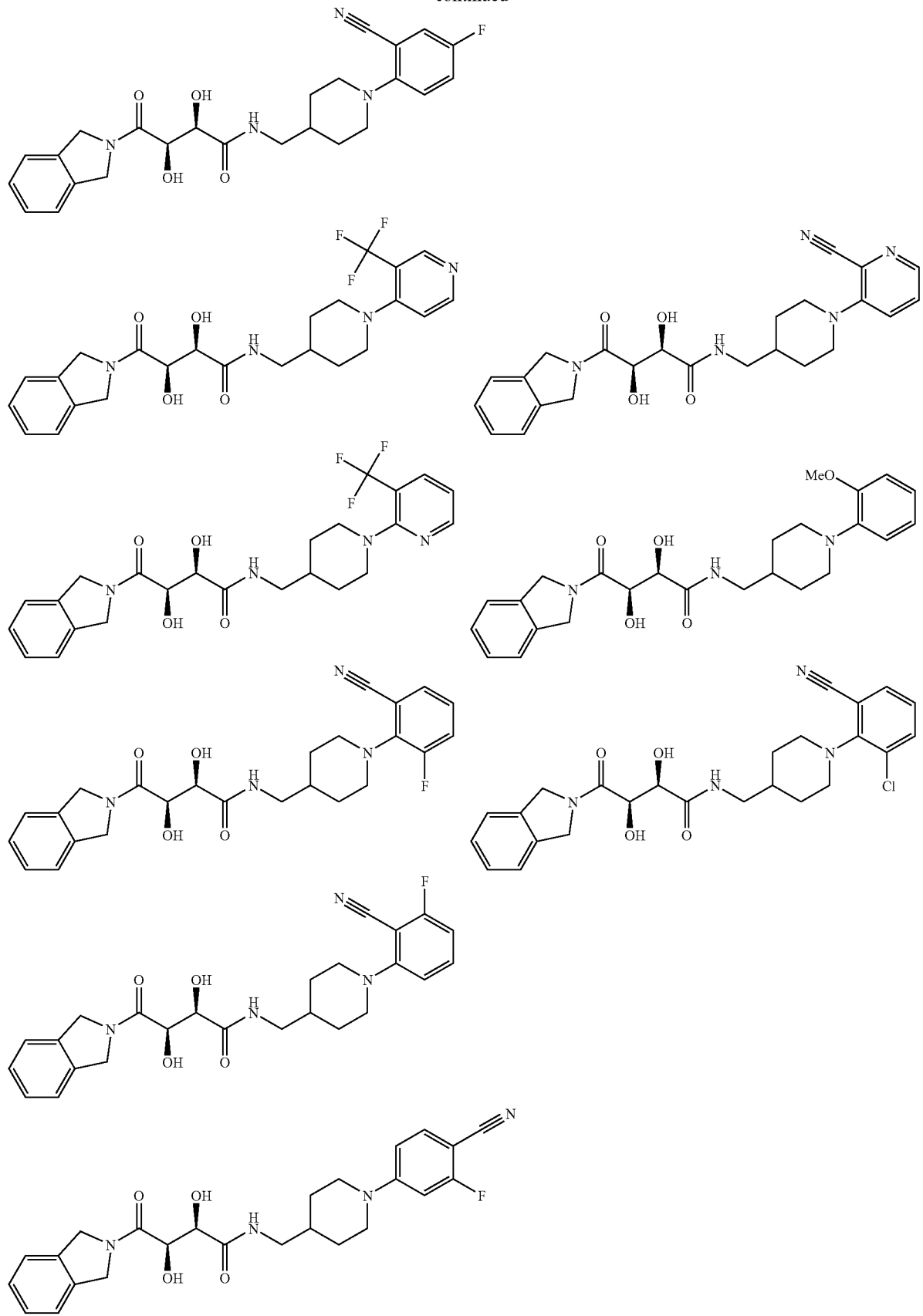

-continued
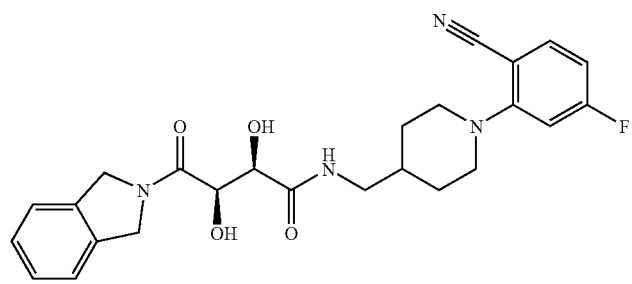
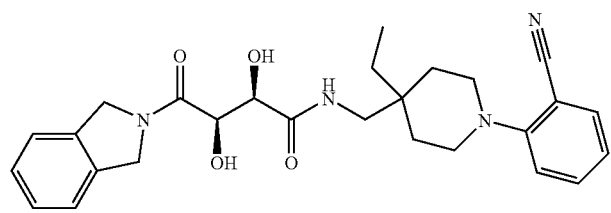
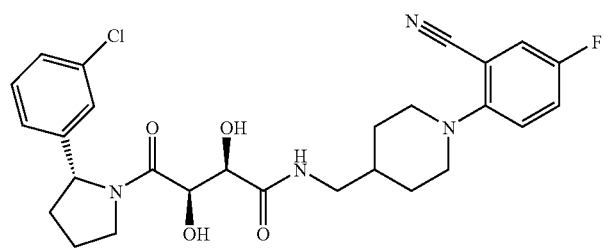
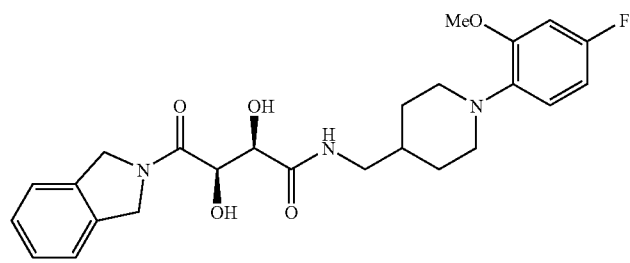
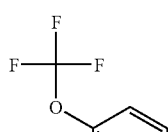
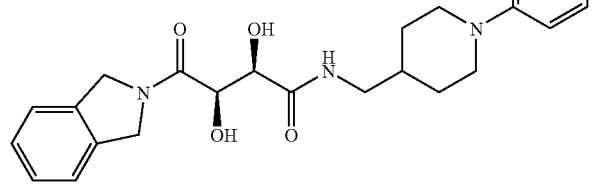
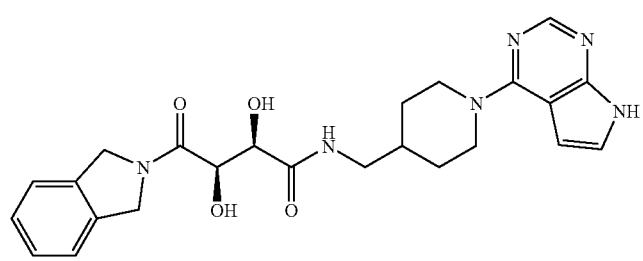

213                                214
-continued
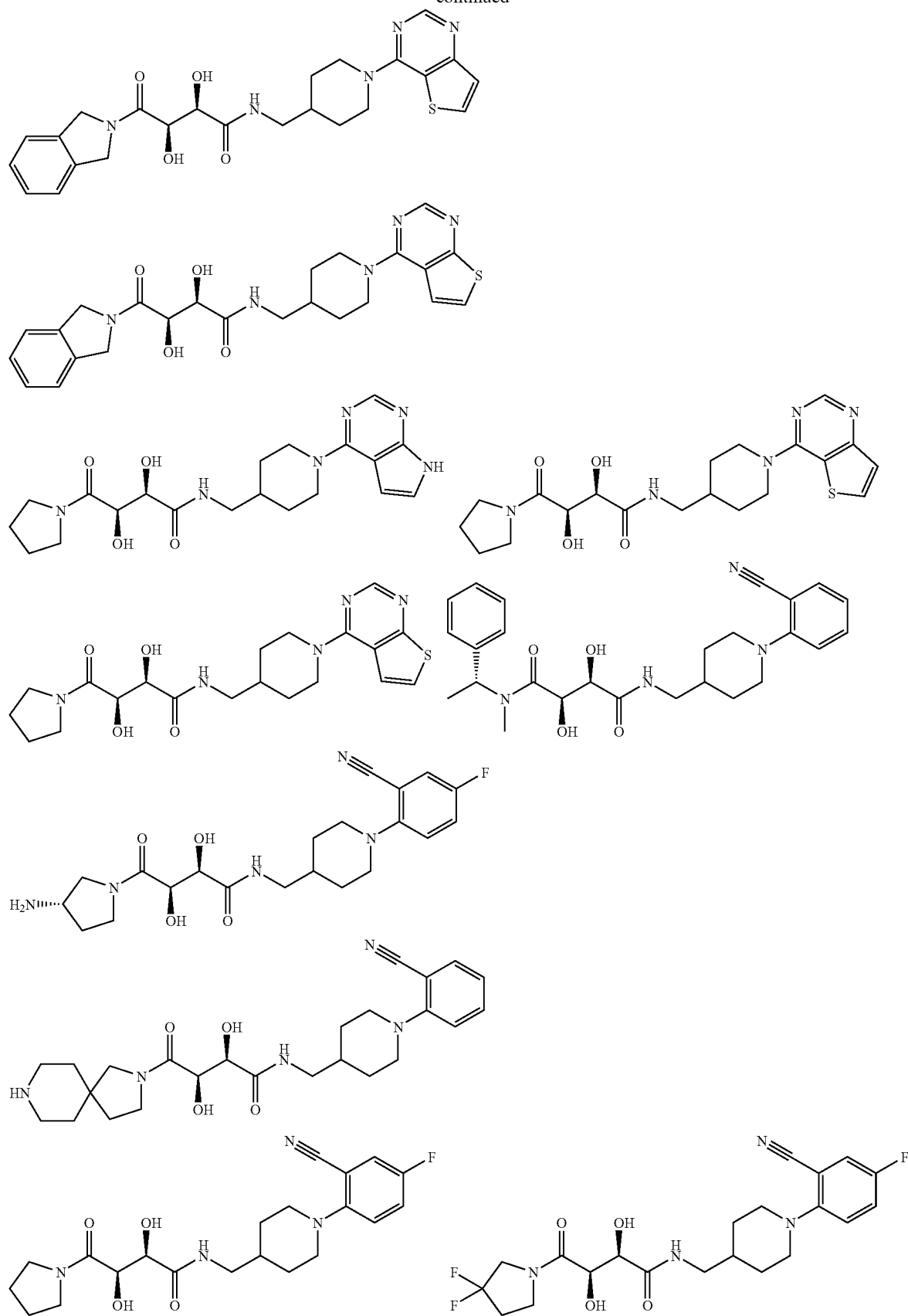

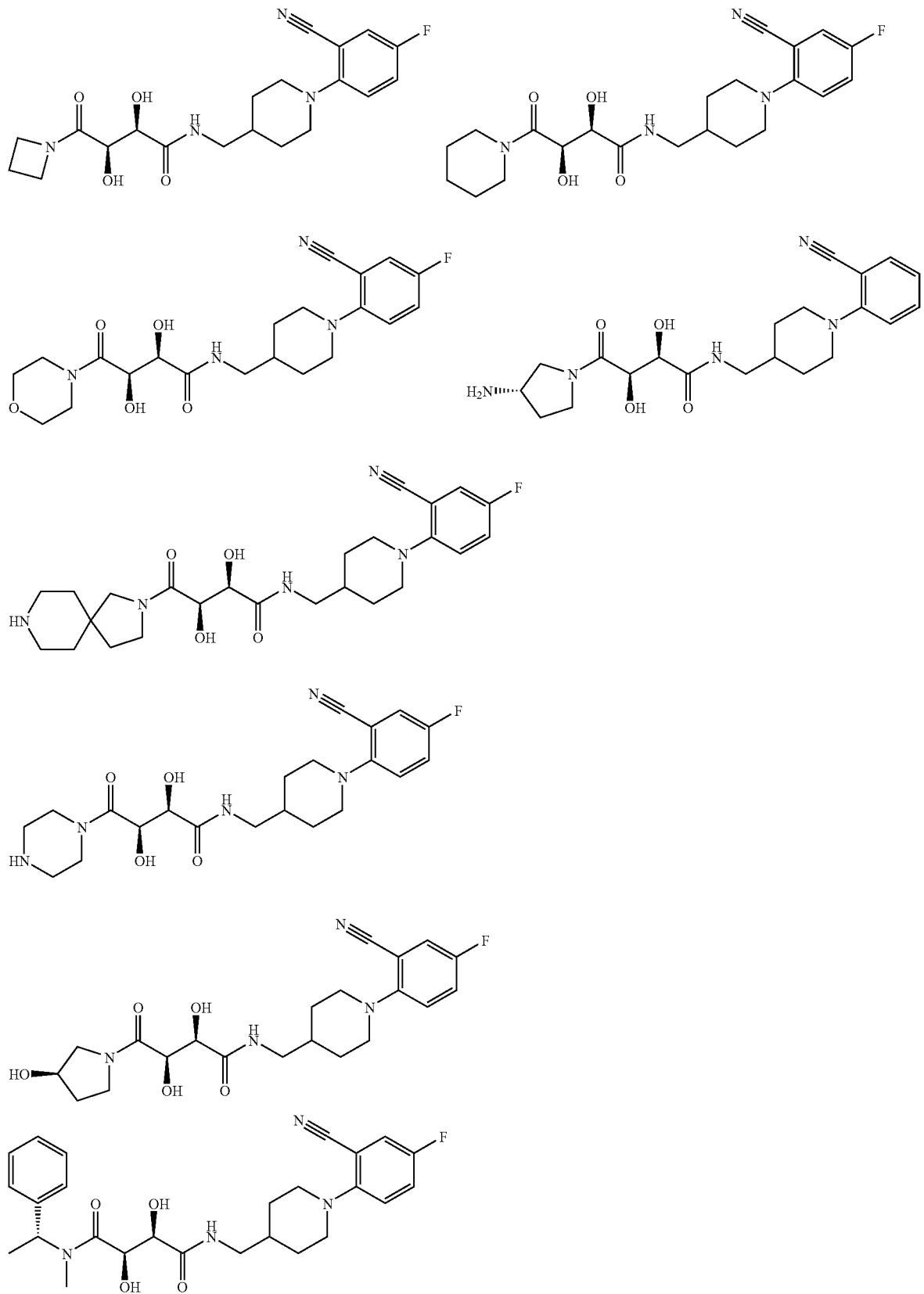

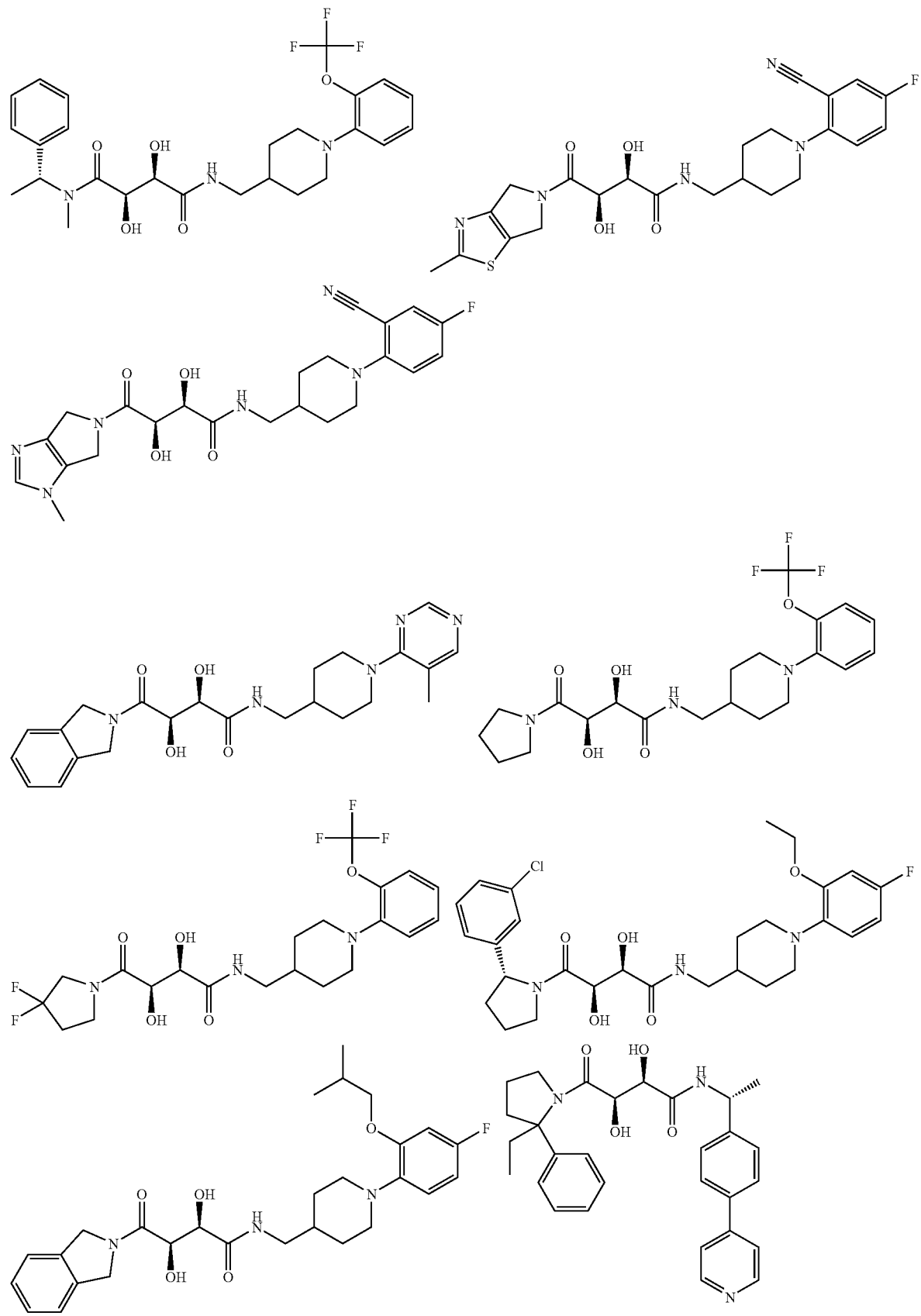

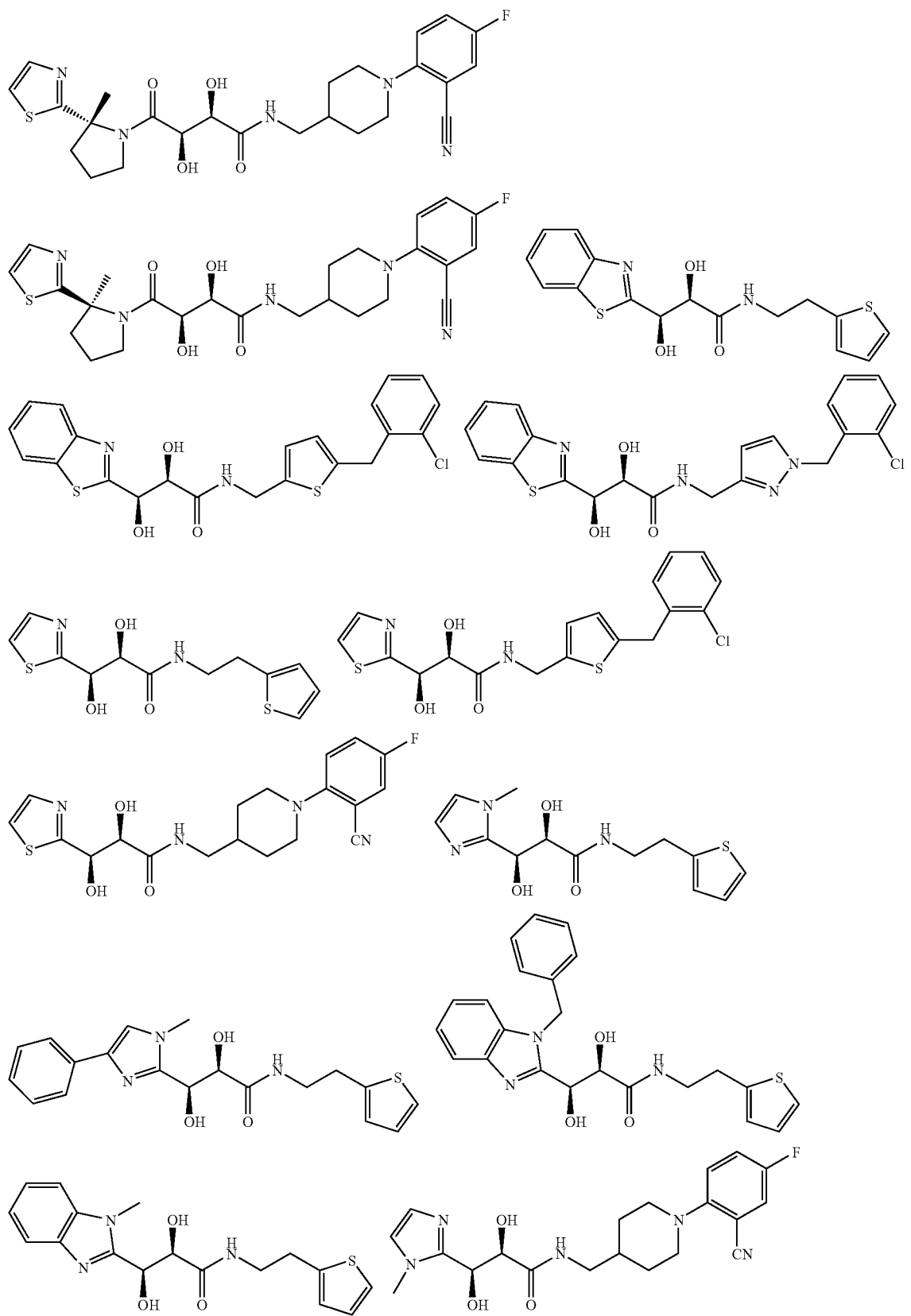

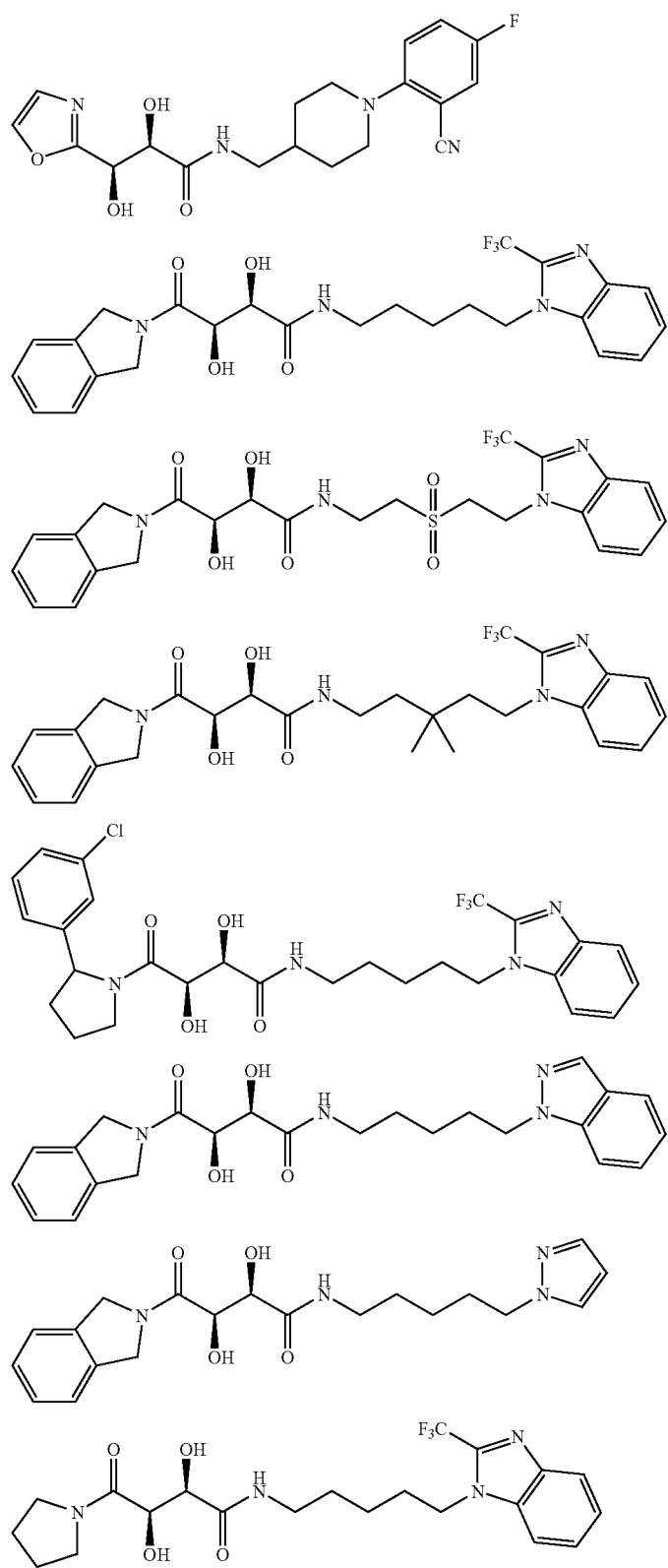

223 224
-continued
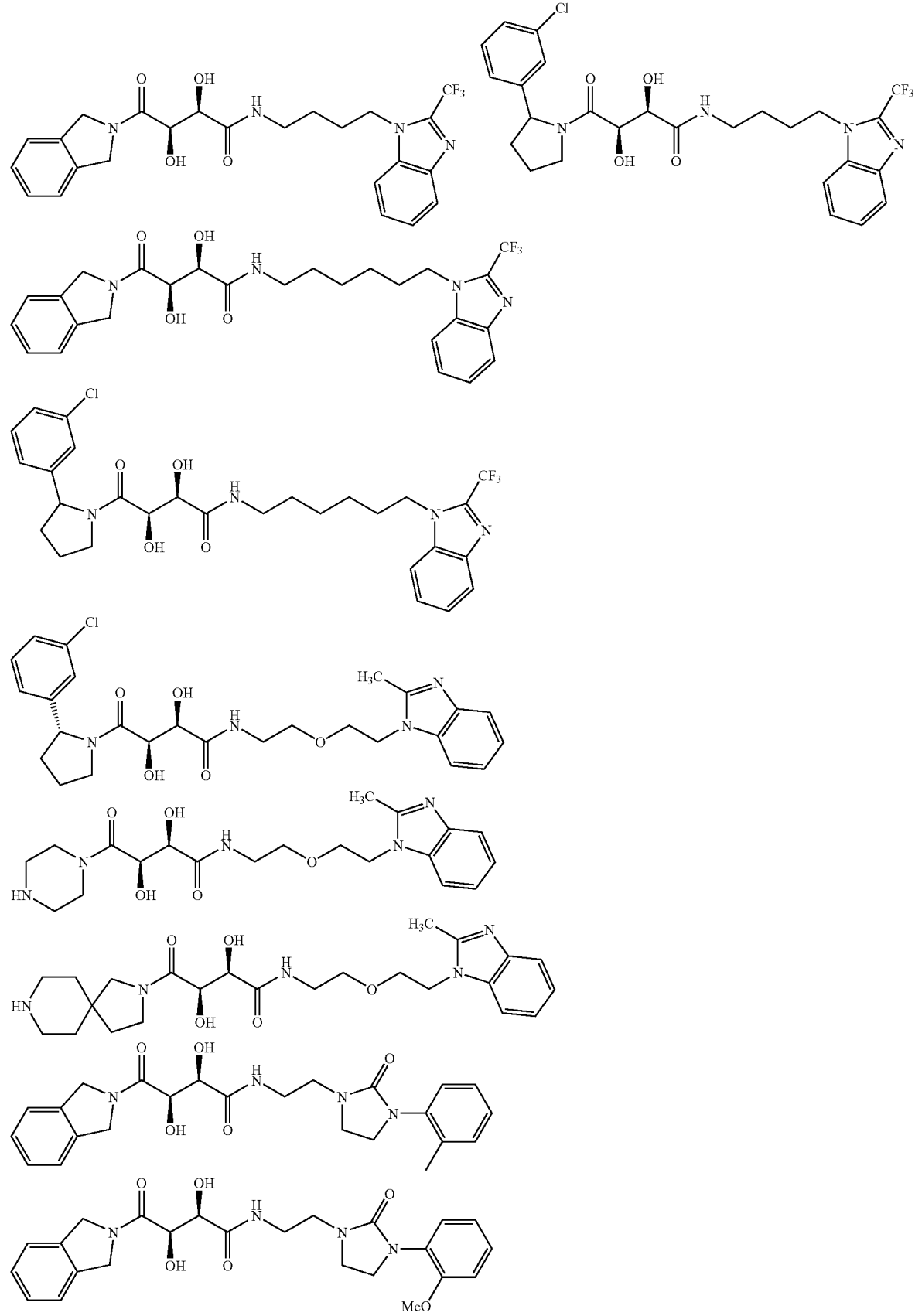

-continued
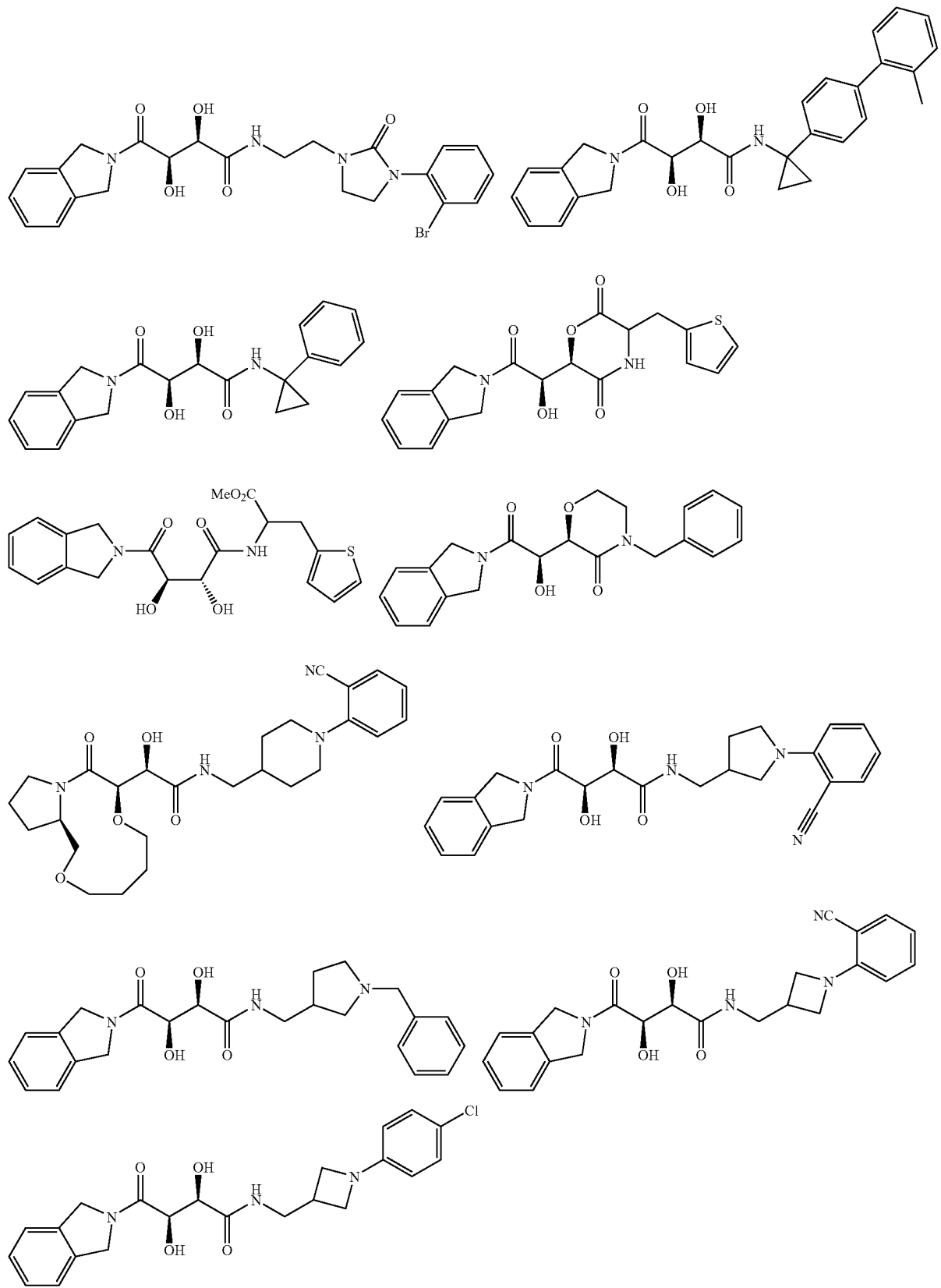

-continued
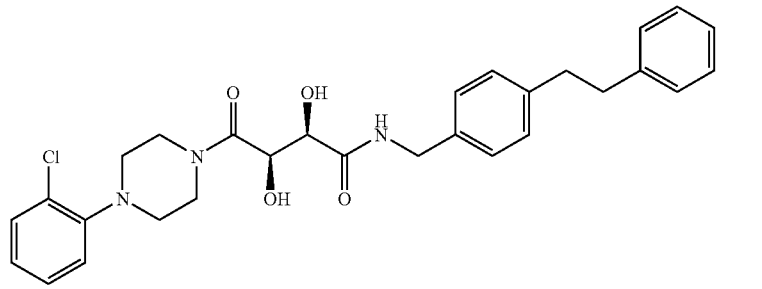
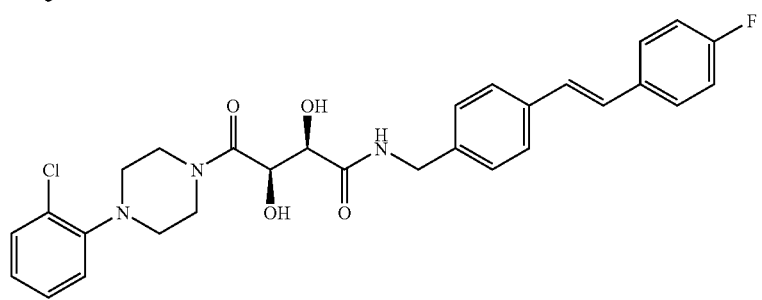
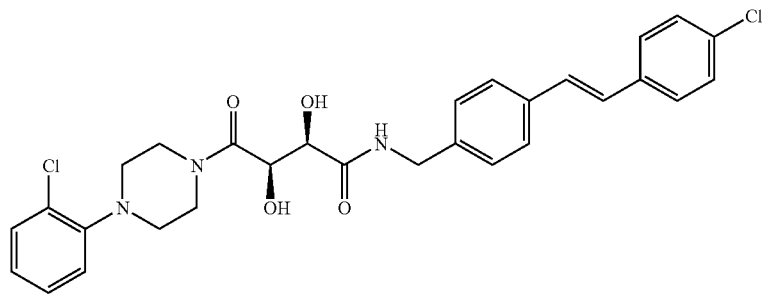
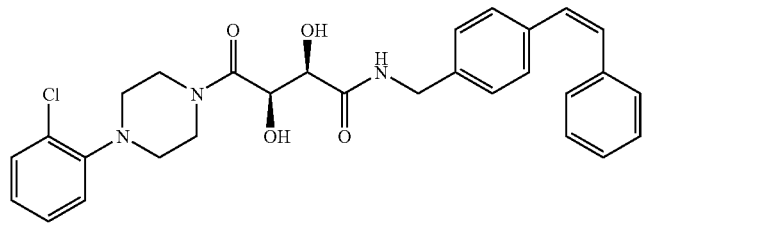
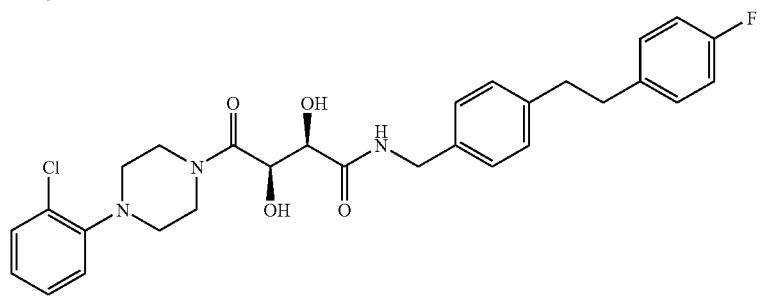
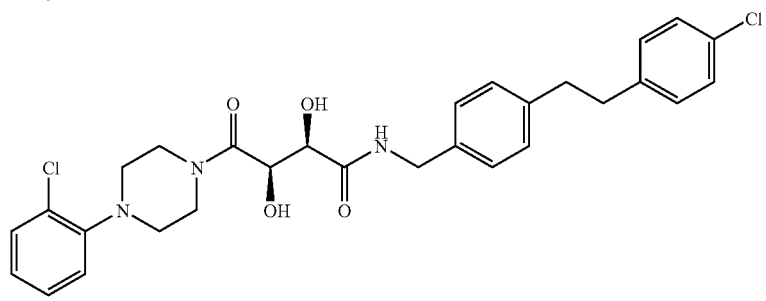

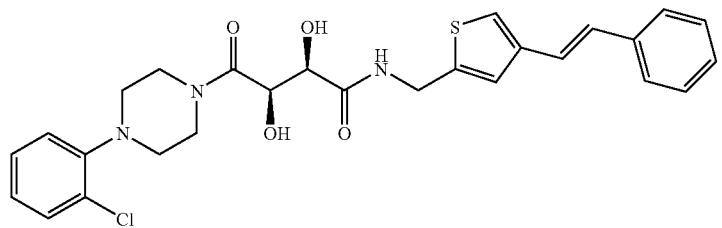
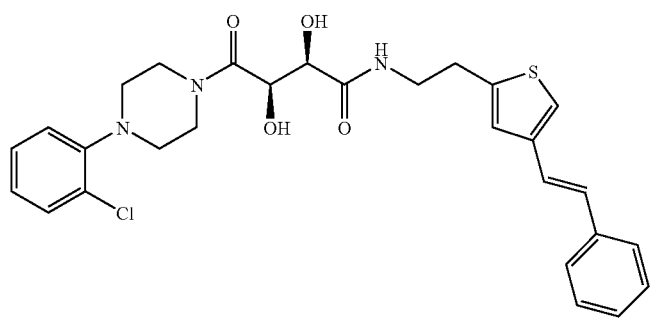
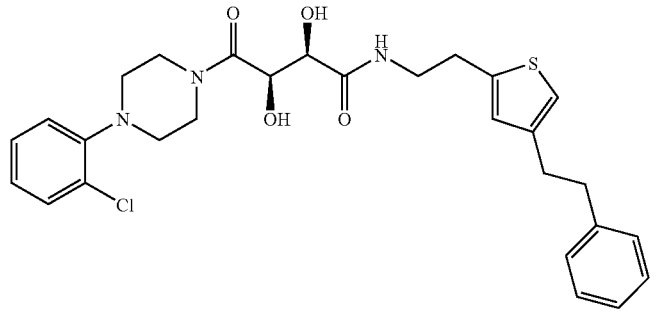
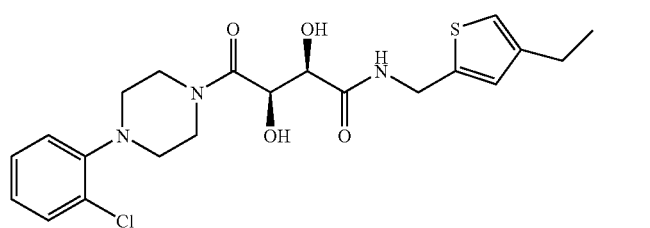
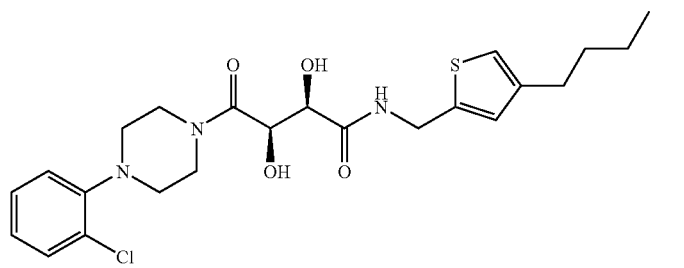
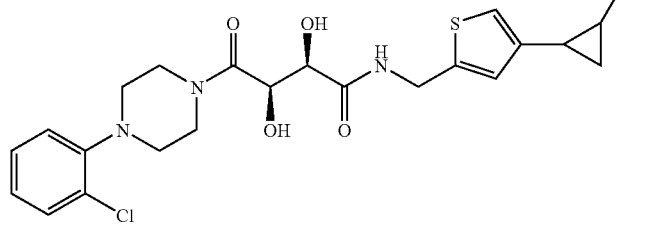

-continued
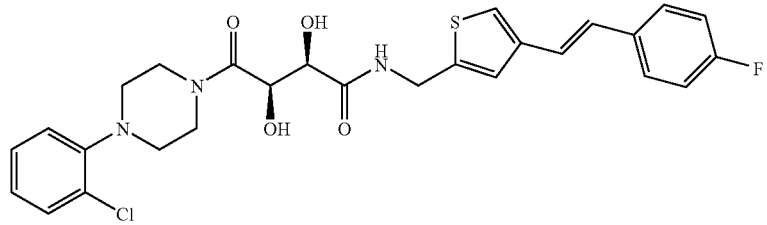
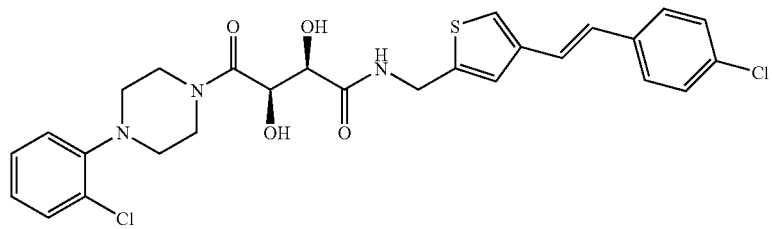
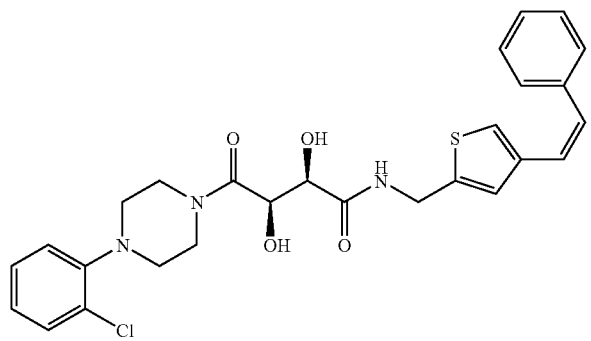
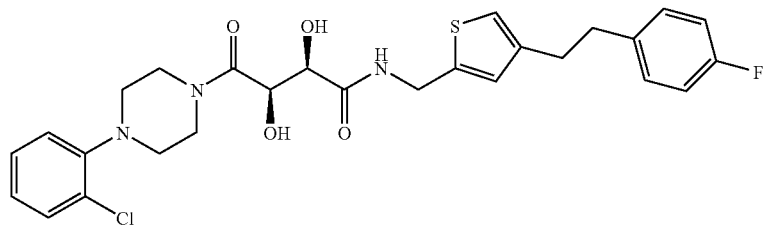
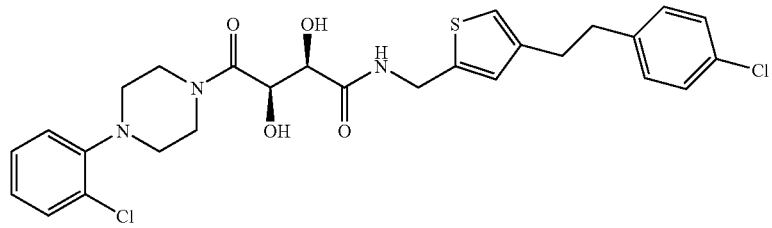
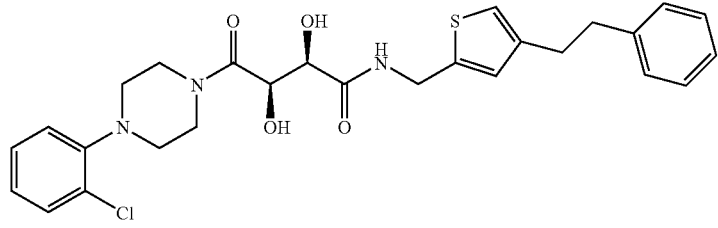
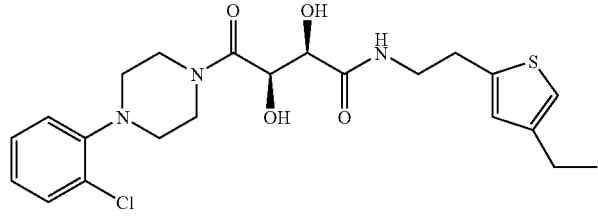

-continued
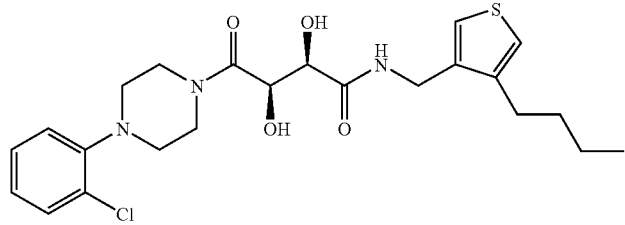
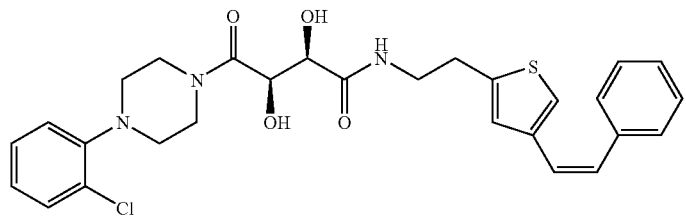
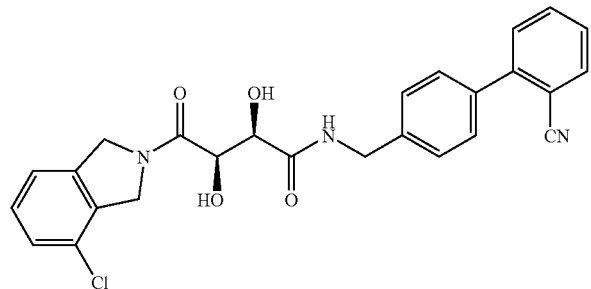
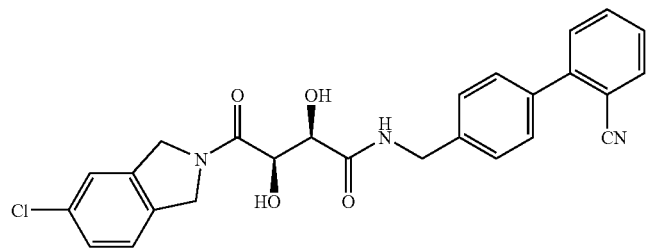
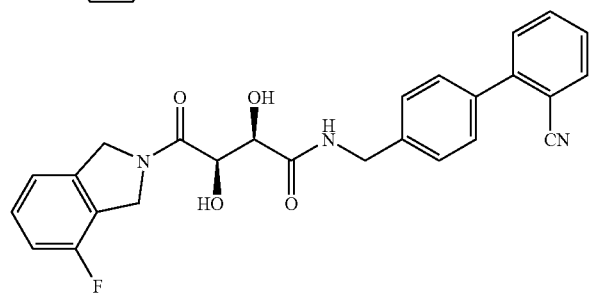
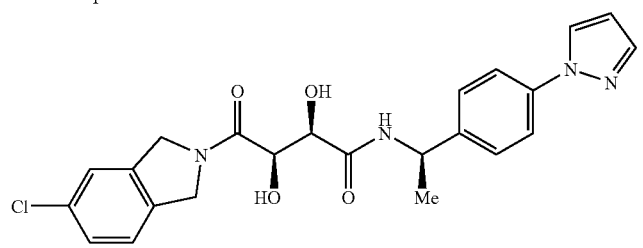

-continued
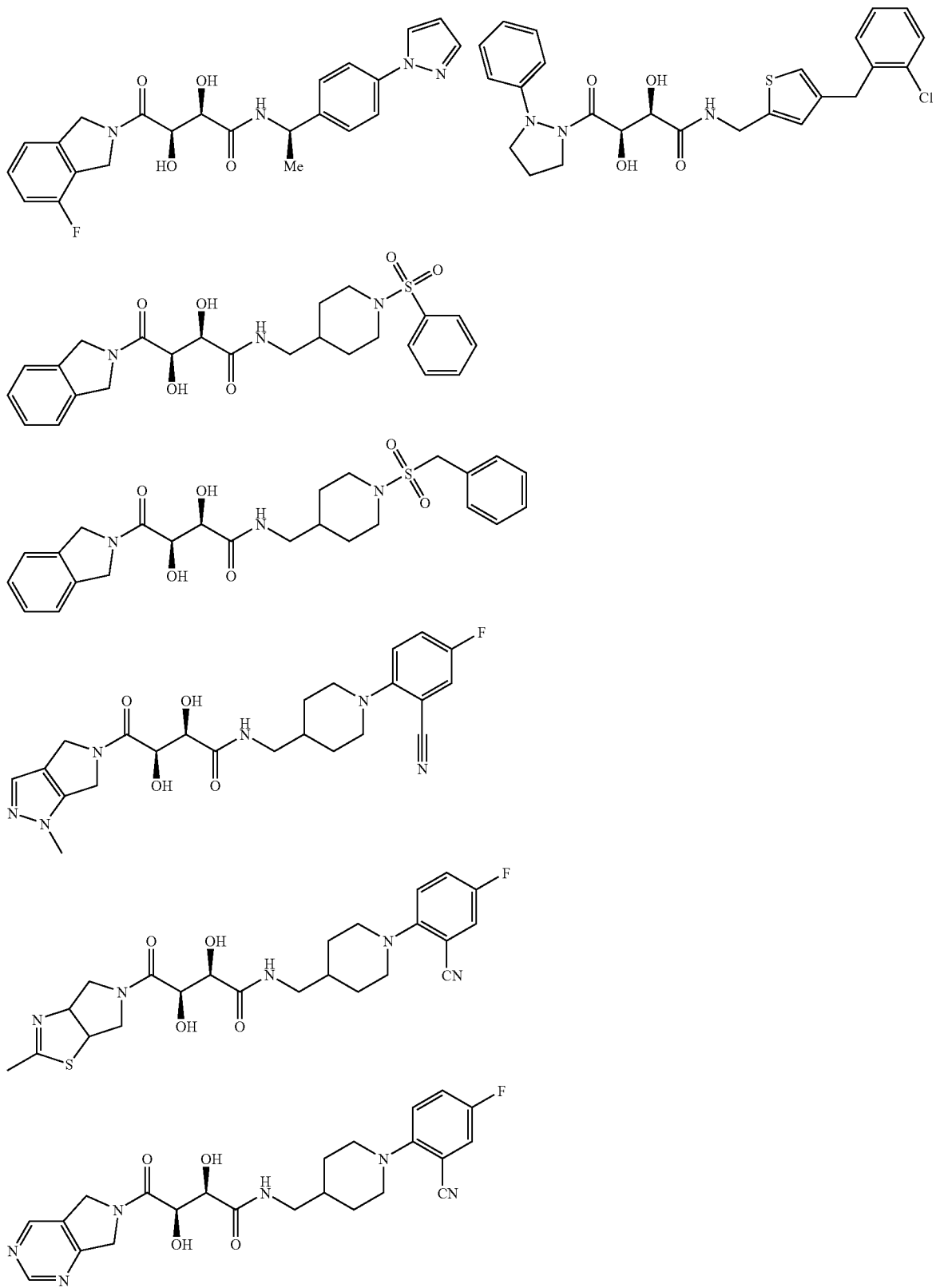

-continued
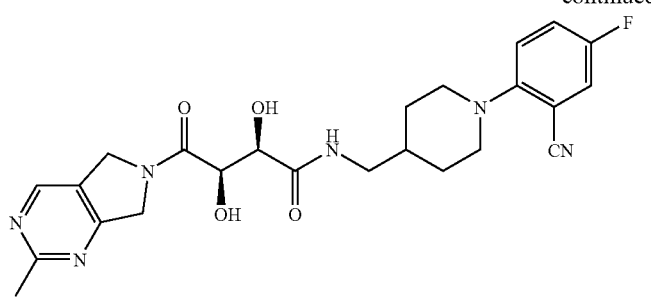
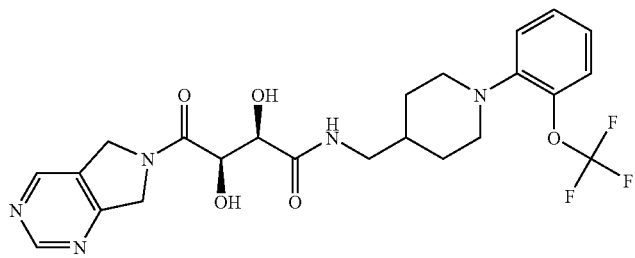
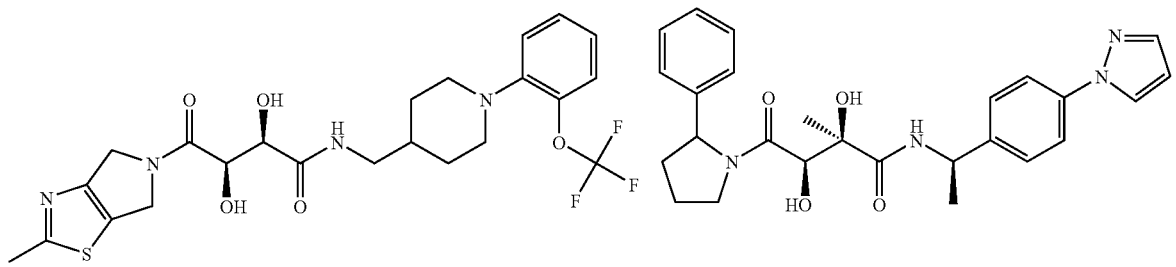
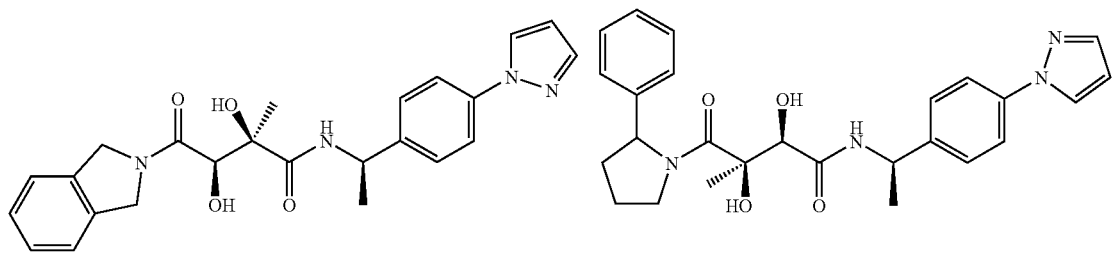
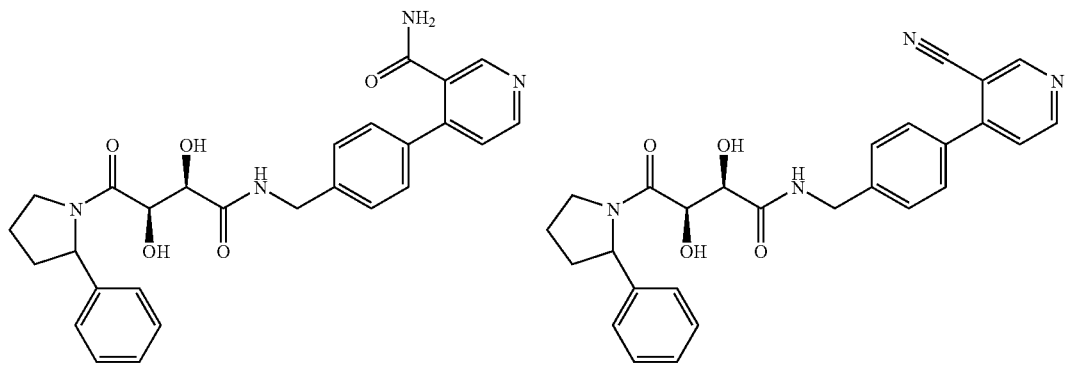

-continued
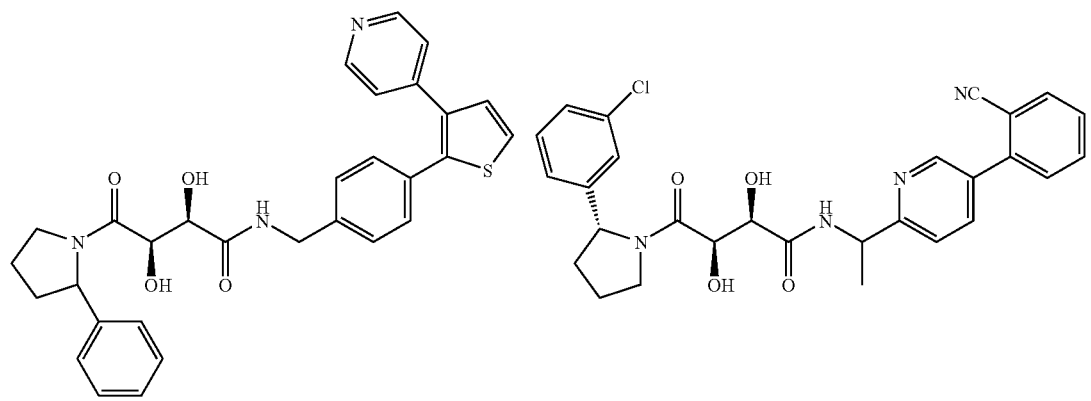
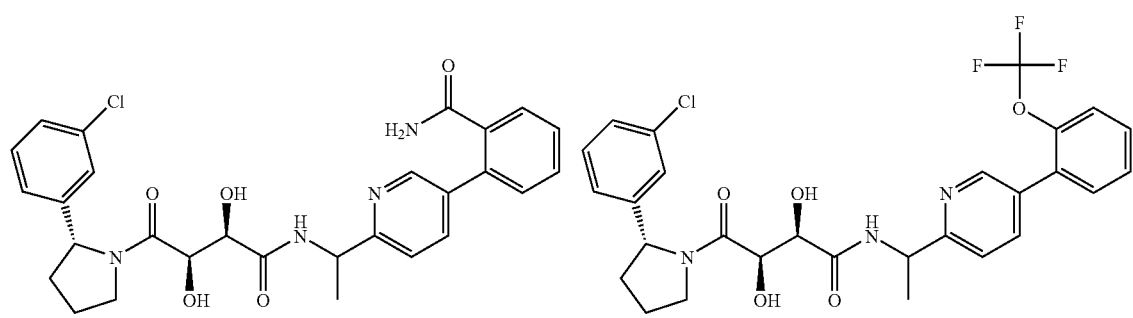
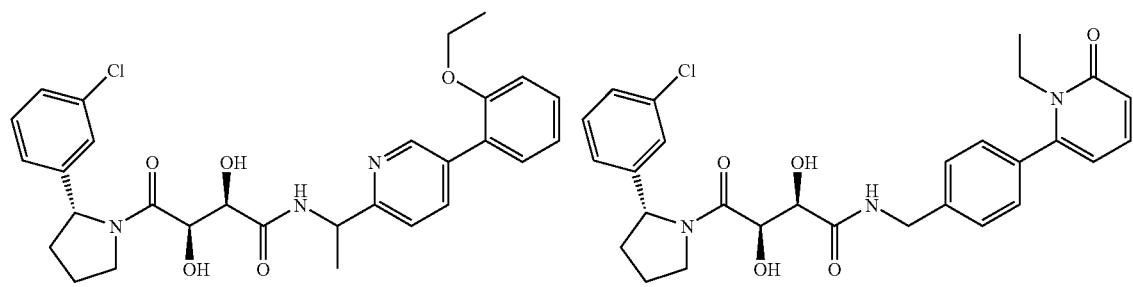
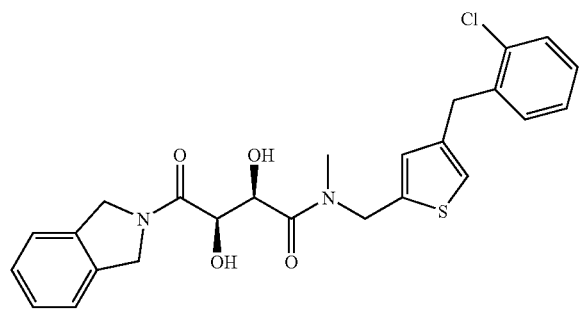
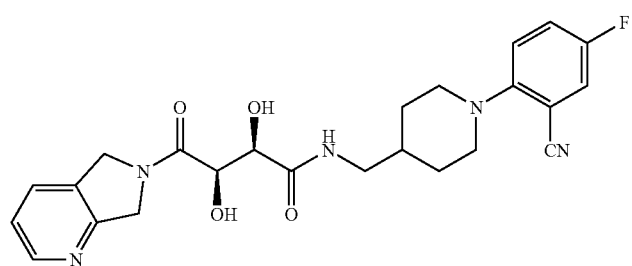

-continued
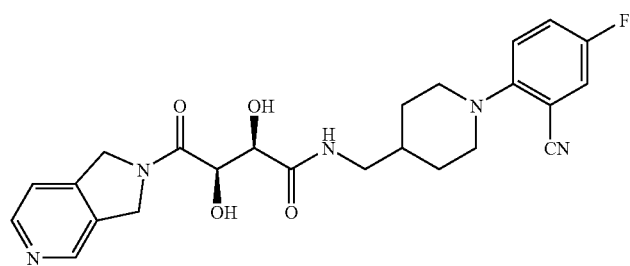
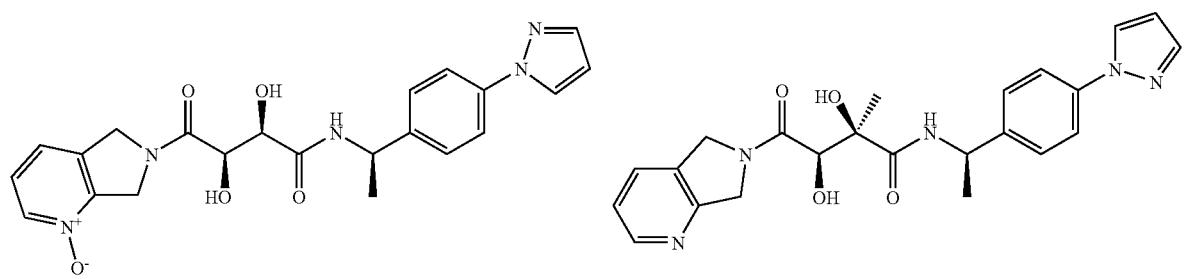
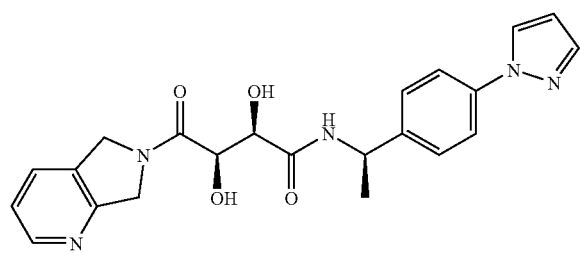
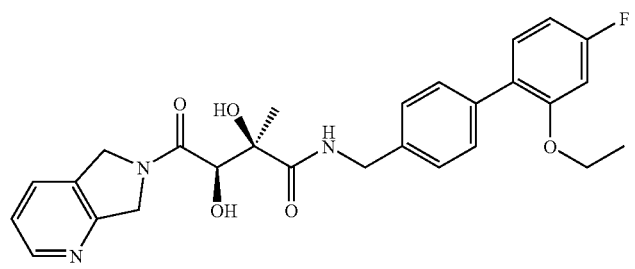
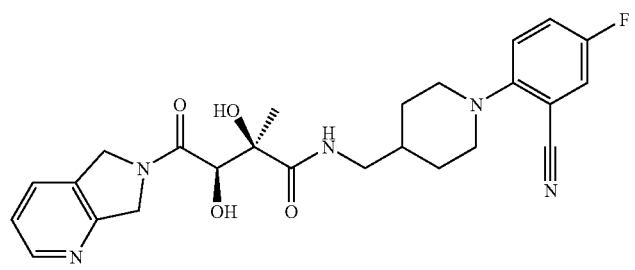
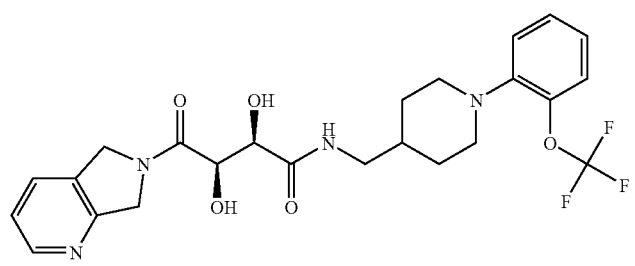

-continued
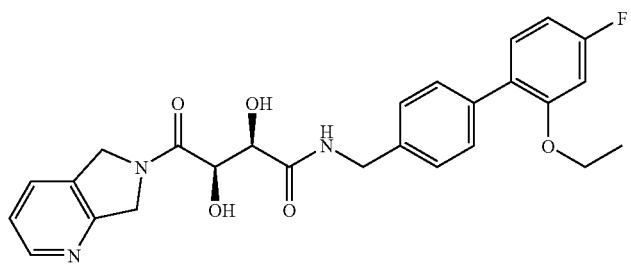
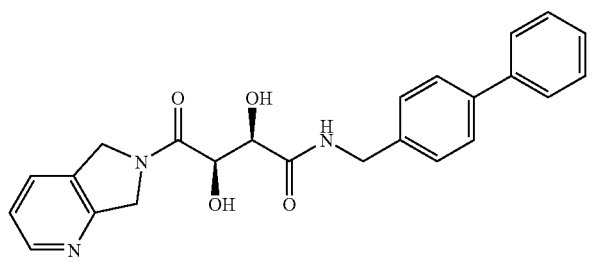
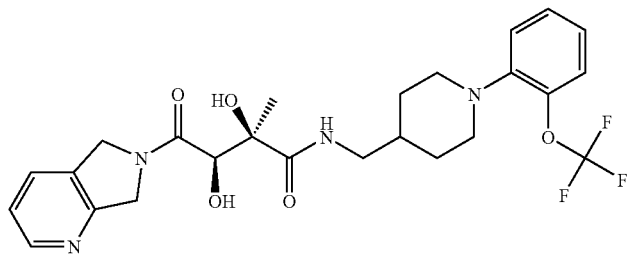
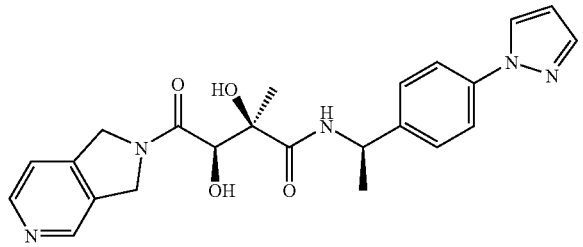
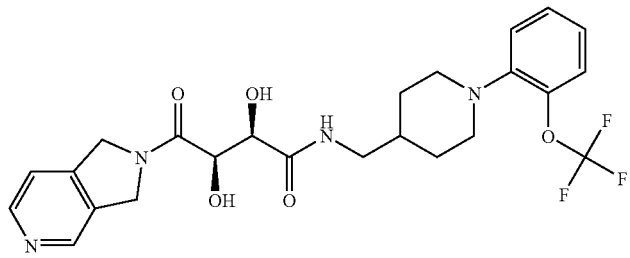
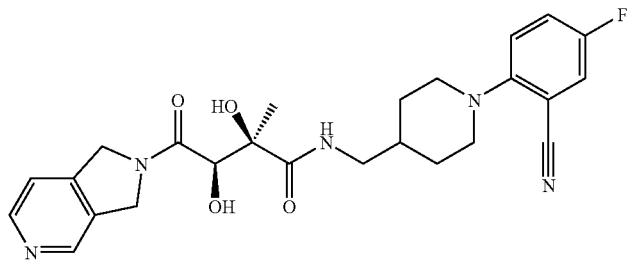

-continued
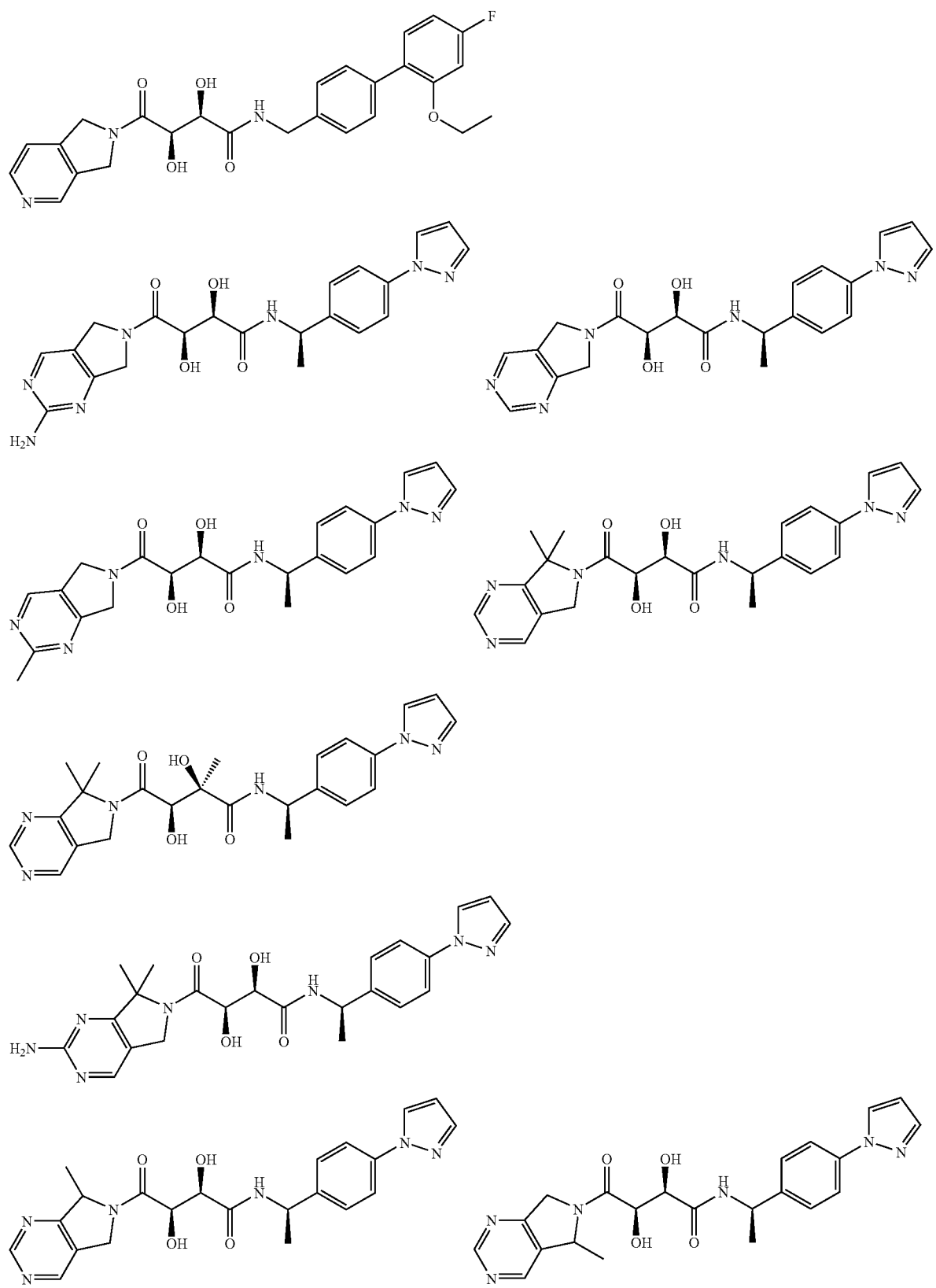

-continued
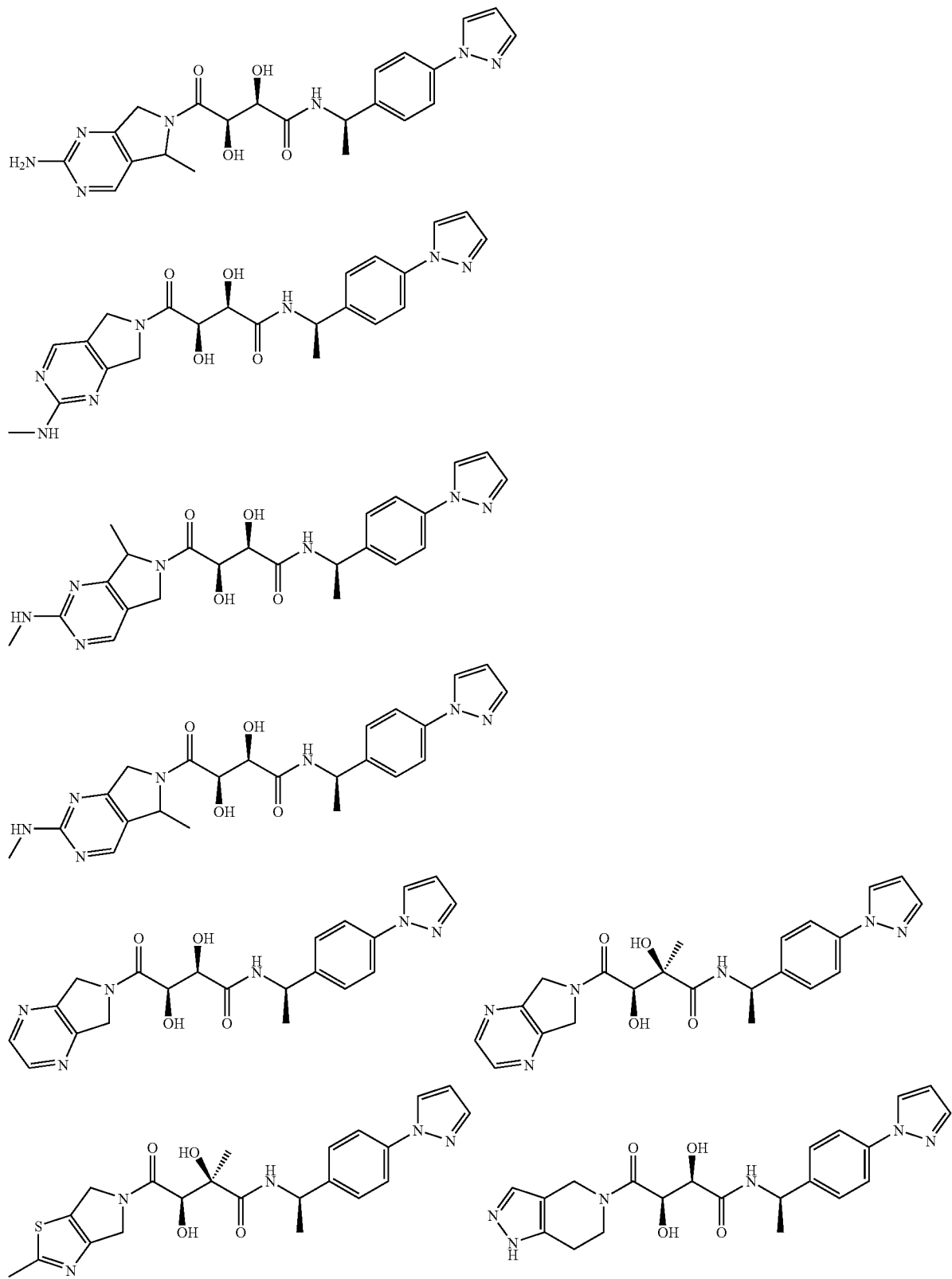

-continued
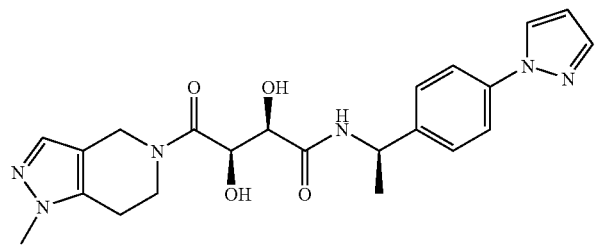
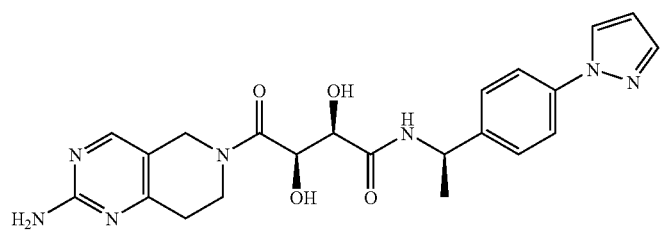
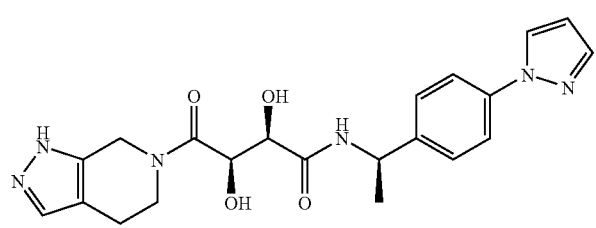
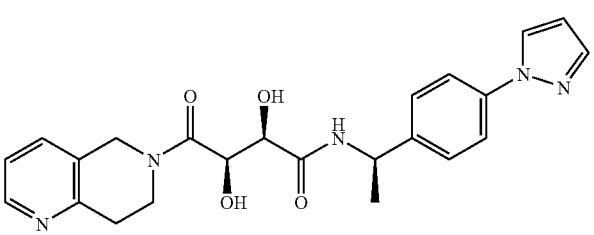
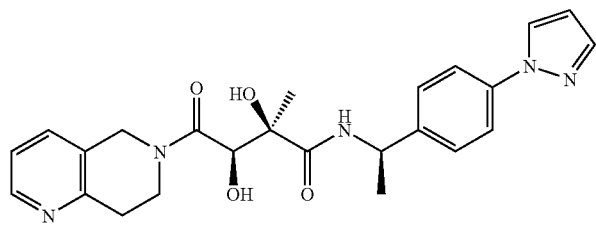
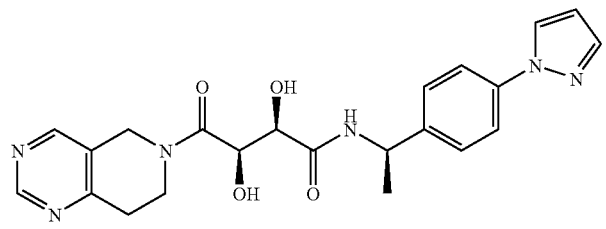
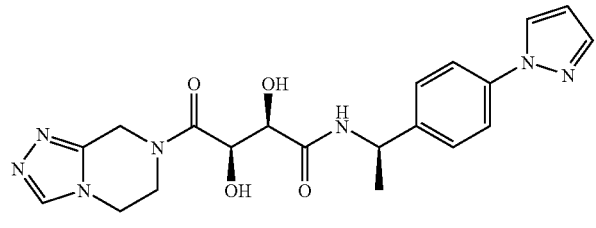
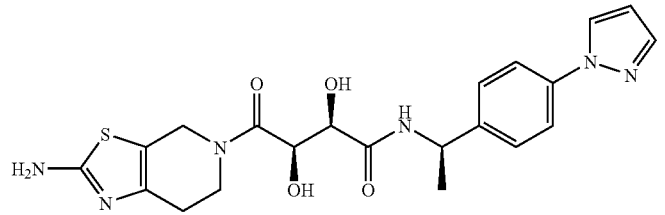

In a preferred embodiment, the compound is selected from the group consisting of:
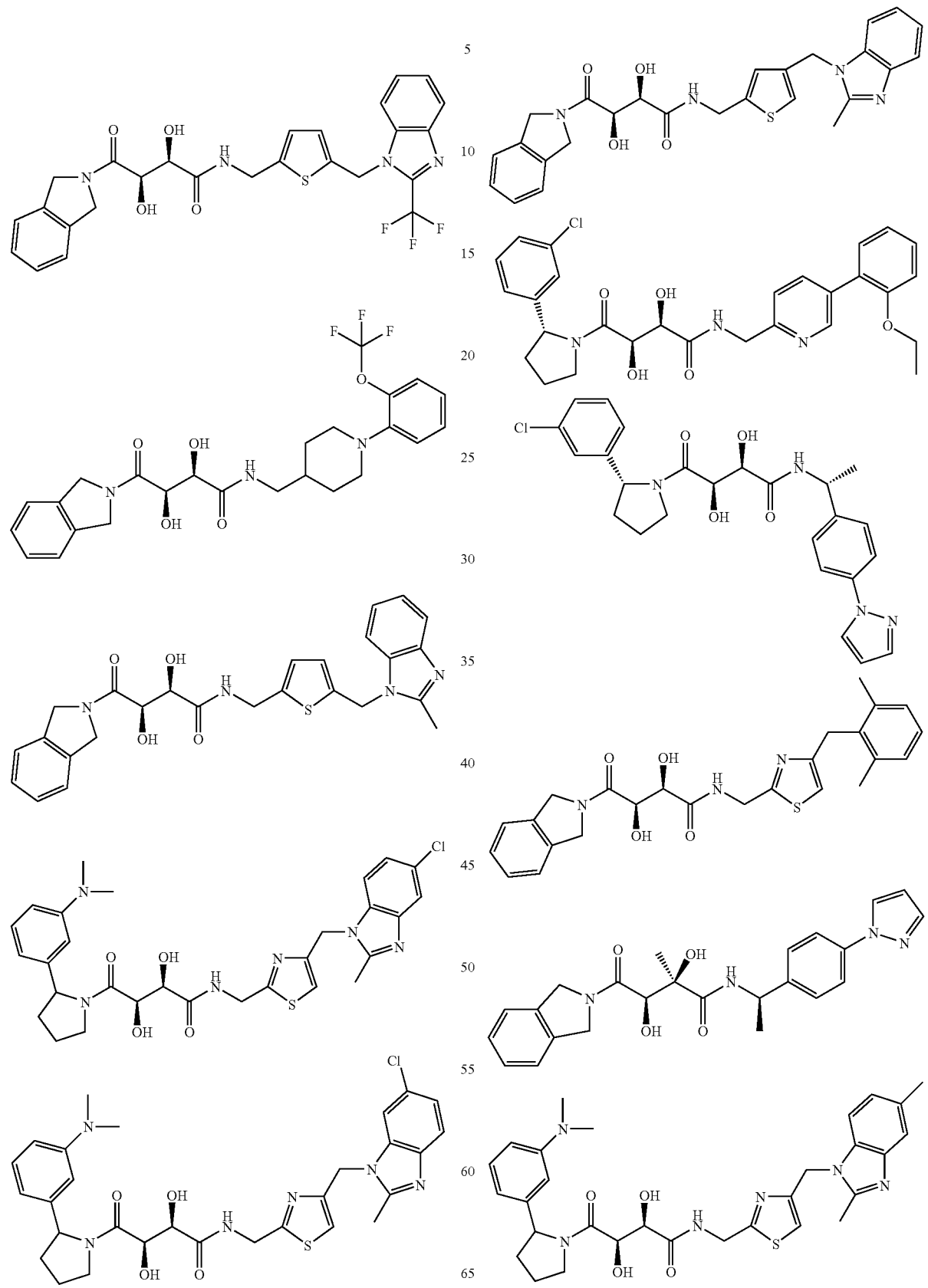

-continued
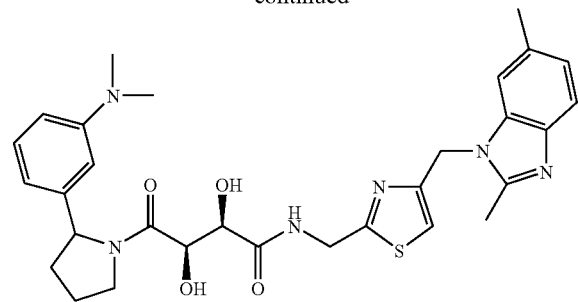
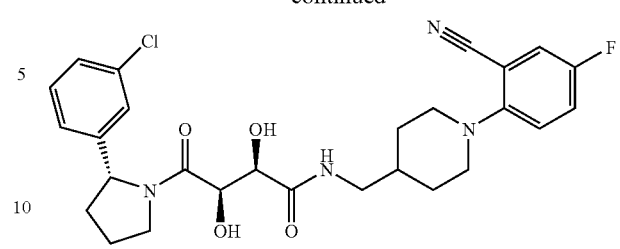
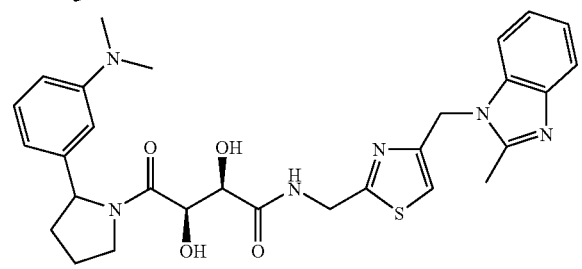
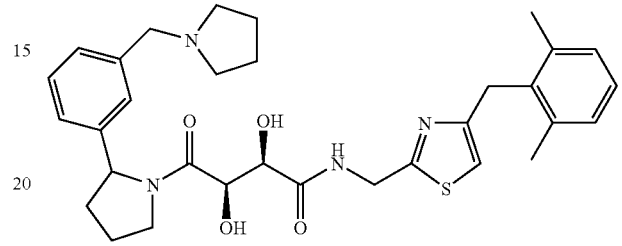
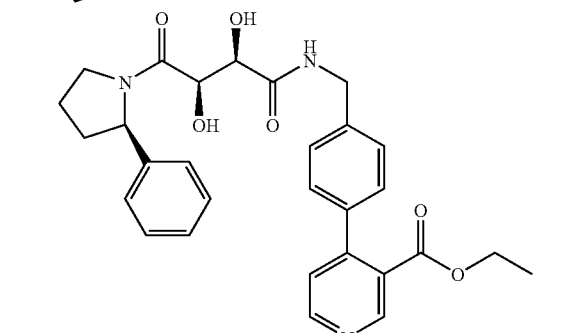
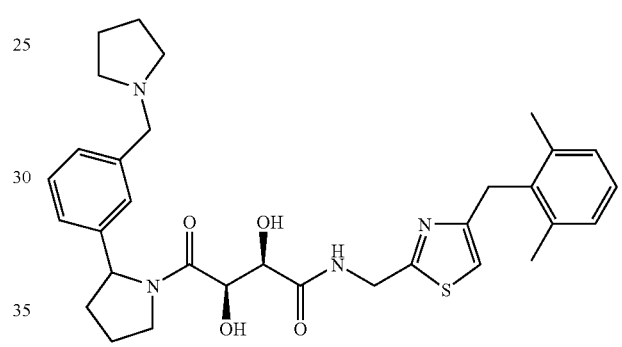
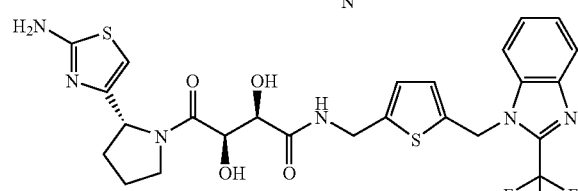
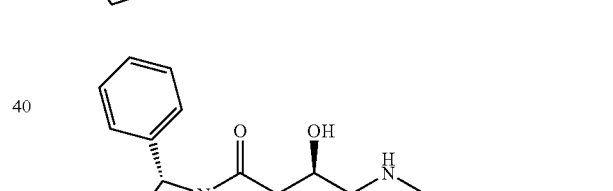
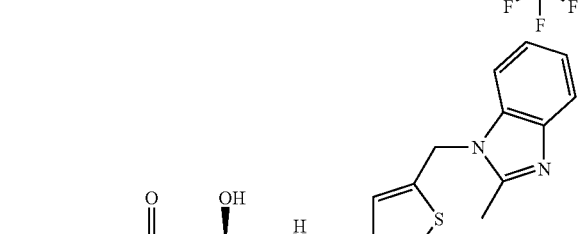
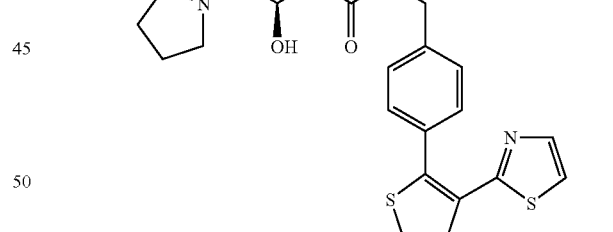
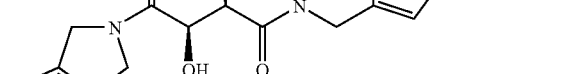
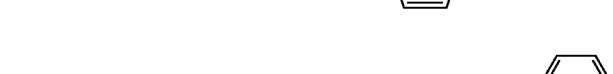
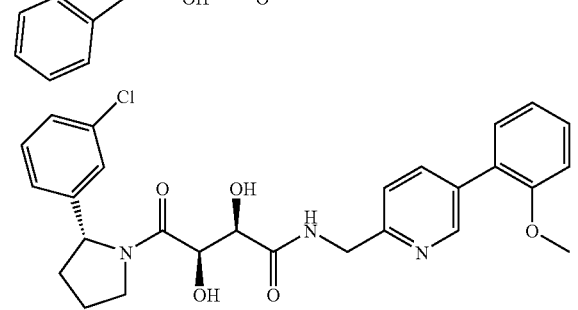
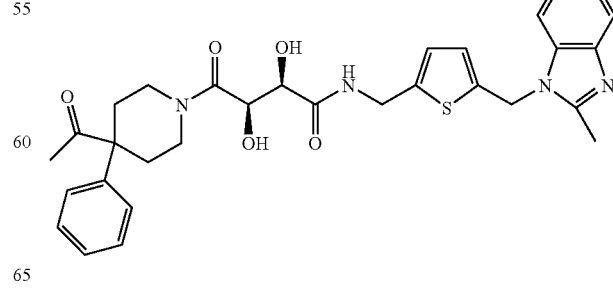

-continued
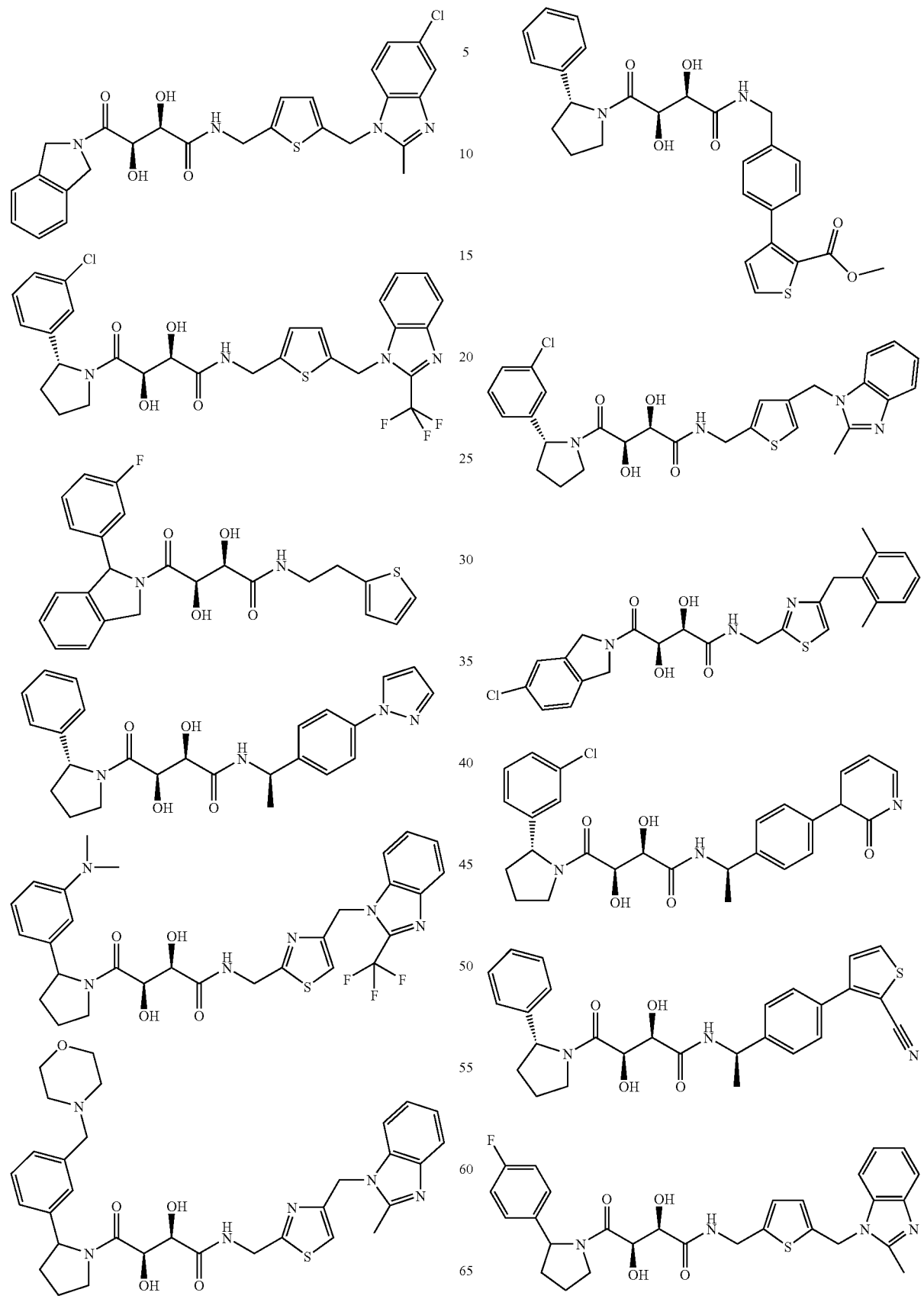

257
-continued
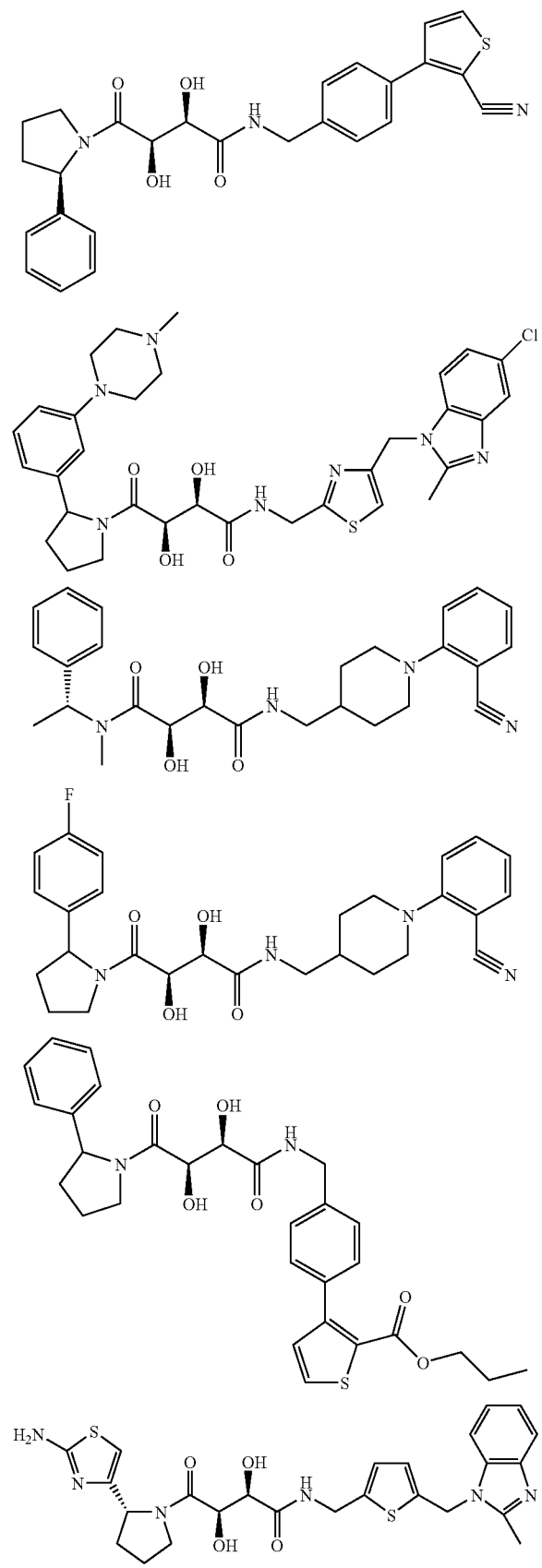
258
-continued
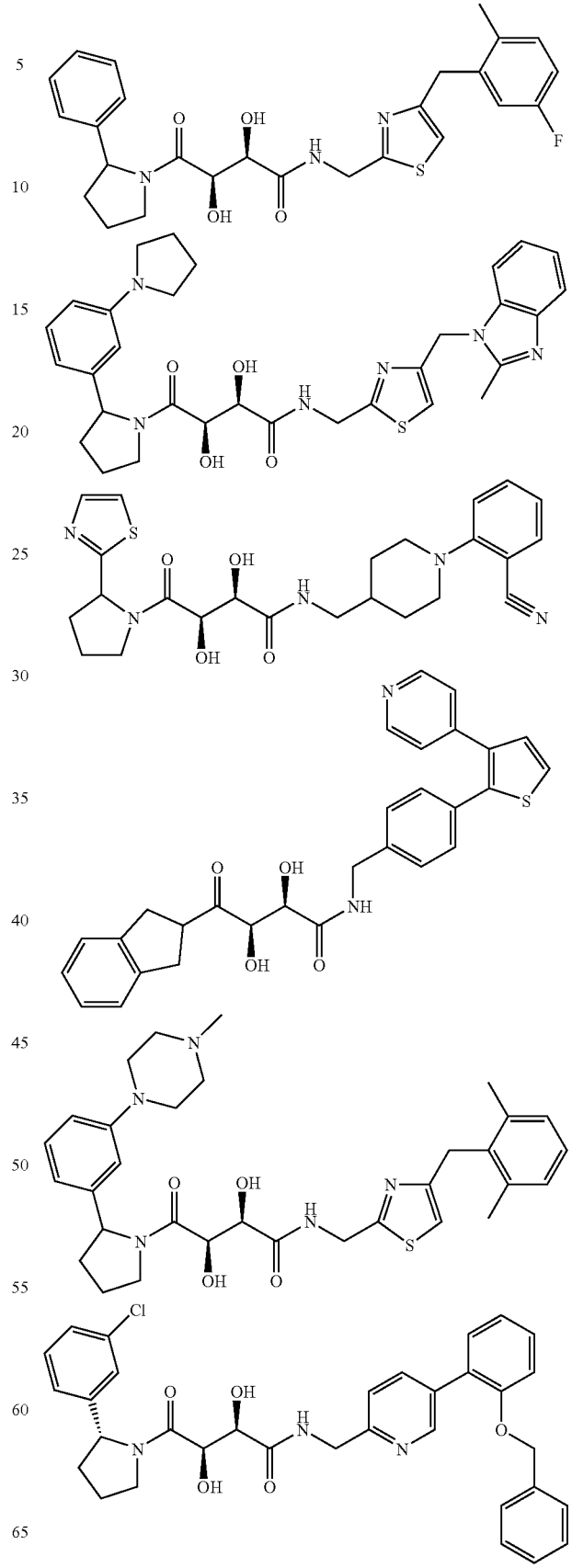

259
-continued
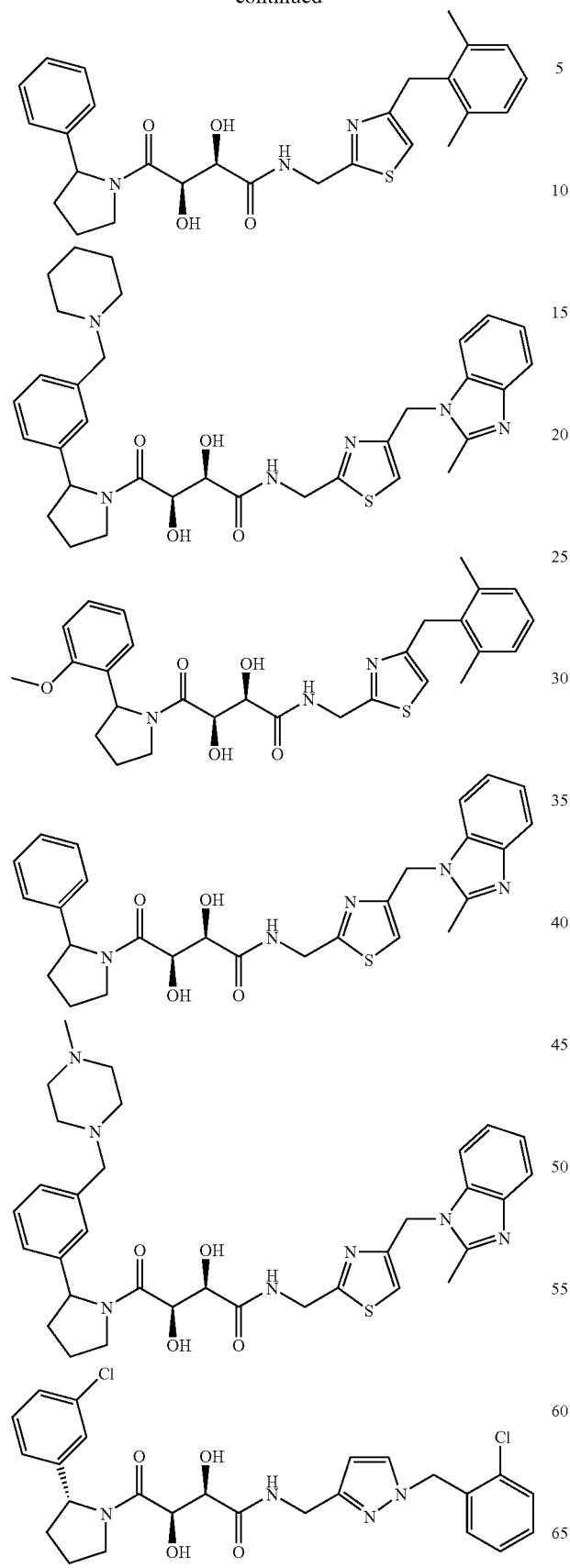
260
-continued
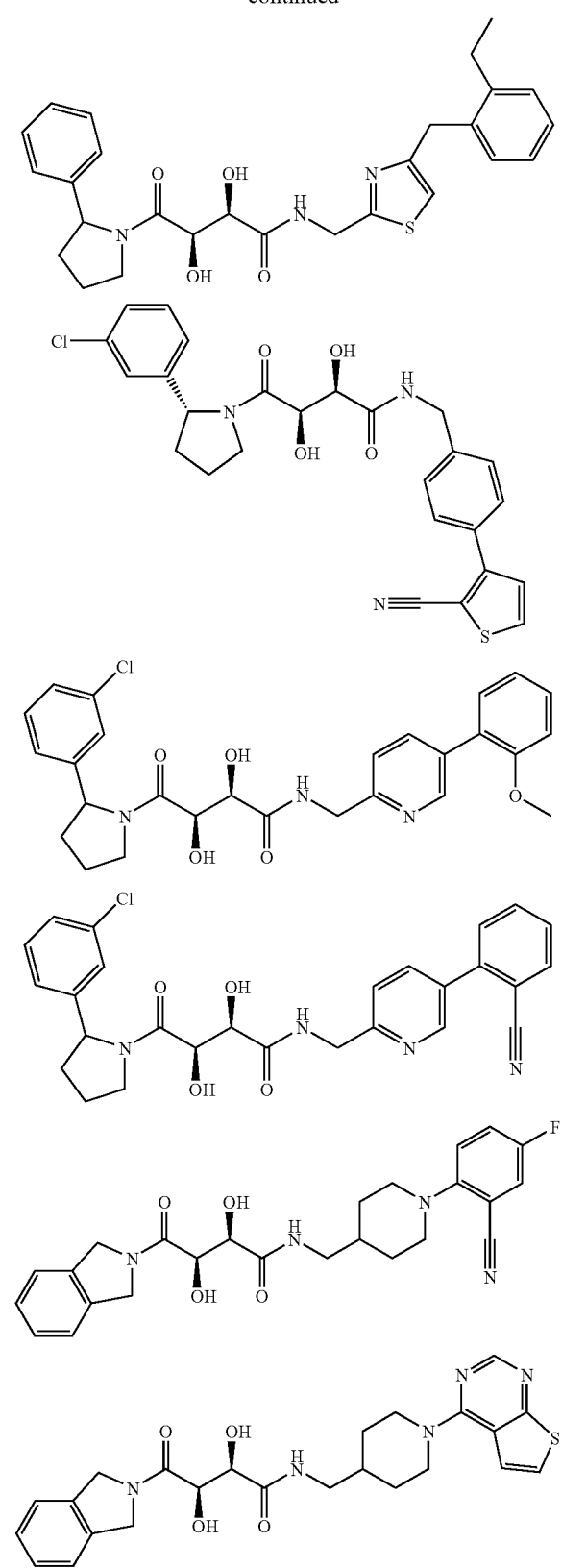

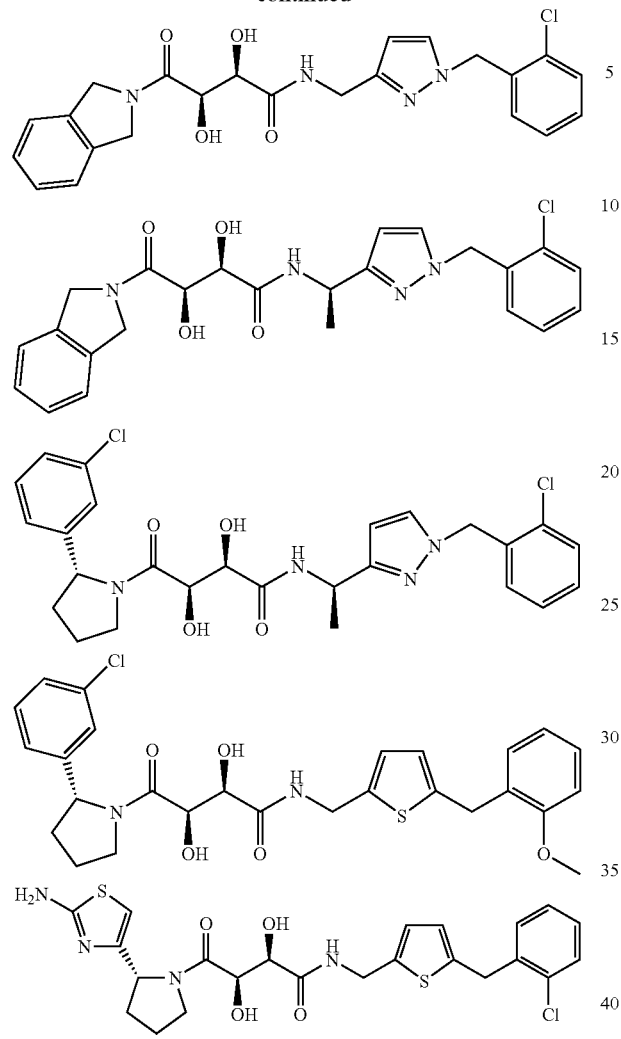
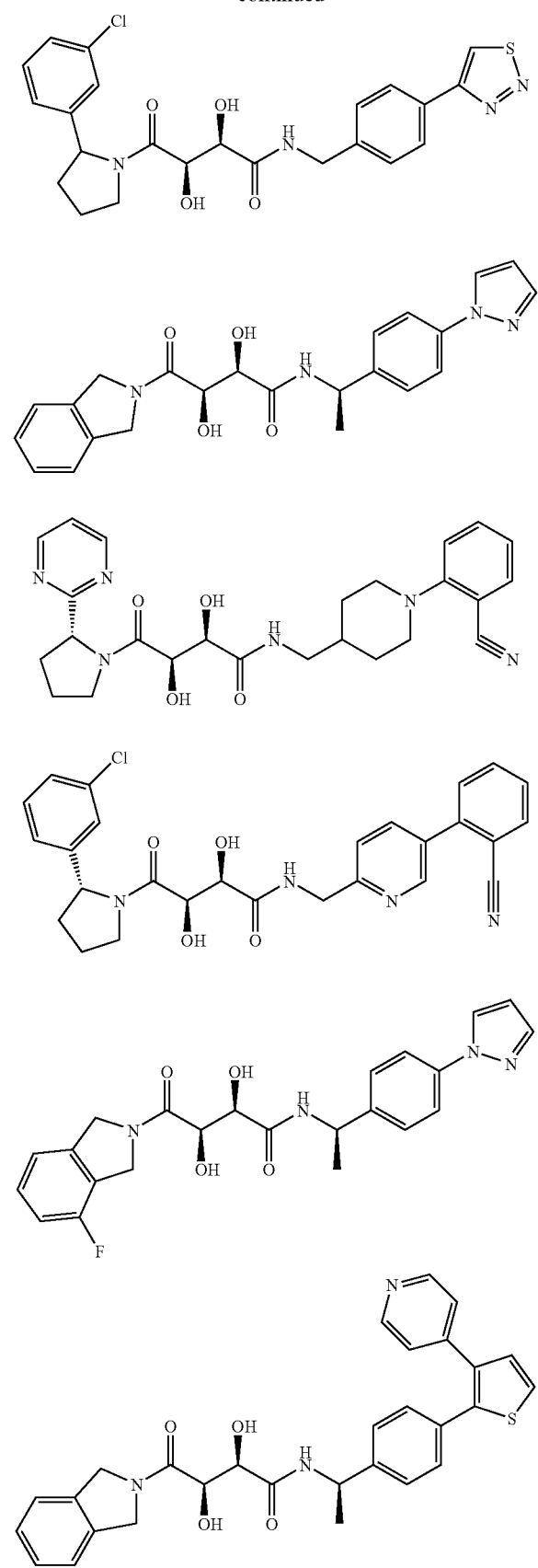

263
-continued
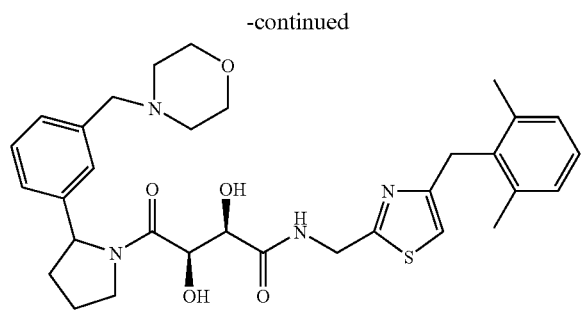
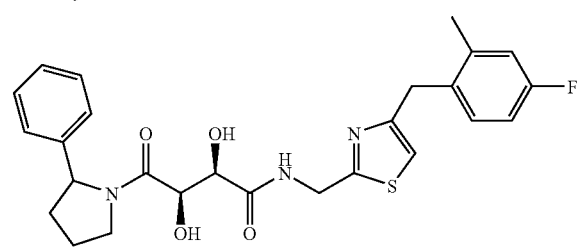
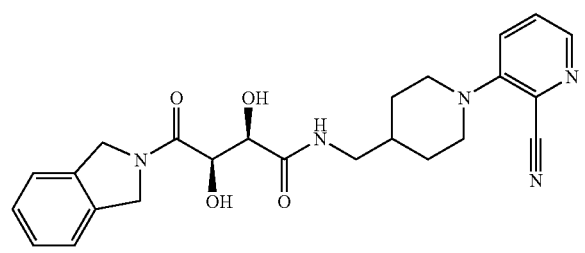
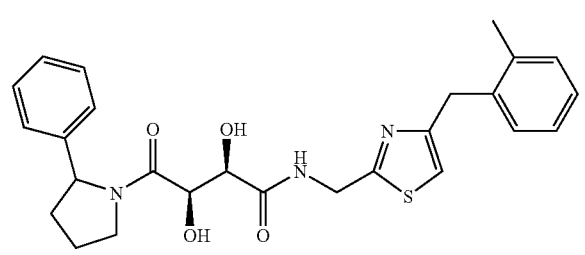
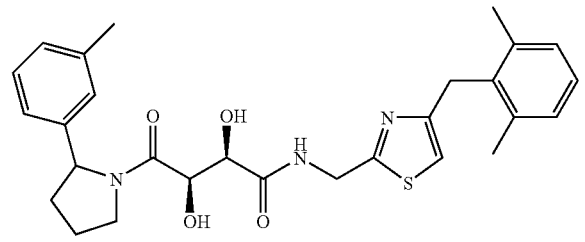
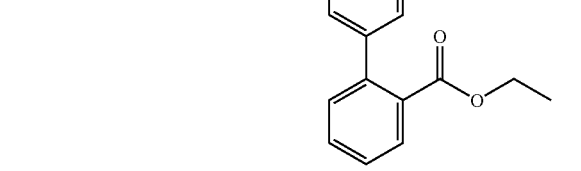
264
-continued
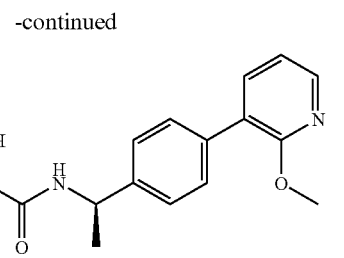
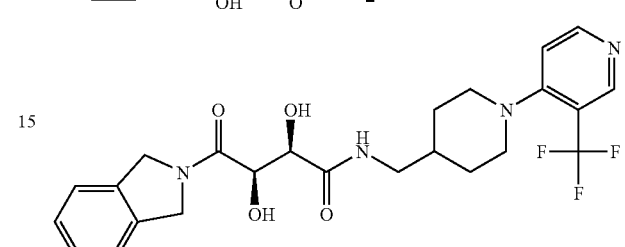
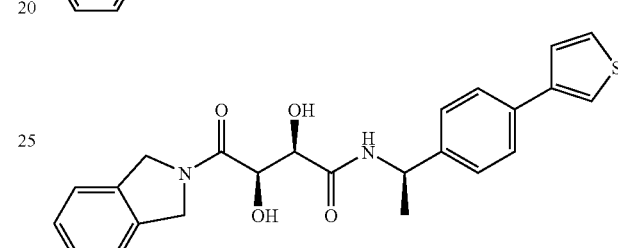

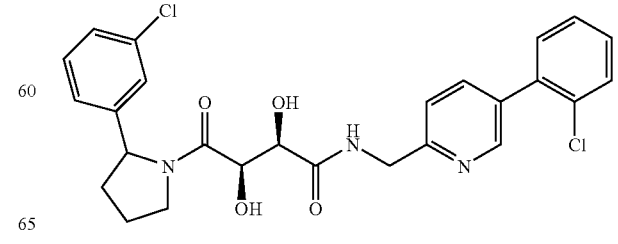

265
-continued
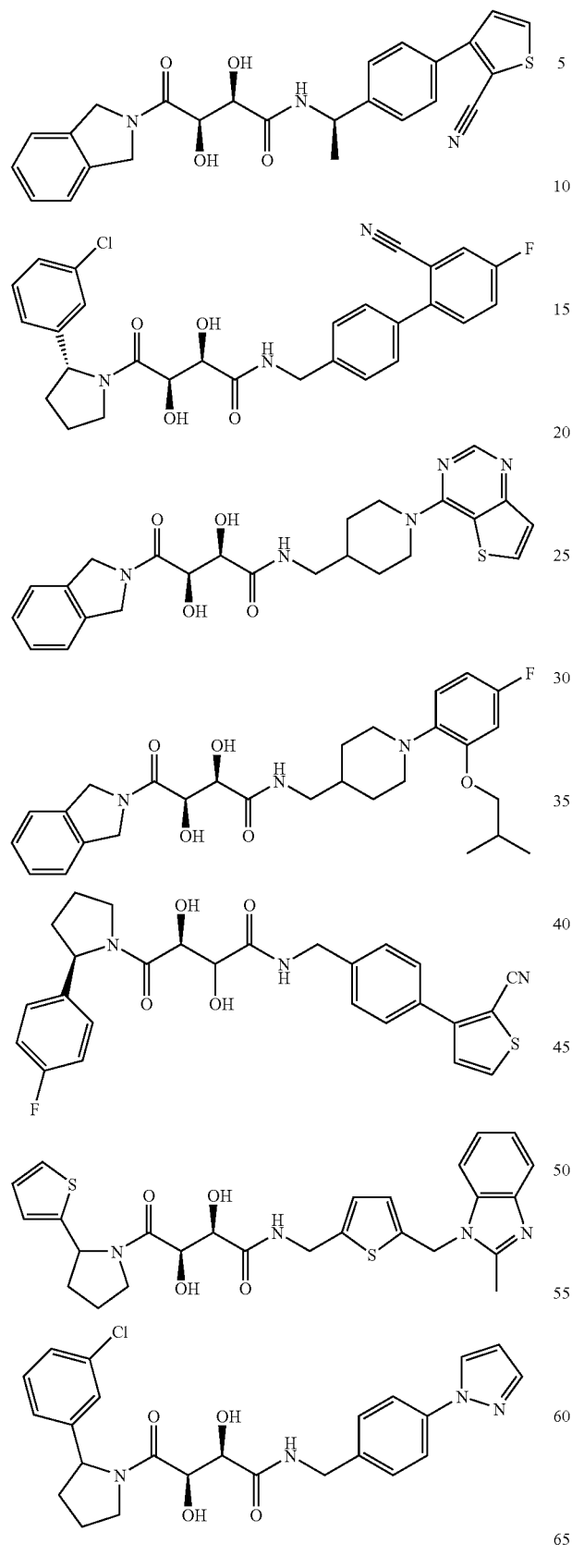
266
-continued
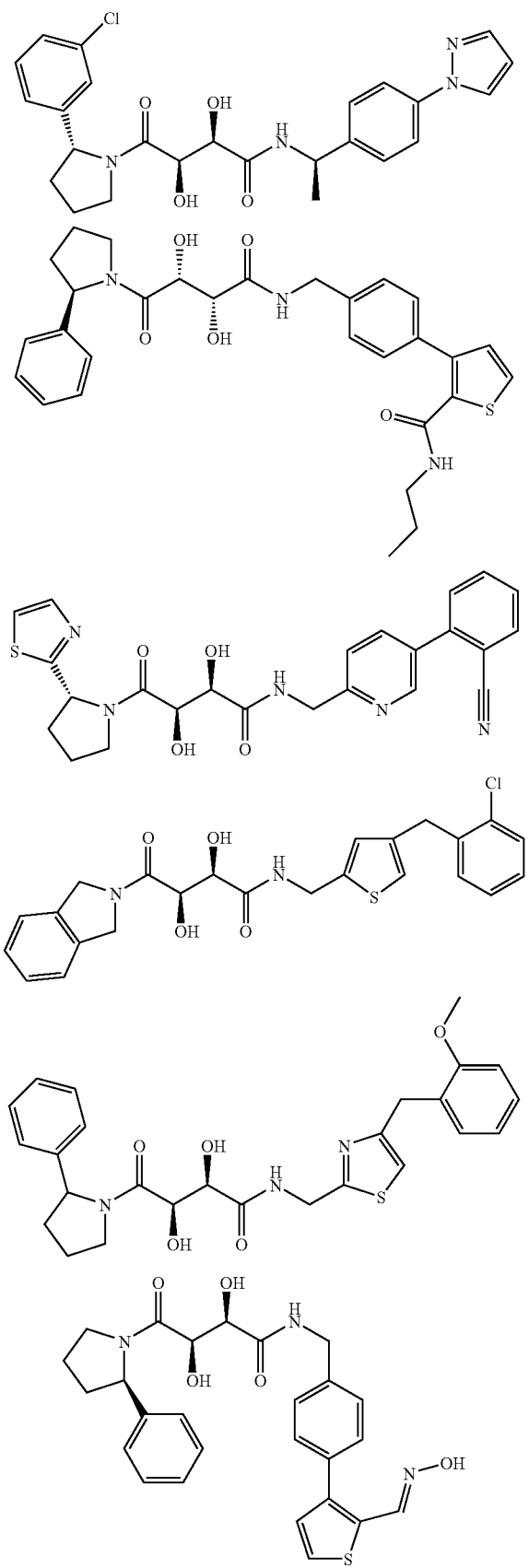

267
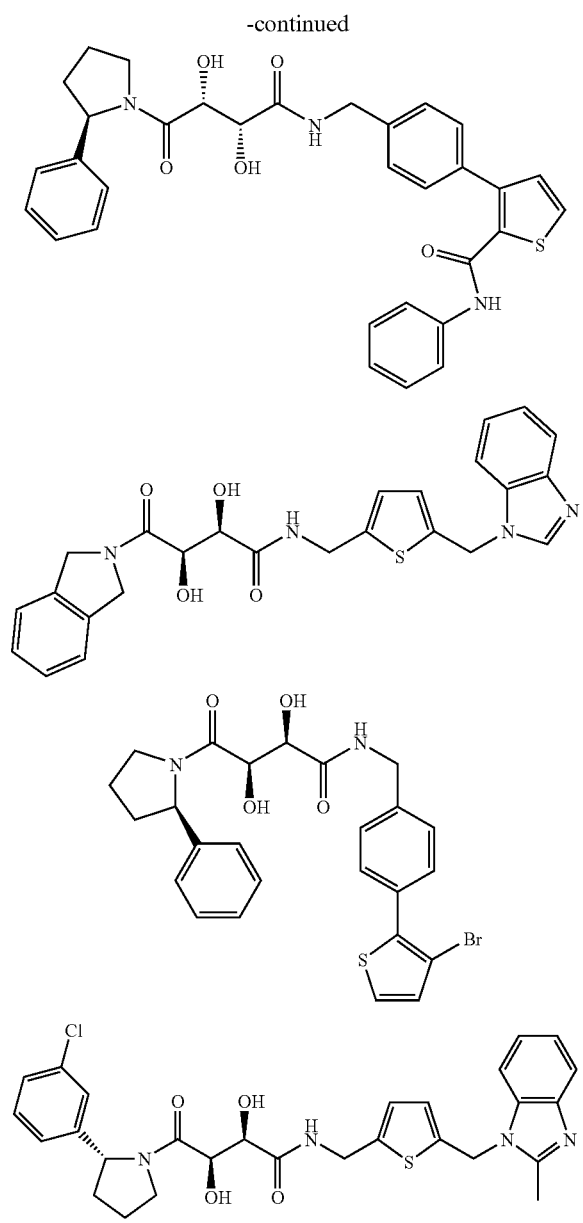
268
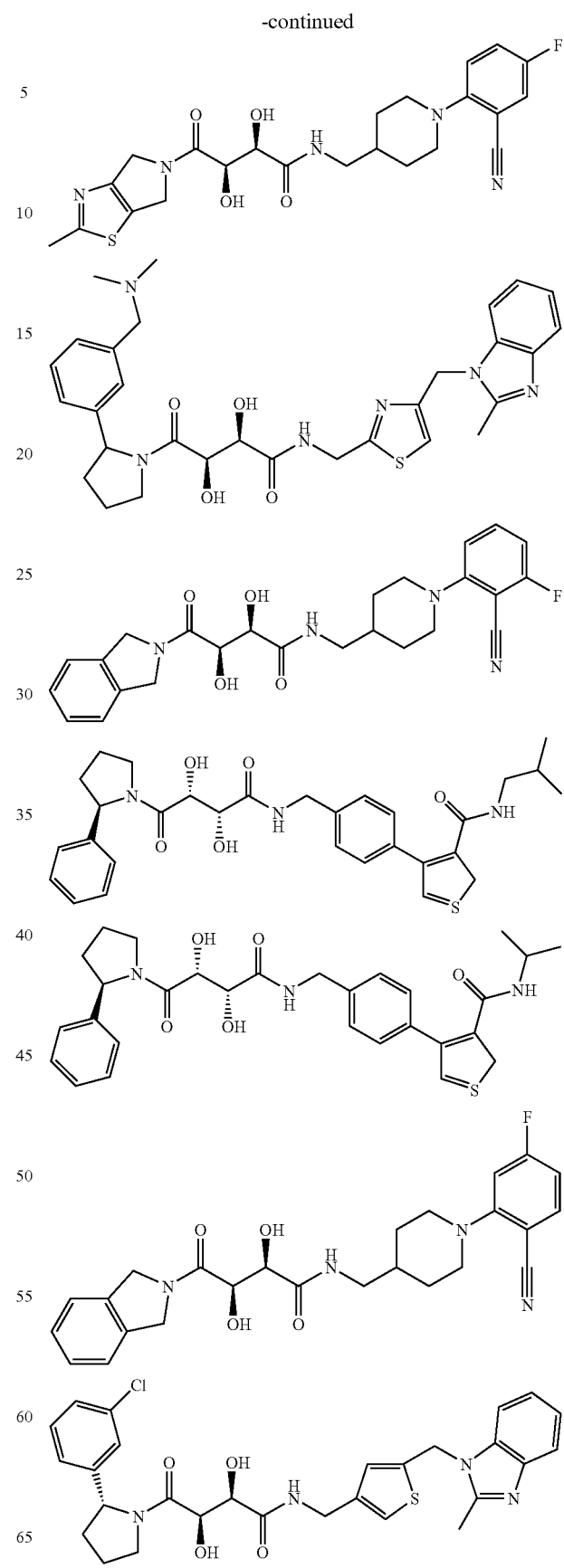

269
-continued
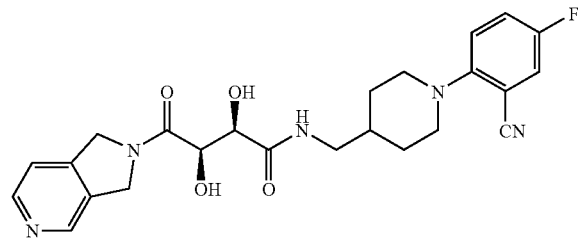
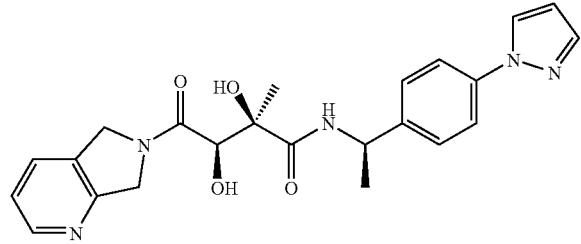
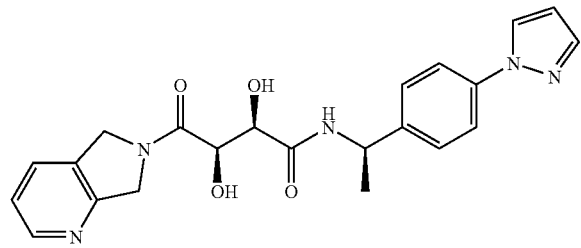
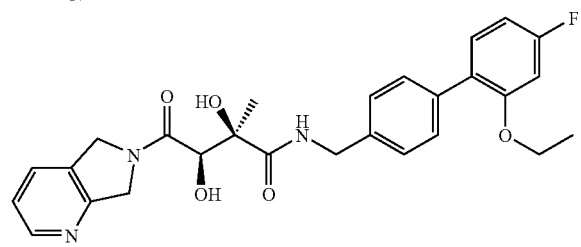
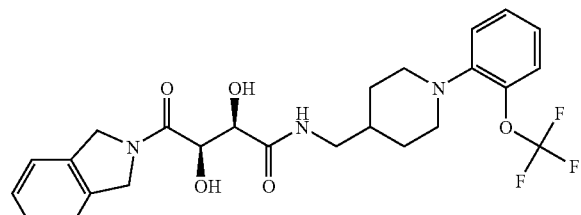
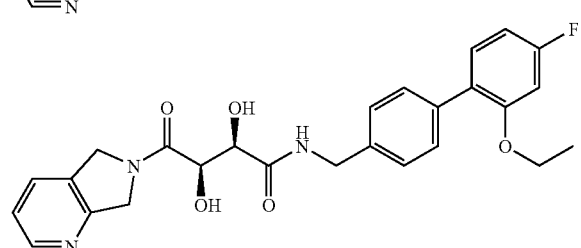
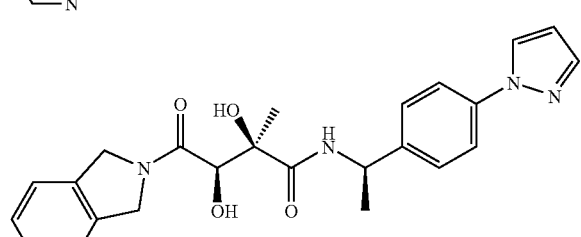
270
-continued
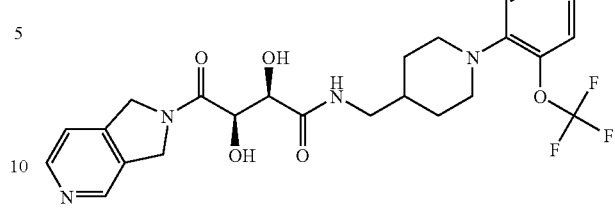
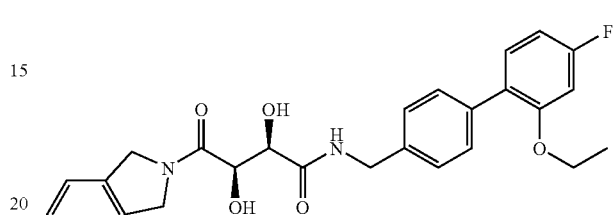
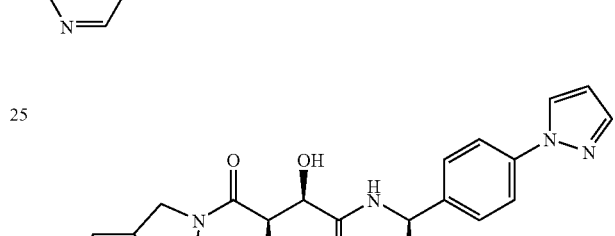
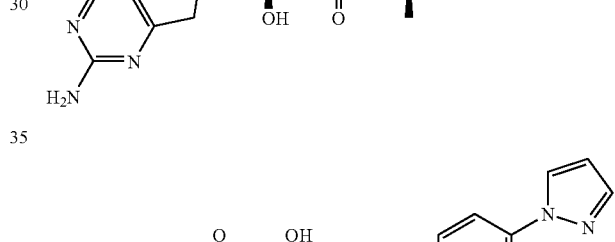
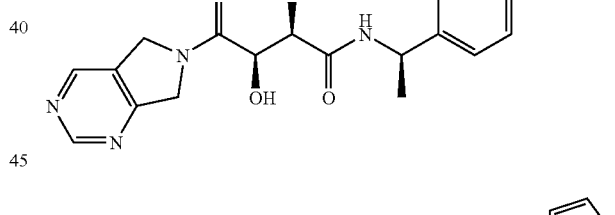
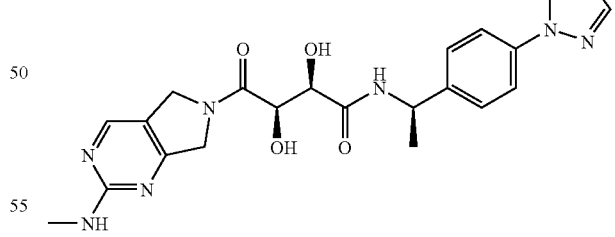
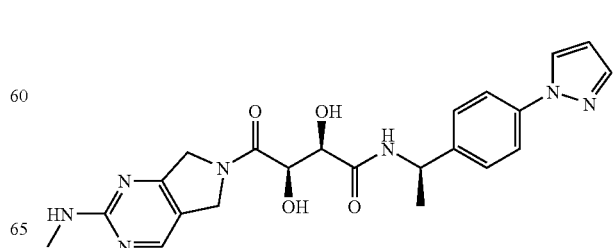

-continued
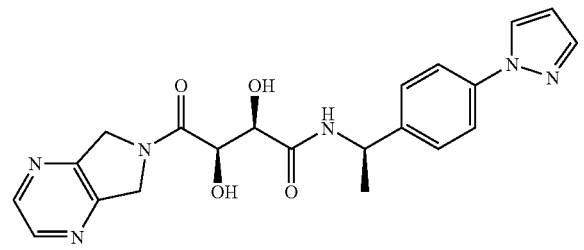
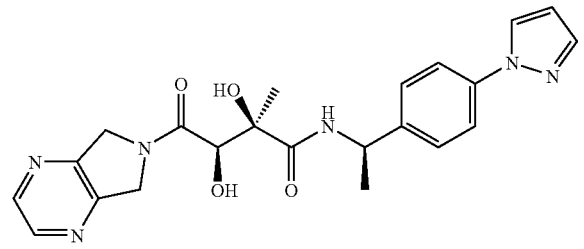
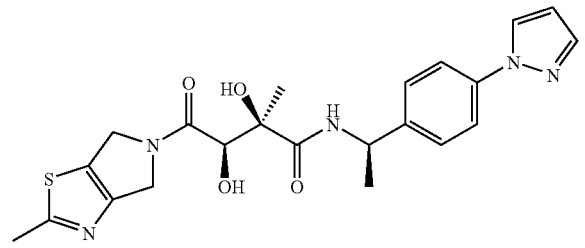
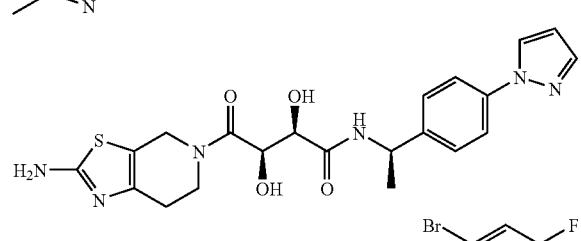
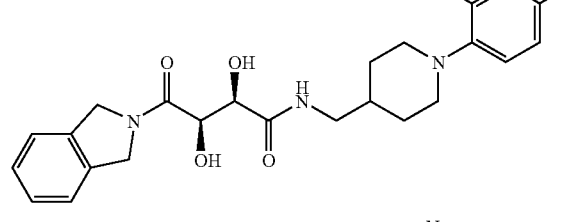
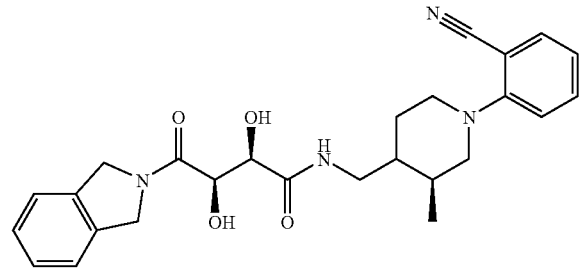
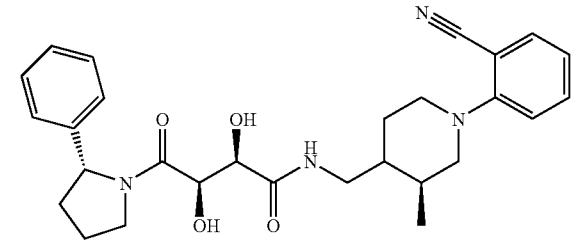
-continued
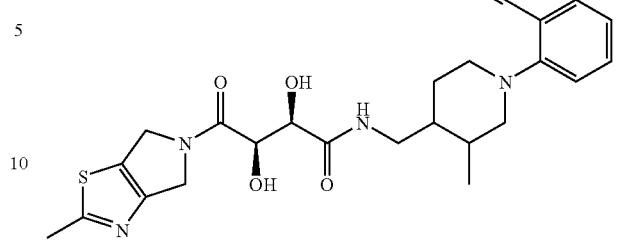
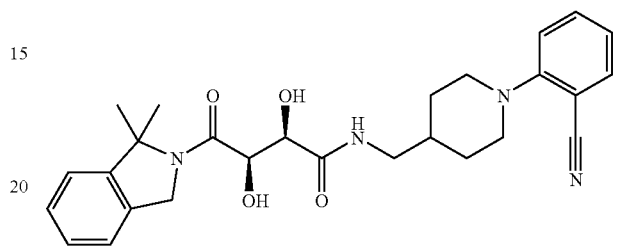
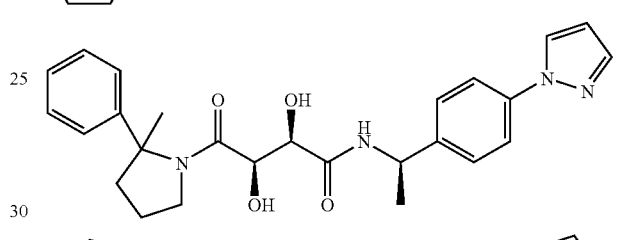

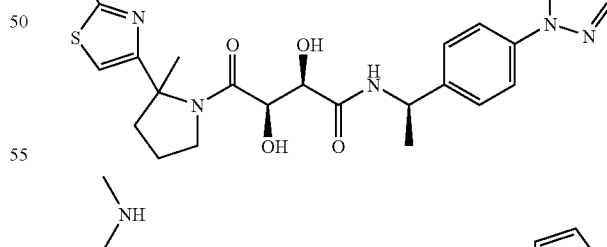

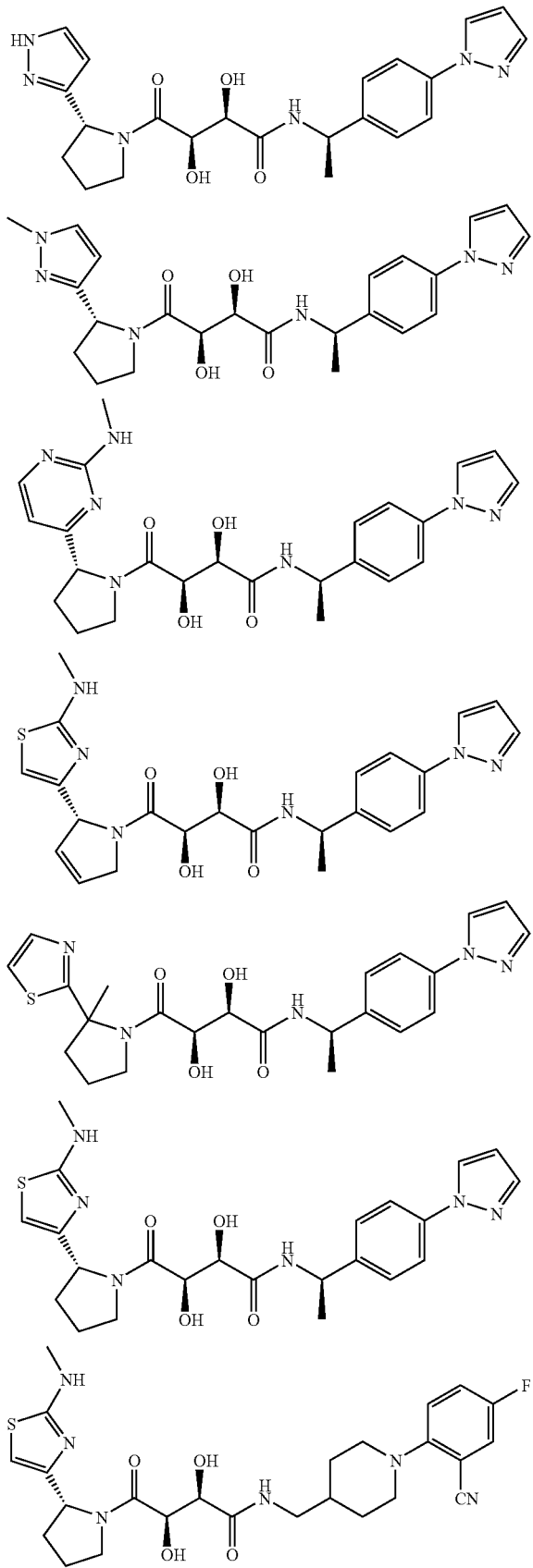

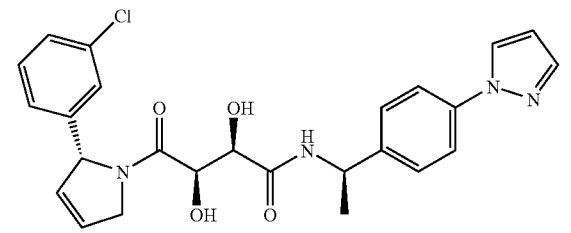
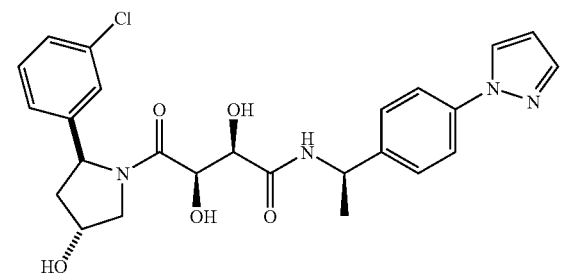
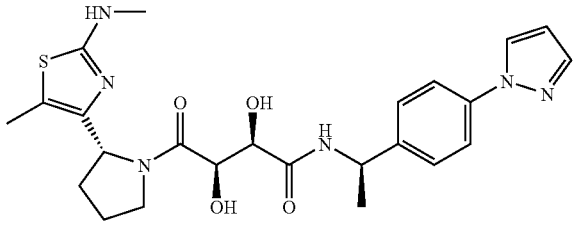
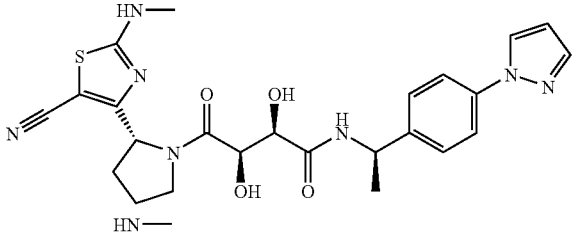
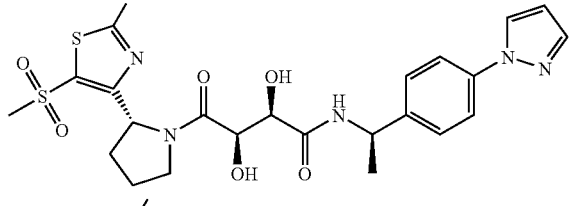
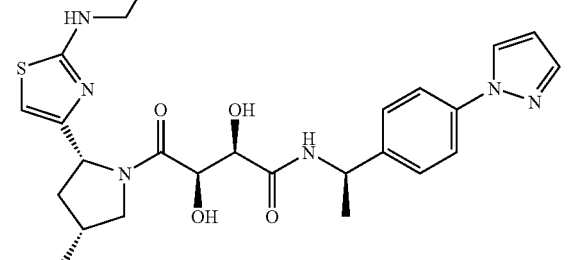

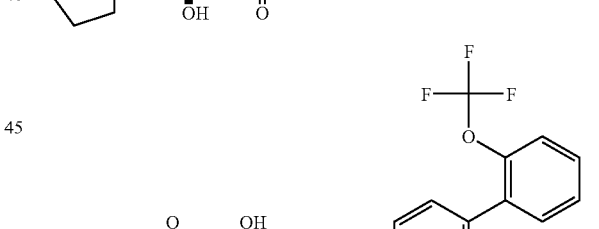
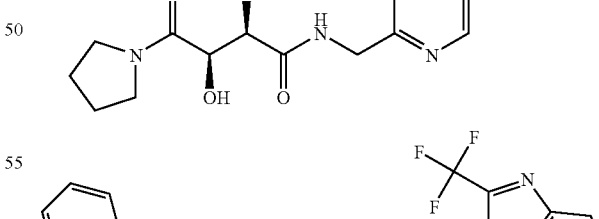
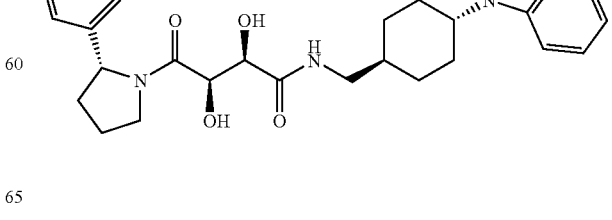

-continued
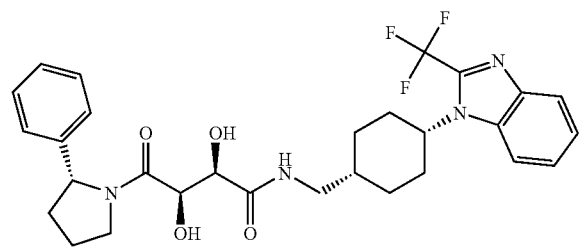
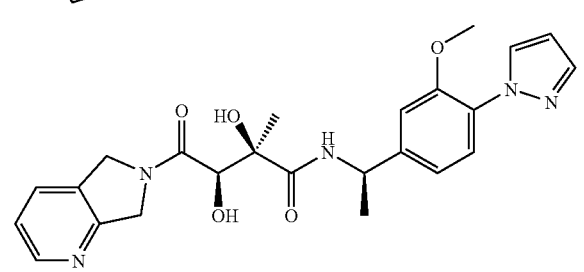
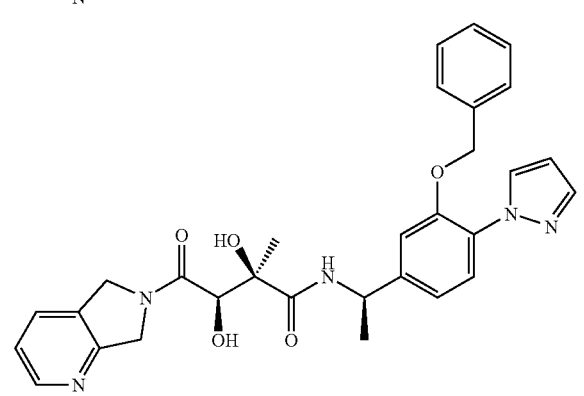
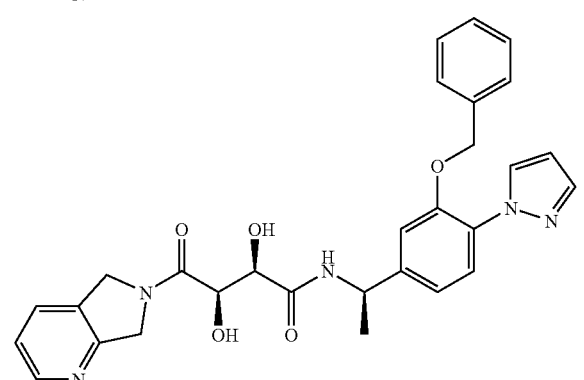
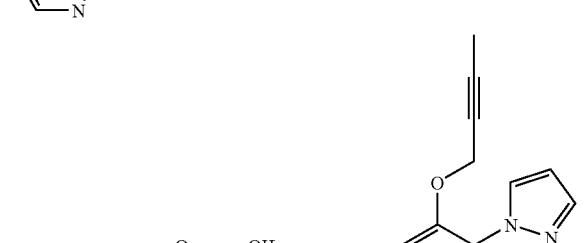
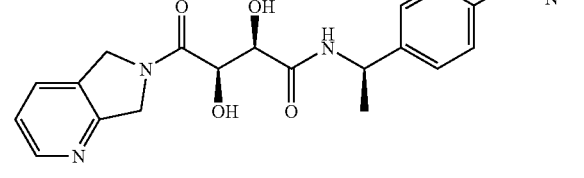
-continued

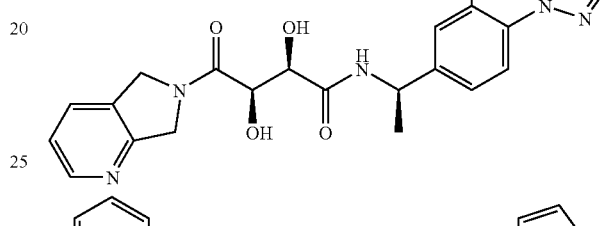

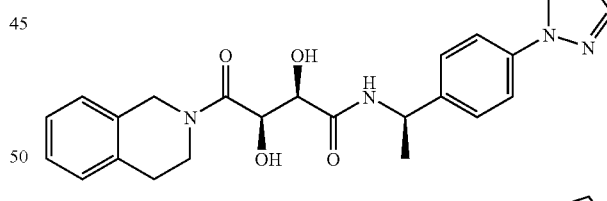
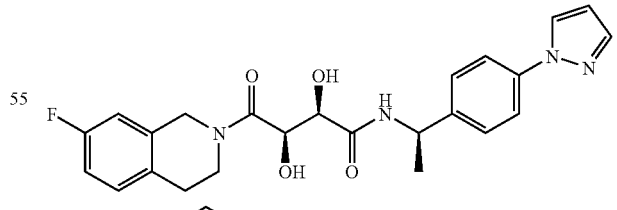
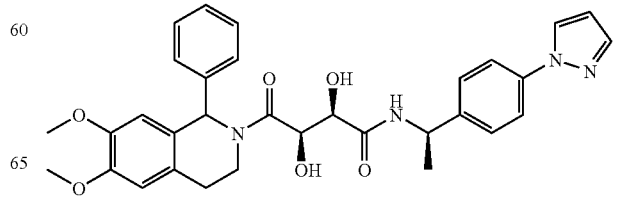

-continued
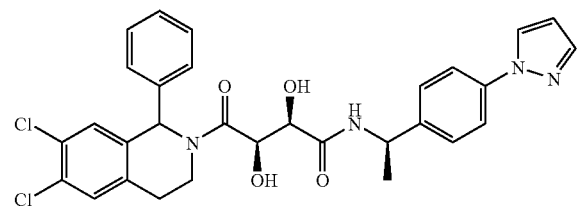
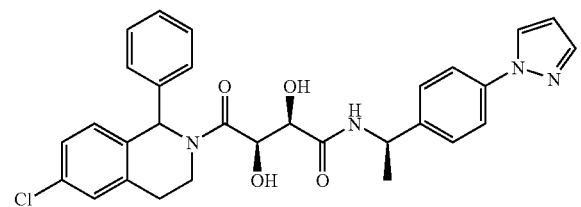
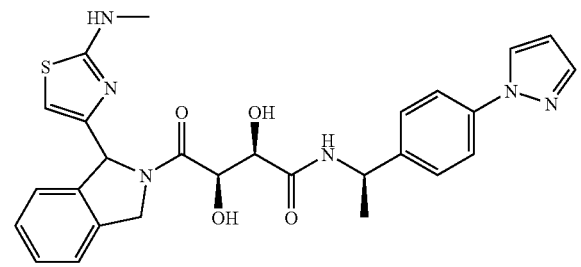
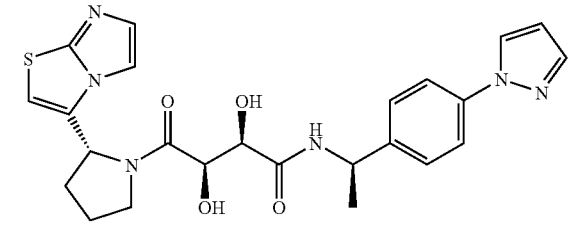
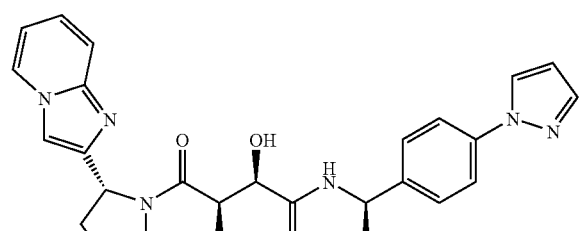
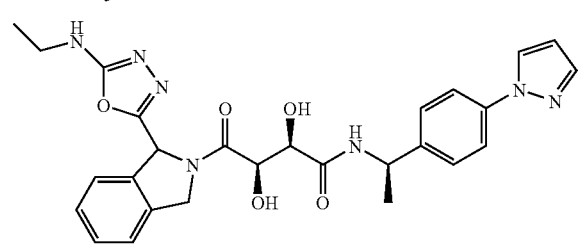
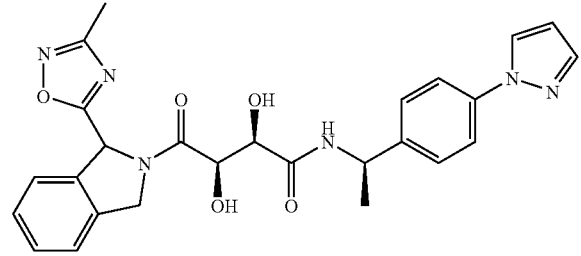
-continued
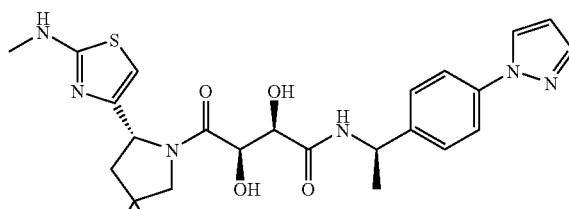
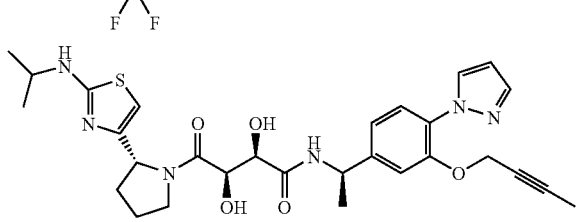
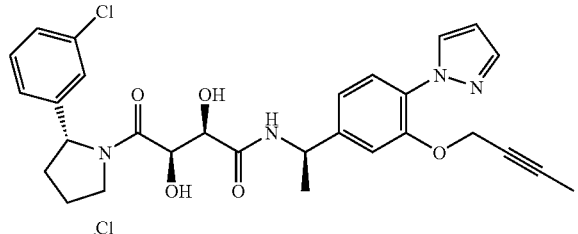
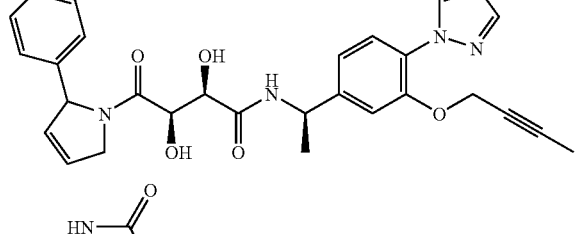
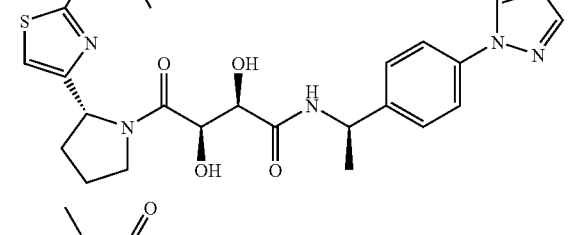
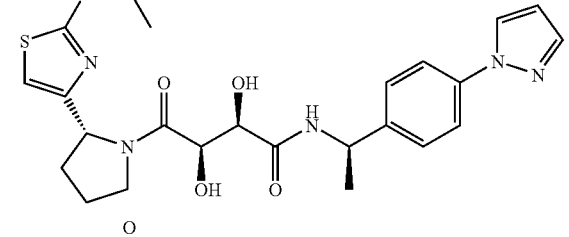
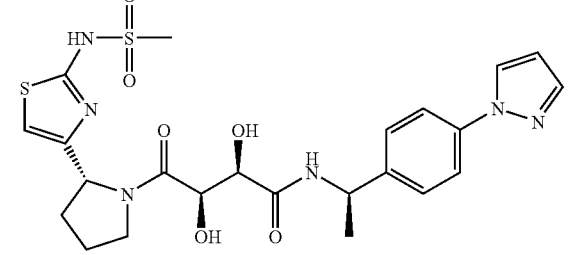

281
-continued
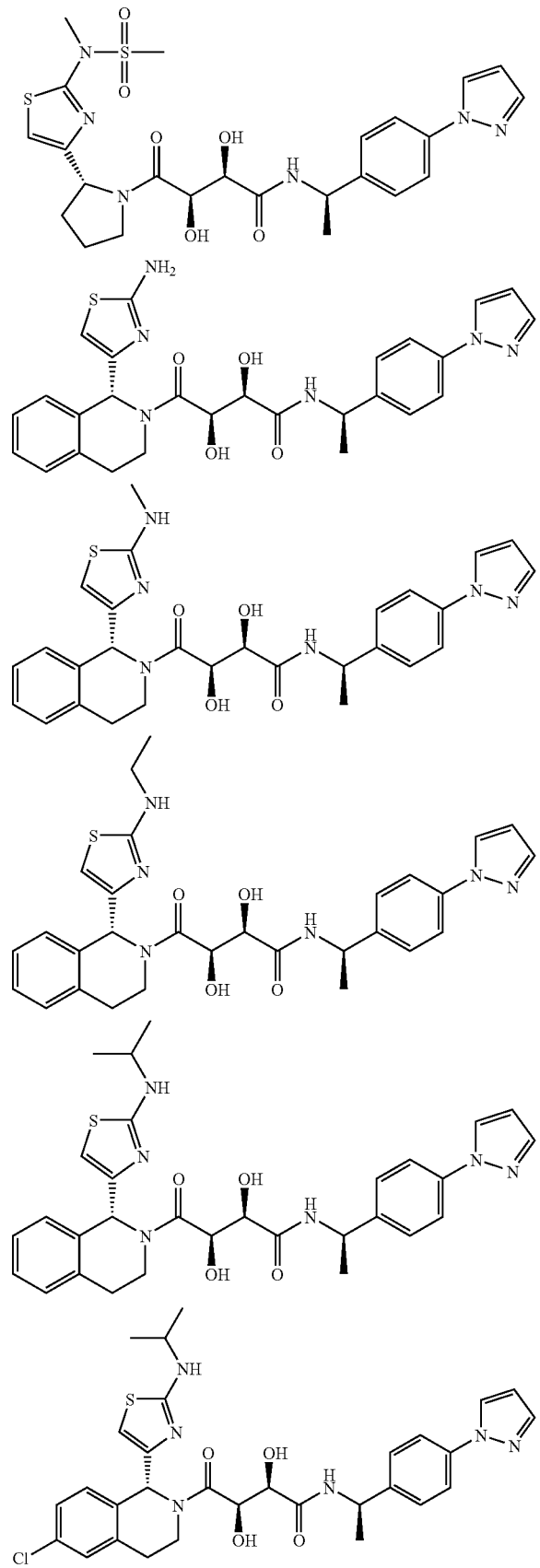
282
-continued
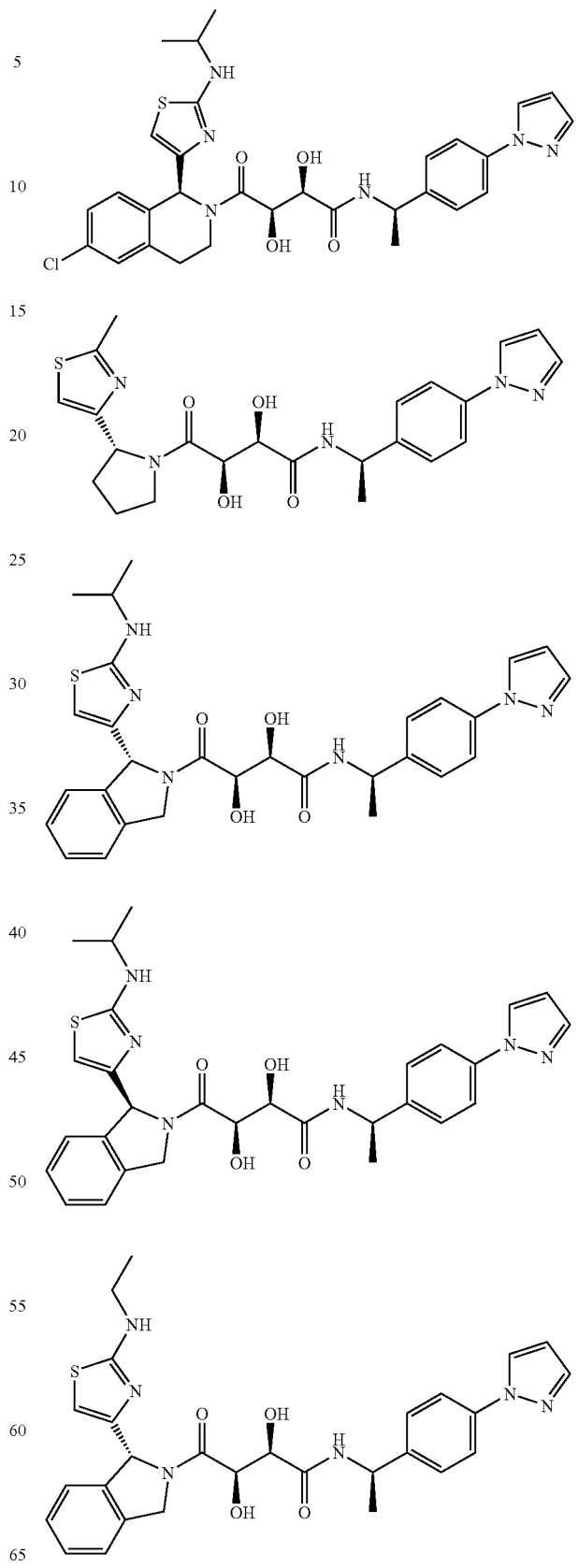

-continued
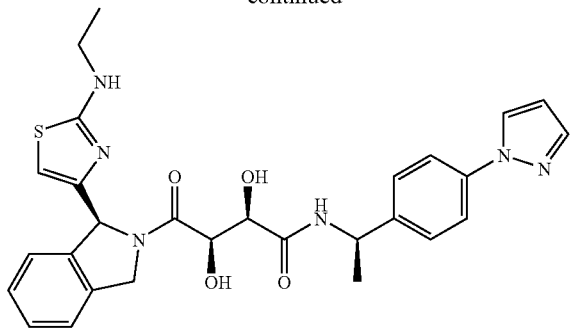
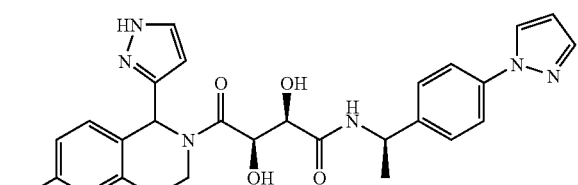
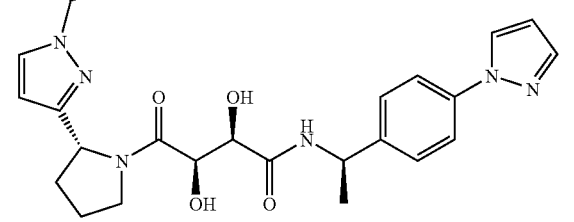
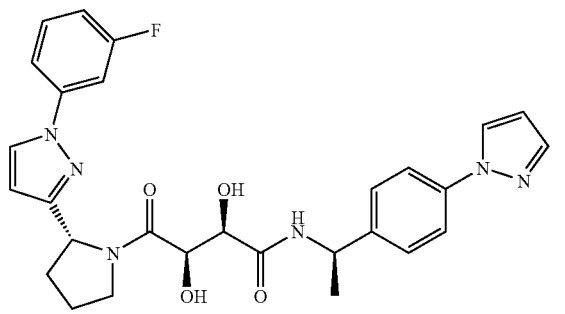
and
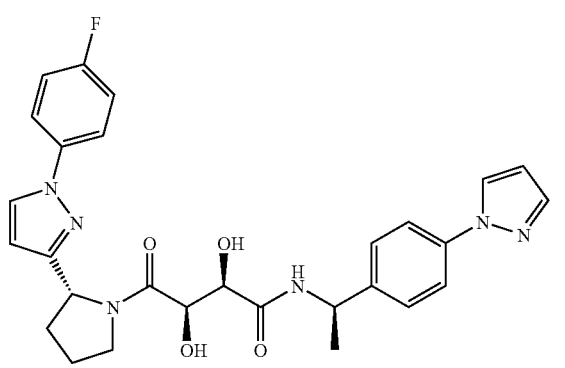
The above preferred compounds have TACE $K_i$ values of less than 20 nM.
In a more preferred embodiment, the compound is selected from the group consting of:
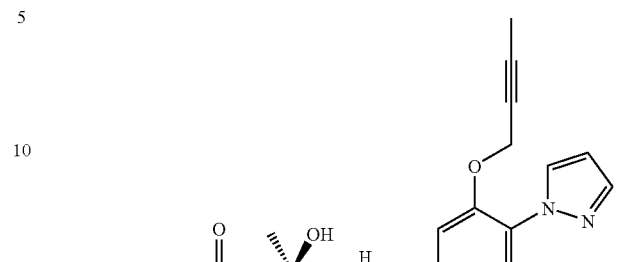
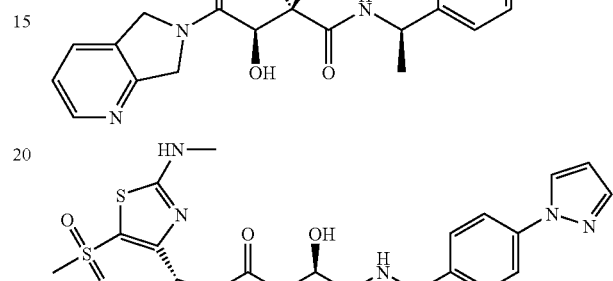
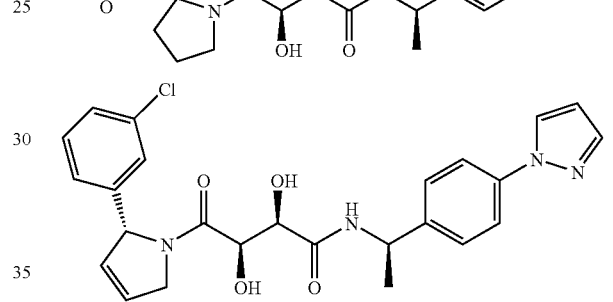
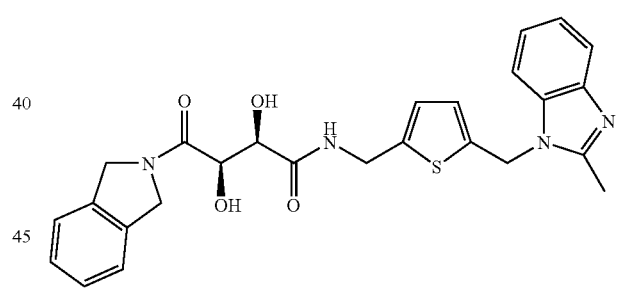
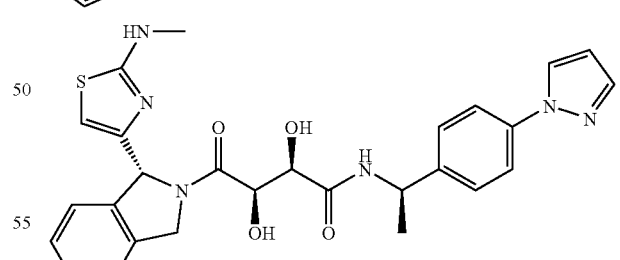
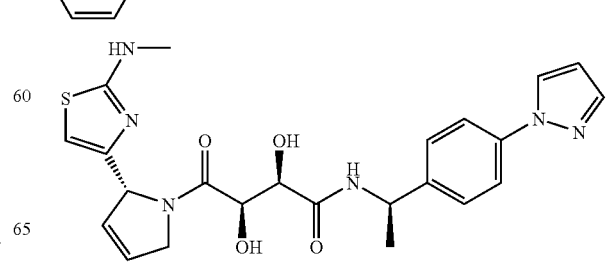

-continued
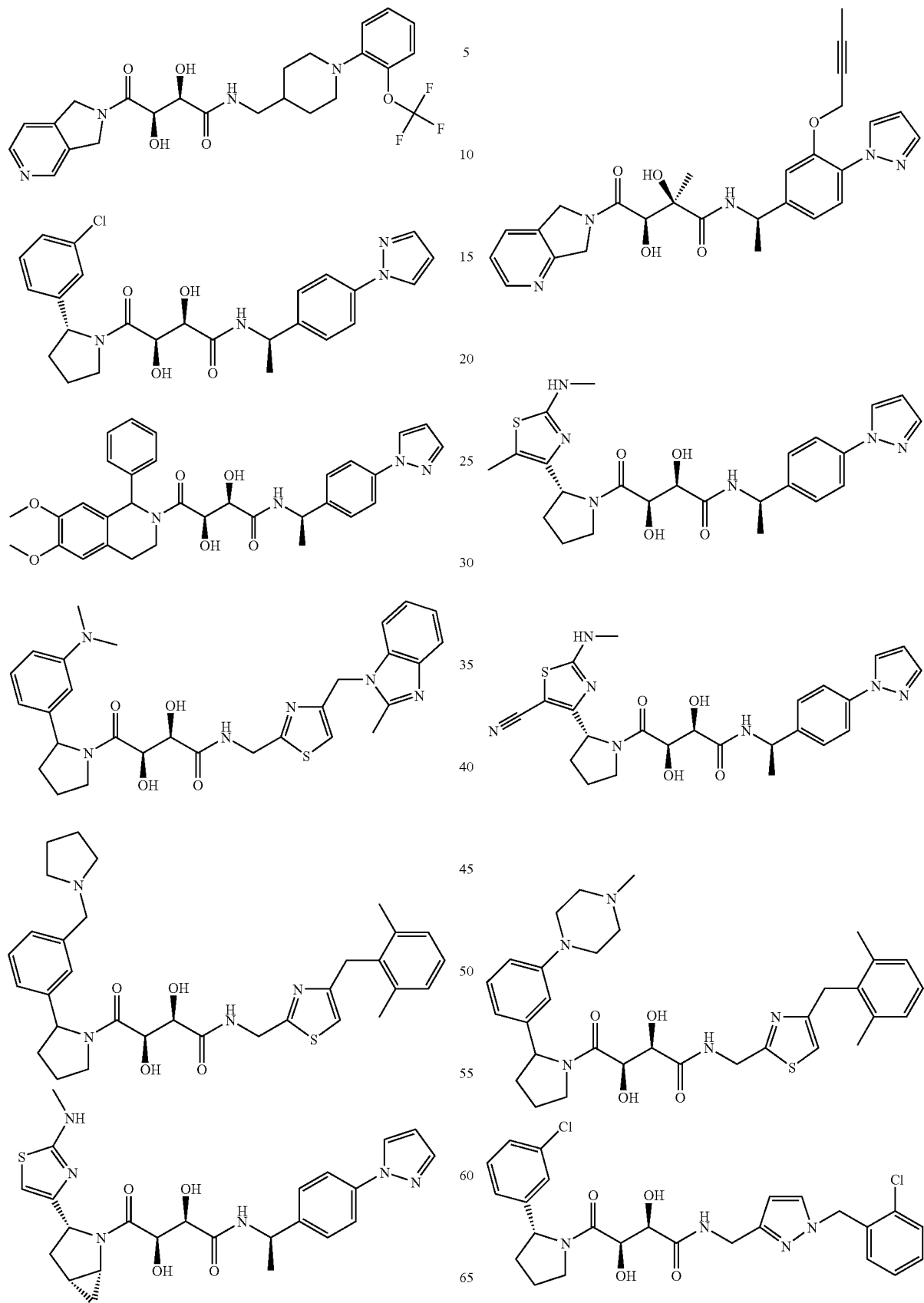

-continued

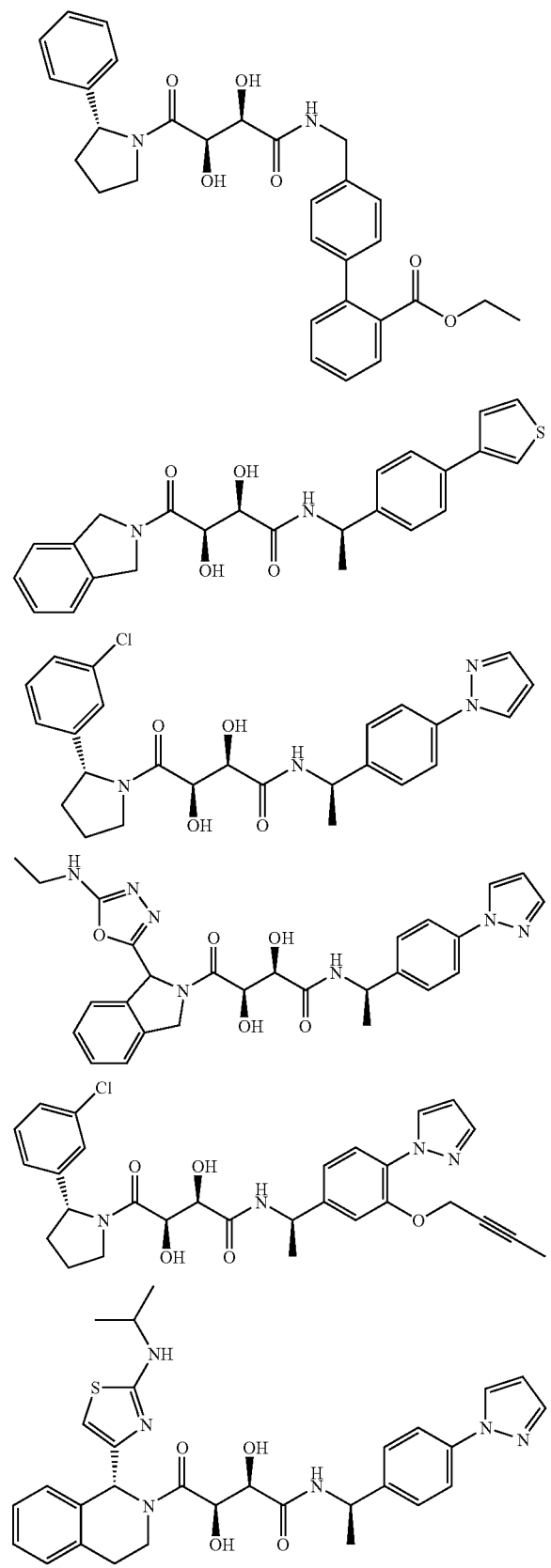

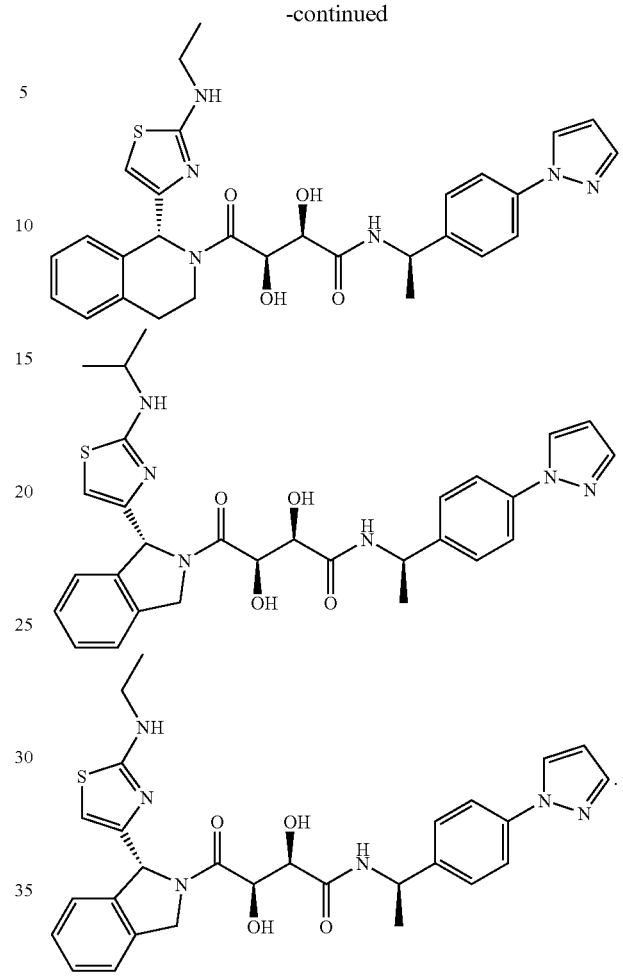

-continued

The above more preferred compounds have TACE $K_i$ values of less than 5 nM.

In another aspect, the invention provides a pharmaceutical composition for treating disorders associated with TACE, TNF-α, MMP, ADAM or any combination thereof in a subject comprising, administering to the subject in need of such treatment a therapeutically effective amount of a compound of formula 1 or a pharmaceutically acceptable salt, solvate or isomer thereof.

In another aspect, the invention provides a compound of formula 1 in purified form.

In another aspect, the invention provides a method of treating a condition or disease mediated by TACE, MMPs, TNF-α, aggrecanase (such as aggrecanase 1 or aggrecanase 2), or any combination thereof in a subject comprising: administering to the subject in need of such treatment a therapeutically effective amount of at least one compound of formula 1 or a pharmaceutically acceptable salt, solvate or isomer thereof.

In another aspect, the invention provides a method of treating a condition or disease selected from the group consisting of rheumatoid arthritis, osteoarthritis, periodontitis, gingivitis, corneal ulceration, solid tumor growth and tumor invasion by secondary metastases, neovascular glaucoma, inflammatory bowel disease, multiple sclerosis and psoriasis in a subject, comprising: administering to the subject in need of such treatment a therapeutically effective amount of at least one compound of formula 1 or a pharmaceutically acceptable salt, solvate or isomer thereof.

In another aspect, the invention provides a method of treating a condition or disease selected from the group consisting of fever, cardiovascular conditions, hemorrhage, coagulation, cachexia, anorexia, alcoholism, acute phase response, acute infection, shock, graft versus host reaction, autoimmune disease and HIV infection in a subject comprising administering to the subject in need of such treatment a therapeutically effective amount of at least one compound of formula 1 or a pharmaceutically acceptable salt, solvate or isomer thereof.

In another aspect, the invention provides a method of treating a condition or disease selected from the group consisting of septic shock, haemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitis, osteo and rheumatoid arthritis, ankylosing spondylitis, psoriatic arthritis, adult Still's disease, ureitis, Wegener's granulomatosis, Behcehe disease, Sjogren's syndrome, sarcoidosis, polymyositis, dermatomyositis, multiple sclerosis, sciatica, complex regional pain syndrome, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, reversible airway obstruction, adult respiratory distress syndrome, asthma, chronic obstructive pulmonary disease (COPD) and bronchitis in a subject comprising administering to the subject in need of such treatment a therapeutically effective amount of at least one compound of formula 1 or a pharmaceutically acceptable salt, solvate or isomer thereof.

In another aspect, the invention provides a method of treating a condition or disease associated with COPD, comprising: administering to the subject in need of such treatment a therapeutically effective amount of at least one compound of claim 1 or a pharmaceutically acceptable salt, solvate or isomer thereof.

In another aspect, the invention provides a method of treating a condition or disease associated with rheumatoid arthritis, comprising: administering to the subject in need of such treatment a therapeutically effective amount of at least one compound of formula 1 or a pharmaceutically acceptable salt, solvate or isomer thereof.

In another aspect, the invention provides a method of treating a condition or disease associated with Crohn's disease, comprising: administering to the subject in need of such treatment a therapeutically effective amount of at least one compound of formula 1 or a pharmaceutically acceptable salt, solvate or isomer thereof.

In another aspect, the invention provides a method of treating a condition or disease associated with psoriasis, comprising: administering to the subject in need of such treatment a therapeutically effective amount of at least one compound of formula 1 or a pharmaceutically acceptable salt, solvate or isomer thereof.

In another aspect, the invention provides a method of treating a condition or disease associated with ankylosing spondylitis, comprising: administering to the subject in need of such treatment a therapeutically effective amount of at least one compound of formula 1 or a pharmaceutically acceptable salt, solvate or isomer thereof.

In another aspect, the invention provides a method of treating a condition or disease associated with sciatica, comprising: administering to the subject in need of such treatment a therapeutically effective amount of at least one compound of formula 1 or a pharmaceutically acceptable salt, solvate or isomer thereof.

In another aspect, the invention provides a method of treating a condition or disease associated with complex regional pain syndrome, comprising: administering to the subject in need of such treatment a therapeutically effective amount of at least one compound of formula 1 or a pharmaceutically acceptable salt, solvate or isomer thereof.

In another aspect, the invention provides a method of treating a condition or disease associated with psoriatic arthritis, comprising: administering to the subject in need of such treatment a therapeutically effective amount of at least one compound of formula 1 or a pharmaceutically acceptable salt, solvate or isomer thereof.

In another aspect, the invention provides a method of treating a condition or disease associated with multiple sclerosis, comprising: administering to the subject in need of such treatment a therapeutically effective amount of at least one compound of formula 1 or a pharmaceutically acceptable salt, solvate or isomer thereof, in combination with a compound selected from the group consisting of Avonex®, Betaseron, Copaxone or other compounds indicated for the treatment of multiple sclerosis.

Additionally, a compound of the present invention may be co-administered or used in combination with disease-modifying antirheumatic drugs (DMARDS) such as methotrexate, azathioprine, leflunomide, pencillinamine, gold salts, mycophenolate mofetil, cyclophosphamide and other similar drugs. They may also be co-administered with or used in combination with NSAIDS such as piroxicam, naproxen, indomethacin, ibuprofen and the like; COX-2 selective inhibitors such as Vioxx® and Celebrex®; immunosuppressives such as steroids, cyclosporin, Tacrolimus, rapamycin and the like; biological response modifiers (BRMs) such as Enbrel®, Remicade®, IL-1 antagonists, anti-CD40, anti-CD28, IL-10, anti-adhesion molecules and the like; and other anti-inflammatory agents such as p38 kinase inhibitors, PDE4 inhibitors, other chemically different TACE inhibitors, chemokine receptor antagonists, Thalidomide and other small molecule inhibitors of pro-inflammatory cytokine production.

Also, a compound of the present invention may be co-administered or used in combination with an H1 antagonist for the treatment of seasonal allergic rhinitis and/or asthma. Suitable H1 antagonists may be, for example, Claritin®, Clarinex®D, Allegra®, or Zyrtec®.

In another aspect, the invention provides a method of treating a condition or disease mediated by TACE, MMPs, TNF-α, aggrecanase, or any combination thereof in a subject comprising: administering to the subject in need of such treatment a therapeutically effective amount of at least one compound of formula 1 or a pharmaceutically acceptable salt, solvate or isomer thereof in combination with a therapeutically effective amount of at least one medicament selected from the group consisting of disease modifying anti-rheumatic drugs (DMARDS), NSAIDs, COX-2 inhibitors, COX-1 inhibitors, immunosuppressives, biological response modifiers (BRMs), anti-infammatory agents and H1 antagonists.

In another aspect, the invention provides a method of treating a condition or disease selected from the group consisting of rheumatoid arthritis, osteoarthritis, periodontitis, gingivitis, corneal ulceration, solid tumor growth and tumor invasion by secondary metastases, neovascular glaucoma, inflammatory bowel disease, multiple sclerosis and psoriasis in a subject, comprising: administering to the subject in need of such treatment a therapeutically effective amount of at least one compound of claim 1 or a pharmaceutically acceptable salt, solvate or isomer thereof in combination with a therapeutically effective amount of at least one medicament selected from the group consisting of DMARDS, NSAIDs, COX-2 inhibitors, COX-1 inhibitors, immunosuppressives, BRMs, anti-infammatory agents and H1 antagonists.

In another aspect, the invention provides a method of treating a condition or disease selected from the group consisting of septic shock, haemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitis, osteo and rheumatoid arthritis, ankylosing spondylitis, psoriatic arthritis, adult Still's disease, ureitis, Wegener's granulomatosis, Behcehe disease, Sjogren's syndrome, sarcoidosis, polymyositis, dermatomyositis, multiple sclerosis, sciatica, complex regional pain syndrome, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, reversible airway obstruction, adult respiratory distress syndrome, asthma, chronic obstructive pulmonary disease (COPD) and bronchitis in a subject comprising administering to the subject in need of such treatment a therapeutically effective amount of at least one compound of claim 1 or a pharmaceutically acceptable salt, solvate or isomer thereof in combination with a therapeutically effective amount of at least one medicament selected from the group consisting of DMARDs, NSAIDs, COX-2 inhibitors, COX-1 inhibitors, immunosuppressives, BRMs, anti-infammatory agents and H1 antagonists.

In another aspect, the invention provides a method for treating RA comprising administering a compound of the formula I in combination with compound selected from the class consisting of a COX-2 inhibitor e.g. Celebrex® or Vioxx®; a COX-1 inhibitor e.g. Feldene®; an immunosuppressive e.g. methotrexate or cyclosporin; a steroid e.g. β-methasone; and anti-TNF-α compound, e.g. Enbrel® or Remicade®; a PDE IV inhibitor, or other classes of compounds indicated for the treatment of RA.

In another aspect, the invention provides a method for treating multiple sclerosis comprising administering a compound of the formula I in combination with a compound selected from the group consisting of Avonex®, Betaseron, Copaxone or other compounds indicated for the treatment of multiple sclerosis.

TACE activity is determined by a kinetic assay measuring the rate of increase in fluorescent intensity generated by TACE catalyzed cleavage of an internally quenched peptide substrate (SPDL-3). The purified catalytic domain of recombinant human TACE (rhTACEc, Residue 215 to 477 with two mutation (S266A and N452Q) and a 6×His tail) is used in the assay. It is purified from the baculovirus/Hi5 cells expression system using affinity chromatography. The substrate SPDL-3 is an internally quenched peptide (MCA-Pro-Leu-Ala-Gln-Ala-Val-Arg-Ser-Ser-Ser-Dpa-Arg-NH2), with its sequence derived from the pro-TNFα cleavage site. MCA is (7-Methoxycoumarin-4-yl)acetyl. Dpa is N-3-(2,4-Dinitrophenyl)-L-2,3-diaminopropionyl.

A 50 µl assay mixture contains 20 mM HEPES, pH 7.3, 5 mM $CaCl_2$, 100 µM $ZnCl_2$, 2% DMSO, 0.04% Methylcellulose, 30 µM SPDL-3, 70 pM rhTACEc and a test compound. RhTACEc is pre-incubated with the testing compound for 90 min. at 25° C. Reaction is started by addition of the substrate. The fluorescent intensity (excitation at 320 nm, emission at 405 nm) was measured every 45 seconds for 30 min. using a fluorospectrometer (GEMINI XS, Molecular Devices). Rate of enzymatic reaction is shown as Units per second. Effect of a test compound is shown as % of TACE activity in the absence of the compound.

TACE inhibitory activities for representative compounds are shown in the table below. $K_i$ values greater than 1000 nM (1 µM) are designated as D class. $K_i$ values between 100 nM (0.1 µM) and 1000 nM (1 µM) are designated as C class. $K_i$ values between 20 nM (0.02 µM) and 100 nM (0.1 µM) are designated as B class. $K_i$ values less than 20 nM (0.02 µM) are designated as A class.

| Compound # | Structure | $K_i$ (nM) |
|---|---|---|
| 5 | 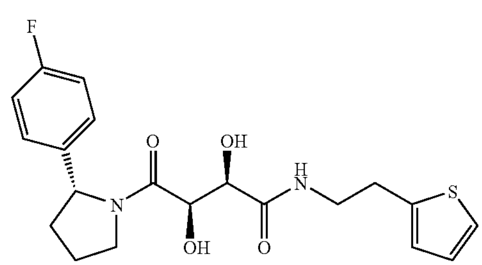 | |

-continued

| Compound # | Structure | $K_i$ (nM) |
|---|---|---|
| 6 | 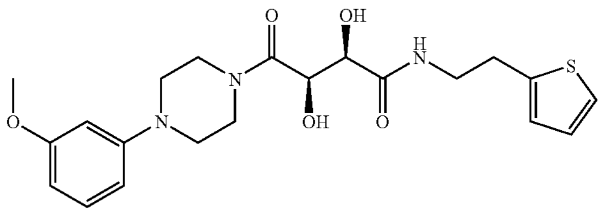 | |
| 7A | 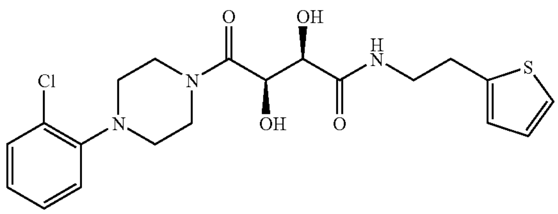 | |
| 7B | 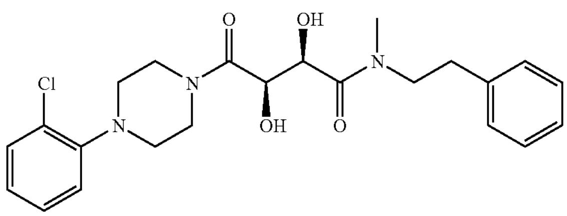 | |
| 8 | 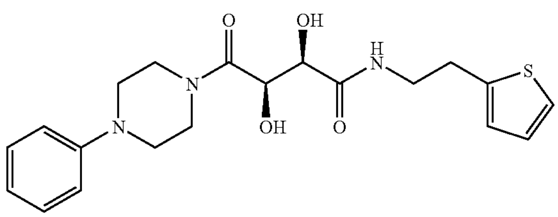 | |
| 9 | 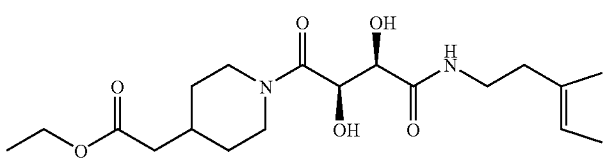 | |
| 10 | 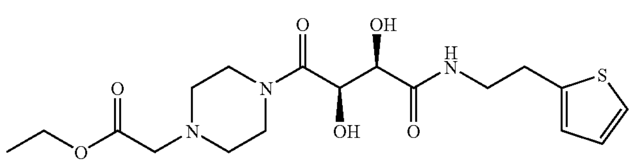 | |
| 11 | 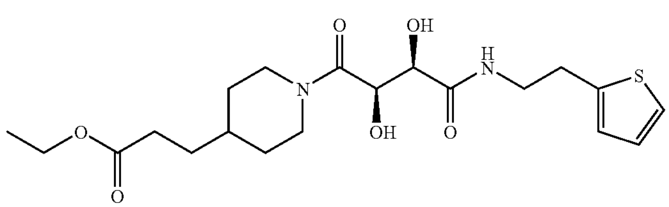 | |

-continued

| Compound # | Structure | $K_i$ (nM) |
|---|---|---|
| 12 | 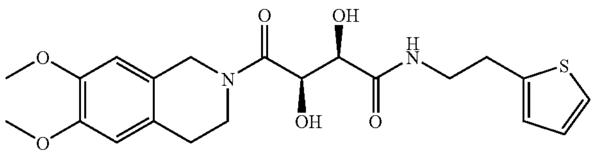 | |
| 13 | 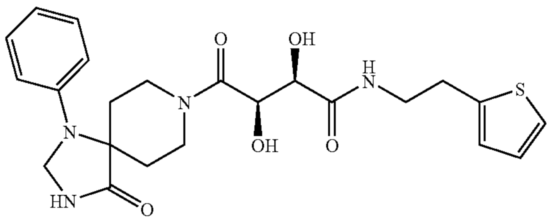 | |
| 14 | 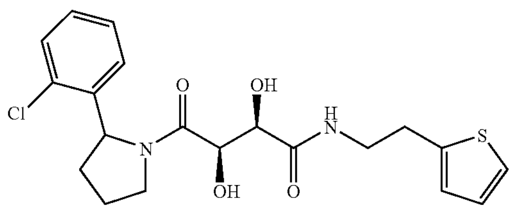 | |
| 15 | 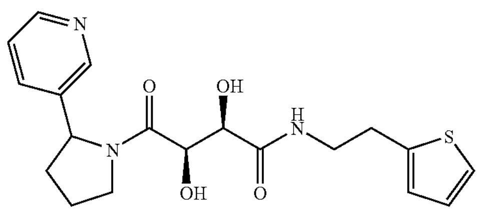 | |
| 16 | 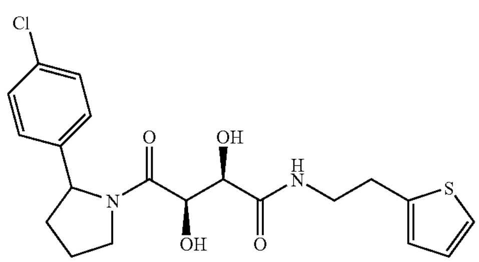 | |
| 17 | 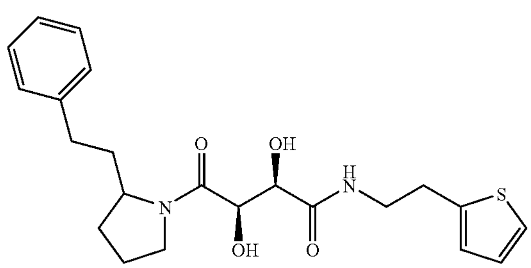 | |
| 18 | 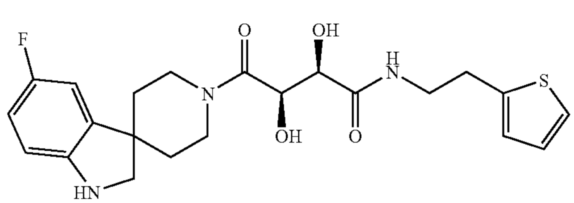 | |

-continued
| Compound # | Structure | $K_i$ (nM) |
|---|---|---|
| 19 | 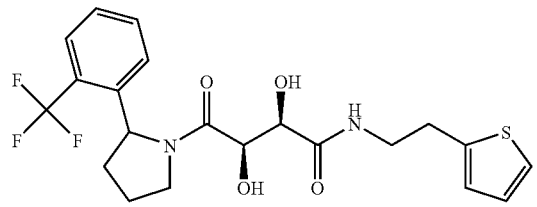 | |
| 20 | 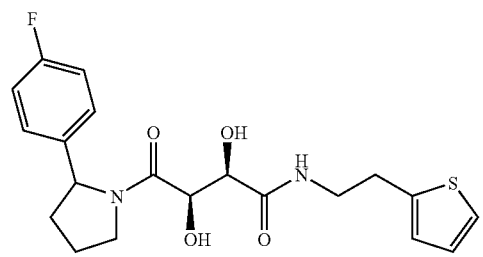 | |
| 21 | 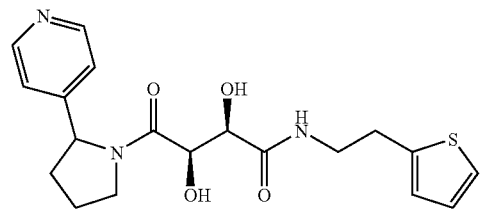 | |
| 22 | 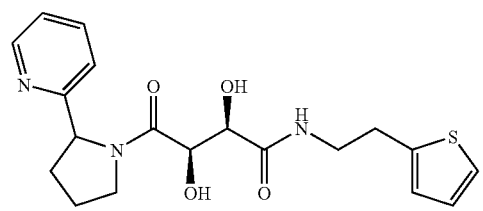 | |
| 23 | 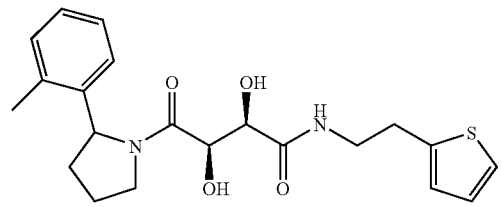 | |
| 24 | 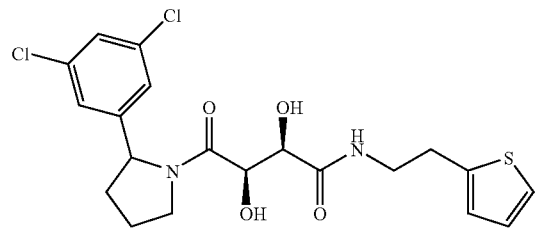 | |

-continued
| Compound # | Structure | $K_i$ (nM) |
|---|---|---|
| 25 | 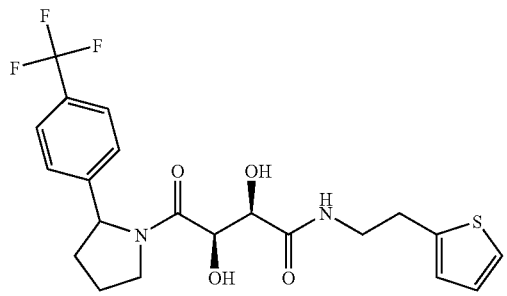 | |
| 26 | 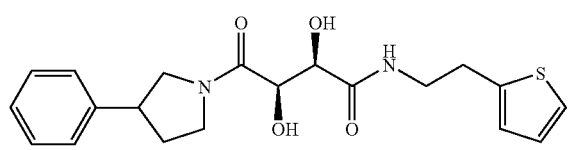 | |
| 27 | 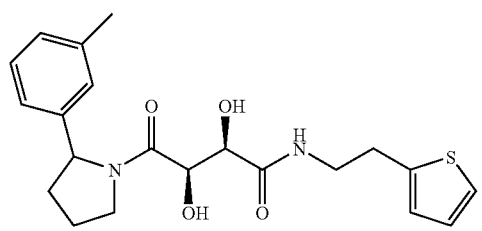 | |
| 28 | 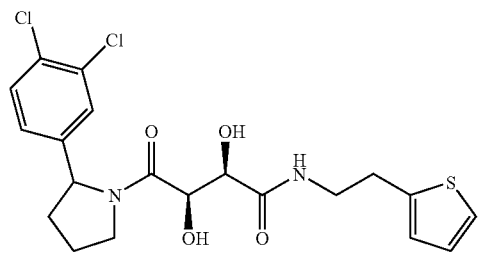 | |
| 29A | 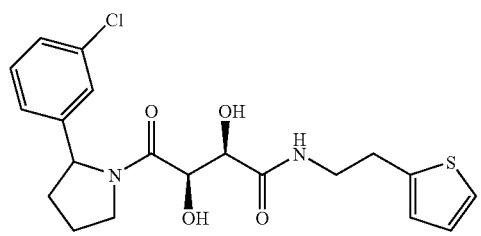 | |
| 29B | 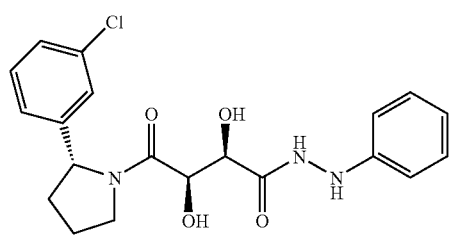 | |

-continued

| Compound # | Structure | $K_i$ (nM) |
|---|---|---|
| 30 | 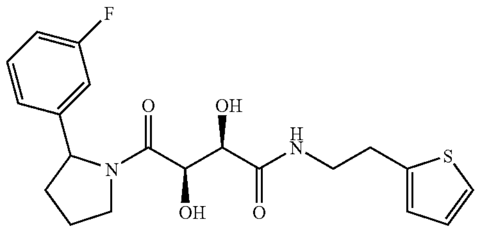 | |
| 31 | 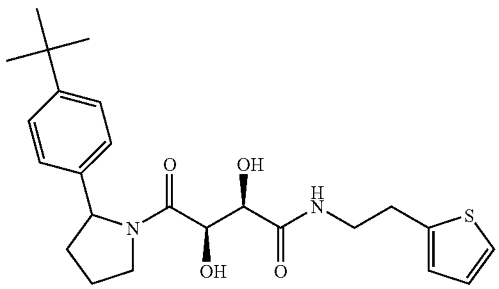 | |
| 32 | 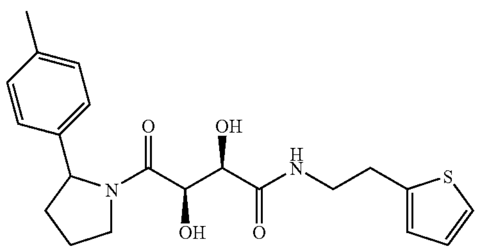 | |
| 33 | 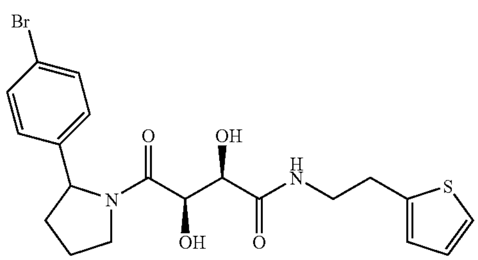 | |
| 34 | 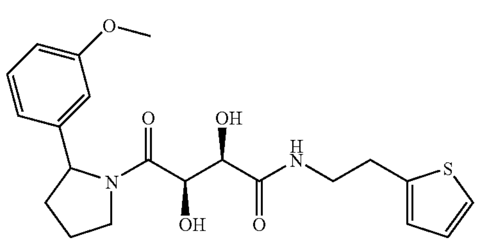 | |
| 35 | 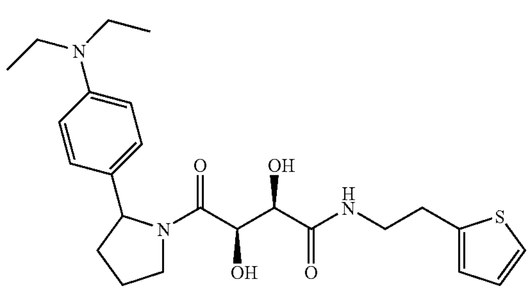 | |

-continued
| Compound # | Structure | $K_i$ (nM) |
|---|---|---|
| 36 | 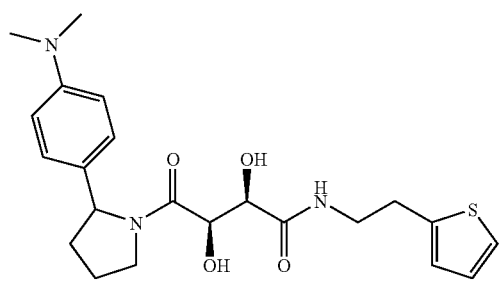 | |
| 37 | 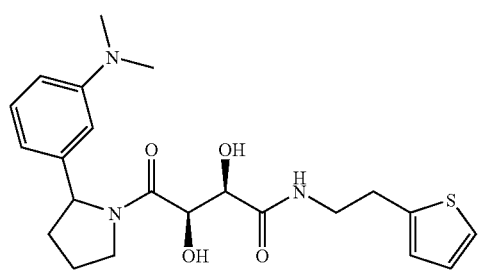 | |
| 38 | 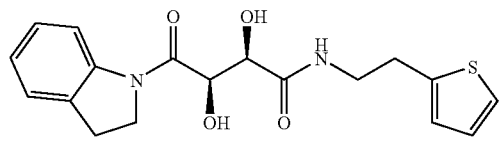 | |
| 39 | 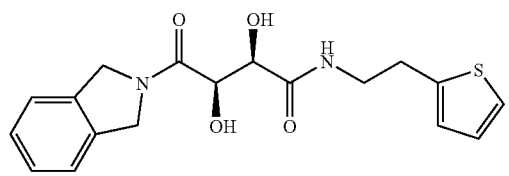 | |
| 40 | 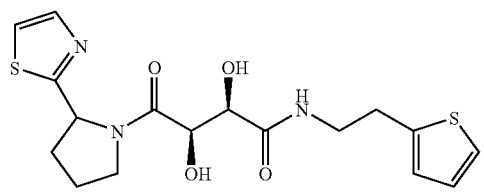 | |
| 41 | 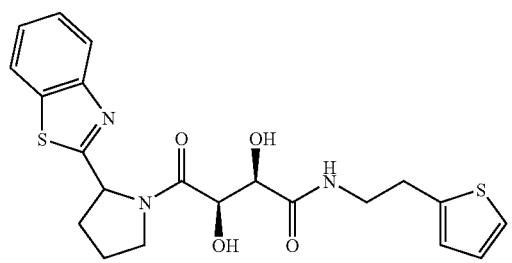 | |

-continued

| Compound # | Structure | $K_i$ (nM) |
|---|---|---|
| 42 | 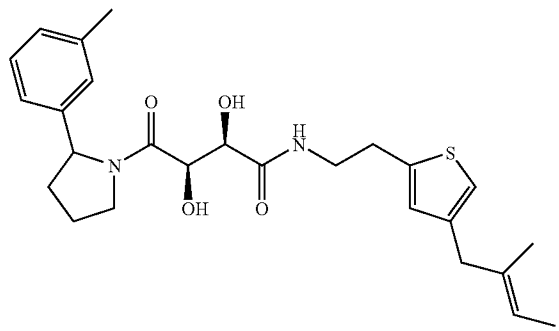 | |
| 43 | 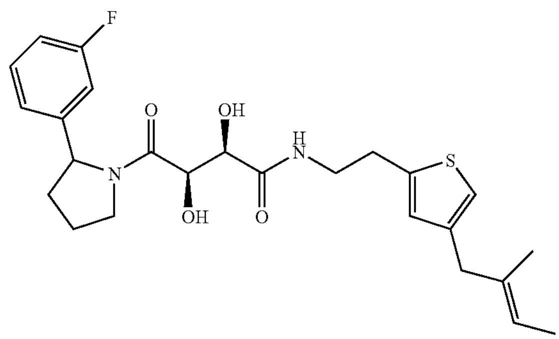 | |
| 44 | 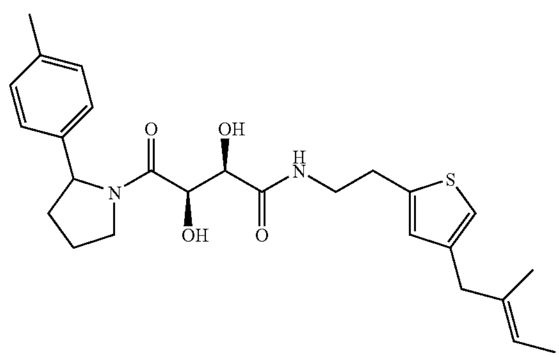 | |
| 46 | 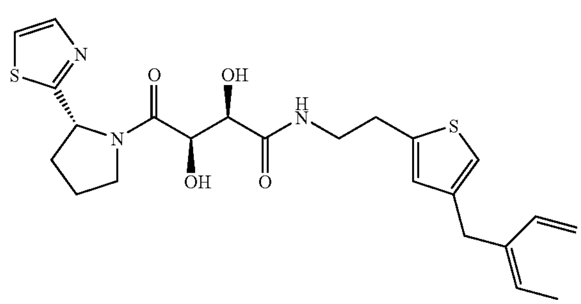 | |

-continued
| Compound # | Structure | $K_i$ (nM) |
|---|---|---|
| 47 | 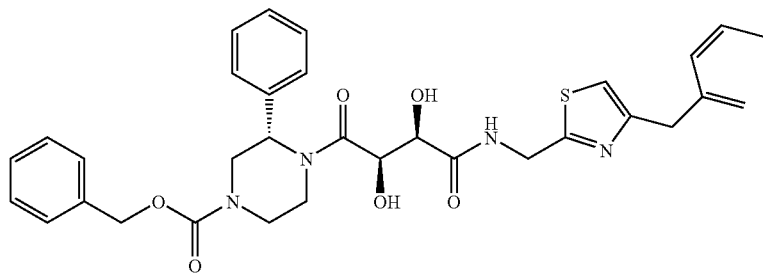 | |
| 50 | 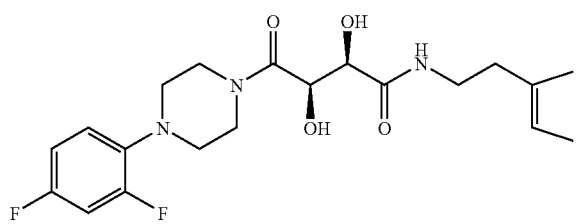 | |
| 52 | 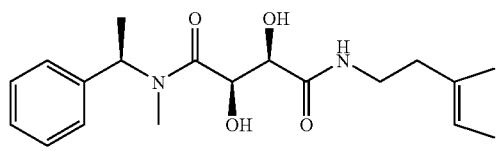 | |
| 55 | 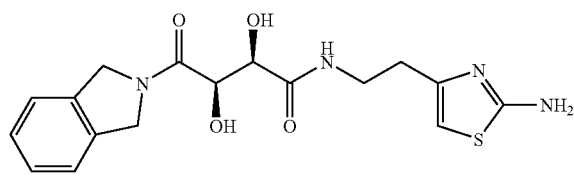 | |
| 56 | 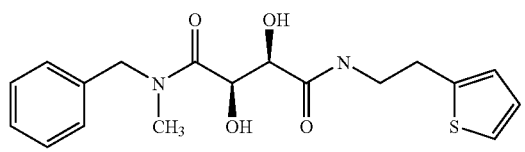 | |
| 57 | 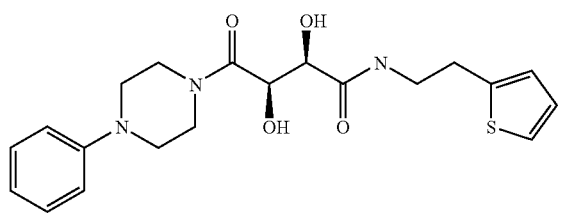 | |
| 58 | 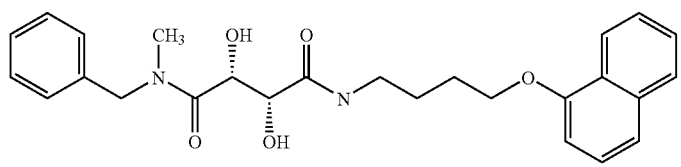 | |

-continued

| Compound # | Structure | $K_i$ (nM) |
|---|---|---|
| 59 | 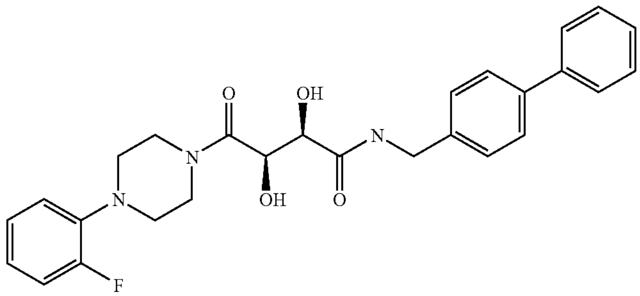 | |
| 60 | 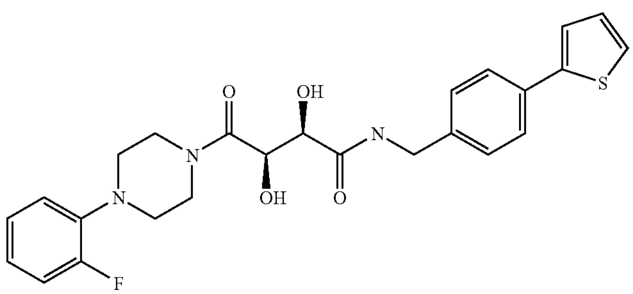 | |
| 61 | 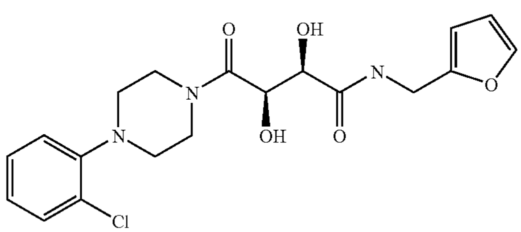 | |
| 62 | 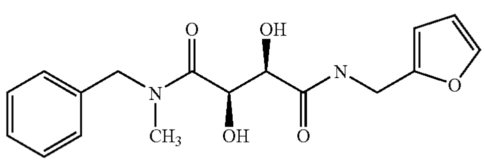 | |
| 63 | 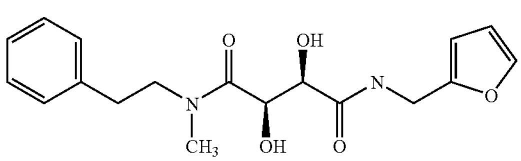 | |
| 64 | 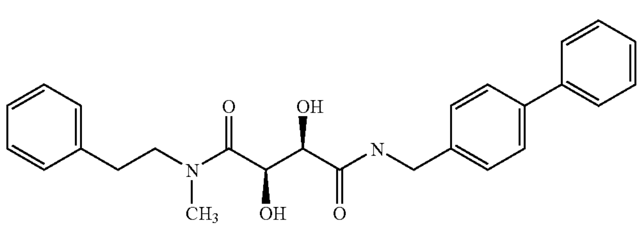 | |

-continued
| Compound # | Structure | $K_i$ (nM) |
|---|---|---|
| 65 | 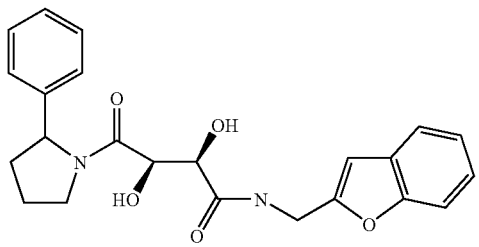 | |
| 66 | 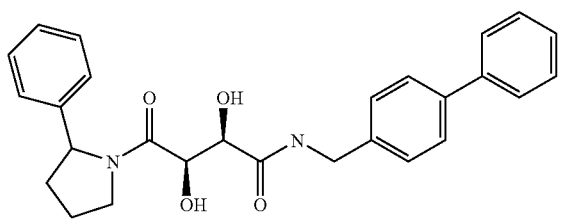 | |
| 67 | 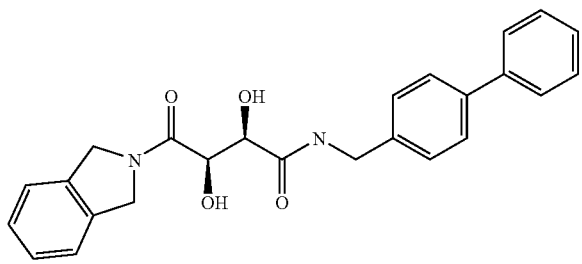 | |
| 68 | 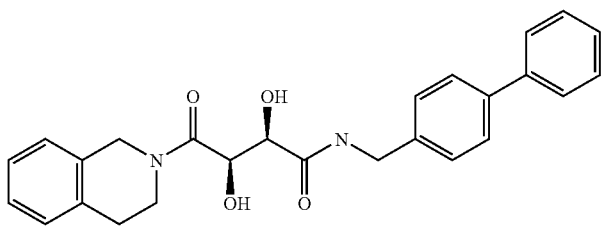 | |
| 69 | 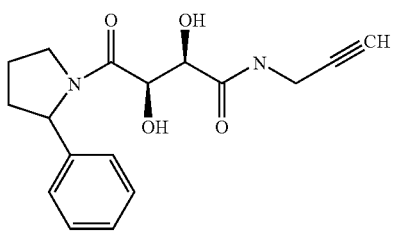 | |
| 70 | 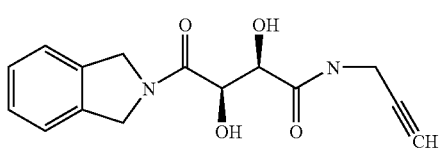 | |

-continued

| Compound # | Structure | $K_i$ (nM) |
|---|---|---|
| 71 | 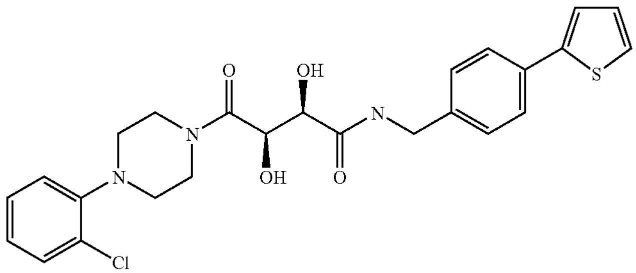 | |
| 72 | 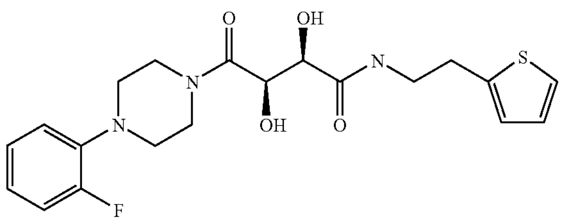 | |
| 73 | 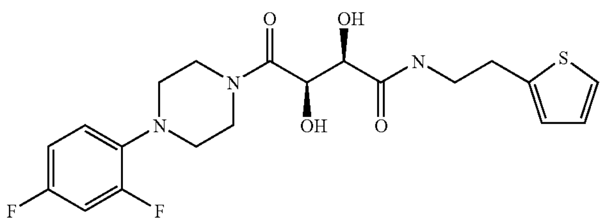 | |
| 74 | 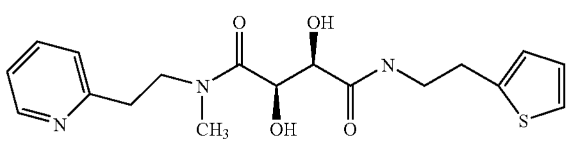 | |
| 75 | 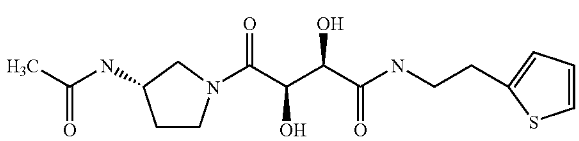 | |
| 76 | 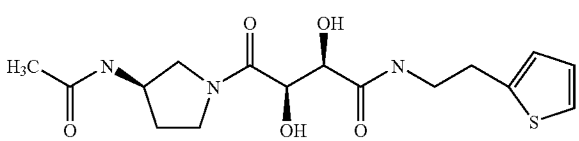 | |
| 77 | 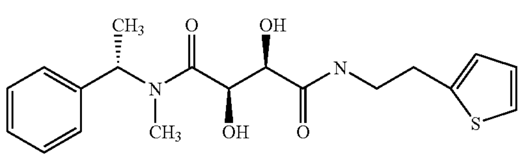 | |
| 78 | 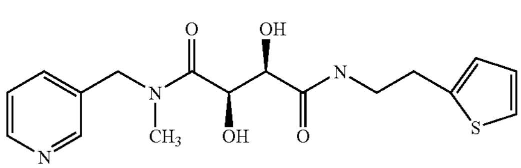 | |

-continued
| Compound # | Structure | $K_i$ (nM) |
|---|---|---|
| 79 | 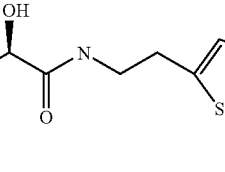 | |
| 80 | 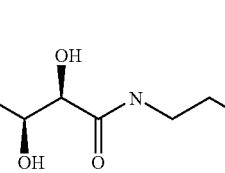 | |
| 81 | 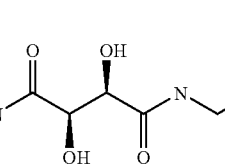 | |
| 82 | 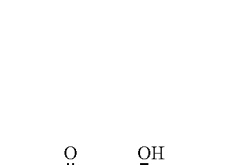 | |
| 83 | 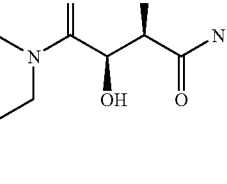 | |
| 84 | 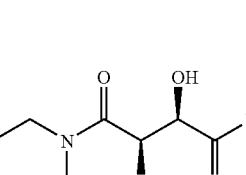 | |

-continued

| Compound # | Structure | $K_i$ (nM) |
|---|---|---|
| 85 | 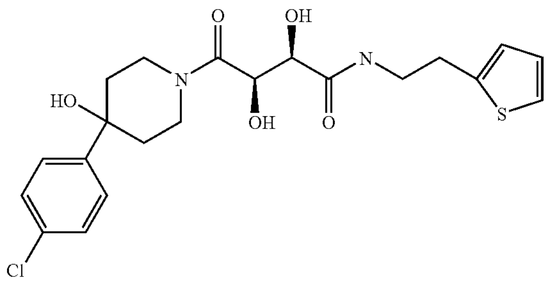 | |
| 86 | 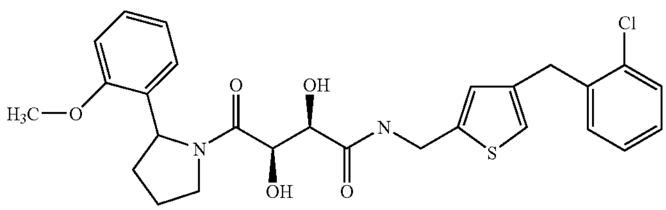 | |
| 87 | 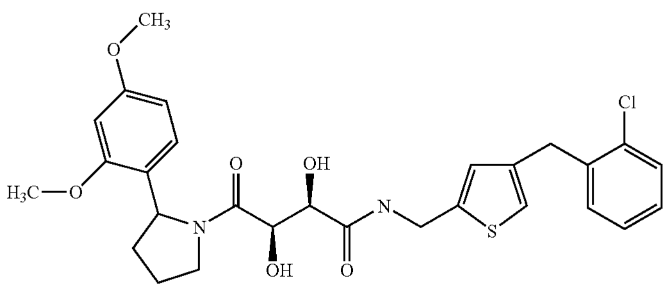 | |
| 88 | 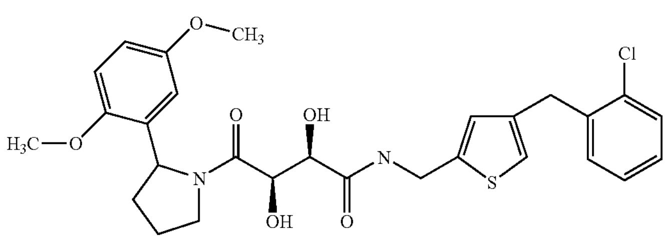 | |
| 89 | 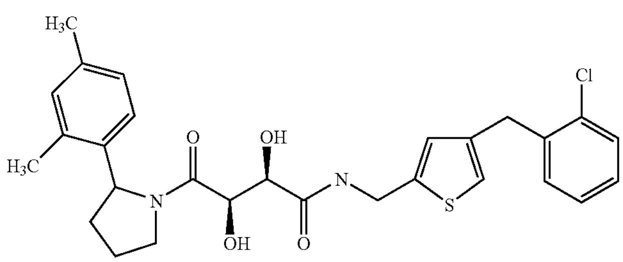 | |
| 90 | 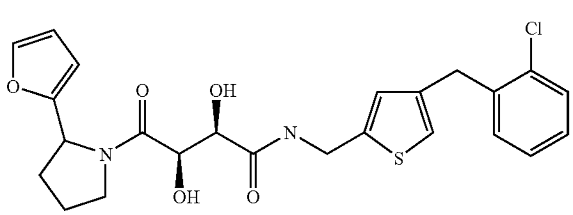 | |

-continued

| Compound # | Structure | $K_i$ (nM) |
|---|---|---|
| 91 | 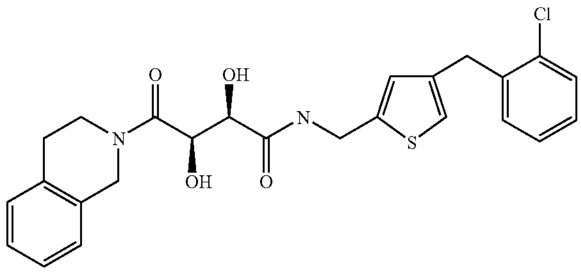 | |
| 92 | 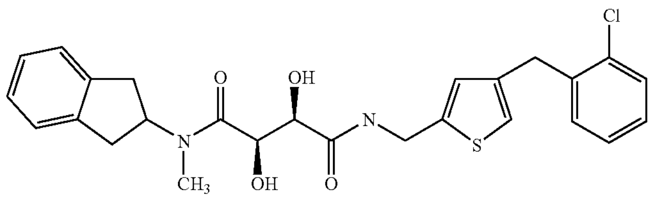 | |
| 93 | 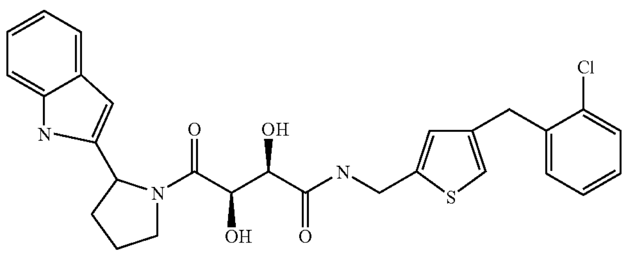 | |
| 94 | 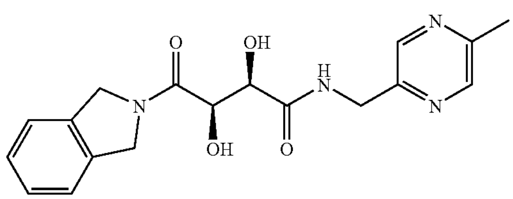 | |
| 95 | 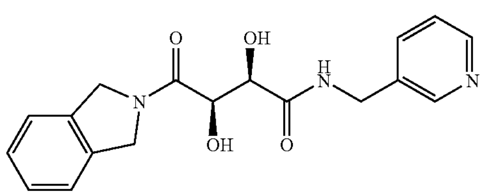 | |
| 96 | 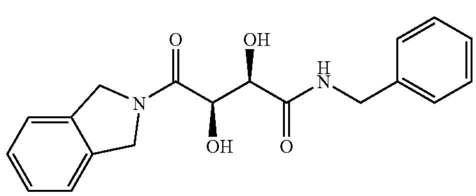 | |
| 97 | 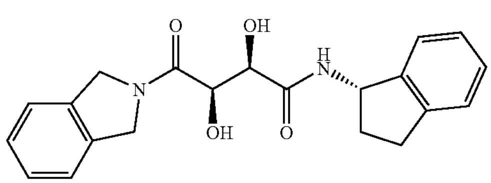 | |

| Compound # | Structure | $K_i$ (nM) |
|---|---|---|
| 98 | 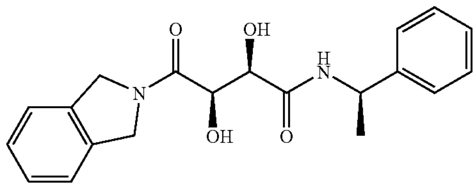 | |
| 99 | 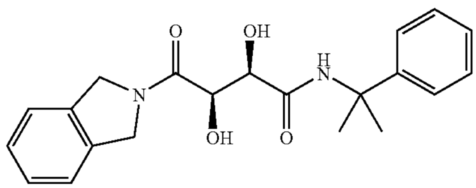 | |
| 100 | 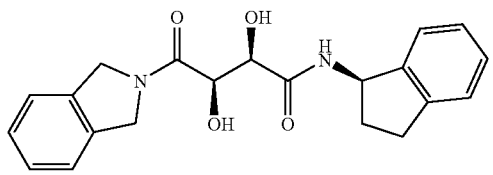 | |
| 101 | 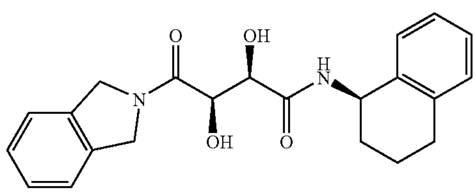 | |
| 102 | 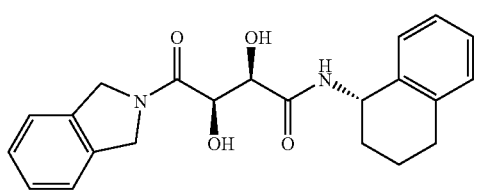 | |
| 103 | 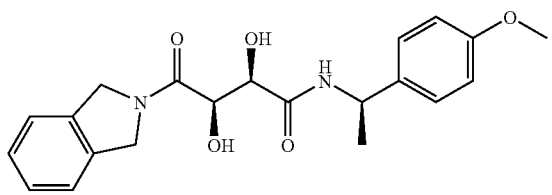 | |
| 104 | 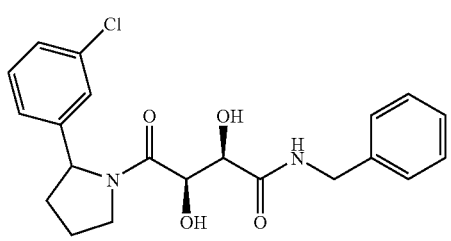 | |

-continued
| Compound # | Structure | $K_i$ (nM) |
|---|---|---|
| 105 | 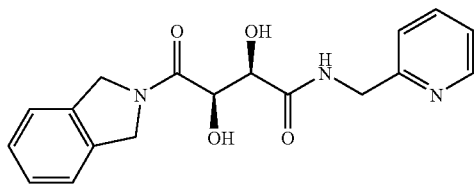 | |
| 108 | 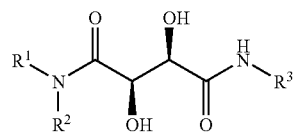<br>(R1 = R2 = CH$_2$Ph, R3 = CH$_2$CH$_2$(C$_4$H$_4$O)) | |
| 109 | 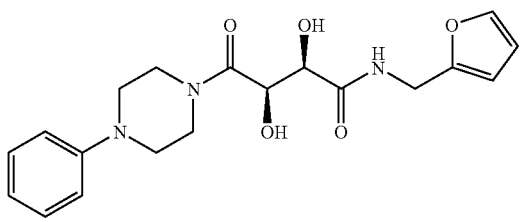 | |
| 110 | 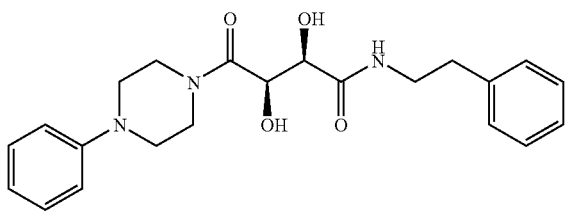 | |
| 111 | 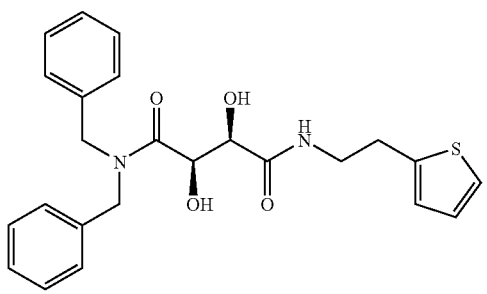 | |
| 112 | 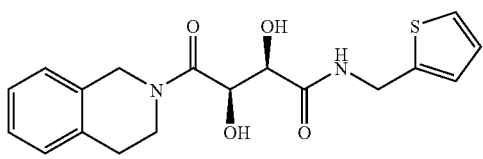 | |
| 113 | 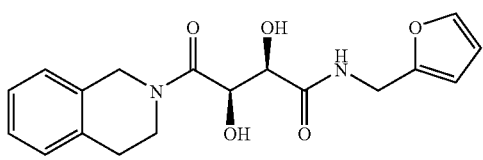 | |

| Compound # | Structure | $K_i$ (nM) |
|---|---|---|
| 114 | 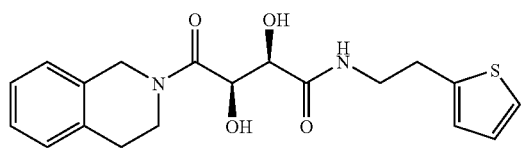 | |
| 115 | 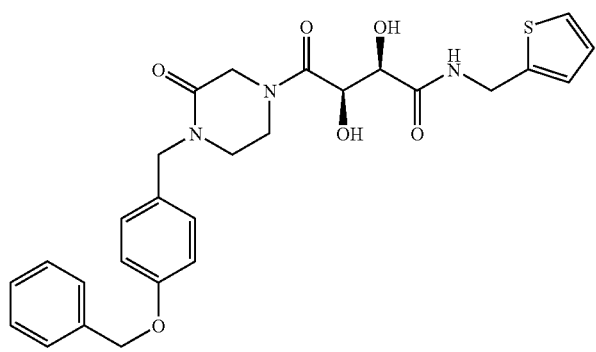 | |
| 116 | 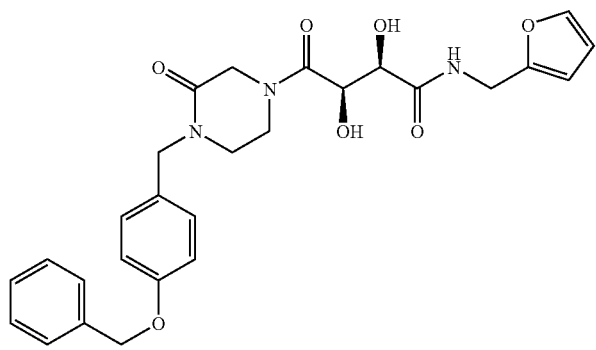 | |
| 117 | 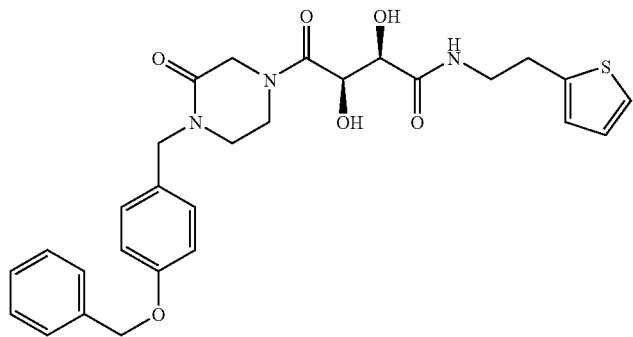 | |
| 118A | 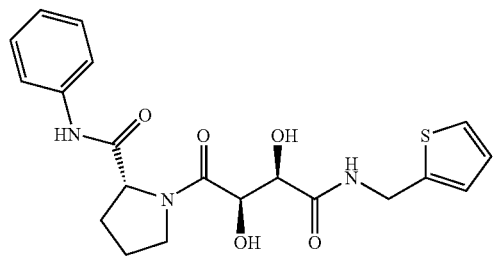 | |

| Compound # | Structure | K$_i$ (nM) |
|---|---|---|
| 118B | 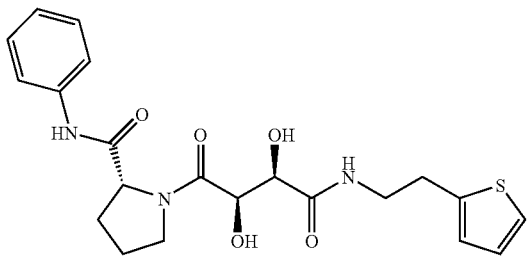 | |
| 119 | 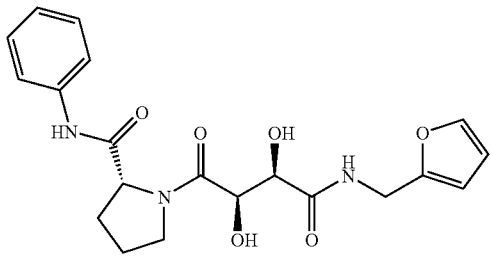 | |
| 120 | 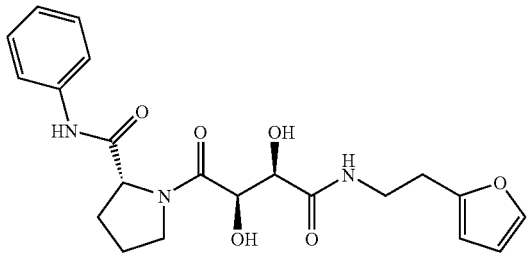 | |
| 121 | 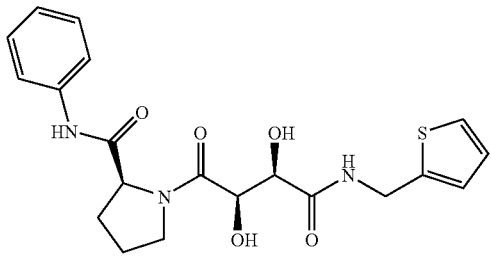 | |
| 122 | 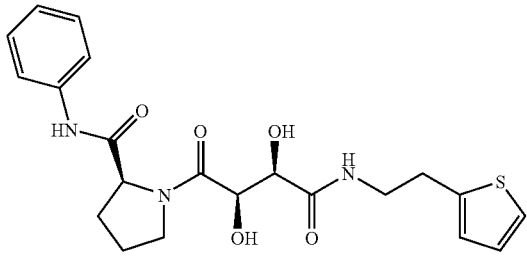 | |

| Compound # | Structure | $K_i$ (nM) |
|---|---|---|
| 123 | 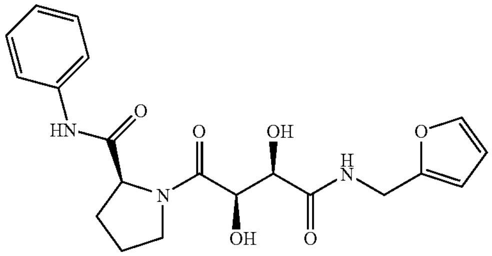 | |
| 124 | 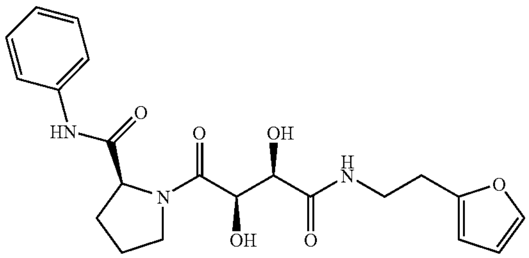 | |
| 108 | 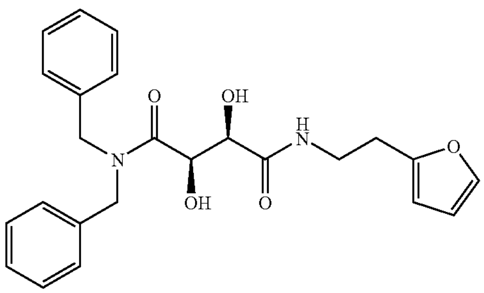 | |
| 125 | 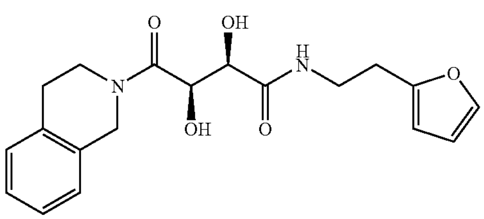 | |
| 38 | 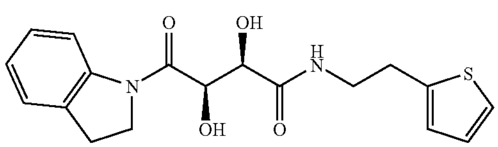 | |
| 39 | 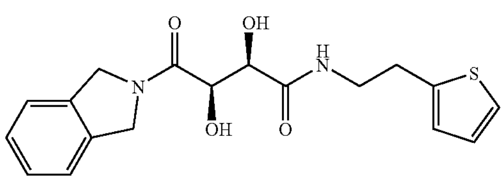 | |
| 126 | 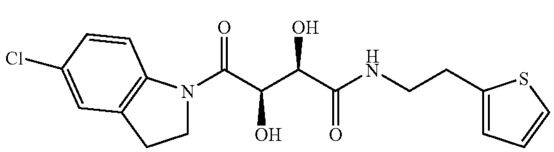 | |

| Compound # | Structure | $K_i$ (nM) |
|---|---|---|
| 127 | 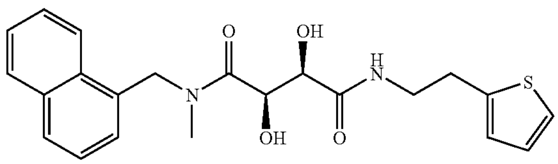 | |
| 128 | 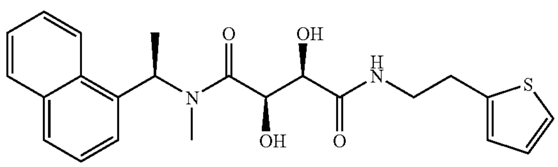 | |
| 129 | 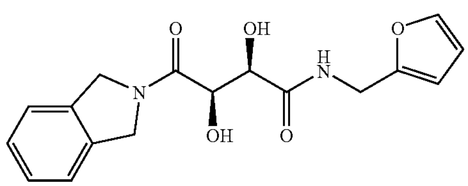 | |
| 130 | 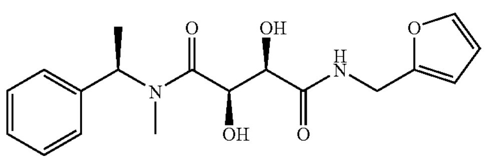 | |
| 131 | 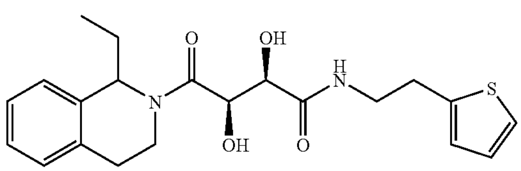 | |
| 132 | 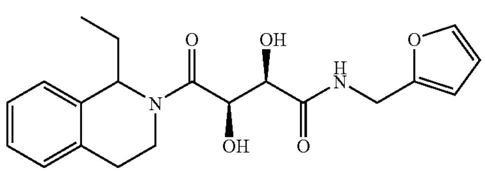 | |
| 133 | 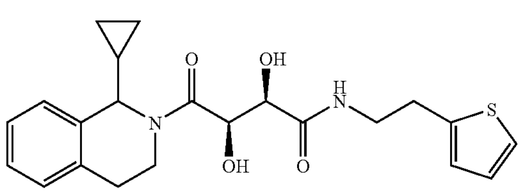 | |
| 134 | 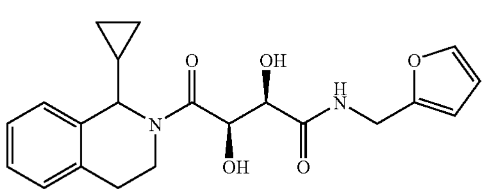 | |

-continued
| Compound # | Structure | $K_i$ (nM) |
|---|---|---|
| 135 | 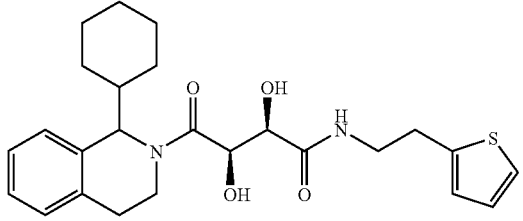 | |
| 136 | 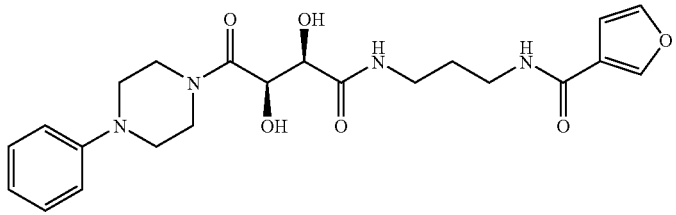 | |
| 137 | 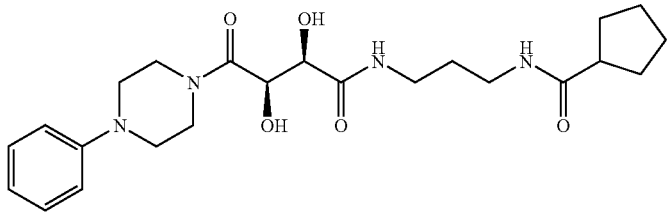 | |
| 138 | 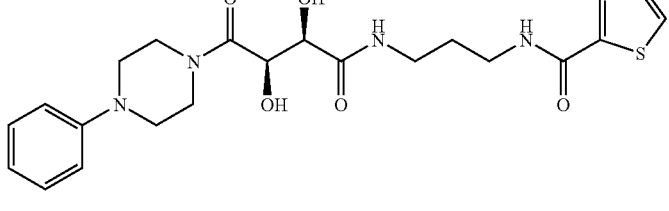 | |
| 139 | 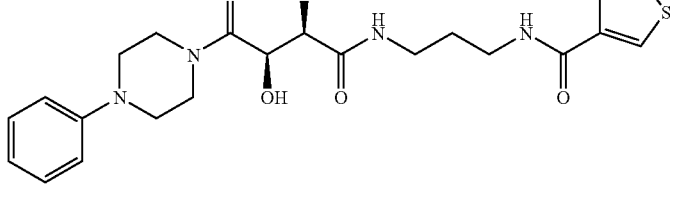 | |
| 140 | 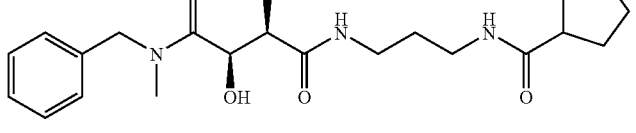 | |
| 141 | 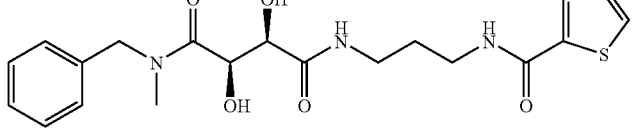 | |

-continued

| Compound # | Structure | K$_i$ (nM) |
|---|---|---|
| 142 | 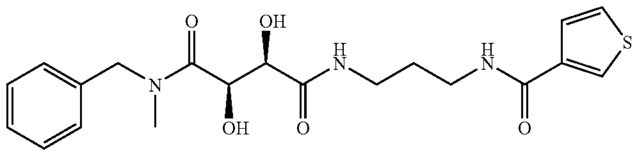 | |
| 143 | 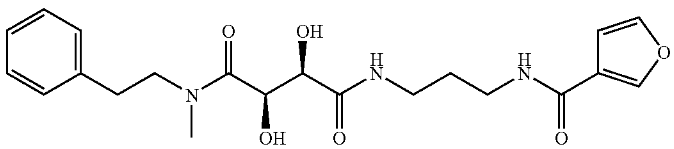 | |
| 144 | 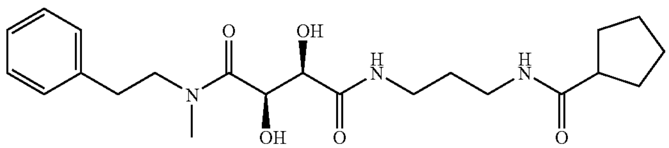 | |
| 145 | 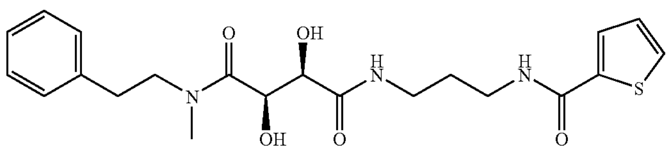 | |
| 146 | 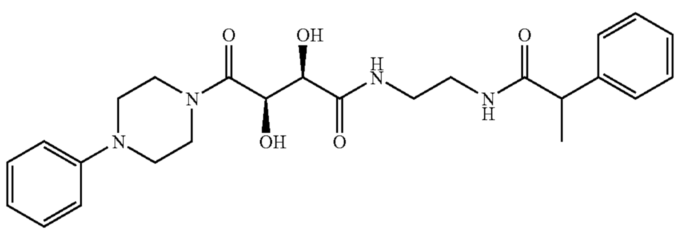 | |
| 147 | 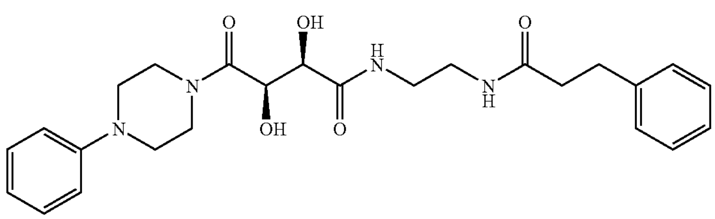 | |
| 148 | 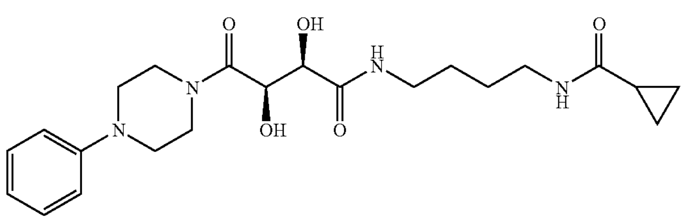 | |
| 149 | 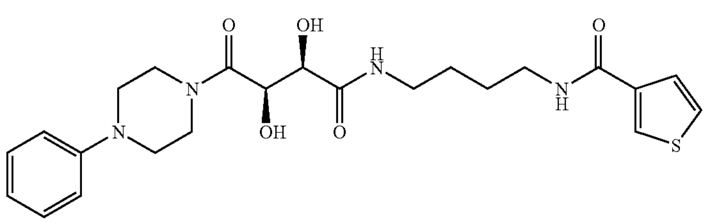 | |

-continued

| Compound # | Structure | $K_i$ (nM) |
|---|---|---|
| 150 | 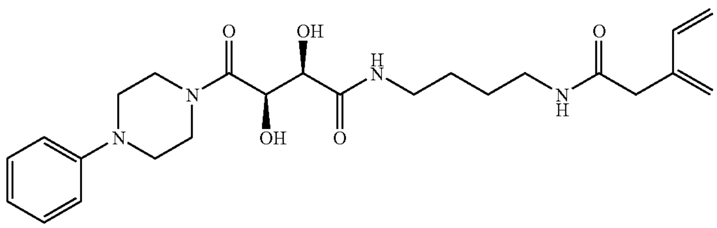 | |
| 151 | 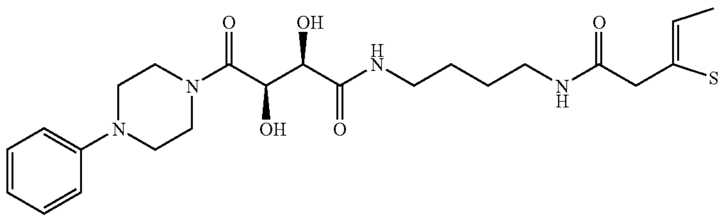 | |
| 152 | 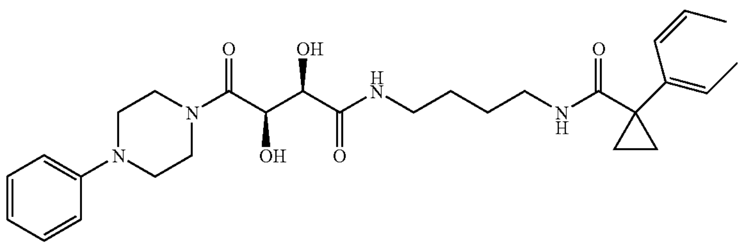 | |
| 157 | 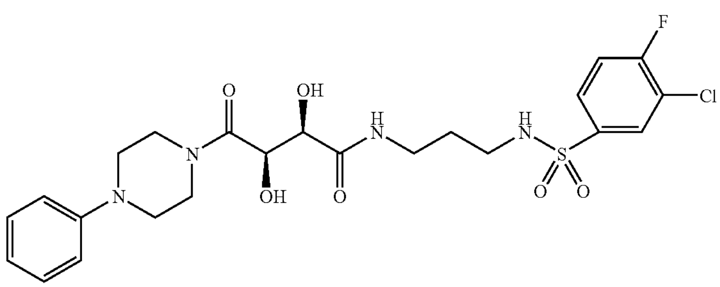 | |
| 158 | 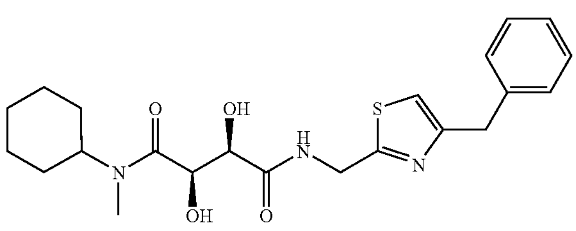 | |
| 159 | 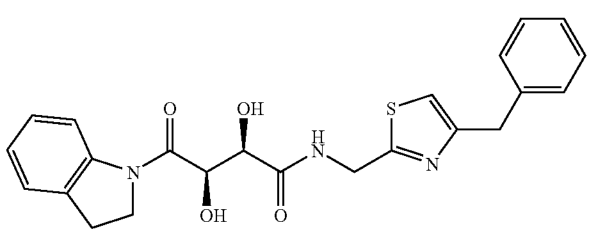 | |

-continued

| Compound # | Structure | $K_i$ (nM) |
|---|---|---|
| 160 | 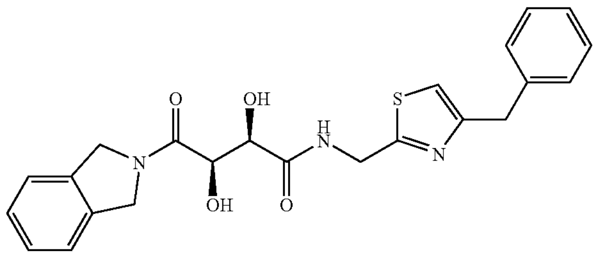 | |
| 161 | 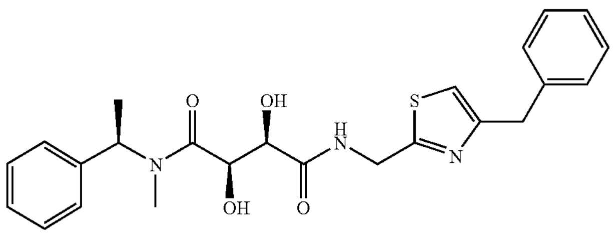 | |
| 162 | 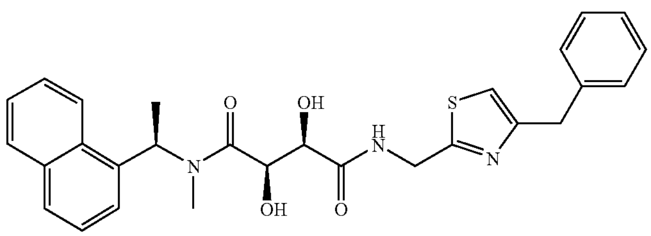 | |
| 163 | 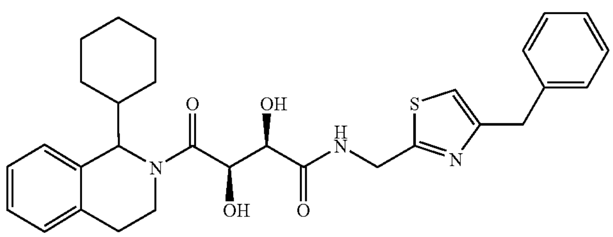 | |
| 164 | 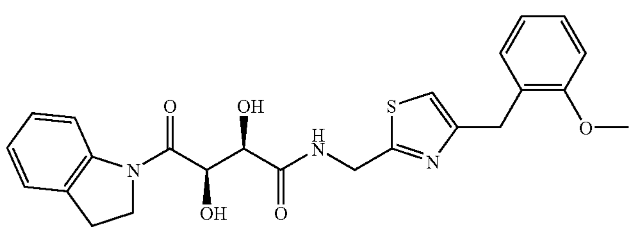 | |
| 165 | 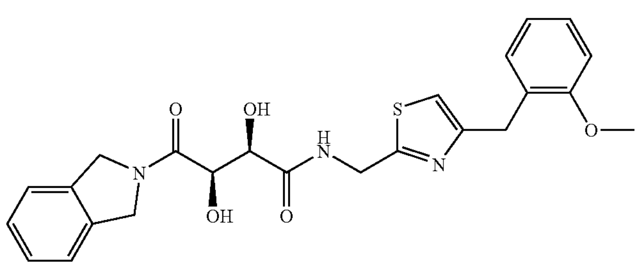 | |

-continued
| Compound # | Structure | $K_i$ (nM) |
|---|---|---|
| 166 | 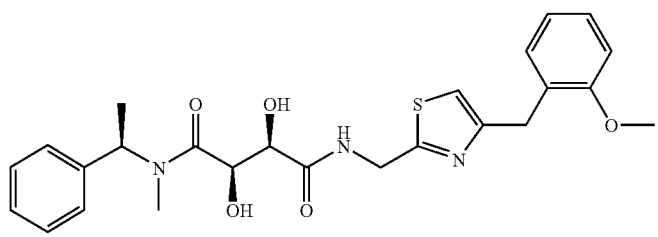 | |
| 167 | 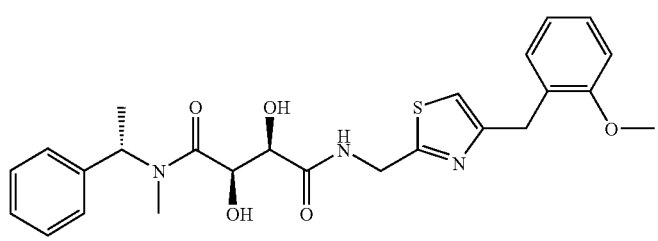 | |
| 168 | 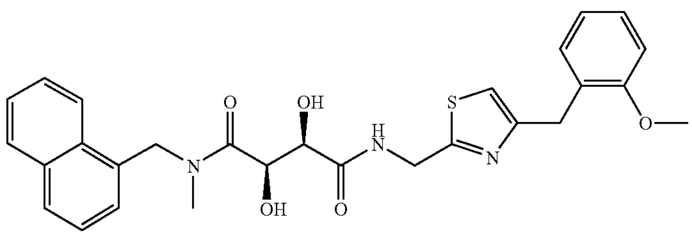 | |
| 169 | 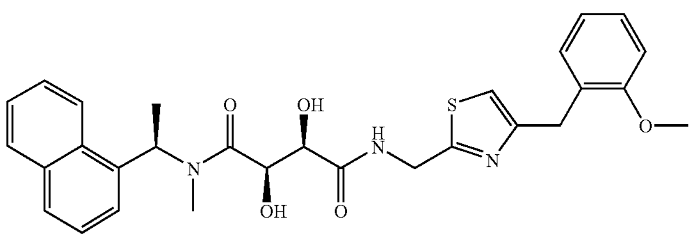 | |
| 170 | 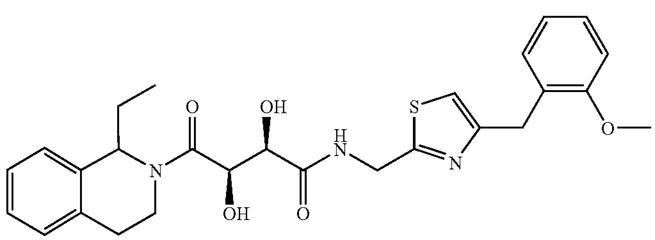 | |
| 171 | 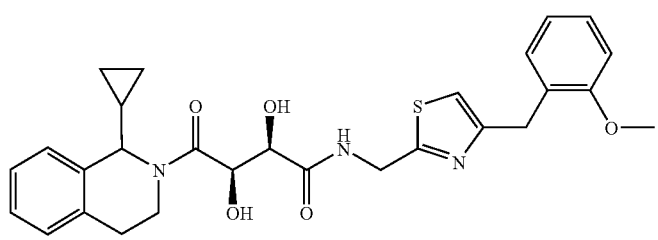 | |

-continued
| Compound # | Structure | $K_i$ (nM) |
|---|---|---|
| 172 | 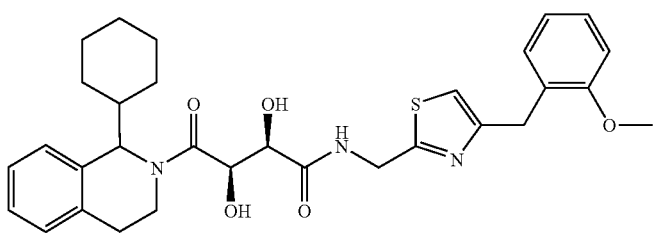 | |
| 173 | 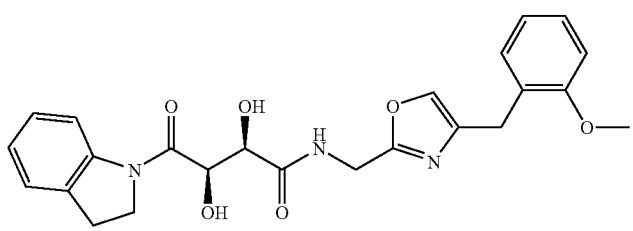 | |
| 174 | 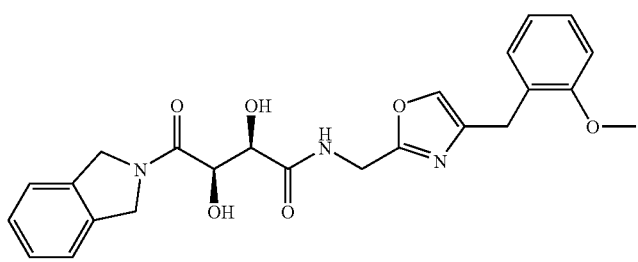 | |
| 175 | 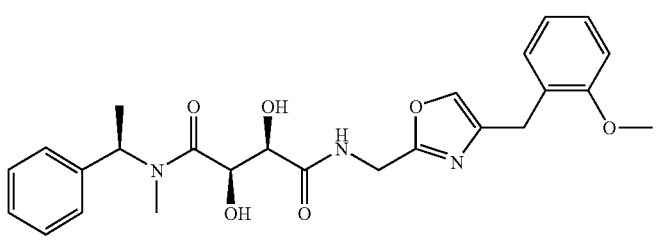 | |
| 176 | 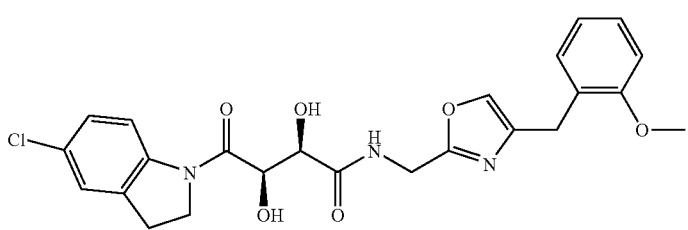 | |
| 177 | 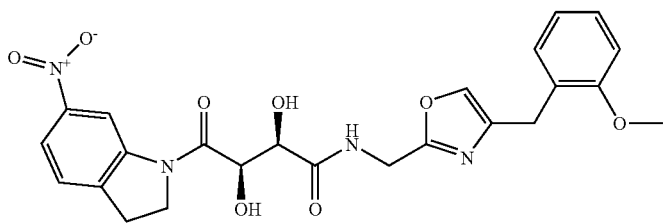 | |

-continued

| Compound # | Structure | $K_i$ (nM) |
|---|---|---|
| 178 | 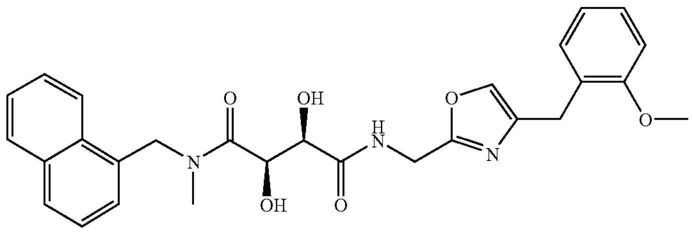 | |
| 179 | 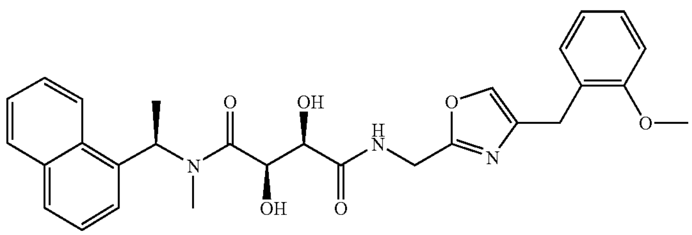 | |
| 180 | 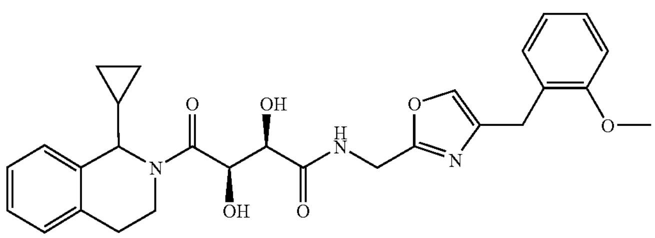 | |
| 181 | 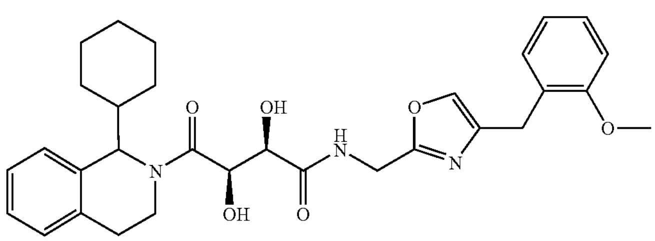 | |
| 182 | 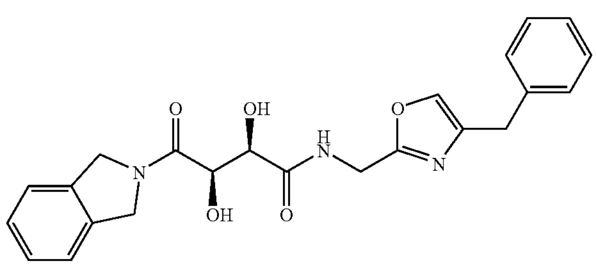 | |
| 191 | 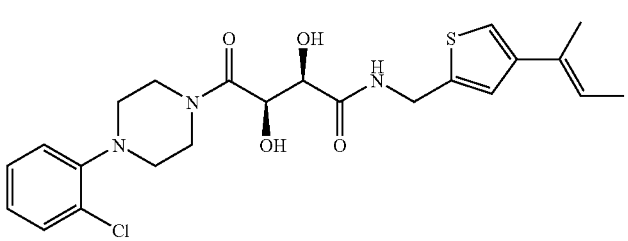 | |

| Compound # | Structure | $K_i$ (nM) |
|---|---|---|
| 192 | 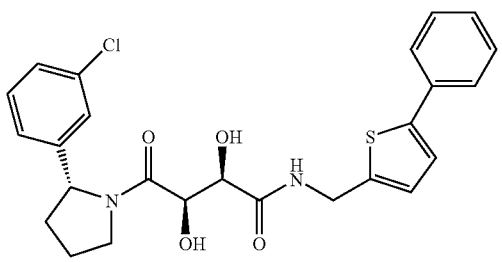 | |
| 197 | 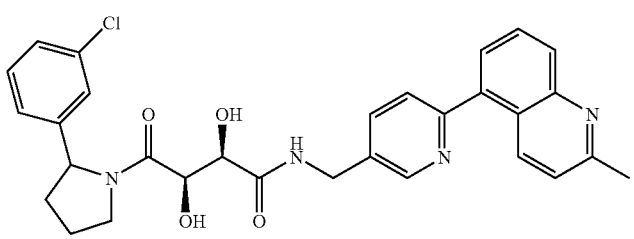 | |
| 198 | 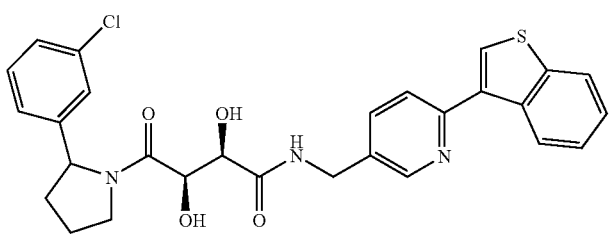 | |
| 199 | 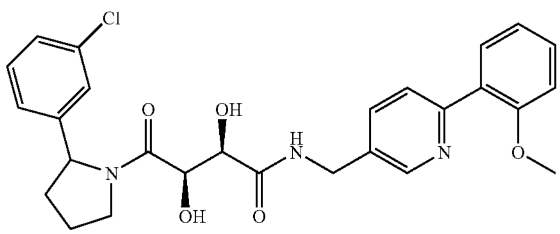 | |
| 200 | 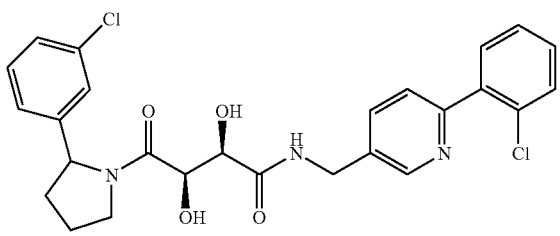 | |
| 201 | 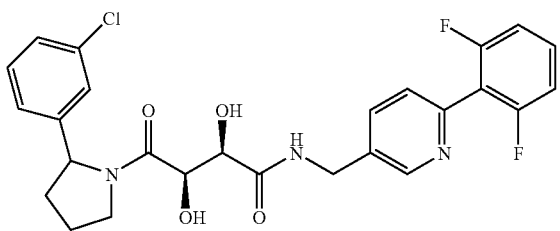 | |

| Compound # | Structure | $K_i$ (nM) |
|---|---|---|
| 202 | 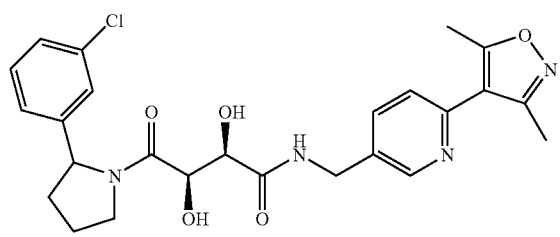 | |
| 203 | 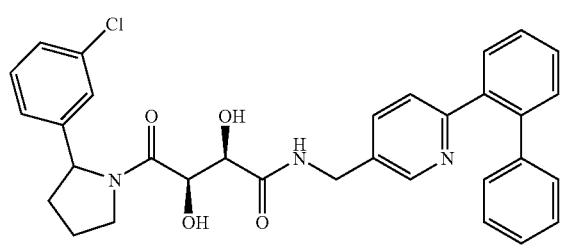 | |
| 204 | 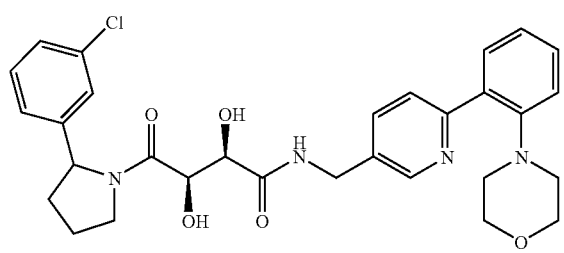 | |
| 205 | 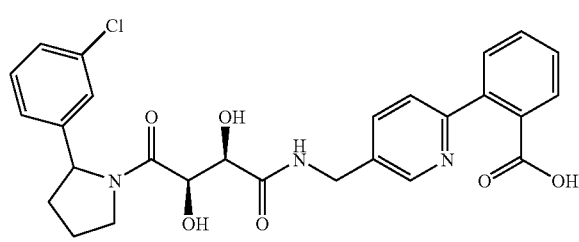 | |
| 206 | 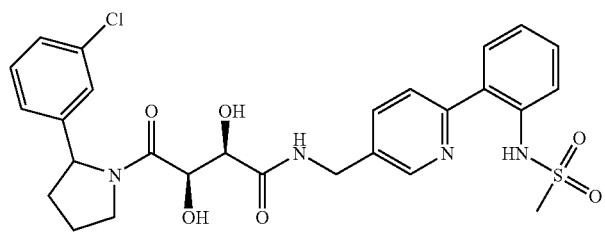 | |
| 207 | 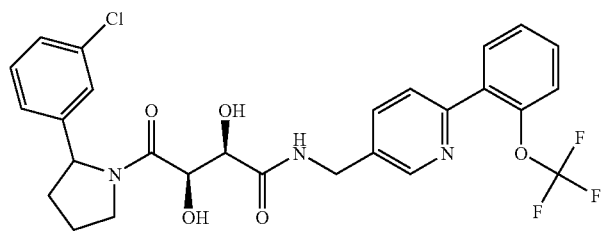 | |

-continued
| Compound # | Structure | $K_i$ (nM) |
|---|---|---|
| 208 | 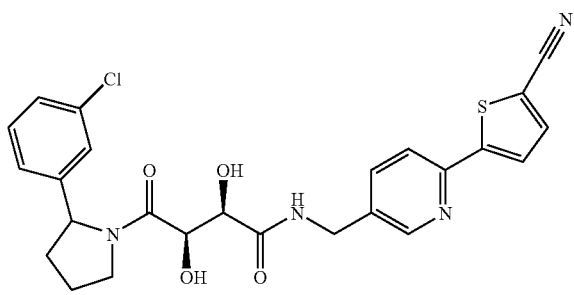 | |
| 212 | 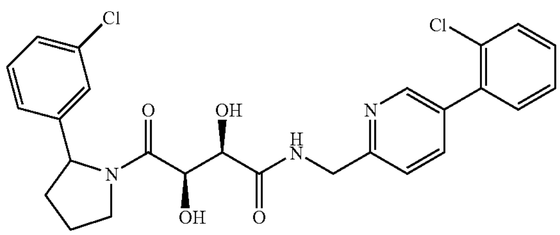 | |
| 213 | 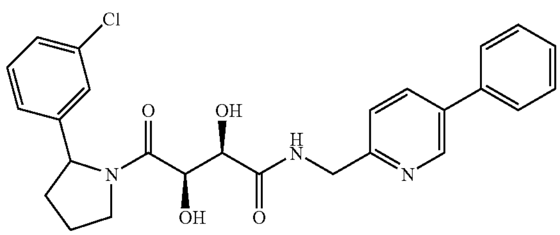 | |
| 214 | 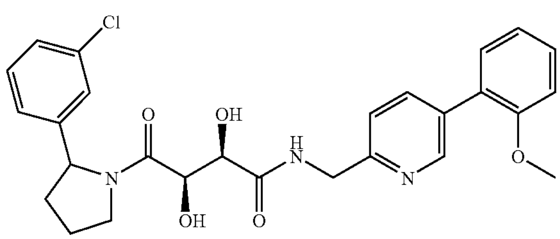 | |
| 215 | 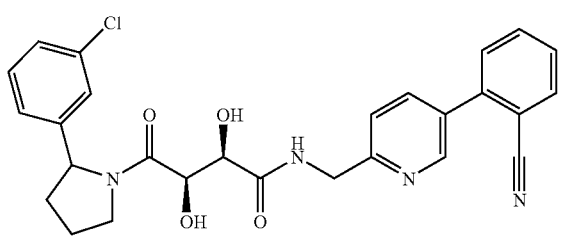 | |
| 216 | 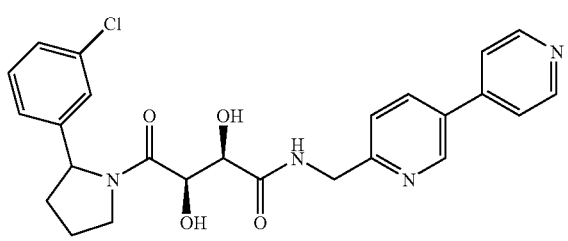 | |

| Compound # | Structure | $K_i$ (nM) |
| --- | --- | --- |
| 217 | 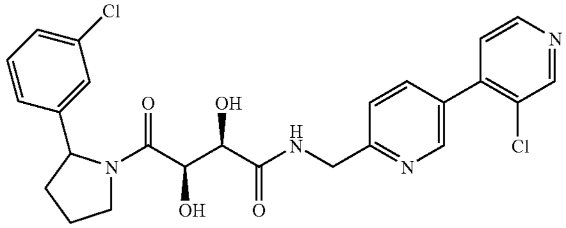 | |
| 218 | 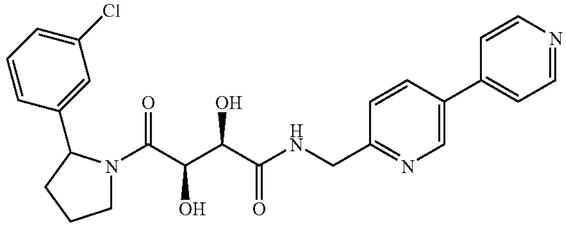 | |
| 219 | 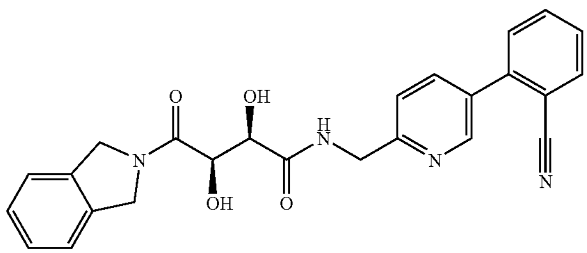 | |
| 220 | 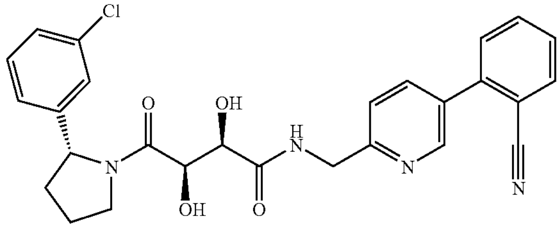 | |
| 221 | 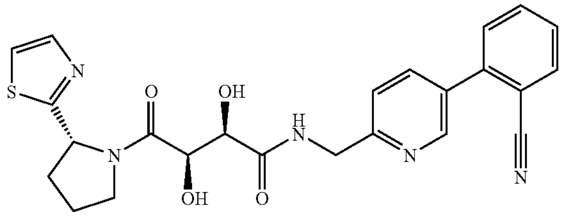 | |
| 222 | 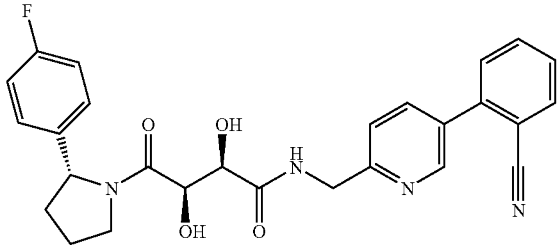 | |

-continued
| Compound # | Structure | $K_i$ (nM) |
|---|---|---|
| 223 | 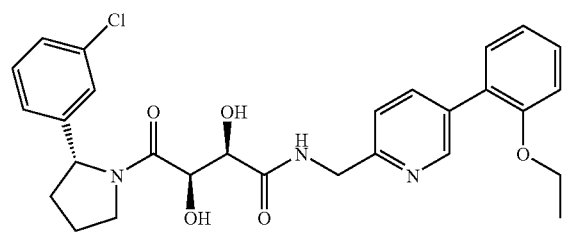 | |
| 224 | 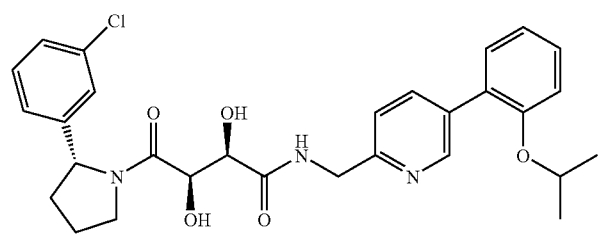 | |
| 225 | 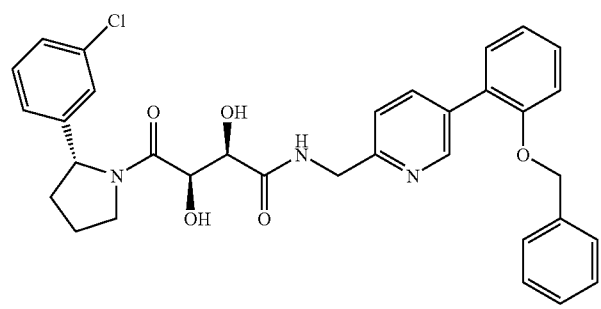 | |
| 226 | 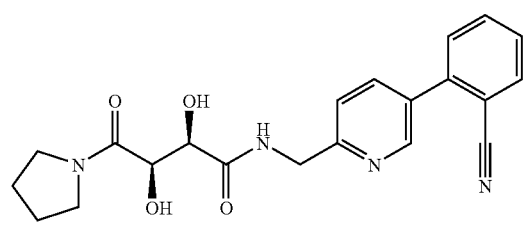 | |
| 227 | 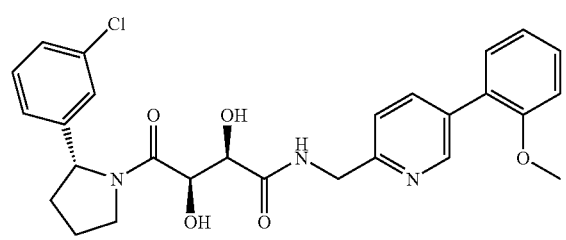 | |
| 232 | 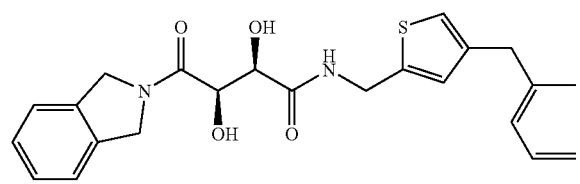 | |

-continued

| Compound # | Structure | $K_i$ (nM) |
|---|---|---|
| 236 | 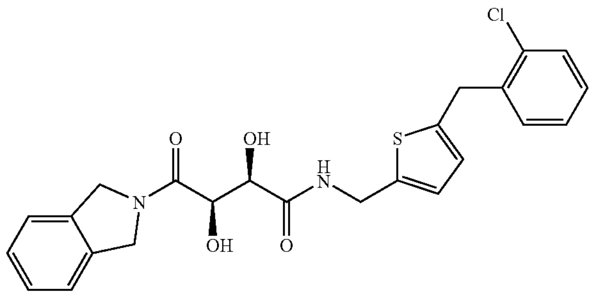 | |
| 242 | 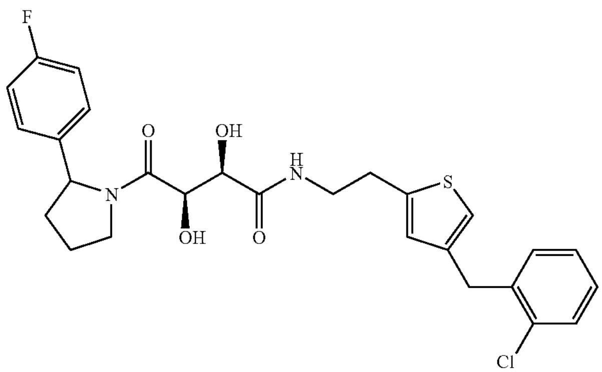 | |
| 243 | 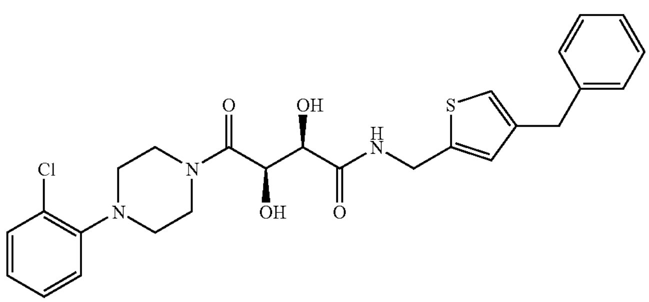 | |
| 244 | 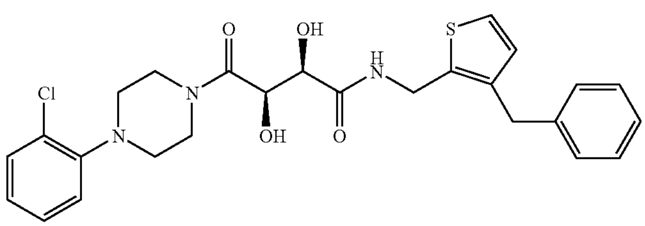 | |
| 245 | 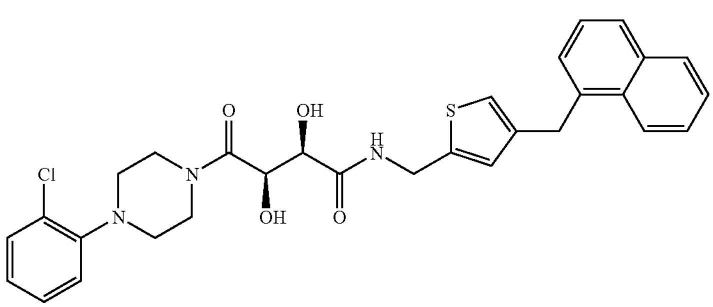 | |

| Compound # | Structure | $K_i$ (nM) |
|---|---|---|
| 246 | 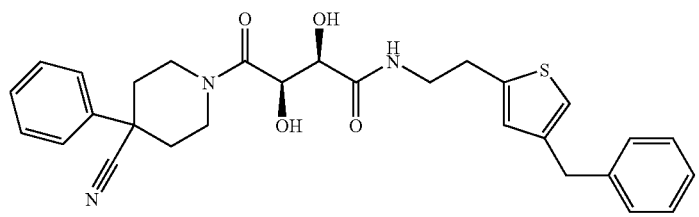 | |
| 247 | 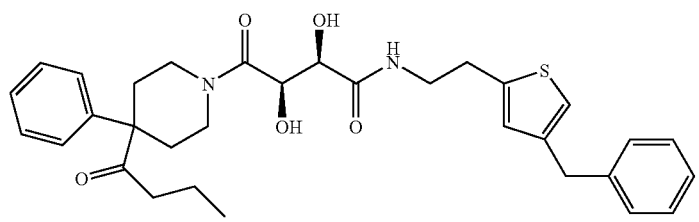 | |
| 248 | 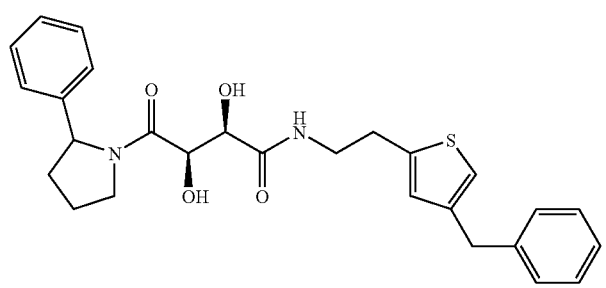 | |
| 249 | 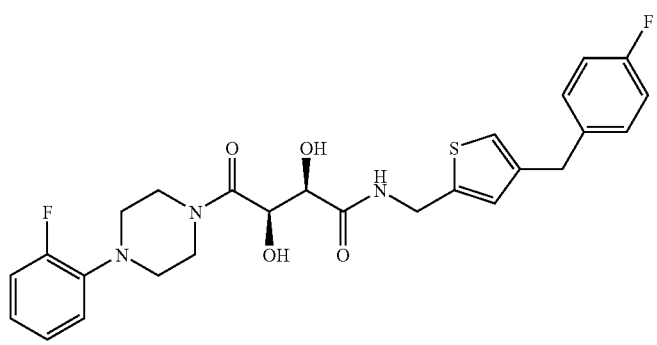 | |
| 250 | 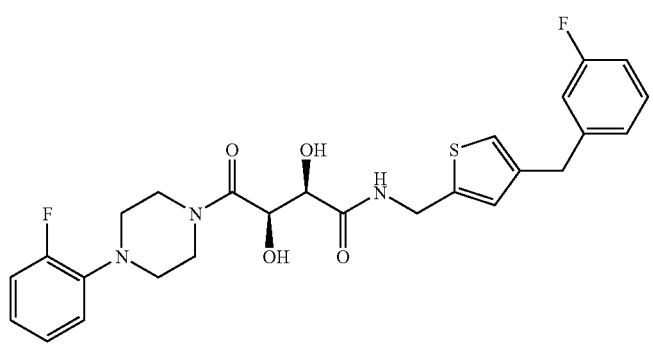 | |

| Compound # | Structure | $K_i$ (nM) |
|---|---|---|
| 251 | 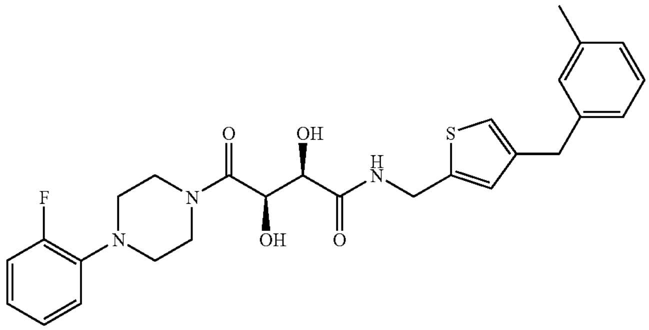 | |
| 252 | 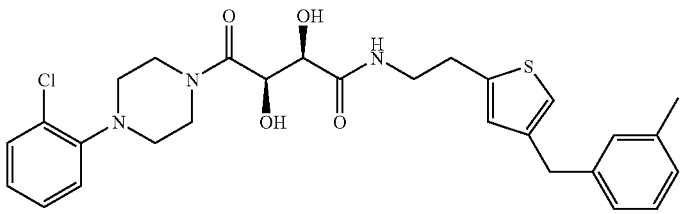 | |
| 253 | 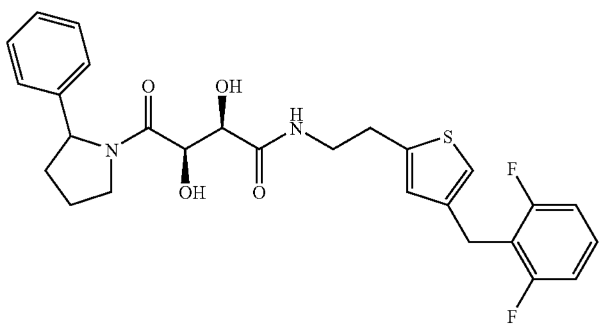 | |
| 254 | 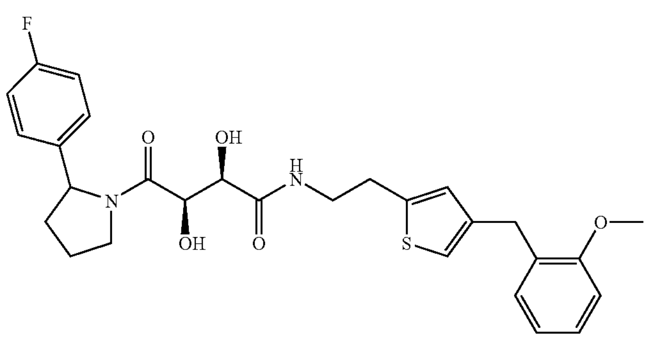 | |
| 255 | 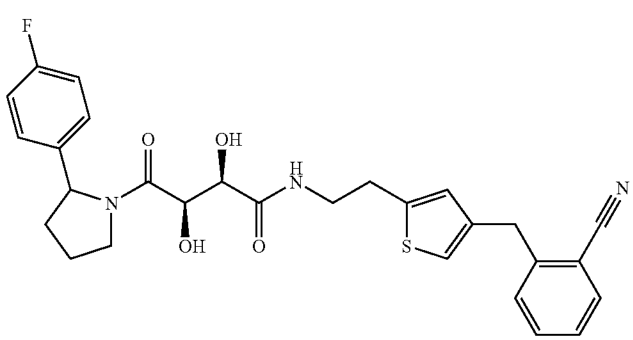 | |

-continued
| Compound # | Structure | $K_i$ (nM) |
|---|---|---|
| 256 | 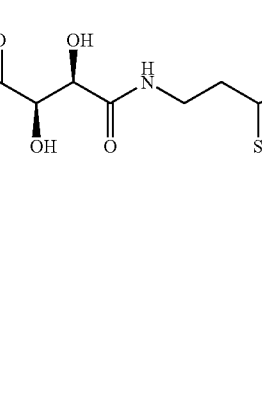 | |
| 257 | 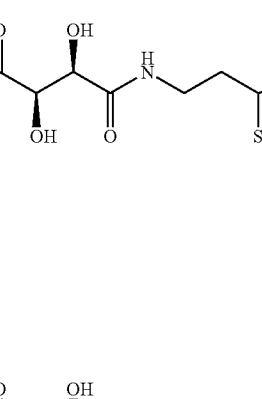 | |
| 258 | 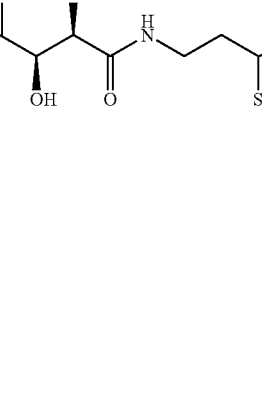 | |
| 259 | 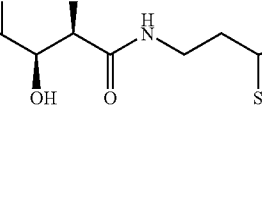 | |

-continued

| Compound # | Structure | K$_i$ (nM) |
|---|---|---|
| 260 | 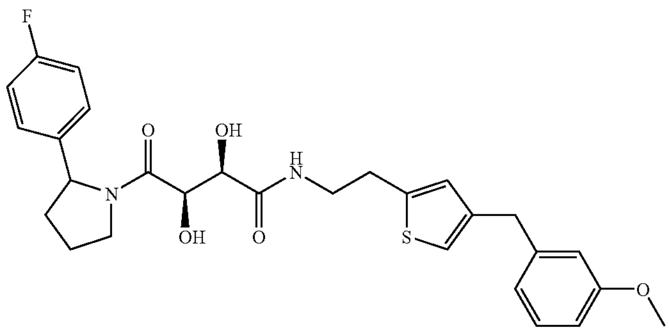 | |
| 261 | 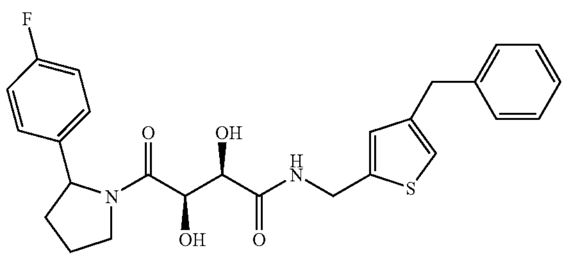 | |
| 262 | 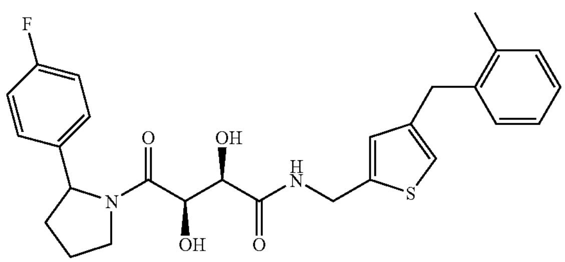 | |
| 263 | 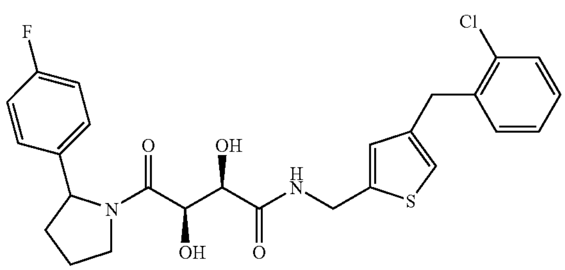 | |
| 264 | 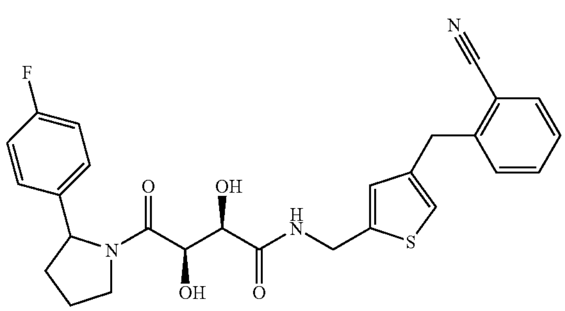 | |

| Compound # | Structure | $K_i$ (nM) |
|---|---|---|
| 265 | 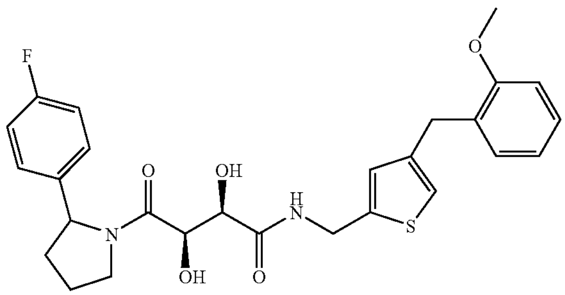 | |
| 266 | 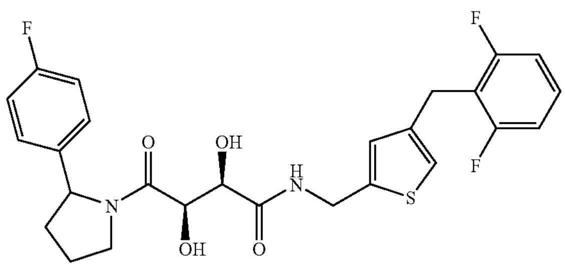 | |
| 267 | 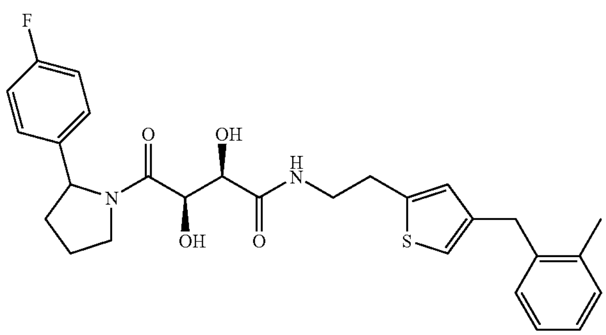 | |
| 268 | 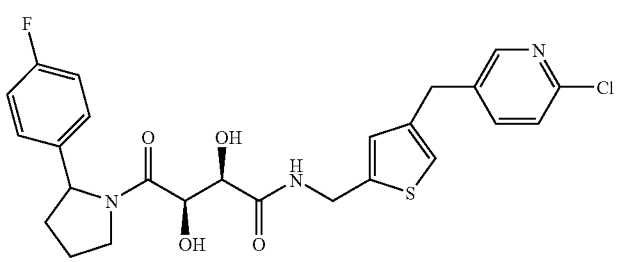 | |
| 269 | 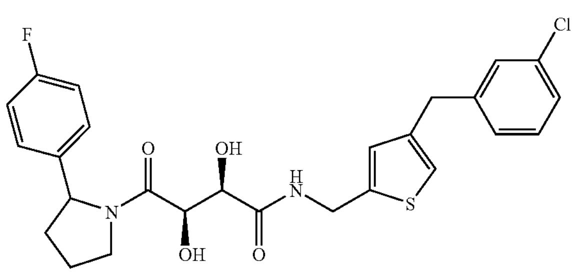 | |

-continued
| Compound # | Structure | $K_i$ (nM) |
|---|---|---|
| 270 | 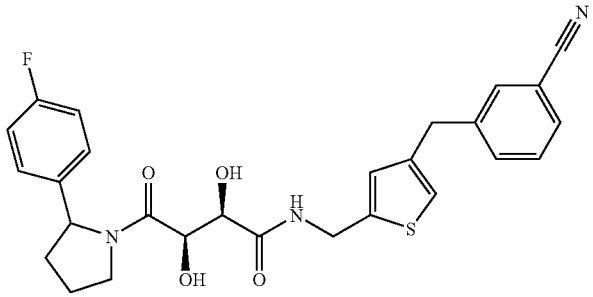 | |
| 271 | 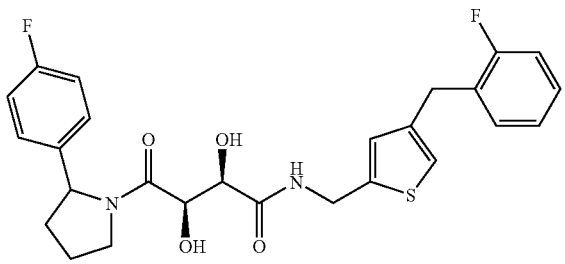 | |
| 272 | 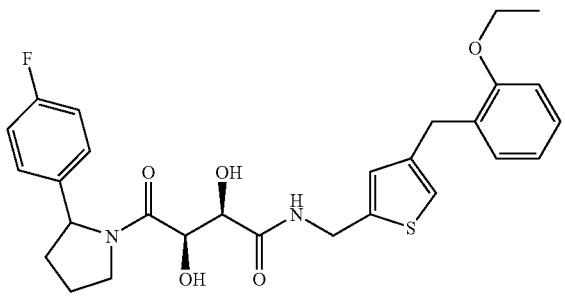 | |
| 273 | 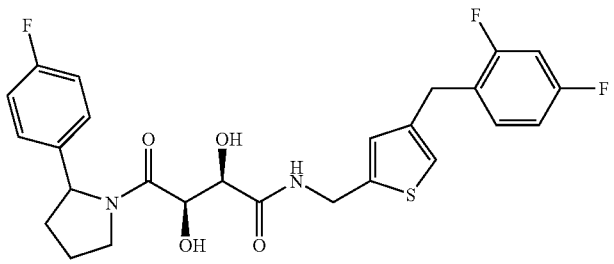 | |
| 274 | 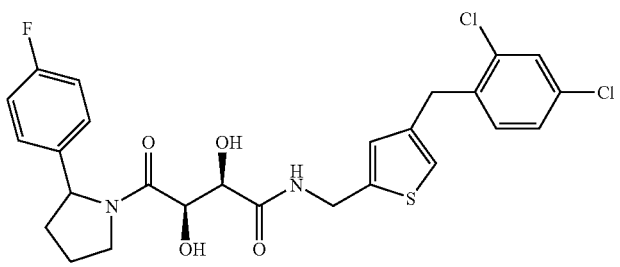 | |

-continued
| Compound # | Structure | $K_i$ (nM) |
|---|---|---|
| 275 | 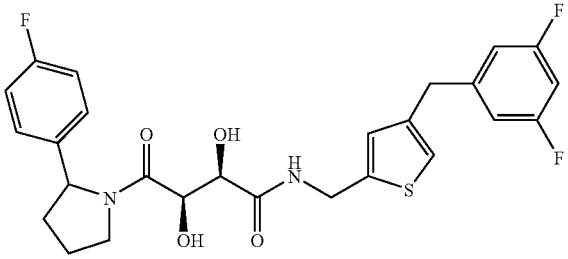 | |
| 276 | 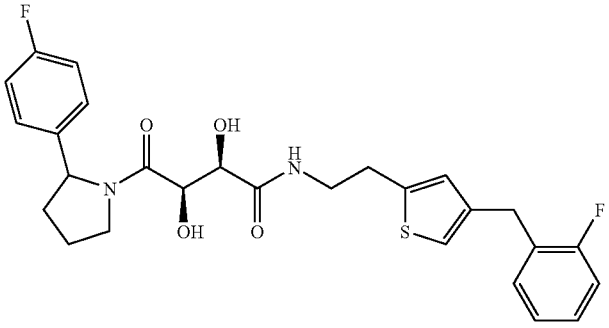 | |
| 277 | 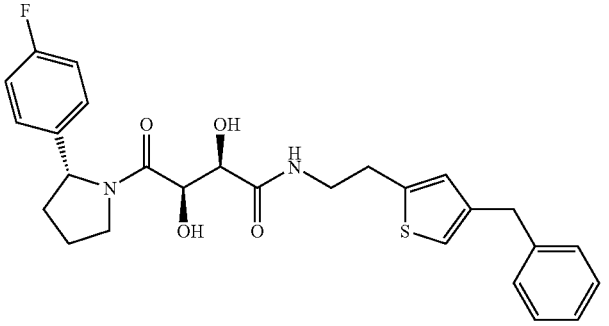 | |
| 278 | 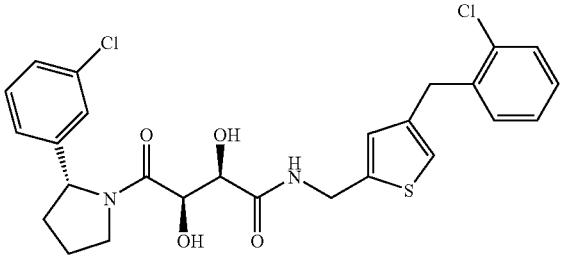 | |
| 279 | 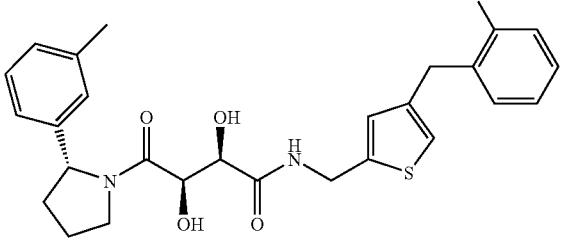 | |

-continued

| Compound # | Structure | $K_i$ (nM) |
|---|---|---|
| 280 | 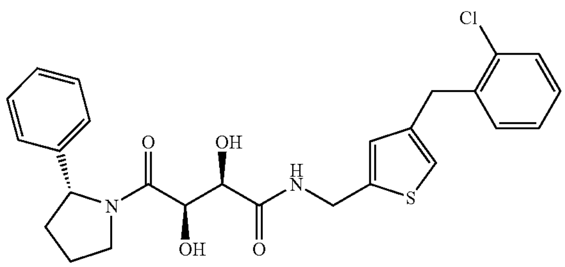 | |
| 281 | 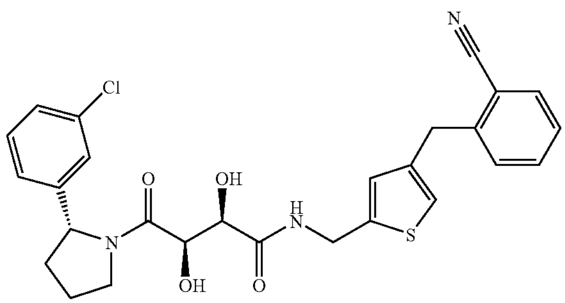 | |
| 282 | 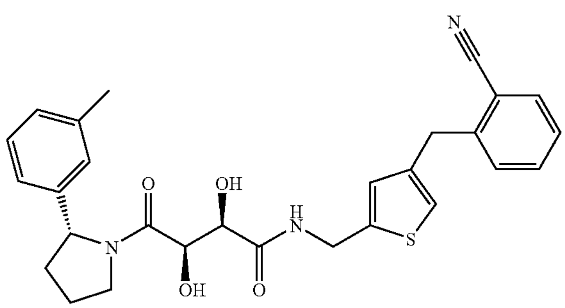 | |
| 283 | 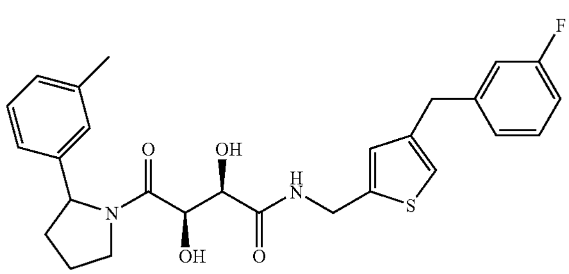 | |
| 284 | 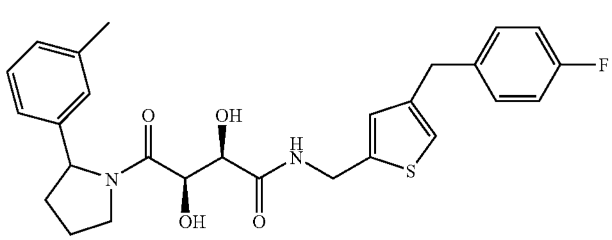 | |

-continued

| Compound # | Structure | $K_i$ (nM) |
|---|---|---|
| 285 | 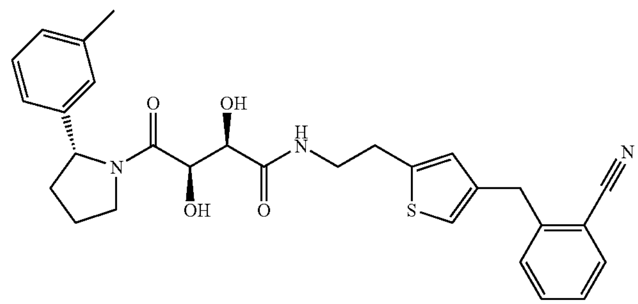 | |
| 286 | 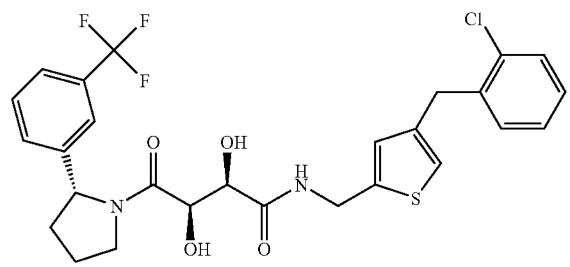 | |
| 287 | 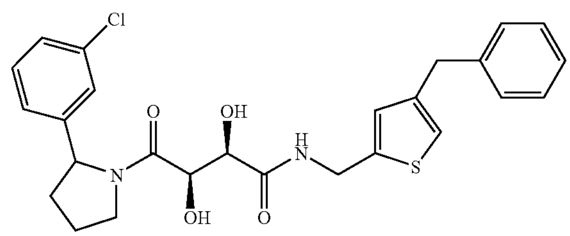 | |
| 288 | 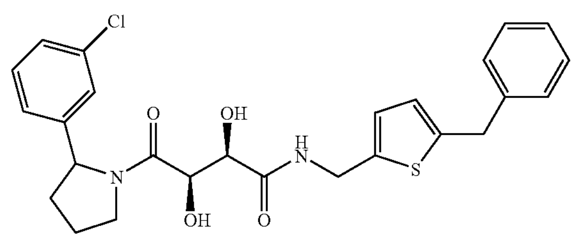 | |
| 289 | 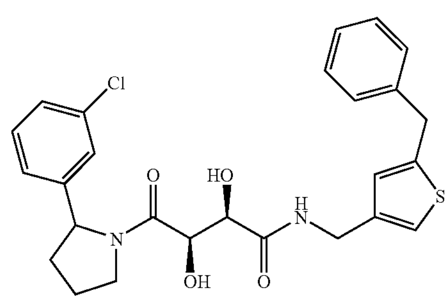 | |

-continued
| Compound # | Structure | $K_i$ (nM) |
|---|---|---|
| 290 | 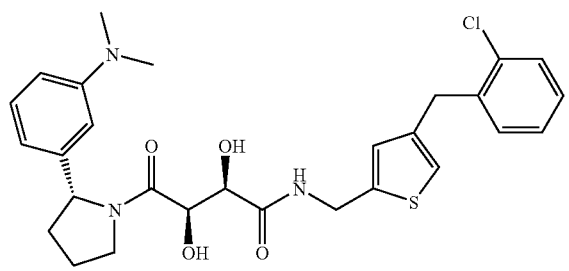 | |
| 291 | 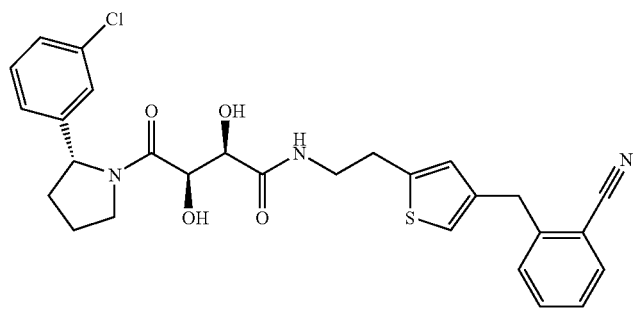 | |
| 292 | 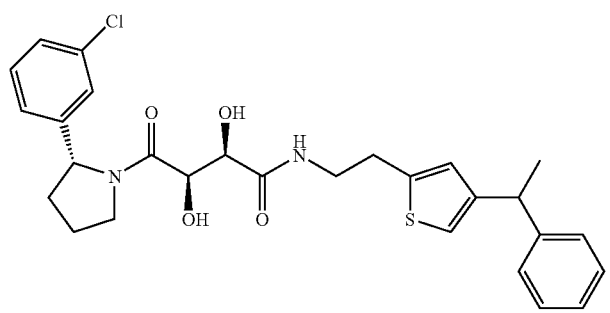 | |
| 293 | 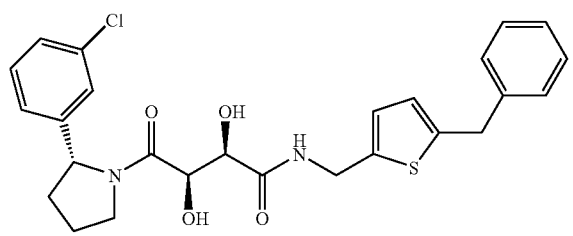 | |
| 294 | 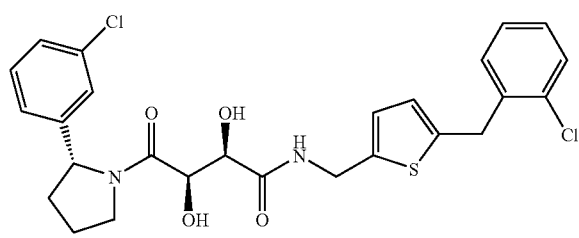 | |

-continued
| Compound # | Structure | $K_i$ (nM) |
|---|---|---|
| 295 | 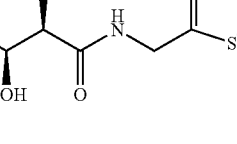 | |
| 296 | 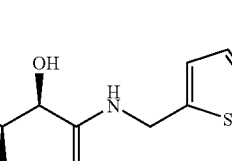 | |
| 297 | 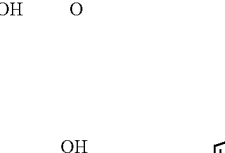 | |
| 298 | 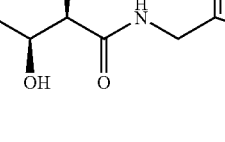 | |
| 299 | 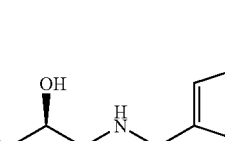 | |
| 300 | 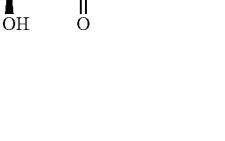 | |

-continued

| Compound # | Structure | $K_i$ (nM) |
|---|---|---|
| 301 | 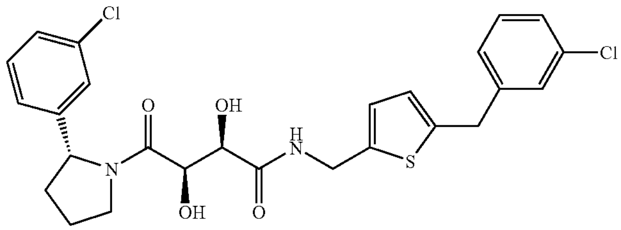 | |
| 302 | 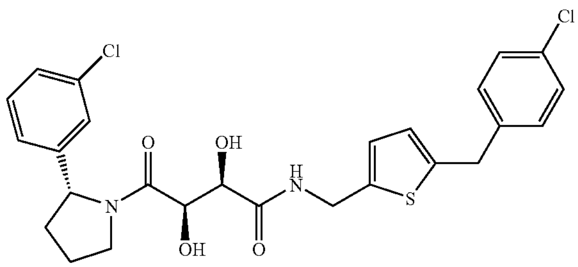 | |
| 303 | 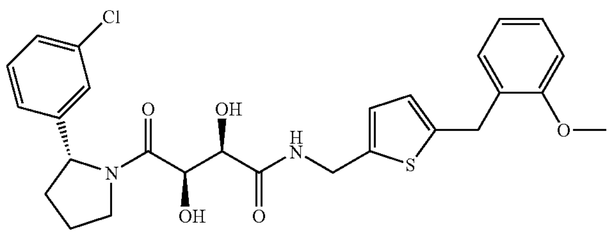 | |
| 304 | 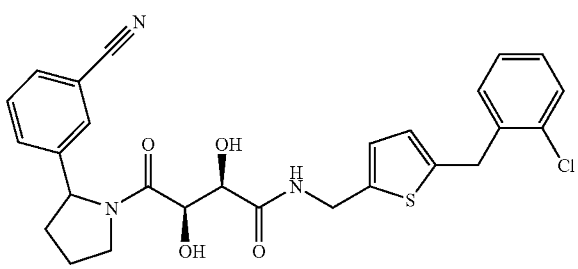 | |
| 309 | 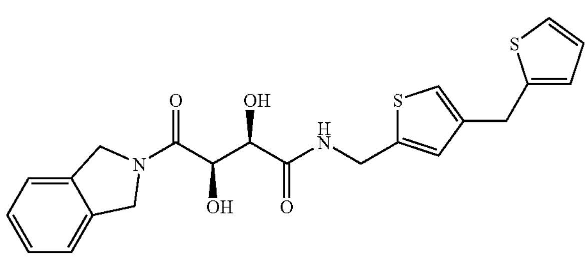 | |
| 310 | 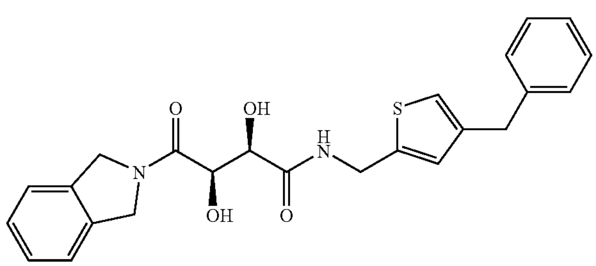 | |

-continued

| Compound # | Structure | $K_i$ (nM) |
|---|---|---|
| 311 | 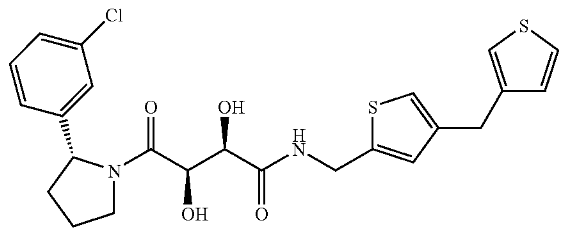 | |
| 312 | 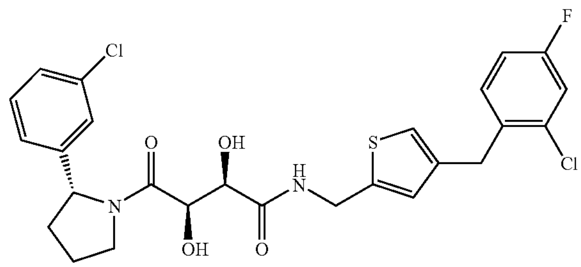 | |
| 313 | 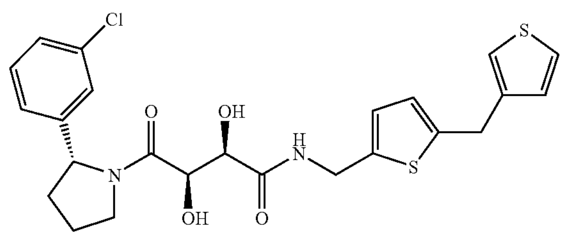 | |
| 314 | 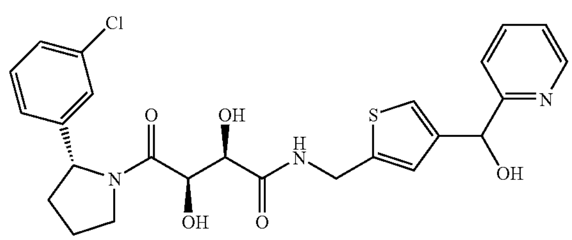 | |
| 315 | 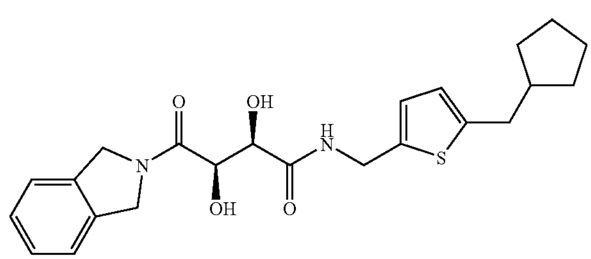 | |
| 316 | 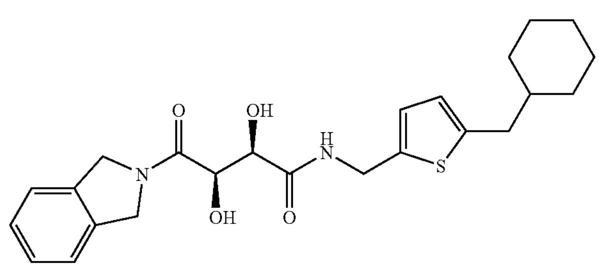 | |

-continued
| Compound # | Structure | $K_i$ (nM) |
|---|---|---|
| 317 | 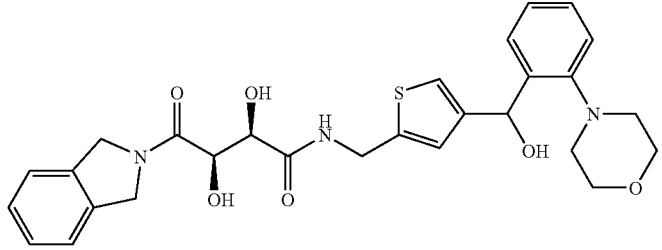 | |
| 318 | 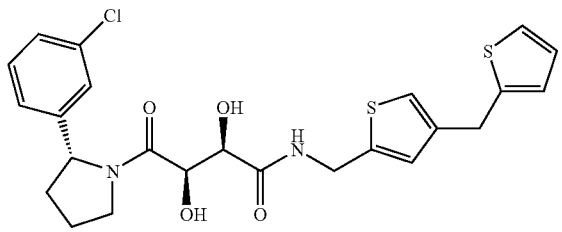 | |
| 325 | 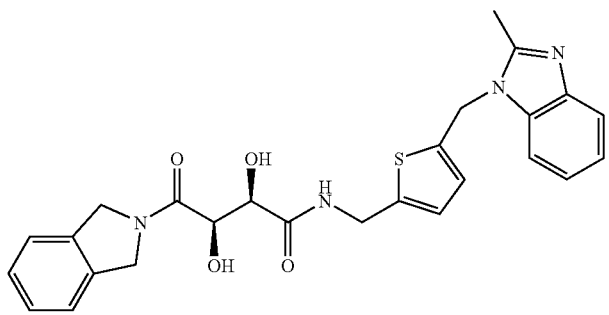 | |
| 329 | 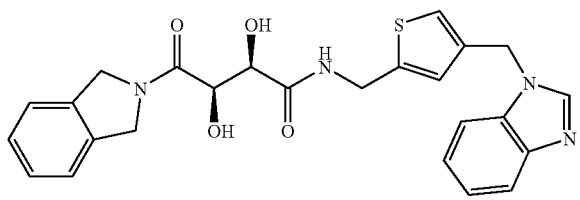 | |
| 327 | 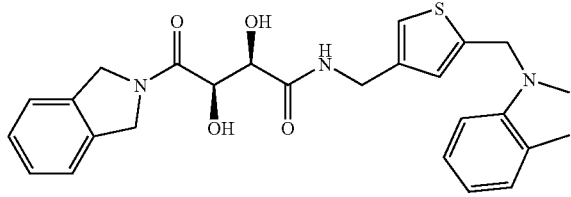 | |
| 338 | 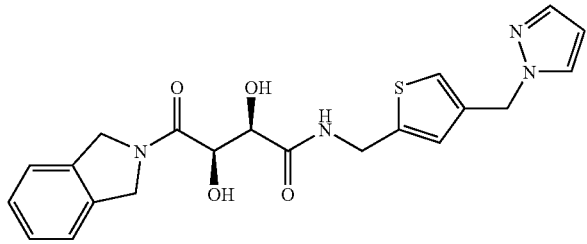 | |

| Compound # | Structure | $K_i$ (nM) |
|---|---|---|
| 339 | 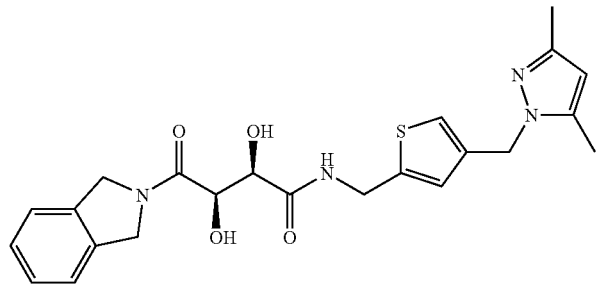 | |
| 340 | 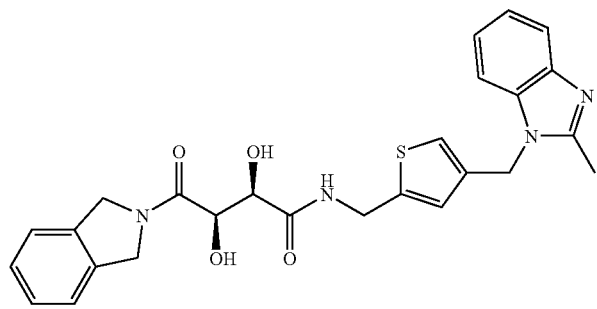 | |
| 341 | 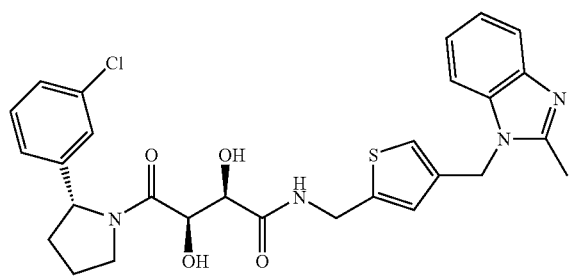 | |
| 342 | 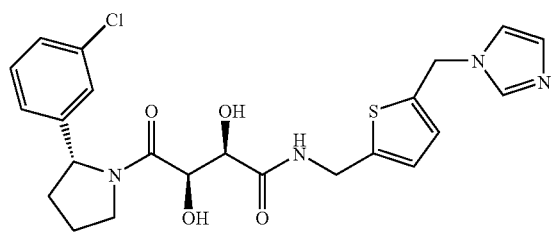 | |
| 343 | 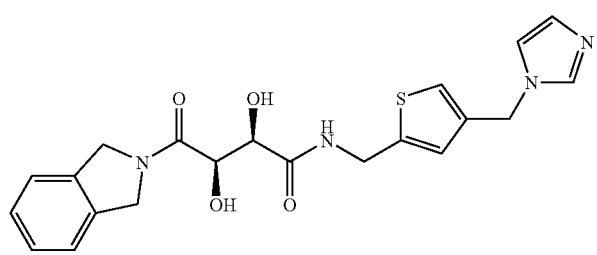 | |

-continued

| Compound # | Structure | $K_i$ (nM) |
|---|---|---|
| 344 | 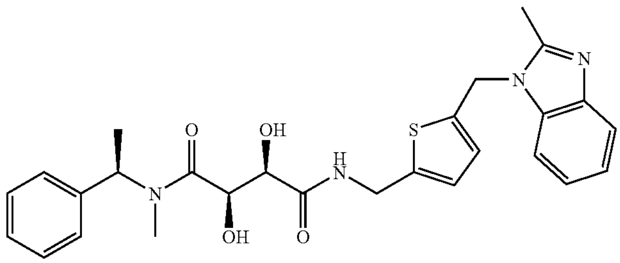 | |
| 345 | 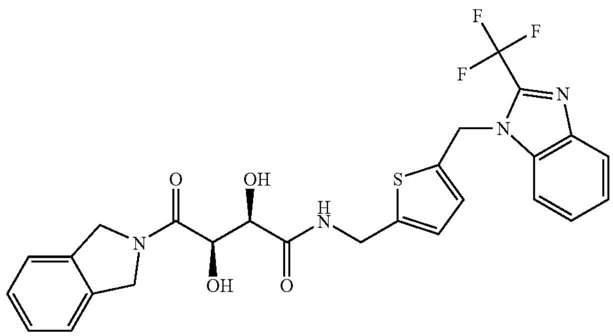 | |
| 346 | 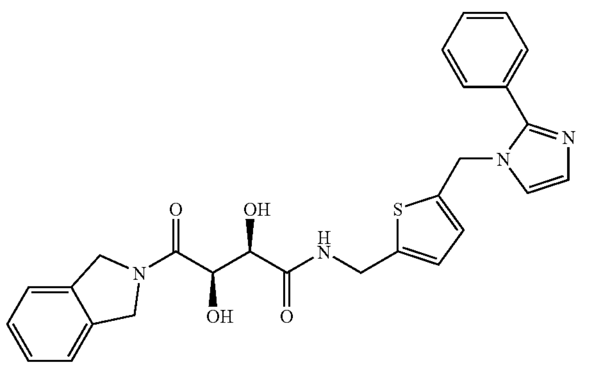 | |
| 347 | 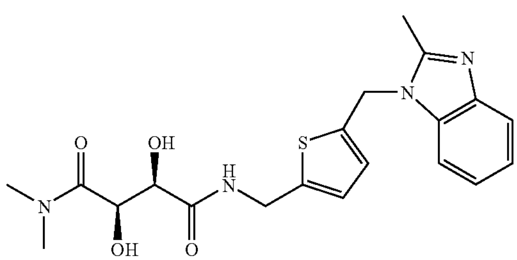 | |
| 348 | 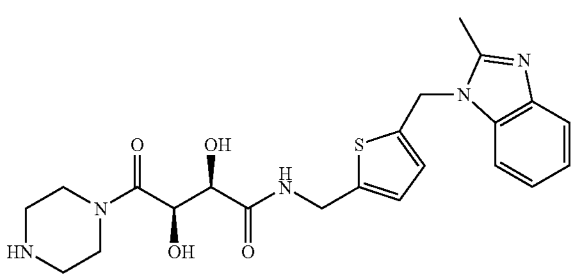 | |

-continued
| Compound # | Structure | $K_i$ (nM) |
|---|---|---|
| 349 | 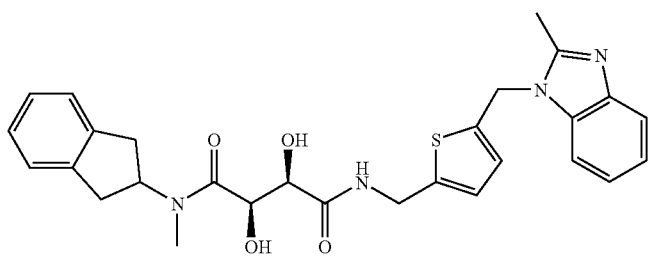 | |
| 350 | 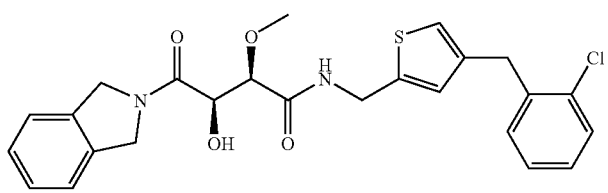 | |
| 351 | 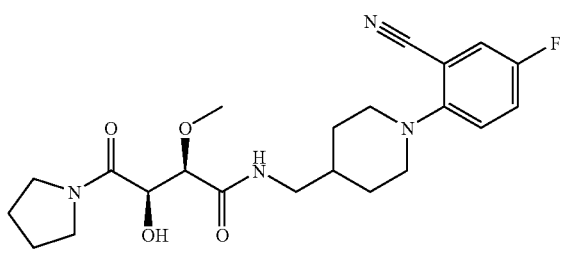 | |
| 352 | 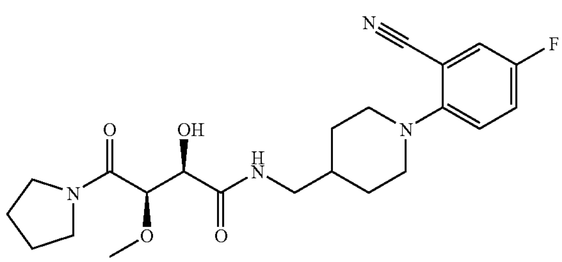 | |
| 375 | 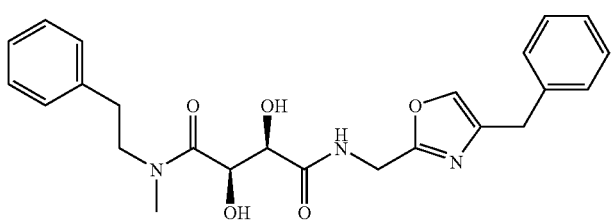 | |
| 376 | 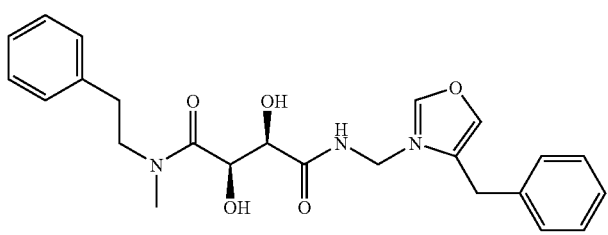 | |

-continued
| Compound # | Structure | K_i (nM) |
|---|---|---|
| 377 | 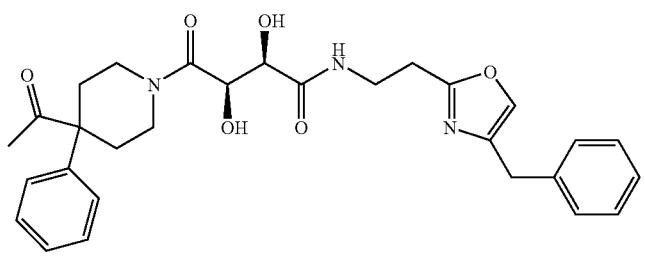 | |
| 378 | 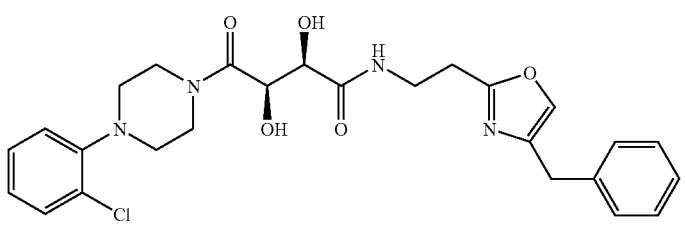 | |
| 379 | 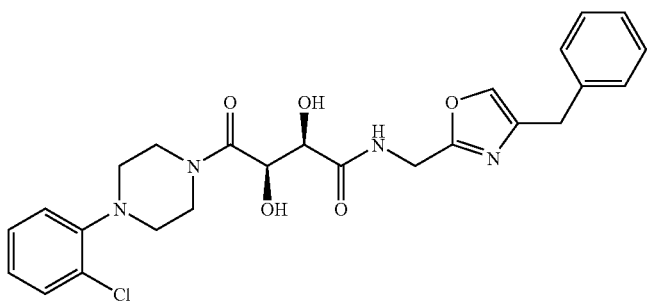 | |
| 380 | 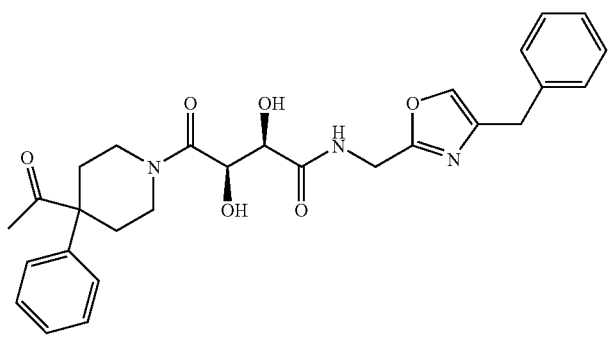 | |
| 381 | 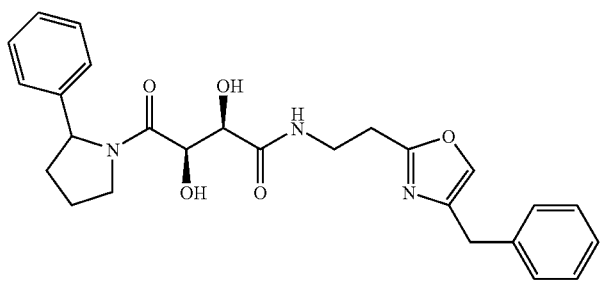 | |

| Compound # | Structure | $K_i$ (nM) |
|---|---|---|
| 382 | 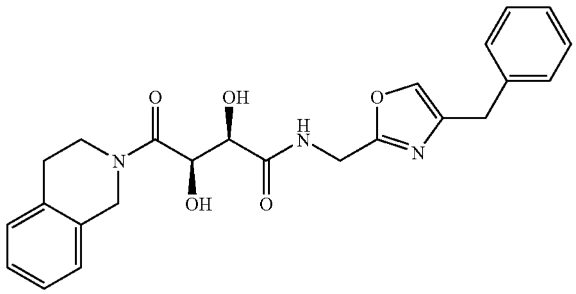 | |
| 383 | 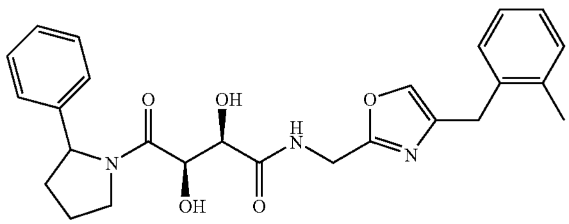 | |
| 384 | 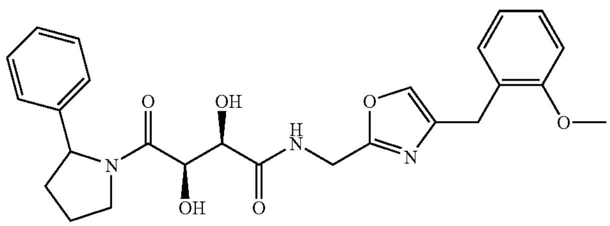 | |
| 174 | 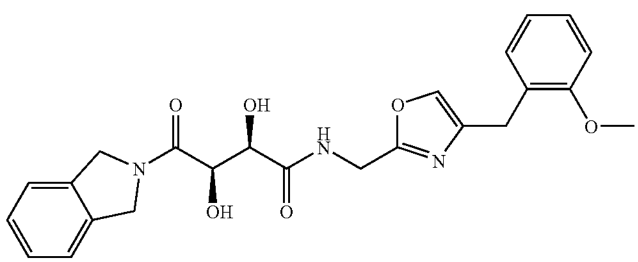 | |
| 175 | 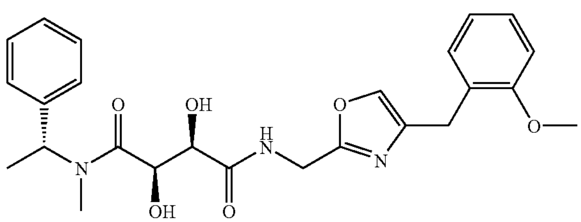 | |
| 179 | 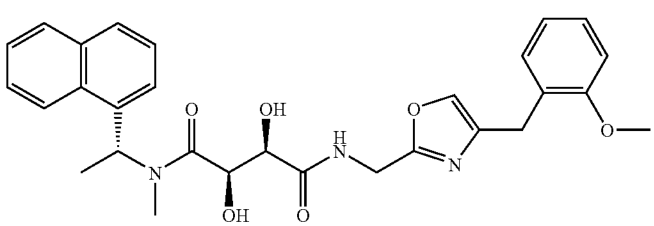 | |

-continued
| Compound # | Structure | $K_i$ (nM) |
|---|---|---|
| 181 | 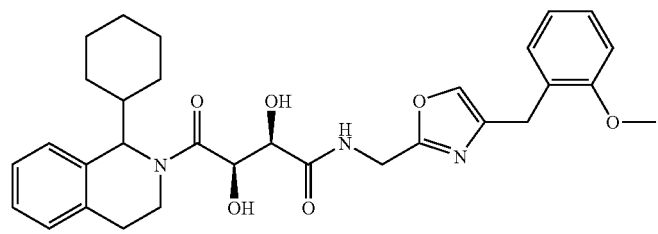 | |
| 182 | 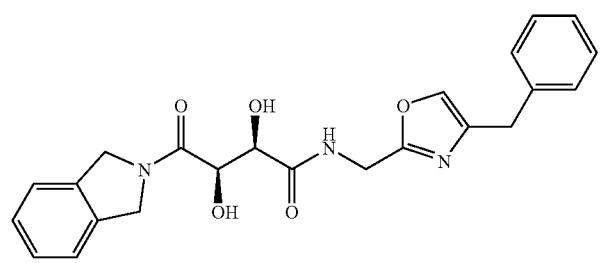 | |
| 396 | 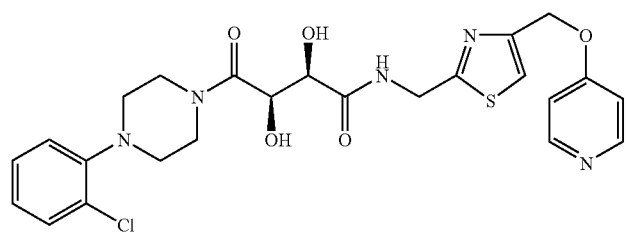 | |
| 397 | 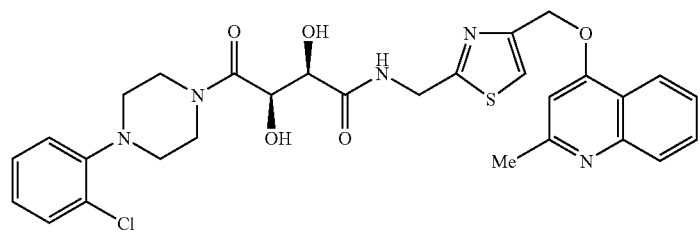 | |
| 398 | 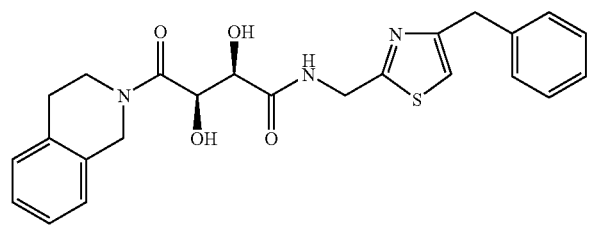 | |
| 399 | 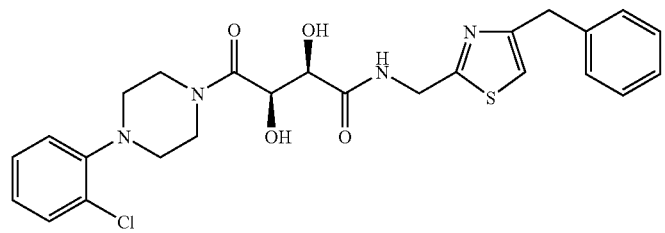 | |

-continued
| Compound # | Structure | $K_i$ (nM) |
|---|---|---|
| 400 | 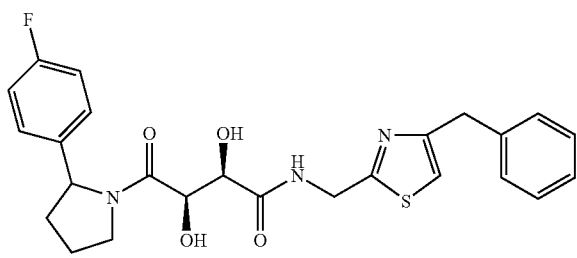 | |
| 401 | 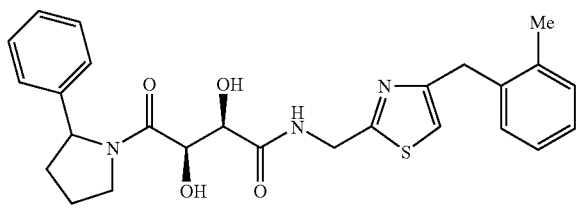 | |
| 402 | 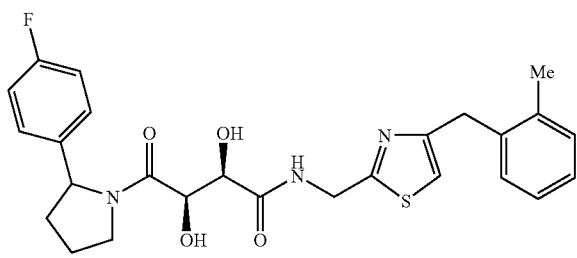 | |
| 403 | 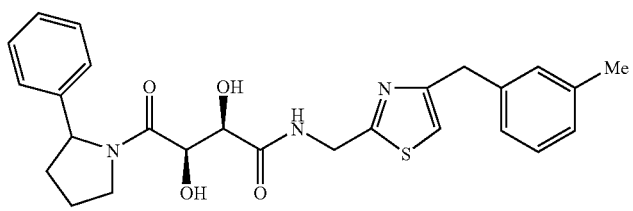 | |
| 404 | 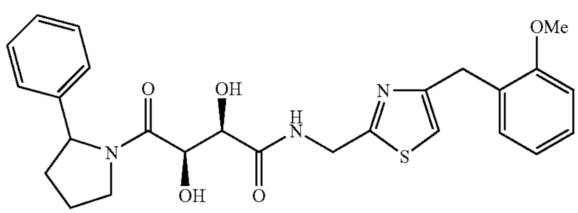 | |
| 405 | 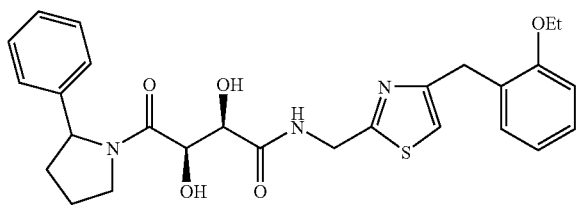 | |

-continued

| Compound # | Structure | $K_i$ (nM) |
|---|---|---|
| 406 | 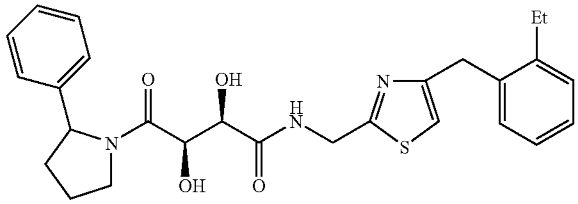 | |
| 407 | 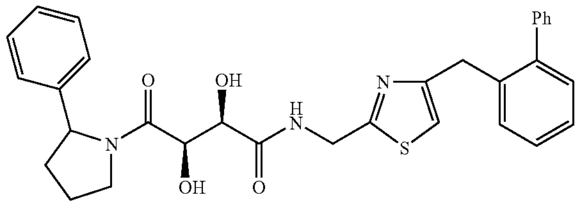 | |
| 408 | 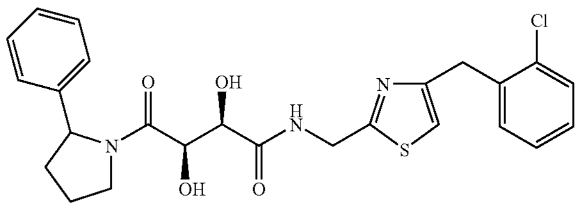 | |
| 409 | 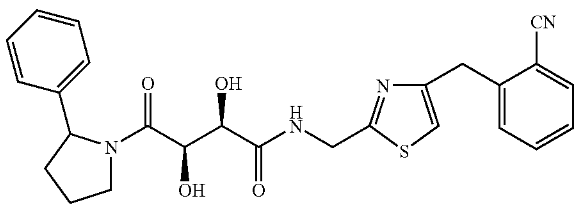 | |
| 410 | 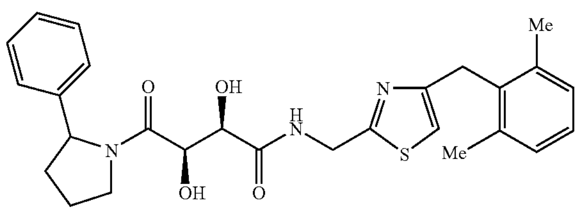 | |
| 411 | 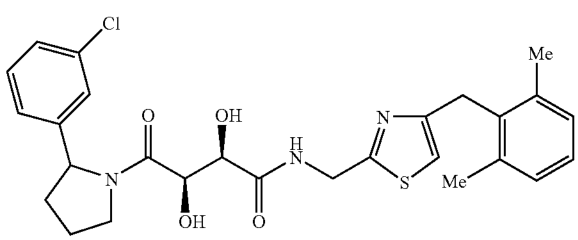 | |
| 412 | 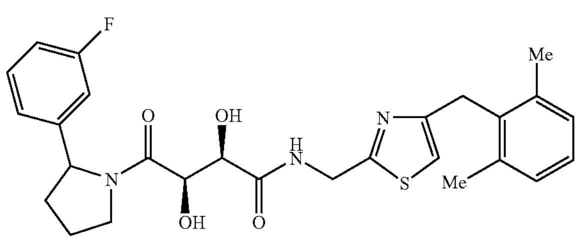 | |

-continued
| Compound # | Structure | $K_i$ (nM) |
|---|---|---|
| 413 | 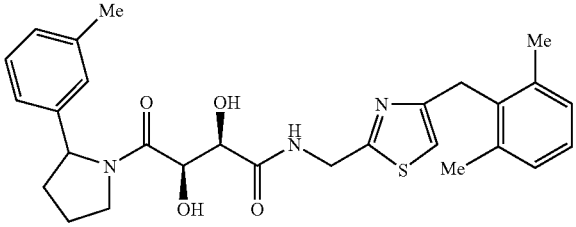 | |
| 414 | 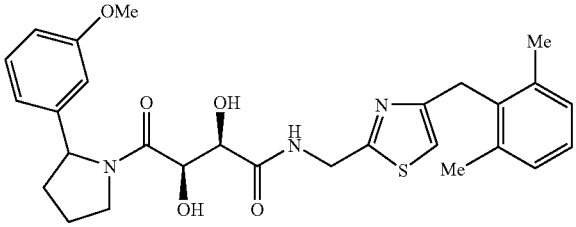 | |
| 415 | 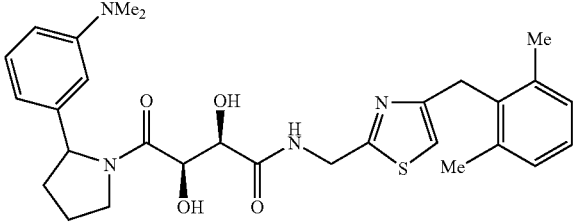 | |
| 416 | 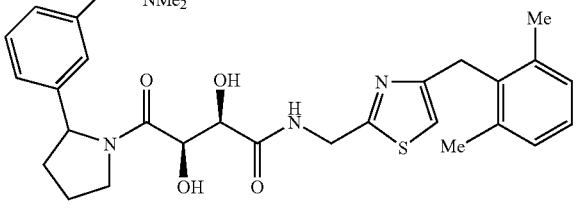 | |
| 417 | 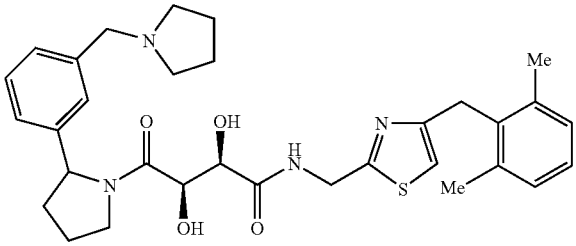 | |
| 418 | 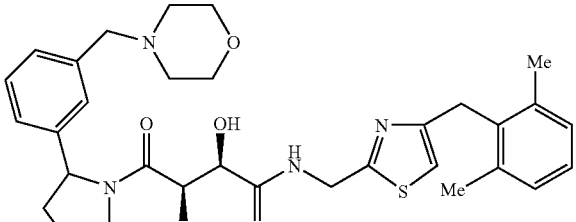 | |

-continued

| Compound # | Structure | $K_i$ (nM) |
|---|---|---|
| 419 | 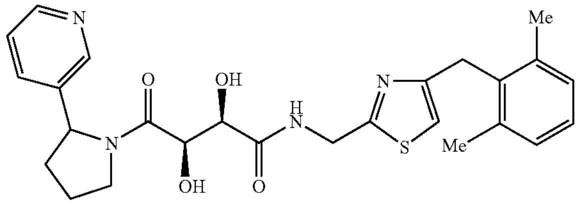 | |
| 420 | 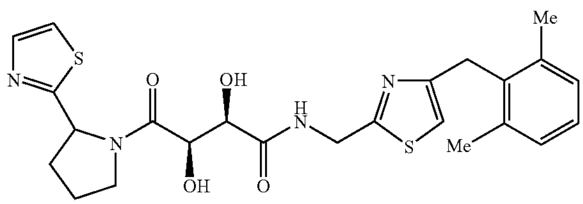 | |
| 421 | 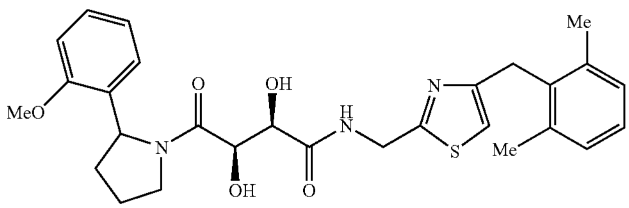 | |
| 422 | 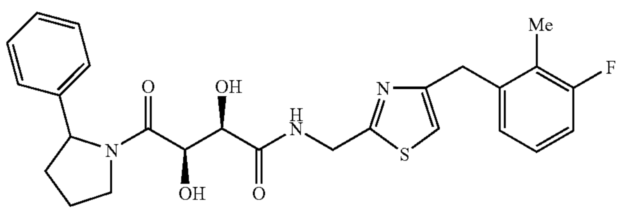 | |
| 423 | 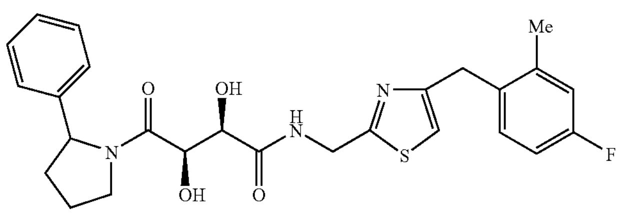 | |
| 424 | 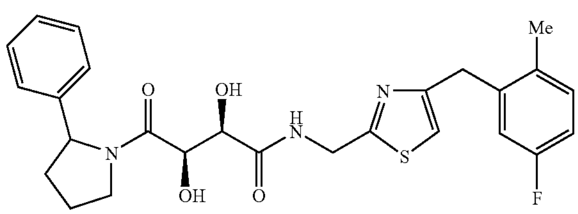 | |
| 425 | 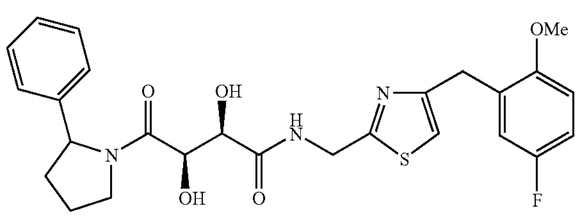 | |

-continued
| Compound # | Structure | $K_i$ (nM) |
|---|---|---|
| 426 | 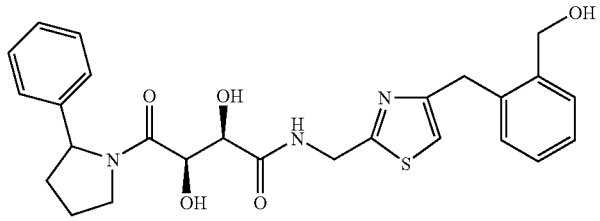 | |
| 427 | 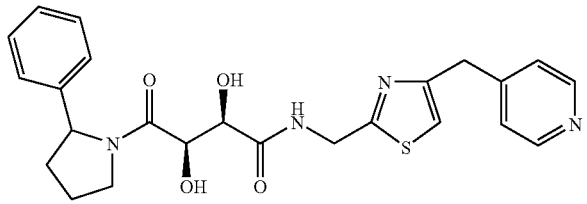 | |
| 428 | 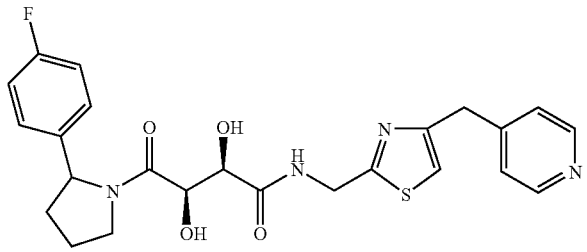 | |
| 429 | 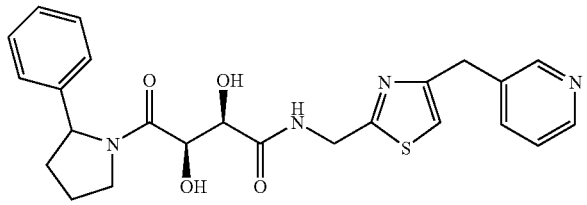 | |
| 430 | 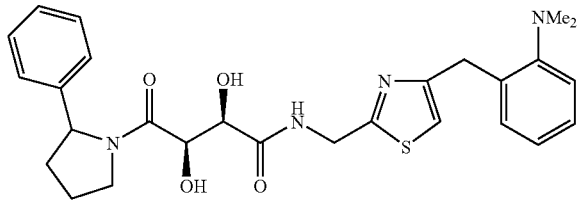 | |
| 431 | 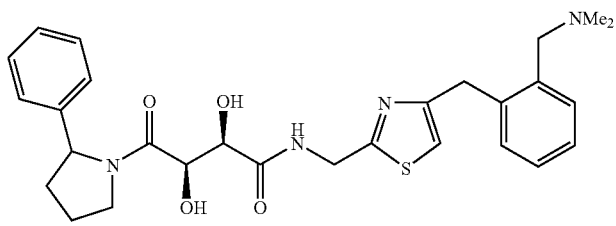 | |

-continued

| Compound # | Structure | $K_i$ (nM) |
|---|---|---|
| 432 | 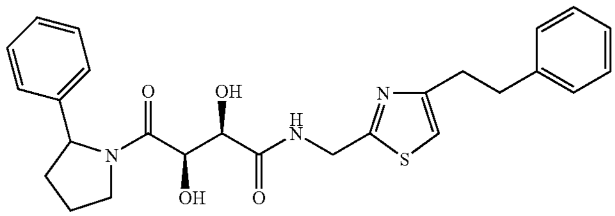 | |
| 433 | 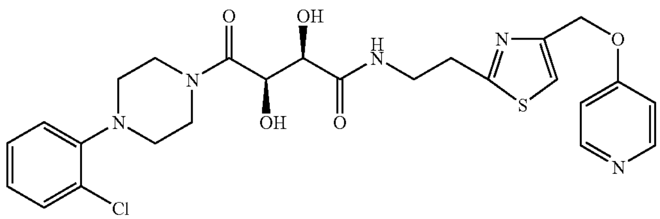 | |
| 434 | 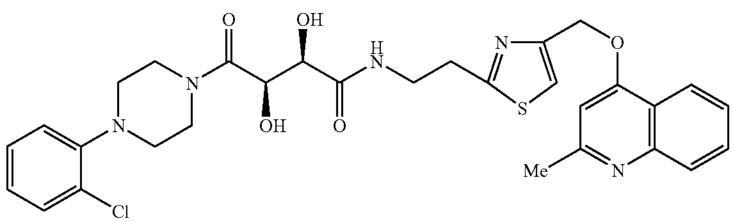 | |
| 435 | 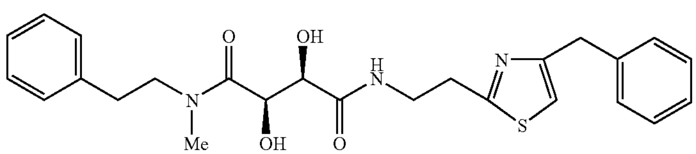 | |
| 436 | 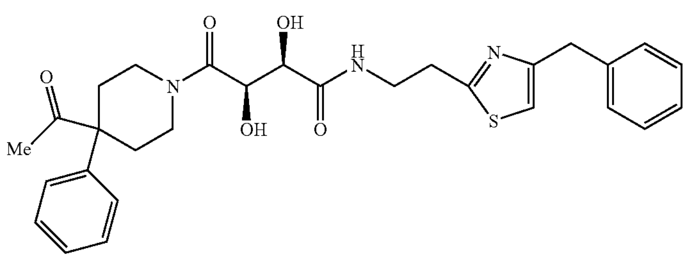 | |
| 437 | 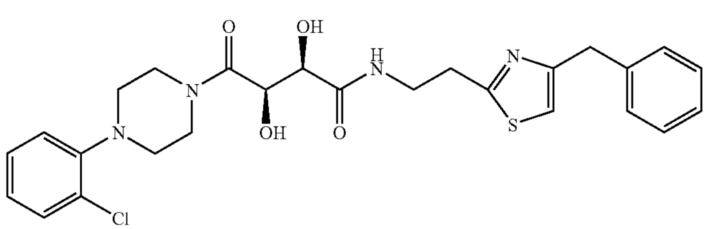 | |
| 438 | 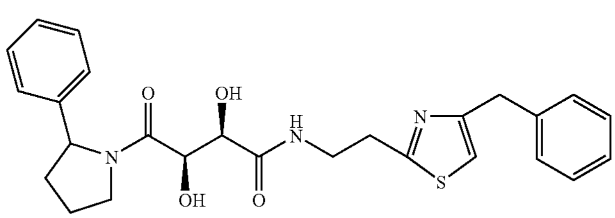 | |

-continued

| Compound # | Structure | $K_i$ (nM) |
|---|---|---|
| 439 | 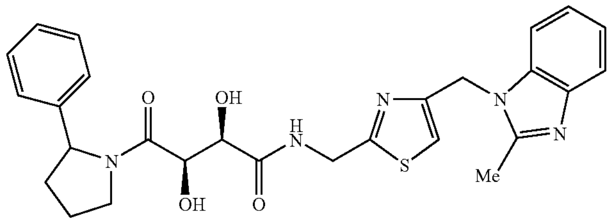 | |
| 440 | 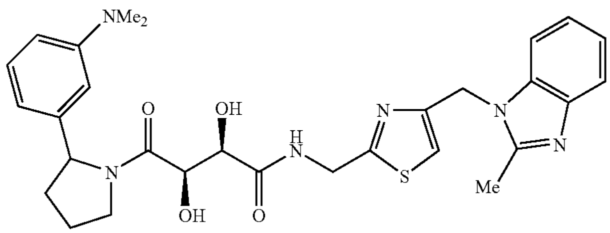 | |
| 441 | 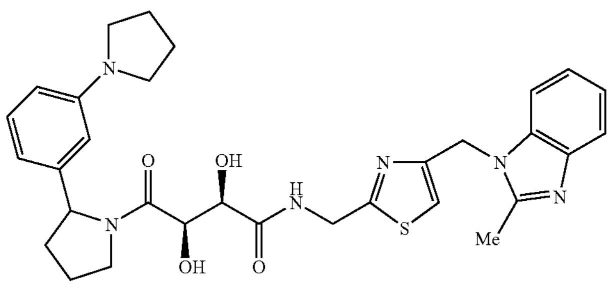 | |
| 442 | 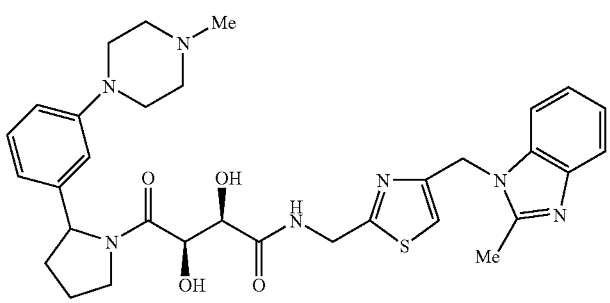 | |
| 443 | 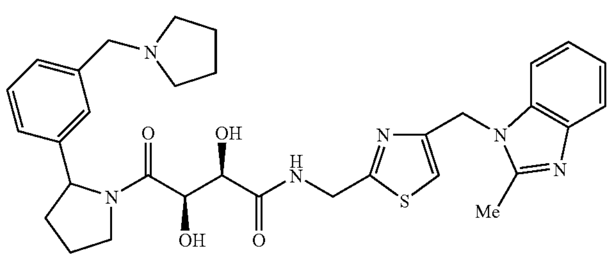 | |
| 444 | 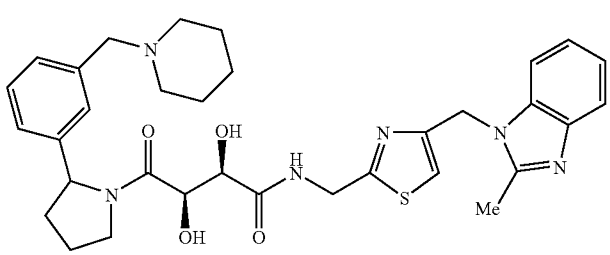 | |

| Compound # | Structure | $K_i$ (nM) |
|---|---|---|
| 445 | 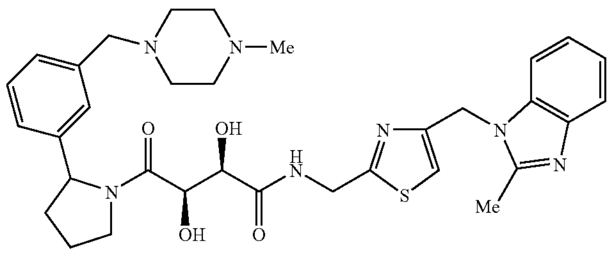 | |
| 446 | 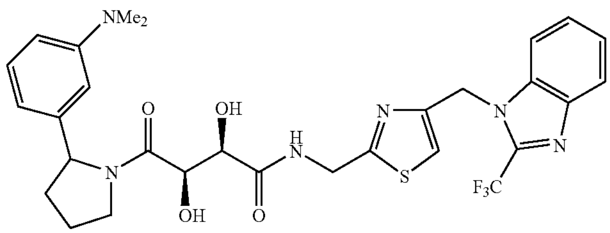 | |
| 447 | 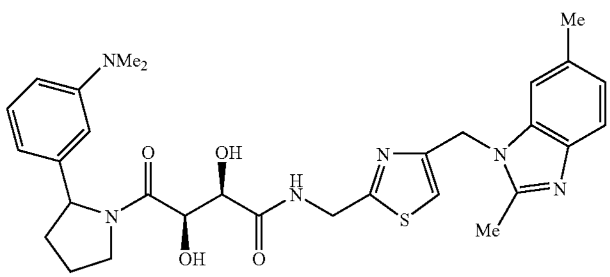 | |
| 448 | 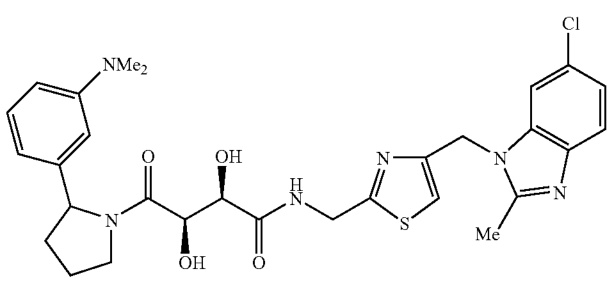 | |

-continued
| Compound # | Structure | $K_i$ (nM) |
|---|---|---|
| 468 | 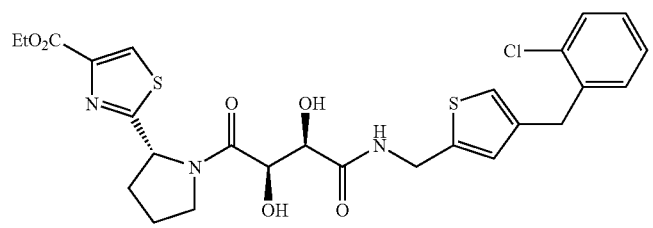 | |
| 473 | 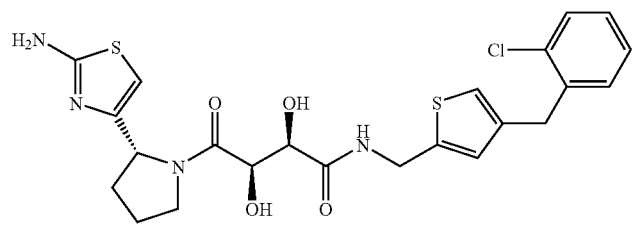 | |
| 477 | 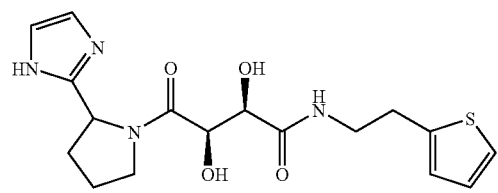 | |
| 478 | 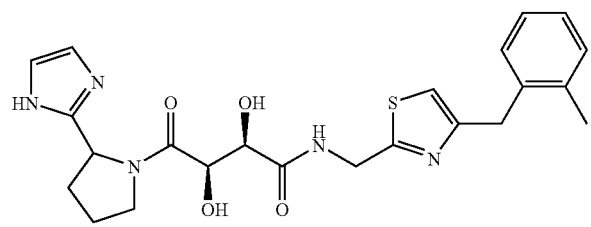 | |
| 479 | 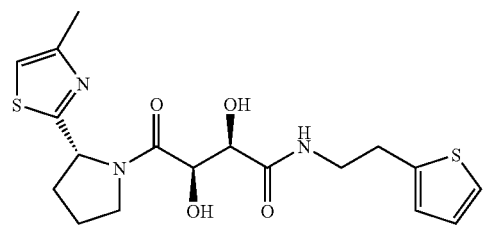 | |
| 480 | 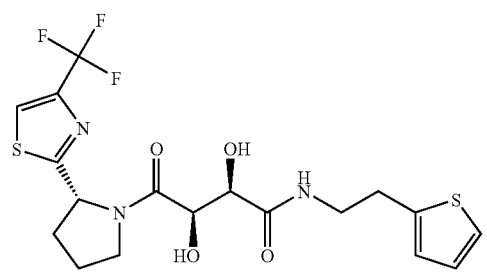 | |

-continued

| Compound # | Structure | K_i (nM) |
|---|---|---|
| 481 | 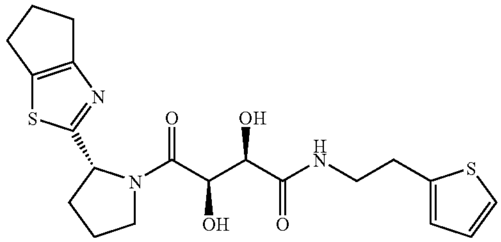 | |
| 482 | 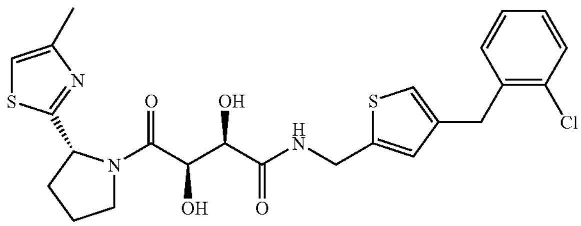 | |
| 483 | 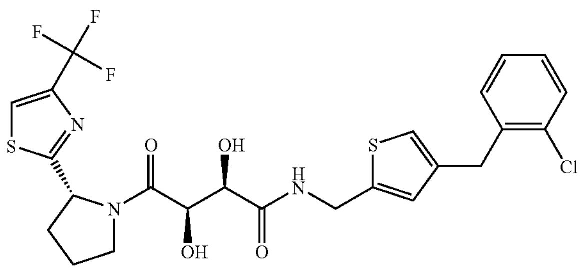 | |
| 484 | 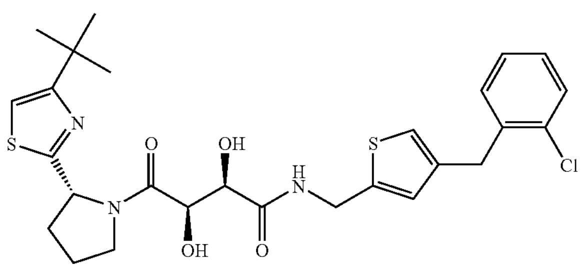 | |
| 485 | 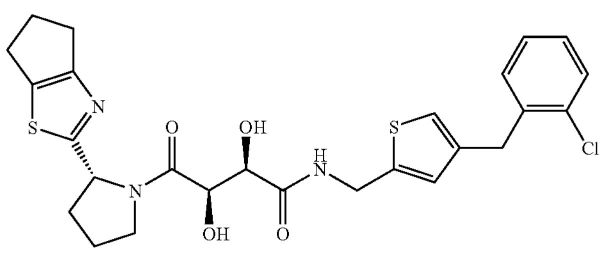 | |
| 486 | 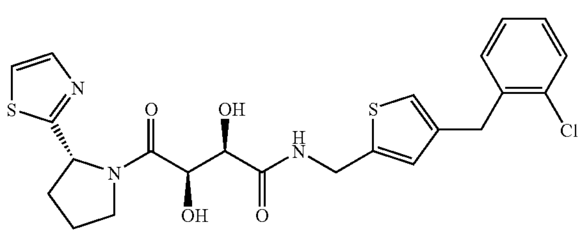 | |

-continued

| Compound # | Structure | $K_i$ (nM) |
|---|---|---|
| 487 | 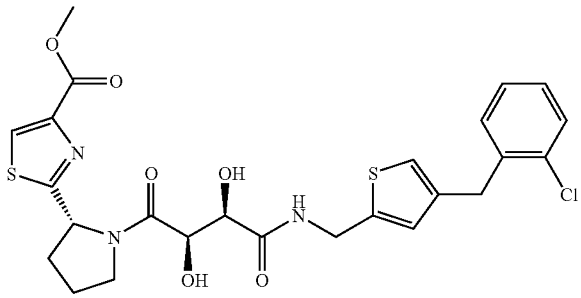 | |
| 488 | 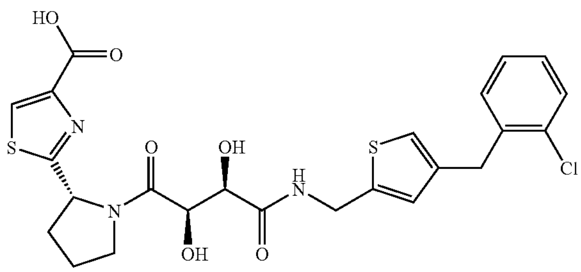 | |
| 489 | 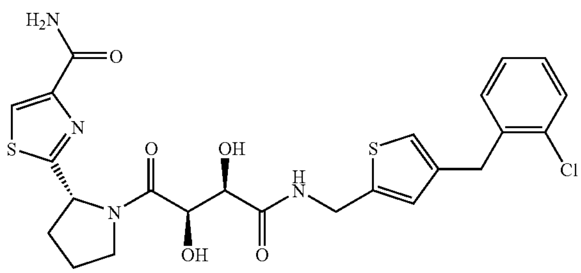 | |
| 490 | 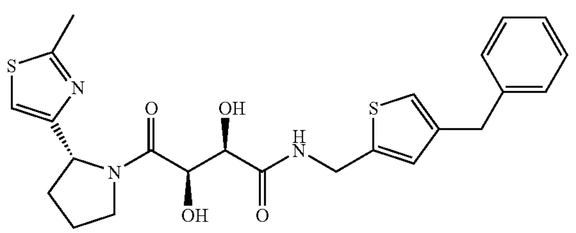 | |
| 491 | 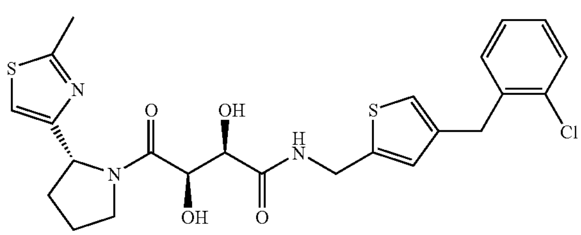 | |
| 492 | 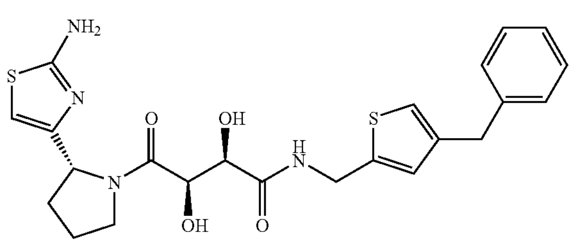 | |

-continued
| Compound # | Structure | $K_i$ (nM) |
|---|---|---|
| 493 | 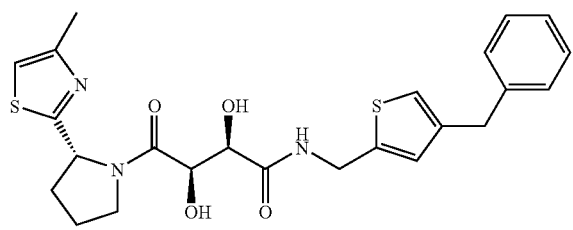 | |
| 494 | 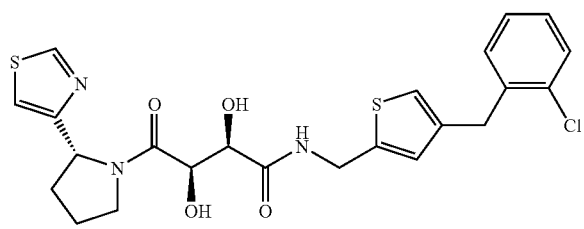 | |
| 495 | 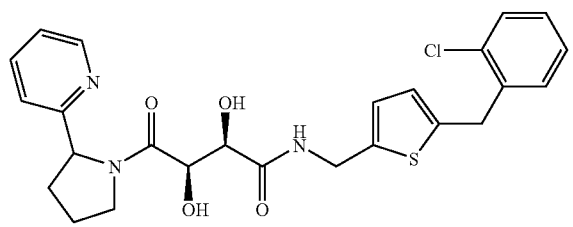 | |
| 496 | 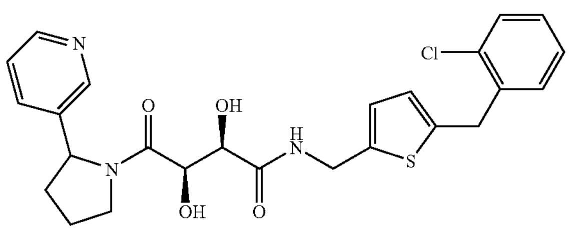 | |
| 497 | 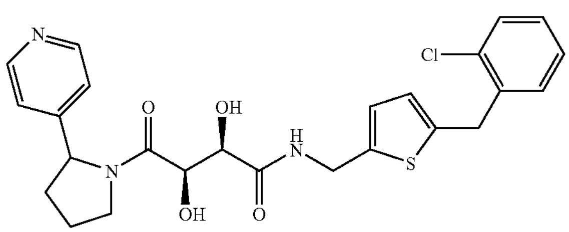 | |
| 498 | 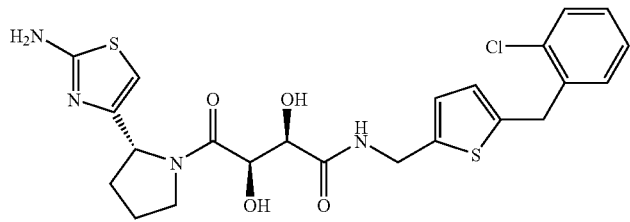 | |

-continued

| Compound # | Structure | $K_i$ (nM) |
|---|---|---|
| 499 | 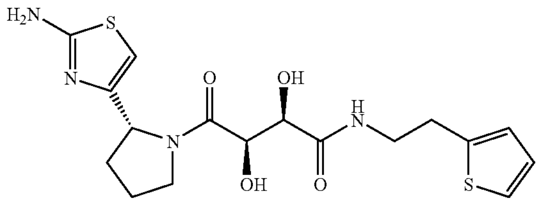 | |
| 500 | 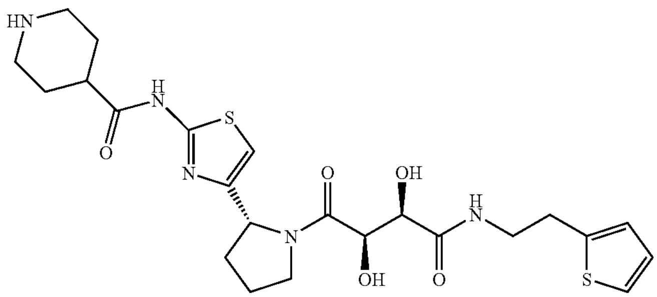 | |
| 501 | 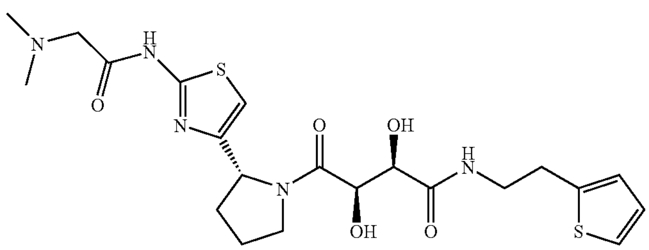 | |
| 502 | 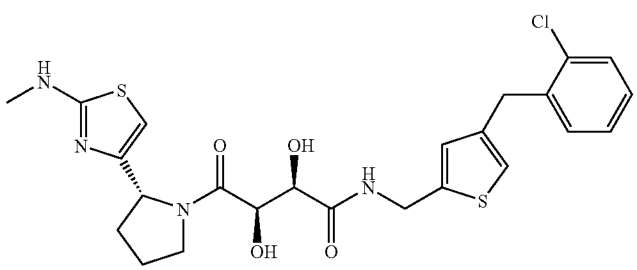 | |
| 416 | 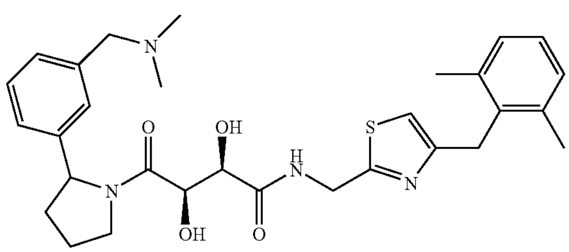 | |
| 417 | 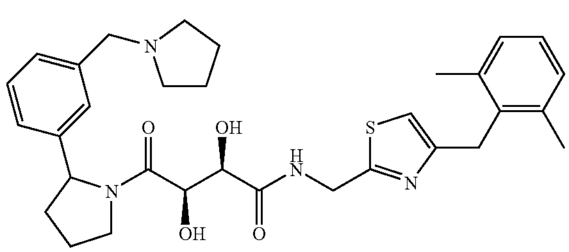 | |

| Compound # | Structure | $K_i$ (nM) |
|---|---|---|
| 418 | 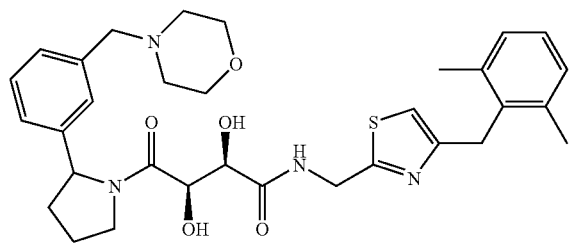 | |
| 529 | 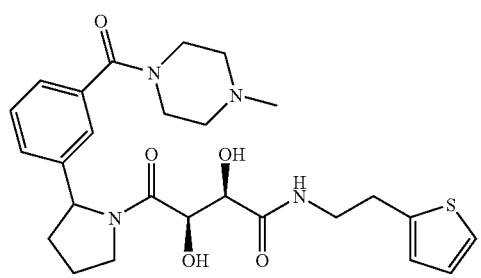 | |
| 530 | 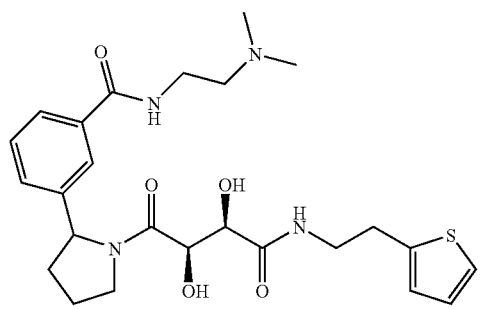 | |
| 531 | 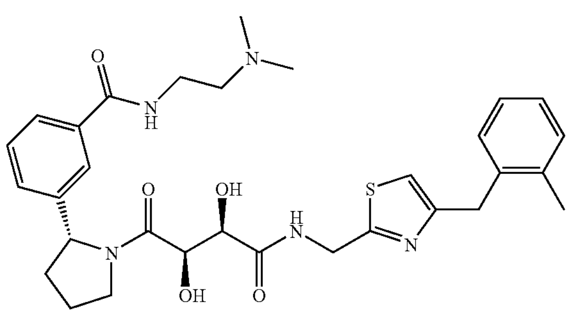 | |
| 532 | 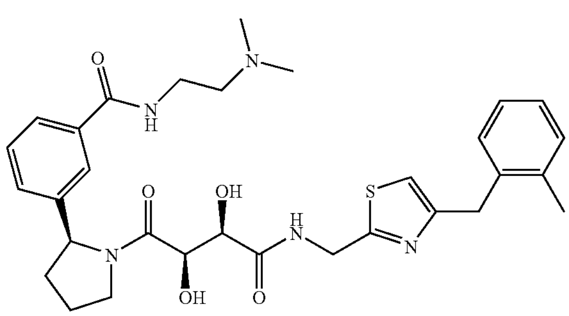 | |

-continued
| Compound # | Structure | $K_i$ (nM) |
|---|---|---|
| 536 | 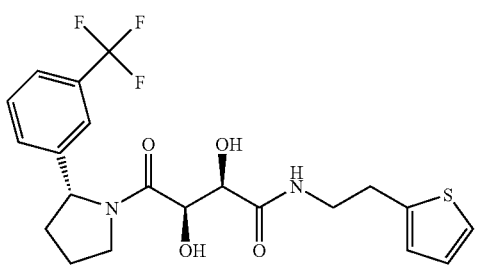 | |
| 537 | 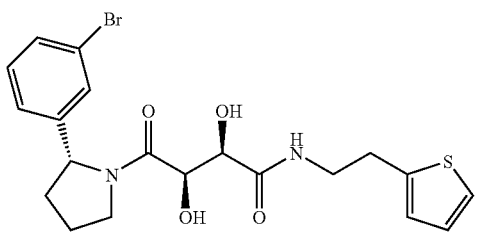 | |
| 538 | 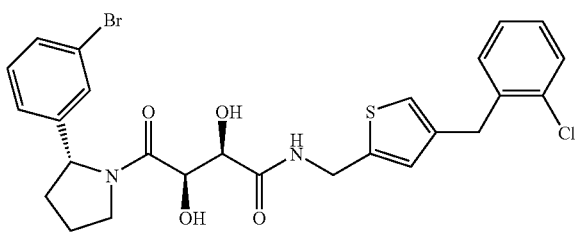 | |
| 539 | 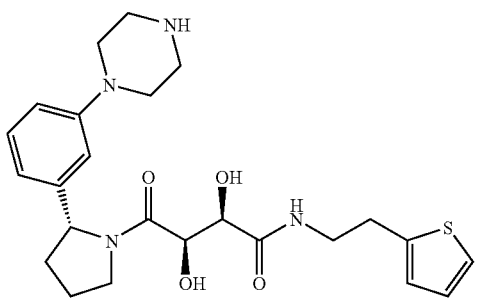 | |
| 540 | 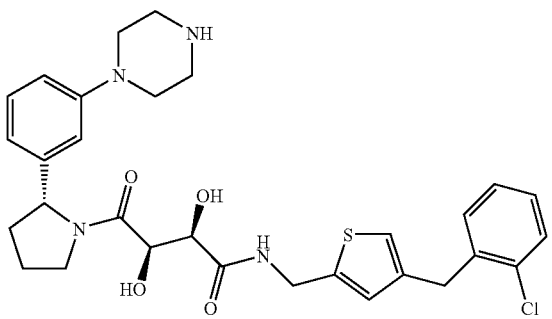 | |

-continued
| Compound # | Structure | $K_i$ (nM) |
|---|---|---|
| 541 | 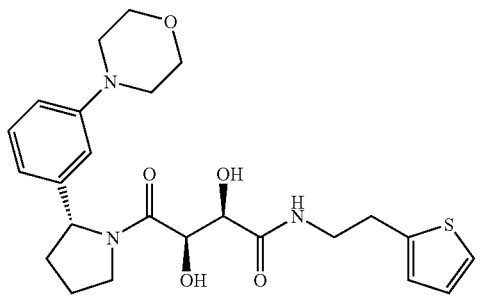 | |
| 542 | 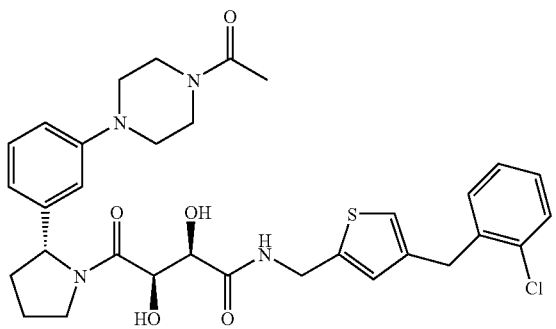 | |
| 546 | 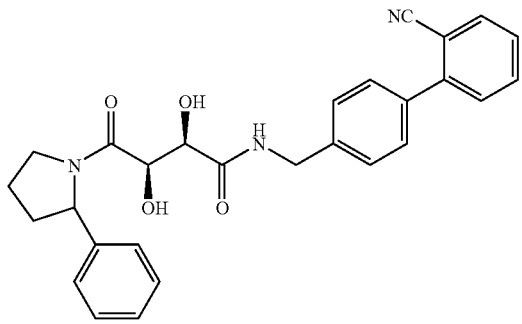 | |
| 553 | 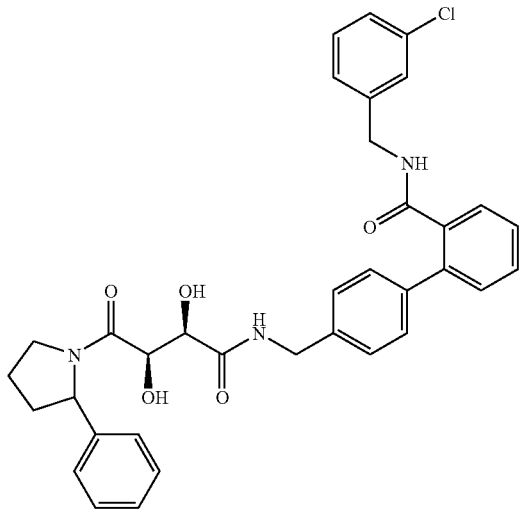 | |

-continued
| Compound # | Structure | $K_i$ (nM) |
|---|---|---|
| 557 | 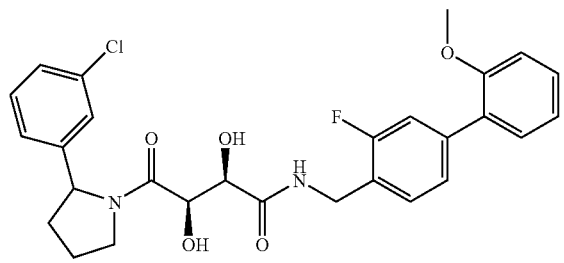 | |
| 565 | 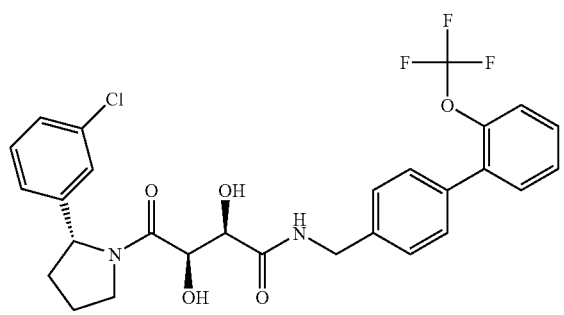 | |
| 572 | 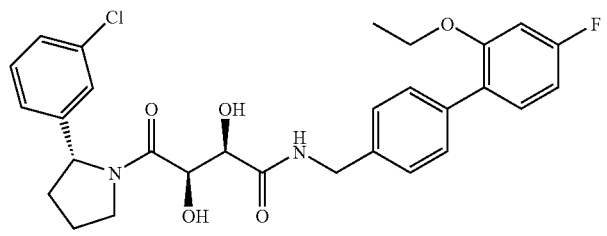 | |
| 578 | 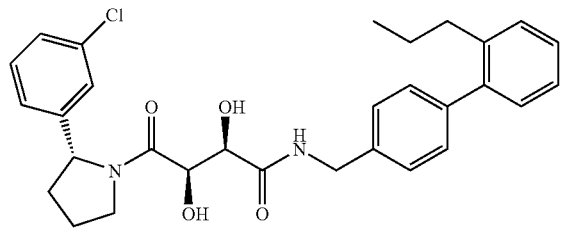 | |
| 585 | 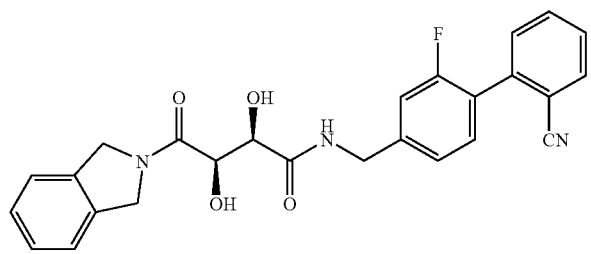 | |

US 7,652,020 B2

-continued

| Compound # | Structure | $K_i$ (nM) |
|---|---|---|
| 586 | 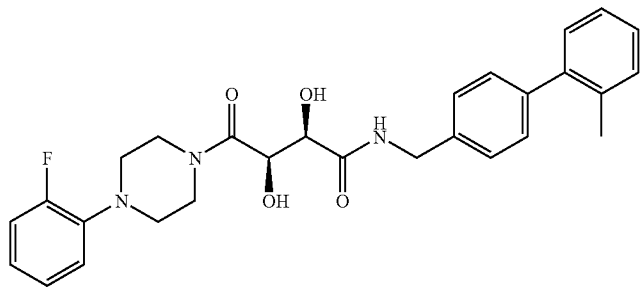 | |
| 587 | 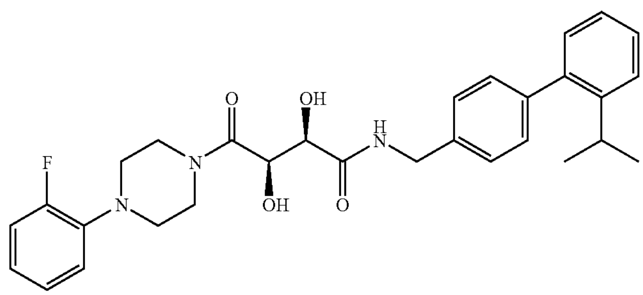 | |
| 588 | 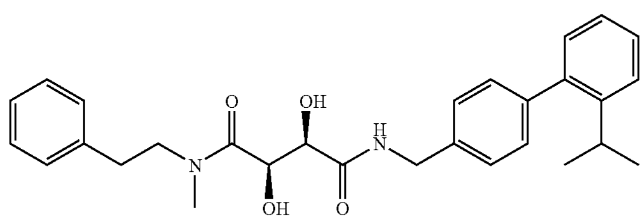 | |
| 589 | 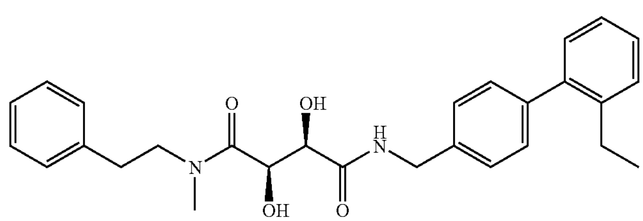 | |
| 590 | 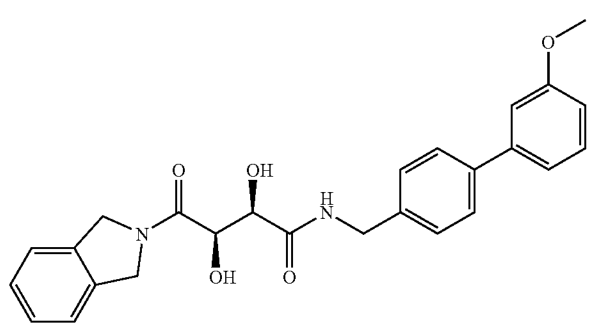 | |

-continued
| Compound # | Structure | $K_i$ (nM) |
|---|---|---|
| 591 | 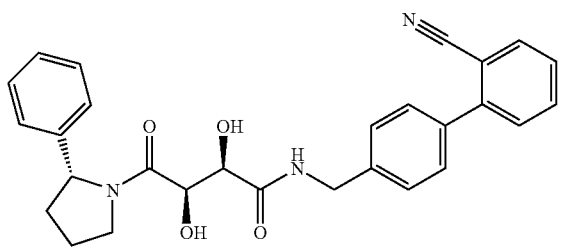 | |
| 592 | 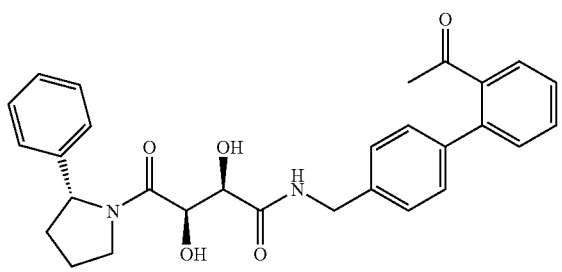 | |
| 593 | 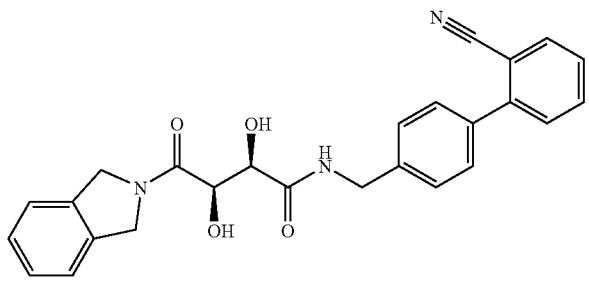 | |
| 594 | 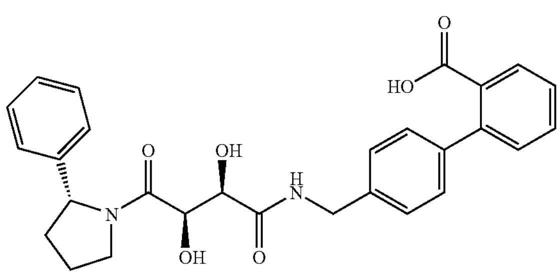 | |
| 595 | 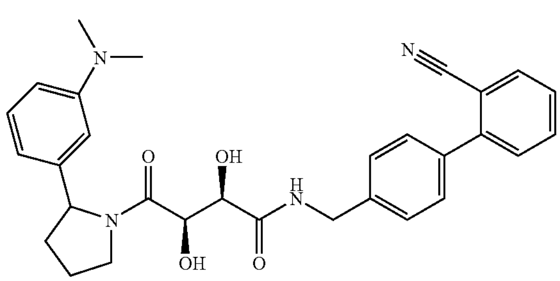 | |

-continued

| Compound # | Structure | $K_i$ (nM) |
|---|---|---|
| 596 | 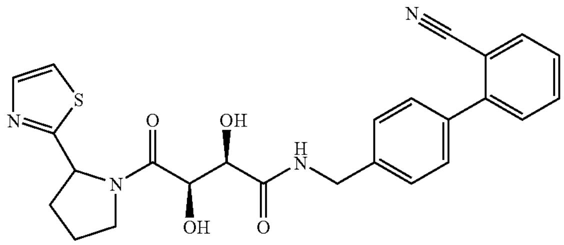 | |
| 597 | 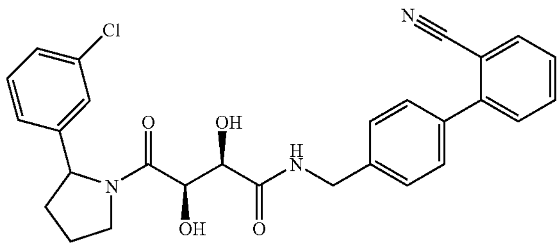 | |
| 598 | 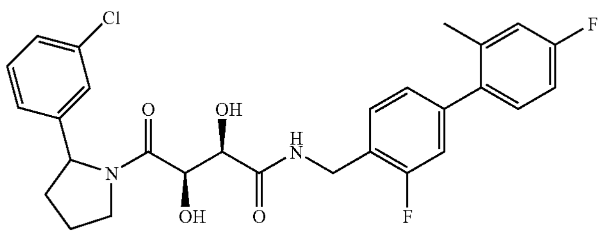 | |
| 599 | 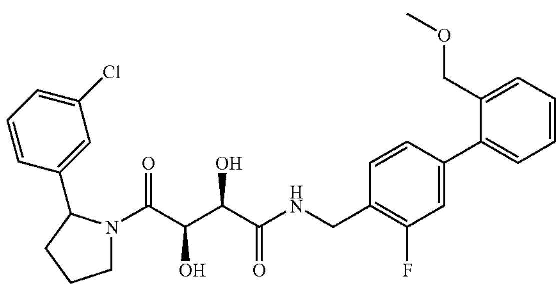 | |
| 600 | 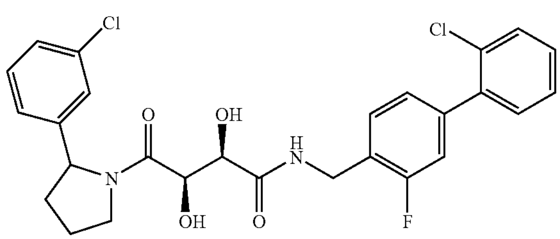 | |
| 601 | 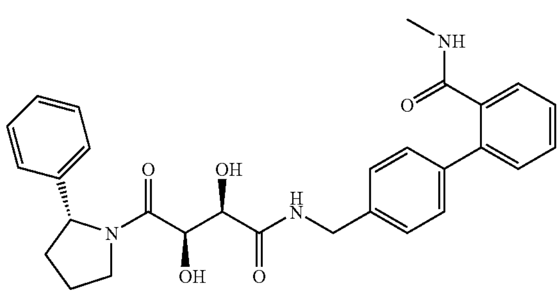 | |

-continued
| Compound # | Structure | $K_i$ (nM) |
|---|---|---|
| 602 | 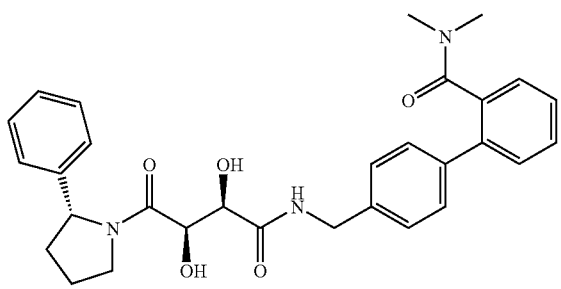 | |
| 603 | 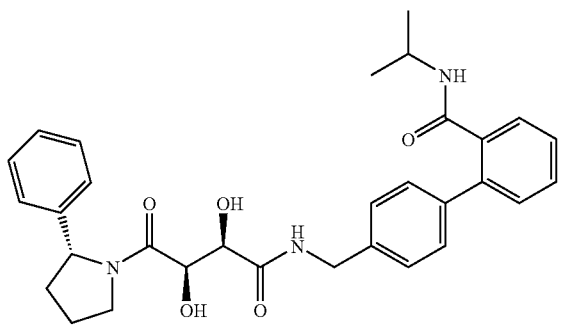 | |
| 604 | 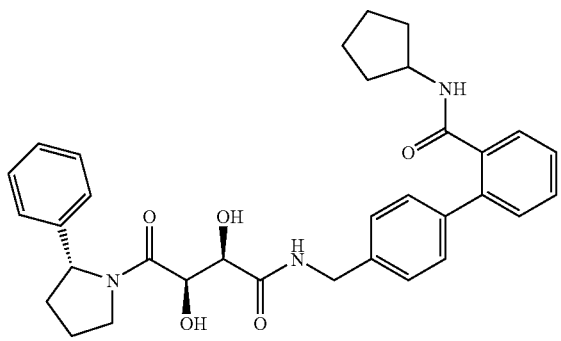 | |
| 605 | 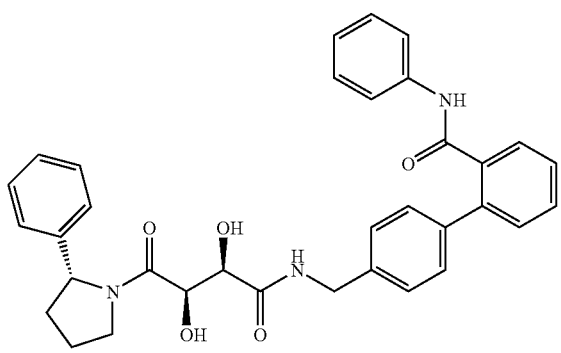 | |

-continued
| Compound # | Structure | $K_i$ (nM) |
|---|---|---|
| 606 | 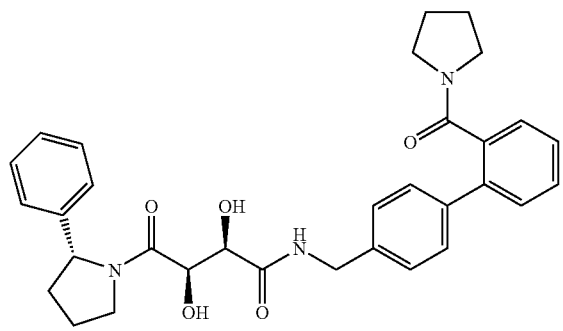 | |
| 607 | 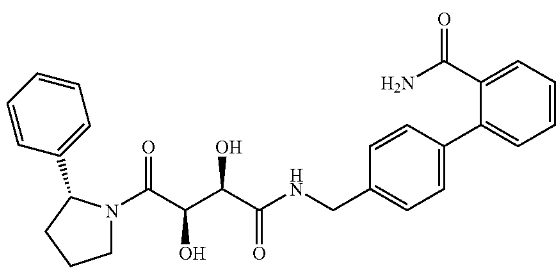 | |
| 608 | 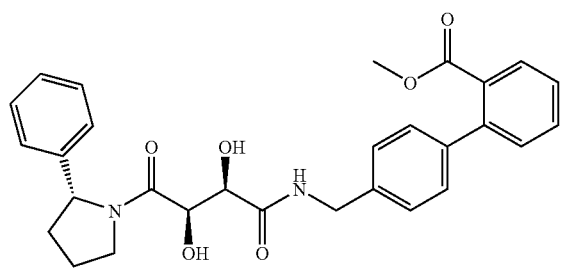 | |
| 609 | 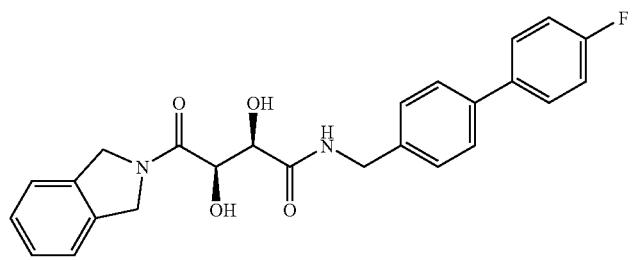 | |
| 610 | 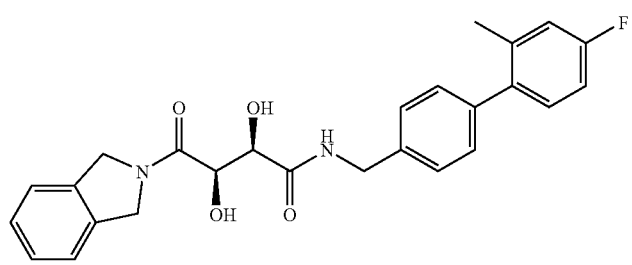 | |

-continued
| Compound # | Structure | K$_i$ (nM) |
|---|---|---|
| 611 | 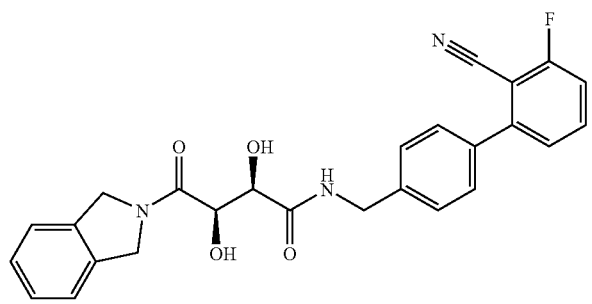 | |
| 612 | 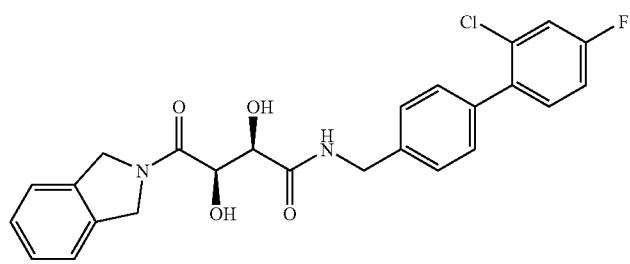 | |
| 613 | 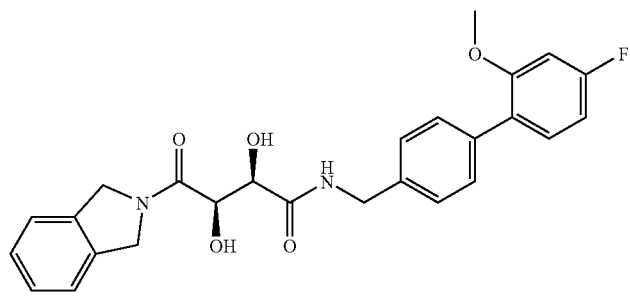 | |
| 614 | 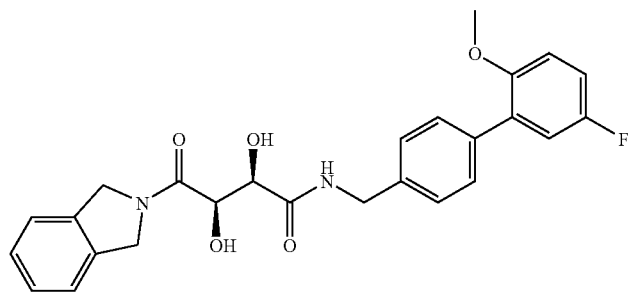 | |
| 615 | 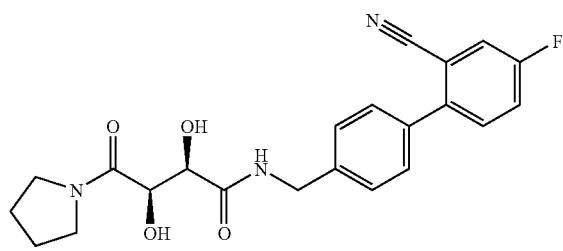 | |

-continued

| Compound # | Structure | $K_i$ (nM) |
|---|---|---|
| 616 | 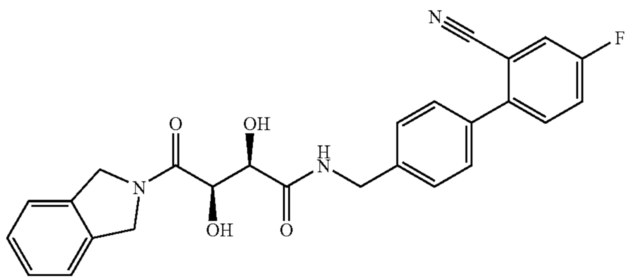 | |
| 617 | 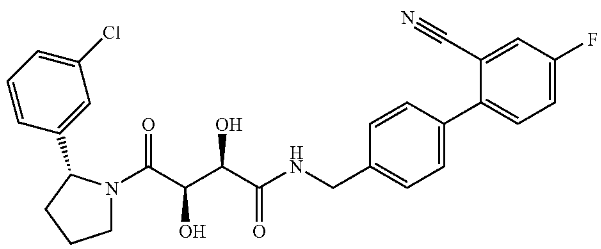 | |
| 618 | 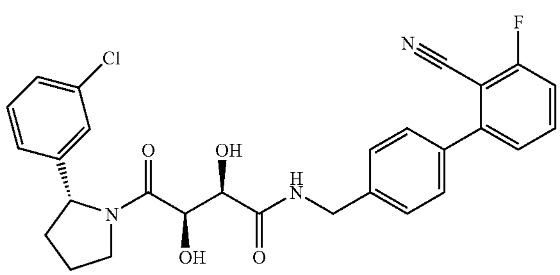 | |
| 619 | 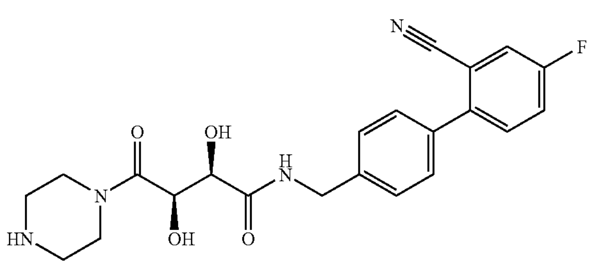 | |
| 620 | 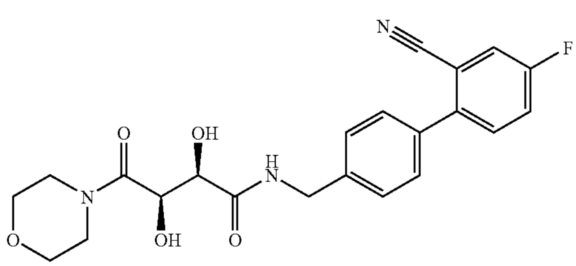 | |

-continued
| Compound # | Structure | $K_i$ (nM) |
|---|---|---|
| 621 | 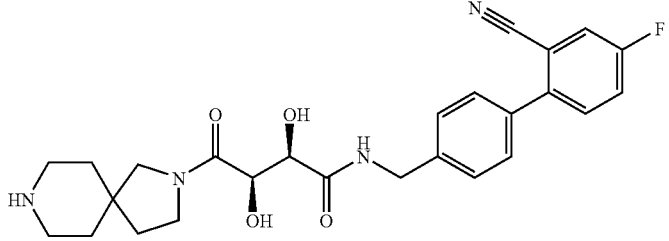 | |
| 622 | 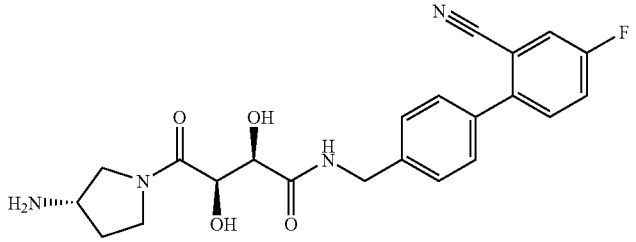 | |
| 623 | 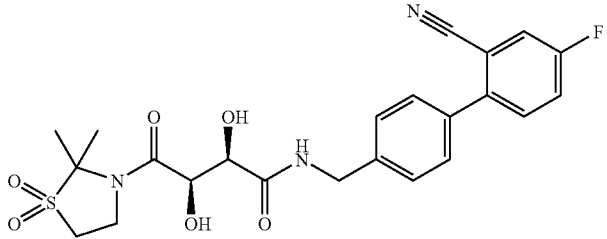 | |
| 624 | 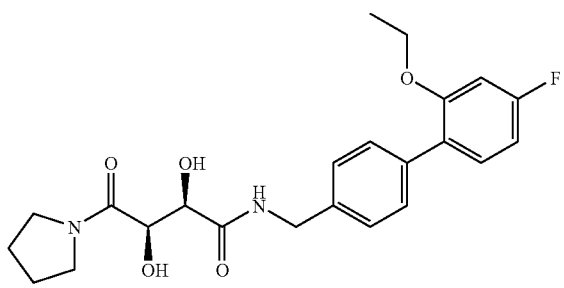 | |
| 625 | 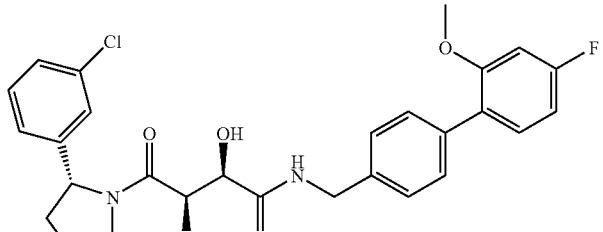 | |

-continued

| Compound # | Structure | $K_i$ (nM) |
|---|---|---|
| 626 | 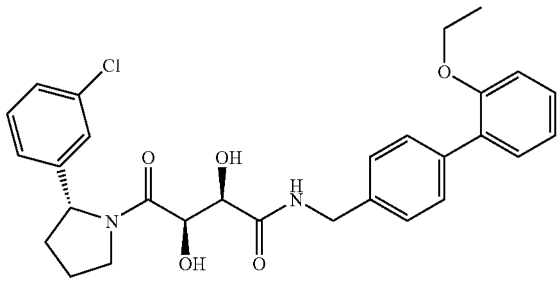 | |
| 627 | 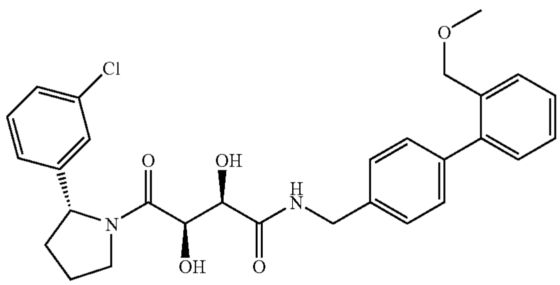 | |
| 628 | 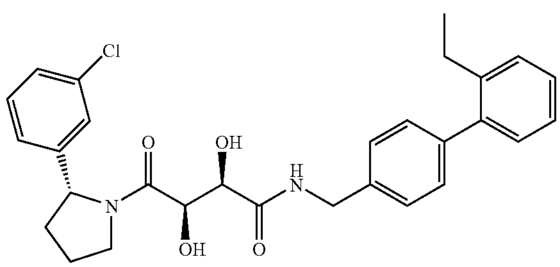 | |
| 629 | 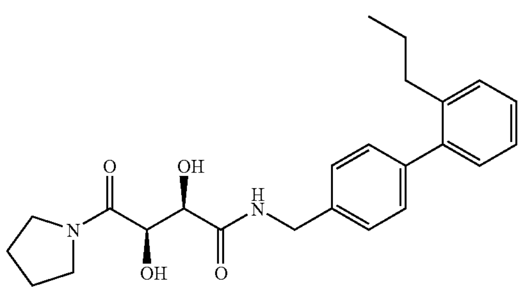 | |
| 630 | 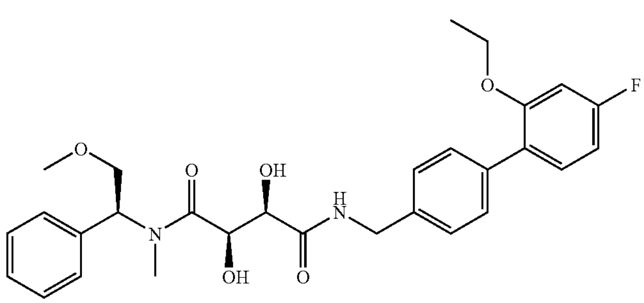 | |

-continued

| Compound # | Structure | $K_i$ (nM) |
|---|---|---|
| 635 | 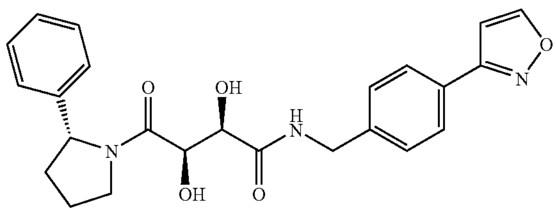 | |
| 636 | 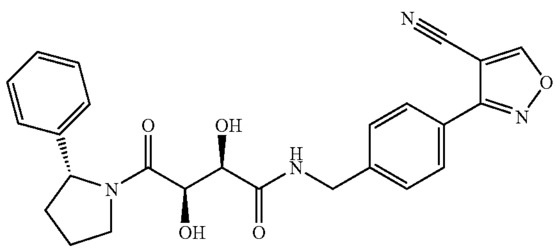 | |
| 637 | 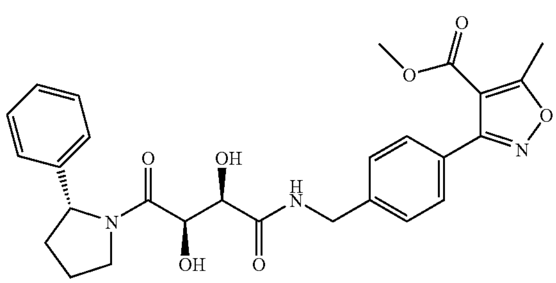 | |
| 638 | 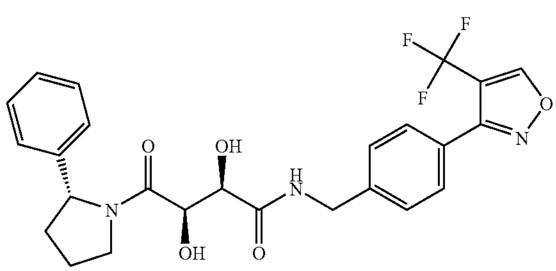 | |
| 639 | 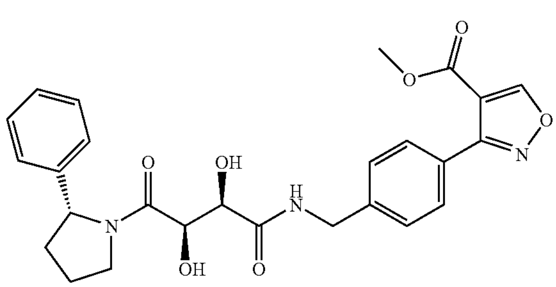 | |

| Compound # | Structure | $K_i$ (nM) |
|---|---|---|
| 640 | 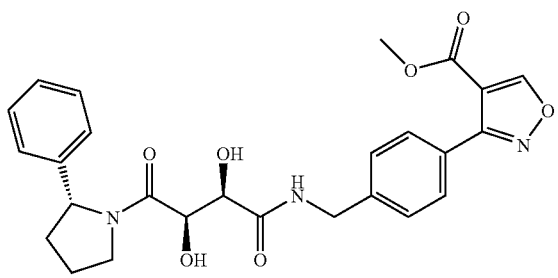 | |
| 646A | 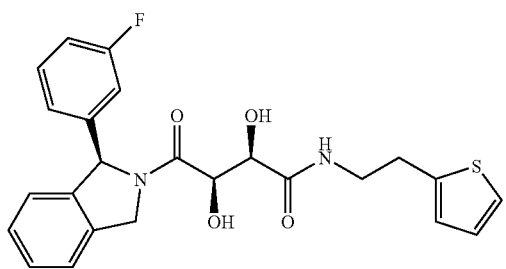 | |
| 646B | 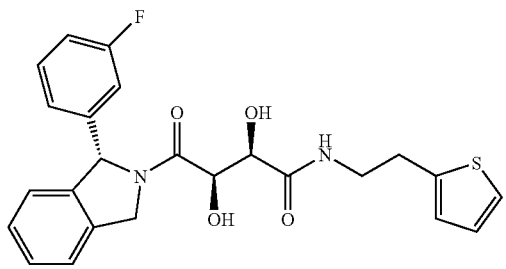 | |
| 647 | 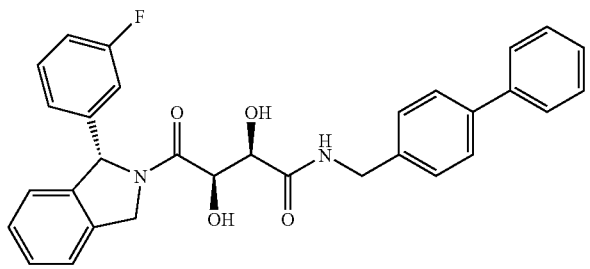 | |
| 648 | 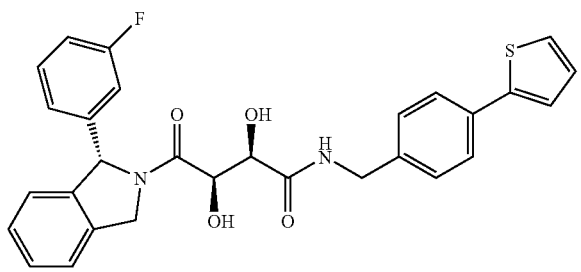 | |

-continued

| Compound # | Structure | $K_i$ (nM) |
|---|---|---|
| 649A | 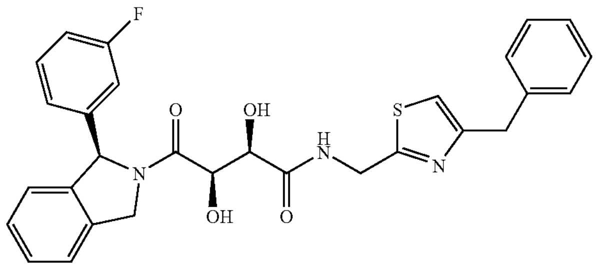 | |
| 649B | 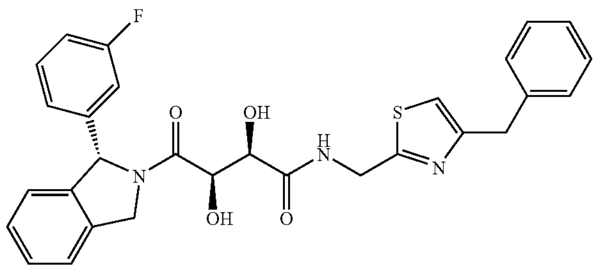 | |
| 655 | 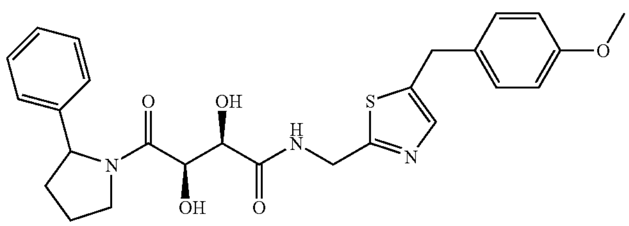 | |
| 656A | 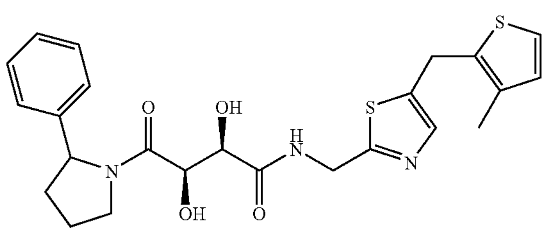 | |
| 656B | 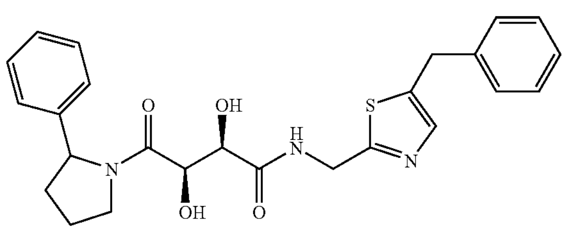 | |
| 657 | 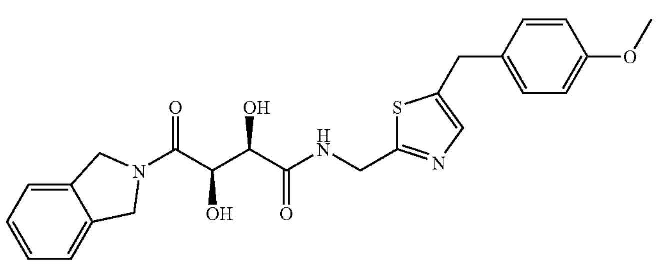 | |

-continued
| Compound # | Structure | $K_i$ (nM) |
|---|---|---|
| 658 | 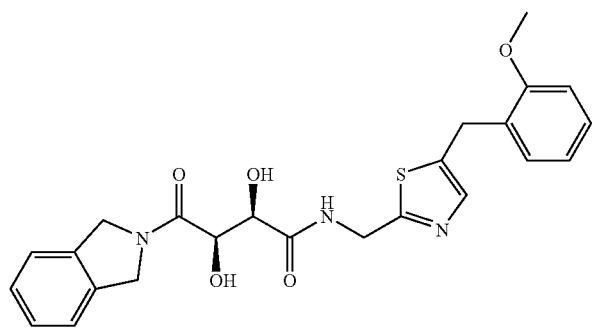 | |
| 659 | 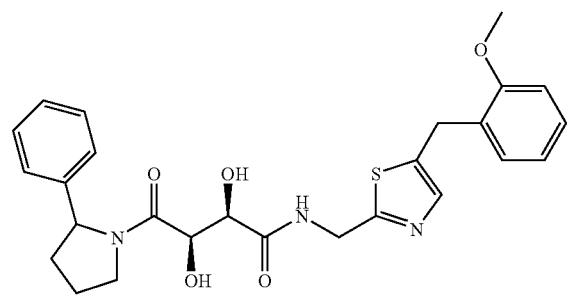 | |
| 660 | 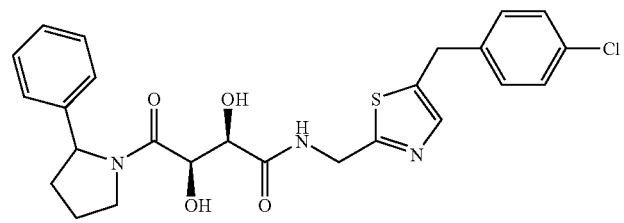 | |
| 661 | 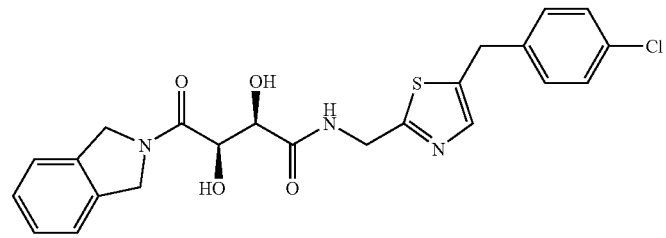 | |
| 662 | 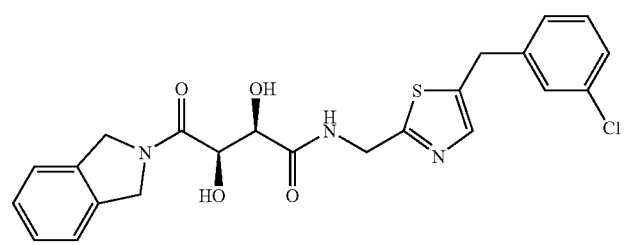 | |

-continued
663
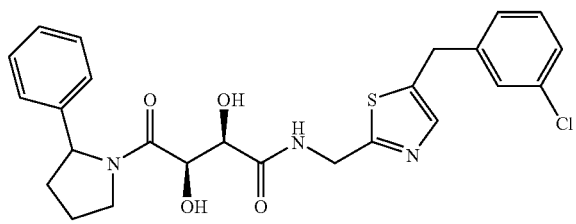
664
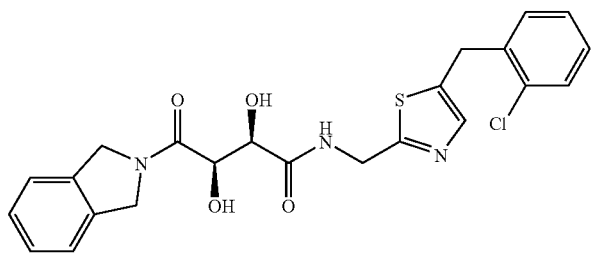
668
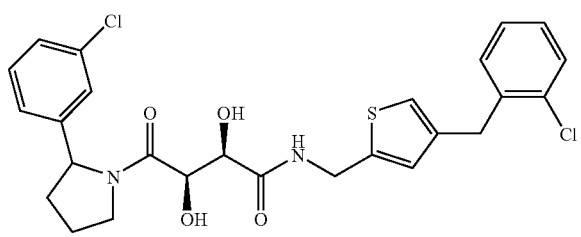
673
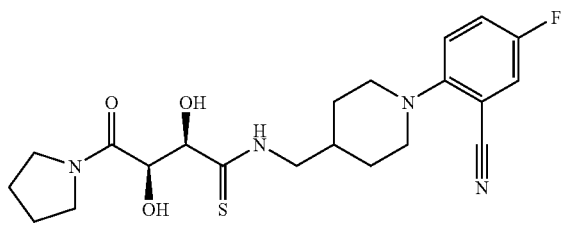
674
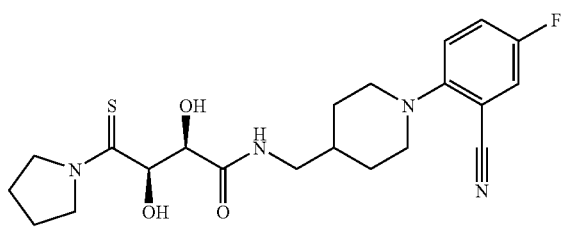
678
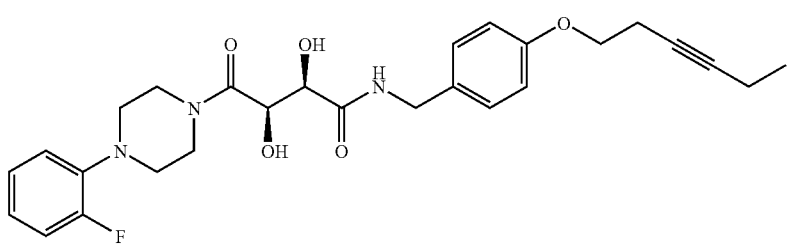

683 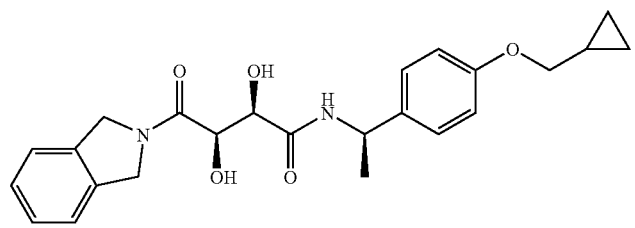
684 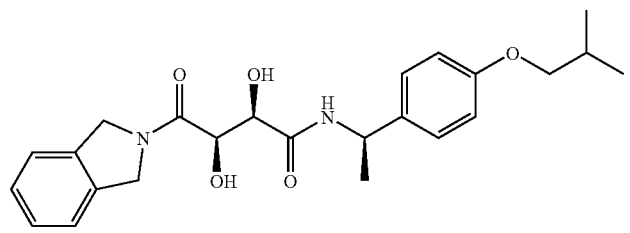
685 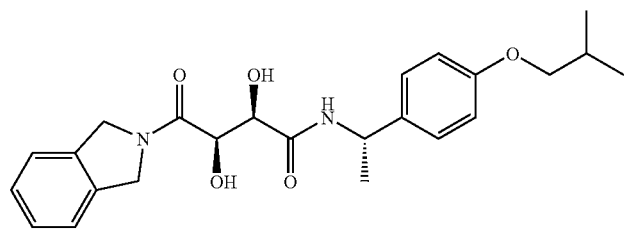
686 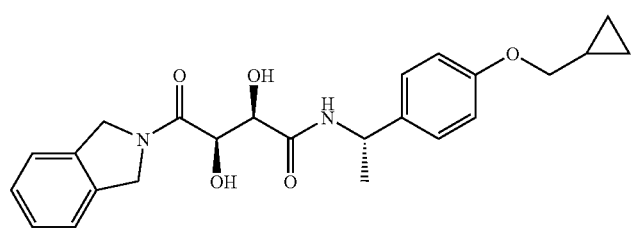
687 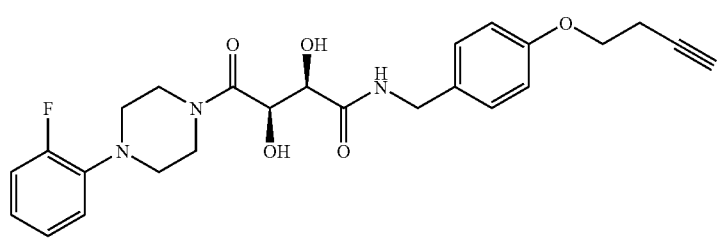
688 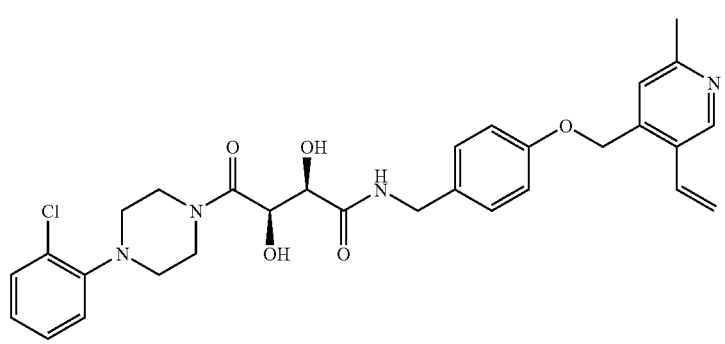

-continued
689
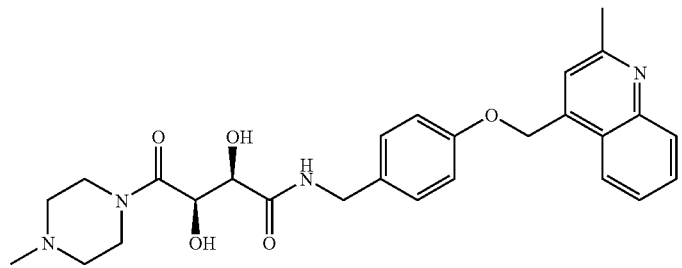
690
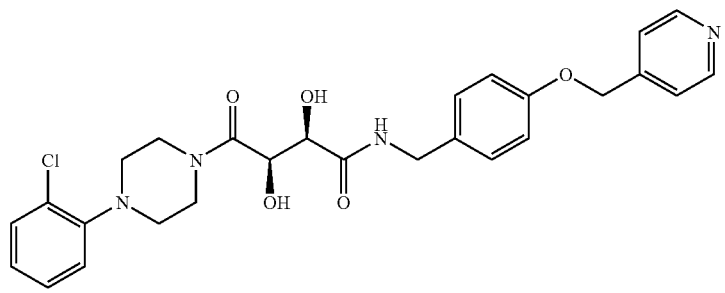
691
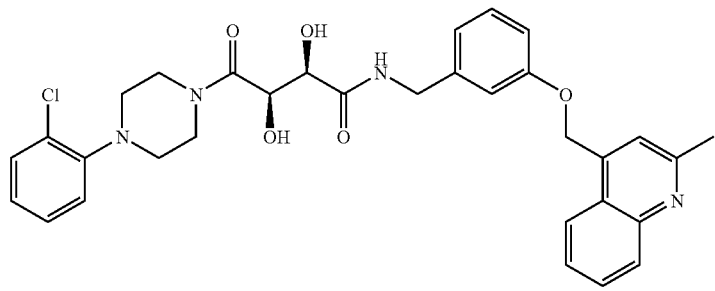
696
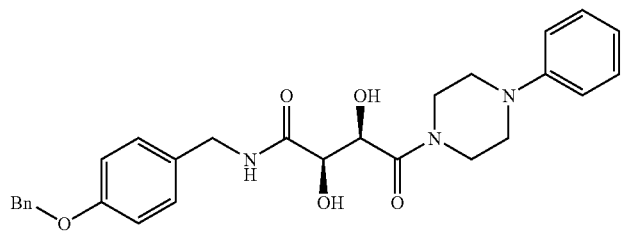
697
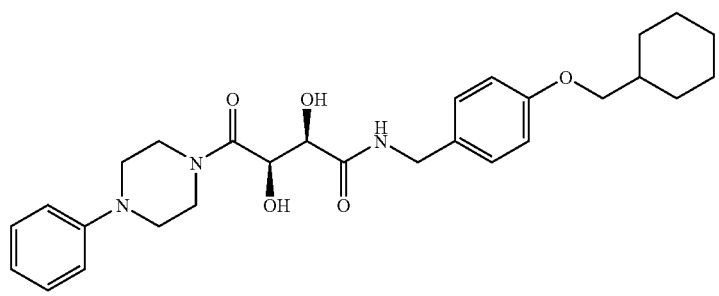

-continued
| | |
|---|---|
| 698 | 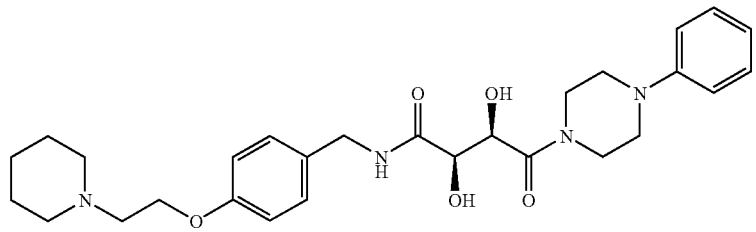 |
| 699 | 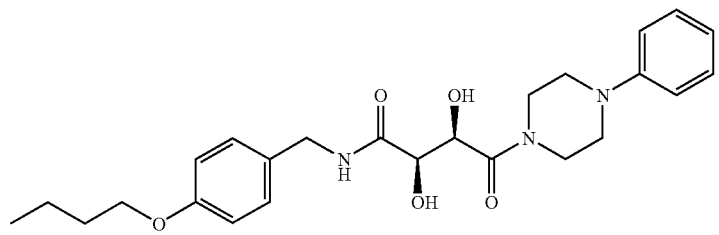 |
| 700 | 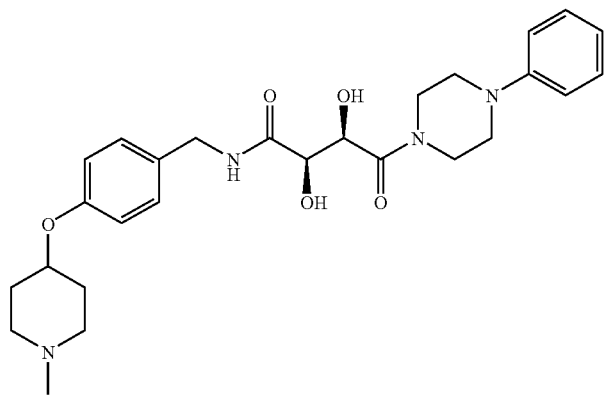 |
| 701 | 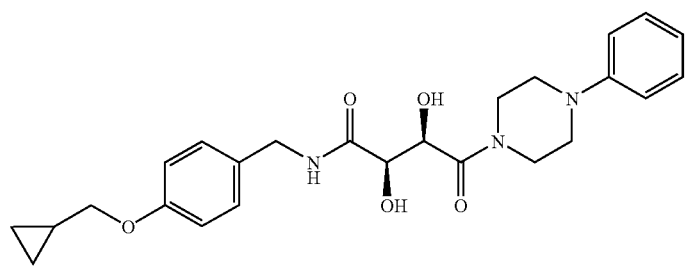 |
| 702 | 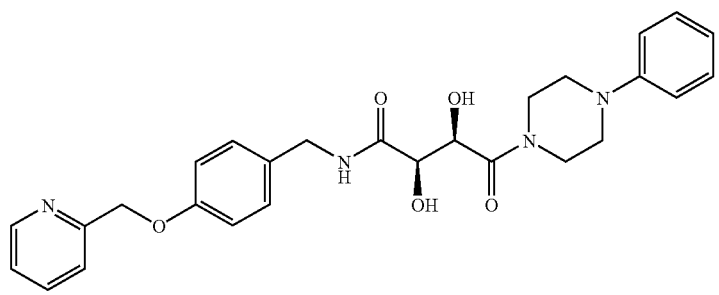 |

703 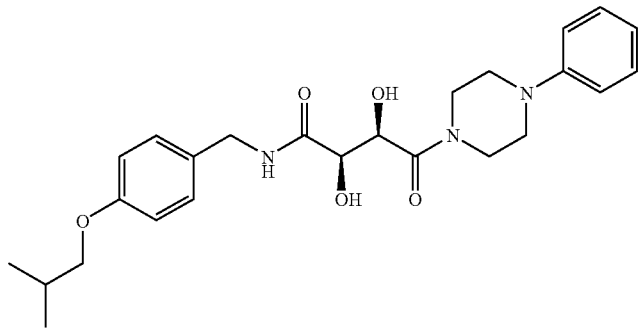
704 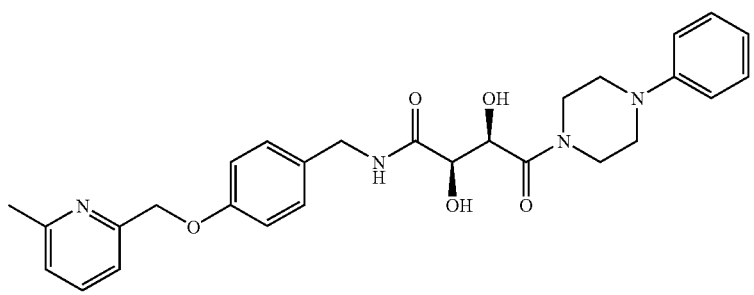
705 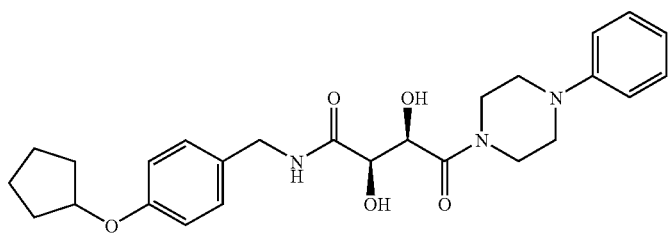
706 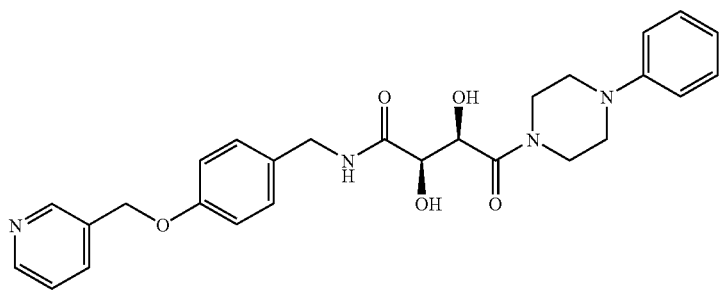
707 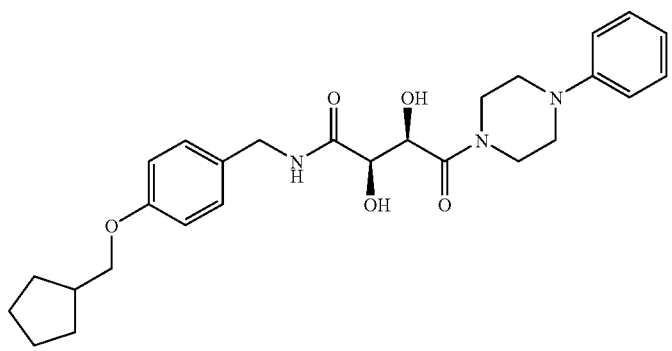

708
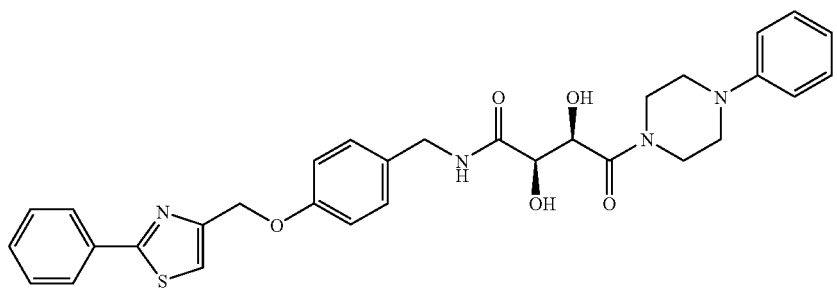
709
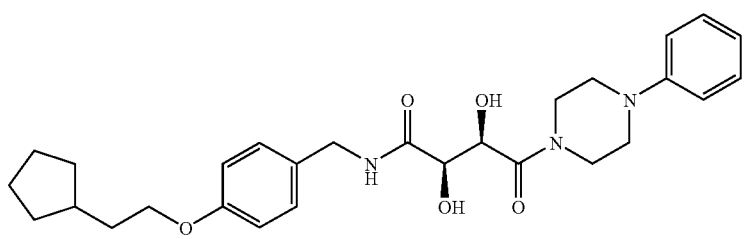
710
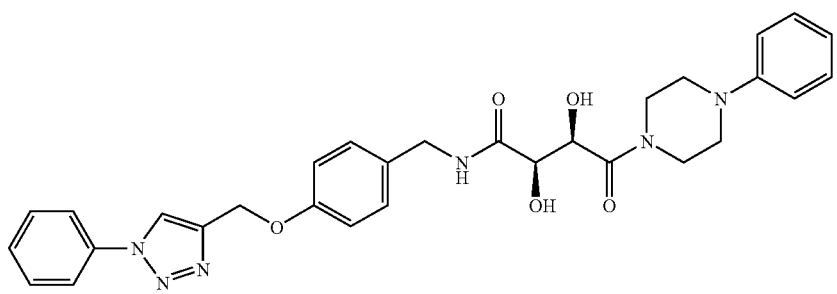
711
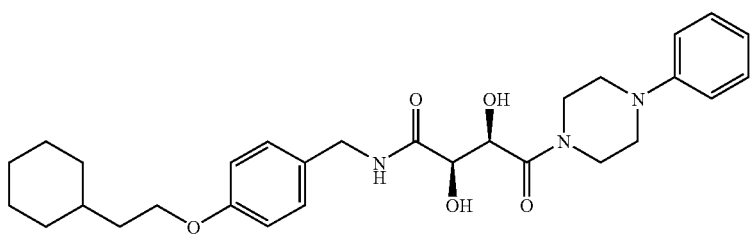
712
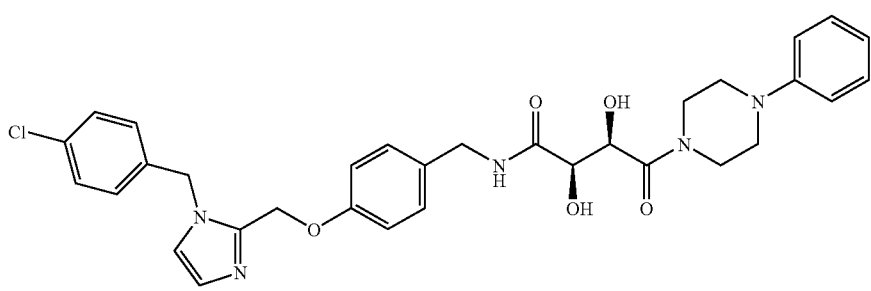

713 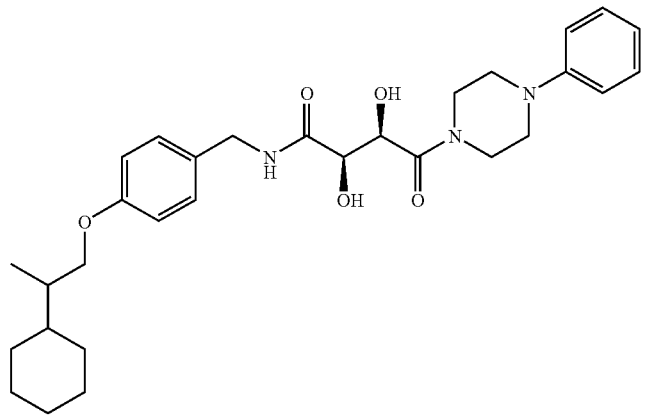
714 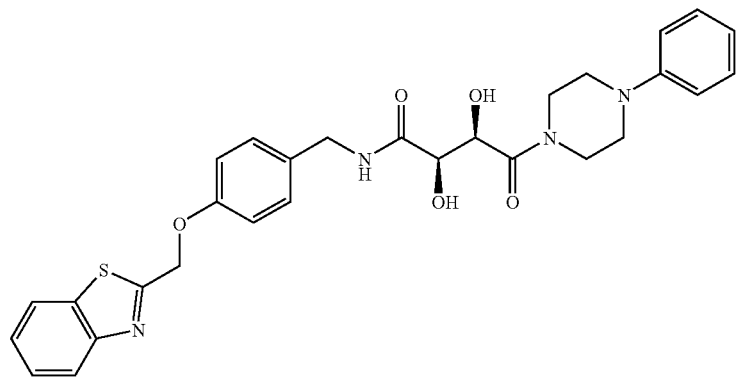
715 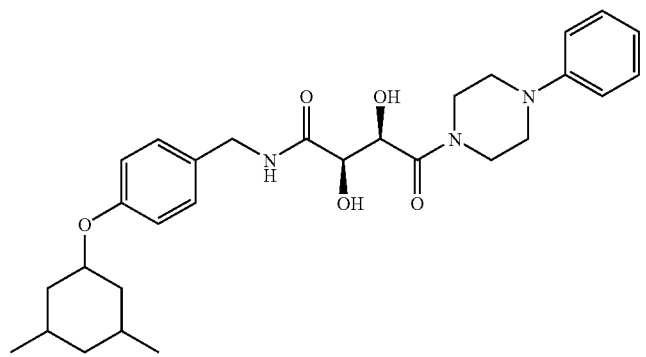
716 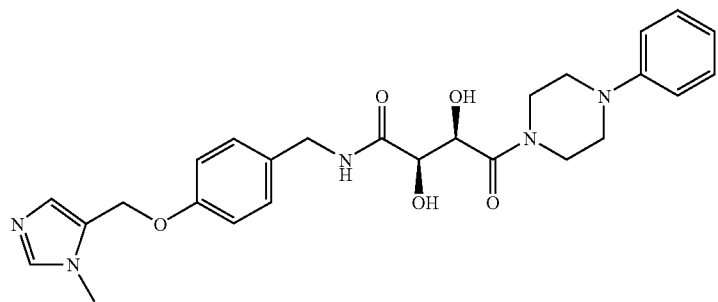

-continued
717
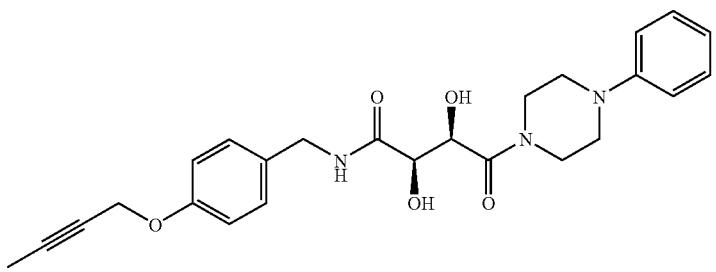
718
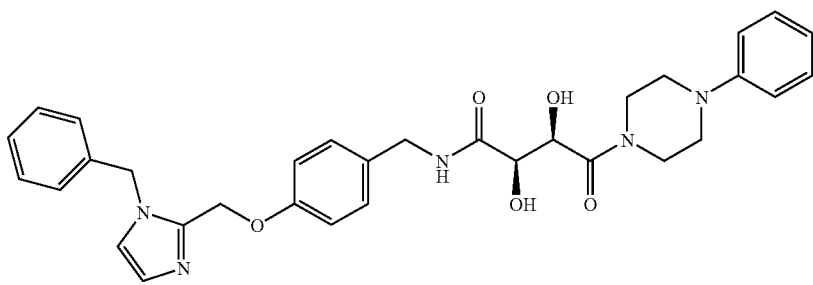
719
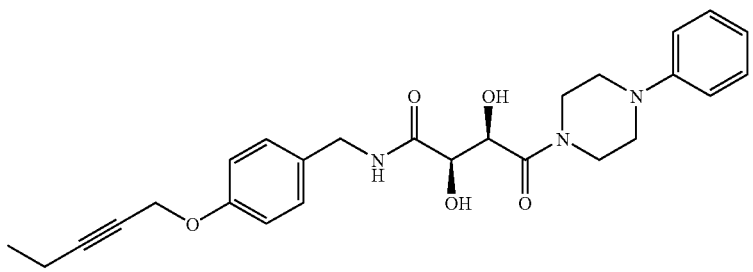
720
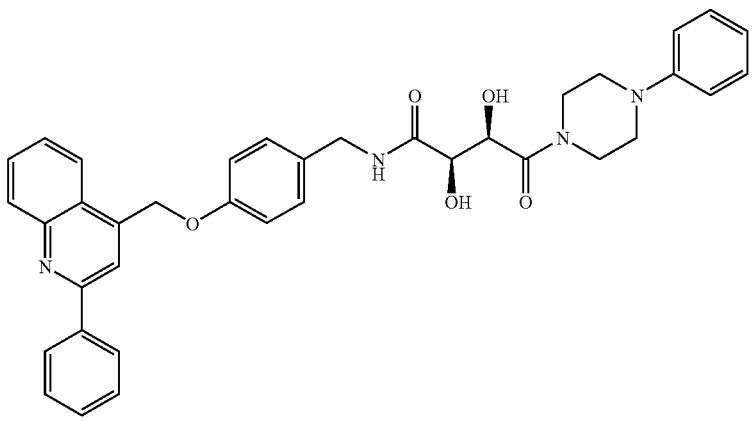
721
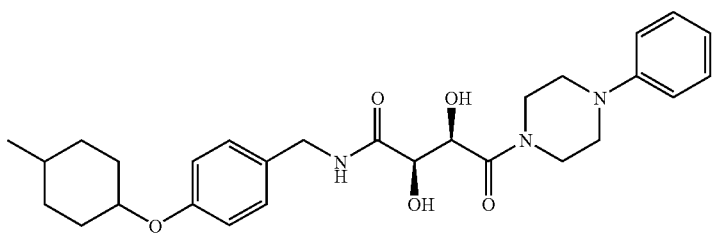

-continued
722
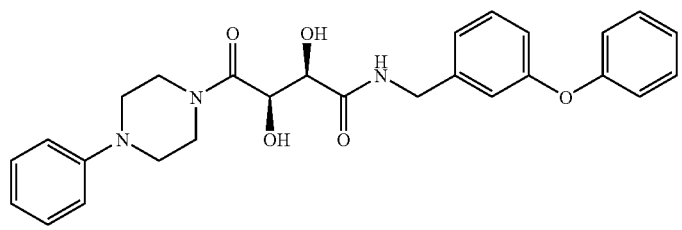
723
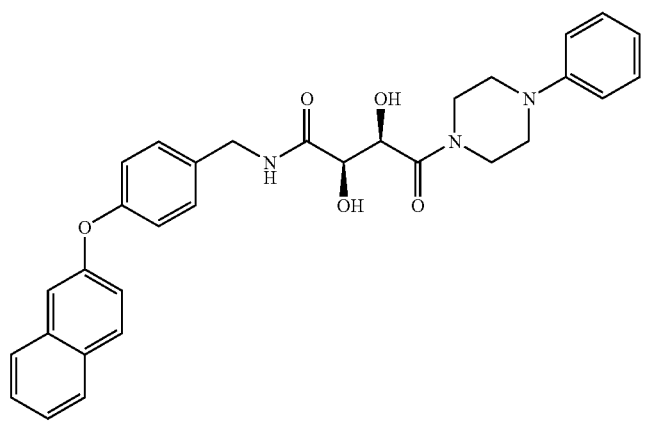
724
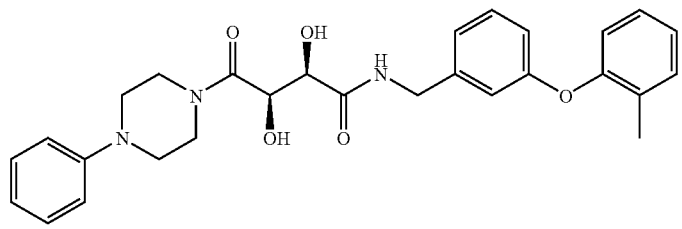
725
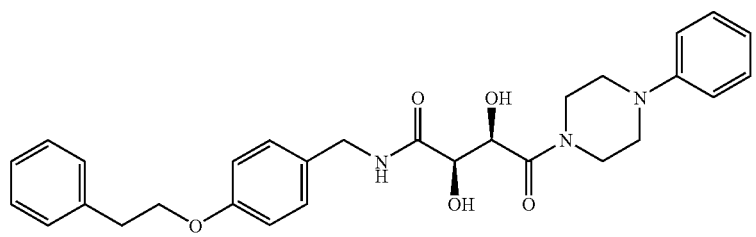
726
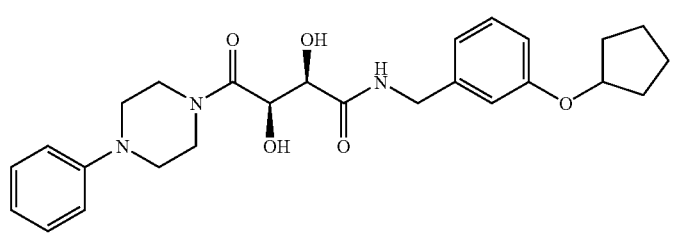

-continued
696
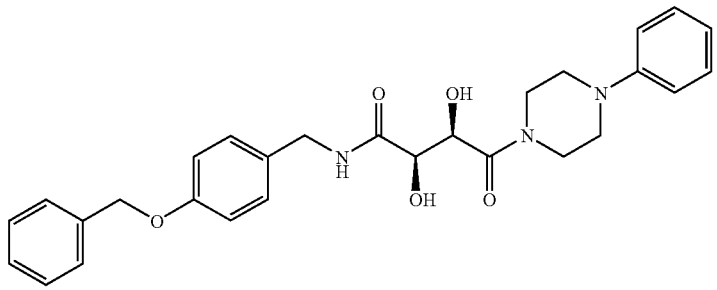
728
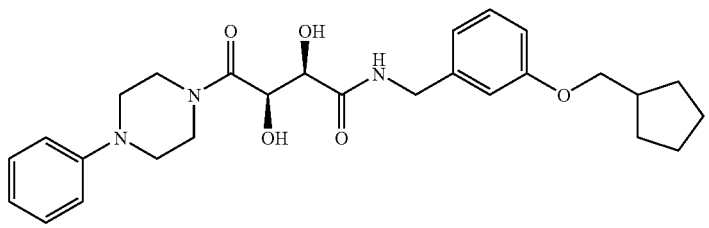
729
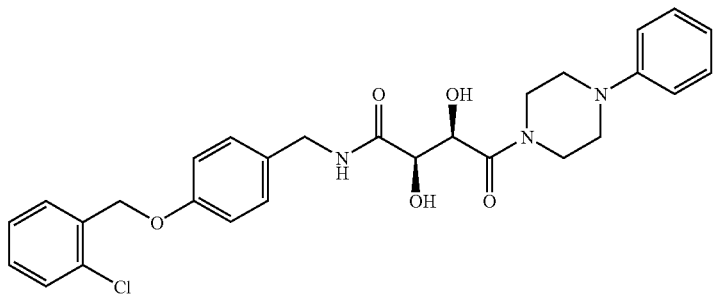
730
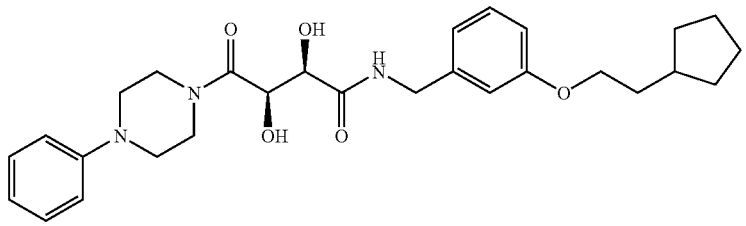
731
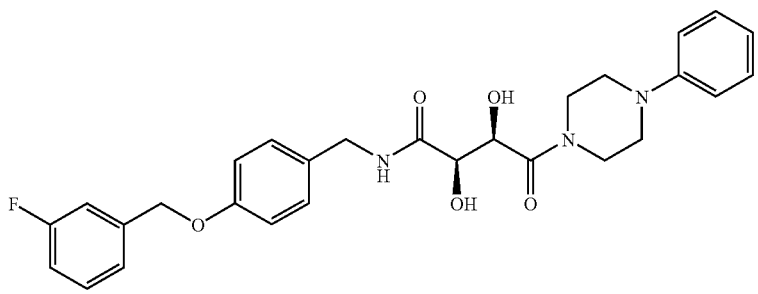
732
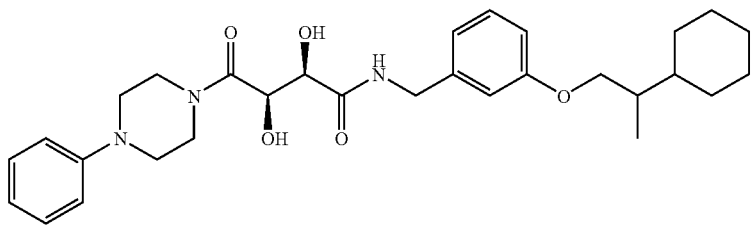

-continued
733
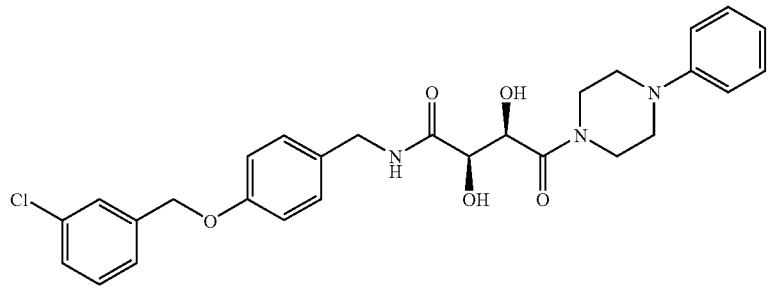
734
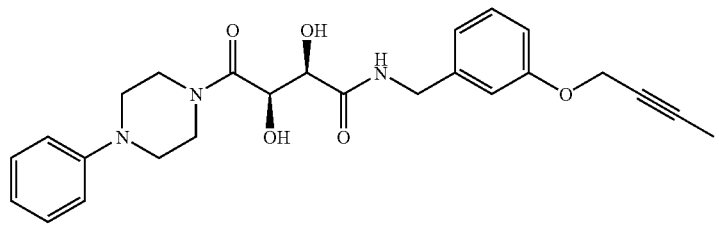
735
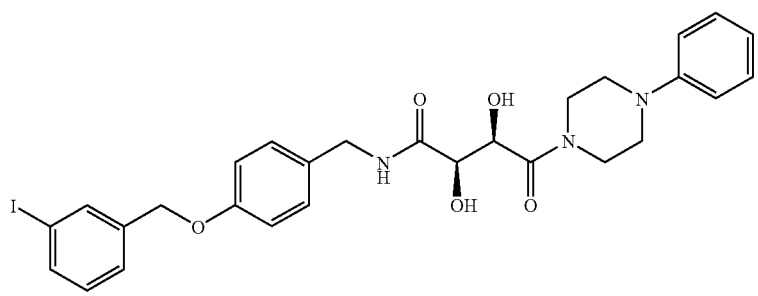
736
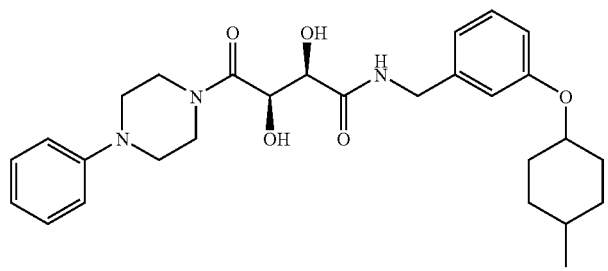
737
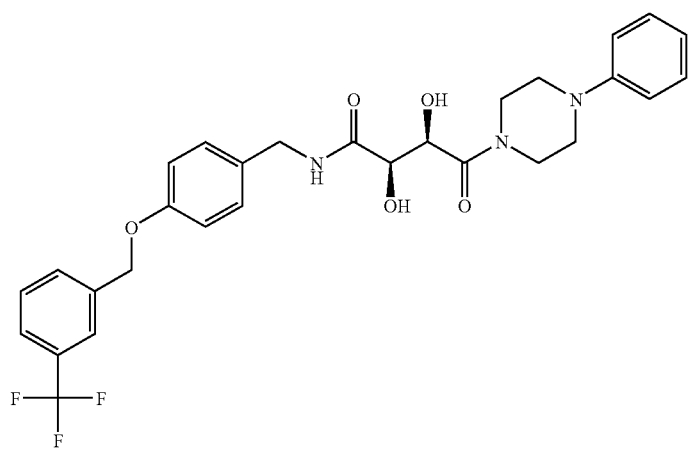

738 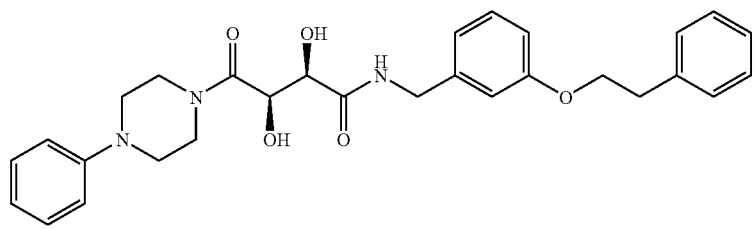
739 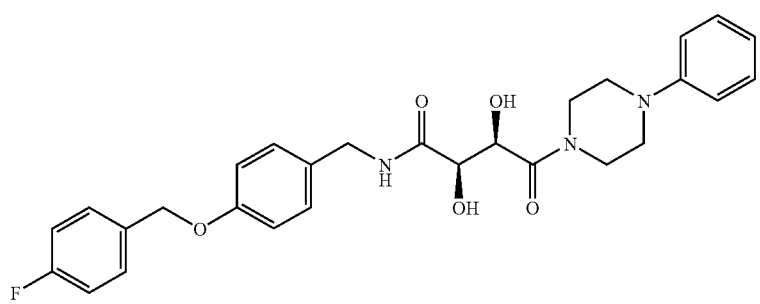
740 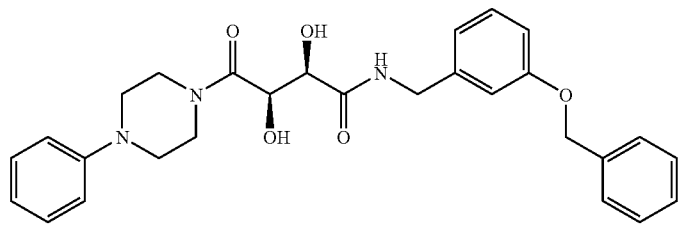
741 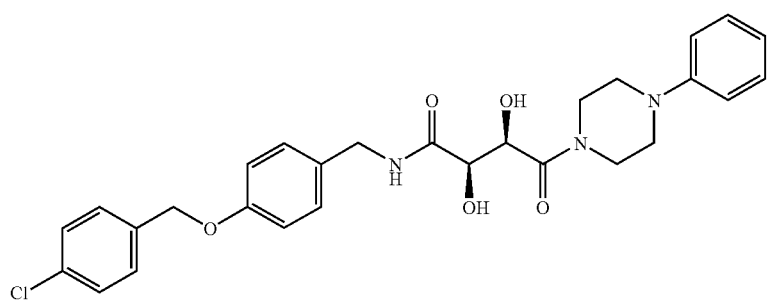
742 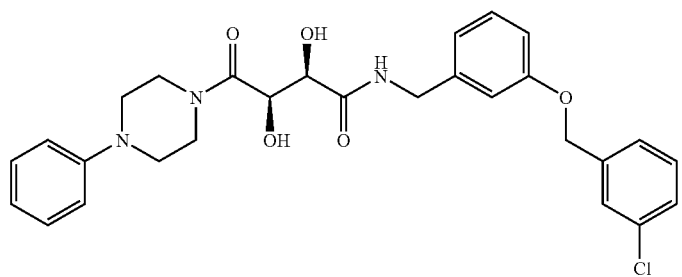

743 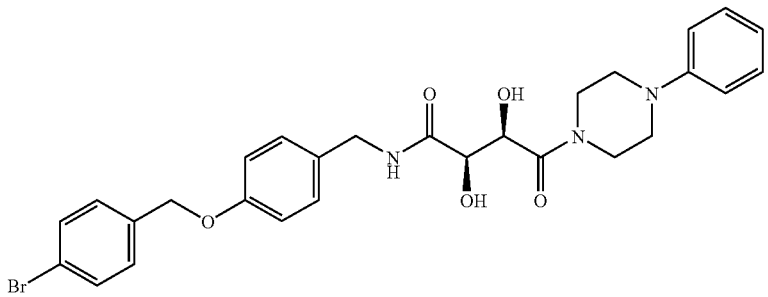
744 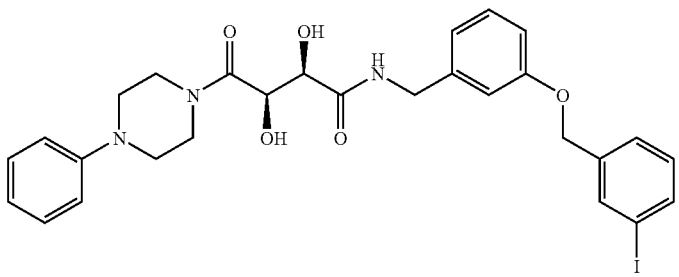
745 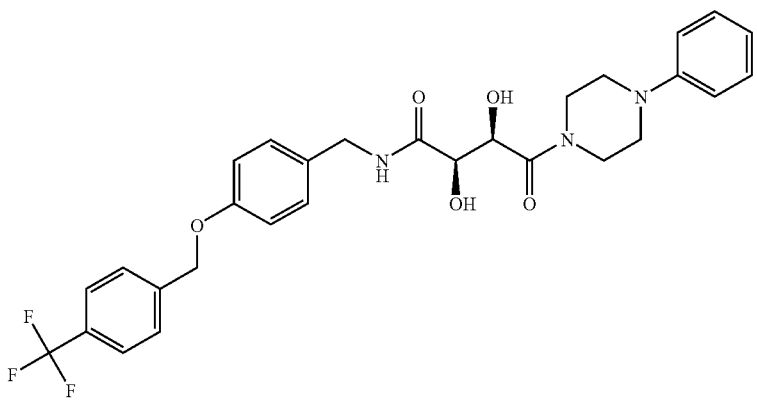
746 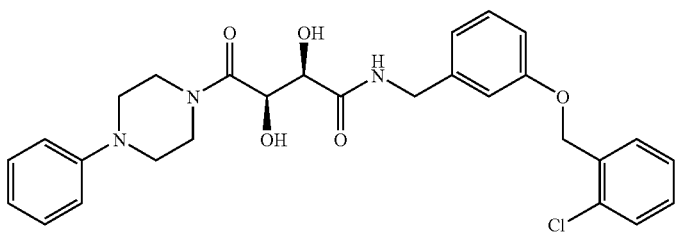
747 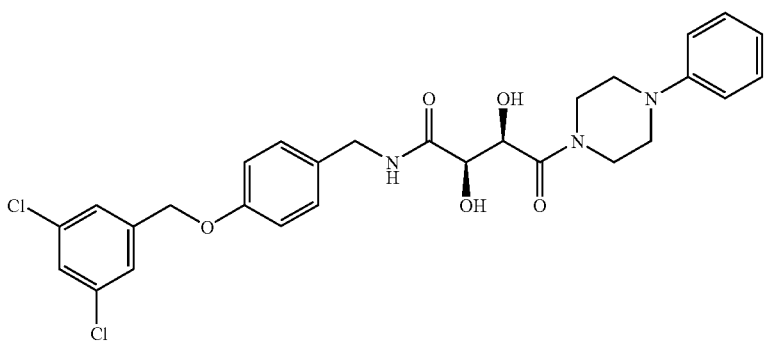

748 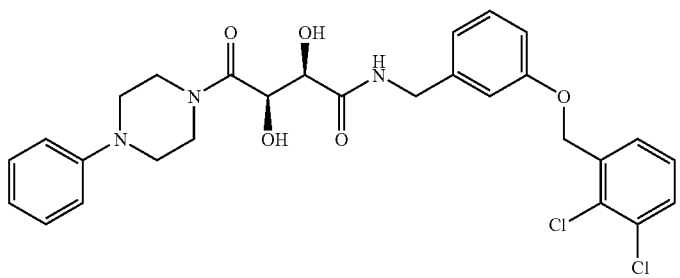
749 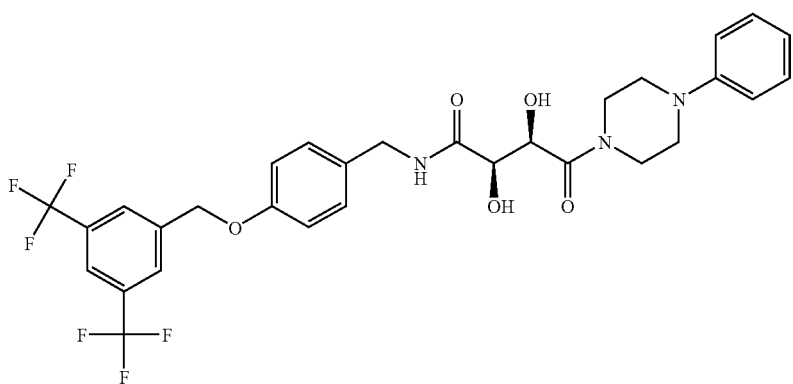
750 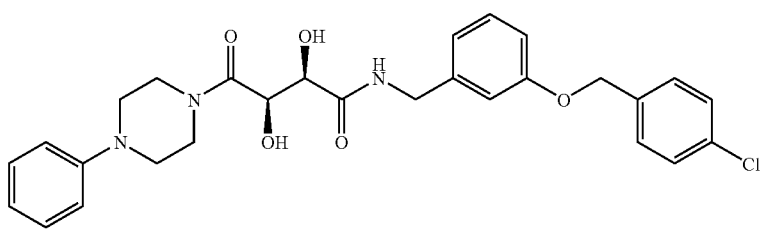
751 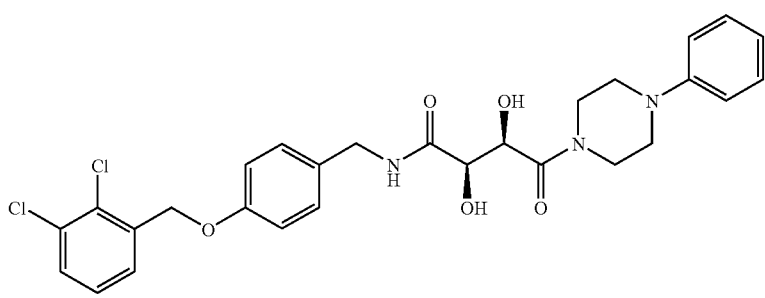
752 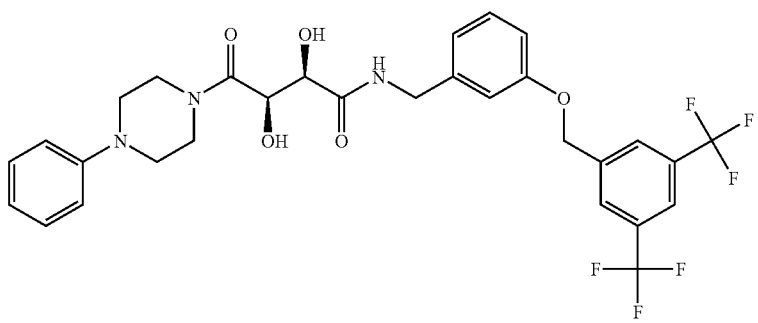

753
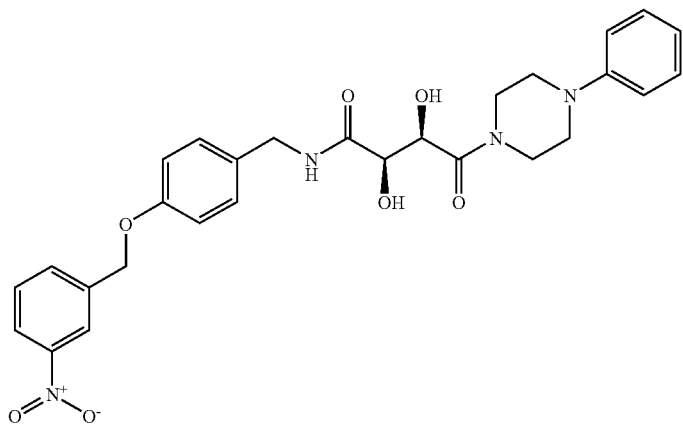
754
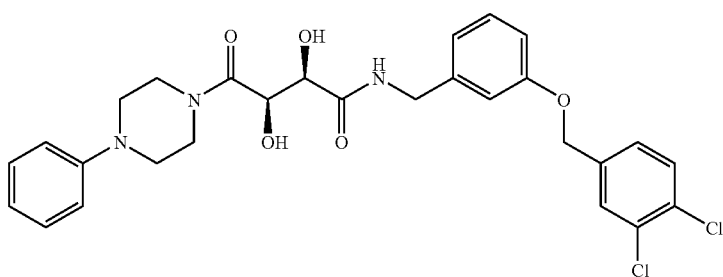
755
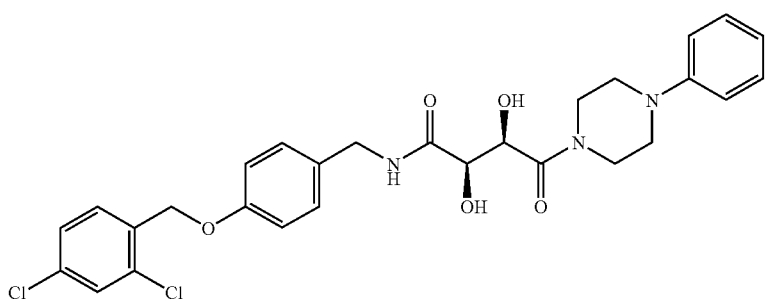
756
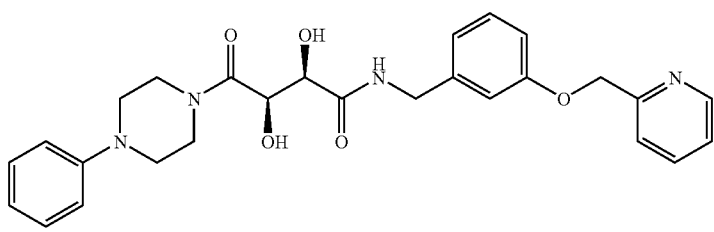

757
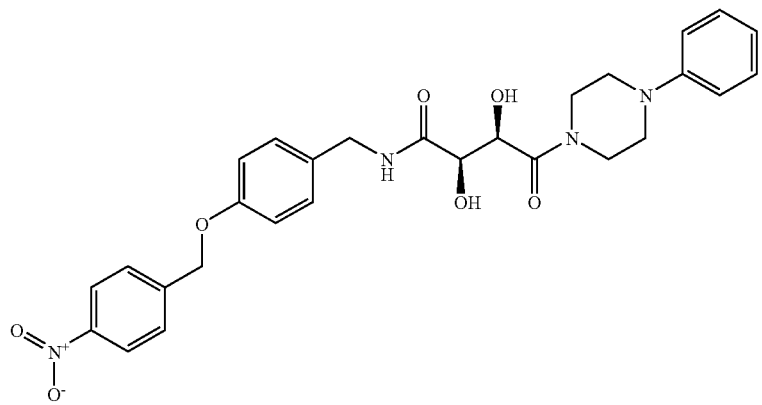
758
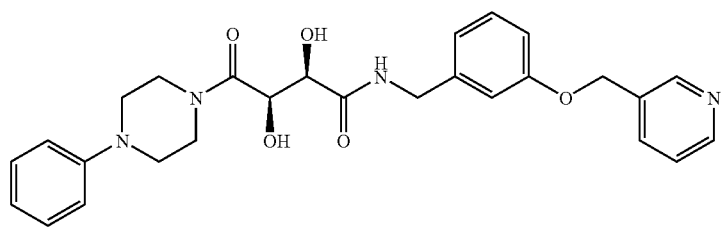
759
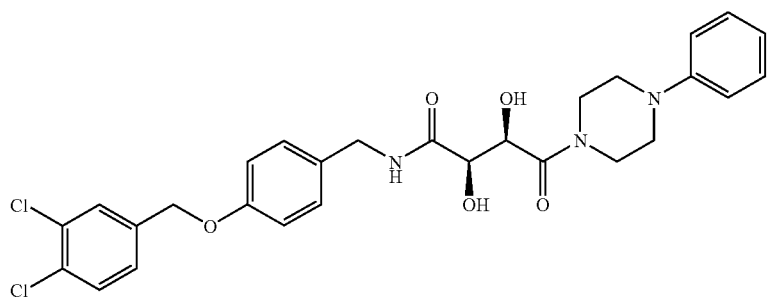
760
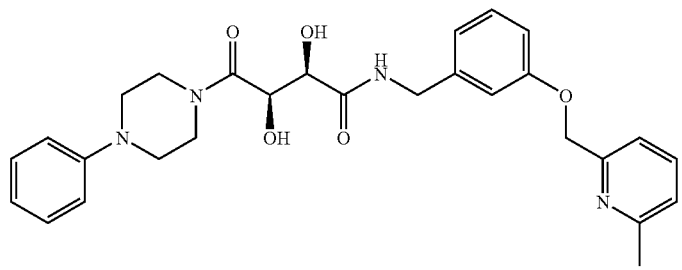
761
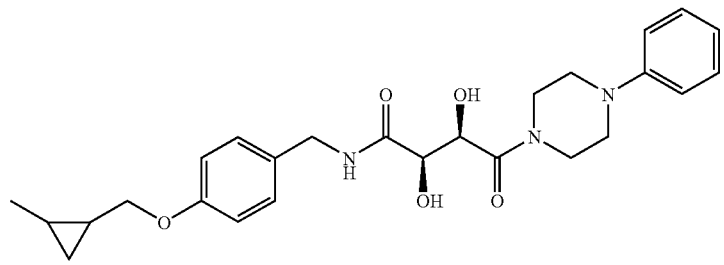

-continued
762
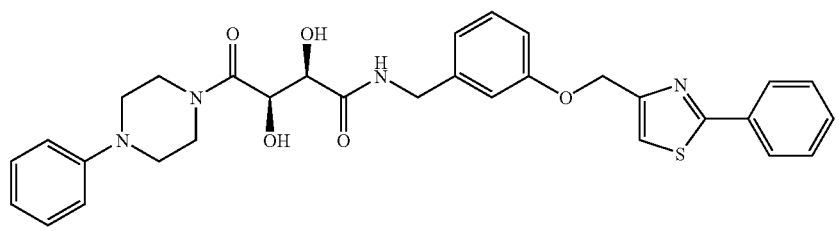
763
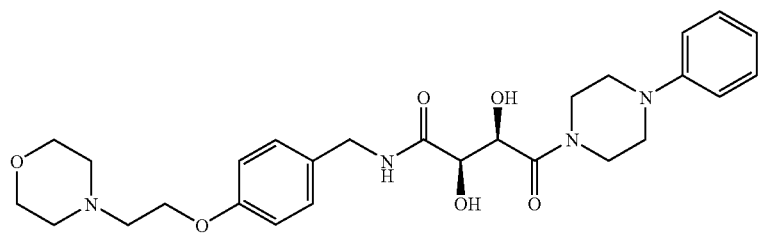
764
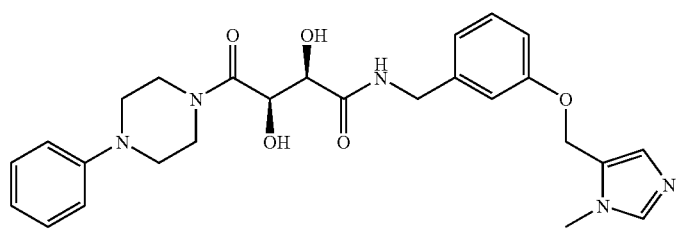
765
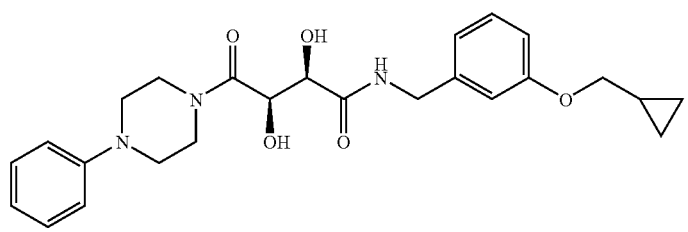
772
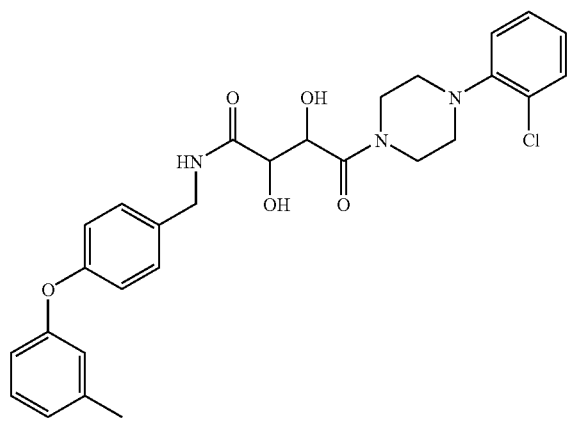
773
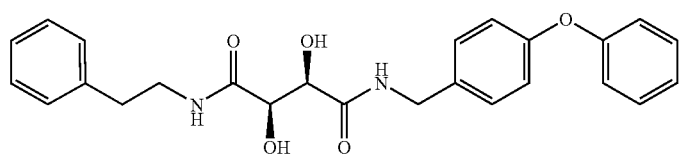

774
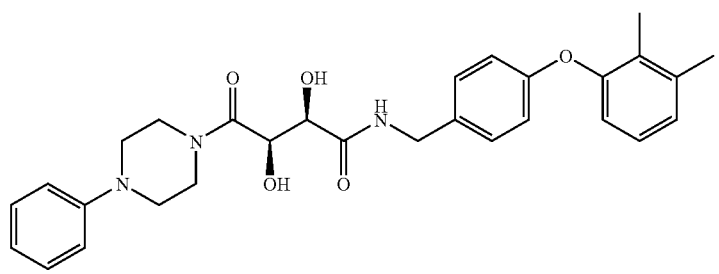
772
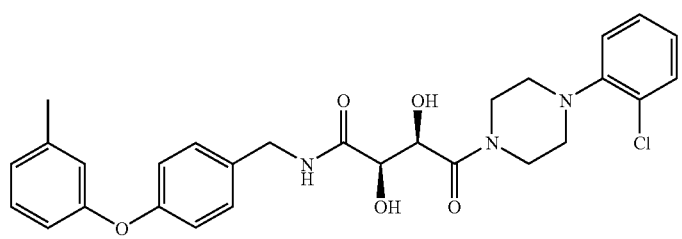
776
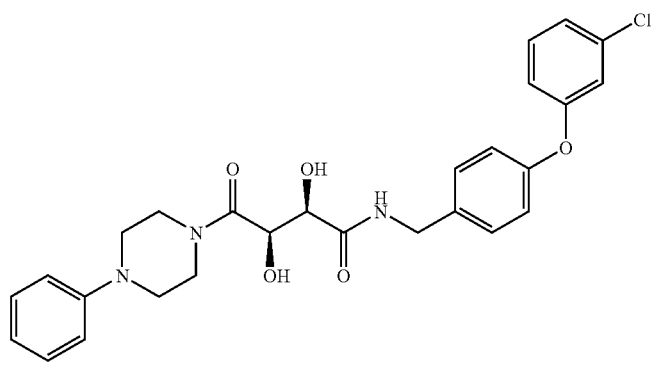
777
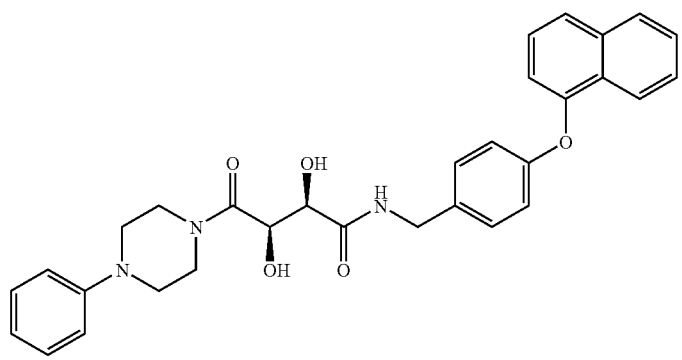

778
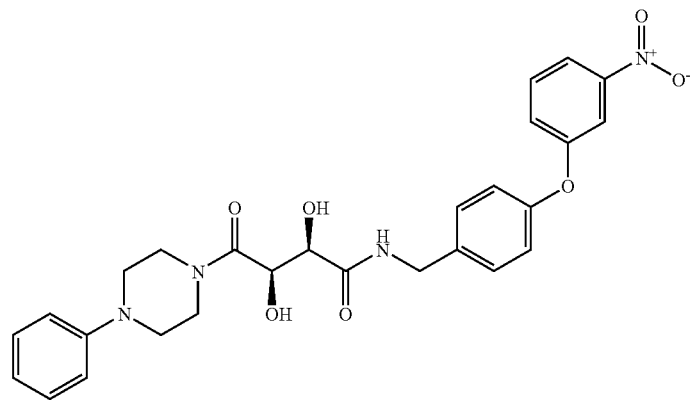
779
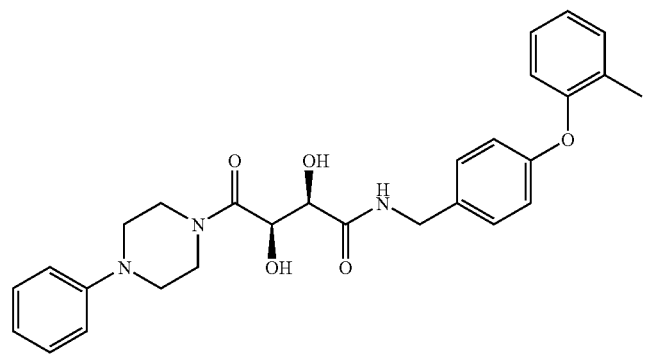
780
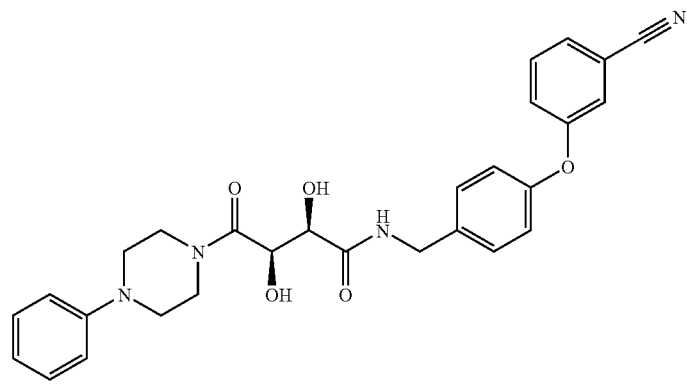
781
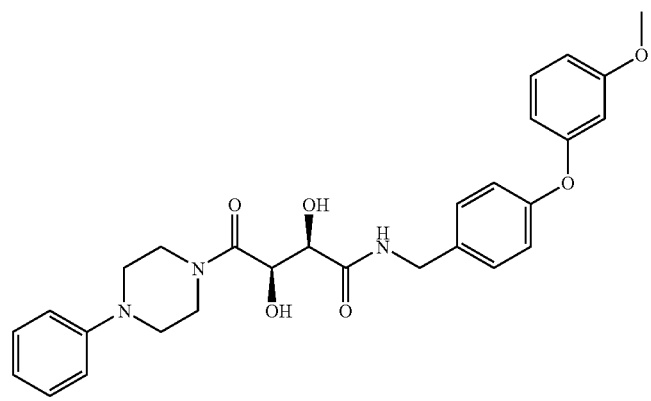

782 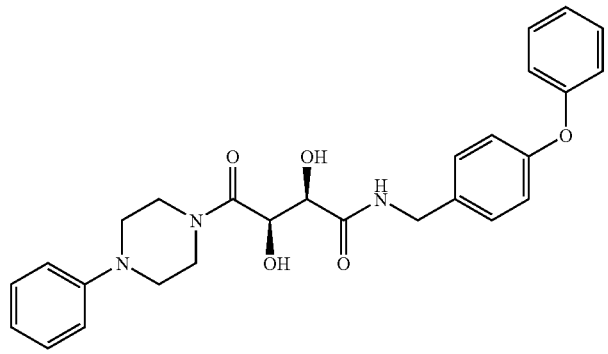
783 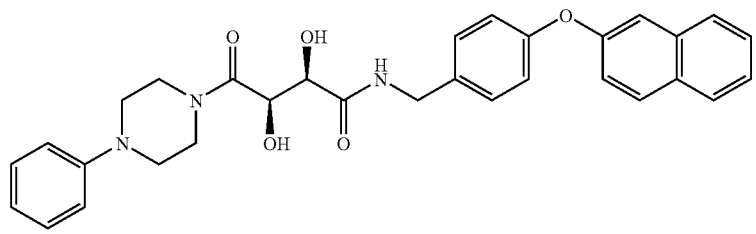
784 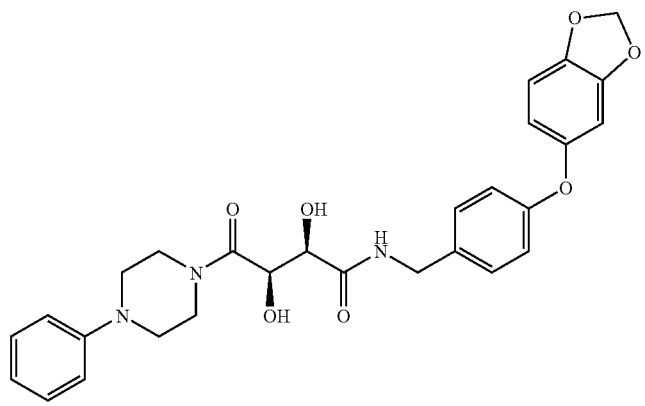
785 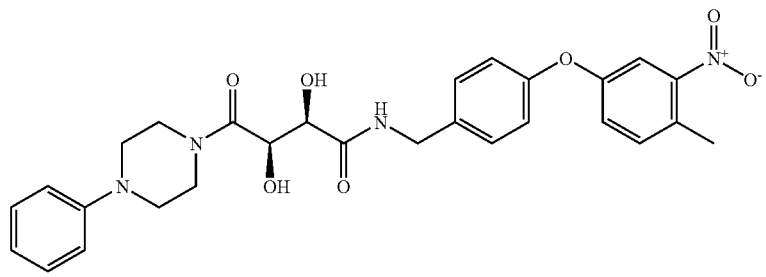

-continued
786
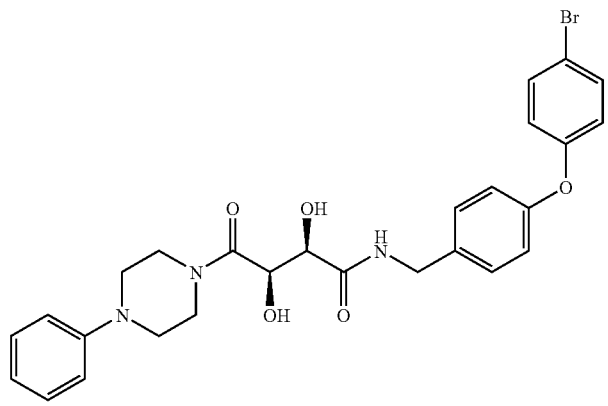
787
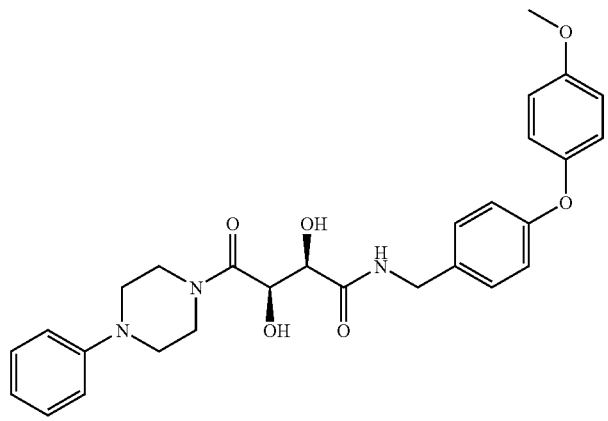
788
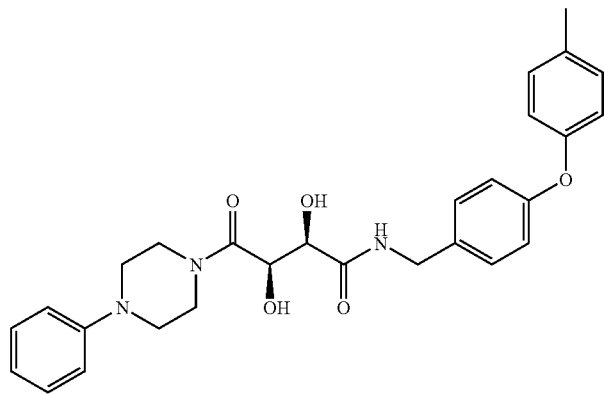
789
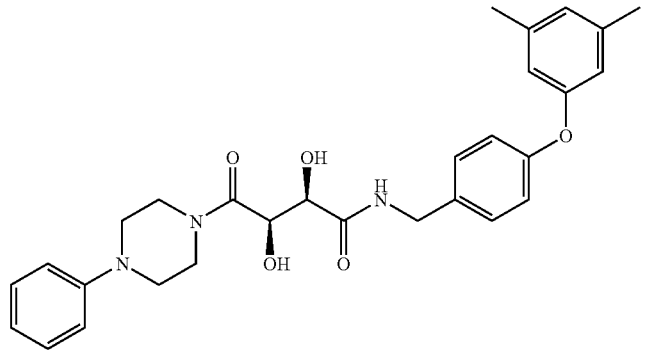

-continued
790
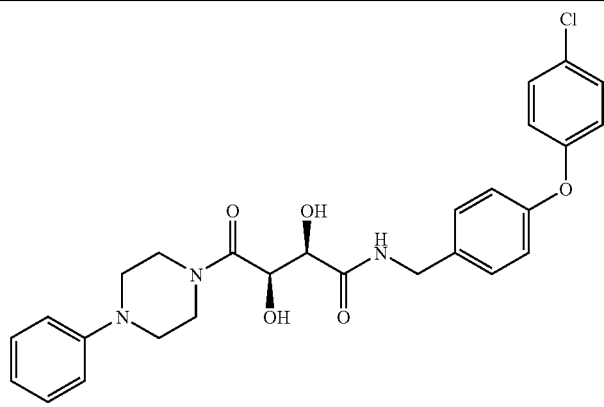
791
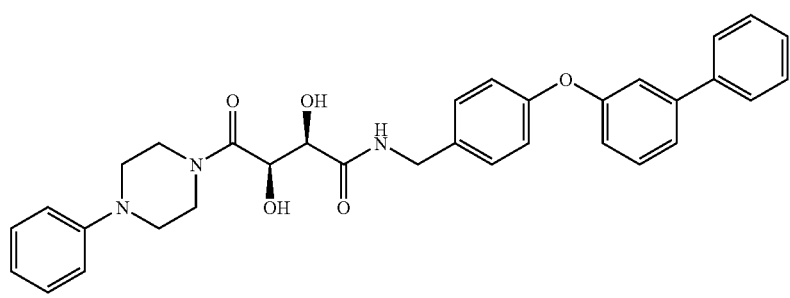
792
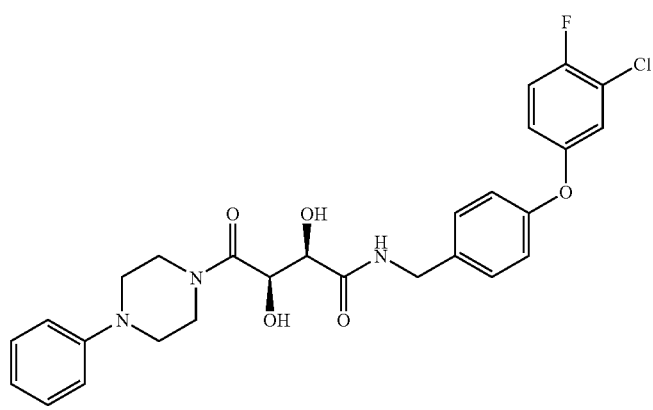
793
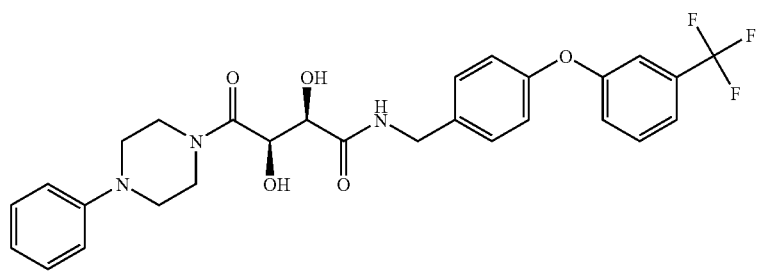
794
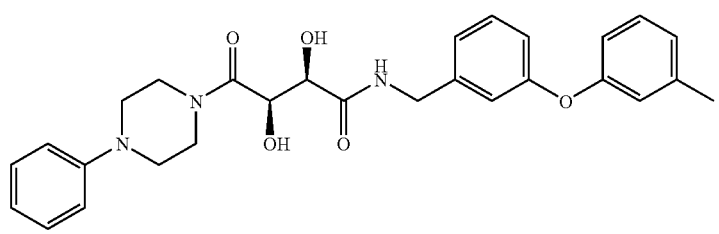

795 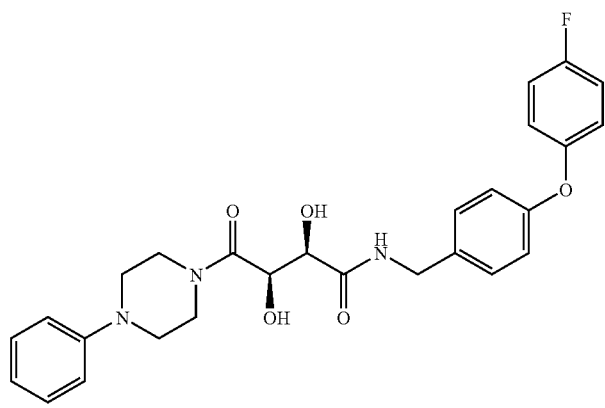
796 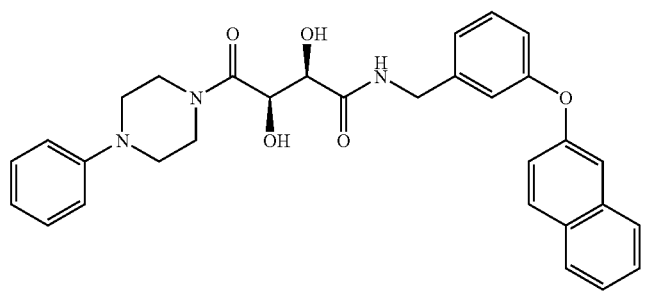
802 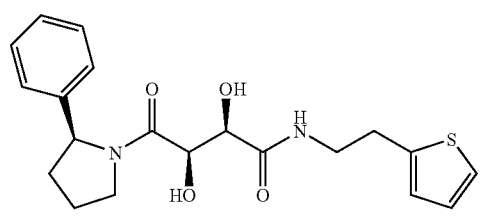
804 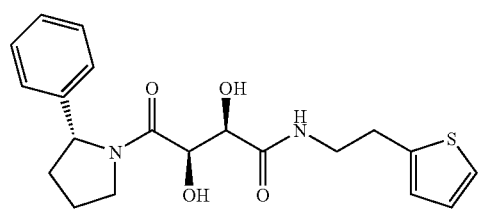
805 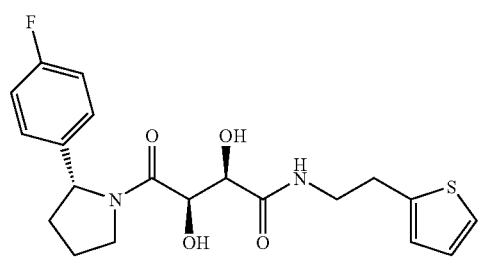

-continued
806 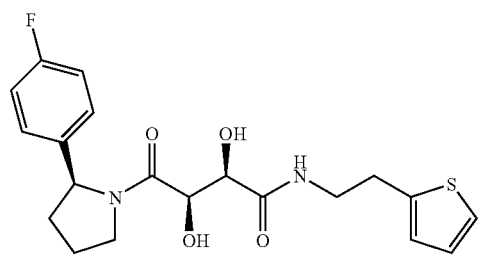
807 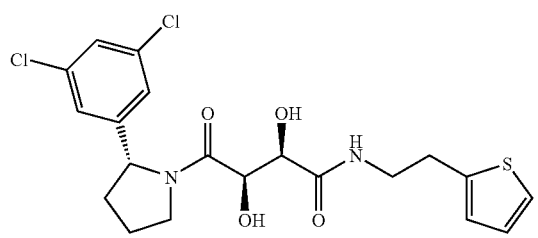
808 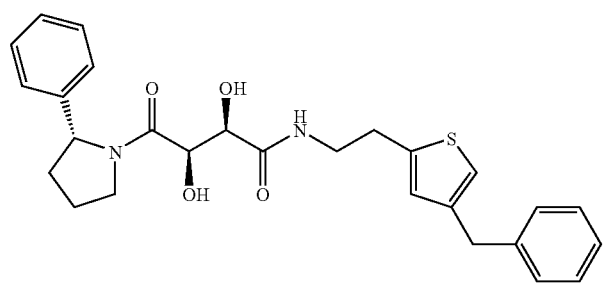
814 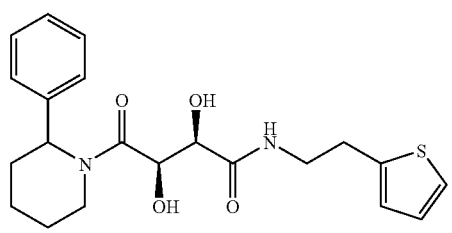
815 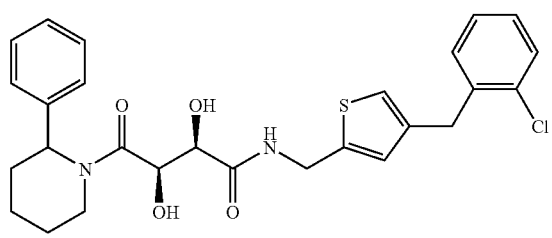
823 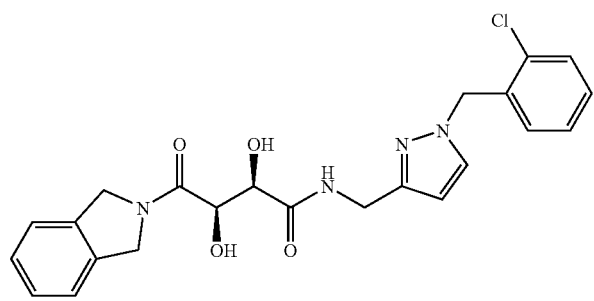

828 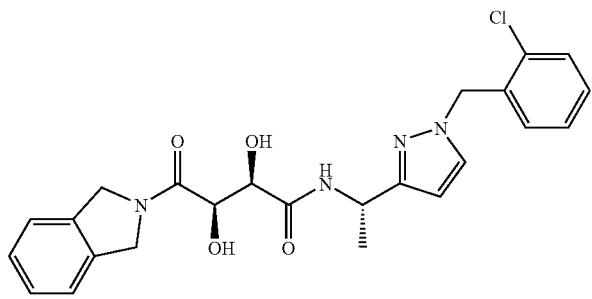
829 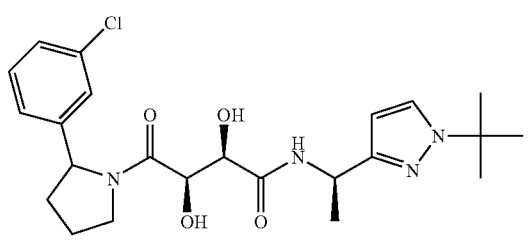
830 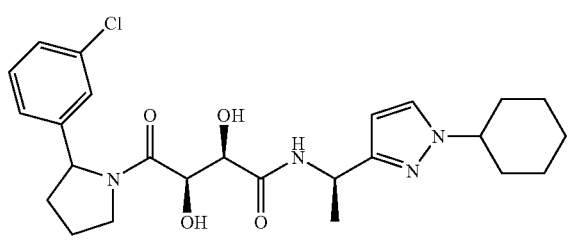
831 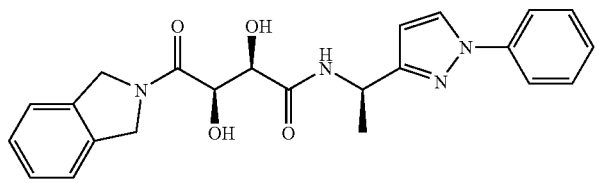
832 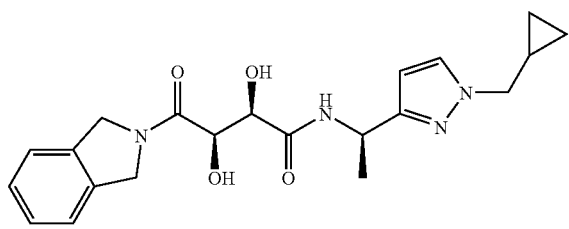
833 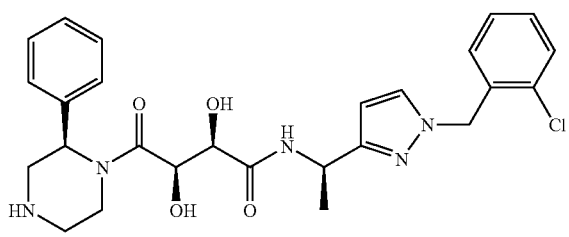

| | |
|---|---|
| 834 | 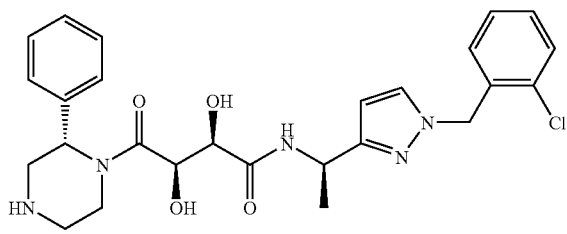 |
| 835 | 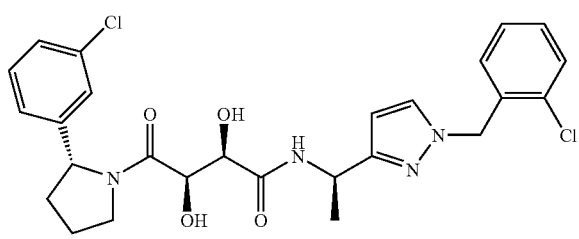 |
| 836 | 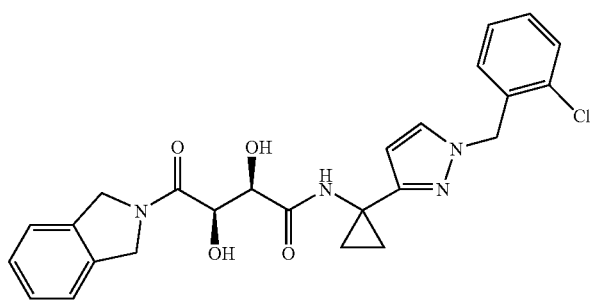 |
| 839 | 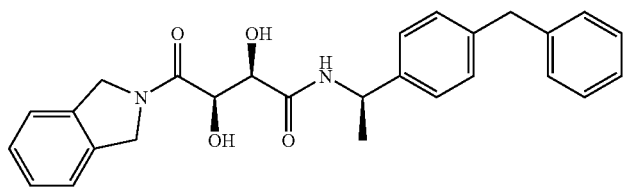 |
| 846 | 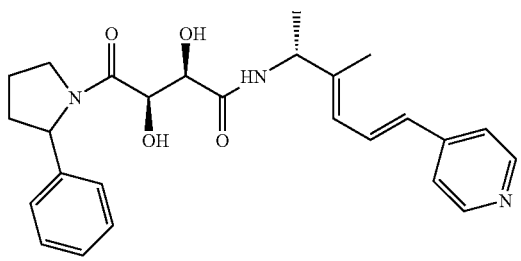 |
| 852 | 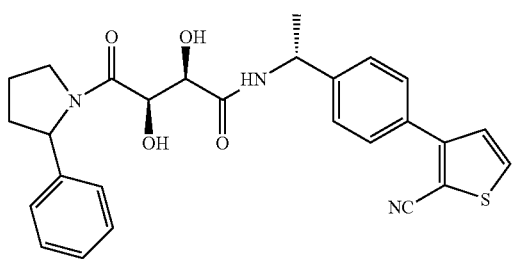 |

-continued
855 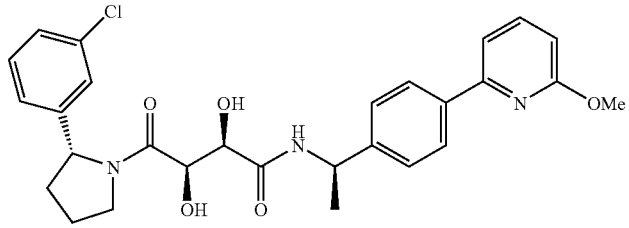
857 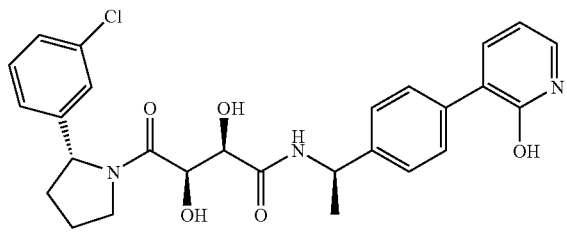
858 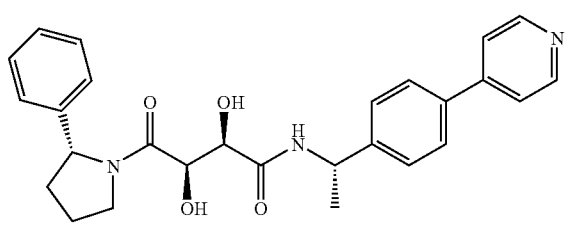
859 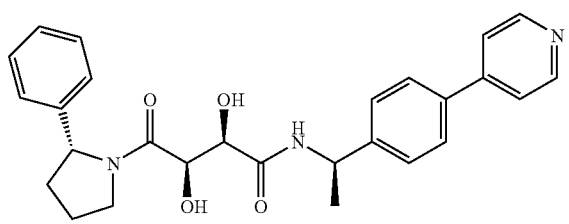
860 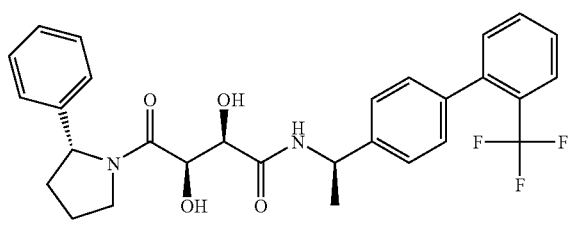
861 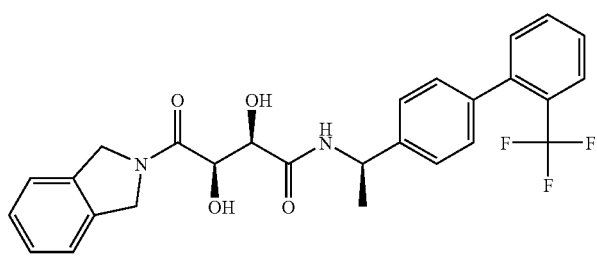

-continued
862
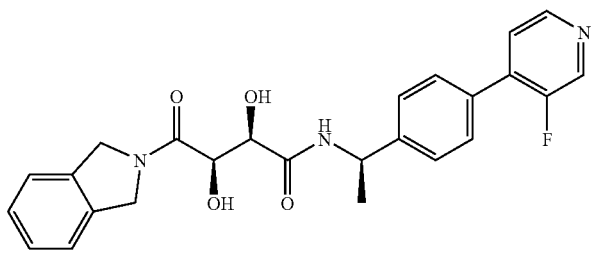
863
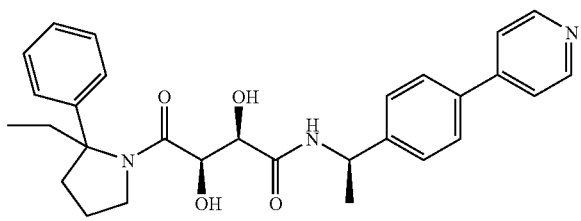
864
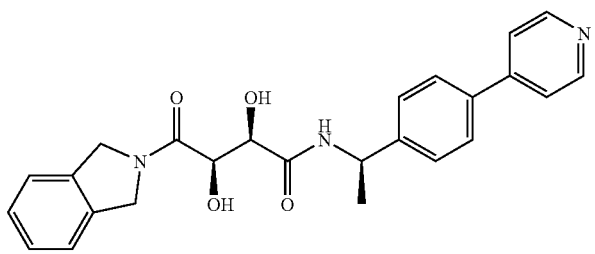
865
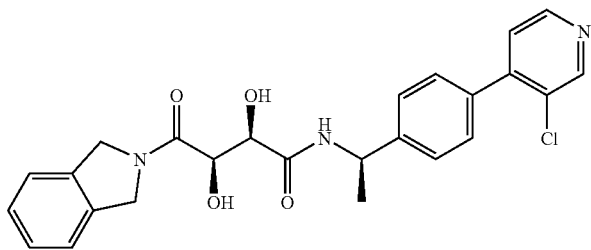
866
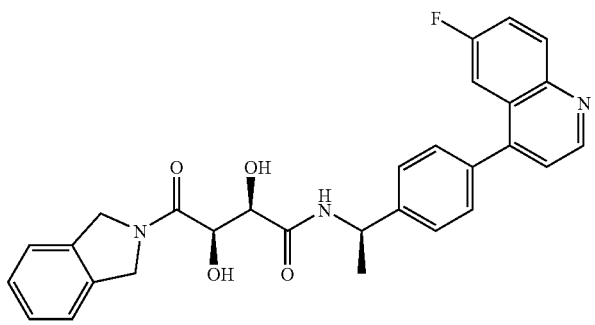
867
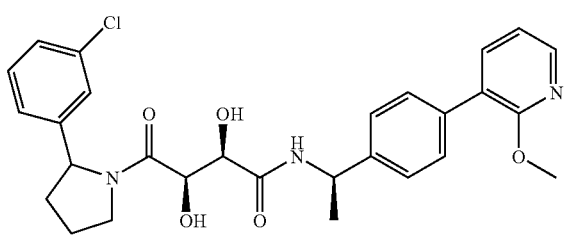

-continued
868 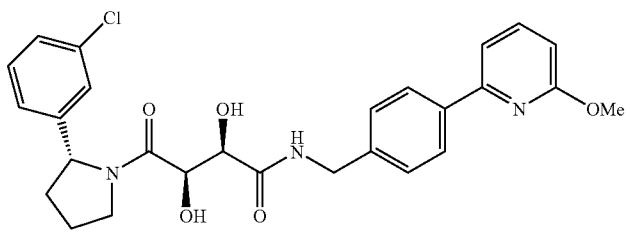
869 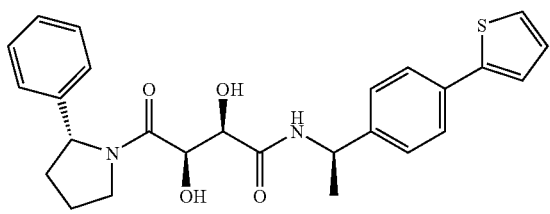
870 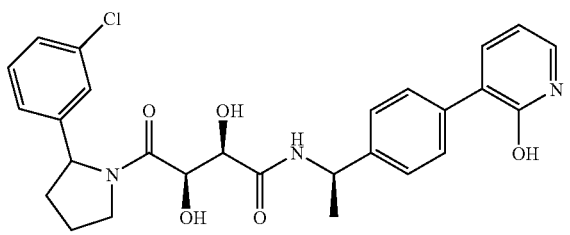
871 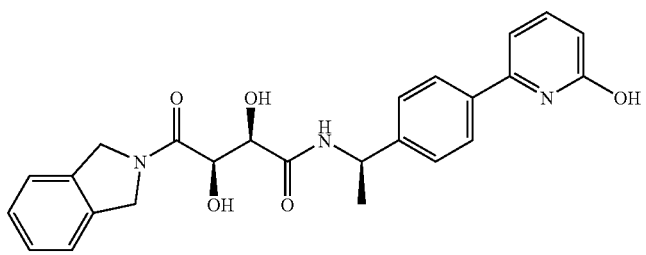
872 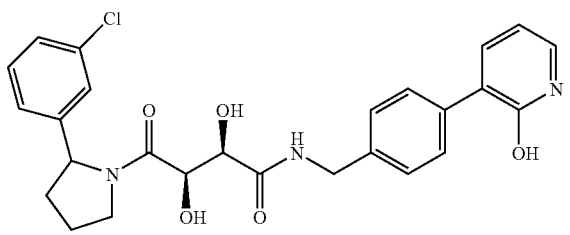
873 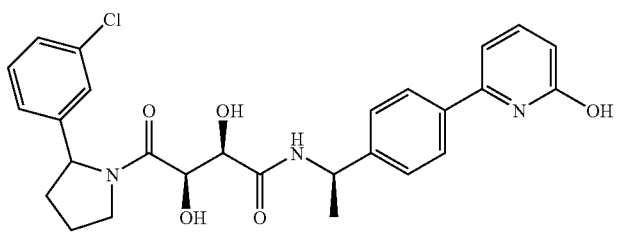

| | |
|---|---|
| 874 | 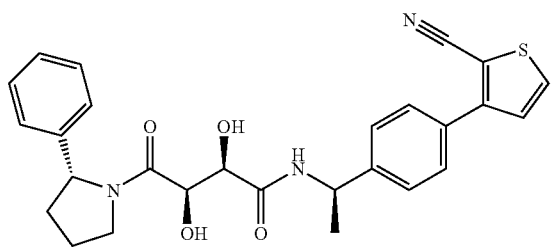 |
| 875 | 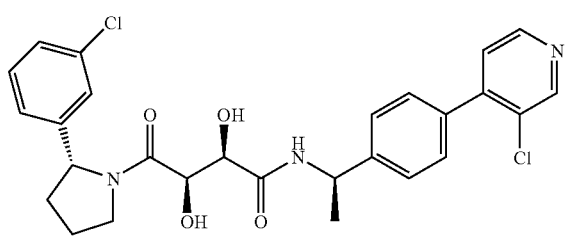 |
| 876 | 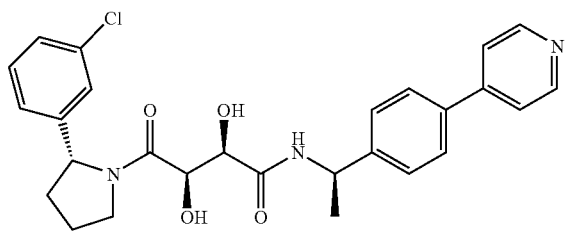 |
| 877 | 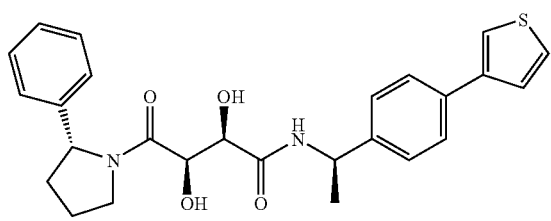 |
| 878 | 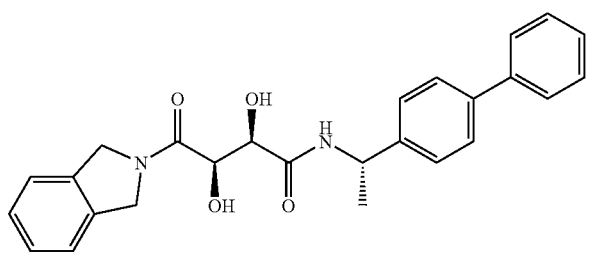 |
| 879 | 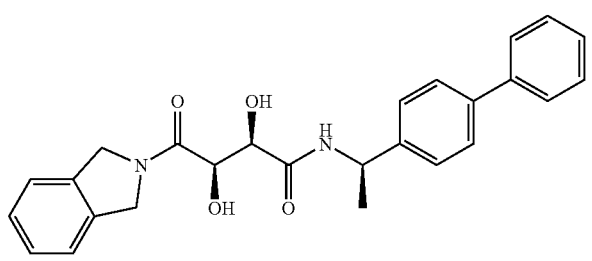 |

-continued
880
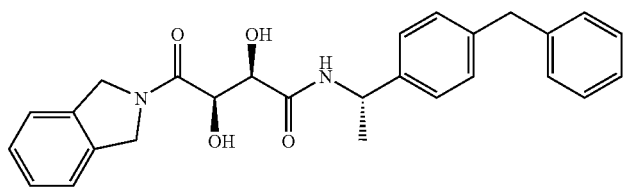
884
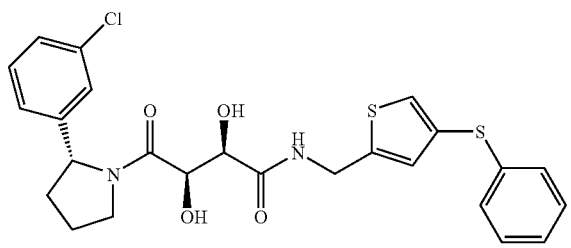
890
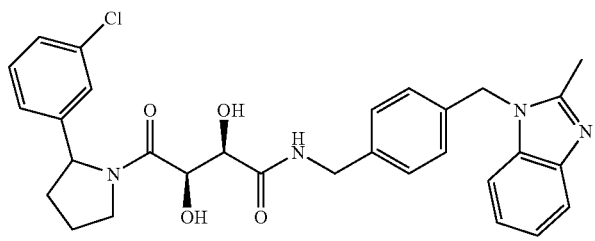
891
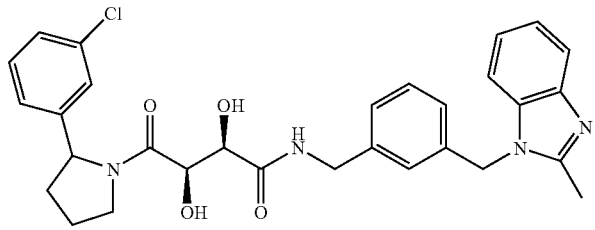
894
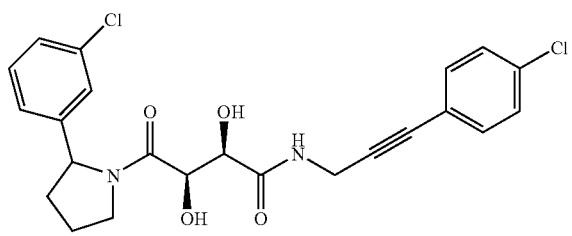
897
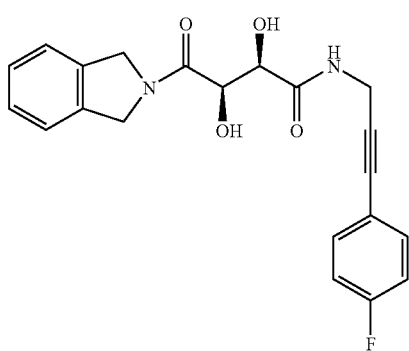

898 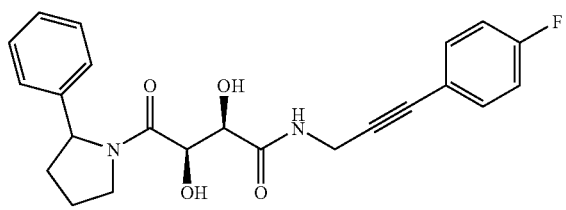
899 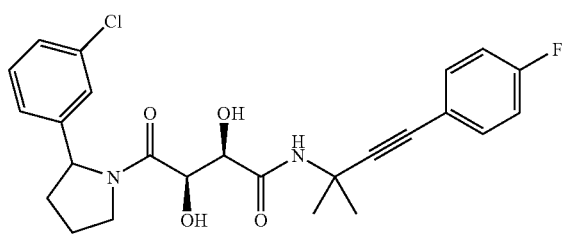
900 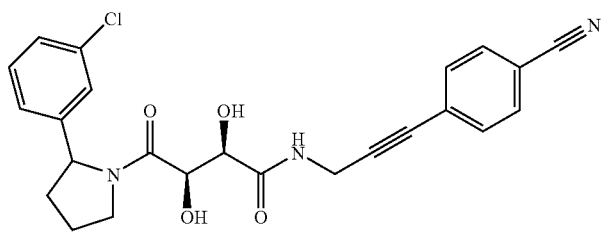
901 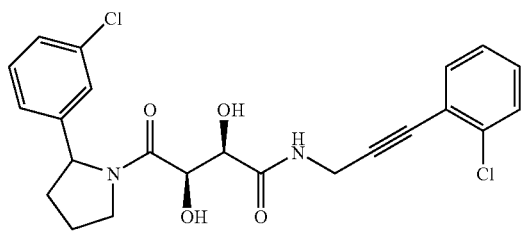
902 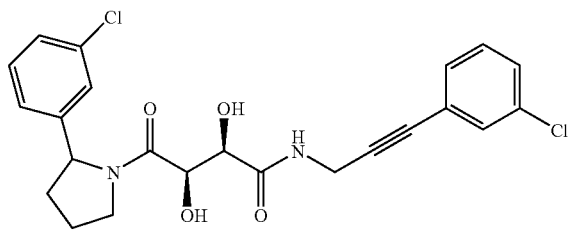
903 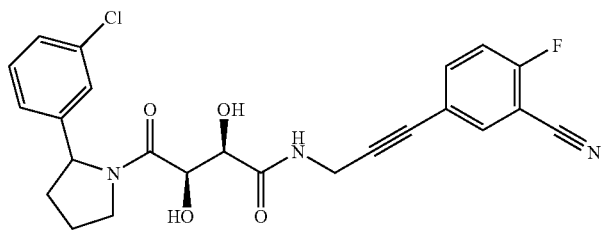

-continued
| | |
|---|---|
| 905 | 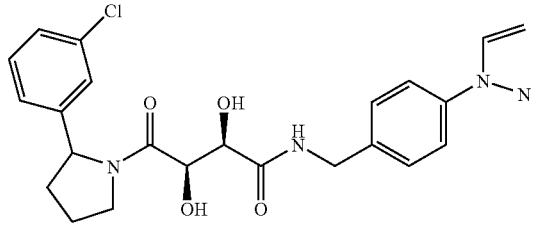 |
| 910 | 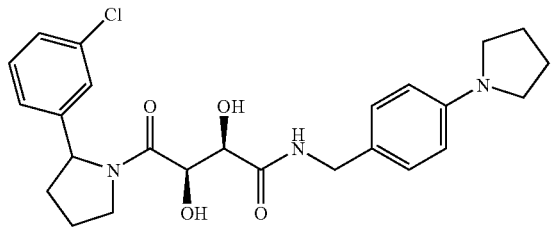 |
| 914 | 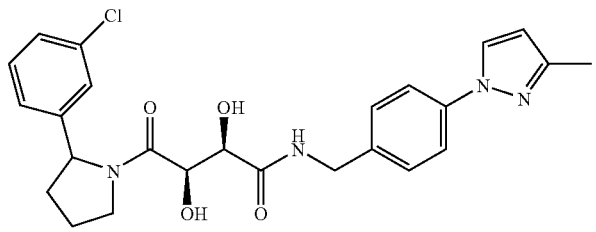 |
| 918 | 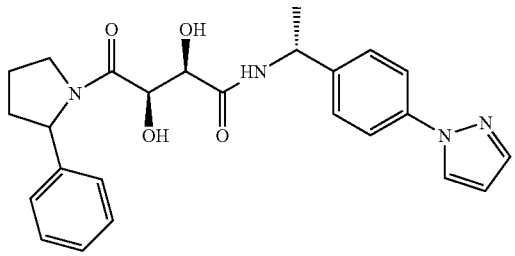 |
| 919 | 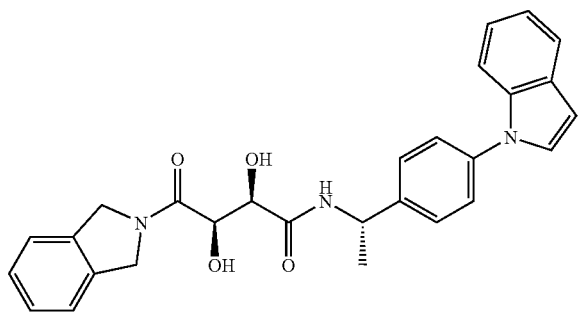 |
| 920 | 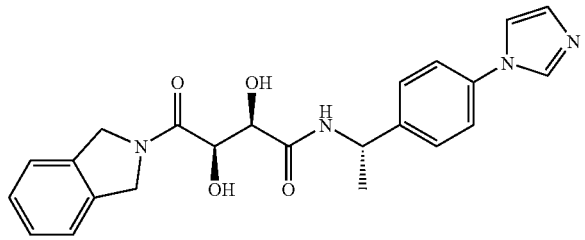 |

921 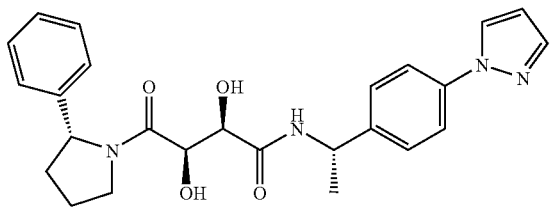
922 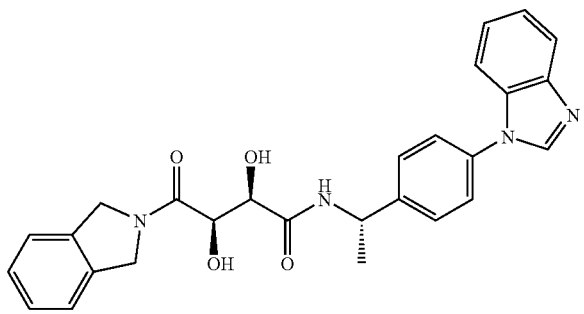
923 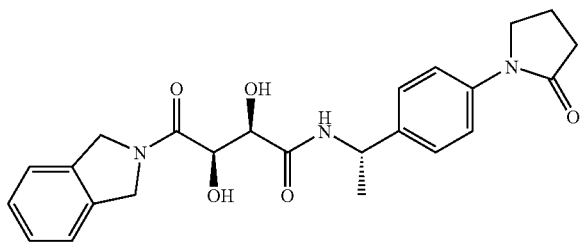
924 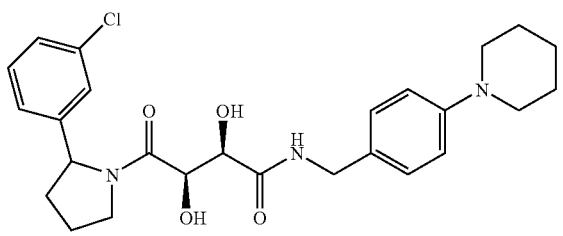
925 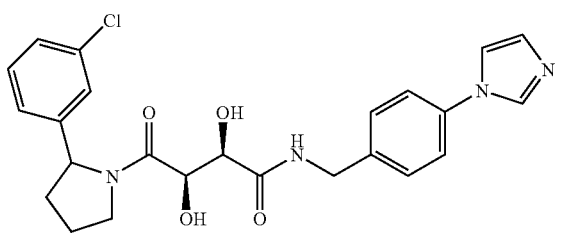
926 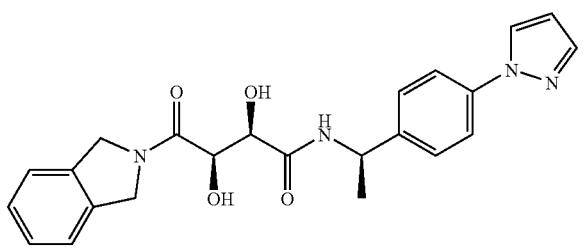

-continued
927 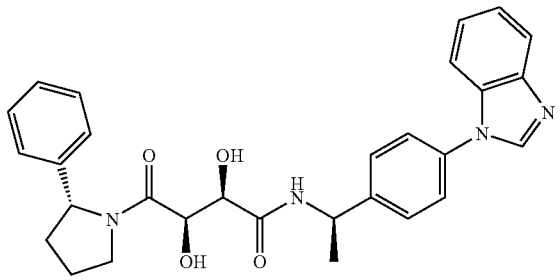
928 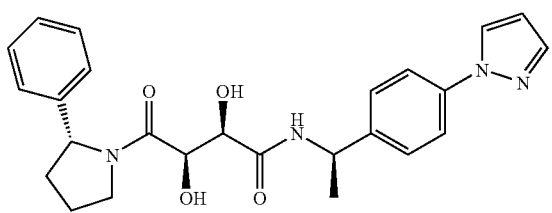
929 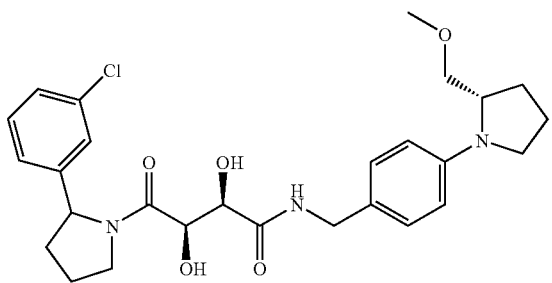
930 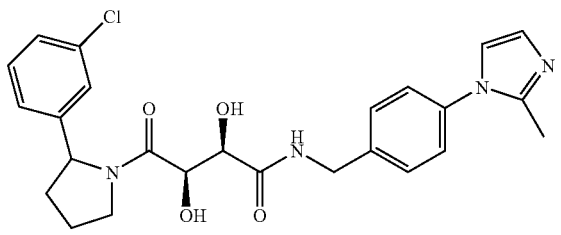
931 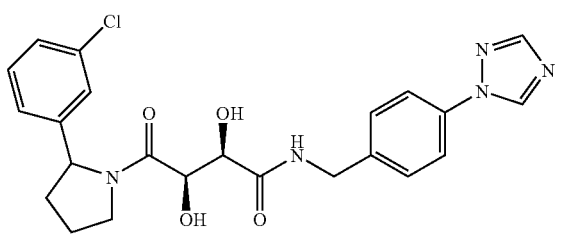
932 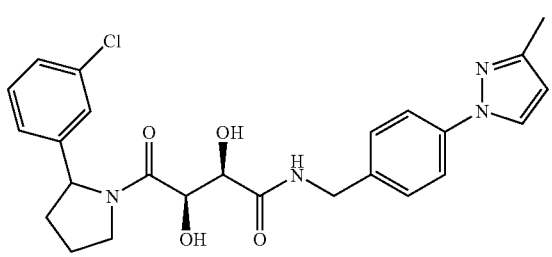

-continued
933 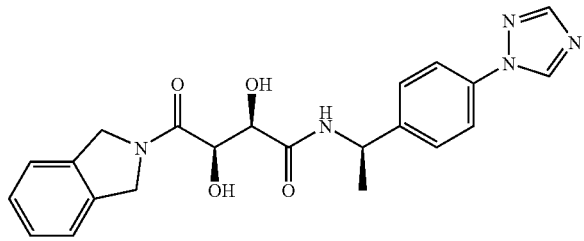
934 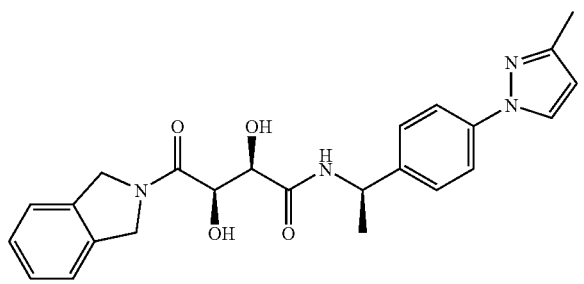
935 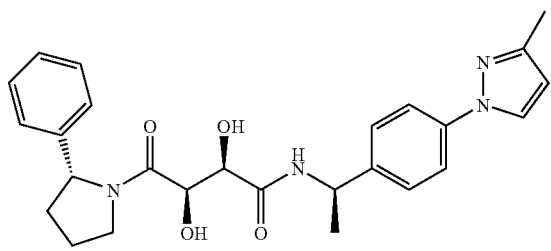
936 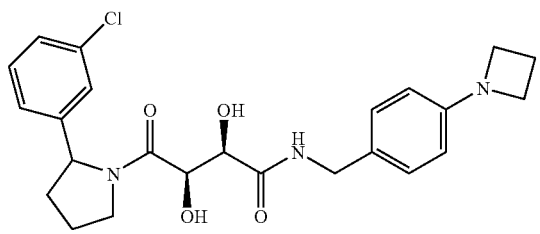
937 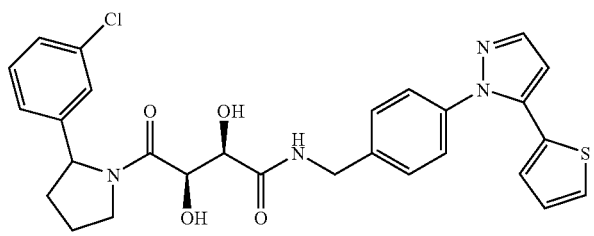
938 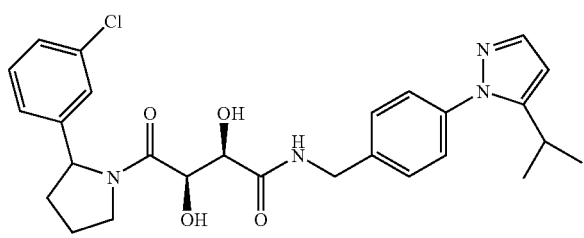

939 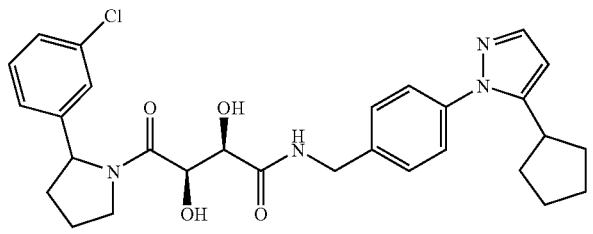
940 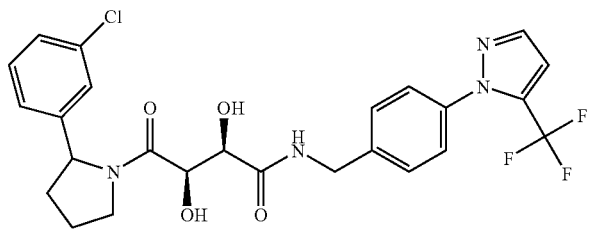
941 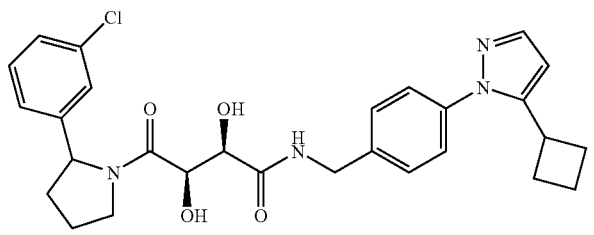
942 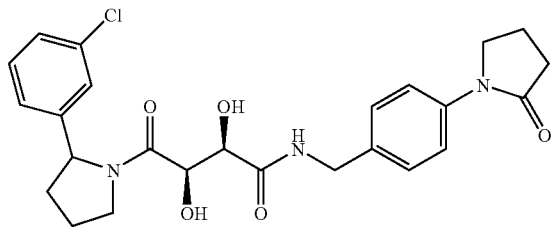
943 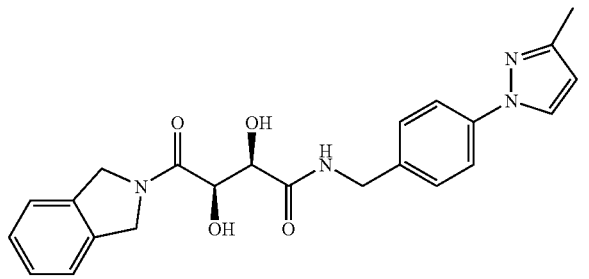
944 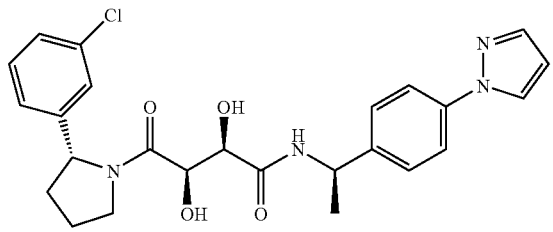
A

| | |
|---|---|
| 945 | 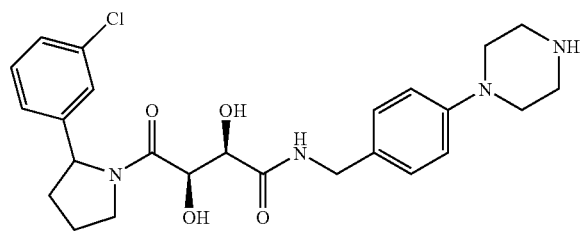 |
| 946 | 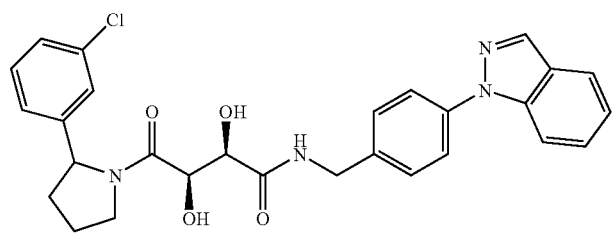 |
| 947 | 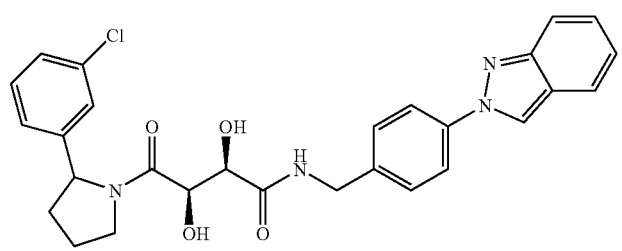 |
| 948 | 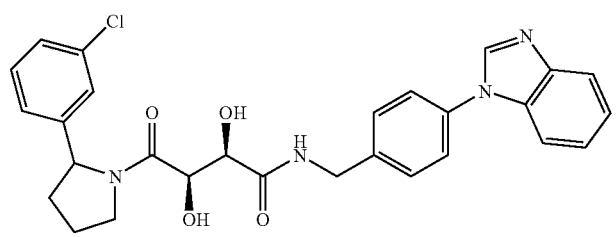 |
| 949 | 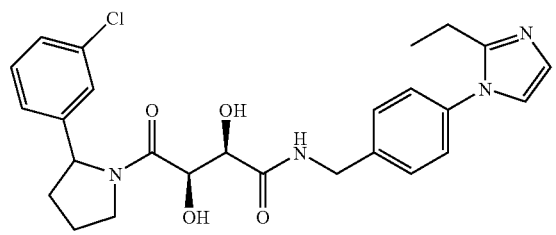 |
| 950 | 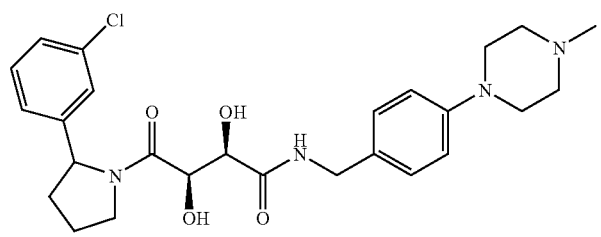 |

-continued
951 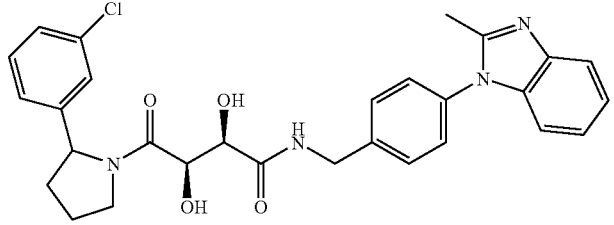
952 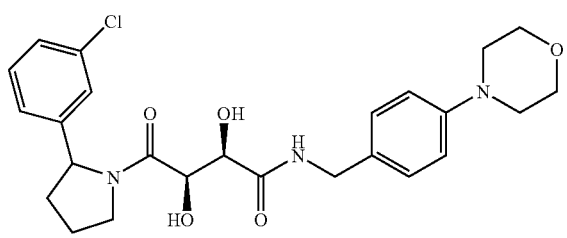
954 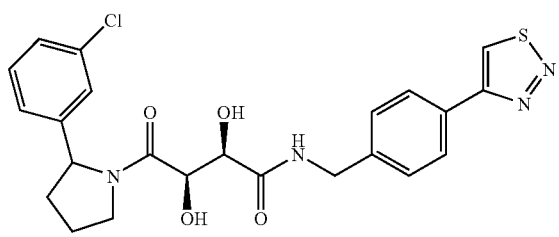
961 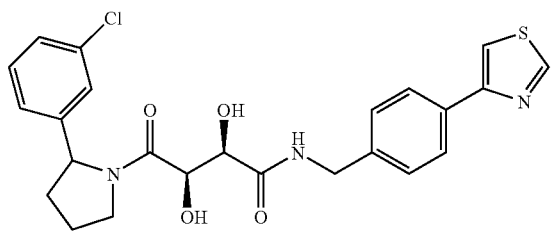
968 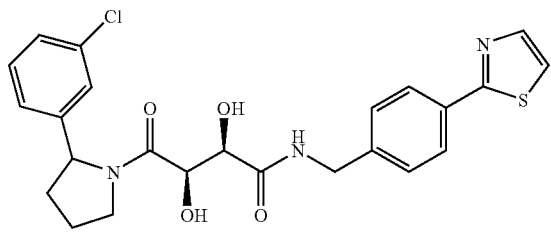
969 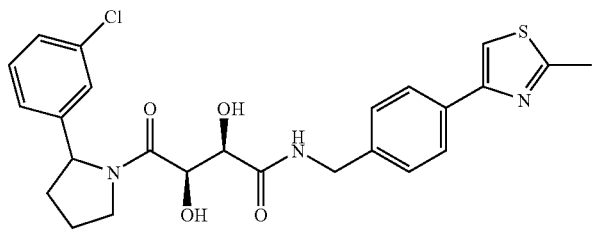

970 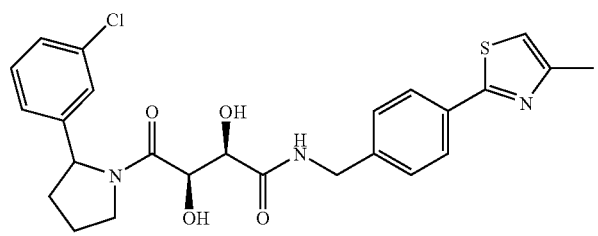
971 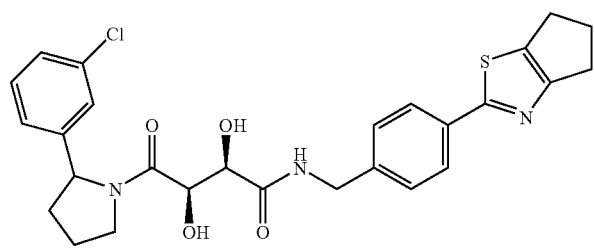
972 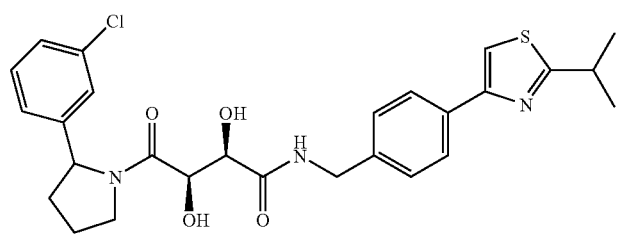
973 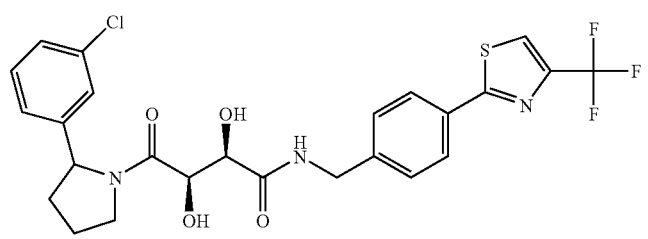
974 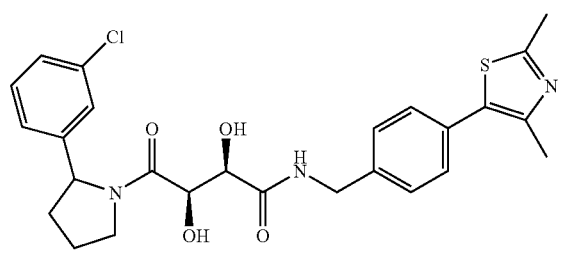
975 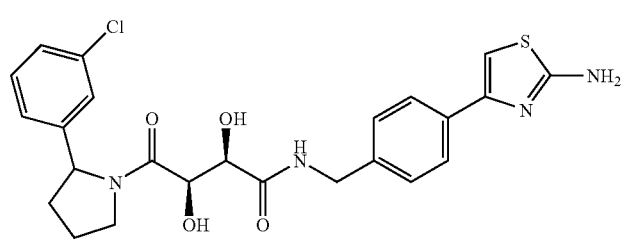

| | |
|---|---|
| 976 | 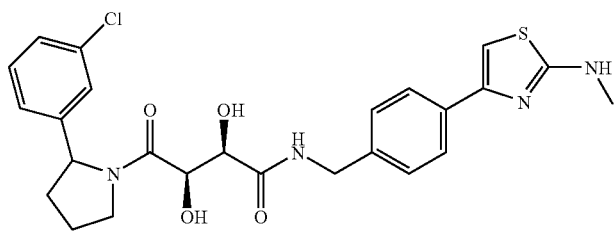 |
| 980 | 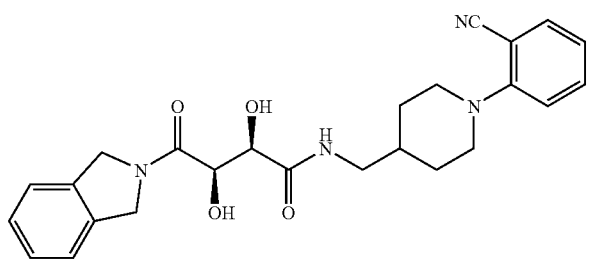 |
| 985 | 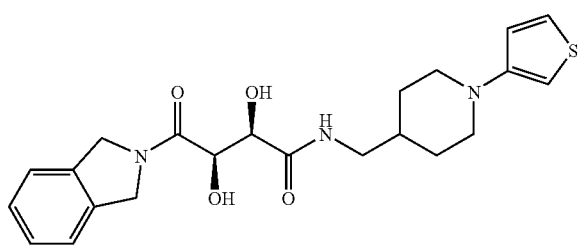 |
| 994 | 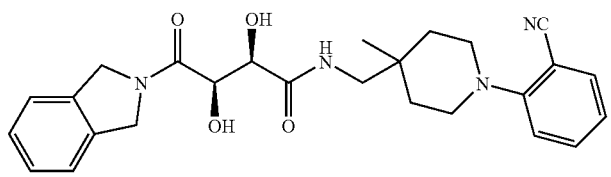 |
| 995 | 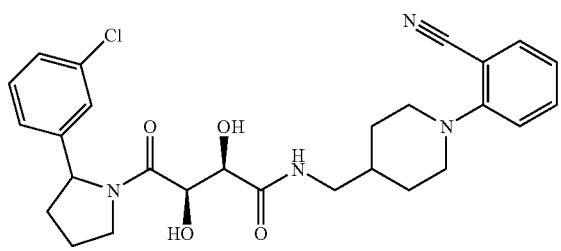 |
| 996 | 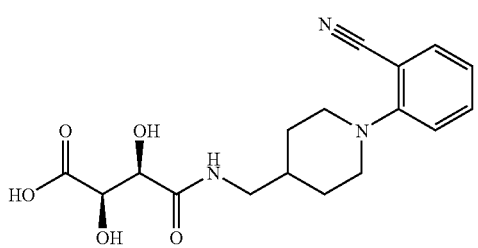 |

| | |
|---|---|
| 997 | 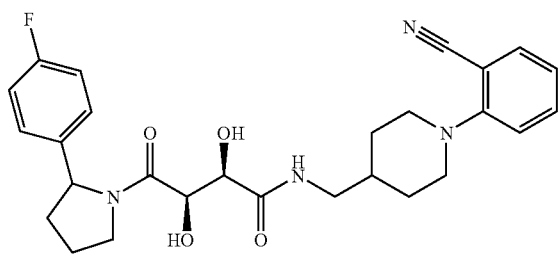 |
| 998 | 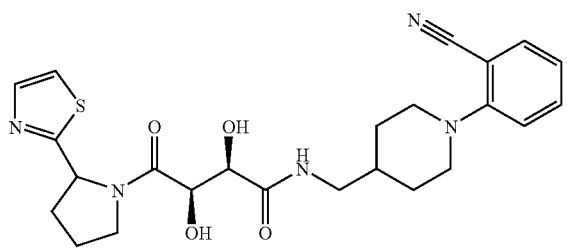 |
| 999 | 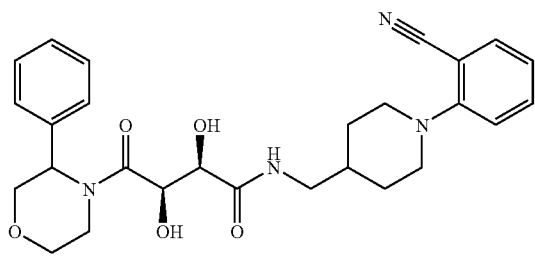 |
| 1000 | 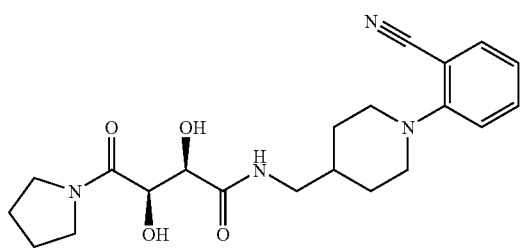 |
| 1001 | 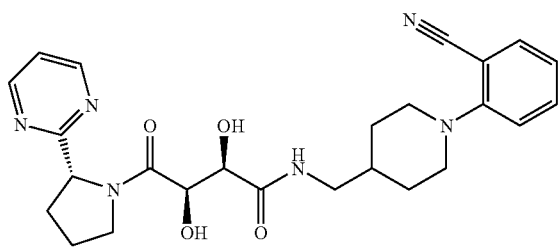 |
| 1002 | 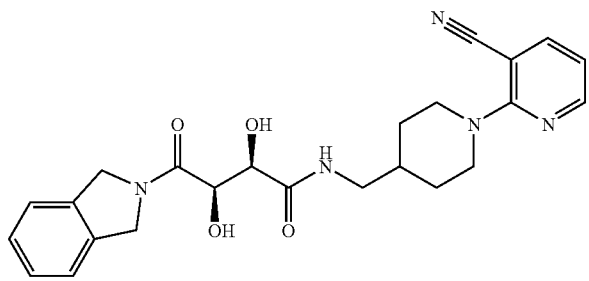 |

-continued
1003
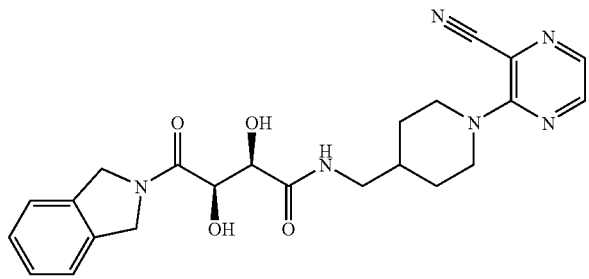
1004
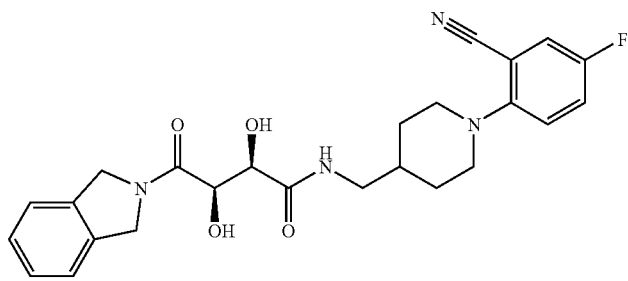
1005
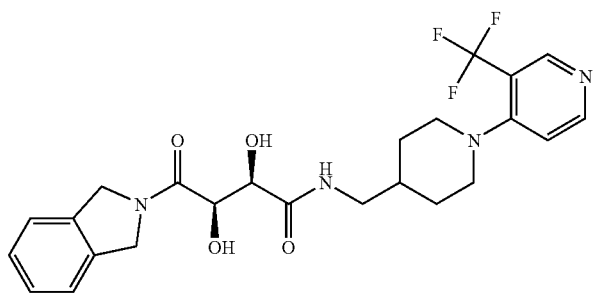
1006
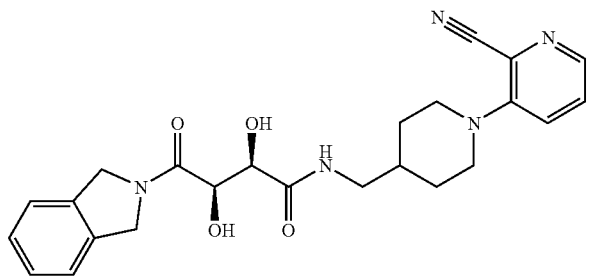
1007
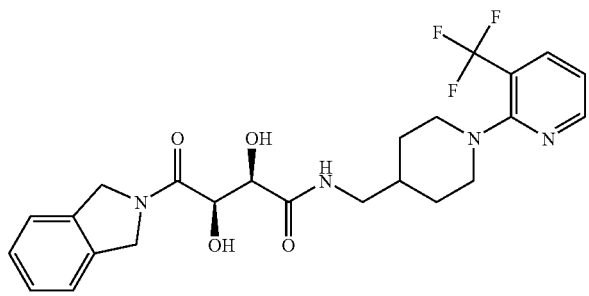

1008 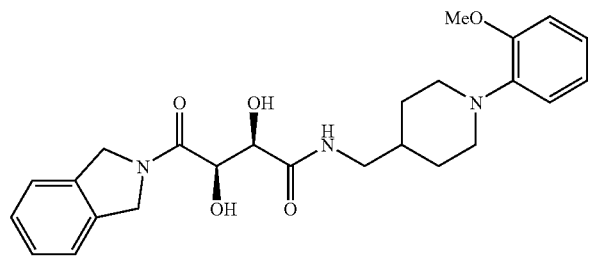
1009 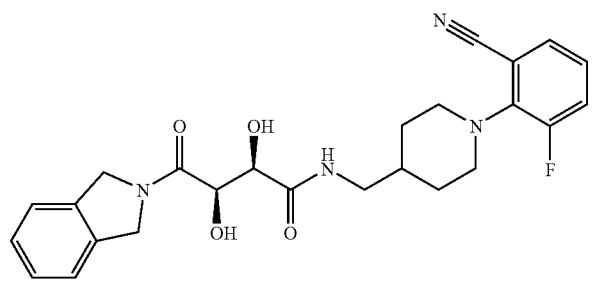
1010 
1011 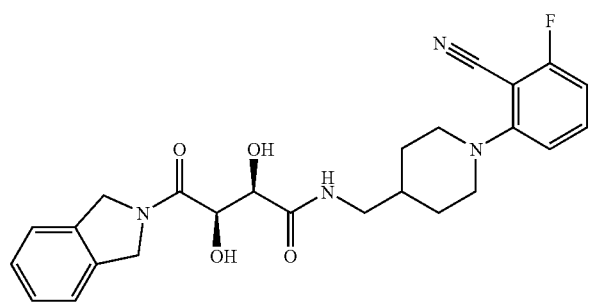
1012 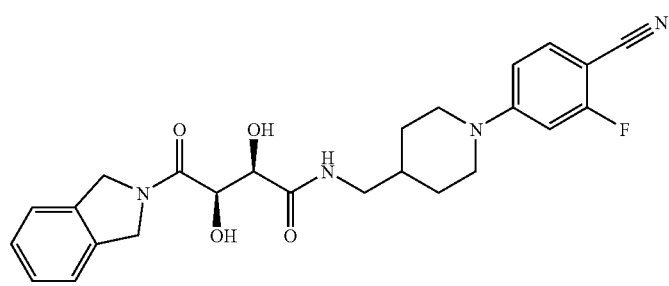

-continued
| | |
|---|---|
| 1013 | 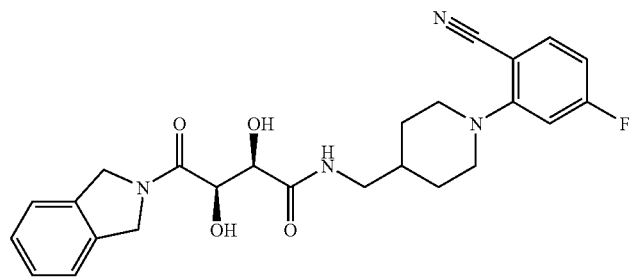 |
| 1014 | 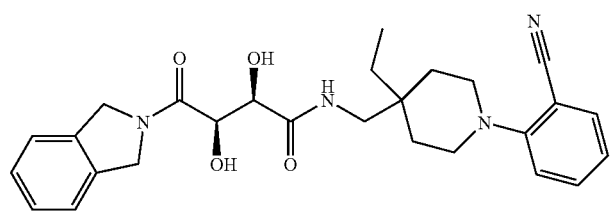 |
| 1015 | 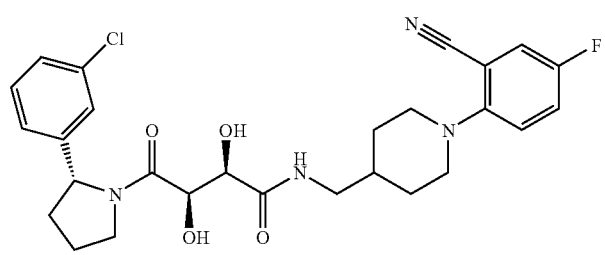 |
| 1016 | 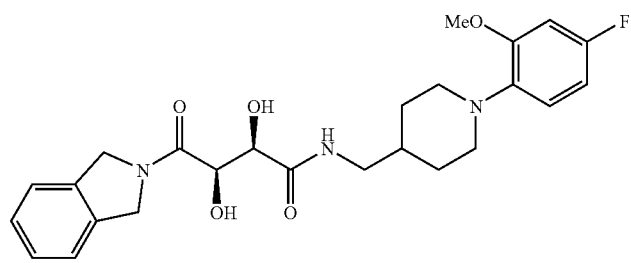 |
| 1017 | 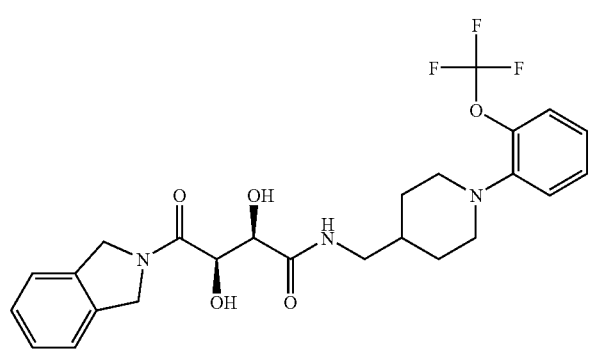 |
| 1018 | 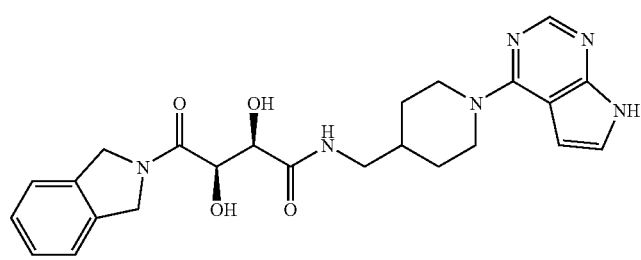 |

1019 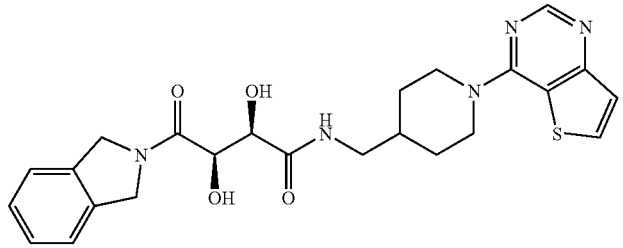
1020 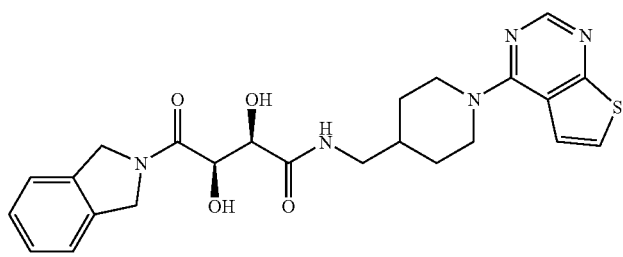
1021 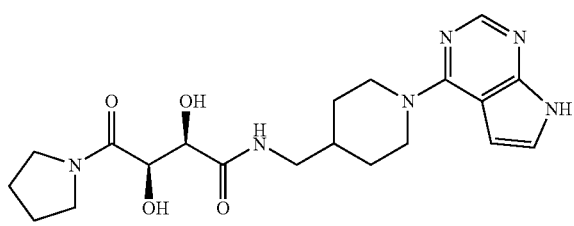
1022 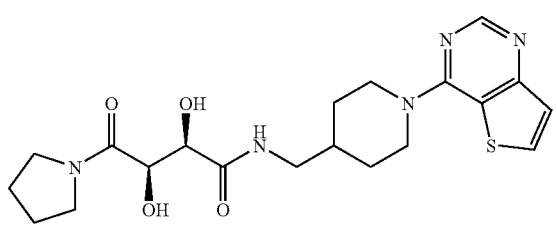
1023 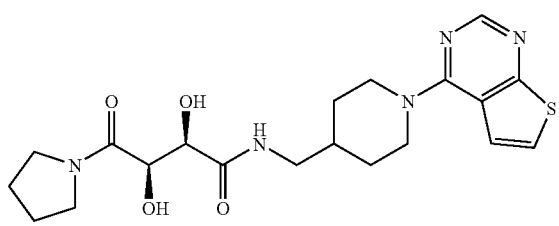
1024 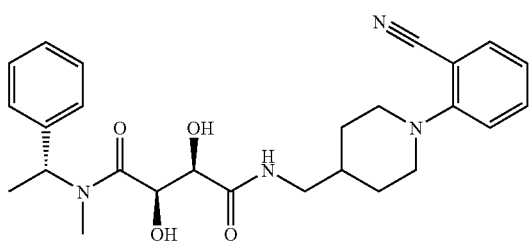

| | |
|---|---|
| 1025 | 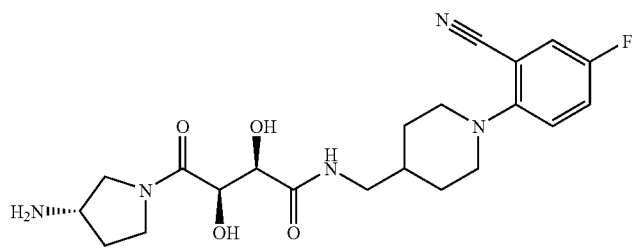 |
| 1026 | 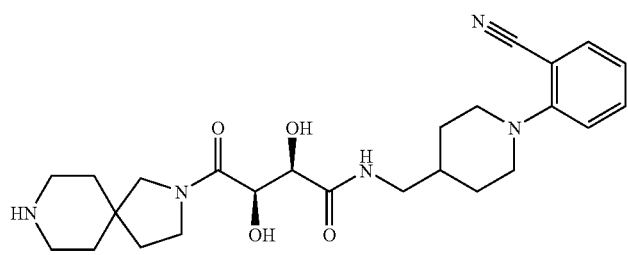 |
| 1027A | 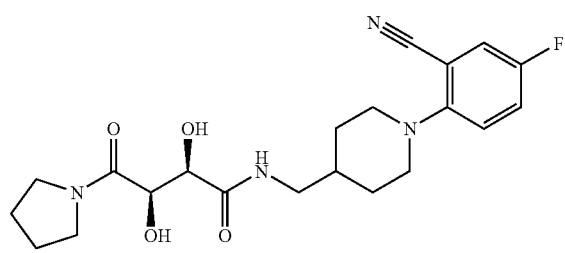 |
| 1027B | 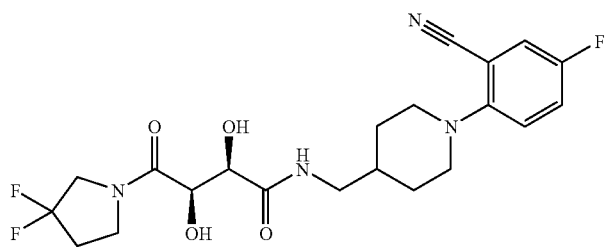 |
| 1027C | 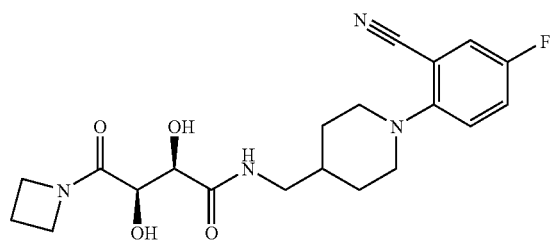 |
| 1028 | 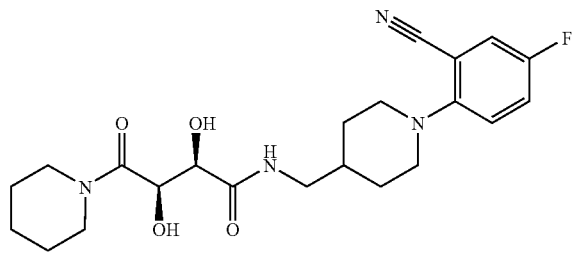 |

-continued
1029 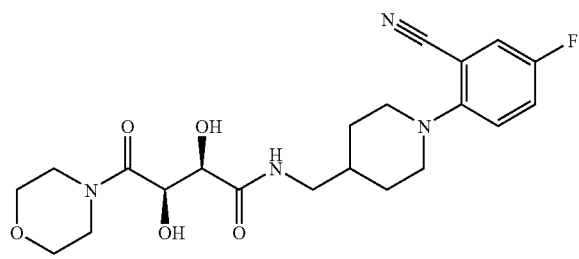
1030 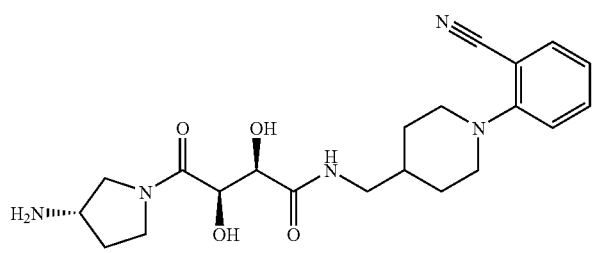
1031 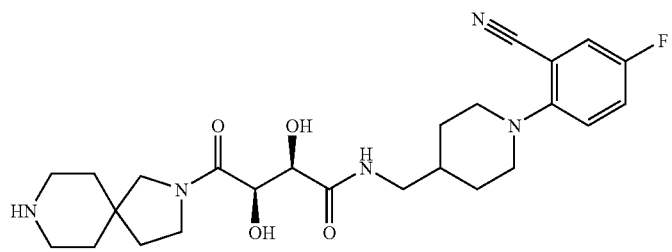
1032 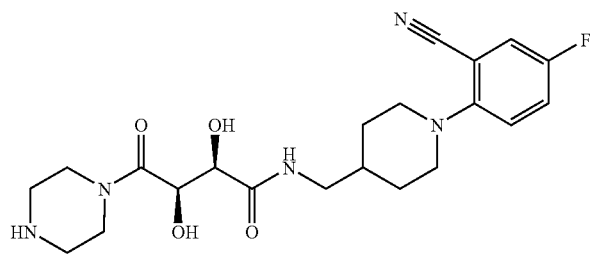
1033 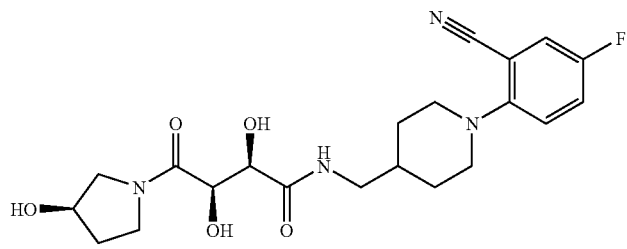
1034A 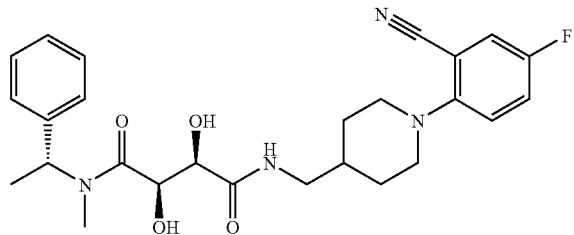

1034B 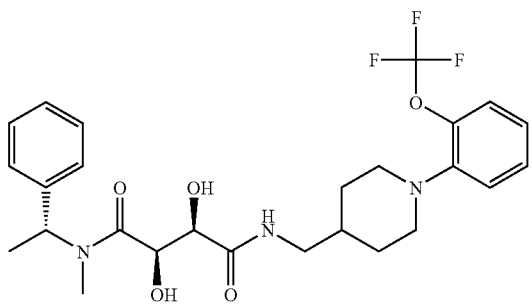
1035 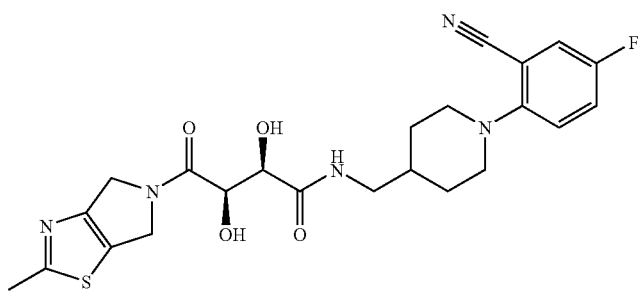
1036 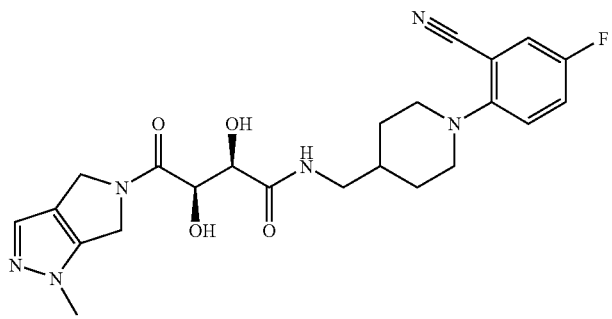
1037 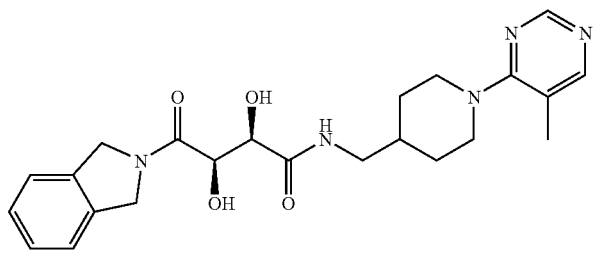
1038A 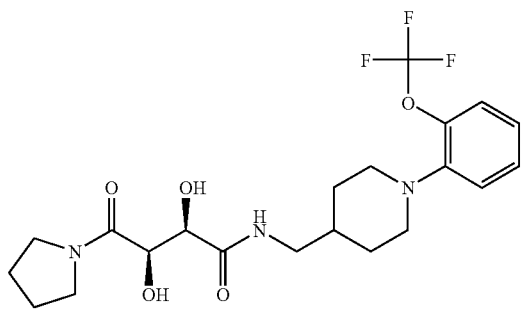

1038B 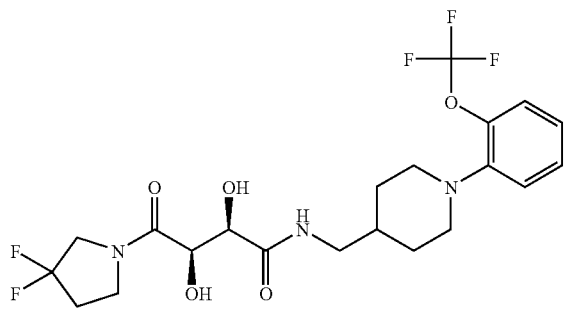
1039 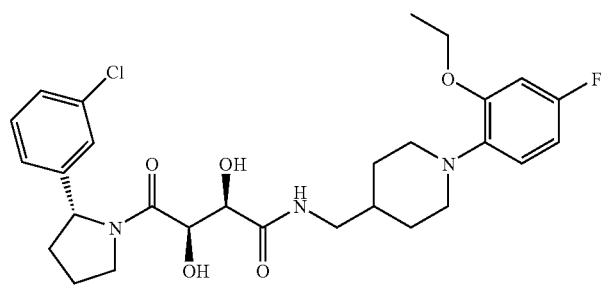
1040 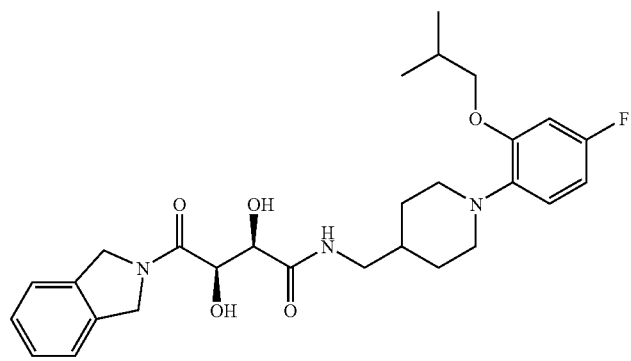
863 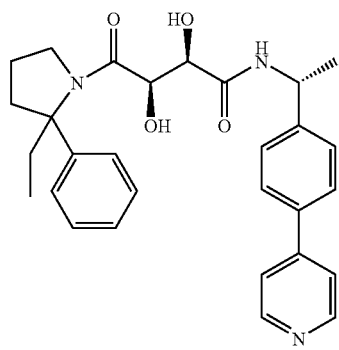
1048A 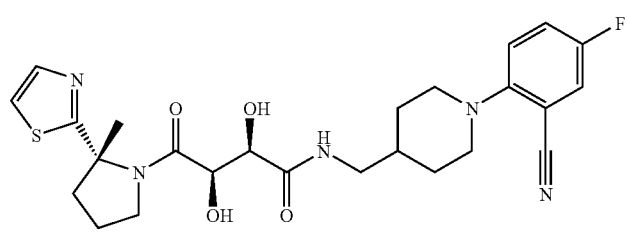

1048B 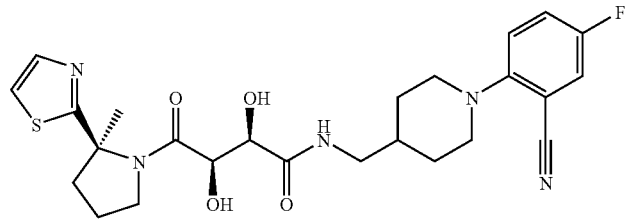
1052 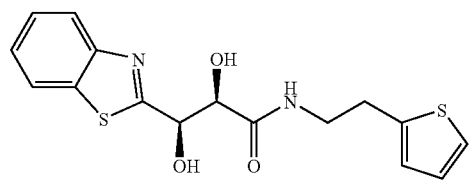
1053 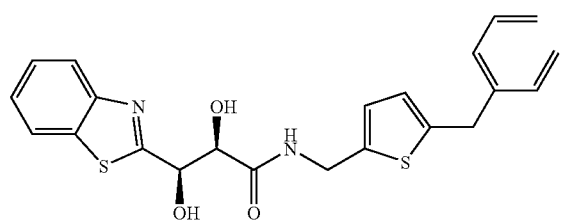
1054 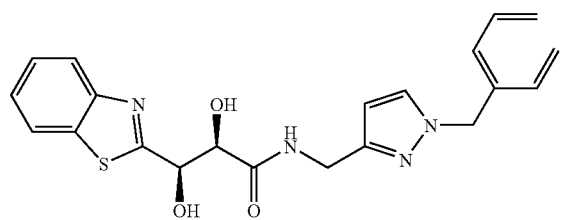
1059 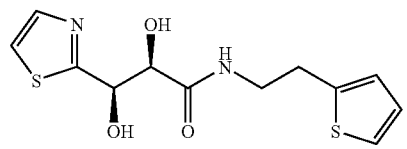
1060 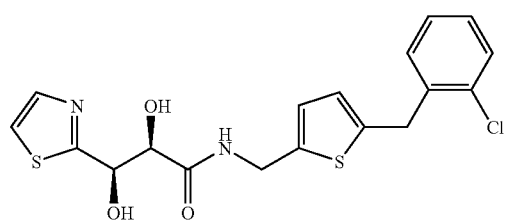
1061 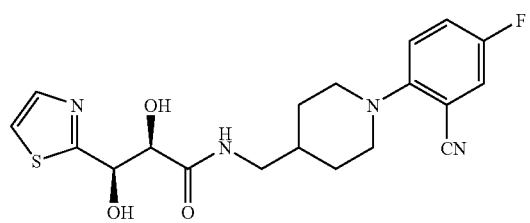

-continued
1063 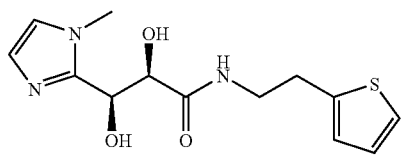
1066 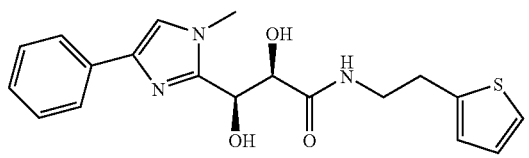
1071 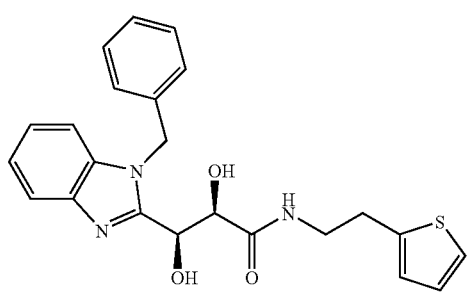
1072 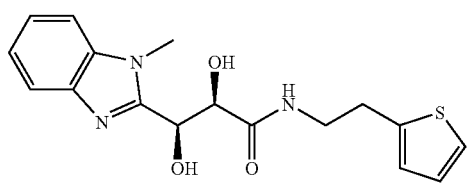
1073 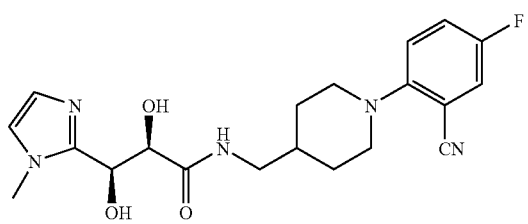
1079 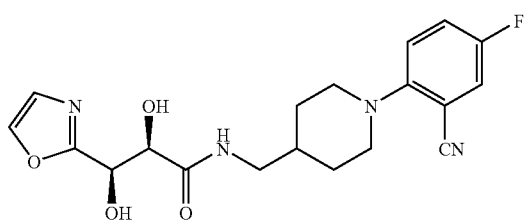
1085 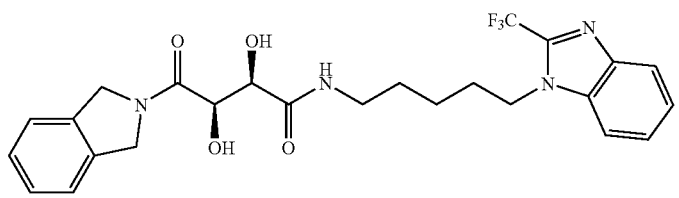

| | |
|---|---|
| 1093 | 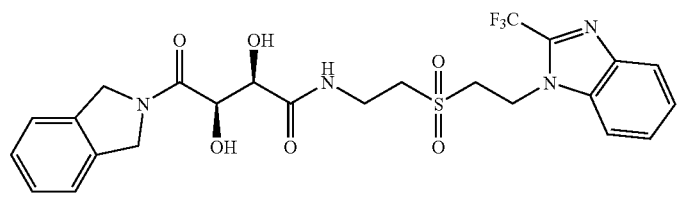 |
| 1103 | 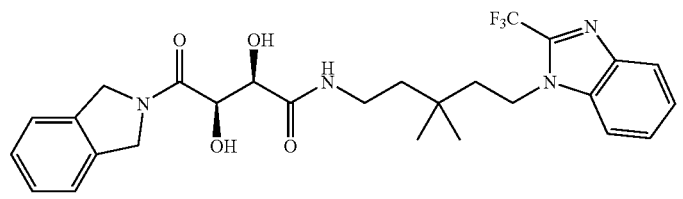 |
| 1104 | 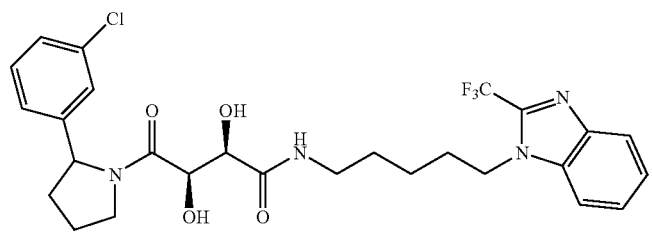 |
| 1105 | 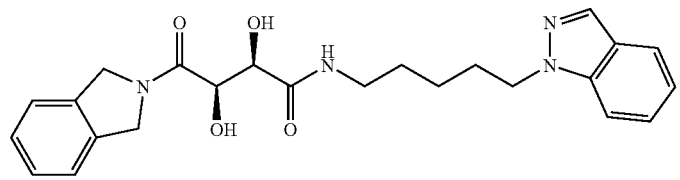 |
| 1106 | 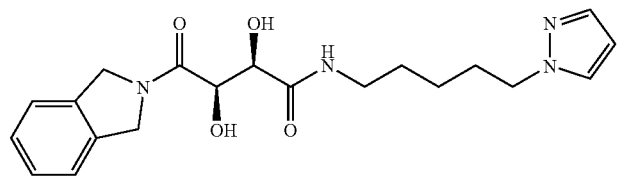 |
| 1107 | 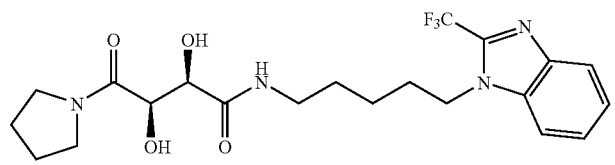 |
| 1108 | 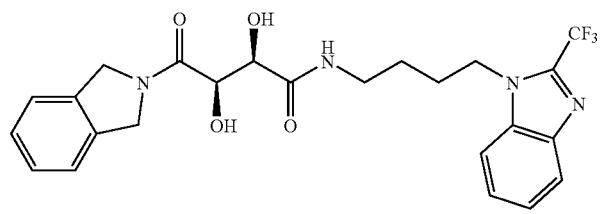 |

-continued
| | |
|---|---|
| 1109 | 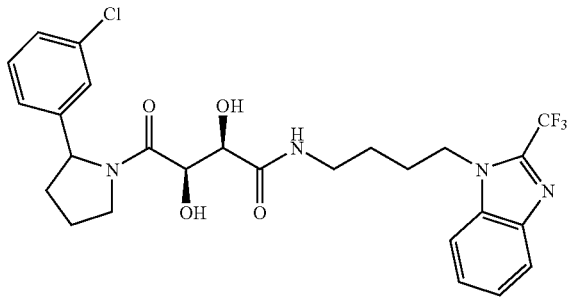 |
| 1110 | 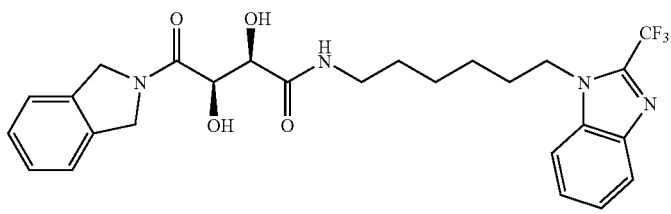 |
| 1111 | 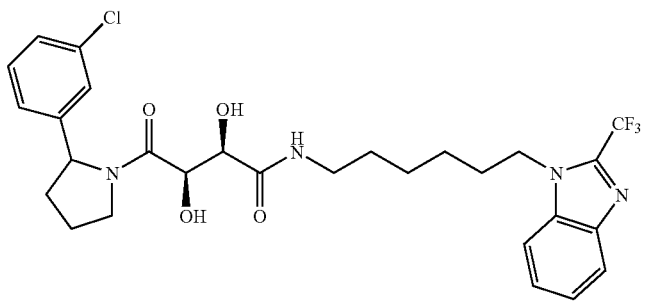 |
| 1112 | 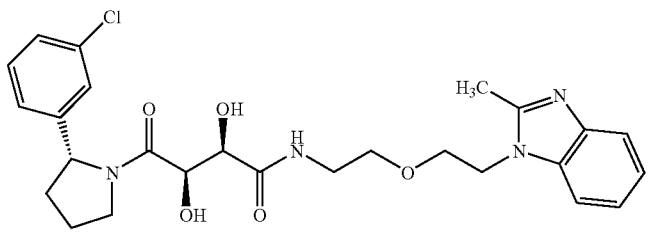 |
| 1113 | 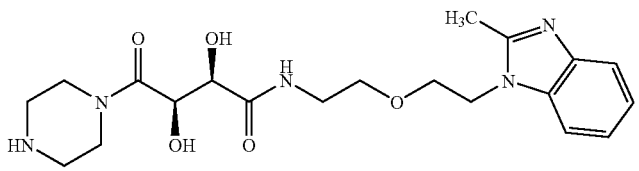 |
| 1114 | 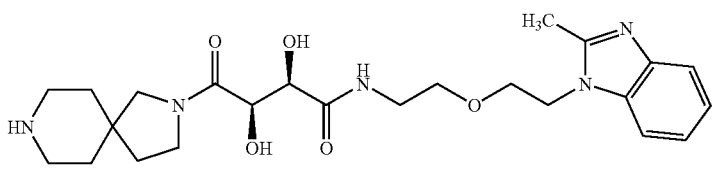 |
| 1121 | 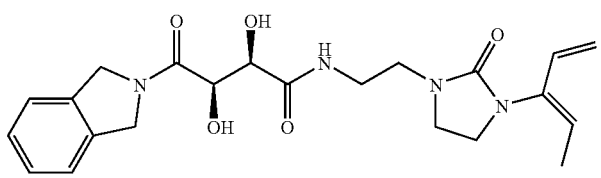 |

-continued
1122 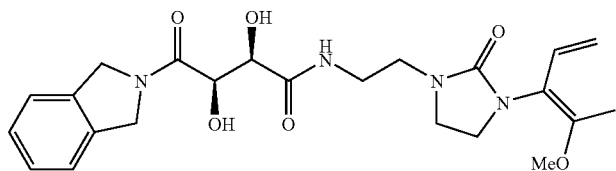
1123 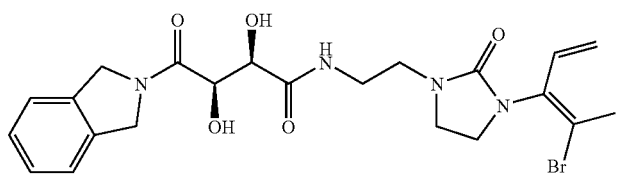
1128 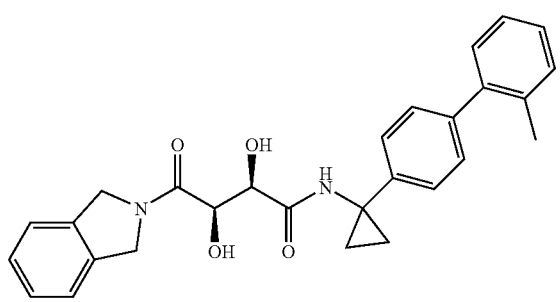
1129 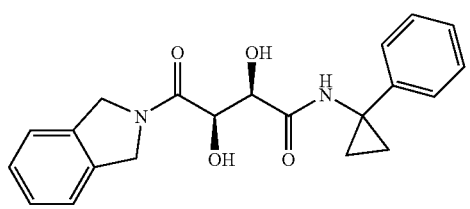
1133 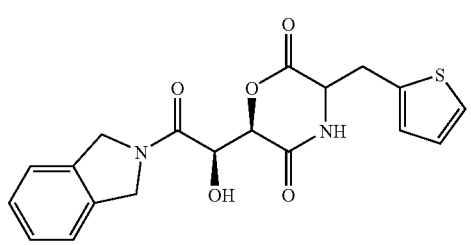
1134 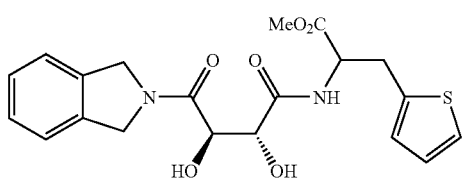
1138 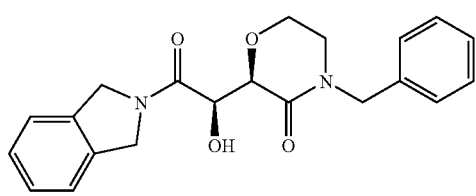

1146 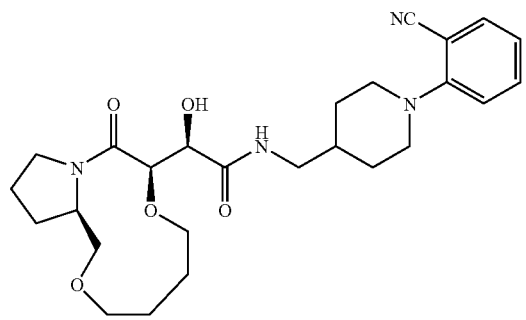
1152 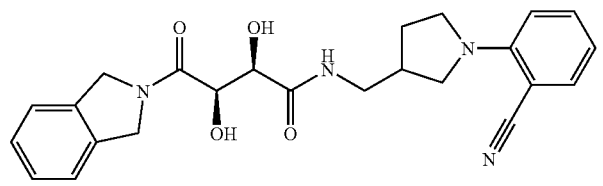
1156 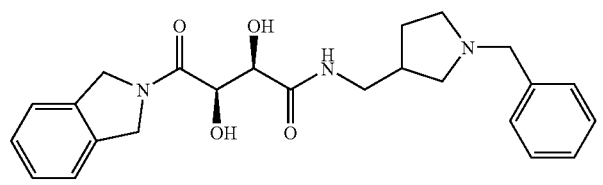
1160 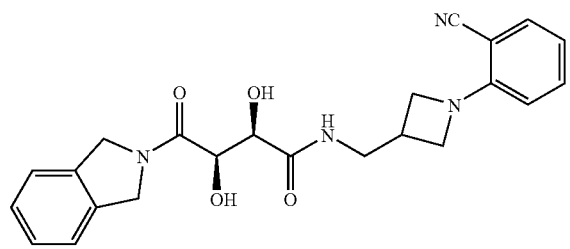
1163 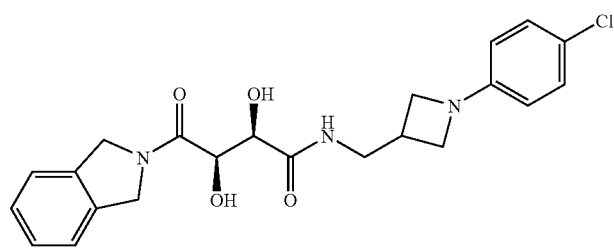
1166 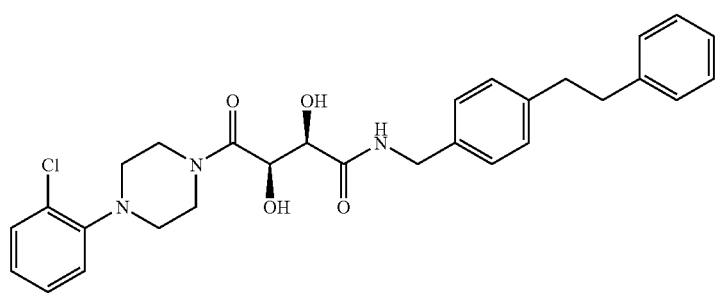

1167 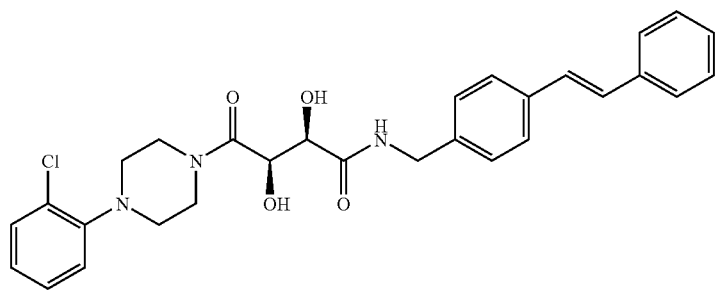
1168 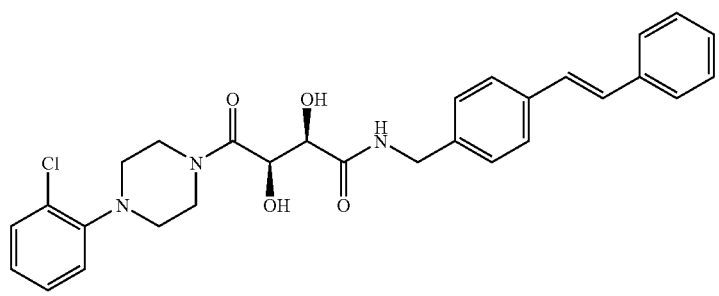
1169 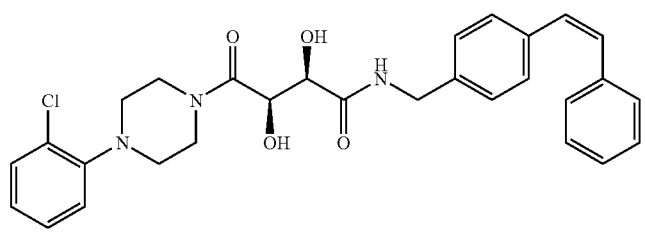
1170 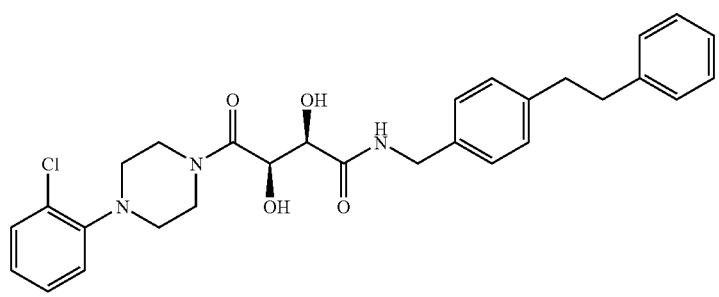
1171 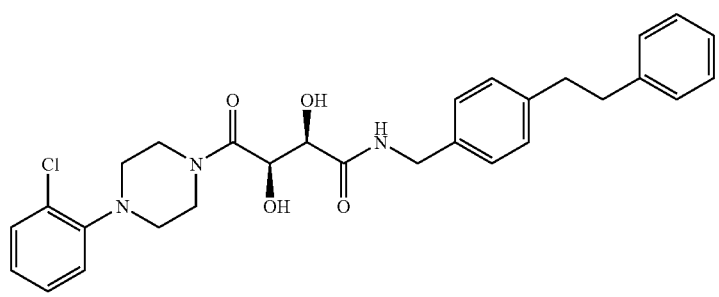

1173 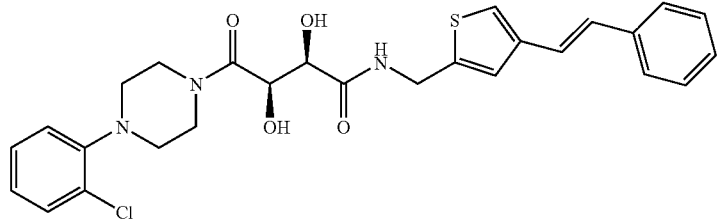
1175 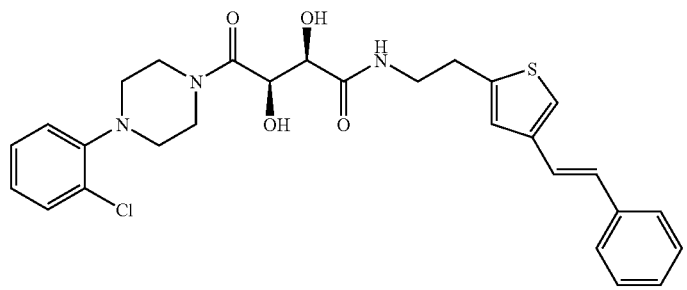
1176 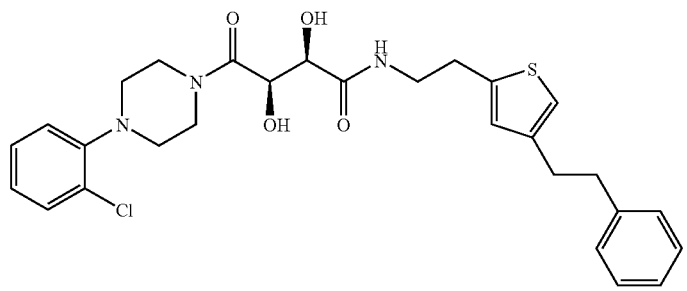
1177 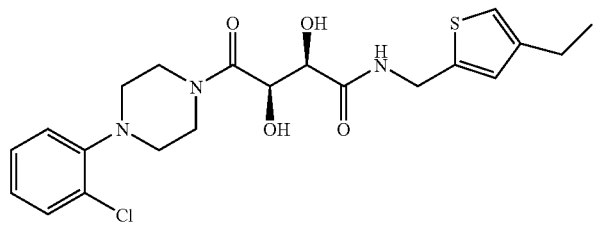
1178 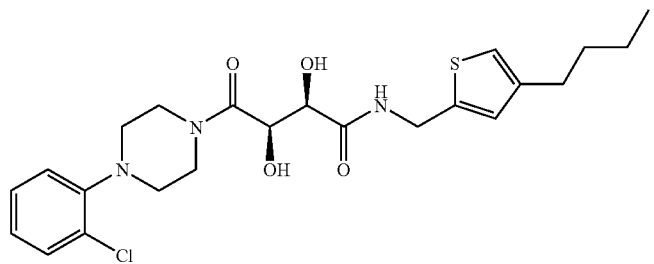

1179 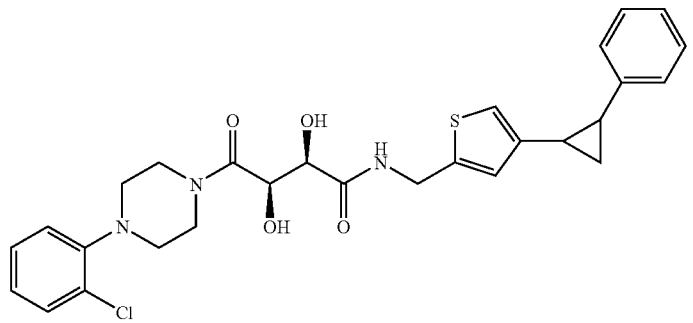
1180 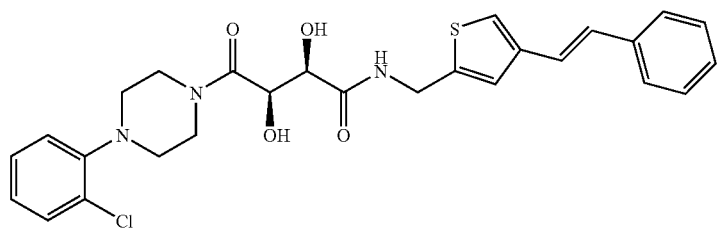
1181 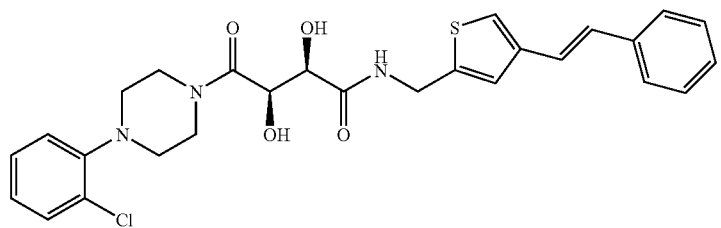
1182 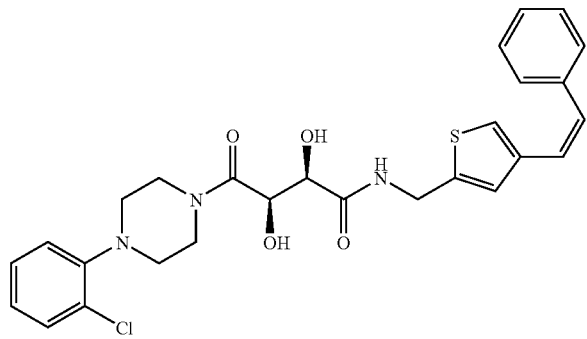
1183 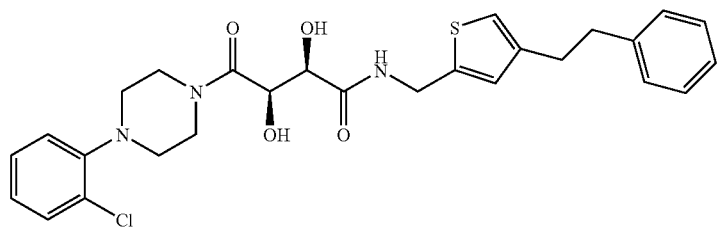
1184 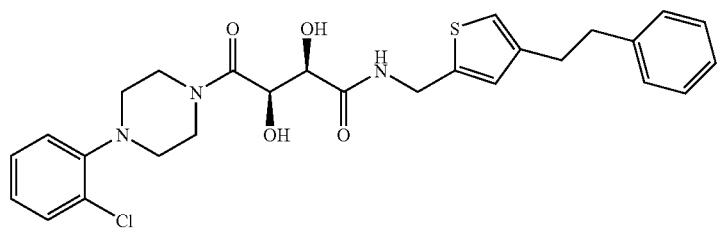

-continued
1185 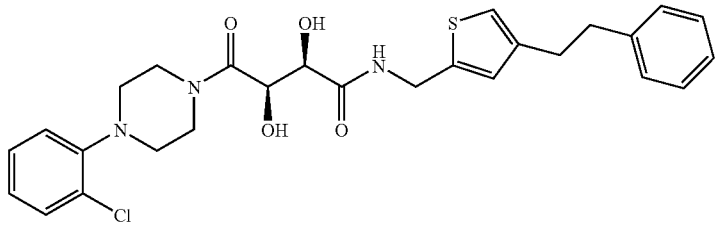
1186 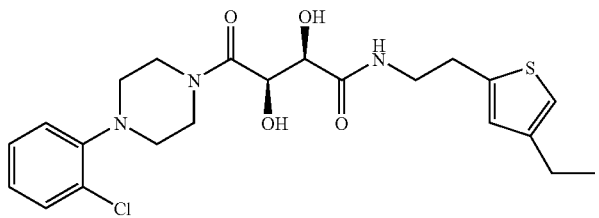
1187 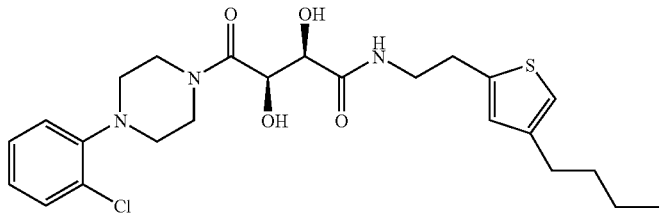
1188 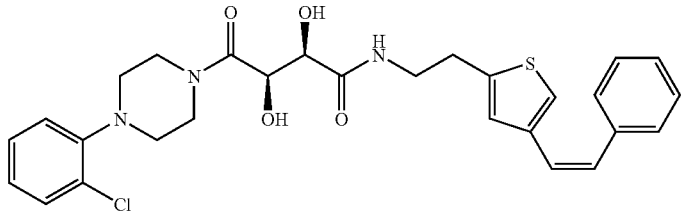
1210 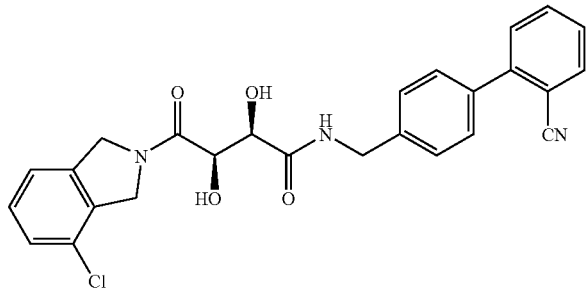
1211 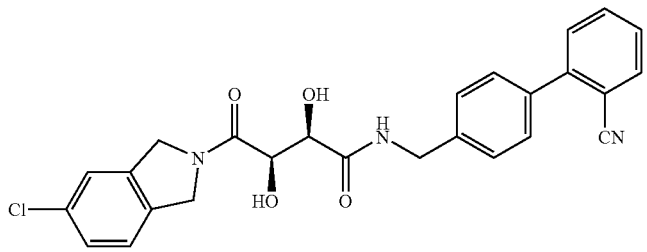

-continued
1212 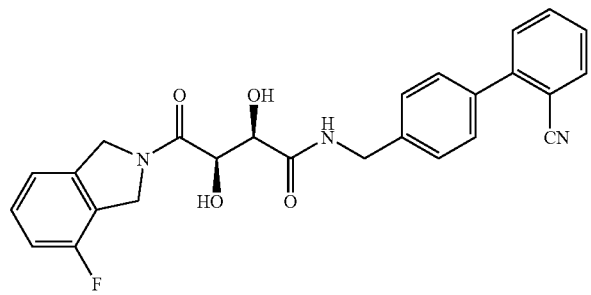
1213 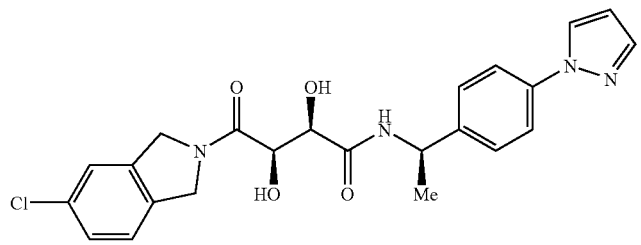
1214 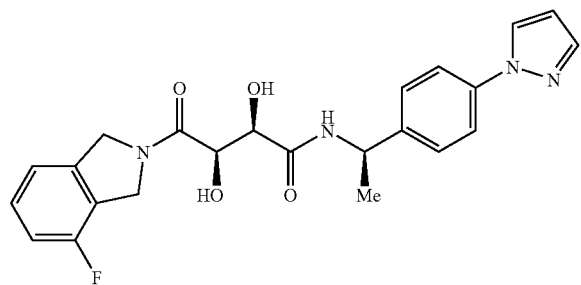
1218 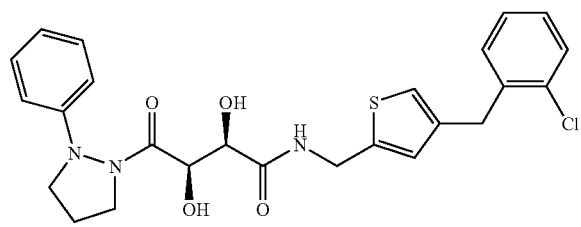
1222 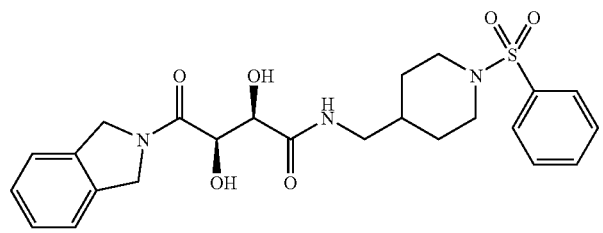
1223 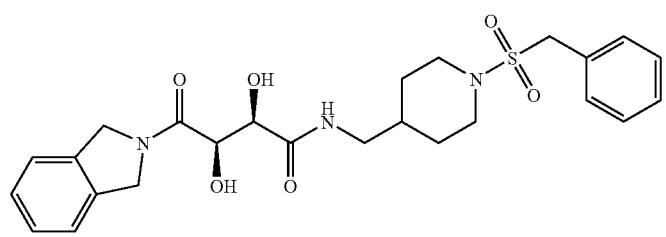

-continued
1036
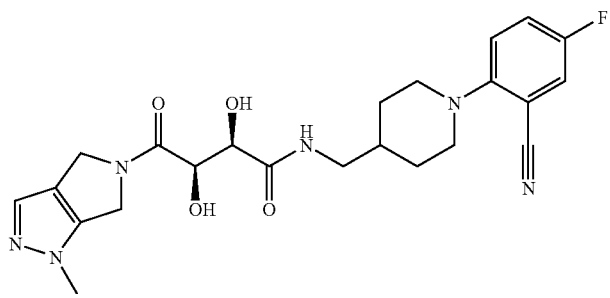
1035
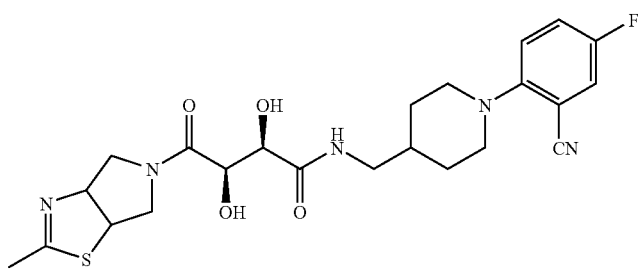
1235A
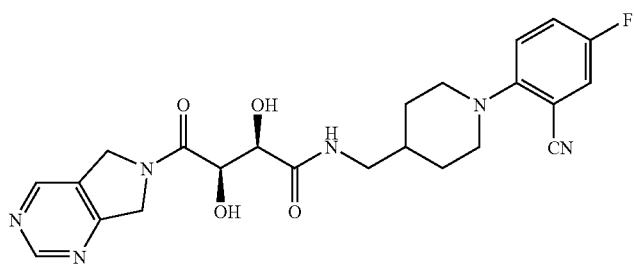
1235B
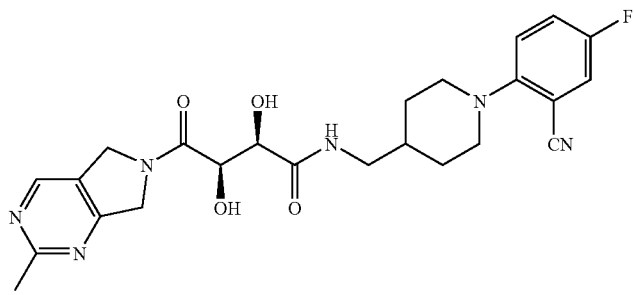
1236A
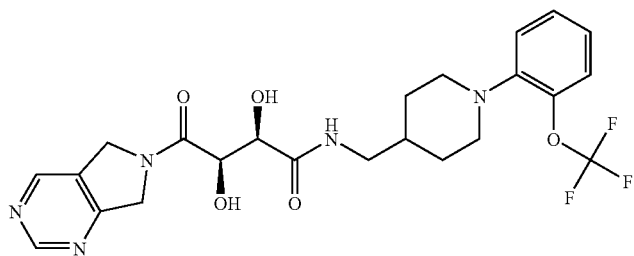

1236B
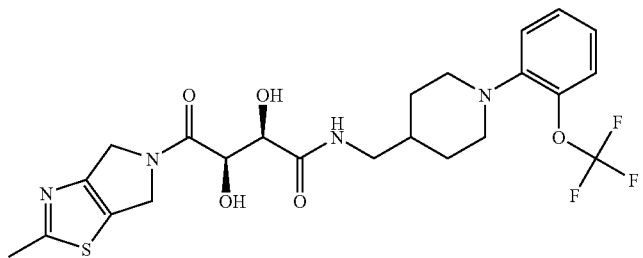
1243A, B
diastereomers)
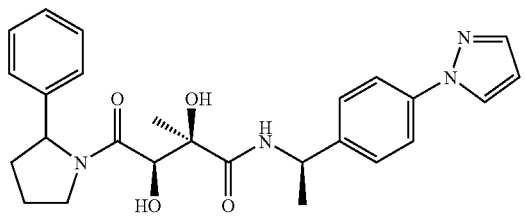
1243C
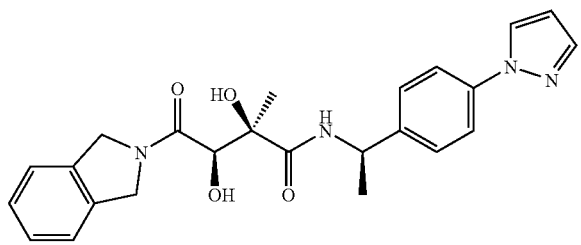
1247A, B
diastereomers)
(?)
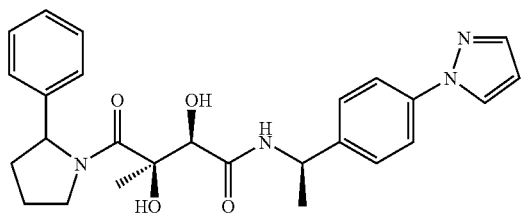
1255
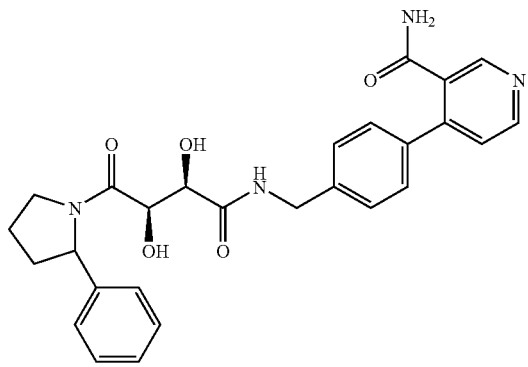

1256 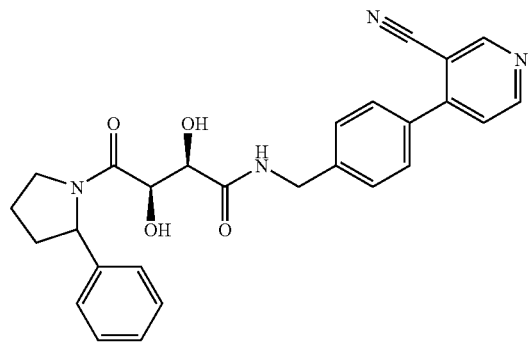
1261 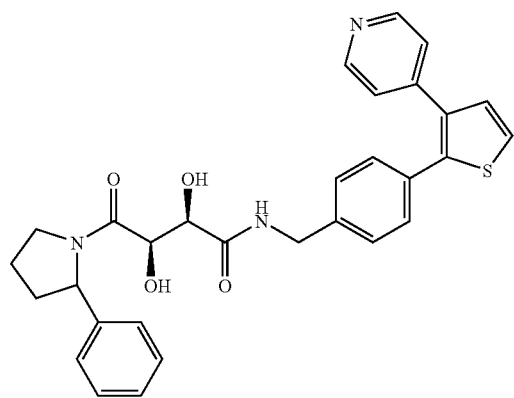
1266 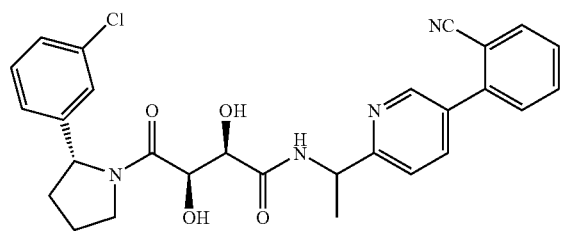
1267 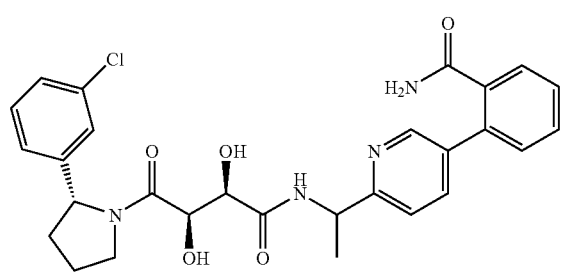
1268 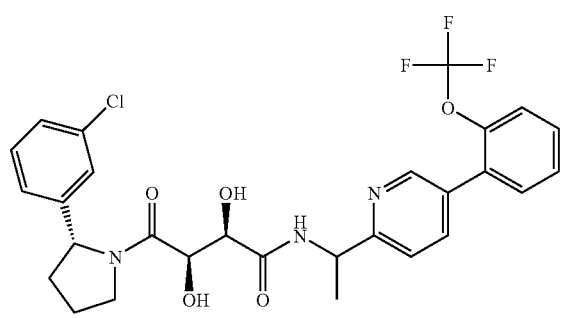

-continued
1269
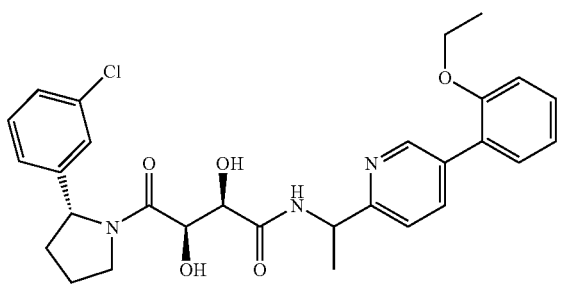
1276
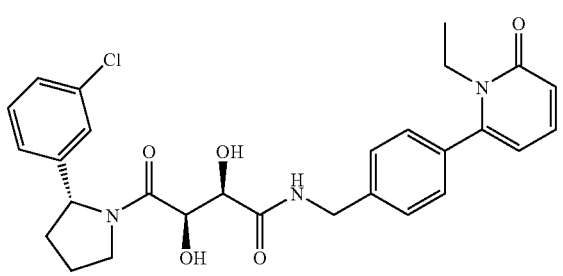
1280
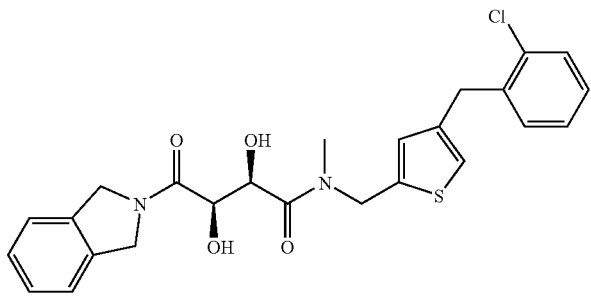
2003 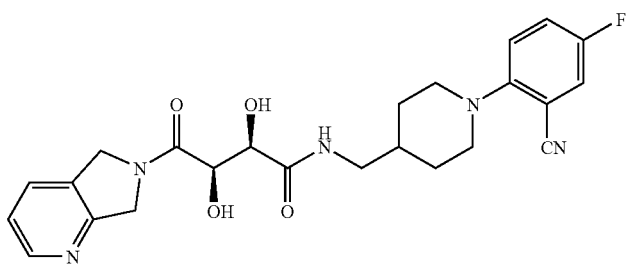 B
2007 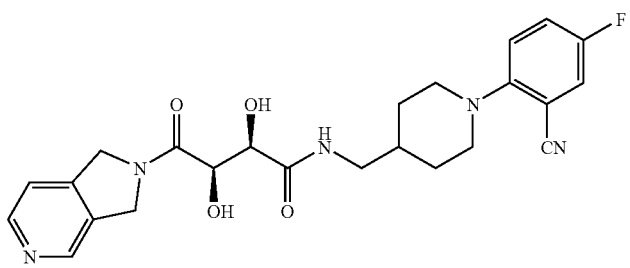 A -continued
| | | |
|---|---|---|
| 2030 | 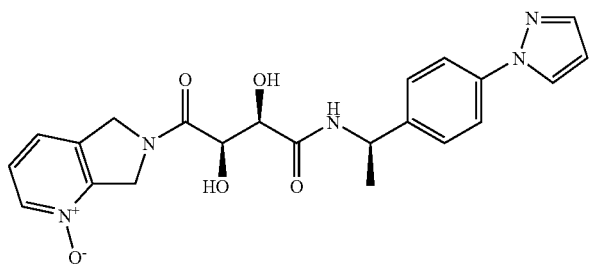 | B |
| 2031 | 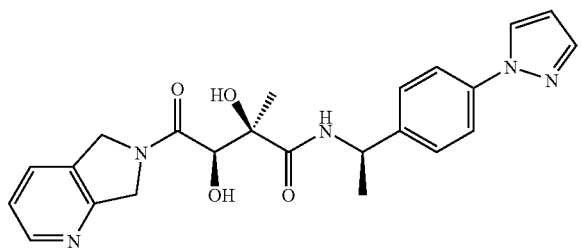 | A |
| 2032 | 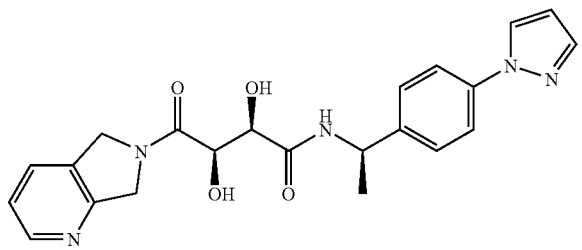 | A |
| 2033 | 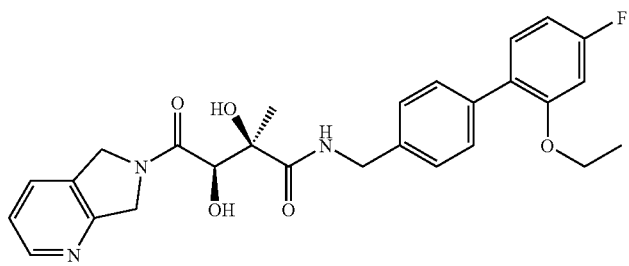 | A |
| 2034 | 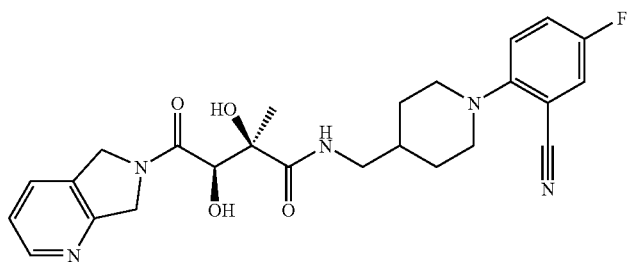 | B |
| 2035 | 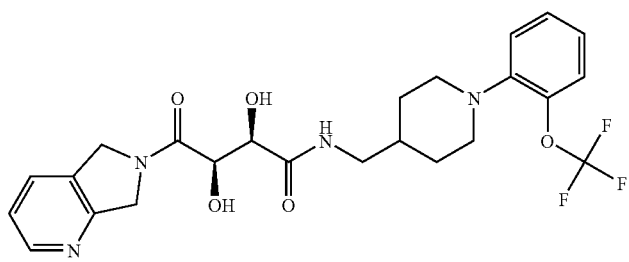 | A |

-continued
| | | |
|---|---|---|
| 2036 | 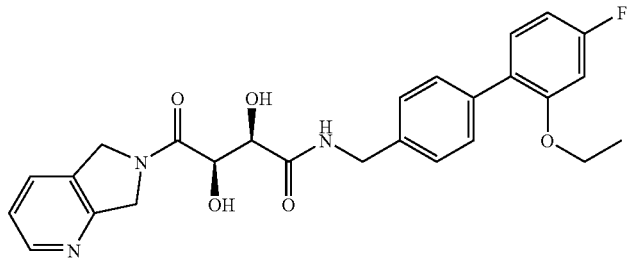 | A |
| 2037 | 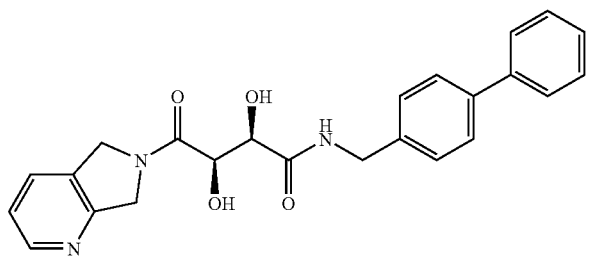 | B |
| 2038 | 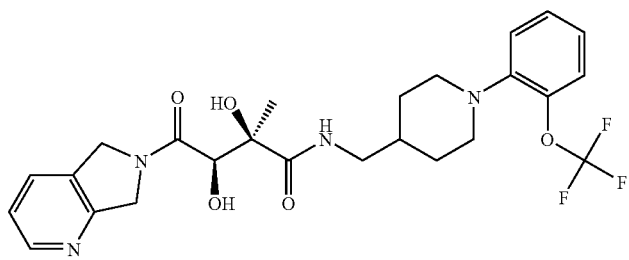 | B |
| 2039 | 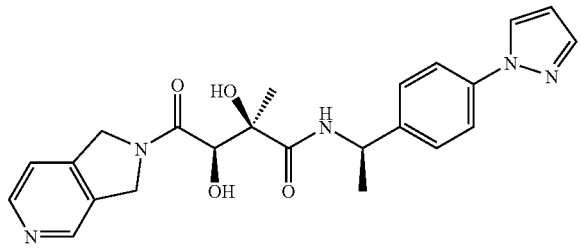 | A |
| 2040 | 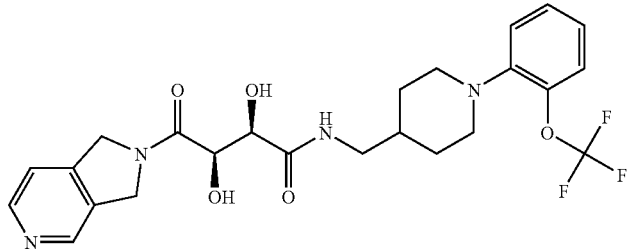 | A |
| 2041 | 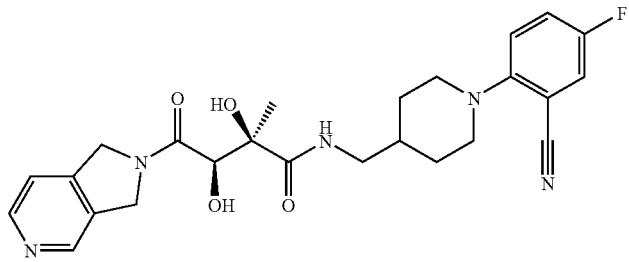 | B |

-continued
| | | |
|---|---|---|
| 2042 | 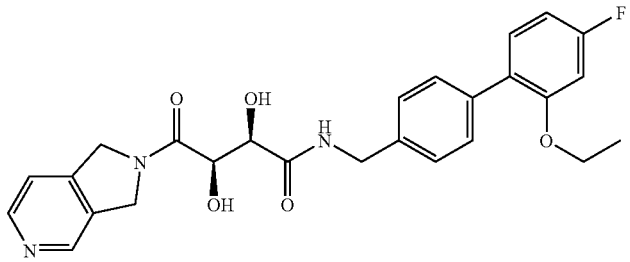 | A |
| 2043 | 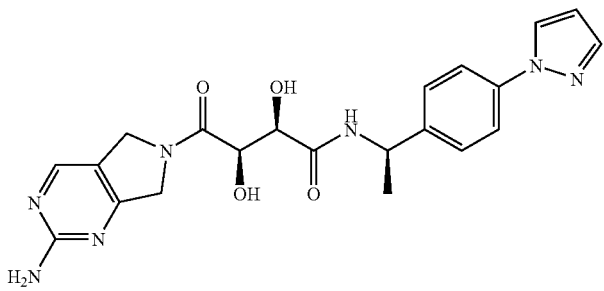 | A |
| 2044 | 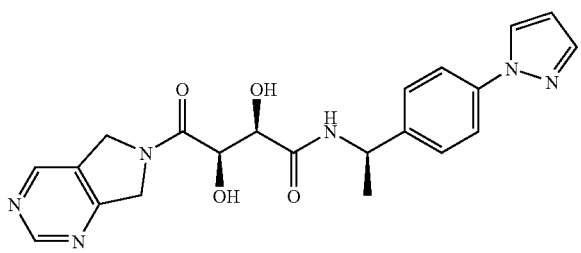 | A |
| 2045 | 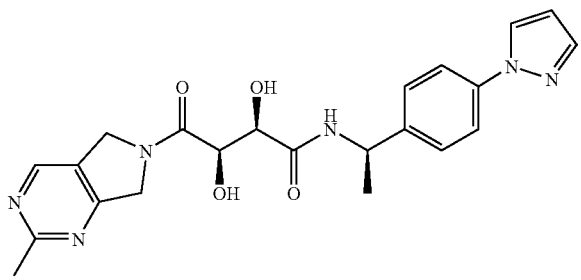 | C |
| 2046 | 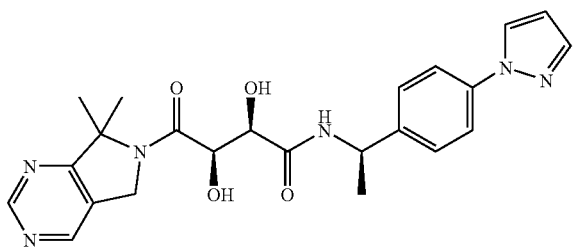 | C |
| 2047 | 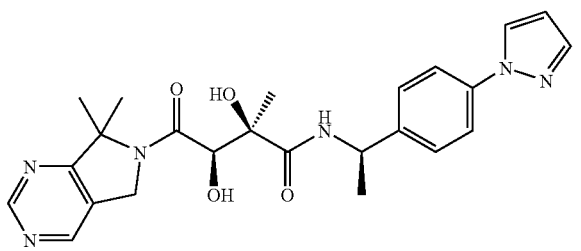 | C |

-continued
2048 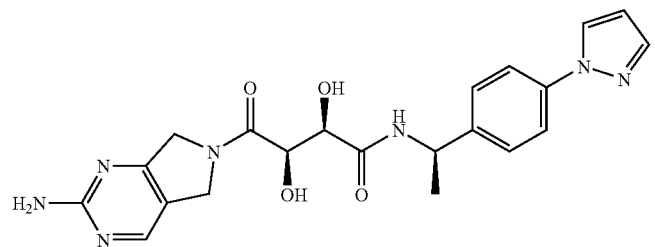 B
2049 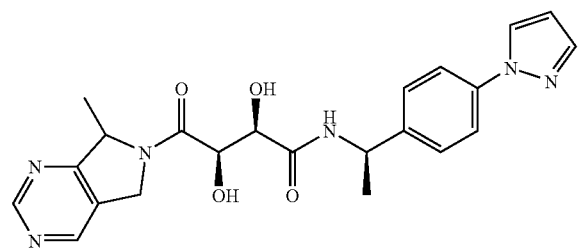 B
2050 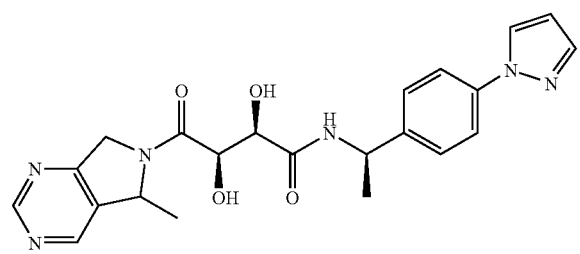 B
2051 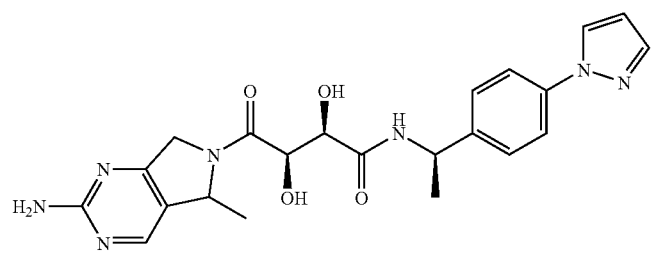 B
2052 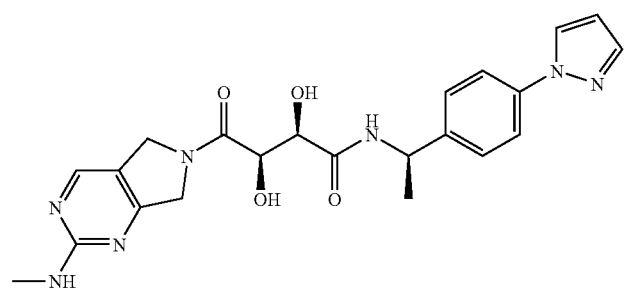 A
2053 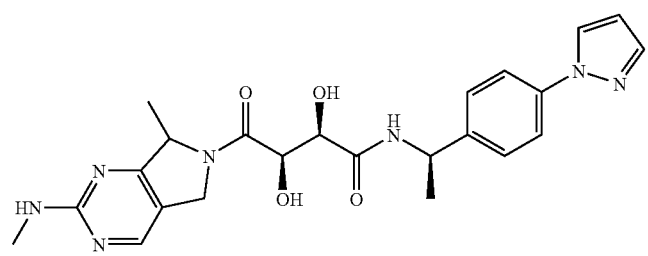 B -continued
| | | |
|---|---|---|
| 2054 | 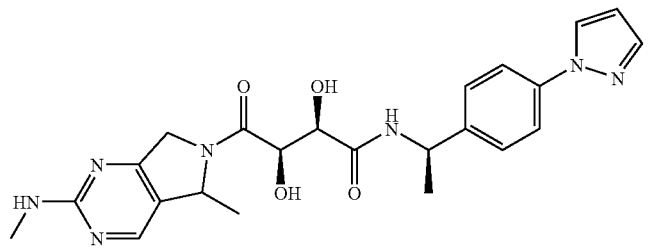 | A |
| 2055 | 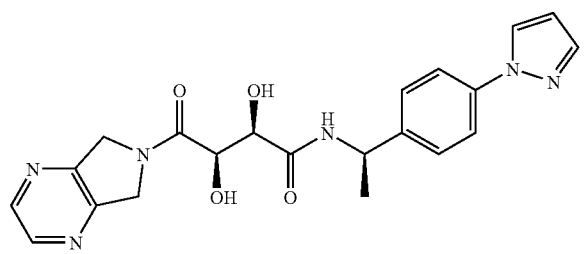 | A |
| 2056 | 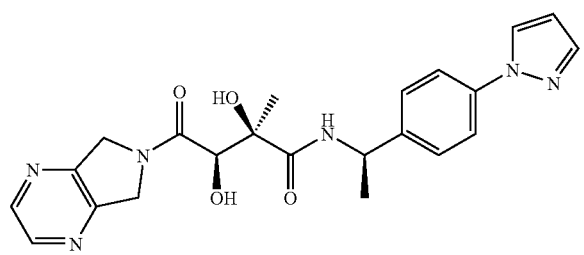 | A |
| 2057 | 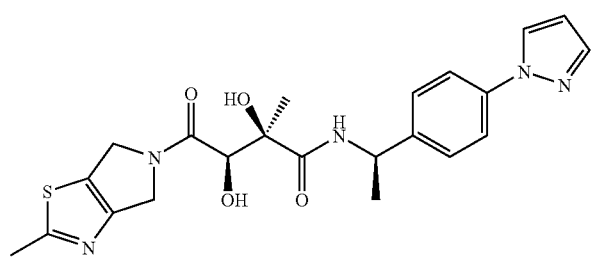 | A |
| 2073 | 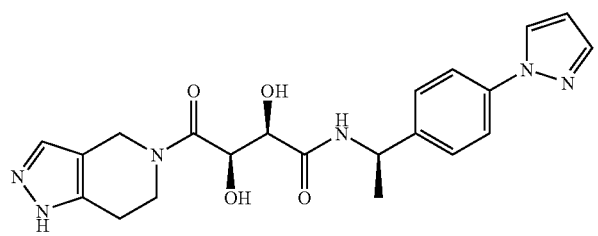 | B |
| 2074 | 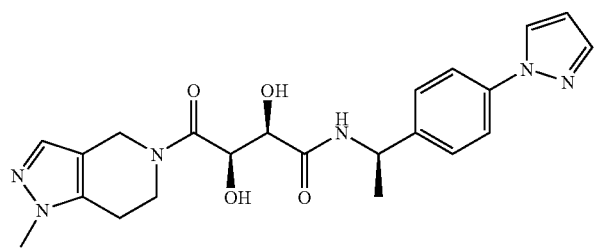 | B |

-continued
| | | |
|---|---|---|
| 2075 | 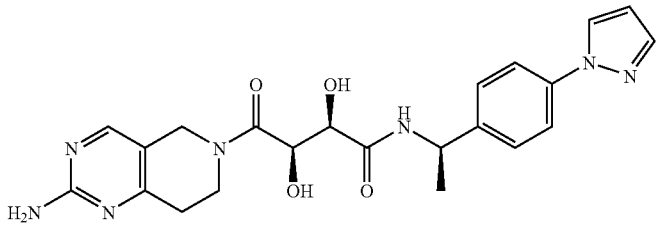 | B |
| 2076 | 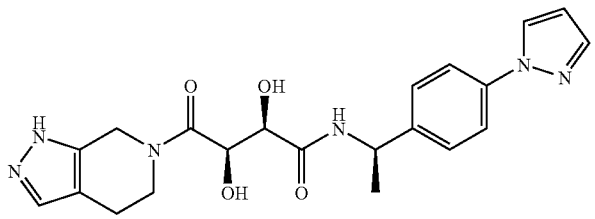 | B |
| 2077 | 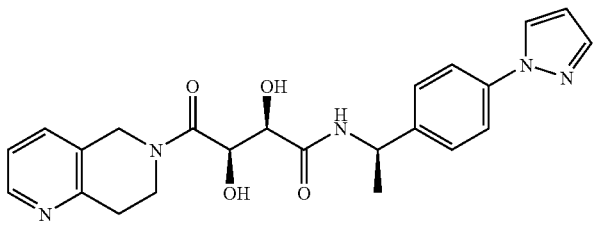 | B |
| 2078 | 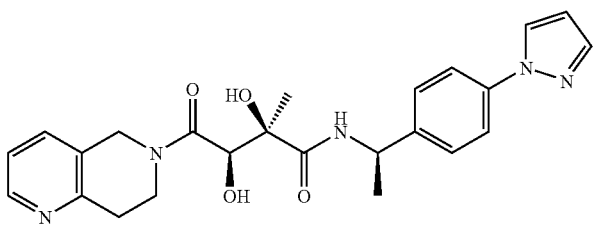 | C |
| 2079 | 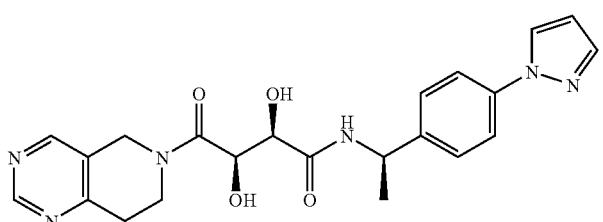 | C |
| 2080 | 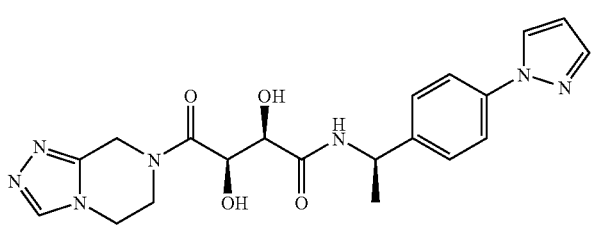 | C |
| 2081 | 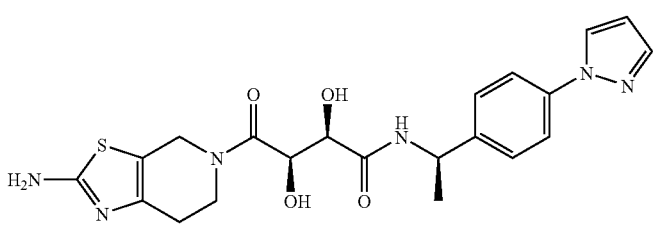 | A |

-continued
| | | |
|---|---|---|
| 2082 | 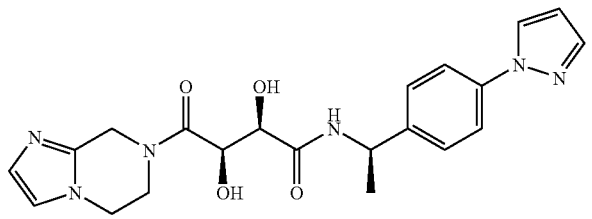 | C |
| 2083 | 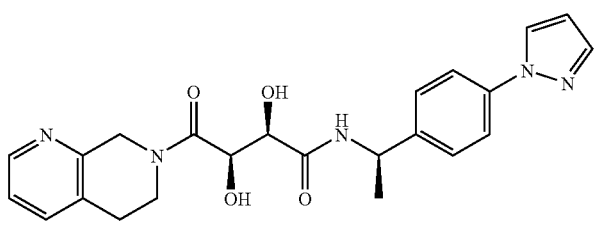 | B |
| 2084 | 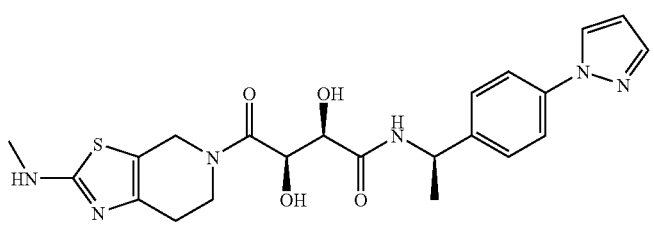 | B |
| 2093 | 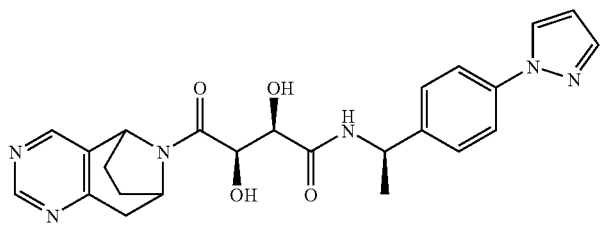 | D |
| 2094 | 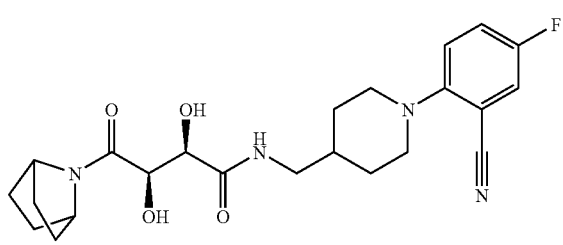 | D |
| 2095 | 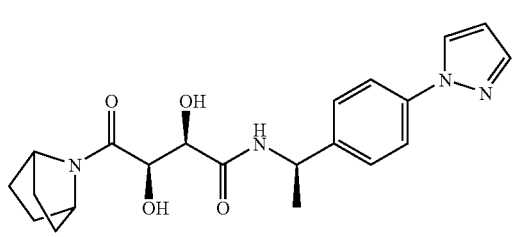 | C |

-continued
| | | |
|---|---|---|
| 2096 | 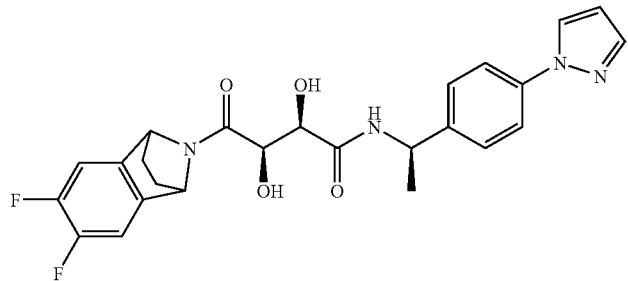 | C |
| 2097 | 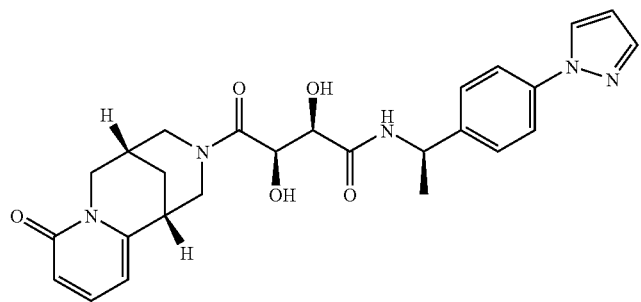 | C |
| 2098 | 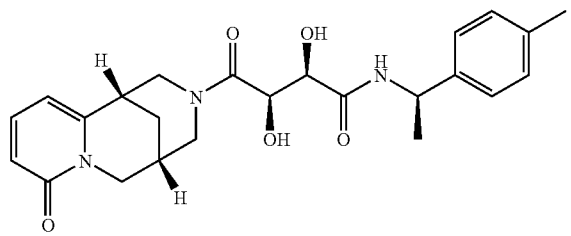 | C |
| 2099 | 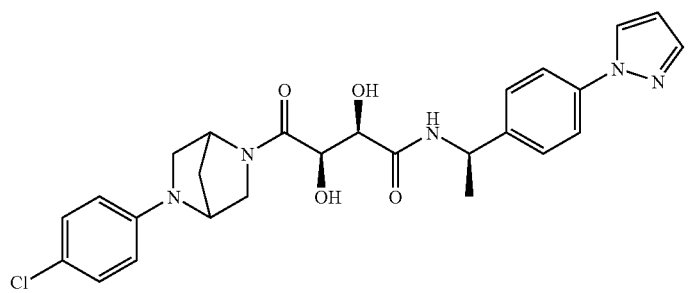 | C |
| 2139 | 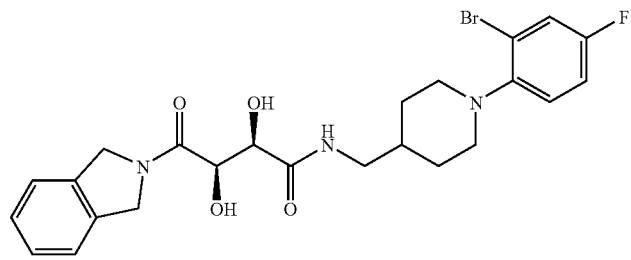 | A |

| | | |
|---|---|---|
| 2140 | 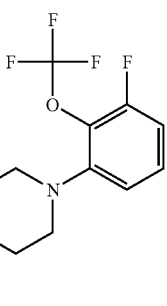 | D |
| 2141 | 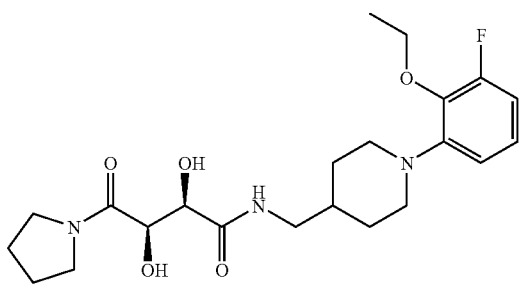 | D |
| 2142 | 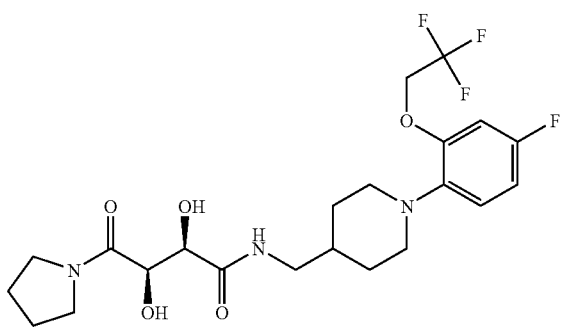 | B |
| 2143 | 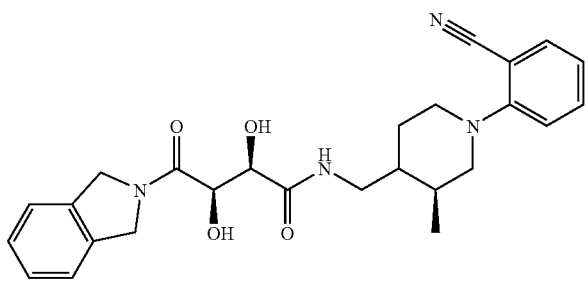 | A |
| 2144 | 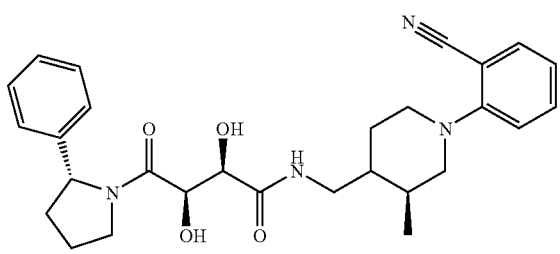 | A |

-continued
| | | |
|---|---|---|
| 2145 | 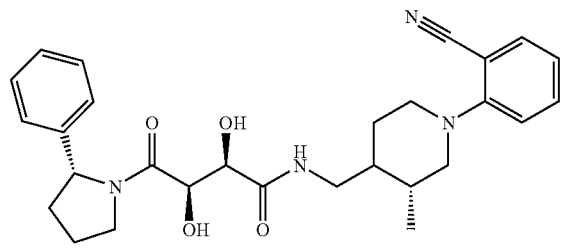 | C |
| 2146 | 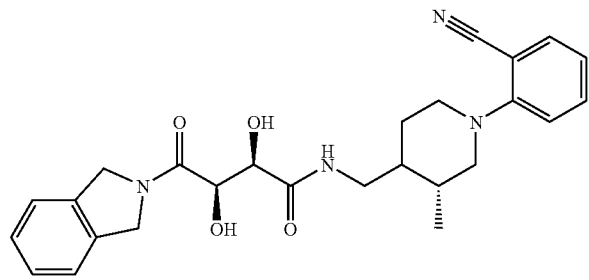 | C |
| 2147 | 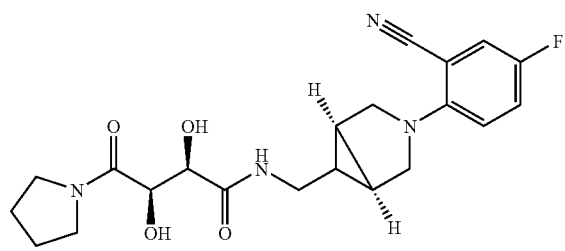 | C |
| 2148 | 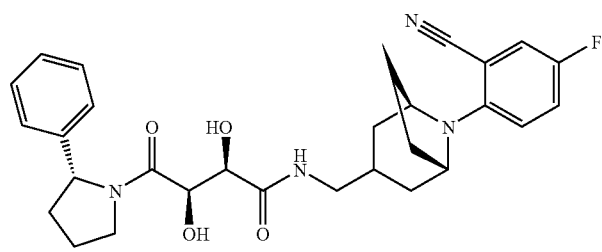 | C |
| 2149 | 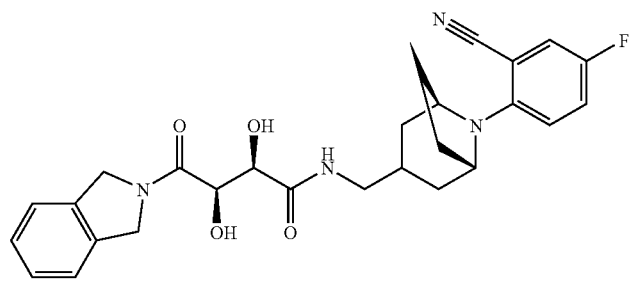 | C |
| 2150 | 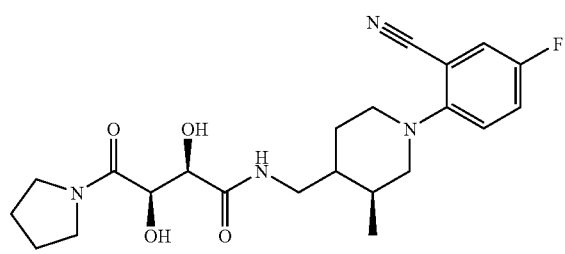 | B |

-continued
2151 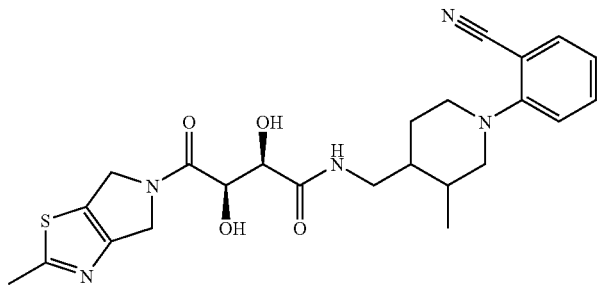 A
2152 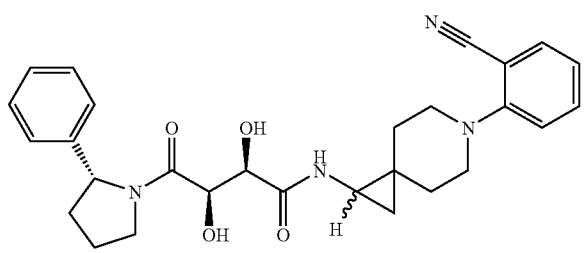 D
2153 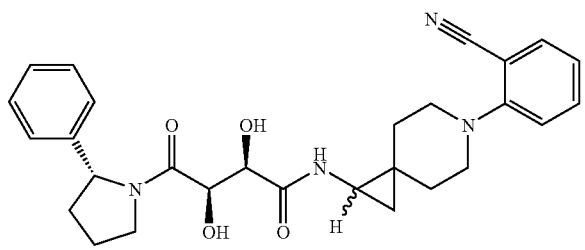 D
2154 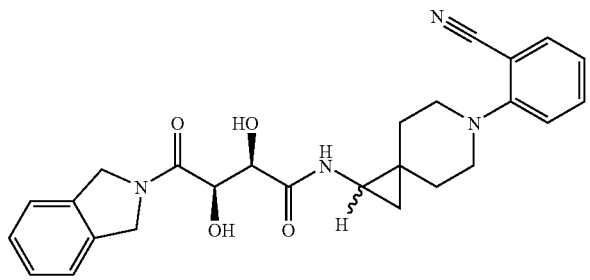 D
2155 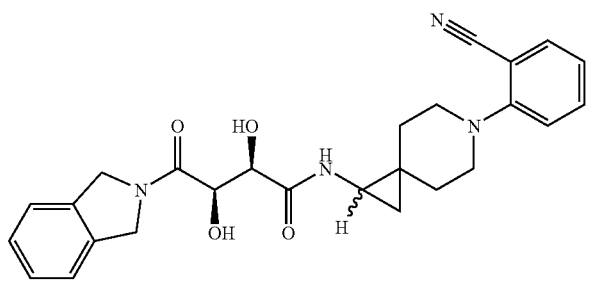 D

| | | |
|---|---|---|
| 2156 | 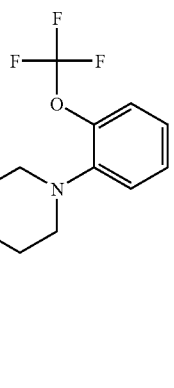 | B |
| 2157 | 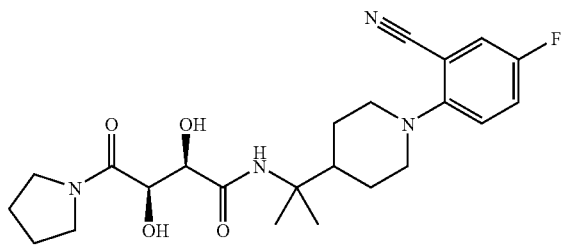 | B |
| 2158 | 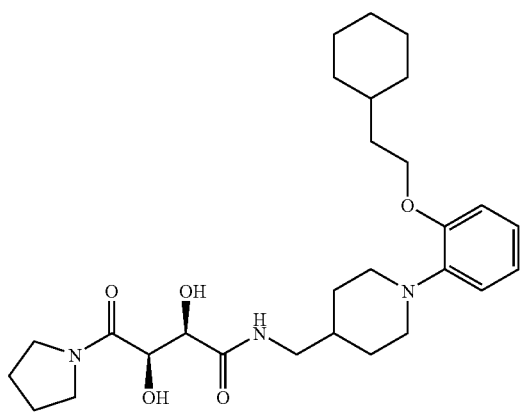 | B |
| 2159 | 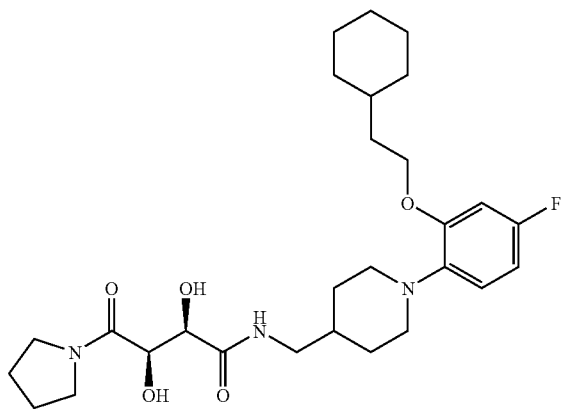 | B |

-continued
| | | |
|---|---|---|
| 2233 | 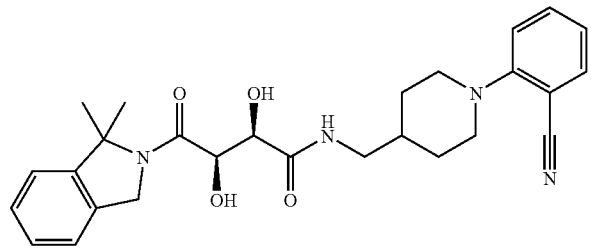 | A |
| 2234 | 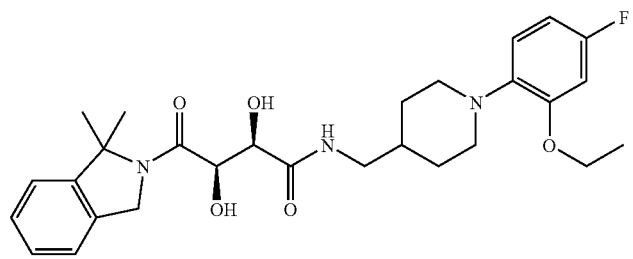 | C |
| 2235 | 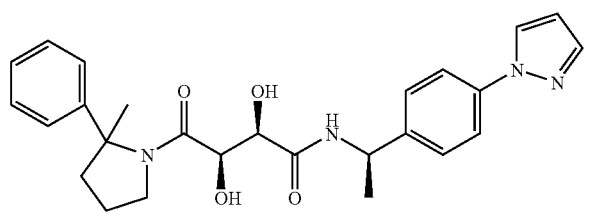 | A |
| 2236 | 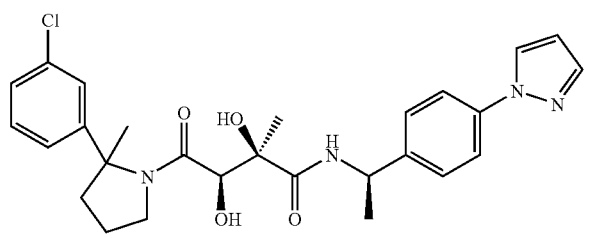 | D |
| 2237 | 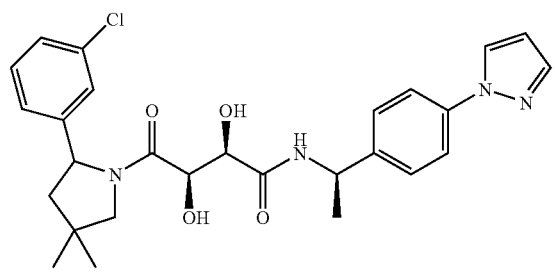 | C |
| 2238 | 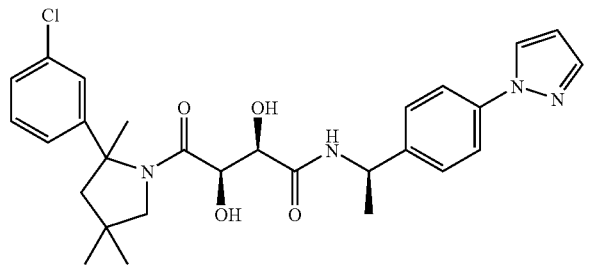 | B |

| | | |
|---|---|---|
| 2239 | 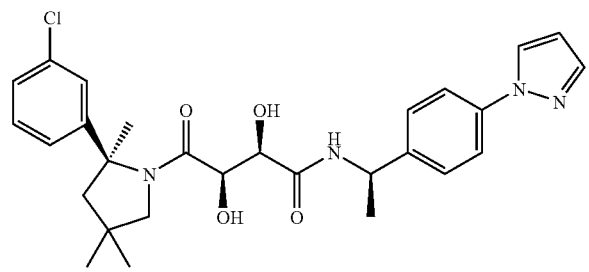 | D |
| 2240 | 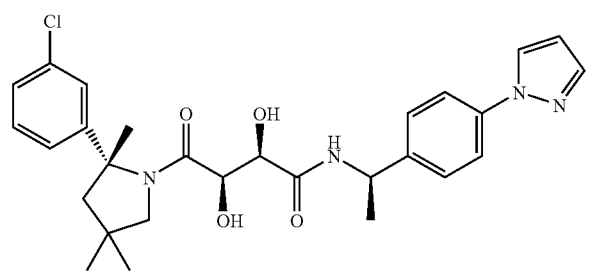 | B |
| 2241 | 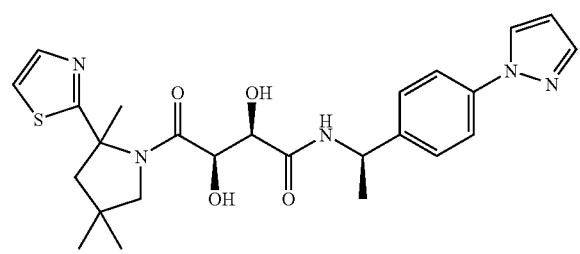 | C |
| 2242 | 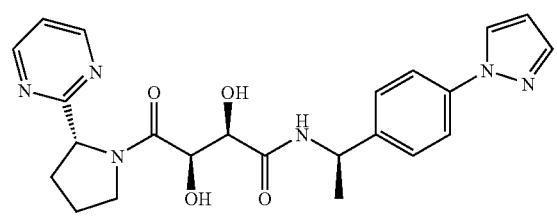 | A |
| 2243 | 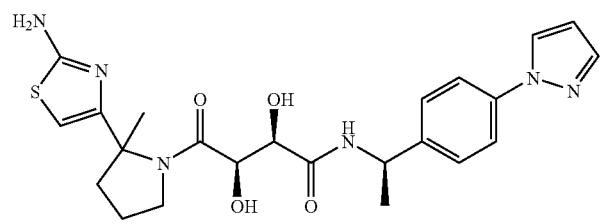 | A |
| 2244 | 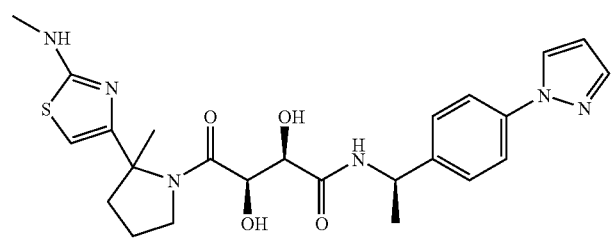 | A |

| | | -continued | |
|---|---|---|---|
| 2245 | 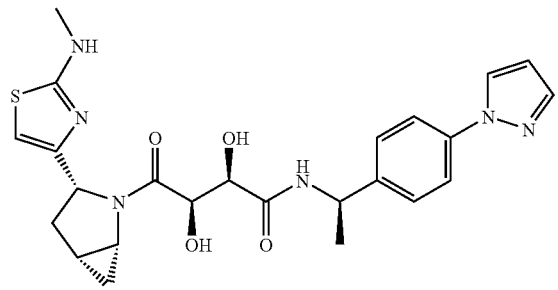 | | A |
| 2246 | 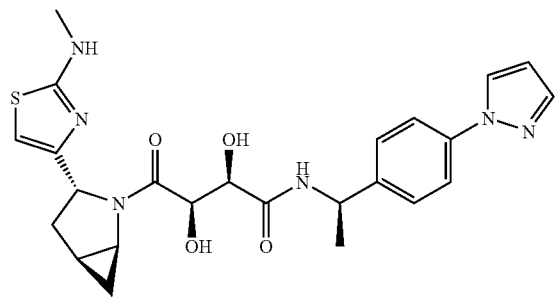 | | B |
| 2247 | 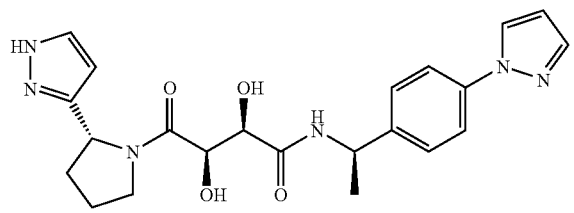 | | A |
| 2248 | 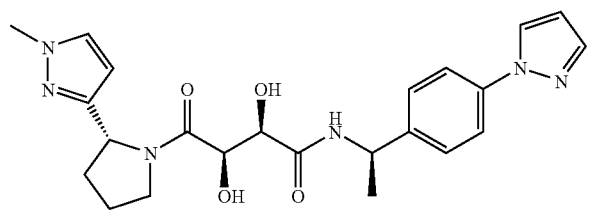 | | A |
| 2249 | 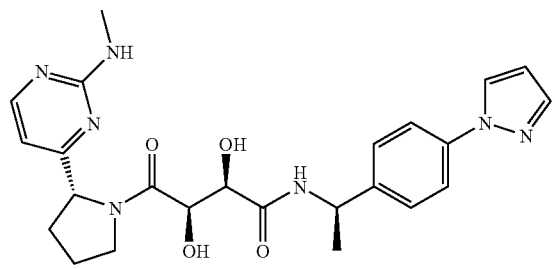 | | A |
| 2250 | 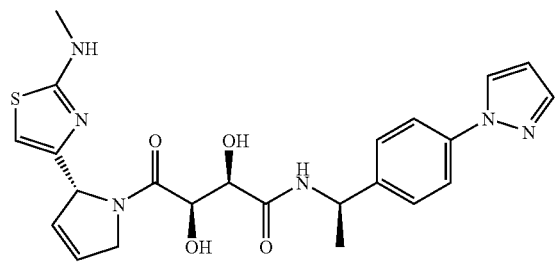 | | A |

| | | |
|---|---|---|
| 2251 | 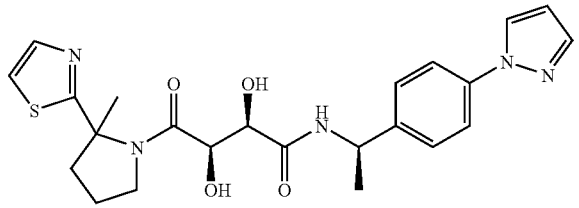 | A |
| 2252 | 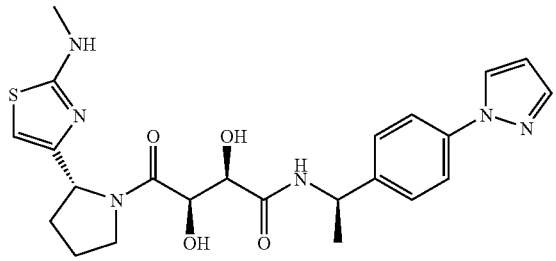 | A |
| 2253 | 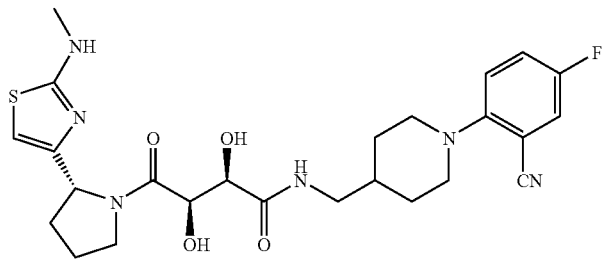 | A |
| 2254 | 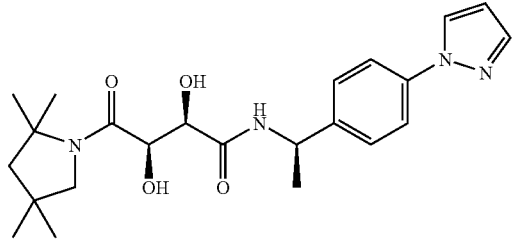 | C |
| 2255 | 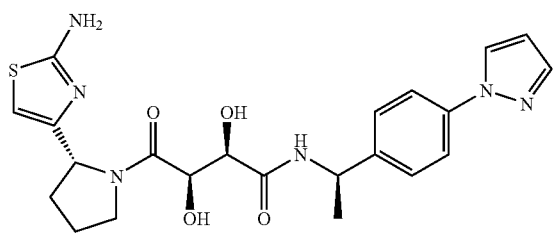 | A |
| 2256 | 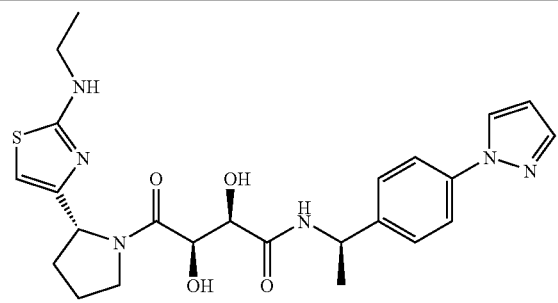 | A |

-continued
| | | |
|---|---|---|
| 2257 | 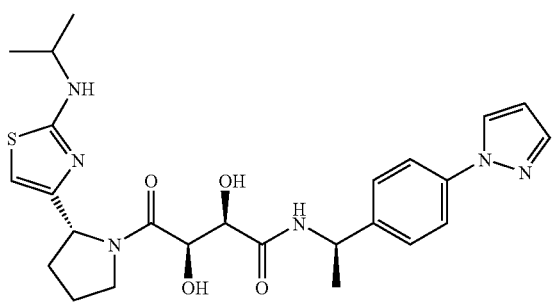 | A |
| 2258 | 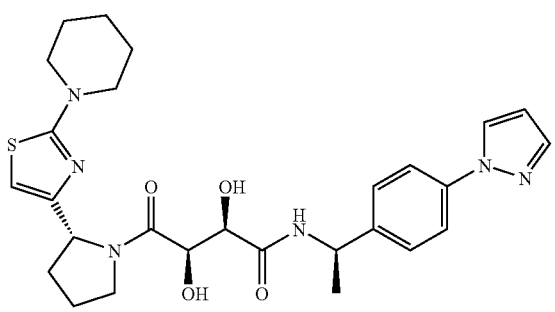 | B |
| 2259 | 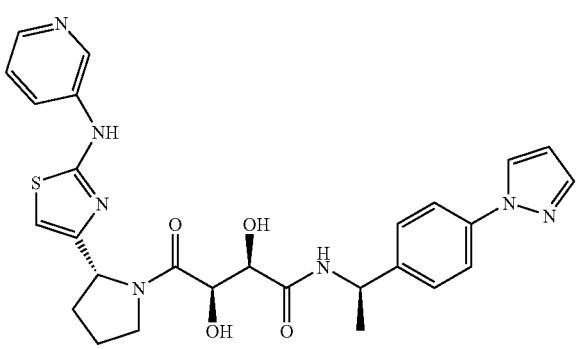 | A |
| 2260 | 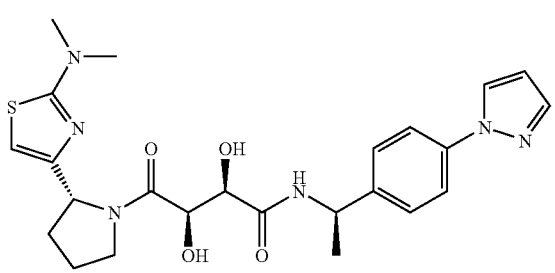 | B |
| 2261 | 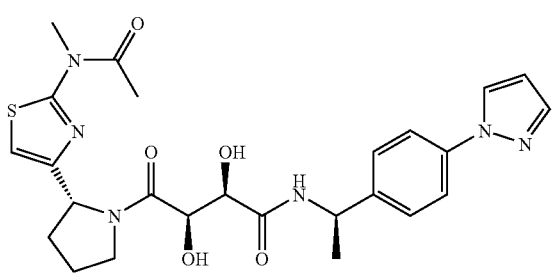 | A |

-continued
| | | |
|---|---|---|
| 2262 | 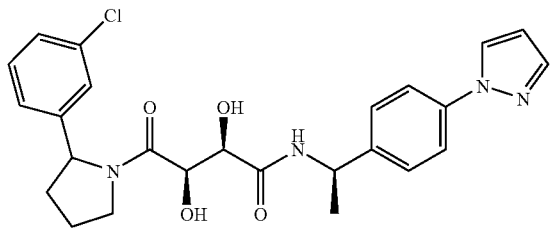 | A |
| 2263 | 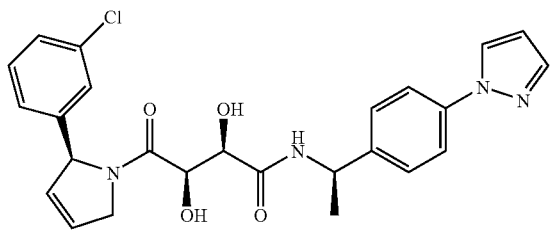 | C |
| 2264 | 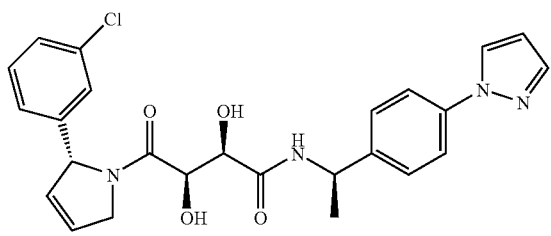 | A |
| 2265 | 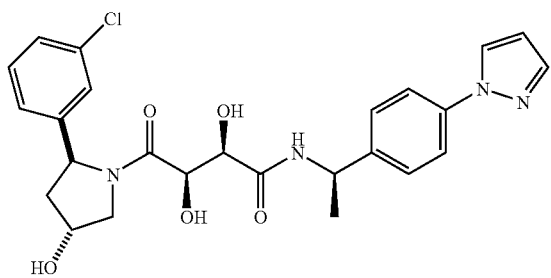 | A |
| 2266 | 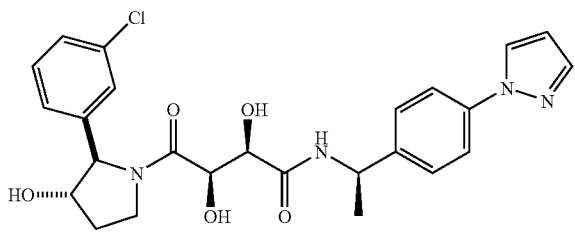 | A |
| 2267 | 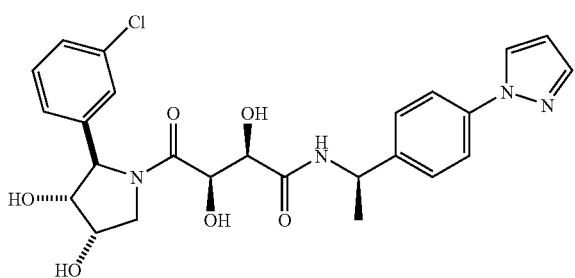 | C |

-continued
| | | |
|---|---|---|
| 2268 | 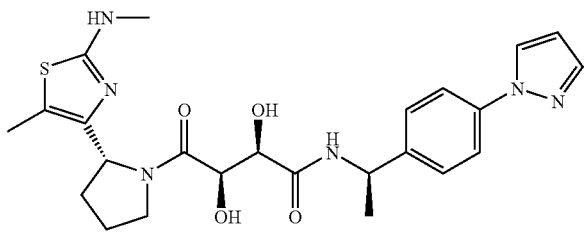 | A |
| 2269 | 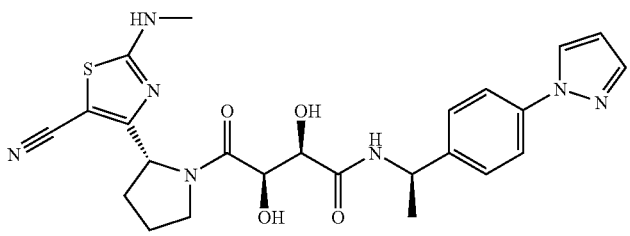 | A |
| 2270 | 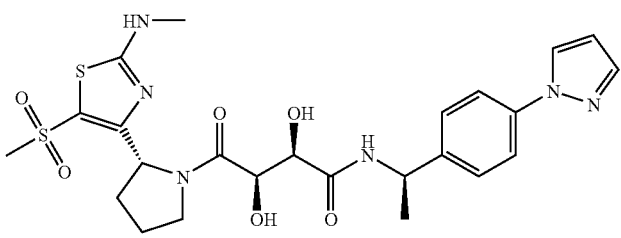 | A |
| 2271 | 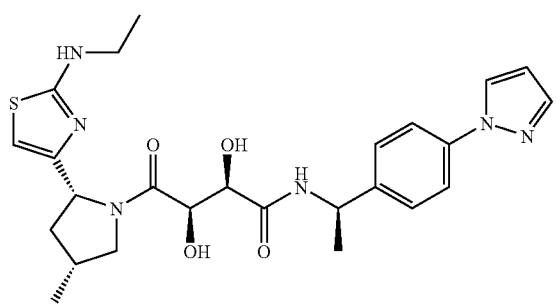 | A |
| 2333 | 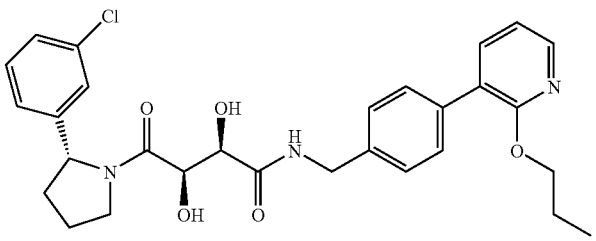 | A |
| 2334 | 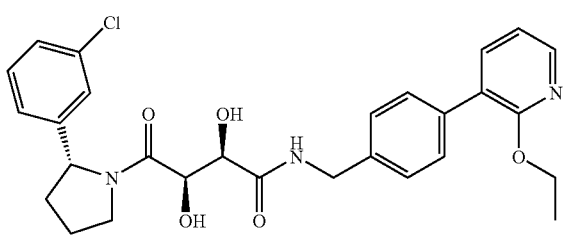 | A |

-continued
| | | |
|---|---|---|
| 2335 | 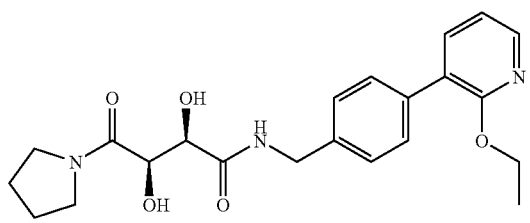 | C |
| 2336 | 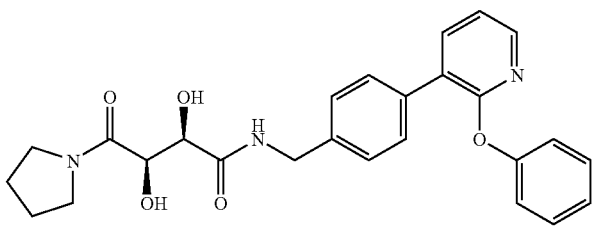 | C |
| 2337 | 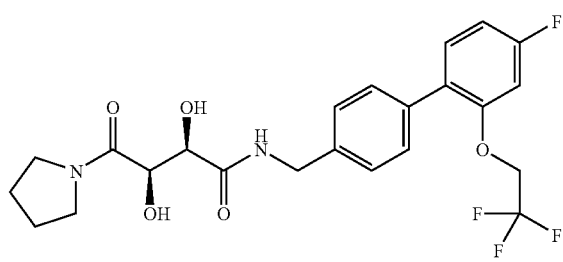 | B |
| 2338 | 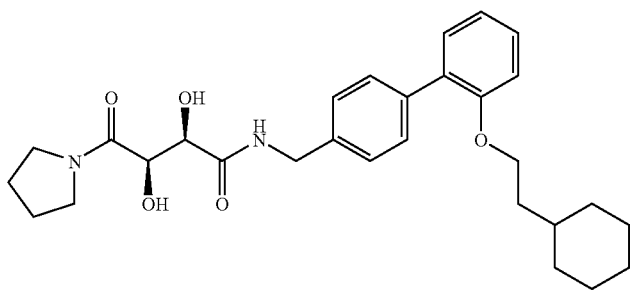 | A |
| 2339 | 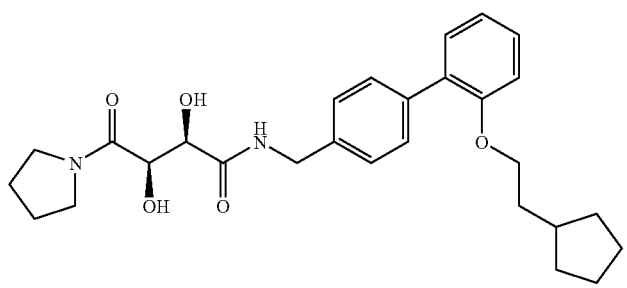 | B |
| 2340 | 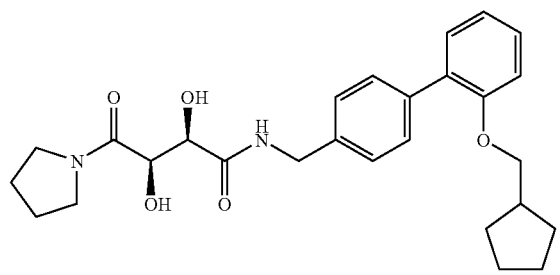 | B |

-continued
| | | |
|---|---|---|
| 2341 | 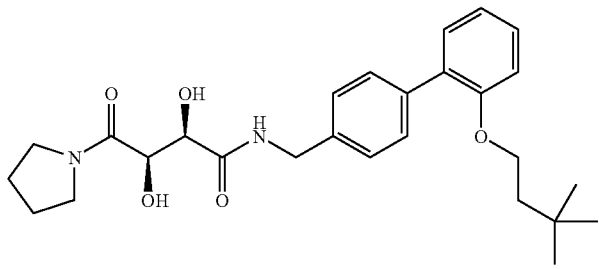 | C |
| 2342 | 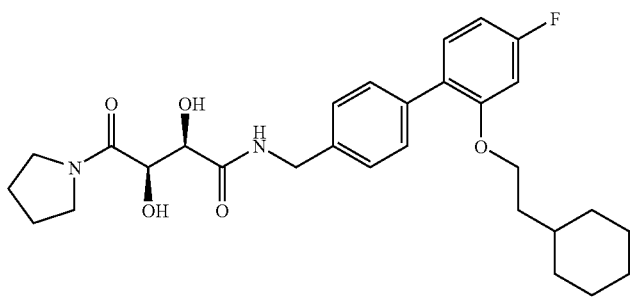 | C |
| 2343 | 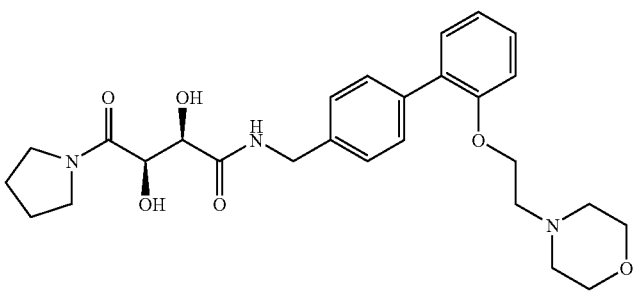 | D |
| 2344 | 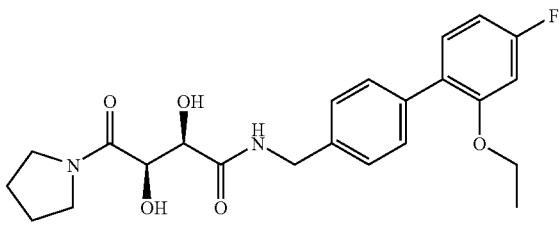 | D |
| 2345 | 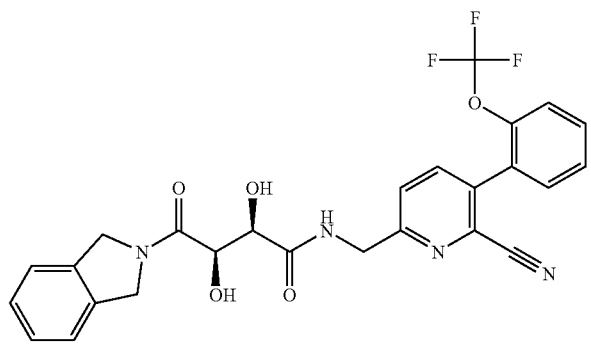 | D |

-continued
| | | |
|---|---|---|
| 2346 | 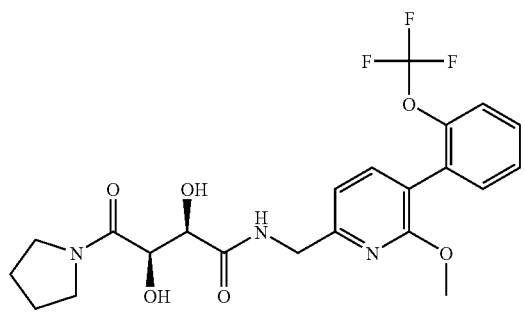 | D |
| 2347 | 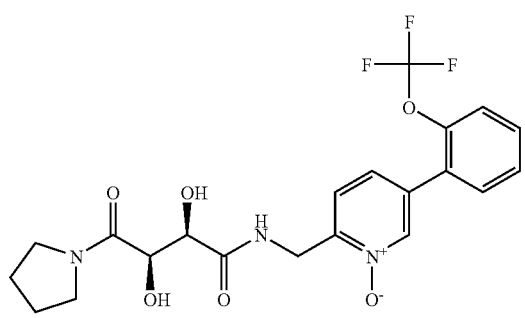 | D |
| 2348 | 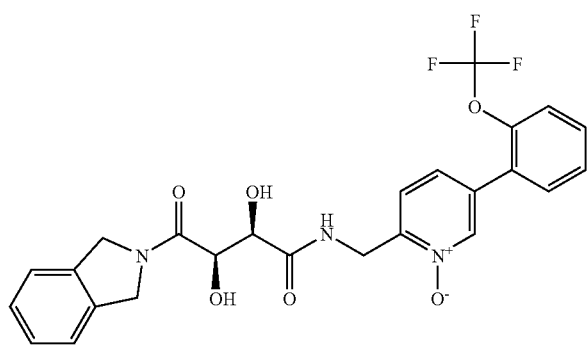 | C |
| 2349 | 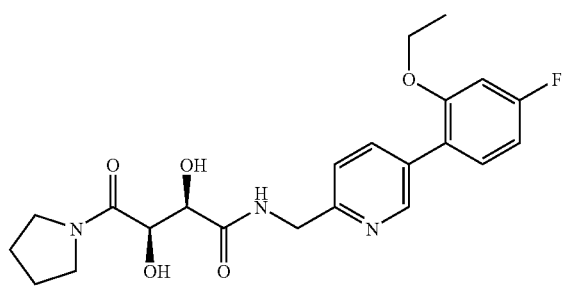 | A |
| 2350 | 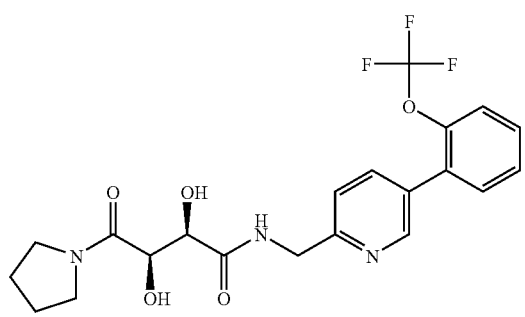 | A |

-continued
2351 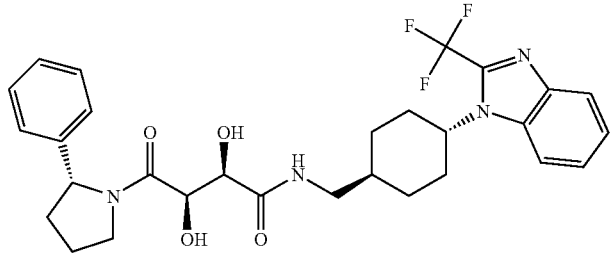 A
2352 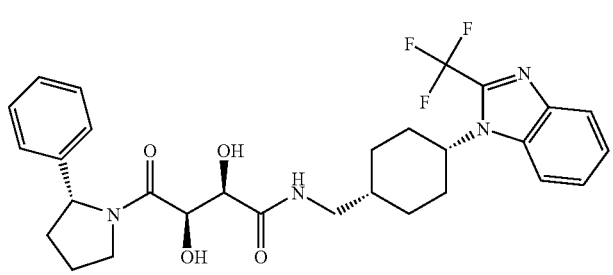 A
2306 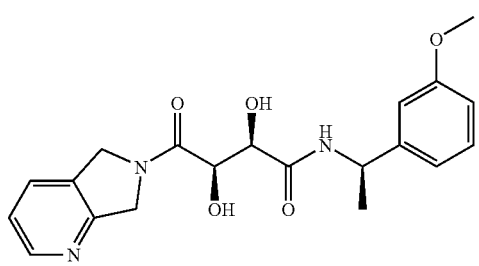 D
2307 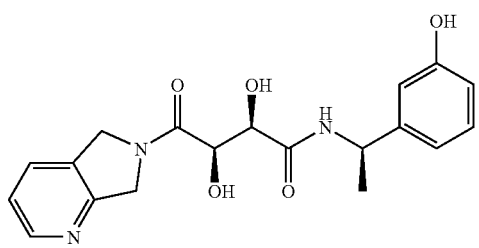 D
2308 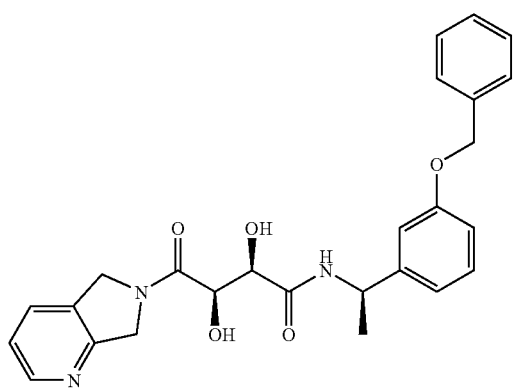 D -continued
2353A 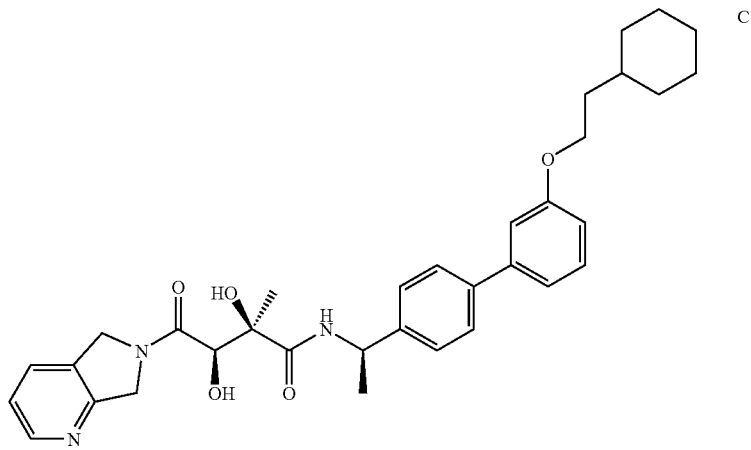 C
2353B 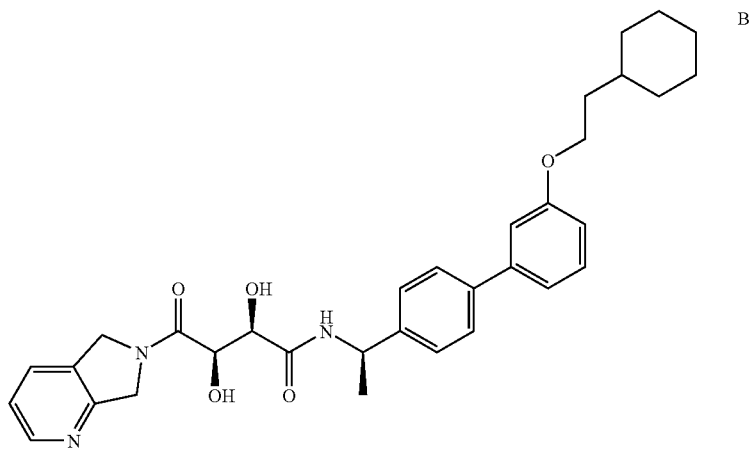 B
2354 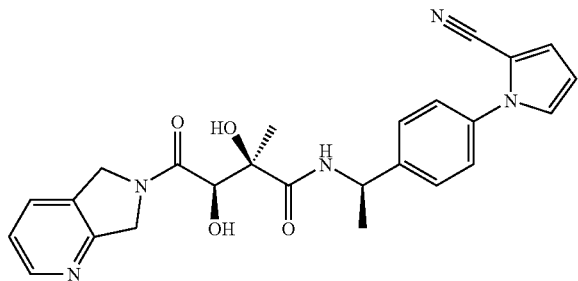 B
2355 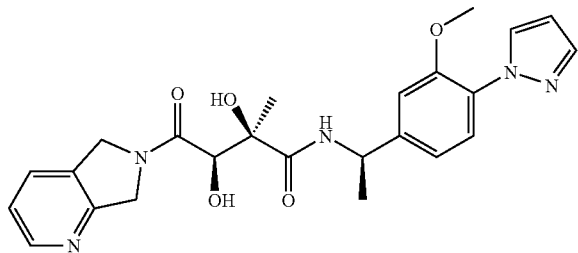 A -continued
| | | |
|---|---|---|
| 2356 | 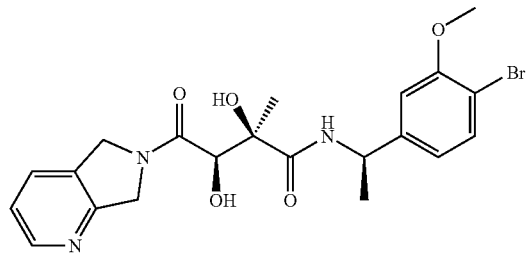 | D |
| 2357 | 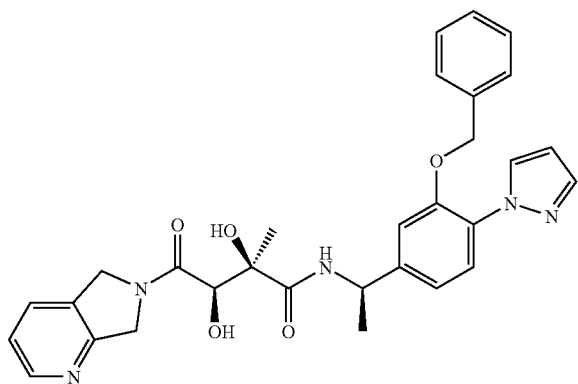 | A |
| 2358 | 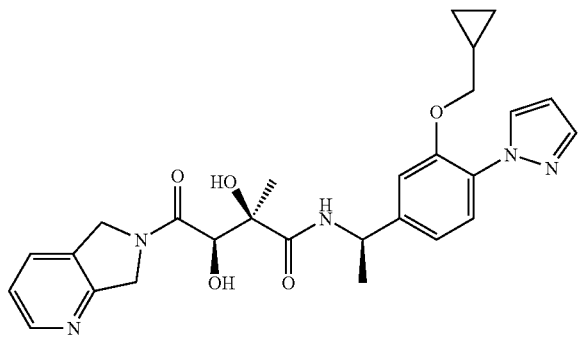 | C |
| 2304 | 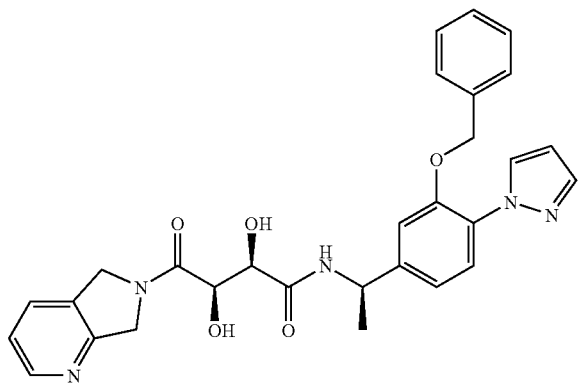 | A |

-continued
| | | |
|---|---|---|
| 2359 | 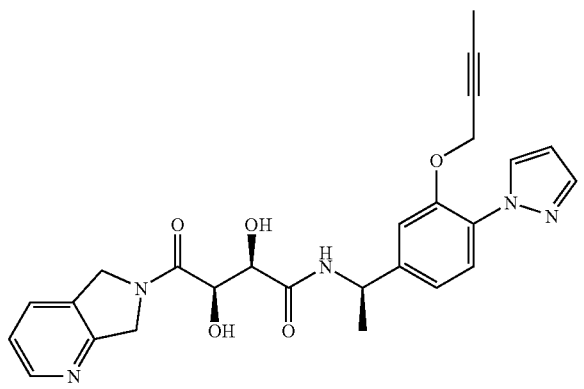 | A |
| 2360 | 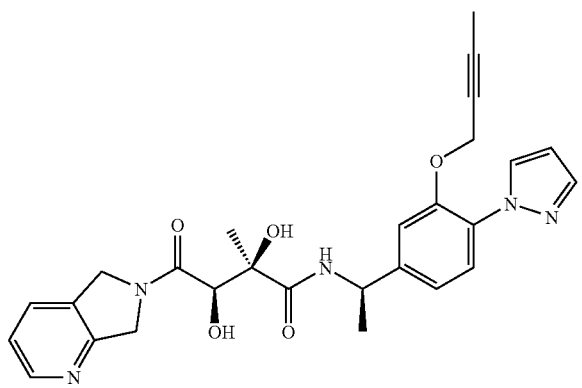 | A |
| 2305 | 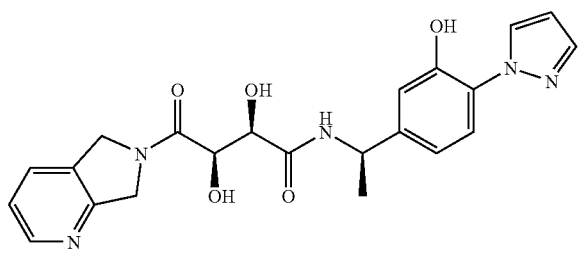 | A |
| 2365 | 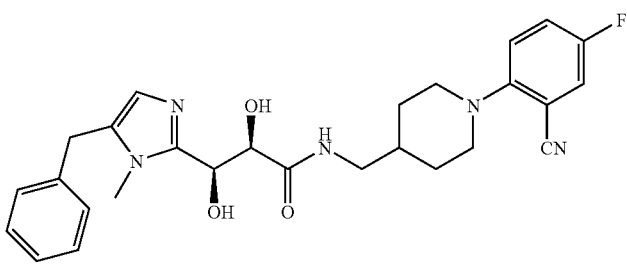 | C |
| 2369 | 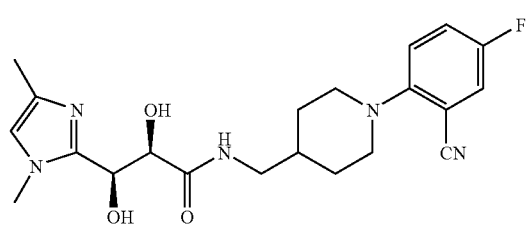 | |

-continued
| | | |
|---|---|---|
| 2372 | 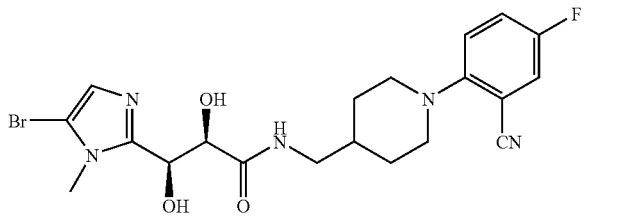 | D |
| 2376 | 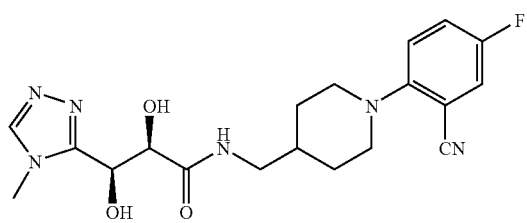 | D |
| 2382 |  | D |
| 2387 | 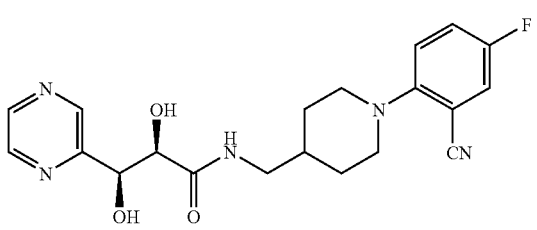 | D |
| 2391 | 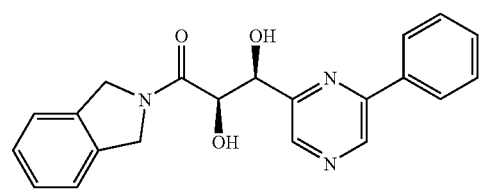 | D |
| 2393 | 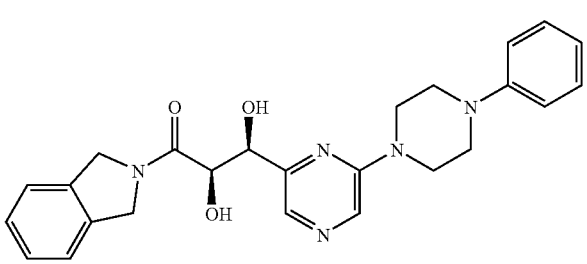 | D |
| 2394 | 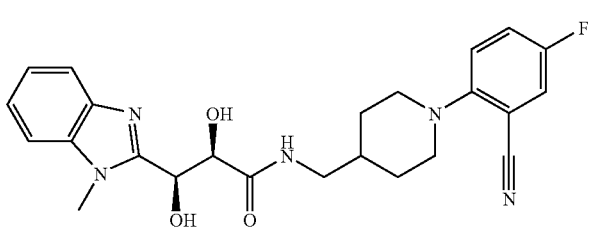 | D |

-continued
| | | |
|---|---|---|
| 2395 | 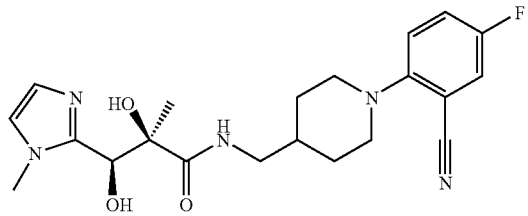 | C |
| 2396 | 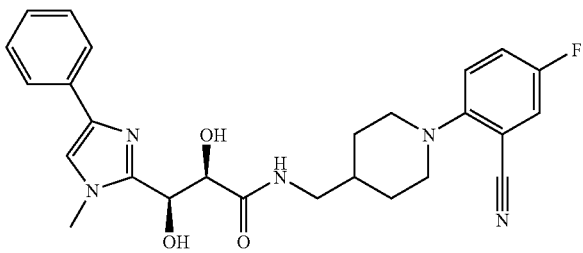 | D |
| 2397 | 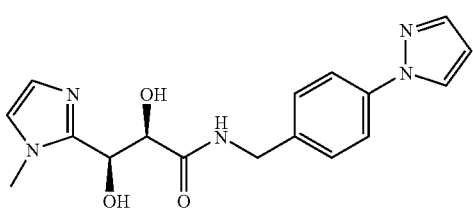 | D |
| 2398 | 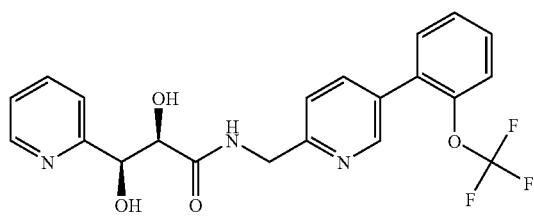 | D |
| 2399 | 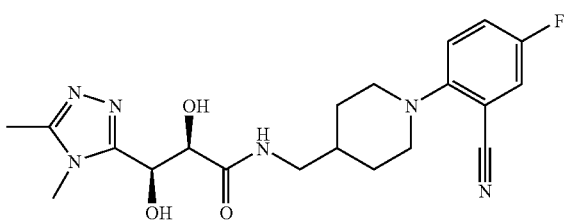 | D |
| 2400 | 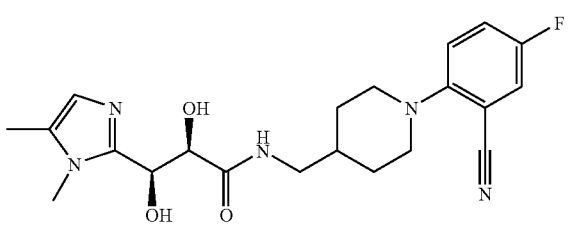 | C |
| 2401 | 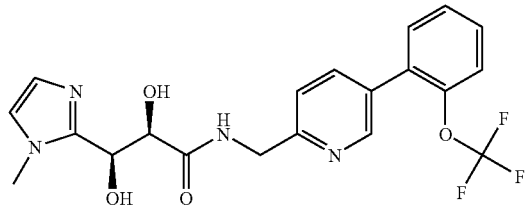 | C |

-continued
| | | |
|---|---|---|
| 2402 | 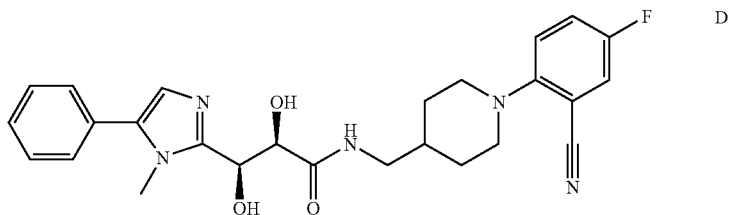 | D |
| 2403 | 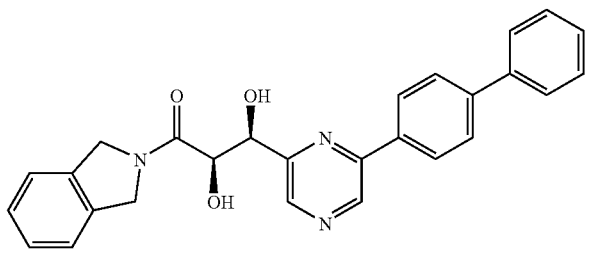 | D |
| 2408 | 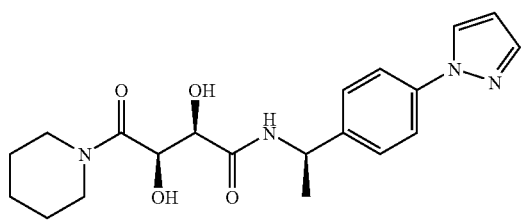 | B |
| 2409 | 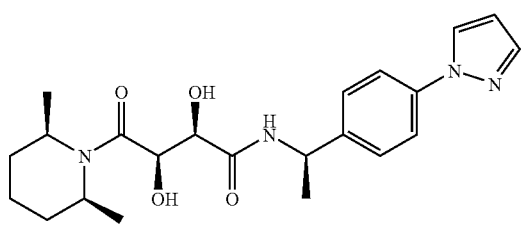 | C |
| 2410 |  | A |
| 2411 | 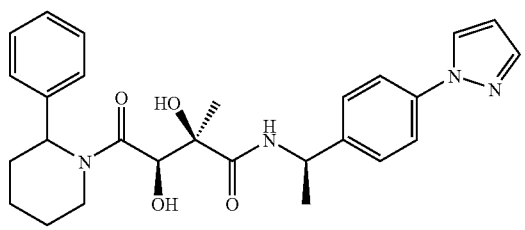 | D |
| 2412 |  | C |

-continued
| | | |
|---|---|---|
| 2413 | 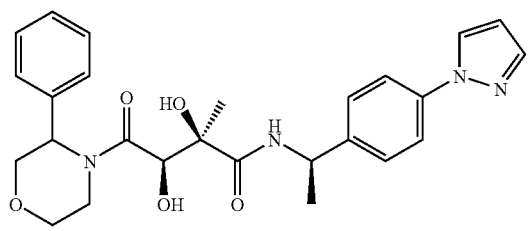 | A |
| 2414 | 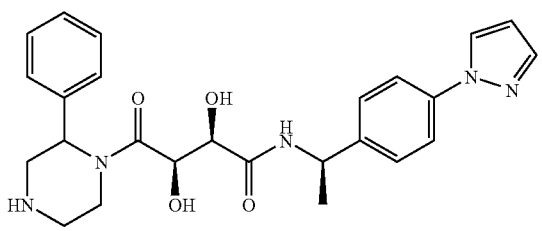 | B |
| 2415 | 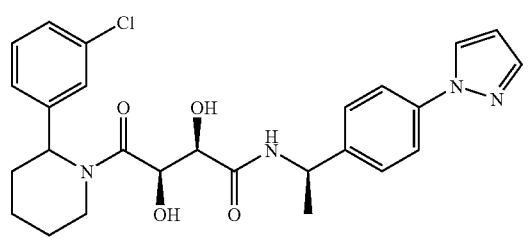 | B |
| 2416 | 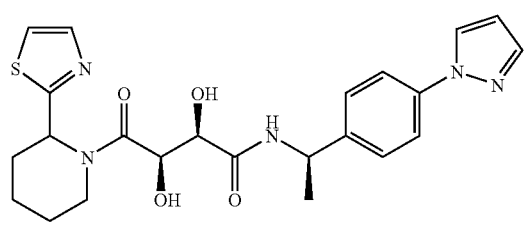 | B |
| 2417 | 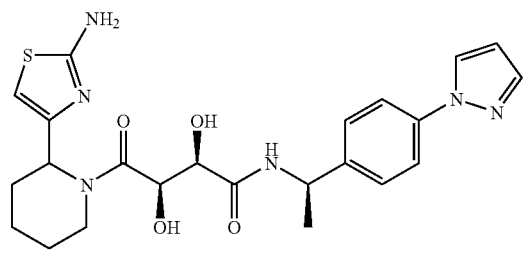 | B |
| 2418 | 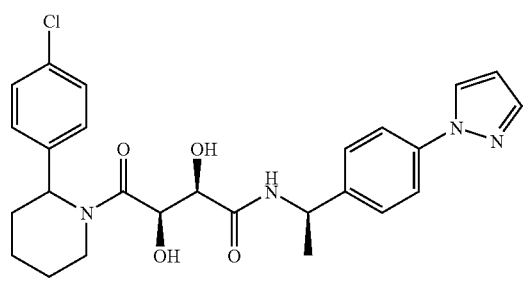 | B |

-continued
| | | |
|---|---|---|
| 2419 | 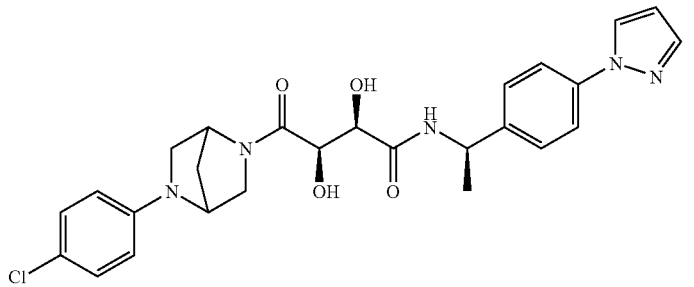 | C |
| 2420 | 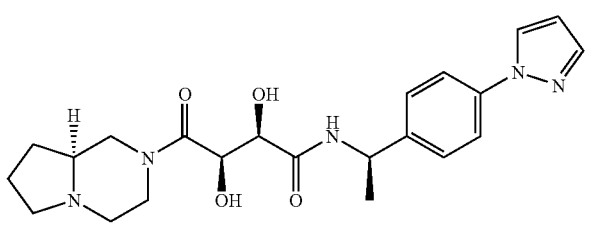 | C |
| 2421 | 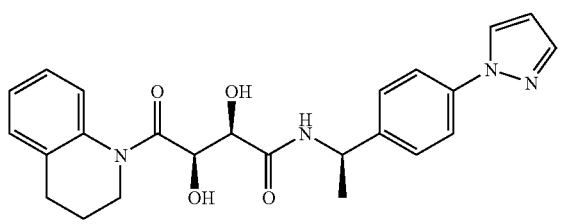 | C |
| 2422 | 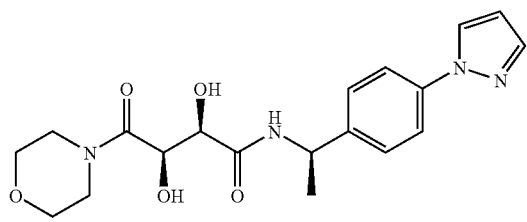 | B |
| 2423 | 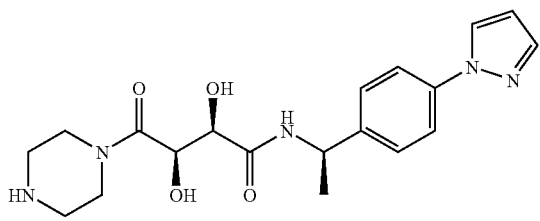 | C |
| 2424 | 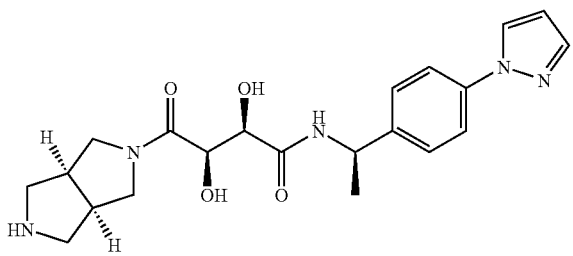 | C |

-continued
| 2425 | 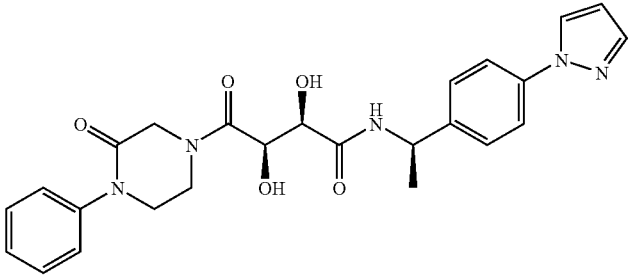 | C |
| 2438 | 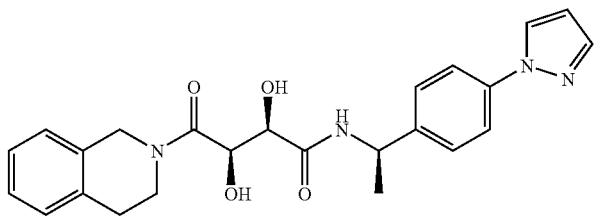 | A |
| 2439 | 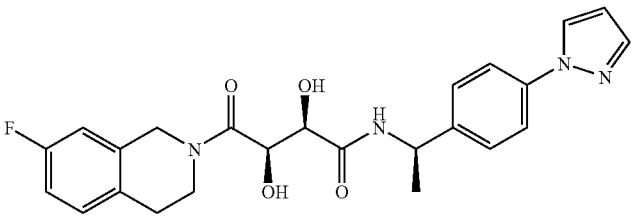 | A |
| 2440 | 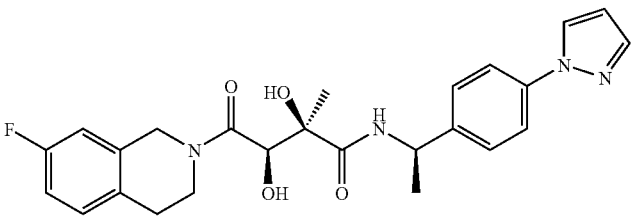 | B |
| 2441 | 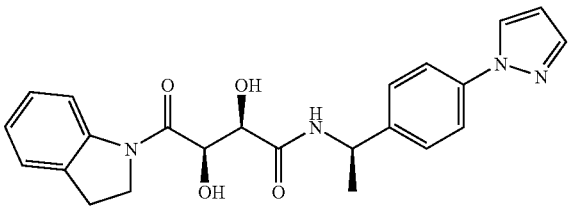 | B |
| 2442 | 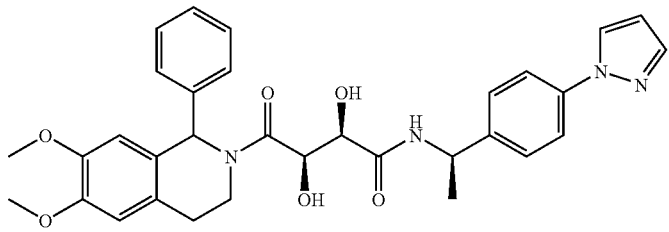 | A |

-continued
| | | |
|---|---|---|
| 2443 | 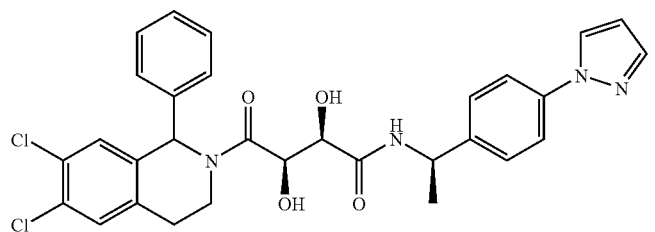 | A |
| 2444 | 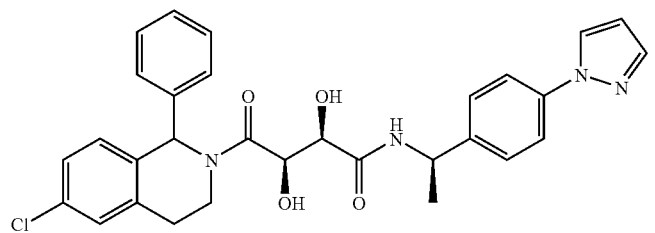 | A |
| 2445 | 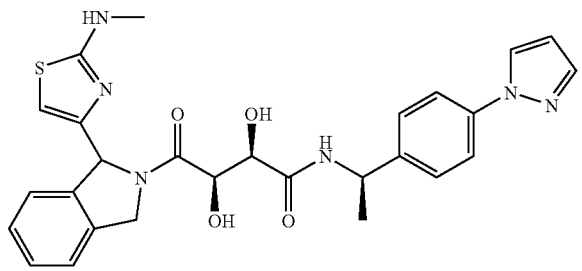 | A |
| 2446 | 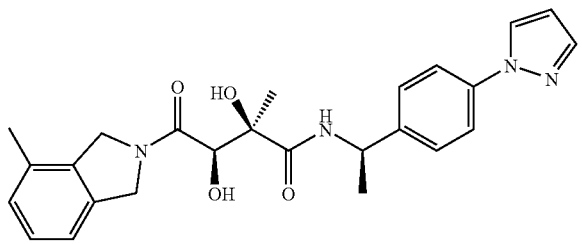 | B |
| 2456 | 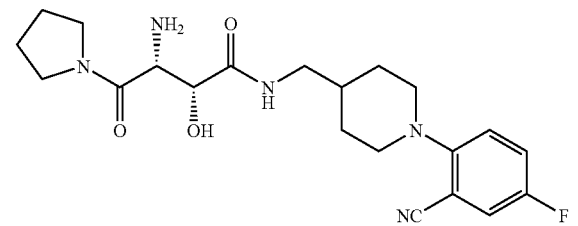 | D |
| 2460 | 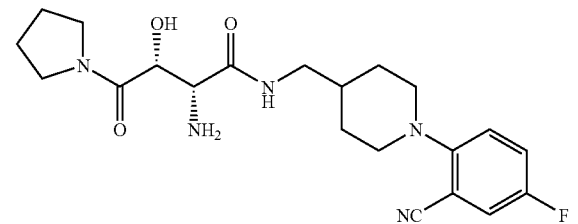 | D |

-continued
| | | |
|---|---|---|
| 2474 | 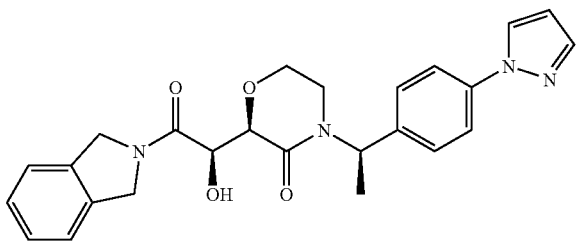 | D |
| 2475 | 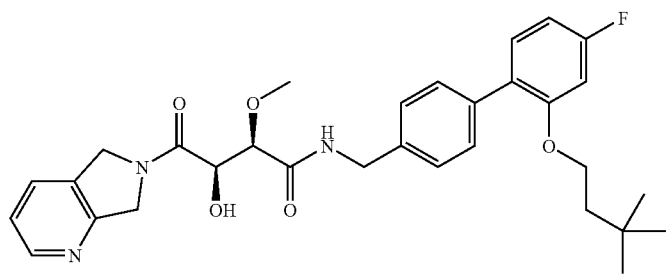 | B |
| 2476 | 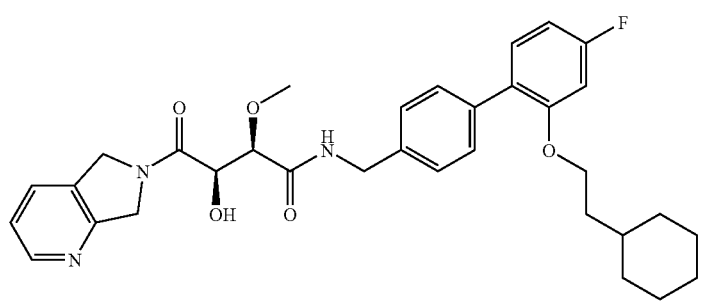 | B |
| 2477 | 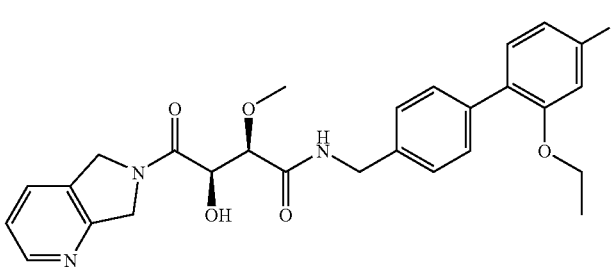 | C |
| 2478 | 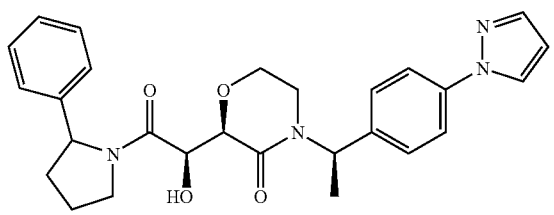 | D |
| 2480 | 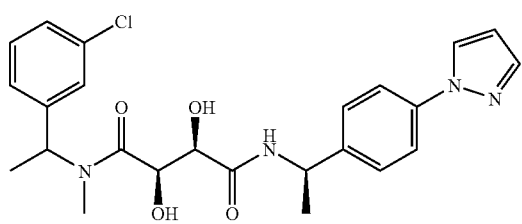 | B |

-continued
| | | |
|---|---|---|
| 2481 | 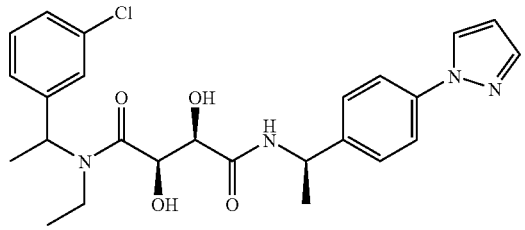 | C |
| 2482 | 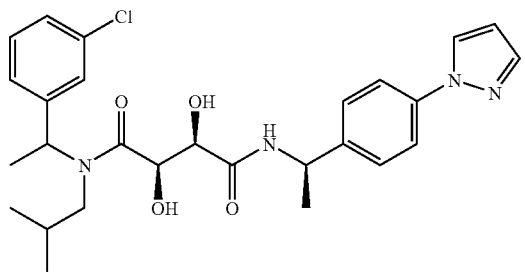 | D |
| 2483 | 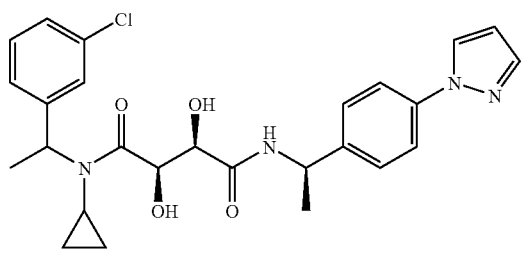 | D |
| 2485 | 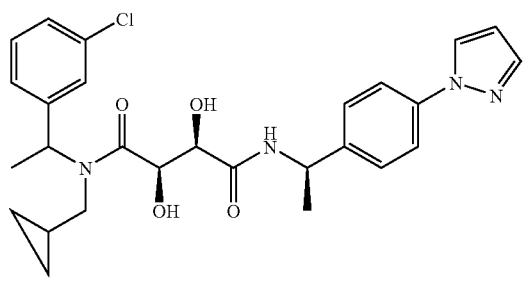 | D |
| 2486 | 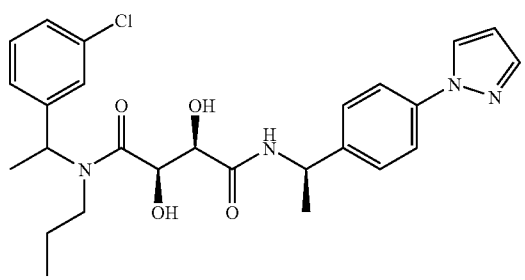 | D |
| 2487 | 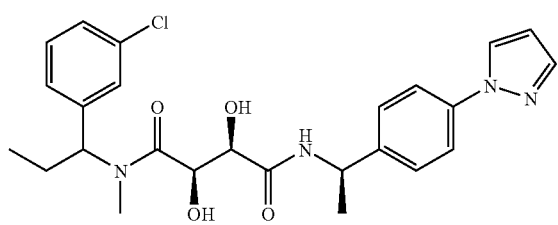 | B |

-continued
| | | |
|---|---|---|
| 2489 | 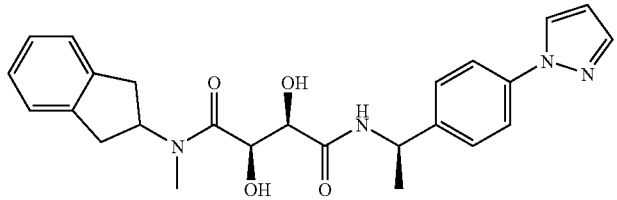 | B |
| 2494 | 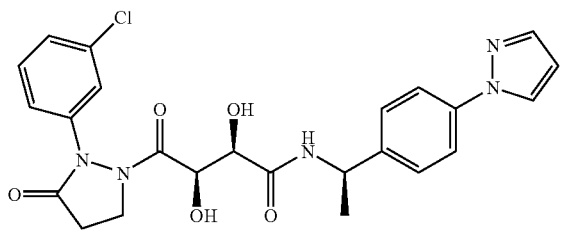 | C |
| 2495 | 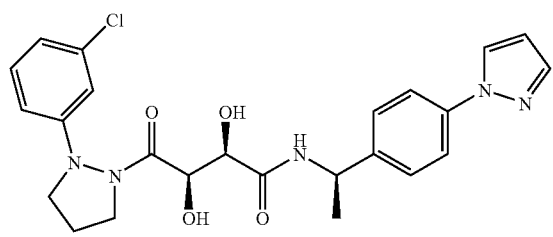 | C |
| 2496 | 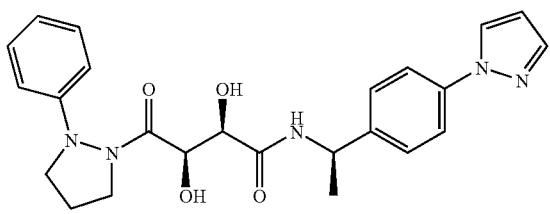 | C |
| 2506 | 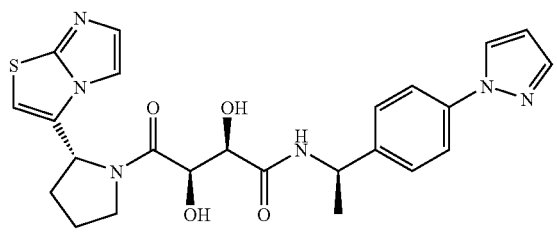 | A |
| 2507 | 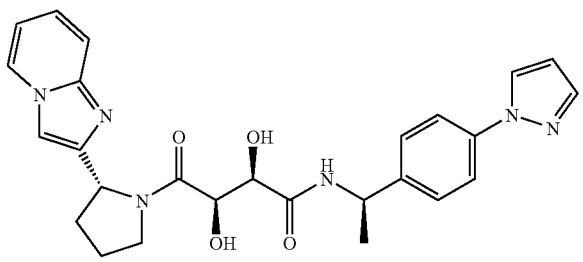 | A |

-continued
| | | |
|---|---|---|
| 2508 | 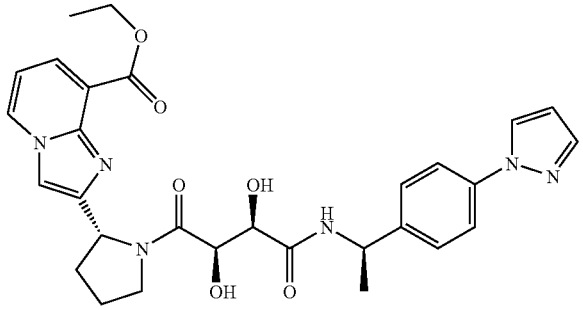 | B |
| 2527 | 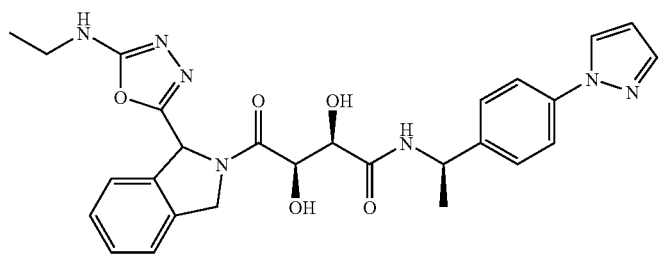 | A |
| 2528 | 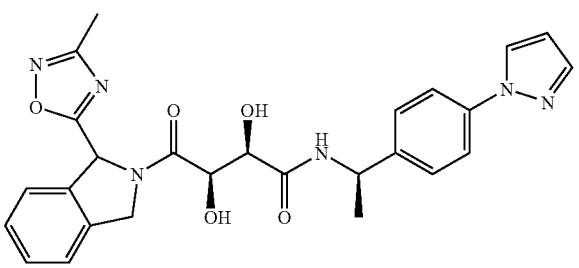 | A |
| 2567 | 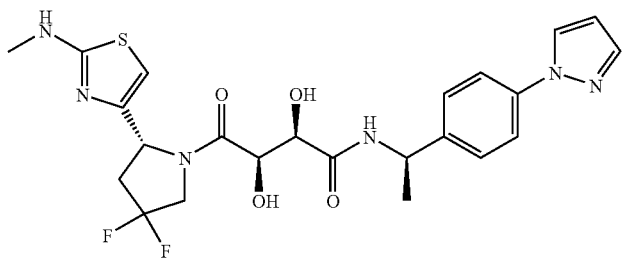 | A |
| 2568 | 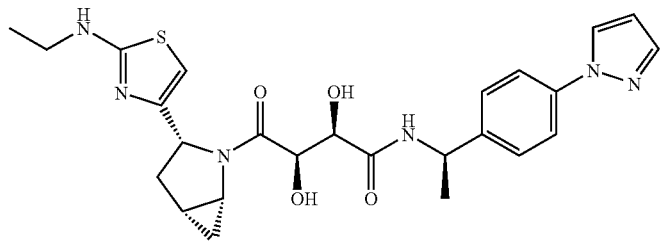 | — |
| 2569 | 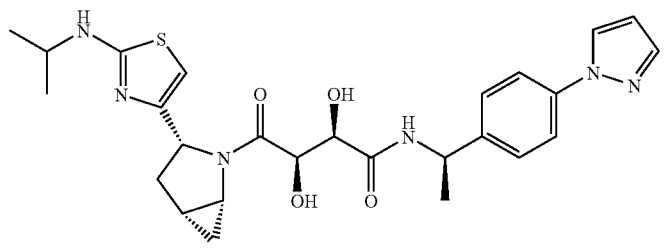 | — |

-continued
| | | |
|---|---|---|
| 2570 | 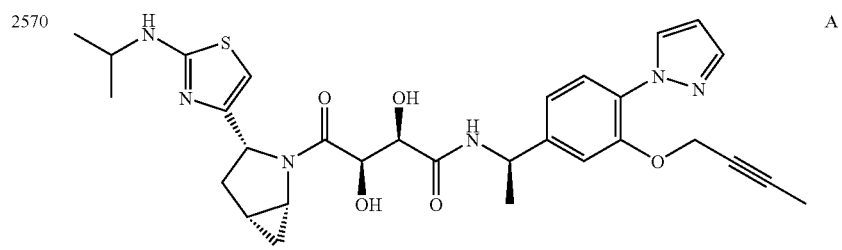 | A |
| 2571 | 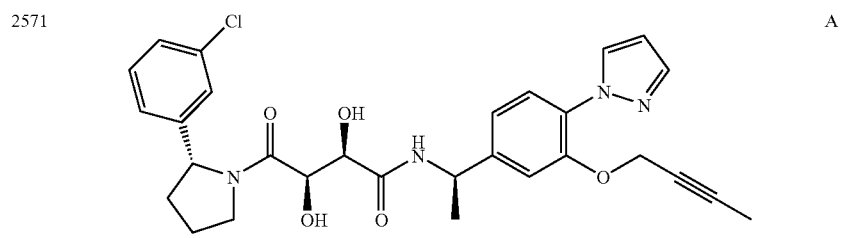 | A |
| 2572 | 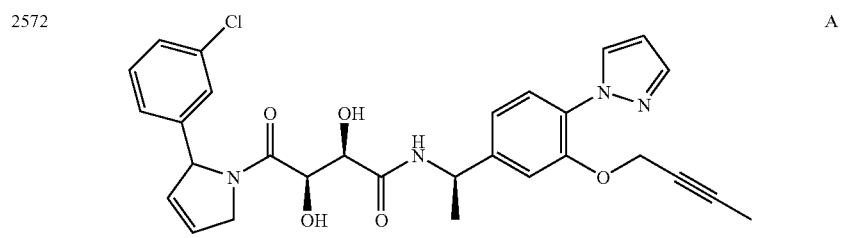 | A |
| 2573 | 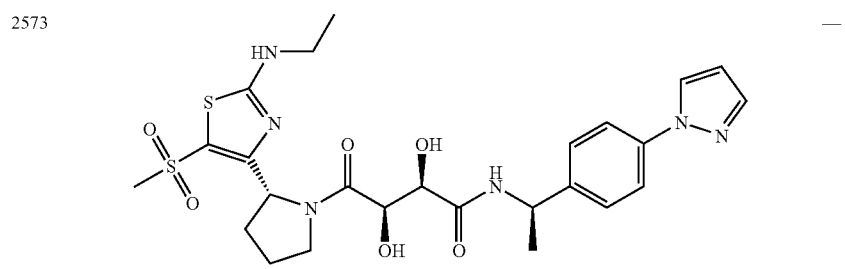 | — |
| 2574 | 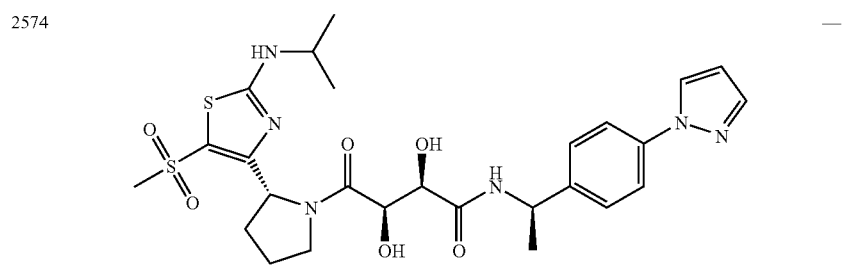 | — |
| 2575 | 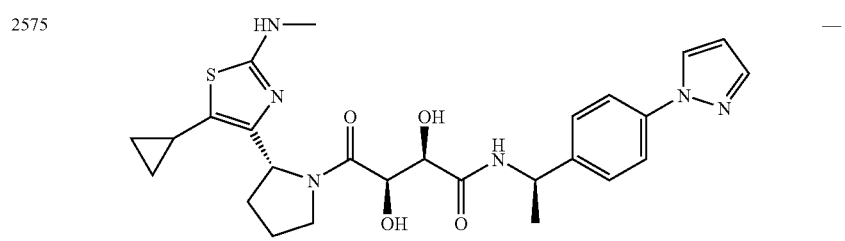 | — |

| | | |
|---|---|---|
| 2576 | 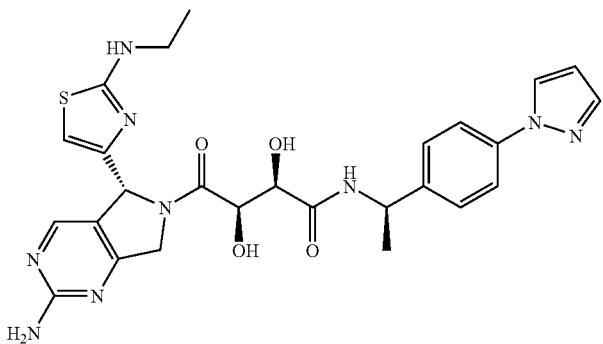 | — |
| 2577 | 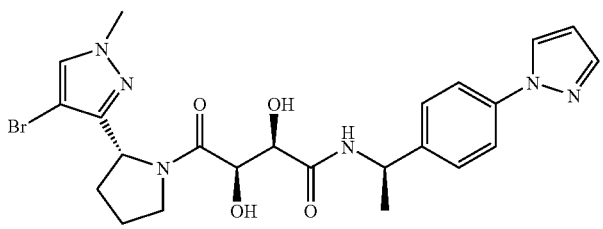 | — |
| 2578 | 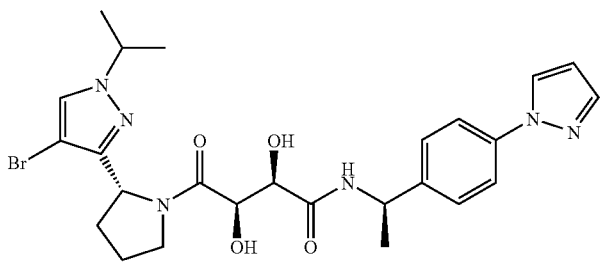 | — |
| 2579 | 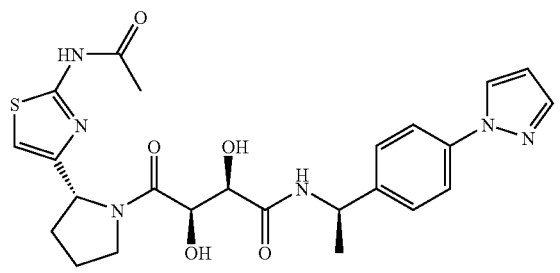 | A |
| 2580 | 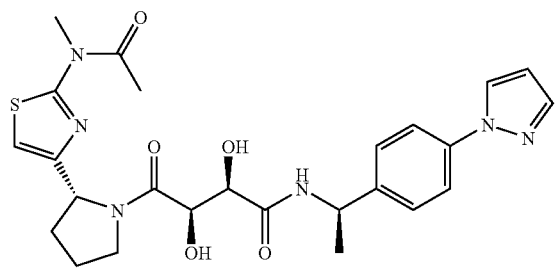 | A |

-continued
| 2581 | 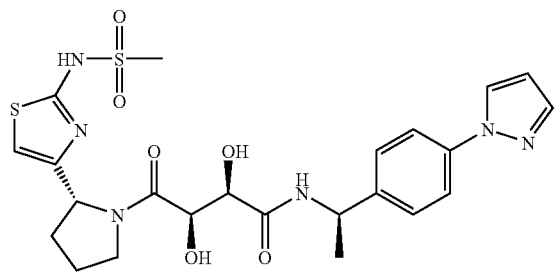 | A |
| 2582 | 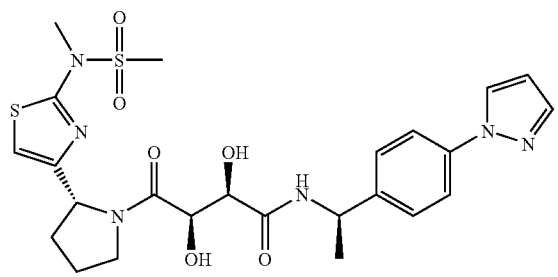 | A |
| 2583 | 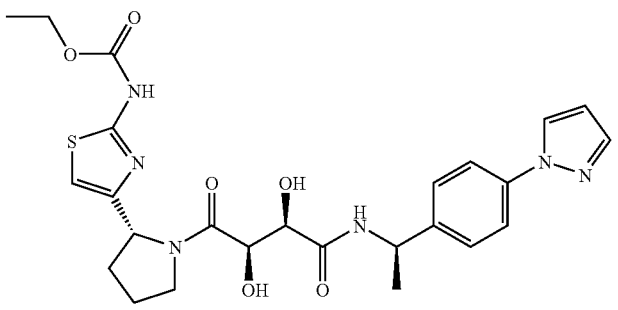 | — |
| 2584 | 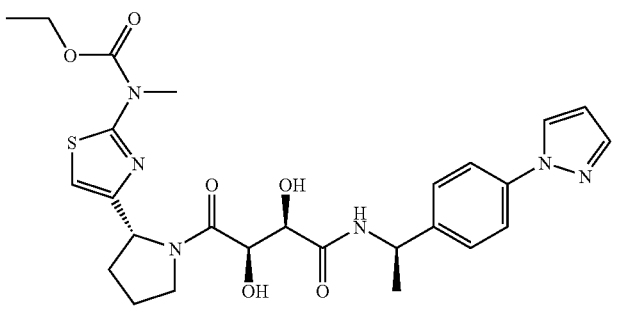 | — |
| 2585 | 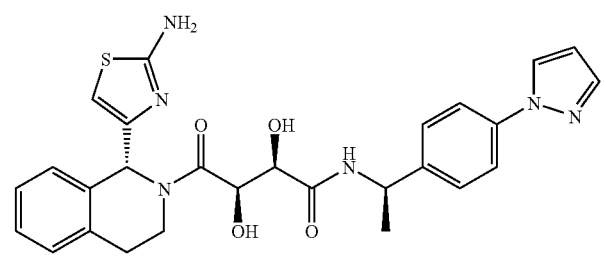 | A |

-continued
2586 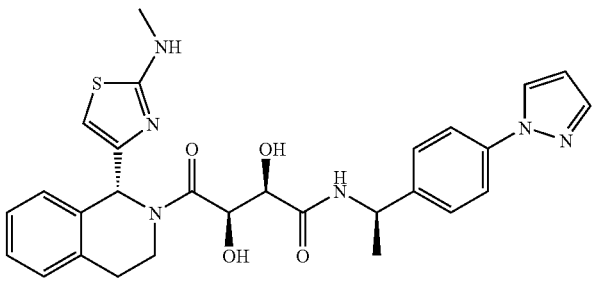 A
2587 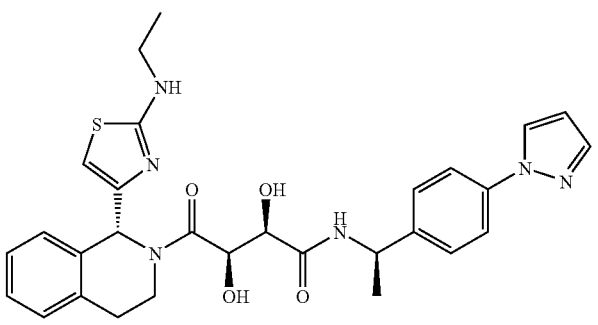 A
2588 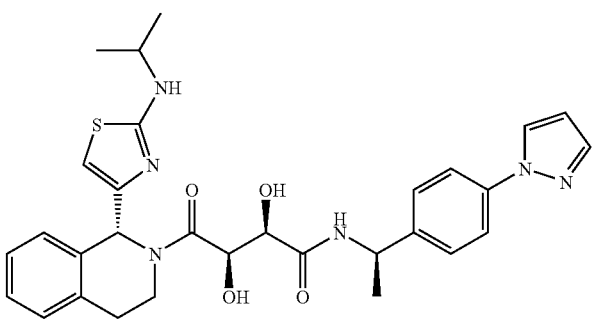 A
2589 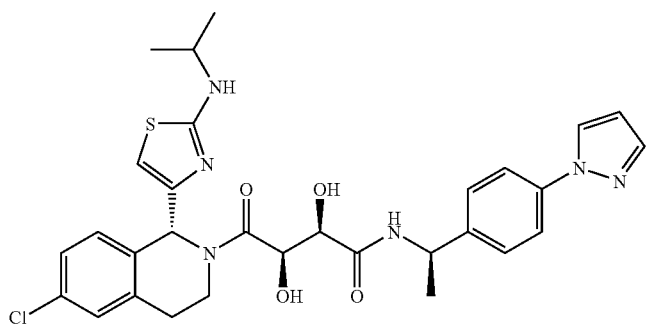 A
2590 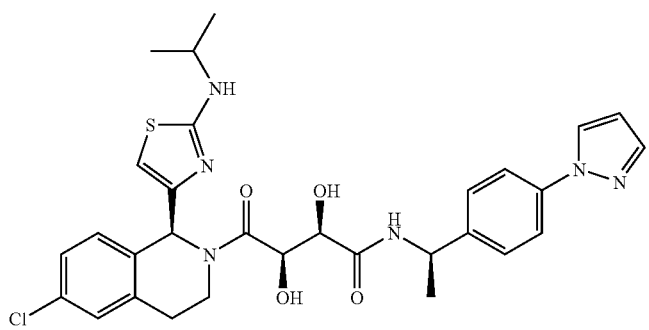 A -continued
| 2591 | 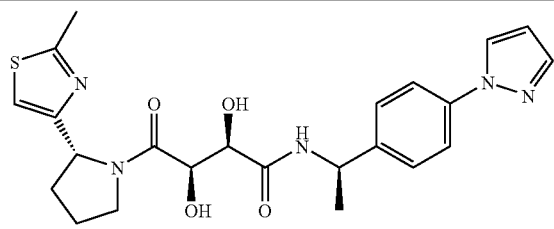 | A |
| 2592 | 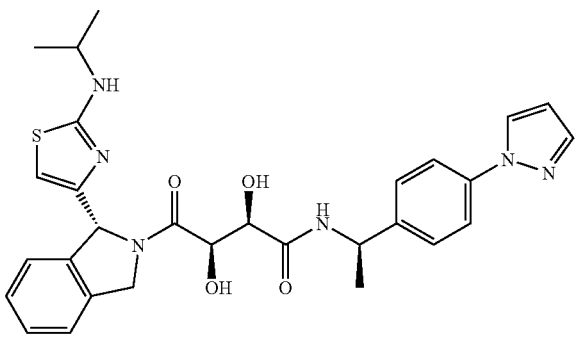 | A |
| 2593 | 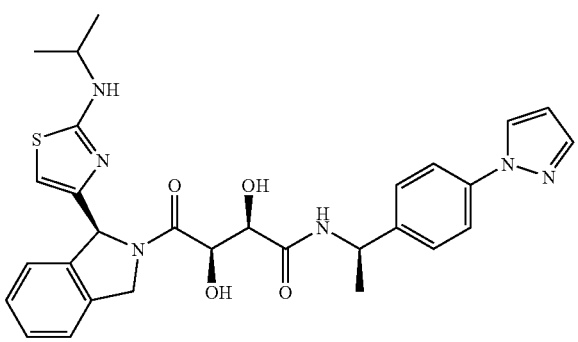 | A |
| 2594 | 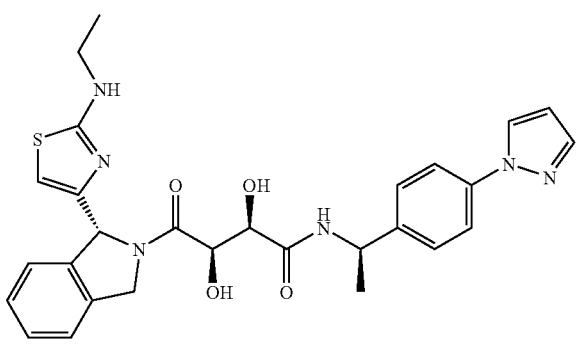 | A |
| 2595 | 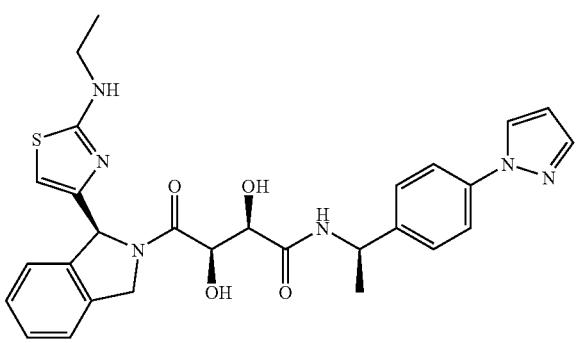 | A |

-continued
| | | |
|---|---|---|
| 2596 | 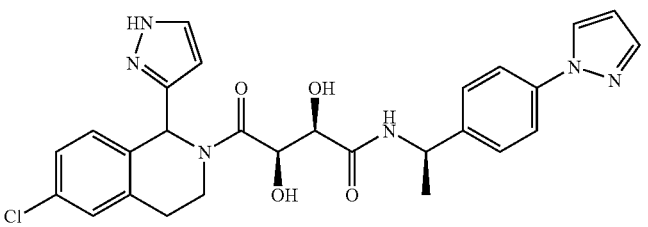 | A |
| 2597 | 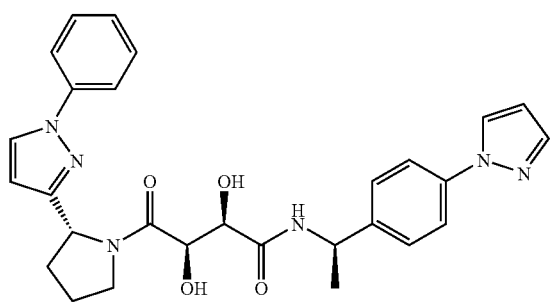 | A |
| 2598 | 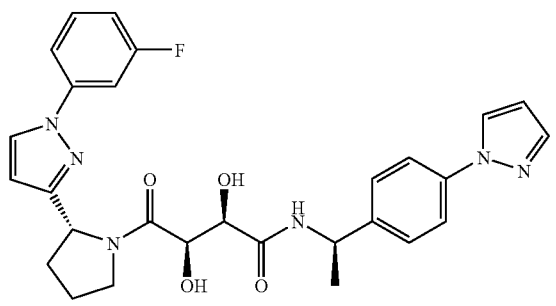 | A |
| 2599 | 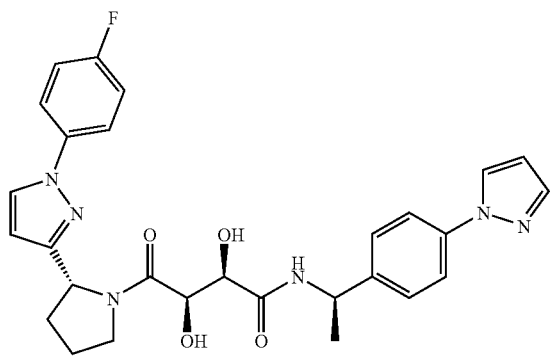 | A |
| 2600 | 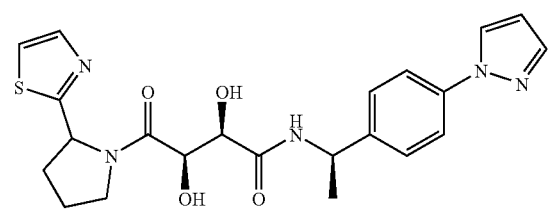 | A |

Representative examples of compounds of the invention with their respective K$_i$ values are listed in the table below:

| Structure | Ki (nM) |
|---|---|
| 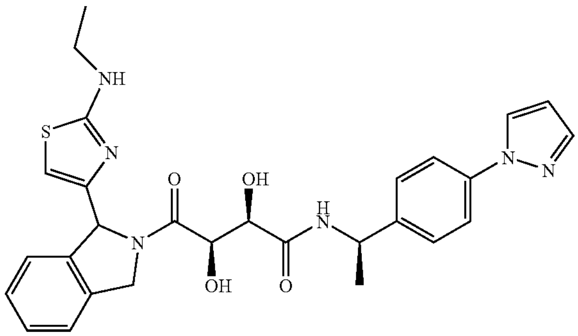 | 0.16 |
| 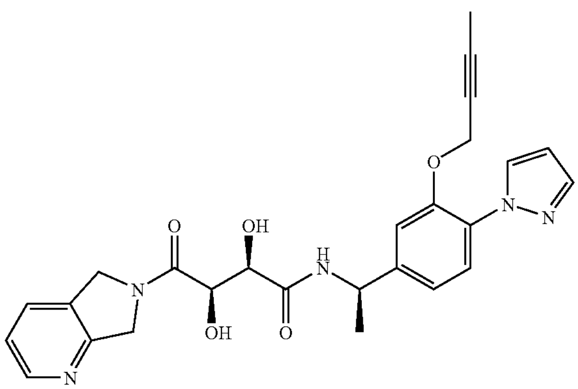 | 0.25 |
| 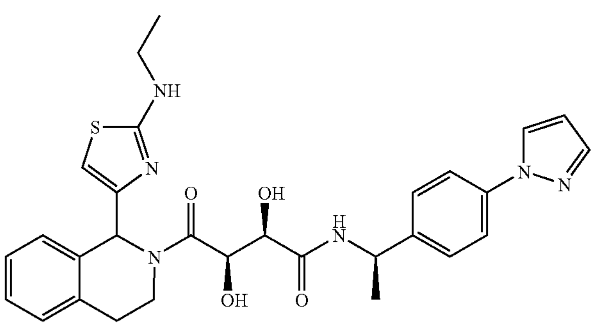 | 0.3 |
| 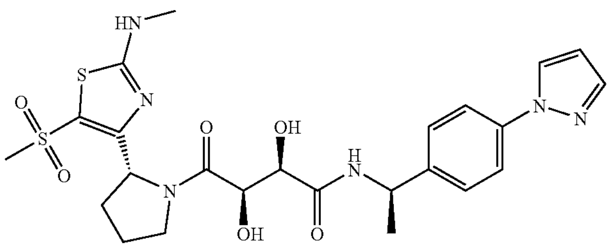 | 0.38 |

-continued
| Structure | Ki (nM) |
|---|---|
| 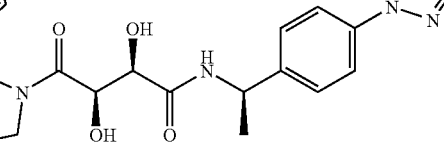 | 0.49 |
| 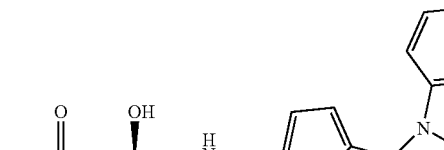 | 0.5 |
| 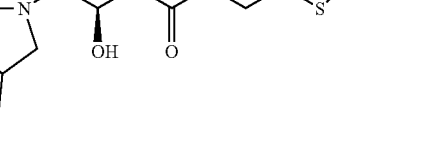 | 0.5 |
| 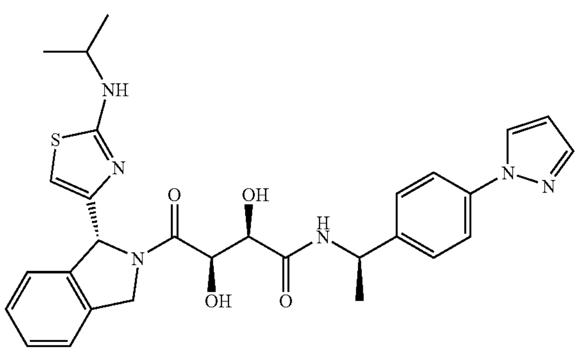 | 0.54 |
| 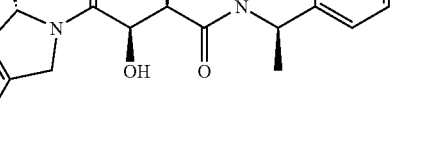 | 0.56 |

| Structure | Ki (nM) |
|---|---|
| *(structure)* | 0.57 |
| *(structure)* | 0.6 |
| *(structure)* | 0.74 |
| *(structure)* | 0.75 |
| *(structure)* | 0.8 |
| *(structure)* | 0.85 |

| Structure | Ki (nM) |
|---|---|
| (structure) | 0.86 |
| (structure) Mixture of diastereomers | 0.89 |
| (structure) | 1 |
| (structure) | 1.1 |
| (structure) One diastereomer | 1.4 |

| Structure | Ki (nM) |
|---|---|
| | 1.4 |
| | 1.4 |
| 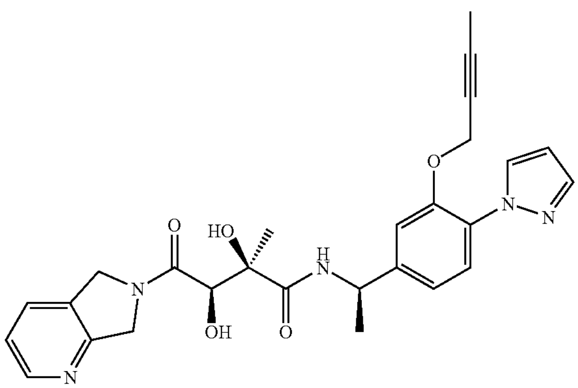 | 1.44 |
| 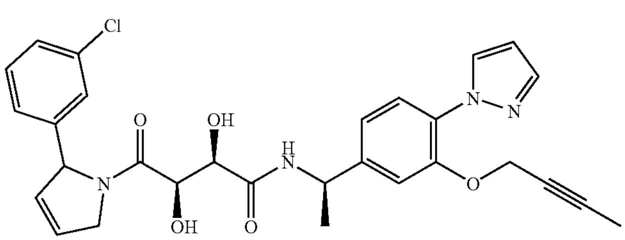 | 1.54 |
| 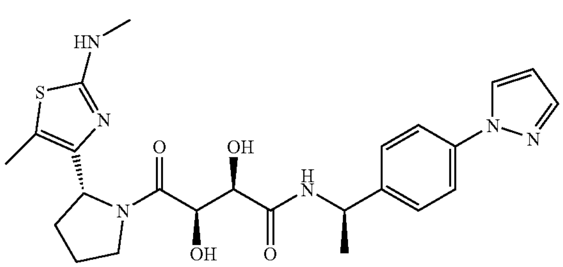 | 2 |

-continued

| Structure | Ki (nM) |
|---|---|
| 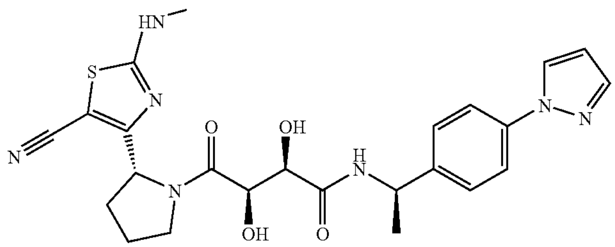 | 2 |
| 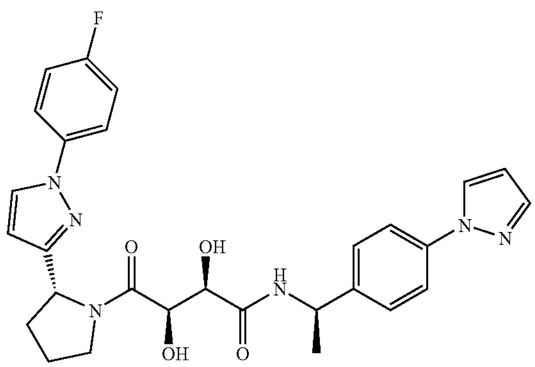 | 2.0 |
| 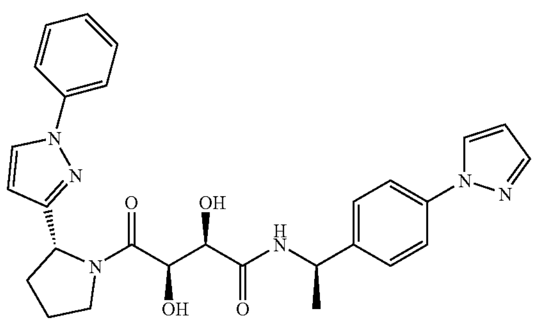 | 2.3 |
| Mixture of diastereomers | |
| 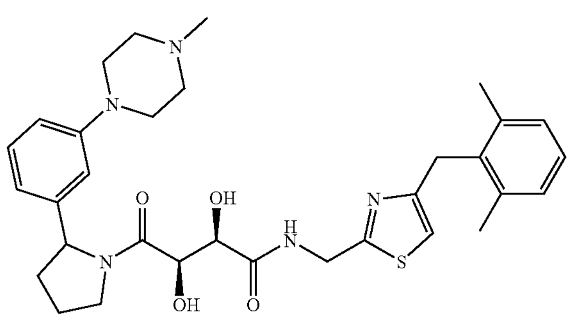 | 2.5 |

-continued
| Structure | Ki (nM) |
|---|---|
| 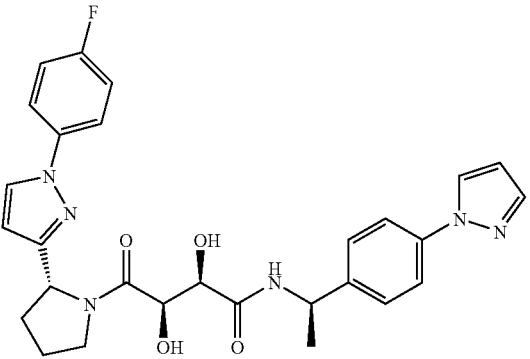 | 2.7 |
| 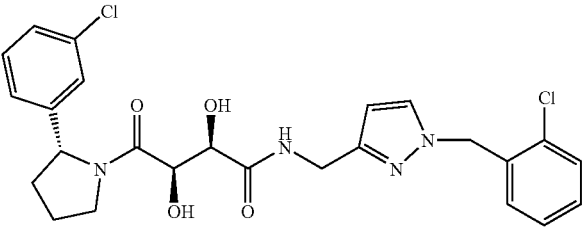 | 2.7 |
| 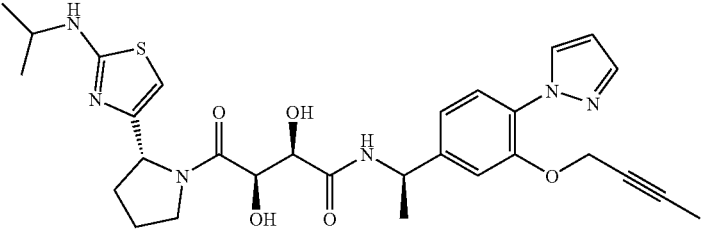 | 2.9 |
| 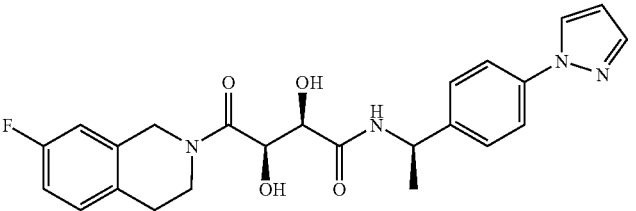 | 3.0 |
| 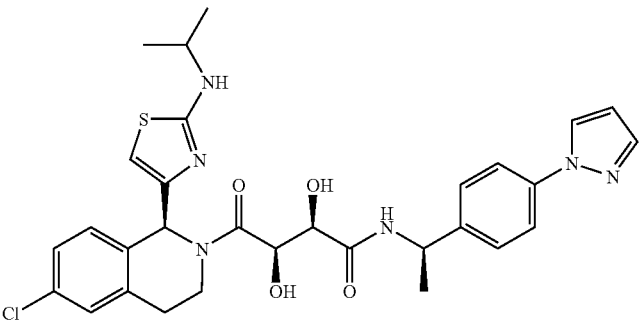 | 3.3 |

| Structure | Ki (nM) |
|---|---|
| [structure: phenyl-pyrrolidine-dihydroxysuccinyl-NH-CH2-biphenyl-CO2Et] | 3.6 |
| [structure: isoindoline-dihydroxysuccinyl-NH-CH(Me)-phenyl-thiophene] | 3.8 |
| [structure: methylaminothiazole-difluoropyrrolidine-dihydroxysuccinyl-NH-CH(Me)-phenyl-pyrazole] | 3.9 |

The pharmaceutical compositions containing the active ingredient may be in a form suitable for oral use, for example, as tablets, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for controlled release.

Formulations for oral use may also be presented as hard gelatin capsules wherein the active ingredients is mixed with an inert solid diluent, for example, calcium carbonate, calcium phosphate or kaolin, or a soft gelatin capsules where in the active ingredient is mixed with water or an oil medium, for example peanut oil, liquid paraffin or olive oil.

Aqueous suspensions contain the active material in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example, heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example, ethyl or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, e.g., sweetening, flavoring and coloring agents, may also be present.

The pharmaceutical compositions of the invention may also be in the form of an oil-in-water emulsion. The oily phase may be a vegetable oil, e.g., olive oil or arachis oil, or a mineral oil, e.g., liquid paraffin or mixtures of these. Suitable emulsifying agents may be naturally-occurring phosphatides, e.g., soy beans, lecithin, and esters or partial esters derived from fatty acids and hexitol anhydrides, for example, sorbitan monooleate, and condensation products of the said partial esters with ethylene oxide, e.g., polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, e.g., as a solution in 1,3-butane diol. Among the acceptable vehicles and solvents that may be employed are water, Ringer's solution and isotonic sodium chloride solution. In addition, sterile fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the invention may also be administered in the form of suppositories for rectal administration of the drug. The compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of The invention are employed. (For purposes of this application, topical application shall include mouthwashes and gargles.)

The compounds for the present invention can be administered in the intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the present invention is selected in accordance with a variety of factors including type, species, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the compound of Formula I useful in the method of the present invention range from 0.01 to 1000 mg per day. More preferably, dosages range from 0.1 to 1000 mg/day. Most preferably, dosages range from 0.1 to 500 mg/day. For oral administration, the compositions are preferably provided in the form of tablets containing 0.01 to 1000 milligrams of the active ingredient, particularly 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. An effective amount of the drug is ordinarily supplied at a dosage level of from about 0.0002 mg/kg to about 50 mg/kg of body weight per day. The range is more particularly from about 0.001 mg/kg to 1 mg/kg of body weight per day.

Advantageously, the active agent of the present invention may be administered in a single daily dose, or the total daily dosage may be administered in dividend doses of two, three or four time daily.

The amount of active ingredient that may be combined with the carrier materials to produce single dosage form will vary depending upon the host treated and the particular mode of administration.

It will be understood, however, that the specific dose level for any particular patient will depend upon a variety of factors including the age, body weight, general health, sex, diet, time of administration, route or administration, rate of excretion, drug combination and the severity of the particular disease undergoing therapy.

The compounds of the invention may be produced by processes known to those skilled in the art and as shown in the following reaction schemes and in the preparations and examples described below.

EXAMPLES

The following abbreviations are used in the procedures and schemes:
ACN Acetonitrile
AcOH Acetic acid
ADDP 1,1¹-(Azodicarbonyl)dipiperidine
Anh. Anhydrous Aq Aqueous
BOC tert-Butoxycarbonyl
° C. degrees Celsius
CBZCl Benzyl chloroformate
CDI Carbodiimide
DBU 1,8-Diazabicyclo[5.4.0]undec-7-ene
DCC Dicyclohexylcarbodiimide
DCM Dichloromethane
DEAD Diethyl azodicarboxylate
(DHQ)2PHAL Hydroquinine 1,4-phthalazinediyl diether
DIAD Diisopropylazodicarboxylate
DIEA Diisopropylethylamine
DMA N,N-Dimethylacetamide
DMAP 4-Dimethylaminopyridine
DME Dimethoxyethane
DMF Dimethylformamide
DMFDMA N,N-Dimethylformamide dimethylacetal
DMPU 1,3-Dimethyl-3,4,5,6-tetrahydro-2(1 h)-pyrimidinone
DMSO Dimethyl sulfoxide
EDC 1-(3-Dimethylaminopropyl)-3-ethylcarbodiimide hydrochloride
EI Electron ionization
Eq Equivalents
EtOAc Ethyl acetate
EtOH Ethanol
g grams
h. hours
$^1$H proton
HATU N,N,N',N'-Tetramethyl-O-(7-Azabenzotriazol-1-yl) Uronium hexafluorophosphate
Hex hexanes
HOBt 1-Hydroxybenzotriazole
HPLC High pressure liquid chromatography
LAH Lithium aluminum hydride
LDA Lithium diisopropylamide
M Molar
mCPBA meta-Chloroperoxybenzoic acid
Me Methyl
MeCN Acetonitrile
MeOH Methanol
min Minutes
mg Milligrams
MHz Megahertz
ml Milliliter
MS Mass Spectroscopy
NMM N-Methylmorpholine
NMP 1-methyl-2-pyrrolidone
ON Overnight
Pd($^t$Bu$_3$P)$_2$ Bis-(tri-tert-butylophosphine)palladium
Pd(TPP)$_4$ Tetrakis-(triphenylphosphine)palladium
Pd(Oac)$_2$ Palladium(II) acetate
PdCl$_2$(TPP)$_2$ Bis-(triphenylphosphine)palladium(II) chloride
PdCl$_2$(ddppf) Dichloro[1,1'-bis(diphenylphosphino)ferrocene]palladium(ii) dichloride
Pd$_2$(dba)$_3$ Tris(dibenzylideneacetone)dipalladium(0)
PyBrOP Bromo-tris-pyrrolidino-phosphonium hexafluorophosphate
Pyr Pyridine
RT Room temperature
SiO$_2$ Silica gel 60 chromatography
sgc Silica gel 60 chromatography
tBOC tert-Butoxycarbonyl
TACE TNF-alpha converting enzyme
TEA Triethylamine
TFA Trifluoroacetic acid
THF Tetrahydrofuran
TLC Thin layer chromatography
TPP Triphenylphosphine
$t_R$ Retention time NMR spectra were acquired on a Mercuryplus 400 MHz NMR Spectrometer (Varian), using CDCl3 or DMSO-d6 as solvents. LC-MS data was obtained using an Agilent 1100 Series LC/MSD (quadrupole, API-ES (Atmospheric Pressure Interface Electrospray)) with a capillary voltage set to 3500 V and running in positive mode. Reported analytical HPLC (LC/MS) retention times were obtained using a C18 (150×4.6 mm) reverse-phase column eluting with a 5 or 10 minute gradient of 0.1% trifluoroacetic acid in water to 95:5 acetonitrile:water at a flow rate of 3 mL/min.

Purification via reverse phase chromatography was accomplished using a C18 reverse phase column with a gradient of 0.1% trifluoroacetic acid in water to 95:5 acetonitrile:water at a flow rate of 20 mL/min. Samples were collected using a UV (Gilson, 254 nm) or mass spectra (Agilent 1100 Series LC/MSD model SL) signal.

Normal phase silica gel chromatography on a Biotage instrument was accomplished using a Quad UV System (P/N 07052) utilizing KP-SIL 32-63 um columns, 60 Å with flash cartridges 12+M or 25+M.

The compounds of formula (I) may be produced by processes known to those skilled in the art and as shown in the following reaction schemes and in the preparations and examples described below. These preparations and examples should not be construed to limit the scope of the disclosure. Alternate mechanistic pathways and analogous structures may be apparent to those skilled in the art. Some of the compounds made by these processes are listed in Table 1. All kinds of isomeric forms of the compounds are considered to be within the scope of this invention.

Example 1

General Synthesis of Tartrate Inhibitors

Two general routes exist for the synthesis of tartrate diamides from amines. The first (Example 1) utilizes an acetonide-protected monoacid/monoester intermediate prepared from the commercially available acetonide dimethyl ester using a literature procedure (J. Am. Chem. Soc. 1978, 100, 48654872). In general either Example 1 or Example 2 could be used interchangeably, although Example 2 was found to be more preferred for compounds that contained functional groups that were unstable towards acidic deprotection conditions (such as 113).

A variety of amide bond coupling reagents were acceptable, including HATU, CDI, EDC, DCC/HOBt, PyBrOP, polymer supported CDI with HOBt, polymer supported carbodiimide, and polymer supported EDC (PS-EDC) with HOBt. These coupling reagents could be used with a variety of bases, including triethylamine (TEA), diisopropylethylamine (DIEA), N-methyl morpholine, pyridine, dimethylaminopyridine (DMAP) and imidazole. In some cases the excess amines in the peptide coupling steps were removed using liquid/liquid extraction or polymeric scavenging resins such as polymer supported isocyanate (PS-NCO) and/or polymer supported tosic acid (MP-TSOH). Unreacted acids could be removed using MP-carbonate resin or polymer resins containing basic functional groups such as trisamine (i.e. PS-trisamine), amberlite, or morpholine. Peptide couplings were conducted in a variety of solvents, including DMF, THF, dioxane, acetonitrile, NMP, and DCM. These solvents can also be combined in various proportions to optimize the reac-

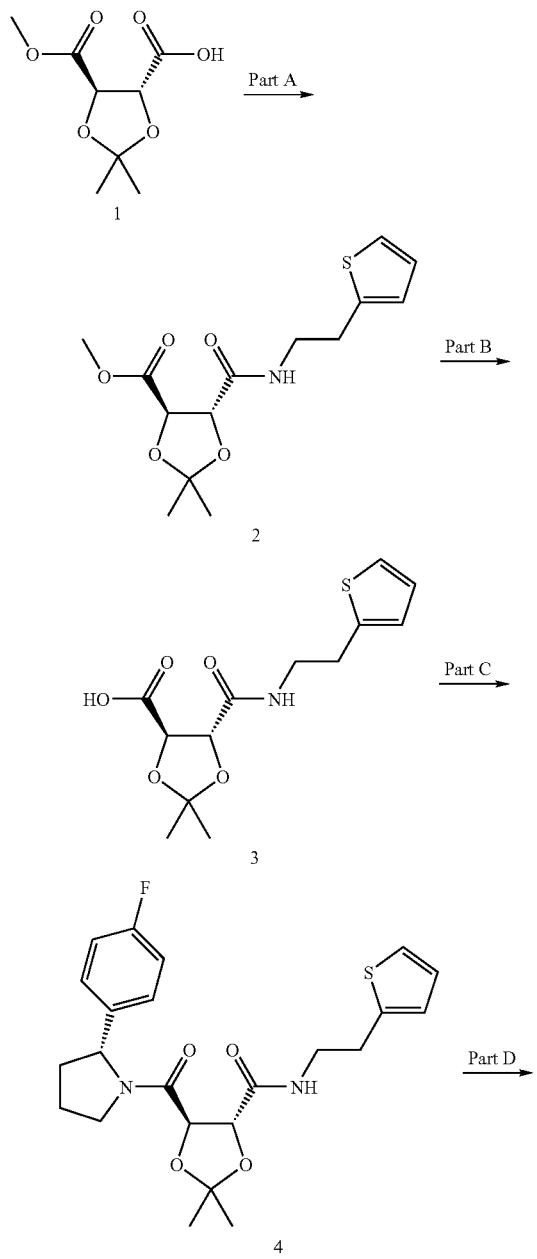

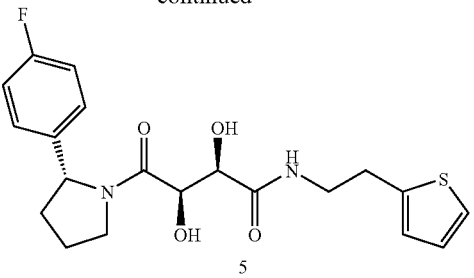

Part A:

To 2,2-dimethyl-[1,3]dioxolane-4R,5R-dicarboxylic acid monomethyl ester (1) (Musich, J. A.; Rapoport, H.; *J. Am. Chem. Soc.* 1978, 100, 4865-4872) (500 mg, 2.45 mmol) in DMF (5 mL) was added 2-thiopheneethylamine (316 µL, 2.70 mmol), DIEA (0.94 mL, 5.4 mmol) and HATU (989 mg, 2.60 mmol). The reaction mixture was stirred overnight and the DMF was removed in vacuo. The residue was dissolved in EtOAc, washed with water, saturated bicarbonate solution, 0.1 N HCl, and brine. The organic layer was dried over sodium sulfate and concentrated. Purification by column chromatography ($SiO_2$, 10% EtOAc/DCM) afforded 2 as an oil (491 mg, 64%). $^1$H NMR (400 MHz, $CDCl_3$) δ 7.17 (dd, 1H, J=1.2, 5.2 Hz), 6.95 (dd, 1H, J=2.1, 5.2 Hz), 6.84 (d, 1H, J=2.4 Hz), 6.66 (bs, 1H, NH), 4.72 (ABq, 2H, J=13.2 Hz), 3.84 (s, 3H), 3.65 (m, 1H), 3.57 (m, 1H), 3.09 (t, 2H, J=6.4 Hz), 1.47 (s, 3H), 1.40 (s, 3H); HPLC-MS $t_R$=1.63 min ($UV_{254\,nm}$); Mass calculated for formula $C_{14}H_{19}NO_5S$ 313.1, observed LCMS m/z 314.2 (M+H).

Part B:

To 2 (869 mg, 2.77 mmol) in THF (10 mL) was added 1.0 M LiOH (3 mL, 3 mmol) and the reaction was stirred overnight at room temperature. The reaction mixture was diluted with water (10 mL) and the THF was removed in vacuo. The basic aqueous layer was extracted with diethyl ether and the ether wash was discarded. The aqueous layer was made acidic with 1.0 N HCl and extracted with diethyl ether. The combined organic layers were dried over sodium sulfate and concentrated to afford 3 as a yellow solid (443 mg, 53%). $^1$H NMR (400 MHz, $CDCl_3$) δ 7.21 (dd, 1H, J=1.2, 5.2 Hz), 6.97 (dd, 1H, J=3.6, 5.2 Hz), 6.90 (bs, 1H, NH), 6.86 (d, 1H, J=3.2 Hz), 4.48 (ABq, 2H, J=9.2 Hz), 3.76 (m, 1H), 3.60 (m, 1H), 3.15 (m, 2H), 1.53 (s, 3H), 1.41 (s, 3H); HPLC-MS $t_R$=1.34 min ($UV_{254\,nm}$); Mass calculated for formula $C_{13}H_{17}NO_5S$ 299.1, observed LCMS m/z 300.1 (M+H).

Part C:

To 3 (150 mg, 0.5 mmol) in DMF (2 mL) was added racemic 2-(4-fluorophenyl)-pyrrolidine (99 mg, 0.6 mmol), DIEA (261 µL, 1.5 mmol), and HATU (228 mg, 0.6 mmol) and the reaction mixture was stirred overnight at room temperature. The DMF was removed in vacuo and the residue was dissolved in ethyl acetate. The organic layer was washed with 0.1 N NaOH, 0.1 N HCl, water, and brine, dried over sodium sulfate and concentrated. Purification by column chromatography ($SiO_2$, 10% to 50% EtOAc/DCM) afforded an oil (220 mg, 99%). The diastereomers were resolved (as described in Example 18) by reverse phase HPLC to afford 4 the desired isomer (78 mg, 35%) after lypholization. HPLC-MS $t_R$=1.93 min ($UV_{254\,nm}$); Mass calculated for formula $C_{23}H_{27}FN_2O_4S$ 446.2, observed LCMS m/z 447.3 (M+H).

Part D:

Compound 4 (78 mg, 0.17 mmol) was dissolved in 90:10 TFA:water (5 mL) and stirred for 4 hours at room temperature. The reaction mixture was quenched with 1:1 ACN:water (10 mL) and concentrated. The residue was re-dissolved in 1:1 ACN:water (10 mL) and concentrated. Lypholization afforded 5 as white solid (62 mg, 87%). $^1$H NMR (400 MHz, CDCl$_3$) mixture of rotomers δ 7.16-6.8 (m, 8H), 5.23-5.11 (m, 1H), 4.85 (m, 1H), 4.40-4.15 (m, 1H), 3.90-3.48 (m, 6H), 3.00 (m, 2H), 2.33 (m, 1H), 2.05-1.83 (m, 3H); HPLC-MS t$_R$=1.50 min (UV$_{254\ nm}$); Mass calculated for formula C$_{20}$H$_{23}$FN$_2$O$_4$S 406.1, observed LCMS m/z 407.2 (M+H).

The following table contains compounds synthesized using the above procedures.

| Compound # | Structure | Exact mass | MS m/z (M + H) |
|---|---|---|---|
| 6 | 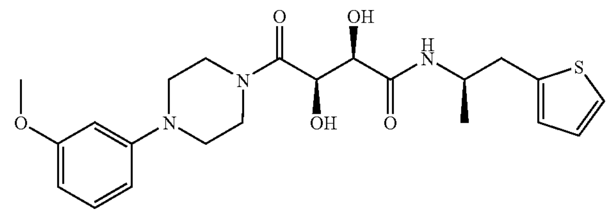 | 433.2 | 434.1 |
| 7A | 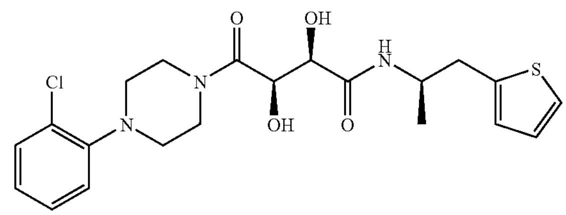 | 437.1 | 438.0 |
| 7B | 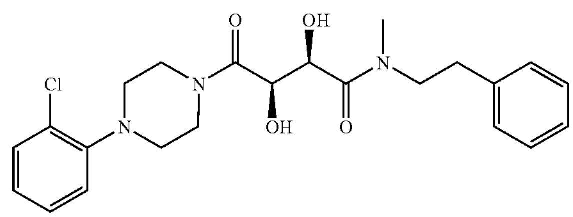 | 445.2 | 446.1 |
| 8 | 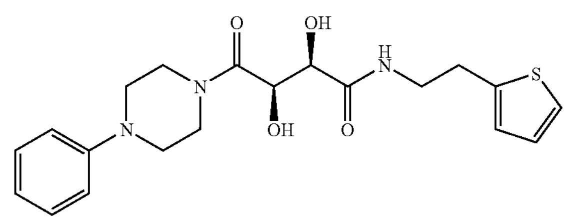 | 403.2 | 404.1 |
| 9 | 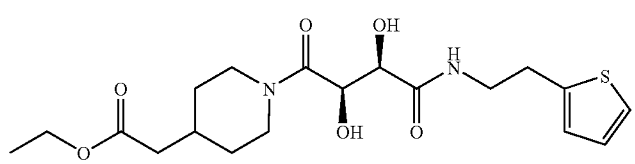 | 412.2 | 413.2 |
| 10 | 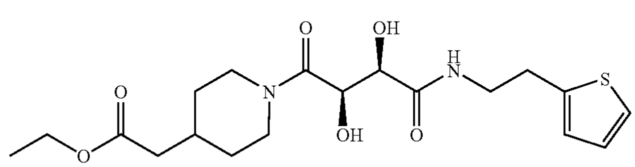 | 413.2 | 414.0 |

-continued

| Compound # | Structure | Exact mass | MS m/z (M + H) |
|---|---|---|---|
| 11 | 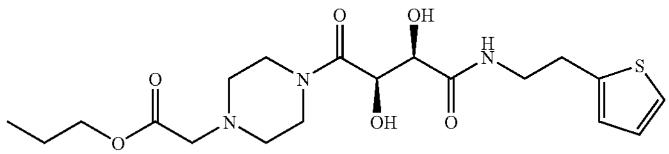 | 427.2 | 428.2 |
| 12 | 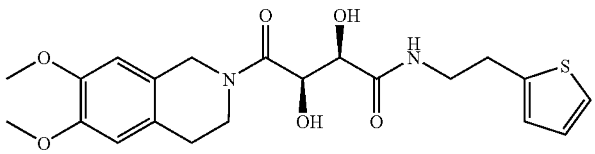 | 434.2 | 435.1 |
| 13 | 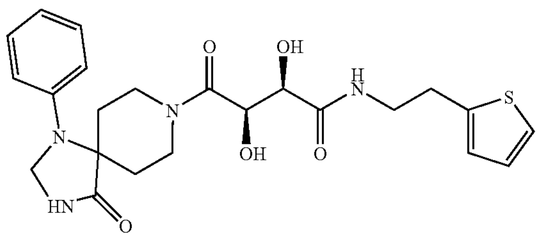 | 472.2 | 473.2 |
| 14 | 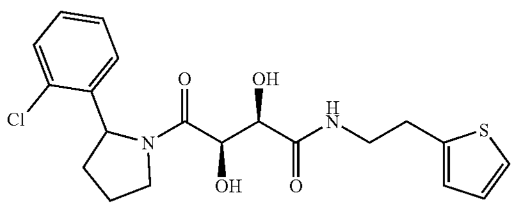 | 422.1 | 423.4 |
| 15 | 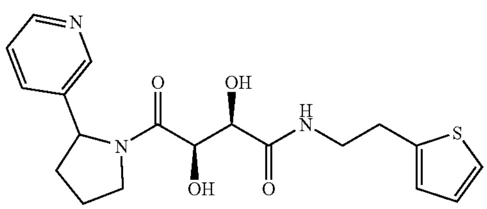 | 389.1 | 390.1 |
| 16 | 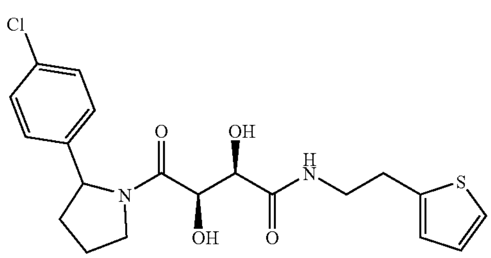 | 422.1 | 423.3 |
| 17 | 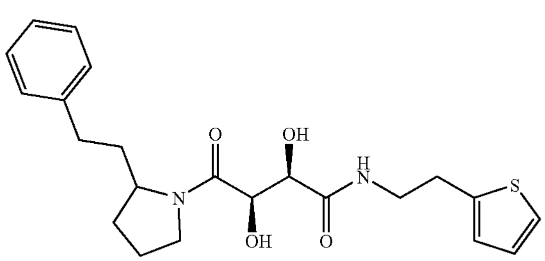 | 416.2 | 417.2 |

-continued

| Compound # | Structure | Exact mass | MS m/z (M + H) |
|---|---|---|---|
| 18 | 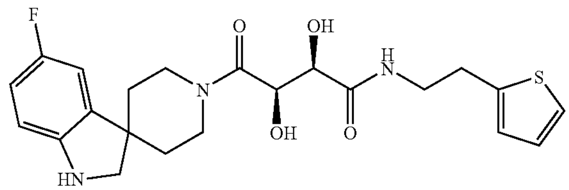 | 447.2 | 448.1 |
| 19 | 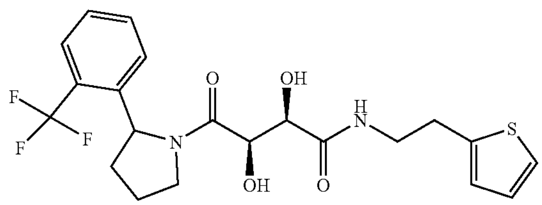 | 456.1 | 457.1 |
| 20 | 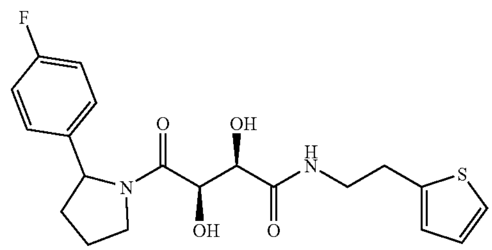 | 406.1 | 407.2 |
| 21 | 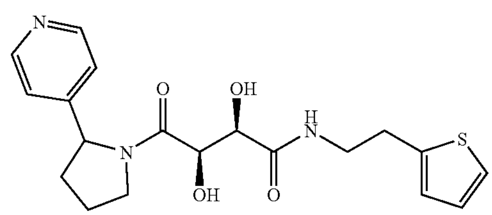 | 389.1 | 390.1 |
| 22 | 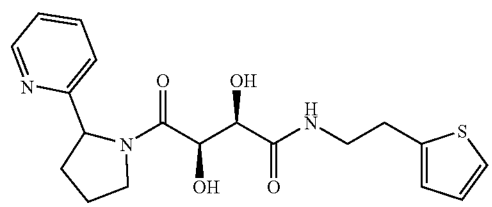 | 389.1 | 390.1 |
| 23 | 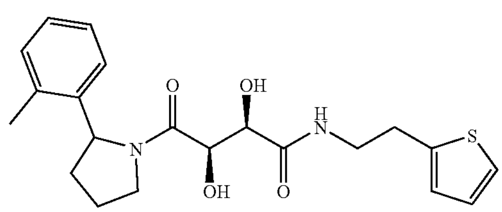 | 402.2 | 403.1 |
| 24 | 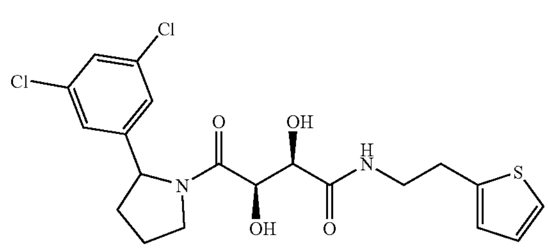 | 456.1 | 457.0 |

-continued

| Compound # | Structure | Exact mass | MS m/z (M + H) |
|---|---|---|---|
| 25 | 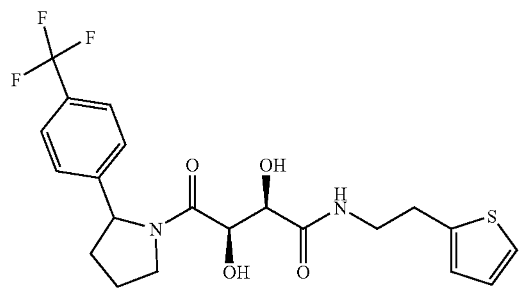 | 456.1 | 457.1 |
| 26 | 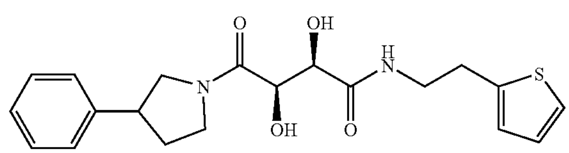 | 388.2 | 389.2 |
| 27 | 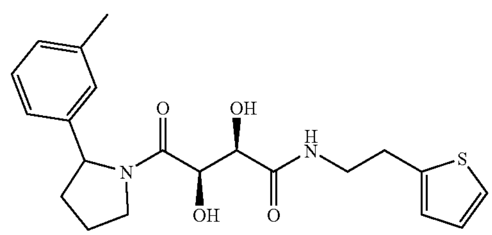 | 402.2 | 403.1 |
| 28 | 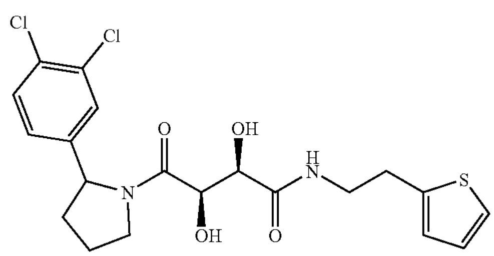 | 456.1 | 457.0 |
| 29A | 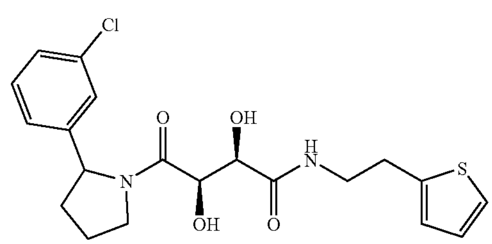 | 422.1 | 423.1 |
| 29B | 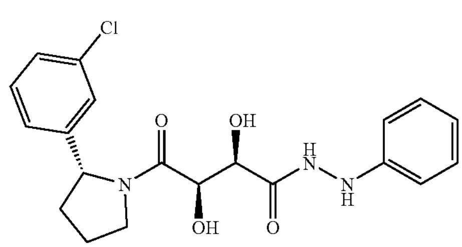 | 403.1 | 404.1 |

-continued

| Compound # | Structure | Exact mass | MS m/z (M + H) |
|---|---|---|---|
| 30 | 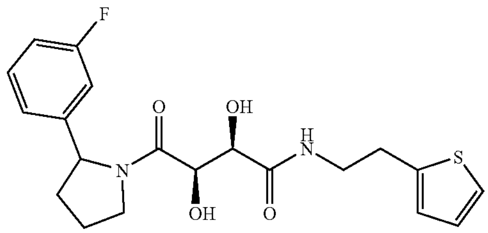 | 406.1 | 407.2 |
| 31 | 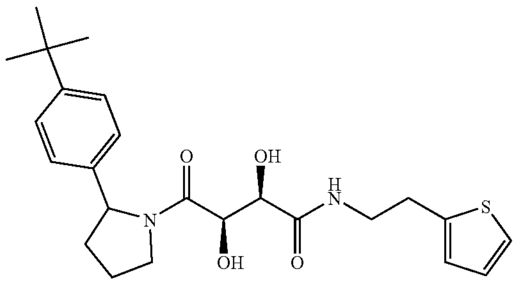 | 444.2 | 445.3 |
| 32 | 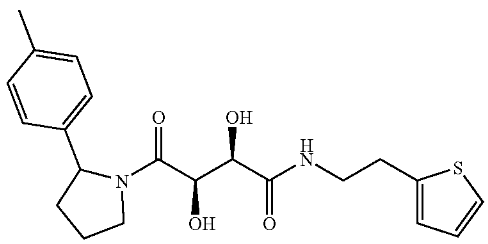 | 402.2 | 403.1 |
| 33 | 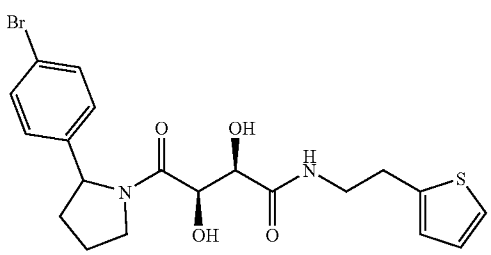 | 466.1 | 467.0 |
| 34 | 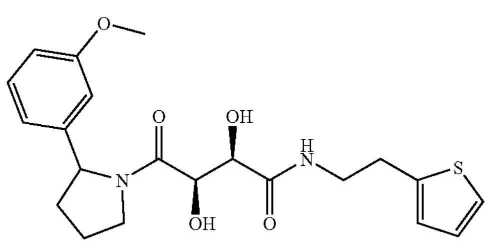 | 418.2 | 419.2 |
| 35 | 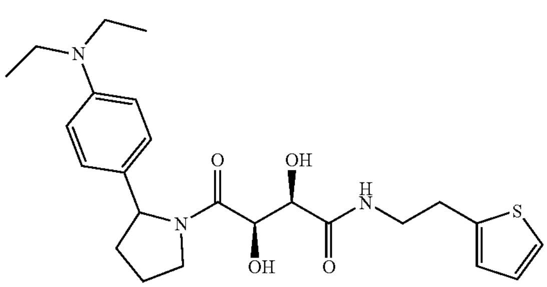 | 459.2 | 460.3 |

-continued

| Compound # | Structure | Exact mass | MS m/z (M + H) |
|---|---|---|---|
| 36 | 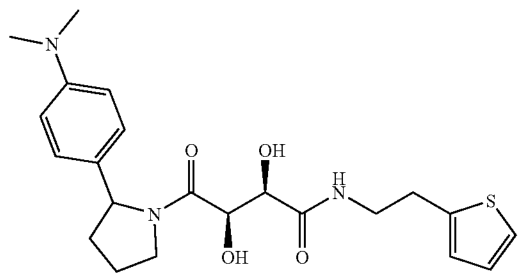 | 431.2 | 432.2 |
| 37 | 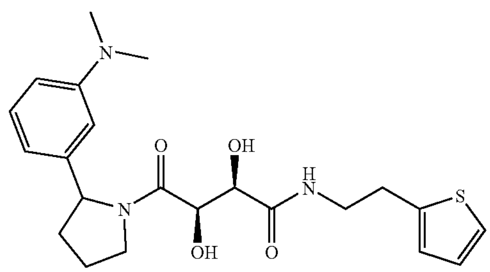 | 431.2 | 432.2 |
| 38 | 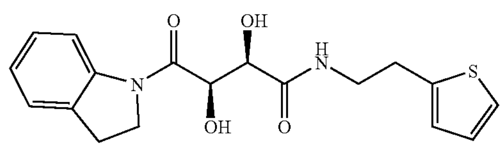 | 360.1 | 361.1 |
| 39 | 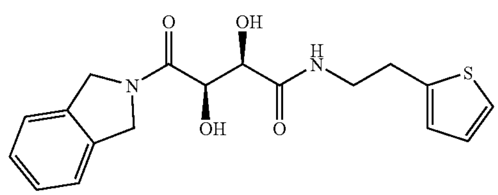 | 360.1 | 361.1 |
| 40 | 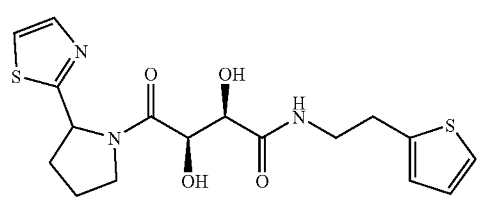 | 395.1 | 396.1 |
| 41 | 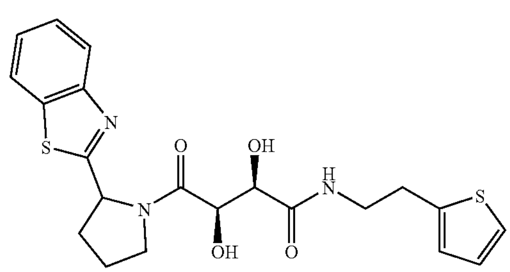 | 445.1 | 446.2 |

-continued

| Compound # | Structure | Exact mass | MS m/z (M + H) |
|---|---|---|---|
| 42 | 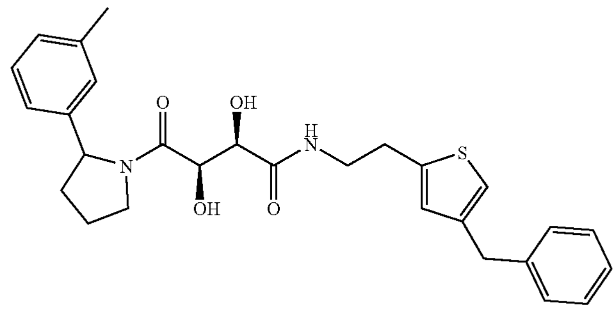 | 492.2 | 493.1 |
| 43 | 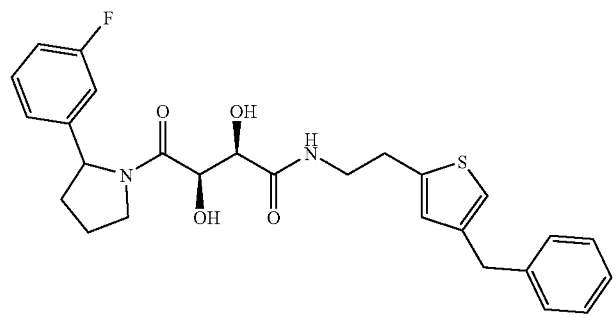 | 496.2 | 497.2 |
| 44 | 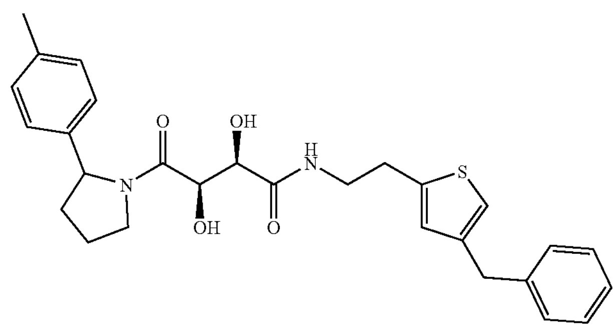 | 492.2 | 493.1 |
| 46 | 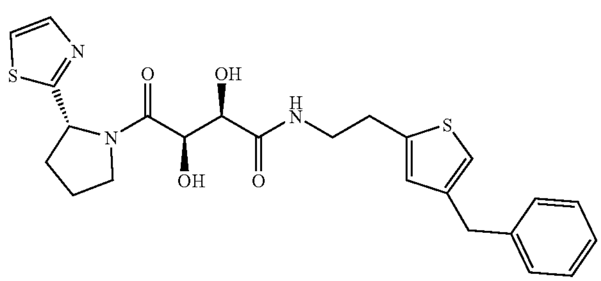 | 485.1 | 486.1 |
| 47 | 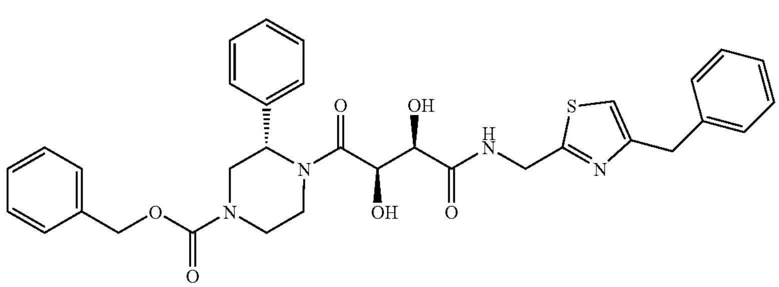 | 614.2 | 615.0 |

Example 2

Anhydride Route to Tartrate Diamide Inhibitors

A second general route to diamide compounds starting from an anhydride intermediate is delineated below in Example 2. (+)-Diacetyl —L-tartaric anhydride (48) is an article of commerce and reacts readily with a variety of amines to generate monoacid/monoamide intermediate. The preferred solvent for the ring opening is DCM; although DMF, THF or dioxane may also be compatible. The subsequent peptide coupling step proceeds under a variety of standard conditions which are given for Example 1. The acetate groups can be removed using a variety of conditions, including hydrazine/methanol, NaOMe in methanol, ammonia/methanol, lithium hydroxide/THF/water (saponification), potassium carbonate in methanol, or MP-carbonate. Often times the preferred set of conditions for parallel synthesis is to use the MP-carbonate. It has also been observed that one or both of the acetate protecting groups can be cleaved during synthetic transformations involving nucleophiles, basic reagents, heating in protic solvents or exposure to organometallic reagents.

Example 2A

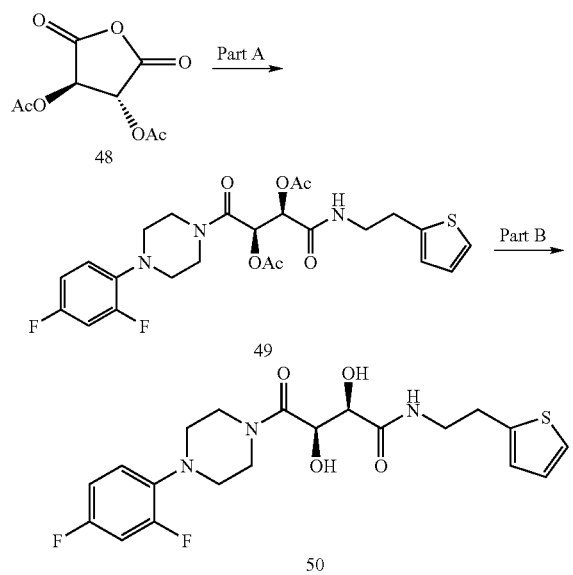

Part A:

To 48 (26 mg, 0.1 mmol) in DMF (1 mL) was added 2,4-difluorophenylpiperazine (20 mg, 0.1 mmol). The reaction mixture was stirred for 1.5 hours. To the crude mixture was added 2-thiopheneethylamine (14 μL, 0.12 mmol), DIEA (38 μL, 0.22 mmol) and HATU (42 mg, 0.11 mmol). The reaction was stirred overnight at room temperature. The reaction mixture was poured into water and extracted with EtOAc. The combined organic layers were washed with 0.1 N NaOH, 0.1 N HCl, and brine; dried over sodium sulfate and concentrated in vacuo to yield 49 as an oil (49 mg, 94%). HPLC-MS $t_R$=2.10 min ($UV_{254\ nm}$); mass calculated for formula $C_{24}H_{27}F_2N_3O_6S$ 523.2, observed LCMS m/z 524.4 (M+H); purity>95% (ELSD).

Part B:

To 49 (49 mg, 0.09 mmol) in MeOH (2 mL) was added anhydrous hydrazine (5 μL, 0.16 mmol). The reaction mixture was stirred overnight at room temperature. The reaction mixture was concentrated in vacuo and freeze-dried to afford 50 as a white powder (40 mg, 100%). $^1$H NMR (400 MHz, CDCl$_3$) δ 7.17 (d, 1H, J=5.2 Hz), 6.96 (m, 2H), 6.85 (m, 4H), 4.87 (s, 1H), 4.24 (s, 1H), 3.90 (m, 2H), 3.72 (m, 2H), 3.60 (m, 4H), 3.08 (m, 4H); HPLC-MS $t_R$=1.85 min ($UV_{254\ nm}$); mass calculated for formula $C_{20}H_{23}F_2N_3O_4S$ 439.1, observed LCMS m/z 440.2 (M+H).

Example 2B

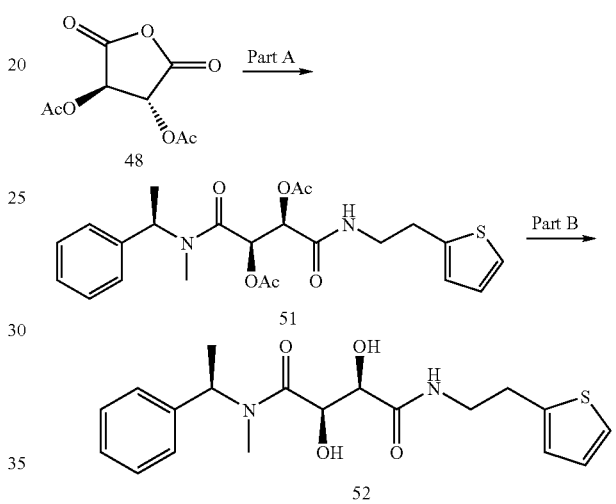

Part A:

To 48 (26 mg, 0.1 mmol) in DMF (1 mL) was added N-methyl-(1R-phenyl-ethyl)-amine (15 μL, 0.1 mmol). The reaction mixture was stirred for 1 hour. To the crude mixture was added 2-thiopheneethylamine (47 μL, 0.4 mmol), HOBt (27 mg, 0.2 mmol), PS-carbodiimide resin (312 mg, 0.4 mmol). To the reaction mixture was added PS-TsOH resin (0.6 mmol) and MP-carbonate resin (0.4 mmol). The reaction was tumbled overnight, filtered and concentrated. Compound 51 was used without further purification. HPLC-MS $t_R$=1.82 min ($UV_{254\ nm}$); mass calculated for formula $C_{23}H_{28}N_2O_6S$ 460.2, observed LCMS m/z 461.1 (M+H).

Part B:

To 51 in MeOH (2 mL) was added anhydrous hydrazine (5 μL, 0.16 mmol). The reaction mixture was stirred overnight at room temperature. The reaction mixture was concentrated in vacuo, purified by reverse phase prep-HPLC and freeze-dried to afford 52 as a white powder (6.7 mg, 18% overall). $^1$H NMR (400 MHz, CDCl$_3$) major rotomer δ 7.40-7.25 (m, 6H), 7.16 (d, 1H, J=4.8 Hz), 6.95 (app. t, 1H, J=4.8 Hz), 6.87 (bs, 1H, NH), 5.96 (q, 1H, J=7.2 Hz), 4.91 (d, 1H, J=1.2 Hz), 4.22 (d, 1H, J=1.2 Hz), 3.60 (m, 2H), 3.08 (m, 2H), 2.79 (s, 3H), 1.56 (d, 3H, J=5.7 Hz); HPLC-MS $t_R$=3.80 min ($UV_{254\ nm}$, 10 min); mass calculated for formula $C_{19}H_{24}N_2O_4S$ 376.2, observed LCMS m/z 377.2 (M+H).

Example 2C
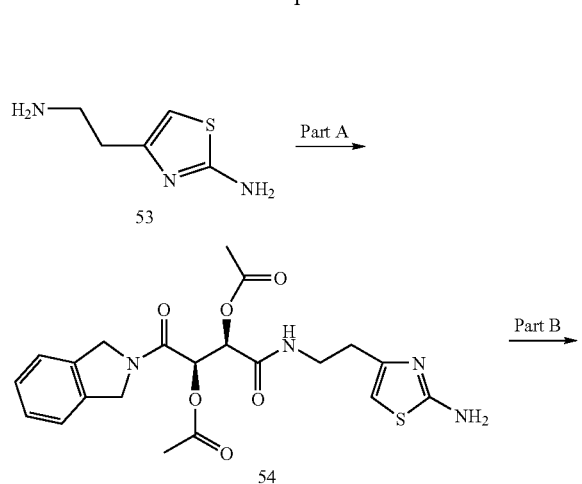
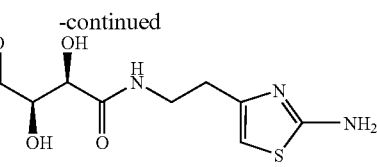
Compound 53 was prepared according to the procedure described by D. Miller et al (*J. Med. Chem.* 1999, 42, 2287).
Parts A & B:
Compound 55 was prepared using procedures similar to those described in Example 14, Parts D & E.
Data for 54: ¹HNMR (400 MHz, CDCl₃) δ 7.51-7.25 (m, 6H), 6.22 (s, 1H), 5.75-5.67 (m, 2H), 5.36 (s, 2H), 5.28-4.61 (m, 4H), 3.69-3.40 (m, 2H), 2.74 (s, 1H), 2.24 (s, 3H), 2.18 (s, 3H). Data for 55: ¹HNMR (400 MHz, CDCl₃) δ 7.54-7.26 (m, 6H), 6.24 (s, 1H), 5.22-5.02 (m, 2H), 4.94-4.82 (m, 3H) 4.42 (s, 1H), 3.72-3.50 (m, 2H), 2.92-2.76 (m, 2H) MS (EI) m/z M+H Obsd 377.1
| Compound # | Structure | Exact mass | MS m/z (M + H) |
|---|---|---|---|
| 56 | 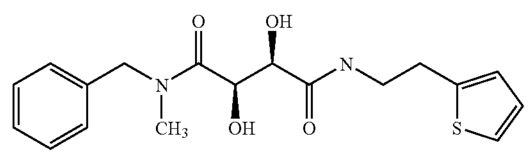 | 362.1 | 363.1 |
| 57 | 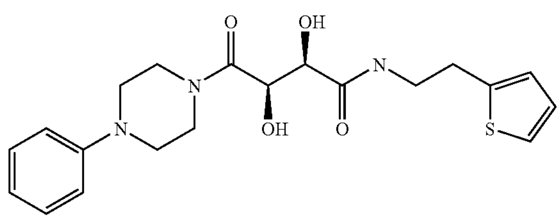 | 403.2 | 404.1 |
| 58 | 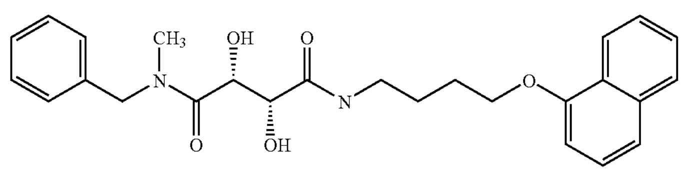 | 450.2 | 451.1 |
| 59 | 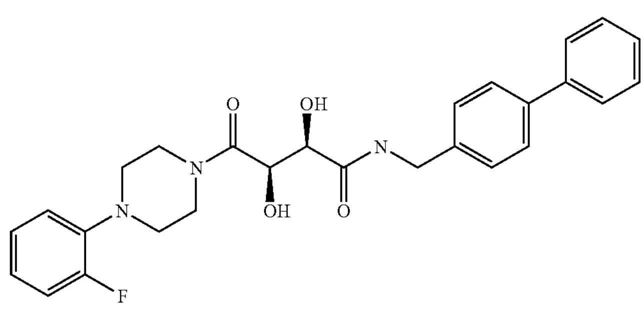 | 477.2 | 478.2 |

| Compound # | Structure | Exact mass | MS m/z (M + H) |
|---|---|---|---|
| 60 | 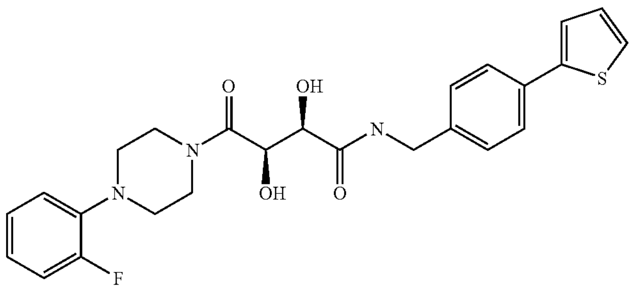 | 483.2 | 484.2 |
| 61 | 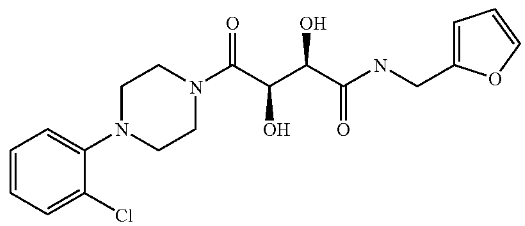 | 407.1 | 408.1 |
| 62 | 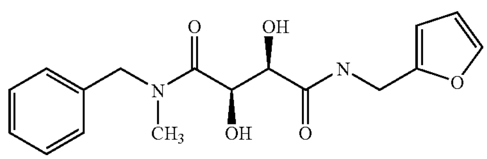 | 332.1 | 333.1 |
| 63 | 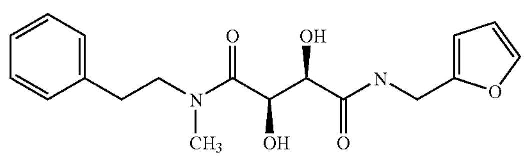 | 346.15 | 347.2 |
| 64 | 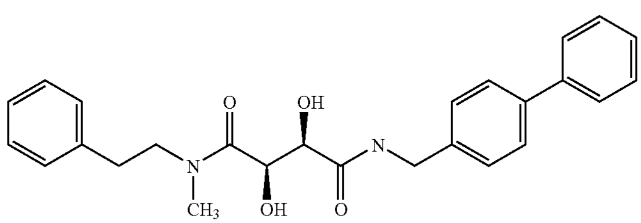 | 432.2 | 433.2 |
| 65 | 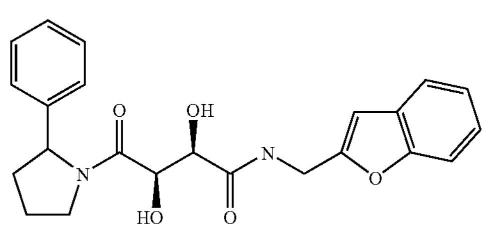 | 408.2 | 409.2 |
| 66 | 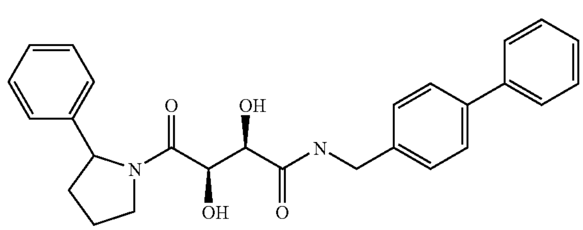 | 444.2 | 445.1 |

-continued

| Compound # | Structure | Exact mass | MS m/z (M + H) |
|---|---|---|---|
| 67 | 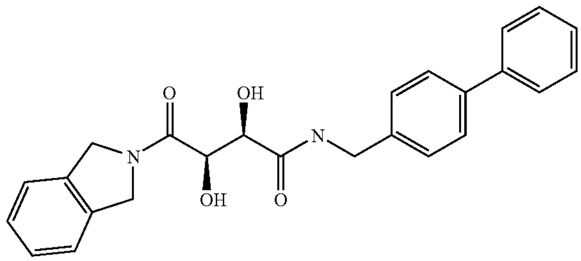 | 416.2 | 417.1 |
| 68 | 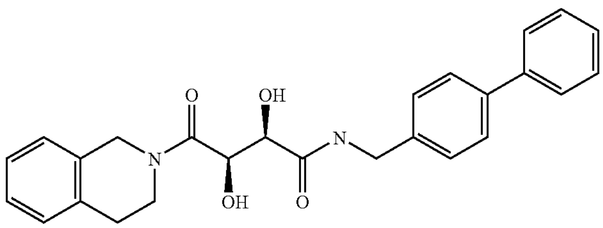 | 430.2 | 431.1 |
| 69 | 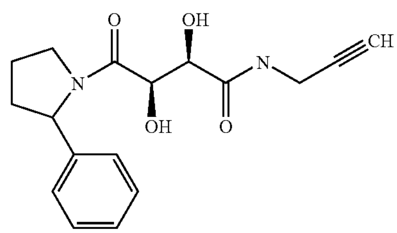 | 316.1 | 317.1 |
| 70 | 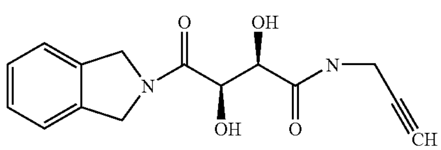 | 288.1 | 289.1 |
| 71 | 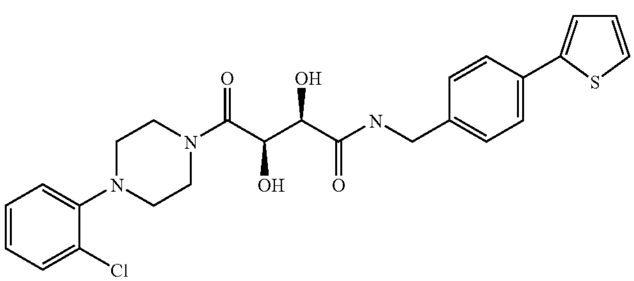 | 499.1 | 500.1 |
| 72 | 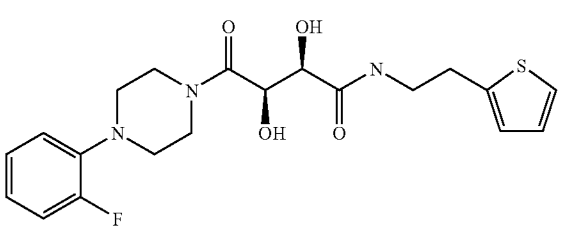 | 421.2 | 422.1 |

-continued

| Compound # | Structure | Exact mass | MS m/z (M + H) |
|---|---|---|---|
| 73 | 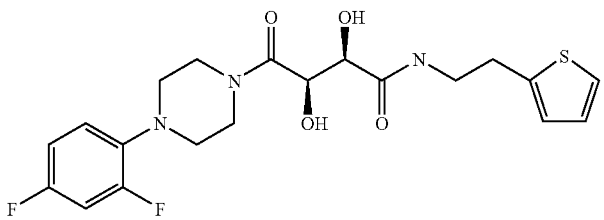 | 439.1 | 440.2 |
| 74 | 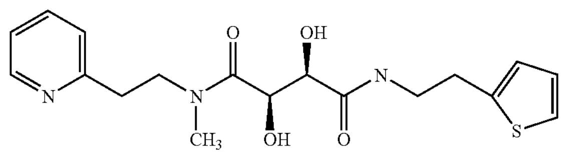 | 377.1 | 378.1 |
| 75 | 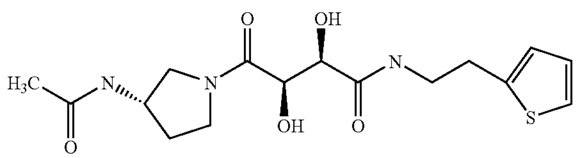 | 369.1 | 370.1 |
| 76 | 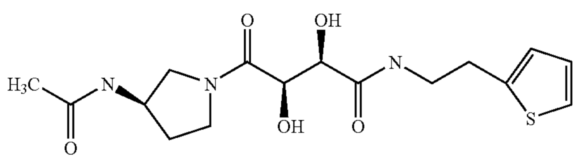 | 369.1 | 370.1 |
| 77 | 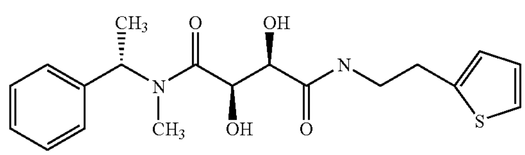 | 376.2 | 377.10 |
| 78 | 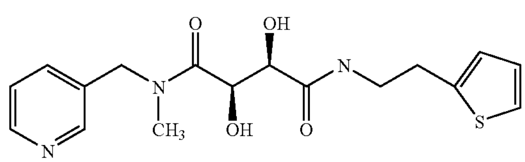 | 363.1 | 364.1 |
| 79 | 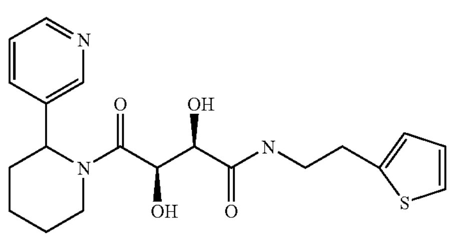 | 403.2 | 404.2 |
| 80 | 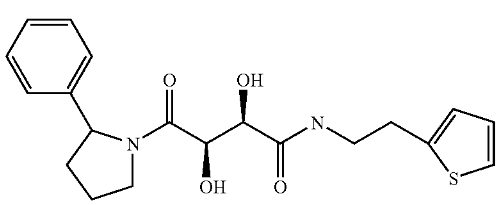 | 388.2 | 389.2 |

-continued

| Compound # | Structure | Exact mass | MS m/z (M + H) |
|---|---|---|---|
| 81 | 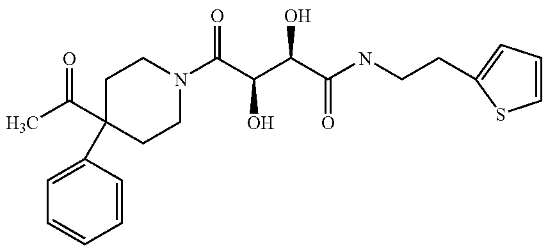 | 444.2 | 445.1 |
| 82 | 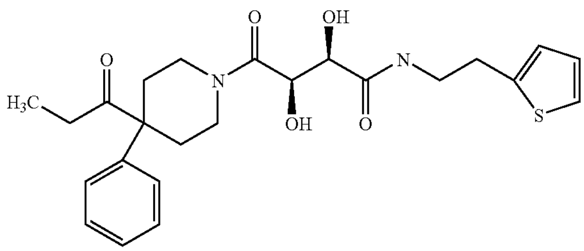 | 458.2 | 459.1 |
| 83 | 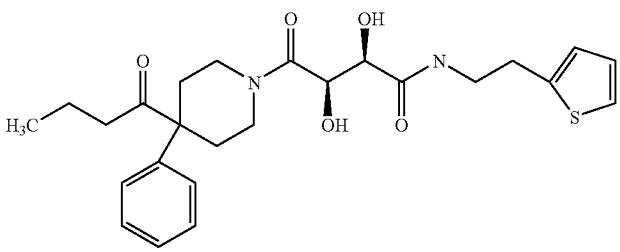 | 472.2 | 473.2 |
| 84 | 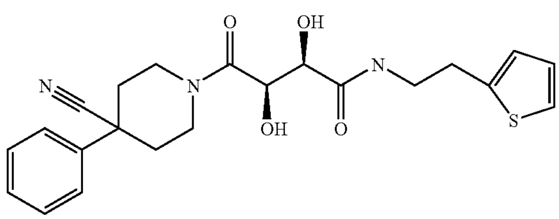 | 427.2 | 428.2 |
| 85 | 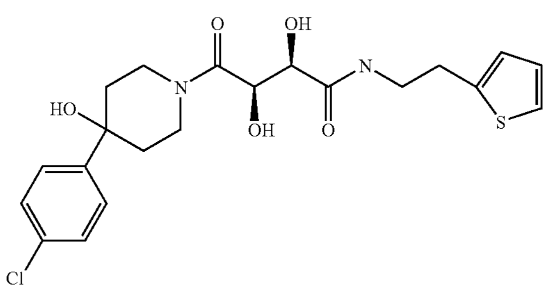 | 452.1 | 453.1 |
| 86 | 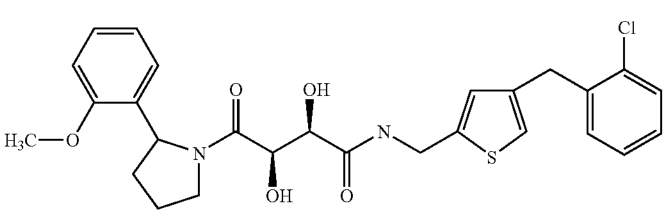 | 528.2 | 529.2 |

-continued

| Compound # | Structure | Exact mass | MS m/z (M + H) |
|---|---|---|---|
| 87 | 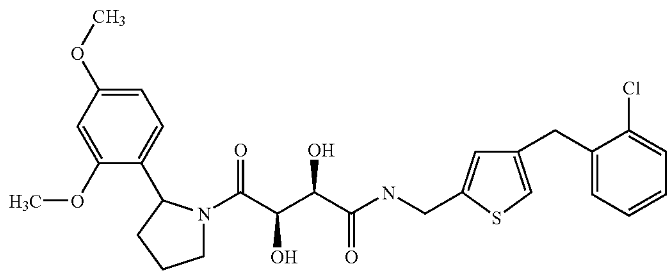 | 558.2 | 559.2 |
| 88 | 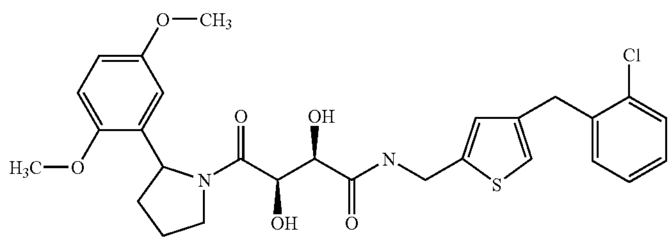 | 558.2 | 559.2 |
| 89 | 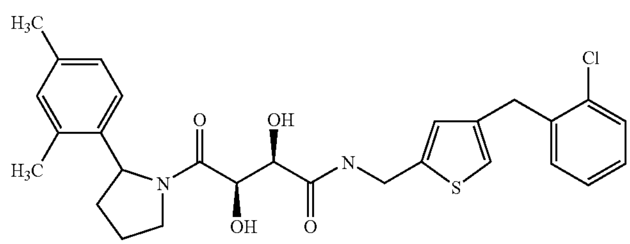 | 526.2 | 527.2 |
| 90 | 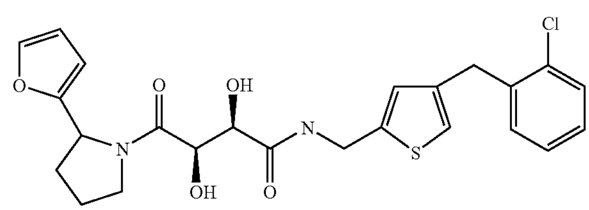 | 488.1 | 489.1 |
| 91 | 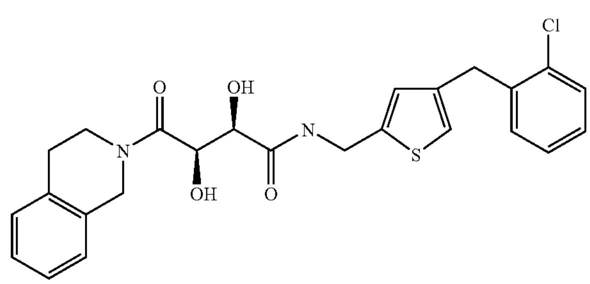 | 484.1 | 485.0 |
| 92 | 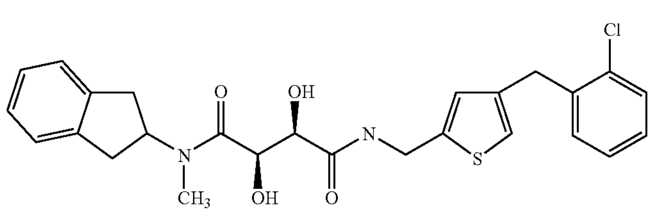 | 498.1 | 499.1 |

-continued

| Compound # | Structure | Exact mass | MS m/z (M + H) |
|---|---|---|---|
| 93 | 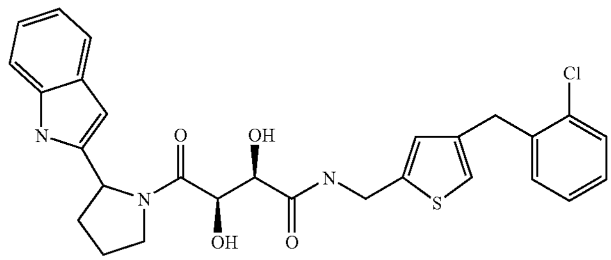 | 537.2 | 538.2 |
| 94 | 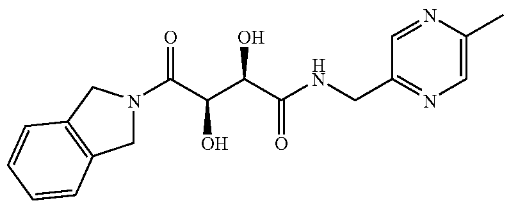 | 356.2 | 357.2 |
| 95 | 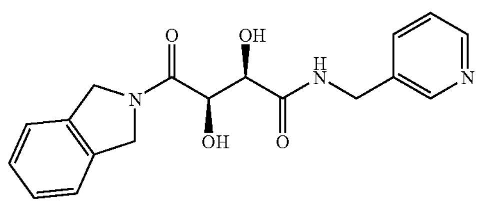 | 341.1 | 342.1 |
| 96 | 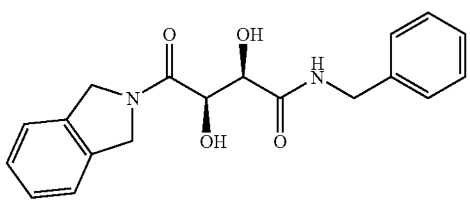 | 340.1 | 341.1 |
| 97 | 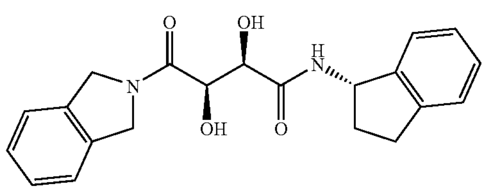 | 366.16 | 367.1 |
| 98 | 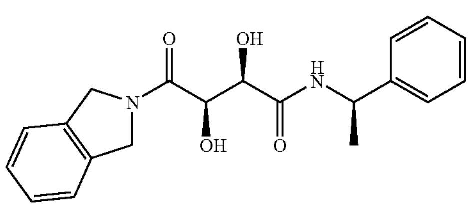 | 354.16 | 355.1 |
| 99 | 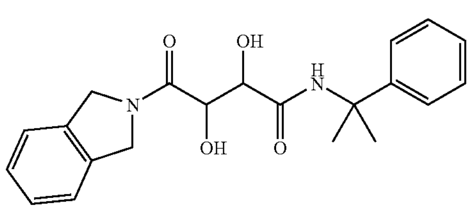 | 368.17 | 369.1 |

-continued

| Compound # | Structure | Exact mass | MS m/z (M + H) |
|---|---|---|---|
| 100 | 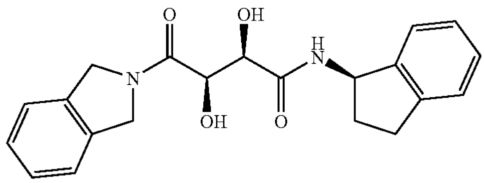 | 366.16 | 367.1 |
| 101 | 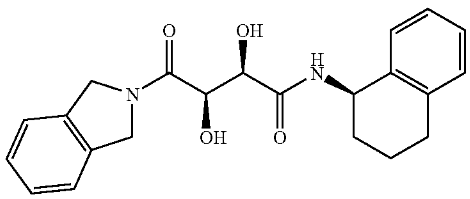 | 380.17 | 381.2 |
| 102 | 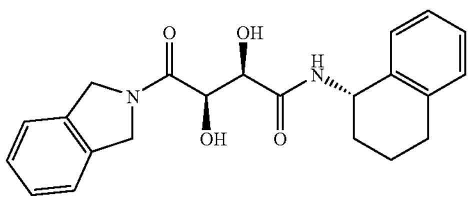 | 380.2 | 381.2 |
| 103 | 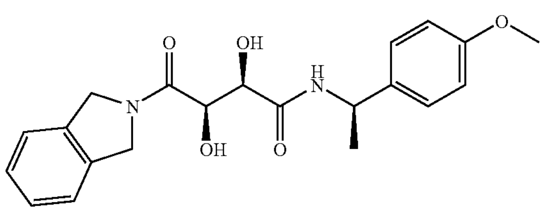 | 384.2 | 385.1 |
| 104 | 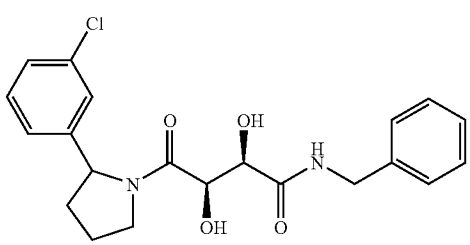 | 402.1 | 403.1 |
| 105 | 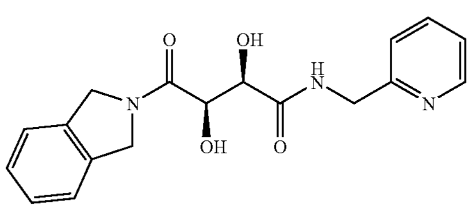 | 341.1 | 342.1 |

Example 2D

Method A

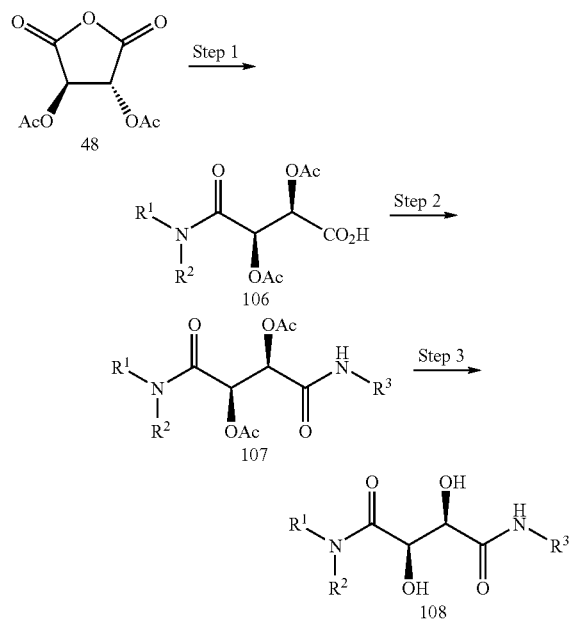

Method A, Step 1:

Compound 106 (R1=R2=CH$_2$Ph) was prepared from 48 following the procedure described in Example 4A, Part C.

Method A, Step 2:

To a THF/MeCN (1:1, 0.5 mL) solution of polystyrene EDC resin (57 mg, 3 eq) in a 6 mL fritted cartridge was added a THF/MeCN (1:1) solution of 106 (0.028 mmol), a THF solution of HOBT (0.3 mL, 1.5 eq) and a 1M THF/MeCN (1:1) solution of 2-furanethylamine (0.056 mL, 2 eq). The cartridge was capped and let shake at 25° C. for 20 h. Polystryrene isocyanate resin (57 mg, 3 eq) and polystyrene trisamine (39 mg, 6 eq) was added followed by 0.5 mL of THF and the mixture was shaken for 6 h. The suspension was filtered and the filtrate was concentrated to afford 107 (R1=R2=CH$_2$Ph, R3=CH$_2$CH$_2$(C$_4$H$_4$O).

Method A, Step 3:

Compound 107 was treated with a 2N solution of NH$_3$ in MeOH (3 mL) for 1.5 h. The solvent was then removed in vacuo to provide 108 (R1=R2=CH$_2$Ph, R3=CH$_2$CH$_2$ (C$_4$H$_4$O).

Example 2D

Table A

| Compound # | Structure | Exact mass | MS m/e (M + H) |
|---|---|---|---|
| 109 | 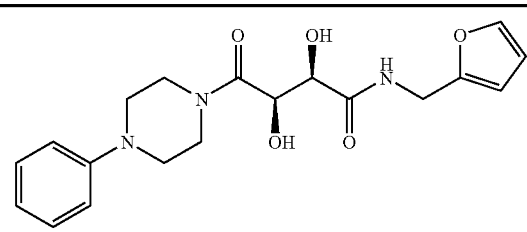 | 373.2 | 374.2 |
| 110 | 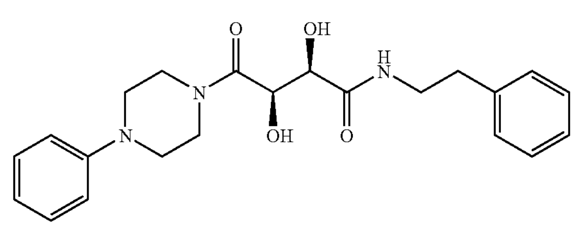 | 397.2 | 398.2 |
| 111 | 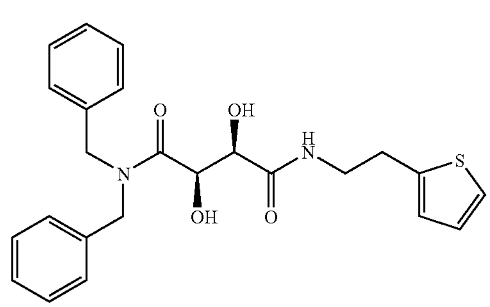 | 438.2 | 439.1 |

-continued

| Compound # | Structure | Exact mass | MS m/e (M + H) |
|---|---|---|---|
| 112 | 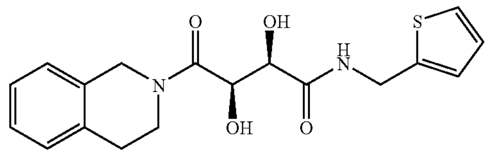 | 360.1 | 361.1 |
| 113 | 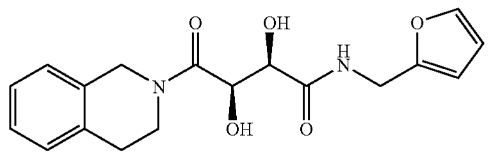 | 344.1 | 345.1 |
| 114 | 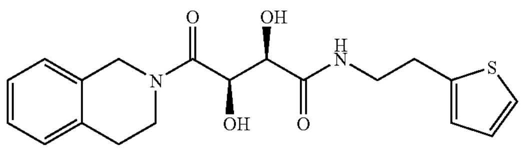 | 374.1 | 375.1 |
| 115 | 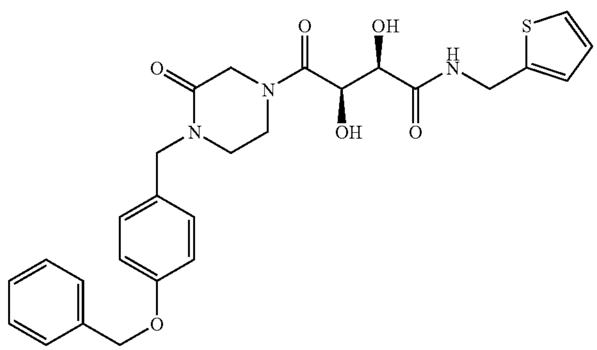 | 523.2 | 524.1 |
| 116 | 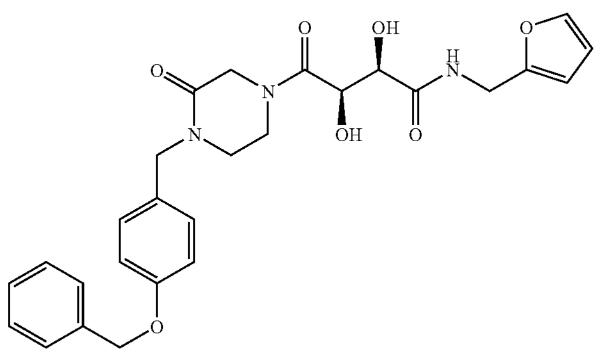 | 507.2 | 508.1 |
| 117 | 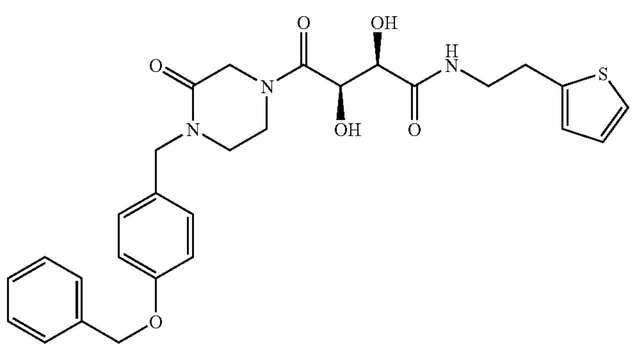 | 537.2 | 538.1 |

-continued

| Compound # | Structure | Exact mass | MS m/e (M + H) |
|---|---|---|---|
| 118A | 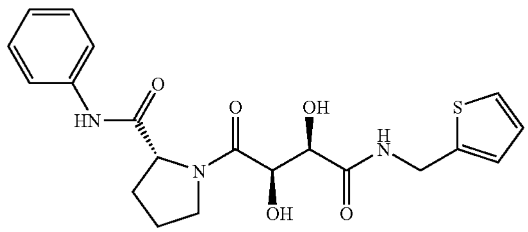 | 417.1 | 418.1 |
| 118B | 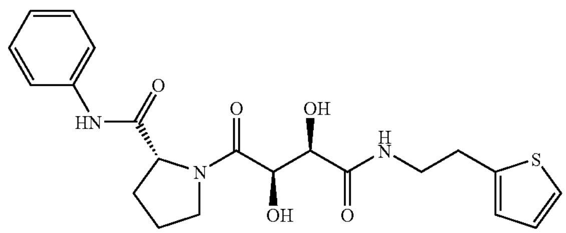 | 431.2 | 432.2 |
| 119 | 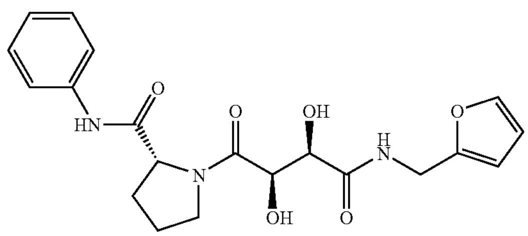 | 401.2 | 402.1 |
| 120 | 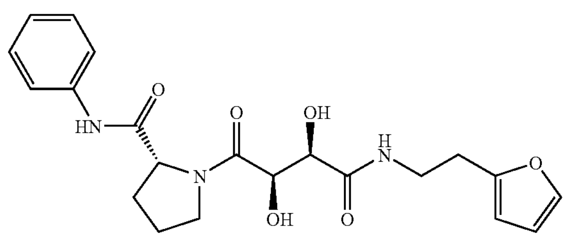 | 415.2 | 416.1 |
| 121 | 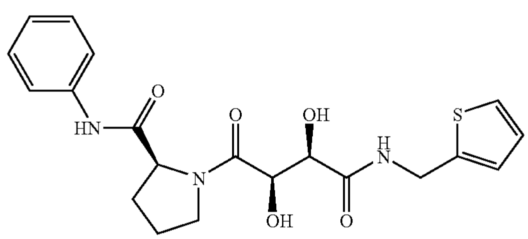 | 417.1 | 418.1 |
| 122 | 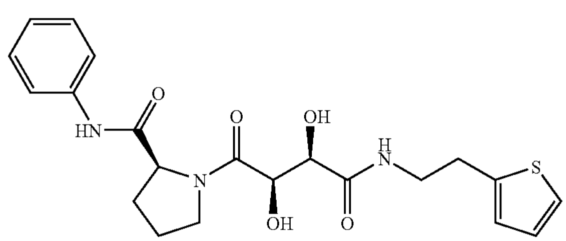 | 431.2 | 432.2 |

-continued

| Compound # | Structure | Exact mass | MS m/e (M + H) |
|---|---|---|---|
| 123 | 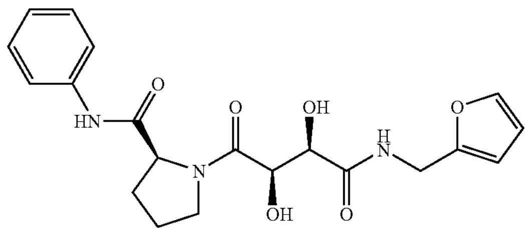 | 401.2 | 402.1 |
| 124 | 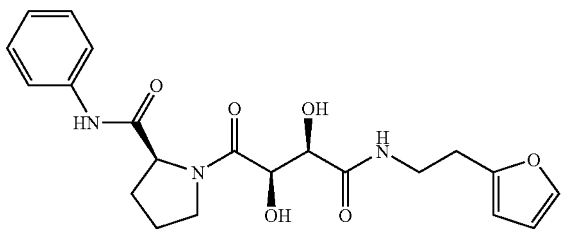 | 415.2 | 416.1 |
| 108 | 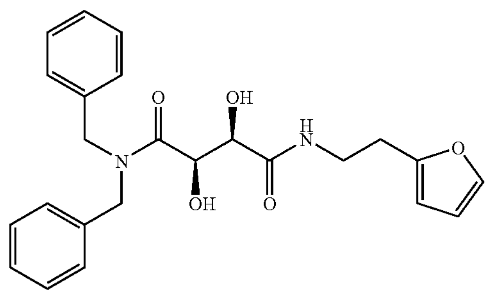 | 422.2 | 423.1 |
| 125 | 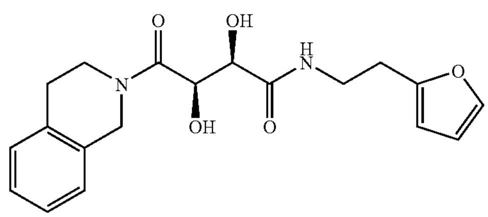 | 358.2 | 359.1 |
| 38 | 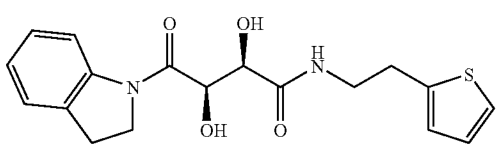 | 360.1 | 361.2 |
| 39 | 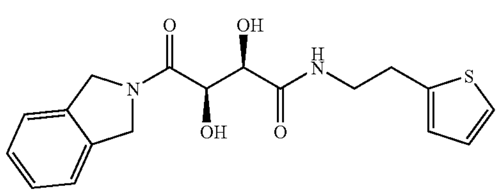 | 360.1 | 361.2 |
| 126 | 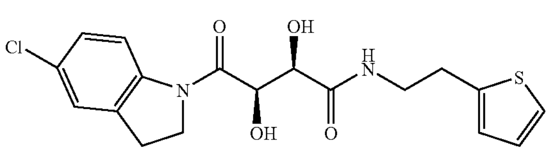 | 394.1 | 395.2 |

-continued
| Compound # | Structure | Exact mass | MS m/e (M + H) |
|---|---|---|---|
| 127 | 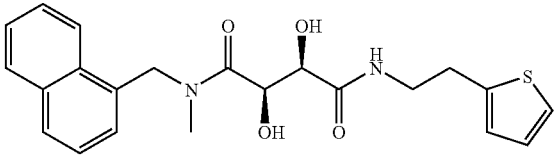 | 412.2 | 413.2 |
| 128 | 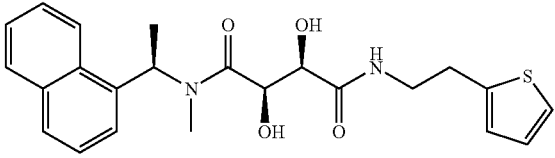 | 426.2 | 427.2 |
| 129 | 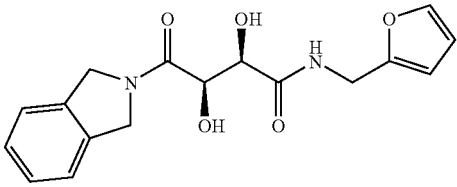 | 330.1 | 331.2 |
| 130 | 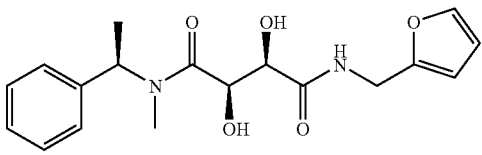 | 346.2 | 347.2 |
| 131 | 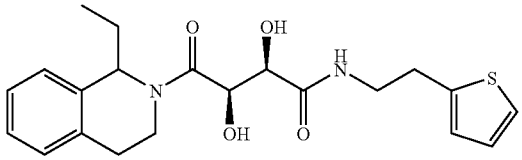 | 402.2 | 403.1 |
| 132 | 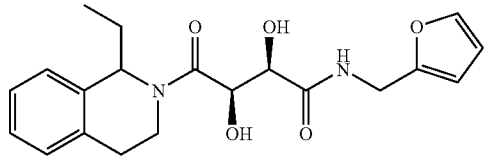 | 372.2 | 373.1 |
| 133 | 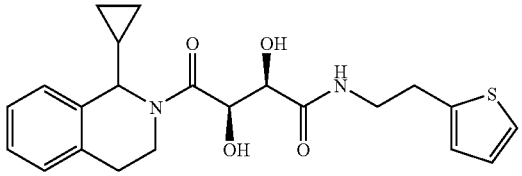 | 414.2 | 415.1 |
| 134 | 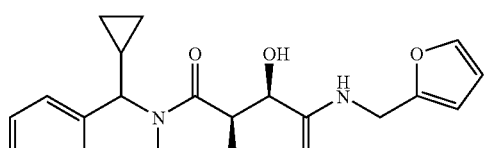 | 384.2 | 385.1 |

-continued

| Compound # | Structure | Exact mass | MS m/e (M + H) |
|---|---|---|---|
| 135 | 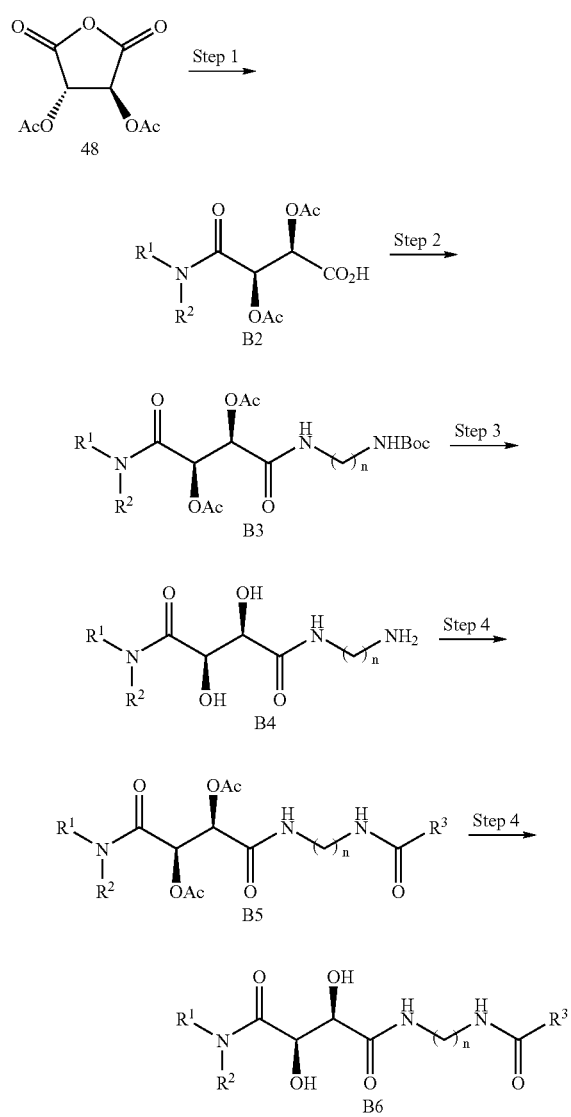 | 456.2 | 457.1 |

Method B

Method B, Step 1:

Compound B2 ($R^1$=$CH_2Ph$, $R^2$=$CH_3$) was prepared from 48 following the procedure described in Example 4A Part C.

Method B, Step 2:

To a DMF (40 mL) solution of B2 (2.0 g, 5.93 mmol), HOBT (880 mg, 6.52 mmol), and N-Boc-1,3-propylenediamine (1.14 g, 6.52 mmol) was added EDCI (1.48 g, 7.61 mmol) at 25° C. under $N_2$. After stirring for 20 h, 1N HCl was added, the products were extracted with ethyl acetate (3×), combined, then washed with sat. $NaHCO_3$, water (3×), and dried over $MgSO_4$. The products were then filtered and concentrated in vacuo to give B3 ($R^1$=$CH_2Ph$, $R^2$=$CH_3$, n=3).

Method B, Step 3:

To a MeCN (30 mL) solution of B3 (1.18 g, 2.4 mmol) at 25° C. was added 20 mL of a 4N solution of HCl in dioxane. The solution was capped and stirred at 25° C. for 2.5 h. The solvent was then removed in vacuo. The product was then dissolved in 45 mL of THF/MeCN/DMF (4:4:1) and polystyrene $NEt_2$ resin (4.5 g, 14.4 mmol) added. After stirring for 1.5 h, the solution was filtered off and the resin washed with THF:MeCN (1:1). The filtrates were then diluted to 120 mL with additional THF/MeCN (1:1) and B4 ($R^1$=$CH_2Ph$, $R^2$=$CH_3$, n=3) was used in the preparation of the following library:

Method B, Step 4:

Polystyrene EDC resin (30 mg, 0.045 mmol) was added to 96-wells of a deep well polypropylene microtiter plate followed by a MeCN/THF/DMF (6:6:1) stock solution (1 mL) of B4 (0.015 mmol) and HOBT (0.0225 mmol). Then 1M stock solutions of each of the individual acids ($R^1$-96COOH) (0.023 mL, 0.021 mmol) were added to the wells, which was then sealed and shaken at 25° C. for 20 h. The solutions were filtered through a polypropylene frit into a 2nd microtiter plate containing polystyrene isocyanate resin (3 equivalents, 0.045 mmol) and polystyrene trisamine resin (6 equivalents, 0.09 mmol). After the top plate was washed with MeCN (0.5 mL), the plate was removed, the bottom microtiter plate sealed and shaken at 25° C. for 16 h. Then the solutions were filtered through a polypropylene frit into a 96-well collection plate. The wells of the top plate were then washed with MeCN (0.5 mL), and the plate removed. Then the resultant solutions in the collection plate were transferred into vials and the solvents removed in vacuo via a SpeedVac to provide amides B5.

Method B, Step 5:

Compounds B6 were prepared from B5 following the procedure described in Method A, Step 3 (see above).

Example 2D

Table B

| Compound # | Structure | Exact mass | MS m/e (M + H) |
|---|---|---|---|
| 136 | 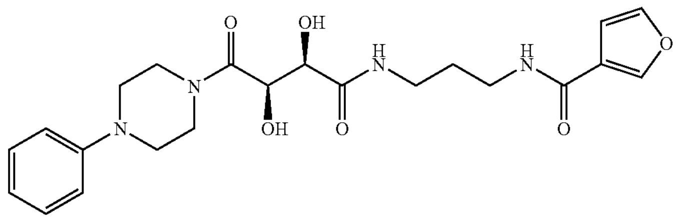 | 444.2 | 445.2 |
| 137 | 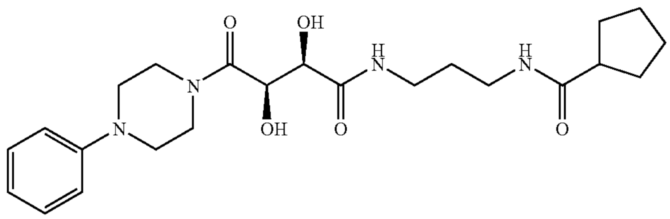 | 446.3 | 447.3 |
| 138 | 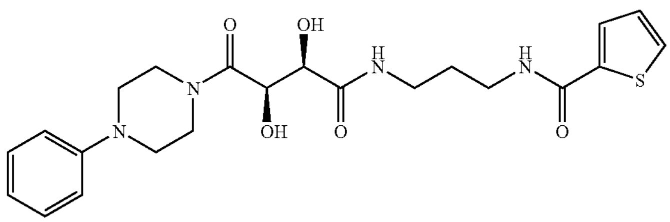 | 460.2 | 461.3 |
| 139 | 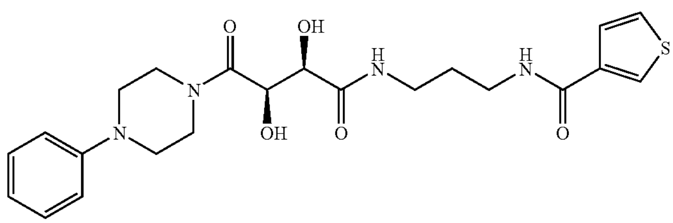 | 460.2 | 461.3 |
| 140 | 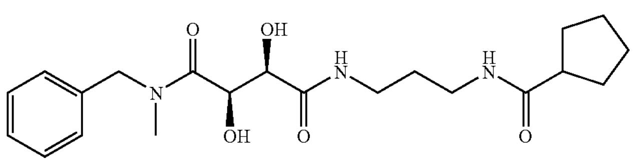 | 405.2 | 406.2 |
| 141 | 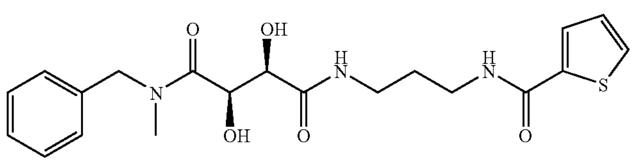 | 419.2 | 420.2 |
| 142 | 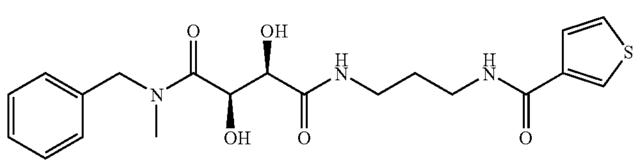 | 419.2 | 420.2 |

-continued

| Compound # | Structure | Exact mass | MS m/e (M + H) |
|---|---|---|---|
| 143 | 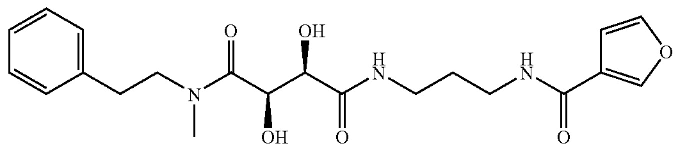 | 417.2 | 418.2 |
| 144 | 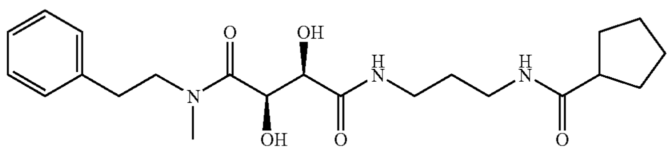 | 419.2 | 420.2 |
| 145 | 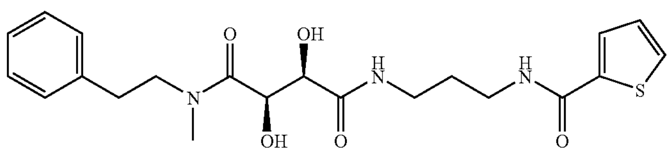 | 433.2 | 434.2 |
| 146 | 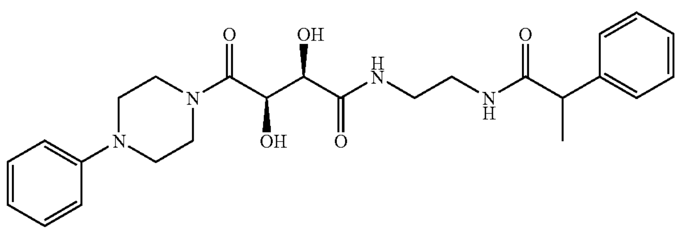 | 468.2 | 469.3 |
| 147 | 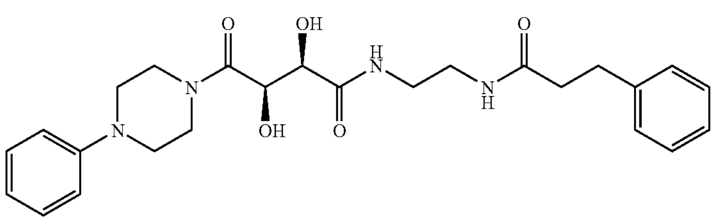 | 468.2 | 469.3 |
| 148 | 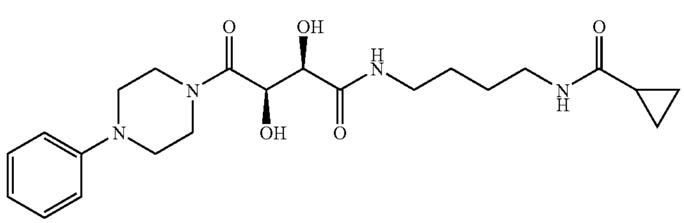 | 432.2 | 433.2 |
| 149 | 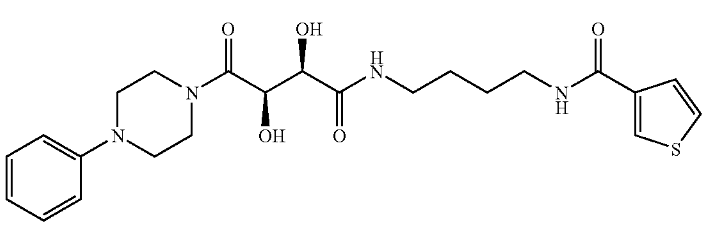 | 474.2 | 475.3 |

| Compound # | Structure | Exact mass | MS m/e (M + H) |
|---|---|---|---|
| 150 | 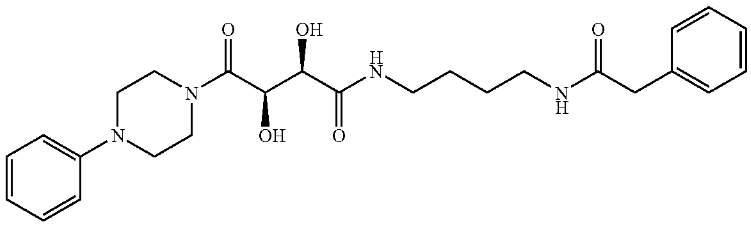 | 482.3 | 483.3 |
| 151 | 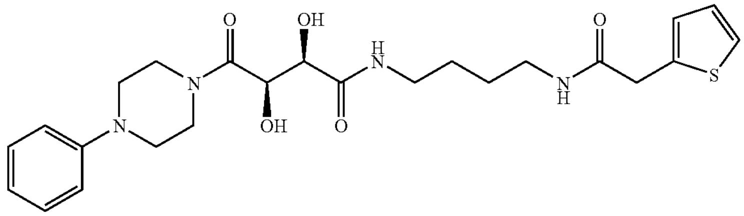 | 488.2 | 489.3 |
| 152 | 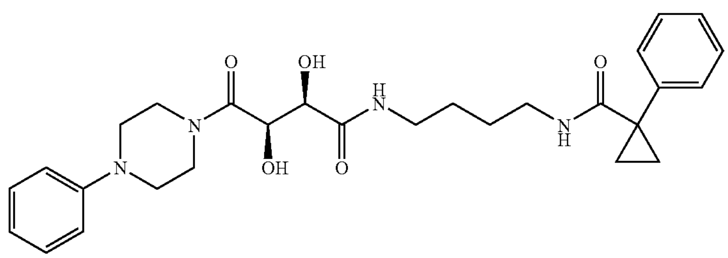 | 508.3 | 509.3 |

Method C

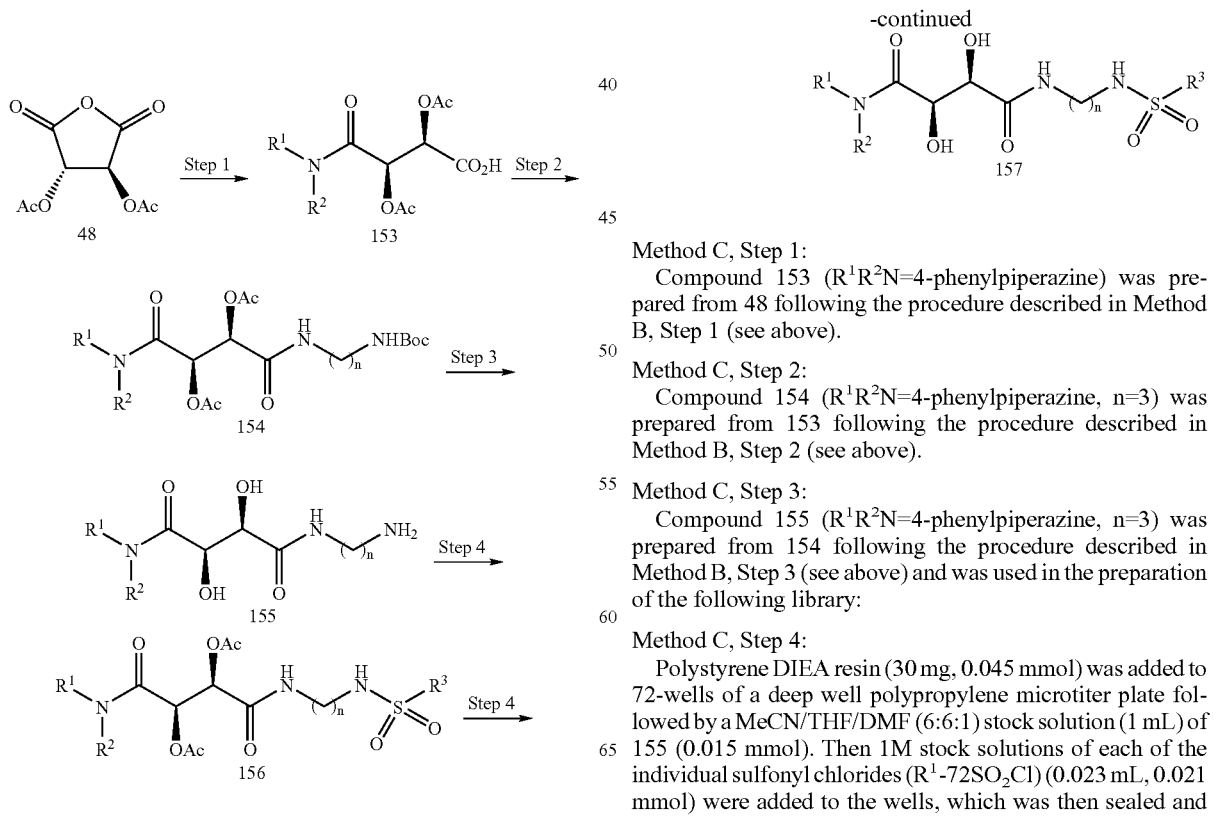

Method C, Step 1:

Compound 153 ($R^1R^2N$=4-phenylpiperazine) was prepared from 48 following the procedure described in Method B, Step 1 (see above).

Method C, Step 2:

Compound 154 ($R^1R^2N$=4-phenylpiperazine, n=3) was prepared from 153 following the procedure described in Method B, Step 2 (see above).

Method C, Step 3:

Compound 155 ($R^1R^2N$=4-phenylpiperazine, n=3) was prepared from 154 following the procedure described in Method B, Step 3 (see above) and was used in the preparation of the following library:

Method C, Step 4:

Polystyrene DIEA resin (30 mg, 0.045 mmol) was added to 72-wells of a deep well polypropylene microtiter plate followed by a MeCN/THF/DMF (6:6:1) stock solution (1 mL) of 155 (0.015 mmol). Then 1M stock solutions of each of the individual sulfonyl chlorides ($R^1$-72SO$_2$Cl) (0.023 mL, 0.021 mmol) were added to the wells, which was then sealed and shaken at 25° C. for 20 h. The solutions were filtered through a polypropylene frit into a 2nd microtiter plate containing polystyrene isocyanate resin (3 equivalents, 0.045 mmol) and polystyrene trisamine resin (6 equivalents, 0.09 mmol). After the top plate was washed with MeCN (0.5 mL), the plate was removed, the bottom microtiter plate sealed and shaken at 25° C. for 16 h. Then the solutions were filtered through a polypropylene frit into a 96-well collection plate. The wells of the top plate were then washed with MeCN (0.5 mL), and the plate removed. Then the resultant solutions in the collection plate were transferred into vials and the solvents removed in vacuo via a SpeedVac to provide sulfonamides 156.

Method C, Step 5:

Compounds 157 were prepared from 156 following the procedure described in Method A, Step 3 (see above).

Example 2D

Table C

| Compound # | Structure | Exact mass | MS m/e (M + H) |
|---|---|---|---|
| 157 | 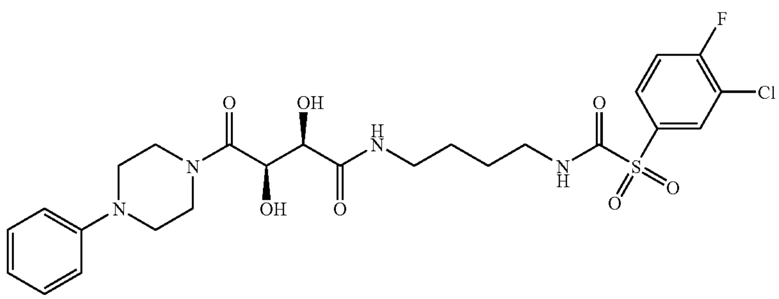 | 542.2 | 543.3 |

These compounds were prepared using Method A:

Example 2D

Table D

| Compound # | Structure | Exact mass | MS m/z (M + H) |
|---|---|---|---|
| 158 | 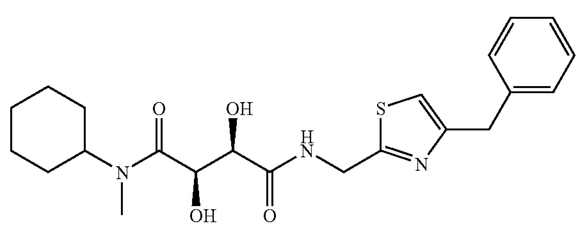 | 431.2 | 432.2 |
| 159 | 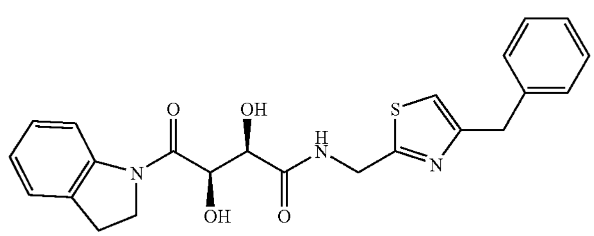 | 437.1 | 438.2 |

-continued

| Compound # | Structure | Exact mass | MS m/z (M + H) |
|---|---|---|---|
| 160 | 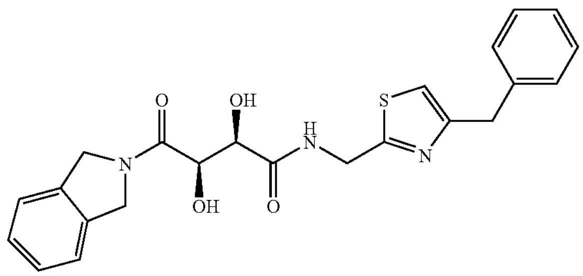 | 437.1 | 438.2 |
| 161 | 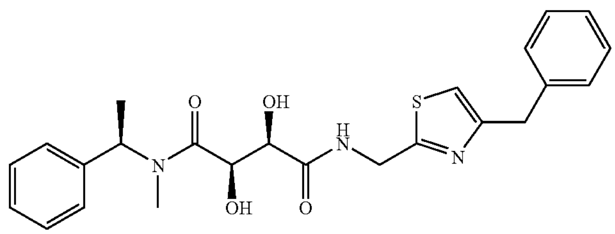 | 453.2 | 454.3 |
| 162 | 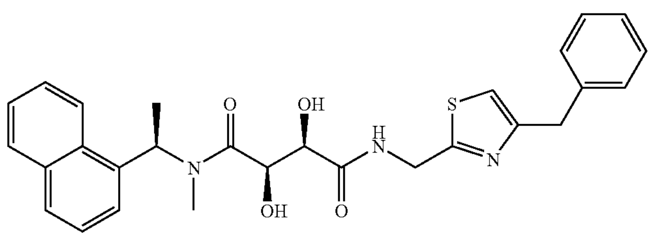 | 503.2 | 504.3 |
| 163 | 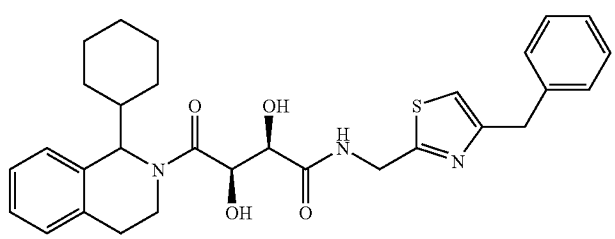 | 533.2 | 534.2 |
| 164 | 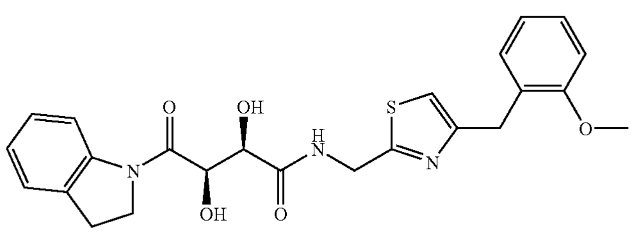 | 467.2 | 468.3 |
| 165 | 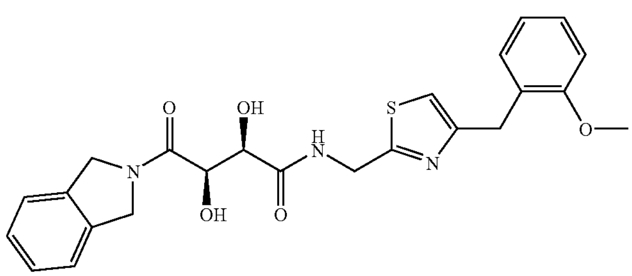 | 467.2 | 468.3 |

| Compound # | Structure | Exact mass | MS m/z (M + H) |
|---|---|---|---|
| 166 | 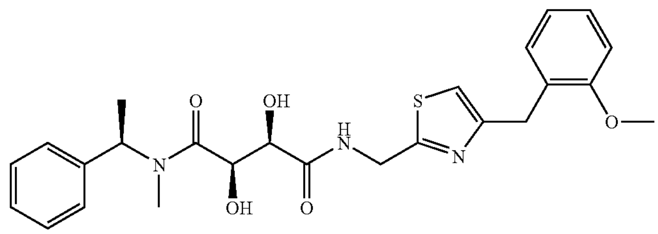 | 483.2 | 484.3 |
| 167 | 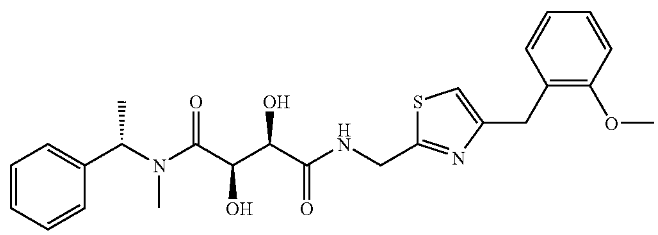 | 483.2 | 484.3 |
| 168 | 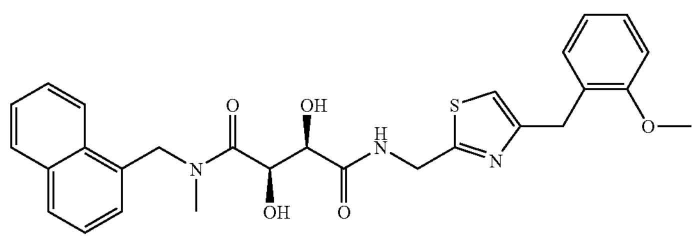 | 519.2 | 520.3 |
| 169 | 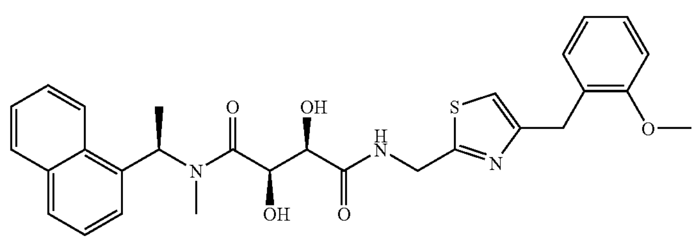 | 533.2 | 534.3 |
| 170 | 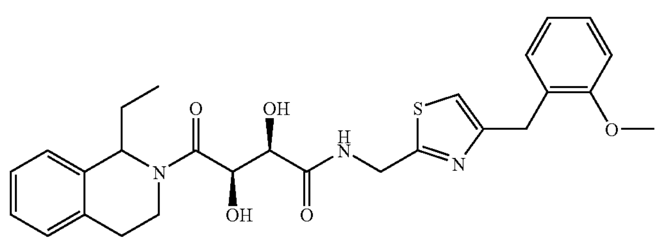 | 509.2 | 510.3 |
| 171 | 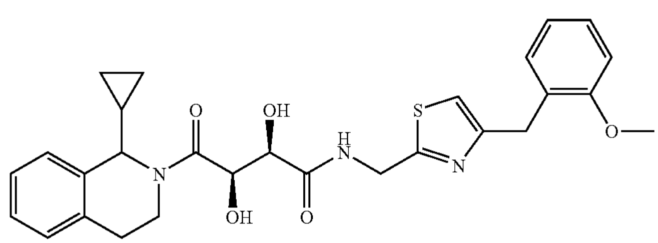 | 521.2 | 522.3 |

-continued
| Compound # | Structure | Exact mass | MS m/z (M + H) |
|---|---|---|---|
| 172 | 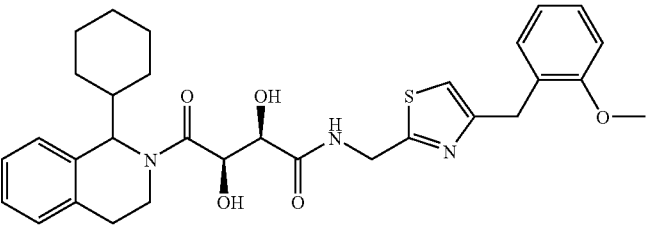 | 563.2 | 564.3 |
These compounds were prepared using Method A:
Example 2D
Table E
| Compound # | Structure | Exact mass | MS m/e (M + H) |
|---|---|---|---|
| 173 | 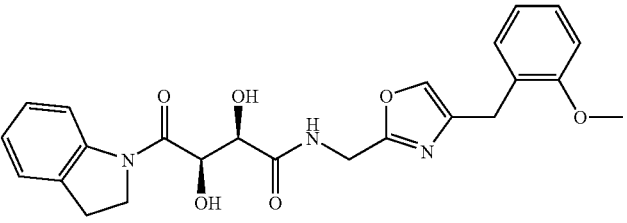 | 451.2 | 452.3 |
| 174 | 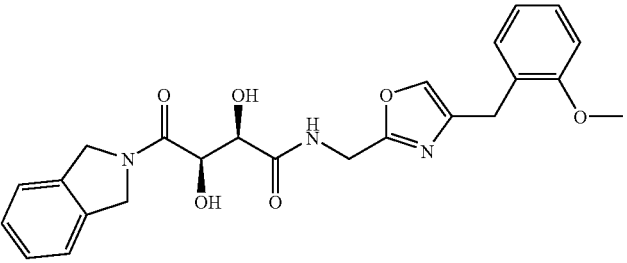 | 451.2 | 452.3 |
| 175 | 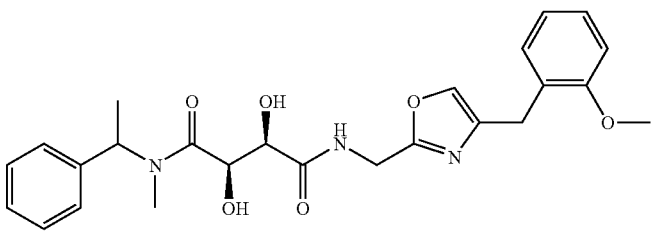 | 467.2 | 468.3 |
| 176 | 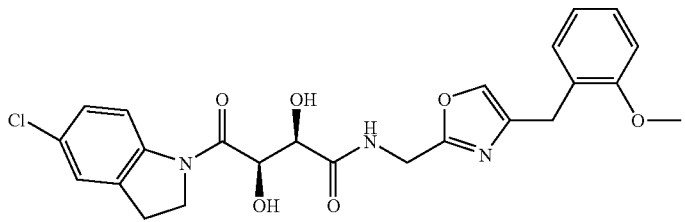 | 485.1 | 486.3 |

-continued

| Compound # | Structure | Exact mass | MS m/e (M + H) |
|---|---|---|---|
| 177 | 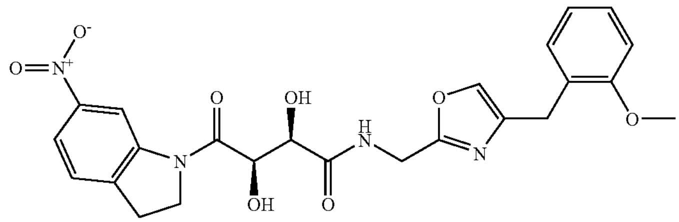 | 496.2 | 497.3 |
| 178 | 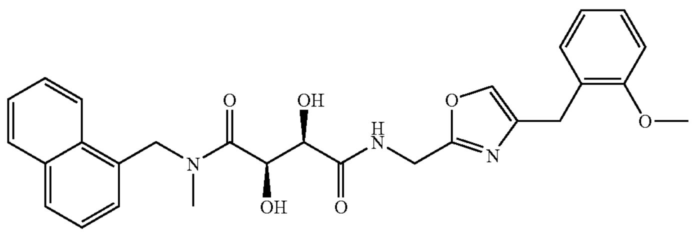 | 503.2 | 504.3 |
| 179 | 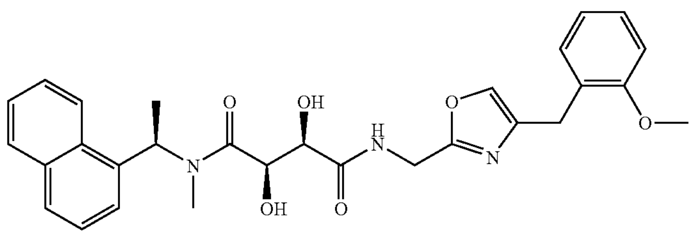 | 517.2 | 518.3 |
| 180 | 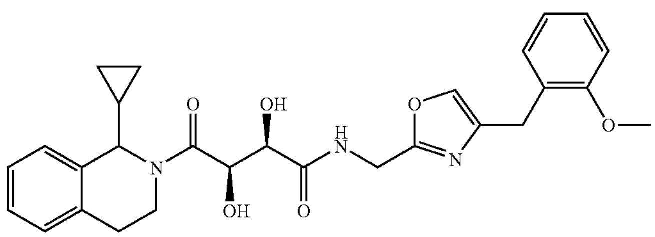 | 505.2 | 506.3 |
| 181 | 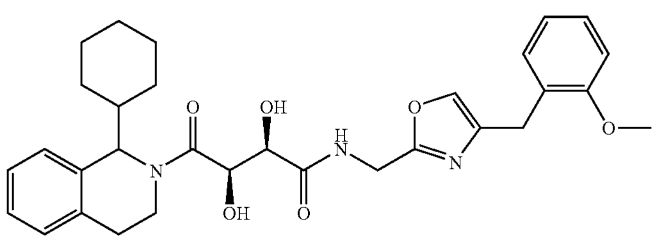 | 547.3 | 548.3 |
| 182 | 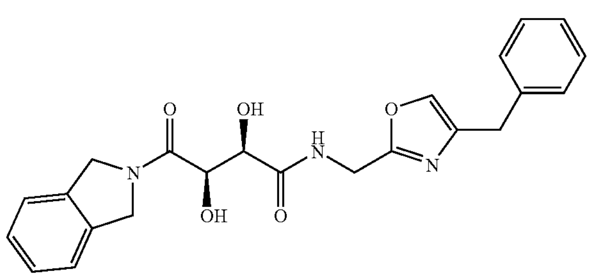 | 421.2 | 422.2 |

Example 3

Heteroaryl Biaryl Compounds

A compound precursor may be prepared such that the synthesis of direct analogs is facilitated. Examples of schemes for biaryl synthesis are listed below. Aryl halides and 'pseudo-halides' (i.e. triflates) are known to react with boronic acids under a variety of established conditions (*Top. Curr. Chem.* 2002, 219, 1249). A variety of bases for this reaction are known in the literature, including sodium carbonate, potassium carbonate, cesium carbonate, potassium t-butoxide, sodium t-butoxide, TEA, DIEA, potassium fluoride, and potassium phosphate. For most applications potassium phosphate was preferred and gave acceptable yields and chemoselectivity. A number of solvents have also been used in the literature for Suzuki reactions, including THF, dioxane, NMP, DMF, DME, DMA, toluene, and water. In general we have found that THF or dioxane are preferred solvents. Solvents may also be mixed in various proportions to enhance reactivity and/or chemoselectivity. Palladium sources for this reaction are numerous as well, including $Pd(TPP)_4$, $Pd(OAc)_2$, $PdCl_2(TPP)_2$, $PdCl_2(dppf)$, $Pd_2(dba)_3$. In general $PdCl_2(dppf)$ was found to be a preferred palladium source.

Example 3A

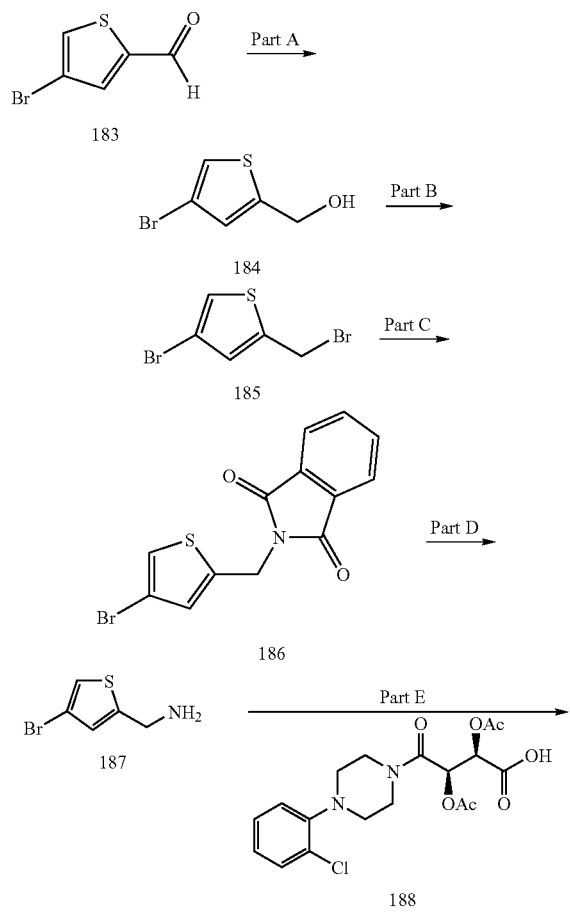

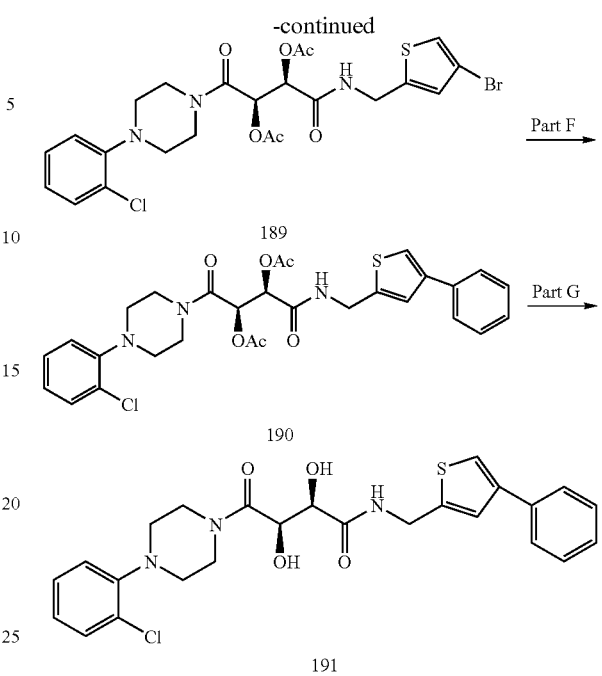

Part A:
To an ice cold methanol (100 mL) solution of 4-bromothiophene-2-carbaldehyde (183) (90%, 11.1 g, 58.1 mmol, 1.00 equiv) was added sodium borohydride in portions (2.20 g, 58.1 mmol, 1.00 equiv) over ca. 10 minutes. The cooling bath was removed and the reaction solution was aged 30 min. The reaction was quenched at rt by the addition of acetone (until evolution of gas ceased), concentrated, and partitioned between ethyl acetate and 0.1 N HCl. The organic phase was washed with water, brine, dried (sodium sulfate), filtered, and then concentrated to give 184 as an orange oil (10.5 g, 95%) that was used without further purification. $^1$H NMR (400 MHz, $CDCl_3$) δ 7.18 (s, 1H), 6.93 (s, 1H), 4.81 (s, 2H).

Part B:
To 184 (4.38 g, 22.7 mmol) in toluene (25 mL) was added phosphorous tribromide (2.36 mL, 25 mmol). The reaction mixture was heated in an oil bath at 90° C. for 15 minutes. After cooling to room temperature the reaction mixture was poured over ice and extracted with ethyl acetate. The combined organic layer was washed with water (2×), saturated sodium bicarbonate solution (1×) and saturated sodium chloride solution, dried over magnesium sulfate and concentrated to afford 185 as a light brown oil (5.51 g, 95%). The material was used without further purification.
$^1$H NMR (400 MHz, $CDCl_3$) δ 7.21 (s, 1H), 7.03 (s, 1H), 4.66 (s, 2H).

Part C:
To 185 (5.51 g, 21.5 mmol) in DMF (20 mL) was added phthalimide (3.80 g, 25.8 mmol) and cesium carbonate (7.72 g, 23.7 mmol). The reaction mixture was stirred overnight at room temperature. The reaction mixture was filtered and the filtrate was concentrated. The residue was dissolved in ethyl acetate and water. The organic layer was separated, washed with saturated sodium chloride solution, dried over sodium sulfate and concentrated to afford a brown solid. Recrystallization from ~30% ethyl acetate/hexanes afforded 186 as a peach solid (6.38 g, 2 crops, 92%). $^1$H NMR (400 MHz, $CDCl_3$) δ 7.86 (m, 2H), 7.72 (m, 2H), 7.11 (s, 1H), 7.07 (s, 1H), 4.97 (s, 2H). HPLC-MS $t_R$=2.02 min ($UV_{254\ nm}$); mass calculated for formula $C_{13}H_8BrNO_2S$ 321.0, observed LCMS m/z 322.0 (M+H).

Part D:

A suspension of 186 (5.76 g, 17.8 mmol) and hydrazine hydrate (3.5 mL, 72 mmol) in ethanol (50 mL) was heated to reflux. The suspension cleared upon heating before a thick white precipitate formed. The reaction mixture was heated for 1 hour and cooled. The white precipitate was broken up by the addition of ethanol (50 mL) and sonication of the mixture. The precipitate was removed by filtration and the solids were thoroughly washed with ethanol and ethyl acetate. The filtrate was concentrated in vacuo. The residue was dissolved in ethyl acetate and water. The layers were separated. The organic layer was washed with saturated sodium chloride solution, dried over sodium sulfate and concentrated to afford 187 as an orange-brown oil (2.66 g, 78%). $^1$H NMR (400 MHz, CDCl$_3$) δ 7.10 (s, 1H), 6.84 (s, 1H), 4.04 (s, 2H). HPLC-MS $t_R$=0.58 min (UV$_{254\ nm}$); Mass calculated for formula C$_5$H$_6$BrNS 190.9, observed LCMS m/z 192.0 (M+H).

Part E:

Following the procedure described in Example 1 part A: To 188 (prepared as described in Example 4 Part C from (+)-diacetyl-L-tartaric anhydride (48) and 2-chlorophenylpiperazine) (916 mg, 2.22 mmol) in DMF (5 mL) was added 187 (502 mg, 2.61 mmol), DIEA (850 μL, 4.88 mmol) and HATU (928 mg, 2.44 mmol). Purification by column chromatography (SiO$_2$, 20% to 50% EtOAc/DCM) afforded 189 as an off-white foam (652 mg, 50%). $^1$H NMR (400 MHz, CDCl$_3$) δ 7.37 (dd, 1H, J=1.2, 7.6 Hz), 7.25 (dt, 1H, J=1.2, 7.6 Hz), 7.14 (d, 1H, J=1.2 Hz), 7.03 (m, 2H), 6.92 (d, 1H, J=1.2 Hz), 6.74 (m, 1H, NH), 5.92 (d, 1H, J=3.6 Hz), 5.70 (d, 1H, J=4.0 Hz), 4.73 (dd, 1H, J=6.4, 15.2 Hz), 4.50 (dd, 1H, J=5.6, 15.6 Hz), 3.83 (m, 3H), 3.65 (m, 1H), 3.20-3.00 (m, 4H), 2.21 (s, 3H), 2.11 (s, 3H); Mass calculated for formula C$_{23}$H$_{25}$BrClN$_3$O$_6$S 585.0, observed LCMS m/z 586.1 (M+H).

Part F:

To 189 (59 mg, 0.1 mmol), phenyl boronic acid (13 mg, 0.11 mmol), potassium phosphate (42 mg, 0.2 mmol), and PdCl$_2$(dppf) (4 mg, 0.005 mmol) was added dioxane (2 mL). The reaction mixture was flushed with argon and heated to 80° C. overnight. The reaction mixture was cooled, poured into water and extracted with EtOAc. The combined organics were washed with brine, dried over sodium sulfate and concentrated. Purification by column chromatography (SiO$_2$, 20% EtOAc/DCM) afforded 190 as an off-white foam (36 mg, 58%, 94% purity). HPLC-MS $t_R$=5.61 min (UV$_{254\ nm}$, 10 min.); mass calculated for formula C$_{29}$H$_{30}$ClN$_3$O$_6$S 583.2, observed LCMS m/z 584.2 (M+H).

Part G:

To 190 (36 mg, 0.062 mmol) in methanol was added 0.5 M sodium methoxide in methanol (6 μL, 0.003 mmol). The reaction mixture was stirred for 1.5 hours at room temperature, quenched with 0.1 N HCl and concentrated. Purification by reverse-phase prep-LC afforded 191 as a white solid (3.2 mg, 10%). $^1$H NMR (400 MHz, CDCl$_3$) δ 7.55 (dd, 2H, J=1.2, 8.4 Hz), 7.40 to 7.20 (m, 9H), 7.09 (m, 1H, NH), 4.91 (d, 1H, J=2.4 Hz), 4.70 (m, 2H), 4.33 (d, 1H, J=2.0 Hz), 4.00 (m, 2H), 3.85 (m, 2H), 3.20 (m, 4H); HPLC-MS $t_R$=1.94 min (UV$_{254\ nm}$); Mass calculated for formula C$_{25}$H$_{26}$ClN$_3$O$_4$S 499.1, observed LCMS m/z 500.2 (M+H).

| Compound # | Structure | Exact mass | MS m/e (M + H) |
|---|---|---|---|
| 192 | 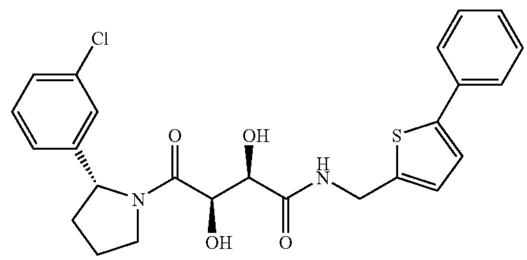 | 484.1 | 485.0 |

Example 3B

3-Pyridyl-Biaryl

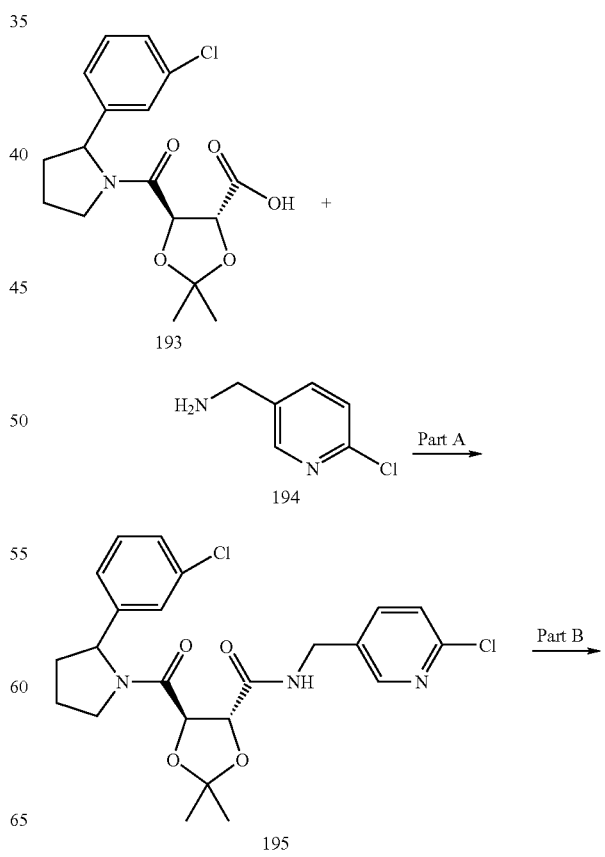

-continued

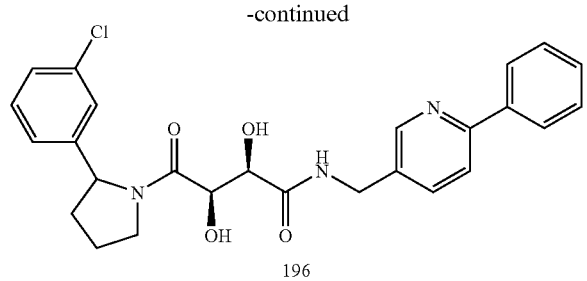

196

Part A:

To 193 (prepared as described in Example 1) (1.5 g, 4.24 mmol) in DMF (10 mL) was added 194 (0.725 g, 5.09 mmol) and HATU (1.94 g, 5.09 mmol). The reaction mixture was stirred overnight at room temperature. The reaction mixture was diluted with ethyl acetate, washed with saturated sodium bicarbonate and brine, dried over sodium sulfate and concentrated. Purification by column chromatography (SiO$_2$, 80% ethyl acetate/hexanes) afforded 195 as a colorless oil (1.73 g, 86%). HPLC-MS $t_R$=1.92 and 1.97 min (UV$_{254\ nm}$); Mass calculated for formula $C_{23}H_{25}Cl_2N_3O_4$ 477.1, observed LCMS m/z 478.1 (M+H).

Part B:

Step 1: To phenyl boronic acid (10 mg, 0.084 mmol), potassium phosphate (36 mg, 0.168 mmol) and PdCl$_2$(dppf) (3.1 mg, 10 mol %) under argon in a 4-mL vial was added 195 (20 mg, 0.042 mmol) in dioxane (0.5 mL). The reaction mixture was heated at 100° C. for 16 hours. The reaction mixture was cooled to room temperature, diluted with ethyl acetate and filtered through celite. The filtrate was concentrated. HPLC-MS $t_R$=2.01 min (UV$_{254\ nm}$); Mass calculated for formula $C_{29}H_{30}ClN_3O_4$ 519.2, observed LCMS m/z 520.2 (M+H).

Step 2: The crude material from Step 1 was dissolved in 80:20 TFA:water (1 mL) at 0° C. and stirred at room temperature for 2 hours. The reaction mixture was quenched with 1:1 water:acetonitrile (2 mL) and concentrated. Purification by reverse phase prep-LC afforded 196 as a solid after lypholization. HPLC-MS $t_R$=3.54 min (UV$_{254\ nm}$, 10 min); Mass calculated for formula $C_{26}H_{26}ClN_3O_4$ 479.2, observed LCMS m/z 480.2 (M+H).

| Compound # | Structure | Exact mass | MS m/z (M + H) |
|---|---|---|---|
| 197 | 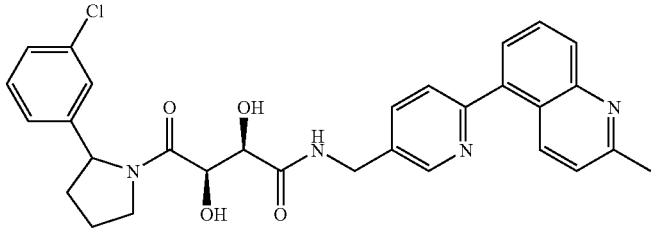 | 544.2 | 454.2 |
| 198 | 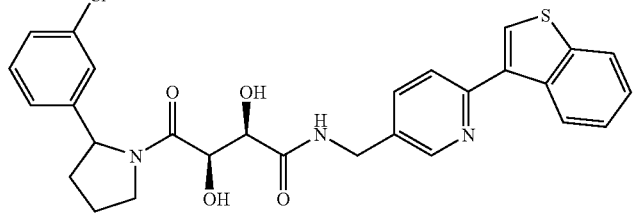 | 535.1 | 536.2 |
| 199 | 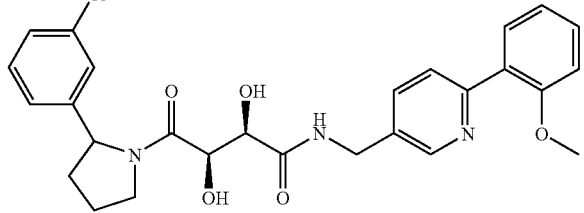 | 509.2 | 510.1 |

-continued

| Compound # | Structure | Exact mass | MS m/z (M + H) |
|---|---|---|---|
| 200 | 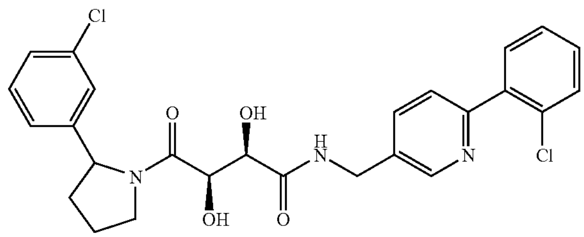 | 513.1 | 514.2 |
| 201 | 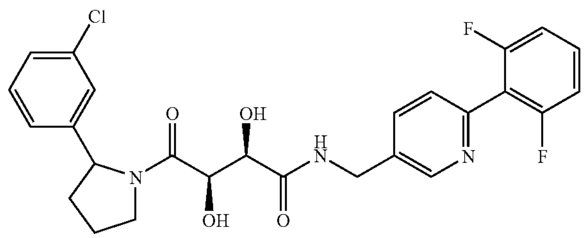 | 515.1 | 516.2 |
| 202 | 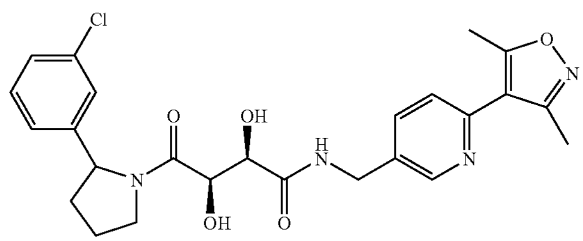 | 498.2 | 499.2 |
| 203 | 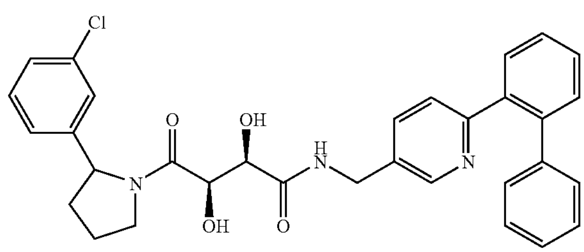 | 555.2 | 556.2 |
| 204 | 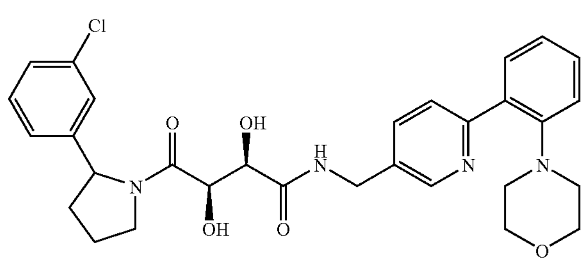 | 564.2 | 565.2 |
| 205 | 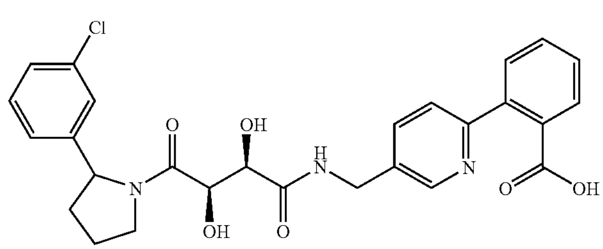 | 523.2 | 524.2 |

-continued
| Compound # | Structure | Exact mass | MS m/z (M + H) |
|---|---|---|---|
| 206 | 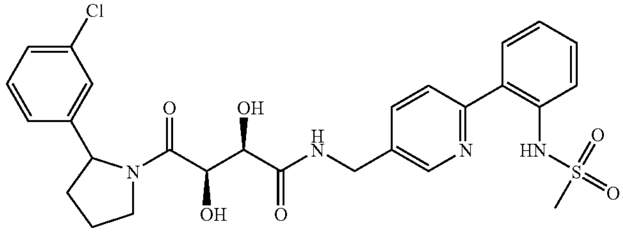 | 572.2 | 573.2 |
| 207 | 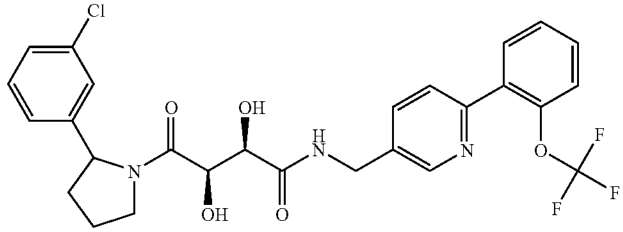 | 563.1 | 564.2 |
| 208 | 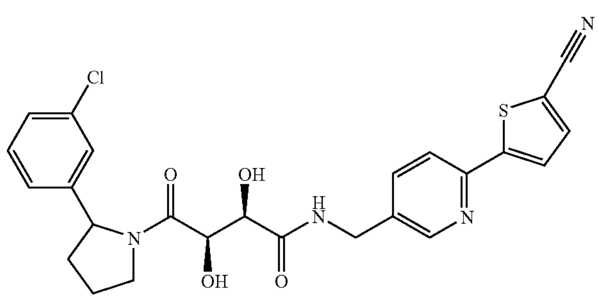 | 510.0 | 511.1 |
Example 3C
2-Pyridyl-Biaryl
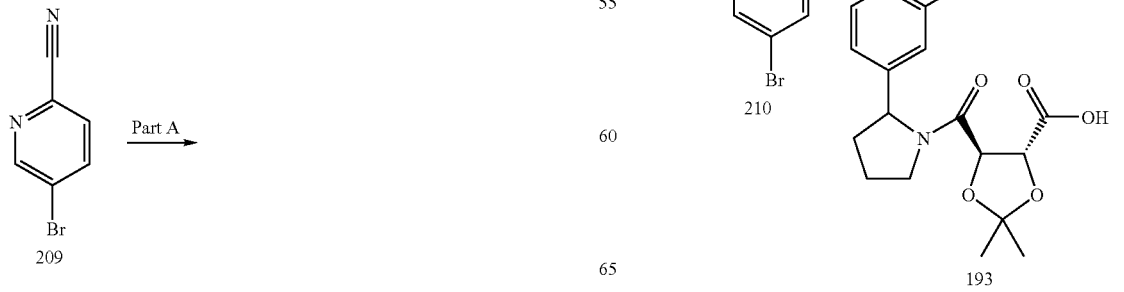

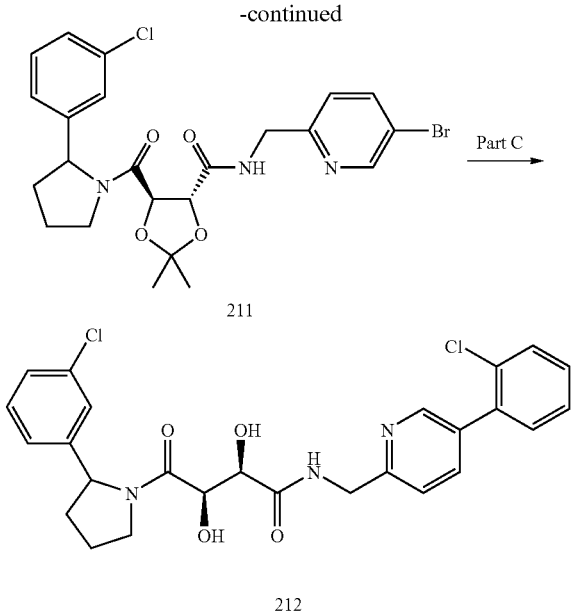

Part A:

To 5-bromo-pyridine-2-carbonitrile (209) (1.0 g, 5.46 mmol) in tetrahydrofuran (10 mL) at −78° C. was added lithium aluminum hydride (1.0 M, 13.66 mL, 13.66 mmol). The reaction was stirred for 2 hours at −78° C. The mixture was quenched at −78° C. with 10:1 THF:water. The mixture was warmed to room temperature, diluted with ethyl acetate and stirred with 1.0 N sodium hydroxide for 10 minutes. The reaction mixture was filtered through celite and the layers were separated. The organic layer was washed with 1.0 N sodium hydroxide and brine, dried over sodium sulfate and concentrated to afford 210 as an oil (600 mg). The material was used without further purification.

Part B:

To 193 (1.13 g, 3.2 mmol) in DMF (10 mL) was added 210 (0.600 g, 3.2 mmol) and HATU (1.34 g, 3.52 mmol). The reaction mixture was stirred for 5 hours at room temperature. The reaction mixture was diluted with ethyl acetate, washed with saturated sodium bicarbonate and brine, dried over sodium sulfate and concentrated to afford 211 as an oil (380 mg). HPLC-MS $t_R$=2.00 and 2.05 min (UV$_{254\ nm}$); Mass calculated for formula $C_{23}H_{25}BrClN_3O_4$ 521.1, observed LCMS m/z 522.1 (M+H).

Part C:

Step 1: To 2-chlorophenyl boronic acid (24 mg, 0.152 mmol), potassium phosphate (65 mg, 0.306 mmol) and PdCl$_2$(dppf) (3.1 mg, 5 mol %) under argon in a 4-mL vial was added 211 (40 mg, 0.076 mmol) in dioxane (0.5 mL). The reaction mixture was heated at 100° C. for 16 hours. The reaction mixture was cooled to room temperature, diluted with ethyl acetate and filtered through celite. The filtrate was concentrated.

Step 2: The crude material from Step 1 was dissolved in 80:20 TFA:water (1 mL) at 0° C. and stirred at room temperature for 2 hours. The reaction mixture was quenched with 1:1 water:acetonitrile (2 mL) and concentrated. Purification by reverse phase prep-LC afforded 212 as a solid after lypholization. HPLC-MS $t_R$=4.10 and 4.13 min (UV$_{254\ nm}$, 10 min); Mass calculated for formula $C_{26}H_{25}Cl_2N_3O_4$ 513.2, observed LCMS m/z 514.2 (M+H).

The following compounds were prepared using the above procedures.

| Compound # | Structure | Exact mass | MS m/e (M + H) |
|---|---|---|---|
| 213 | 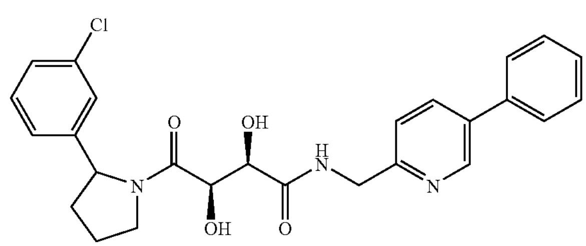 | 479.2 | 480.1 |
| 214 | 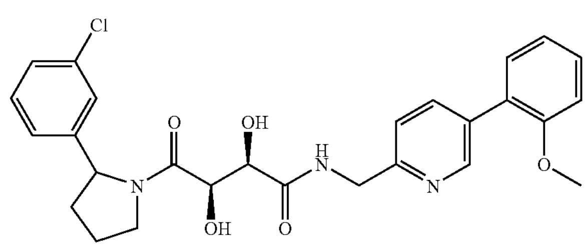 | 509.2 | 510.1 |

-continued

| Compound # | Structure | Exact mass | MS m/e (M + H) |
|---|---|---|---|
| 215 | 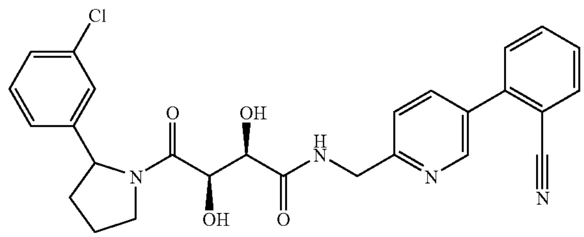 | 504.2 | 505.1 |
| 216 | 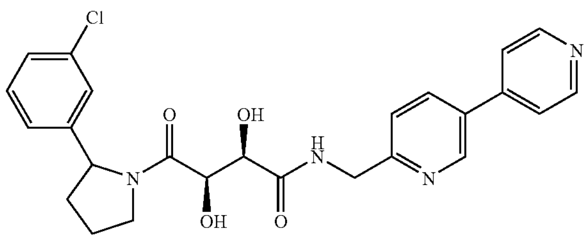 | 480.2 | 481.1 |
| 217 | 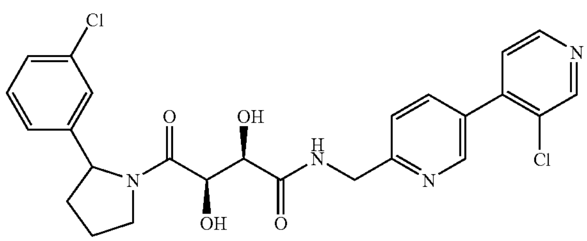 | 514.1 | 515.0 |
| 218 | 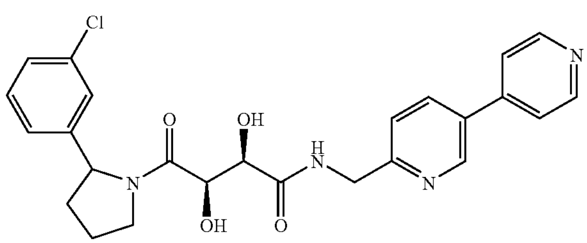 | 481.2 | 482.2 |
| 219 | 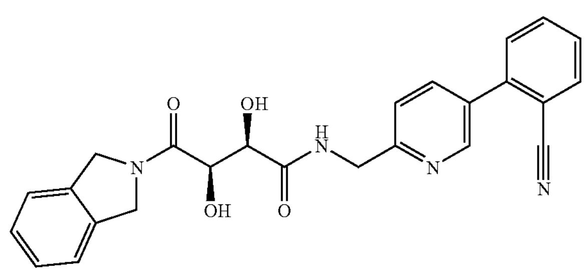 | 442.2 | 443.2 |
| 220 | 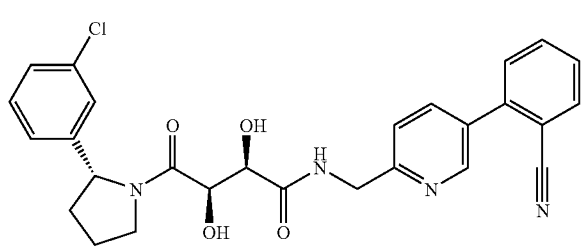 | 504.2 | 505.1 |

-continued

| Compound # | Structure | Exact mass | MS m/e (M + H) |
|---|---|---|---|
| 221 | 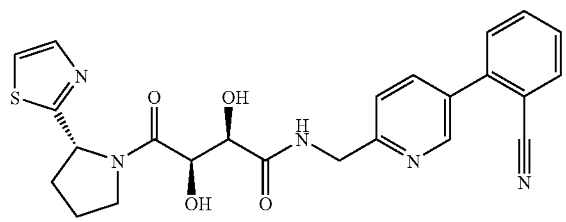 | 477.2 | 478.1 |
| 222 | 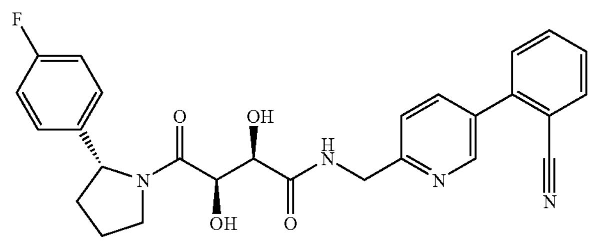 | 488.2 | 489.1 |
| 223 | 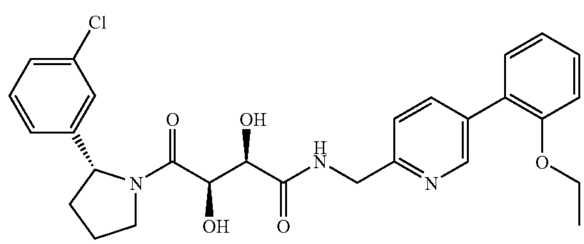 | 523.2 | 524.2 |
| 224 | 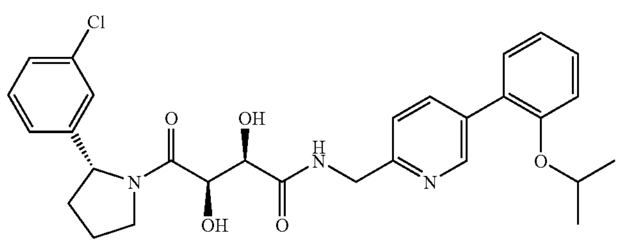 | 537.2 | 538.2 |
| 225 | 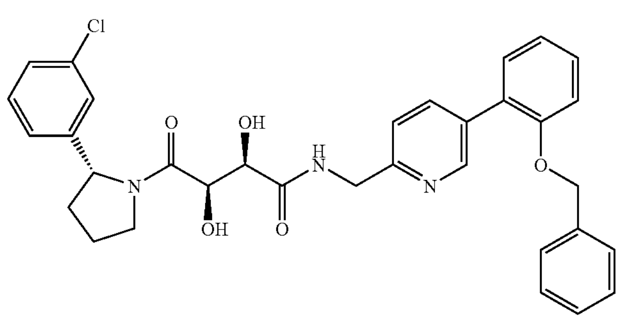 | 585.2 | 586.2 |
| 226 | 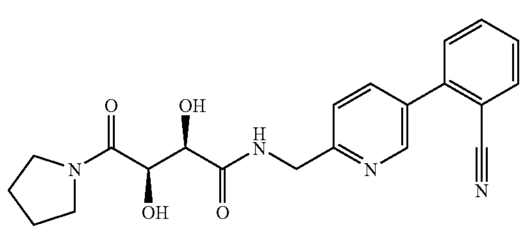 | 394.2 | 395.2 |

-continued

| Compound # | Structure | Exact mass | MS m/e (M + H) |
|---|---|---|---|
| 227 | 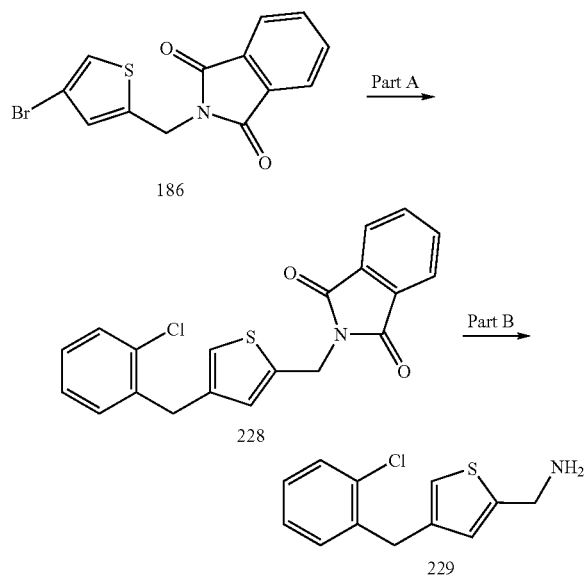 | 509.2 | 510.1 |

Example 4

Thiophene-Benzyl Compounds

Pd-mediated Negishi-type couplings were an efficient way to generate a set of relevant compounds for this series where Ar was a phenyl ring. While a range of palladium sources are known we found that $Pd(P^tBu_3)_2$ was preferred. The reaction can be run in a variety of solvent systems, including dioxane, THF, or DMA. A preferred method utilized the solvent from the zinc reagent, which was typically available as a THF stock solution. Removal of the t-BOC group can be completed using a range of acidic conditions including TFA/water, HCl in methanol, and HCl in dioxane; all of which proceeded equally well with most reaction substrates. The reactions are typically concentrated and freeze-dried to give HCl or TFA salts. The Negishi reactions proceed comparably, and in many cases better, when the amine was protected by a phthalimide. The phthalimide protecting group could be removed by heating in ethanol containing hydrazine hydrate.

Example 4A

Part A:

To 186 (3.47 g, 10.8 mmol) and bis-(tri-tert-butyl-phosphine) palladium (0.28 g, 0.54 mmol) in a flask under argon was added 2-chlorobenzyl zinc chloride (0.5 M in THF, 54 mL, 27 mmol). The reaction was stirred at room temperature for 3 hours. The reaction mixture was diluted with EtOAc (200 mL) and washed with saturated ammonium chloride solution (100 mL), bicarbonate solution (100 mL) and brine (100 mL). The organic layer was dried over sodium sulfate and concentrated. Purification by column chromatography ($SiO_2$, 20% EtOAc/Hex) afforded 228 as a white solid (3.59 g, 91%). $^1$H NMR (400 MHz, $CDCl_3$) δ 7.85 (dd, 2H, J=3.2, 5.6 Hz), 7.71 (dd, 2H, J=3.2, 5.6 Hz), 7.36 (m, 1H), 7.17 (m, 3H), 6.99 (d, 1H, J=1.0 Hz), 6.78 (d, 1H, J=1.0 Hz), 4.95 (s, 2H), 4.00 (s, 2H).

Part B:

To 228 (3.55 g, 9.72 mmol) suspended in ethanol (35 mL) was added hydrazine monohydrate (1.9 mL, 38.9 mmol). The reaction mixture was heated at reflux for 2 hours. After cooling the solids were removed by filtration and washed with ethanol (100 mL) and ethyl acetate (50 mL). The filtrate was concentrated and the residue was dissolved in ethyl acetate (150 mL) and water (100 mL). The organic layer was separated, washed with brine (100 ml), dried over sodium sulfate and concentrated to yield 229 as a yellow oil (2.54 g, 99%).

Part C:

To 48 (2.16 mg, 10.0 mmol) in DCM (10 mL) was added isoindoline (1.13 mL, 10.0 mmol). The reaction was stirred at room temperature for 2 hours. The solvent was removed in vacuo and the residue was partitioned between ethyl acetate and 1.0 N HCl. The organic layer was separated, washed with water and brine, dried over sodium sulfate and concentrated to afford 230 as a dark solid (3.35 g, 100%). $^1$H NMR (400 MHz, DMSO-$d_6$) δ 13.63 (bs, 1H), 7.38-7.28 (m, 4H), 5.01 (d, 1H, J=13.2 Hz), 4.93 (d, 1H, J=14.0 Hz), 4.71 (d, 1H, J=16.4 Hz), 4.56 (d, 1H, J=15.6 Hz), 2.12 (s, 3H), 2.07 (s, 3H); HPLC-MS $t_R$=1.10 min (UV$_{254\,nm}$); mass calculated for formula $C_{16}H_{17}NO_7$ 335.1, observed LCMS m/z 336.1 (M+H).

Part D:

To 230 (18 mg, 0.053 mmol) in NMP (2 mL) was added 229 (19 mg, 0.08 mmol), DIEA (26 µL, 0.148 mmol) and HATU (30 mg, 0.08 mmol). The reaction mixture was stirred overnight. The reaction mixture was poured into water and extracted with ethyl acetate. The combined organic layer was washed with 0.1 N NaOH, 0.1 N HCl and brine, dried over sodium sulfate and concentrated to afford 231.

Part E:

To 231 (118 mg, 0.216 mmol) in methanol (3 mL) and DCM (3 mL) was added MP-carbonate resin (2.54 mmol/g, 85 mg). The reaction was stirred for 3 hours, filtered and concentrated to afford 232 as a white solid (94 mg, 92%). $^1$H NMR (400 MHz, DMSO-$d_6$) δ 8.34 (t, 1H, J=2.0 Hz) 7.79 (dd 1H, J=0.8, 8.0 Hz), 7.64 (dt, 1H, J=1.6, 8.0 Hz), 7.47 (d, 1H, J=7.6 Hz), 7.40 (dt, 1H, J=0.8, 7.6 Hz), 7.35-7.27 (m, 4H), 6.97 (d, 1H, J=1.6 Hz), 6.81 (d, 1H, J=1.2 Hz), 5.67 (d, 1H, J=6.4 Hz), 5.05 (d, 1H, J=12.8 Hz), 4.97 (d, 1H, J=8.0 Hz), 4.90 (d, 1H, J=13.2 Hz), 4.75 (d, 1H, J=13.2 Hz), 4.60 (m, 2H), 4.36 (m, 2H, J=6.4, 15.2 Hz) 4.24 (dd, 1H, J=3.2, 6.8 Hz); HPLC-MS $t_R$=1.85 (UV$_{254\,nm}$); mass calculated for formula $C_{24}H_{23}ClN_2O_4S$ 470.1, observed LCMS m/z 471.1

Example 4B

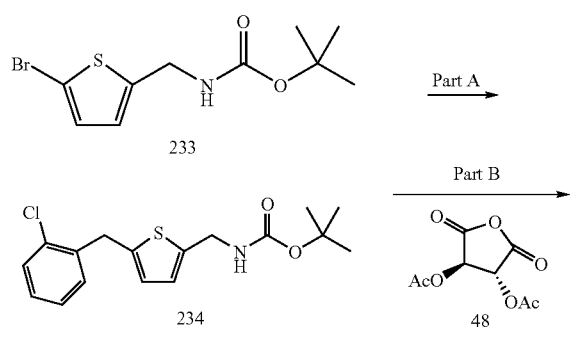

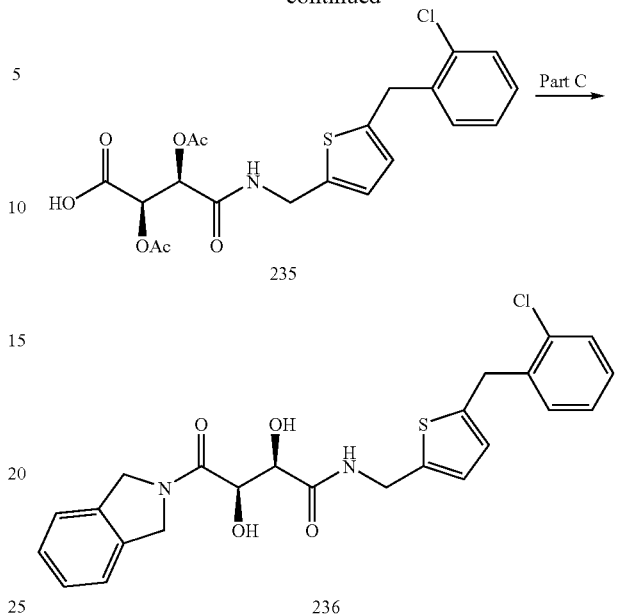

Part A:

To 233 (4.00 g, 13.7 mmol) and bis-(tri-tert-butyl-phosphine) palladium (0.28 g, 0.54 mmol) in a flask under argon was added 2-chlorobenzyl zinc chloride (0.5 M in THF, 69 mL, 34.5 mmol). The reaction was stirred at room temperature overnight. The reaction mixture was diluted with EtOAc (200 mL) and washed with saturated ammonium chloride solution (100 mL), bicarbonate solution (100 mL) and brine (100 mL). The organic layer was dried over sodium sulfate and concentrated. Purification by column chromatography (SiO$_2$, 15% EtOAc/Hex) afforded 234 as a white solid (4.5 g, 95%). $^1$H NMR (400 MHz, CDCl$_3$) δ 7.36 (d, 1H J=3.6 Hz), 7.25-7.18 (m, 4H), 6.74 (s, 1H), 6.64 (d, 1H, J=3.6 Hz), 4.40 (d, 2H, J=5.2 Hz), 4.22 (s, 2H).

Part B:

To 234 (450 mg, 1.34 mmol) was added 4M HCl in dioxane (1.5 mL) and the reaction was stirred for 30 minutes. The dioxane was removed in vacuo. The residue was dissolved in THF (10 mL) and DIEA (500 µL, 2.68 mmol) and 48 (275 mg, 1.27 mmol) were added. The reaction was stirred overnight at room temperature. The reaction mixture was diluted with ethyl acetate (60 mL) and washed with 1.0 N HCl. The organic layer was dried over sodium sulfate and concentrated to afford 235 as a yellow foam (505 mg, 90%).

Part C:

To 235 (40 mg, 0.09 mmol) in DMF (2 mL) were added DIEA (50 µL, 0.29 mmol), isoindoline (14 mg, 0.12 mmol), and HATU (45 mg, 0.12 mmol). The reaction mixture was stirred for 6 hours. The reaction mixture was diluted with ethyl acetate (30 mL) and washed with 0.1 N NaOH, 0.1 N HCl and brine. The organic layer was dried over sodium sulfate. The crude product was dissolved in methanol (3 mL) and potassium carbonate (100 mg) in water (1 mL) was added. After stirring for 30 minutes the reaction mixture was diluted with ethyl acetate (20 mL) and washed with brine. The organic layer was dried over sodium sulfate and concentrated. Purification by reverse phase prep-LC afforded 236 as a white solid. $^1$H NMR (400 MHz, DMSO-$d_6$) δ 8.29 (t, 1H, J=6.4

Hz) 7.42 (dd, 1H, J=1.6, 7.8 Hz), 7.37-7.23 (m, 7H), 6.74 (d, 1H, J=3.6 Hz), 6.65 (d, 1H, J=3.2 Hz), 5.66 (d, 1H, J=5.6 Hz), 5.04 (d, 1H, J=14.8 Hz), 4.97 (bs, 1H), 4.89 (d, 1H, J=15.2 Hz), 4.75 (d, 1H, J=16.4 Hz), 4.60 (m, 2H), 4.38 (dd, 1H, J=6.4, 15.2 Hz), 4.23 (bs, 1H), 4.15 (s, 2H); HPLC-MS $t_R$=4.92 min ($UV_{254\ nm}$, 10 min); mass calculated for formula $C_{24}H_{23}ClN_2O_4S$ 470.1, observed LCMS m/z 471.1

Example 4C

Thiophene-Benzyl

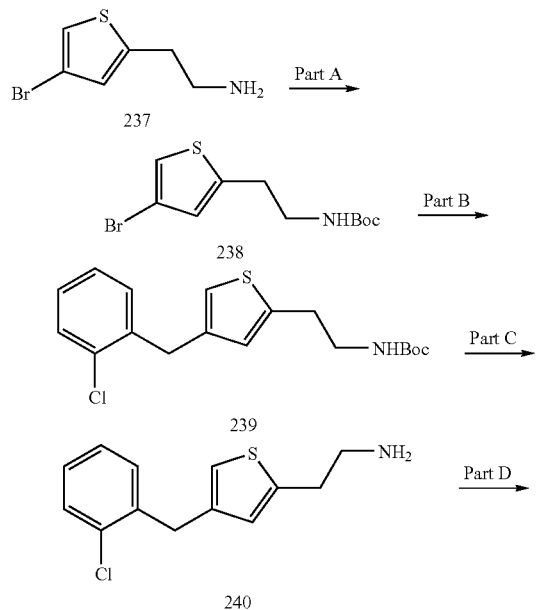

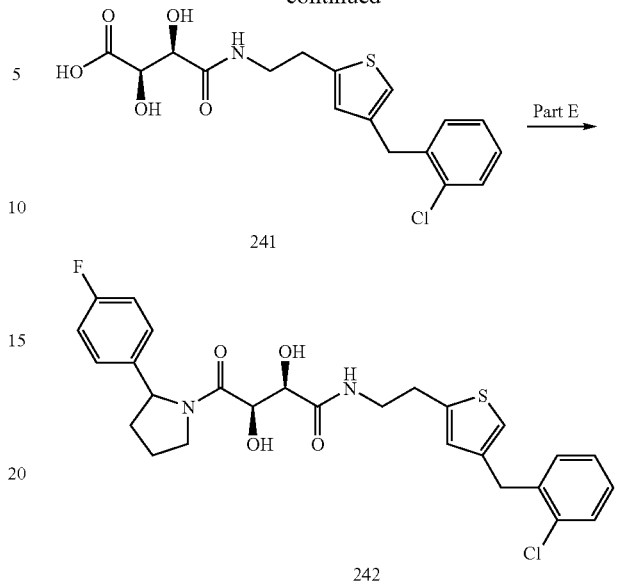

Compound 237 was prepared according to the procedure described by A. J. Hutchison et al (European Patent 0323807 A2, Dec. 7, 1989)

Parts A:

Compound 238 was prepared by procedures similar to those described in Example 5 Part A.

Parts B-E:

Compound 242 was prepared by procedures similar to those described in Example 4B Parts A to C. HPLC-MS $t_R$=2.05 min ($UV_{254\ nm}$); mass calculated for formula $C_{27}H_{28}ClFN_2O_4S$ 530.1, observed LCMS m/z 531.1 (M+H).

The following compounds were prepared by the procdures desribed in Example 4A-4C.

| Compound # | Structure | Exact mass | MS m/z (M + H) |
|---|---|---|---|
| 243 | 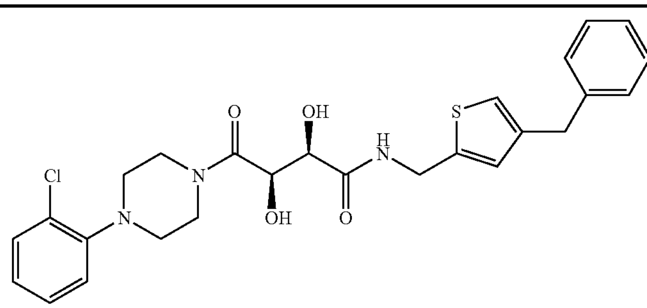 | 513.2 | 514.2 |
| 244 | 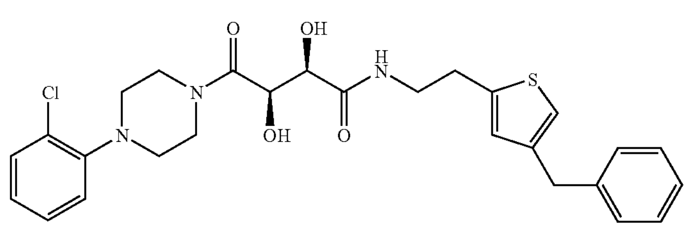 | 527.2 | 528.1 |

-continued

| Compound # | Structure | Exact mass | MS m/z (M + H) |
|---|---|---|---|
| 245 | 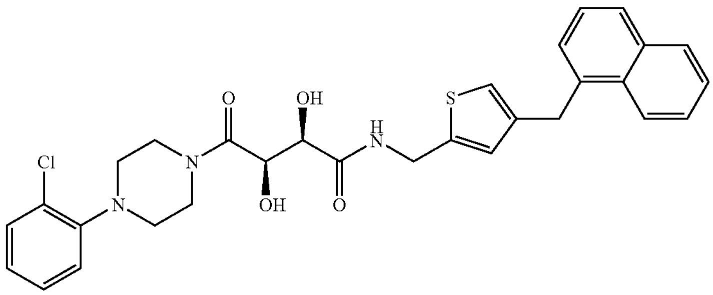 | 563.2 | 564.2 |
| 246 | 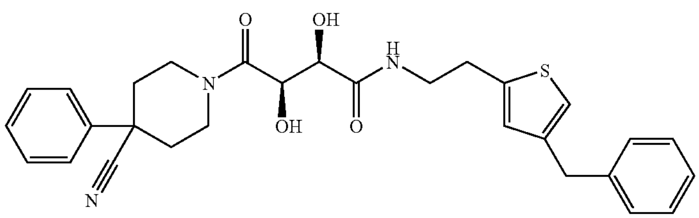 | 517.2 | 518.2 |
| 247 | 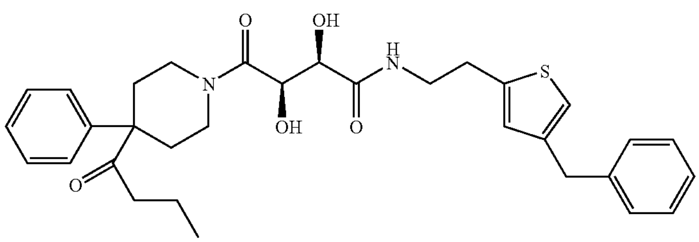 | 562.3 | 563.2 |
| 248 | 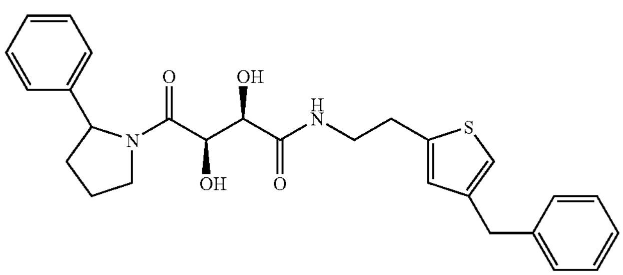 | 478.2 | 479.2 |
| 249 | 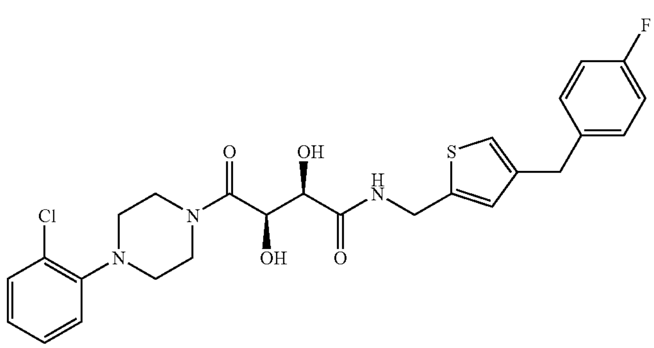 | 515.2 | 516.0 |

-continued

| Compound # | Structure | Exact mass | MS m/z (M + H) |
|---|---|---|---|
| 250 | 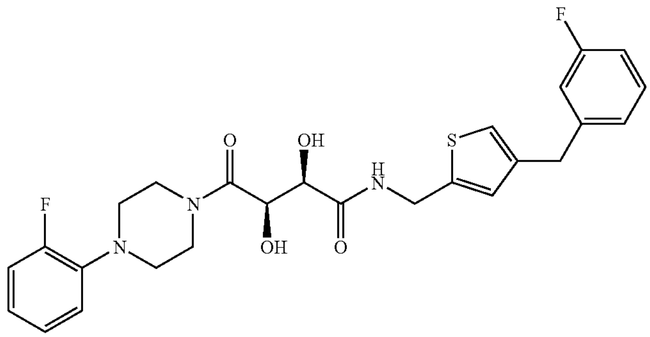 | 515.2 | 516.0 |
| 251 | 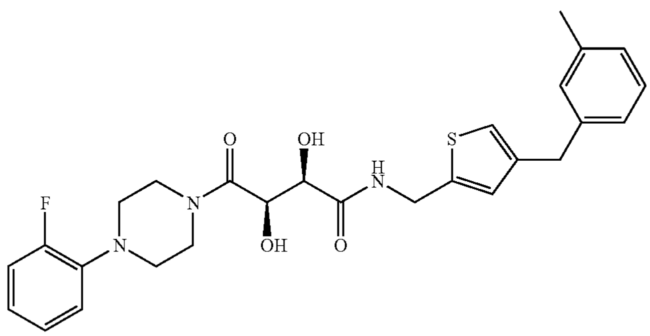 | 511.2 | 512.2 |
| 252 | 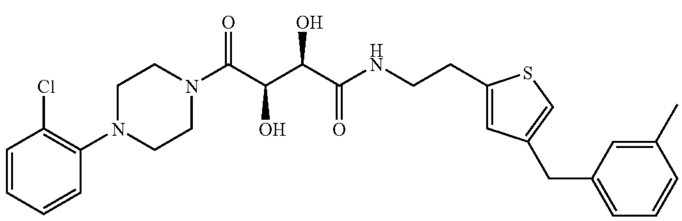 | 541.2 | 542.2 |
| 253 | 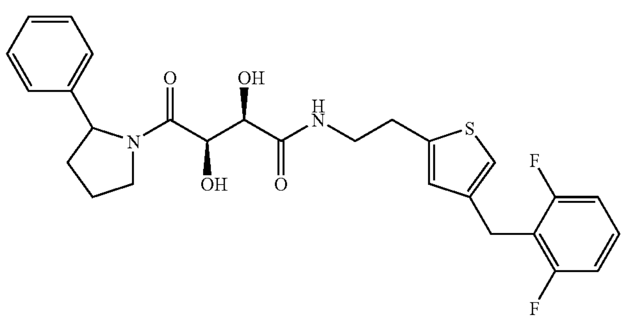 | 514.2 | 515.2 |
| 254 | 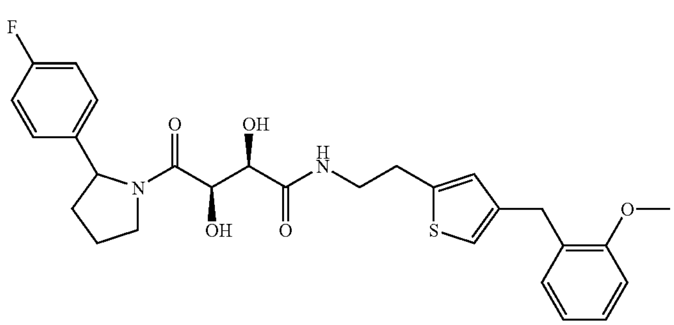 | 526.2 | 527.2 |

-continued

| Compound # | Structure | Exact mass | MS m/z (M + H) |
|---|---|---|---|
| 255 | 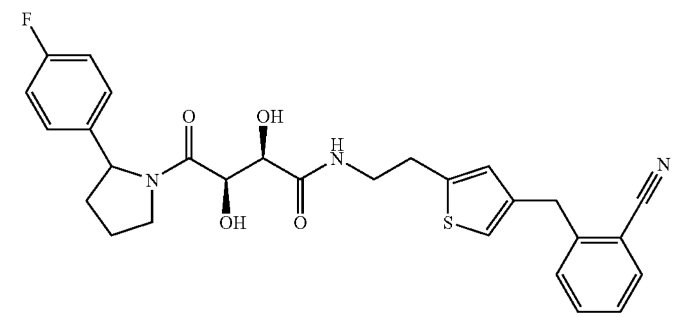 | 521.2 | 522.1 |
| 256 | 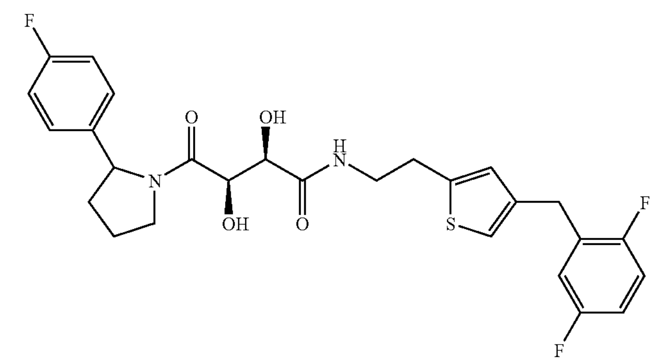 | 532.2 | 533.2 |
| 257 | 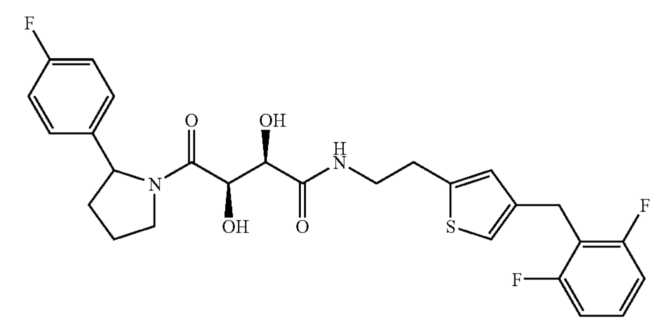 | 532.2 | 533.2 |
| 258 | 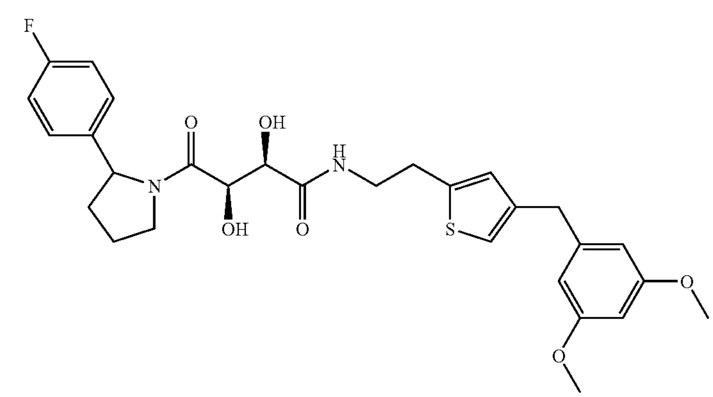 | 556.2 | 557.2 |

-continued

| Compound # | Structure | Exact mass | MS m/z (M + H) |
|---|---|---|---|
| 259 | 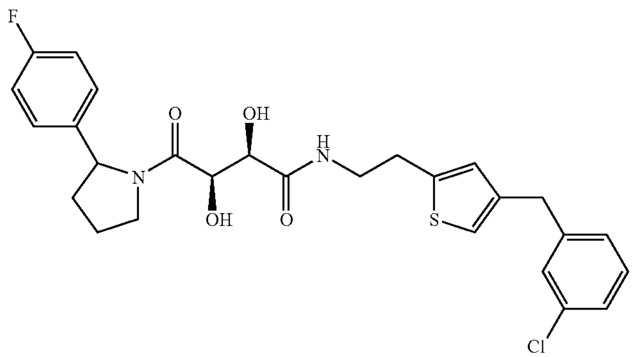 | 530.1 | 531.1 |
| 260 | 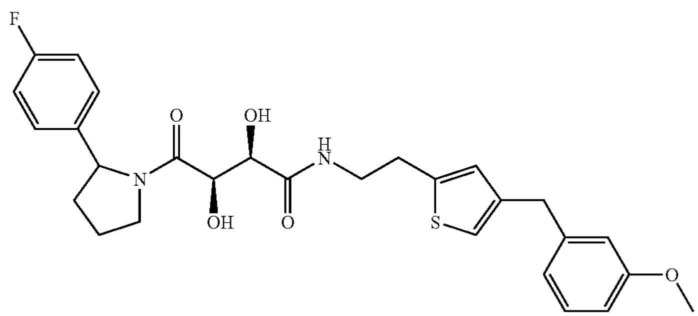 | 526.2 | 527.2 |
| 261 | 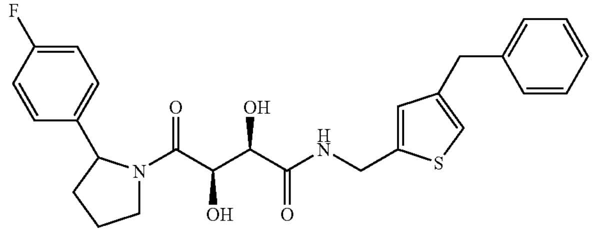 | 482.2 | 483.1 |
| 262 | 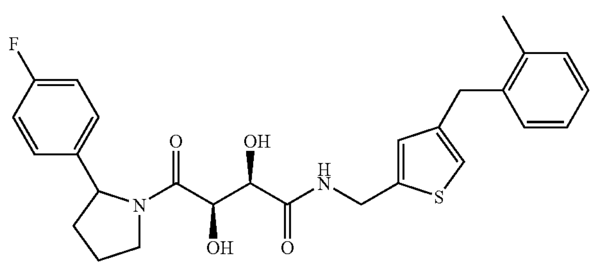 | 496.2 | 497.2 |
| 263 | 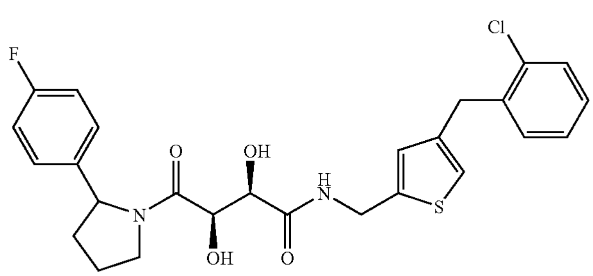 | 516.1 | 517.2 |

-continued
| Compound # | Structure | Exact mass | MS m/z (M + H) |
|---|---|---|---|
| 264 | 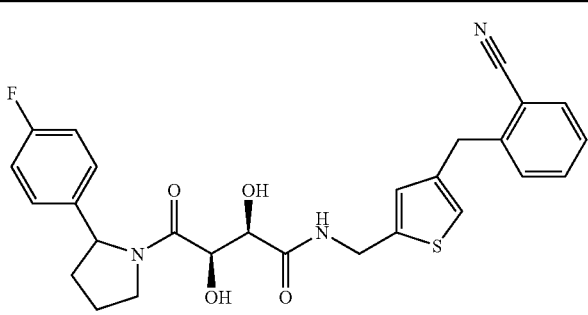 | 507.2 | 508.1 |
| 265 | 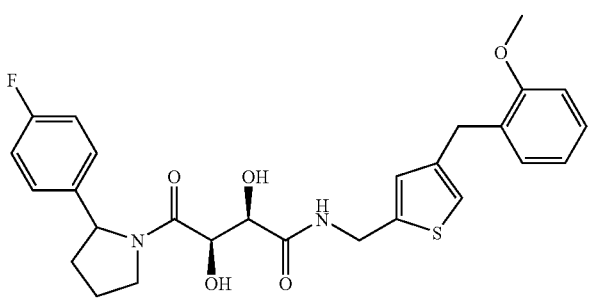 | 512.2 | 513.2 |
| 266 | 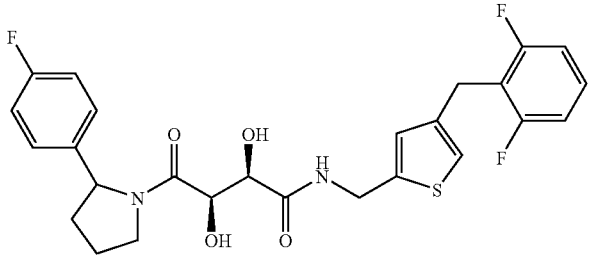 | 518.2 | 519.1 |
| 267 | 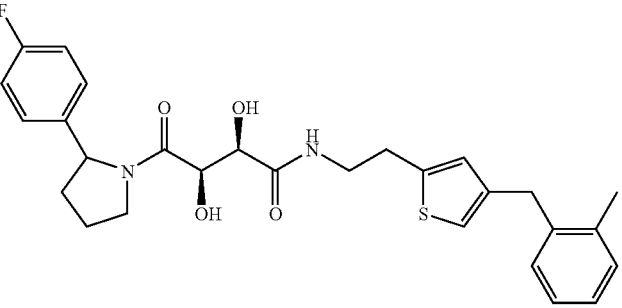 | 510.2 | 511.1 |
| 268 | 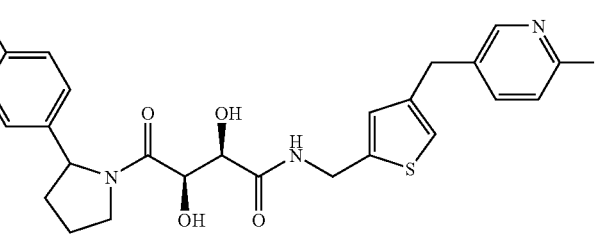 | 517.1 | 518.0 |

-continued

| Compound # | Structure | Exact mass | MS m/z (M + H) |
|---|---|---|---|
| 269 | 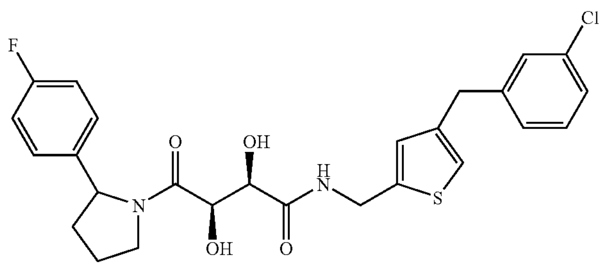 | 516.1 | 517.2 |
| 270 | 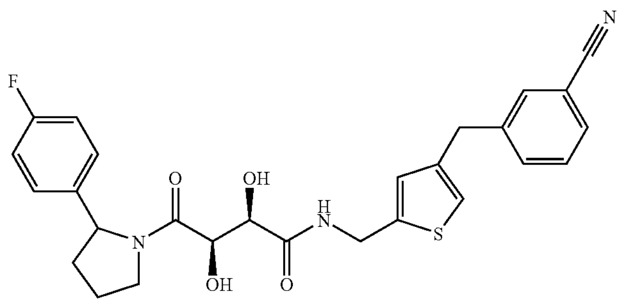 | 507.2 | 508.1 |
| 271 | 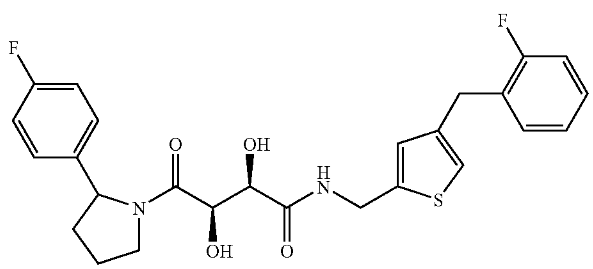 | 500.2 | 501.1 |
| 272 | 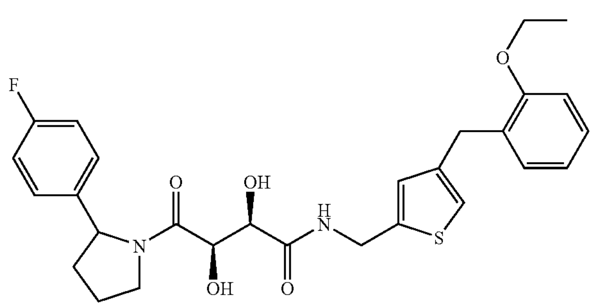 | 526.2 | 527.2 |
| 273 | 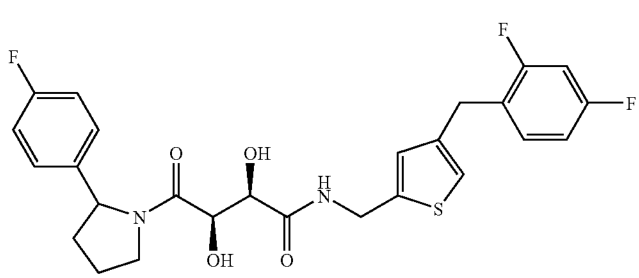 | 518.2 | 519.1 |

-continued

| Compound # | Structure | Exact mass | MS m/z (M + H) |
|---|---|---|---|
| 274 | 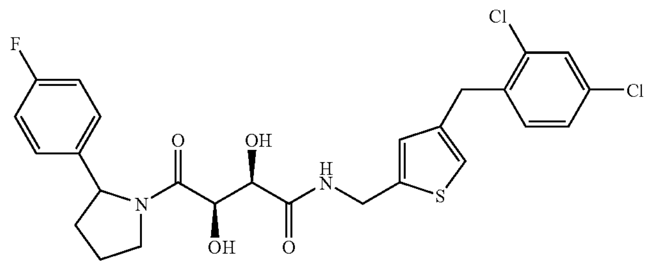 | 550.1 | 551.0 |
| 275 | 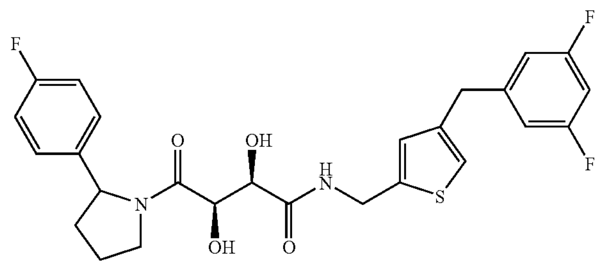 | 518.2 | 519.1 |
| 276 | 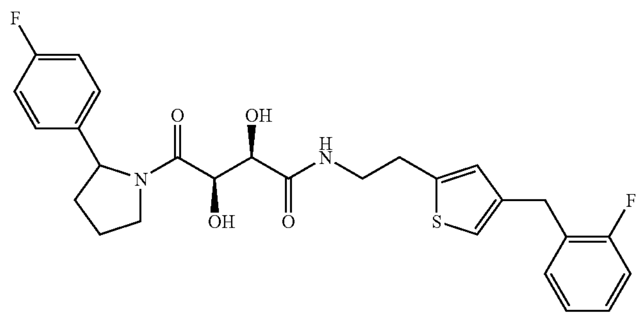 | 514.2 | 515.2 |
| 277 | 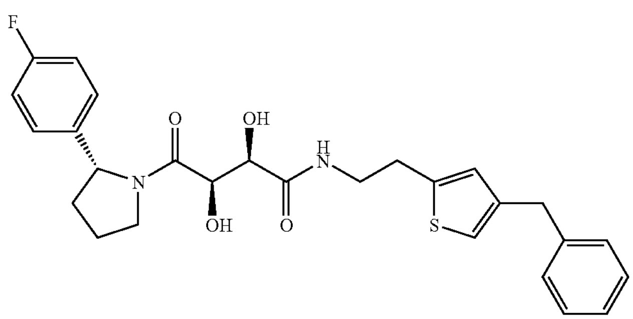 | 496.2 | 497.1 |
| 278 | 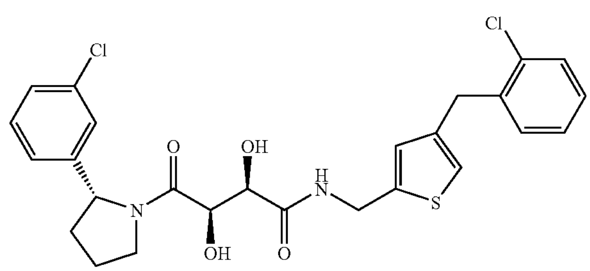 | 532.1 | 533.0 |

-continued

| Compound # | Structure | Exact mass | MS m/z (M + H) |
|---|---|---|---|
| 279 | 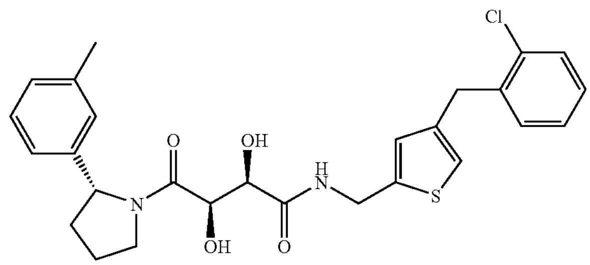 | 512.2 | 513.1 |
| 280 | 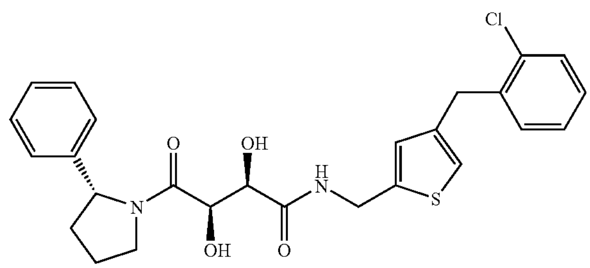 | 498.1 | 499.0 |
| 281 | 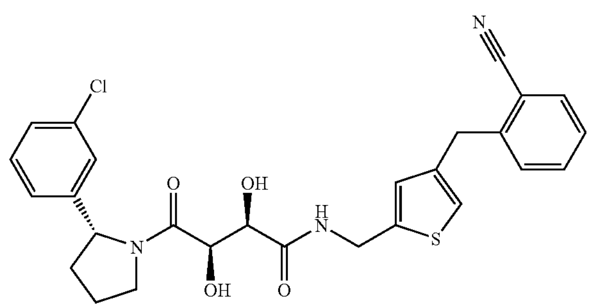 | 523.1 | 524.1 |
| 282 | 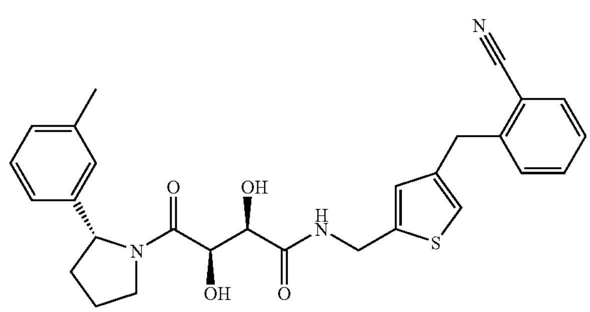 | 503.2 | 504.1 |
| 283 | 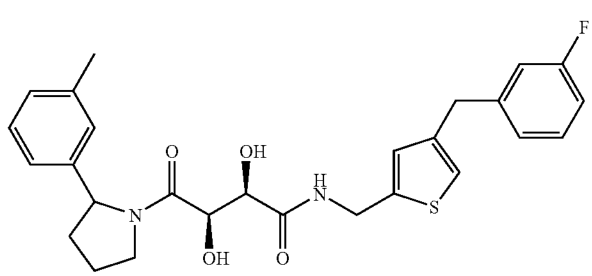 | 496.2 | 497.2 |

-continued
| Compound # | Structure | Exact mass | MS m/z (M + H) |
|---|---|---|---|
| 284 | 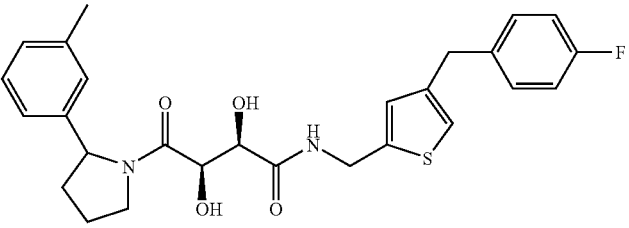 | 496.2 | 497.2 |
| 285 | 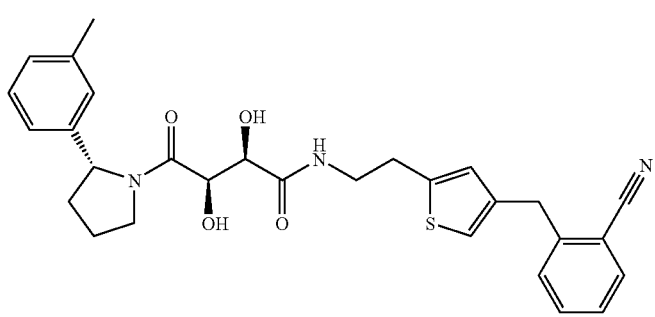 | 517.2 | 518.2 |
| 286 | 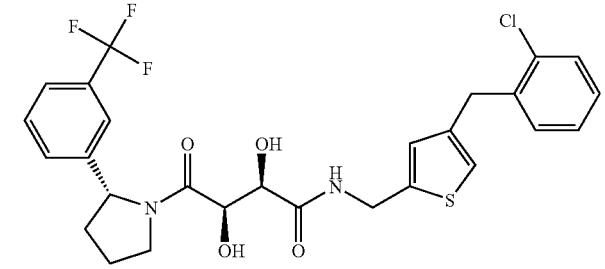 | 566.12 | 567.1 |
| 287 | 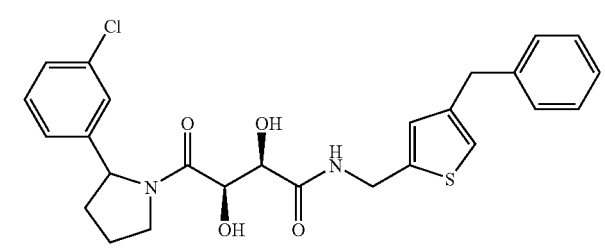 | 498.1 | 499.1 |
| 288 | 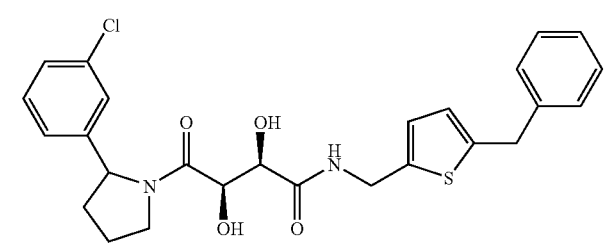 | 498.1 | 499.1 |

| Compound # | Structure | Exact mass | MS m/z (M + H) |
|---|---|---|---|
| 289 | 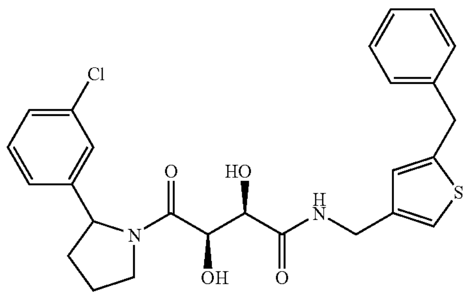 | 498.1 | 499.1 |
| 290 | 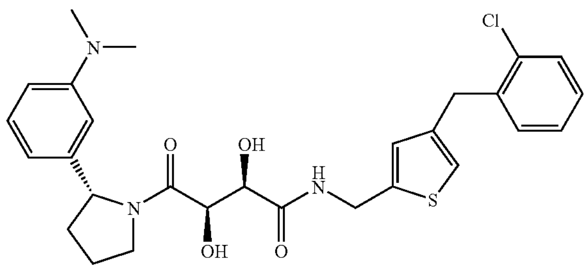 | 541.2 | 542.2 |
| 291 | 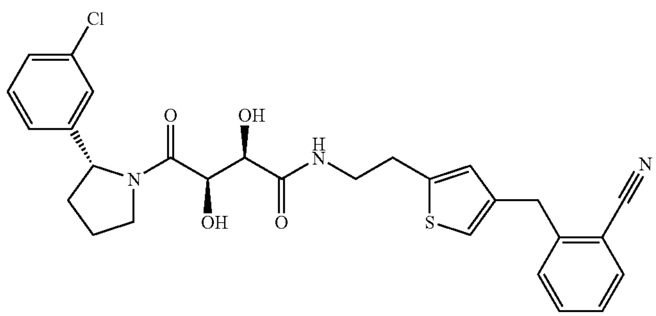 | 537.2 | 538.2 |
| 292 | 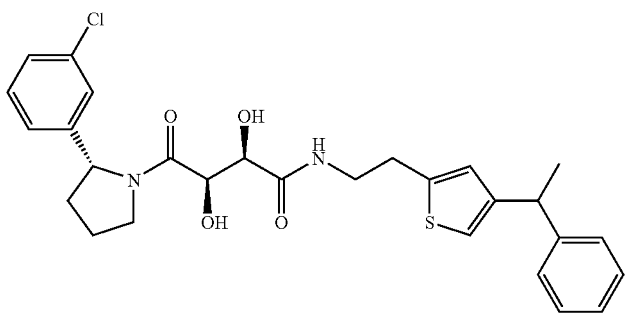 | 526.2 | 527.0 |
| 293 | 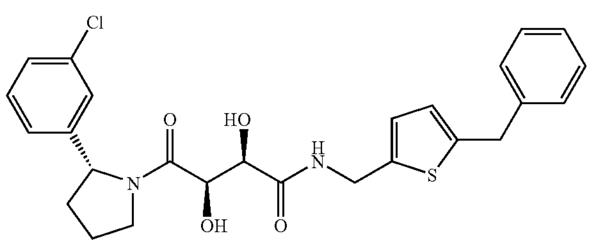 | 498.1 | 499.1 |

-continued

| Compound # | Structure | Exact mass | MS m/z (M + H) |
|---|---|---|---|
| 294 | 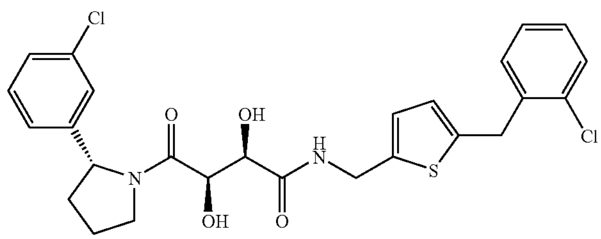 | 532.1 | 533.0 |
| 295 | 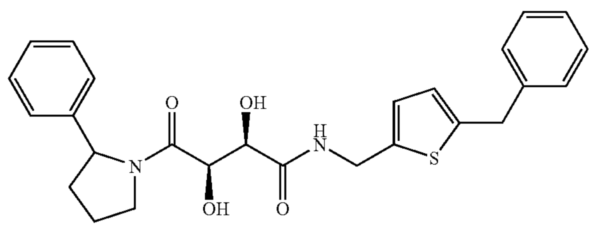 | 464.2 | 465.1 |
| 296 | 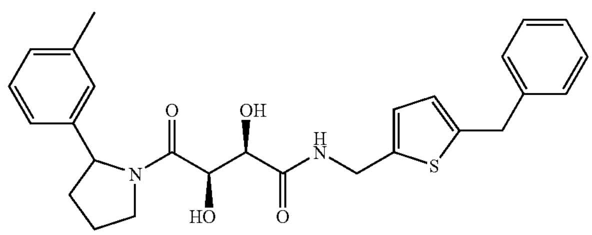 | 478.2 | 479.2 |
| 297 | 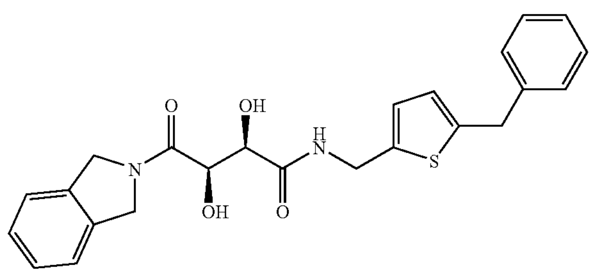 | 436.2 | 437.2 |
| 298 | 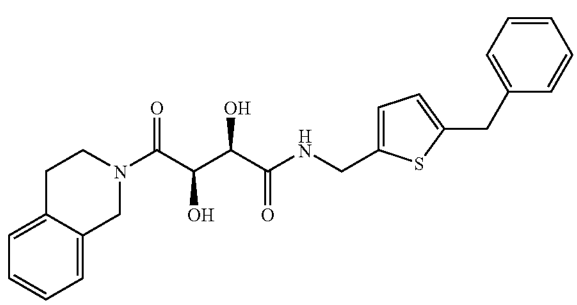 | 450.2 | 451.1 |

-continued

| Compound # | Structure | Exact mass | MS m/z (M + H) |
|---|---|---|---|
| 299 | 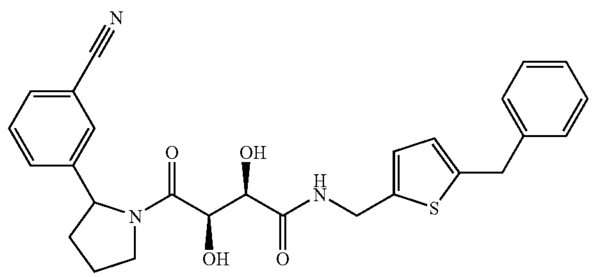 | 489.2 | 490.1 |
| 300 | 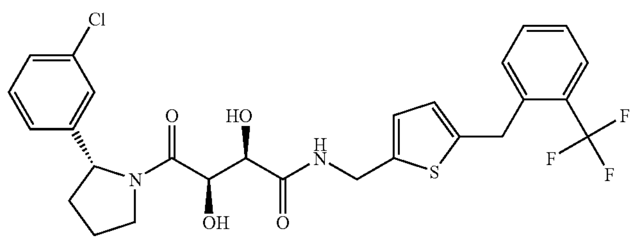 | 566.1 | 567.1 |
| 301 | 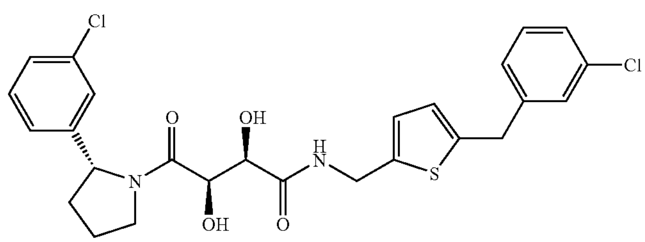 | 532.1 | 533.0 |
| 302 | 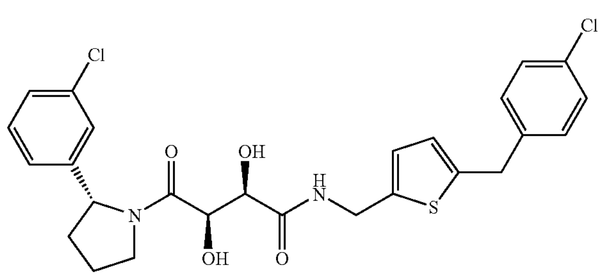 | 532.1 | 533.0 |
| 303 | 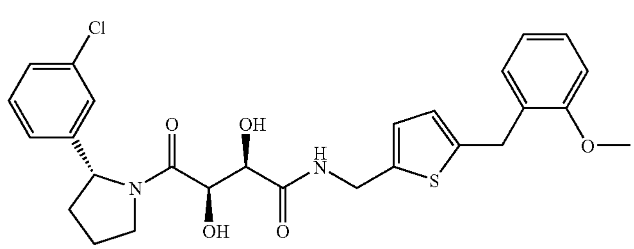 | 528.2 | 529.2 |

-continued

| Compound # | Structure | Exact mass | MS m/z (M + H) |
|---|---|---|---|
| 304 | 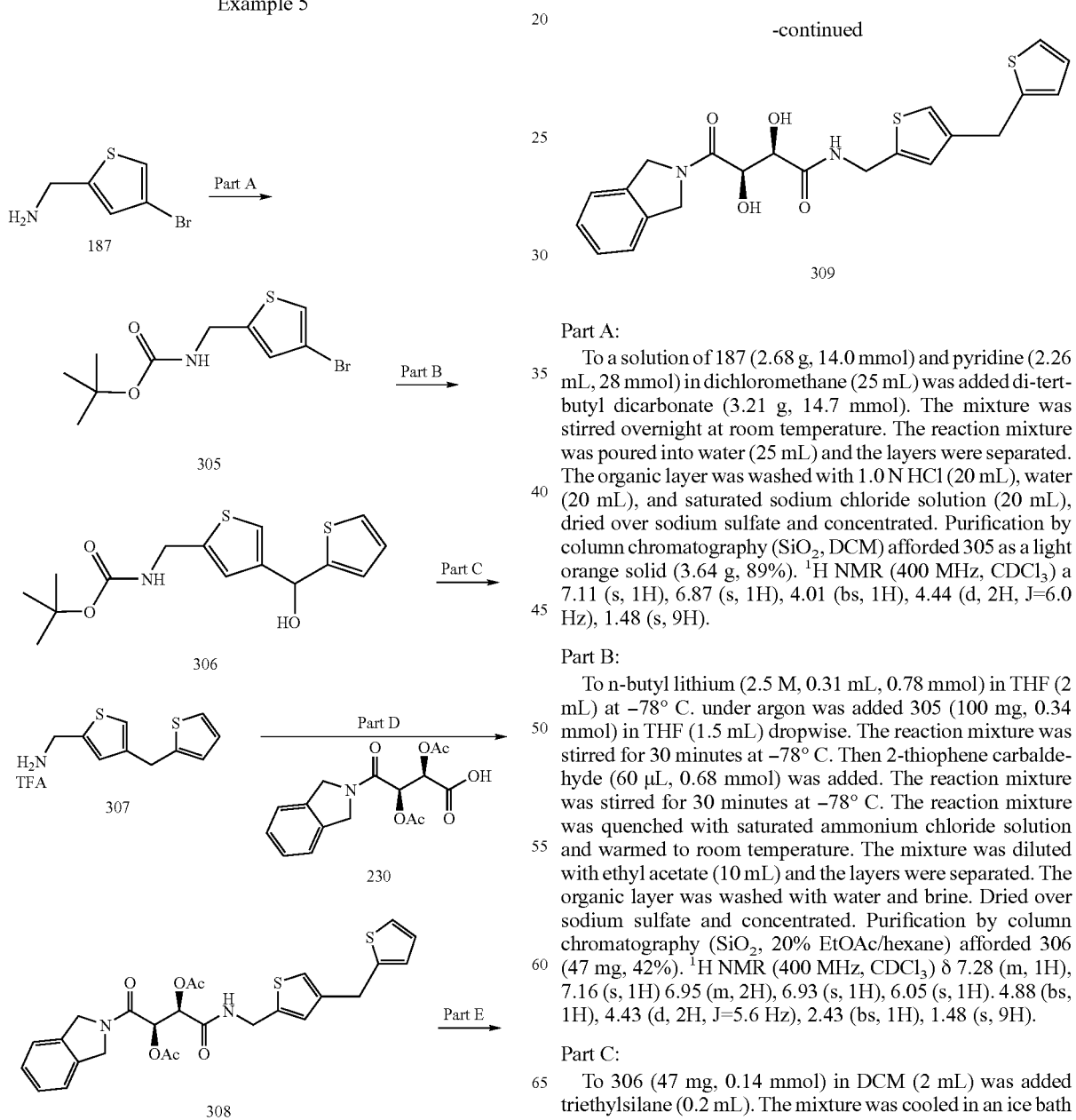 | 523.1 | 524.2 |

Example 5

Part A:

To a solution of 187 (2.68 g, 14.0 mmol) and pyridine (2.26 mL, 28 mmol) in dichloromethane (25 mL) was added di-tert-butyl dicarbonate (3.21 g, 14.7 mmol). The mixture was stirred overnight at room temperature. The reaction mixture was poured into water (25 mL) and the layers were separated. The organic layer was washed with 1.0 N HCl (20 mL), water (20 mL), and saturated sodium chloride solution (20 mL), dried over sodium sulfate and concentrated. Purification by column chromatography (SiO$_2$, DCM) afforded 305 as a light orange solid (3.64 g, 89%). $^1$H NMR (400 MHz, CDCl$_3$) a 7.11 (s, 1H), 6.87 (s, 1H), 4.01 (bs, 1H), 4.44 (d, 2H, J=6.0 Hz), 1.48 (s, 9H).

Part B:

To n-butyl lithium (2.5 M, 0.31 mL, 0.78 mmol) in THF (2 mL) at −78° C. under argon was added 305 (100 mg, 0.34 mmol) in THF (1.5 mL) dropwise. The reaction mixture was stirred for 30 minutes at −78° C. Then 2-thiophene carbaldehyde (60 μL, 0.68 mmol) was added. The reaction mixture was stirred for 30 minutes at −78° C. The reaction mixture was quenched with saturated ammonium chloride solution and warmed to room temperature. The mixture was diluted with ethyl acetate (10 mL) and the layers were separated. The organic layer was washed with water and brine. Dried over sodium sulfate and concentrated. Purification by column chromatography (SiO$_2$, 20% EtOAc/hexane) afforded 306 (47 mg, 42%). $^1$H NMR (400 MHz, CDCl$_3$) δ 7.28 (m, 1H), 7.16 (s, 1H) 6.95 (m, 2H), 6.93 (s, 1H), 6.05 (s, 1H). 4.88 (bs, 1H), 4.43 (d, 2H, J=5.6 Hz), 2.43 (bs, 1H), 1.48 (s, 9H).

Part C:

To 306 (47 mg, 0.14 mmol) in DCM (2 mL) was added triethylsilane (0.2 mL). The mixture was cooled in an ice bath and TFA (0.2 mL) was added. The mixture was warmed to room temperature and stirred overnight. The solvents were removed in vacuo and 307 was used without further purification. $^1$H NMR (400 MHz, CD$_3$OD) a 7.20 (m, 2H), 7.09 (s, 1H) 6.90 (m, 1H), 6.86 (m, 1H), 4.26 (s, 2H), 4.15 (s, 2H).

Part D:

To 230 (19 mg, 0.06 mmol) in DMF (2 mL) was added 307 (18 mg, 0.06 mmol), DIEA (29 μL, 0.17 mmol) and HATU (28 mg, 0.07 mmol). The reaction mixture was stirred overnight at room temperature. The reaction mixture was diluted with ethyl acetate (20 mL) and water (20 mL). The layers were separated and the aqueous layer was extracted with ethyl acetate. The combined organic layers were washed with sodium bicarbonate solution and brine, dried over sodium sulfate and concentrated. Compound 308 was used without further purification. HPLC-MS t$_R$=1.91 min (UV$_{254\ nm}$); mass calculated for formula C$_{26}$H$_{26}$N$_2$O$_6$S$_2$ 526.1, observed LCMS m/z 269.9 (M+H).

Part E:

Compound 308 and potassium carbonate (20 mg) were mixed in methanol (2.5 mL) and water (0.5 mL) and were stirred for 30 minutes. The reaction mixture was diluted with ethyl acetate, washed with water and brine, dried over sodium sulfate and concentrated. Purification by reverse phase prep-LC afforded 309 as a white solid. $^1$H NMR (400 MHz, DMSO-d$_6$) δ 8.33 (t, 1H, J=5.6 Hz), 7.30 (m, 5H), 7.03 (s, 1H), 6.92 (s, 1H), 6.67 (s, 1H), 6.82 (s, 1H), 5.04 (d, 1H, J=14.0 Hz), 4.90 (d, 1H, J=14.0 Hz), 4.75 (d, 1H, J=16.0 Hz), 4.60 (m, 2H), 4.41 (dd, 1H, J=6.8, 14.8 Hz), 4.33 (dd, 1H, J=5.6, 14.4 Hz), 4.25 (s, 1H), 4.04 (s, 2H); HPLC-MS t$_R$=4.45 min (UV$_{254\ nm}$, 10 min); mass calculated for formula C$_{22}$H$_{22}$N$_2$O$_4$S$_2$ 442.1, observed LCMS m/z 443.0 (M+H).

The following compounds were prepared using the procedures described above. Part C did not result in dehydration for compounds like 314 and 317.

| Compound # | Structure | Exact mass | MS m/z (M + H) |
|---|---|---|---|
| 310 | 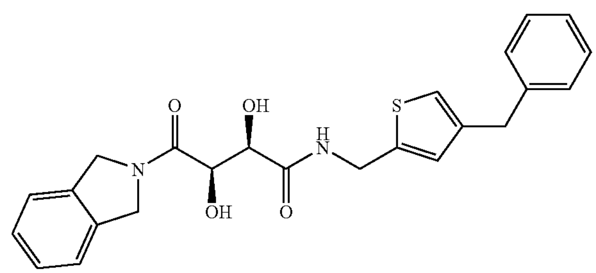 | 436.2 | 437.3 |
| 311 | 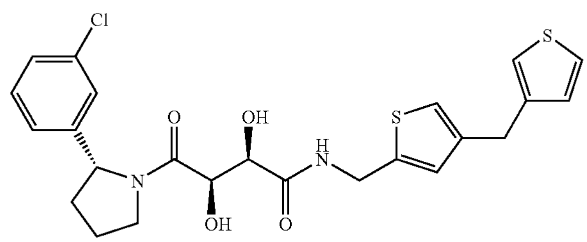 | 504.1 | 505.1 |
| 312 | 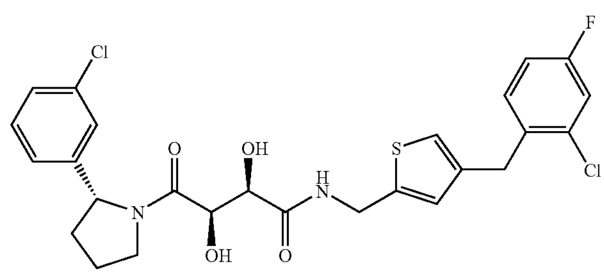 | 550.1 | 551.0 |
| 313 | 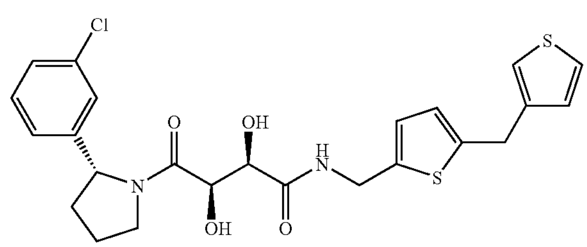 | 504.1 | 505.1 |

-continued

| Compound # | Structure | Exact mass | MS m/z (M + H) |
|---|---|---|---|
| 314 | 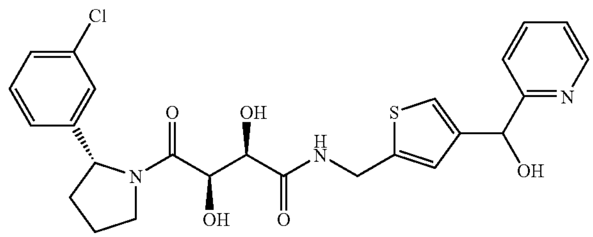 | 515.1 | 516.1 |
| 315 | 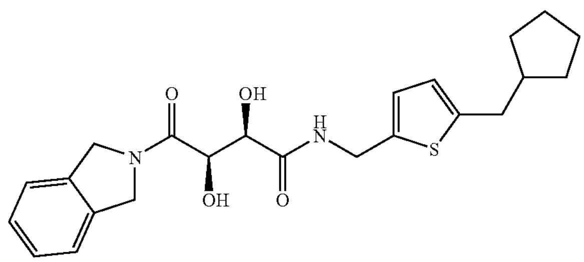 | 428.2 | 429.1 |
| 316 | 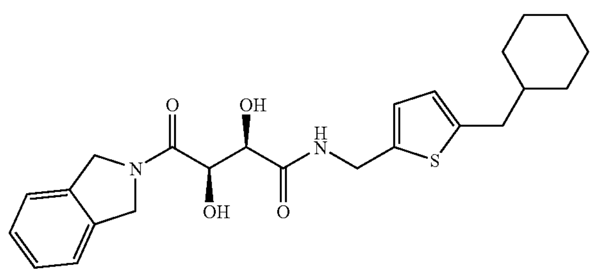 | 442.2 | 443.0 |
| 317 | 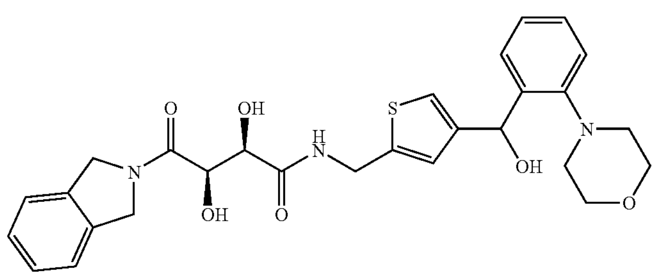 | 537.2 | 538.0 |
| 318 | 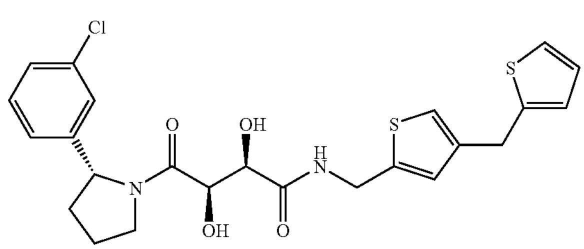 | 504.09 | 505.0 |

Example 6

Example 6A

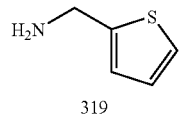
319

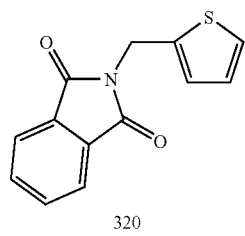
320

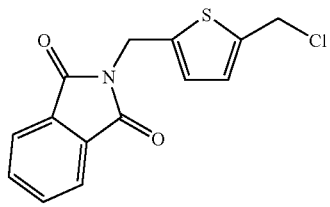
321

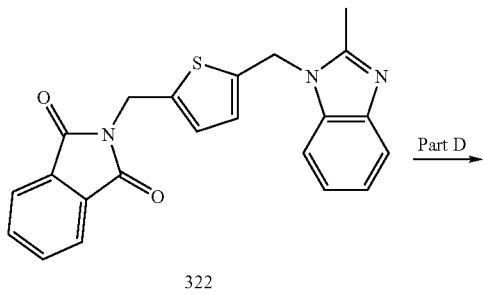
322

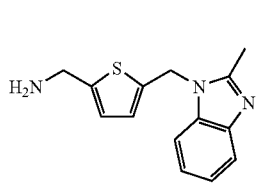
323

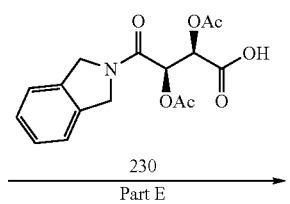
230

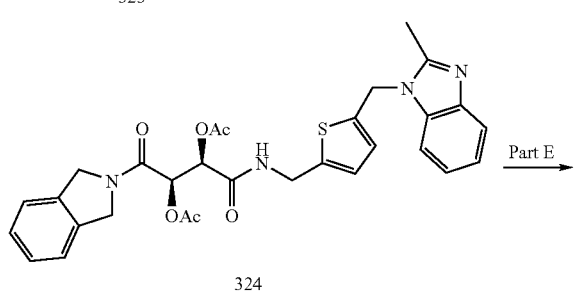
324

-continued

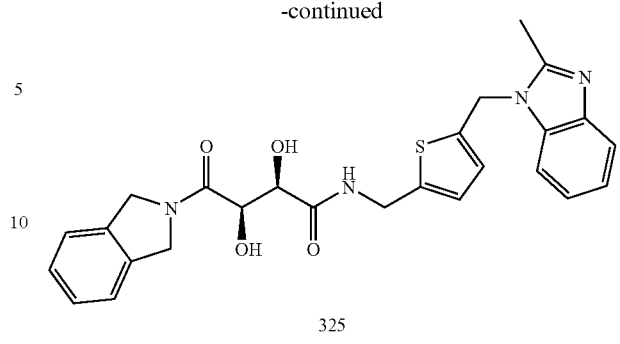
325

Part A:

A mixture of 2-(aminomethyl)thiophene (319) (1.57 g, 13.8 mmol), monomethyl phthalate (2.75 g, 15.3 mmol), EDC (3.26 g, 16.6 mmol), HOBt (2.79 g, 20.7 mmol) and triethylamine (5 mL, 27.6 mmol) in DCM (40 mL) was stirred for 12 hours. The reaction mixture was partitioned between ethyl acetate and water. The aqueous layer was extracted with ethyl acetate (2×50 mL). The combined organic layers were washed with 1.0 N HCl, bicarbonate solution and brine, dried over sodium sulfate and concentrated. Recrystallization of the mixture from ethyl acetate/hexanes afforded 320 as a solid (2.20 g, 67%). $^1$H NMR (400 MHz, CDCl$_3$) δ 7.85 (m, 2H), 7.71 (m, 2H), 7.21 (m, 1H), 7.15 (m, 1H), 6.94 (m, 1H), 5.03 (s, 2H).

Part B: (Feigel, M., Lugert, G., Heichert, C.; *Liebigs Ann. Chem.* 1987, 367)

To paraformaldehyde (250 mg) in HCl (conc., 5 mL) was added 0.5 M zinc chloride in THF (1.7 mL, 0.85 mmol). To this mixture was added 320 (235 mg, 0.85 mmol) in portions and then dioxane (3 mL). The reaction mixture was stirred at 60° C. for 45 minutes. The reaction mixture was cooled and diluted with water (50 mL) and ethyl acetate (50 mL). The layers were separated and the aqueous layer was extracted with ethyl acetate (2×30 mL). The combined organic layers were dried over sodium sulfate and concentrated. Recrystallization from ethyl acetate/hexane afforded 321 as a solid (190 mg, 78%). $^1$H NMR (400 MHz, CDCl$_3$) δ 7.86 (dd, 2H, J=3.2, 5.6 Hz), 7.72 (dd, 2H, J=3.2, 5.6 Hz), 6.98 (d, 1H, J=3.6 Hz), 6.90 (d, 1H, J=3.6 Hz), 4.98 (s, 2H), 4.72 (s, 2H).

Part C:

A mixture 321 (190 mg, 0.65 mmol), 2-methylbenzimidazole (112 mg, 0.85 mmol), sodium iodide (catalytic) and cesium carbonate (275 mg, 0.85 mmol) in DMF (6 mL) were stirred overnight at room temperature. The reaction mixture was partitioned between ethyl acetate and water. The layers were separated and the aqueous layer was extracted with ethyl acetate (2×50 mL). The combined organic layers were washed with sodium bicarbonate solution and brine, dried over sodium sulfate and concentrated. Recrystallization from ethyl acetate/hexane afforded 322 (65 mg) and 322 contaminated with 2-methylbenzimidazole (120 mg). $^1$H NMR (400 MHz, CDCl$_3$) δ 7.83 (dd, 2H, J=3.2, 5.6 Hz), 7.70 (dd, 2H, J=3.2, 5.6 Hz), 7.68 (m, 1H), 7.29 (m, 1H), 7.23 (m, 2H), 6.95 (d, 1H, J=3.6 Hz), 6.70 (d, 1H, J=3.6 Hz), 5.36 (s, 2H), 4.91 (s, 2H), 2.64 (s, 3H); HPLC-MS $t_R$=1.14 min (UV$_{254\ nm}$); mass calculated for formula C$_{22}$H$_{17}$N$_3$O$_2$S 387.1, observed LCMS m/z 388.1 (M+H).

Part D:

Compound 322 (90 mg, 0.23 mmol) and hydrazine hydrate (50 μL, 0.93 mmol) in ethanol (10 mL) and DCM (5 mL) were refluxed for 1.5 hours. The reaction mixture was cooled and filtered. The filtrate was concentrated and the crude product was used without further purification.

Part E:

To 230 (83 mg, 0.24 mmol) in DMF (5 mL) was added 323 (82 mg, 0.32 mmol), DIEA (300 µL, 1.6 mmol) and HATU (135 mg, 0.36 mmol). The reaction mixture was stirred overnight at room temperature. The reaction mixture was diluted with ethyl acetate (50 mL) and water (50 mL). The layers were separated and the aqueous layer was extracted with ethyl acetate. The combined organic layers were washed with sodium bicarbonate solution and brine, dried over sodium sulfate and concentrated. Compound 324 was used without further purification. HPLC-MS $t_R$=1.13 min (UV$_{254\ nm}$); mass calculated for formula $C_{30}H_{30}N_4O_6S$ 574.2, observed LCMS m/z 575.1 (M+H).

Part F:

Compound 324 (~120 mg, 0.21 mmol) and potassium carbonate (100 mg) were mixed in methanol (5 mL) and water (1 mL). After 5 minutes a solid precipitated and the reaction was stirred for 30 minutes. The solid was collected by filtration. Purification by reverse phase prep-LC afforded 325 as a white solid. $^1$H NMR (400 MHz, DMSO-d$_6$) δ 8.35 (t, 1H, J=6.0 Hz), 7.93 (d, 1H, J=8.0 Hz), 7.73 (d, 1H, J=6.8 Hz), 7.48 (m, 2H), 7.33 (m, 1H), 7.27 (m, 3H), 7.08 (d, 1H, J=3.6 Hz), 6.82 (d, 1H, J=3.6 Hz), 5.80 (s, 2H), 5.02 (d, 1H, J=14.4 Hz), 4.86 (d, 1H, J=15.2 Hz), 4.74 (d, 1H, J=16.8 Hz), 4.58 (d, 1H, J=16.4 Hz), 4.57 (s, 1H), 4.33 (m, 2H), 4.22 (s, 1H), 2.84 (s, 3H); HPLC-MS $t_R$=2.74 min (UV$_{254\ nm}$, 10 min); mass calculated for formula $C_{26}H_{26}N_4O_4S$ 490.2, observed LCMS m/z 491.2 (M+H).

Example 6B

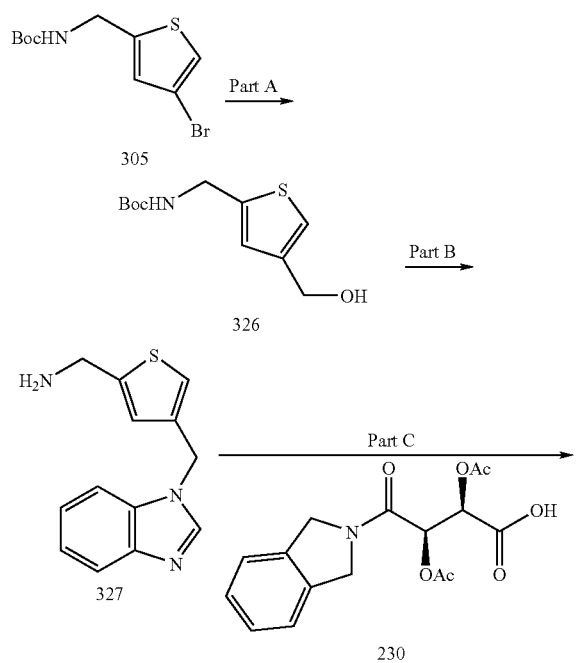

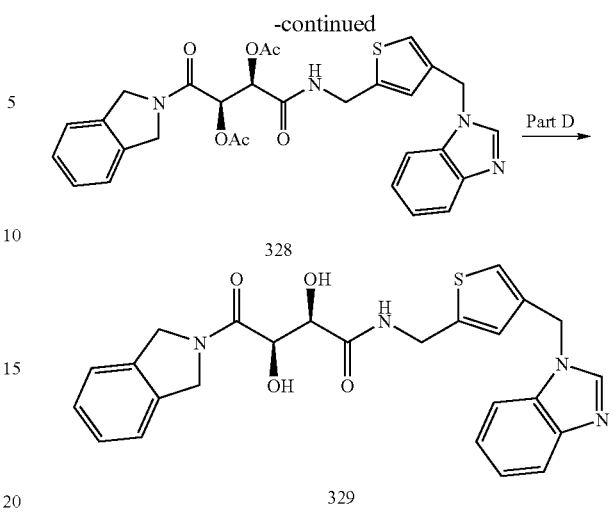

Part A:

To n-butyl lithium (2.5 M, 0.91 mL, 2.28 mmol) in THF (5 mL) at −78° C. under argon was added 305 (300 mg, 1.03 mmol) in THF (5 mL) dropwise. The reaction mixture was stirred for 30 minutes at −78° C. Then dimethyl formamide (151 mg, 2.06 mmol) was added. The reaction mixture was stirred for 30 minutes at −78° C. The reaction mixture was quenched with saturated ammonium chloride solution and warmed to room temperature. The mixture was diluted with ethyl acetate (10 mL) and the layers were separated. The organic layer was washed with water and brine. Dried over sodium sulfate and concentrated. The residue was dissolved in methanol and sodium borohydride (156 mg, 4.12 mmol) was added. The reaction mixture was stirred overnight at room temperature. The reaction mixture was diluted with ethyl acetate and washed with 0.1 N HCl, water and brine. The organic layer was dried over sodium sulfate and concentrated. Purification by column chromatography (SiO$_2$, 25% EtOAc/hexane) afforded 326 (147 mg, 58%). $^1$H NMR (400 MHz, CDCl$_3$) δ 7.10 (s, 1H), 6.94 (s, 1H), 4.63 (s, 2H), 4.45 (d, 2H, J=4.7 Hz), 1.48 (s, 9H).

Part B:

To 326 (30 mg, 0.12 mmol) in THF (2 mL) was added benzimidazole (19 mg, 0.16 mmol), triphenylphosphine (42 mg, 0.16 mmol) and DIAD (32 mg, 0.16 mmol). The reaction mixture was stirred overnight at room temperature. The reaction mixture was concentrated. The residue was dissolved in dichloromethane (2 mL) and TFA (0.5 mL) was added. The reaction mixture was stirred for 30 minutes and concentrated. The residue was dissolved in diethyl ether and washed twice with water. The combined aqueous layer was made basic DIEA and extracted with ethyl acetate. The combined organic layer was washed with brine, dried and concentrated to afford 327 as a film (41 mg). The material was used without further purification.

Part C:

To 230 (20 mg, 0.06 mmol) in DMF (2 mL) was added 327 (19 mg, 0.08 mmol), DIEA (31 µL, 0.18 mmol), DMAP (1 mg) and HATU (30 mg, 0.08 mmol). The reaction mixture was stirred overnight. The mixture was poured into water and extracted with ethyl acetate. The combined organic layers were washed with 0.1 N NaOH, water and brine, dried over sodium sulfate and concentrated. Compound 328 was used without further purification. Mass calculated for formula $C_{29}H_{28}N_4O_6S$ 560.2, observed LCMS m/z 561.2 (M+H).

Part D:

Compound 328 and potassium carbonate (20 mg) were mixed in methanol (2.5 mL) and water (0.5 mL) and were stirred for 30 minutes. The reaction mixture was diluted with ethyl acetate, washed with water and brine, dried over sodium sulfate and concentrated. Purification by reverse phase prep-LC afforded 329 as a white solid (8 mg). HPLC-MS $t_R$=2.77 min ($UV_{254\ nm}$, 10 min); mass calculated for formula $C_{25}H_{24}N_4O_4S$ 476.2, observed LCMS m/z 477.1 (M+H).

Example 6C

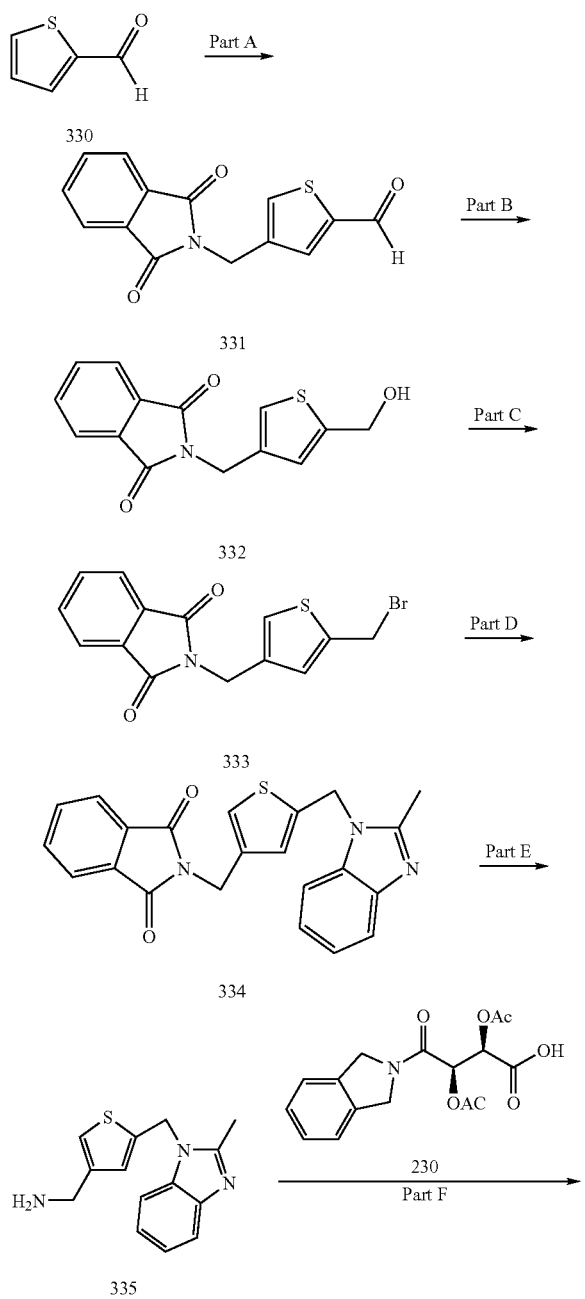

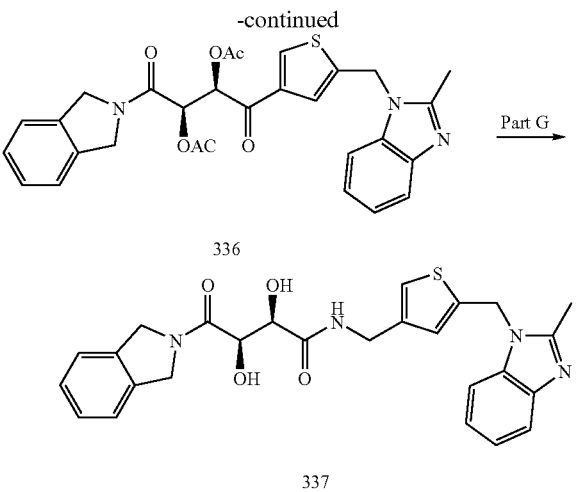

Part A:

N-(Hydroxymethyl)phthalimide (1.0 g, 5.6 mmol) was dissolved in 1% triflic acid in trifluoroacetic acid (10 mL) at 0° C. To this mixture was added 330 (0.52 mL, 5.6 mmol). The reaction mixture was warmed to room temperature slowly and stirred overnight. The reaction mixture was poured into ice water (100 mL) and extracted with DCM. The combined organic layers were washed with sodium bicarbonate solution and brine, dried over sodium sulfate and concentrated. Purification by column chromatography ($SiO_2$, 30% EtOAc/Hex) afforded 331 (619 mg, 41%). $^1$H NMR (400 MHz, $CDCl_3$) δ 9.85 (d, 1H, J=1.6 Hz), 7.86 (m, 2H), 7.81 (d, 1H, J=1.6 Hz), 7.76 (s, 1H), 7.73 (m, 2H), 4.87 (s, 2H).

Part B:

Compound 331 (315 mg, 1.16 mmol) was dissolved in 1:1 methylene chloride:methanol (10 mL) and cooled in an ice bath. To this solution was added sodium borohydride (11 mg, 0.29 mmol) and the reaction was stirred for 30 minutes. Additional sodium borohydride (3 mg, 0.08 mmol) was added and the reaction was stirred for 30 minutes. The reaction mixture was diluted with methylene chloride and washed with saturated ammonium chloride solution, water and brine. The reaction mixture was dried over sodium sulfate and concentrated to afford 332 as a white solid (310 mg, 98%). $^1$H NMR (400 MHz, $CD_3OD$) δ 7.83 (m, 2H), 7.79 (m, 2H), 7.24 (s, 1H), 6.97 (s, 1H), 4.76 (s, 2H), 4.65 (s, 2H).

Part C:

A mixture of 332 (97 mg, 0.36 mmol) and phosphorous tribromide (34 μL, 0.39 mmol) in DCM (5 mL) was stirred for 30 minutes at room temperature. The reaction mixture was poured into ice water and extracted with ethyl acetate. The combined organic layers were washed with sodium bicarbonate solution and brine, dried over sodium sulfate and concentrated to afford 333 as a white solid (104 mg, 87%). $^1$H NMR (400 MHz, $CDCl_3$) δ 7.85 (dd, 2H, J=2.8, 5.2 Hz), 7.72 (dd, 2H, J=2.8, 5.2 Hz), 7.32 (s, 1H), 7.15 (s, 1H), 4.77 (s, 2H), 4.66 (s, 2H).

Part D:

A mixture of 333 (450 mg, 1.34 mmol), 2-methyl-benzimidazole (355 mg, 2.69 mmol) and cesium carbonate (875 mg, 2.69 mmol) in DMF (5 mL) was stirred overnight at room temperature. The reaction mixture was diluted with ethyl acetate and washed with water and brine, dried over sodium sulfate and concentrated. Recrystallization from ethyl acetate/hexanes afforded 334 as a white solid (252 mg, 49%). ¹H NMR (400 MHz, CDCl₃) δ 7.84 (dd, 2H, J=2.8, 5.2 Hz), 7.72 (dd, 2H, J=2.8, 5.2 Hz), 7.68 (m, 1H), 7.23 (m, 3H), 7.19 (s, 1H), 7.05 (s, 1H), 5.38 (s, 2H), 4.75 (s, 2H), 2.66 (s, 3H).

Part E:

A mixture of 334 (225 mg, 0.58 mmol) and hydrazine hydrate (113 µL, 2.32 mmol) in ethanol (4 mL) was refluxed for 4 hours. The reaction mixture was cooled and filtered. The filtrate was concentrated and the residue was dissolved in ethyl acetate. The organic layer was washed with water and brine, dried over sodium sulfate and concentrated to afford a 335 as yellow solid (148 mg, 99%).

Part F:

To 230 (12 mg, 0.036 mmol) in DMF (2 mL) was added 335 (12 mg, 0.045 mmol), DIEA (18 µL, 0.11 mmol) and HATU (17 mg, 0.045 mmol). The reaction mixture was stirred overnight at room temperature. The reaction mixture was diluted with ethyl acetate (20 mL) and water (20 mL). The layers were separated and the aqueous layer was extracted with ethyl acetate. The combined organic layers were washed with sodium bicarbonate solution and brine, dried over sodium sulfate and concentrated. Compound 336 was used without further purification. HPLC-MS $t_R$=1.22 min (UV$_{254\,nm}$); mass calculated for formula $C_{30}H_{30}N_4O_6S$ 574.2, observed LCMS m/z 575.0 (M+H).

Part G:

Compound 336 and potassium carbonate (20 mg) were mixed in methanol (1.5 mL) and stirred for 30 minutes. The reaction mixture was diluted with ethyl acetate, washed with water and brine, dried over sodium sulfate and concentrated. Purification by reverse phase prep-LC afforded 337 as a white solid. ¹H NMR (400 MHz, DMSO-d₆) δ 8.23 (t, 1H, J=6.4 Hz), 7.89 (m, 1H), 7.70 (m, 1H), 7.44 (m, 2H), 7.33 (m, 1H), 7.27 (m, 3H), 7.20 (s, 1H), 7.14 (s, 1H), 5.80 (s, 2H), 5.04 (d, 1H, J=13.2 Hz), 4.88 (d, 1H, J=15.2 Hz), 4.73 (m, 2H), 4.60 (m, 2H), 4.25 (m, 2H), 2.83 (s, 3H); HPLC-MS $t_R$=2.04 min (UV$_{254\,nm}$, 10 min); mass calculated for formula $C_{26}H_{26}N_4O_4S$ 490.2, observed LCMS m/z 491.1 (M+H).

The following compounds were prepared using the procedures described in Example 6A to 6C.

| Compound # | Structure | Exact mass | MS m/z (M + H) |
|---|---|---|---|
| 338 | 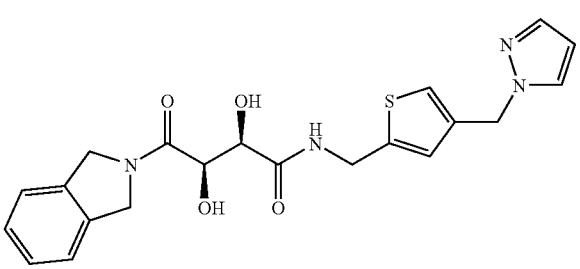 | 426.1 | 427.1 |
| 339 | 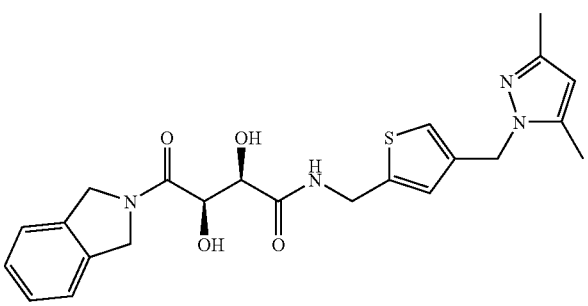 | 454.2 | 455.2 |
| 340 | 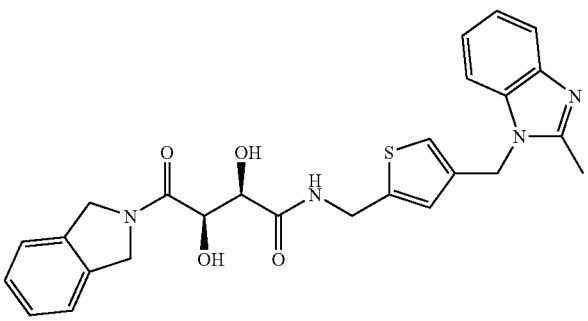 | 490.2 | 491.2 |

-continued
| Compound # | Structure | Exact mass | MS m/z (M + H) |
|---|---|---|---|
| 341 | 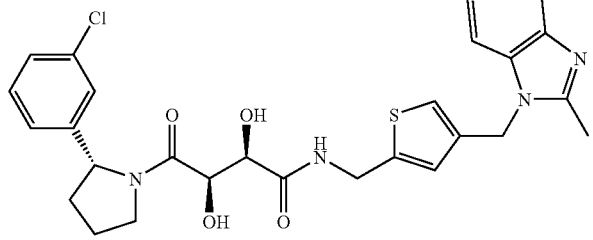 | 552.2 | 553.2 |
| 342 | 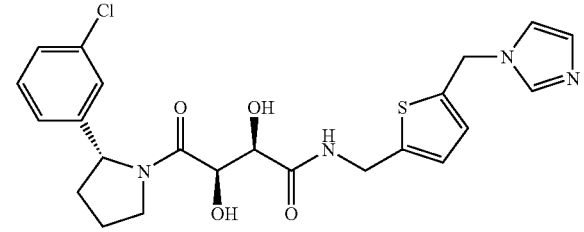 | 488.1 | 489.0 |
| 343 | 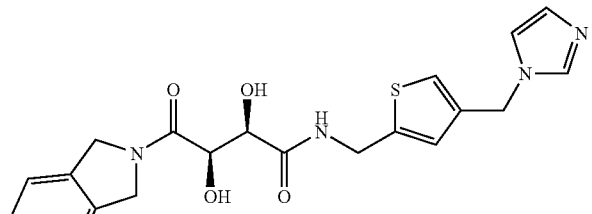 | 426.1 | 427.1 |
| 344 | 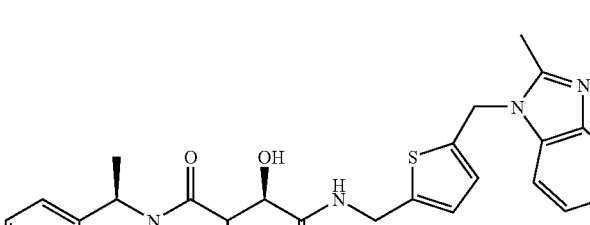 | 506.2 | 507.2 |
| 345 | 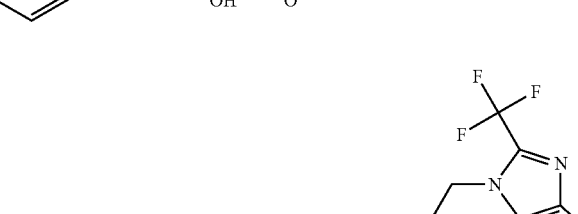 | 544.1 | 545.1 |

-continued
| Compound # | Structure | Exact mass | MS m/z (M + H) |
|---|---|---|---|
| 346 | 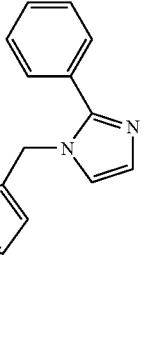 | 502.2 | 503.2 |
| 347 | 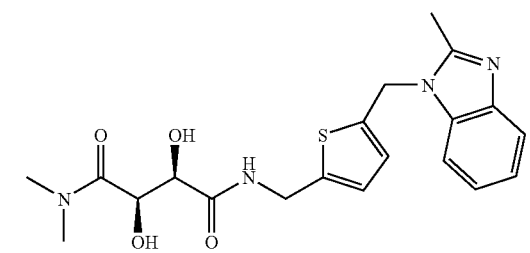 | 416.2 | 417.2 |
| 348 | 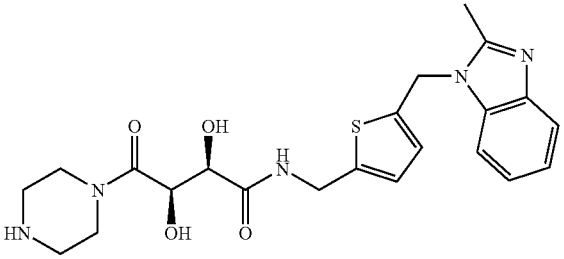 | 457.2 | 458.1 |
| 349 | 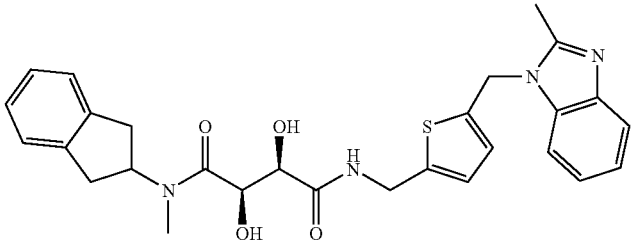 | 518.2 | 519.2 |
Example 7
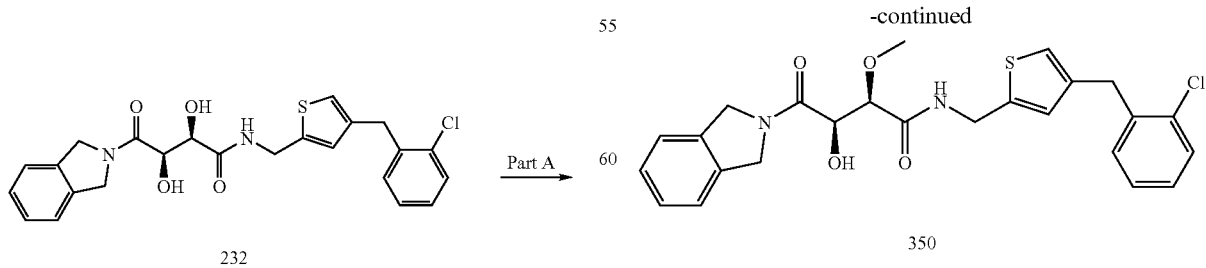

Part A:

To 232 (26 mg, 0.056 mmol) in toluene (5 mL) was added dibutyltin oxide (20 mg, 0.08 mmol). The mixture was heated for 3 hours at reflux with a Dean Stark trap. The mixture was concentrated. The residue was dissolved in NMP (3 mL) and treated with cesium fluoride (8.5 mg, 0.056 mmol) and iodomethane (14 μL, 0.224 mmol). The reaction mixture was heated at 50° C. overnight. The reaction mixture was poured into water and extracted with ethyl acetate. The combined organic layers were washed with brine, dried over sodium sulfate and concentrated. Purification by prep-HPLC afforded 350 (3.4 mg, 13%). HPLC-MS $t_R$=5.26 min (UV$_{254\ nm}$, 10 min.); mass calculated for formula $C_{25}H_{25}ClN_2O_4S$ 484.1, observed LCMS m/z 485.0 (M+H).

| Compound # | Structure | Exact mass | MS m/e (M + H) |
|---|---|---|---|
| 351 | 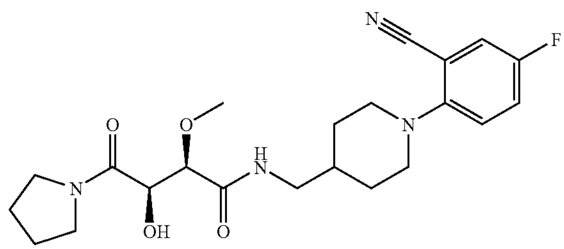 | 432.2 | 433.2 |
| 352 | 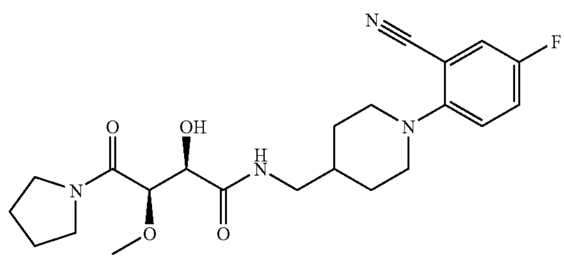 | 432.2 | 433.2 |

Example 8

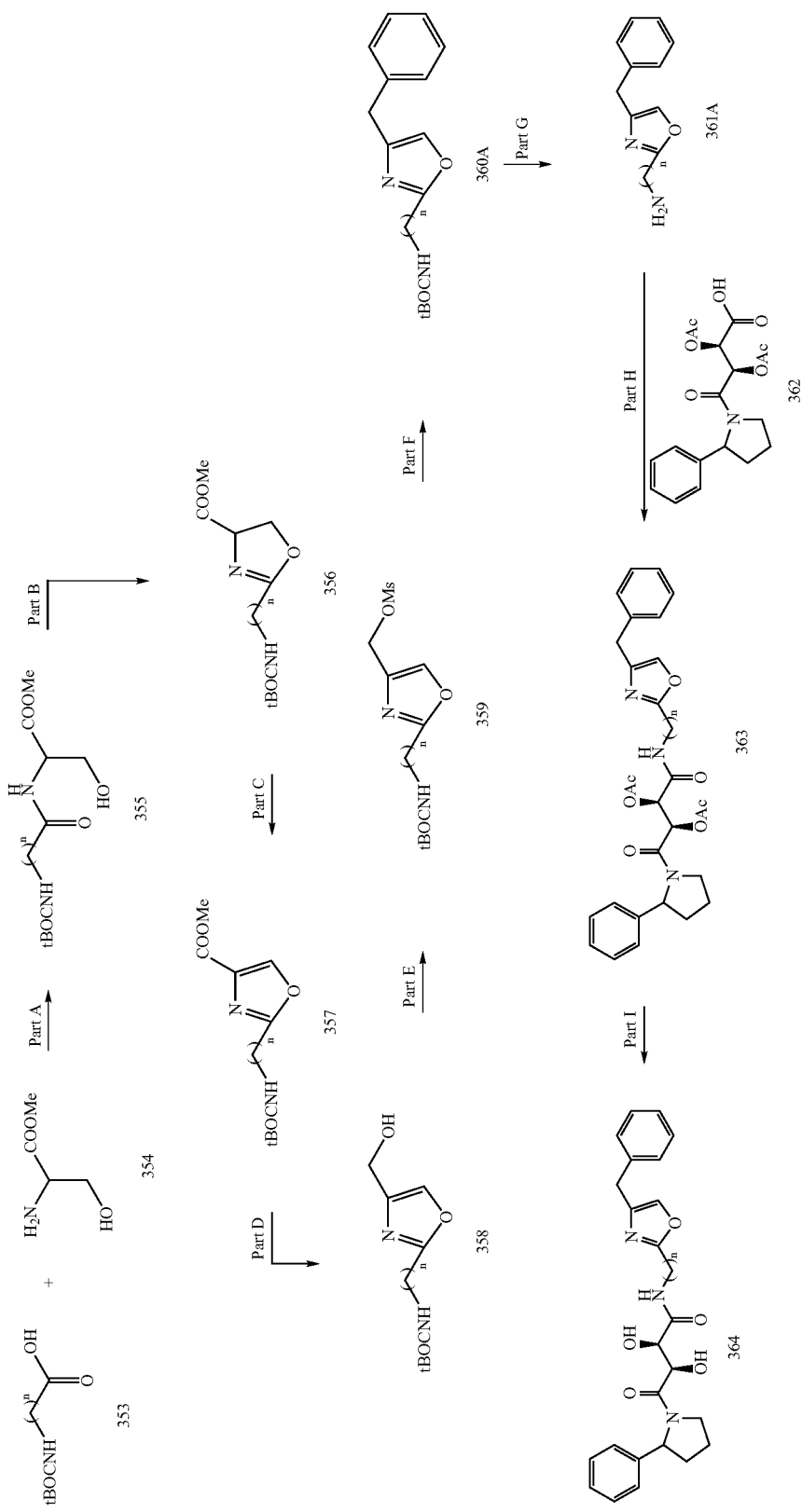

Part A:

To BOC-glycine (353) (25.0 g, 0.143 mol) dissolved in dry THF (100 mL) and cooled to −20° C. under a nitrogen atmosphere was added Hunig's base (23.1 g, 31.1 mL, 0.357 mol) then isobutylchloroformate (21.4 g, 20.4 mL, 0.157 mol). Stirred at −20° C. for 60 mins. Serine methyl ester (354) (24.4 g, 0.157 mol) then Hunig's base (23.1 g, 31.1 mL, 0.357 mol) was added. The reaction mixture was warmed to room temperature, stirred for 18 h and concentrated. The residue was partitioned between 0.5 N NaOH (300 mL) CH$_2$Cl$_2$. The layers were separated and the acqueous layer was extracted with CH$_2$Cl$_2$. The combined organic layer was dried over magnesium sulfate and concentrated. Purified by silica gel chromatography (eluant: 1% MeOH—CH$_2$Cl$_2$ to 3% MeOH—CH$_2$Cl$_2$) to give 20.5 g (52%) of the product 355 as a yellow oil. MS m/e: 277 (M+H).

For n=2: MS m/e: 291 (M+H)

Part B:

To compound 355 (4.55 g, 16.5 mmol) dissolved in CH$_2$Cl$_2$ (200 mL) and cooled to −50° C. under a nitrogen atmosphere was added diethylaminosulfur trifluoride (3.19 g, 2.4 mL, 19.8 mmol) dropwise via syringe. Stirred at −50° C. for 2 h, added potassium carbonate (3.88 g, 28.1 mmol), and warmed slowly to room temperature over 2 h. Added 0.2 N NaOH (100 mL) and separated layers. Extracted aqueous layer with CH$_2$Cl$_2$, dried combined organic extracts (MgSO$_4$), filtered, and concentrated. Purified by silica gel chromatography (eluant: 2% MeOH—CH$_2$Cl$_2$ to 4% MeOH—CH$_2$Cl$_2$) to give 3.06 g (72%) of the product 356 as a yellow oil. MS m/e: 259 (M+H).

For n=2: MS m/e: 273 (M+H)

Part C:

To compound 356 (6.10 g, 23.6 mmol) dissolved in CH$_2$Cl$_2$ (250 mL) and cooled to 0° C. was added DBU (12.59 g, 12.4 mL, 82.7 mmol) and bromotrichloromethane (16.40 g, 8.1 mL, 82.7 mmol). Warmed slowly to room temperature over 2 h and stirred for 16 h. Added 0.1 N NaOH (200 mL) and separated layers. Extracted aqueous layer with CH$_2$Cl$_2$, dried combined organic extracts (MgSO$_4$), filtered, and concentrated. Purified by silica gel chromatography (eluant: 2% MeOH—CH$_2$Cl$_2$ to 3% MeOH—CH$_2$Cl$_2$) to give 4.27 g (71%) of the product 357 as an orange oil. MS m/e: 257 (M+H).

For n=2: MS m/e: 271 (M+H)

Part D:

To compound 357 (4.25 g, 16.6 mmol) dissolved in Et$_2$O (100 mL) was added lithium borohydride (1.44 g, 66.3 mmol) and MeOH (2.13 g, 2.7 mL, 66.3 mmol). Refluxed for 3 h, cooled to room temperature, and concentrated. Added water (100 mL), extracted with CH$_2$Cl$_2$, dried combined organic extracts (MgSO$_4$), filtered, and concentrated. Purified by silica gel chromatography (eluant: 5% MeOH—CH$_2$Cl$_2$ to 10% MeOH—CH$_2$Cl$_2$) to give 2.43 g (64%) of the product 358 as a yellow oil. MS m/e: 229 (M+H).

For n=2: MS m/e: 243 (M+H)

Part E:

To compound 358 (1.41 g, 6.18 mmol) dissolved in CH$_2$Cl$_2$ (35 mL) and cooled to −25° C. was added triethylamine (1.25 g, 1.7 mL, 12.4 mmol) then mesyl chloride (0.85 g, 0.57 mL, 7.41 mmol) dropwise. Warmed to 0° C. slowly over 60 mins. Added water (50 mL), extracted with CH$_2$Cl$_2$, dried combined organic extracts (MgSO$_4$), filtered, and concentrated to give 1.89 g (100%) of the product 359 as a yellow oil. MS m/e: 251 (M+2−tBu).

For n=2: MS m/e: 265 (M+2−tBu)

Part F:

Suspended copper cyanide (1.66 g, 18.5 mmol) in dry THF (70 mL) under a nitrogen atmosphere and cooled to −25° C. Added phenyl magnesium bromide (3.0 M in Et$_2$O, 12.3 mL, 37.0 mmol) dropwise via syringe such that internal temperature <−20° C. Stirred at −20° C. for 30 mins then at 0° C. for 30 mins. Warmed to 15° C. internal temperature then recooled to −25° C. Added compound 359 (1.89 g, 6.18 mmol) dissolved in dry THF (20 mL) dropwise via syringe. Stirred at −25° C. internal temperature for 2 h then at 0° C. for 16 h. Concentrated, added 2 N NH$_4$OH (100 mL), extracted with CH$_2$Cl$_2$, dried combined organic extracts (MgSO$_4$), filtered, and concentrated. Purified by silica gel chromatography (eluant: 5% EtOAc-hexane to 20% EtOAc-hexane) to give 0.82 g (46%) of the product 360A as a yellow oil. MS m/e: 289 (M+H).

The following intermediates were prepared according to the above procedure:

| Compound # | Intermediate Structure | MS |
|---|---|---|
| 360B | tBOCNH—[oxazole]—CH$_2$—[2-Me-phenyl] | 303 (M + H) |
| 360C | tBOCNH—[oxazole]—CH$_2$—[2-OMe-phenyl] | 319 (M + H) |
| 360D | tBOCNH—CH$_2$CH$_2$—[oxazole]—CH$_2$—[phenyl] | 303 (M + H) |

Part G:

To compound 360A (1.00 g, 3.47 mmol) dissolved in 1:1 CH$_2$Cl$_2$:MeOH (30 mL) was added 4 N HCl in dioxane (7.8 mL, 31.2 mmol). Stirred at room temperature for 4 h then concentrated to give 0.78 g (100%) of the product 361A (hydrochloride salt) as a yellow solid. MS m/e: 189 (M+H).

The following intermediates were prepared according to the above procedure:

| Compound # | Intermediate Structure | MS |
|---|---|---|
| 361B | H$_2$N—[oxazole]—CH$_2$—[2-Me-phenyl] | 303 (M + H) |

-continued

| Compound # | Intermediate Structure | MS |
|---|---|---|
| 361C | (aminomethyl-oxazole with 2-methoxybenzyl) | 219 (M + H) |
| 361D | (aminoethyl-oxazole with benzyl) | 203 (M + H) |

Part H: (JFL 80324-023)

Combined compound 361A (0.20 g, 0.677 mmol), compound 362 (0.30 g, 0.812 mmol), HATU (0.51 g, 1.35 mmol), and triethylamine (0.21 g, 0.28 mL, 2.03 mmol) in dry DMF (8 mL). Stirred at room temperature for 16 h. Concentrated, added 0.5 N NaOH (15 mL), extracted with $CH_2Cl_2$, dried combined organic extracts ($MgSO_4$), filtered, and concentrated. Purified by silica gel chromatography (eluant: 3% MeOH—$CH_2Cl_2$) to give 0.25 g (70%) of the product 363 as a beige oil. MS m/e: 534 (M+H).

The following intermediates were prepared according to the above procedure:

| Compound # | Intermediate Structure | MS |
|---|---|---|
| 365 | | 522 (M + H) |
| 366 | | 590 (M + H) |
| 367 | | 520 (M + H) |
| 368 | | 583 (M + H) |
| 369 | | 548 (M + H) |

-continued

| Compound # | Intermediate Structure | MS |
|---|---|---|
| 370 | | 564 (M + H) |
| 371 | | 536 (M + H) |
| 372 | | 604 (M + H) |
| 373 | | 597 (M + H) |
| 374 | | 548 (M + H) |

Part I:

To compound 363 (0.24 g, 0.450 mmol) dissolved in MeOH (10 mL) was added 0.5 M NaOMe in MeOH (0.09 mL, 0.045 mmol). Stirred at room temperature for 60 mins. Added 4 N HCl in dioxane (0.11 mL, 0.450 mmol) and concentrated to give 0.20 g (100%) of the product 364 as a brown foam. MS m/e: 450 (M+H).

The following compounds were prepared according to Example 8:

| Compound # | Structure | Exact mass | MS m/z (M + H) |
|---|---|---|---|
| 375 | 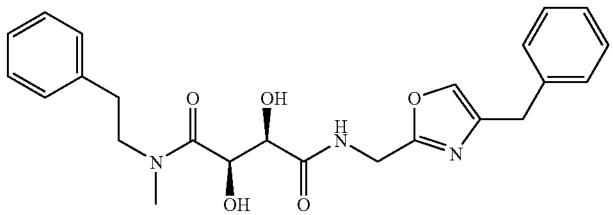 | 437.2 | 438.0 |
| 376 | 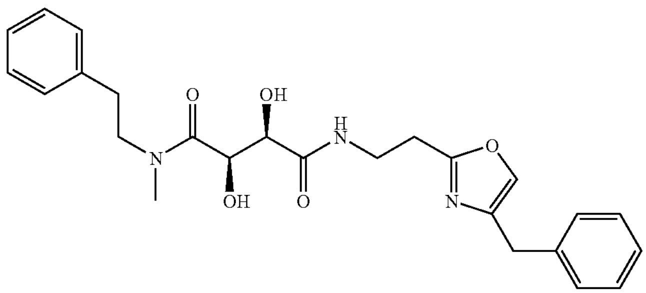 | 451.2 | 452.0 |
| 377 | 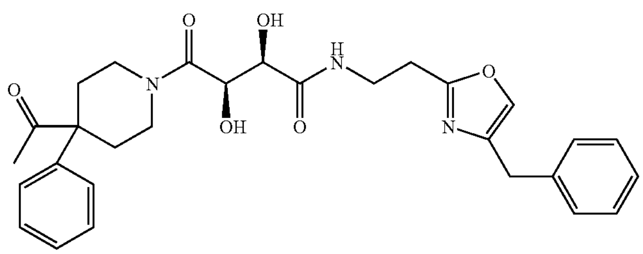 | 519.2 | 520.0 |
| 378 | 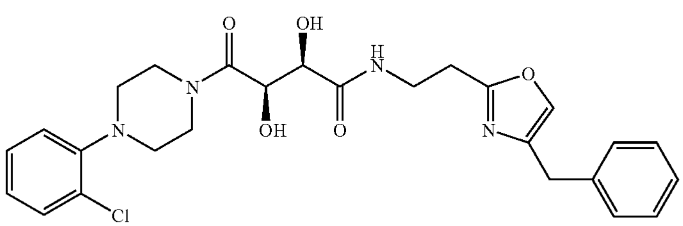 | 512.2 | 513.0 |
| 379 | 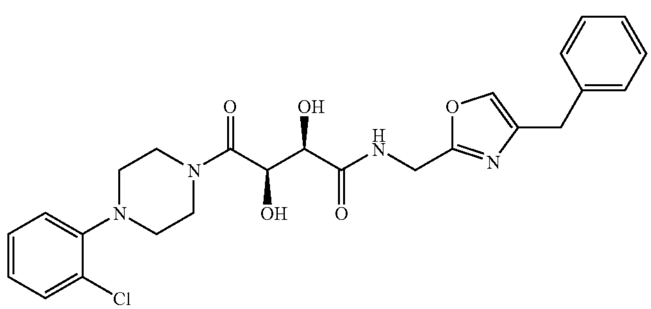 | 498.2 | 499.2 |

-continued

| Compound # | Structure | Exact mass | MS m/z (M + H) |
|---|---|---|---|
| 380 | 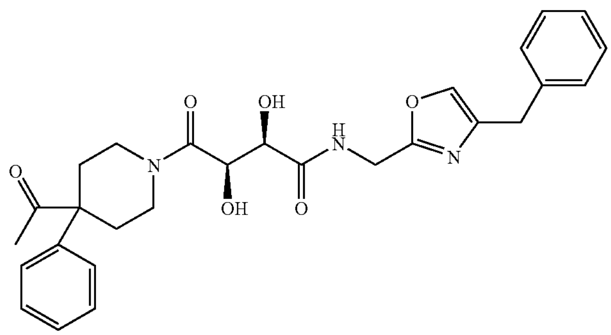 | 505.2 | 506.3 |
| 381 | 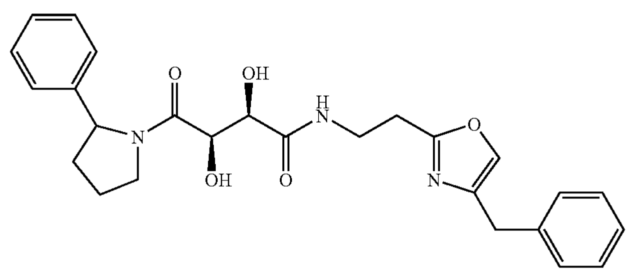 | 463.2 | 464.2 |
| 382 | 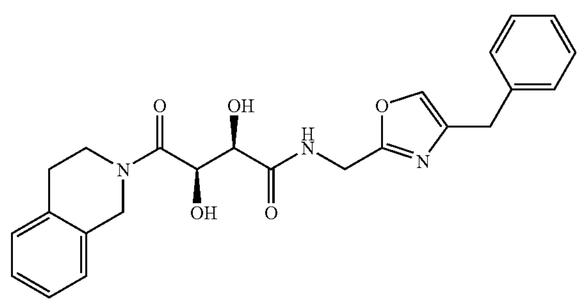 | 435.2 | 436.2 |
| 383 | 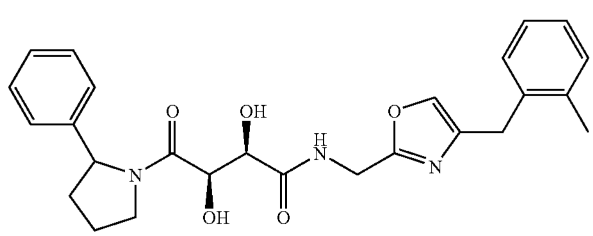 | 463.2 | 464.2 |
| 384 | 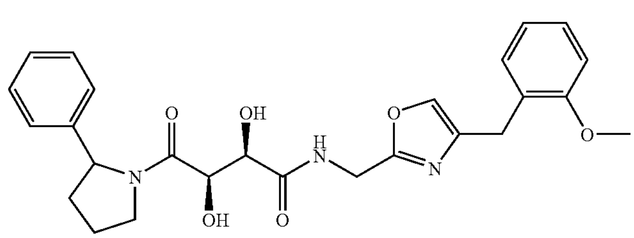 | 479.2 | 480.2 |

-continued

| Compound # | Structure | Exact mass | MS m/z (M + H) |
|---|---|---|---|
| 174 | 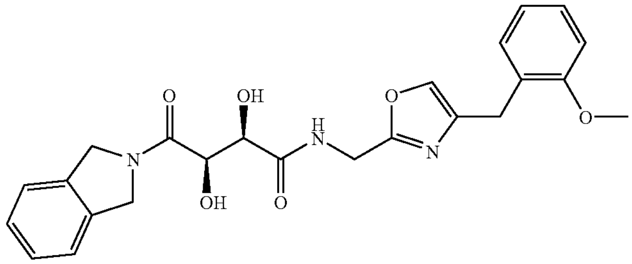 | 451.2 | 452.2 |
| 175 | 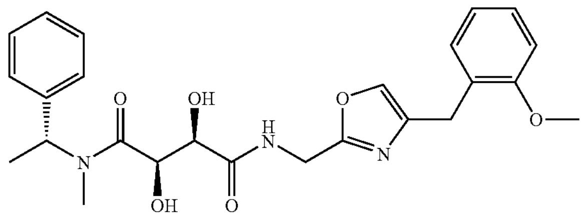 | 467.2 | 468.3 |
| 179 | 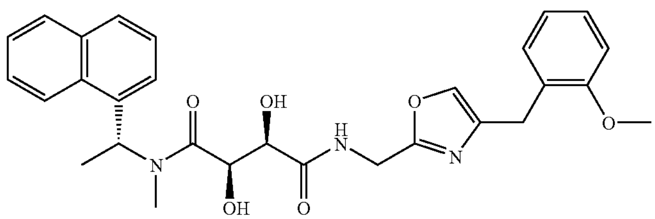 | 517.2 | 518.3 |
| 181 | 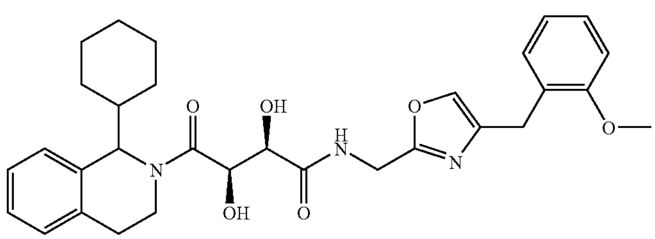 | 547.3 | 548.3 |
| 182 | 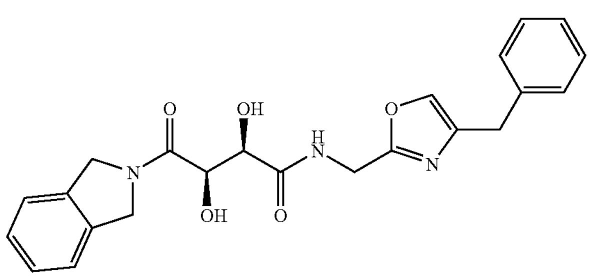 | 421.2 | 422.2 |

Example 9

Thiazole-Benzyl Inhibitors

Example 9A

Scheme 1

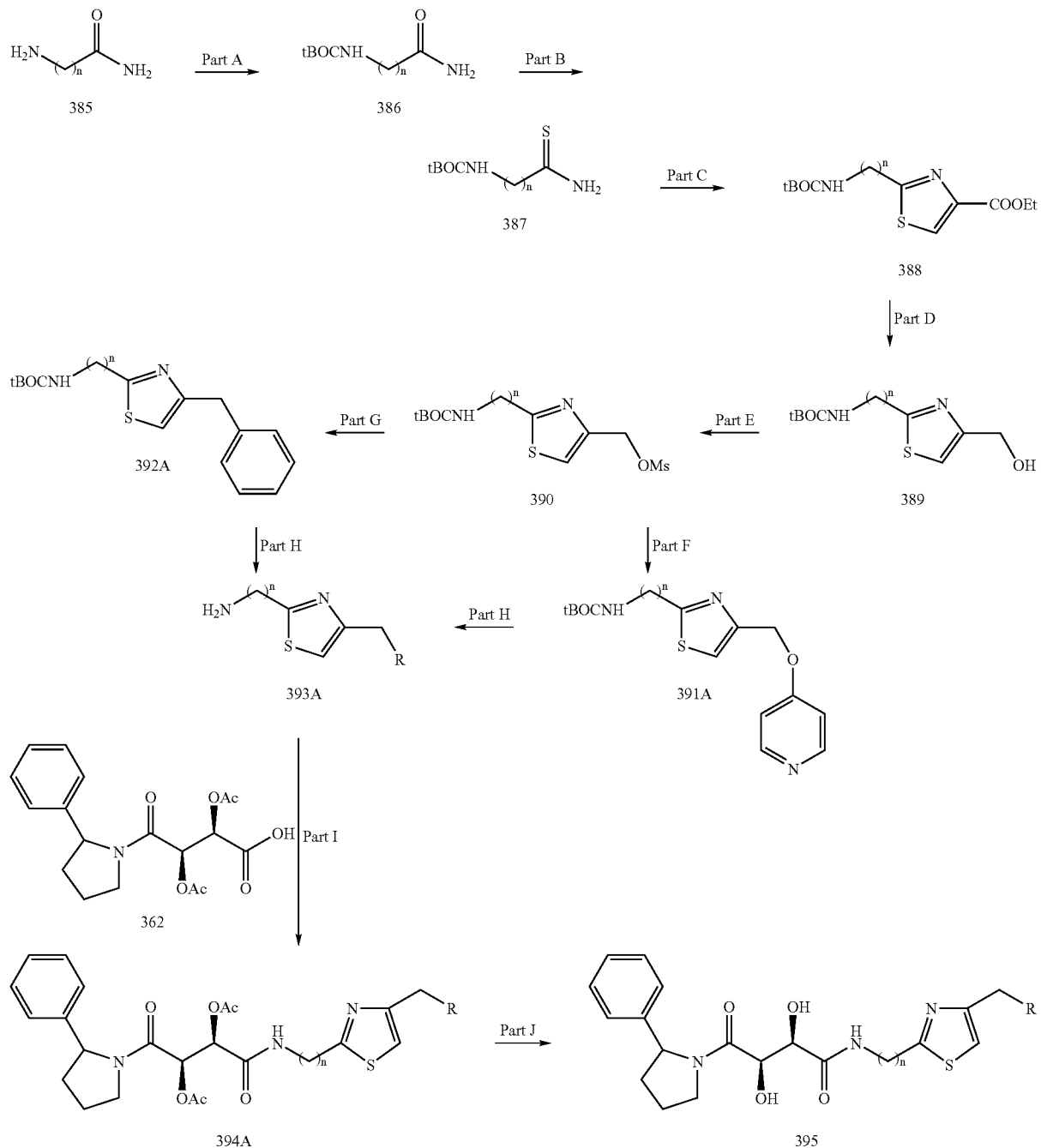

ture and stirred for 24 h. Concentrated, added 1 N NaOH (600 mL), extracted with $CH_2Cl_2$, dried combined organic extracts ($MgSO_4$), filtered, and concentrated to give 53.0 g (56%) of the product 396 as a white solid. MS m/e: 175 (M+H).

For n=2: MS m/e: 189 (M+H)

Part A:

To glycinamide HCl 385 (60.0 g, 0.543 mol) suspended in MeOH (1000 mL) and cooled to 0° C. was added triethylamine (109.9 g, 151.4 mL, 1.09 mol) and tBOC anhydride (148.0 g, 0.678 mol) portionwise. Warmed to room tempera- Part B:

To compound 386 (21.63 g, 0.124 mol) dissolved in THF (400 mL) was added Lawesson reagent (30.13 g, 0.074 mol). Stirred at room temperature for 16 h then concentrated. Purified by silica gel chromatography (eluant: 3% MeOH—

CH$_2$Cl$_2$) then re-purified by silica gel chromatography (eluant: 2% MeOH—CH$_2$Cl$_2$) to give 23.59 g (100%) of the product 387 as a light green solid. MS m/e: 135 (M+2-tBu).

For n=2: MS m/e: 149 (M+2-tBu)

Part C:

To compound 387 (6.00 g, 31.5 mmol) dissolved in CH$_2$Cl$_2$ (150 mL) was added ethyl bromopyruvate (6.76 g, 4.4 mL, 34.7 mmol). Stirred at room temperature for 5 h then concentrated. Added 3 A sieves (6 g) and EtOH (150 mL) and refluxed for 16 h. Filtered and concentrated to give a dark foam. Dissolved foam in 1:1 CH$_2$Cl$_2$:EtOH (100 mL) and added triethylamine (6.40 g, 8.8 mL, 63.1 mmol) and tBOC anhydride (7.60 g, 34.7 mmol). Stirred at room temperature for 5 h then concentrated. Added 0.25 N NaOH (100 mL), extracted with CH$_2$Cl$_2$, dried combined organic extracts (MgSO$_4$), filtered, and concentrated. Purified by silica gel chromatography (eluant: 10% EtOAc-CH$_2$Cl$_2$ to 30% EtOAc-CH$_2$Cl$_2$) to give 6.00 g (67%) of the product 388 as a brown oil. MS m/e: 287 (M+H).

For n=2: MS m/e: 301 (M+H)

Part D:

To compound 388 (4.70 g, 16.4 mmol) dissolved in Et$_2$O (140 mL) was added lithium borohydride (1.43 g, 65.7 mmol) and MeOH (2.10 g, 2.7 mL, 65.7 mmol). Refluxed for 16 h, cooled to room temperature, and concentrated. Added water (100 mL), extracted with CH$_2$Cl$_2$, dried combined organic extracts (MgSO$_4$), filtered, and concentrated. Purified by silica gel chromatography (eluant: 2% MeOH—CH$_2$Cl$_2$ to 5% MeOH—CH$_2$Cl$_2$) to give 3.70 g (92%) of the product 389 as a yellow solid. MS m/e: 245 (M+H).

For n=2: MS m/e: 259 (M+H)

Part E:

To compound 389 (5.30 g, 21.7 mmol) dissolved in CH$_2$Cl$_2$ (130 mL) and cooled to -25° C. was added triethylamine (4.40 g, 6.0 mL, 43.4 mmol) then mesyl chloride (3.00 g, 2.0 mL, 26.0 mmol) dropwise. Warmed to 0° C. slowly over 60 mins. Added water (100 mL), extracted with CH$_2$Cl$_2$, dried combined organic extracts (MgSO$_4$), filtered, and concentrated to give 7.00 g (100%) of the product 390 as a yellow oil. MS m/e: 223 (M+2-tBOC).

For n=2: MS m/e: 237 (M+2-tBOC)

Part F:

To compound 390 (0.60 g, 1.86 mmol) dissolved in dry DMF (25 mL) was added 4-hydroxypyridine (0.22 g, 2.30 mmol) and cesium carbonate (1.20 g, 3.72 mmol). Stirred at room temperature for 16 h then concentrated. Added water (25 mL), extracted with CH$_2$Cl$_2$, dried combined organic extracts (MgSO$_4$), filtered, and concentrated. Purified by silica gel chromatography (eluant: 10% MeOH with NH$_3$—CH$_2$Cl$_2$) to give 0.40 g (68%) of the product 391A as a colorless oil. MS m/e: 322 (M+H).

The following intermediates were prepared according to the above procedure:

| Compound # | Intermediate Structure | MS |
|---|---|---|
| 391B | tBOCNH-thiazole-CH$_2$-O-(2-methylquinolin-4-yl) | 386 (M + H) |
| 391C | tBOCNH-thiazole-CH$_2$-(2-methylbenzimidazol-1-yl) | 359 (M + H) |
| 391D | tBOCNH-thiazole-CH$_2$-(2-trifluoromethylbenzimidazol-1-yl) | 413 (M + H) |
| 391E | tBOCNH-thiazole-CH$_2$-(2,5-dimethylbenzimidazol-1-yl) and tBOCNH-thiazole-CH$_2$-(2,6-dimethylbenzimidazol-1-yl) mixture | 373 (M + H) |

-continued

| Compound # | Intermediate Structure | MS |
|---|---|---|
| 391F | (mixture) | 393 (M + H) |
| 391G | | 336 (M + H) |
| 391H | | 400 (M + H) |

Part G:

Suspended copper cyanide (1.65 g, 18.4 mmol) in dry THF (70 mL) under a nitrogen atmosphere and cooled to −25° C. Added phenyl magnesium bromide (3.0 M in Et$_2$O, 12.3 mL, 37.0 mmol) dropwise via syringe such that internal temperature <−20° C. Stirred at −20° C. for 30 mins then at 0° C. for 30 mins. Warmed to 15° C. internal temperature then recooled to −25° C. Added compound 390 (1.98 g, 6.14 mmol) dissolved in dry THF (20 mL) dropwise via syringe. Stirred at −25° C. internal temperature for 2 h then at 0° C. for 16 h. Concentrated, added 2 N NH$_4$OH (100 mL), extracted with CH$_2$Cl$_2$, dried combined organic extracts (MgSO$_4$), filtered, and concentrated. Purified by silica gel chromatography (eluant: 5% EtOAc-hexane to 20% EtOAc-hexane) to give 1.14 g (66%) of the product 392A as a yellow oil. MS m/e: 305 (M+H).

The following intermediates were prepared according to the above procedure:

| Compound # | Intermediate Structure | MS |
|---|---|---|
| 392B | | 319 (M + H) |
| 392C | | 319 (M + H) |
| 392D | | 333 (M + H) |
| 392E | | 335 (M + H) |
| 392F | | 381 (M + H) |
| 392G | | 333 (M + H) |

| Compound # | Intermediate Structure | MS |
|---|---|---|
| 392H | tBOCNH—[thiazole]—CH2—[phenyl with Me, F] | 337 (M + H) |
| 392I | tBOCNH—[thiazole]—CH2—[phenyl with Me, F] | 337 (M + H) |
| 392J | tBOCNH—[thiazole]—CH2—[phenyl with Me, F] | 337 (M + H) |
| 392K | tBOCNH—[thiazole]—CH2—[phenyl with OMe, F] | 353 (M + H) |
| 392L | tBOCNH—[thiazole]—CH2—[4-pyridyl] | 306 (M + H) |
| 392M | tBOCNH—[thiazole]—CH2—[3-pyridyl] | 306 (M + H) |
| 392N | tBOCNH—[thiazole]—CH2—[phenyl with NMe2] | 348 (M + H) |
| 392O | tBOCNH—[ethyl-thiazole]—CH2—[phenyl] | 319 (M + H) |

Part H:

To compound 392A (0.30 g, 0.986 mmol) dissolved in 1:1 $CH_2Cl_2$:MeOH (10 mL) was added 4 N HCl in dioxane (2.4 mL, 9.86 mmol). Stirred at room temperature for 16 h then concentrated to give 0.23 g (100%) of the product 393A (hydrochloride salt) as a beige foam. MS m/e: 205 (M+H).

The following intermediates were prepared according to the above procedure:

| Compound # | Intermediate Structure | MS |
|---|---|---|
| 393B | H2N—CH2—[thiazole]—CH2—[phenyl with 2-Me] | 219 (M + H) |
| 393C | H2N—CH2—[thiazole]—CH2—[phenyl with 3-Me] | 219 (M + H) |
| 393D | H2N—CH2—[thiazole]—CH2—[phenyl with 2-Et] | 233 (M + H) |
| 393E | H2N—CH2—[thiazole]—CH2—[phenyl with 2-OMe] | 235 (M + H) |

-continued

| Compound # | Intermediate Structure | MS |
|---|---|---|
| 393F | 2-(aminomethyl)-4-(2-ethoxybenzyl)thiazole | 249 (M + H) |
| 393G | 2-(aminomethyl)-4-(2-phenylbenzyl)thiazole | 281 (M + H) |
| 393H | 2-(aminomethyl)-4-(2-chlorobenzyl)thiazole | 239 (M + H) |
| 393I | 2-(aminomethyl)-4-(2-cyanobenzyl)thiazole | 230 (M + H) |
| 393J | 2-(aminomethyl)-4-(2,6-dimethylbenzyl)thiazole | 233 (M + H) |
| 393K | 2-(aminomethyl)-4-(3-fluoro-2-methylbenzyl)thiazole | 237 (M + H) |
| 393L | 2-(aminomethyl)-4-(4-fluoro-2-methylbenzyl)thiazole | 237 (M + H) |
| 393M | 2-(aminomethyl)-4-(5-fluoro-2-methylbenzyl)thiazole | 237 (M + H) |
| 393N | 2-(aminomethyl)-4-(5-fluoro-2-methoxybenzyl)thiazole | 253 (M + H) |

-continued

| Compound # | Intermediate Structure | MS |
|---|---|---|
| 393O | | 206 (M + H) |
| 393P | | 206 (M + H) |
| 393Q | | 248 (M + H) |
| 393R | | 219 (M + H) |
| 393S | | 219 (M + H) |
| 393T | | 286 (M + H) |
| 393U | | 259 (M + H) |
| 393V | | 313 (M + H) |
| 393W | mixture | 273 (M + H) |

| Compound # | Intermediate Structure | MS |
|---|---|---|
| 393X | mixture | 293 (M + H) |
| 393Y | | 236 (M + H) |
| 393Z | | 300 (M + H) |

Part I:

Combined compound 393A (100 mg, 0.416 mmol), compound 362 (181 mg, 0.499 mmol), HATU (316 mg, 0.832 mmol), and triethylamine (126 mg, 0.17 mL, 1.25 mmol) in dry DMF (6 mL). Stirred at room temperature for 16 h. Concentrated, added 0.5 N NaOH (15 mL), extracted with $CH_2Cl_2$, dried combined organic extracts ($MgSO_4$), filtered, and concentrated. Purified by silica gel chromatography (eluant: 3% MeOH—$CH_2Cl_2$) to give 120 mg (52%) of the product 394A as a colorless oil. MS m/e: 550 (M+H).

The following intermediates were prepared according to the above procedure:

| Compound # | Intermediate Structure | MS |
|---|---|---|
| 394B | | 616(M + H) |
| 394C | | 680(M + H) |

-continued
| Compound # | Intermediate Structure | MS |
|---|---|---|
| 394D | 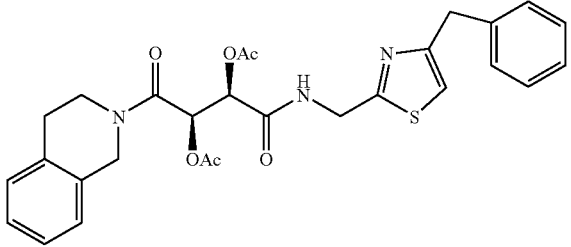 | 536(M + H) |
| 394E | 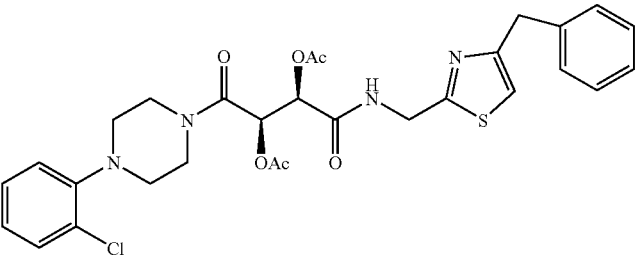 | 600(M + H) |
| 394F | 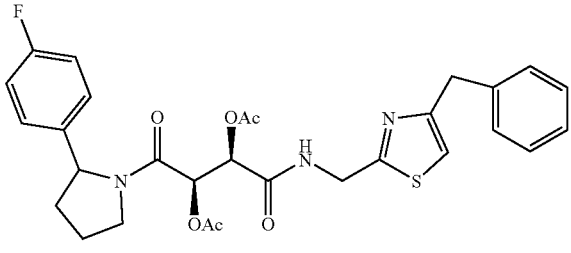 | 568(M + H) |
| 394G | 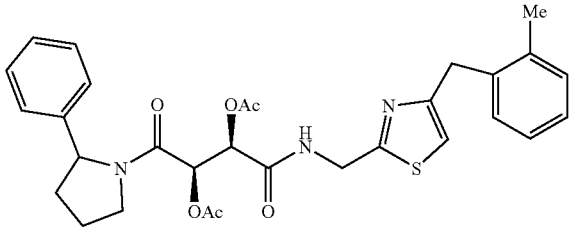 | 564(M + H) |
| 394H | 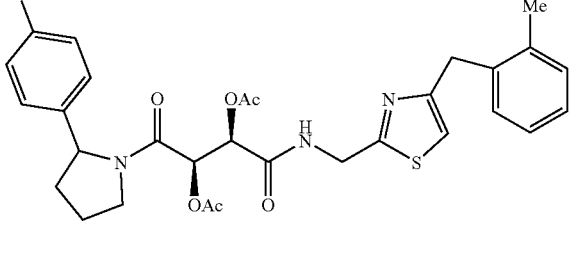 | 582(M + H) |
| 394I | 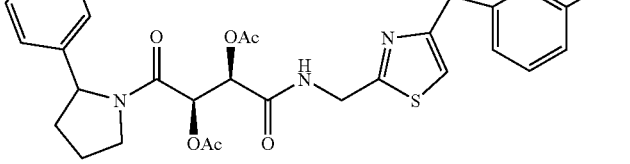 | 564(M + H) |

-continued

| Compound # | Intermediate Structure | MS |
|---|---|---|
| 394J | | 580(M + H) |
| 394K | | 594(M + H) |
| 394L | | 578(M + H) |
| 394M | | 626(M + H) |
| 394N | | 584(M + H) |
| 394O | | 575(M + H) |

-continued

| Compound # | Intermediate Structure | MS |
|---|---|---|
| 394P | | 578(M + H) |
| 394Q | | 612(M + H) |
| 394R | | 596(M + H) |
| 394S | | 592(M + H) |
| 394T | | 608(M + H) |
| 394U | | 621(M + H) |

-continued

| Compound # | Intermediate Structure | MS |
| --- | --- | --- |
| 394V | | 635(M + H) |
| 394W | | 661(M + H) |
| 394X | | 677(M + H) |
| 394Y | | 579(M + H) |
| 394Z | | 585(M + H) |
| 394AA | | 608(M + H) |

-continued

| Compound # | Intermediate Structure | MS |
|---|---|---|
| 394BB | | 582(M + H) |
| 394CC | | 582(M + H) |
| 394DD | | 582(M + H) |
| 394EE | | 598(M + H) |
| 394FF | | 580(M + H) |
| 394GG | | 551(M + H) |

| Compound # | Intermediate Structure | MS |
|---|---|---|
| 394HH | | 569(M + H) |
| 394II | | 551(M + H) |
| 394JJ | | 593(M + H) |
| 394KK | | 607(M + H) |
| 394LL | | 564(M + H) |
| 394MM | | 630(M + H) |

-continued

| Compound # | Intermediate Structure | MS |
|---|---|---|
| 394NN | | 694(M + H) |
| 394OO | | 552(M + H) |
| 394PP | | 620(M + H) |
| 394QQ | | 613(M + H) |
| 394RR | | 564(M + H) |
| 394SS | | 604(M + H) |
| 394TT | | 647(M + H) |

| Compound # | Intermediate Structure | MS |
|---|---|---|
| 394UU | 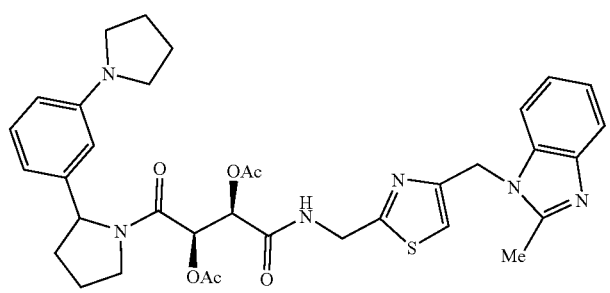 | 673(M + H) |
| 394VV | 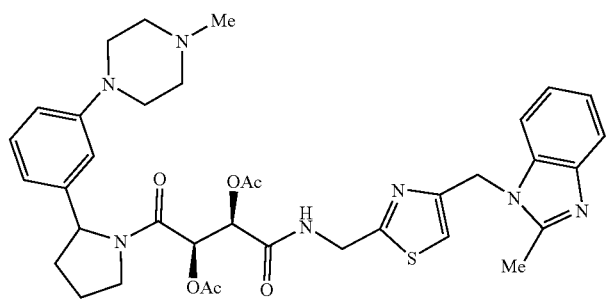 | 702(M + H) |
| 394WW | 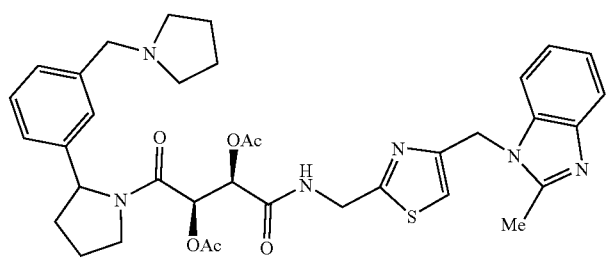 | 687(M + H) |
| 394XX | 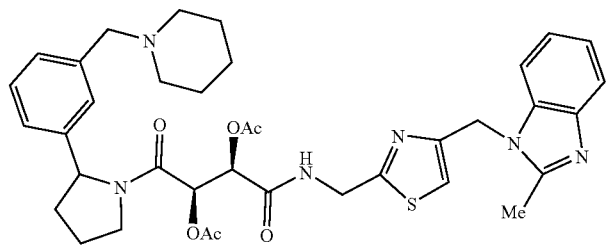 | 701(M + H) |
| 394YY | 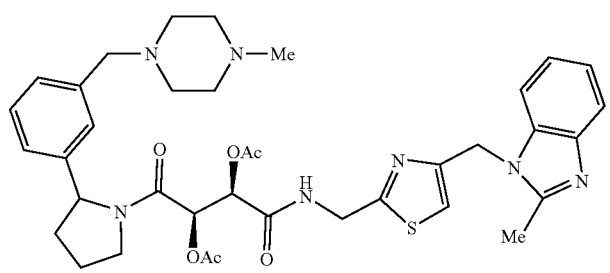 | 716(M + H) |

| Compound # | Intermediate Structure | MS |
|---|---|---|
| 394ZZ | | 701(M + H) |
| 394AAA | | 661(M + H) |
| | | |
| 394BBB | | 682(M + H) |
| | | |

Part J:

To compound 394A (0.12 g, 0.218 mmol) dissolved in MeOH (6 mL) was added 0.5 M NaOMe in MeOH (0.044 mL, 0.0218 mmol). Stirred at room temperature for 60 mins. Added 4 N HCl in dioxane (0.055 mL, 0.218 mmol) and concentrated to give 0.10 g (100%) of the product 395 as a light yellow foam. MS m/e: 466 (M+H).

The following compounds were prepared according to the above procedure:

| Compound # | Compound | MS |
|---|---|---|
| 396 | 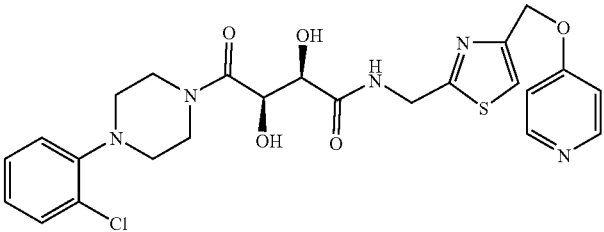 | 532(M + H) |
| 397 | 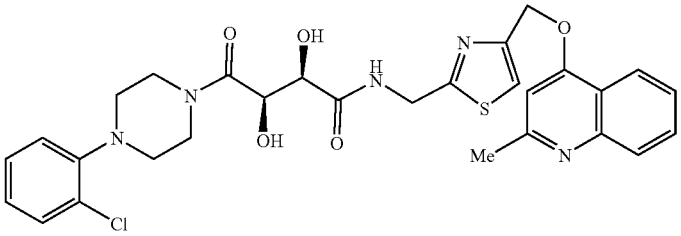 | 596(M + H) |
| 398 | 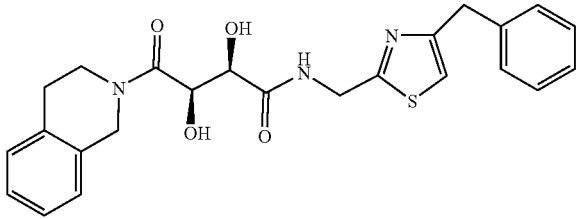 | 452(M + H) |
| 399 | 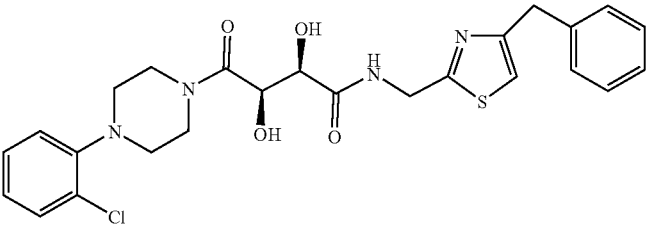 | 515(M + H) |
| 400 | 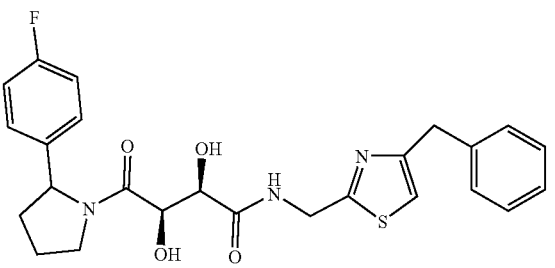 | 484(M + H) |
| 401 | 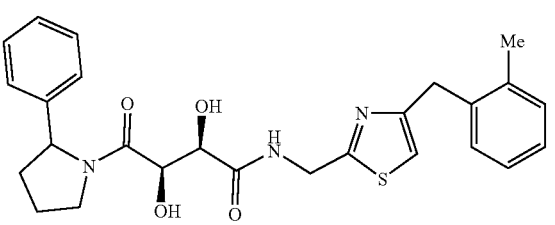 | 480(M + H) |

-continued

| Compound # | Compound | MS |
|---|---|---|
| 402 | | 498(M + H) |
| 403 | | 480(M + H) |
| 404 | | 496(M + H) |
| 405 | | 510(M + H) |
| 406 | | 494(M + H) |
| 407 | | 542(M + H) |

-continued
| Compound # | Compound | MS |
|---|---|---|
| 408 | 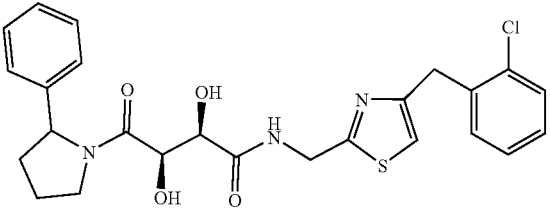 | 500(M + H) |
| 409 | 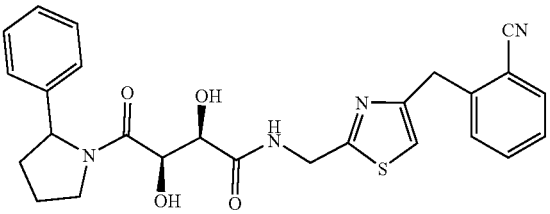 | 491(M + H) |
| 410 | 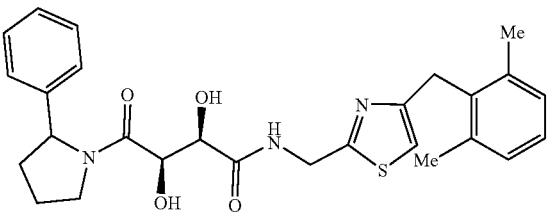 | 494(M + H) |
| 411 | 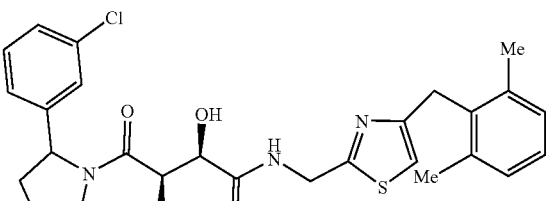 | 528(M + H) |
| 412 | 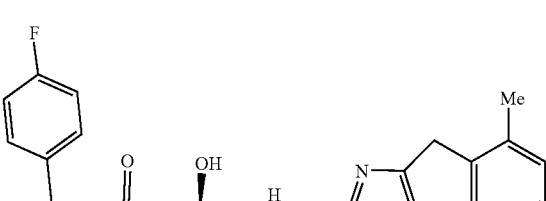 | 512(M + H) |
| 413 | 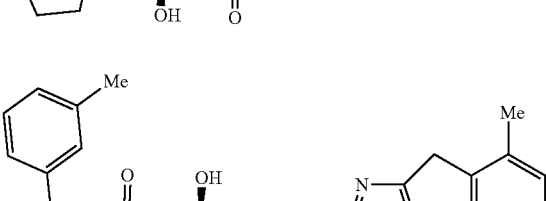 | 508(M + H) |

-continued

| Compound # | Compound | MS |
|---|---|---|
| 414 | (3-OMe-phenyl-pyrrolidine tartrate amide with 2,6-dimethylbenzyl thiazole) | 524(M + H) |
| 415 | (3-NMe2-phenyl analog) | 537(M + H) |
| 416 | (3-CH2NMe2-phenyl analog) | 551(M + H) |
| 417 | (3-CH2-pyrrolidinyl-phenyl analog) | 577(M + H) |
| 418 | (3-CH2-morpholinyl-phenyl analog) | 593(M + H) |
| 419 | (3-pyridyl analog) | 495(M + H) |

-continued

| Compound # | Compound | MS |
|---|---|---|
| 420 | | 501(M + H) |
| 421 | | 524(M + H) |
| 422 | | 498(M + H) |
| 423 | | 498(M + H) |
| 424 | | 498(M + H) |
| 425 | | 514(M + H) |
| 426 | | 496(M + H) |

-continued

| Compound # | Compound | MS |
|---|---|---|
| 427 | | 467(M + H) |
| 428 | | 485(M + H) |
| 429 | | 467(M + H) |
| 430 | | 509(M + H) |
| 431 | | 523(M + H) |
| 432 | | 480(M + H) |

-continued

| Compound # | Compound | MS |
|---|---|---|
| 433 | | 546(M + H) |
| 434 | | 610(M + H) |
| 435 | | 468(M + H) |
| 436 | | 536(M + H) |
| 437 | | 529(M + H) |
| 438 | | 480(M + H) |
| 439 | | 520(M + H) |

| Compound # | Compound | MS |
|---|---|---|
| 440 | 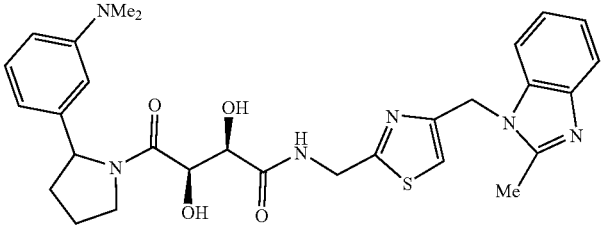 | 563(M + H) |
| 441 | 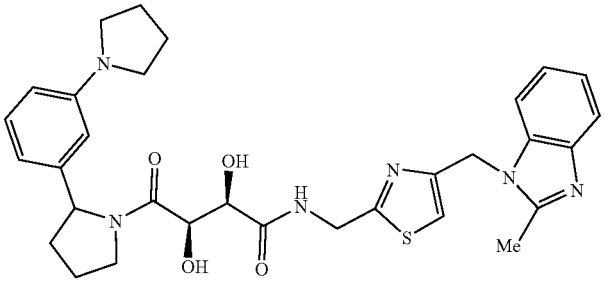 | 589(M + H) |
| 442 | 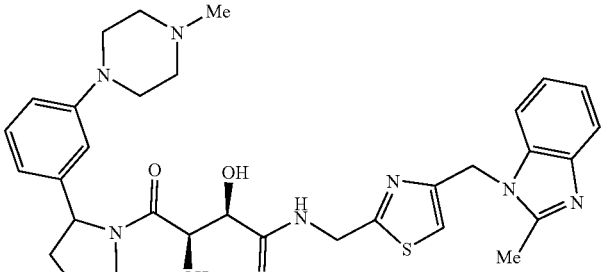 | 618(M + H) |
| 443 | 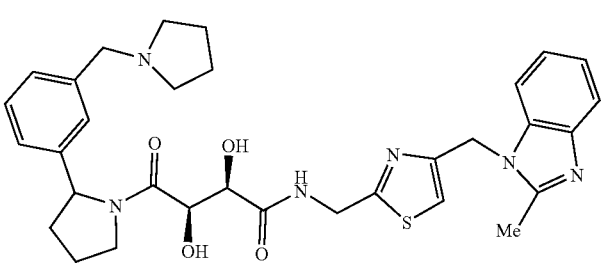 | 603(M + H) |
| 444 | 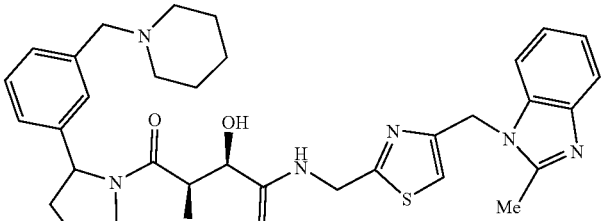 | 617(M + H) |

-continued

| Compound # | Compound | MS |
|---|---|---|
| 445 | | 632(M + H) |
| 446 | | 617(M + H) |
| 447 | | 577(M + H) |
| 448 | | 597(M + H) |

Example 9B

Scheme 1

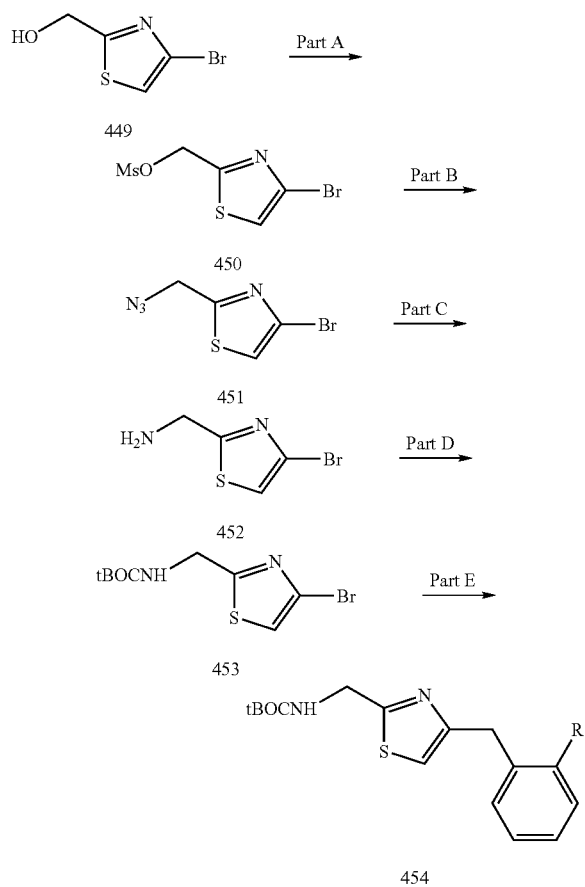

Reference for compound 449:
K. C. Nicolaou, N. P. King, M. R. V. Finlay, Y. He, F. Roschangar, D. Vourloumis, H. Vallberg, F. Sarabia, S. Ninkovic, D. Hepworth; *Bioorg. Med. Chem.* 1999, 7, 665-697.

Part A:
To compound 449 (4.86 g, 25.0 mmol) dissolved in $CH_2Cl_2$ (200 mL) and cooled to −30° C. was added triethylamine (5.07 g, 7.0 mL, 50.1 mmol) and then mesyl chloride (3.44 g, 2.3 mL, 30.1 mmol) dropwise via syringe. Warmed slowly to 0° C. over 60 mins. Added water (200 mL), extracted with $CH_2Cl_2$, dried combined organic extracts (MgSO$_4$), filtered, and concentrated to give 6.80 g (100%) of the product 450 as an orange oil. MS m/e: 272 (M+H).

Part B:
To compound 450 (6.80 g, 25.0 mmol) dissolved in DMF (100 mL) was added sodium azide (3.25 g, 50.0 mmol) and heated at 80° C. for 2 h. Cooled to room temperature and concentrated. Added water (200 mL), extracted with $CH_2Cl_2$, dried combined organic extracts (MgSO$_4$), filtered, and concentrated. Purified by silica gel chromatography (eluant: 5% EtOAc-hexane to 10% EtOAc-hexane) to give 4.18 g (76%) of the product 451 as an orange oil. MS m/e: 219 (M+H).

Part C:
To compound 451 (4.18 g, 19.1 mmol) dissolved in 10:1 THF:water by volume (150 mL) was added triphenylphosphine (20.0 g, 76.3 mmol) and refluxed for 2 h. Cooled to room temperature and concentrated. Purified by silica gel chromatography (eluant: 3% MeOH with $NH_3$—$CH_2Cl_2$) to give 6.18 g of the product 452 (with triphenylphosphine oxide) as a yellow solid. 100% yield of product 452 would be 3.68 g. MS m/e: 194 (M+H).

Part D:
To compound 452 (3.68 g, 19.1 mmol) dissolved in $CH_2Cl_2$ (100 mL) was added tBOC anhydride (5.21 g, 23.9 mmol). Stirred at room temperature for 2 h then concentrated. Purified by silica gel chromatography (eluant: 3% MeOH—$CH_2Cl_2$) to give 3.97 g (71%) of the product 453 as a yellow oil. MS m/e: 293 (M+H).

Part E:
To compound 453 (1.07 g, 3.65 mmol) dissolved in dry THF (10 mL) under a nitrogen atmosphere was added 2-chlorobenzylzinc chloride (0.5 M in THF, 14.6 mL, 7.30 mmol) and bis(tri-t-butylphosphine)palladium (0.14 g, 0.274 mmol). Heated at 60° C. for 2 h. Cooled to room temperature and concentrated. Added 0.2 N HCl (30 mL), extracted with $CH_2Cl_2$, dried combined organic extracts (MgSO$_4$), filtered, and concentrated. Purified by silica gel chromatography (eluant: 5% EtOAc-hexane to 15% EtOAc-hexane) to give 0.61 g (49%) of the product 454 as a yellow oil. MS m/e: 339 (M+H).

Scheme 2

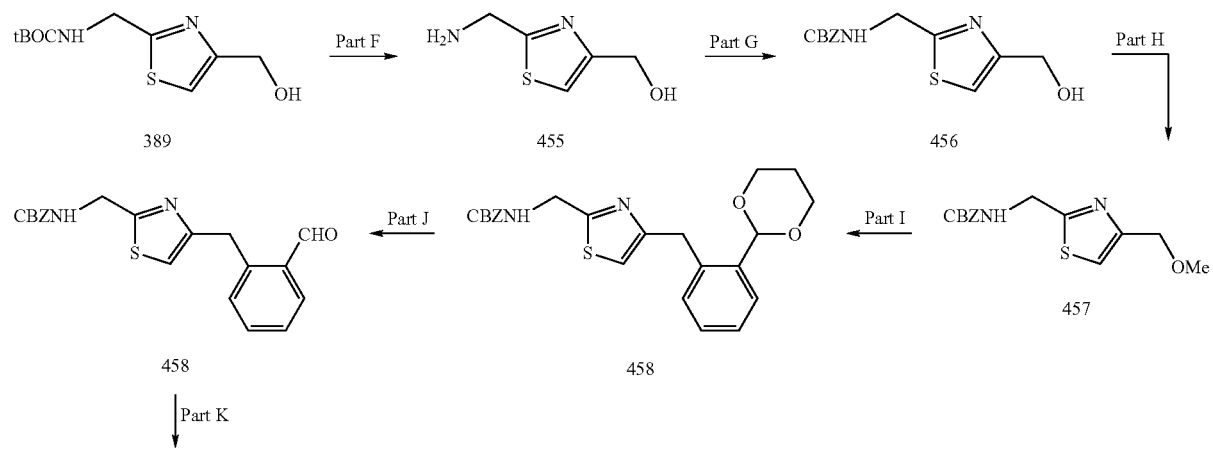

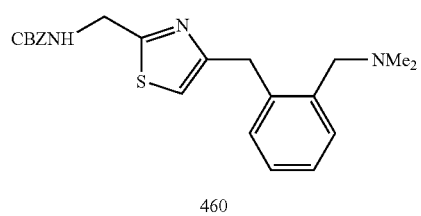

460

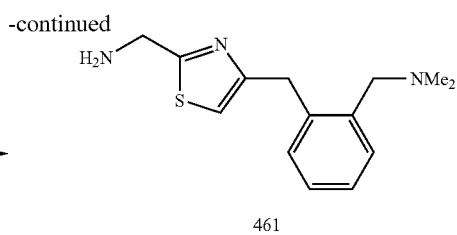

461

Part F:

To compound 389 (2.00 g, 8.18 mmol) dissolved in MeOH (40 mL) was added 4 N HCl in dioxane (20.5 mL, 81.8 mmol). Stirred at room temperature for 3 h. Concentrated to give 1.48 g (100%) of the product 455 as a white solid. MS m/e: 145 (M+H).

Part G:

To compound 455 (1.48 g, 8.18 mmol) suspended in $CH_2Cl_2$ (50 mL) was added triethylamine (2.48 g, 3.4 mL, 24.5 mmol) and cooled to 0° C. Added CBZCl (1.54 g, 1.3 mL, 9.00 mmol) dissolved in $CH_2Cl_2$ (10 mL) dropwise via addition funnel. Stirred at 0° C. for 30 mins then at room temperature for 2 h. Added 0.2 N NaOH (100 mL), extracted with $CH_2Cl_2$, dried combined organic extracts ($MgSO_4$), filtered, and concentrated. Purified by silica gel chromatography (eluant: 5% MeOH—$CH_2Cl_2$ to 10% MeOH—$CH_2Cl_2$) to give 1.41 g (62%) of the product 456 as a white solid. MS m/e: 279 (M+H).

Part H:

To compound 456 (1.40 g, 5.03 mmol) dissolved in $CH_2Cl_2$ (40 mL) and cooled to −30° C. was added triethylamine (1.02 g, 1.4 mL, 10.1 mmol) and then mesyl chloride (0.69 g, 0.47 mL, 6.04 mmol) dropwise via syringe. Warmed slowly to 0° C. over 60 mins. Added water (50 mL), extracted with $CH_2Cl_2$, dried combined organic extracts ($MgSO_4$), filtered, and concentrated to give 1.79 g (100%) of the product 457 as a yellow oil. MS m/e: 357 (M+H).

Part I:

To 2-(1,3-dioxan-2-yl)phenylmagnesium bromide (0.25 M in THF, 100 mL, 25.0 mmol) under a nitrogen atmosphere and cooled to −25° C. internal temperature was added copper cyanide (1.12 g, 12.5 mmol). Stirred at −25° C. for 1 h then at 0° C. for 1 h. Warmed to 15° C. internal temperature then recooled to −25° C. Added compound 457 (1.78 g, 4.99 mmol) dissolved in dry THF (15 mL) dropwise via syringe. Stirred at −25° C. internal temperature for 1 h then at 0° C. for 16 h. Concentrated, added 2 N $NH_4OH$ (100 mL) and $CH_2Cl_2$ (100 mL), and filtered through celite. Separated layers of filtrate, extracted with $CH_2Cl_2$, dried combined organic extracts ($MgSO_4$), filtered, and concentrated. Purified by silica gel chromatography (eluant: 10% EtOAc-hexane to 40% EtOAc-hexane) to give 1.35 g (64%) of the product 458 as a white solid. MS m/e: 425 (M+H).

Part J:

To compound 458 (1.34 g, 3.16 mmol) dissolved in $CH_2Cl_2$ (10 mL) was added water (2 mL) and TFA (8 mL). Stirred at room temperature for 5 h then concentrated. Added 1 N NaOH (50 mL), extracted with $CH_2Cl_2$, dried combined organic extracts ($MgSO_4$), filtered, and concentrated. Purified by silica gel chromatography (eluant: 20% EtOAc-$CH_2Cl_2$ to 30% EtOAc-$CH_2Cl_2$) to give 1.05 g (91%) of the product 459 as a yellow oil. MS m/e: 367 (M+H).

Part K:

To compound 459 (0.74 g, 2.02 mmol) dissolved in $CH_2Cl_2$ (20 mL) was added dimethylamine (2 M in THF, 2.0 mL, 4.04 mmol), 3A sieves (0.60 g), glacial acetic acid (0.12 g, 0.12 mL, 2.02 mmol), then sodium triacetoxyborohydride (0.64 g, 3.03 mmol). Stirred at room temperature for 16 h. Added 0.5 N NaOH (25 mL), extracted with $CH_2Cl_2$, dried combined organic extracts ($MgSO_4$), filtered, and concentrated. Purified by silica gel chromatography (eluant: 5% MeOH with $NH_3$—$CH_2Cl_2$ to 15% MeOH with $NH_3$—$CH_2Cl_2$) to give 0.65 g (81%) of the product 460 as a yellow oil. MS m/e: 396 (M+H).

Part L:

To compound 460 (0.64 g, 1.62 mmol) dissolved in MeOH (5 mL) was added THF (2 mL) and 6.25 N NaOH (5 mL). Refluxed for 3 h. Cooled to room temperature and concentrated. Purified by silica gel chromatography (eluant: 10% MeOH with $NH_3$—$CH_2Cl_2$ to 15% MeOH with $NH_3$—$CH_2Cl_2$) to give 0.31 g (74%) of the product 461 as an orange oil. MS m/e: 262 (M+H).

Select compounds prepared using the procedures from Example 9B are exemplified in the preceding table.

Example 10

2-Heteroaryl Pyrrolidines & Derivatives

Example 10A

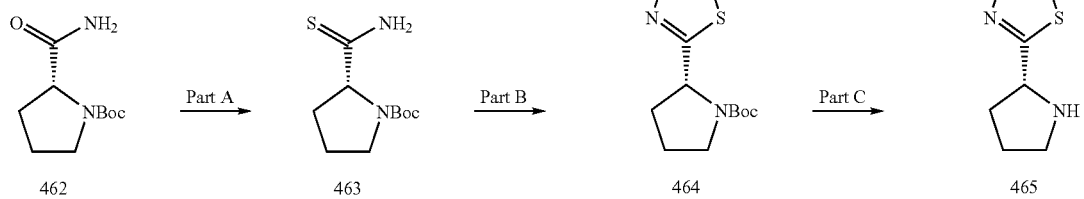

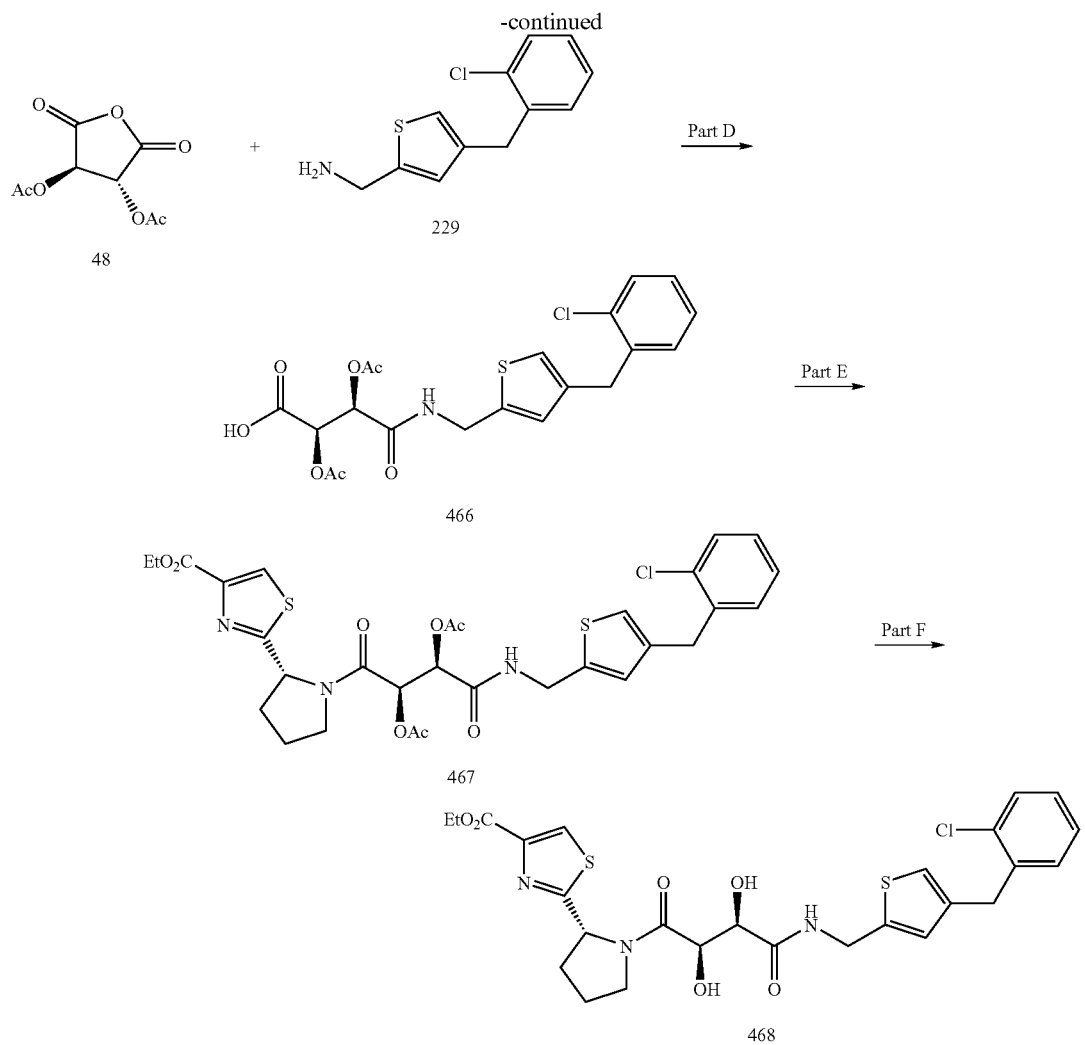

Part A:

To D-1-N-Boc-prolinamide (462) (2.5 g, 11.7 mmol) in THF (15 mL) was added Lawesson's reagent (2.36 g, 5.8 mmol) portionwise at room temperature. The reaction mixture was stirred for 3.5 hours under argon atmosphere. The solvents were removed in vacuo. Purification by column chromatography (SiO$_2$, 5% MeOH/DCM) afforded 463 as a light yellow solid (2.5 g, 93%).

Part B:

A mixture of 463 (500 mg, 2.15 mmol) and potassium hydrogencarbonate (1.74 g, 17.35 mmol) in DME (12 mL) was stirred for 10 minutes. Ethyl bromopyruvate (0.81 mL, 6.45 mmol) was added dropwise via a syringe to the reaction mixture. The reaction mixture was stirred for 30 minutes. The reaction mixture was cooled to 0° C. and a mixture of trifluoroacetic anhydride (1.21 mL, 8.6 mmol) and 2,6-lutidine (2.12 mL, 18.3 mmol) was added dropwise via syringe over 10 minutes. The reaction mixture was stirred for 30 minutes at 0° C. The solvents were removed in vacuo. The residue was dissolved in chloroform, washed with 1.0 N HCl, bicarbonate solution and brine, dried over sodium sulfate and concentrated. Purification by column chromatography (SiO$_2$, 30% EtOAc/hexane) afforded 464 as a light yellow solid (520 mg, 74%). HPLC-MS $t_R$=1.88 min (UV$_{254\ nm}$); Mass calculated for formula C$_{15}$H$_{22}$N$_2$O$_4$S 326.1, observed LCMS m/z 327.1 (M+H).

Part C:

To 464 (486 mg, 1.49 mmol) in dioxane (1 mL) was added 4 N HCl in dioxane (1 mL). The reaction mixture was stirred for 1 hour at room temperature and concentrated. HPLC-MS $t_R$=0.60 min (UV$_{254\ nm}$); Mass calculated for formula C$_{10}$H$_{14}$N$_2$O$_2$S 226.1, observed LCMS m/z 227.1 (M+H).

Part D:

To 48 (216 mg, 1.0 mmol) in THF (2 mL) was added material from 229 (238 mg, 1 mmol). The reaction mixture was stirred overnight at room temperature. The reaction mixture was concentrated and freeze-dried to afford a white powder (410 mg, 90%). HPLC-MS $t_R$=1.74 min (UV$_{254\ nm}$); Mass calculated for formula C$_{20}$H$_{20}$ClNO$_7$S 453.0, observed LCMS m/z 454.0 (M+H).

Part E:

To 465 (26 mg, 0.1 mmol) in DMF (0.5 mL) was added DIEA (35 µL, 0.2 mmol), 466 (54 mg, 0.12 mmol) in DMF (1 mL) and then HATU (57 mg, 0.15 mmol). The reaction mixture was stirred overnight at room temperature. The reaction mixture was diluted with ethyl acetate (20 mL) and water (20 mL) and the layers were separated. The organic layer was washed with 0.1 N NaOH, 0.1 N HCl and brine, dried over sodium sulfate and concentrated. Compound 467 was used without further purification. HPLC-MS $t_R$=2.06 min (UV$_{254\ nm}$); Mass calculated for formula $C_{30}H_{32}ClN_3O_8S_2$ 661.1, observed LCMS m/z 662.0 (M+H).

Part F:

To 467 in methanol (1 mL) was added 7.0 M ammonia in methanol (1 mL). The reaction mixture was stirred for 1 hour at room temperature and concentrated. Purification by reverse phase prep-LC afforded 468 as a white powder (2 mg). HPLC-MS $t_R$=5.04 min (UV$_{254\ nm}$, 10 min); Mass calculated for formula $C_{26}H_{28}ClN_3O_6S_2$ 577.1, observed LCMS m/z 578.0 (M+H).

Example 10B

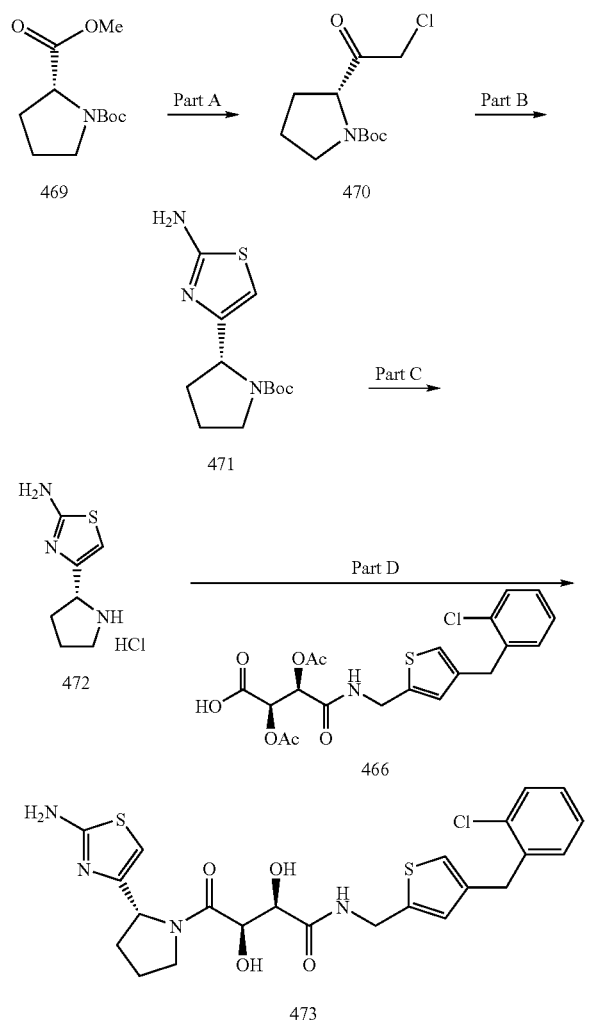

Part A:

A solution of LDA was formed by the addition of 1.6 M n-butyl lithium (34 mL, 54.5 mmol) to diisopropylamine (8.47 mL, 60 mmol.) in THF (20 mL) at −78° C. The reaction mixture was stirred at −78° C. for 20 minutes and warmed to 0° C. gradually. The LDA solution was added dropwise to a mixture of N-Boc-D-proline methyl ester (469) (2.5 g, 10.9 mmol) and chloroiodomethane (3.17 mL, 43.6 mmol) in THF (20 mL) at −78° C. via a cannula over 30 minutes. The reaction mixture was stirred at −78° C. for 30 minutes. A solution of acetic acid (15 mL) in THF (15 mL) was added slowly over 20 minutes at −78° C. The reaction mixture was stirred for 20 minutes and then warmed to room temperature. The reaction mixture was diluted with ethyl acetate and washed with water, sodium bicarbonate solution and brine. The organic layer was dried over sodium sulfate and concentrated. Purification by column chromatography (SiO$_2$, 20% EtOAc/hexane) afforded 470 as a light brown solid (2.0 g, 74%). HPLC-MS $t_R$=1.80 min (UV$_{254\ nm}$); Mass calculated for formula $C_{11}H_{18}ClNO_3$ 247.1, observed LCMS m/z 248.1 (M+H).

Part B:

A mixture of 470 (250 mg, 1.0 mmol) and thiourea (152 mg, 2 mmol) were stirred for 72 hours. The reaction mixture was diluted with ethyl acetate and washed with sodium bicarbonate solution and brine. The organic layer was dried over sodium sulfate and concentrated. Purification by column chromatography (SiO$_2$, 80% EtOAc/hexane) afforded 471 as a white solid (201 mg, 75%). HPLC-MS $t_R$=0.67 min (UV$_{254\ nm}$); Mass calculated for formula $C_{12}H_{19}N_3O_2S$ 269.1, observed LCMS m/z 270.1 (M+H).

Part C:

To 471 (201 mg, 0.75 mmol) in dioxane (1 mL) was added 4 N HCl in dioxane (1 mL). The reaction mixture was stirred for 1 hour at room temperature and concentrated.

Part D:

A mixture of 466 (45 mg, 0.1 mmol), 472 (29 mg, 0.12 mmol), DIEA (50 μL, 0.28 mmol) and HATU (57 mg, 0.15 mmol) in DMF (2 mL) was stirred overnight at room temperature. The reaction mixture was diluted with ethyl acetate (20 mL) and water (20 mL) and the layers were separated. The organic layer was washed with 0.1 N NaOH, 0.1 N HCl and brine, dried over sodium sulfate and concentrated. The residue was dissolved in methanol (1 mL) and 7.0 M ammonia in methanol (1 mL) was added. The reaction mixture was stirred for 1 hour at room temperature and concentrated. Purification by reverse phase prep-LC afforded 473 as a white powder. HPLC-MS $t_R$=1.42 min (UV$_{254\ nm}$); Mass calculated for formula $C_{23}H_{25}ClN_4O_4S_2$ 520.1, observed LCMS m/z 521.1 (M+H).

Example 10C

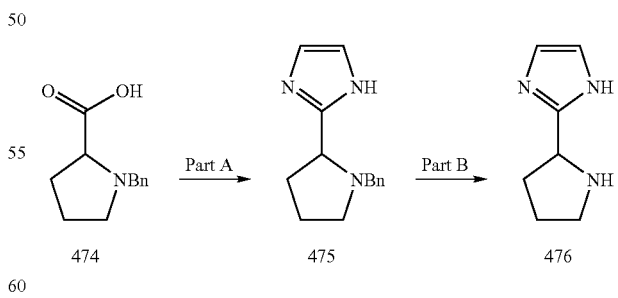

Part A:

To 1-Benzyl-pyrrolidine-2-carboxylic acid (474) (Belokon, Y. N. at al; Tetrahedron Asymmetry 1998, 9, 4249-4252) in CH$_2$Cl$_2$ (20 mL) was added 2,2-dimethoxy-ethylamine (614 mg, 5.84 mmol), EDCI (1.12 g, 5.84 mmol), HOBT (658 mg, 4.87 mmol), and NMM (1.08 mL, 9.8 mmol). The reaction mixture was stirred overnight at 25° C. Saturated aqueous NaHCO₃ solution (50 mL) was added. The aqueous layer was extracted with CH₂Cl₂ (50 mL×3). The combined organic layers was washed with brine (50 mL), dried over Na₂SO₄, and concentrated by rotary evaporator to give 1-benzyl-pyrrolidine-2-carboxylic acid (2,2-dimethoxy-ethyl)-amide as yellow oil. To 1-benzyl-pyrrolidine-2-carboxylic acid (2,2-dimethoxy-ethyl)-amide was added acetic acid (10 mL) and ammonium acetate (11 g). The reaction mixture was heated to 140° C. overnight. After it was cooled down, it was poured into 100 mL ice-water with stirring. Solid NaHCO₃ was added in small portion with stirring to adjust the pH of the solution to 8-9. The aqueous solution was extracted with EtOAc (100 mL×2). The combined organic layers was washed with brine, dried over Na₂SO₄, and concentrated with rotary evaporator. Compound 475 (110 mg) was isolated by SiO₂ chromatography (CH₂Cl₂/MeOH/NH₃: 40:1:0.1 to 20:1:0.1). MS: m/z 228.3 [M+H]⁺.

Part B: 5-Pyrrolidine-2-yl-1H-imidazole:

To 475 (110 mg) in 10 mL EtOH was added Pd/C (10%, 50 mg). The reaction mixture was hydrogenated under hydrogen (50 psi) for 24 hours. The solid was filtrated and the solution was evaporated by rotary evaporator to give 5-Pyrrolidine-2-yl-1H-imidazole (476) (67 mg). MS m/z 138.2 [M+H]⁺. ¹H-NMR (300 MHz, CDCl₃): δ ppm: 6.95 (s, 2H), 4.35 (t, 1H, J=7.4 Hz), 3.00 (m, 2H), 2.22-18 2.03 (m, 2H), 1.85 (m, 3H).

The following compounds were prepared by procedures described in Example 11. The 2-(pyridyl)-pyrrolidines are commericial amines (entries 495-497). The amino-thiazole of 471 was further functionalized via acylation chemistry to afford 500-501.

| Compound # | Structure | Exact mass | MS m/z (M + H) |
|---|---|---|---|
| 477 | 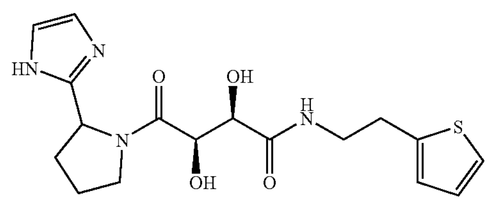 | 378.1 | 379.1 |
| 478 | 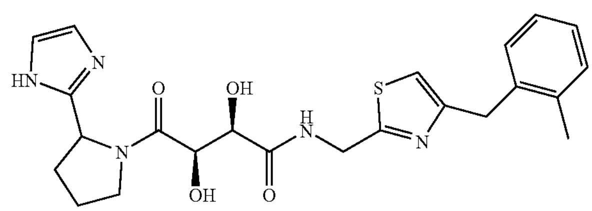 | 469.2 | 470.1 |
| 479 | 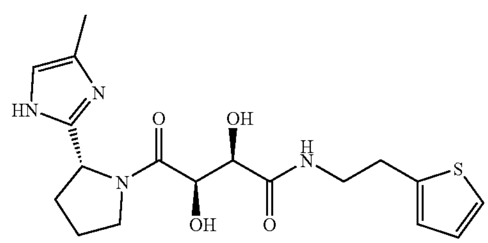 | 409.1 | 410.1 |
| 480 | 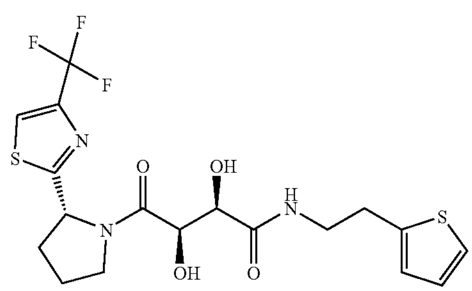 | 463.1 | 464.0 |

-continued
| Compound # | Structure | Exact mass | MS m/z (M + H) |
|---|---|---|---|
| 481 | 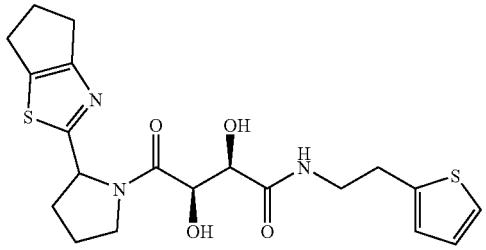 | 435.1 | 436.1 |
| 482 | 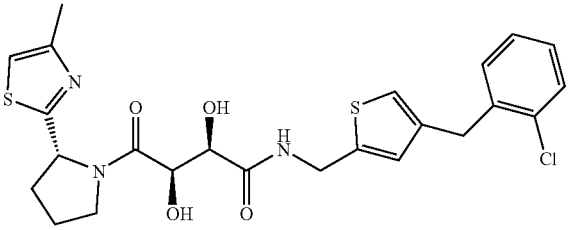 | 519.1 | 520.0 |
| 483 | 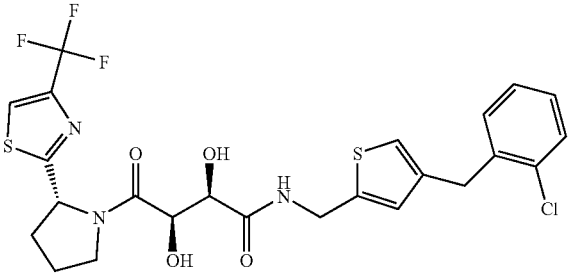 | 573.1 | 574.0 |
| 484 | 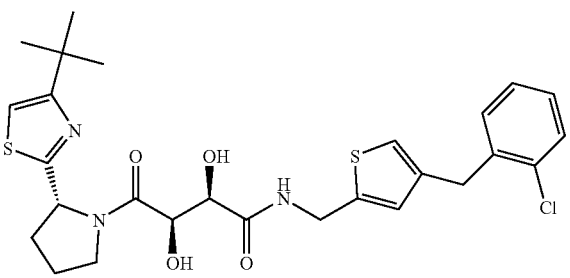 | 561.2 | 562.2 |
| 485 | 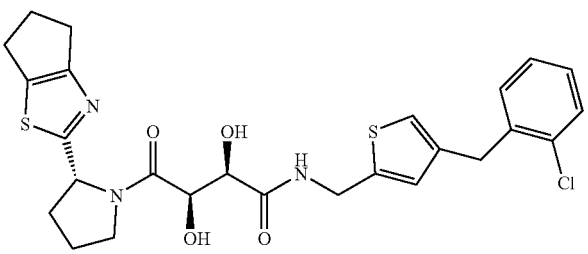 | 545.1 | 546.1 |
| 486 | 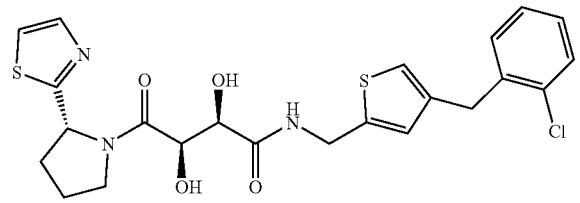 | 505.1 | 506.0 |

-continued
| Compound # | Structure | Exact mass | MS m/z (M + H) |
|---|---|---|---|
| 487 | 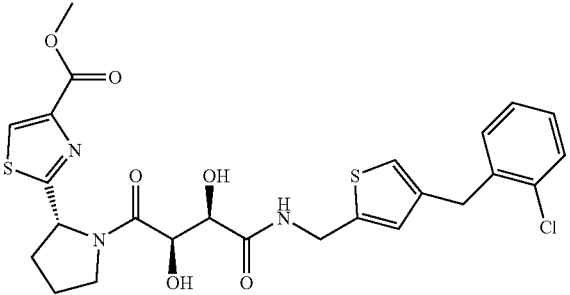 | 563.1 | 564.1 |
| 488 | 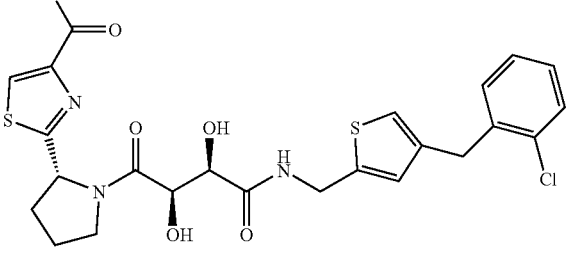 | 549.1 | 550.0 |
| 489 | 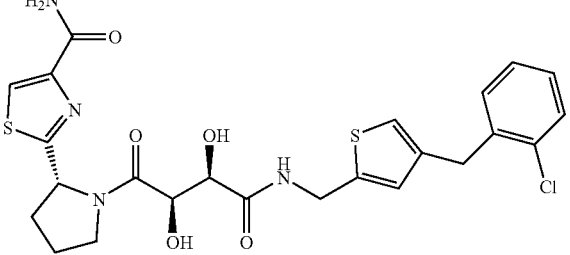 | 548.1 | 549.1 |
| 490 | 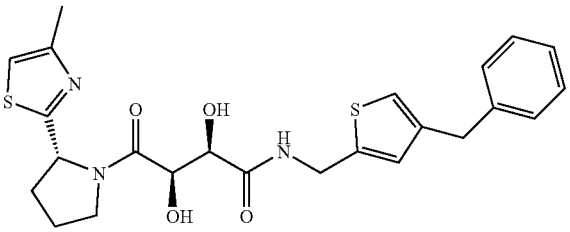 | 485.1 | 486.1 |
| 491 | 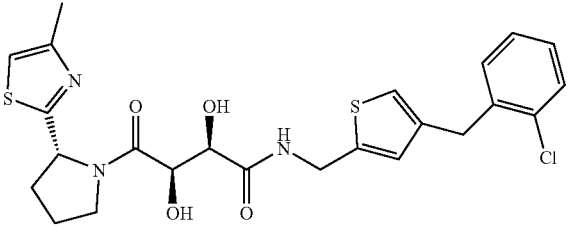 | 519.1 | 520.0 |

| Compound # | Structure | Exact mass | MS m/z (M + H) |
|---|---|---|---|
| 492 | 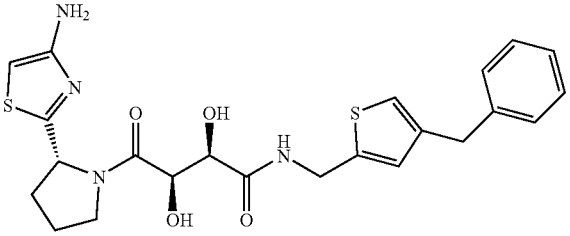 | 486.1 | 487.1 |
| 493 | 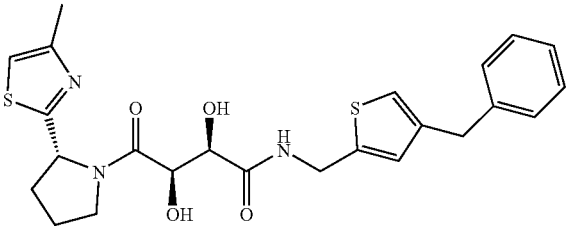 | 485.1 | 486.1 |
| 494 | 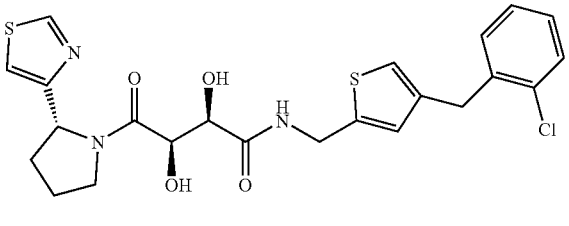 | 505.1 | 505.9 |
| 495 | 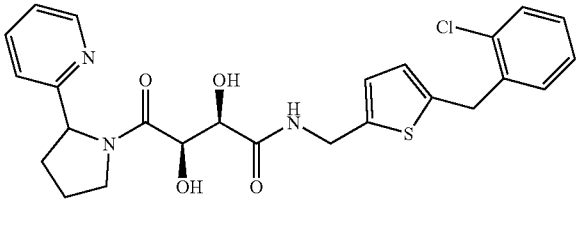 | 499.1 | 499.9 |
| 496 | 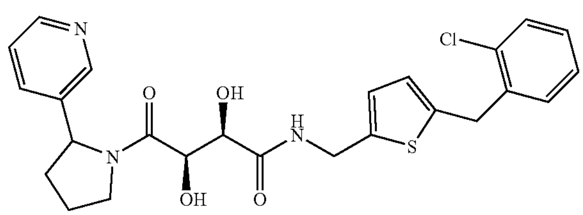 | 499.1 | 499.9 |
| 497 | 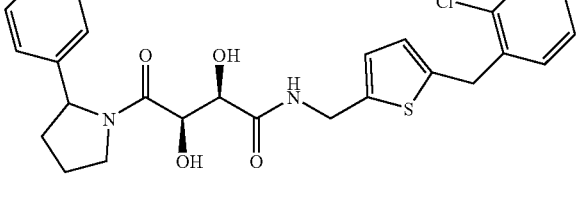 | 499.1 | 499.9 |

-continued
| Compound # | Structure | Exact mass | MS m/z (M + H) |
|---|---|---|---|
| 498 | 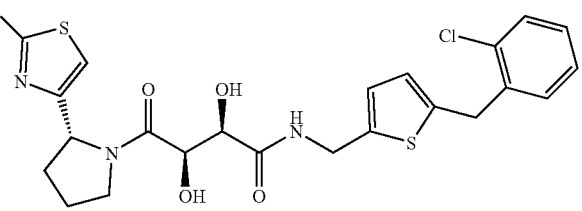 | 520.1 | 520.9 |
| 499 | 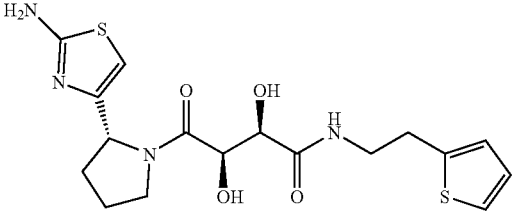 | 521.2 | 522.1 |
| 500 | 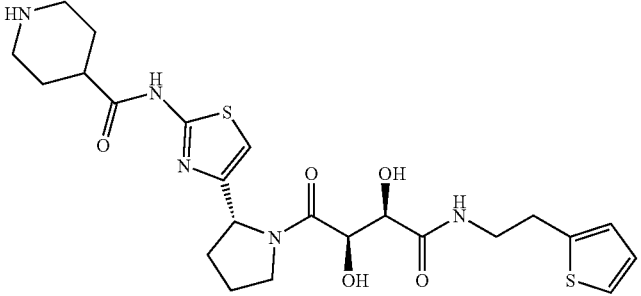 | 522.2 | 522.1 |
| 501 | 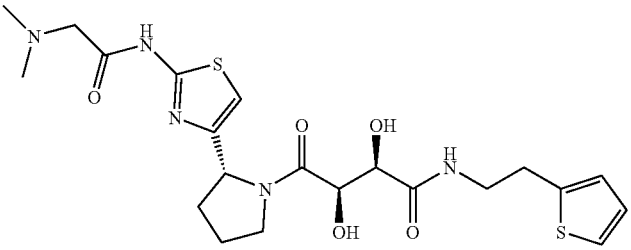 | 495.2 | 496.1 |
| 502 | 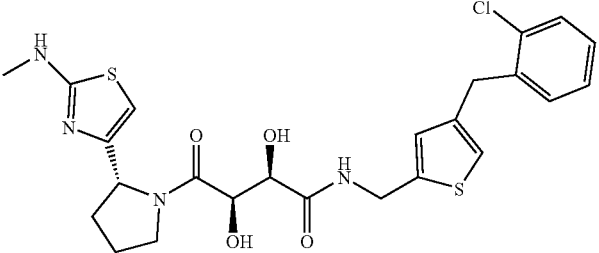 | 534.1 | 535.0 |

Example 11

2-Phenyl Pyrrolidines & Derivatives

Example 11A

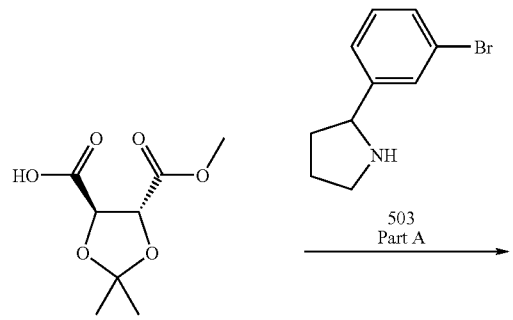

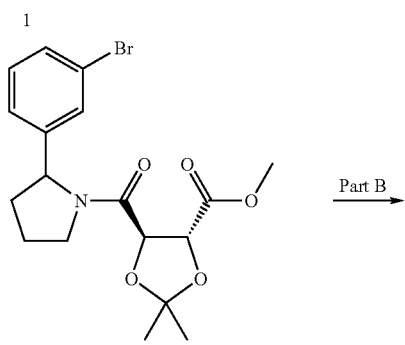

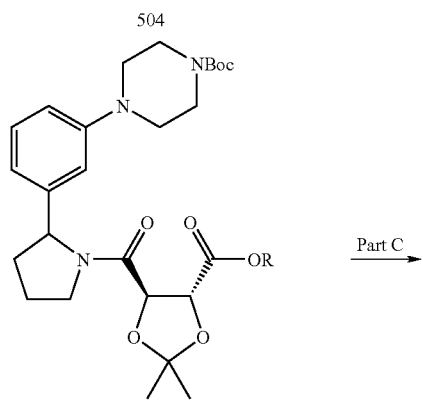

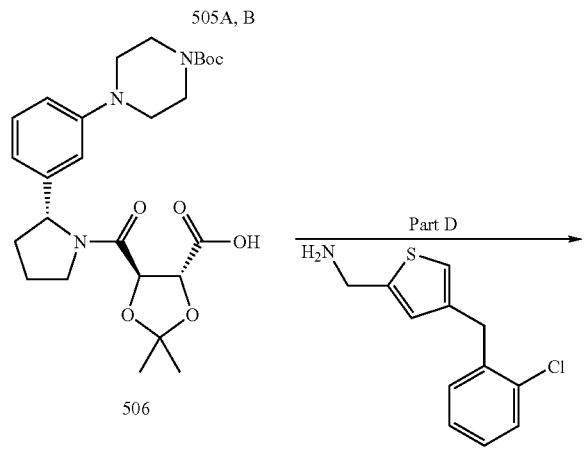

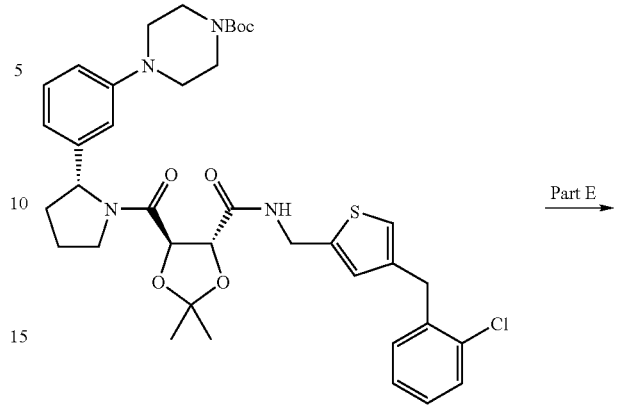

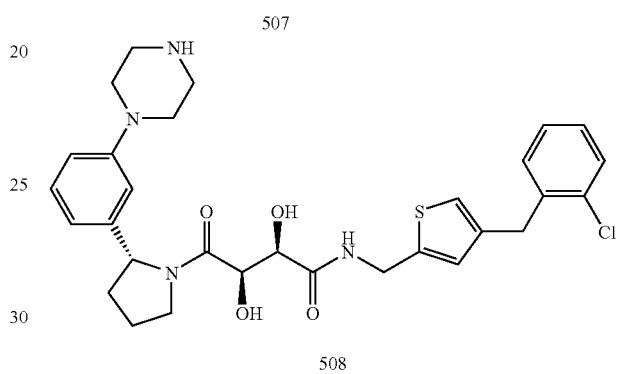

Part A:

To 1 (925 mg, 4.53 mmol) in DMF (5 mL) was added 2-(3-bromophenyl)-pyrrolidine (503) (prepared by the method of Sorgi, K. L.; Maryanoff, C. A.; McComsey, D. F.; Graden, D. W.; Maryanoff, B. E.; *J. Am. Chem. Soc.* 1990, 112, 3567) (1.12 g, 4.95 mmol), DIEA (1.75 mL, 10.0 mmol) and HATU (1.88 g, 4.95 mmol). The reaction mixture was stirred overnight at room temperature. The DMF was removed in vacuo and the residue was partitioned between ethyl acetate (20 mL) and water (20 mL). The layers were separated and the aqueous layer was extracted with ethyl acetate. The combined organic layers were washed with sodium bicarbonate solution, 1.0 N HCl and brine, dried over sodium sulfate and concentrated. Purification by column chromatography (SiO$_2$, 10-20% EtOAc/DCM) afforded 504 (1.22 g, 65%). HPLC-MS $t_R$=2.00 min (UV$_{254\ nm}$); mass calculated for formula C$_{18}$H$_{22}$BrNO$_5$ 411.1, observed LCMS m/z 412.2 (M+H).

Part B:

To piperazine-1-carboxylic acid tert-butyl ester (279 mg, 1.5 mmol), potassium phosphate (530 mg, 2.5 mmol), Pd$_2$(dba)$_3$ (23 mg, 0.025 mmol) and 2-(dicyclohexylphosphino)biphenyl (35 mg, 0.1 mmol) under argon atmosphere was added the material from Part A (414 mg, 1.0 mmol). The reaction mixture was evacuated and flushed with argon. The mixture was heated overnight at 90° C. The reaction mixture was diluted with ethyl acetate, filtered through celite and concentrated to give a mixture of methyl ester 505A and acid 505B as an orange film (679 mg). The material was used without further purification. 505A: HPLC-MS $t_R$=2.08 & 2.14 min (ester, UV$_{254\ nm}$); mass calculated for formula C$_{27}$H$_{39}$N$_3$O$_7$ 517.3, observed LCMS m/z 518.0 (M+H).

505B: HPLC-MS $t_R$=1.83 & 1.91 min (acid, $UV_{254\,nm}$); mass calculated for formula $C_{26}H_{37}N_3O_7$ 503.3, observed LCMS m/z 504.1 (M+H)

Part C:

To the mixture of 505A and 505B (~1 mmol) in THF (4 mL) and water (1 mL) was added 1.0 M lithium hydroxide (1.2 mL, 1.2 mmol). The reaction mixture was stirred overnight at room temperature. The reaction mixture was diluted with water (10 mL) and the THF was removed in vacuo. The aqueous layer was washed with diethyl ether (3×10 mL), made acidic with 1.0 N HCl and extracted with ethyl acetate (3×10 mL). The combined ethyl acetate layers were dried over sodium sulfate and concentrated. Purification by reverse phase prep-LC afforded the desired isomer 506 (107 mg, 96% purity). HPLC-MS $t_R$=1.83 min ($UV_{254\,nm}$); mass calculated for formula $C_{26}H_{37}N_3O_7$ 503.3, observed LCMS m/z 504.1 (M+H).

Part D:

To 506 (107 mg, 0.21 mmol) in DMF (5 mL) was added 229 (55 mg, 0.23 mmol), DIEA (80 µL, 0.46 mmol) and HATU (87 mg, 0.23 mmol). The reaction mixture was stirred overnight at room temperature. The DMF was removed in vacuo and the residue was partitioned between ethyl acetate and water. The layers were separated. The organic layer was washed with 0.1 N NaOH, 0.1 N HCl, and brine, dried over sodium sulfate and concentrated.

Purification by column chromatography ($SiO_2$, 50% EtOAc/hexane) afforded 507 (98 mg, 64%). HPLC-MS $t_R$=2.49 min ($UV_{254\,nm}$); mass calculated for formula $C_{38}H_{47}ClN_4O_6S$ 722.2, observed LCMS m/z 723.1 (M+H).

Part E:

To 507 (98 mg, 0.14 mmol) was added 80:20 TFA:water (4 mL) and the mixture was stirred for 4 hours at room temperature. The reaction was quenched with 1:1 acetonitrile:water (10 mL) and concentrated. The residue was dissolved in ethyl acetate and washed with sodium bicarbonate solution. To the aqueous layer was added sodium chloride and it was extracted with ethyl acetate. The combined organic layer was dried over sodium sulfate and concentrated. The residue was dissolve in acetonitrile (2 mL) and 1.0 N HCl (0.3 mL) and concentrated. The material was lyophilized to afford 508 as the HCl salt as a white powder (75 mg, 86%). HPLC-MS $t_R$=1.27 min ($UV_{254\,nm}$); mass calculated for formula $C_{30}H_{35}ClN_4O_4S$ 582.2, observed LCMS m/z 583.2 (M+H).

Example 11B

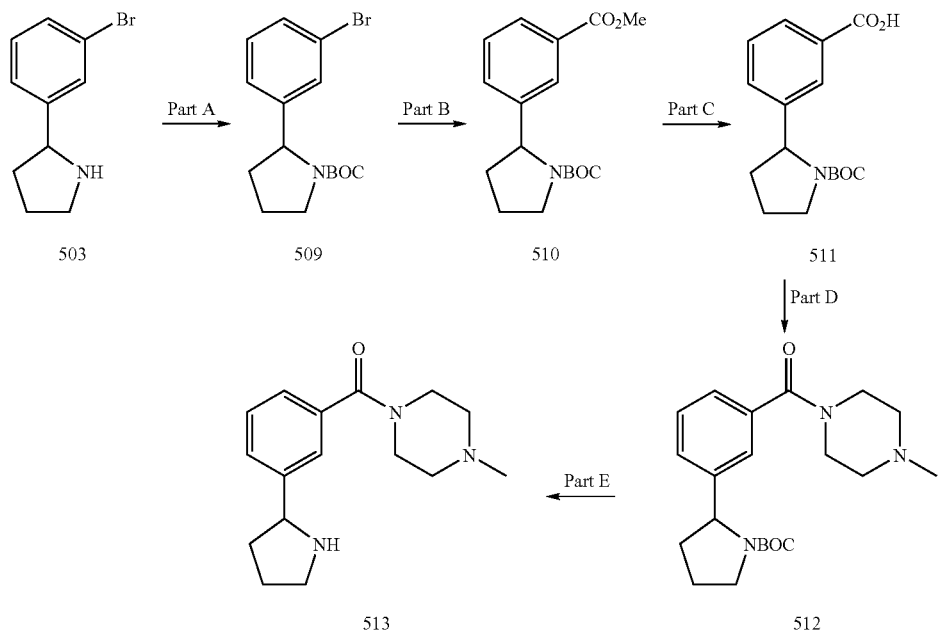

Part A

To a solution of compound 503 (5.0 g, 22.1 mmol) in dry $CH_2Cl_2$ (80 mL) was added di-tert-butyl dicarbonate (5.55 g, 25.4 mmol). The solution was stirred at room temperature for 2 hours. The solvent was removed by rotary evaporator. The product was isolated by silica gel chromatography (Hexane/EtOAc 5:1 to 3:1) to give compound 509 (5.7 g, 79%).

Part B

To a two neck flask was charged with compound 509 (1.0 g, 3.06 mmol), MeOH (8 mL), triethylamine (6 mL), DMF (6 mL), and $Pd(PPh_3)_2Cl_2$. A condenser with a three-way-valve on the top was attached to the flask. A balloon and a carbon monoxide tank were attached to the three-way-valve. The balloon was filled with CO and flashed the system twice. Then the balloon was filled with CO and was connected to the flask system. The flask was heated in a 80° C. oil bath for 36 hours. After cooling down to room temperature, water (50 mL) and EtOAc (100 mL) were added. The organic phase was separated, washed with water (50 mL) twice and brine, dried over $Na_2SO_4$, concentrated with rotary evaporator, the product was isolated with silica gel chromatography (Hexane/EtOAc 10:1 to 5:1) to give compound 510 (610 mg, 65%).

Part C

Compound 510 (384 mg, 1.26 mmol) was dissolved in dioxane/water (3:1, 4 mL) and LiOH (100 mg. 2.38 mmol) was added. The solution was stirred at room temperature for four hours. Saturated $NH_4Cl$ solution (20 mL) was added.

The aqueous phase was extracted with EtOAc (25 mL) twice. The organic phases were combined, washed with brine, dried over $Na_2SO_4$, concentrated by rotary evaporator, and dried under vacuum to give compound 511 (368 mg, 100%).

Part E

Compound 511 (76 mg, 0.26 mmol) was dissolved in dry $CH_2Cl_2$ (1.5 mL). N-methyl piperazine (0.035 mL, 0.31 mmol), EDCI (75 mg, 0.39 mmol), HOBT (43 mg, 0.31 mmol), and NMM (0.086 mL, 0.78 mmol) were added. The solution was stirred at room temperature for 16 hours. Saturated $NaHCO_3$ solution (5 mL) and $CH_2Cl_2$ (5 mL) was added and the layers were separated. The aqueous phase was extracted with $CH_2Cl_2$ (5 mL) twice. The organic phases were combined, dried over $Na_2SO_4$, concentrated by rotary evaporator. The product was isolated by silica gel chromatography to give compound 512 (90 mg, 92%).

Part F

Compound 512 (90 mg, 0.24 mmol) was dissolved in MeOH (1 mL) and HCl (4M in dioxane, 0.25 mL, 1 mmol) was added. The solution was stirred at room temperature for overnight. The solvent was removed by rotary evaporator to give compound 513 (83 mg, 100%).

Example 11C

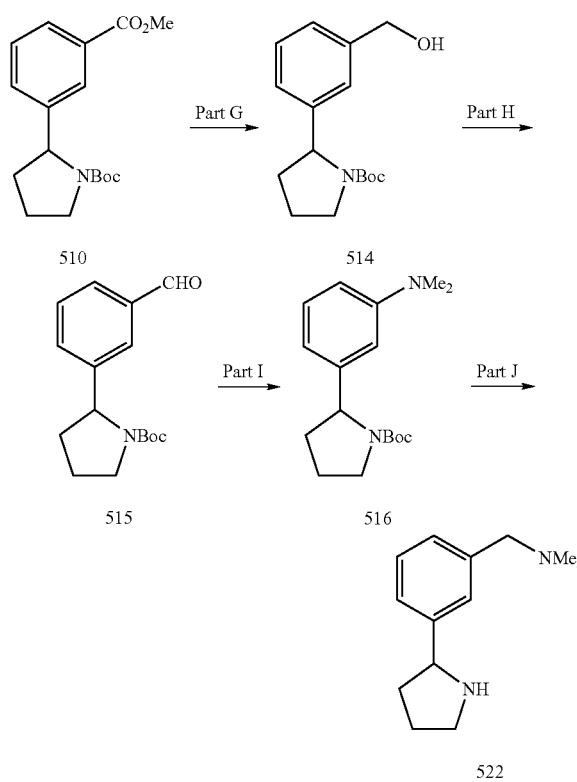

Part G:

Compound 510 (3.68 g, 12.0 mmol) was dissolved in dry THF (60 mL), and lithium borohydride (0.78 g, 36.2 mmol) was added. The solution was heated at reflux for 16 h then cooled to room temperature. MeOH (4 mL) was added, and the solvent was removed by rotary evaporator. Water (75 mL) was added, and the aqueous solution was extracted with $CH_2Cl_2$ (75 mL) three times. The combined organic extracts were dried ($MgSO_4$), filtered, and concentrated. The product was purified by silica gel chromatography (eluant: 5% MeOH—$CH_2Cl_2$ to 10% MeOH—$CH_2Cl_2$) to give 3.28 g (98%) of compound 514. MS (m/e for M+1): 278.

Part H:

Oxalyl chloride (1.87 g, 1.3 mL, 14.7 mmol) was dissolved in dry $CH_2Cl_2$ (35 mL) and cooled to −78° C. under a nitrogen atmosphere. DMSO (2.30 g, 2.1 mL, 29.5 mmol) dissolved in dry $CH_2Cl_2$ (5 mL) was added dropwise via addition funnel. The solution was stirred at −78° C. for 15 mins then compound 514 (3.27 g, 11.8 mmol) dissolved in $CH_2Cl_2$ (15 mL) was added. The reaction mixture was stirred at −78° C. for 60 mins then triethylamine (3.58 g, 4.9 mL, 35.4 mmol) was added. The reaction mixture was stirred at −78° C. for 15 mins then warmed to 0° C. Water (75 mL) was added, and the layers separated. The aqueous phase was extracted with $CH_2Cl_2$ (75 mL) two times. The combined organic extracts were dried ($MgSO_4$), filtered, and concentrated. The product was purified by silica gel chromatography (eluant: 5% EtOAc-$CH_2Cl_2$ to 10% EtOAc-$CH_2Cl_2$) to give 2.94 g (90%) of the product 515. MS (m/e for M+1): 276.

Part I:

Compound 515 (0.50 g, 1.82 mmol) was dissolved in $CH_2Cl_2$ (10 mL), and 3A sieves (0.50 g), dimethylamine in THF (2 M, 1.8 mL, 3.64 mmol), glacial acetic acid (0.109 g, 1.82 mmol), and sodium triacetoxyborohydride (0.579 g, 2.73 mmol) were added. The reaction mixture was stirred at room temperature for 24 h. 1 N NaOH (25 mL) was added, and the aqueous solution was extracted with $CH_2Cl_2$ (25 mL) four times. The combined organic extracts were dried ($MgSO_4$), filtered, and concentrated. The product was purified by silica gel chromatography (eluant: 5% MeOH—$CH_2Cl_2$ to 15% MeOH—$CH_2Cl_2$) to give 0.396 g (72%) of the product 516. MS (m/e for M+1): 305.

The following intermediates were also prepared.

| Compound # | Intermediate | MS(m/e for M + 1) |
|---|---|---|
| 517 | | 347 |
| 518 | | 331 |
| 519 | | 345 |

-continued

| Compound # | Intermediate | MS(m/e for M + 1) |
|---|---|---|
| 520 | (structure: 3-(N-methylpiperazinylmethyl)phenyl-NBOC-pyrrolidine) | 360 |
| 521 | (structure: 3-(azetidinylmethyl)phenyl-NBOC-pyrrolidine) | 317 |

Part J:
The following compounds were prepared using procedure described in Example 11B Part F.

| Compound # | Intermediate | MS(m/e for M + 1) |
|---|---|---|
| 522 | (structure: 3-(NMe₂-methyl)phenyl-NH-pyrrolidine) | 205 |
| 523 | (structure: 3-(morpholinylmethyl)phenyl-NH-pyrrolidine) | 247 |
| 524 | (structure: 3-(pyrrolidinylmethyl)phenyl-NH-pyrrolidine) | 231 |
| 525 | (structure: 3-(piperidinylmethyl)phenyl-NH-pyrrolidine) | 245 |
| 526 | (structure: 3-(N-methylpiperazinylmethyl)phenyl-NH-pyrrolidine) | 260 |
| 527 | (structure: 3-(azetidinylmethyl)phenyl-NH-pyrrolidine) | 217 |

The following compounds were prepared using the procedures described in Example 11.

| Compound # | Structure | Exact mass | MS m/e (M + H) |
|---|---|---|---|
| 416 | (structure shown) | 550.3 | 551.3 |

-continued

| Compound # | Structure | Exact mass | MS m/e (M + H) |
|---|---|---|---|
| 417 | 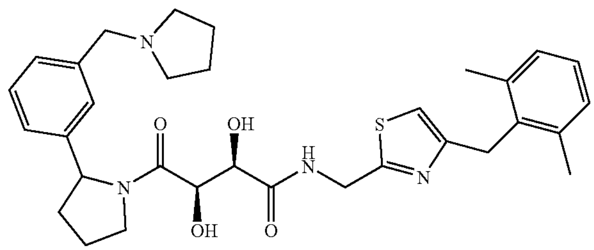 | 576.3 | 577.3 |
| 418 | 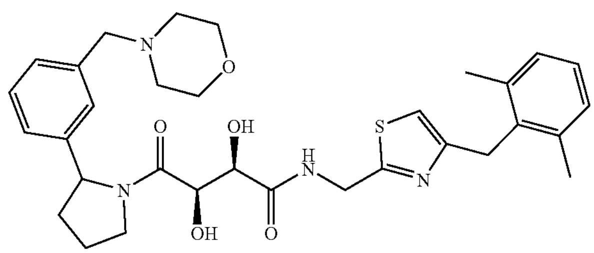 | 592.3 | 593.3 |
| 529 | 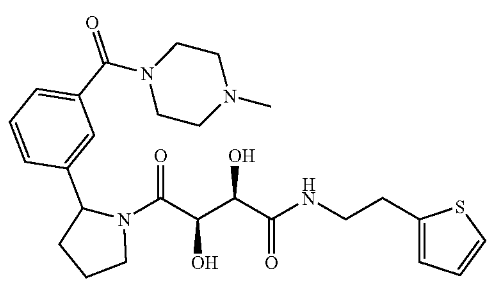 | 514.2 | 515.0 |
| 530 | 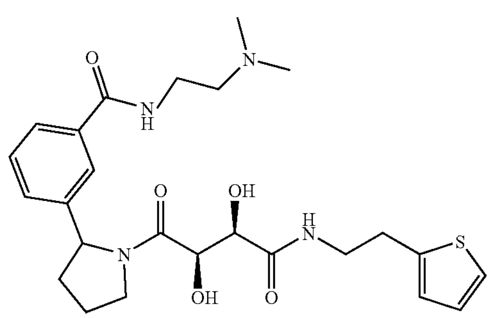 | 502.2 | 503.1 |
| 531 | 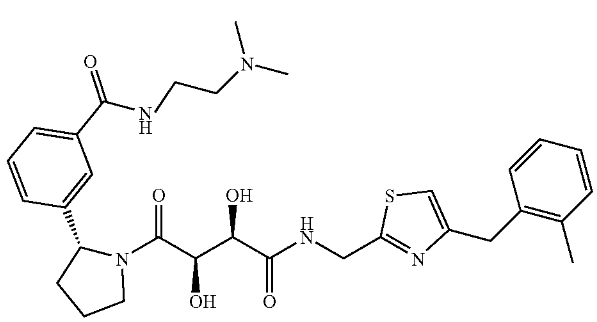 | 593.3 | 594.1 |

-continued

| Compound # | Structure | Exact mass | MS m/e (M + H) |
|---|---|---|---|
| 532 | 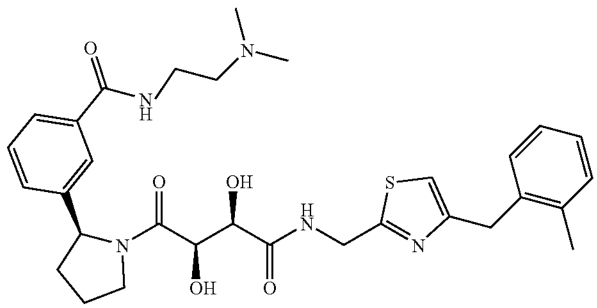 | 593.3 | 594.1 |
| 536 | 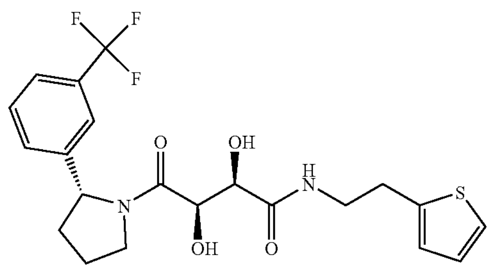 | 456.1 | 457.1 |
| 537 | 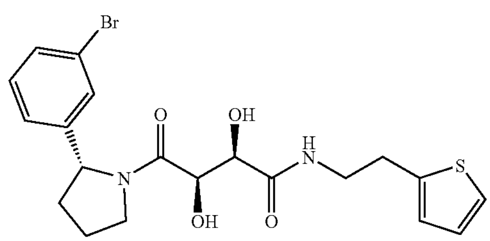 | 466.1 | 467.0 |
| 538 | 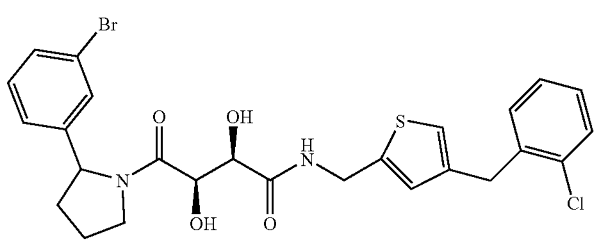 | 576.1 | 577.0 |
| 539 | 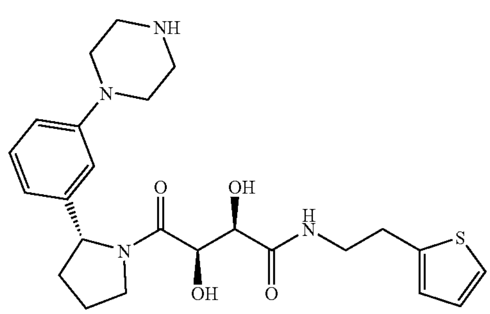 | 472.2 | 473.2 |

-continued
| Compound # | Structure | Exact mass | MS m/e (M + H) |
|---|---|---|---|
| 540 | 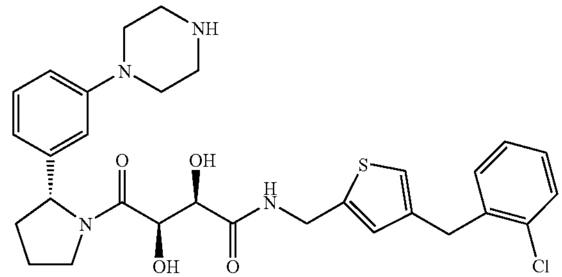 | 582.2 | 583.2 |
| 541 | 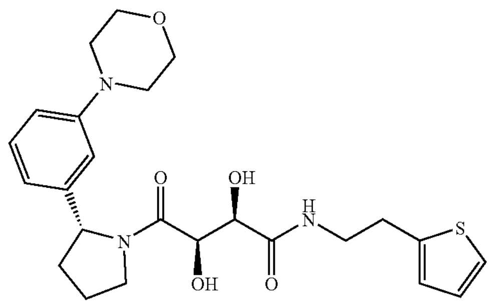 | 473.2 | 474.2 |
| 542 | 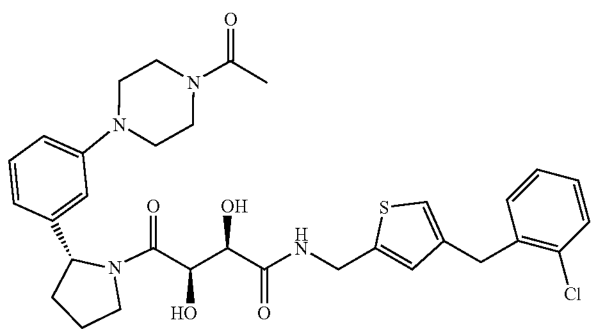 | 624.2 | 625.1 |
Example 12
Suzuki Aryl-Aryl Couplings
Example 12A
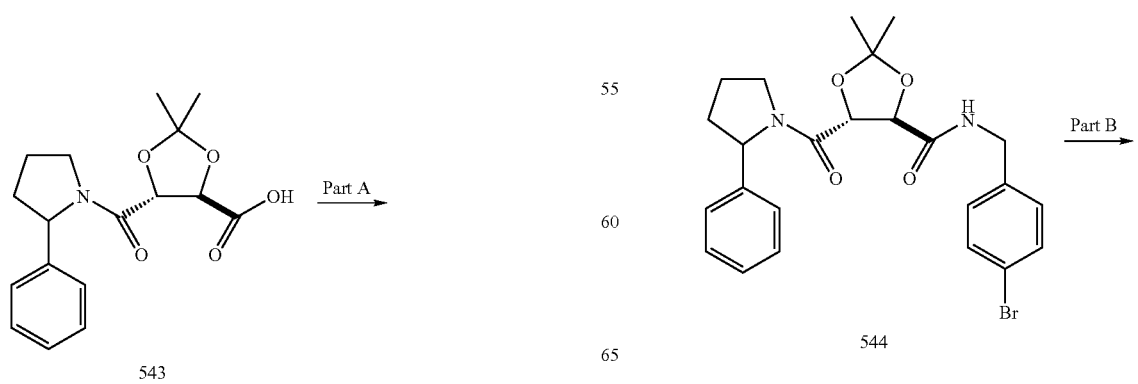

-continued

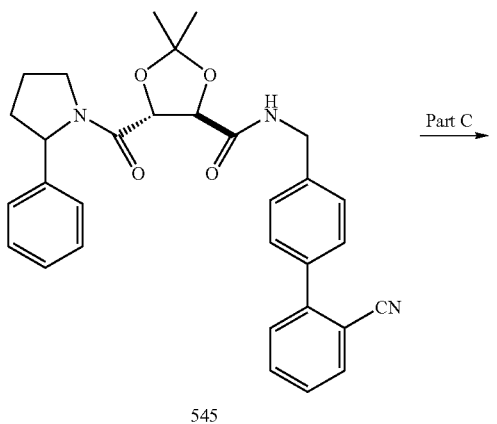

545

→ Part C

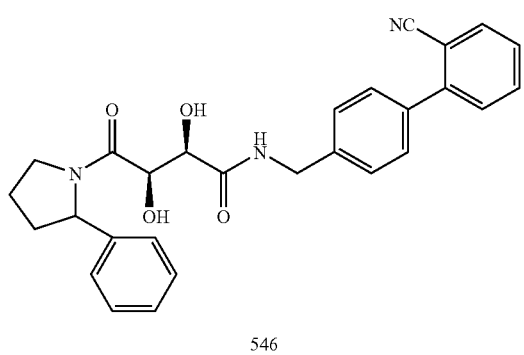

546

Compound 543 was prepared by procedures described in Example 1.

Part A:

To a solution of 543 (1.01 g, 3.17 mmol) and 4-bromobenzyl amine (0.71 g, 3.83 mmol) in CH$_2$Cl$_2$ (10 mL) cooled to 0° C. was added DIEA (1.10 mL, 6.31 mmol) followed by PyBrOP (1.10 g, 3.43 mmol). The reaction was warmed to room temperature and stirred for 16 hours. The liquid was concentrated, and the thick oil was taken up in EtOAc. The organic layer was washed with 0.5 N KHSO$_4$ (1×), sat. NaHCO$_3$ (1×), dried (Na$_2$SO$_4$), filtered, and concentrated. The residue was purified by silica gel chromatography (eluting 0% to 100% EtOAc/hexanes) to furnish 544 (1.27 g, 2.61 mmol, 82% yield) as a tan oil. MS m/e: 487.1 (M+H).

Part B:

A solution of 544 (0.105 g, 0.215 mmol), 2-cyanophenyl boronic acid (0.032 g, 0.215 mmol), and Pd(dppf)Cl$_2$ (0.016 g, 0.021 mmol) in CH$_3$CN (1 mL) and 1 N K$_2$CO$_3$ (1 mL) was heated in a SmithCreator microwave (2-5 mL vessel, 150° C. for 10 minutes). The mixture was concentrated and the residue was purified by silica gel chromatography (eluting 0% to 100% EtOAc/hexanes) to furnish 545 (0.062 g, 0.12 mmol, 56% yield) as a tan oil. MS m/e: 510.1 (M+H).

Part C:

A solution of 545 (0.049 g, 0.096 mmol) in a 70% TFA/ 20% CH$_2$Cl$_2$/10% H$_2$O mixture was stirred at room temperature for 2 hours. The mixture was concentrated, and the residue was purified by reverse phase HPLC (eluting 5:95 to 95:5 CH$_3$CN/H$_2$O (0.1% HCO$_2$H)) to provide 546 (0.023 g, 0.049 mmol, 51% yield) as a white solid. MS m/e: 470.1 (M+H).

Example 12B

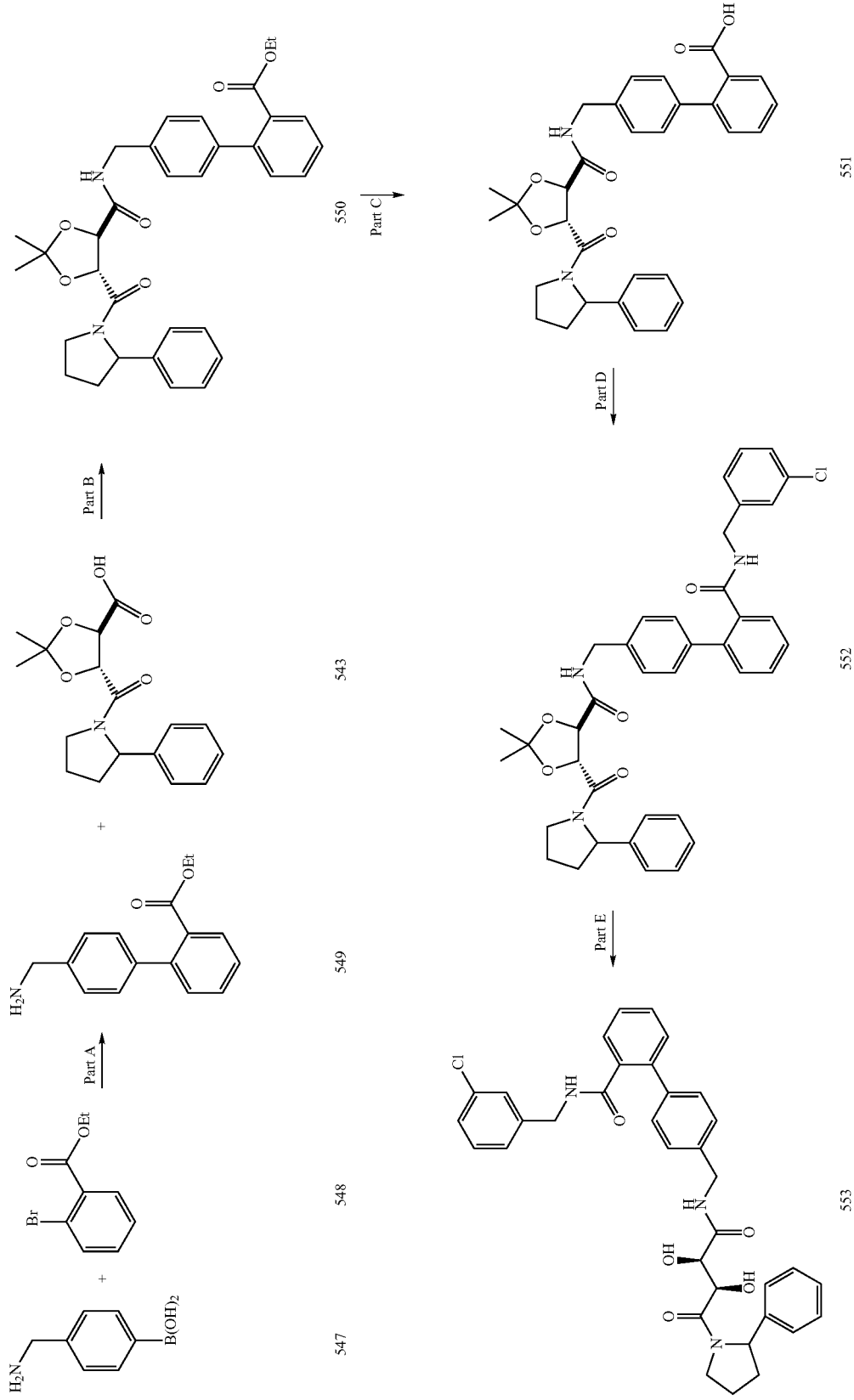

Part A:

A solution of ethyl 2-bromobenzoate (548) (0.25 g, 1.1 mmol), (4-aminomethylphenyl)boronic acid (547) (0.20 g, 1.1 mmol), and Pd(dppf)Cl$_2$ (0.040 g, 0.055 mmol) in CH$_3$CN (1 mL) and 1 N K$_2$CO$_3$ (1 mL) was heated in a SmithCreator microwave (2-5 mL vessel, 100° C. for 5 minutes). The reaction was diluted with H$_2$O and EtOAc. The organic layer was removed, and the aqueous phase was extracted with EtOAc (3×). The combined organics were dried (Na$_2$SO$_4$), filtered, and concentrated. The residue was purified by silica gel chromatography (eluting 0% to 20% CH$_2$Cl$_2$/MeOH) to furnish 549 (0.14 g, 0.55 mmol, 50% yield) as a brown oil. MS m/e: 256.1 (M+H).

Part B:

To a solution of 549 (0.21 g, 0.82 mmol) and 543 (0.19 g, 0.59 mmol) in CH$_2$Cl$_2$ (5 mL) cooled to 0° C. was added DIEA followed by PyBrOP. The reaction was stirred for 20 hours gradually warming to room temperature. The mixture was concentrated, and the brown oil was taken up in EtOAc. The organic phase was washed with 0.5 N KHSO$_4$ (1×), sat. NaHCO$_3$ (1×), dried (Na$_2$SO$_4$), filtered, and concentrated. The residue was purified by silica gel chromatography (eluting 0% to 100% EtOAc/hexanes) to furnish 550 (0.29 g, 0.51 mmol, 87% yield) as a brown oil. MS m/e: 557.1 (M+H).

Part C:

To a solution of 550 (0.26 g, 0.47 mmol) in a THF (2 mL)/MeOH (2 mL)/H$_2$O (1 mL) mixture was added LiOH·H$_2$O (0.052 g, 1.24 mmol) in one solid portion. The reaction was stirred overnight and then acidified to pH 3 with 1N HCl. After dilution with EtOAc, the organic layer was removed, and the aqueous phase was extracted with EtOAc (3×). The combined organics were dried (Na$_2$SO$_4$), filtered, and concentrated. The residue was purified by reverse phase HPLC (eluting 10:90 to 100:0 CH$_3$CN/H$_2$O (0.1% HCO$_2$H) to furnish 551 (0.22 g, 0.38 mmol, 88% yield). MS m/e: 529.1 (M+H).

Part D:

To a solution of 551 (55 mg, 0.104 mmol) in CH$_2$Cl$_2$ (1 mL) was added polystyrene-bound HOBt (109 mg, 0.095 mmol), DIC (0.067 mL, 0.427 mmol), and DMAP (7 mg, 0.057 mmol) and was shaken overnight. The mixture was filtered, then washed with DMF (3×3 mL), CH$_2$Cl$_2$ (3×3 mL), DMF (3×3 mL), and THF (3×3 mL). The resin was dried under vacuum overnight. To the dried resin-bound acid (82 mg, 0.034 mmol) was added 3-chlorobenzylamine (8.33 µL, 0.068 mmol) in CH$_2$Cl$_2$ (1 mL) and the mixture was shaken overnight. To the mixture was added polystyrene-bound isocyanate resin (70 mg, 0.102 mmol) and shaken for 5 hours. Filter the desired product and wash the filtrate with CH$_2$Cl$_2$ (3×3 mL) and THF (3×3 mL). Concentrate the organic portions in vacuo to afford 552 (14.6 mg, 0.022 mmol, 66% yield). MS m/e: 652.2 (M+H).

Part E:

To 552 (14.6 mg, 0.022 mmol) was added a 2 mL of a mixture of TFA/CH$_2$Cl$_2$/H$_2$O (7/2/1) and stirred at room temperature for 2 h. The mixture was concentrated in vacuo. The mixture was purified via reverse-phase HPLC to furnish 553 (3.7 mg, 0.006 mmol, 27% yield). MS m/e: 612.1 (M+H).

Example 12C

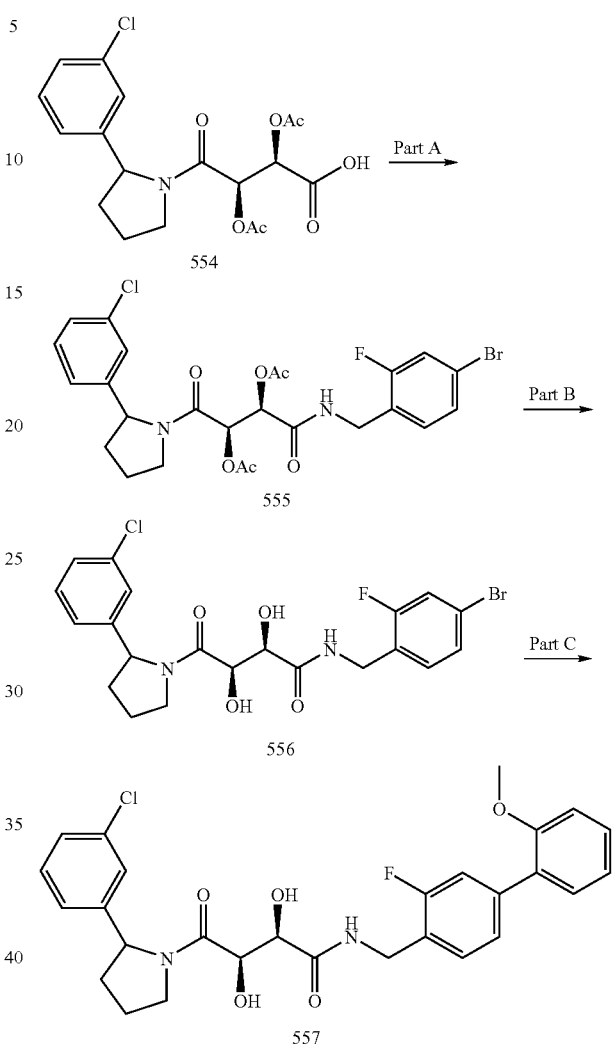

Compound 554 was prepared by the procedure desribed in Example 4 Part C. HPLC-MS t$_R$=1.39 min (UV$_{254\,nm}$); mass calculated for formula C$_{14}$H$_{16}$ClNO$_5$ 397.1, observed LCMS m/z 398.1 (M+H).

Part A:

To 554 (355 mg, 0.89 mmol) in DMF (5 mL) was added 2-fluoro-4-bromobenzylamine hydrochloride (257 mg, 1.07 mmol), DIEA (530 uL, 3.03 mmol) and HATU (407 mg, 1.07 mmol). The reaction was stirred overnight at room temperature. The reaction mixture was poured into water and extracted with EtOAc. The combined organic layers were washed with 0.1 N NaOH, 0.1 N HCl, and brine; dried over sodium sulfate and concentrated. Purification by column chromatography (SiO$_2$, 80% ethyl acetate/hexanes) afforded 555 as a foam (320 mg, 62%). HPLC-MS t$_R$=2.03 min (UV$_{254\,nm}$); mass calculated for formula C$_{25}$H$_{25}$BrClFN$_2$O$_6$ 582.1, observed LCMS m/z 583.0 (M+H).

Part B:

To 555 (320 mg, 0.55 mmol) in MeOH (5 mL) was added anhydrous hydrazine (28 µL, 0.88 mmol). The reaction mixture was stirred overnight at room temperature. The reaction mixture was concentrated in vacuo and lypholized to afford 556 as a white powder (275 mg, 100%). HPLC-MS $t_R$=1.81 min (UV$_{254\ nm}$); mass calculated for formula $C_{21}H_{21}BrClFN_2O_4$ 498.0, observed LCMS m/z 499.0 (M+H).

Part C:

Compound 556 (46 mg, 0.092 mmol) in dioxane (1 mL) was added to a solution of 2-methoxyphenyl boronic acid (22 mg, 0.14 mmol), potassium phosphate (42 mg, 0.2 mmol), and PdCl$_2$(dppf) (4 mg, 0.005 mmol) under argon atmosphere. The reaction mixture was heated to 80° C. overnight. After cooling the mixture was filtered through celite and the pad was rinsed with ethyl acetate. The filtrate was concentrated. Purification by reverse phase prep-LC afforded 557 as a white solid (26 mg) after lypholization. HPLC-MS $t_R$=1.97 min (UV$_{254\ nm}$); mass calculated for formula $C_{28}H_{28}ClFN_2O_5$ 526.2, observed LCMS m/z 527.0 (M+H).

Example 12D

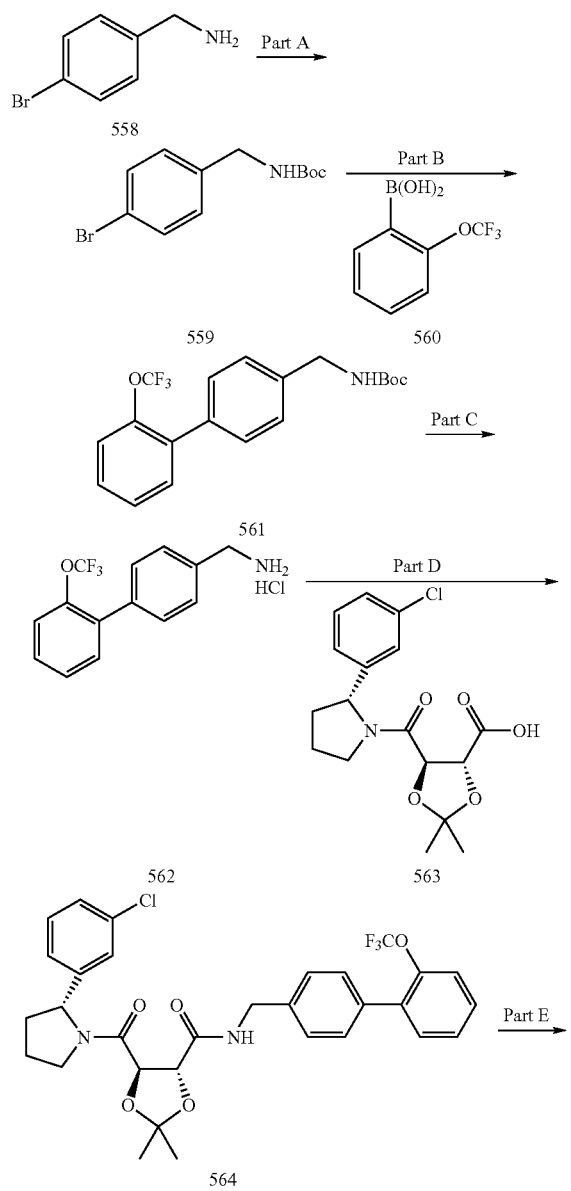

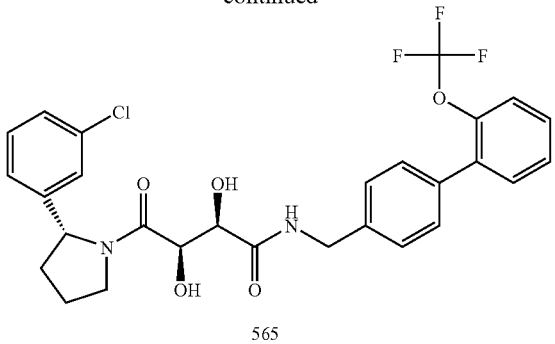

Part A:

A mixture of 4-bromo-benzylamine hydrochloride (558) (1.0 g, 4.5 mmol), di-tert-butyl dicarbonate (1.48 g, 6.8 mmol) and DIEA (2.4 mL, 13.8 mmol) in chloroform (40 mL) was stirred overnight at room temperature. The reaction mixture was washed with 1.0 N HCl, water and brine, dried over sodium sulfate and concentrated. Purification by column chromatography (SiO$_2$, 20% ethyl acetate/hexane) afforded a mixture of 559 (1.17 g, 91%). $^1$H NMR (400 MHz, CDCl$_3$) δ 7.44 (d, 2H, J=8.8 Hz), 7.15 (d, 2H, J=8.83 Hz), 4.85 (bs, e H), 4.27 (d, 2H, J=5.7 Hz), 1.48 (s, 9H).

Part B:

A mixture of 559 (100 mg, 0.35 mmol), 560 (107 mg, 0.52 mmol) potassium phosphate (223 mg, 1.05 mmol) and PdCl$_2$(dppf) (14 mg, 0.018 mmol) in dioxane (5 mL) was under argon atmosphere was heated to 80° C. overnight. The reaction mixture was cooled and filtered through celite. The celite pad was washed with ethyl acetate. The filtrate was washed with saturated sodium bicarbonate, water and brine, dried over sodium sulfate and concentrated. Purification by column chromatography (SiO$_2$, 20% ethyl acetate/hexane) afforded slightly impure 561 (146 mg). HPLC-MS $t_R$=2.35 min (UV$_{254\ nm}$); mass calculated for formula $C_{19}H_{20}F_3NO_3$ 367.1, observed LCMS m/z 390.1 (M+Na).

Part C:

Compound 561 (129 mg, 0.35 mmol) in 3:1 DCM:TFA (4 mL) was stirred for 1 hour. The residue was dissolved in DCM (5 mL) and concentrated. The residue was dissolved in diethyl ether (20 mL) and treated with 1.0 M HCl in diethyl ether (2 mL). The resulting white solid was collected by filtration and washed with diethyl ether to afford 562 (90 mg, 85% 2 steps). $^1$H NMR (400 MHz, DMSO-d$_6$) δ 8.3 (bs, 3H), 7.50 (m, 8H), 4.09 (s, 2H).

Part D:

Compound 563 was prepared using procedures similar to those described in Example 11A. Compound 564 was prepared from 562 and 563 using procedures similar to those described in Example 1 Part A. HPLC-MS $t_R$=2.49 min (UV$_{254\ nm}$); mass calculated for formula $C_{31}H_{30}ClF_3N_2O_5$ 602.2, observed LCMS m/z 603.2 (M+H).

Part E:

Compound 565 was prepared using the procedures described in Example 1 Part B. HPLC-MS $t_R$=2.16 min (UV$_{254\ nm}$); mass calculated for formula C$_{28}$H$_{26}$ClF$_3$N$_2$O$_5$ 562.2, observed LCMS m/z 563.0 (M+H).

Example 12E

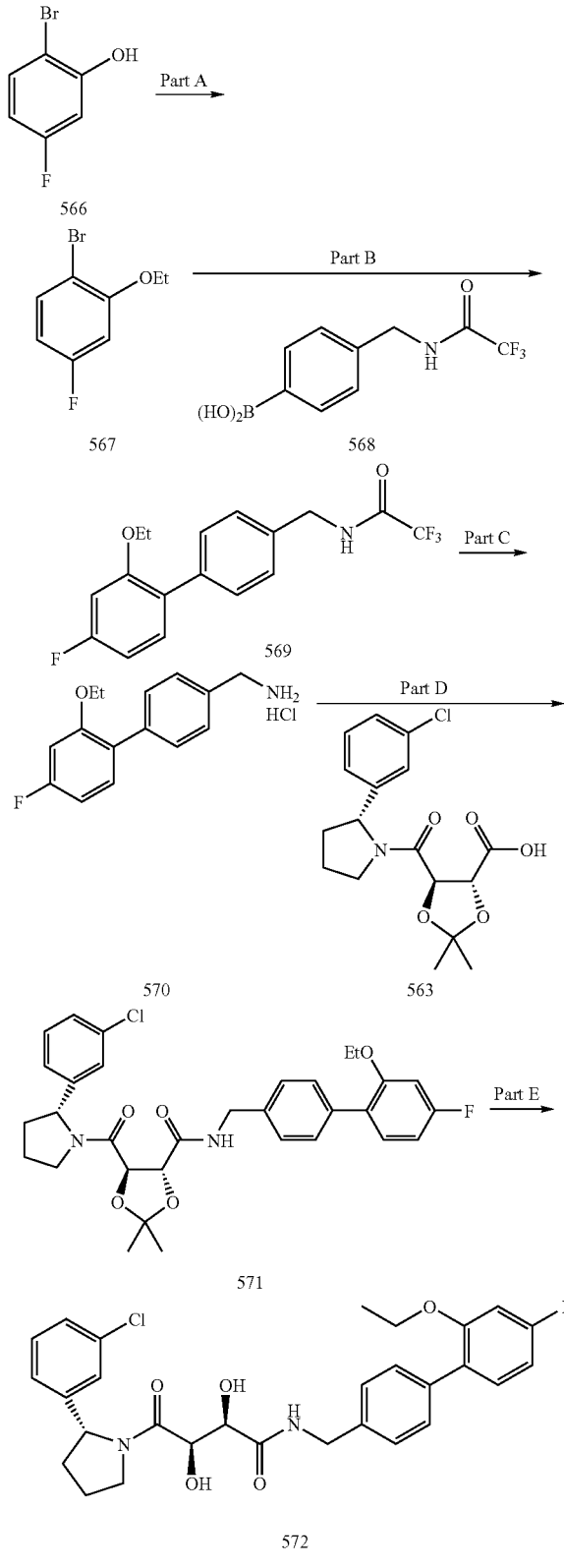

Part A:

To 2-bromo-5-fluoro-phenol (566) (2.28 g, 11.94 mmol) in DMF (15 mL) was added iodoethane (1.16 mL, 14.32 mmol) and cesium carbonate (4.28 g, 13.13 mmol). The reaction mixture was stirred for 72 hours. The mixture was filtered and the DMF was removed in vacuo. The residue was partitioned in ethyl acetate and water. The layers were separated and the organic layer was washed with water and brine, dried over sodium sulfate and concentrated to afford 567 (1.76 g, 67%) as a colorless oil. $^1$H NMR (400 MHz, CDCl$_3$) δ 7.46 (dd, 1H, J=6.3, 8.8 Hz), 6.62 (dd, 1H, J=2.7, 10.5 Hz), 6.57 (m, 1H, J=2.7), 4.08 (q, 2H, J=6.9 Hz), 1.50 (t, 3H, J=7.0 Hz).

Part B:

Compound 569 (607 mg, 58%) was prepared from 567 and 568 (prepared by the procedures of Maku, S. et. al. (*J. Comb. Chem.* 2003, 5, 379)) using the procedures described in Example 12D Part B. HPLC-MS t$_R$=2.13 min (UV$_{254\ nm}$); mass calculated for formula C$_{17}$H$_{15}$F$_4$NO$_2$ 341.1, observed LCMS m/z 342.1 (M+H).

Part C:

To 569 (607 mg, 1.78 mmol) in methanol (6 mL) was added 10% potassium carbonate in 2:1 methanol:water (20 ml). To obtain a clear solution additional water (5 mL) was added. The reaction mixture was stirred overnight at room temperature. The methanol was removed in vacuo. The residue was portioned between water and ethyl acetate. The layers were separated and the aqueous layer was extracted with ethyl acetate. The combined organic layers were washed with brine, dried over sodium sulfate and concentrated. The residue was dissolved in diethyl ether (20 mL) and treated with 1.0 M HCl in diethyl ether (5 mL). The resulting white solid was collected by filtration and washed with diethyl ether to afford 570 (377 mg, 75%). $^1$H NMR (400 MHz, DMSO-d$_6$) δ 8.27 (bs, 3H), 7.49 (m, 4H), 7.29 (dd, 1H, J=6.9, 8.3 Hz), 7.00 (dd, 1 h J=2.5, 11.4 Hz), 6.83 (dt, 1H, J=2.8, 8.6, 10.8 Hz) 4.05 (m, 4H), 1.27 (t, 3H, J=6.5 Hz).

Part D:

Compound 571 was prepared using procedures described in Example 12E Part D. Purification by column chromatography (SiO$_2$, 20% ethyl acetate/hexane) afforded 571 (104 mg, 95%). HPLC-MS t$_R$=2.40 min (UV$_{254\ nm}$); mass calculated for formula C$_{32}$H$_{34}$ClFN$_2$O$_5$ 580.2, observed LCMS m/z 581.2 (M+H).

Part E:

Compound 572 was prepared using the procedures described in Example 12D Part E. HPLC-MS t$_R$=2.06 min (UV$_{254\ nm}$); mass calculated for formula C$_{29}$H$_{30}$ClFN$_2$O$_5$ 540.2, observed LCMS m/z 541.2 (M+H).

Example 12F

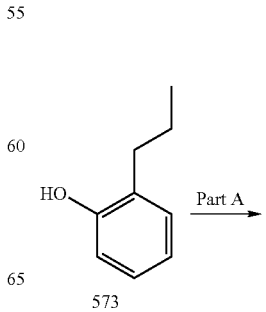

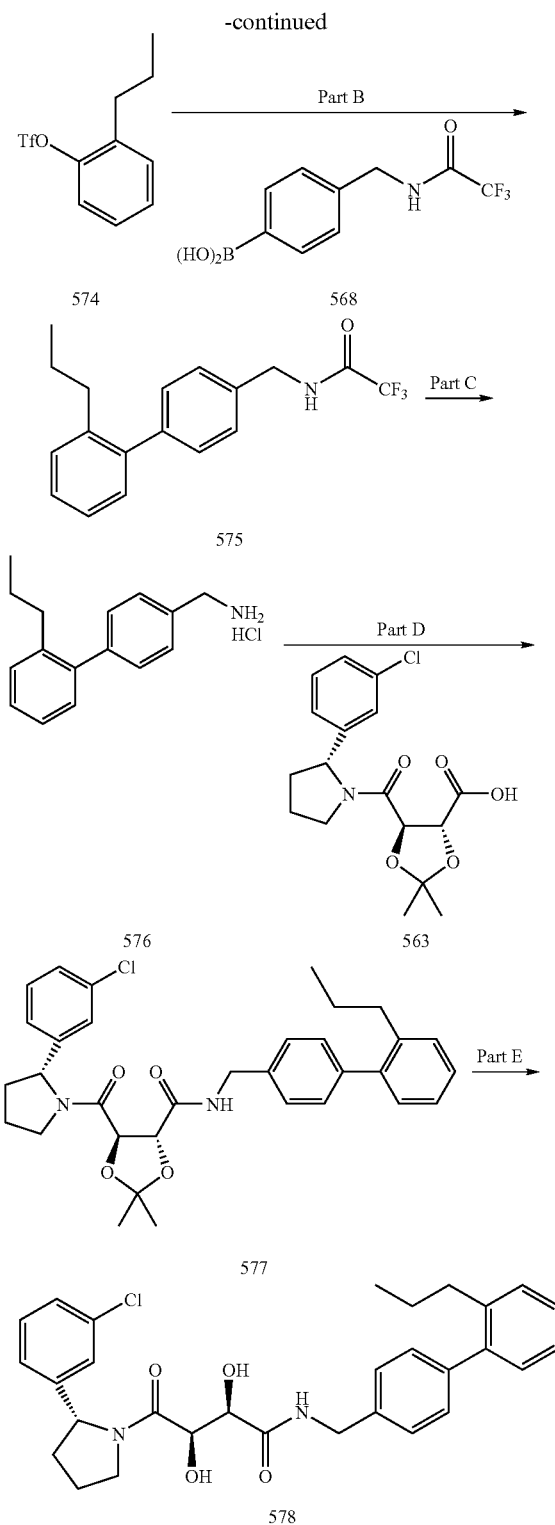

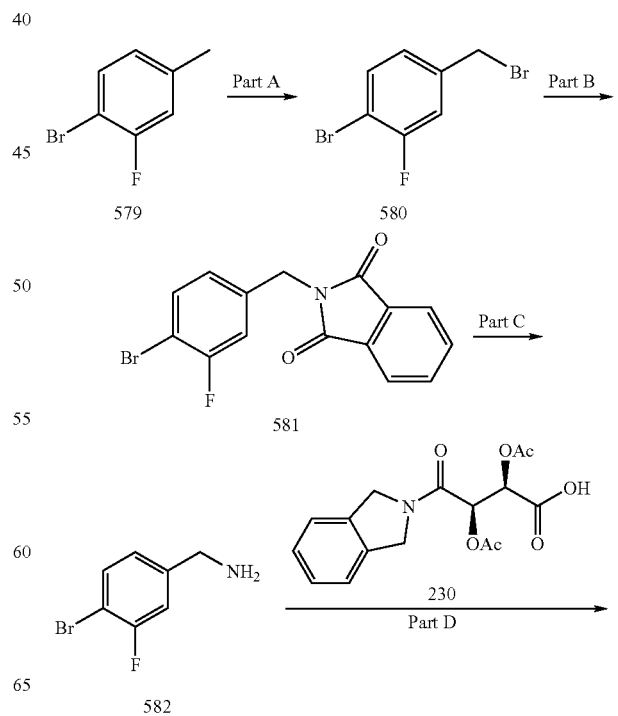

The layers were separated and the organic layer was washed with saturated sodium bicarbonate solution and brine, dried over sodium sulfate and concentrated. Purification by column chromatography (SiO$_2$, 5% ethyl acetate/hexane) afforded 574 (916 mg, 100%). $^1$H NMR (400 MHz, CDCl$_3$) δ 7.30 (m, 2H), 7.26 (m, 2H), 2.70 (m, 2H), 1.68 (m, 2H), 1.00 (t, 3H, J=7.3 Hz).

Part B:

Compound 575 (288 mg, 89%) was prepared using the procedures described in Example 12D Part B and a reaction temperature of 100° C. HPLC-MS $t_R$=2.30 min (UV$_{254\ nm}$); mass calculated for formula C$_{18}$H$_{18}$F$_3$NO 321.1, observed LCMS m/z 322.2 (M+H).

Part C:

Compound 576 (203 mg, 86%) was prepared using the procedure described in Example 12E Part C. $^1$H NMR (400 MHz, DMSO-d$_6$) δ 8.27 (bs, 3H), 7.52 (d, 2H, J=8.0 Hz), 7.32 (d, 2H, J=8.1 Hz), 7.31 (m, 2H), 7.22 (m, 1H), 7.10 (d, 1H, J=7.1 Hz), 4.08 (s, 2H,) 2.54 (m, 2H), 1.44 (m, 2H), 0.75 (t, 3H, J=7.7 Hz).

Part D:

Compound 577 (62 mg, 92%) was prepared according to the procedure described in Example 12D Part D. HPLC-MS $t_R$=2.55 min (UV$_{254\ nm}$); mass calculated for formula C$_{33}$H$_{37}$ClN$_2$O$_4$ 560.2, observed LCMS m/z 561.2 (M+H).

Part E:

Compound 578 (53 mg, 93%) was prepared according to the procedure described in Example 12D Part E. HPLC-MS $t_R$=2.21 min (UV$_{254\ nm}$); mass calculated for formula C$_{30}$H$_{33}$ClN$_2$O$_4$ 520.2, observed LCMS m/z 521.2 (M+H).

Example 12G

Part A:

To a mixture of 2-propyl phenol (573) (0.5 mL, 3.63 mmol) and DIEA (0.950 mL, 5.45 mmol) in DCM (20 mL) at 0° C. was added triflic anhydride (0.734 mL, 4.36 mmol) in DCM (10 mL) via an addition funnel. The reaction mixture was stirred for 45 minutes. The mixture was poured into water.

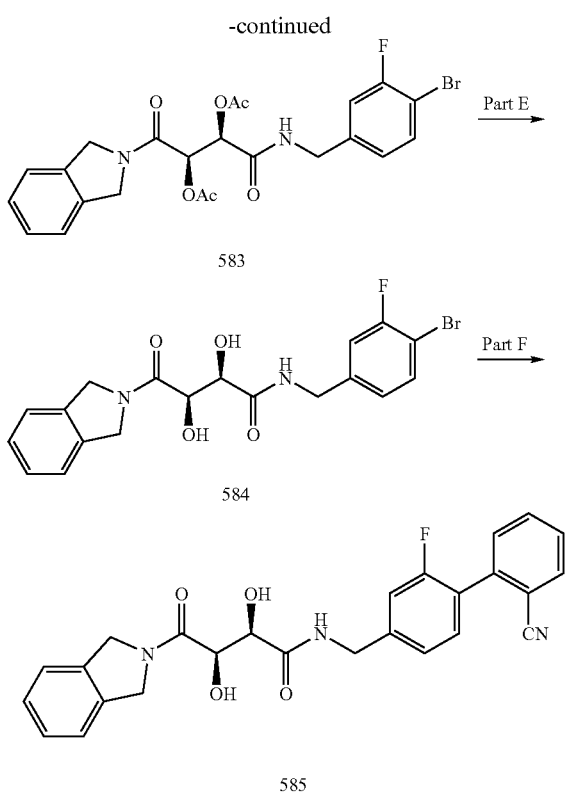

Part A:

A mixture of 4-bromo-3-fluoro-toluene (579) (2.0 mL, 15.8 mmol), N-bromosuccinimide (3.38 g, 19.0 mmol) and benzoylperoxide (48 mg, 0.2 mmol) in carbon tetrachloride (50 mL) was heated to reflux under a nitrogen atmosphere for 16 hours. The reaction mixture was cooled and filtered. The filtrate was washed with water (2×), saturated sodium bicarbonate solution and brine, dried over sodium sulfate and concentrated to afford a mixture of 580 and dibromonated product (4.02 g). The material was used without further purification. $^1$H NMR (400 MHz, CDCl$_3$) δ 7.52 (dd, 1H, J=6.6, 7.6 Hz), 7.17 (dd, 1H, J=2.0, 8.9 Hz), 7.11 (dd, 1H, J=2.0, 8.2 Hz), 4.42 (s, 2H).

Part B:

A mixture of 580 (4.02 g, 15.0 mmol), phthalimide (2.65 g, 18 mmol) and cesium carbonate (5.38 g, 16.5 mmol) in DMF (30 mL) was stirred for 72 hours. The reaction mixture was poured into water (100 mL) and extracted with ethyl acetate. The combined organic layers were washed with water (3×) and brine, dried over sodium sulfate and concentrated. Recrystallization from 30% ethyl acetate/hexanes afforded slightly impure 581 (3.28 g) as a yellow solid. $^1$H NMR (400 MHz, CDCl$_3$) δ 7.86 (m, 2H), 7.74 (m, 2H), 7.49 (dd, 1H, J=7.3, 8.4 Hz), 7.20 (dd, 1H, J=1.9, 9.3 Hz), 7.06 (dd, 1H, J=2.0, 7.9 Hz), 4.80 (s, 2H).

Part C:

A mixture of 581 (1.00 g, 3.0 mmol) and hydrazine monohydrate (580 uL, 12.0 mmol) in ethanol (25 mL) was heated to reflux for 1 hour. The reaction mixture was diluted with ethyl acetate and filtered. The precipitate was washed with ethyl acetate. The filtrate was concentrated and the residue was dissolved in water and ethyl acetate. The layers were separated. The organic layer was washed with saturated sodium bicarbonate solution, water and brine, dried over sodium sulfate and concentrated to afford 582 (375 mg) as a yellow oil. $^1$H NMR (400 MHz, CDCl$_3$) δ 7.48 (t, 1H, J=8.5 Hz), 7.12 (dd, 1H, J=2.2, 9.5 Hz), 6.99 (dd, 1H, J=1.6, 8.2 Hz), 3.86 (s, 2H).

Part D:

Compound 583 was prepared using procedures similar to those described in Example 12C Part A. HPLC-MS $t_R$=1.82 min (UV$_{254\ nm}$); mass calculated for formula C$_{23}$H$_{22}$BrFN$_2$O$_6$ 520.0, observed LCMS m/z 521.0 (M+H).

Part E:

Compound 584 was prepared using the procedures described in Example 12C Part B. HPLC-MS $t_R$=1.81 min (UV$_{254\ nm}$); mass calculated for formula C$_{19}$H$_{18}$BrFN$_2$O$_4$ 436.0, observed LCMS m/z 437.0 (M+H).

Part F:

Compound 585 was prepared using procedures similar to those described in Example 12C Part C. HPLC-MS $t_R$=4.12 min (UV$_{254\ nm}$, 10 min); mass calculated for formula C$_{26}$H$_{22}$FN$_3$O$_4$ 459.2, observed LCMS m/z 460.1 (M+H).

The following table contains compounds prepared using the procedures described in Example 12A-G.

| Compound # | Structure | Exact mass | MS m/e (M + H) |
|---|---|---|---|
| 586 | 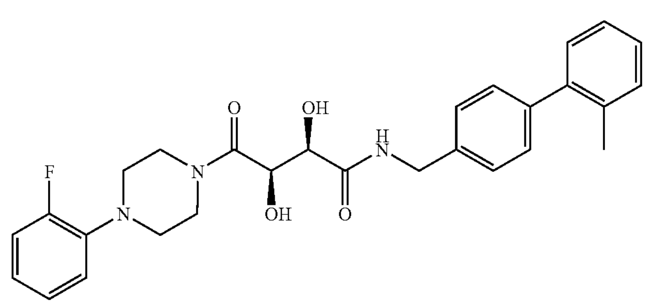 | 491.2 | 492.2 |

-continued

| Compound # | Structure | Exact mass | MS m/e (M + H) |
|---|---|---|---|
| 587 | 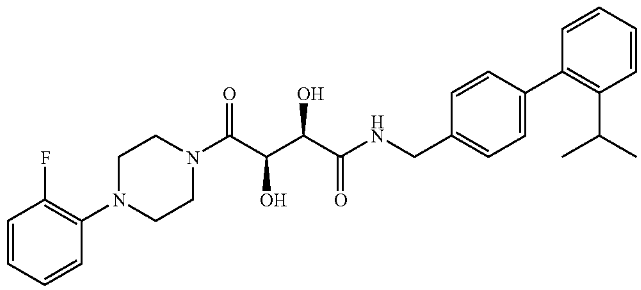 | 519.3 | 520.3 |
| 588 | 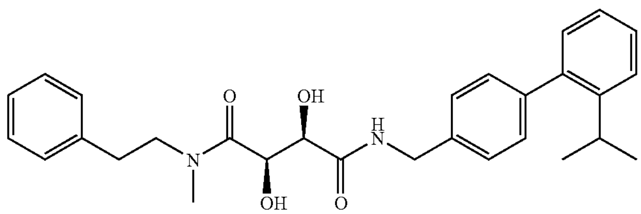 | 474.3 | 475.3 |
| 589 | 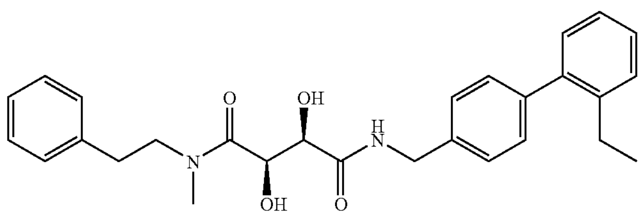 | 460.2 | 461.2 |
| 590 | 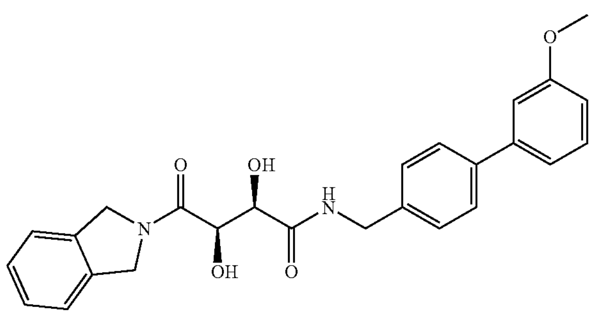 | 446.2 | 447.2 |
| 591 | 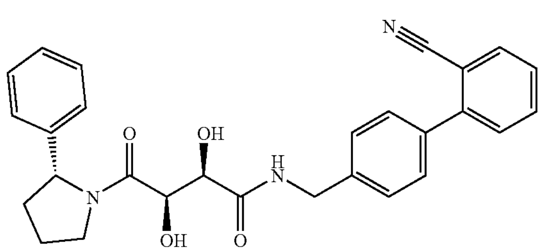 | 469.2 | 470.1 |

-continued

| Compound # | Structure | Exact mass | MS m/e (M + H) |
|---|---|---|---|
| 592 | 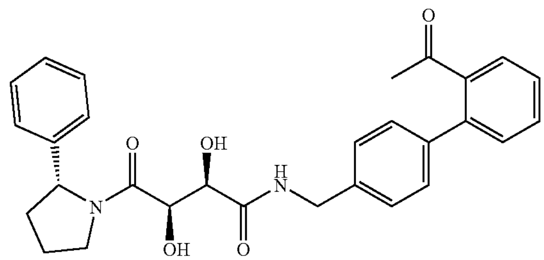 | 486.2 | 487.1 |
| 593 | 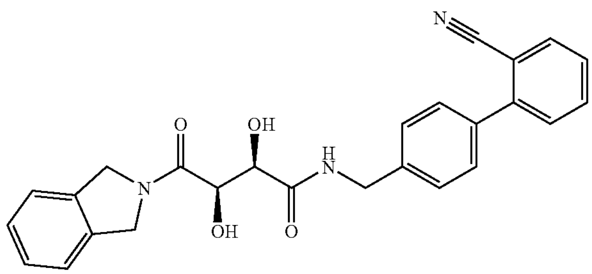 | 441.2 | 442.1 |
| 594 | 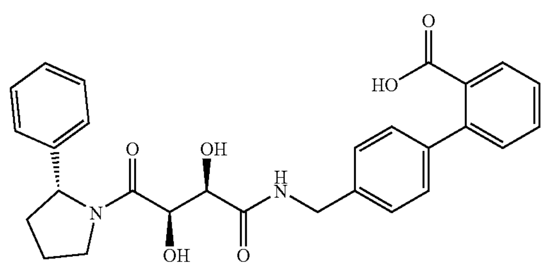 | 488.2 | 489.1 |
| 595 | 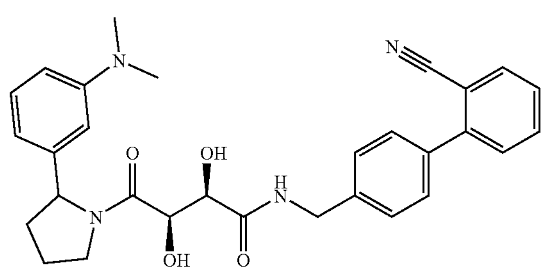 | 512.2 | 513.3 |
| 596 | 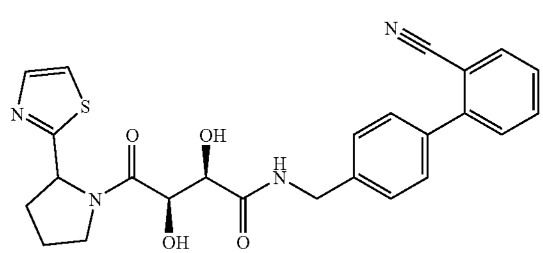 | 476.2 | 477.2 |

| Compound # | Structure | Exact mass | MS m/e (M + H) |
|---|---|---|---|
| 597 | 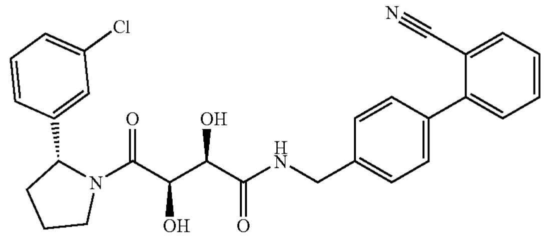 | 503.2 | 504.2 |
| 598 | 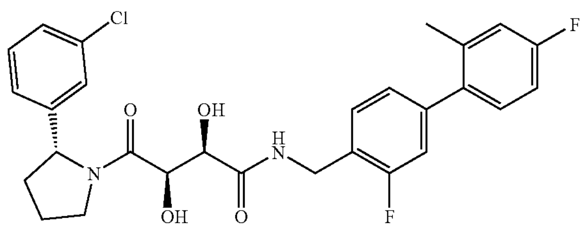 | 528.2 | 529.2 |
| 599 | 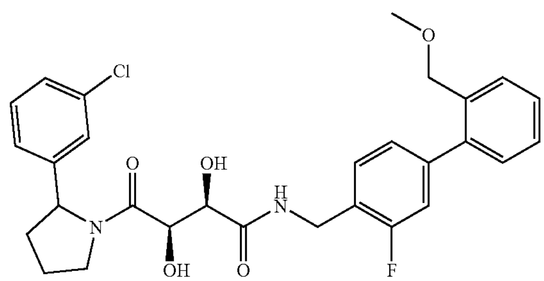 | 540.2 | 541.2 |
| 600 | 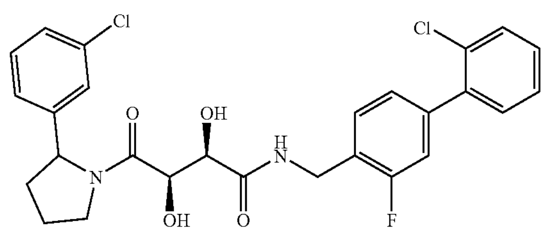 | 530.1 | 531.0 |
| 601 | 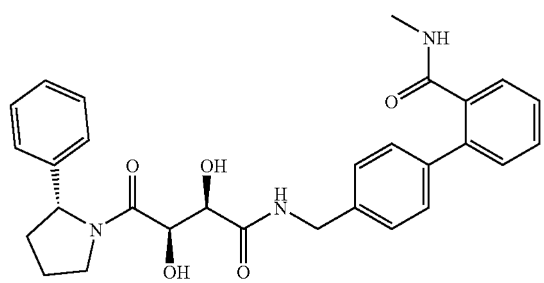 | 501.2 | 502.3 |
| 602 | 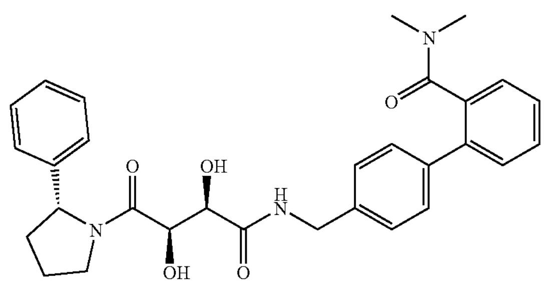 | 515.2 | 516.3 |

-continued

| Compound # | Structure | Exact mass | MS m/e (M + H) |
|---|---|---|---|
| 603 | 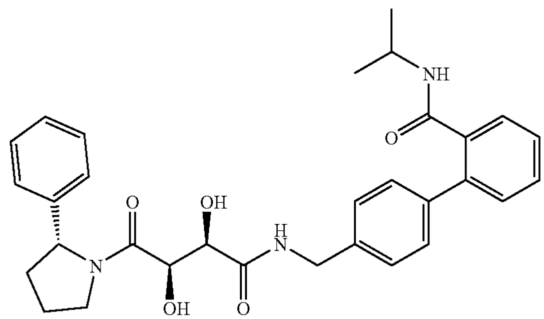 | 529.3 | 530.3 |
| 604 | 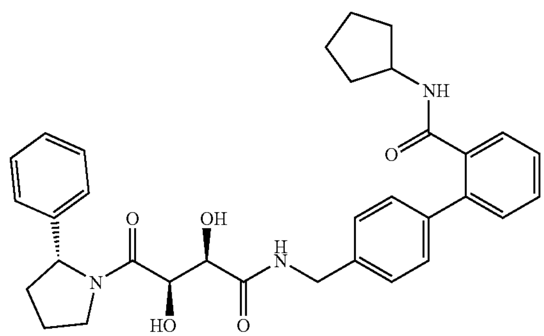 | 555.3 | 556.3 |
| 605 | 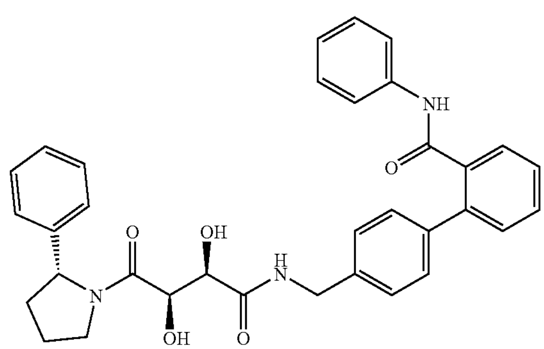 | 563.2 | 564.3 |
| 606 | 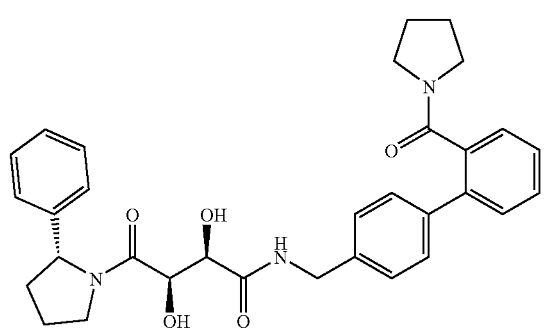 | 541.3 | 542.3 |

-continued

| Compound # | Structure | Exact mass | MS m/e (M + H) |
|---|---|---|---|
| 607 | 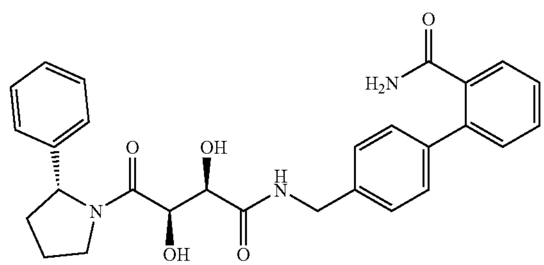 | 487.2 | 488.1 |
| 608 | 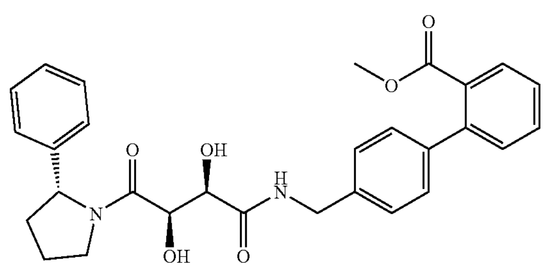 | 502.2 | 503.1 |
| 609 | 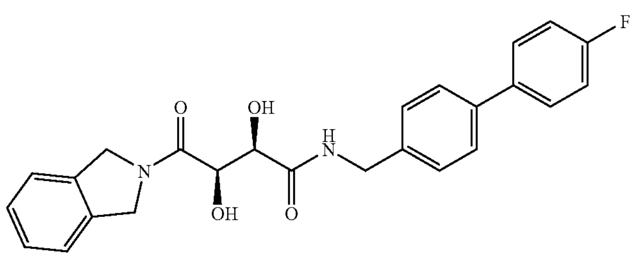 | 434.2 | 435.2 |
| 610 | 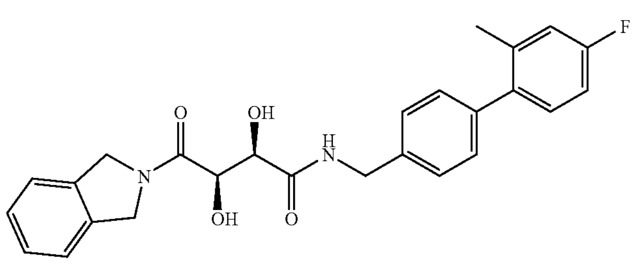 | 448.2 | 449.2 |
| 611 | 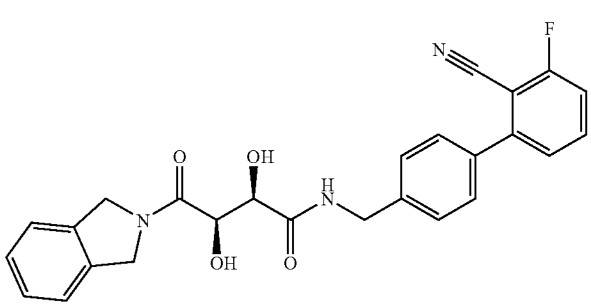 | 459.2 | 460.1 |

-continued

| Compound # | Structure | Exact mass | MS m/e (M + H) |
|---|---|---|---|
| 612 | 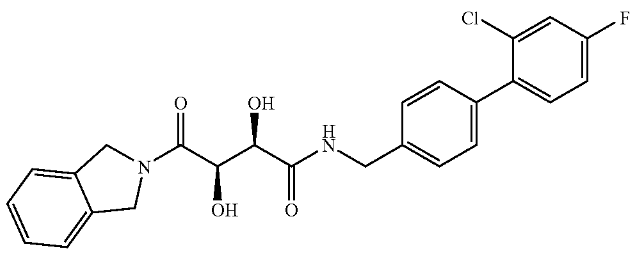 | 468.1 | 469.1 |
| 613 | 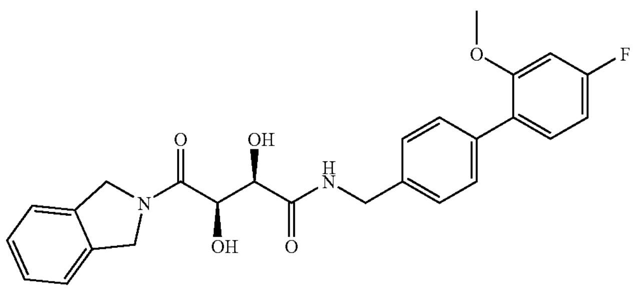 | 464.2 | 465.1 |
| 614 | 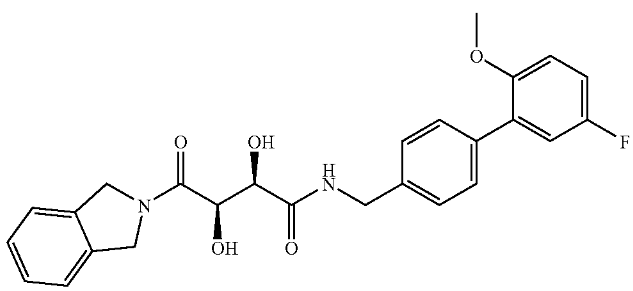 | 464.2 | 465.1 |
| 615 | 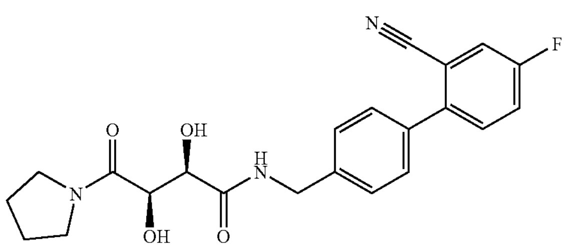 | 411.2 | 412.1 |
| 616 | 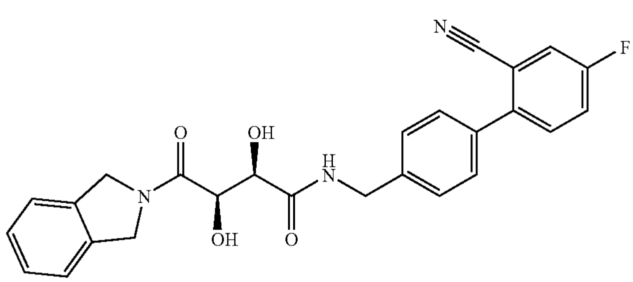 | 459.2 | 460.1 |

-continued

| Compound # | Structure | Exact mass | MS m/e (M + H) |
|---|---|---|---|
| 617 | 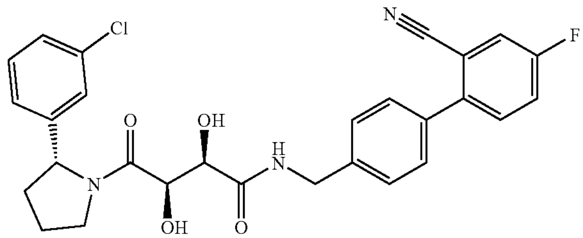 | 521.2 | 522.1 |
| 618 | 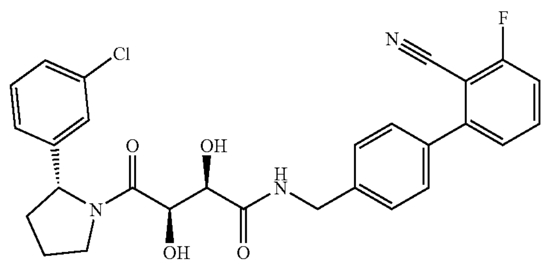 | 521.2 | 522.1 |
| 619 | 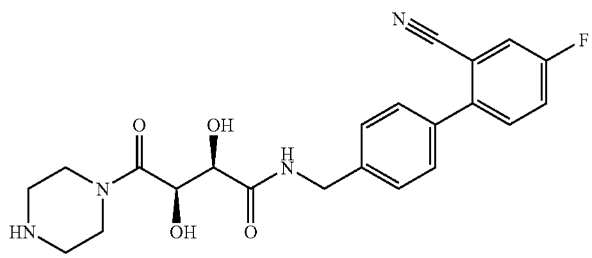 | 426.2 | 427.1 |
| 620 | 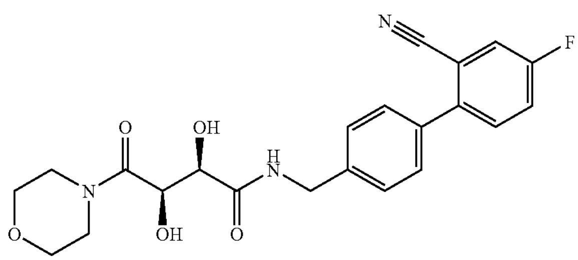 | 427.2 | 428.1 |
| 621 | 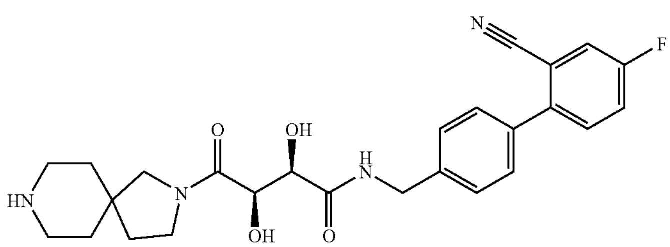 | 480.2 | 481.2 |
| 622 | 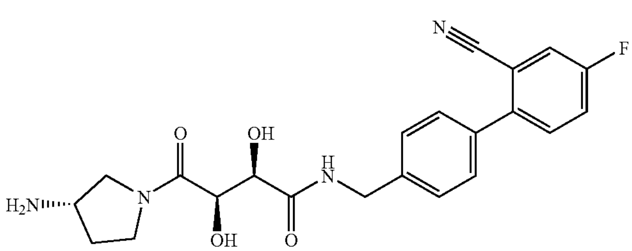 | 426.2 | 427.1 |

| Compound # | Structure | Exact mass | MS m/e (M + H) |
|---|---|---|---|
| 623 | 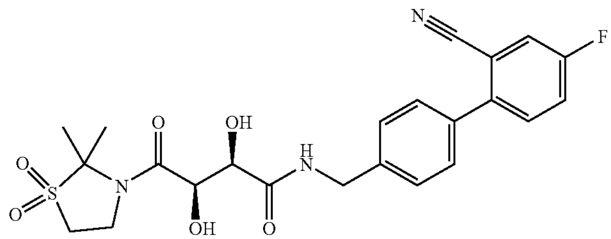 | 489.1 | 490.1 |
| 624 | 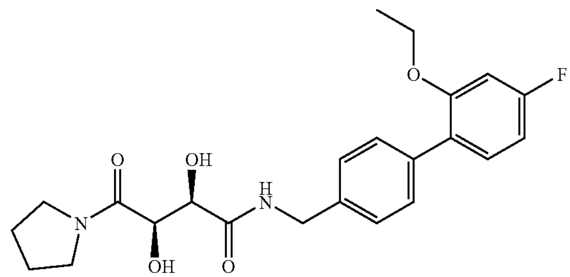 | 430.2 | 431.2 |
| 625 | 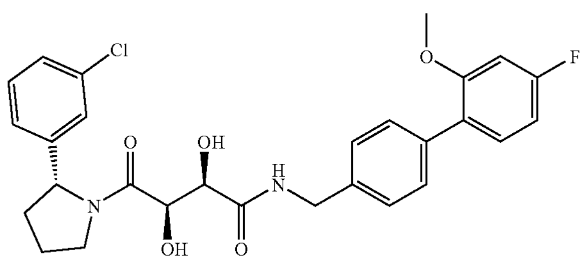 | 526.2 | 527.2 |
| 626 | 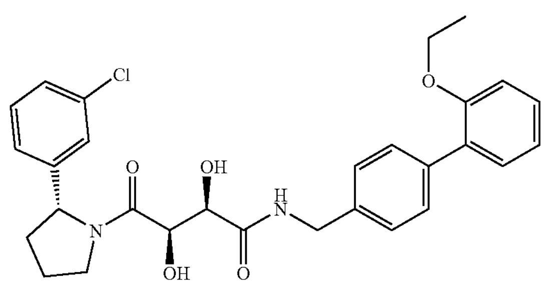 | 522.2 | 523.2 |
| 627 | 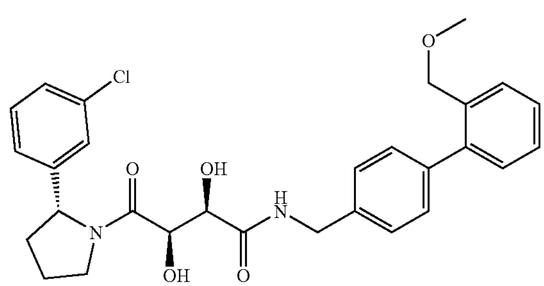 | 522.2 | 523.2 |

-continued
| Compound # | Structure | Exact mass | MS m/e (M + H) |
|---|---|---|---|
| 628 | 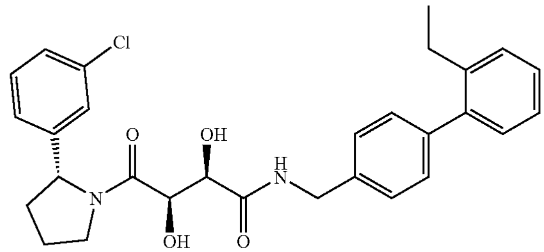 | 506.2 | 507.2 |
| 629 | 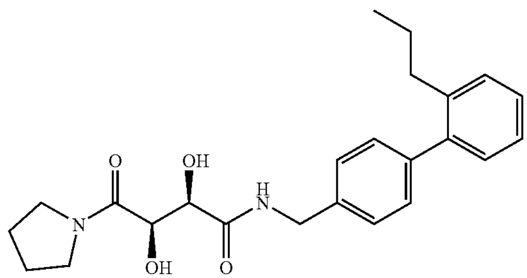 | 410.2 | 411.2 |
| 630 | 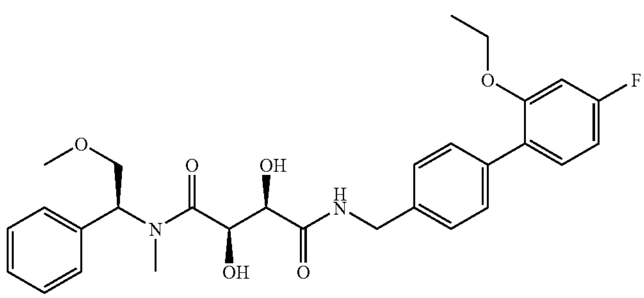 | 524.2 | 525.2 |
Example 13
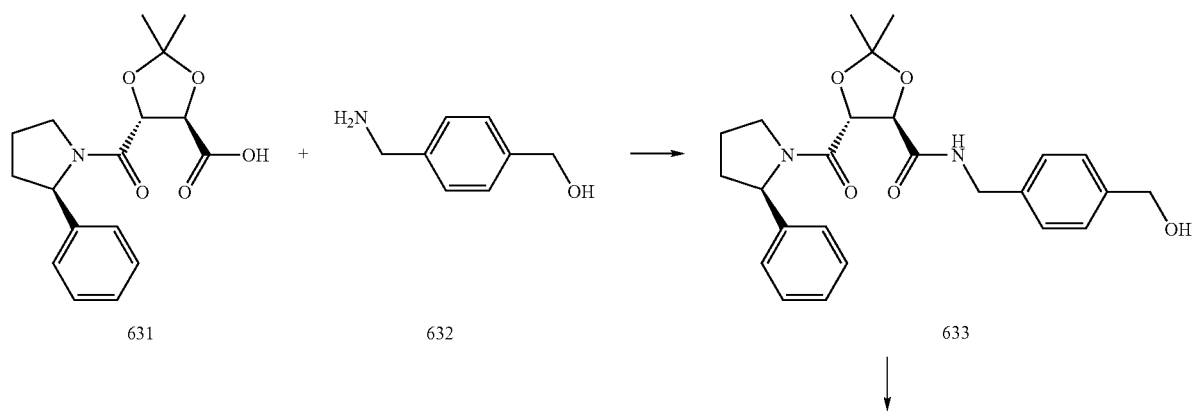

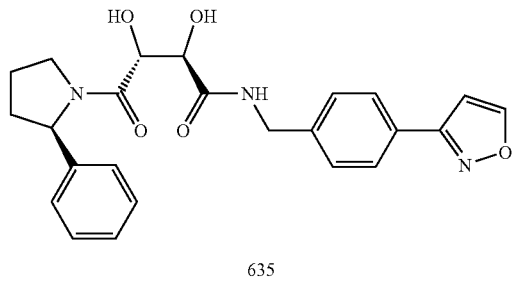

635

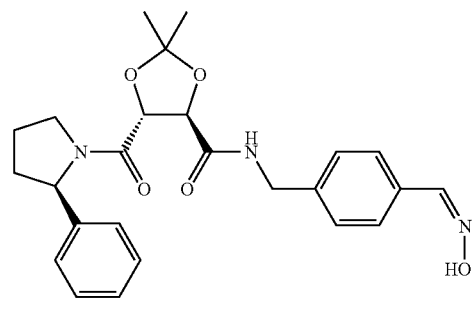

634

Compound 631 was prepared by the procedures described in Example 11A.

Part A.

To a solution of 631 (0.46 g) and 632 (1.2 eq) in 10 ml DMF at OC were added HATU (1.5 eq) and HOBt (1.5 eq). The reaction was stirred at r.t. overnight before the solvent was removed in vacuo and residue chromatographed using Ethyl Acetate in Hexane (0-100%) to give 0.46 gram of desired product 633.

Part B.

To a solution of 0.46 g of 633 in 10 ml of DCM was added Dess-Martin Reagent (1.1 eq) and the reaction was stirred at r.t. for 30 min before it was treated with sat. aqueous solution of sodium bicarbonate and sodium thiosulfate 7:1 (w/w). The aqueous layer was extracted with DCM (2×) and the combined organic layers was dried over anhydrous sodium sulfate. After removal of solvent, the crude reaction product was dissolved in 2 ml pyridine. To the solution was added 1.5 eq of hydroxylamine hydrochloride and the solution was heated to reflux for 30 min before the solvent was removed in vacuo and residue chromatographed using Ethyl Acetate in Hexane (0-100%) to give 0.4 gram of product 634.

Part C.

To a flask containing 634 (0.42 g) in anhydrous DMF at 0° C. was added NBS (1 eq) and the solution was allowed to warm up to r.t. overnight before another equivalent of NBS was added and solution stirred for another overnight. The final reaction mixture was poured over ice and extracted with DCM. The organic phase was washed with water and brine, dried over sodium sulfate. After removal of the solvent, the residue was chromatographed using Ethyl Acetate in Hexane (0-100%) to give 0.38 gram of desired product.

To a solution of 0.035 gram of above compound in 2 ml DCM was added vinylacetate (2 eq) and DIEA (3.5 eq) and the solution was stirred at r.t. overnight. After removal of solvent, the residue was chromatographed using Ethyl Acetate in Hexane (0-100%) to give 20 mg product which was treated with 50% TFA in DCM for 2 h. before it was purified using a RP HPLC system to give 10 mg of desired product 635.

The following compounds were generated using similar procedures.

| Compound # | Structure | Exact mass | MS m/z (M + H) |
|---|---|---|---|
| 635 | 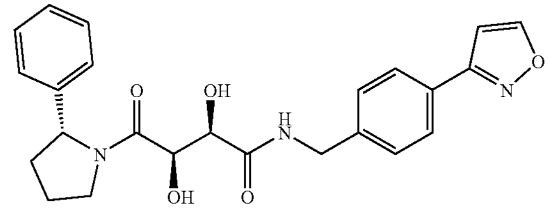 | 435.2 | 436.0 |
| 636 | 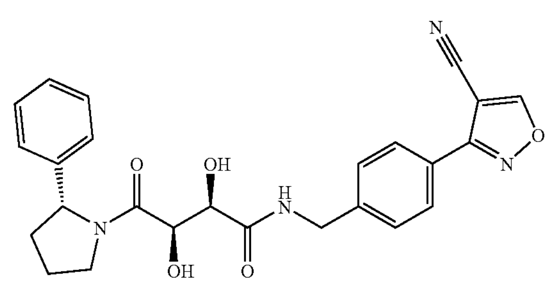 | 460.2 | 461.0 |

-continued
| Compound # | Structure | Exact mass | MS m/z (M + H) |
|---|---|---|---|
| 637 | 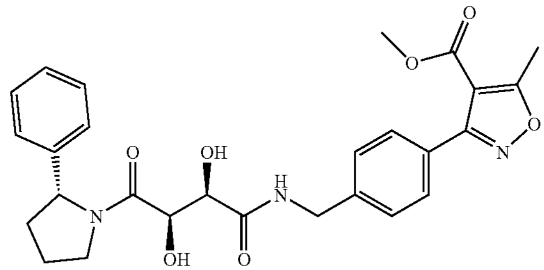 | 507.2 | 508.0 |
| 638 | 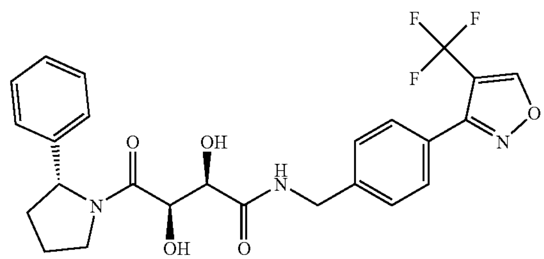 | 503.2 | 504.0 |
| 639 | 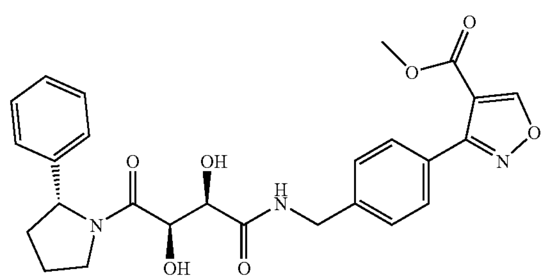 | 493.2 | 494.0 |
Example 14
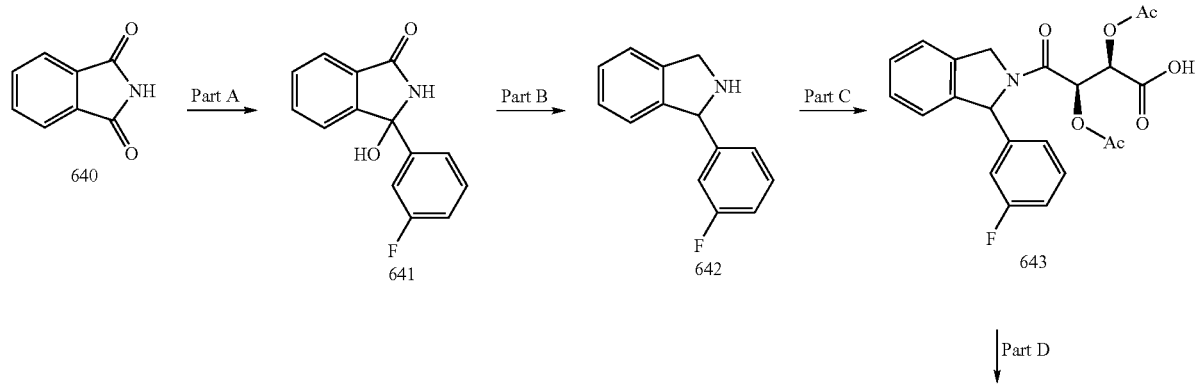

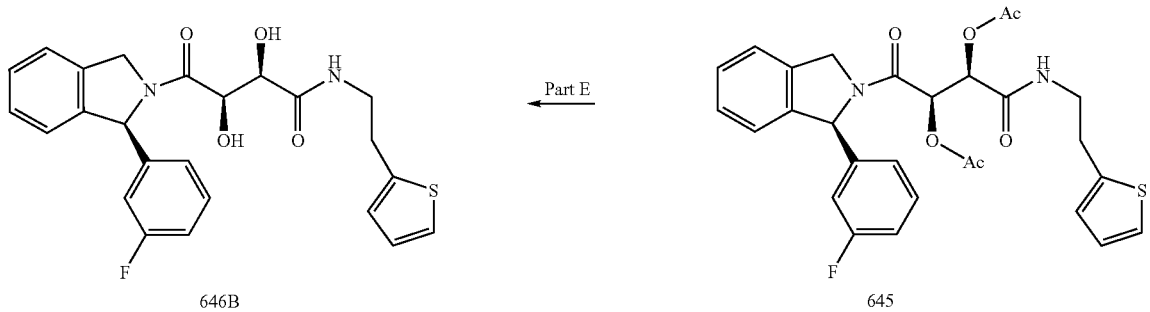

Part A:

A Schlenck flask was flame dried under N₂ flow, capped with a septum, and allowed to cool to rt. Phthalimide (640) (4.13 g, 28.1 mmol) was added followed by anhydrous THF (100 mL). After the phthalimide had dissolved, the flask was placed in an ice water bath and allowed to cool for 20 min. A 1 M solution of 3-fluorophenyl magnesium bromide in THF (25 mL) was added causing a precipitate to form. DMPU (5 mL) was added, causing the reaction mixture to become clear again. Additional 3-fluorophenyl magnesium bromide was added (35 mL) over 10 min. The reaction mixture was stirred at 0° C. for 3.5 h, then quenched with 1.0 M pH 6.5 sodium phosphate buffer. The resulting mixture was diluted with EtOAc and the layers were separated. The organic layer was washed with water and brine, then dried with MgSO₄. Evaporation of the solvent gave and off white solid (7.4 g). This material was triturated in CH₂Cl₂/hexanes to give 4.0 g of pure 641. MS (EI) m/z Obsd. M+H 244.0

Part B:

A Schlenck flask was flame dried under N₂ flow, capped with a septum, and allowed to cool to rt. LiAlH₄ (1.26 g, 33.2 mmol) and AlCl₃ (1.47 g, 11.0 mmol) were added to the flask, followed by anhydrous THF. The flask was placed in an ice-water bath immediately and allowed to cool with stirring. Compound 641 was added to the flask in portions. The reaction mixture was stirred for 3 h during which time it warmed to 15° C. The reaction was recooled to 0° C. and water (3 mL) was added. Aqueous 3.0 N sodium hydroxide was added (6 mL) followed by water (9 mL). The reaction mixture was filtered through a pad of Celite which was rinsed with EtOAc. The resulting filtrate was concentrated to dryness giving a green solid. The crude product was partially purified via flash sgc using a 40%-50% EtOAc/hexanes gradient, followed by 98% EtOAc/2% Et₃N. The fractions containing the impure desired product were combined to give a blue oil. This material was dissolved in CH₂Cl₂ (6 mL). TFA (4 mL) and triethyl silane (2 mL) were added and the reaction mixture was left stirring ON. The reaction mixture was concentrated to give a green oil. This material was purified via flash sgc using 2:1 hexanes:EtOAc, followed by 98% EtOAc/2% Et₃N as the mobile phase. Compound 642 was isolated as a yellow oil (0.56 g). MS (EI) m/z Obsd M+H 214.2.

Part C:

Compound 642 (0.56 g, 2.6 mmol) was dissolved in CH₂Cl₂ (8 mL). Triethyl amine was added (1 mL) followed by (+)-diacetyl-(L)-tartaric anhydride (0.65 g, 3.00 mmol). The reaction mixture was left stirring at rt ON. The reaction mixture was concentrated to dryness and purified via sgc using 2%-5% MeoH/CH₂Cl₂ mobile phase with 1% acetic acid added to it. After evaporating the solvent and azeotopic removal of the acetic acid with heptane, compound 643 was obtained as a white solid (0.33 g). MS (EI) m/z Obsd M+H 430.1

Part D:

Compound 643 (92 mg, 0.214 mmol), HOBT (36 mg, 0.26 mmol), DMF (1.5 mL), 2-thiophene ethylamine (44 mg, 0.34 mmol), and N-methylmorpholine (50 µL) were added to a flask. EDC was added and the reaction mixture was left stirring ON at rt. The reaction mixture was diluted with EtOAc and washed with aqueous NaHCO₃, citric acid, water, and brine. The organic layer was dried with MgSO₄ and concentrated to give a brown oil. The crude product was purified via flash sgc using a 10%-80% EtOAc/Hexanes gradient. Two diastereomeric compounds were isolated-644 Diastereomer A (0.02 g) MS (EI) m/z Obsd M+H 539.06 and 645 Diastereomer B (0.03 g) MS (EI) m/z Obsd M+H 539.03.

Part E:

Compound 645 was dissolved in 2 M methanolic ammonia and stirred at rt for 30 m. The reaction was purified to dryness. The crude product was purified via prep TLC on silica plates using 1:1 EtOAc: Hexanes as the mobile phase. 646B: MS (EI) m/z Obsd M+H 455.1.

| Compound # | Structure | Exact mass | MS m/z(M + H) |
|---|---|---|---|
| 646A | 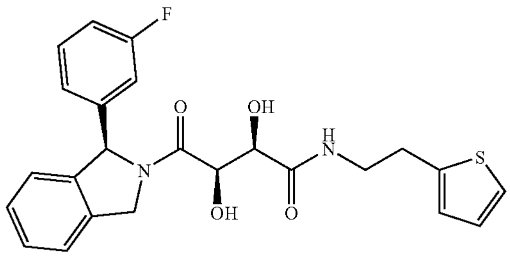 | 454.1 | 455.1 |
| 646B | 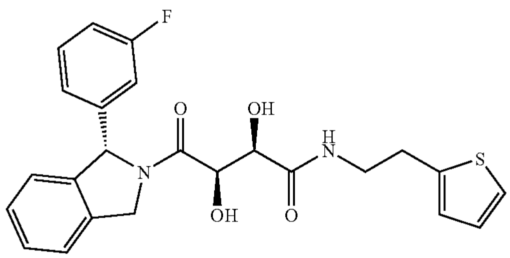 | 454.1 | 455.1 |
| 647 | 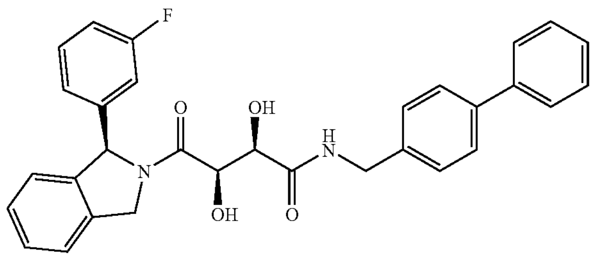 | 510.2 | 511.1 |
| 648 | 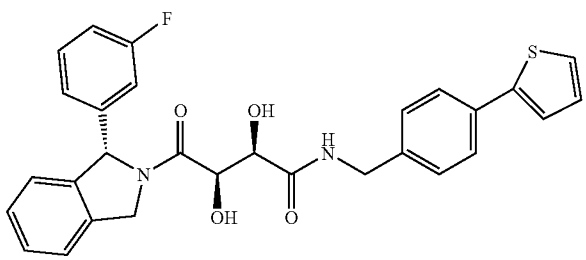 | 516.2 | 517.1 |
| 649A | 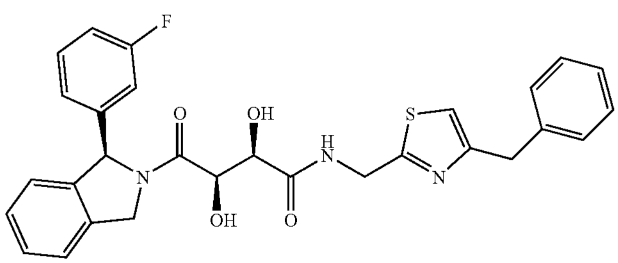 | 531.2 | 532.1 |
| 649B | 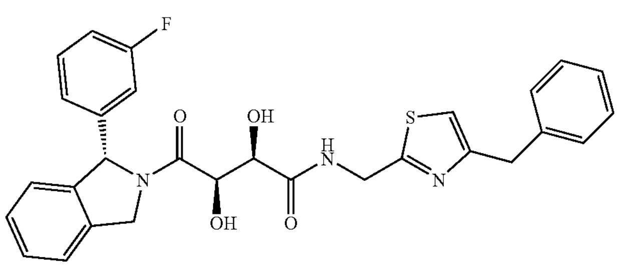 | 531.2 | 532.1 |

Example 15

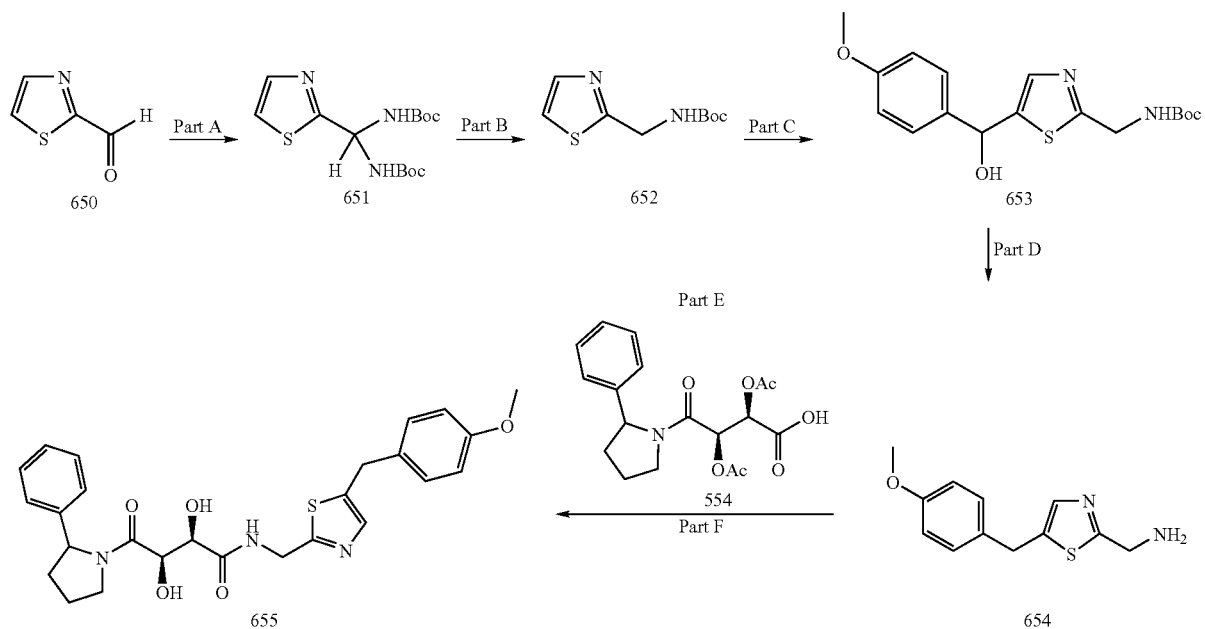

Part A:

Compound 650 (8.36 g, 73.9 mmol) and tert-butyl carbamate (25.96 g, 222 mmol) were dissolved in acetonitrile (300 mL) and trifluoroacetic acid was added. The reaction was stirred overnight at rt under $N_2$, then concentrated. The resulting mixture was dissolved in EtOAc and washed with water. The organic layer was dried with $Na_2SO_4$ and concentrated to dryness. The crude product was purified via flash sgc using 1:3 EtOAc: Hexanes as the mobile phase to give 30.27 g of product 651. $^1$HNMR (400 MHz, CDCl$_3$) δ 7.78 (s, 1H), 7.40 (s, 1H), 6.38-6.30 (m, 1H), 1.51 (s, 18H) MS (EI) m/z Obsd M+H 330.1

Part B:

Compound 651 (30.27 g, 91.89 mmol) was dissolved in 2-propanol (1500 mL) and sodium borohydride (17.0 g, 46 mmol) was added. The reaction mixture was refluxed for 3 h, then concentrated on the rotovap. The resulting material was diluted with EtOAc, washed with water, and dried with $Na_2SO_4$. The solvents were evaporated and the crude product was purified via flash sgc using 1:2 EtOAc: Hexanes as the mobile phase to give 11.58 g of 652. Yield=73% over steps one and two. $^1$HNMR (400 MHz, CDCl$_3$) δ 7.78 (s, 1H), 7.33 (s, 1H), 5.35 (s, 1H), 4.69 (s, 2H), 1.53 (s, 9H); MS (EI) MS (EI) m/z Obsd M+H 215.0

Part C:

Compound 652 (0.30 g, 1.40 mmol) was dissolved in 5 mL of anhydrous THF (5 mL). The flask was capped with a septum, placed under $N_2$ blanket, and cooled in a dry ice/2-propanol bath. A solution of LDA (1.71 mL, 1.8 M) was added via syringe and the reaction mixture was stirred for 0.5 h. A solution of 4-methoxy benzaldehyde (0.21 g, 1.54 mmol) in 5 mL of anhydrous THF was added via syringe. The reaction mixture was stirred for 1 h. The ice bath was removed and the reaction was left stirring overnight at rt. Water was added and the reaction mixture was diluted with EtOAc. The layers were separated. The organic layer was washed with water and dried with $Na_2SO_4$. The solvent was evaporated and the crude product was purified via flash sgc using 1:1 EtOAc: Hexanes to give 0.28 g of 653. $^1$HNMR (400 MHz, CDCl$_3$) δ 7.42 (s, 1H), 7.37-7.32 (m, 2H), 6.89-6.94 (m, 2H), 6.02 (s, 1H), 5.38 (broad s, 1H), 4.55 (s, 2H), 3.86 (s, 3H) 3.28 (s, 1H), 1.49 (s, 9H).

Part D:

Compound 653 (0.28 g, 0.80 mmol) was dissolved in triethylsilane (2 mL) and TFA (0.6 mL). The reaction mixture was refluxed for 3 h then allowed to cool to rt and stirred overnight. The reaction mixture was concentrated. Methanol was added and the reaction mixture was concentrated. Lithium hydroxide (10 mL, 1.0 M aq) and dioxane (10 mL) were added. The reaction mixture was stirred for 3 h then partially concentrated. EtOAc was added and the layers were separated. The organic layer was washed with water and dried with $Na_2SO_4$. The reaction mixture was concentrated to give 0.23 g of compound 654. $^1$HNMR (400 MHz, CDCl$_3$) δ 7.44 (s, 1H), 7.19 (d, J=9 Hz, 2H), 6.89 (d, J=9 Hz, 2H), 4.16 (s, 2H), 4.11 (s, 2H), 3.84 (s, 3H), 1.77 (broad s, 2H).

Parts E and F:

Compound 654 was converted to compound 655 using procedures described in Example 2. Data for 655: $^1$HNMR (400 MHz, CDCl$_3$) δ 7.41-7.26 (m, 5H), 7.22-7.14 (M, 4H), 6.89-6.81 (m, 2H), 5.50-5.17 (m, 1H), 4.98-4.54 (m, 4H), 4.53-4.31 (m, 2H), 4.06-3.98 (m, 2H), 3.84 (s, 3H), 2.47-2.27 (m, 1H), 2.12-1.75 (m, 1H). MS (EI) m/z Obsd M+H 496.1.

| Compound # | Structure | Exact mass | MS m/z (M + H) |
|---|---|---|---|
| 656A | 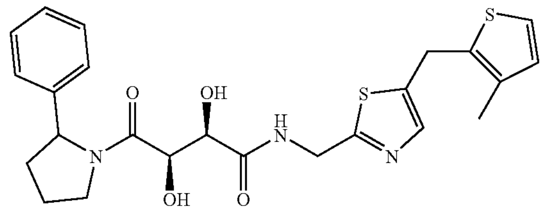 | 485.1 | 486.3 |
| 656B | 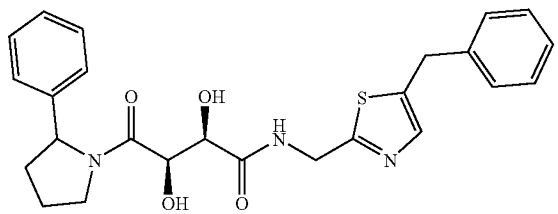 | 465.2 | 466.1 |
| 657 | 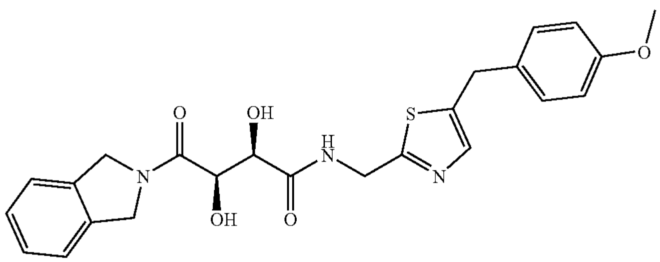 | 467.2 | 468.1 |
| 658 | 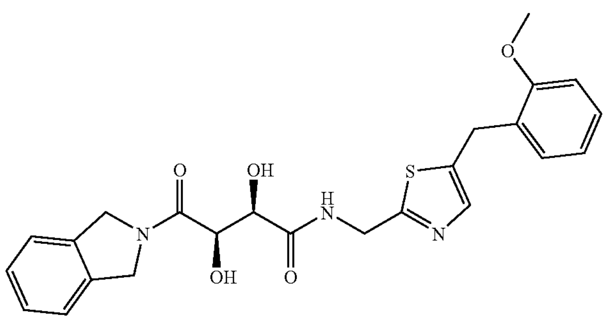 | 467.2 | 468.1 |
| 659 | 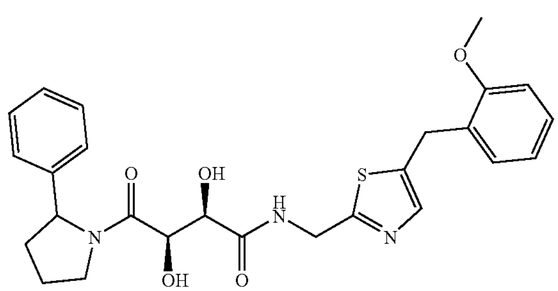 | 495.2 | 496.1 |
| 660 | 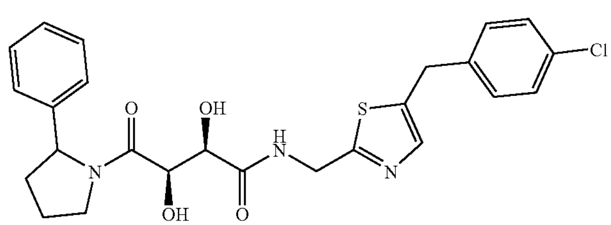 | 499.1 | 500.1 |

-continued
| Compound # | Structure | Exact mass | MS m/z (M + H) |
|---|---|---|---|
| 661 | 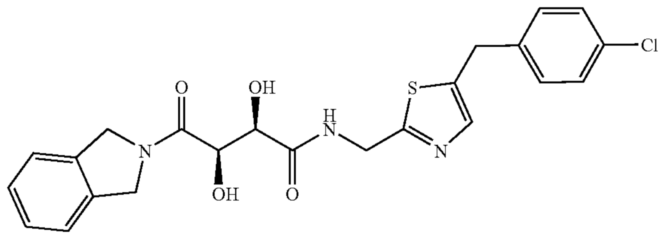 | 471.1 | 472.1 |
| 662 | 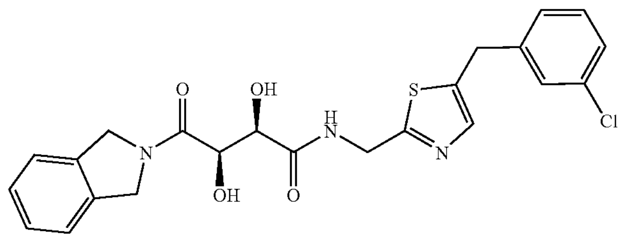 | 471.1 | 472.1 |
| 663 | 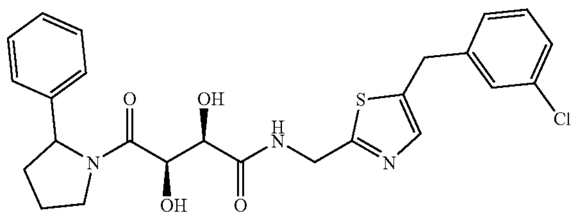 | 499.1 | 500.1 |
| 664 | 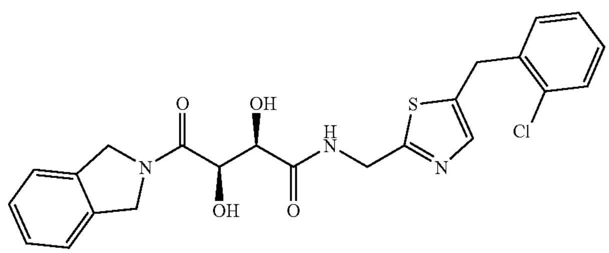 | 471.1 | 472.1 |
Example 16
Thioamides
Example 16A
-continued
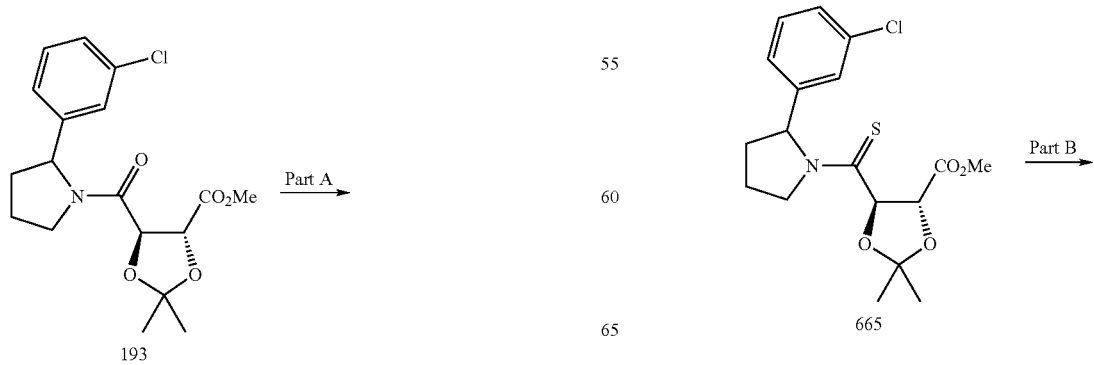
193
665

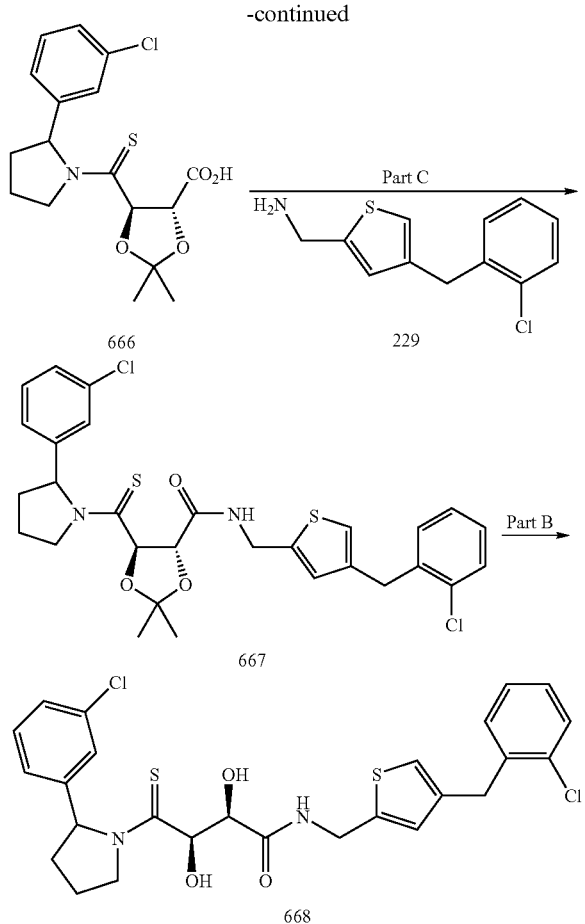

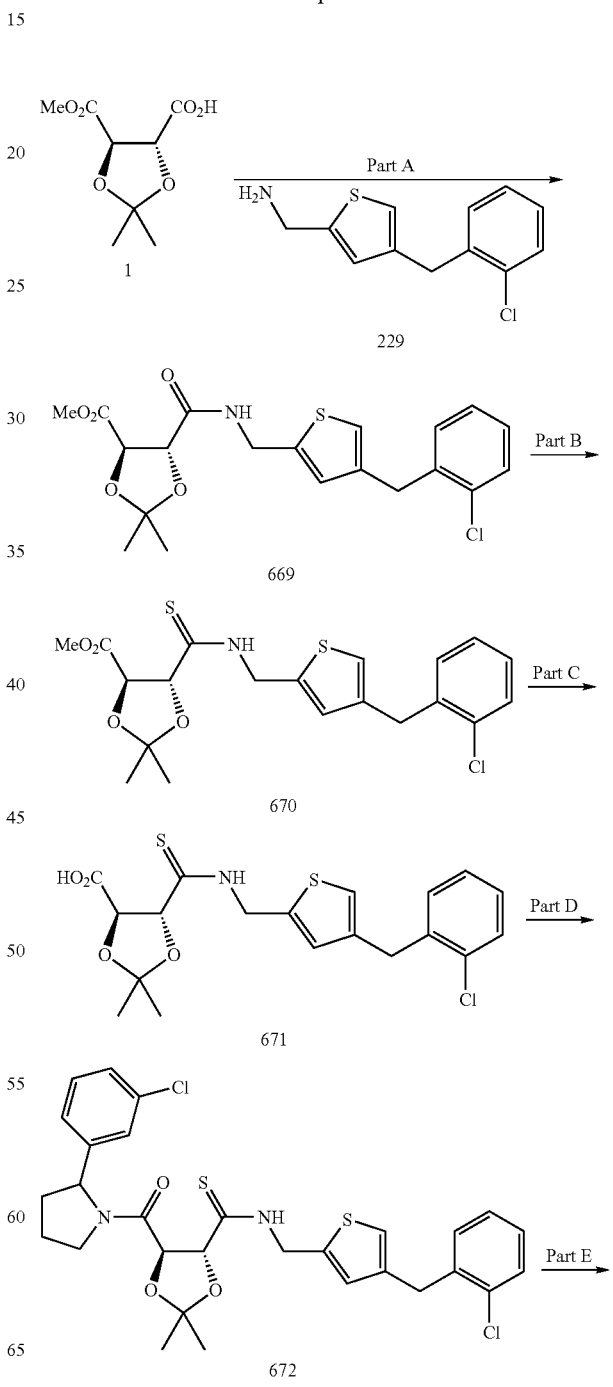

in compound 667 as an oil. Mass calculated for formula $C_{29}H_{30}Cl_2N_2O_3S_2$ 588.1, observed LCMS m/z 589.1 (M+H).

Part E:

Compound 667 was dissolved in 0.5 mL of TFA/$H_2O$ (80:20) and stirred at room temperature for 2 h. The reaction mixture was quenched with ACN/$H_2O$ (50:50) and concentrated in vacuo. Purification by reverse phase prep-LC afforded compound 668 as a white solid. HPLC-MS $t_R$=6.97 min (UV$_{254\ nm}$, 10 min), Mass calculated for formula $C_{26}H_{26}Cl_2N_2O_3S_2$ 548.1, observed LCMS m/z 549.1 (M+H).

Example 16B

Part A:

To a solution of compound 193 (200 mg, 0.54 mmol) in THF (5 mL) was added portionwise of Lawesson's reagent (203 mg, 0.5 mmol). The reaction mixture was stirred overnight under argon at room temperature, and diluted with EtOAc. The organic layer was washed with saturated NaHCO$_3$, brine, dried over Na$_2$SO$_4$, and concentrated. Column chromatography over silica gel (EtOAc/hexane, 20:80) afforded compound 665. Mass calculated for formula $C_{18}H_{22}ClNO_4S$ 383.1, observed LCMS m/z 384.1 (M+H).

Part B:

To compound 665 in MeOH (5 mL) was added powdered K$_2$CO$_3$ (50 mg). Mixture was stirred at room temperature for 1 h and the solvent was removed in vacuo. The residue was dissolved in water and acidified with 1 N HCl. It was extracted with EtOAc, the combined organic layers was washed with 1N HCl, brine, dried over Na$_2$SO$_4$, and concentrated to afford compound 666 as an oil (45 mg). Mass calculated for formula $C_{17}H_{20}ClNO_4S$ 369.1, observed LCMS m/z 370.1 (M+H).

Part D:

To compound 666 (10 mg, 0.027 mmol) in DMF (0.5 mL) was 229 (11 mg, 0.041 mmol) and HATU (20.5 mg, 0.054 mmol). The reaction mixture was stirred at room temperature for 4 h, and diluted with ethyl acetate and water. The organic layer was washed with 1 N HCl, saturated NaHCO$_3$, and brine. It was dried over Na$_2$SO$_4$, and concentrated, resulting

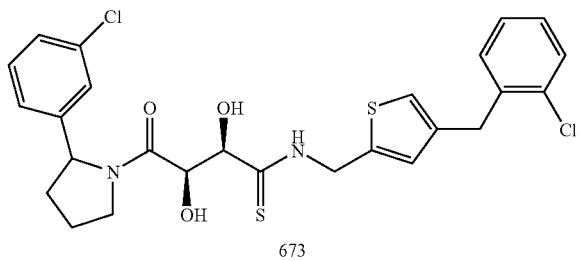

673

Part A:
To 1 (204 mg, 1 mmol) in DMF (2 mL) was added 229 (320 mmol, 1.2 mmol) and HATU (570 mg, 1.5 mmol). The reaction mixture was stirred overnight at room temperature, and diluted with ethyl acetate and water. The organic layer was washed with 1 N HCl, saturated NaHCO$_3$, and brine. It was dried over Na$_2$SO$_4$, and concentrated, resulting in 669 as a slightly yellow oil (280 mg, 66%).

Part B:
To a solution of 669 (280 mg, 0.54 mmol) in THF (5 mL) was added portionwise of Lawesson's reagent (202 mg, 0.5 mmol). The reaction mixture was stirred overnight under argon at room temperature, and diluted with EtOAc. The organic layer was washed with saturated NaHCO$_3$, brine, dried over Na$_2$SO$_4$, and concentrated. Column chromatography over silica gel (EtOAc/hexane, 20:80) afforded compound 670. Mass calculated for formula C$_{20}$H$_{22}$ClNO$_4$S 439.1, observed LCMS m/z 440.1 (M+H).

Part C:
To 670 in MeOH (5 mL) was added powdered K$_2$CO$_3$ (50 mg). The mixture was stirred at room temperature for 1 h and the solvent was removed in vacuo. The residue was dissolved in water and acidified with 1 N HCl. It was extracted with EtOAc, the combined organic layers was washed with 1N HCl, Brine, dried over Na$_2$SO$_4$, and concentrated to afford compound 671 as an oil (80 mg). Mass calculated for formula C$_{17}$H$_{20}$ClNO$_4$S 425.1, observed LCMS m/z 426.1 (M+H).

Part D:
To compound 671 (10 mg, 0.027 mmol) in DMF (0.5 mL) was added racemic 2-(3-chlorophenyl)pyrrolidine (6.5 mg, 0.035 mmol) and HATU (17.5 mg, 0.046 mmol). The reaction mixture was stirred at room temperature for 4 h, and diluted with ethyl acetate and water. The organic layer was washed with 1 N HCl, saturated NaHCO$_3$, and brine. It was dried over Na$_2$SO$_4$, and concentrated, resulting in compound 672 as an oil. Mass calculated for formula C$_{29}$H$_{30}$Cl$_2$N$_2$O$_3$S$_2$ 588.1, observed LCMS m/z 589.1 (M+H).

Part E:
Compound 672 was dissolved in 0.5 mL of TFA/H$_2$O (80:20) and stirred at room temperature for 2 h. The reaction mixture was quenched with ACN/H$_2$O (50:50) and concentrated in vacuo. Purification by reverse phase prep-LC afforded compound 673 as a white solid. HPLC-MS t$_R$=7.04 min (UV$_{254\ nm}$, 10 min), Mass calculated for formula C$_{26}$H$_{26}$Cl$_2$N$_2$O$_3$S$_2$ 548.1, observed LCMS m/z 549.1 (M+H).

The following compounds were prepared by the methods described above. Belleau's reagent was substituted for Lawesson's reagent.

| Compound # | Structure | Exact mass | MS m/e (M + H) |
|---|---|---|---|
| 673 | 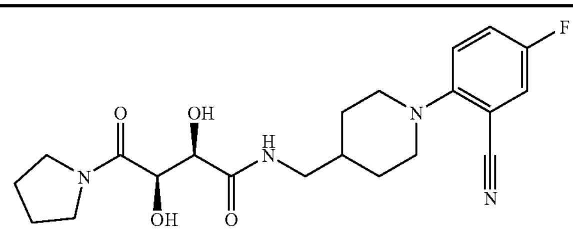 | 434.2 | 435.2 |
| 674 | 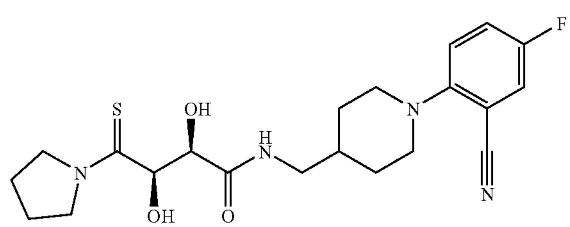 | 434.2 | 435.1 |

Example 17

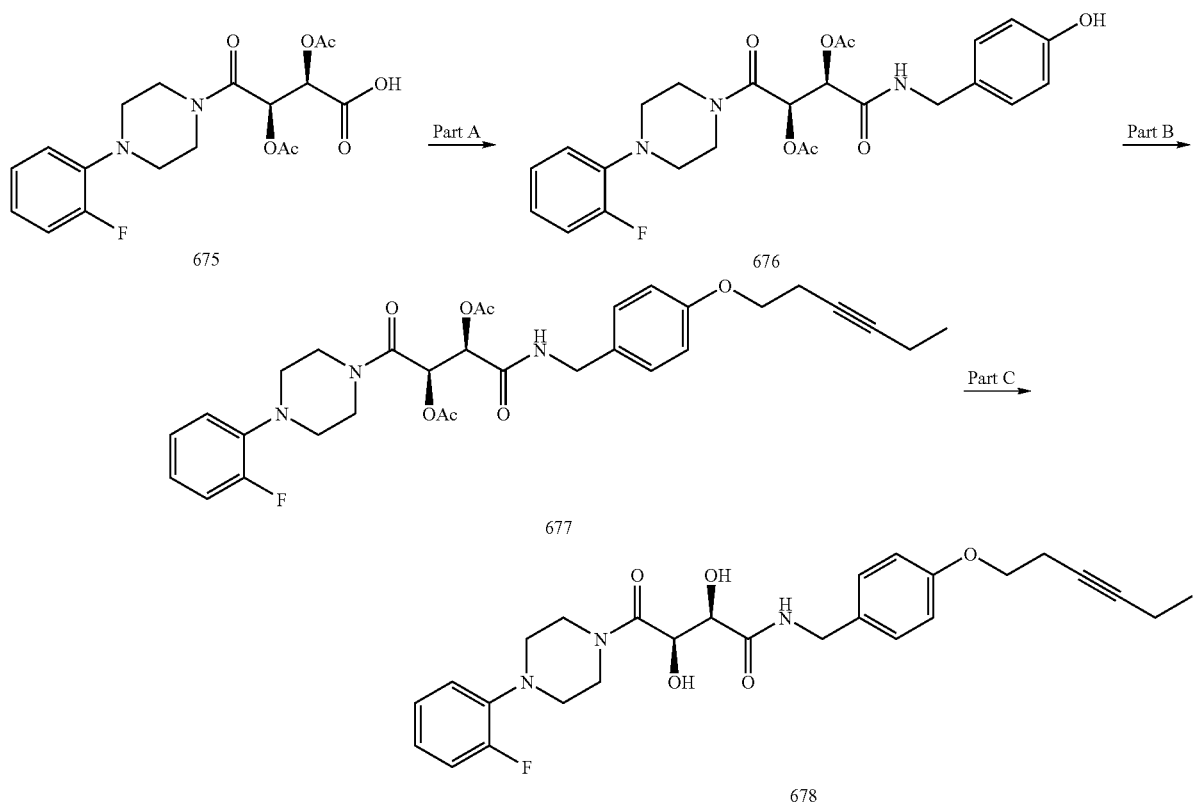

Compound 675 was prepared as described in Example 4A Part C.

Part A:
To 675 (1.34 g, 3.38 mmol) in DMF (20 mL) was added 4-hydroxybenzylamine (0.5 g, 4.06 mmol), DIEA (0.71 mL, 4.06 mmol) and HATU (1.54 g, 4.06 mmol). The reaction mixture was stirred overnight at room temperature. The reaction mixture was diluted with water and the aqueous layer was extracted with ethyl acetate. The combined organic layers were dried over sodium sulfate and concentrated. Purification by column chromatography (SiO$_2$, 80% EtOAc/hexane) afforded 676 (1.41 g, 83%). HPLC-MS $t_R$=1.56 min (UV$_{254\ nm}$); Mass calculated for formula $C_{25}H_{28}FN_3O_7$ 501.2, observed LCMS m/z 502.1 (M+H).

Part B:
To a mixture of 676 (50 mg, 0.1 mmol), triphenylphosphine (79 mg, 0.3 mmol), 3-hexyn-1-ol (33 µL, 0.3 mmol) in THF (0.5 mL) at 0° C. was added DEAD (47 µL, 0.3 mmol). The reaction mixture was warmed to room temperature and stirred for 5 hours. The reaction mixture was diluted with water and extracted with ethyl acetate. The combined organic layers were dried over sodium sulfate and concentrated. Purification by column chromatography (SiO$_2$, 20% EtOAc/hexane to 100% EtOAc) afforded 677 (9 mg, 15%). HPLC-MS $t_R$=2.09 min (UV$_{254\ nm}$); Mass calculated for formula $C_{31}H_{36}FN_3O_7$ 581.3, observed LCMS m/z 582.2 (M+H).

Part C:
To 677 (9 mg, 0.02 mmol) in methanol (0.5 mL) was added anhydrous hydrazine (2 µL, 0.04 mmol). The reaction mixture was stirred overnight at room temperature. The solvents were removed in vacuo and the material was freeze-dried to yield 678 as a white powder (2 mg). HPLC-MS $t_R$=1.89 min (UV$_{254\ nm}$); Mass calculated for formula $C_{27}H_{32}FN_3O_5$ 497.2, observed LCMS m/z 498.2 (M+H).

Example 17B

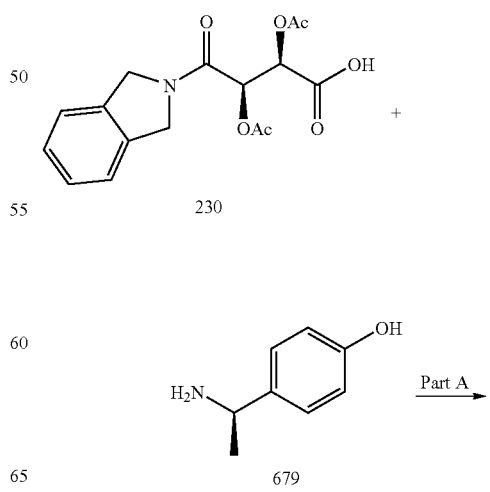

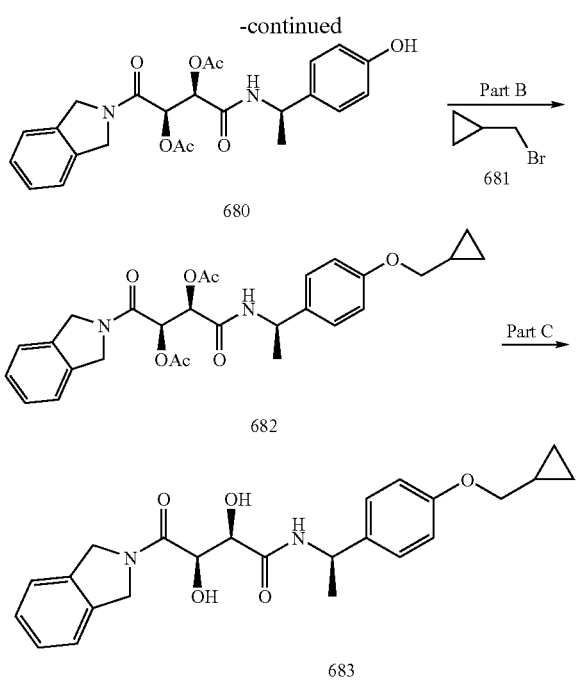

Part A:

Compound 680 was prepared from compounds 230 & 679 using procedures described in Example 17A Part A. HPLC-MS $t_R$=1.37 min (UV$_{254\ nm}$); Mass calculated for formula $C_{24}H_{26}N_2O_7$ 454.2, observed LCMS m/z 455.2 (M+H).

Part B:

A mixture of 680 (49 mg, 0.11 mmol), 681 (14 uL, 0.14 mmol) and cesium carbonate (46 mg, 0.14 mmol) in DMF (2 mL) was stirred 24 hours. The reaction mixture was poured into water and extracted with ethyl acetate. The combined organic layers were washed with brine, dried over sodium sulfate and concentrated to afford 682 (33 mg). The material was used without further purification. HPLC-MS $t_R$=1.91 min (UV$_{254\ nm}$); Mass calculated for formula $C_{28}H_{32}N_2O_7$ 508.2, observed LCMS m/z 509.2 (M+H).

Part C:

To compound 682 (33 mg, 0.06 mmol) in methanol (2 mL) was added 7.0 M ammonia in methanol (2 ml). The reaction mixture was stirred for 1 hour and concentrated. Purification by reverse phase prep-HPLC afforded 683 (8 mg). HPLC-MS $t_R$=4.28 min (UV$_{254\ nm}$, 10 min); Mass calculated for formula $C_{24}H_{28}N_2O_5$ 424.2, observed LCMS m/z 425.2 (M+H).

The following compounds were prepared using procedures described in Example 17A & 17B.

| # | Structure | Exact Mass | Mass Obsvd |
|---|---|---|---|
| 684 | 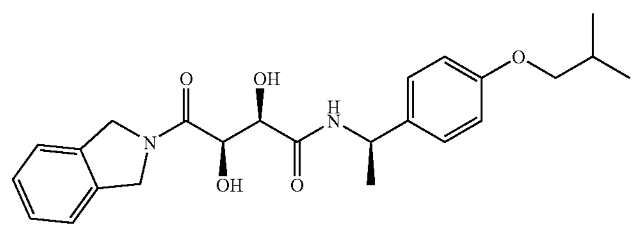 | 426.2 | 427.1 |
| 685 | 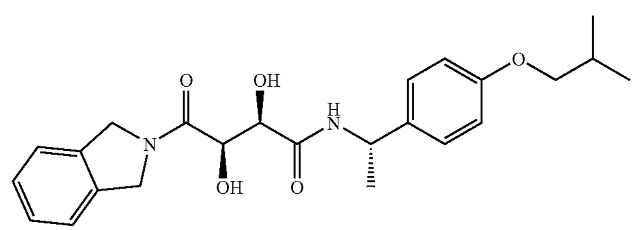 | 426.2 | 427.1 |
| 686 | 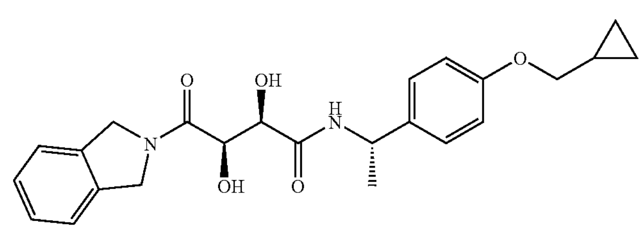 | 424.2 | 425.2 |

-continued

| # | Structure | Exact Mass | Mass Obsvd |
|---|---|---|---|
| 687 | 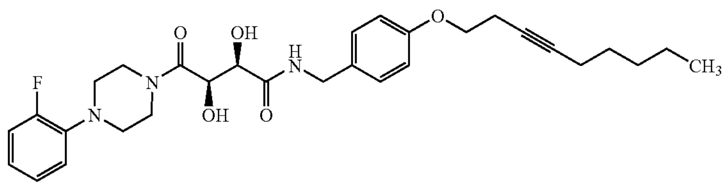 | 539.3 | 540.3 |
| 688 | 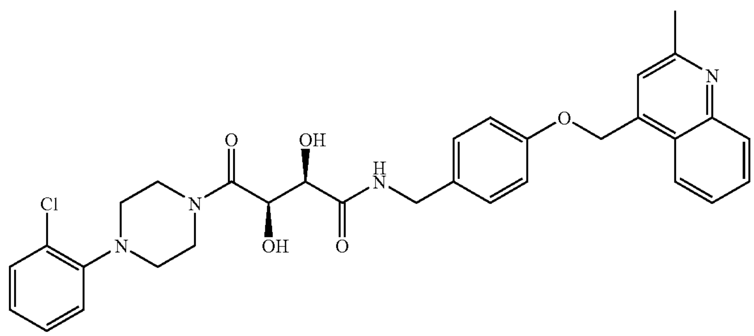 | 588.2 | 589 |
| 689 | 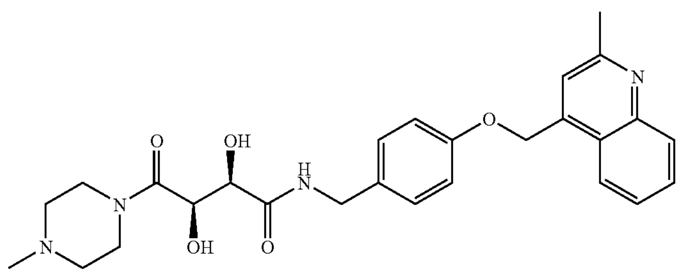 | 492.2 | 493 |
| 690 | 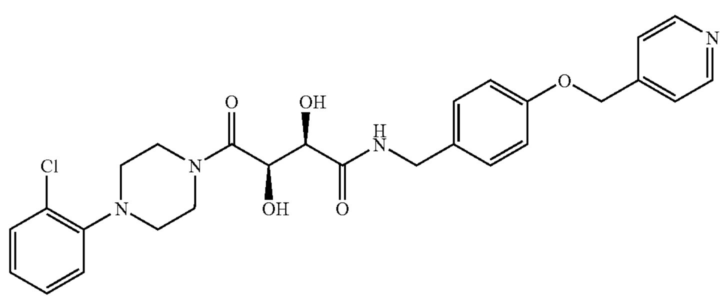 | 524.1 | 525 |
| 691 | 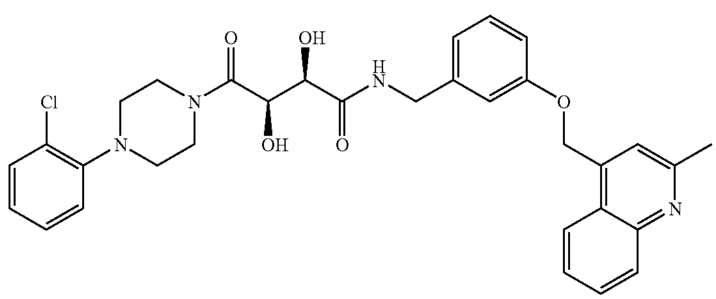 | 588.2 | 589 |

Example 17C

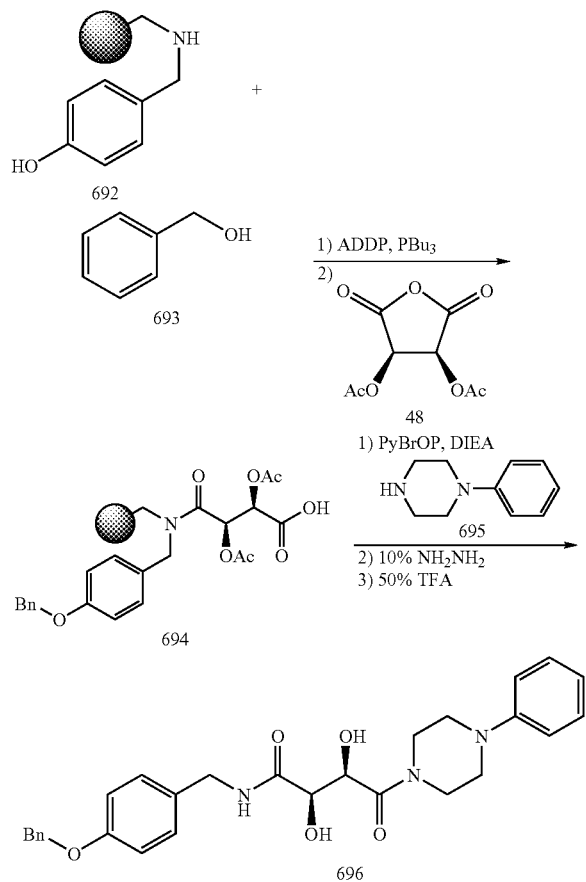

Step A1:

To pre-swelled MB-CHO resin (5.0 g, 1.0 mmol/g) in 40 ml DCE was added 4-hydroxybenzylamine (1.5 eq) and triacetoxyborohydride (2 eq) and the mixture was agitated overnight before the solution was drained and resin washed with MeOH, DCM and THF 5 cycles to give resin 692 after drying in vacuo overnight.

Step A2:

To a pre-swelled resin 692 (150 mg, 1 mmol/g) in anhydrous THF was added benzylalcohol (5 eq) and $PPh_3$ (7 eq) in 1.5 ml of THF and ADDP (5 eq) in 0.5 ml of DCM. The reaction was agitated at room temperature over the weekend. The reaction solution was drained and resin washed with 5 cycles of MeOH, DCM and THF and dried in vaccuo before it was swelled in NMP followed by addition of 1.5 ml 1M NMP solution of compound 48. The reaction mixture was agitated overnight before the solution was drained and resin washed with 5 cycles of MeOH, DCM and THF and dried in vacuo to give resin 694.

Step B:

Resin 694 was pre-swelled in DCM, before 1-phenylpiperazine hydrochloric salt (695)(6 eq) was added followed by addition of PyBrop (3 eq) and DIEA (9 eq) in 3 ml of DCM. The reaction solution was agitated overnight before it was drained and resin washed with 5 cycles of MeOH, DCM and THF before it was treated with 10% hydrazine in methanol for 2 h. The resin was then further washed with 5 cycles of MeOH, DCM and THF followed by cleavage using 50% of TFA in DCM. The cleavage solution was evaporated and residue purified with a RP-HPLC system to give 5 mg of desired product 696.

The following compounds were generated using similar methods.

| Compound # | Structure | Obs. MS |
|---|---|---|
| 697 | 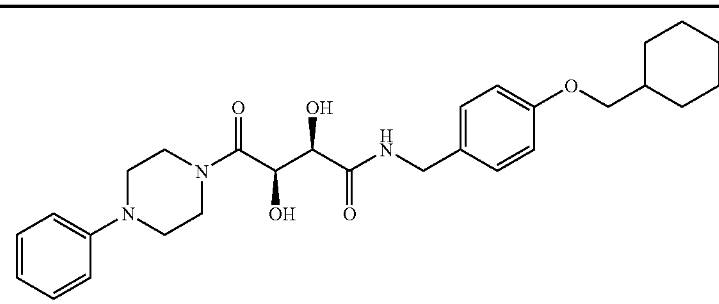 | 496 |
| 698 | 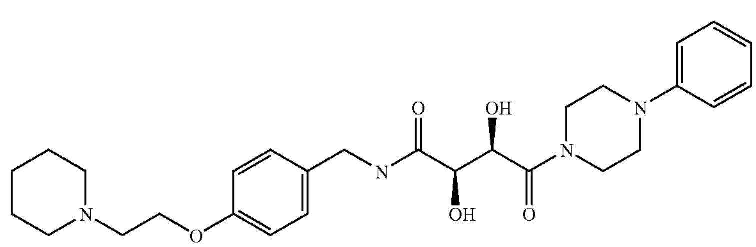 | 511 |

-continued

| Compound # | Structure | Obs. MS |
|---|---|---|
| 699 | 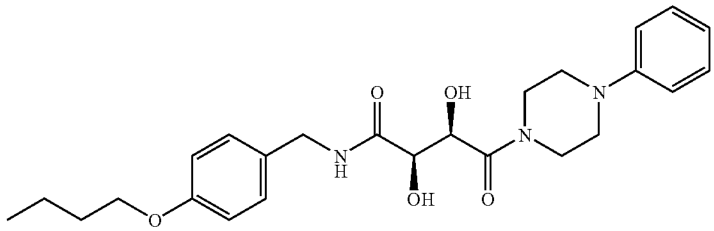 | 456 |
| 700 | 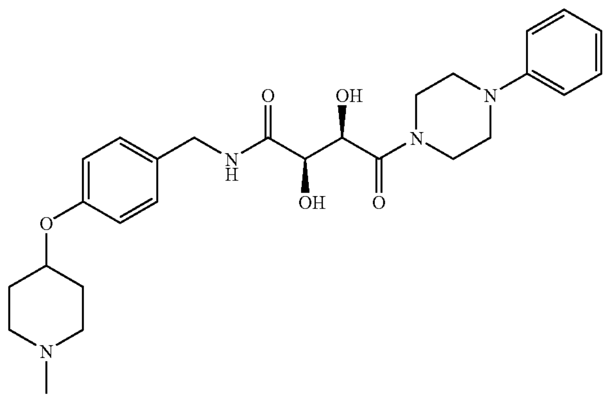 | 497 |
| 701 | 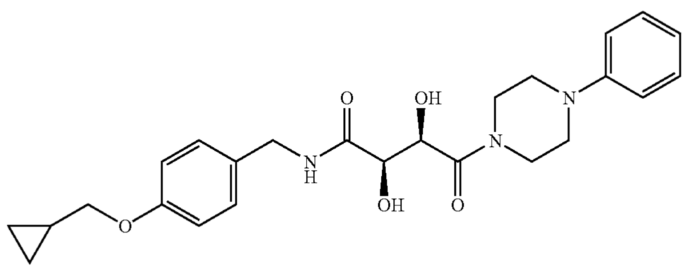 | 454 |
| 702 | 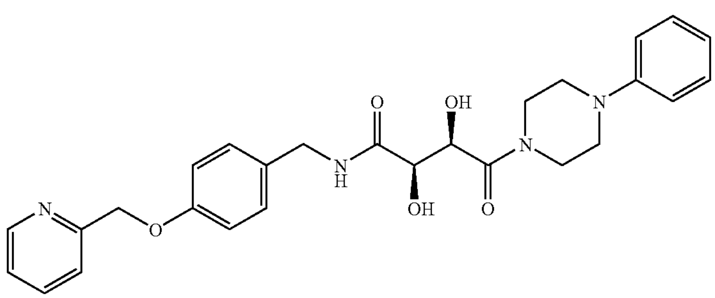 | 491 |
| 703 | 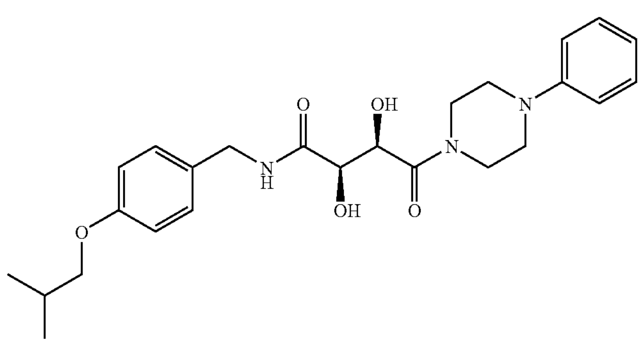 | 456 |

-continued

| Compound # | Structure | Obs. MS |
|---|---|---|
| 704 | 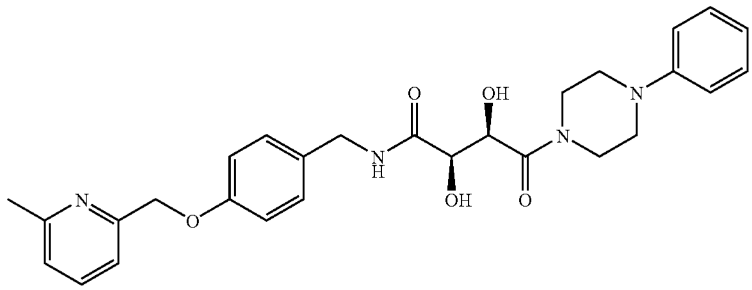 | 505 |
| 705 | 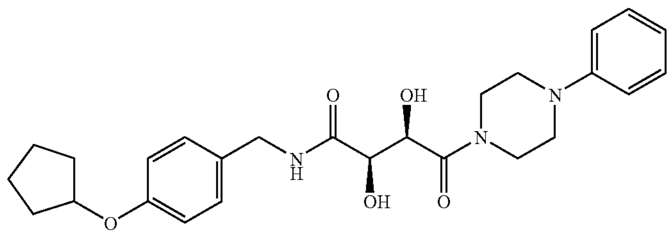 | 468 |
| 706 | 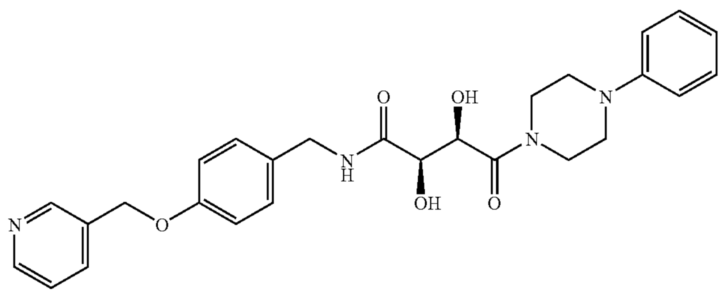 | 491 |
| 707 | 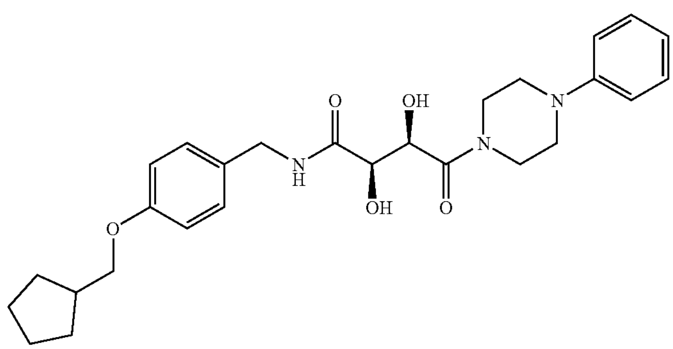 | 482 |
| 708 | 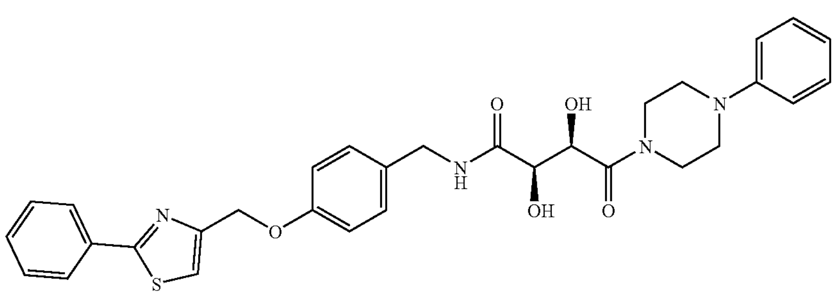 | 573 |

-continued

| Compound # | Structure | Obs. MS |
|---|---|---|
| 709 | 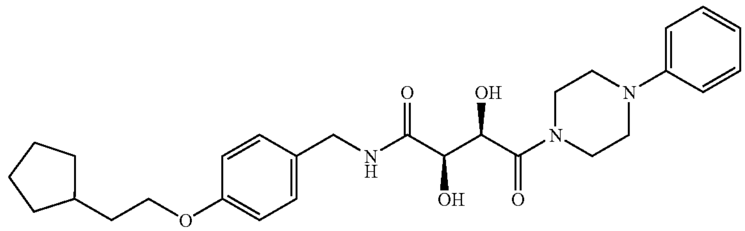 | 496 |
| 710 | 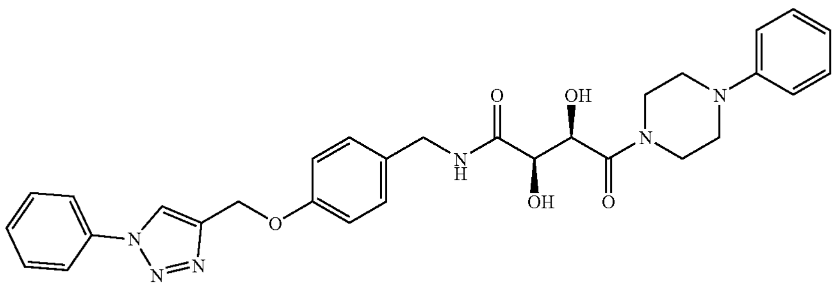 | 557 |
| 711 | 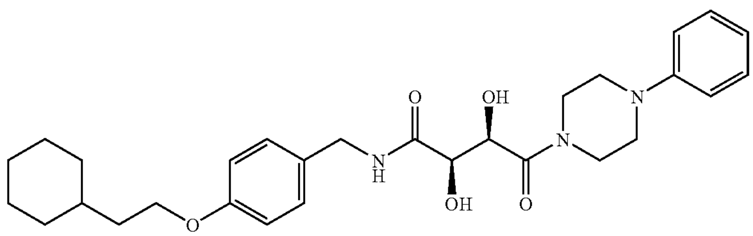 | 510 |
| 712 | 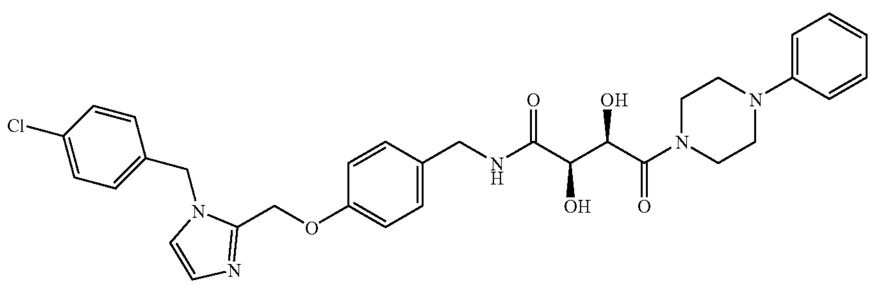 | 604 |
| 713 | 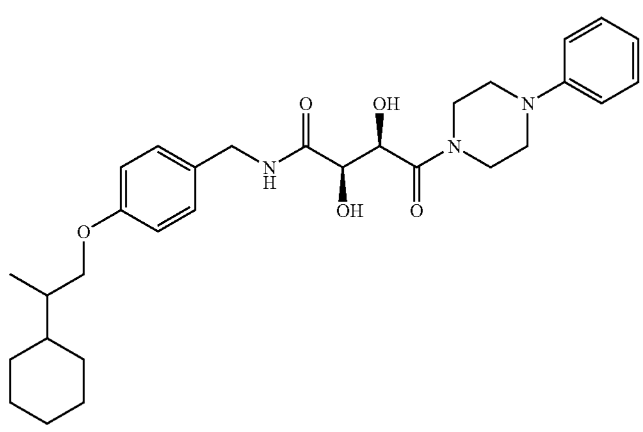 | 524 |

-continued

| Compound # | Structure | Obs. MS |
|---|---|---|
| 714 | 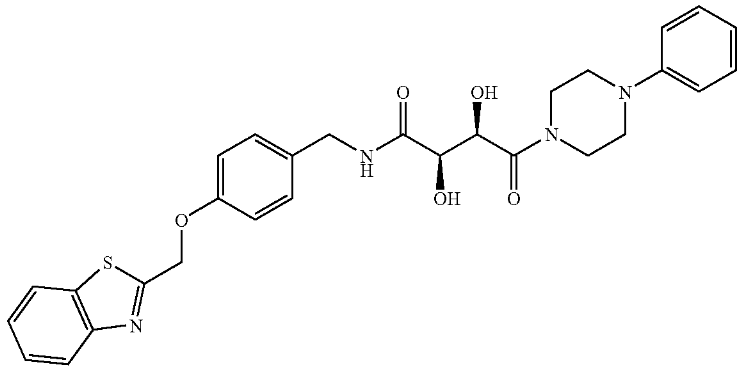 | 547 |
| 715 | 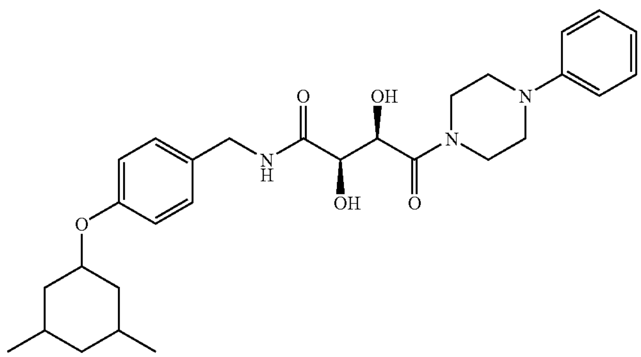 | 510 |
| 716 | 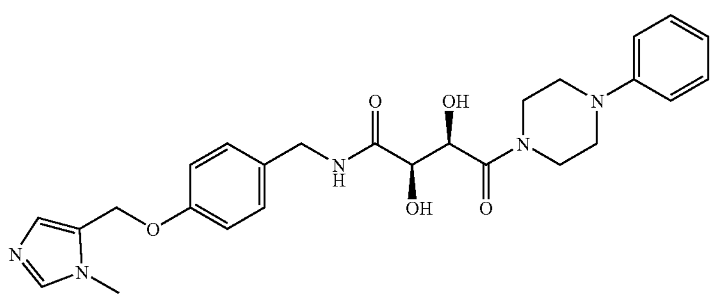 | 494 |
| 717 | 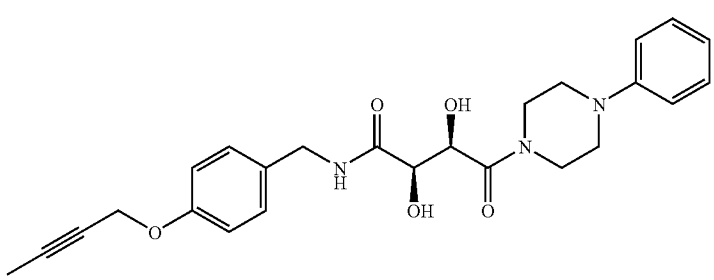 | 452 |

-continued

| Compound # | Structure | Obs. MS |
|---|---|---|
| 718 | 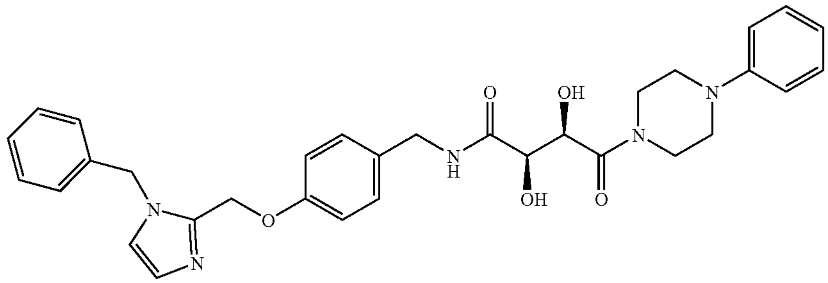 | 570 |
| 719 | 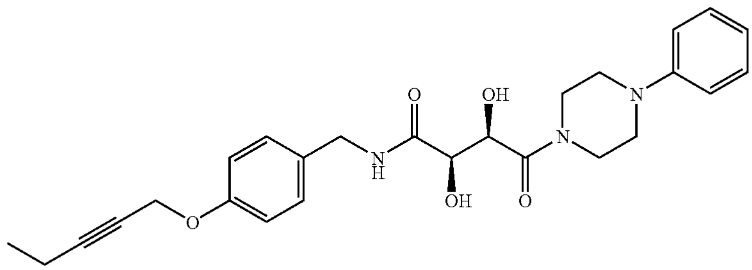 | 466 |
| 720 | 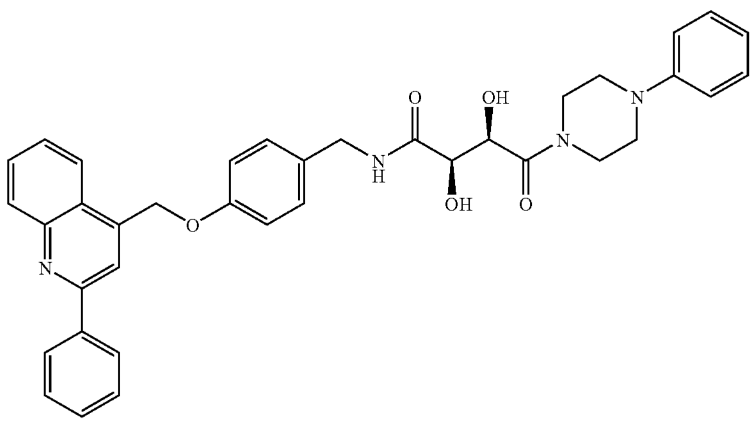 | 617 |
| 721 | 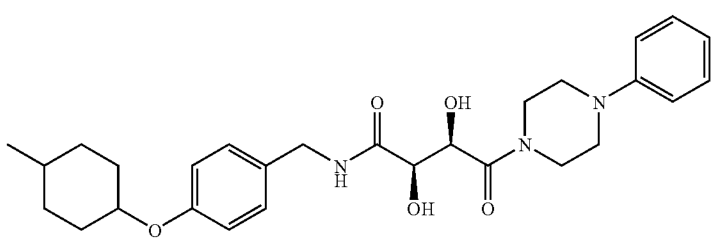 | 496 |
| 722 | 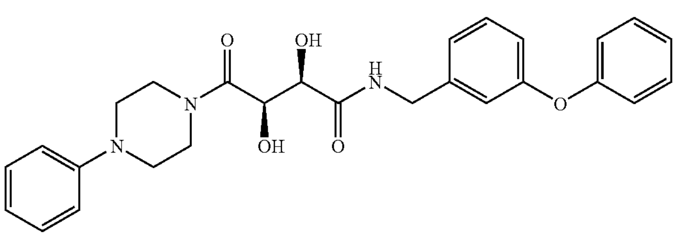 | 476 |

-continued

| Compound # | Structure | Obs. MS |
|---|---|---|
| 723 | 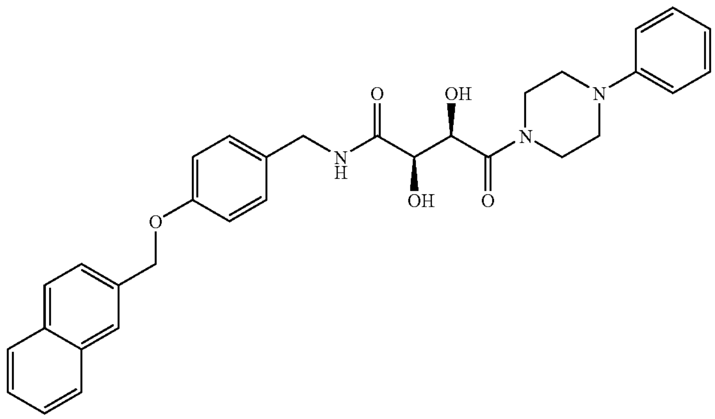 | 540 |
| 724 | 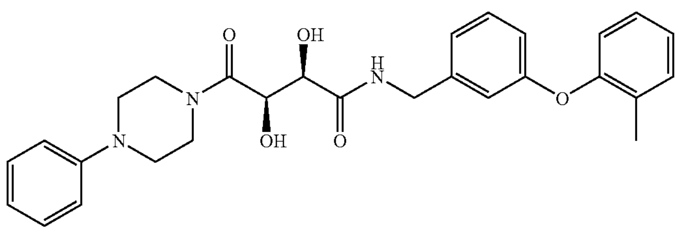 | 490 |
| 725 | 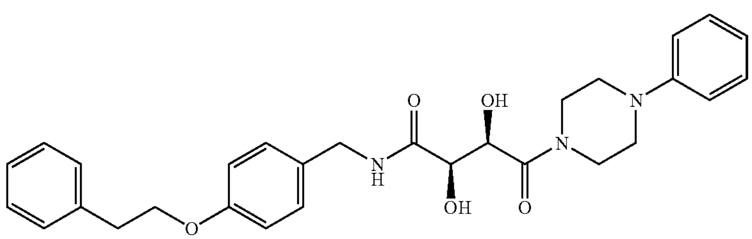 | 504 |
| 726 | 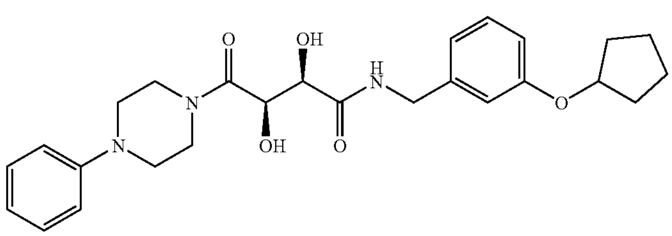 | 468 |
| 696 | 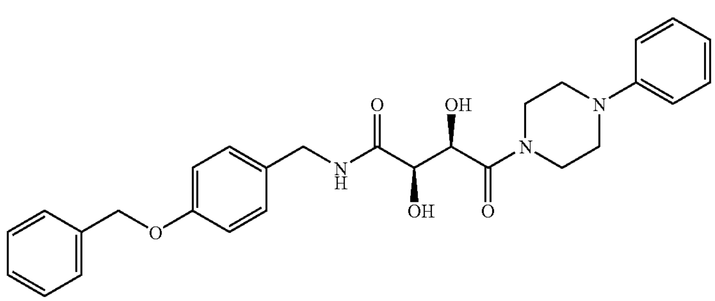 | 490 |

-continued

| Compound # | Structure | Obs. MS |
|---|---|---|
| 728 | 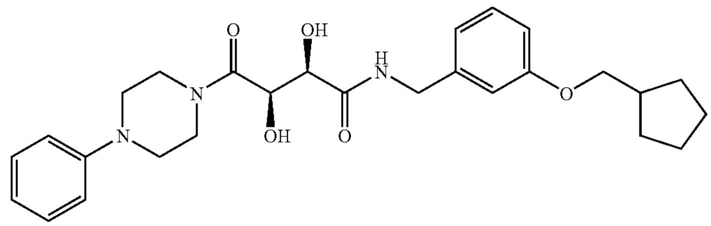 | 482 |
| 729 | 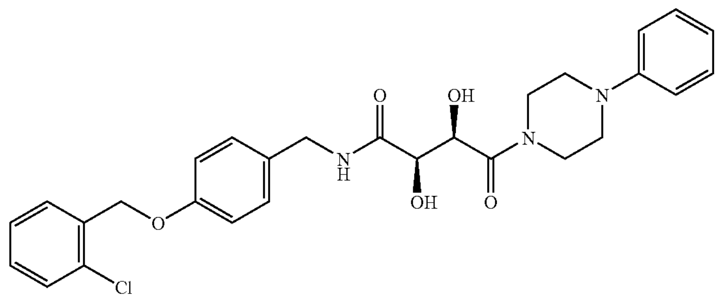 | 524 |
| 730 | 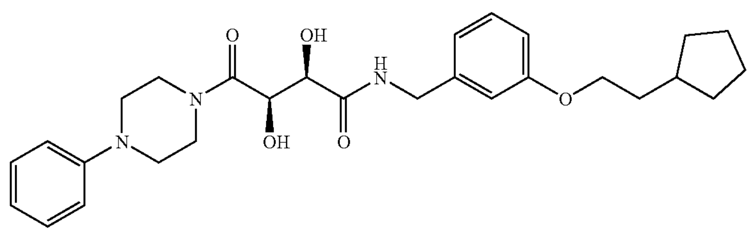 | 496 |
| 731 | 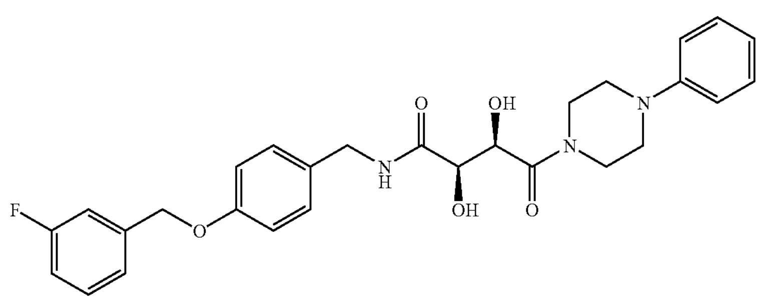 | 508 |
| 732 | 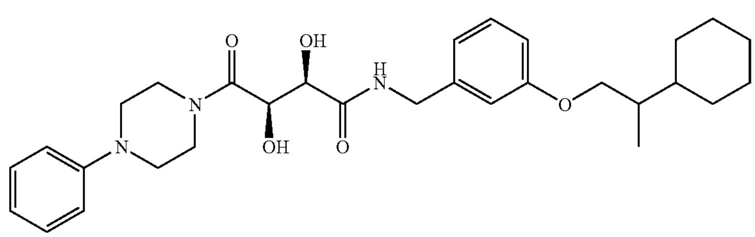 | 524 |

| Compound # | Structure | Obs. MS |
|---|---|---|
| 733 | 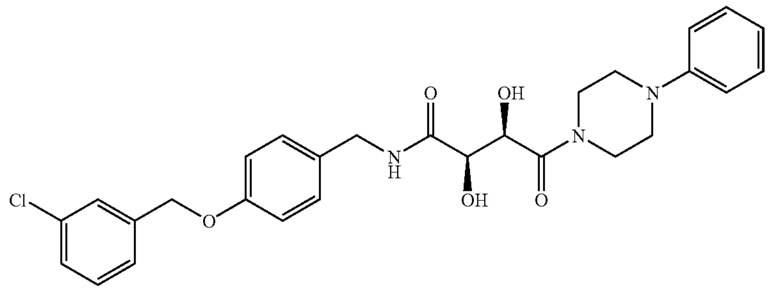 | 524 |
| 734 | 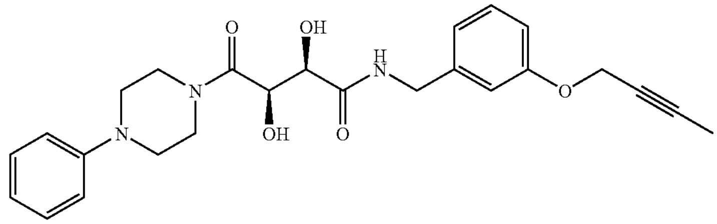 | 452 |
| 735 | 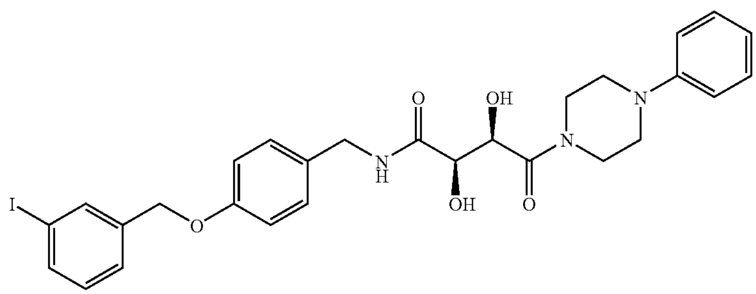 | 616 |
| 736 | 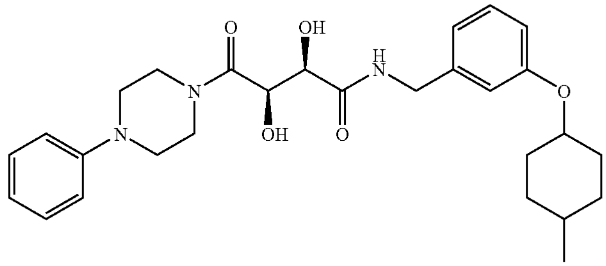 | 496 |
| 737 | 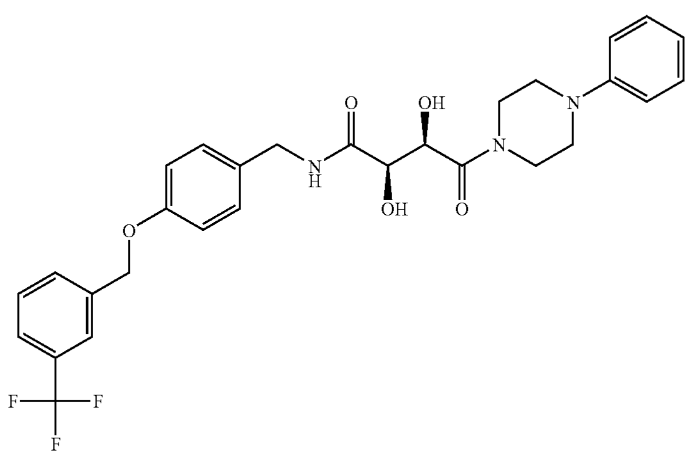 | 558 |

-continued

| Compound # | Structure | Obs. MS |
|---|---|---|
| 738 | 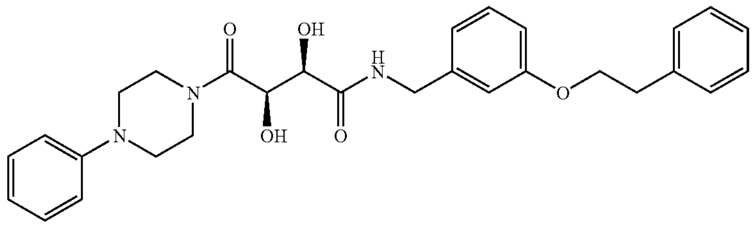 | 504 |
| 739 | 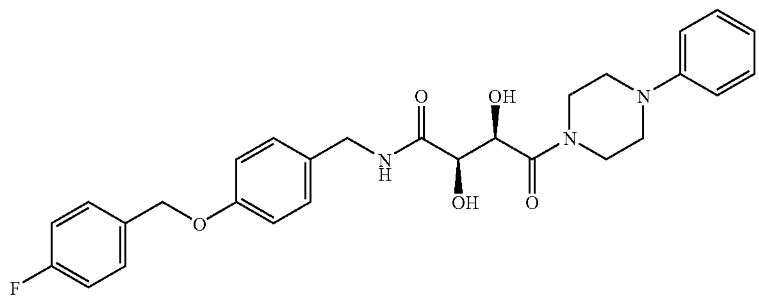 | 508 |
| 740 | 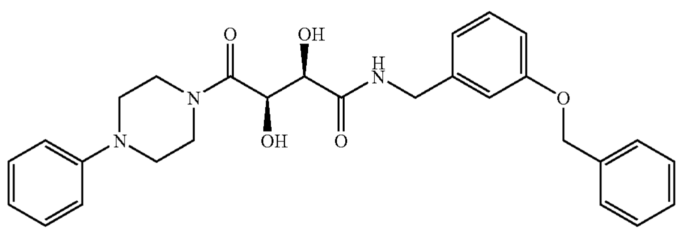 | 490 |
| 741 | 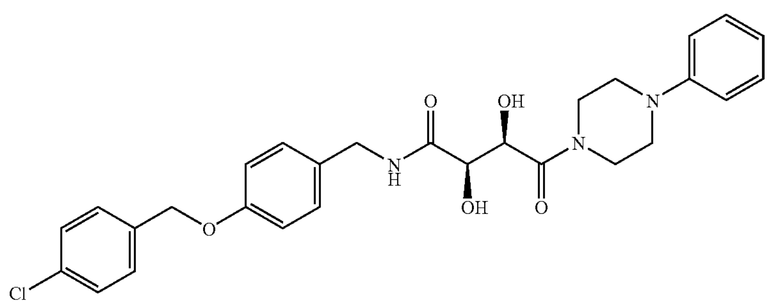 | 524 |
| 742 | 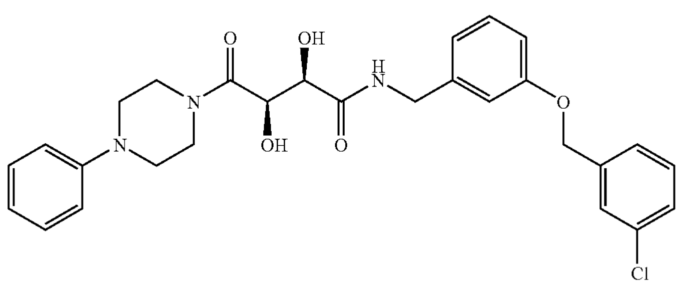 | 524 |

| Compound # | Structure | Obs. MS |
|---|---|---|
| 743 | 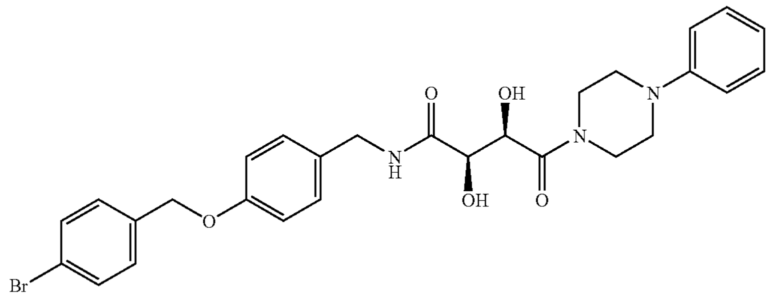 | 569 |
| 744 | 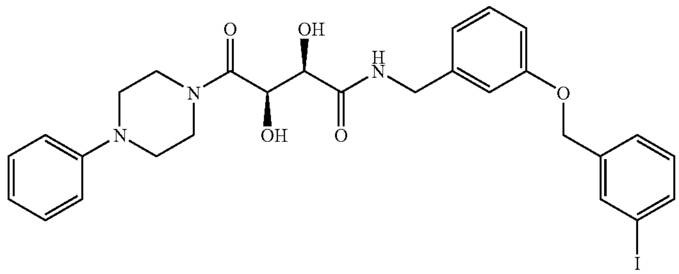 | 616 |
| 745 | 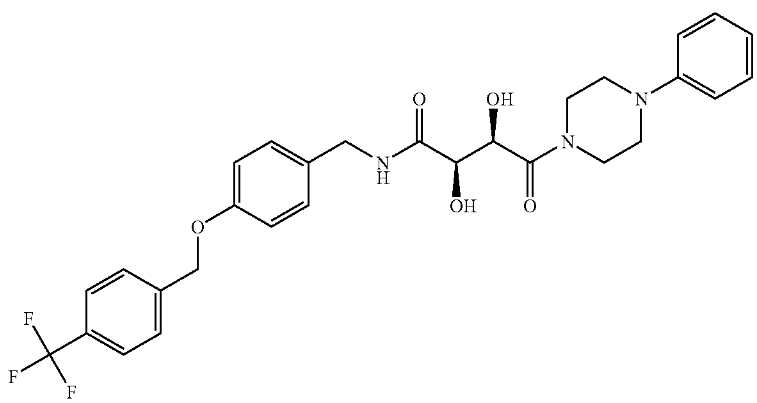 | 558 |
| 746 | 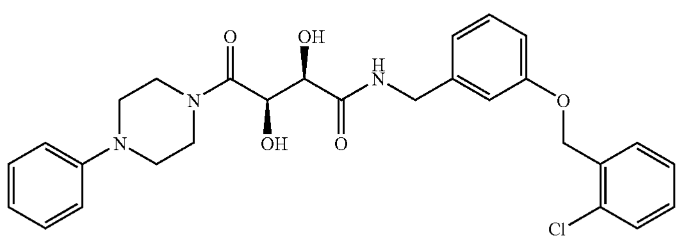 | 524 |
| 747 | 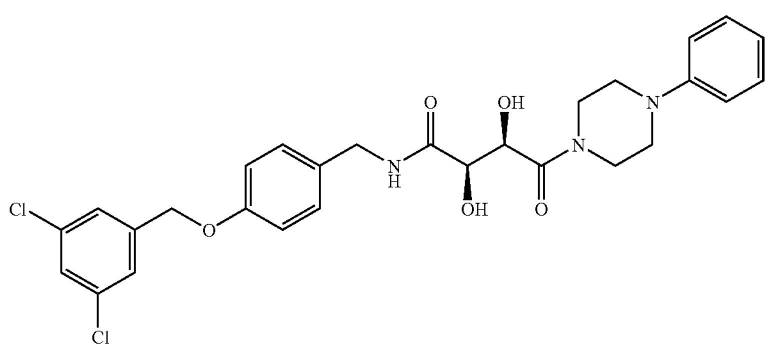 | 558 |

-continued

| Compound # | Structure | Obs. MS |
|---|---|---|
| 748 | 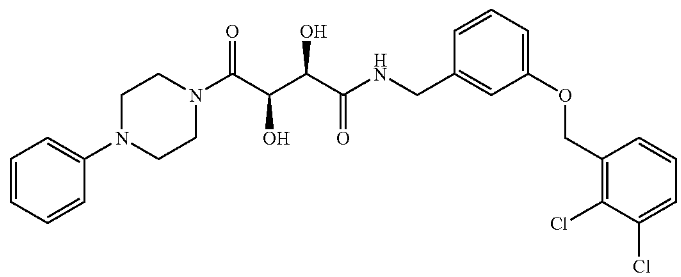 | 558 |
| 749 | 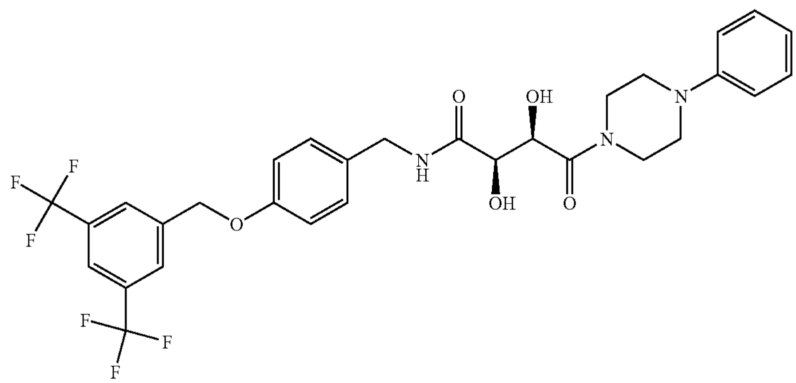 | 626 |
| 750 | 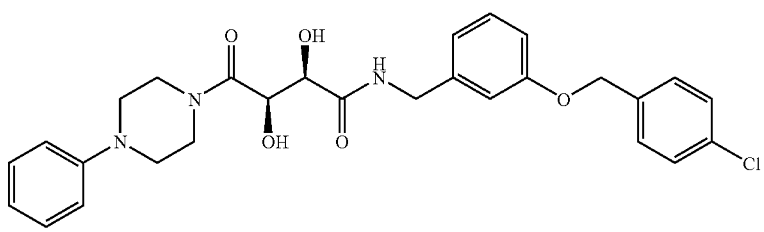 | 524 |
| 751 | 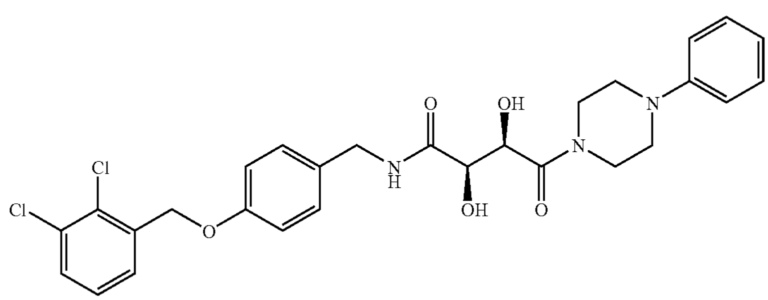 | 558 |
| 752 | 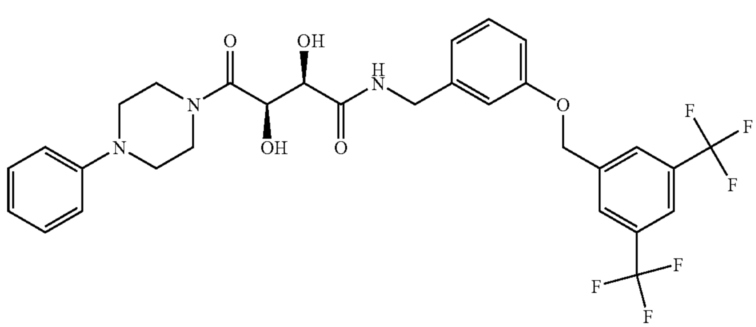 | 626 |

| Compound # | Structure | Obs. MS |
|---|---|---|
| 753 | 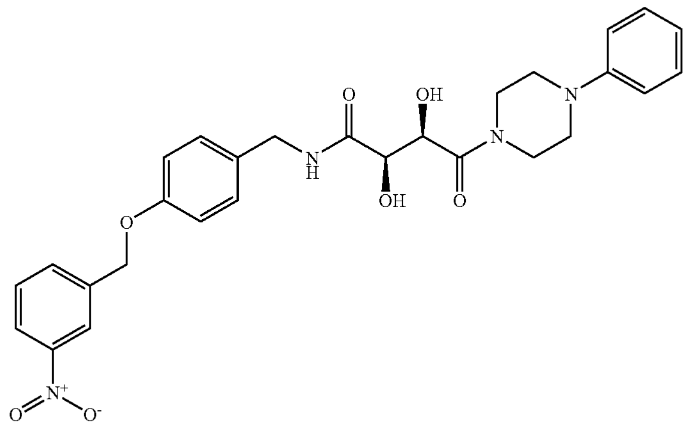 | 535 |
| 754 | 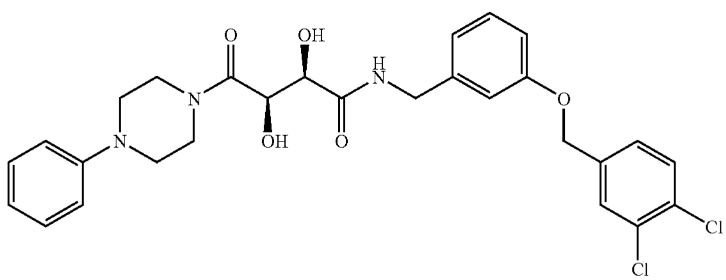 | 558 |
| 755 | 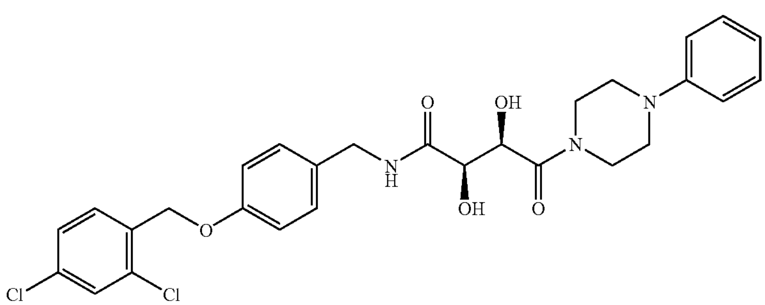 | 558 |
| 756 | 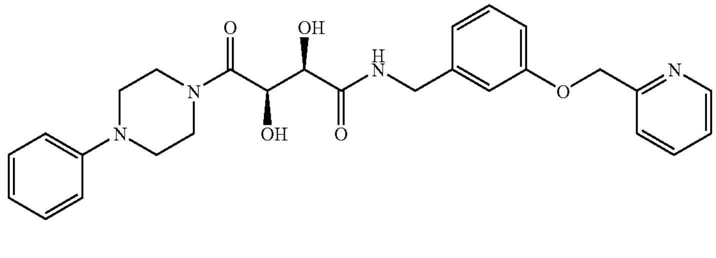 | 491 |

-continued
| Compound # | Structure | Obs. MS |
|---|---|---|
| 757 | 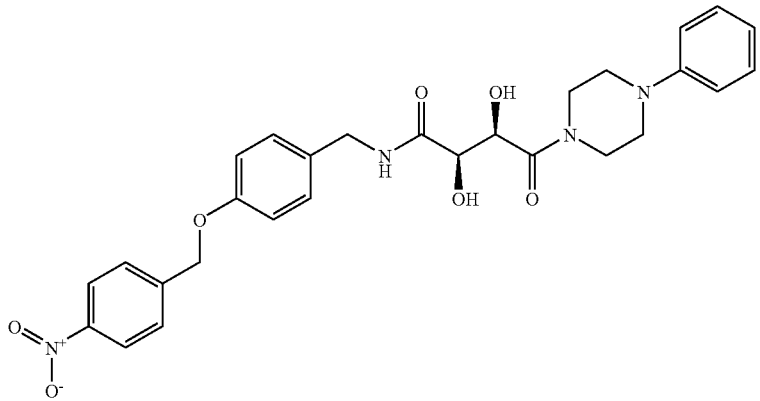 | 535 |
| 758 | 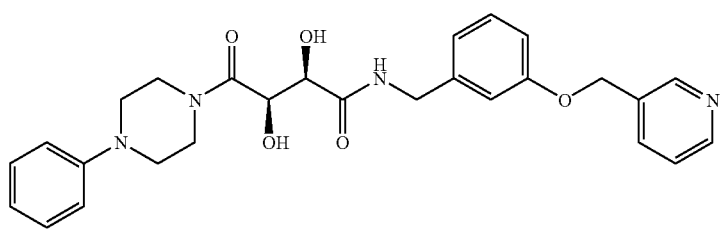 | 491 |
| 759 | 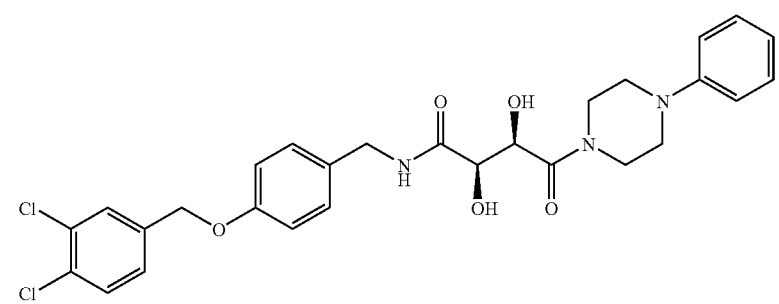 | 558 |
| 760 | 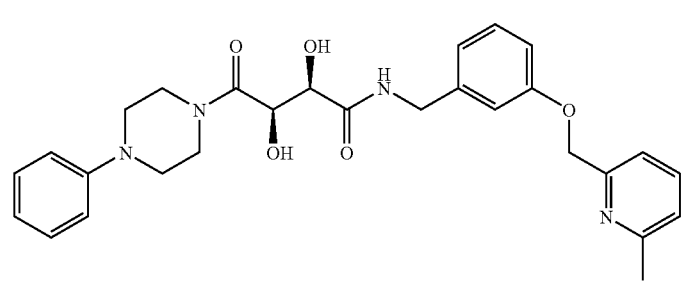 | 505 |
| 761 | 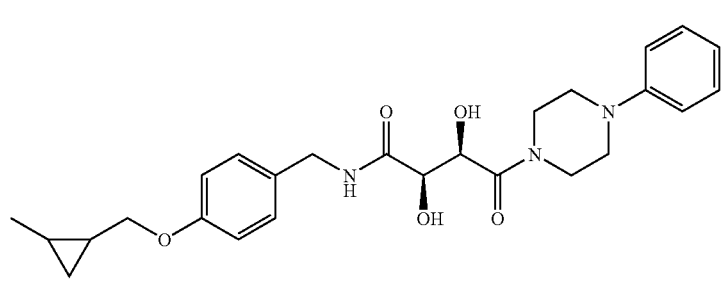 | 468 |

-continued
| Compound # | Structure | Obs. MS |
|---|---|---|
| 762 | 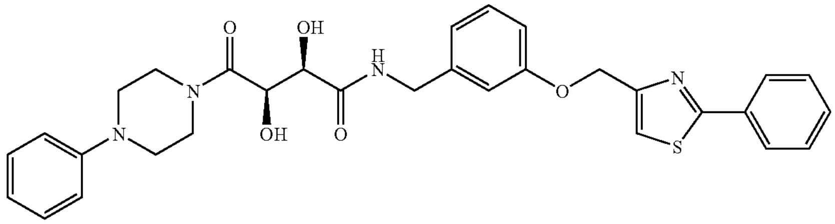 | 573 |
| 763 | 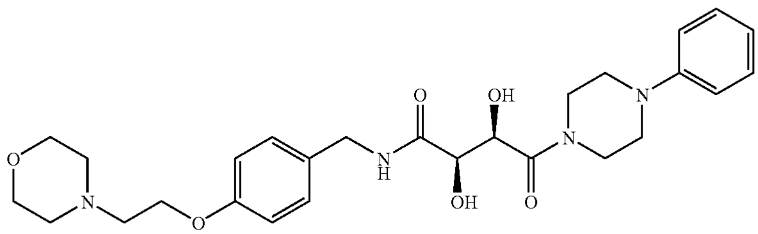 | 513 |
| 764 | 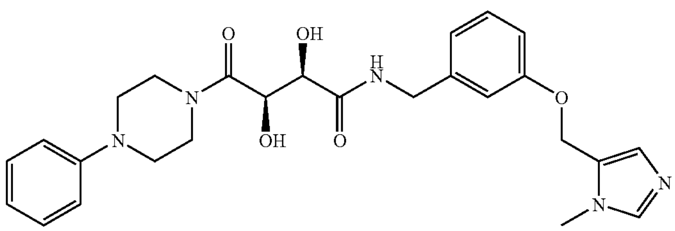 | 494 |
| 765 | 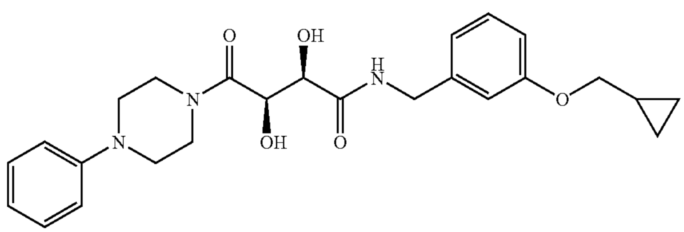 | 454 |
Example 17D
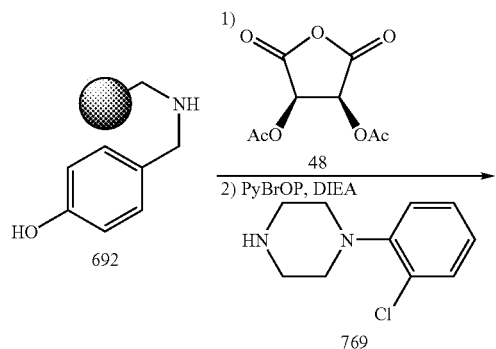

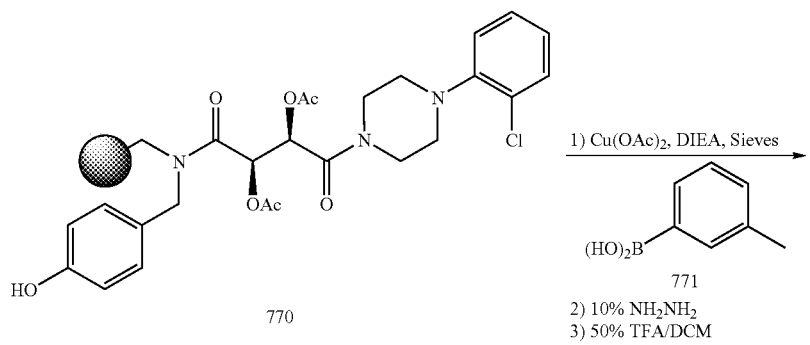

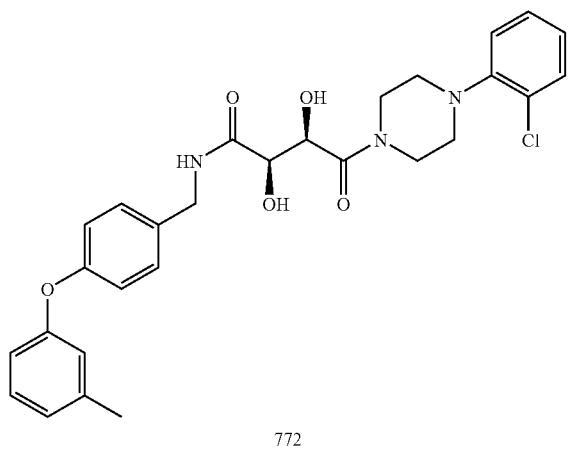

Step A.

To resin 692 (2.6 g, 1 mmol/g), preswelled in NMP was added 48 (5 eq) and the mixture was agitated for 48 h. before the solution was drained and resin washed with 5 cycles of MeOH, DCM and THF and dried in vacuo. The resin was then swelled in anhydrous DCM (25 ml) before 769 (6 eq, HCl salt) and DIEA (9 eq) were added followed by addition of PyBrop. The reaction was agitated at r.t. overnight before the solution was drained and resin washed with 5 cycles of MeOH, DCM and THF and dried in vacuo to give resin 770 (0.9 mmol/g loading).

Step B.

To a pre-swelled resin 770 (0.095 g, 0.9 mmol/g) in anhydrous DCM was added anhydrous Cu(OAc)$_2$ (3 eq), 771 (5 eq), 4 A molecular sieves (5 micron particle size, 100 mg) and DIEA (7 eq) in 2 ml anh. DCM. The reaction was agitated for 48 h. before the mixture was drained and resin washed with 5 cycles of H$_2$O, MeOH, DCM and THF before it was treated with 10% hydrazine in Methanol for 2 h. The resin was then further washed with 5 cycles of MeOH, DCM and THF followed by cleavage using 50% of TFA in DCM. The cleavage solution was evaporated and residue purified with a RP-HPLC system to give 5 mg of desired product 772.

The following compounds were synthesized in similar fashion.

| Compound # | Structure | OBS. Mass |
|---|---|---|
| 773 | ![structure] | 435 |

-continued

| Compound # | Structure | OBS. Mass |
|---|---|---|
| 774 | 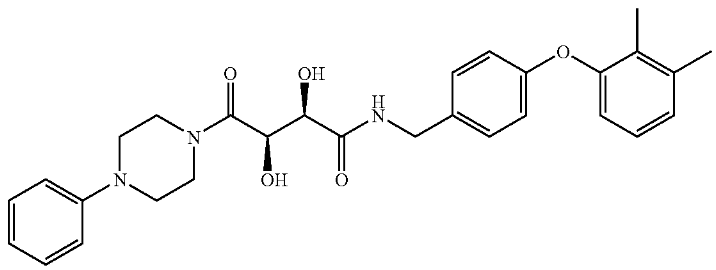 | 504 |
| 772 | 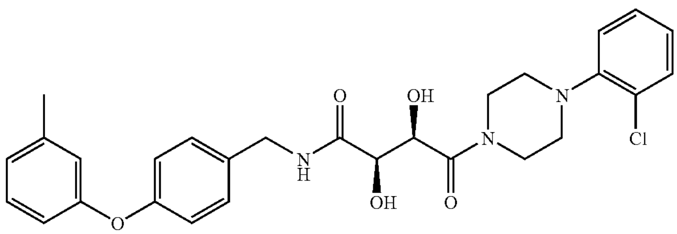 | 524 |
| 776 | 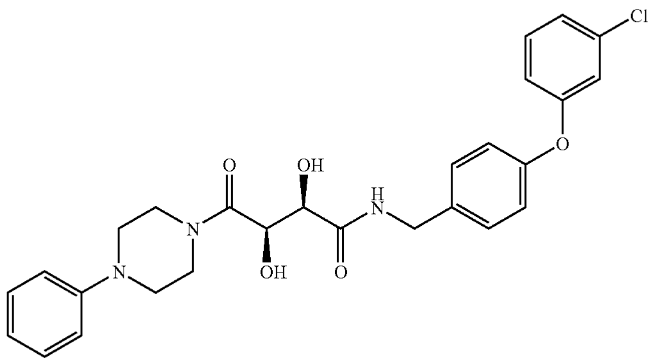 | 510 |
| 777 | 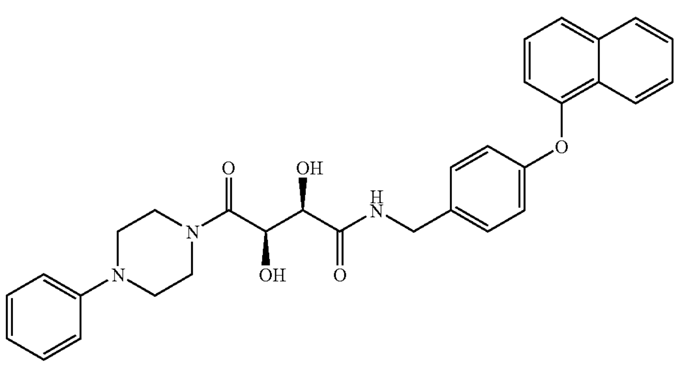 | 526 |

-continued
| Compound # | Structure | OBS. Mass |
|---|---|---|
| 778 | 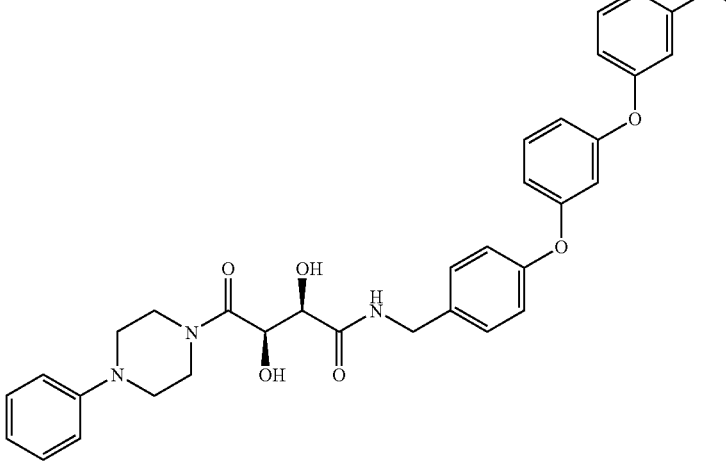 | 521 |
| 779 | 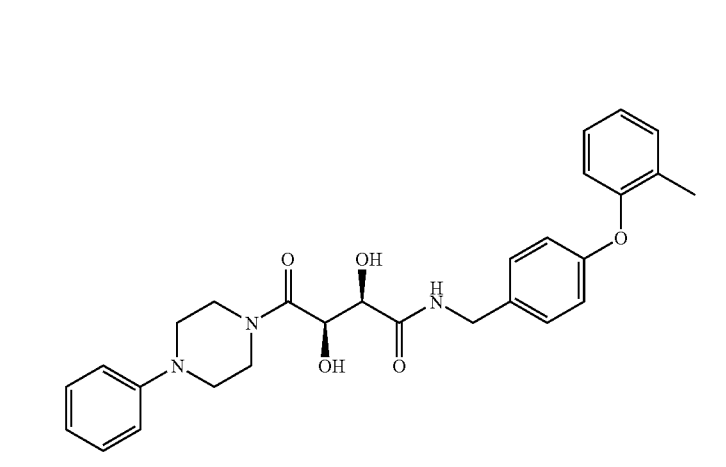 | 490 |
| 780 | 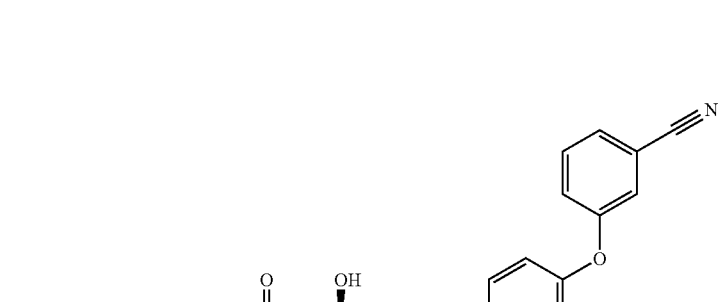 | 501 |

-continued

| Compound # | Structure | OBS. Mass |
|---|---|---|
| 781 | 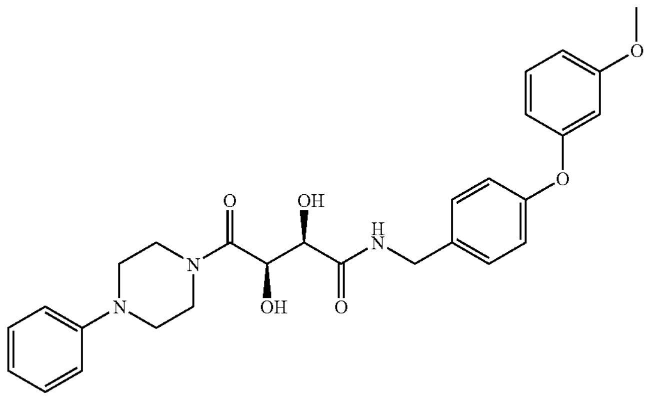 | 506 |
| 782 | 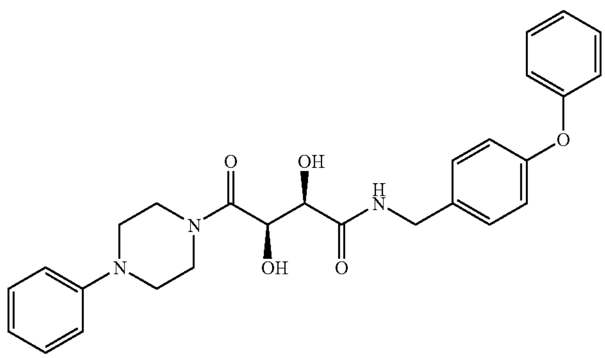 | 476 |
| 783 | 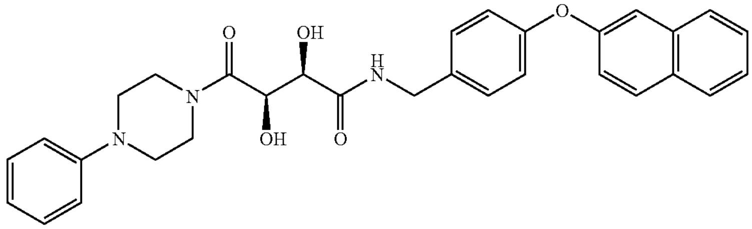 | 526 |
| 784 | 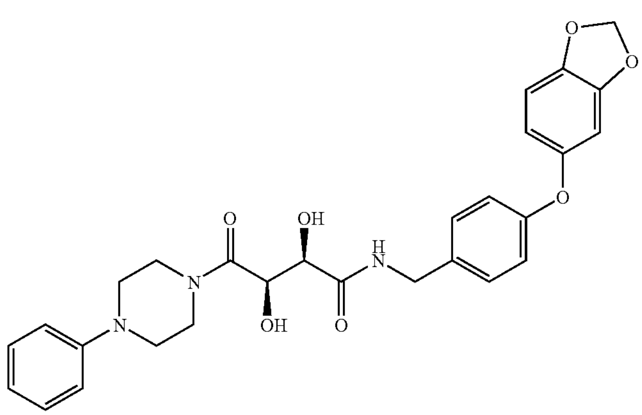 | 520 |

-continued
| Compound # | Structure | OBS. Mass |
|---|---|---|
| 785 | 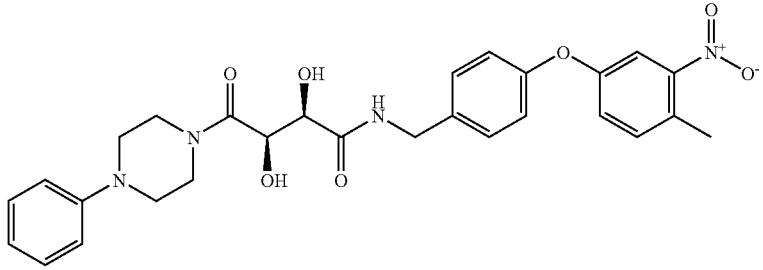 | 535 |
| 786 | 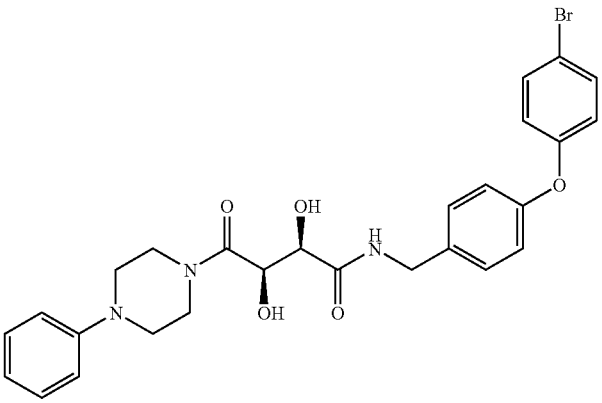 | 555 |
| 787 | 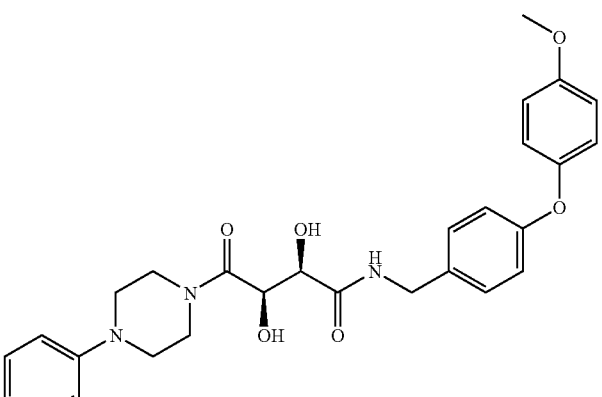 | 506 |
| 788 | 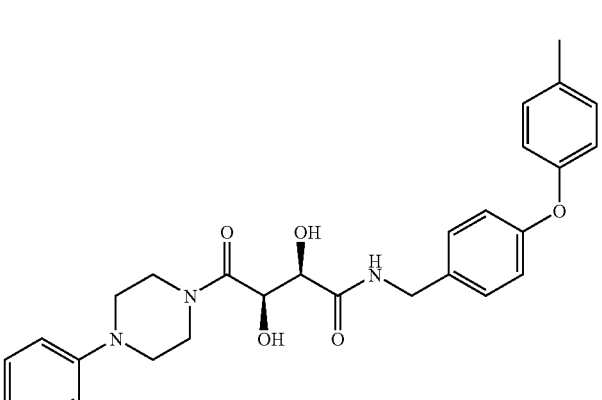 | 490 |

-continued

| Compound # | Structure | OBS. Mass |
|---|---|---|
| 789 | 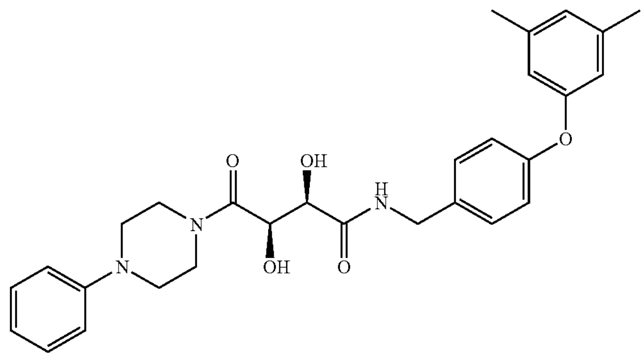 | 504 |
| 790 | 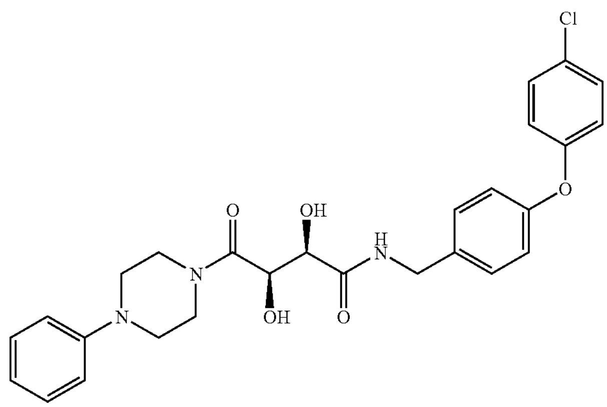 | 510 |
| 791 | 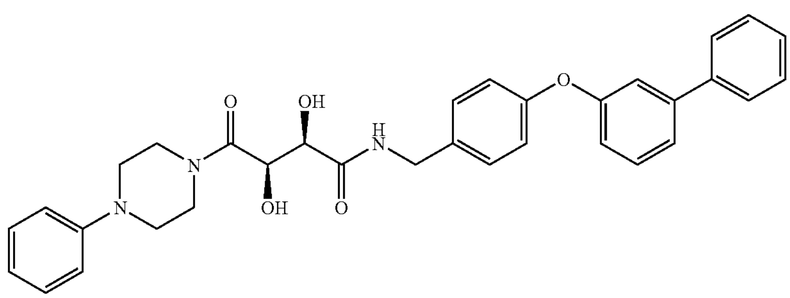 | 552 |
| 792 | 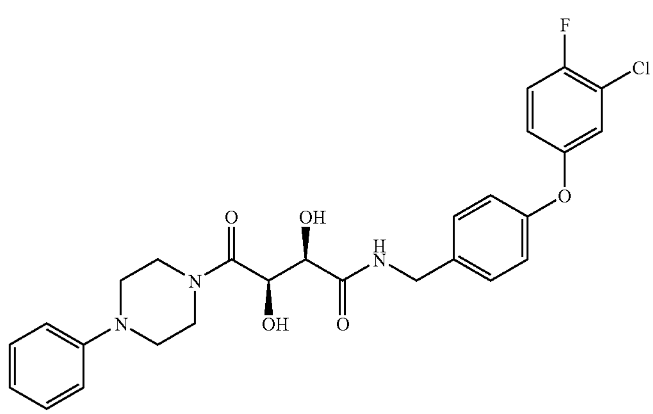 | 528 |

-continued

| Compound # | Structure | OBS. Mass |
|---|---|---|
| 793 | 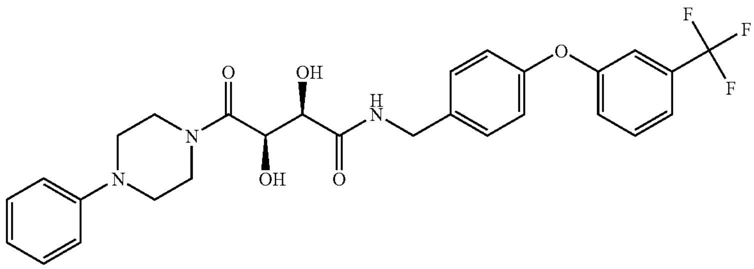 | 544 |
| 794 | 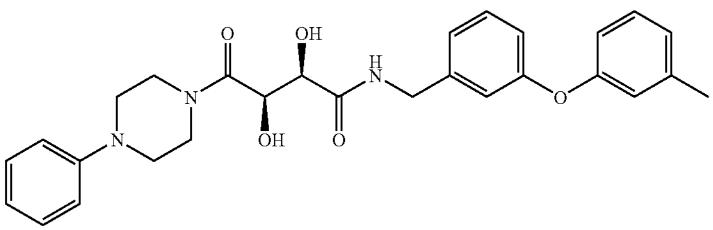 | 490 |
| 795 | 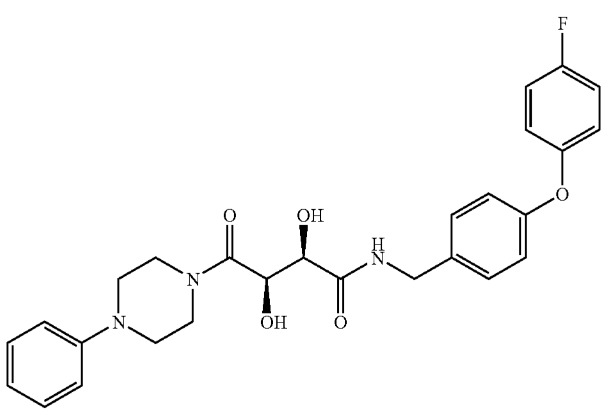 | 494 |
| 796 | 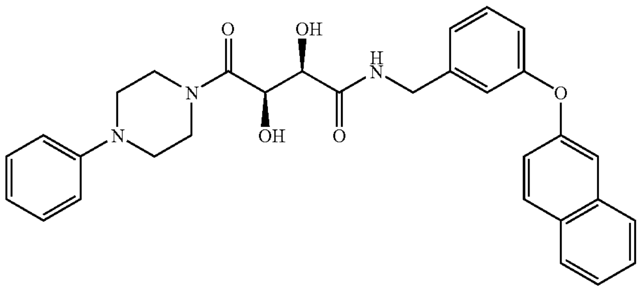 | 526 |

Example 18

Example 18A

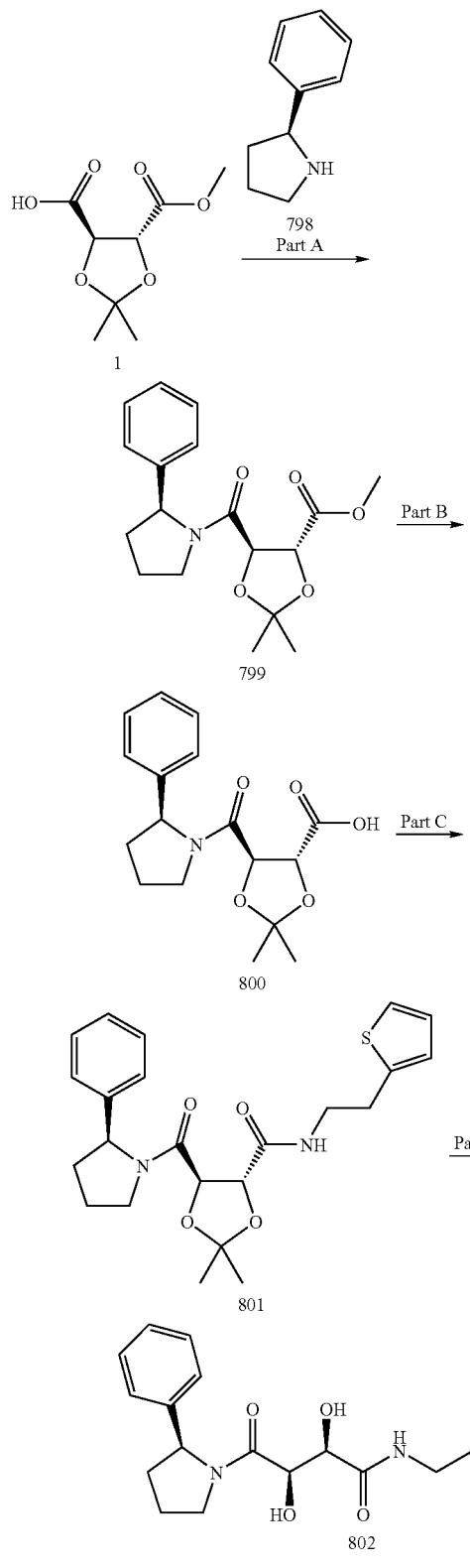

Part A:

Following the procedure described in Example 1 Part A, 1 (163 mg, 0.8 mmol), 2S-phenyl-pyrrolidine (798) (Burgess, L. E.; Meyers, A. I.; *J. Org. Chem.* 1991, 56, 2294) (147 mg, 0.8 mmol), DIEA (560 µL, 3.2 mmol) and HATU (304 mg, 0.8 mmol) were mixed together in DMF (2 mL). Purification by column chromatography (SiO$_2$, 5%-20% EtOAc/DCM) afforded 799 as an oil (115 mg, 43%). HPLC-MS $t_R$=1.82 min (UV$_{254\ nm}$); Mass calculated for formula C$_{18}$H$_{23}$NO$_5$ 333.2, observed LCMS m/z 334.1 (M+H).

Part B:

Following the procedure in Example 1 Part B the material from Part A was saponified. 800: HPLC-MS $t_R$=1.54 min (UV$_{254\ nm}$); Mass calculated for formula C$_{17}$H$_{21}$NO$_5$ 319.1, observed LCMS m/z 320.2 (M+H).

Part C:

Compound 800, 2-thiopheneethylamine (6 µL, 0.05 mmol), DIEA (18 µL, 0.103 mmol) and HATU (19 mg, 0.05 mmol) were mixed together following the procedure described in Example 1 Part A. 801: HPLC-MS $t_R$=2.01 min (UV$_{254\ nm}$); Mass calculated for formula C$_{23}$H$_{28}$N$_2$O$_4$S 428.2, observed LCMS m/z 429.2 (M+H).

Part D:

Compound 801 was dissolved in 90:10 TFA:water (2 mL) and stirred for 4 hours. The reaction mixture was quenched with 1:1 acetonitrile:water (4 mL) and concentrated. Purification by reverse phase prep-LC afforded 802 as a white powder (9 mg, 50%, 2 steps). HPLC-MS $t_R$=1.54 min (UV$_{254\ nm}$); Mass calculated for formula C$_{20}$H$_{24}$N$_2$O$_4$S 388.2, observed LCMS m/z 389.2 (M+H).

Example 18B

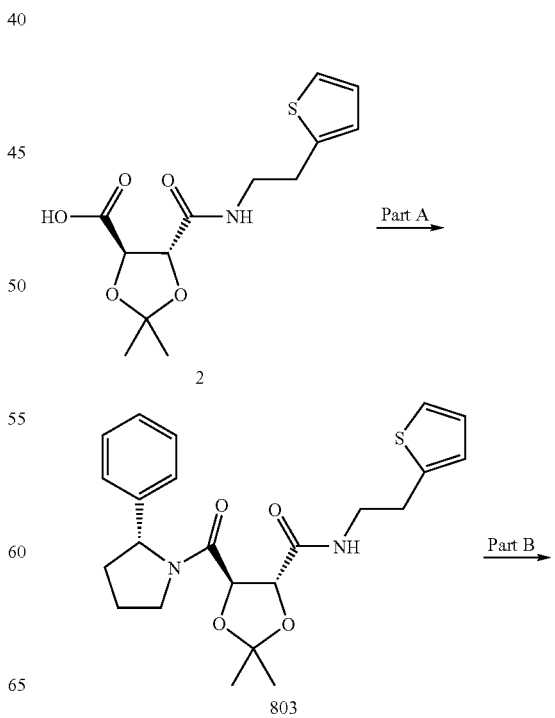

-continued

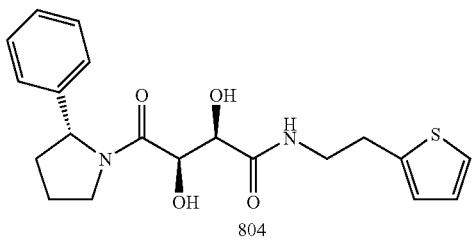
804

Part A:
Compound 2 (42 mg, 0.14 mmol), 2-phenyl pyrrolidine (22 mg, 0.15 mmol), DIEA (63 μL, 0.36 mmol) and HATU (61 mg, 0.16 mmol) were mixed together following the procedure described in Example 1 Part A. The desired isomer was separated by reverse phase prep-LC to afford 803 as a white solid. HPLC-MS $t_R$=1.96 min ($UV_{254\ nm}$); Mass calculated for formula $C_{23}H_{28}N_2O_4S$ 428.2, observed LCMS m/z 429.1 (M+H).

Part B:
Compound 803 was deprotected using the procedure described in Example 1 Part D to afford 804 as a white powder (5 mg, 19% 2 steps). HPLC-MS $t_R$=1.50 min ($UV_{254\ nm}$); Mass calculated for formula $C_{20}H_{24}N_2O_4S$ 388.2, observed LCMS m/z 389.2 (M+H).

| Compound # | Structure | Exact mass | MS m/e (M + H) |
|---|---|---|---|
| 805 | 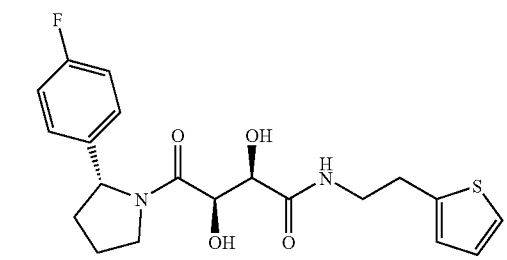 | 406.1 | 407.2 |
| 806 | 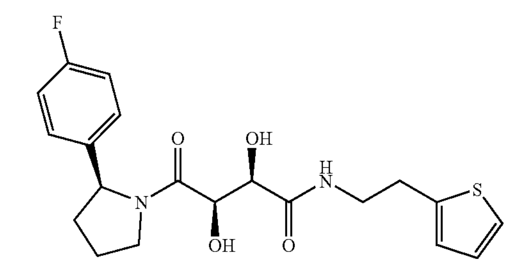 | 406.1 | 407.2 |
| 807 | 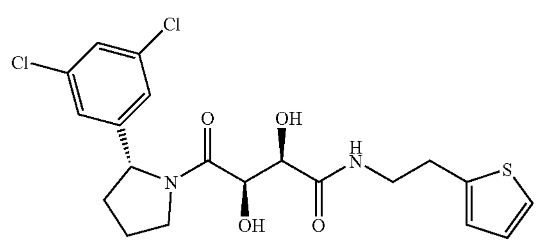 | 456.1 | 457.1 |
| 808 | 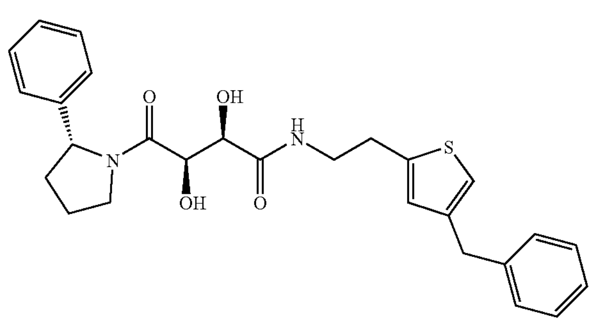 | 478.2 | 479.2 |

Example 19

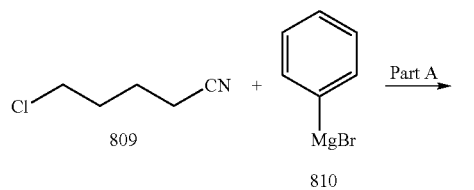

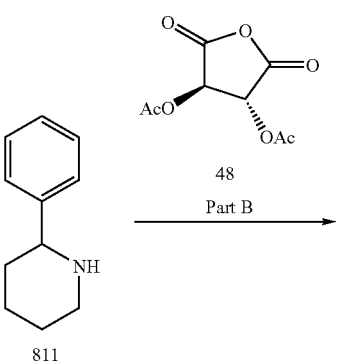

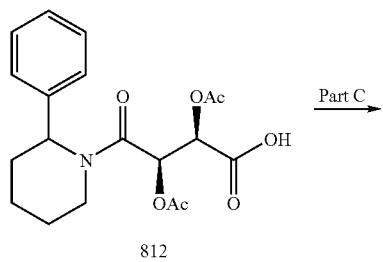

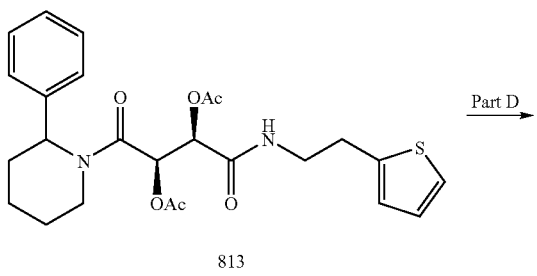

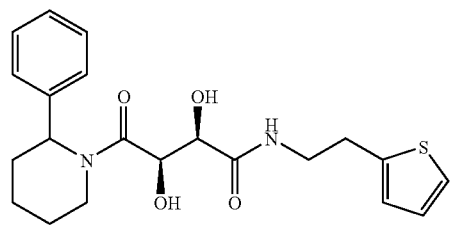

Part A: 2-Phenyl Piperidine

To 5-chlorovaleronitrile (809) (1.23 mL, 11 mmol) and trimethylsilylchloride (4.32 mL, 34 mmol) in toluene (50 mL) under argon at 0° C. was added phenylmagnesium bromide (810) (3M in diethyl ether, 3.67 mL, 11 mmol) dropwise. The reaction mixture was stirred at 0° C. for 1 hour. To the reaction mixture was added methanol (50 mL). Sodium borohydride (1.04 g, 27.5 mmol) was added portionwise. After the vigorous bubbling had subsided the reaction mixture was stirred for 1 hour at room temperature. A solution of 50% sodium hydroxide (5 mL) was added to the mixture and it was stirred overnight. The reaction mixture was filtered to remove the precipitate and the solids were washed with ethyl acetate. The filtrate was concentrated in vacuo. The crude reaction mixture was dissolved in ethyl acetate and water. The aqueous layer had a pH of 9. The layers were separated and the organic layer was washed with brine solution, dried over sodium sulfate and concentrated in vacuo to afford an orange oil. The product was purified by column chromatography (SiO$_2$, 20% ethyl acetate/hexane to 20% ethyl acetate hexane+2% triethylamine) to afford 811 as a polar yellow oil (927 mg, 52%). $^1$H NMR (400 MHz, CDCl$_3$) δ 7.4-7.3 (m, 4H), 7.24 (m, 1H), 3.60 (dd, 1H, J=2.4, 10.4 Hz), 3.21 (m, 1H), 2.81 (dt, 1H, J=3.2, 10.8 Hz), 1.90 (m, 1H), 1.81 (m, 1H), 1.68 (m, 1H), 1.56 (m, 3H); HPLC-MS $t_R$=0.73 min (MS); mass calculated for formula C$_{11}$H$_{15}$N 161.1, observed LCMS m/z 162.1 (M+H).

Part B:

To 48 (108 mg, 0.5 mmol) in DCM (3 mL) was added 811 (80 mg, 0.5 mmol). The reaction mixture was stirred overnight before being poured into 1.0 N HCl and extracted with DCM. The combined organic layers were dried over sodium sulfate, concentrated and freeze-dried to afford 812 as a white solid (119 mg, 63%). Mass calculated for formula C$_{19}$H$_{23}$NO$_7$ 377.2, observed LCMS m/z 378.1 (M+H).

Part C:

Prepared as described in Example 1 Part A using 812 (19 mg, 0.05 mmol) to afford a foam 813 (24 mg, 100%). Mass calculated for formula C$_{19}$H$_{23}$NO$_7$ 486.2, observed LCMS m/z 487.1 (M+H).

Part D:

Compound 813 (24 mg, 0.05 mmol) was deprotected using the procedure described in Example 2A Part B. Purification by reverse-phase prep-LC afforded 814 as a white powder (9 mg, 45%). HPLC-MS $t_R$=4.38 and 4.42 min (UV$_{254\,nm}$, 10 min); Mass calculated for formula C$_{21}$H$_{26}$N$_2$O$_4$S 402.2, observed LCMS m/z 403.1 (M+H).

| Compound # | Structure | Exact mass | MS m/e (M + H) |
|---|---|---|---|
| 815 | 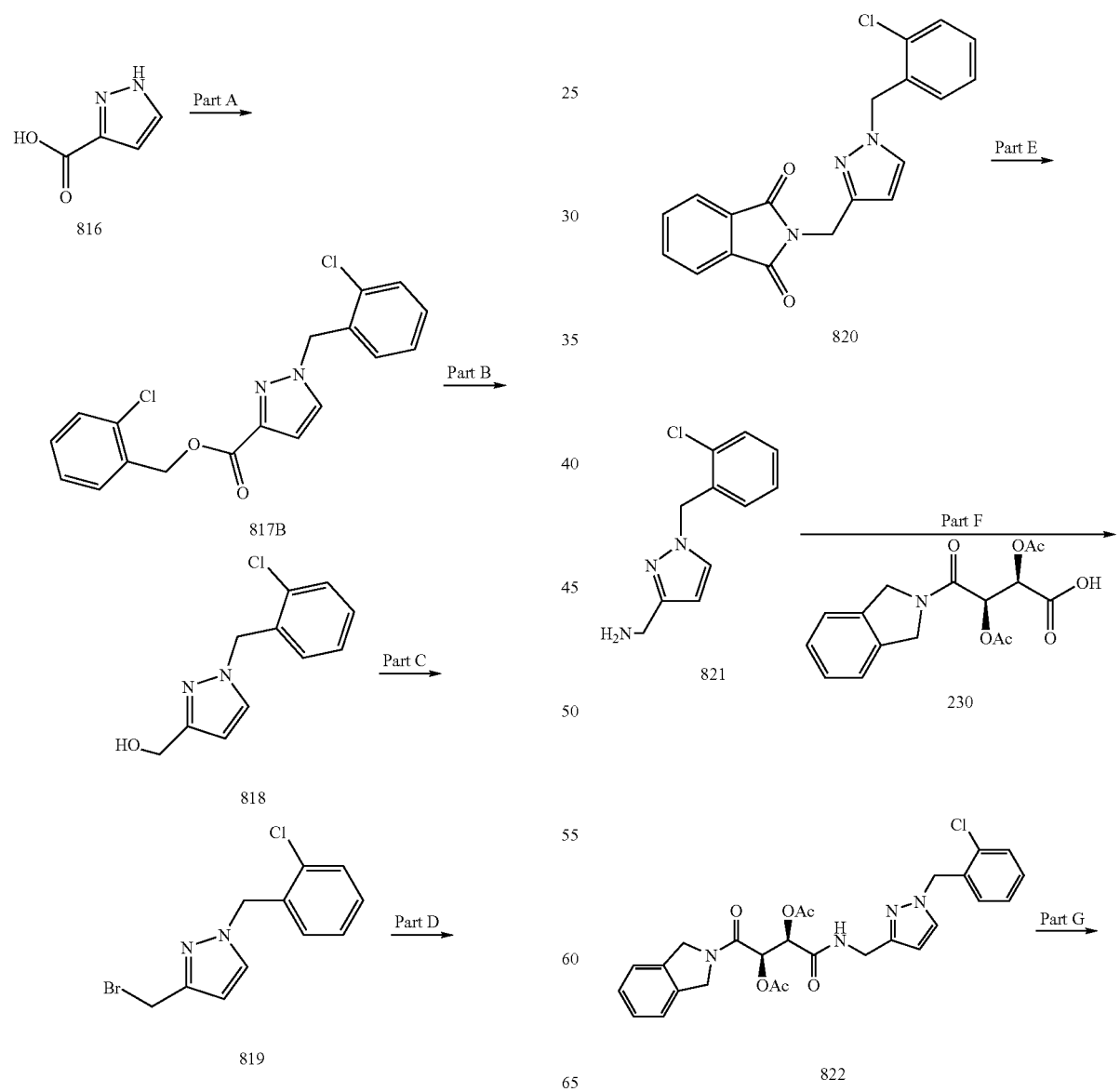 | 512.2 | 513.1 |
Example 20
Example 20A
-continued -continued

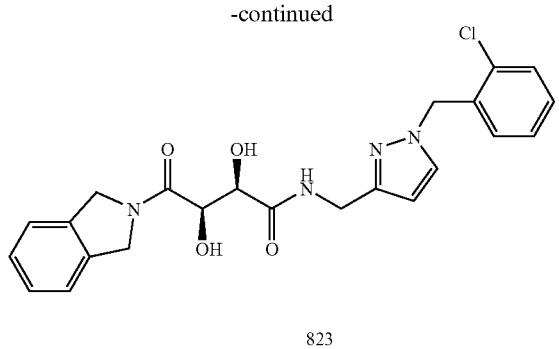

823

Part A:

To 1H-Pyrazole-3-carboxylic acid (816) (274 mg, 2.44 mmol) in DMF (10 mL) was added 2-chlorobenzyl bromide (698 µL, 5.38 mmol) and cesium carbonate (1.67 g, 5.12 mmol). The reaction mixture was stirred overnight at room temperature. The solids were removed by filtration and the filtrate was concentrated. Purification by column chromatography (SiO$_2$, 20% to 30% EtOAc/Hex) separated the regioisomers to afford the 817A as an oil (136 mg, 15%) and 817B as a white solid (685 mg, 78%).

1-(2-Chloro-benzyl)-1H-pyrazole-5-carboxylic acid 2-chloro-benzyl ester (817A): $^1$H NMR (400 MHz, CDCl$_3$) δ 7.61 (d, 1H, J=2.0 Hz), 7.37 (m, 3H), 7.31-7.11 (m, 4H), 7.02 (d, 1H, J=2.0 Hz), 6.53 (dd. 1H, J=2.0, 7.6 Hz), 5.91 (s, 2H), 5.39 (s, 2H). HPLC-MS t$_R$=2.40 min (UV$_{254\ nm}$); mass calculated for formula C$_{18}$H$_{14}$Cl$_2$N$_2$O$_2$ 360.0, observed LCMS m/z 361.0 (M+H).

1-(2-Chloro-benzyl)-1H-pyrazole-3-carboxylic acid 2-chloro-benzyl ester (817B): $^1$H NMR (400 MHz, CDCl$_3$) δ 7.51 (m, 1H), 7.44 (d, 1H, J=2.4 Hz), 7.40 (m, 2H), 7.27 (m, 4H), 7.08 (dd, 1H, J=1.6, 7.6 Hz), 6.87 (d, 1H, J=2.4 Hz), 5.54 (s, 2H), 5.51 (s, 2H); HPLC-MS t$_R$=2.22 min (UV$_{254}$ nM); mass calculated for formula C$_{18}$H$_{14}$Cl$_2$N$_2$O$_2$ 360.0, observed LCMS m/z 361.0 (M+H).

Part B:

To 817B (685 mg, 1.90 mmol) in THF (10 mL) was added 1.0 M LiAlH$_4$ (1.14 mL, 1.14 mmol) with ice cooling. The reaction mixture was stirred for 1 hour. The reaction was quenched with water (1 mL), 3 M NaOH (1 mL) and water (3 mL). The organic layer was decanted and the precipitate was washed with EtOAc. The combined organic layers were washed with brine, dried over sodium sulfate and concentrated. Purification by column chromatography (SiO$_2$, 1:1 DCM:EtOAc) yielded 818 as an oil (350 mg, 83%). $^1$H NMR (400 MHz, CDCl$_3$) δ 7.42 (d, 1H, J=2.4 Hz), 7.39 (dd, 1H, J=2.4, 8.0 Hz), 7.25 (m, 2H), 7.02 (dd, 1H, J=1.6, 7.2 Hz), 6.30 (d, 1H, J=2.4 Hz), 5.43 (s, 2H), 4.73 (s, 2H), 2.5 (bs, 1H, OH); HPLC-MS t$_R$=1.29 min (UV$_{254\ nm}$); mass calculated for formula C$_{11}$H$_{11}$ClN$_2$O 222.1, observed LCMS m/z 223.1 (M+H).

Part C:

To 818 (350 mg, 1.57 mmol) in toluene (5 mL) was added phosphorous tribromide (163 µL, 1.73 mmol). The reaction mixture was heated to reflux in a pre-heated oil bath for 15 minutes. The mixture was cooled, poured over ice and extracted with EtOAc. The combined organic layer was washed with bicarbonate solution and brine, dried over sodium sulfate and concentrated to yield 819 as a white solid (414 mg, 93%). $^1$H NMR (400 MHz, CDCl$_3$) δ 7.39 (m, 2H), 7.25 (m, 2H), 7.00 (dd, 1H, J=2.0, 7.2 Hz), 6.36 (d, 1H, J=2.4 Hz), 5.41 (s, 2H), 4.53 (s, 2H); HPLC-MS t$_R$=1.96 min (UV$_{254\ nm}$); mass calculated for formula C$_{11}$H$_{10}$BrClN$_2$ 284.0, observed LCMS m/z 285.1 (M+H).

Part D:

To 819 (412 mg, 1.44 mmol) in DMF (5 mL) was added phthalimide (255 mg, 1.73 mmol) and cesium carbonate (515 mg, 1.58 mmol). The reaction mixture was stirred overnight at room temperature. The solids were removed by filtration and the filtrate was concentrated. The residue was dissolved in EtOAc and water. The layers were separated. The organic layer was washed with brine, dried over sodium sulfate and concentrated. Purification by column chromatography (SiO$_2$, 5% EtOAc/DCM) yielded 820 as a solid (418 mg, 82%). HPLC-MS t$_R$=1.96 min (UV$_{254\ nm}$); mass calculated for formula C$_{19}$H$_{14}$ClN$_3$O$_2$ 351.1, observed LCMS m/z 352.2 (M+H).

Part E:

To 820 (418 mg, 1.19 mmol) in ethanol (20 mL) was added hydrazine monohydrate (231 µL, 4.75 mmol) and the reaction was heated to reflux for 3 hours. The mixture was cooled and diluted with 50% EtOAc/hexanes (40 mL). The solids were removed by filtration and were thoroughly washed with 50% EtOAc/hexanes (30 mL). The filtrate was concentrated. The residue was dissolved in EtOAc and washed with water and brine, dried over sodium sulfate and concentrated to afford 821 as a semi-solid (205 mg, 78%). $^1$H NMR (400 MHz, CDCl$_3$) δ 7.39 (m, 1H), 7.38 (d, 1H, J=2.0 Hz), 7.23 (m, 2H), 6.92 (dd, 1H, J=2.0, 7.2 Hz), 6.22 (d, 1H, J=2.0 Hz), 5.39 (s, 2H), 3.91 (s, 2H); HPLC-MS t$_R$=0.91 min (UV$_{254\ nm}$); mass calculated for formula C$_{11}$H$_{12}$ClN$_3$ 221.07, observed LCMS m/z 222.1 (M+H).

Part F:

To 821 (49 mg, 0.22 mmol) in DMF (2 ml) was added 230 (67 mg, 0.2 mmol), DIEA (77 µL, 0.44 mmol) and HATU (84 mg, 0.22 mmol). The reaction mixture was stirred overnight. The DMF was removed in vacuo and the residue was dissolved in EtOAc. The organic layer was washed with bicarbonate solution, 0.1 N HCl, and brine, dried over sodium sulfate and concentrated. Purification by column chromatography (SiO$_2$, 80% EtOAc/Hex) yielded 822 as a solid (70 mg, 65%). HPLC-MS t$_R$=1.80 min (UV$_{254\ nm}$); mass calculated for formula C$_{27}$H$_{27}$ClN$_4$O$_6$ 538.2, observed LCMS m/z 539.2 (M+H).

Part G:

A mixture of 822 (70 mg, 0.13 mmol) and potassium carbonate (90 mg, 0.65 mmol) in MeOH (2 mL) was stirred 1 hour. The reaction was diluted with EtOAc and poured into brine solution. Additional salt was added and the layers were separated. The aqueous layer was extracted with EtOAc. The combined organic layer was dried over sodium sulfate and concentrated to yield 823 as a white solid (45 mg, 76%). $^1$H NMR (400 MHz, DMSO-d$_6$) δ 8.05 (t, 1H, J=6.0 Hz), 7.70 (d, 1H, J=2.0 Hz), 7.46 (dd, 1H, J=2.0, 8.0 Hz), 7.36-7.27 (m, 6H), 6.94 (dd, 1H, J=2.0, 7.6 Hz), 6.20 (d, 1H, J=2.0 Hz), 5.68 (d, 1H, J=6.8 Hz), 5.35 (s, 2H), 5.06 (d, 1H, J=14.4 Hz), 5.03 (d, 1H, J=7.6 Hz), 4.91 (d, 1H, J=14.4 Hz), 4.76 (d, 1H, J=15.6 Hz), 4.62 (dd, 1H, J=2.8, 7.6 Hz), 4.61 (d, 1H, J=14.8

Hz), 4.26 (m, 3H); HPLC-MS $t_R$=1.55 min (UV$_{254\,nm}$); mass calculated for formula $C_{23}H_{23}ClN_4O_4$ 454.1, observed LCMS m/z 455.2 (M+H).

Example 20B

Pyrazole Spacer

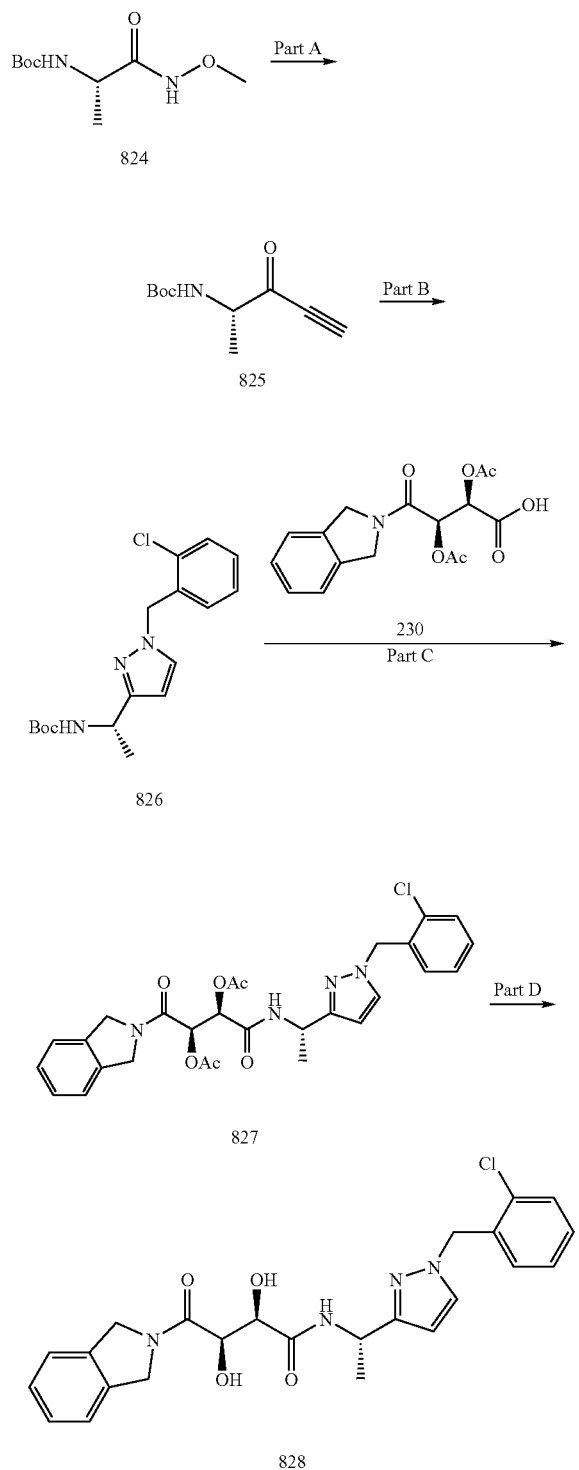

Part A:

To the Weinreb amide 824 (prepared using the method of De Luca, L.; Giacomelli, G.; Taddei, M. *J. Org. Chem.* 2001, 66, 2534) (200 mg, 0.85 mmol) in THF (15 mL) was added lithium (trimethylsilyl)acetylide (4.3 mL, 2.14 mmol) dropwise at 0° C. The reaction mixture was stirred for 1 hour then diluted with EtOAc (50 mL). The mixture was washed with 0.1 N HCl (50 mL), dried over sodium sulfate and concentrated. Purification by column chromatography (SiO$_2$, 20% EtOAc/Hex) afforded 825 (91 mg, 54%).

Part B:

A mixture of 825 (71 mg, 0.33 mmol), (2-chloro-phenyl)-hydrazine dihydrochloride (89 mg, 0.39 mmol) and potassium carbonate (200 mg, 1.64 mmol) in methanol (5 mL) were stirred at reflux for 12 hours. The reaction mixture was cooled and diluted with EtOAc (50 mL) and water (50 mL). The organic layer was separated, dried over sodium sulfate and concentrated. Purification by column chromatography (SiO$_2$, 20% EtOAc/Hex) afforded 826 (50 mg, 15%). HPLC-MS $t_R$=2.10 min (ELSD); mass calculated for formula $C_{17}H_{22}ClN_3O_2$ 335.1, observed LCMS m/z 336.2 (M+H).

Part C:

Compound 826 (45 mg, 0.13 mmol) was dissolved in 25% TFA/DCM (4 mL) and stirred for 30 minutes. The solvents were removed in vacuo and the material was used without further purification. The residue was dissolved in DMF (5 mL) and 230 (25 mg, 0.07 mmol), DIEA (300 µL, 1.68 mmol) and HATU (32 mg, 0.09 mmol) were added. The reaction mixture was stirred overnight. The DMF was removed in vacuo and the residue was dissolved in EtOAc and water. The organic layer was separated and washed with 0.1 N NaOH, 0.1 N HCl and brine, dried over sodium sulfate and concentrated. Compound 827 was used without further purification.

Part D:

Compound 827 (25 mg, 0.05 mmol) was dissolved in methanol (5 mL) and a solution on potassium carbonate (50 mg) in water (1 mL) was added. The reaction was stirred for 30 minutes. The reaction mixture was diluted with ethyl acetate and brine. The organic layer was separated, dried over sodium sulfate and concentrated. Purification by reverse phase prep-LC afforded 828 as a white powder (15 mg, 65%). $^1$H NMR (400 MHz, DMSO-d$_6$) δ 7.81 (d, 1H, J=8.0 Hz), 7.70 (d, 1H, J=1.6 Hz), 7.47 (dd, 1H, J=1.6, 7.6 Hz), 7.35-7.26 (m, 6H), 6.89 (dd, 1H, J=1.6, 7.2 Hz), 6.29 (d, 1H, J=2.0 Hz), 5.38 (s, 2H), 5.04 (d, 1H, J=15.2 Hz), 4.97 (m, 2H), 4.90 (d, 1H, J=14.0 Hz), 4.76 (d, 1H, J=16.4 Hz), 4.61 (m, 2H), 4.27 (d, 1H, J=2.4 Hz), 1.39 (d, 3H, J=6.8 Hz); HPLC-MS $t_R$=4.25 min (UV$_{254\,nm}$, 10 min); mass calculated for formula $C_{24}H_{25}ClN_4O_4$ 468.2, observed LCMS m/z 469.1 (M+H).

| Compound # | Structure | Exact mass | MS m/e (M + H) |
|---|---|---|---|
| 829 | 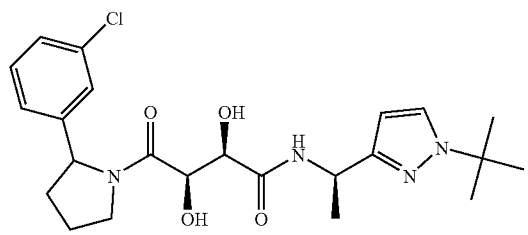 | 462.2 | 463.1 |
| 830 | 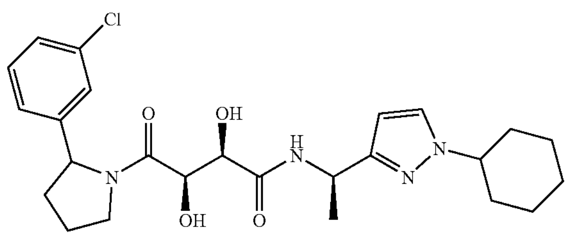 | 488.2 | 489.2 |
| 831 | 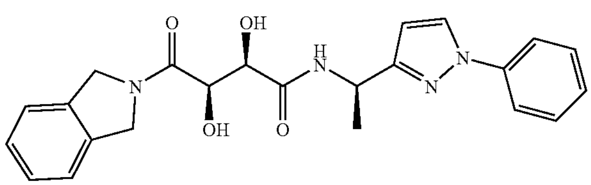 | 420.2 | 421.1 |
| 832 | 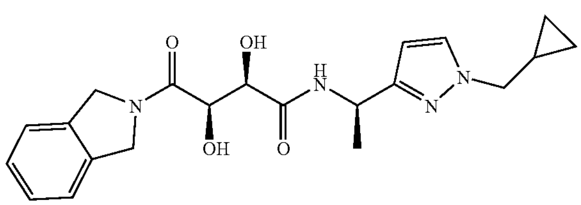 | 398.2 | 399.1 |
| 833 | 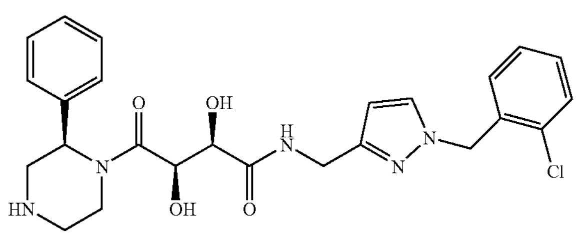 | 511.2 | 512.2 |
| 834 | 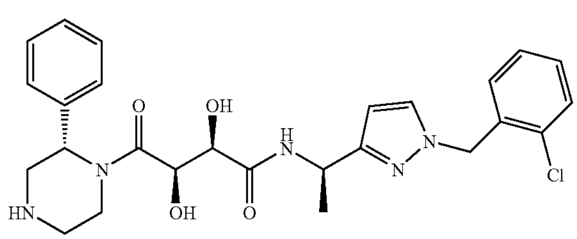 | 511.2 | 512.2 |
| 835 | 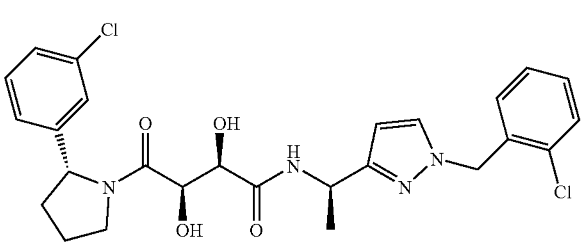 | 530.2 | 531.1 |

| Compound # | Structure | Exact mass | MS m/e (M + H) |
|---|---|---|---|
| 836 | 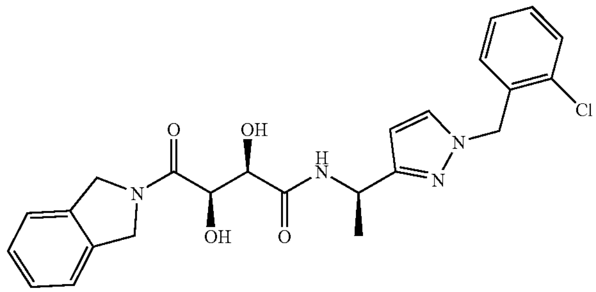 | 480.2 | 481.1 |

Example 21

α-Methyl Benzyl Amines

Example 21A

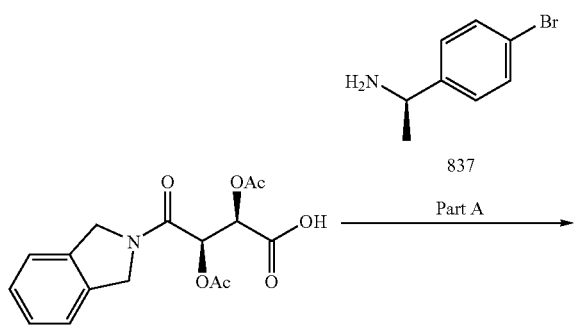

230

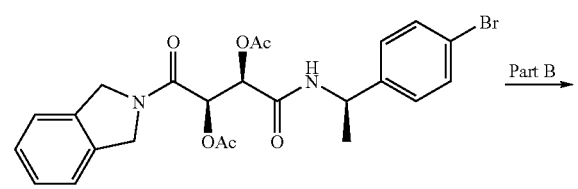

838

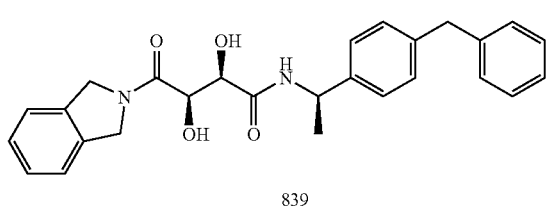

839

Part A:

A mixture of 1R-(4-bromo-phenyl)-ethylamine (837) (0.18 mL, 1.25 mmol), 230 (349 mg, 1.0 mmol), DIEA (357 μL, 2.0 mmol) and HATU (456 mg, 1.2 mmol) in NMP (10 mL) was stirred overnight at room temperature. The reaction mixture was poured into water and extracted with EtOAc. The organic layer was washed with bicarbonate solution, 0.1 N HCl, and brine, dried over sodium sulfate and concentrated. 838: $^1$H NMR (400 MHz, DMSO-$d_6$) δ 8.72 (d, 1H, J=7.6 Hz), 7.49 (dd, 2H, J=2.0, 6.8 Hz), 7.37-7.25 (m, 6H), 5.56 (ABq, 2H, J=6.8 Hz), 4.99 (d, 1H. J=13.2 Hz), 4.89 (m, 2H), 4.70 (d, 1H, J=16.0 Hz), 4.51 (d, 1H, J=16.4 Hz), 2.09 (s, 3H), 2.03 (s, 3H), 1.32 (d, 3H, J=7.2 Hz).

Part B:

To 838 (135 mg, 0.26 mmol), PdCl$_2$(dppf) (22 mg, 0.03 mmol), potassium phosphate (166 mg, 0.78 mmol) in dioxane (5 mL) under argon atmosphere was added benzyl-9-BBN (0.5 M in THF, 1.3 mL, 0.65 mmol). The reaction mixture was heated to 60° C. overnight. The reaction mixture was filtered through a celite pad and the pad was rinsed with ethyl acetate. The filtrate was concentrated. The crude product was dissolved in methanol (5 mL) and potassium carbonate (4 mg) was added. The reaction mixture was stirred for 1 hour, filtered and concentrated to afford 839 as a solid (50 mg, 42%). $^1$H NMR (400 MHz, DMSO-$d_6$) 67.97 (d, 1H, J=7.6 Hz), 7.34-7.10 (m, 13H), 5.03 (d, 1H. J=14.4 Hz), 4.90 (m, 2H), 4.72 (d, 1H, J=16.8 Hz), 4.58 (m, 2H), 4.20 (d, 1H, J=3.2 Hz), 3.87 (s, 2H), 1.37 (d, 3H, J=7.2 Hz); HPLC-MS $t_R$=1.89 min (UV$_{254\,nm}$); mass calculated for formula $C_{27}H_{28}N_2O_4$ 444.2, observed LCMS m/z 445.1 (M+H).

Example 21B

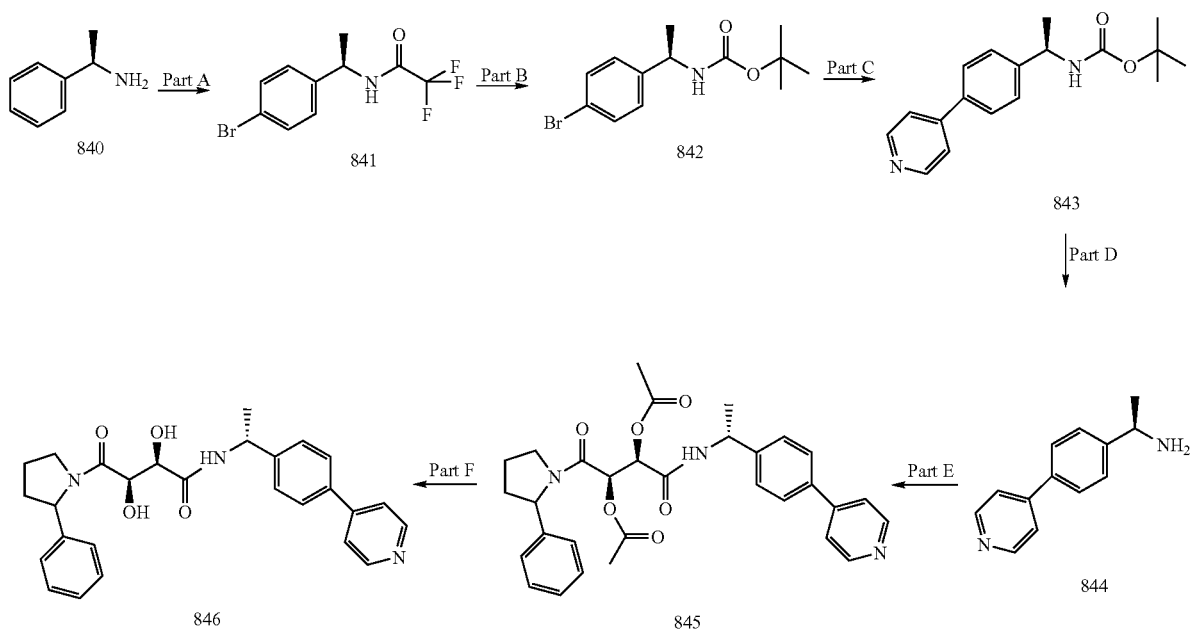

Part A:

CH$_2$Cl$_2$ (300 mL) and trifluoroacetic anhydride (100 g, 0.476 mol) were added to a 2 liter 3-necked flask. The flask was equipped with a drying tube and cooled in an ice-water bath. A solution of (R)-α-methylbenzylamine (840) (53.72 g, 0.443 mol) dissolved in 100 mL of CH$_2$Cl$_2$ was added over 40 min. The ice bath was removed and the reaction mixture was stirred at rt for 3 h. The reaction mixture was cooled with an ice-water bath and methanesulfonic acid (110 mL, 1.69 mol) was added. Dibromodimethylhydantoin (65 g, 0.227 mol) was added in portions over 1 hr 15 min. The reaction mixture was left stirring overnight then poured into a solution prepared from 60 mL of 1 M NaHSO$_3$ and 500 mL of ice and water. The layers were separated and the aqueous layer was extracted with 100 mL of CH$_2$Cl$_2$. The combined organic layer was washed with water and brine, then dried with MgSO$_4$. The solvent was evaporated to give a white solid. This material was recrystallized from Et$_2$O/Hexanes to give compound 841. MS (EI) m/z M+H Obsd 297.16

Part B:

Compound 841 (8.09 g, 27.3 mmol) was dissolved in 40 mL of dioxane, 10 mL of methanol, and 40 mL of 1 M aqueous LiOH. The reaction mixture was stirred at rt for 2.5 h under N$_2$. Boc anhydride (7.45 g, 34.1 mmol) and EtOAc (25 mL) were added and the reaction mixture was stirred at rt under N$_2$ for 1.5 h. The reaction mixture was diluted with EtOAc and brine. The layers were separated and the aqueous layer was extracted with EtOAc. The combined organic layer was washed with citric acid, water, and brine, then dried with MgSO$_4$. The solvents were evaporated and the crude product was purified via flash sgc using a 5%-10% EtOAc/Hexanes gradient as the mobile phase. White solid 842 (7.95 g) was obtained as product. MS (EI) m/z M+Na Obsd 324.01

Part C:

Compound 842 (1.11 g, 3.69) and 4-pyridine boronic acid (0.55 g, 4.48 mmol) were suspended in 1-propanol (8 mL) and stirred for 25 min at 40° C. Palladium (II) acetate (55 mg, 0.24 mmol) and water (4 mL), were added, followed by sodium carbonate (0.47 g, 4.43 mmol) and triphenyl phosphine (197 mg 0.75 mmol). The reaction mixture was stirred under N$_2$ at 80° C. for 21 h. The reaction mixture was allowed to cool to rt and diluted with EtOAc and 0.5 M NaHCO$_3$. The layers were separated and the aqueous layer was extracted with EtOAc. The combined organic layer was washed with brine, dried with MgSO$_4$, filtered, and concentrated to give an orange solid. The crude product was purified via sgc using 30% EtOAc/Hexanes, followed by 30% EtOAc/Hexanes with 2% added diisopropylethylamine added, followed by 40% EtOAc/Hexanes as the mobile phase. White solid 843 was obtained as product (0.71 g). MS (EI) m/z M+H Obsd 299.10.

Part D:

Compound 843 (0.70, 2.3 mmol) was suspended in 22 mL of 4 M HCl in dioxane and 8 mL of CH$_2$Cl$_2$. The reaction mixture was stirred under N$_2$ at rt for 6 h, then concentrated to give white solid 844 (0.70 g). MS (EI) m/z M+H Obsd 199.09.

Parts E & F:

Compound 846 was prepared using procedures similar to those described in Example 14, Steps E&F. MS (EI) m/z M+H Obsd 460.1

Example 21C

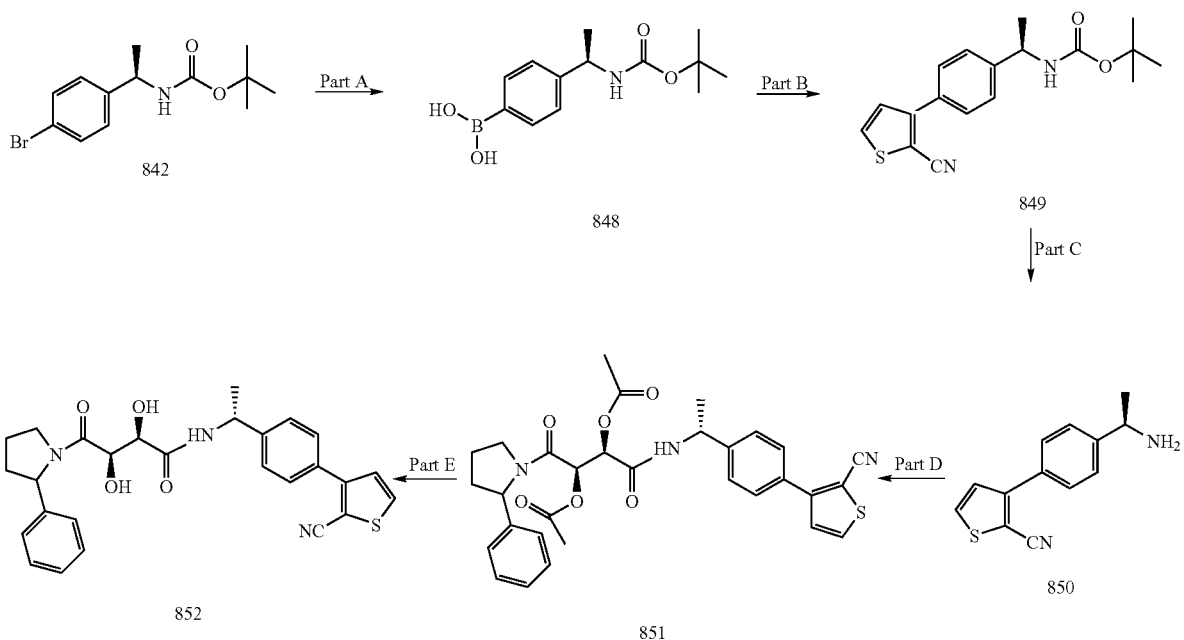

Part A:

A 500 mL Schlenck Flask equipped with a stir bar was flame dried under $N_2$ flow, capped with a septum, and allowed to cool to rt. A solution of n-butyl lithium in hexanes (55 mL, 2.5 Molar, 137.4 mmol) was added via syringe. The flask was cooled in a dry ice/2-propanol bath. Tetramethylethylene diamine (TMEDA-19.0 g, 167 mmol) was added. Compound 842 (20 g, 66.8 mmol) was dissolved in anhydrous THF (200 mL) and added to the reaction mixture over 30 min via addition funnel. The reaction mixture was stirred at −78 C for 15 min. Triethyl borate was added (21.4 mL, 176 mmol) as a solution in 40 mL of anhydrous THF. The reaction mixture was stirred for 30 min. The reaction mixture was quenched at −78° C. with 1.0 M aq HCl to a pH of 2, then allowed to warm to rt. The reaction mixture was extracted with EtOAc. The organic layer was dried with $MgSO_4$ and concentrated to dryness. The crude product was purified via sgc using 5:95 MeOH:$CH_2Cl_2$ as the mobile phase. White solid 848 was obtained as product (3.8 grams). Data for 848: $^1$HNMR (400 MHz, $CD_3OD$) δ 7.56 (d, J=8 Hz, 2H), 7.29 (d, J=8 Hz, 2H), 4.58-4.64 (m, 1H), 1.41-1.36 (m, 12H).

Part B:

Compound 848 (300 mg, 1.13 mmol), 3-bromo-2-cyanothiophene (192 mg, 1.02 mmol), acetonitrile (4 mL), Dichloro[1,1'-bis(diphenylphosphino) ferrocene] palladium (II) dichloride (Strem, 171 mg, 0.23 mmol), and 1.25 mL of 1 M aq $K_2CO_3$ were added to a microwave tube equipped with a stir bar. $N_2$ was bubbled through the soln. and the tube was capped. The reaction mixture was irradiated at 150° C. for 5 min in a Personal Chemistry "Companion" microwave oven. The resulting material was filtered through Celite which was washed with EtOAc. The filtrate was partitioned between EtOAc and water. The organic layer was washed with water and treated with $Na_2SO_4$ and Darco activated carbon. The mixture was filtered and concentrated to dryness. The crude product was purified via sgc using 60:40 Hexanes: EtOAc as the mobile phase. Compound 849 was obtained as a yellow oil (224 mg) which crystallized on standing. m/z Obsd. M+Na 350.93

Part C:

Compound 849 (224 mg, 0.682 mmol) was dissolved in 2.8 mL of $CH_2Cl_2$ and 1.2 mL of trifluoroacetic acid. The reaction mixture was stirred at rt for 2 hours, then concentrated to dryness. The crude product was purified via sgc using 9:1 $CH_2Cl_2$:MeOH($NH_3$) as the mobile phase to give 110 mg of 850 as an oil. m/z Obsd. M+H 229.10

Parts D and E:

Compounds 851 and 852 were prepared via procedures similar to those described in Example 14, Parts D and E. Data for 851: m/z Obsd. M+H 574.05. Data for 852: m/z Obsd. M+Na 511.91.

Example: 21D

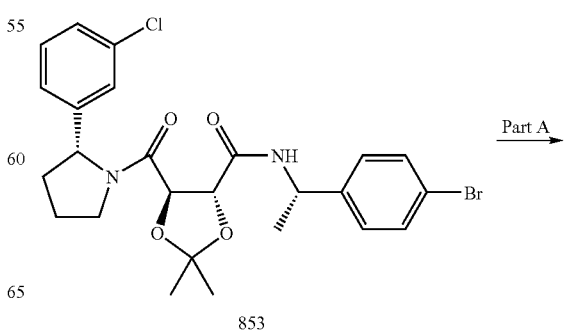

-continued

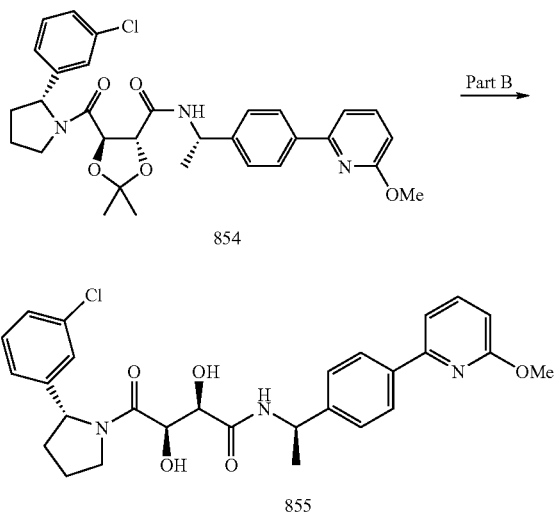

854

855

Compound 853 was synthesized using the procedures described in Example 1.

Part A:

Compound 853 (25 mg, 0.050 mmol) was dissolved in THF (1 mL) and PdP(t-Bu$_3$)$_2$ (5 mg, 0.0097 mmol) was added under an argon atmosphere. 6-Methoxy-2-pyridylzinc bromide (0.5 M in THF, 0.2 mL) was added and the reaction was stirred at 50° C. overnight. The reaction mixture was filtered over a bed of celite and then evaporated under reduced pressure. Purification by reverse phase prep-LC afforded an off-white solid 854 (10 mg, 38%) after lyophilization. HPLC-MS $t_R$=6.138 min (UV$_{254\ nm}$, 10 min); mass calculated for formula $C_{31}H_{34}ClN_3O_5$ 563.2, observed LCMS m/z 564.1 (M+H).

Part B:

Compound 854 (10 mg, 0.0188 mmol) was dissolved in MeOH (0.3 mL) and TFA (4 mL) and stirred for 2 hours at room temperature. The solvent was removed to provide the pure product 855 (9.36 mg, 95%). HPLC-MS $t_R$=5.098 min (UV$_{254\ nm}$, 10 min); mass calculated for formula $C_{28}H_{30}ClN_3O_5$ 523.1, observed LCMS m/z 524.1 (M+H).

Example: 21 E

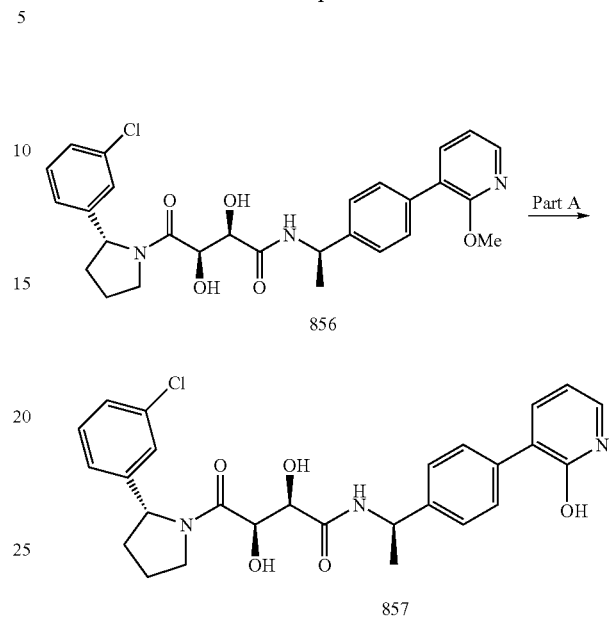

856

857

Compound 856 was synthesized using the Suzuki procedures desribed in Example 12.

Part A:

Compound 856 (160 mg, 0.30 mmol) was dissolved in acetonitrile (5 mL) and sodium iodide (140 mg, 1.0 mmol) was added followed by trimethylsilylchloride (105 mg, 1.0 mmol). Water (0.1 mL) was added and the reaction mixture was stirred at reflux for 4 hours. The reaction was quenched with water and extracted with ethyl acetate. The combined organic layers were washed with bicarbonate solution and brine; dried over sodium sulfate and concentrated. Purification by reverse phase prep-LC afforded an off-white solid 857 (86 mg, 56%) after lyophilization. HPLC-MS $t_R$=3.72 min (UV$_{254\ nm}$, 10 min); mass calculated for formula $C_{27}H_{28}ClN_3O_5$ 509.1, observed LCMS m/z 510.1 (M+H).

The following table contains compounds made using the procedures described in Example 21A-E.

| Compound # | Structure | Exact mass | MS m/e (M + H) |
|---|---|---|---|
| 858 | 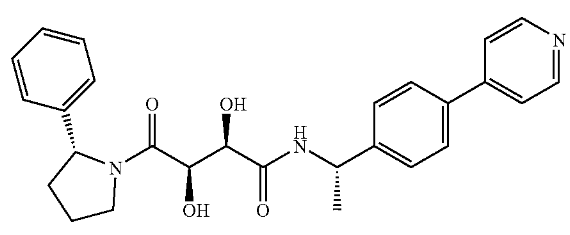 | 459.2 | 460.1 |

-continued

| Compound # | Structure | Exact mass | MS m/e (M + H) |
|---|---|---|---|
| 859 | 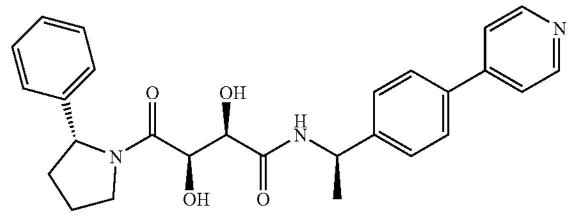 | 459.2 | 460.1 |
| 860 | 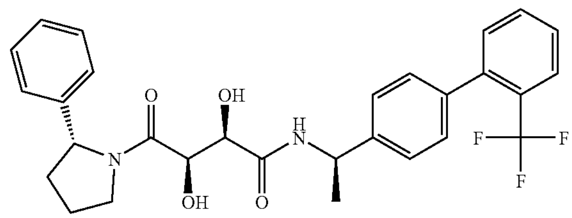 | 526.2 | 527.7 |
| 861 | 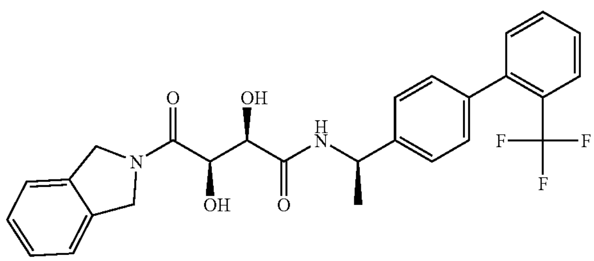 | 498.2 | 499.0 |
| 862 | 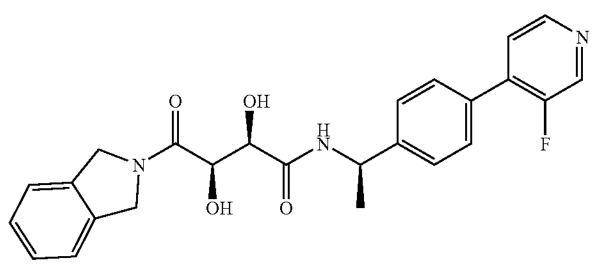 | 449.2 | 450.0 |
| 863 | 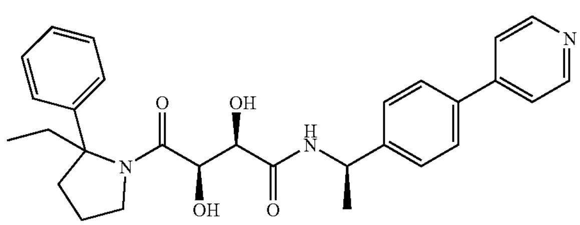 | 487.3 | 488.1 |
| 864 | 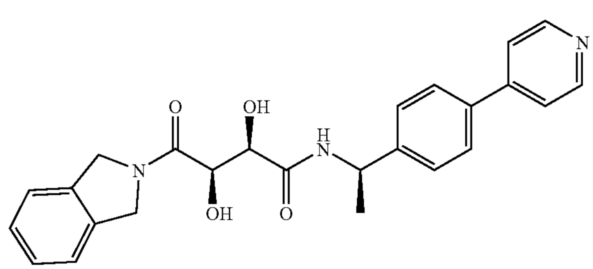 | 431.2 | 432.1 |

-continued

| Compound # | Structure | Exact mass | MS m/e (M + H) |
|---|---|---|---|
| 865 | 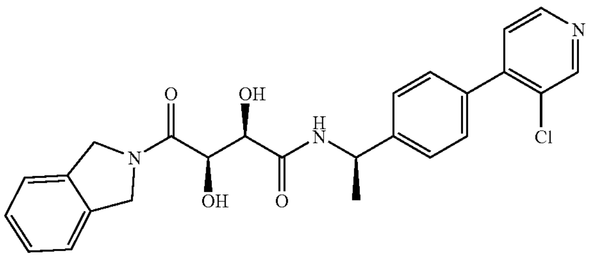 | 465.2 | 466.1 |
| 866 | 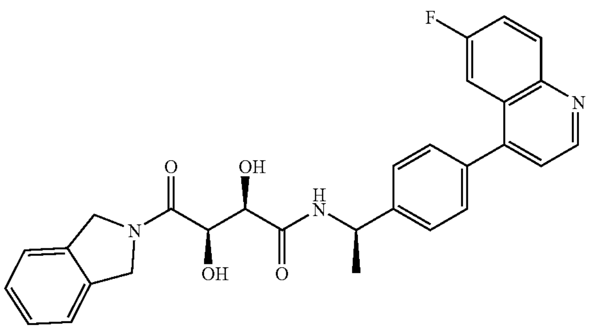 | 499.2 | 500.0 |
| 867 | 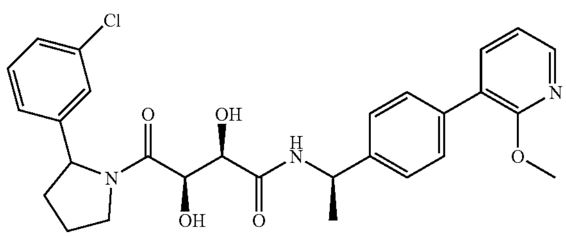 | 523.2 | 524.2 |
| 868 | 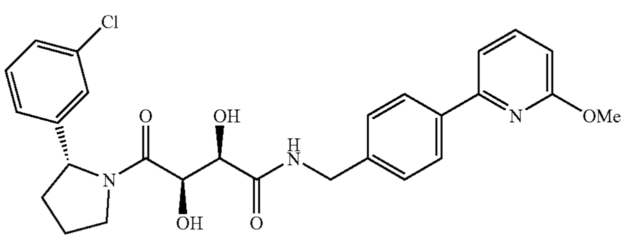 | 509.2 | 510.1 |
| 869 | 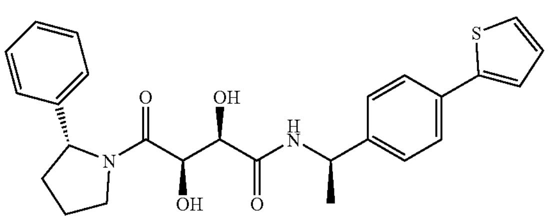 | 464.2 | 464.9 |
| 870 | 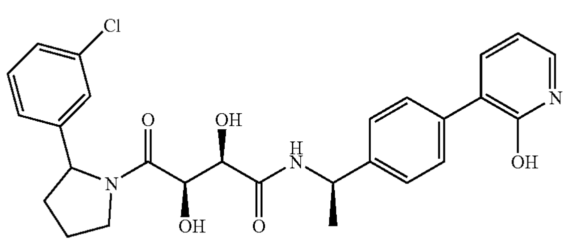 | 509.2 | 510.2 |

-continued

| Compound # | Structure | Exact mass | MS m/e (M + H) |
|---|---|---|---|
| 871 | 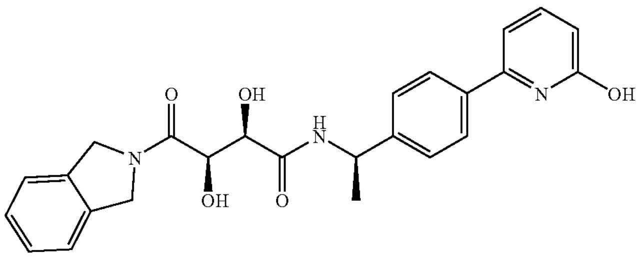 | 447.2 | 448.2 |
| 872 | 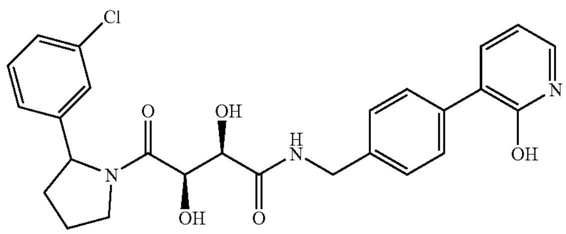 | 495.2 | 496.2 |
| 873 | 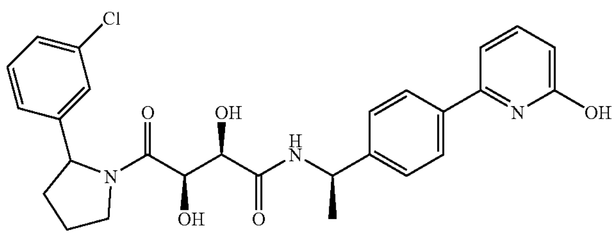 | 509.2 | 510.2 |
| 874 | 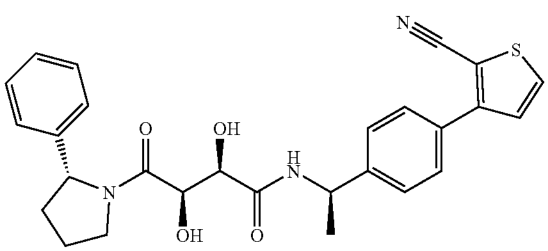 | 489.2 | 511.9 (M + Na) |
| 875 | 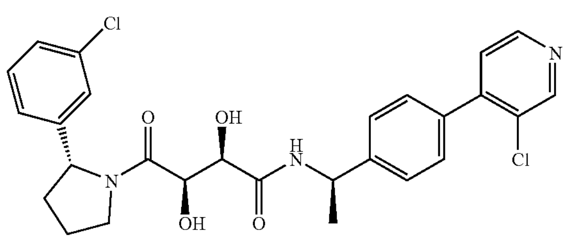 | 527.1 | 528.1 |
| 876 | 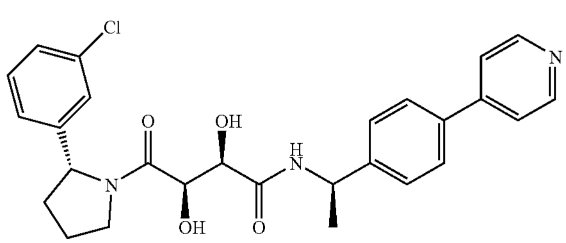 | 493.1 | 494.1 |

-continued
| Compound # | Structure | Exact mass | MS m/e (M + H) |
|---|---|---|---|
| 877 | 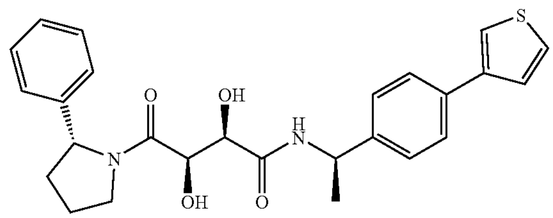 | 464.2 | 464.9 |
| 878 | 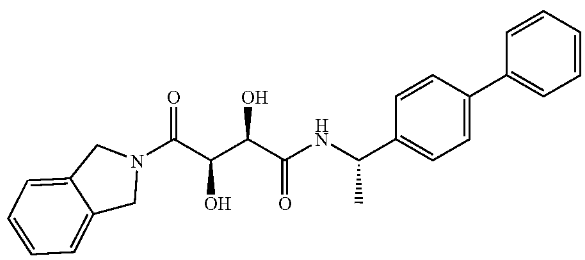 | 430.2 | 431.2 |
| 879 | 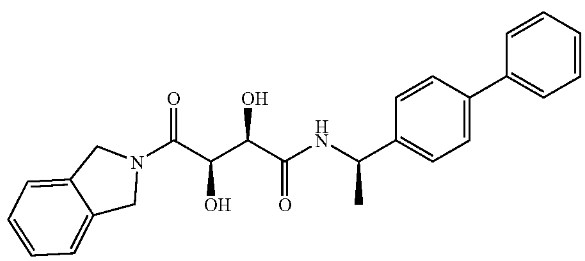 | 430.2 | 431.2 |
| 880 | 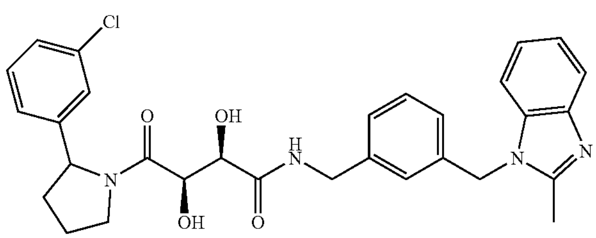 | 444.2 | 445.2 |
Example 22
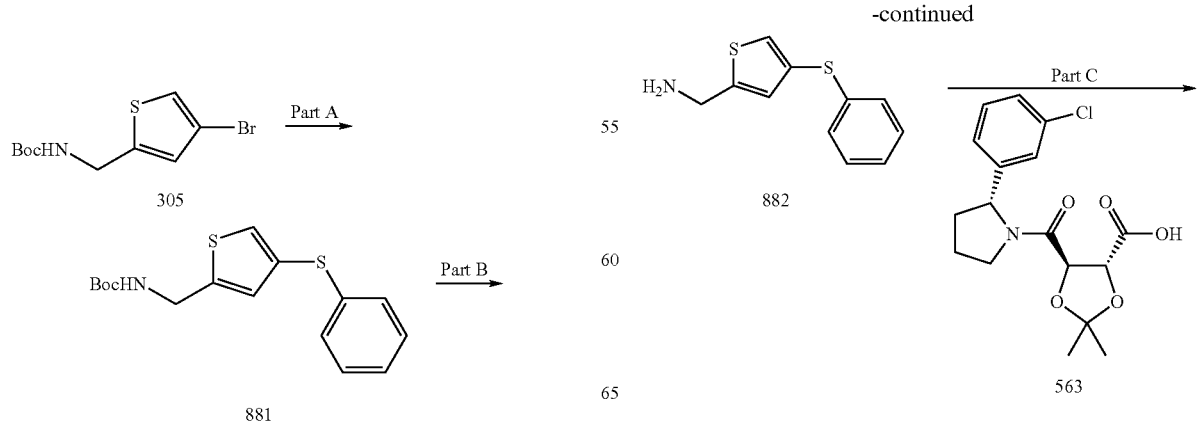

-continued

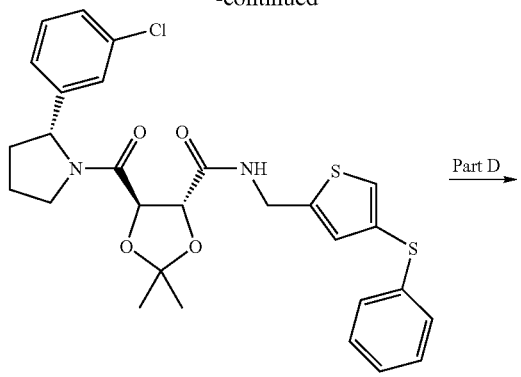

883

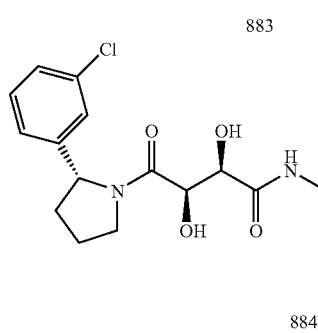

884

Part A:
To 305 (100 mg, 0.34 mmol) in THF (2 mL) at −90° C. under argon was added n-butyl lithium (1.6 M, 0.140 mL, 0.22 mmol) dropwise. The reaction mixture was stirred for 30 minutes at −90° C. Then diphenyl disulfide (90 mg, 0.4 mmol) in THF (1 mL) was added slowly. The reaction mixture was stirred for 30 minutes at −90° C. The reaction mixture was quenched with saturated ammonium chloride solution and warmed to room temperature. The mixture was diluted with ethyl acetate (10 mL) and the layers were separated. The organic layer was washed with water and brine. Dried over sodium sulfate and concentrated. Purification by column chromatography (SiO$_2$, 5% EtOAc/hexane) afforded 881 (19 mg, 59%). HPLC-MS $t_R$=2.28 min (UV$_{254\ nm}$); mass calculated for formula C$_{16}$H$_{19}$NO$_2$S$_2$ 321.09, observed LCMS m/z 322.2 (M+H).

Part B:
To 881 (66 mg, 0.2 mmol) was added 4N HCl in dioxane (1 mL). The reaction mixture was stirred for 1 hour. The solvents were removed in vacuo and the crude product was used without further purification. HPLC-MS $t_R$=1.12 min (UV$_{254\ nm}$); mass calculated for formula C$_{11}$H$_{11}$NS$_2$ 221.0, observed LCMS m/z 222.1 (M+H).

Part C:
To 563 (56 mg, 0.16 mmol) in DMF (2 mL) was added 882 (66 mg, 0.26 mmol), DIEA (82 µL, 0.46 mmol) and HATU (78 mg, 0.24 mmol). The reaction mixture was stirred overnight at room temperature. The reaction mixture was diluted with ethyl acetate (20 mL) and water (20 mL). The layers were separated and the aqueous layer was extracted with ethyl acetate. The combined organic layers were washed with sodium bicarbonate solution and brine, dried over sodium sulfate and concentrated. Compound 883 (43 mg, 48%) was used without further purification. HPLC-MS $t_R$=2.40 min (UV$_{254\ nm}$); mass calculated for formula C$_{28}$H$_{29}$ClN$_2$O$_4$S$_2$ 556.1, observed LCMS m/z 557.0 (M+H).

Part D:
Compound 883 (25 mg, 0.04 mmol) was dissolved in 80:20 TFA:water (1 mL) and stirred for 1.5 hours. The reaction was quenched with 1:1 water:acetonitrile (1 mL) and the solvents were removed in vacuo. Purification by reverse phase prep-LC afforded 884 as a white solid (5 mg, 22%). HPLC-MS $t_R$=2.04 min (UV$_{254\ nm}$); mass calculated for formula C$_{25}$H$_{25}$ClN$_2$O$_4$S$_2$ 516.1, observed LCMS m/z 517.1 (M+H).

Example 23

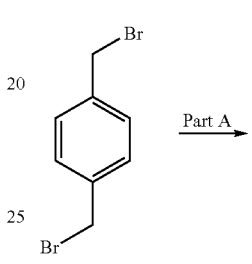

885

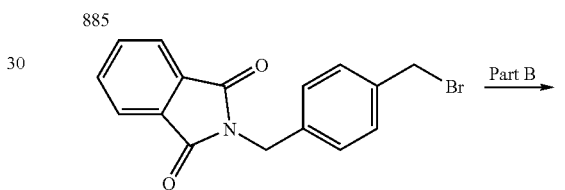

886

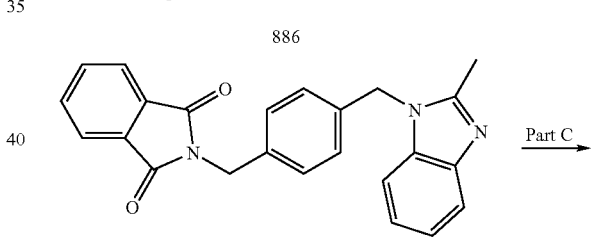

887

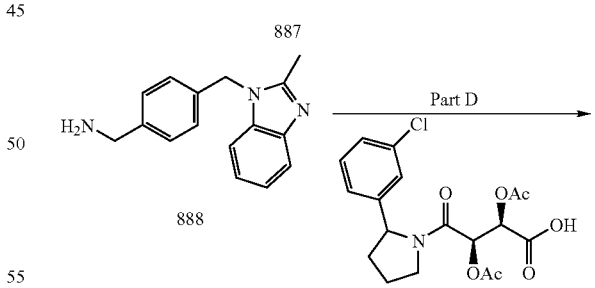

888        554

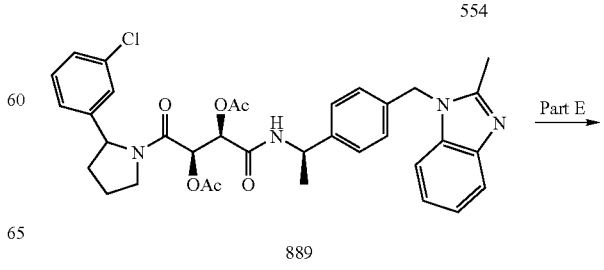

889

-continued

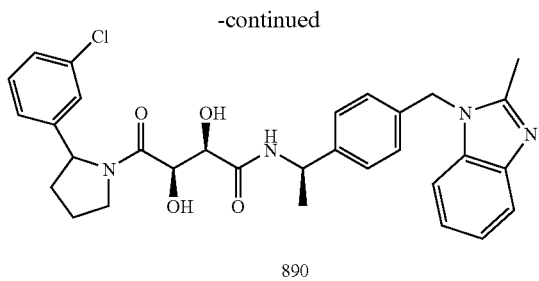

890

Part A:

A mixture of ☐,☐'-dibromo-p-xylene (885) (528 mg, 2.0 mmol), phthalimide (294 mg, 2.0 mmol) and cesium carbonate (717 mg, 2.2 mmol) in DMF (5 mL) was stirred for 4 hours. The reaction mixture was filtered and the filtrate was concentrated. The residue was dissolved in DCM and washed with bicarbonate solution and brine. The organic layer was dried over sodium sulfate and concentrated. Recrystallization from 75% EtOAc/hexanes removed the dialkylated product. The mother liquor was concentrated and the monoalkylated product 886 was isolated by column chromatography (SiO$_2$, 50% DCM/Hex) as a white solid (110 mg, 16%). $^1$H NMR (400 MHz, CDCl$_3$) δ 7.84 (d, 2H, J=2.4 Hz), 7.72 (d, 2H, J=2.4 Hz), 7.41 (d, 2H, J=7.2 Hz), 7.34 (d, 2H, J=7.2 Hz), 4.84 (s, 2H), 4.46 (s, 2H).

Part B:

A mixture of 886 (110 mg, 0.33 mmol), 2-methyl benzimidazole (44 mg, 0.33 mmol) and cesium carbonate (114 mg, 0.35 mmol) in DMF (5 mL) was stirred overnight at room temperature. The reaction mixture was filtered and concentrated. The residue was partitioned between bicarbonate solution and ethyl acetate. The layers were separated and the aqueous layer was extracted with ethyl acetate. The combined organic layer was washed with brine, dried over sodium sulfate and concentrated to afford 887 as an off-white solid (120 mg, 95%). $^1$H NMR (400 MHz, CDCl$_3$) δ 7.82 (m, 2H), 7.70 (m, 2H), 7.37 (d, 2H, J=8.0 Hz), 7.25-7.18 (m, 4H), 7.00 (d, 2H, J=8.7 Hz), 5.30 (s, 2H), 4.82 (s, 2H), 2.57 (s, 3H).

Part C:

A mixture of 887 (120 mg, 0.31 mmol) and hydrazine hydrate (61 µL, 1.26 mmol) in ethanol (10 mL) was heated to reflux for 3 hours. The reaction mixture was concentrated. The residue was dissolved in ethyl acetate and washed with bicarbonate solution. The aqueous layer was extracted with ethyl acetate. The combined organic layer was washed with brine, dried over sodium sulfate and concentrated to afford 888 as a yellow oil (31 mg, 40%). $^1$H NMR (400 MHz, CDCl$_3$) δ 7.72 (dd, 1H, J=1.2, 8.4 Hz), 7.51 (dd, 1H, J=3.2, 6.4 Hz), 7.26-7.17 (m, 4H), 7.01 (d, 2H, J=8 Hz), 5.30 (s, 2H), 3.85 (s, 2H), 2.60 (s, 2H), 2.57 (s, 3H).

Part D:

A mixture of 888 (31 mg, 0.12 mmol), 554 (40 mg, 0.1 mmol), DIEA (38 µL, 0.22 mmol) and HATU (46 mg, 0.12 mmol) in DMF (2 mL) was stirred overnight. The DMF was removed in vacuo. The residue was dissolved in ethyl acetate, washed with bicarbonate solution and brine, dried over sodium sulfate and concentrated to afford 889 as a film (61 mg, 96%). HPLC-MS t$_R$=1.38 min (UV$_{254nm}$); mass calculated for formula C$_{34}$H$_{35}$ClN$_4$O$_6$ 630.2, observed LCMS m/z 631.2 (M+H).

Part E:

To 889 (61 mg, 0.097 mmol) in methanol (2 mL) was added anhydrous hydrazine (5 µL, 0.16 mmol). The reaction mixture was stirred overnight, concentrated, purified by reverse phase prep-LC and treated with HCl to afford 890 as an HCl salt (19 mg, 33%). HPLC-MS t$_R$=3.42 min (UV$_{254\ nm}$, 10 min); mass calculated for formula C$_{30}$H$_{31}$ClN$_4$O$_4$ 546.2, observed LCMS m/z 547.2 (M+H).

| Compound # | Structure | Exact mass | MS m/e (M + H) |
|---|---|---|---|
| 891 | 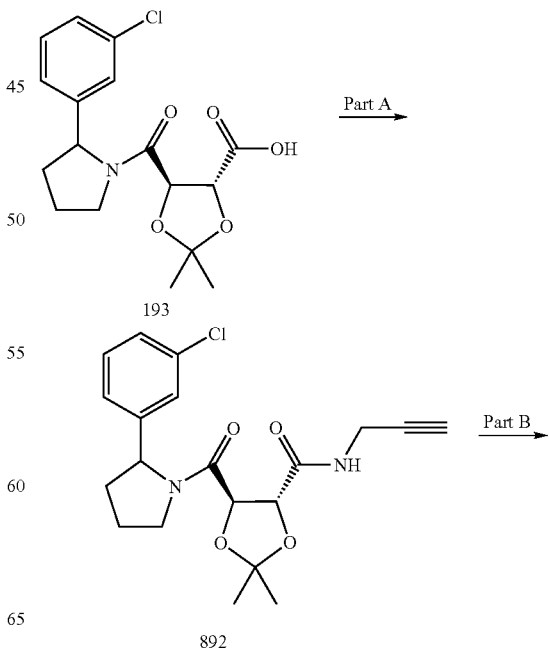 | 546.2 | 547.2 |

Example 24

Alkyne Linkages

Example 24A

1053
-continued

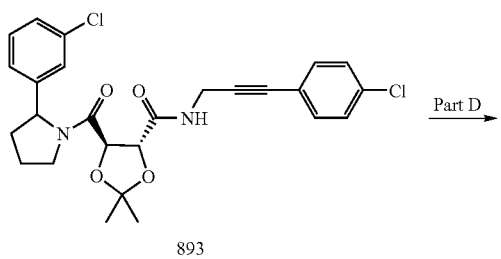

893

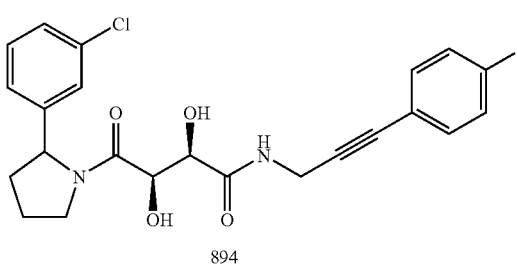

894

Part A:

To 193 (200 mg, 0.57 mmol) in DCM (5 mL) was added propargyl amine (62 mg, 1.13 mmol), DIEA (396 μL, 1.71 mmol), DMAP (7 mg, 0.06 mmol) and EDC (140 mg, 0.74 mmol). The reaction mixture was stirred overnight at room temperature. The reaction mixture was diluted with ethyl acetate, washed with water and brine, dried over sodium sulfate and concentrated. Purification by column chromatography (SiO$_2$, 60% ethyl acetate/hexanes) afforded 892 as an oil (136 mg, 62%). HPLC-MS $t_R$=1.76 and 1.83 min (UV$_{254\ nm}$); Mass calculated for formula C$_{20}$H$_{23}$ClN$_2$O$_4$ 390.1, observed LCMS m/z 391.1 (M+H).

Part B:

To 892 (20 mg, 0.05 mmol) in DMF (1 mL) was added 4-chloro-iodobenzene (24 mg, 0.10 mmol), copper(I) iodide (1 mg, 0.005 mmol), PdCl$_2$(Ph$_3$P)$_2$ (1.8 mg, 0.003 mmol) and triethylamine (1 mL). The reaction mixture was stirred overnight at 50° C. under argon atmosphere. The reaction mixture was diluted with ethyl acetate, washed with 0.1 N HCl, dried over sodium sulfate and concentrated. The material was used without further purification. 893: HPLC-MS $t_R$=2.28 and 2.32 min (UV$_{254\ nm}$); Mass calculated for formula C$_{26}$H$_{26}$Cl$_2$N$_2$O$_4$ 500.1, observed LCMS m/z 501.1 (M+H).

Part C:

Compound 893 was dissolved in 4:1 TFA:water (2 mL) and stirred at room temperature for 1.5 hours. The reaction was quenched with 1:1 water:acetonitrile (2 mL) and concentrated. Purification by reverse phase prep-LC afforded 894 as a solid (2 mg). HPLC-MS $t_R$=5.02 min (UV$_{254\ nm}$, 10 min); Mass calculated for formula C$_{23}$H$_{22}$Cl$_2$N$_2$O$_4$ 460.1, observed LCMS m/z 461.2 (M+H).

1054
Example 24B

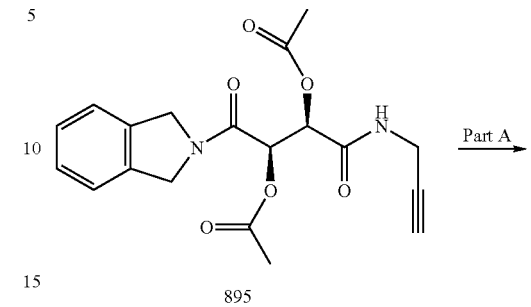

895

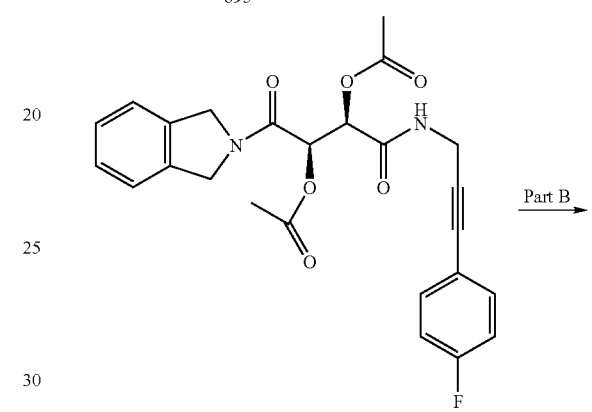

896

897

Compound 895 was obtained via procedures described in Example 2A Part A using isoindoline to open the (+)-diacetyl-L-tartaric anhydride and propargyl amine in the coupling procedure.

Part A:

Compound 895 (138 mg, 0.371 mmol), p-bromofluorobenzene (244 mg, 1.39 mmol), and dichlorobis(triphenylphosphine) palladium (II) (26 mg, 0.037 mmol) were dissolved in 1.5 mL CH$_3$CN and 1.5 mL Et$_3$N. The reaction mixture was heated in a sealed tube under N$_2$ at 80° C. for 2 h. The reaction mixture was allowed to cool to rt. EOAc and 1.0 M pH 7.0 sodium phosphate buffer were added. The layers were separated. The organic layer was washed with water and dried with MgSO$_4$. The solvent was evaporated and the crude product was purified via sgc using 3:1 EtOAc:hexanes as the mobile phase to give 20 mg of compound 896. MS (EI) m/z Obsd M+H 467.19

Part B:

Compound 896 (20 mg, 0.043 mmol) was dissolved in 3 mL of 2 M methanolic ammonia. The reaction mixture was stirred at rt for 1 h. The reaction mixture was concentrated to dryness. The crude product was purified via prep TLC on silica plates using 97:3 CH$_2$Cl$_2$:MeOH as the mobile phase to give 12 mg of 897. MS (EI) m/z Obsd M+H 383.2.

| Compound # | Structure | Exact mass | MS m/z (M + H) |
|---|---|---|---|
| 898 | 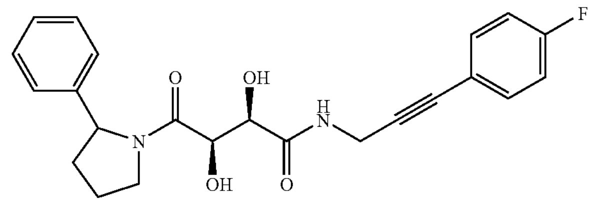 | 410.2 | 411.1 |
| 899 | 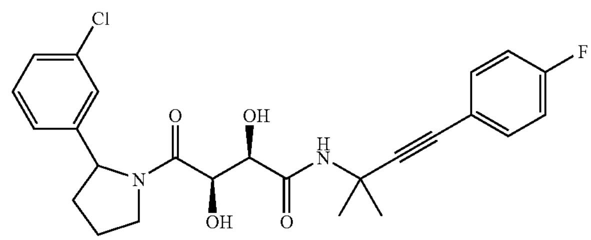 | 472.2 | 473.2 |
| 900 | 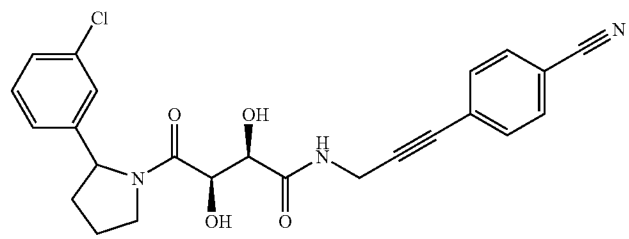 | 451.1 | 452.1 |
| 901 | 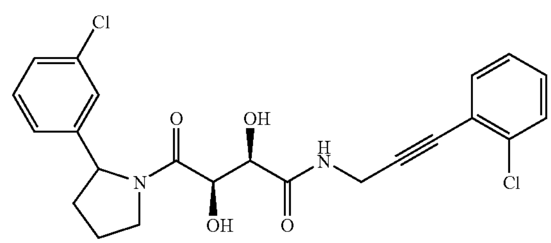 | 460.1 | 461.2 |
| 902 | 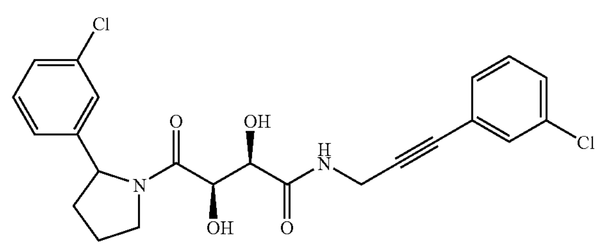 | 460.1 | 461.2 |
| 903 | 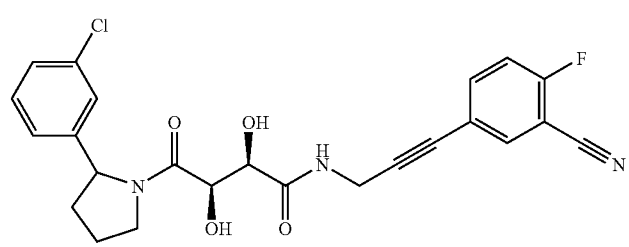 | 469.1 | 470.2 |

Example 25

N-Linked Biaryls

Example 25A

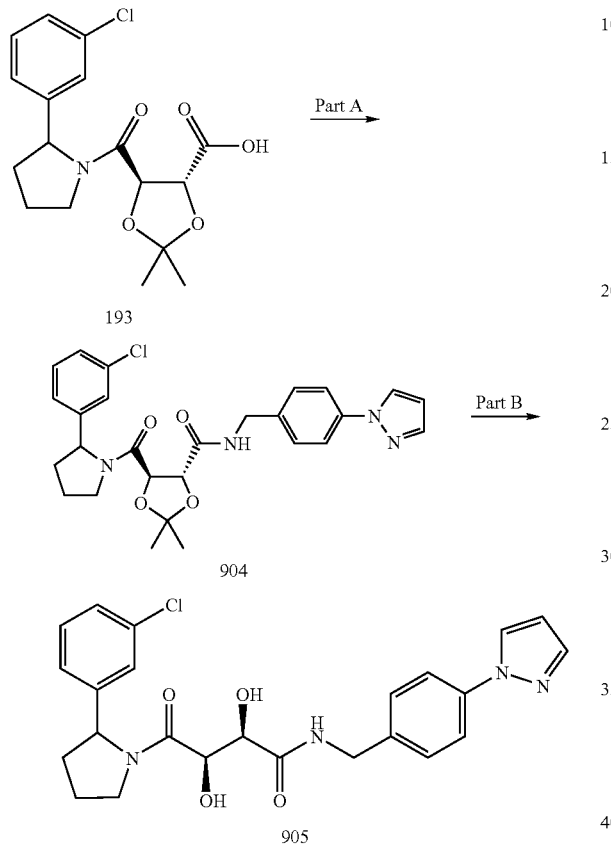

Example 25B

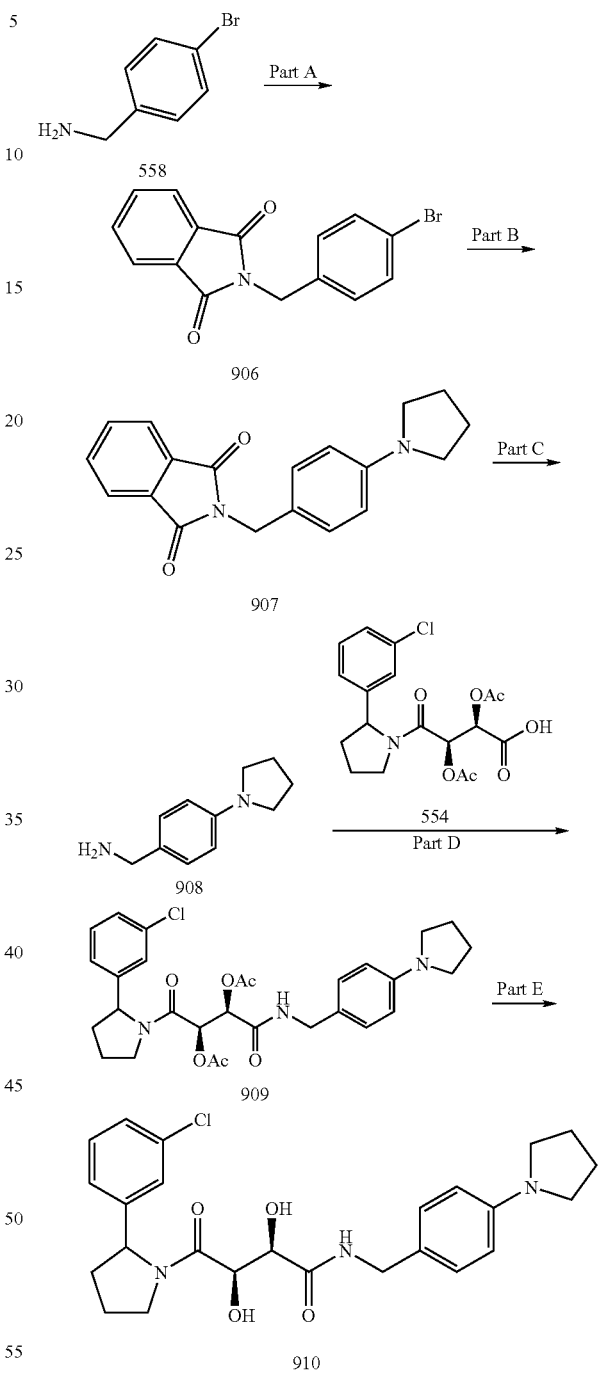

Part A:

To 193 (42 mg, 0.12 mmol) in DMF (2 mL) was added 4-pyrazol-1-yl-benzylamine (25 mg, 0.14 mmol), DIEA (50 µL, 0.29 mmol) and HATU (53 mg, 0.13 mmol). The reaction mixture was stirred overnight at room temperature. The reaction mixture was poured into water and extracted with ethyl acetate. The combined organic layers were washed with 0.1 N NaOH and brine, dried over sodium sulfate and concentrated. The crude material was used without further purification. 904: HPLC-MS $t_R$=1.97 and 2.03 min ($UV_{254\ nm}$); Mass calculated for formula $C_{27}H_{29}ClN_4O_4$ 508.2, observed LCMS m/z 509.2 (M+H).

Part B:

Compound 904 was dissolved in 4:1 TFA:water (2 mL) and stirred at room temperature for 2 hours. The reaction was quenched by the addition of 1:1 acetonitrile:water (4 mL) and the solvents were removed in vacuo. Purification by reverse phase prep-LC afforded 905 as a white solid (33 mg). HPLC-MS $t_R$=4.16 min ($UV_{254\ nm}$, 10 min); Mass calculated for formula $C_{24}H_{25}ClN_4O_4$ 468.2, observed LCMS m/z 469.2 (M+H).

Part A:

A mixture of 4-bromobenzyl amine hydrochloride (558) (2.0 g, 9.0 mmol), monomethyl phthalate (1.94 g, 10.8 mmol), EDC (2.07 g, 10.8 mmol), HOBt (1.82 g, 13.5 mmol) and triethylamine (3.8 mL, 27.0 mmol) in DCM (50 mL) was stirred overnight. The reaction mixture was diluted DCM and washed with 1.0 N HCl, water, bicarbonate solution and brine, dried over sodium sulfate and concentrated. Recrystallization of the mixture from ethyl acetate afforded 906 as a solid (1.72 g, 61%). $^1$H NMR (400 MHz, CDCl$_3$) δ 7.83 (m, 2H), 7.70 (m, 2H), 7.42 (d, 2H, J=8.2 Hz), 7.29 (d, 2H, J=8.2 Hz), 4.79 (s, 2H). HPLC-MS $t_R$=2.05 min (UV$_{254\ nm}$); Mass calculated for formula C$_{15}$H$_{10}$BrNO$_2$ 315.0, observed LCMS m/z 316.0 (M+H).

Part B:

A mixture of 906 (100 mg, 0.32 mmol), pyrrolidine (34 mg, 0.48 mmol), potassium phosphate (171 mg, 0.80 mmol), Pd$_2$(dba)$_3$ (8 mg, 0.008 mmol) and 2-(dicyclohexylphosphino)biphenyl (11 mg, 0.032 mmol) in dioxane (3 mL) were stirred under argon atmosphere at 90° C. overnight. The reaction mixture was filtered through celite and concentrated. The yellow residue was purified by column chromatography (SiO$_2$, 5% EtOAc/DCM) to afford 907 (82 mg, 84%). HPLC-MS $t_R$=2.13 min (UV$_{254\ nm}$); Mass calculated for formula C$_{19}$H$_{18}$N$_2$O$_2$ 306.1, observed LCMS m/z 307.2 (M+H).

Part C:

To 907 (82 mg, 0.268 mmol) in 1:1 ethanol:DCM (4 mL) was added hydrazine monohydrate (52 μL, 1.07 mmol). The reaction mixture was heated to reflux overnight. The precipitate was removed by filtration and the filtrate was concentrated. The residue was dissolved in ethyl acetate, washed with water and brine, dried over sodium sulfate and concentrated to afford 908 as a white solid (23 mg, 49%). HPLC-MS $t_R$=0.86 min (UV$_{254\ nm}$); Mass calculated for formula C$_{11}$H$_{16}$N$_2$ 176.1, observed LCMS m/z 177.1 (M+H).

Part D:

A mixture of 554 (30 mg, 0.076 mmol), 908 (17.3 mg, 0.098 mmol), DIEA (40 μL, 0.226 mmol), DMAP (1 mg) and HATU (37 mg, 0.098 mmol) in DMF (1 mL) was stirred overnight. The reaction mixture was poured in water and extracted with ethyl acetate. The combined organic layers were washed with 0.1 N NaOH, water and brine, dried over sodium sulfate and concentrated. Compound 909 was used without further purification.

Part E:

To 909 in 3:1 methanol:water (2 mL) was added potassium carbonate (20 mg). The reaction mixture was stirred for 30 minutes. The reaction mixture was partitioned between ethyl acetate and water. The organic layer was separated, washed with brine, dried over sodium sulfate and concentrated. Purification by reverse phase prep-LC afforded 910 as a solid (2 mg). HPLC-MS $t_R$=3.57 min (UV$_{254\ nm}$ 10 min); Mass calculated for formula C$_{25}$H$_{30}$ClN$_3$O$_4$ 471.2, observed LCMS m/z 472.2 (M+H).

Example 25C

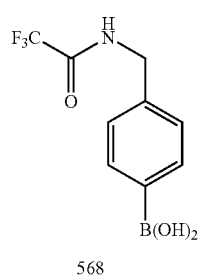
568

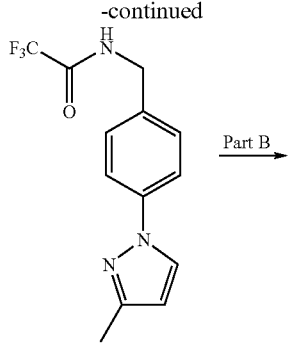
911

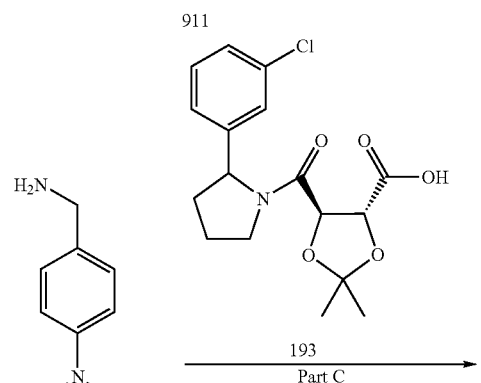
912

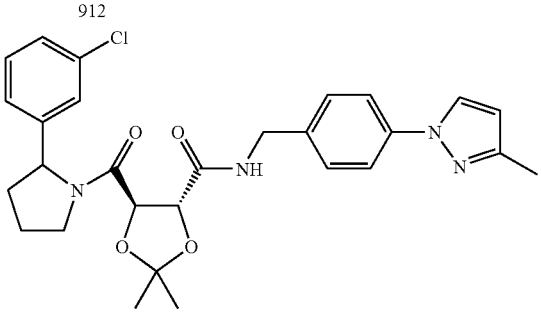

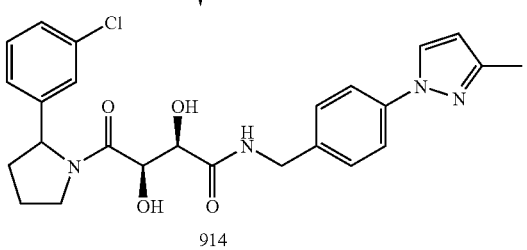
914

Compound 568 was prepared according to the procedure of Maku, S. et. al. (*J. Comb. Chem.* 2003, 5, 379)

Part A:

A mixture of compound 568 (740 mg, 3 mmol), 3-methylpyrazole (123 mg, 1.5 mmol), copper (II) acetate (409 mg, 2.25 mmol), pyridine (0.25 ml), 3 mmol) in tetrahydrofuran (10 mL) was stirred at room temperature open to the air for 60 hours. The reaction mixture was diluted with ethyl acetate, filtered through celite and concentrated. Purification by column chromatography (SiO$_2$, 30% ethyl acetate/hexanes to 50% ethyl acetate/hexane) afforded the product as an impure white solid (450 mg). Further purification by column chromatography (SiO$_2$, dichloromethane to 5% ethyl acetate/dichloromethane) afforded 911 as a solid (295 mg, 70% purity). $^1$H NMR (400 MHz, acetone-d$_6$) δ 8.97 (bs, 1H, NH), 8.16 (d, 1H, J=2.4 Hz), 7.76 (d, 2H, J=8.4 Hz), 7.42 (d, 2H, Part D:

Compound 913 was dissolved in 4:1 TFA:water (2 mL) and stirred at room temperature for 2 hours. The reaction was quenched by the addition of 1:1 acetonitrile:water (4 mL) and the solvents were removed in vacuo. Purification by reverse phase prep-LC afforded 914 as a white solid (35 mg). HPLC-MS t$_R$=4.31 min (UV$_{254\ nm}$, 10 min); Mass calculated for formula C$_{25}$H$_{27}$ClN$_4$O$_4$ 482.1, observed LCMS m/z 483.1 (M+H).

Example 25D

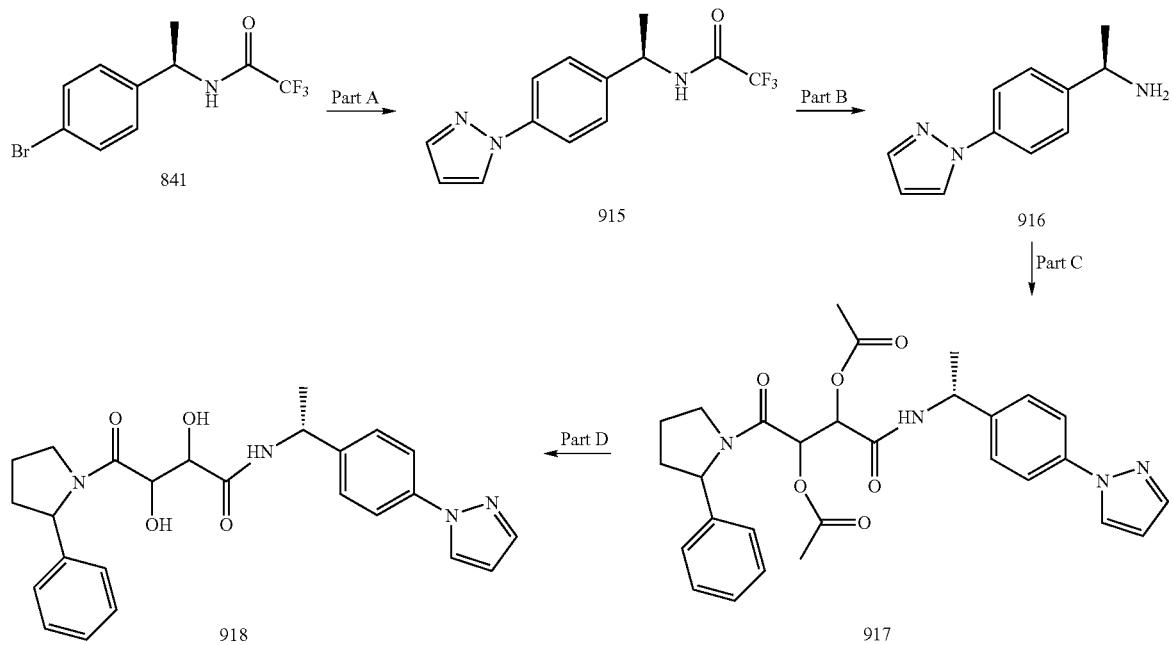

J=8.8 Hz), 6.27 (d, 1H, J=2.4 Hz), 4.55 (d, 2H, J=5.6 Hz), 2.28 (s, 3H); HPLC-MS t$_R$=1.62 min (UV$_{254\ nm}$); Mass calculated for formula C$_{13}$H$_{12}$F$_3$N$_3$O 283.1, observed LCMS m/z 284.2 (M+H).

Part B:

To 911 (165 mg, 0.43 mmol) in 1:1 methanol: water (2 mL) was added 10% potassium carbonate in 2:1 methanol:water (7 mL). The reaction mixture was stirred overnight at room temperature. The reaction mixture was concentrated and the residue was dissolved in ethyl acetate. The ethyl acetate layer was washed with water and brine, dried over sodium sulfate and concentrated to afford 912 as a white solid (69 mg, 86%). HPLC-MS t$_R$=0.75 min (UV$_{254\ nm}$); Mass calculated for formula C$_{11}$H$_{13}$N$_3$ 187.1, observed LCMS m/z 188.1 (M+H).

Part C:

To 193 (65 mg, 0.18 mmol) in DMF (2 mL) was added 912 (38 mg, 0.2 mmol), DIEA (70 µL, 0.4 mmol) and HATU (76 mg, 0.21 mmol). The reaction mixture was stirred overnight at room temperature. The reaction mixture was poured into water and extracted with ethyl acetate. The combined organic layers were washed with 0.1 N NaOH and brine, dried over sodium sulfate and concentrated. Compound 913 was used without further purification. HPLC-MS t$_R$=2.05 and 2.09 min (UV$_{254\ nm}$); Mass calculated for formula C$_{28}$H$_{31}$ClN$_4$O$_4$ 522.2, observed LCMS m/z 523.2 (M+H).

Part A:

Compound 841 (0.5 g, 1.69 mmol), pyrazole (0.14 g, 2.05 mmol), CuI (0.064 g, 0.336 mmol), 1,10-phenanthroline (0.12 g, 0.66 mmol), and Cs$_2$CO$_3$ (1.1 g, 3.37 mmol) were dissolved in dimethylacetamide and stirred for 20 h at 140° C. under N$_2$. The reaction mixture was allowed to cool to rt and diluted with EtOAc. The resulting mixture was washed with water and concentrated to dryness. The resulting material was purified via flash sgc using CH$_2$Cl$_2$:MeOH:conc NH$_4$OH— (200:10:1) as the mobile phase to give 0.30 g of 915. Data for 915: $^1$HNMR (400 MHz, CDCl$_3$) δ 7.98 (s, 1H), 7.80-7.74 (m, 3H), 7.48 (d, 2H), 6.55 (s, 1H), 5.23 (m, 1H), 1.68 (d, J=4 Hz, 2H). MS (EI) of m/z Obsd. M+H 283.97

Part B:

Compound 915 (0.20 g, 0.67 mmol) was dissolved in 10 mL of MeOH. Aqueous LiOH (10 mL/1.0 M) was added. The reaction mixture was stirred at rt for 4 h. The solution was partially concentrated in vacuo to remove the MeOH. The resulting material was extracted with EtOAc. The organic layer was washed with water, dried with Na$_2$SO$_4$, filtered, and concentrated to give 0.14 g of 916. Data for 916: $^1$HNMR (400 MHz, CDCl$_3$) δ 7.94 (s, 1H), 7.75 (s, 1H), 7.68 (d, J=9 Hz, 2H), 7.47 (d, J=9 Hz, 2H), 4.26-4.13 (m, 1H), 1.44 (d, J=7 Hz, 3H).

Parts C and D:

Compounds 917 and 918 were prepared via procedures similar to those described in Example 14-Parts D and E. Data for 917: ¹HNMR (400 MHz, CDCl₃) δ 7.98-7.62 (m, 4H), 7.46-7.13 (m, 8H), 6.68-6.47 (m, 2H), 5.86-5.41 (m, 2H), 5.24-5.10 (m, 2H), 4.05-3.48 (m, 2H), 2.22-1.79 (m, 10H), 1.58-1.55 (m, 2H). Data for 918: ¹HNMR (400 MHz, CDCl₃) δ 7.96 (s, 1H), 7.80 (s, 1H), 7.75-7.59 (m, 2H), 7.48-6.95 (m, 8H), 6.52 (s, 1H), 5.32-5.13 (m, 2H), 4.97-4.05 (m, 2H), 3.99-3.68 (m, 3H), 2.46-1.80 (m, 4H), 1.62-1.51 (m, 3H); MS (EI) m/z Obsd. M+H 449.1.

| Compound # | Structure | Exact mass | MS m/e (M + H) |
|---|---|---|---|
| 919 | 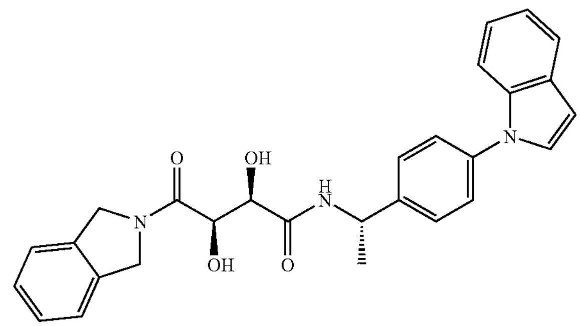 | 469.2 | 470.1 |
| 920 | 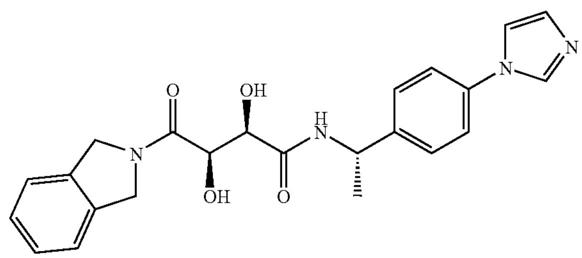 | 420.2 | 421.1 |
| 921 | 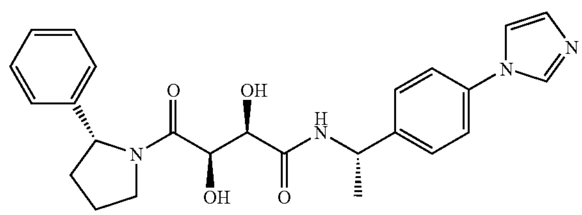 | 448.2 | 449.1 |
| 922 | 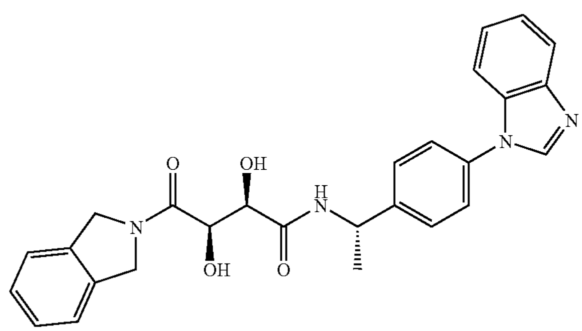 | 470.2 | 471.1 |
| 923 | 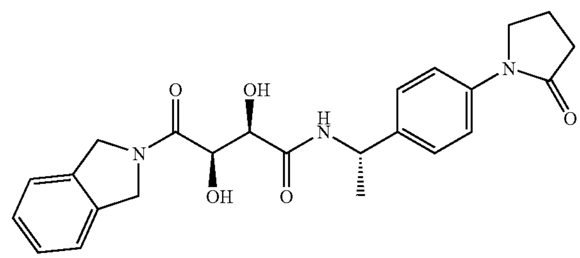 | 437.2 | 438.2 |

-continued

| Compound # | Structure | Exact mass | MS m/e (M + H) |
|---|---|---|---|
| 924 | 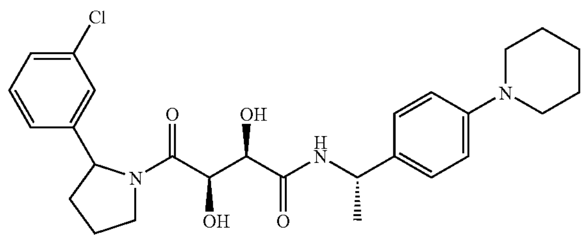 | 485.2 | 486.2 |
| 925 | 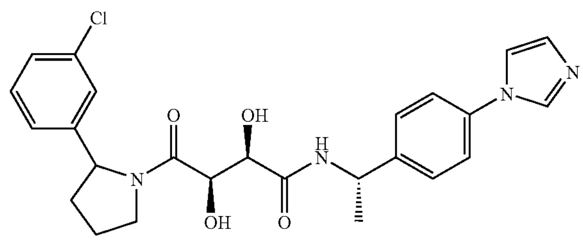 | 468.2 | 469.1 |
| 926 | 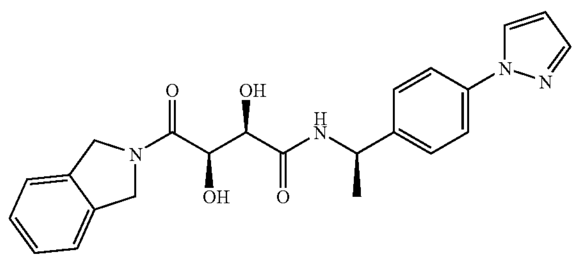 | 420.2 | 421.1 |
| 927 | 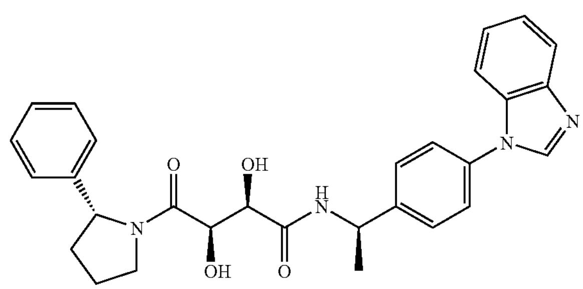 | 498.2 | 499.1 |
| 928 | 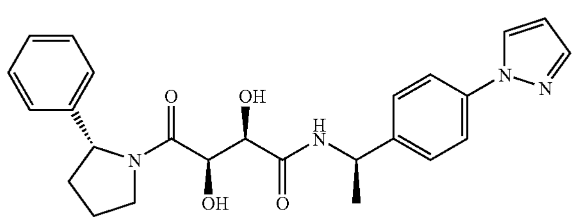 | 448.2 | 449.1 |
| 929 | 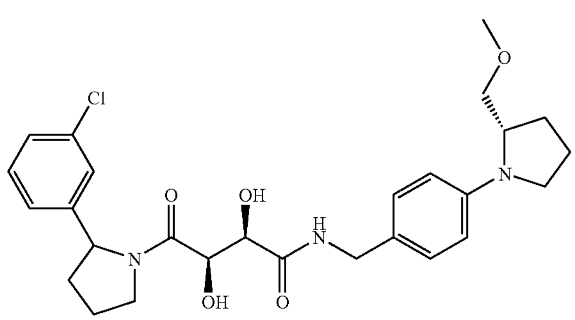 | 515.2 | 516.3 |

-continued
| Compound # | Structure | Exact mass | MS m/e (M + H) |
|---|---|---|---|
| 930 | 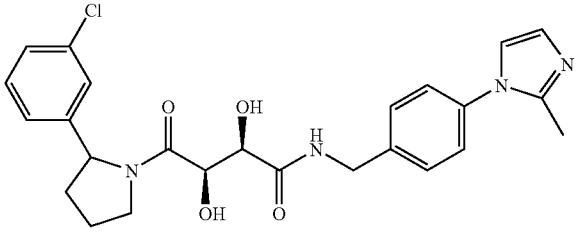 | 482.2 | 483.1 |
| 931 | 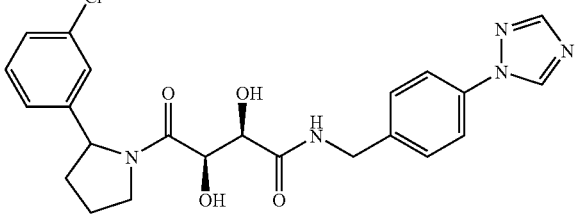 | 469.2 | 470.0 |
| 932 | 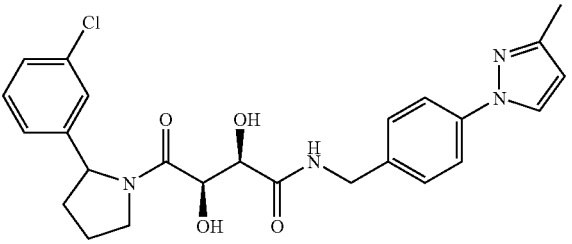 | 482.2 | 483.1 |
| 933 | 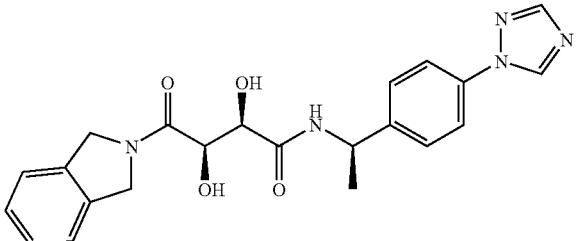 | 421.2 | 422.1 |
| 934 | 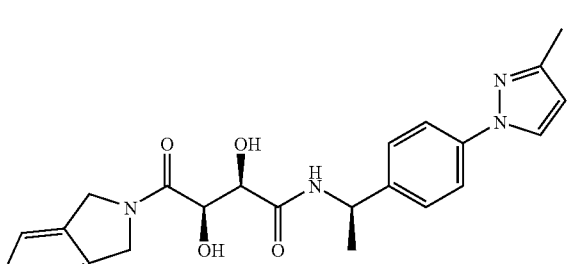 | 434.2 | 435.1 |
| 935 | 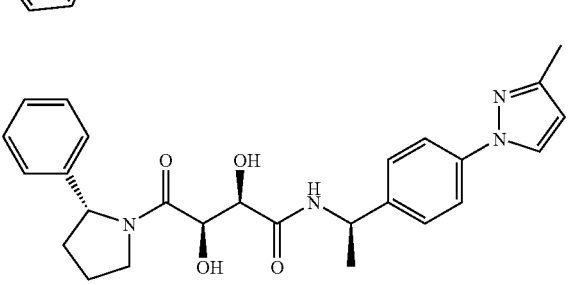 | 462.2 | 463.1 |

-continued

| Compound # | Structure | Exact mass | MS m/e (M + H) |
|---|---|---|---|
| 936 | 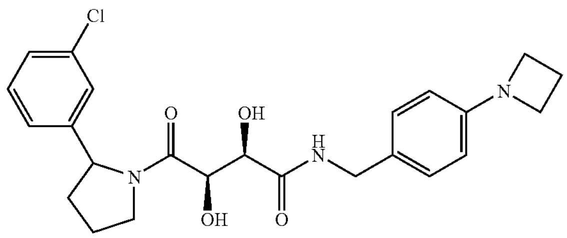 | 457.2 | 458.2 |
| 937 | 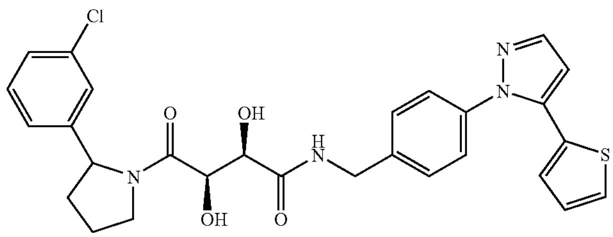 | 550.1 | 551.0 |
| 938 | 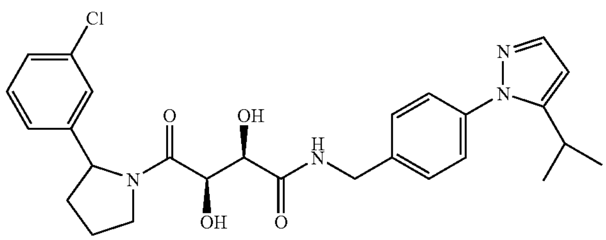 | 510.2 | 511.1 |
| 939 | 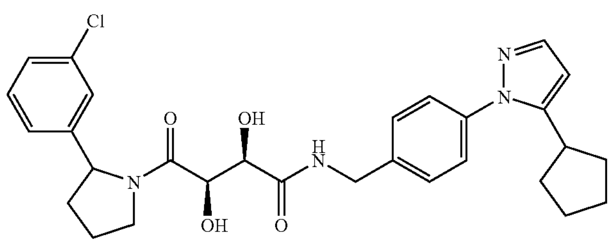 | 536.2 | 537.1 |
| 940 | 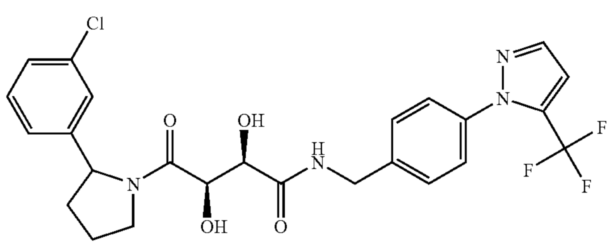 | 536.1 | 537.1 |
| 941 | 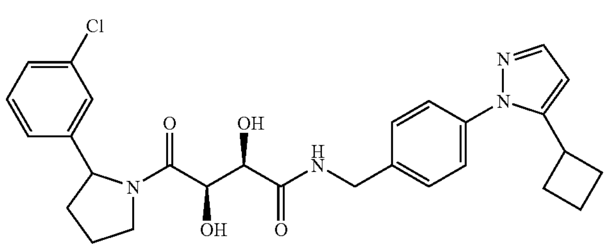 | 522.2 | 523.2 |

-continued

| Compound # | Structure | Exact mass | MS m/e (M + H) |
|---|---|---|---|
| 942 | 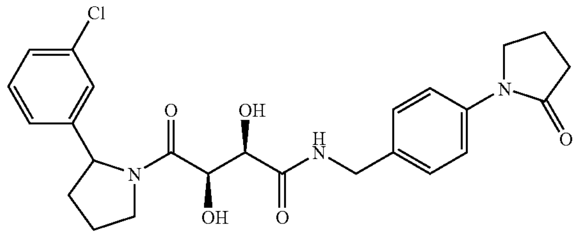 | 485.2 | 486.1 |
| 943 | 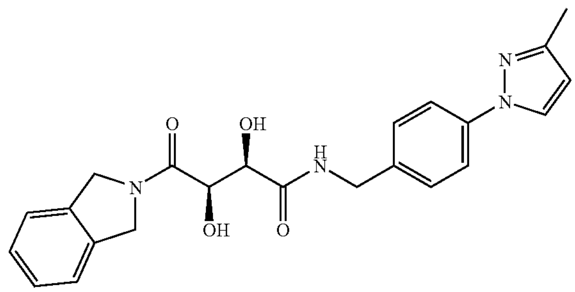 | 420.2 | 421.1 |
| 944 | 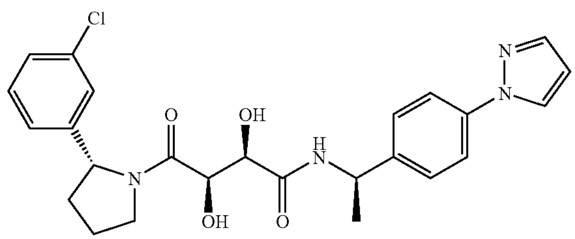 | 482.1 | 483.1 |
| 945 | 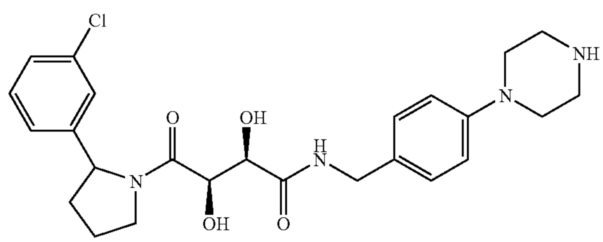 | 486.2 | 487.3 |
| 946 | 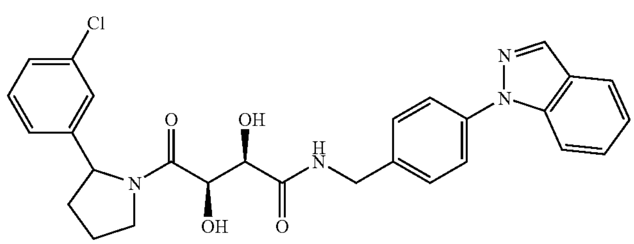 | 518.2 | 519.2 |
| 947 | 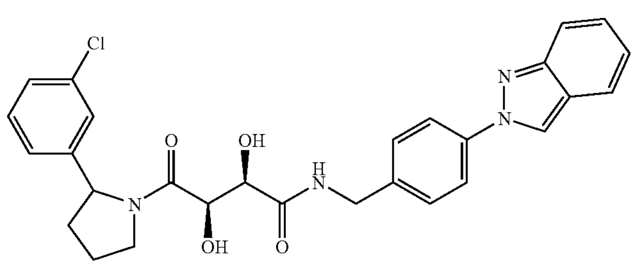 | 518.2 | 519.2 |

-continued

| Compound # | Structure | Exact mass | MS m/e (M + H) |
|---|---|---|---|
| 948 | 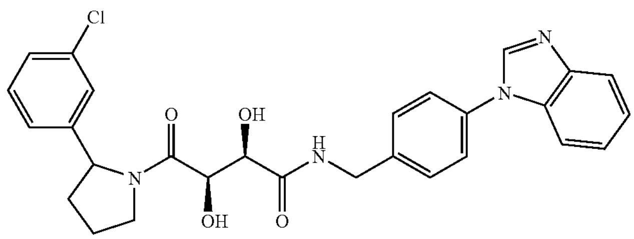 | 518.2 | 519.2 |
| 949 | 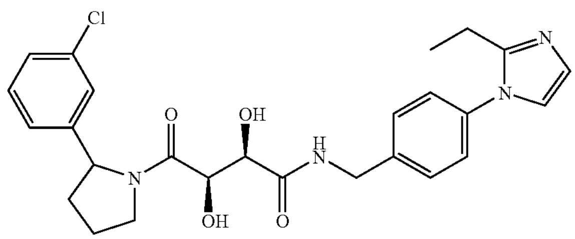 | 496.2 | 497.2 |
| 950 | 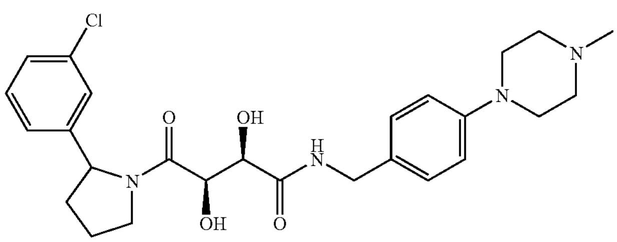 | 500.2 | 501.2 |
| 951 | 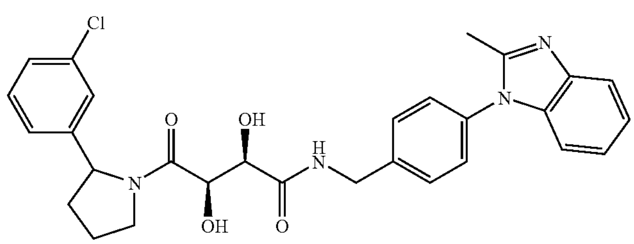 | 532.2 | 533.2 |
| 952 | 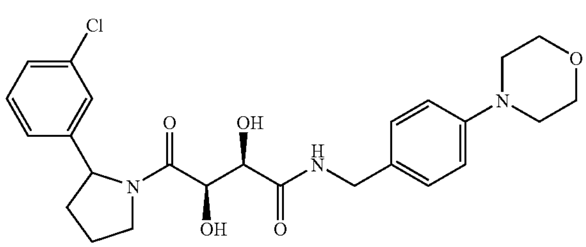 | 487.2 | 488.2 |

Example 26

Aryl-Heteroaryl Biaryl Compounds

Example 26A

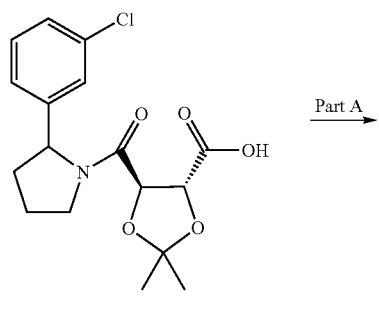

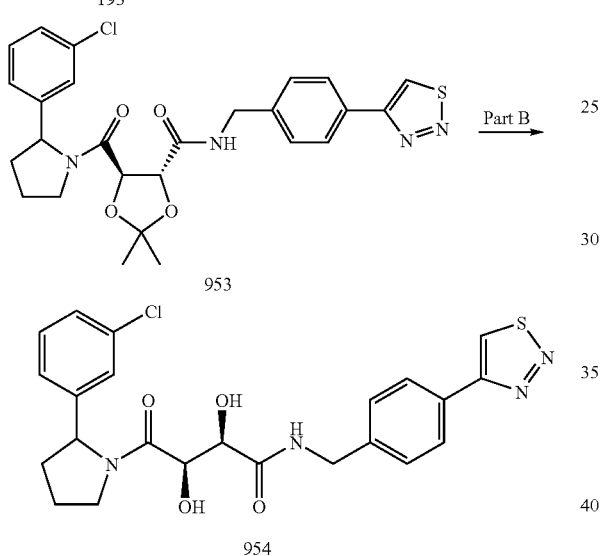

Part A:

To 193 (42 mg, 0.12 mmol) in DMF (2 mL) was added 4-[1,2,3]thiadiazol-4-yl-benzylamine (25 mg, 0.13 mmol), DIEA (45 μL, 0.26 mmol) and HATU (50 mg, 0.13 mmol). The reaction mixture was stirred overnight at room temperature. The reaction mixture was poured into water and extracted with ethyl acetate. The combined organic layers were washed with 0.1 N NaOH and brine, dried over sodium sulfate and concentrated. The crude material was used without further purification. 953: Mass calculated for formula C26H27ClN4O4S 526.1, observed LCMS m/z 527.1 (M+H).

Part B:

Compound 953 was dissolved in 4:1 TFA:water (2 mL) and stirred at room temperature for 2 hours. The reaction was quenched by the addition of 1:1 acetonitrile:water (4 mL) and the solvents were removed in vacuo. Purification by reverse phase prep-LC afforded 954 as a white solid (21 mg). HPLC-MS $t_R$=4.21 min (UV$_{254\ nm}$, 10 min); Mass calculated for formula C$_{23}$H$_{23}$ClN$_4$O$_4$S 486.1, observed LCMS m/z 487.1 (M+H).

Example 26B

Biaryl C—C Linkage

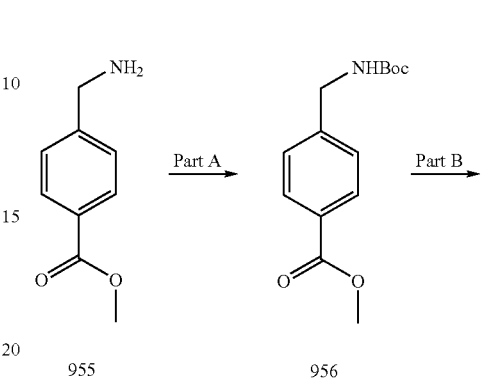

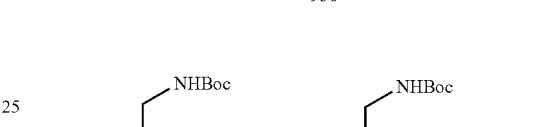

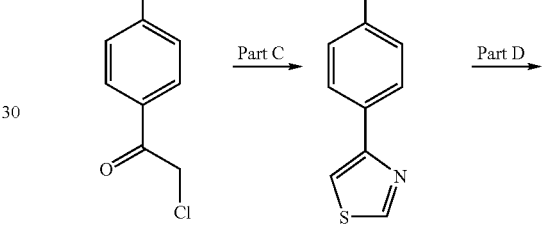

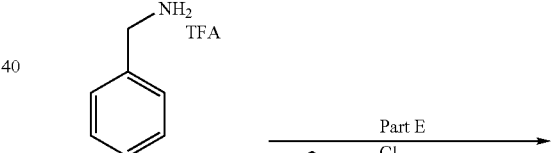

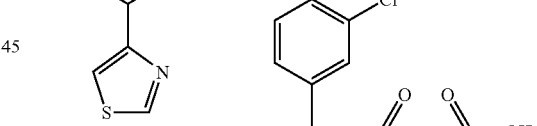

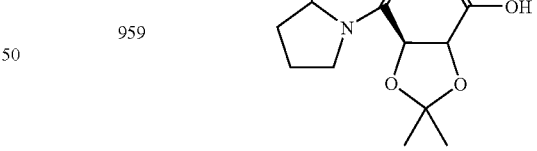

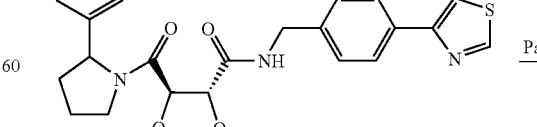

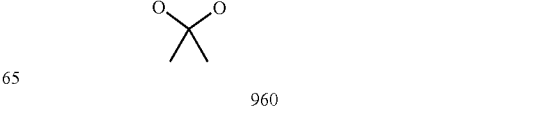

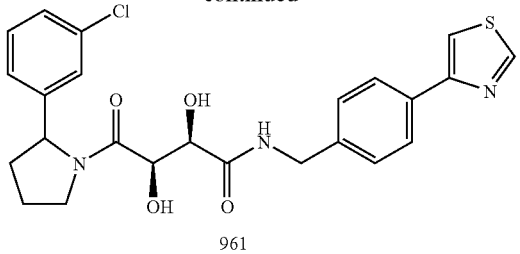

961

Part A:

To 4-aminomethyl-benzoic acid methyl ester (955) (2 g, 9.92 mmol) in dichloromethane (25 mL) was added Boc anhydride (2.27 g, 10.4 mmol) and triethylamine (2.76 mL, 19.84 mmol). The reaction mixture was stirred overnight. The reaction mixture was diluted with dichloromethane, washed with water and brine, dried over sodium sulfate and concentrated to afford 956 as a white solid (2.40 g, 91%). HPLC-MS $t_R$=1.76 min (UV$_{254nm}$); Mass calculated for formula $C_{14}H_{19}NO_4$ 265.1, observed LCMS m/z 288.2 (M+Na).

Part B:

Compound 957 (257 mg, 80%) was synthesized following the procedure described in Example 10B Part A. HPLC-MS $t_R$=1.77 min (UV$_{254\ nm}$); Mass calculated for formula $C_{14}H_{18}ClNO_3$ 283.1, observed LCMS m/z 306.1 (M+Na).

Part C:

To 957 (49 mg, 0.17 mmol) in DMF (2 mL) was added thioformamide (21 mg, 0.35 mmol) and pyridine (50 μL). The reaction mixture was stirred for 72 hours. The mixture diluted with ethyl acetate, washed with 0.1 N sodium hydroxide, water and brine, dried over sodium sulfate and concentrated. Purification by column chromatography (SiO$_2$, 25% ethyl acetate/hexanes) afforded 958 (25 mg, 50%). HPLC-MS $t_R$=1.80 min (UV$_{254\ nm}$); Mass calculated for formula $C_{15}H_{18}N_2O_2S$ 290.1, observed LCMS m/z 291.1 (M+H).

Part D:

Compound 958 (25 mg, 0.084 mmol) was stirred in dichloromethane (2 mL) and TFA (1 mL) at room temperature for 1 hour. The solvents were removed in vacuo to afford 959 as an oil (26 mg). $^1$H NMR (400 MHz, CD$_3$OD) δ 9.07 (d, 1H, J=2.0 Hz), 8.03 (d, 2H, J=8.4 Hz), 7.96 (d, 1H, J=1.6 Hz), 7.52 (d, 2H, J=8.0 Hz), 4.16 (s, 2H).

Part E:

To 193 (23 mg, 0.065 mmol) in DMF (2 mL) was added 959 (26 mg, 0.084 mmol), DIEA (34 μL, 0.20 mmol) and HATU (32 mg, 0.084 mmol). The reaction mixture was stirred overnight at room temperature. The reaction mixture was poured into water and extracted with ethyl acetate. The combined organic layers were washed with 0.1 N NaOH and brine, dried over sodium sulfate and concentrated. The crude material was used without further purification. 960: HPLC-MS $t_R$=2.00 and 2.05 min (UV$_{254\ nm}$); Mass calculated for formula $C_{27}H_{28}ClN_3O_4S$ 525.2, observed LCMS m/z 526.1 (M+H).

Part F:

Compound 960 was dissolved in 4:1 TFA:water (2 ml) and stirred at room temperature for 2 hours. The reaction was quenched by the addition of 1:1 acetonitrile:water (4 mL) and the solvents were removed in vacuo. Purification by reverse phase prep-LC afforded 961 as a white solid (14 mg). HPLC-MS $t_R$=4.17 min (UV$_{254\ nm}$, 10 min); Mass calculated for formula $C_{24}H_{24}ClN_3O_4S$ 485.1, observed LCMS m/z 486.1 (M+H).

Example 26C

Biaryl C—C Linkage

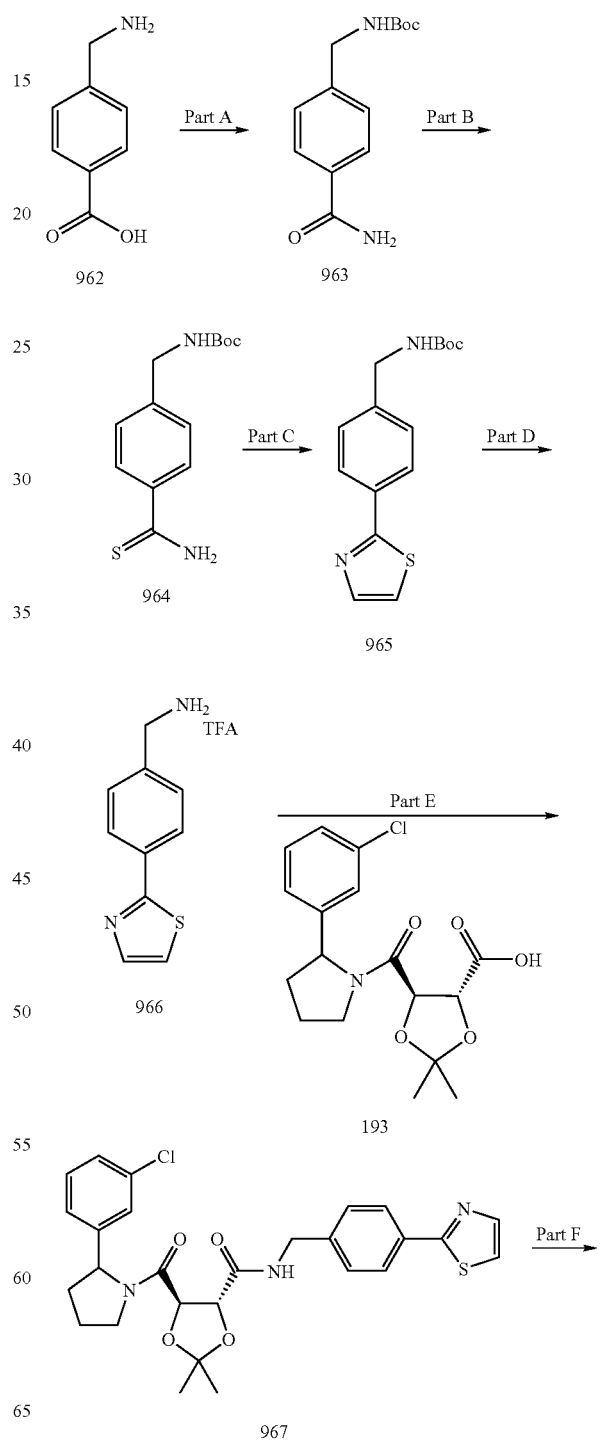

-continued

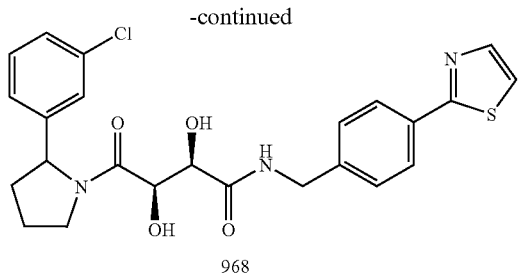

968

Part A:

To 4-(tert-butoxycarbonylamino-methyl)-benzoic acid (962) (500 mg, 1.99 mmol) in tetrahydrofuran (5 mL) in an ice bath was added DIEA (347 µL, 1.99 mmol). The reaction mixture was stirred for 15 minutes and ethyl chloroformate (190 µL, 1.99 mmol) was added. The reaction mixture was stirred for an additional 15 minutes and ammonia in dioxane (0.5 M, 4.18 mL, 2.09 mmol) was added. The reaction mixture was warmed to room temperature and stirred for 2 hours. The solvent was removed in vacuo and the residue was partitioned between ethyl acetate and water. The layers were separated and the aqueous layer was saturated with sodium chloride and extracted with ethyl acetate. The combined organic layers were washed brine, dried over sodium sulfate and concentrated to afford 963 as a white solid (540 mg), which contained some mixed anhydride as an impurity. $^1$H NMR (400 MHz, CD$_3$OD) δ7.81 (d, 2H, J=8.0 Hz), 7.35 (d, 2H, J=8.4 Hz), 7.21 (bs, 1H, NH), 4.28 (s, 2H), 1.47 (s, 9H).

Part B:

To 963 (500 mg, 2.0 mmol) in tetrahydrofuran (20 mL) was added Lawesson's reagent (485 mg, 1.2 mmol). The reaction mixture was stirred overnight at room temperature. The solvent was removed in vacuo and the residue was dissolved in ethyl acetate. The mixture was washed with 0.1 N sodium hydroxide, water and brine, dried over sodium sulfate and concentrated to a yellow residue. Purification by column chromatography (SiO$_2$, 40% ethyl acetate/hexanes) afforded 964 as a pale yellow solid (432 mg, 81%). $^1$H NMR (400 MHz, CDCl$_3$) δ 7.84 (d, 2H, J=8.4 Hz), 7.32 (d, 2H, J=8.4 Hz), 4.36 (d, 2H, J=5.6 Hz), 1.48 (s, 9H).

Part C:

To 964 (70 mg, 0.263 mmol) in DMF (2 mL) was added chloroacetaldehyde (50% in water, 41 mg, 0.526 mmol). The reaction was stirred overnight at room temperature. An additional 2 equivalents of chloroacetaldehyde was added and the reaction was stirred for 24 hours. The reaction was still not complete so the mixture was heated to 50° C. for 2 days. The mixture diluted with ethyl acetate, washed with 0.1 N sodium hydroxide, water and brine, dried over sodium sulfate and concentrated. Purification by column chromatography (SiO$_2$, 25% ethyl acetate/hexanes) afforded 965 (31 mg). HPLC-MS $t_R$=1.84 min (UV$_{254\ nm}$); Mass calculated for formula $C_{15}H_{18}N_2O_2S$ 290.1, observed LCMS m/z 291.1 (M+H).

Part D:

Compound 965 (31 mg, 0.106 mmol) was stirred in dichloromethane (2 mL) and TFA (1 mL) at room temperature for 1 hour. The solvents were removed in vacuo to afford 966 as an oil (60 mg). $^1$H NMR (400 MHz, CD$_3$OD) δ 8.03 (d, 2H, J=8.8 Hz), 7.90 (d, 1H, J=3.2 Hz), 7.65 (d, 1H, J=3.6 Hz), 7.56 (d, 2H, J=8.8 Hz), 4.18 (s, 2H).

Part E:

To 193 (29 mg, 0.082 mmol) in DMF (2 mL) was added 966 (32 mg, 0.106 mmol), DIEA (43 µL, 0.25 mmol) and HATU (40 mg, 0.106 mmol). The reaction mixture was stirred overnight at room temperature. The reaction mixture was poured into water and extracted with ethyl acetate. The combined organic layers were washed with 0.1 N NaOH and brine, dried over sodium sulfate and concentrated. The crude material was used without further purification. 967: HPLC-MS $t_R$=2.03 and 2.08 min (UV$_{254\ nm}$); Mass calculated for formula $C_{27}H_{28}ClN_3O_4S$ 525.2, observed LCMS m/z 526.1 (M+H).

Part F:

Compound 967 was dissolved in 4:1 TFA:water (2 mL) and stirred at room temperature for 2 hours. The reaction was quenched by the addition of 1:1 acetonitrile:water (4 mL) and the solvents were removed in vacuo. Purification by reverse phase prep-LC afforded 968 as a white solid (15 mg). HPLC-MS $t_R$=4.21 min (UV$_{254\ nm}$, 10 min); Mass calculated for formula $C_{24}H_{24}ClN_3O_4S$ 485.1, observed LCMS m/z 486.1 (M+H).

| Compound # | Structure | Exact mass | MS m/e (M + H) |
|---|---|---|---|
| 969 | 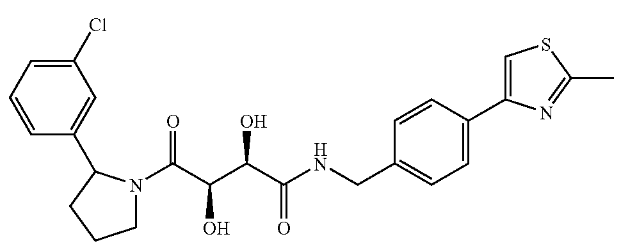 | 499.1 | 500.1 |

-continued

| Compound # | Structure | Exact mass | MS m/e (M + H) |
|---|---|---|---|
| 970 | 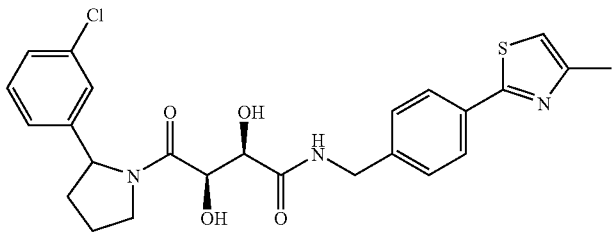 | 499.1 | 500.1 |
| 971 | 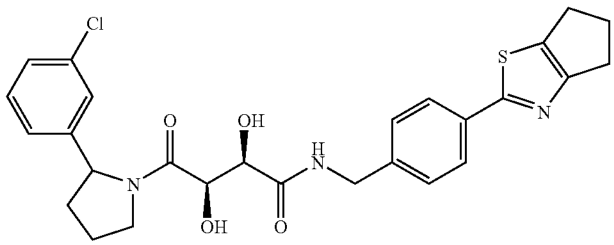 | 525.2 | 526.2 |
| 972 | 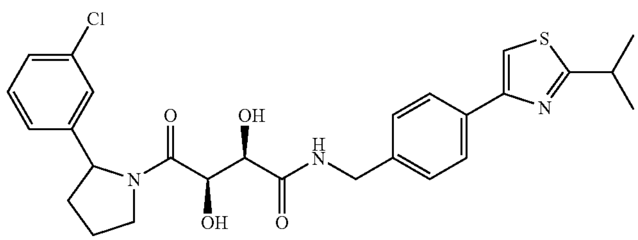 | 527.2 | 528.1 |
| 973 | 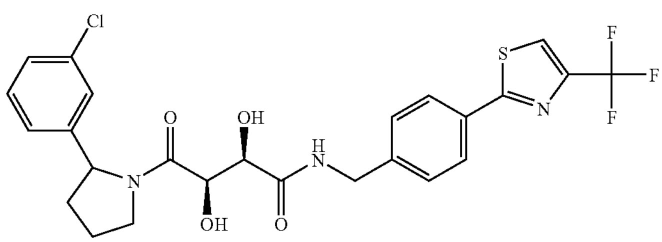 | 553.1 | 554.0 |
| 974 | 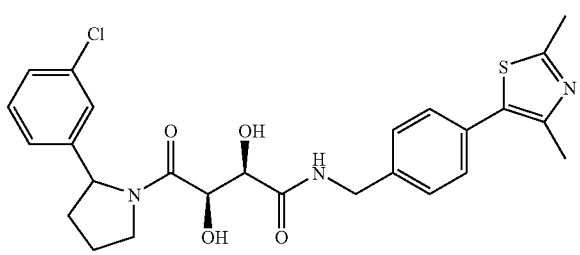 | 513.2 | 514.2 |
| 975 | 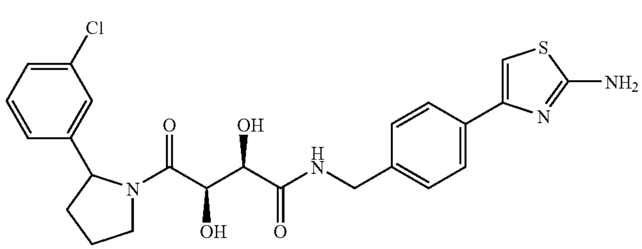 | 500.1 | 501.1 |

-continued

| Compound # | Structure | Exact mass | MS m/e (M + H) |
| --- | --- | --- | --- |
| 976 | 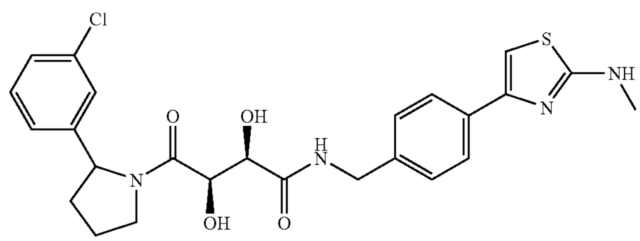 | 514.1 | 515.1 |

Example 27

Piperidine-Aryl Compounds

Example 27A

Piperidine-Aryl

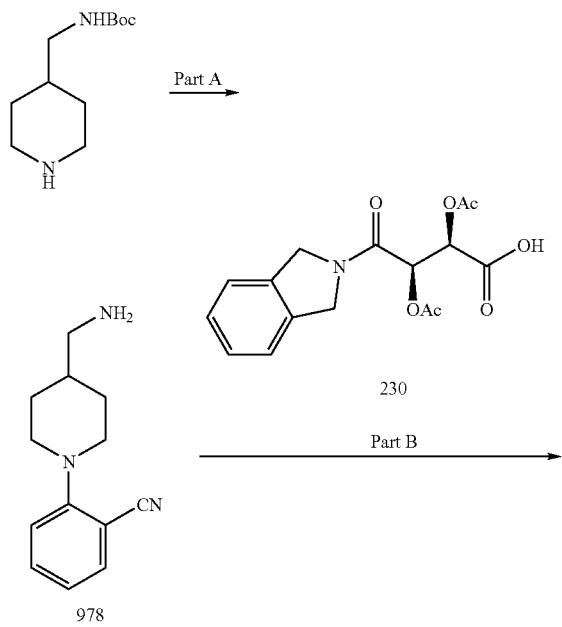

Part A:

Step 1: A mixture of piperidin-4-ylmethyl-carbamic acid tert-butyl ester (977) (2.5 g, 11.66 mmol), 2-fluoro-3-cyanobenzene (1.55 g, 12.8 mmol) and DIEA (3 mL, 17.5 mmol) in NMP (5 mL) under argon atmosphere was stirred overnight at 120° C. The reaction mixture was diluted with ethyl acetate, washed with water and brine, dried over sodium sulfate and concentrated. Purification by column chromatography (SiO$_2$, 25% ethyl acetate/hexanes) afforded a white solid (3.1 g).

Step 2: To the material from Step 1 (2 g) in dichloromethane (5 mL) at 0° C. was added TFA (5 mL). The mixture was stirred at room temperature for 1 hour. The mixture was quenched with acetonitrile and concentrated. The residue was dissolved in ethyl acetate, washed with sodium carbonate solution and brine, dried over sodium sulfate and concentrated to yield 978 as an oil which solidified to a waxy solid (920 mg). HPLC-MS $t_R$=0.63 min (UV$_{254\,nm}$); Mass calculated for formula C$_{13}$H$_{17}$N$_3$ 215.1, observed LCMS m/z 216.2 (M+H).

Part B:

To 978 (120 mg, 0.55 mmol) in DMF (2 mL) was added 230 (167 mg, 0.5 mmol), DIEA (0.21 mL, 1.2 mmol) and HATU (211 mg, 0.55 mmol). The mixture was stirred for 3 hours at room temperature. The reaction mixture was diluted with ethyl acetate, washed with saturated sodium bicarbonate and brine, dried over sodium sulfate and concentrated. The material was used without further purification.

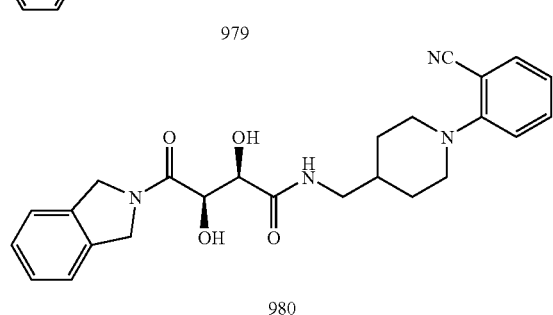

Part C:

To 979 in methanol (4 mL) was added 7.0 N ammonia in methanol (2 mL) was added. The mixture was stirred for 2 hours at room temperature and concentrated. Purification by reverse phase prep-LC afforded 980 as a white powder (80 mg) upon lypholization. HPLC-MS $t_R$=4.03 min (UV$_{254\,nm}$); Mass calculated for formula C$_{25}$H$_{28}$N$_4$O$_4$ 448.2, observed LCMS m/z 449.2 (M+H).

Example 27B

Piperidine-Aryl

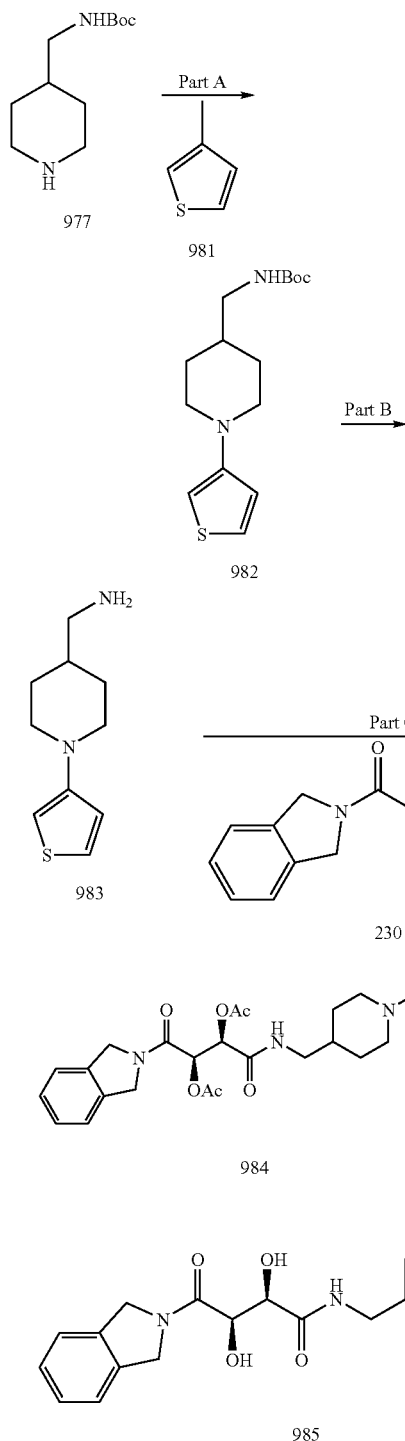

night at 80° C. in a 4 mL vial. The reaction mixture was diluted with ethyl acetate and washed with water (3×) and brine, dried over sodium sulfate and concentrated. Purification by column chromatography (SiO$_2$, 25% ethyl acetate/hexanes) afforded 982 (94 mg, 34%).

Part B:

Compound 982 (42 mg, 0.14 mmol) was dissolved in DCM (2 mL) and TFA (1 mL). The mixture was stirred for 1 hour and concentrated to afford 983 in quantitative yield. HPLC-MS $t_R$=0.35 min (UV$_{254\ nm}$); Mass calculated for formula $COH_{16}N_2S$ 196.1, observed LCMS m/z 197.2 (M+H).

Part C:

Compound 984 was prepared according to the procedure described in Example 27A Part B. HPLC-MS $t_R$=1.36 min (UV$_{254\ nm}$); Mass calculated for formula $C_{26}H_{31}N_3O_6S$ 513.2, observed LCMS m/z 514.2 (M+H).

Part D:

Compound 985 was prepared according to the method described in Example 25 Part E. HPLC-MS $t_R$=2.85 min (UV$_{254\ nm}$, 10 min.); Mass calculated for formula $C_{22}H_{27}N_3O_4S$ 429.2, observed LCMS m/z 430.1 (M+H).

Example 27C

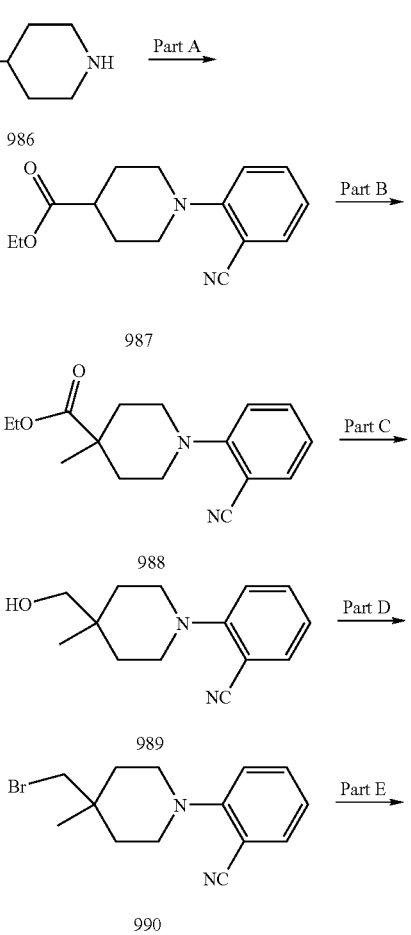

Part A:

A mixture of 977 (200 mg, 0.93 mmol), 3-iodothiophene (981) (294 mg, 1.4 mmol), copper(I)iodide (36 mg, 0.19 mmol), proline (43 mg, 0.37 mmol) and potassium carbonate (258 mg, 1.87 mmol) in DMSO (1.5 mL) was stirred over- -continued

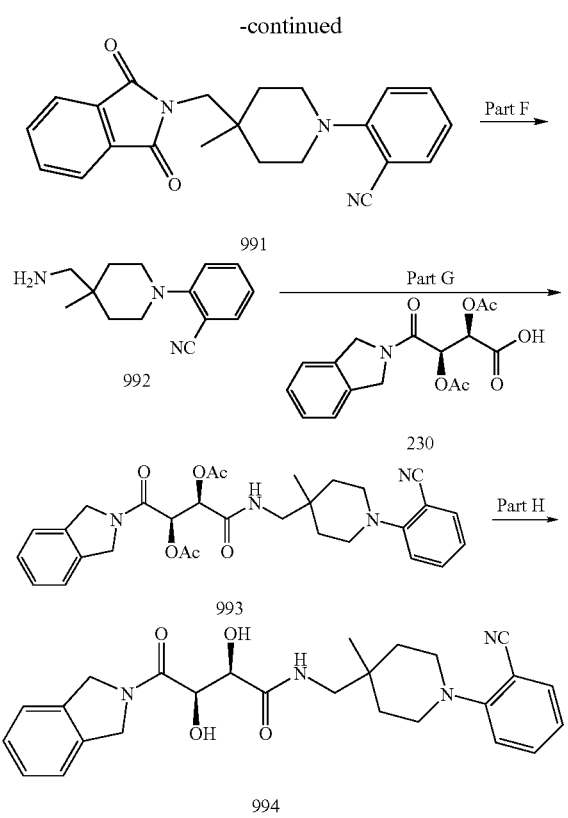

Part A:

Compound 986 (1.13 g, 7.23 mmol) was dissolved in N-methylpyrrolidinone (4 mL) and 2-fluorobenzonitrile (0.90 g, 7.5 mmol) was added followed by DIEA (2.5 mL, 14.4 mmol). The reaction was stirred at 120° C. overnight. The cooled reaction mixture was quenched with water and extracted with ethyl acetate. The combined organic layers were washed with bicarbonate solution and brine; dried over sodium sulfate and concentrated. Purification by column chromatography (SiO$_2$, 25% ethyl acetate/hexanes) afforded a white solid 987 (1.5 g, 81%). HPLC-MS $t_R$=1.95 (UV$_{254\ nm}$); mass calculated for formula $C_{15}H_{18}N_2O_2$ 258.14, observed LCMS m/z 259.1 (M+H).

Part B:

Diisopropylamine (0.330 mL, 2.32 mmol) was dissolved in THF (20 mL) and cooled in an ice bath. A solution of n-BuLi (2.5M in hexanes, 1 mL) was added dropwise and stirred for 15 minutes. The reaction mixture was then cooled to −78° C. and a solution of compound 987 (400 mg, 1.6 mmol) in THF (10 mL) was added dropwise. Stirring was continued at this temperature for 30 minutes before a solution of iodomethane (450 mg, 3.2 mmol) in THF (10 mL) was added dropwise. The reaction was stirred for 30 minutes at this temperature and then 1 hour at room temperature. The reaction was quenched with water and extracted with ethyl acetate. The combined organic layers were washed with bicarbonate solution and brine; dried over sodium sulfate and concentrated to provide the product 988 that was used without purification. HPLC-MS $t_R$=2.10 (UV$_{254\ nm}$); mass calculated for formula $C_{16}H_{20}N_2O_2$ 272.15, observed LCMS m/z 273.2 (M+H).

Part C:

Compound 988 was dissolved in THF (20 mL) and lithium borohydride (60 mg, 2.6 mmol) was added. The reaction mixture was refluxed for 5 hours. The cooled reaction mixture was quenched with water and extracted with ethyl acetate. The combined organic layers were washed with bicarbonate solution and brine; dried over sodium sulfate and concentrated. Purification by column chromatography (SiO$_2$, 50% ethyl acetate/hexanes) afforded a white solid 989 (300 mg). HPLC-MS $t_R$=1.57 (UV$_{254\ nm}$); mass calculated for formula $C_{14}H_{18}N_2O$ 230.1, observed LCMS m/z 231.3 (M+H).

Part D:

Compound 989 (300 mg, 1.3 mmol) was dissolved in toluene (5 mL) and phosphorus tribromide (0.06 mL, 0.52 mmol) was added. The reaction was stirred at reflux for 3 hours. The cooled reaction was quenched with water and extracted with ethyl acetate. The combined organic layers were washed with bicarbonate solution and brine; dried over sodium sulfate and concentrated to provide the product 990 that was used without purification.

Part E:

Compound 990 was dissolved in DMF (10 mL) and cesium carbonate (850 mg, 2.6 mmol) and phthalimide (190 mg, 1.3 mmol) were added and stirred overnight. The reaction was quenched with water and extracted with ethyl acetate. The combined organic layers were washed with bicarbonate solution and brine; dried over sodium sulfate and concentrated. Purification by column chromatography (SiO$_2$, 25% ethyl acetate/hexanes) afforded a white solid 991 (90 mg). HPLC-MS $t_R$=2.14 min (UV$_{254\ nm}$); mass calculated for formula $C_{22}H_{21}N_3O_2$ 359.1, observed LCMS m/z 360.1.

Part F:

Compound 991 (90 mg, 0.25 mmol) was dissolved in ethanol (3 mL) and hydrazine hydrate (0.5 mL) was added. The reaction was stirred for 3 hours and the solids were filtered. The solvent was evaporated to provide the desired product 992 that was used without purification.

Part G:

Compound 992 was dissolved in DMF (5 mL) and compound 230 (84 mg, 0.25 mmol) and HATU (114 mg, 0.30 mmol) were added and stirred overnight. The reaction was quenched with water and extracted with ethyl acetate. The combined organic layers were washed with bicarbonate solution and brine; dried over sodium sulfate and concentrated. Purification by column chromatography (SiO$_2$, ethyl acetate) afforded a white foam 993 (100 mg). HPLC-MS $t_R$=1.99 min (UV$_{254\ nm}$); mass calculated for formula $C_{30}H_{34}N_4O_6$ 546.2, observed LCMS m/z 547.2.

Part H:

Compound 993 (100 mg, 0.182 mmol) was dissolved in methanol (5 mL) and potassium carbonate (100 mg) was added and stirred for 30 minutes. The reaction was quenched with water and extracted with ethyl acetate. The combined organic layers were washed with bicarbonate solution and brine; dried over sodium sulfate and concentrated. Purification by reverse phase prep-LC afforded a white solid 994 (7 mg, 8%) after lyophilization. HPLC-MS $t_R$=4.32 min (UV$_{254\ nm}$, 10 min); mass calculated for formula $C_{26}H_{30}N_4O_4$ 462.23, observed LCMS m/z 463.1 (M+H).

The following table contains compounds that were prepared using the procedures described in Example 27A-C. Compounds such as 1002 were made from the chloropyridyl precursor using the procedures described in Example 27A Part A.

| Compound # | Structure | Exact mass | MS m/z (M + H) |
|---|---|---|---|
| 995 | 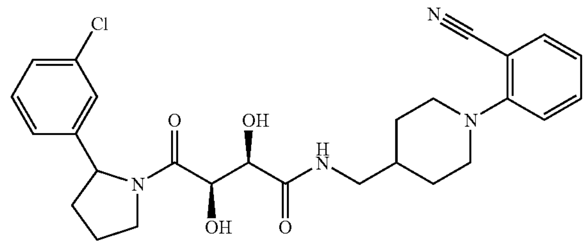 | 510.2 | 511.1 |
| 996 | 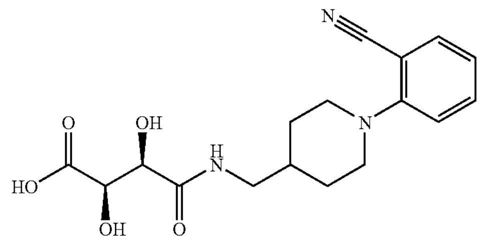 | 347.1 | 348.3 |
| 997 | 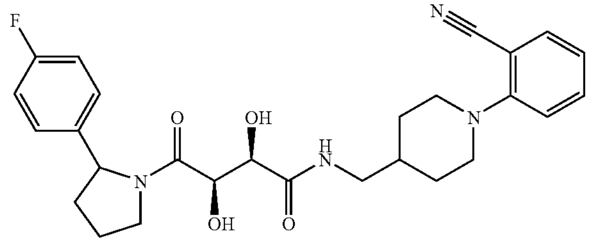 | 494.2 | 495.2 |
| 998 | 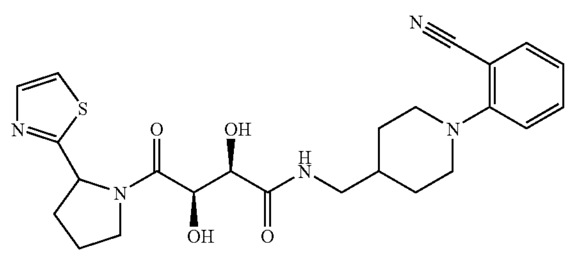 | 483.2 | 484.1 |
| 999 | 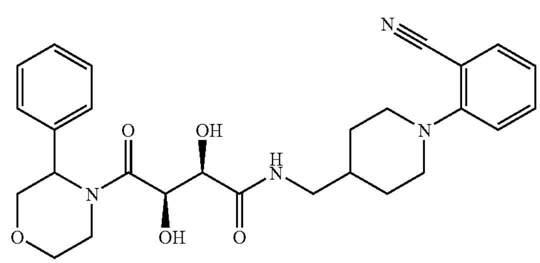 | 492.2 | 493.1 |
| 1000 | 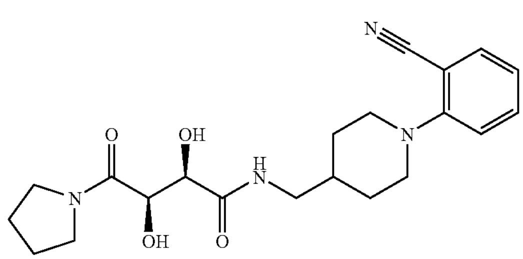 | 400.2 | 401.2 |

-continued

| Compound # | Structure | Exact mass | MS m/z (M + H) |
|---|---|---|---|
| 1001 | 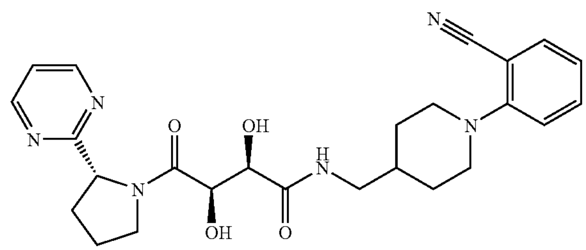 | 478.2 | 479.2 |
| 1002 | 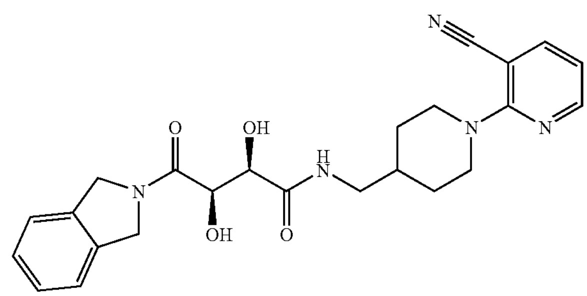 | 449.2 | 450.2 |
| 1003 | 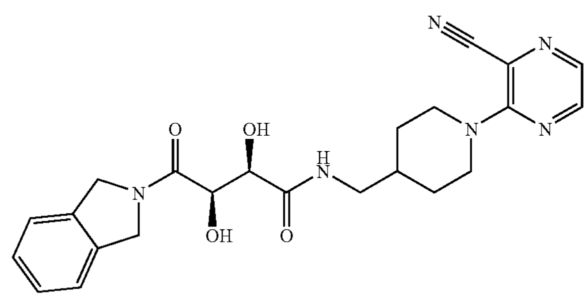 | 450.2 | 451.1 |
| 1004 | 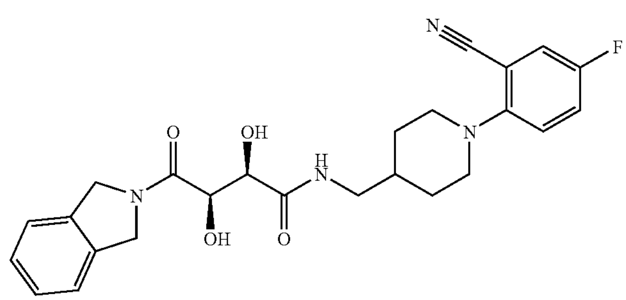 | 466.2 | 467.2 |
| 1005 | 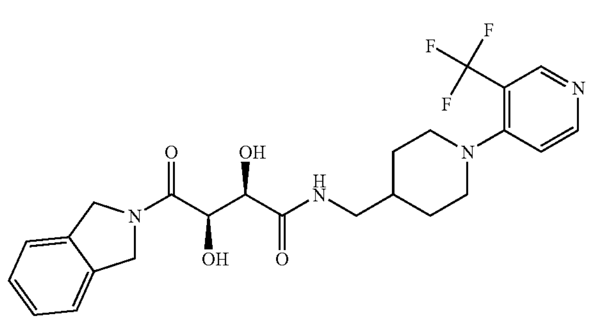 | 492.2 | 493.1 |

-continued
| Compound # | Structure | Exact mass | MS m/z (M + H) |
|---|---|---|---|
| 1006 | 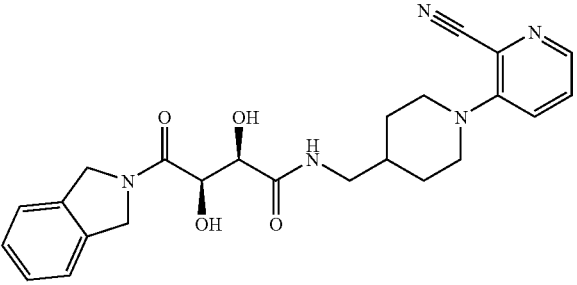 | 449.2 | 450.1 |
| 1007 | 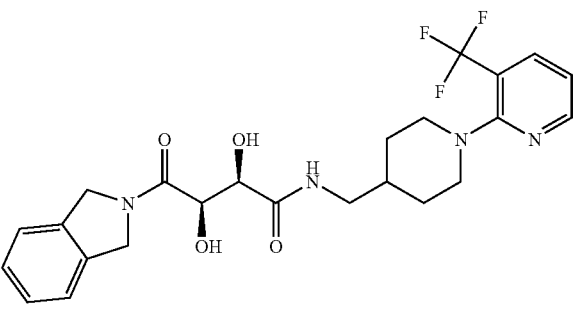 | 492.2 | 493.1 |
| 1008 | 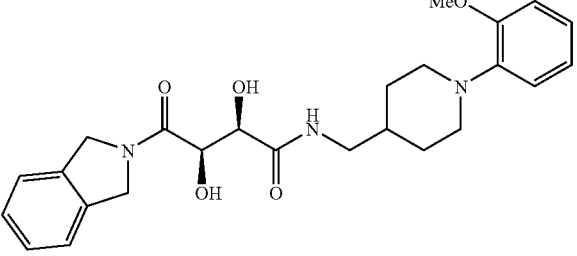 | 453.2 | 454.2 |
| 1009 | 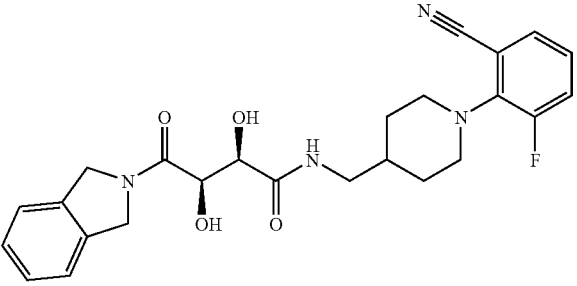 | 466.2 | 467.2 |
| 1010 | 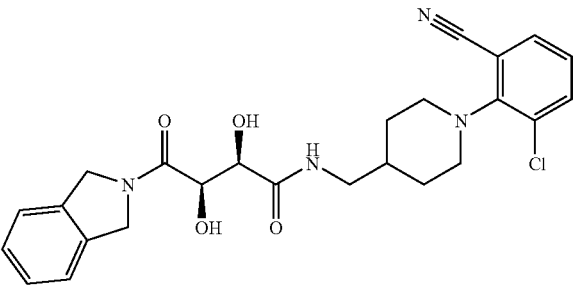 | 482.2 | 483.1 |

-continued
| Compound # | Structure | Exact mass | MS m/z (M + H) |
|---|---|---|---|
| 1011 | 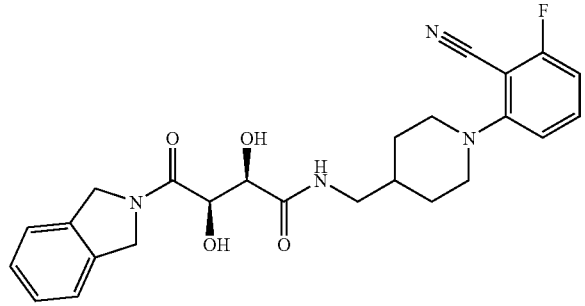 | 466.2 | 467.2 |
| 1012 | 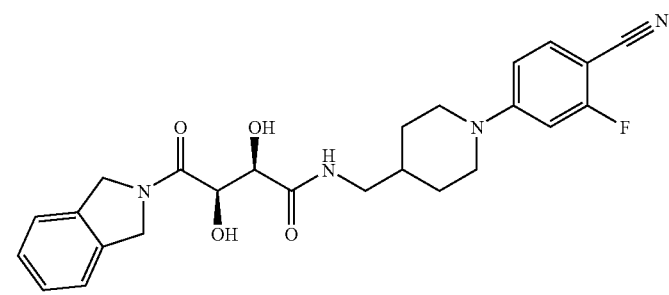 | 466.2 | 467.2 |
| 1013 | 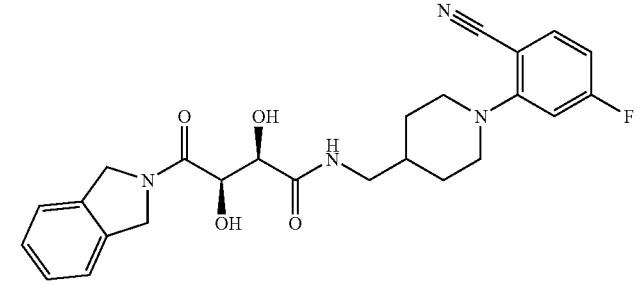 | 466.2 | 467.2 |
| 1014 | 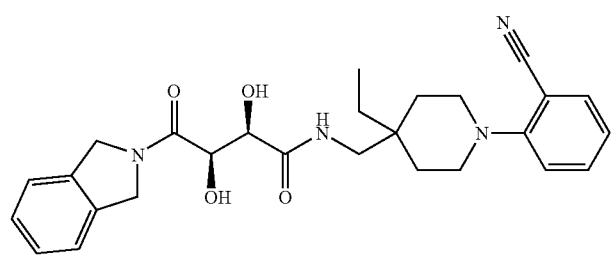 | 476.2 | 477.1 |
| 1015 | 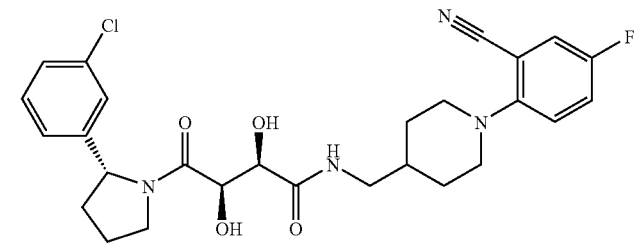 | 528.2 | 529.2 |

-continued
| Compound # | Structure | Exact mass | MS m/z (M + H) |
|---|---|---|---|
| 1016 | 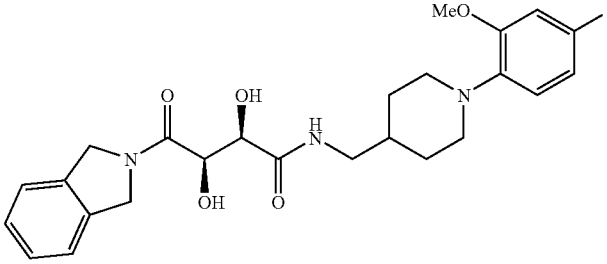 | 471.2 | 472.1 |
| 1017 | 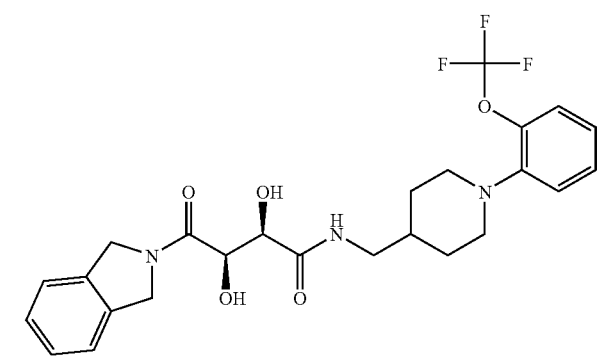 | 507.2 | 508.2 |
| 1018 | 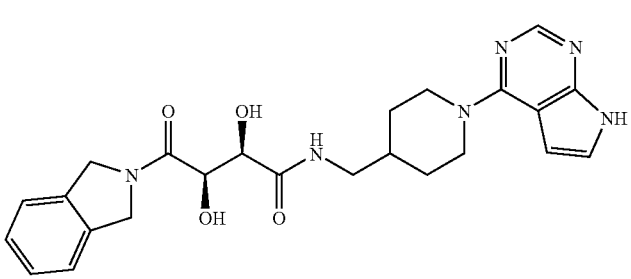 | 464.2 | 465.2 |
| 1019 | 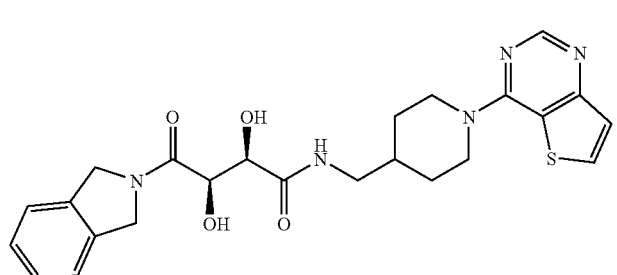 | 481.2 | 482.2 |
| 1020 | 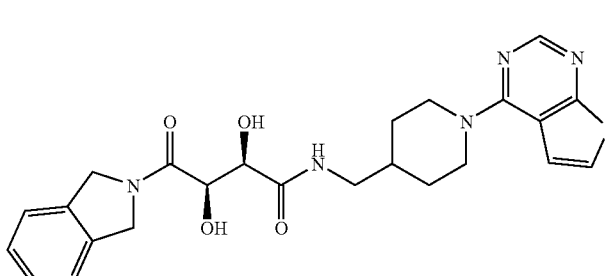 | 481.2 | 482.2 |

-continued

| Compound # | Structure | Exact mass | MS m/z (M + H) |
|---|---|---|---|
| 1021 | 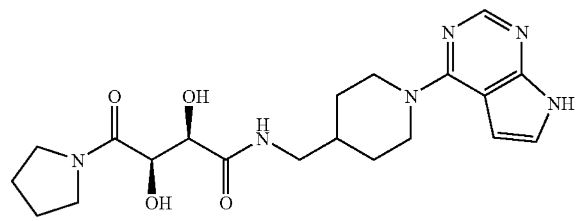 | 416.2 | 417.3 |
| 1022 | 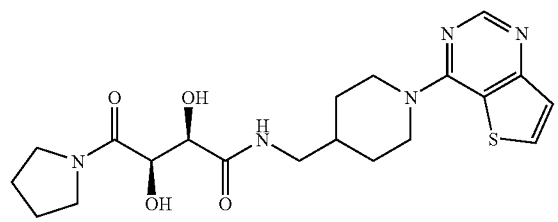 | 433.2 | 434.2 |
| 1023 | 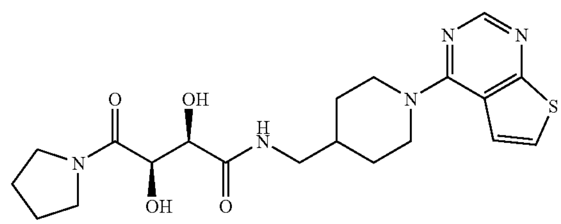 | 433.2 | 434.2 |
| 1024 | 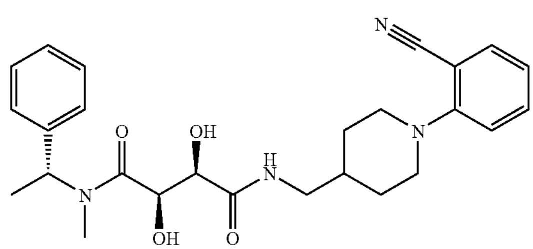 | 464.2 | 465.2 |
| 1025 | 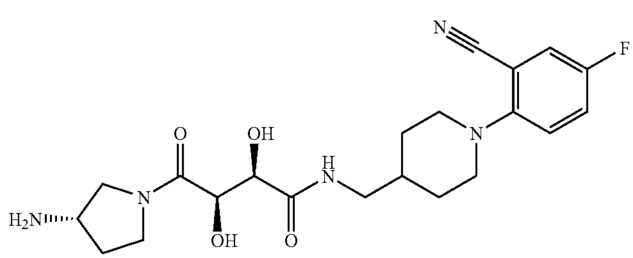 | 433.2 | 434.2 |
| 1026 | 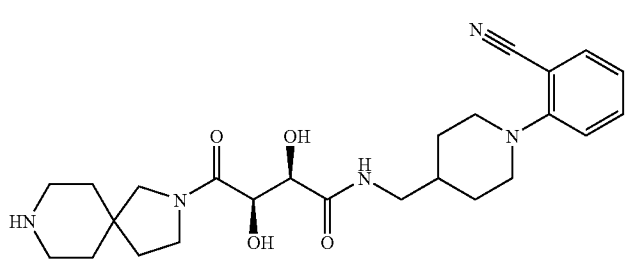 | 469.3 | 470.2 |

-continued

| Compound # | Structure | Exact mass | MS m/z (M + H) |
|---|---|---|---|
| 1027A | 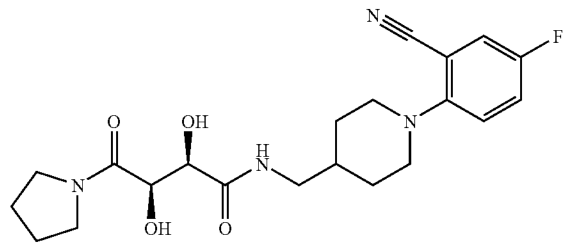 | 418.2 | 419.2 |
| 1027B | 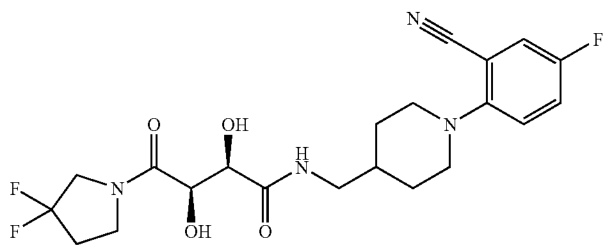 | 454.2 | 455.2 |
| 1027C | 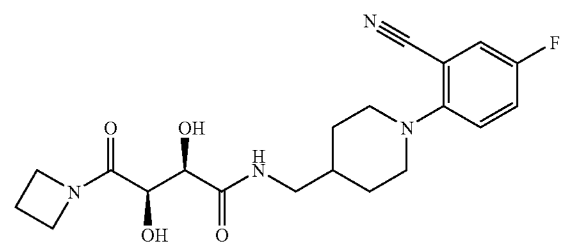 | 404.2 | 405.2 |
| 1028 | 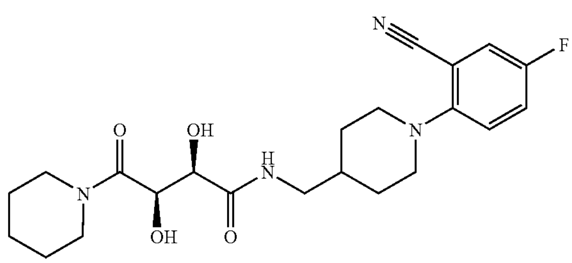 | 432.2 | 433.2 |
| 1029 | 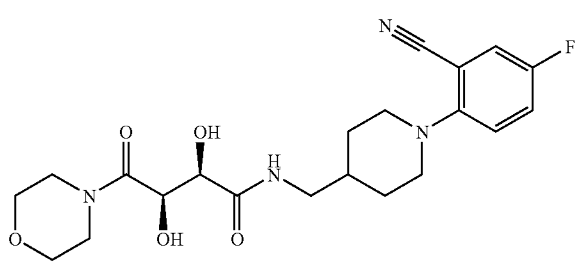 | 434.2 | 435.2 |
| 1030 | 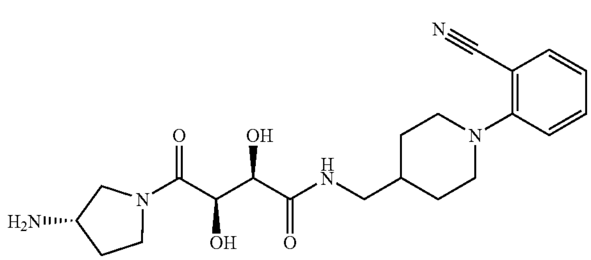 | 415.2 | 416.2 |

-continued

| Compound # | Structure | Exact mass | MS m/z (M + H) |
|---|---|---|---|
| 1031 | 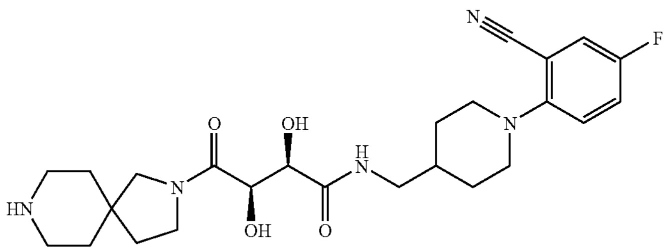 | 487.3 | 488.2 |
| 1032 | 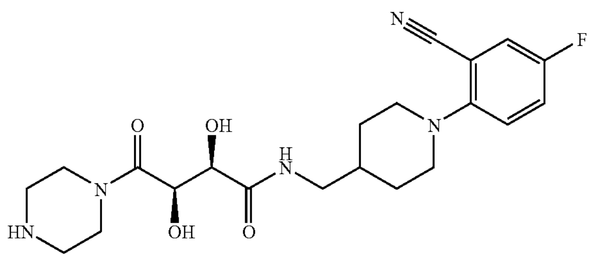 | 433.2 | 434.2 |
| 1033 | 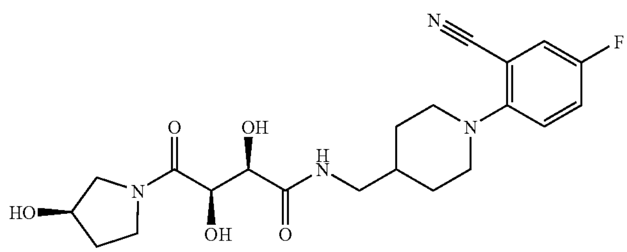 | 434.2 | 435.2 |
| 1034A | 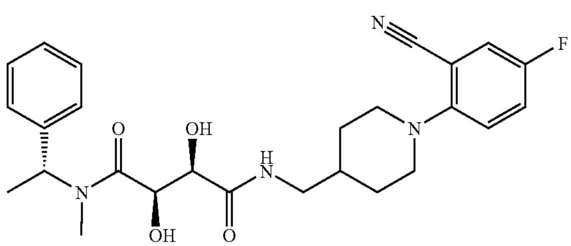 | 482.2 | 483.3 |
| 1034B | 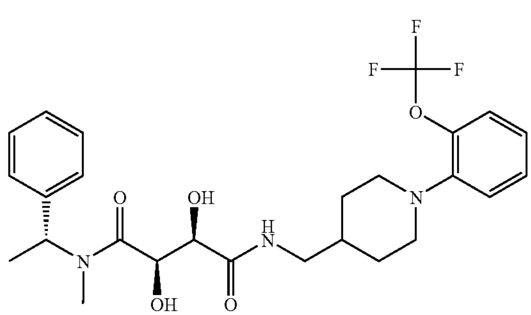 | 523.2 | 524.2 |

| Compound # | Structure | Exact mass | MS m/z (M + H) |
|---|---|---|---|
| 1035 | 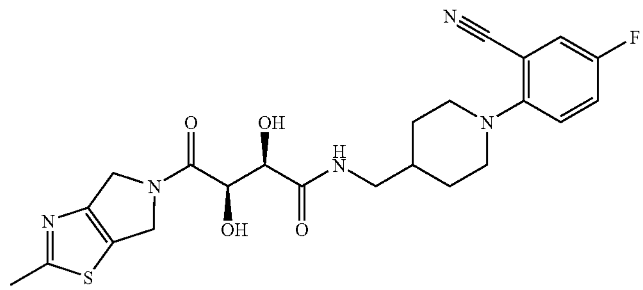 | 487.2 | 488.2 |
| 1036 | 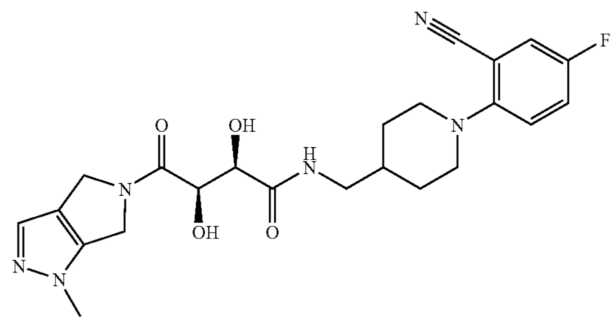 | 470.2 | 471.2 |
| 1037 | 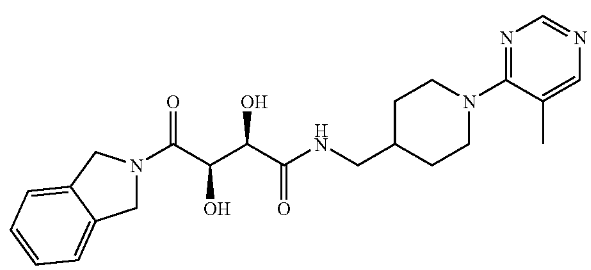 | 439.2 | 440.2 |
| 1038A | 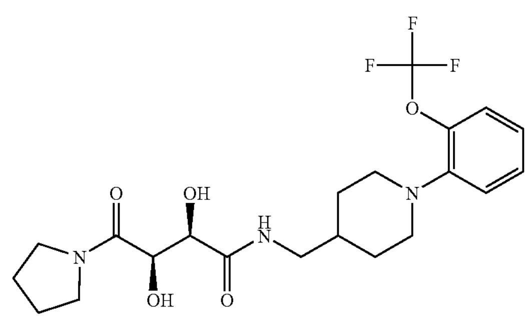 | 459.2 | 460.1 |
| 1038B | 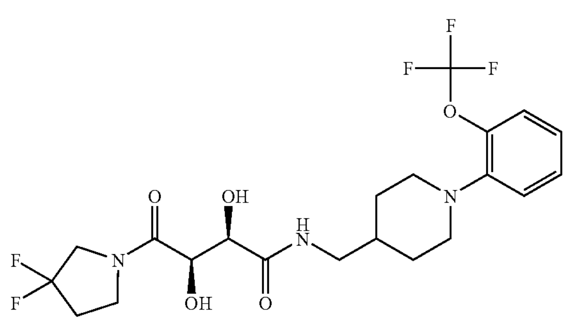 | 495.2 | 496.2 |

-continued

| Compound # | Structure | Exact mass | MS m/z (M + H) |
|---|---|---|---|
| 1039 | 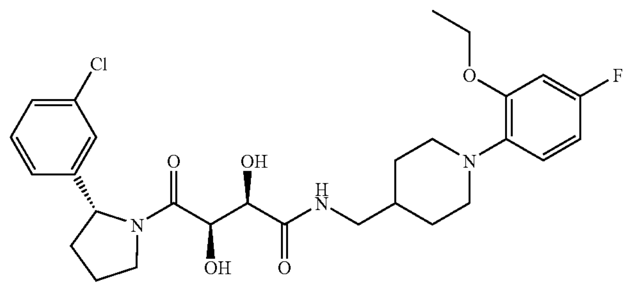 | 547.2 | 548.2 |
| 1040 | 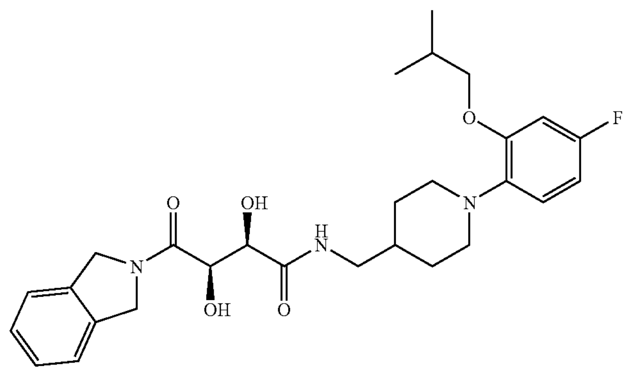 | 513.3 | 514.3 |

Example 28

Alkylated Phenyl Pyrrolidines

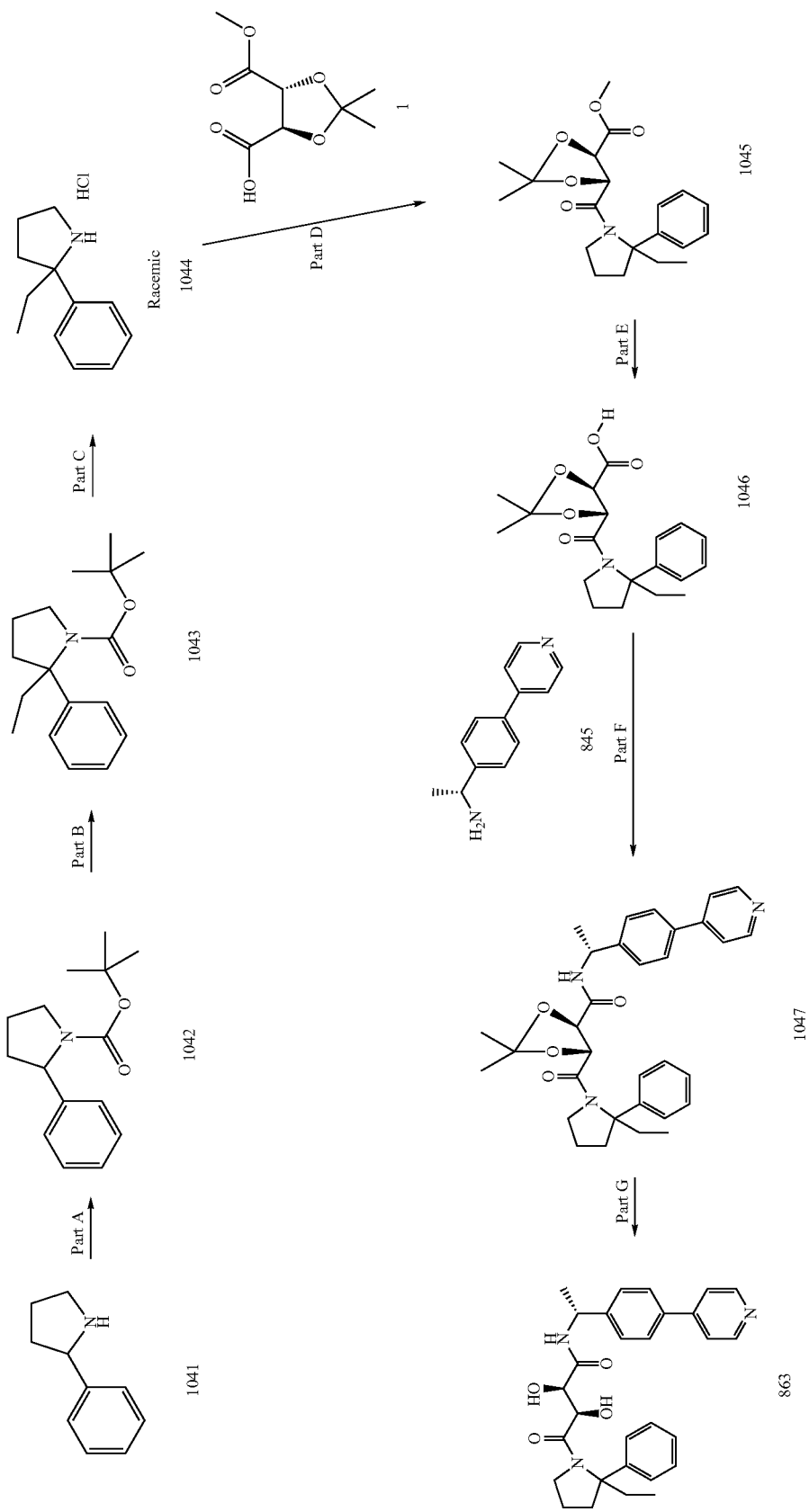

Part A:

2-Phenyl pyrrolidine (1041) (3.14 g, 21.4 mmol) was dissolved in THF (40 mL). Aqueous NaOH (12 mL, 25%) was added, followed by Boc anhydride. The reaction mixture was stirred at rt for 70 h. The layers were separated. The aqueous layer was extracted with EtOAc. The combined organic layer was washed with 1.0 M pH=7.0 sodium phosphate buffer and brine, then dried with MgSO$_4$. Evaporation of the solvents gave a yellow oil which was purified by column chromatography (SiO$_2$, 9:1 Hexanes:EtOAc) to give a 5.1 g of a clear oil as product 1042. MS (EI) m/z M+Na Obsd 270.08

Part B:

A 100 mL Schlenck flask was equipped with a stir bar, flame dried under N$_2$ flow, capped with a septum, and allowed to cool to rt. Compound 1042 (0.50 g, 2.02 mmol) was added and the flask was recapped. Anhydrous THF (8.5 mL) was added via syringe and the flask was cooled in a dry ice/2-propanol bath. Sec butyl lithium (1.6 mL, 2.34 mmol) was added via syringe. The reaction mixture was left stirring at −78° C. for 30 m. Iodoethane (180 μL, 2.25 mmol) was added and the reaction mixture was stirred for 2 hr. Additional iodoethane was added (80 μL, 1.0 mmol) was added and the reaction mixture was stirred for 45 minutes. The reaction mixture was quenched with 1.0 M pH 7.0 sodium phosphate buffer and diluted with EtOAc. The layers were separated and the aqueous layer was extracted with EtOAc. The combined organic layer was washed with water and brine, then dried with MgSO$_4$ and concentrated to a clear oil. The crude product was purified by column chromatography (SiO$_2$, 0%-20% EtOAc/Hexanes) to give 0.12 g of compound 1043. MS (EI) m/z M+Na Obsd 298.15.

Part C:

Compound 1043 (0.12 g, 0.43 mmol) was dissolved in 10 mL of 4 M HCl in dioxane. The reaction mixture was stirred at rt for 2.25 h. The reaction mixture was concentrated to dryness giving white solid 1044 (112 mg). MS (EI) m/z Obsd M+H 176.12.

Part D:

Compound 1044 (104 mg, 0.49 mmol) and 1 (0.120 g, 0.588 mmol) were dissolved in CH$_2$Cl$_2$ (2 mL). Diisopropyl ethylamine (200 μL, 1.12 mmol) was added, followed by PyBrop (249 mg, 0.78 mmol). The reaction mixture was left stirring overnight at rt under N$_2$. The reaction mixture was diluted with CH$_2$Cl$_2$ then washed with 1.0 m pH 7.0 sodium phosphate buffer, aq NaHCO$_3$, and brine. The organic layer was dried with MgSO$_4$ and concentrated to a clear oil. The crude product was purified purified by column chromatography (SiO$_2$, 0%-40% EtOAc/Hexanes) to give 0.16 g of compound 1045. MS (EI) m/z Obsd M+H 362.08

Part E:

Compound 1045 (0.15 g, 0.42 mmol) was dissolved in dioxane (1.6 mL) and water (0.4 mL). Lithium hydroxide was added (19 mg, 0.45 mmol). The reaction mixture was stirred at rt for 2 h 15 m. The solution was concentrated to give 1046 as a clear oil. MS (EI) m/z Obsd M+H 348.09

Part F:

Compound 1046 (69 mg, 0.19 mmol) and 845 (51 mg, 0.22 mmol) were dissolved in DMF (1 mL) and diisopropylamine (100 μL, 0.58 mmol). PyBrop was added (108 mg, 0.338 mmol) and the reaction was stirred overnight at rt. The reaction mixture was diluted with EtOAc and washed with 1.0 M pH 8.0 sodium phosphate buffer and brine. The organic layer was dried with MgSO$_4$ and concentrated to a yellow oil. The crude product was purified via prep TLC on silica plates using 95:5 CH$_2$Cl$_2$:MeOH as the mobile phase. Compound 1047 was obtained as a clear oil (74 mg). MS (EI) m/z Obsd M+H 528.20.

Part G:

Compound 1047 (74 mg, 0.14 mmol) was dissolved in 5 mL of 9:1 trifluoroacetic acid:water solution. The reaction mixture was stirred at rt for 3 h 10 m, then concentrated to dryness. The crude product was purified purified by column chromatography (SiO$_2$, 0%-7% MeOH/CH$_2$Cl$_2$) to give 26 mg of compound 863. MS (EI) m/z Obsd M+H 488.1.

Compound 1048A,B was prepared from Boc-proline OMe using the above alkylation procedures and the thiazole ring was constructed as described in Example 10A.

| Compound # | Structure | Exact mass | MS m/e (M + H) |
|---|---|---|---|
| 1048A | 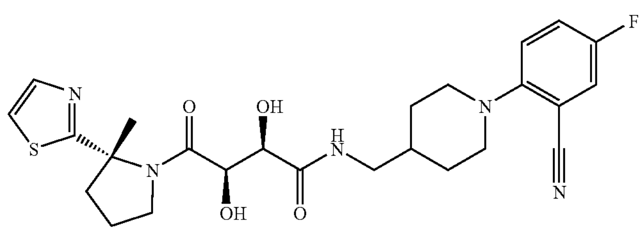 | 515.2 | 516.2 |
| 1048B | 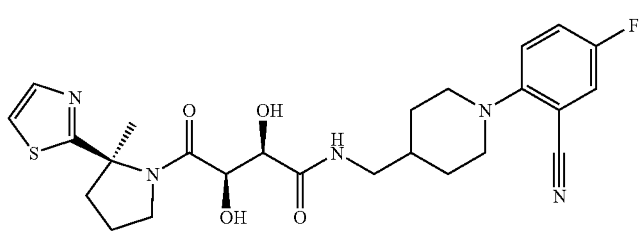 | 515.2 | 516.2 |

Example 29

Example 29A

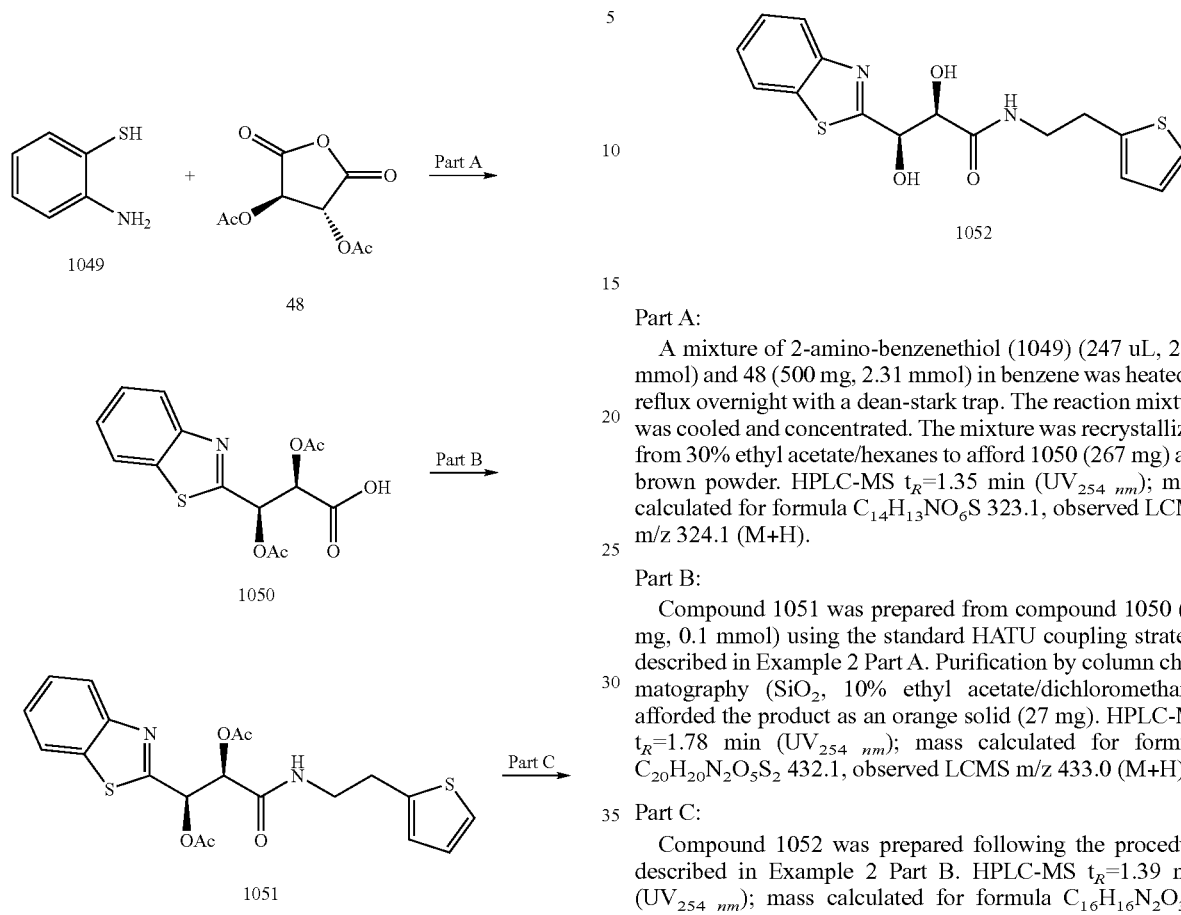

Part A:

A mixture of 2-amino-benzenethiol (1049) (247 uL, 2.31 mmol) and 48 (500 mg, 2.31 mmol) in benzene was heated at reflux overnight with a dean-stark trap. The reaction mixture was cooled and concentrated. The mixture was recrystallized from 30% ethyl acetate/hexanes to afford 1050 (267 mg) as a brown powder. HPLC-MS $t_R$=1.35 min ($UV_{254\ nm}$); mass calculated for formula $C_{14}H_{13}NO_6S$ 323.1, observed LCMS m/z 324.1 (M+H).

Part B:

Compound 1051 was prepared from compound 1050 (32 mg, 0.1 mmol) using the standard HATU coupling strategy described in Example 2 Part A. Purification by column chromatography ($SiO_2$, 10% ethyl acetate/dichloromethane) afforded the product as an orange solid (27 mg). HPLC-MS $t_R$=1.78 min ($UV_{254\ nm}$); mass calculated for formula $C_{20}H_{20}N_2O_5S_2$ 432.1, observed LCMS m/z 433.0 (M+H).

Part C:

Compound 1052 was prepared following the procedure described in Example 2 Part B. HPLC-MS $t_R$=1.39 min ($UV_{254\ nm}$); mass calculated for formula $C_{16}H_{16}N_2O_3S_2$ 348.1, observed LCMS m/z 349.0 (M+H).

| Compound # | Structure | Exact mass | MS m/z (M + H) |
|---|---|---|---|
| 1053 | 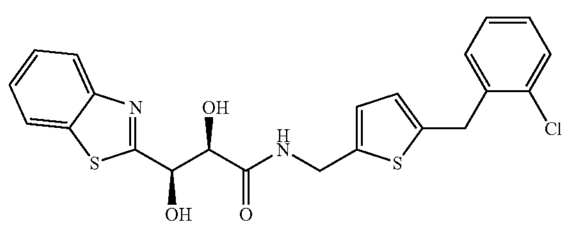 | 458.1 | 459.0 |
| 1054 | 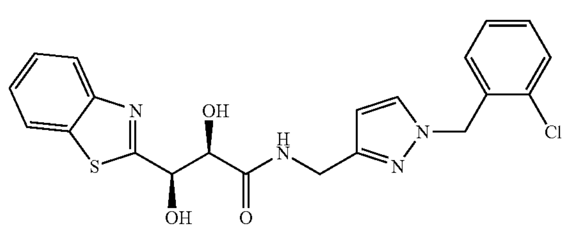 | 442.1 | 443.0 |

Example 29B

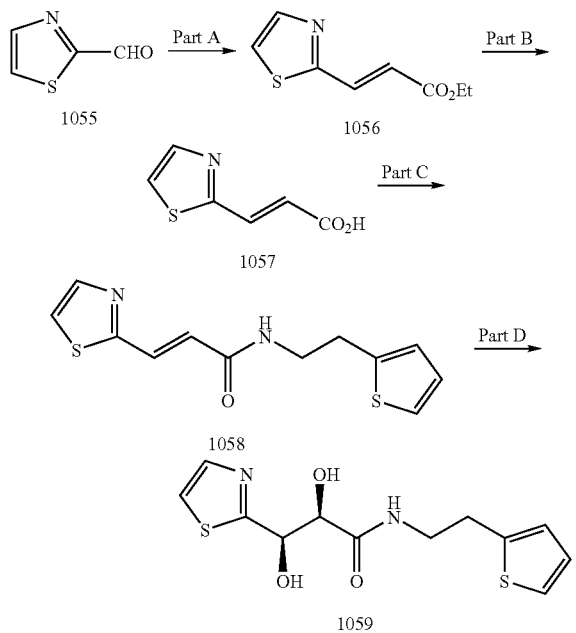

Part A:

To sodium hydride (95%, 115 mg, 4.55 mmol) in DME (10 mL) under argon was added triethylphophonacetate dropwise. Within a few minutes the reaction mixture was clear. After 1 hour the aldehyde 1055 (400 uL, 4.55 mmol) was added. After 15 minutes water and diethyl ether were added to the reaction mixture. The layers were separated and the aqueous layer was extracted with diethyl ether. The combined organic layer was washed with brine, dried over sodium sulfate and concentrated to afford 1056 as an orange oil (666 mg, 80%). $^1$H NMR (400 MHz, CDCl$_3$) δ 7.92 (d, 1H, J=3.2 Hz), 7.79 (d, 1H, J=16.0 Hz), 7.43 (d, 1H, J=3.2 Hz), 6.71 (d, 1H, J=16.0 Hz), 4.29 (q, 2H, J=7.5 Hz), 1.36 (t, 3H, J=7.5 Hz).

Part B:

To ester 1056 (84 mg, 0.46 mmol) in THF (2 mL) was added 1.0 M lithium hydroxide solution (0.5 mL, 0.5 mmol). The reaction mixture was stirred overnight. The reaction mixture was made acidic with 1.0 N HCl solution and extracted with ethyl acetate. Sodium chloride was added to the aqueous layer during the extractions. The combined organic layer was dried over sodium sulfate and concentrated to afford 1057 as a film (65 mg, 92%). $^1$H NMR (400 MHz, CDCl$_3$) δ 7.97 (d, 1H, J=3.0 Hz), 7.89 (d, 1H, J=15.7 Hz), 7.49 (d, 1H, J=3.0 Hz), 6.75 (d, 1H, J=15.7 Hz).

Part C:

Compound 1058 was prepared from Compound 1057 (32 mg, 0.21 mmol) using the standard HATU coupling strategy described in Example 2 Part A. Purification by column chromatography (SiO$_2$, 50% ethyl acetate/hexane) afforded the product as a film (35 mg, 63%). HPLC-MS $t_R$=1.35 min (UV$_{254\ nm}$); mass calculated for formula C$_{12}$H$_{12}$N$_2$OS$_2$ 264.0, observed LCMS m/z 265.1 (M+H).

Part D:

Compound 1059 was prepared using a modified Sharpless dihydroxylation procedure (Chem. Rev. 1994, 94, 2483). A flask was charged with (DHQ)$_2$PHAL (10 mg, 10 mol %), K$_3$Fe(CN)$_6$ (128 mg, 0.39 mmol), postassium carbonate (54 mg, 0.39 mmol), methane sulfonamide (24 mg, 0.26 mmol) and potassium osmium tetraoxide dihydrate (1 mg, 2 mol %). To the solids was added alkene 4 (35 mg, 0.13 mmol) in tert-butanol:water (1:1, 2.5 mL). The reaction mixture was stirred overnight at room temperature. The reaction mixture was cooled in an ice bath and sodium metabisulfite (38 mg, 0.2 mmol) was added. The mixture was stirred for 30 minutes. The reaction mixture was diluted with ethyl acetate and water. The layers were separated and the aqueous layer was extracted with ethyl acetate. The combined organic layer was washed with 2.0 N potassium hydroxide solution and brine, dried over sodium sulfate and concentrated. Purification by column chromatography (SiO$_2$, 80% ethyl acetate/hexane) afforded the product as a white solid after lypholization (5 mg, 13%). HPLC-MS $t_R$=1.00 min (UV$_{254\ nm}$); mass calculated for formula C$_{12}$H$_{14}$N$_2$O$_3$S$_2$ 298.0, observed LCMS m/z 299.0 (M+H).

| Compound # | Structure | Exact mass | MS m/z (M + H) |
|---|---|---|---|
| 1060 | 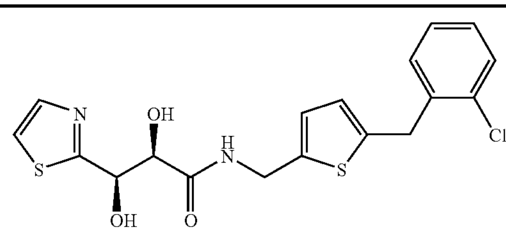 | 408.0 | 409.0 |
| 1061 | 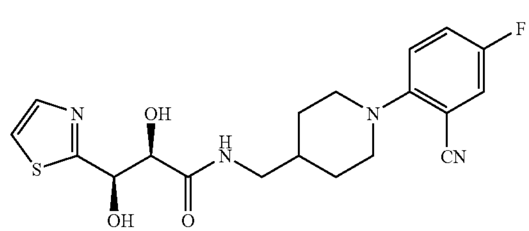 | 404.1 | 405.1 |

Example 29C

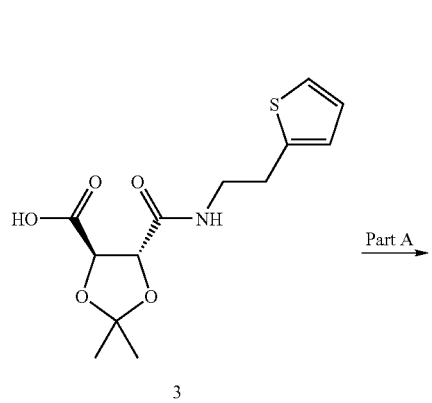

3

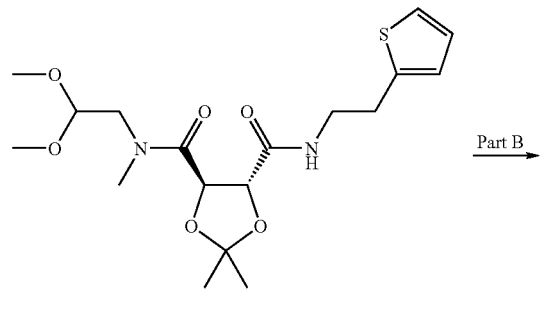

1062

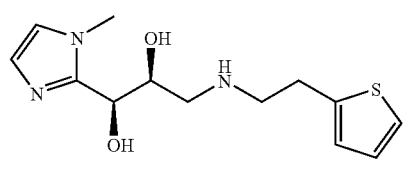

1063

Example 29D

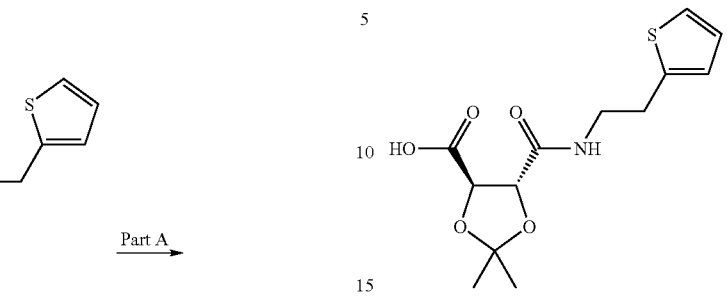

3

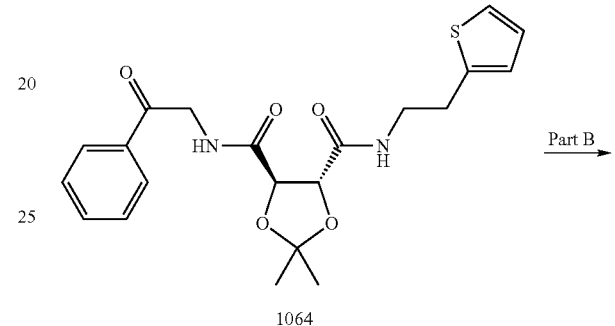

1064

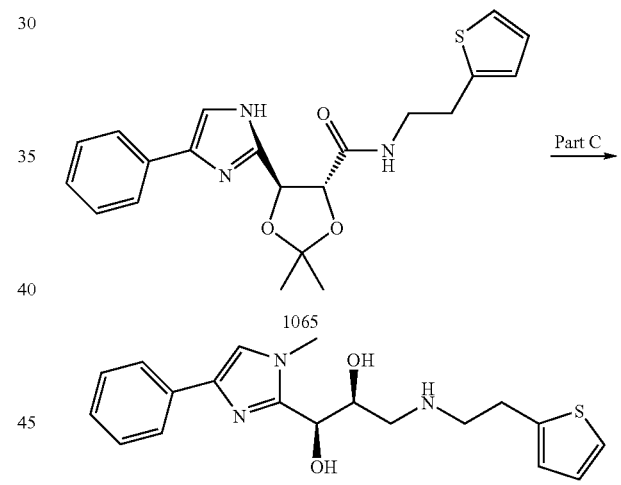

1065

1066

Part A:

Compound 1062 was prepared following the procedures described in Example 1.

HPLC-MS $t_R$=1.69 min (UV$_{254\ nm}$); mass calculated for formula $C_{18}H_{28}N_2O_6S$ 400.2, observed LCMS m/z 401.2 (M+H).

Part B:

Compound 1062 (198 mg, 0.69 mmol) and ammonium acetate (1.9 g, 24.7 mmol) in acetic acid (6 ml) were heated overnight at 110° C. The reaction mixture was concentrated. The residue was suspended in DCM and the solids removed by filtration. The filtrate was concentrated to afford a mixture of acetonide protected product and 1063. The residue was treated with 80% TFA:water (2 mL) and stirred overnight. The solvents were removed. Purification by prep-HPLC afforded 1063 (11 mg, 4%) as a TFA salt. HPLC-MS $t_R$=0.79 min (UV$_{254\ nm}$); mass calculated for formula C13H17N3O3S 295.1, observed LCMS m/z 296.1 (M+H).

Part A:

Compound 1064 was prepared following the procedures described in Example 1.

HPLC-MS $t_R$=1.77 min (UV$_{254\ nm}$); mass calculated for formula $C_{21}H_{24}N_2O_5S$ 416.14, observed LCMS m/z 417.1 (M+H).

Part B:

Compound 1064 (216 mg, 0.52 mmol) and ammonium acetate (2 g, 25.9 mmol) in acetic acid (6 ml) were heated overnight at 110° C. The reaction mixture was concentrated. The residue was suspended in DCM and the solids removed by filtration. The filtrate was concentrated and purified by reverse phase chromatography (Gilson) to afford 1065 (80 mg, 30%) as a TFA salt (80% purity). HPLC-MS $t_R$=1.38 min (UV$_{254\ nm}$); mass calculated for formula $C_{21}H_{23}N_3O_3S$ 397.1, observed LCMS m/z 398.2 (M+H).

Part C:

A mixture of compound 1065 (63 mg, 0.127 mmol), iodomethane (10 µL, 0.16 mmol) and cesium carbonate (206 mg, 0.634 mmol) in DMF (6 ml) was stirred overnight at room temperature. The reaction mixture was concentrated. The residue was suspended in ethyl acetate and the solids removed by filtration. The filtrate was concentrated to afford the crude acetonide protected product. The residue was treated with 90% TFA:water (3 mL) and stirred for 3 h at 50° C. The solvents were removed. Purification by prep-HPLC afforded 1066 (12 mg, 19%) as a TFA salt. HPLC-MS $t_R$=2.87 min (10 min; $UV_{254\ nm}$); mass calculated for formula $C_{19}H_{21}N_3O_3S$ 371.1, observed LCMS m/z 372.1 (M+H).

Example 29E

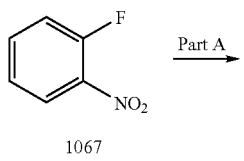

1067

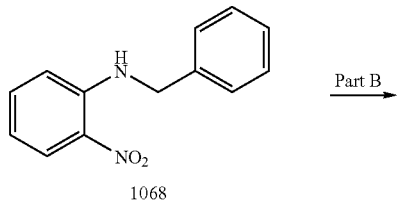

1068

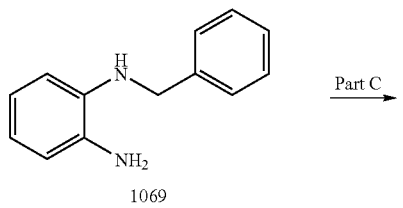

1069

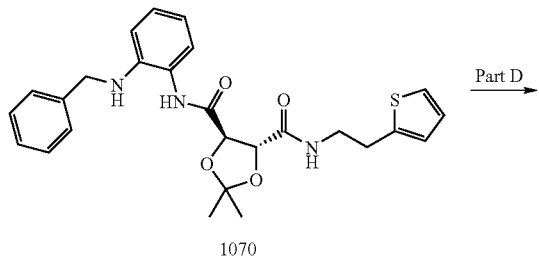

1070

-continued

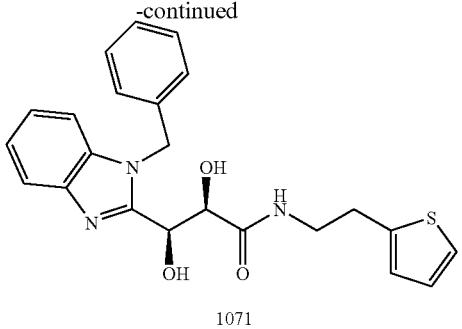

1071

Part A:

According to a modification of a procedure by Goker, H. et. al. (*Il Farmaco* 1998, 53, 415-420) a mixture of 1-fluoro-2-nitro-benzene (1067) (1.1 mL, 10.4 mmol) and benzylamine (2.35 mL, 21.5 mmol) in DMF (5 mL) was heated overnight at 80° C. The reaction mixture was concentrated to give an orange solid which was filtered, washed with water and dried to afford benzyl-(2-nitro-phenyl)-amine (1068) (2.5 g, 100%). $^1$H NMR δ (400 MHz, CDCl$_3$) 8.44 (b, 1H, NH), 8.22-8.19 (dd, 1H), 7.41-7.27 (m, 6H), 6.84-6.81 (dd, 1H), 6.70-6.66 (m, 1H), 4.58-4.57 (d, 2H).

Part B:

To a solution of benzyl-(2-nitro-phenyl)-amine (1068) (2.5 g, 10.43 mmol) in ethanol (150 mL) and water (10 mL) was added iron (8.7 g, 155.7 mmol) followed by 30 drops of concentrated HCl, and the resulting mixture was heated overnight at reflux. The reaction mixture was quenched with water, diluted with DCM and the layers were separated. The organic layer was washed with saturated sodium bicarbonate solution, brine, dried over sodium sulfate and concentrated to give a brown oily residue. Further purification by column chromatography (SiO$_2$, 20% ethyl acetate/hexanes) afforded N-benzyl-benzene-1,2-diamine (1069) as a dark yellow oil (1.18 g, 57%). $^1$H NMR (400 MHz, CDCl$_3$) δ 7.41-7.24 (m, 5H), 6.82-6.67 (m, 4H), 4.32 (s, 2H), 3.56 (b, 3H, NH).

Part C:

Compound 1070 was prepared following the procedures described in Example 29C Part A. HPLC-MS $t_R$=2.13 min ($UV_{254\ nm}$); mass calculated for formula $C_{26}H_{29}N_3O_4S$ 479.2, observed LCMS m/z 480.1 (M+H).

Part D:

A mixture of compound 1070 (75 mg, 0.156 mmol) and p-toluenesulfonic acid monohydrate (30 mg, 0.156 mmol) in toluene (3 ml) was heated overnight at reflux. The reaction mixture was concentrated to a residue identified as the acetonide deprotected product by LC-MS. Further purification by reverse phase chromatography afforded 1071 (40 mg, 48%) as a TFA salt (95% purity). HPLC-MS $t_R$=3.52 min (10 min; $UV_{254\ nm}$); mass calculated for formula $C_{23}H_{23}N_3O_3S$ 421.1, observed LCMS m/z 422.2 (M+H).

The following compounds were synthesized by procedures described in Example 29C-E.

| Compound # | Structure | Exact mass | MS m/z (M + H) |
|---|---|---|---|
| 1072 | 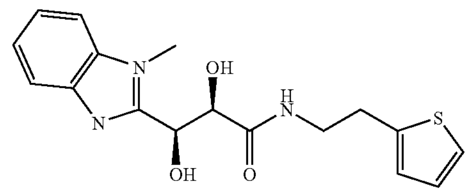 | 345.1 | 346.1 |
| 1073 | 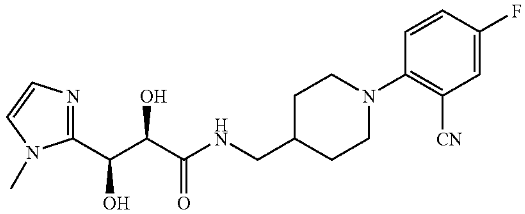 | 401.2 | 402.2 |

Example 29F

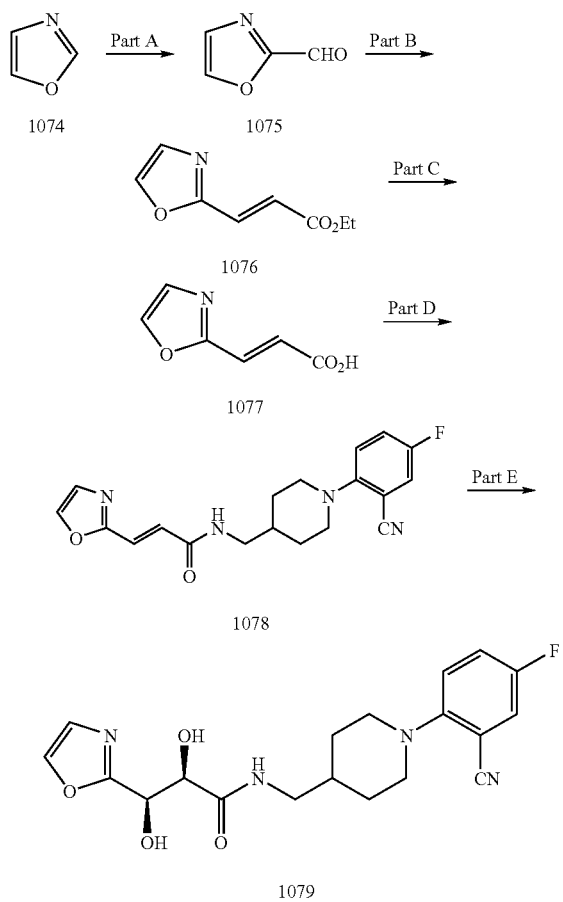

Part A:

According to a procedure Hodges, J. C. et al (*J. Org. Chem.* 1991, 56, 449-452) to a cold (−78° C.) solution of oxazole (1074) (1 g, 14.4 mmol) in 45 mL of THF was added dropwise nBuLi (9 mL, 14.4 mmol, 1.6 M soln in hexane), and the resulting solution was stirred at −78° C. for 25 min. Then DMF (1.12 mL, 14.4 mmol) was added dropwise, followed by THF (5 mL) and the resulting mixture was allowed to warm up slowly to room temperature, and was stirred overnight. The reaction mixture was quenched by the addition of silica gel (3 g), concentrated, and the resulting slurry was diluted with DCM and loaded on a silica gel column. Flash chromatography (3% ethyl acetate/DCM) afforded oxazole-2-carbaldehyde (1075) (165 mg, 12%) as a yellow oil; $^1$H NMR (400 MHz, CDCl$_3$) δ 9.79 (s, 1H), 7.9 (s, 1H), 7.46 (s, 1H).

Part B:

Compound 1076 was prepared from compound 1075 (165 mg, 1.7 mmol) using the procedure described in Example 29B Part A. Purification by column chromatography (SiO$_2$, 20% ethyl acetate/hexane) afforded the product as a yellow solid (107 mg, 34%); $^1$H NMR (400 MHz, CDCl$_3$) δ 7.69 (s, 1H), 7.45 (d, 1H, J=16.0 Hz), 7.27 (s, 1H), 6.74 (d, 1H, J=16.0 Hz), 4.29 (q, 2H, J=7.3 Hz), 1.36 (t, 3H, J=7.3 Hz).

Part C:

Compound 1077 was prepared from compound 1076 (107 mg, 0.58 mmol) using the procedure described in Example 29B Part B. Work-up afforded the product as a pale yellow solid (77 mg, 85%). $^1$H NMR (400 MHz, DMSO-d$_6$) δ 12.9 (s, 1H), 8.25 (s, 1H), 7.44 (s, 1H), 7.27 (d, 1H, J=16.0 Hz), 6.62 (d, 1H, J=16.0 Hz).

Part D:

Compound 1078 was prepared from compound 1077 (165 mg, 1.7 mmol) using the procedure described in Example 29B Part C. After standard HATU coupling work-up the solid residue was triturated with 1:1 DCM/hexane, filtered and washed with 1:1 DCM/hexane to give 1078 (123 mg, 70%) as a pale yellow solid; $^1$H NMR (400 MHz, DMSO-d$_6$) δ 8.49 (t, 1H), 8.20 (s, 1H), 7.69-7.66 (dd, 1H), 7.49-7.44 (m, 1H), 7.38 (s, 1H), 7.20-7.16 (dd, 1H), 7.14 (d, 1H, J=16.0 Hz), 6.94 (d, 1H, J=16.0 Hz), 3.41-3.38 (d, 2H), 3.16 (t, 2H), 2.72 (t, 2H), 1.81-1.78 (d, 2H), 1.64-1.58 (m, 1H), 1.40-1.30 (m, 2H). HPLC-MS $t_R$=1.63 min (UV$_{254\,nm}$); mass calculated for formula C$_{19}$H$_{19}$FN$_4$O$_2$ 354.15, observed LCMS m/z 355.1 (M+H).

Part E:

Compound 1079 was prepared from compound 1078 (118 mg, 0.33 mmol) using the procedure described in Example 29B Part D. Purification by column chromatography (SiO$_2$, 5% MeOH/DCM) afforded the product as a white solid (28 mg, 22%); $^1$H NMR (400 MHz, DMSO-d$_6$) δ 8.02 (s, 1H), 7.88 (t, 1H), 7.69-7.66 (dd, 1H), 7.48-7.43 (m, 1H), 7.20-7.16 (dd, H), 7.14 (s, 1H), 5.83-5.81 (d, 1H), 5.72-5.70 (d, 1H), 4.93-4.90 (dd, 1H), 4.23-4.21 (d of d, 1H), 3.38-3.36 (d, 2H), 3.04 (t, 2H), 2.69 (t, 2H), 1.77-1.72 (d, 2H), 1.62-1.56 (m, 1H), 1.32-1.23 (m, 2H). $^{19}$F NMR (400 MHz, DMSO-d$_6$) δ-120.6 ppm. HPLC-MS $t_R$=3.32 min (10 min; UV$_{254\ nm}$); mass calculated for formula C$_{19}$H$_{21}$FN$_4$O$_4$ 388.15, observed LCMS m/z 389.2 (M+H).

Example 30

Example 30A

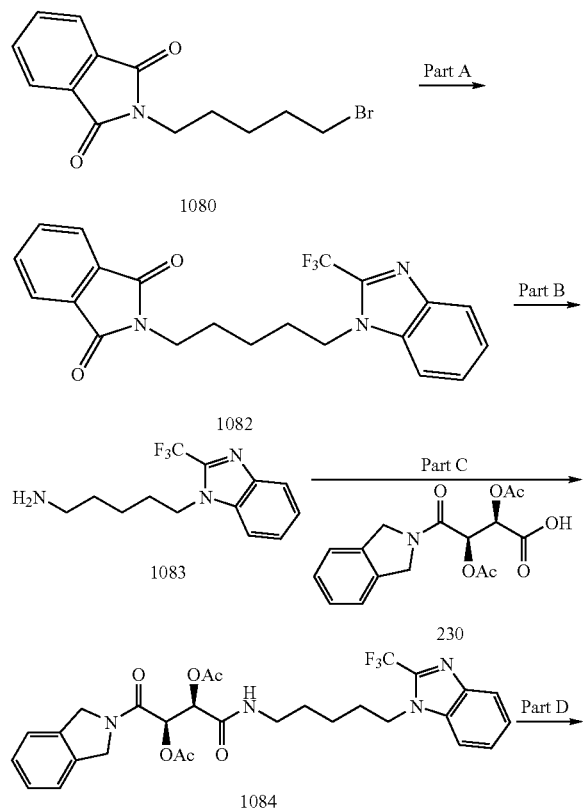

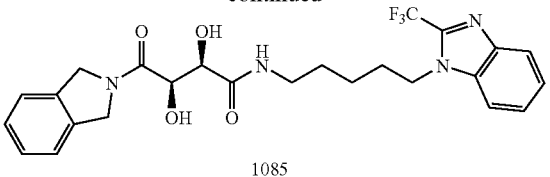

1085

Part A:

A mixture of 2-(5-bromo-pentyl)-isoindole-1,3-dione (1080) (2.0 g, 6.77 mmol), 2-trifluoromethyl-1H-benzoimidazole (1.2 g, 6.45 mmol) and potassium carbonate (1.78 g, 12.9 mmol) in NMP (5 ml) was stirred overnight at room temperature. The reaction mixture was partitioned between ethyl acetate and water, and the resulting organic layer was washed with water, brine, dried over sodium sulfate and concentrated to give an oil. Further purification by column chromatography (SiO$_2$, 25% ethyl acetate/hexanes) afforded compound 1082 as a colorless oil (1.88 g, 73%). $^1$H NMR (400 MHz, CDCl$_3$) δ 7.88-7.86 (d, 1H), 7.85-7.83 (m, 2H), 7.73-7.71 (m, 2H), 7.49-7.34 (m, 3H), 4.31 (t, 2H), 3.72 (t, 2H), 1.99-1.92 (m, 2H), 1.80-1.73 (m, 2H), 1.53-1.45 (m, 2H).

Part B:

To a solution of compound 1082 (1.88 g, 4.68 mmol) in EtOH (50 mL) was added hydrazine monohydrate (0.45 mL, 9.36 mmol) and the resulting mixture was heated for 3 h at 60° C., during which time a white precipitate formed. The reaction mixture was filtered, washed with EtOH and the filtrate was concentrated. The residue was suspended in ether, stirred for 10 min at room temperature, filtered and washed with ether, and the resulting filtrate was concentrated to afford compound 1083 as an oil (1.10 g, 87%). $^1$H NMR (400 MHz, CDCl$_3$) δ 7.90-7.88 (d, 1H), 7.46-7.37 (m, 3H), 4.33 (t, 2H), 2.76 (t, 2H), 2.02-1.40 (m, 6H).

Part C:

Compound 1084 was prepared from 1083 and 230 following the procedures described in Example 2.

Part D:

Compound 1085 was prepared following the procedures described in Example 2. HPLC-MS $t_R$=4.14 min (10 min; UV$_{254\ nm}$); mass calculated for formula C$_{25}$H$_{27}$F$_3$N$_4$O$_4$ 504.2, observed LCMS m/z 505.1 (M+H).

Example 30B

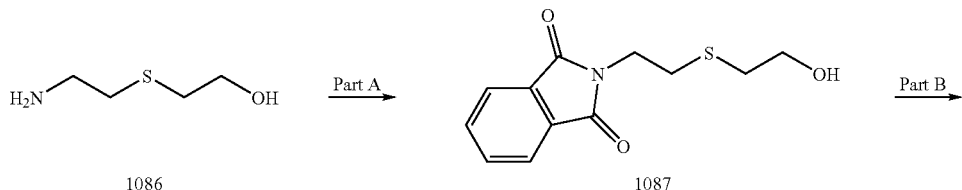

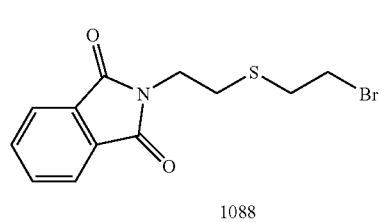 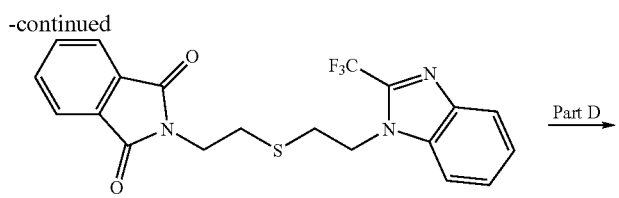

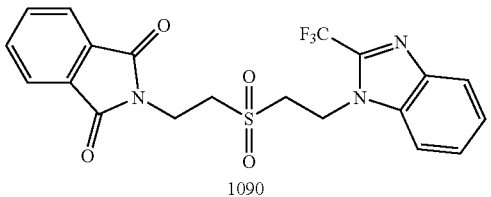 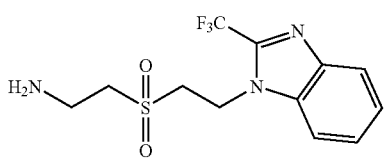

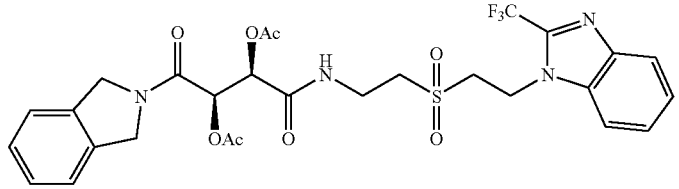

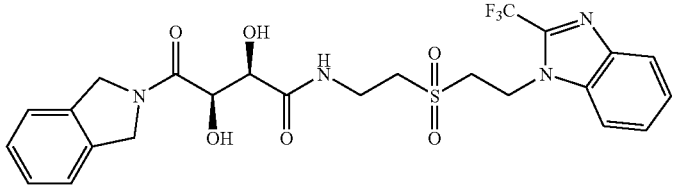

Part A:

According to a modification of a procedure by Lown, J. W. et. al. (*J. Org. Chem.* 1982, 47, 2027-2033) a mixture of 2-(2-amino-ethylsulfanyl)-ethanol (1086) (1.82, 15 mmol) and phthalimide (2.22 g, 15 mmol) in toluene (35 ml) was heated overnight at reflux. The reaction mixture was concentrated to a residue, which was purified by column chromatography (SiO$_2$, 25% ethyl acetate/DCM to 50% ethyl acetate/DCM) to afford compound 1087 as an off-white solid (2.98 g, 79%). $^1$H NMR (400 MHz, CDCl$_3$) δ 7.87-7.85 (m, 2H), 7.75-7.72 (m, 2H), 3.94 (t, 2H), 3.80 (t, 2H), 2.89-2.82 (m, 4H).

Part B:

According to a modification of a procedure by Nair, S. A. et. al. (*Synthesis* 1995, 810-814) to an ice-cold solution of compound 1087 (628 mg, 2.5 mmol) and carbon tetrabromide (1.04 g, 3.12 mmol) in DCM (25 mL) was added triphenylphosphine (920 mg, 3.5 mmol) in two portions over 10 min. The reaction mixture was allowed to warm up to room temperature and stirred overnight at room temperature. The mixture was concentrated and the resulting residue was purified by column chromatography (SiO$_2$, 30% ethyl acetate/hexanes) to afford compound 1088 as a white solid (733 mg, 93%).

$^1$H NMR (400 MHz, CDCl$_3$) δ7.88-7.86 (m, 2H), 7.75-7.73 (m, 2H), 3.92 (t, 2H), 3.53 (t, 2H), 3.04 (t, 2H), 2.90 (t, 2H).

Part C:

Compound 1089 was prepared following the procedures described in Example 30A, Part A. $^1$H NMR (400 MHz, CDCl$_3$) δ7.89-7.87 (d, 1H), 7.86-7.84 (m, 2H), 7.74-7.72 (m, 2H), 7.58-7.56 (d, 1H), 7.46 (t, 1H), 7.38 (t, 1H), 4.52 (t, 2H), 3.92 (t, 2H), 3.02 (t, 2H), 2.89 (t, 2H); $^{19}$F NMR (400 MHz, CDCl$_3$) δ-4.7 ppm.

Part D:

To a solution of compound 1089 (250 mg, 0.6 mmol) in DCM (5 mL) was added m-chloroperoxybenzoic acid (336 mg, 1.5 mmol) and the resulting mixture was stirred overnight at room temperature. The reaction mixture was diluted with DCM, washed with saturated sodium bicarbonate solution, brine, dried over sodium sulfate and concentrated to give compound 1090 (284 mg) as a white solid which was used without further purification. $^1$H NMR (400 MHz, CDCl$_3$) δ7.92-7.90 (d, 1H), 7.90-7.88 (m, 2H), 7.78-7.76 (m, 2H), 7.66-7.62 (d of t, 1H), 7.54-7.51 (t of d, 1H), 7.46-7.44 (t of d, 1H), 4.89 (t, 2H), 4.20 (t, 2H), 3.65 (t, 2H), 3.46 (t, 2H); $^{19}$F NMR (400 MHz, CDCl$_3$) δ-62.5 ppm.

Part E:

Compound 1091 was prepared following the procedures described in Example 30A, Part B. $^1$H NMR (400 MHz, CDCl$_3$) δ7.91-7.89 (d, 1H), 7.63-7.61 (d, 1H), 7.51-7.48 (t of d, 1H), 7.44-7.40 (t of d, 1H), 4.90 (t, 2H), 3.71 (t, 2H), 3.31 (t, 2H), 3.12 (t, 2H); $^{19}$F NMR (400 MHz, CDCl$_3$) δ-62.5 ppm.

Part F:

Compound 1092 was prepared following the procedures described in Example 27A, Part B, and used without further purification. HPLC-MS t$_R$=1.65 min (UV$_{254\,nm}$); mass calculated for formula C$_{28}$H$_{29}$F$_3$N$_4$O$_8$S 638.17, observed LCMS m/z 639.1 (M+H).

Part G:

Compound 1093 was prepared following the procedures described in Example 27A, Part C. HPLC-MS $t_R$=3.57 min (10 min; $UV_{254\ nm}$); mass calculated for formula $C_{24}H_{25}F_3N_4O_6S$ 554.14, observed LCMS m/z 555.1 (M+H).

Example 30C

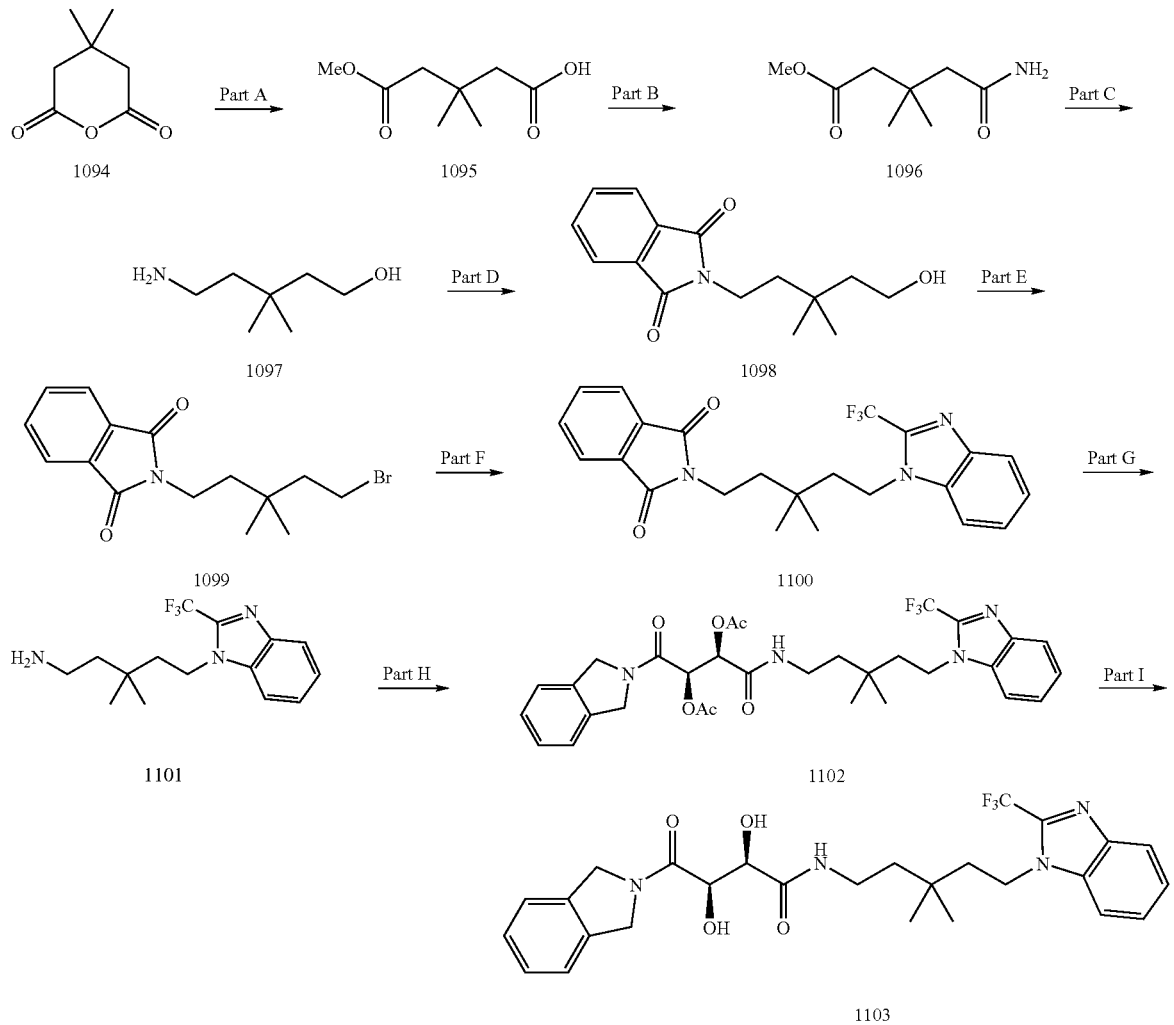

Part A:

According to a modification of a procedure by Brown, R. F. et. al. (*J. Am. Chem. Soc.* 1955, 77, 1083-1089) a mixture of 3,3-dimethyl glutaric anhydride (1094) (7.1 g, 50 mmol) and methanol (40 mL) was heated overnight at reflux. The reaction mixture was concentrated to give compound 1095 as a colorless oil (8.46 g, 97%). $^1$H NMR (400 MHz, CDCl$_3$) δ 3.70 (s, 3H), 2.50 (s, 2H), 2.48 (s, 2H), 1.16 (s, 6H).

Part B:

To an ice-cold solution of compound 1095 (8.46 g, 48.5 mmol) in DCM (30 mL) was added dropwise oxalyl chloride (7 mL, 80 mmol), followed by DMF (2 drops) and the resulting mixture was heated for 3.5 h at reflux. The reaction mixture was concentrated to give the corresponding acid chloride (4-chlorocarbonyl-3,3-dimethyl-butyric acid methyl ester) as a brown oil (7.89 g, 84%) which was used without further purification in the next step. To an ice-cold solution of ammonia in 1,4-dioxane (30 mL of a solution containing 2.2 g ammonia dissolved in 100 mL of 1,4-dioxane, 38.8 mmol approx) was added dropwise a solution of 4-chlorocarbonyl-3,3-dimethyl-butyric acid methyl ester (3 g, 15.5 mmol) in 1,4-dioxane (3 mL) and after the addition was complete the resulting white slurry was stirred 45 min at room temperature. The reaction mixture was diluted with ethyl acetate, filtered and concentrated to give compound 1096 as a viscous yellow oil (2.62 g, 97%). $^1$H NMR (400 MHz, CDCl$_3$) δ 3.71 (s, 3H), 2.43 (s, 2H), 2.31 (s, 2H), 1.14 (s, 6H).

Part C:

To an ice-cold solution of LAH (42 mL, 1 M sol in THF, 42 mmol) was added dropwise a solution of compound 1096 (2.02 g, 11.6 mmol) in THF and the resulting mixture was heated overnight at reflux. The reaction mixture was cooled to 0° C. and quenched by dropwise addition of brine, when a paste-like solid formed. This solid was triturated and sonicated several times with ethyl acetate, and the combined organic extracts were concentrated to give compound 1097 as an oil (1.17 g, 76%). $^1$H NMR (400 MHz, CDCl$_3$) δ 3.71 (t, 2H), 2.71 (t, 2H), 1.53 (t, 2H), 1.41 (t, 2H), 0.92 (s, 6H).

Part D:
  Compound 1098 was prepared following the procedures described in Example 30B, Part A. HPLC-MS $t_R$=1.88 min (UV$_{254\,nm}$); mass calculated for formula $C_{15}H_{19}NO_3$ 261.14, observed LCMS m/z 262.0 (M+H).

Part E:
  Compound 1099 was prepared following the procedures described in Example 30B, Part B. $^1$H NMR (400 MHz, CDCl$_3$) δ 7.84-7.82 (m, 2H), 7.71-7.69 (m, 2H), 3.70-3.66 (m, 2H), 3.47-3.42 (m, 2H), 1.97-1.92 (m, 2H), 1.61-1.57 (m, 2H), 1.03 (s, 6H).

Part F:
  Compound 1100 was prepared following the procedures described in Example 30B, Part C. $^1$H NMR (400 MHz, CDCl$_3$) δ 7.89-7.87 (d, 1H), 7.86-7.84 (m, 2H), 7.73-7.71 (m, 2H), 7.5-7.57 (d, 1H), 7.47-7.43 (t of d, 1H), 7.39-7.35 (t of d, 1H), 4.46-4.41 (m, 2H), 3.79-3.75 (m, 2H), 1.89-1.85 (m, 2H), 1.74-1.69 (m, 2H), 1.18 (s, 6H); $^{19}$F NMR (400 MHz, CDCl$_3$) δ2.7 ppm.

Part G:
  Compound 1101 was prepared following the procedures described in Example 30B, Part E. HPLC-MS $t_R$=1.13 min (UV$_{254\,nm}$); mass calculated for formula $C_{15}H_{20}F_3N_3$ 299.16, observed LCMS m/z 300.1 (M+H).

Part H:
  Compound 1102 was prepared following the procedures described in Example 27A, Part B, and used without further purification. HPLC-MS $t_R$=2.0 min (UV$_{254\,nm}$); mass calculated for formula $C_{31}H_{35}F_3N_4O_6$ 616.25, observed LCMS m/z 617.2 (M+H).

Part I:
  Compound 1103 was prepared following the procedures described in Example 27A, Part C. HPLC-MS $t_R$=4.52 min (10 min, UV$_{254\,nm}$); mass calculated for formula $C_{27}H_{31}F_3N_4O_4$ 532.23, observed LCMS m/z 533.2 (M+H).

The following compounds were synthesized using procedures described in Example 30 A-C.

| Compound # | Structure | Exact mass | MS m/e (M + H) |
| --- | --- | --- | --- |
| 1104 | 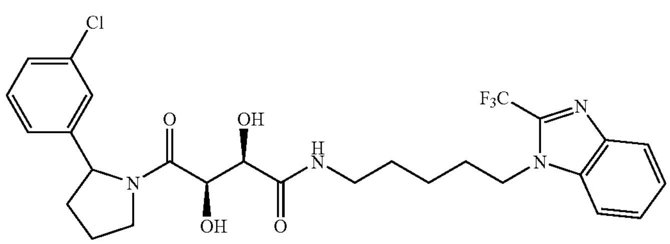 | 566.2 | 567.2 |
| 1105 | 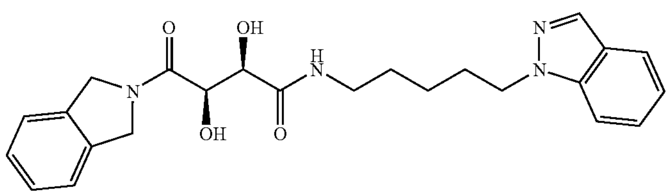 | 436.21 | 437.2 |
| 1106 | 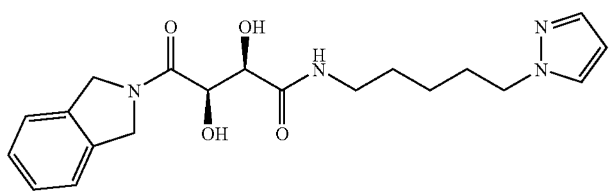 | 386.2 | 387.2 |
| 1107 | 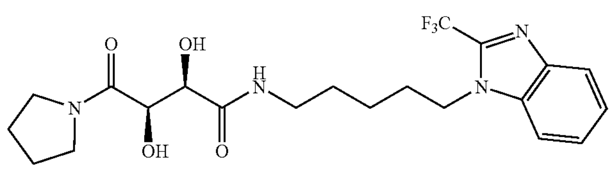 | 456.2 | 457.1 |
| 1108 | 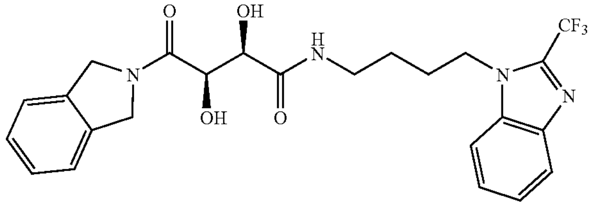 | 490.18 | 491.1 |

-continued

| Compound # | Structure | Exact mass | MS m/e (M + H) |
|---|---|---|---|
| 1109 | 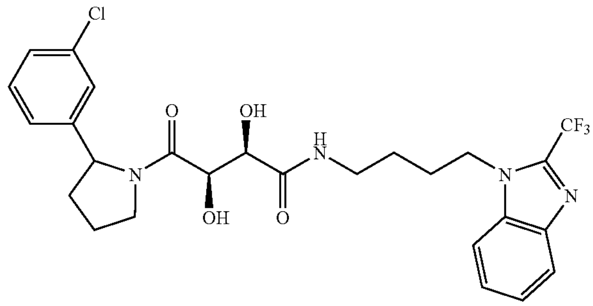 | 552.18 | 553.2 |
| 1110 | 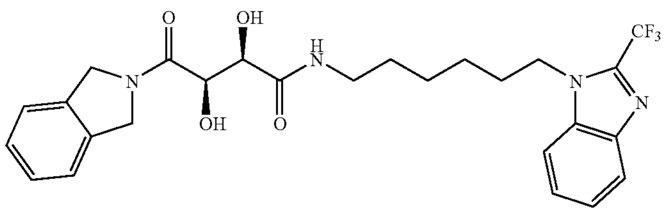 | 518.2 | 519.1 |
| 1111 | 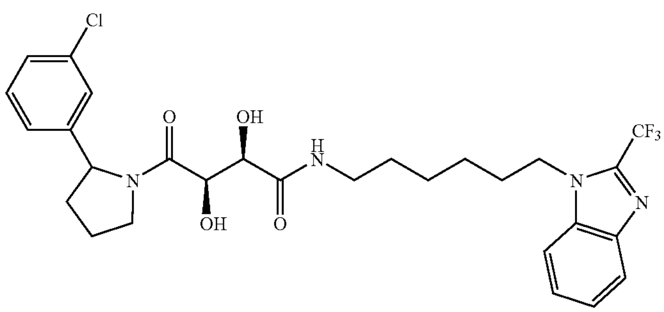 | 580.21 | 581.2 |
| 1112 | 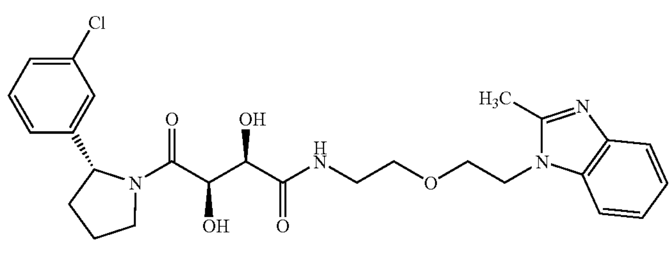 | 514.2 | 515.2 |
| 1113 | 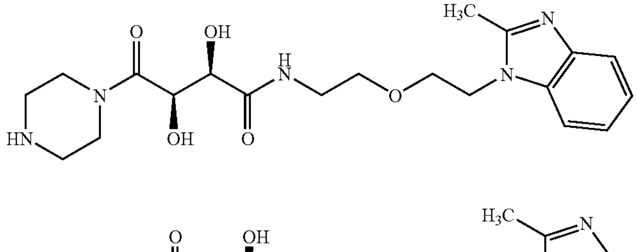 | 419.2 | 420.2 |
| 1114 | 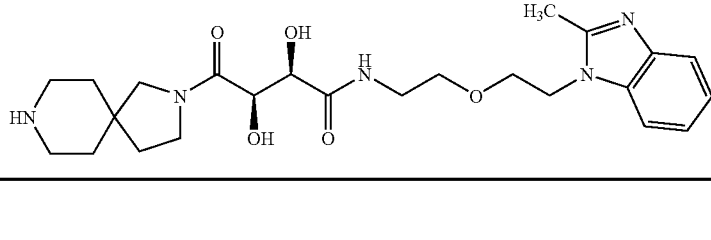 | 473.3 | 474.3 |

Example 31

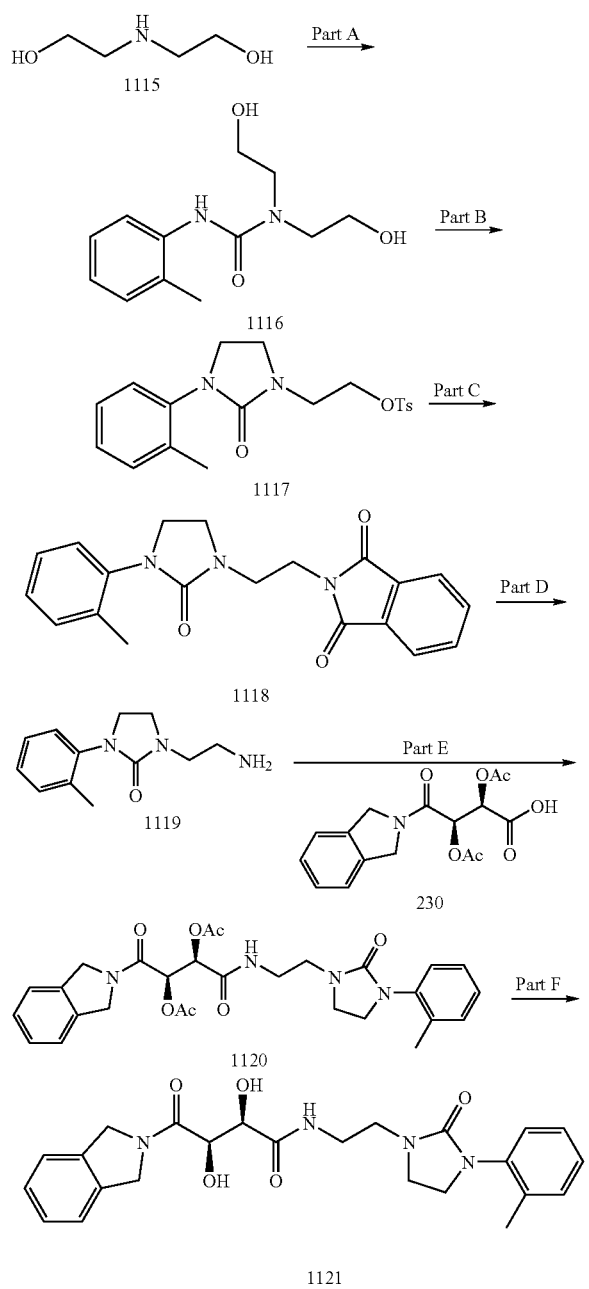

Part A:

Compound 1115 (790 mg, 7.5 mmol) was dissolved in THF (10 mL) and cooled in an ice bath. 2-Methylphenylisocyanate (500 mg, 3.75 mmol) was added in portions and the resulting solution was stirred at room temperature for 2 hours. The reaction mixture was quenched with water and extracted with ethyl acetate. The combined organic layers were washed with 1 N HCl solution, bicarbonate solution and brine; dried over sodium sulfate and concentrated. Purification by column chromatography (SiO$_2$, 50% ethyl acetate/hexanes) afforded a white solid 1116 (1.02 g, 56%). HPLC-MS $t_R$=0.95 (UV$_{254\ nm}$); mass calculated for formula C$_{12}$H$_{18}$N$_2$O$_3$ 238.1, observed LCMS m/z 239.2 (M+H).

Part B:

Compound 1116 (1.02 g, 4.2 mmol) was dissolved in THF (25 mL) and cooled in an ice bath. Potassium t-butoxide (1.5 g, 13.2 mmol) was added in portions and the reaction mixture was stirred for 10 minutes. A solution of p-toluenesulfonyl chloride (1.91 g, 10.8 mmol) in THF (5 mL) was added dropwise and the reaction was stirred 30 minutes at 0° C. and 30 minutes at room temperature. The reaction was quenched with water and extracted with ethyl acetate. The combined organic layers were washed with 1 N HCl solution, bicarbonate solution and brine; dried over sodium sulfate and concentrated. Purification by column chromatography (SiO$_2$, 50% ethyl acetate/hexanes) afforded a white solid 1117 (0.750 g, 48%). HPLC-MS $t_R$=1.87 min (UV$_{254\ nm}$); mass calculated for formula C$_{19}$H$_{22}$N$_2$O$_4$S 374.1, observed LCMS m/z 375.1 (M+H).

Part C:

Compound 1117 (750 mg, 2.0 mmol) was dissolved in DMF (10 mL) and phthalimide (441 mg, 3.0 mmol) and cesium carbonate (1.95 g, 6.0 mmol) were added and stirred overnight. The reaction mixture was quenched with water and extracted with ethyl acetate. The combined organic layers were washed with 1 N HCl solution, bicarbonate solution and brine; dried over sodium sulfate and concentrated. The solid residue was recrystallized from ethyl acetate/hexanes to provide 1118 (500 mg, 72%) as a white solid. HPLC-MS $t_R$=1.63 (UV$_{254\ nm}$); mass calculated for formula C$_{20}$H$_{19}$N$_3$O$_3$ 349.1, observed LCMS m/z 350.2 (M+H).

Part D:

Compound 1118 (110 mg, 0.29 mmol) was dissolved in ethanol (3 mL) and hydrazine hydrate (0.10 mL) was added. The reaction was stirred for 3 hours at room temperature. The solids were removed by filtration and the solution was evaporated under reduced pressure. The residue was dissolved in 1 N NaOH solution and extracted with ethyl acetate. The combined organic layers were washed with brine; dried over sodium sulfate and concentrated to provide compound 1119 that was used without purification.

Part E:

Compound 1119, 230 (97 mg, 0.29 mmol), DIEA (0.125 mL, 0.7 mmol) and HATU (133 mg, 0.348 mmol) were combined in DMF (3 ml) and stirred overnight. The reaction was quenched with water and extracted with ethyl acetate. The combined organic layers were washed with 1 N HCl solution, bicarbonate solution and brine; dried over sodium sulfate and concentrated to provide compound 1120 that was used in the next step without purification. HPLC-MS $t_R$=1.68 min (UV$_{254\ nm}$); mass calculated for formula C$_{28}$H$_{32}$N$_4$O$_7$ 536.2, observed LCMS m/z 537.3 (M+H).

Part F:

Compound 1120 was dissolved in methanol (5 mL) and potassium carbonate (150 mg) was added and stirred for 30 minutes. The reaction was quenched with water and extracted with ethyl acetate. The combined organic layers were washed with 1 N HCl solution, bicarbonate solution and brine; dried over sodium sulfate and concentrated. Purification by reverse phase prep-LC afforded 1121 as a white solid (16 mg) after lyophilization. HPLC-MS $t_R$=3.48 min (UV$_{254\ nm}$, 10 min); mass calculated for formula C$_{24}$H$_{28}$N$_4$O$_5$ 452.2, observed LCMS m/z 453.1 (M+H).

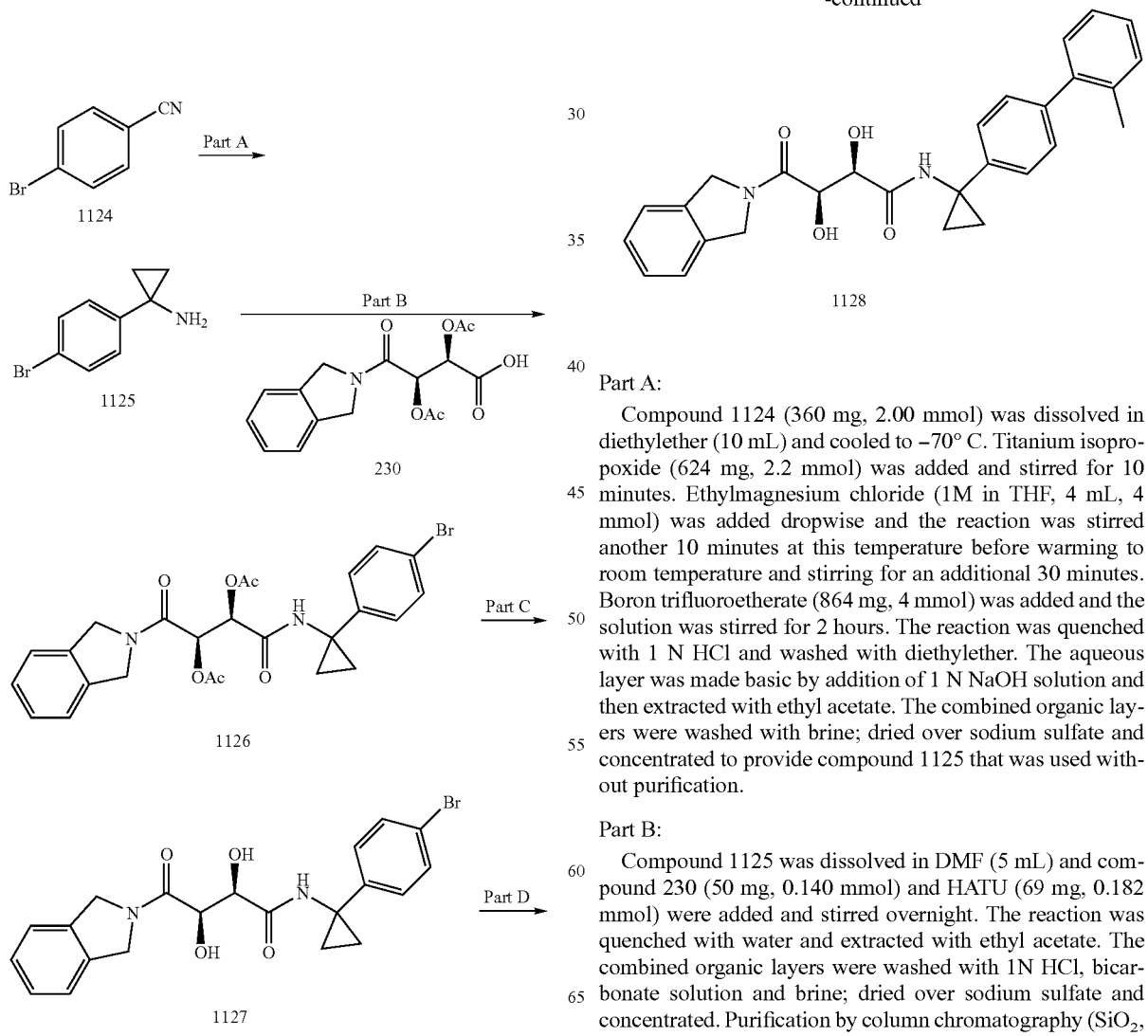

| Compound # | Structure | Exact mass | MS m/e (M + H) |
|---|---|---|---|
| 1122 | 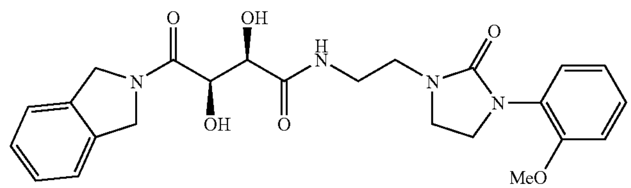 | 468.20 | 469.1 |
| 1123 | 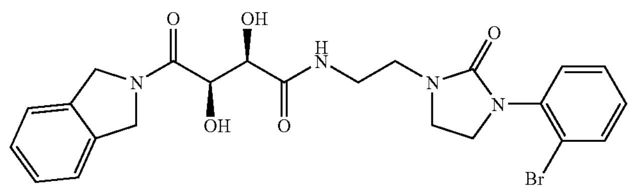 | 516.10 | 517.0 |

Example 32

Part A:

Compound 1124 (360 mg, 2.00 mmol) was dissolved in diethylether (10 mL) and cooled to −70° C. Titanium isopropoxide (624 mg, 2.2 mmol) was added and stirred for 10 minutes. Ethylmagnesium chloride (1M in THF, 4 mL, 4 mmol) was added dropwise and the reaction was stirred another 10 minutes at this temperature before warming to room temperature and stirring for an additional 30 minutes. Boron trifluoroetherate (864 mg, 4 mmol) was added and the solution was stirred for 2 hours. The reaction was quenched with 1 N HCl and washed with diethylether. The aqueous layer was made basic by addition of 1 N NaOH solution and then extracted with ethyl acetate. The combined organic layers were washed with brine; dried over sodium sulfate and concentrated to provide compound 1125 that was used without purification.

Part B:

Compound 1125 was dissolved in DMF (5 mL) and compound 230 (50 mg, 0.140 mmol) and HATU (69 mg, 0.182 mmol) were added and stirred overnight. The reaction was quenched with water and extracted with ethyl acetate. The combined organic layers were washed with 1N HCl, bicarbonate solution and brine; dried over sodium sulfate and concentrated. Purification by column chromatography (SiO$_2$, 50% ethyl acetate/hexanes) afforded a white solid 1126 (60 mg, 81%). HPLC-MS $t_R$=1.928 (UV$_{254\ nm}$); mass calculated for formula $C_{25}H_{25}BrN_2O_6$ 528.0, observed LCMS m/z 529.1 (M+H).

Part C:
Compound 1126 (60 mg, 0.1427 mmol) was dissolved in MeOH (5 mL) and potassium carbonate (100 mg) was added followed by stirring for 30 minutes. The reaction was quenched with water and extracted with ethyl acetate. The combined organic layers were washed with bicarbonate solution and brine; dried over sodium sulfate and concentrated. Purification by reverse phase prep-LC afforded a white solid 1127 (10 mg, 15.8%) after lyophilization. HPLC-MS $t_R$=4.192 min (UV$_{254\ nm}$, 10 min); mass calculated for formula $C_{21}H_{21}BrN_2O_4$ 444.0, observed LCMS m/z 445.1 (M+H).

Part D:
Compound 1127 (7.6 mg, 0.017 mmol) was dissolved in dioxane (2 mL) and Pd(dba)$_3$ (3 mg), triphenylphosphine (4.4 mg, 0.017 mmol), potassium phosphate (8 mg, 0.0377 mmol), and 2-methylphenylboronic acid (4.3 mg, 0.034 mmol) were added under a nitrogen atmosphere. The reaction mixture was heated to 90° C. overnight and then filtered over a bed of celite and concentrated. Purification by reverse phase prep-LC afforded a white solid 1128 (5 mg, 65%) after lyophilization. HPLC-MS $t_R$=4.095 min (UV$_{254\ nm}$, 10 min); mass calculated for formula $C_{28}H_{28}N_2O_4$ 456.2, observed LCMS m/z 457.3 (M+H).

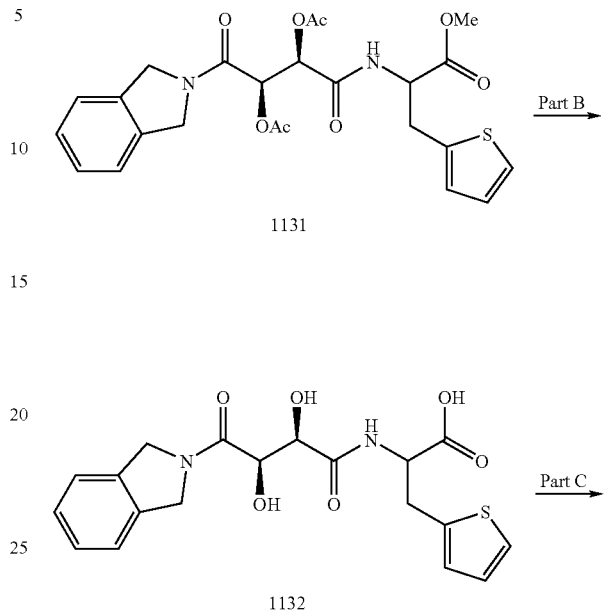

| Compound # | Structure | Exact mass | MS m/e (M + H) |
|---|---|---|---|
| 1129 | 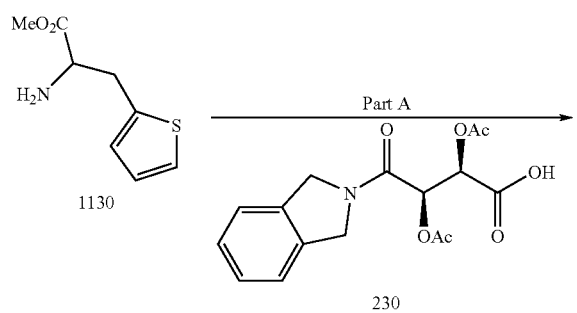 | 366.16 | 367.1 |

Example 33

Constrained Analogs

Example 33A

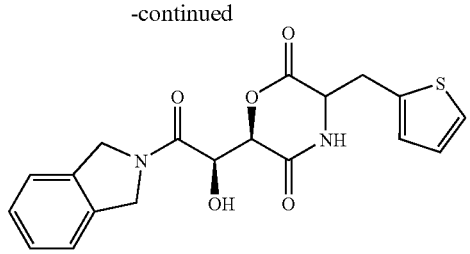

Part A:
To 2-amino-3-thiophen-2-yl-propionic acid methyl ester hydrochloride (1130) (120 mg, 0.54 mmol) in DMF (2 mL) was added 230 (150 mg, 0.45 mmol), DIEA (160 □M, 0.9 mmol) and HATU (205 mg, 0.54 mmol). The reaction mixture was stirred overnight at room temperature, and diluted with ethyl acetate and water. The organic layer was washed with 1 N HCl, saturated NaHCO$_3$, and brine. It was dried over Na$_2$SO$_4$, and concentrated, resulting in compound 1131.

Part B:

Compound 1131 was dissolved in 5 mL of MeOH, 10 mL of 10% $K_2CO_3$ aqueous solution was added. After stirring at room temperature for 1 h, the reaction mixture was concentrated in vacuo, and then acified with 1N HCL to PH 2. The solution was then extracted with EtOAc, the organic layer was washed with brine, dried over $Na_2SO_4$, and concentrated, affording compound 1132 as a white solid. Mass calculated for formula $C_{19}H_{20}N_2O_6S$ 404.1, observed LCMS m/z 405.0.0 (M+H).

Part C:

Compound 1132 (40 mg, 0.1 mmol) in 1 mL of DMF was added with PS carbodiimide resin (117 mg, 1.28 mmol/g loading, 0.15 mmol) and dimethylaminopyridine (3 mg, 0.024 mmol). After stirring overnight at 50° C., the solid was filtered off, and the solution was concentrated in vacuo. Purification by reverse phase prep-LC afforded compound 1133 as a white solid. HPLC-MS $t_R$=3.59 min ($UV_{254\ nm}$, 10 min), Mass calculated for formula $C_{25}H_{26}ClN_3O_4S$ 386.1, observed LCMS m/z 387.0 (M+H). Compound Structure Exact mass MS m/e (M+H)

-continued

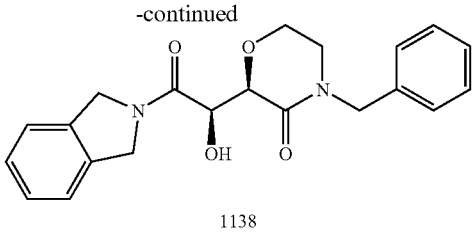

1138

Part A:

2-Benzylamino-ethanol (1135) (0.676 g, 4.5 mmol) in DMF (10 mL) was added 230 (1.0 g, 3 mmol), and HATU (1.71 g, 4.5 mmol). The reaction mixture was stirred overnight at room temperature, and diluted with ethyl acetate and water. The organic layer was washed with 1 N HCl, saturated $NaHCO_3$, and brine. It was dried over $Na_2SO_4$, and concentrated, resulting in compound 1136 (1.1 g, 80%). Mass calculated for formula $C_{25}H_{28}N_2O_7$ 468.2, observed LCMS m/z 469.1 (M+H).

| Compound # | Structure | Exact mass | MS m/e (M + H) |
|---|---|---|---|
| 1134 | 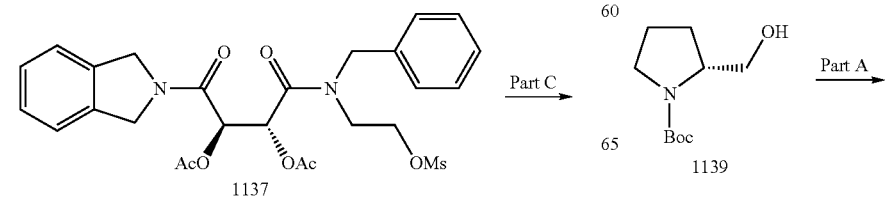 | 418.1 | 419.0 |

Example 33B

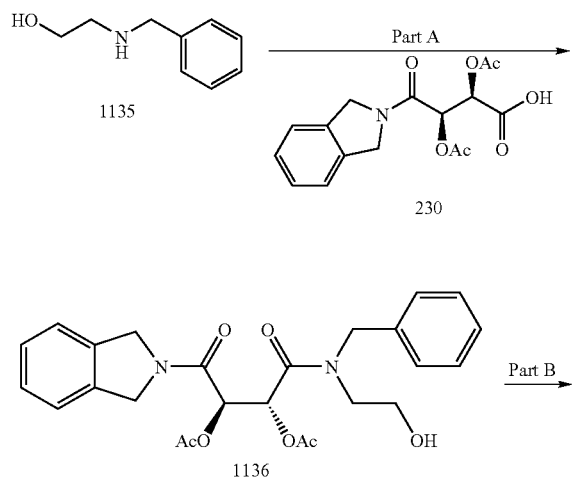

Part B:

Compound 1136 (468 mg, 1 mmol) and DIEA (261 mL, 1.5 mmol) in $CH_2Cl_2$ (5 mL) was added dropwise with mesyl chloride (116 mL, 1.5 mmol) at 0° C. After stirring at 0° C. for 10 min, the reaction mixture was allowed to stir at room temperature for 1.5 h, then concentrated to dryness. The residue was extracted with ethyl acetate, washed with 1 N HCl, saturated $NaHCO_3$, and brine. It was dried over $Na_2SO_4$, and concentrated, resulting in 1137 (511 mg, 93%).

Part C:

Compound 1137 (389 mg, 0.71 mmol) in MeOH (20 mL) was added with solid $K_2CO_3$ (323 mg, 2.34 mmol). After stirring at room temperature for 2 h, it was concentrated to remove the solvent, then dissolved in EtOAc and water. The organic layer was washed with 1 N HCl, saturated $NaHCO_3$, brine, and concentrated. Purification by reverse phase prep-LC afforded 1138 as a white solid. HPLC-MS $t_R$=3.89 min ($UV_{254\ nm}$, 10 min), Mass calculated for formula $C_{21}H_{22}N_2O_4$ 366.16, observed LCMS m/z 367.1 (M+H).

Example 33C

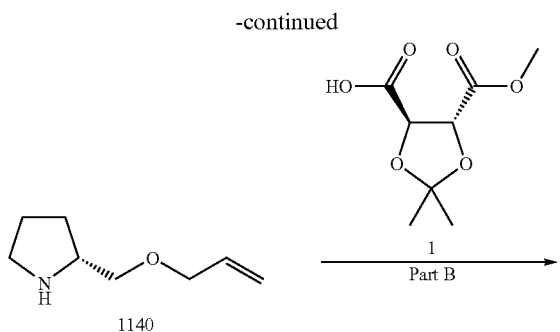

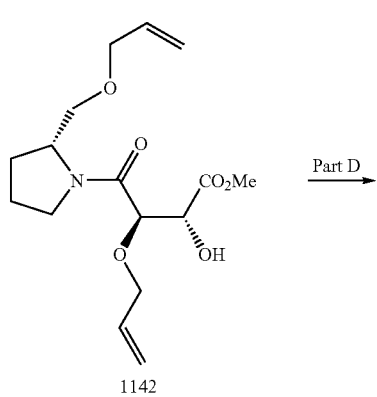

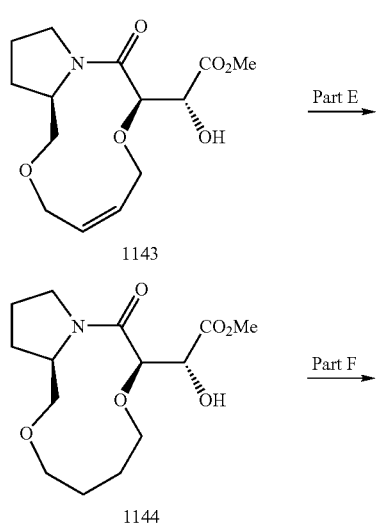

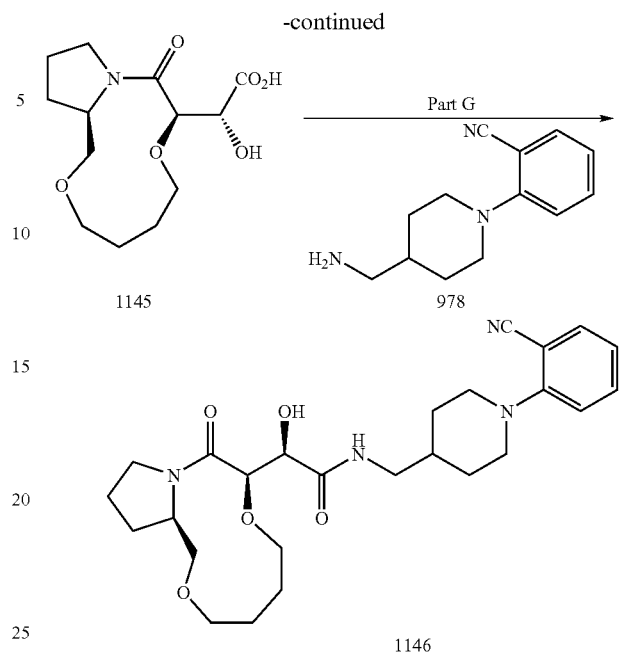

Part A:
Step 1: (R)-Boc-prolinol (1139) (2.0 g, 9.94 mmol) in THF (5 mL) was added into NaH (0.437 g, 60% in mineral oil, 10.93 mmol) in 10 mL of THF at 0° C. After stirring at 0° C. for 10 min, allyl bromide (1.32 g, 10.93 mmol) was added. Te reaction mixture was allowed to stir overnight at room temperature. After filtration, the solution was concentrated to dryness, the residue was taken up with EtOAc, washed with 1N citric acid, saturated NaHCO$_3$, and brine, dried over Na$_2$SO$_4$, and concentrated, resulting in a colorless oil (2.30 g, 96%).

Step 2: The above material in CH$_2$Cl$_2$ (10 mL) was added dropwise with 3 mL of TFA at 0° C. After stirring at room temperature for 1 h, the solution was concentrated. The residue was dissolved in EtOAc, washed with concentrated Na$_2$CO$_3$, brine, dried over over Na$_2$SO$_4$, and concentrated, resulting in compound 1140 as a colorless oil (1.06 g, 75% for two steps).

Part B:
Step 1: To compound 1140 (500 mg, 3.54 mmol) in DMF (10 mL) was added 1 (867 mg, 4.25 mmol) DIEA (1.48 mL, 8.5 mmol) and HATU (1.616 g, 4.25 mmol) at 0° C. After stirring at room temperature for 5 h, the reaction mixture was diluted with ethyl acetate and water. The organic phase was washed with 1 N citric acid, saturated NaHCO$_3$, and brine. It was dried over Na$_2$SO$_4$, and concentrated. Column purification (SiO$_2$, EtOAc/Hexane 40:60) afforded a colorless oil (650 mg, 57%).

Step 2: The above material was treated with 5 mL of TFA/H$_2$O (80:20) at 0° C. After stirring at room temperature for 2 h, it was concentrated to dryness. Column purification (SiO$_2$, EtOAc/Hexane 70:30) afforded compound 1141 (500 mg, 88%) as a colorless oil.

Part C:
Step 1: To compound 1141 (250 mg, 0.87 mmol) in toluene (20 mL) was added dibutyltin oxide (217 mg, 0.87 mmol). The reaction mixture was refluxed for 1 h, using Dean-stark apparatus for azotropic removal of water. After cooling to room temperature, the solvent was stripped to dryness under reduced pressure. The resulting oil was dried in vacuo for 2 h.

Step 2: To the above oil was added CsF (198 mg, 1.30 mmol). The mixture was then placed in vacuo for 2 h. Allyl bromide (220 mg, 1.83 mmol) in DMF (10 mL) was added at 0° C. After stirring at room temperature under argone for 30 h, the reaction mixture was concentrated, and then taken up with EtOAc. The solution was washed with saturated KF solution, and brine, dried over $Na_2SO_4$, and concentrated. The organic layer was washed with 1 N HCl, saturated $NaHCO_3$, brine, and concentrated. Column chromatography ($SiO_2$, EtOAc/Hexane 60:40) afforded compound 1142 as a colorless oil (130 mg, 45%). Mass calculated for formula $C_{16}H_{25}NO_6$ 327.17, observed LCMS m/z 328.1 (M+H).

Part D:

Compound 1142 (110 mg, 0.33 mmol) in dichloromethane (200 mL) was added with Grubbs' second-generation catalyst (Scholl, M.; Ding, S.; Lee, C. W.; Grubbs, R. H., *Org. Lett*, 1999, 1, 953-956.). After stirring at room temperature under argone for 3.5 h, the solution was concentrated under reduced pressure. Column chromatography ($SiO_2$, EtOAc) afforded 1143 as a white solid (60 mg, 60%), Mass calculated for formula $C_{14}H_{21}NO_6$ 299.14, observed LCMS m/z 300.1 (M+H).

Part E:

To 1143 (60 mg, 0.2 mmol) in EtOAc (10 mL) was added 10% Pd/C (10 mg). The reaction mixture was allowed to stir at room temperature under $H_2$ for 2 h, then concentrated. Column chromatography ($SiO_2$, EtOAc) afforded 1144 as a white solid (50 mg, 83%), Mass calculated for formula $C_{14}H_{23}NO_6$ 301.15, observed LCMS m/z 302.1 (M+H).

Part F:

Compound 1144 (20 mg, 0.067 mmol) in MeOH (2 mL) was mixed with solid $K_2CO_3$ (20 mg, 0.14 mmol). After stirring at room temperature for 5 h, the reaction mixture was concentrated, and then taken up with EtOAc and water. It was acidified with 1N HCl. The organic layer was separated, washed with brine, dried over $Na_2SO_4$, and concentrated to afford 1145 as a white solid (12 mg, 63%), Mass calculated for formula $C_{13}H_{21}NO_6$ 287.1, observed LCMS m/z 288.1 (M+H).

Part G:

A mixture of 1145 (12 mg, 0.042 mmol), 978 (13.5 mg, 0.063 mmol), DIEA (0.018 mL, 0.1 mmol) and HATU (24 mg, 0.063 mmol) in DMF (1 mL) was stirred overnight at room temperature, and then diluted with ethyl acetate and water. The organic layer was washed with 1 N HCl, saturated $NaHCO_3$, and brine. It was dried over $Na_2SO_4$, and concentrated. Purification by reverse phase prep-LC afforded 1146 as a white solid. HPLC-MS $t_R$=4.22 min ($UV_{254\ nm}$, 10 min), mass calculated for formula $C_{21}H_{22}N_2O_4$ 484.3, observed LCMS m/z 485.2 (M+H).

Example 34

Example 34A

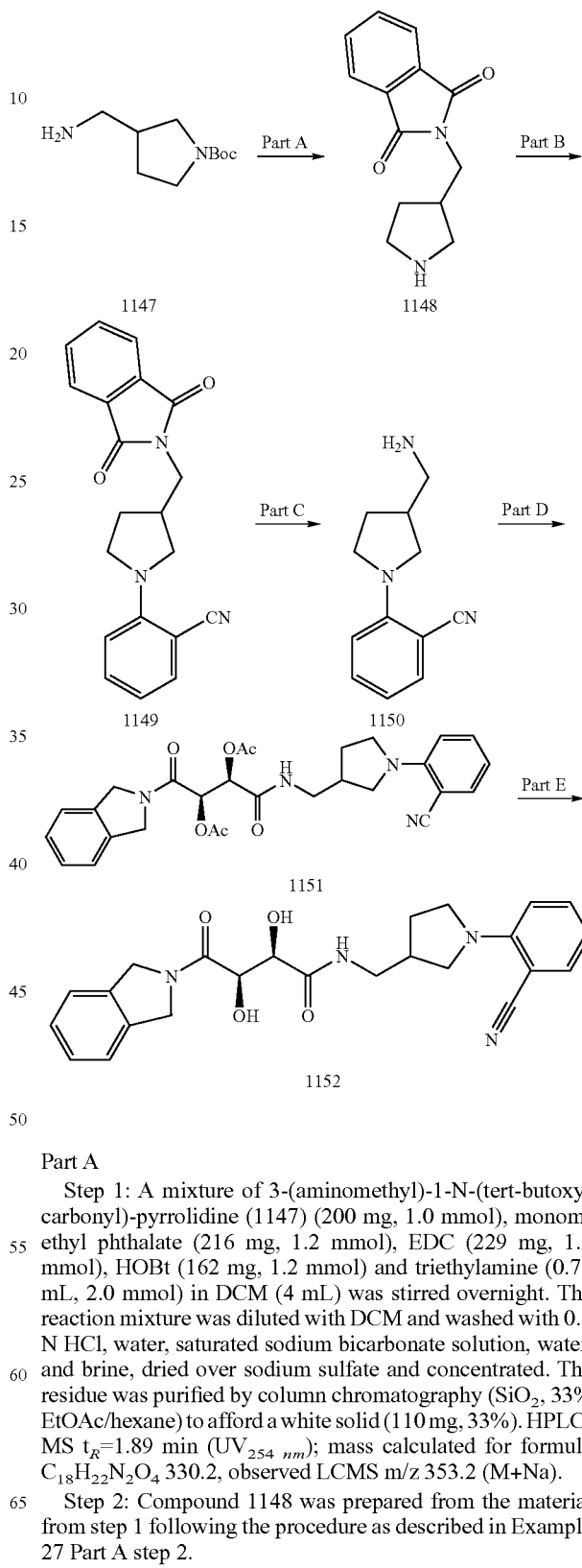

Part A

Step 1: A mixture of 3-(aminomethyl)-1-N-(tert-butoxycarbonyl)-pyrrolidine (1147) (200 mg, 1.0 mmol), monomethyl phthalate (216 mg, 1.2 mmol), EDC (229 mg, 1.2 mmol), HOBt (162 mg, 1.2 mmol) and triethylamine (0.79 mL, 2.0 mmol) in DCM (4 mL) was stirred overnight. The reaction mixture was diluted with DCM and washed with 0.1 N HCl, water, saturated sodium bicarbonate solution, water, and brine, dried over sodium sulfate and concentrated. The residue was purified by column chromatography ($SiO_2$, 33% EtOAc/hexane) to afford a white solid (110 mg, 33%). HPLC-MS $t_R$=1.89 min ($UV_{254\ nm}$); mass calculated for formula $C_{18}H_{22}N_2O_4$ 330.2, observed LCMS m/z 353.2 (M+Na).

Step 2: Compound 1148 was prepared from the material from step 1 following the procedure as described in Example 27 Part A step 2.

Part B

Compound 1149 was prepared following the procedure as described in Example 27 Part A step 1. HPLC-MS $t_R$=1.96 min (UV$_{254\ nm}$); mass calculated for formula $C_{20}H_{17}N_3O_2$ 331.1, observed LCMS m/z 332.2 (M+H).

Part C

Compound 1149 (0.33 mmol) and hydrazine hydrate (65 μL, 1.34 mmol) in ethanol (3 mL) were refluxed for 2 hours. The reaction mixture was cooled and filtered. The filtrate was concentrated and 1150 was used without further purification.

Part D and E

Compounds 1151 and 1152 were prepared following the procedures described in Example 5 Part D and E. Data for 1151: HPLC-MS $t_R$=1.78 min (UV$_{254\ nm}$); mass calculated for formula $C_{28}H_{30}N_4O_6$ 518.2, observed LCMS m/z 519.2 (M+H). Data for 1152: HPLC-MS $t_R$=1.52 min (UV$_{254\ nm}$); mass calculated for formula $C_{24}H_{26}N_4O_4$ 434.2, observed LCMS m/z 435.2 (M+H).

Example 34B

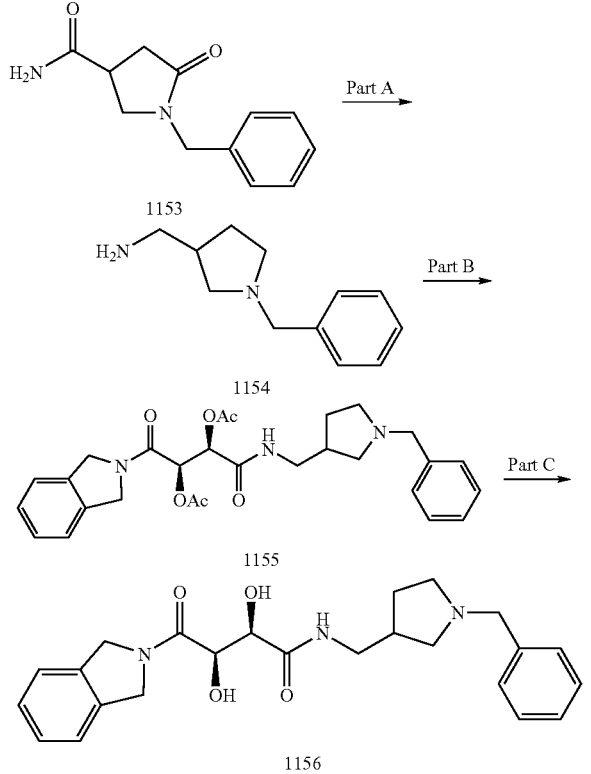

Part A

To a solution of 1-benzyl-5-oxo-3-pyrrolidinecarboxamide (1153) (50 mg, 0.23 mmol) in THF (1 mL) was added 1M solution of lithium aluminum hydride in THF (0.69 mL, 0.69 mmol). The reaction mixture was stirred at 50° C. for 3 hours, cooled, quenched with aqueous ammonium chloride solution. After addition of 1 N sodium hydroxide solution, the mixture was diluted with ethyl acetate, stirred for 20 minutes, and filtered through a pad of Celite. The filtrate was washed with 1N sodium hydroxide solution and brine, dried over sodium sulfate and concentrated to give 1154 as an oil (14 mg, 32%). HPLC-MS $t_R$=0.22 min (UV$_{254\ nm}$); mass calculated for formula $C_{12}H_{18}N_2$ 190.2, observed LCMS m/z 191.2 (M+H).

Part B and C

Compounds 1155 and 1156 were prepared following the procedures described in Example 5 Part D and E. Data for 1156: HPLC-MS $t_R$=0.91 min (UV$_{254\ nm}$); mass calculated for formula $C_{24}H_{29}N_3O_4$ 423.2, observed LCMS m/z 424.1 (M+H).

Example 35

Example 35A

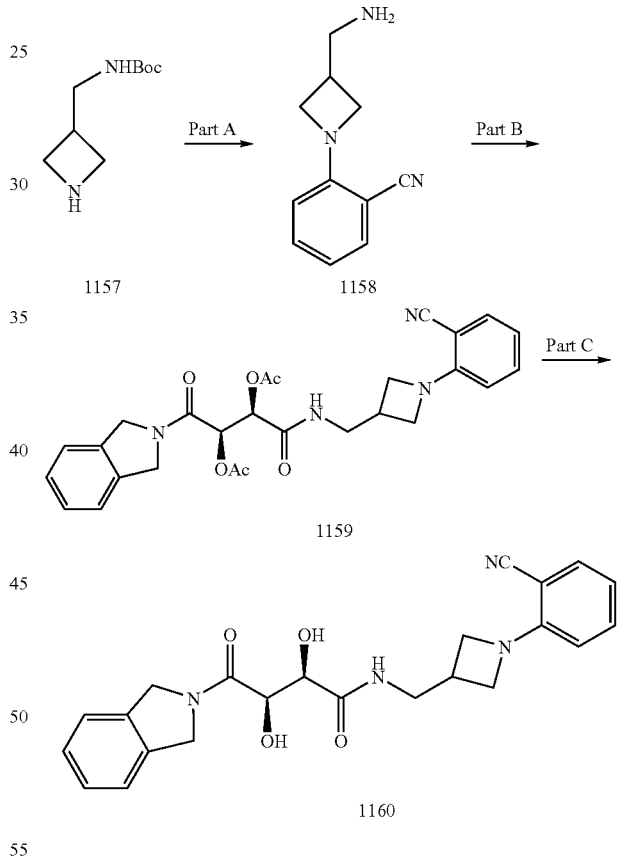

Part A and B and C:

Compounds 1158, 1159 and 1160 were prepared following the procedures described in Example 27 Part A, B and C. Data for 1158: HPLC-MS $t_R$=0.76 min (UV$_{254\ nm}$); mass calculated for formula $C_{11}H_{13}N_3$ 187.1, observed LCMS m/z 188.1 (M+H). Data for 1159: HPLC-MS $t_R$=1.72 min (UV$_{254\ nm}$); mass calculated for formula $C_{27}H_{28}N_4O_6$ 504.2, observed LCMS m/z 505.1 (M+H). Data for 1160: HPLC-MS $t_R$=1.43 min (UV$_{254\ nm}$); mass calculated for formula $C_{23}H_{24}N_4O_4$ 420.2, observed LCMS m/z 421.1 (M+H).

Example 35B

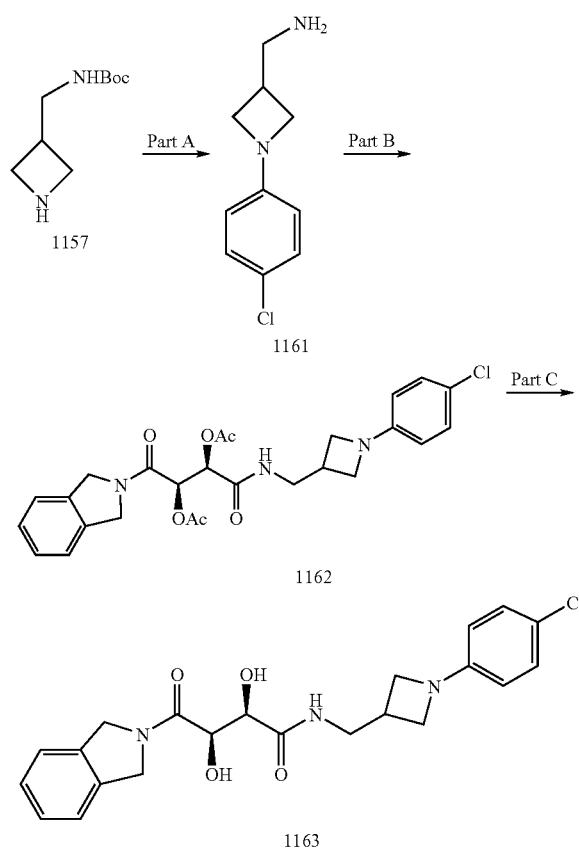

Part A

Step 1: A mixture of azetidin-3-ylmethyl-carbamic acid tert-butyl ester (1157) (20 mg, 0.107 mmol), 4-chloro-1-iodobenzene (38.4 mg, 0.161 mmol), copper iodide (4.0 mg, 0.021 mmol), L-proline (4.8 mg, 0.042 mmol) and potassium carbonate (29.6 mg, 0.214 mmol) in DMSO (2 mL) under Argon atmosphere was stirred at 80° C. overnight. The reaction mixture was diluted with EtOAc, washed with water and brine, dried over sodium sulfate and concentrated. HPLC-MS $t_R$=2.13 min ($UV_{254\ nm}$); mass calculated for formula $C_{15}H_{21}ClN_2O_3$ 296.1, observed LCMS m/z 297.2 (M+H).

Step 2: Compound 1161 was prepared from the material from step 1 following the procedure as described in Example 27 Part A step 2.

Part B and C

Compounds 1162 and 1163 were prepared following the procedures described in Example 5 Part D and E. Data for 1162: HPLC-MS $t_R$=1.93 mm ($UV_{254\ nm}$); mass calculated for formula C26H28ClN3O6 513.2, observed LCMS m/z 514.2 (M+H). Data for 1163: HPLC-MS $t_R$=1.63 nm ($UV_{254\ nm}$); mass calculated for formula $C_{22}H_{24}ClN_3O_4$ 429.2, observed LCMS m/z 430.1 (M+H).

Example 36

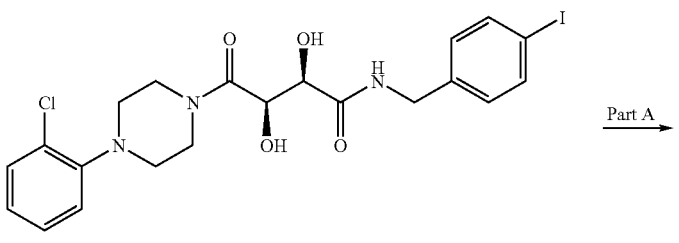

1164

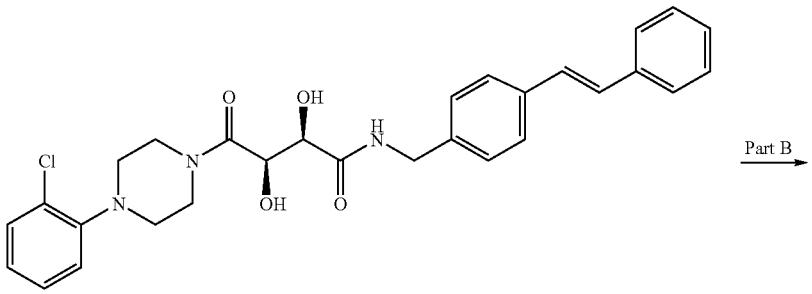

1159

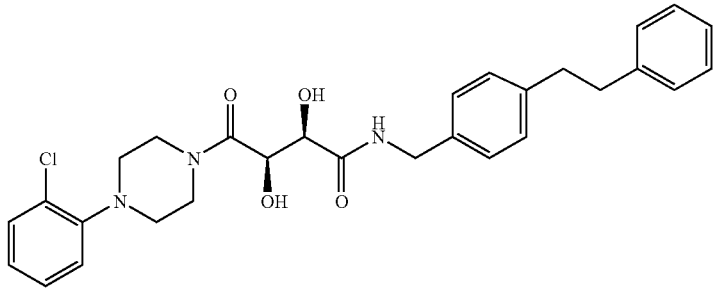

1166

Compound 1164 was prepared using procedures described in Example 2. HPLC-MS $t_R$=1.88 min (UV$_{254\ nm}$); mass calculated for formula $C_{21}H_{23}ClIN_3O_4$ 543.0, observed LCMS m/z 544.0 (M+H).

Part A:

Compound 1165 was prepared from 1164 and styrenyl boronic acid using the coupling conditions described in Example 3 Part F. HPLC-MS $t_R$=2.11 min (UV$_{254\ nm}$); mass calculated for formula $C_{29}H_{30}ClN_3O_4$ 519.2, observed LCMS m/z 520.0 (M+H).

Part B:

A mixture of 1165 (10 mg, 0.02 mmol) and palladium on carbon (10 wt %, 2 mg) in THF (2 mL) under hydrogen (atmospheric pressure) was stirred overnight. The reaction mixture was filtered through celite and concentrated. Purification by prep-LC afforded 1166 as an off-white solid (5 mg). HPLC-MS $t_R$=5.42 min (UV$_{254\ nm}$, 10 min); mass calculated for formula $C_{29}H_{32}ClN_3O_4$ 521.2, observed LCMS m/z 522.2 (M+H).

| Compound # | Structure | Exact mass | MS m/e (M + H) |
|---|---|---|---|
| 1167 | 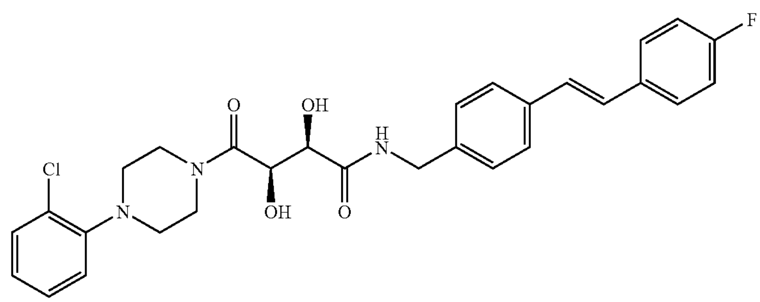 | 537.2 | 538.1 |
| 1168 | 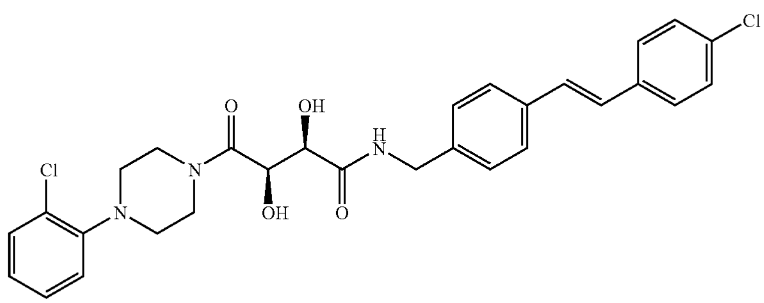 | 553.2 | 554.0 |
| 1169 | 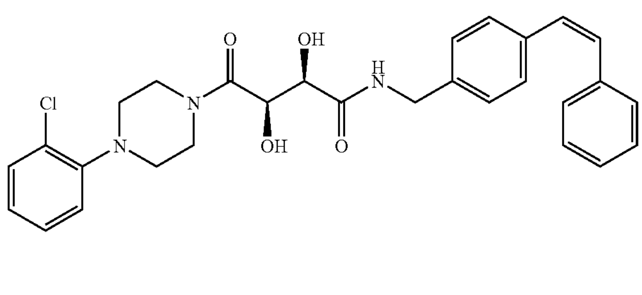 | 519.2 | 520.2 |

-continued

| Compound # | Structure | Exact mass | MS m/e (M + H) |
|---|---|---|---|
| 1170 | 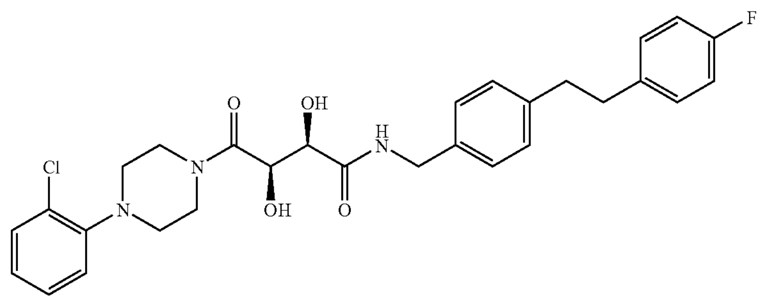 | 539.2 | 540.2 |
| 1171 | 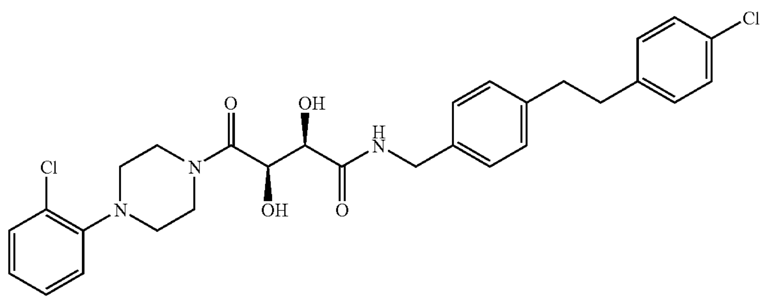 | 555.2 | 556.0 |

Example 37

Alkyl Suzuki

Example 37A

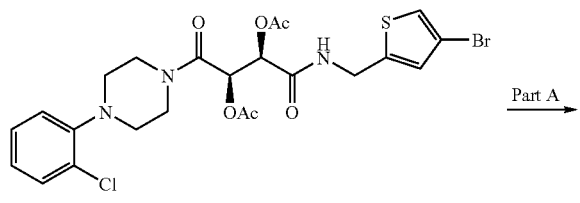

Part A:

Compound 1172 was prepared from 189 using the procedures described in Example 2A Part B. HPLC-MS $t_R$=4.83 min (UV$_{254\ nm}$, 10 min); mass calculated for formula $C_{19}H_{21}BrClN_3O_4S$ 501.0, observed LCMS m/z 502.0 (M+H).

Part B:

Compound 1173 was prepared using the procedures described in Example 36 Part A. HPLC-MS $t_R$=5.37 min (UV$_{254\ nm}$, 10 min); mass calculated for formula $C_{27}H_{28}ClN_3O_4S$ 525.2, observed LCMS m/z 526.2 (M+H).

Example 37B

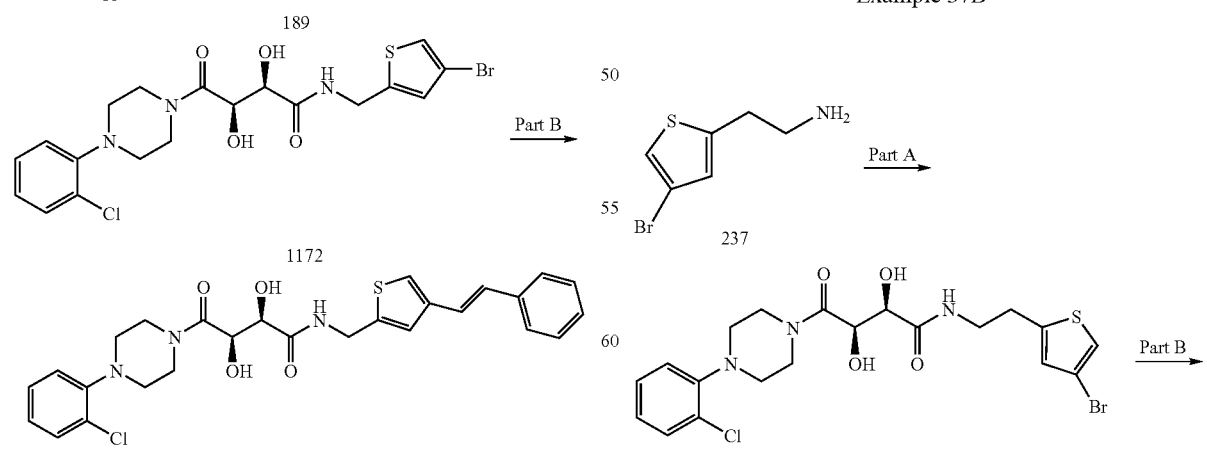

-continued

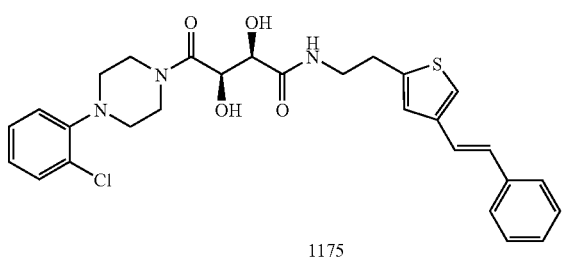

1175

Part A:

Compound 1174 was prepared from 237 using the procedures described in Example 2. HPLC-MS $t_R$=4.76 min (UV$_{254\ nm}$, 10 min); Mass calculated for formula $C_{20}H_{23}BrClN_3O_4S$ 515.0, observed LCMS m/z 516.0 (M+H).

Part B:

Compound 1175 was prepared using the procedures described in Example 36 Part A. HPLC-MS $t_R$=2.29 min (UV$_{254\ nm}$); mass calculated for formula $C_{28}H_{30}ClN_3O_4S$ 539.2, observed LCMS m/z 540.2 (M+H).

Example 37C

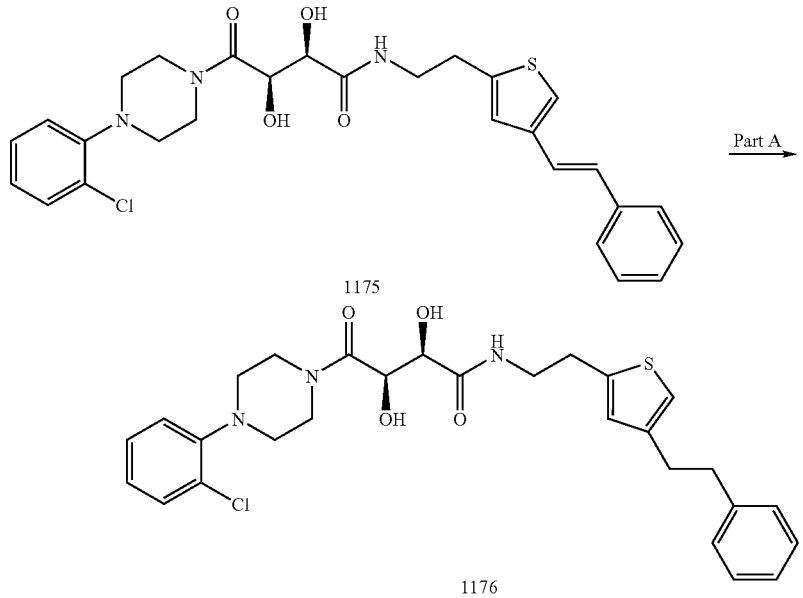

Part A:

Compound 1176 was prepared using procedures described in Example 36 Part B.

HPLC-MS $t_R$=5.50 min (UV$_{254\ nm}$, 10 min); mass calculated for formula $C_{28}H_{32}ClN_3O_4S$ 541.2, observed LCMS m/z 542.2 (M+H).

| Compound # | Structure | Exact mass | MS m/e (M + H) |
|---|---|---|---|
| 1177 | 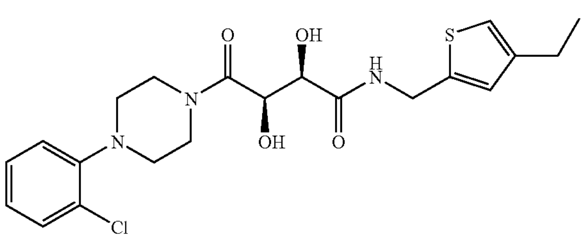 | 451.1 | 452.2 |

-continued

| Compound # | Structure | Exact mass | MS m/e (M + H) |
|---|---|---|---|
| 1178 | 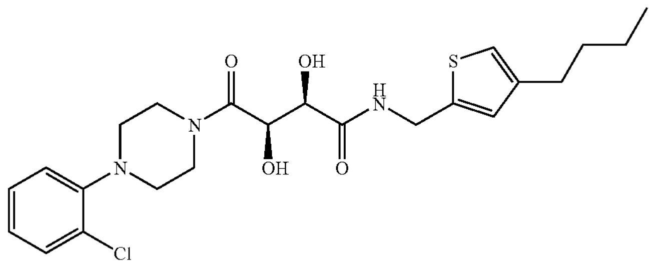 | 479.2 | 480.2 |
| 1179 | 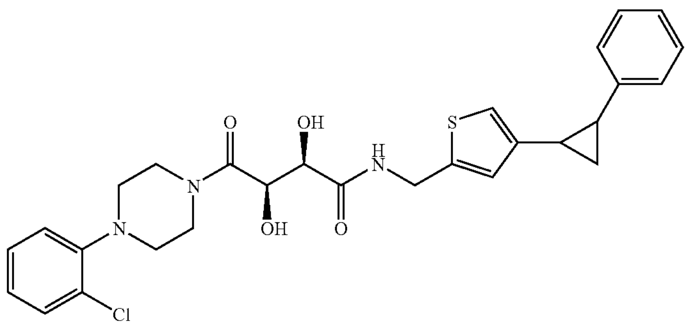 | 539.2 | 540.1 |
| 1180 | 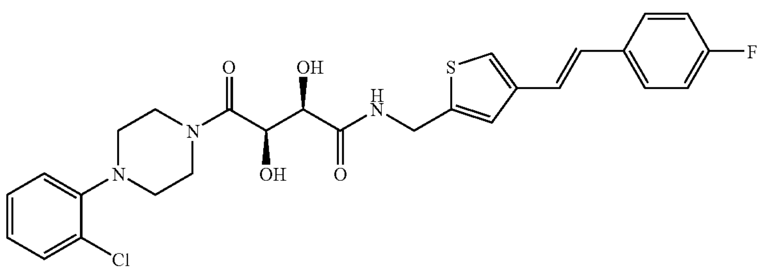 | 543.1 | 544.0 |
| 1181 | 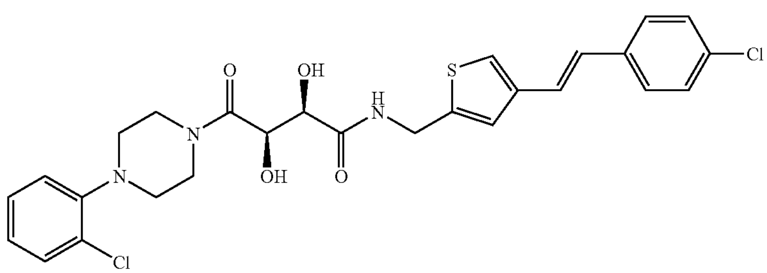 | 559.1 | 560.0 |
| 1182 | 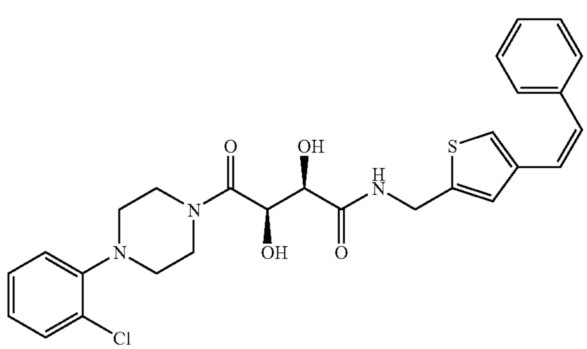 | 525.2 | 526.2 |

-continued

| Compound # | Structure | Exact mass | MS m/e (M + H) |
|---|---|---|---|
| 1183 | 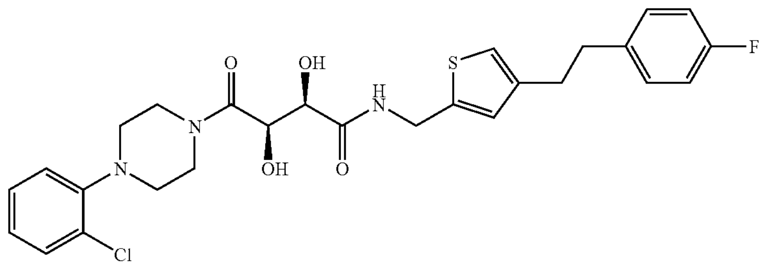 | 545.2 | 546.1 |
| 1184 | 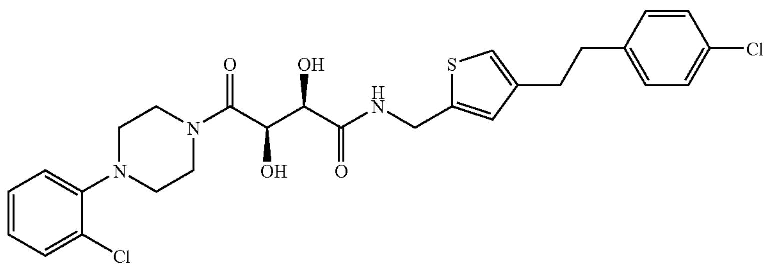 | 561.1 | 562.0 |
| 1185 | 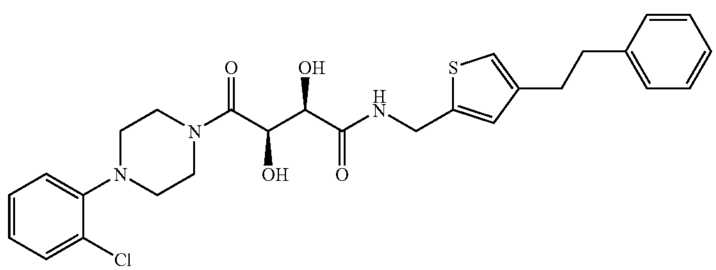 | 527.2 | 528.1 |
| 1186 | 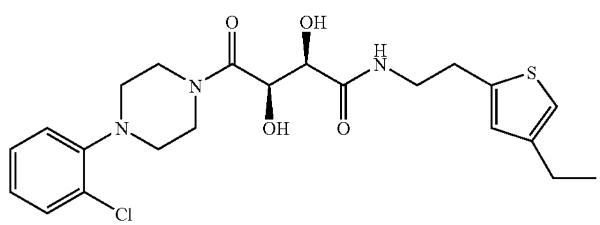 | 465.2 | 466.1 |
| 1187 | 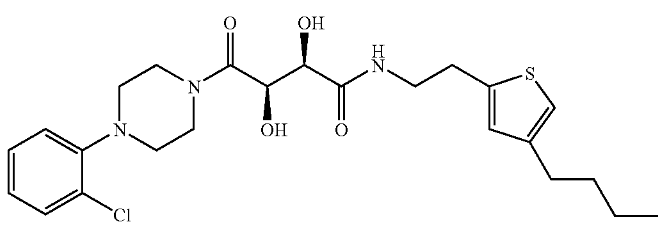 | 493.2 | 494.1 |
| 1188 | 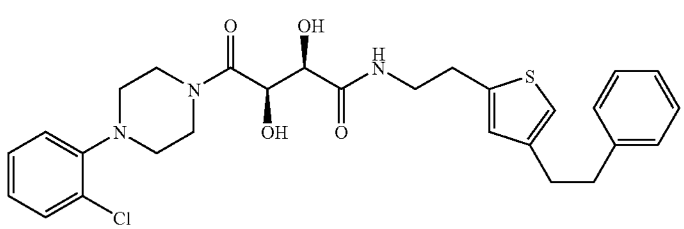 | 539.2 | 540.1 |

Example 38

Isoindoline Analogs

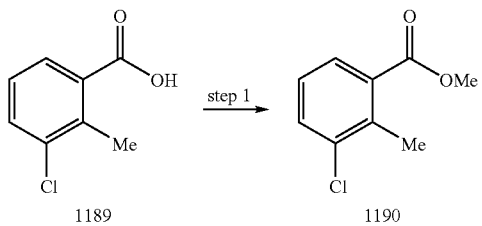

Step 1

To 3-chloro-2-methylbenzoic acid 1189 (4.95 g, 0.0290 mol) dissolved in DMF (70 mL) was added cesium carbonate (14.18 g, 0.0435 mol) and methyl iodide (0.35 g, 2.3 mL, 0.0377 mol). The reaction mixture was stirred at room temperature for 20 h. The reaction mixture was concentrated, and EtOAc (200 mL) was added. The organic solution was washed with water (2×100 mL), dried (MgSO$_4$), filtered, and concentrated to give 4.43 g (83%) of the product 1190 as a yellow oil. MS for M-Cl:149

| Compound # | Structure | MS |
|---|---|---|
| 1191 | 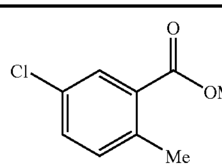 | M-Cl: 149 |
| 1192 | 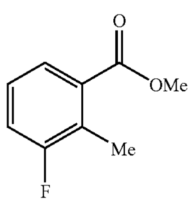 | M + 1: 169 |

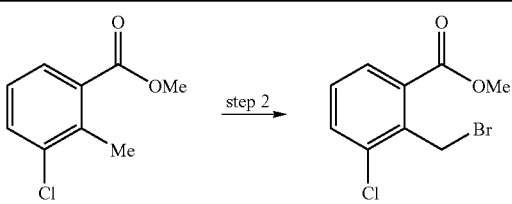

Step 2

To compound 1190 (4.42 g, 0.0239 mol) dissolved in CCl$_4$ (100 mL) was added n-bromosuccinimide (5.11 g, 0.287 mol) and benzoyl peroxide (0.58 g, 0.00239 mol). The reaction mixture was heated at reflux for 16 h then cooled to room temperature. The solid was removed by filtration and washed with CH$_2$Cl$_2$. The filtrate was concentrated to give 7.80 g of the product 1193 with succinimide as a yellow oil and solid mixture.

| Compound # | Structure |
|---|---|
| 1194 | 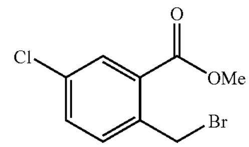 |
| 1195 | 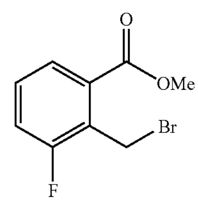 |

Step 3

Compound 1193 (6.31 g, 0.0239 mol) was dissolved in 7 N NH$_3$ in MeOH (50 mL) and stirred at room temperature for 3 h then heated at reflux for 4 h. The reaction mixture was cooled to room temperature and concentrated. The residue was suspended in CH$_2$Cl$_2$ (150 mL), and the solid was removed by filtration and washed with CH$_2$Cl$_2$. The filtrate was concentrated, and the crude product was purified by silica gel flash chromatography (eluant: 5% MeOH—CH$_2$Cl$_2$ to 10% MeOH—CH$_2$Cl$_2$) to give 3.68 g (92%) of the product 1196 as a white solid. MS for M+1: 168.

| Compound # | Structure | MS (M + 1) |
|---|---|---|
| 1197 | 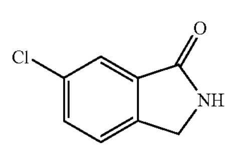 | 168 |

| Compound # | Structure | MS (M + 1) |
|---|---|---|
| 1198 | 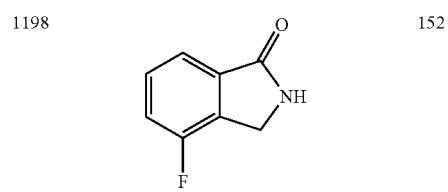 | 152 |

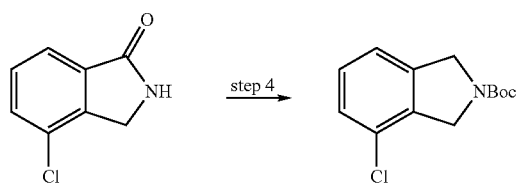

Step 4

To compound 1196 (1.00 g, 5.97 mmol) suspended in dry THF (15 mL) was added borane (1 M in THF, 14.9 mL, 14.0 mmol). The reaction mixture was heated at reflux for 5 h then cooled to 0° C. EtOH (15 mL) and potassium carbonate (2 g) were carefully added portionwise. The reaction mixture was heated at reflux for 16 h then cooled to 0° C., and (tBOC)$_2$O (1.95 g, 8.95 mmol) was added. The reaction mixture was stirred at room temperature for 3 h then concentrated. Water (30 mL) was added, and the aqueous solution was extracted with 3×30 mL of CH$_2$Cl$_2$. The combined organic extracts were dried (MgSO$_4$), filtered, and concentrated. The crude product was purified by silica gel flash chromatography (eluant: 5% EtOAc-CH$_2$Cl$_2$) to give 0.56 g (37%) of the product 1199 as a yellow oil. MS for M+1-tBu: 198.

| Compound # | Structure | MS |
|---|---|---|
| 1200 | 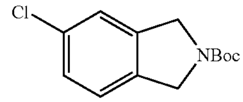 | M + 2-tBu = 198 |
| 1201 | 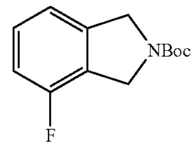 | M + 2-tBu: 182 |

The following intermediates were prepared according to the procedure of Example 11B Part F.

| Compound # | Structure | MS (M + 1) |
|---|---|---|
| 1202 | 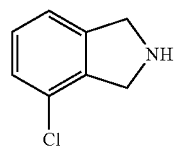 | 154 |
| 1203 | 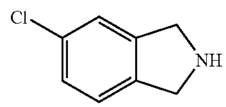 | 154 |
| 1204 | 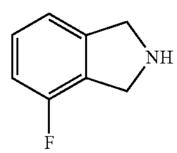 | 138 |

The following intermediates were prepared according to the procedure of Example 2

| Compound # | Structure | MS (M + 1) |
|---|---|---|
| 1205 | 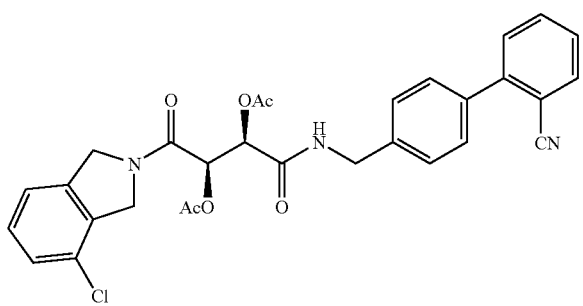 | 560 |

-continued
| Compound # | Structure | MS (M + 1) |
|---|---|---|
| 1206 | 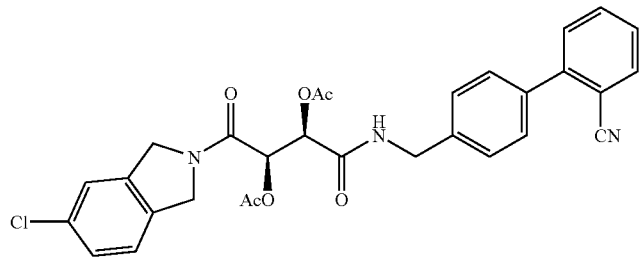 | 560 |
| 1207 | 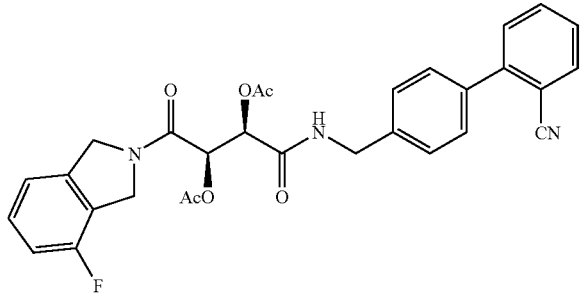 | 544 |
| 1208 | 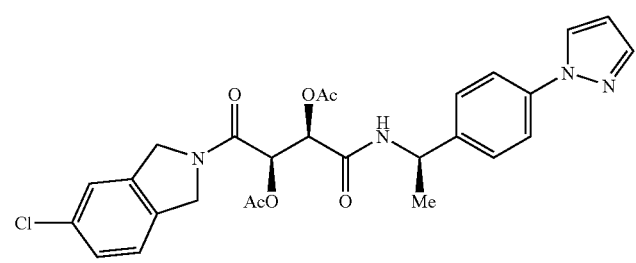 | 539 |
| 1209 | 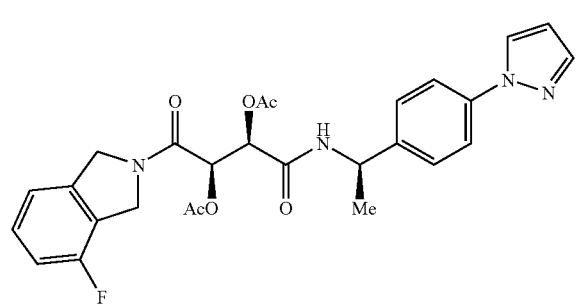 | 523 |

The following compounds were prepared according to the procedure of Example 2

| Compound # | Structure | MS (M + 1) |
|---|---|---|
| 1210 | 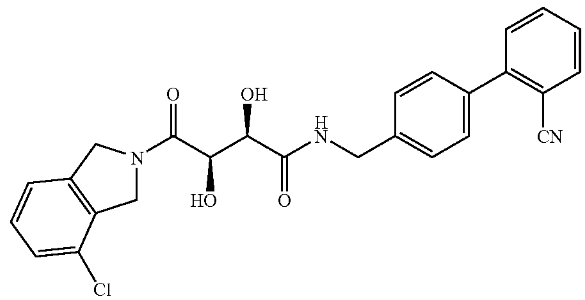 | 476 |
| 1211 | 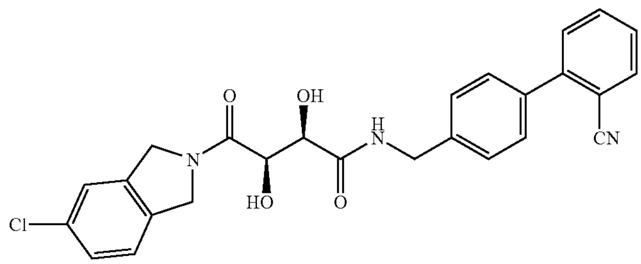 | 476 |
| 1212 | 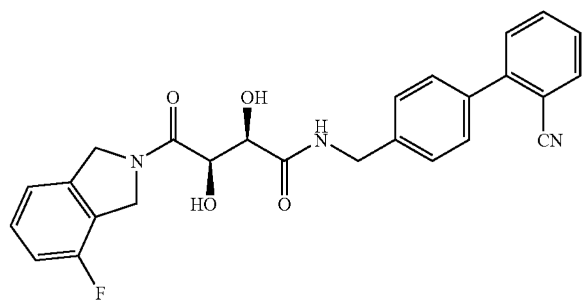 | 460 |
| 1213 | 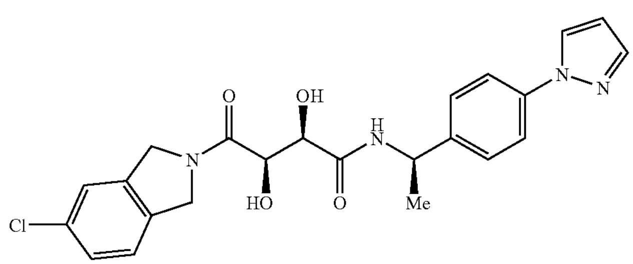 | 455 |
| 1214 | 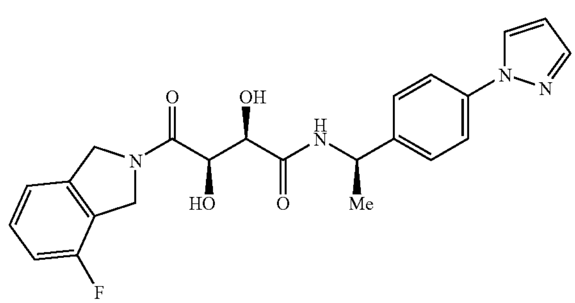 | 439 |

Example 39

Hydrazinoamides

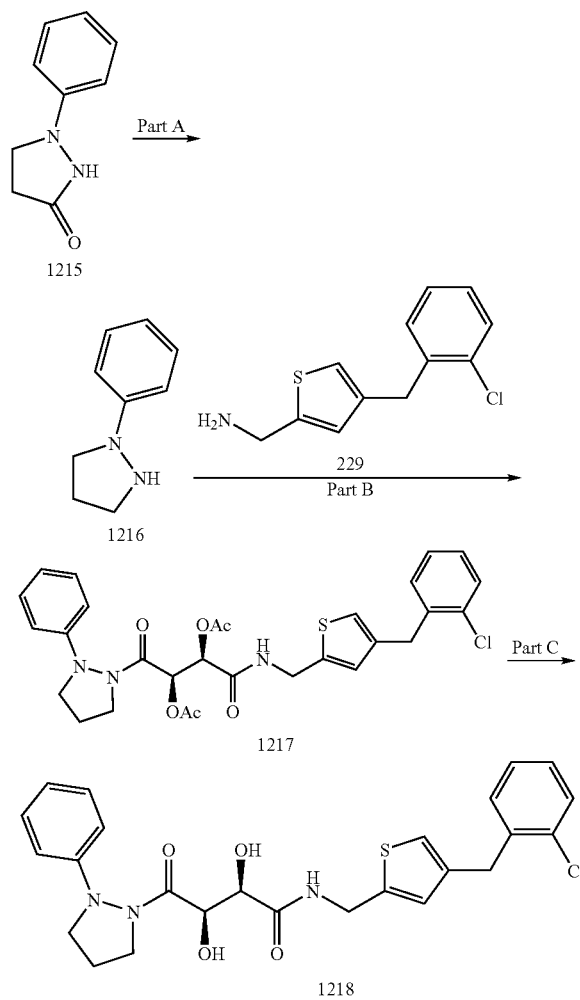

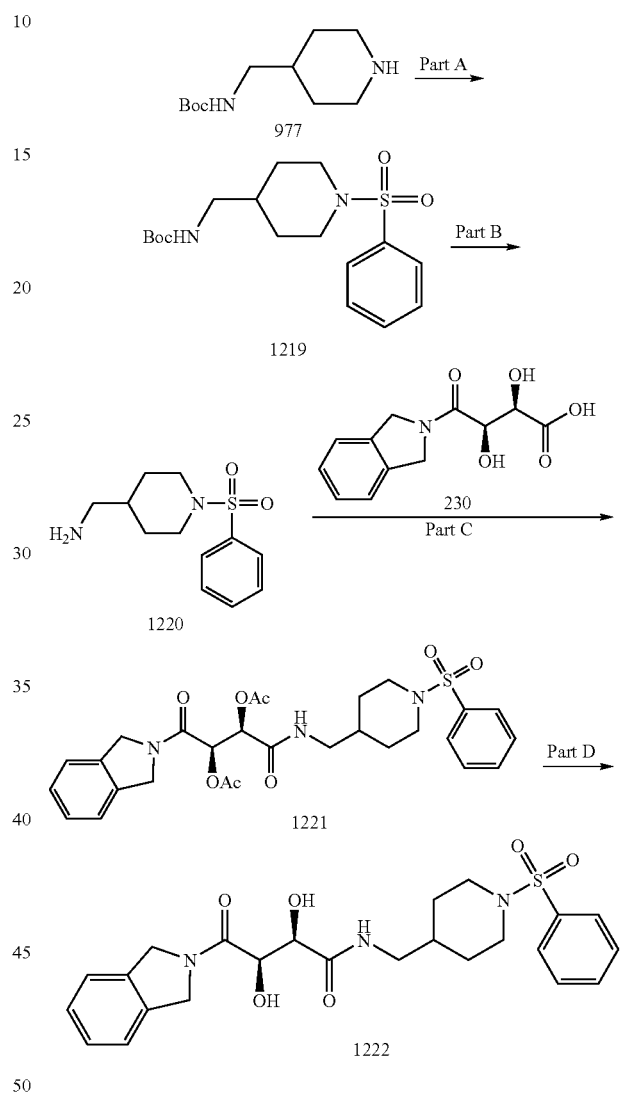

Part A:
1-Phenyl-pyrazolidin-3-one (1215) (1.0 g, 6.16 mmol) in 15 mL of THF was added dropwise to the mixture of AlCl₃ (0.82 g, 6.16 mmol) and 12 mL of 1 M LiAlH₄ (12 mmol) in THF at 0° C. under argone. The reaction mixture was then allowed to stir at room temperature for 4 h. It was quenched with 10 mL of 1N NH4Cl solution, diluted with EtOAc and 15% NaOH aqueous solution. After filtration, the organic layer was separated, dried over Na₂SO₄, and concentrated. Column chromatography (SiO₂, EtOAc/Hexane, 20:80) afforded 1216 as colorless oil.

Part B:
Compound 1217 was prepared according to the procedure described in Example 2A Part A from 1216 (15 mg, 0.1 mmol).

Part C:
Compound 1217 was dissolved in 1 mL of MeOH, 0.5 mL of 7N NH₃ in MeOH was added. After stirring at room temperature for 1 h, the reaction mixture was concentrated in vacuo. Purification by reverse phase prep-LC afforded compound 1218 as a white solid. HPLC-MS $t_R$=5.09 min (UV$_{254\,nm}$, 10 min), Mass calculated for formula $C_{25}H_{26}ClN_3O_4S$ 499.1, observed LCMS m/z 500.0 (M+H).

Example 40

Piperidine Sulfonamides

Part A:
Phenylsulfonyl chloride (212 mg, 1.2 mmol) was slowly added to a solution of 4-(Boc-aminomethyl)piperidine (977) (214 mg, 1 mmol) in 1.0 mL of pyridine at 0° C. The reaction mixture was allowed to stir at room temperature overnight, and diluted with ethyl acetate and water. The organic layer was washed with 1 N citric acid, saturated NaHCO₃, and brine. It was dried over Na₂SO₄, and concentrated, resulting in 1219 (320 mg, 90%). Mass calculated for formula $C_{17}H_{26}N_2O_4S$ 354.2, observed LCMS m/z 355.2 (M+H), 299.2 (M−55)

Part B:
To the solution of 1219 (200 mg, 0.54 mmol) in THF (5 mL) was added 2 mL of 4 N HCl in dioxane. The reaction mixture was stirred at room temperature for 1 h, and concentrated to afford 1220 (105 mg, 66%).

Part C:

To 1220 (105 mg, 0.36 mmol) in DMF (2 mL) was added 230 (100 mg, 0.3 mmol), DIEA (750 µL, 0.6 mmol) and HATU (137 mg, 0.36 mmol). The reaction mixture was stirred overnight at room temperature, and diluted with ethyl acetate and water. The organic layer was washed with 1 N HCl, saturated NaHCO$_3$, and brine. It was dried over Na$_2$SO$_4$, and concentrated, resulting in 1221.

Part D:

Compound 1221 was dissolved in 4 mL of MeOH, 2 mL of 7N NH$_3$ in MeOH was added. After stirring at room temperature for 1 h, the reaction mixture was concentrated in vacuo. Purification by reverse phase prep-LC afforded 1222 as a white solid. HPLC-MS t$_R$=3.59 min (UV$_{254\ nm}$, 10 min), Mass calculated for formula C$_{24}$H$_{29}$N$_3$O$_6$S 488.2, observed LCMS m/z 488.1 (M+H).

| Compound # | Structure | Overall yield |
|---|---|---|
| 1226 | 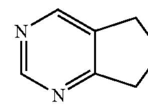 | 47% |
| 1227 | 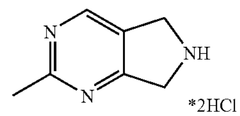 | 66% |

| Compound # | Structure | Exact mass | MS m/e (M + H) |
|---|---|---|---|
| 1223 | 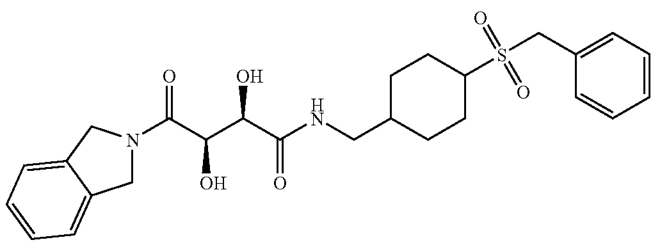 | 501.2 | 502.1 |

Example 41

Heterocyclic Isoindoline Analogs

Example 41A

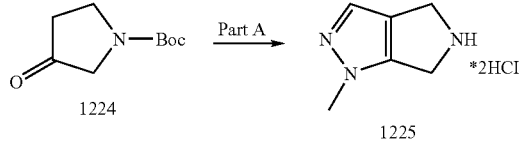

Part A:

Compound 1225 (70% overall yield) was prepared from 1 according to the procedures of Fukui, H. et. al. (*Heterocycles* 2002, 56, 257)

The following analogs were prepared according to this reference:

| Compound # | Structure | Overall yield |
|---|---|---|
| 1225 | | 73% |
| 1225 | | |
| 1228 | | |
| 1229 | | |

Part B:

Compound 1228 was prepared according to procedures described in Example 27A. HPLC-MS $t_R$=0.95 min (UV$_{254nm}$); mass calculated for formula C13H16FN3 233.1, observed LCMS m/z 234.2 (M+H). Compound 1229 was prepared according to the procedures described in Example 2A Part A. HPLC-MS $t_R$=1.57 min (UV$_{254\ nM}$); mass calculated for formula $C_{27}H_{31}FN_6O_6$ 554.23, observed LCMS m/z 555.2 (M+H).

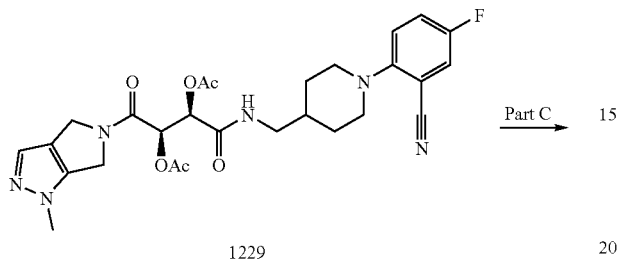

1229

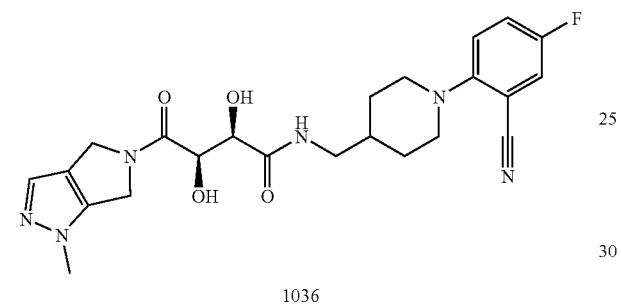

1036

Part C:

Comppound 1036 was synthesized using the procedure found in Example 2A, Part B. Purification by reverse phase prep-LC afforded a white solid after lyophilization. HPLC-MS $t_R$=3.39 min (UV$_{254\ nM}$, 10 min); mass calculated for formula $C_{23}H_{27}FN_6O_4$ 470.21, observed LCMS m/z 471.2 (M+H).

Example 41B

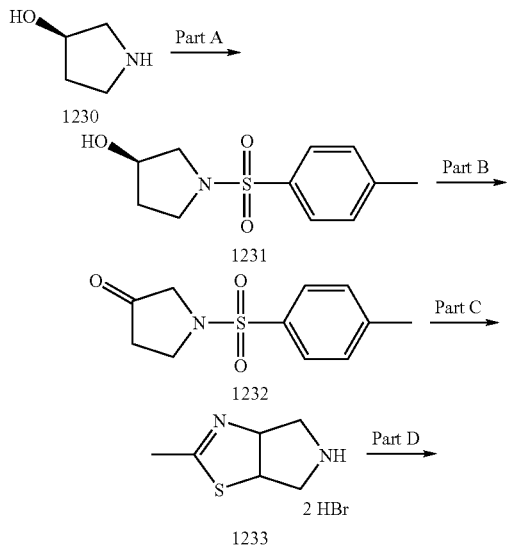

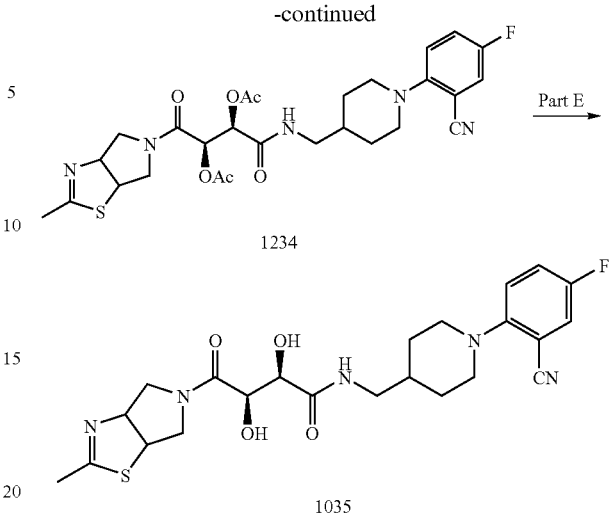

1234

1035

Part A:

Compound 1230 (2.18 g, 17.7 mmol) was dissolved in methylene chloride (35 mL) and cooled in an ice bath. Triethylamine (5 mL, 35.4 mmol) was added followed by p-toluenesulfonyl chloride (3.35 g, 17.7 mmol) in portions. The reaction mixture was stirred for 3 hours at room temperature and then quenched with water and extracted with methylene chloride. The combined organic layers were washed with 1 N HCl solution, bicarbonate solution and brine; dried over sodium sulfate and concentrated to provide the desired product 1231 (3.85 g), that was used without purification. HPLC-MS $t_R$=1.26 min (UV$_{254nm}$); mass calculated for formula $C_{11}H_{15}NO_3S$ 241.08, observed LCMS m/z 242.2 (M+H).

Part B:

Compound 1231 (3.82 g, 15.78 mmol) was dissolved in methylene chloride (100 mL) and pyridinium chlorochromate (6.7 g, 31 mmol) was added followed by crushed molecular sieves (3.5 g). The reaction was stirred overnight and then diethylether (150 mL) was added and stirring was continued for an additional hour. The solids were filtered and the solvent was evaporated under reduced pressure. Purification by column chromatography (SiO$_2$, 50% ethyl acetate/hexanes) afforded a white solid 1232 (3.20 g, 84%). HPLC-MS $t_R$=1.43 min (UV$_{254\ nM}$); mass calculated for formula $C_{11}H_{13}NO_3S$ 239.06, observed LCMS m/z 240.1 (M+H).

Part C:

Reactions were performed using procedures from Heterocycles, Vol. 41, No. 7, 1995.

Part D:

Reaction was performed using the procedure found in Example 2A, Part A. 1234: HPLC-MS $t_R$=1.702 min (UV$_{254\ nM}$); mass calculated for formula $C_{27}H_{30}FN_5O_6S$ 571.19, observed LCMS m/z 572.2 (M+H).

Part E:

Reaction was performed using the procedure found in Example 2A, Part B. Purification by reverse phase prep-LC afforded a white solid after lyophilization. 1035: HPLC-MS $t_R$=3.66 min (UV$_{254\ nM}$, 10 min); mass calculated for formula $C_{23}H_{26}FN_5O_4S$ 487.2, observed LCMS m/z 488.2 (M+H).

| Compound # | Structure | Exact mass | MS m/e (M + H) |
|---|---|---|---|
| 1235A | 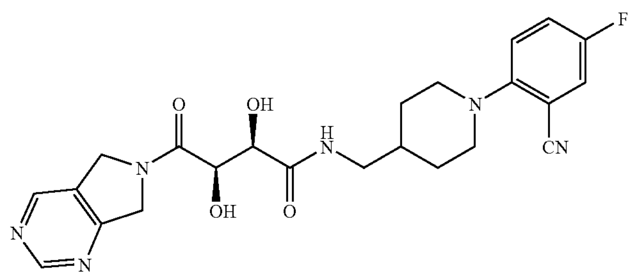 | 468.2 | 469.2 |
| 1235B | 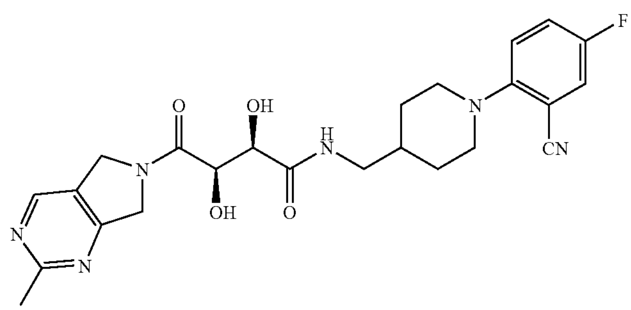 | 482.2 | 483.2 |
| 1236A | 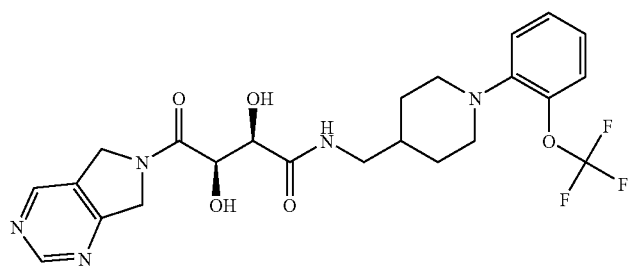 | 509.2 | 510.2 |
| 1236B | 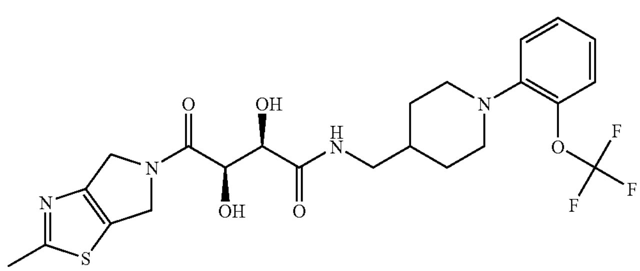 | 528.2 | 529.2 |
Example 42
Example 42A
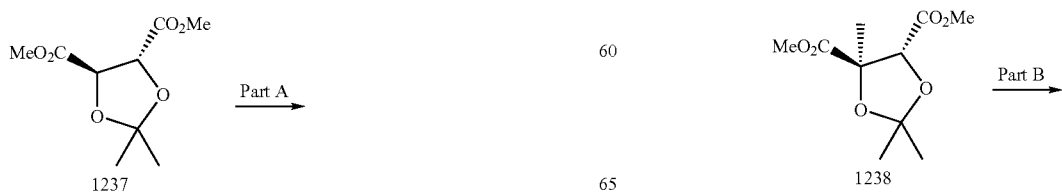
-continued

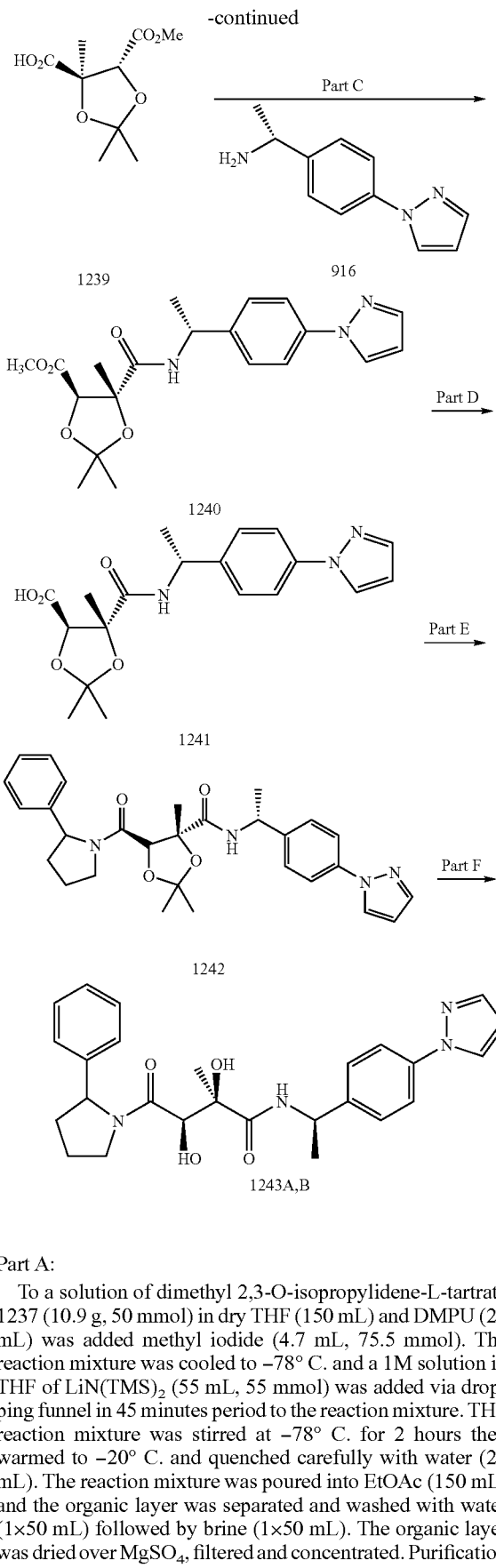

by column chromatography (SiO$_2$, 10% Et$_2$O/hexane followed by 15% Et$_2$O/hexane) afforded the desired compound 1238 as clear oil (9.7 g, 83%). LCMS m/z: 233.1 (M+H).

Part B:

A pH 8 buffer solution was prepared by titrating a solution of 0.1 M sodium phosphate (300 mL) with 1M HCl to final pH of 8. To a mixture of compound 1238 in pH 8 buffer solution was added esterase (41 units/mg, 15 mg, 615 units). Added aq. 1 N NaOH (6.5 mL) slowly via syringe during a period of 3.5 hours to the reaction mixture to maintain the pH of the reaction mixture in the range of 7.9-8.2. The reaction mixture was extracted with Et$_2$O (2×50 mL). The aqueous layer was acidified to pH 3 using 12N HCl then extracted with EtOAc (4×25 mL). The combined organic layers were dried over MgSO$_4$, filtered and concentrated in vacuo to afford the desired compound 1239 (1.36 g, 72%). LCMS m/z: 219.1 (M+H).

Part C:

To a solution of compound 916 (0.1 g, 0.535 mmol) in DMF (1.5 mL) was added compound 1239 (0.092 g, 0.5 mmol), triethyl amine (0.2 mL, 1.4 mmol) and HATU (0.365 g, 0.96 mmol). The reaction mixture was stirred for 18 hours and then diluted with CH$_2$Cl$_2$ (5 mL) and washed with aq. 0.5N NaOH solution (3 mL). The organic layer was dried over MgSO$_4$ and concentrated. Purification by column chromatography (SiO$_2$, 30% EtOAc/hexane followed by 40% EtOAc/hexane) afforded the compound 1240 as a white foam (0.162 g, 67%). LCMS m/z 388.1 (M+H).

Part D:

To a solution of compound 1240 (0.175 g, 0.452 mmol) in THF (2 mL) and MeOH (2 mL) at 0° C. was added aq. 1.0 M LiOH (0.91 mL, 0.91 mmol). The reaction mixture was warmed to room temperature and stirred for 1 hour. The reaction mixture was acidified with aq. 1N HCl (0.95 mL) and diluted with brine (1.5 mL) and extracted with EtOAc (2×10 mL). The combined organic layers were dried over MgSO$_4$ and concentrated to afford compound 1241 as a white foam (0.182 g, 100%). LCMS m/z: 374.1 (M+H).

Part E:

To a solution of compound 1241 (0.179 g, 0.48 mmol) in DMF (3 mL) was added 2-phenylpyrrolidine hydrogen chloride salt (0.092 g, 0.5 mmol), triethyl amine (0.2 mL, 1.4 mmol) and HATU (0.365 g, 0.96 mmol). The reaction mixture was stirred for 4.5 hours and then diluted with EtOAc (10 mL) and washed with water (1.5 mL) followed by brine (1.5 mL). The organic layer was dried over MgSO$_4$ and concentrated. The residue was purified by prep. plate chromatography (SiO$_2$, 66% EtOAc/hexane). Two diastereomeric compounds 1242 were isolated. Diastereomer compound 1242A (0.067 g, 28%), LCMS m/z 503.1 (M+H) and diastereomer compound 1242B (0.095 g, 28%), LCMS m/z 503.1 (M+H).

Part F:

To a solution of compound 1242A (0.06 g, 0.119 mmol) in CH$_2$Cl$_2$ (1 mL) was added TFA (4 mL) followed by water (0.5 mL). The reaction mixture was stirred at 80° C. temperature for 3 hours and then concentrated. The residue was purified by column chromatography (SiO$_2$, 5% MeOH/CH$_2$Cl$_2$) to afford 1243A (0.012 g, 22%), LCMS m/z 463.1 (M+H).

To a solution of compound 1242B (0.088 g, 0.18 mmol) in CH$_2$Cl$_2$ (1 mL) was added TFA (4 mL) followed by water (0.5 mL). The reaction mixture was stirred at 23° C. temperature for 18 hours and then concentrated. The residue was purified by column chromatography (SiO$_2$, 5% MeOH/CH$_2$Cl$_2$) to afford 1243B (0.05 g, 66%), LCMS m/z 463.1 (M+H).

Part A:

To a solution of dimethyl 2,3-O-isopropylidene-L-tartrate 1237 (10.9 g, 50 mmol) in dry THF (150 mL) and DMPU (25 mL) was added methyl iodide (4.7 mL, 75.5 mmol). The reaction mixture was cooled to −78° C. and a 1M solution in THF of LiN(TMS)$_2$ (55 mL, 55 mmol) was added via dropping funnel in 45 minutes period to the reaction mixture. THF reaction mixture was stirred at −78° C. for 2 hours then warmed to −20° C. and quenched carefully with water (20 mL). The reaction mixture was poured into EtOAc (150 mL) and the organic layer was separated and washed with water (1×50 mL) followed by brine (1×50 mL). The organic layer was dried over MgSO$_4$, filtered and concentrated. Purification

| Compound # | Structure | Exact mass | MS m/z (M + H) |
|---|---|---|---|
| 1243C | 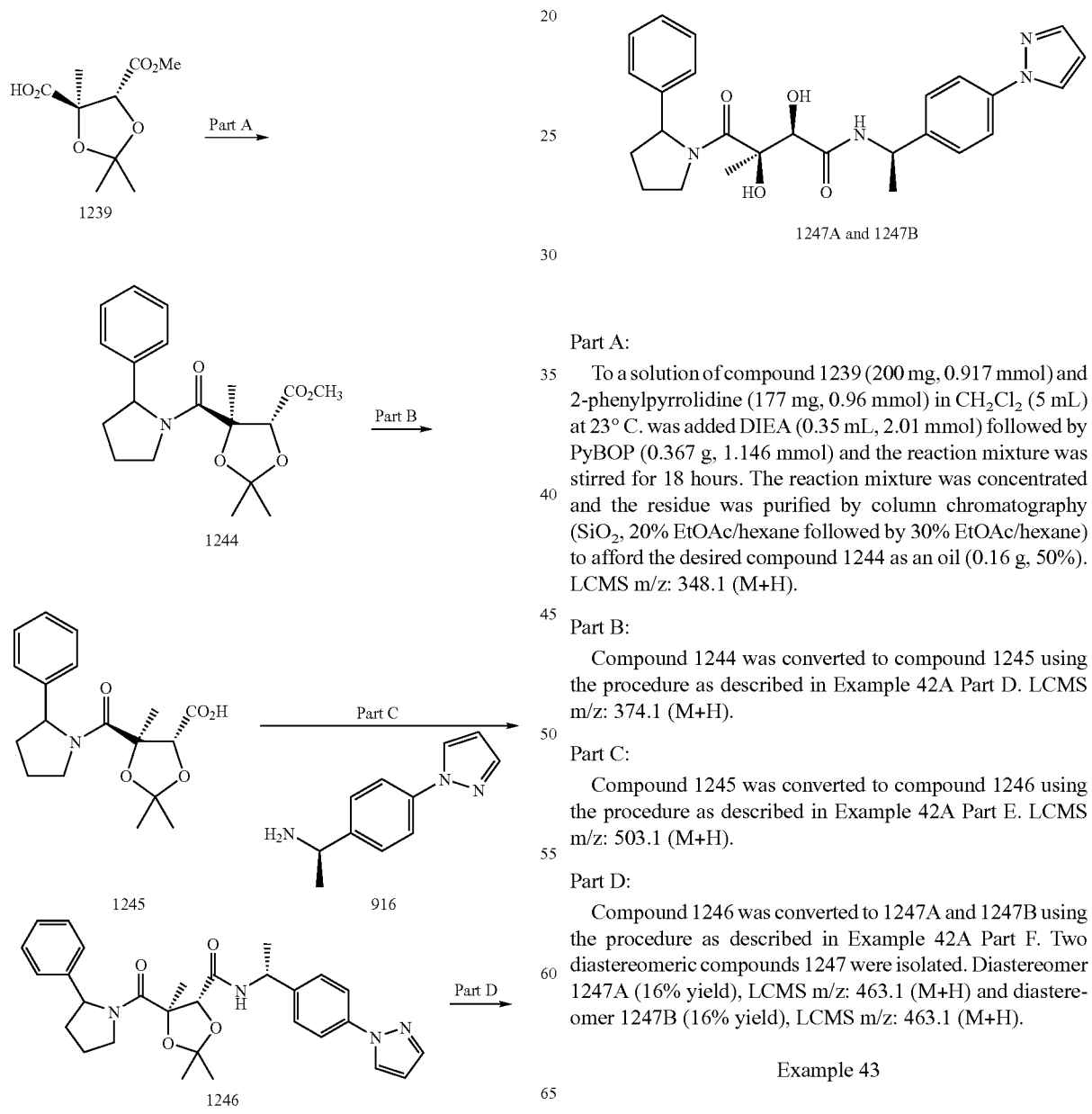 | 434.2 | 435.1 |

Example 42B

Part A:

To a solution of compound 1239 (200 mg, 0.917 mmol) and 2-phenylpyrrolidine (177 mg, 0.96 mmol) in $CH_2Cl_2$ (5 mL) at 23° C. was added DIEA (0.35 mL, 2.01 mmol) followed by PyBOP (0.367 g, 1.146 mmol) and the reaction mixture was stirred for 18 hours. The reaction mixture was concentrated and the residue was purified by column chromatography ($SiO_2$, 20% EtOAc/hexane followed by 30% EtOAc/hexane) to afford the desired compound 1244 as an oil (0.16 g, 50%). LCMS m/z: 348.1 (M+H).

Part B:

Compound 1244 was converted to compound 1245 using the procedure as described in Example 42A Part D. LCMS m/z: 374.1 (M+H).

Part C:

Compound 1245 was converted to compound 1246 using the procedure as described in Example 42A Part E. LCMS m/z: 503.1 (M+H).

Part D:

Compound 1246 was converted to 1247A and 1247B using the procedure as described in Example 42A Part F. Two diastereomeric compounds 1247 were isolated. Diastereomer 1247A (16% yield), LCMS m/z: 463.1 (M+H) and diastereomer 1247B (16% yield), LCMS m/z: 463.1 (M+H).

Example 43

Example 43A

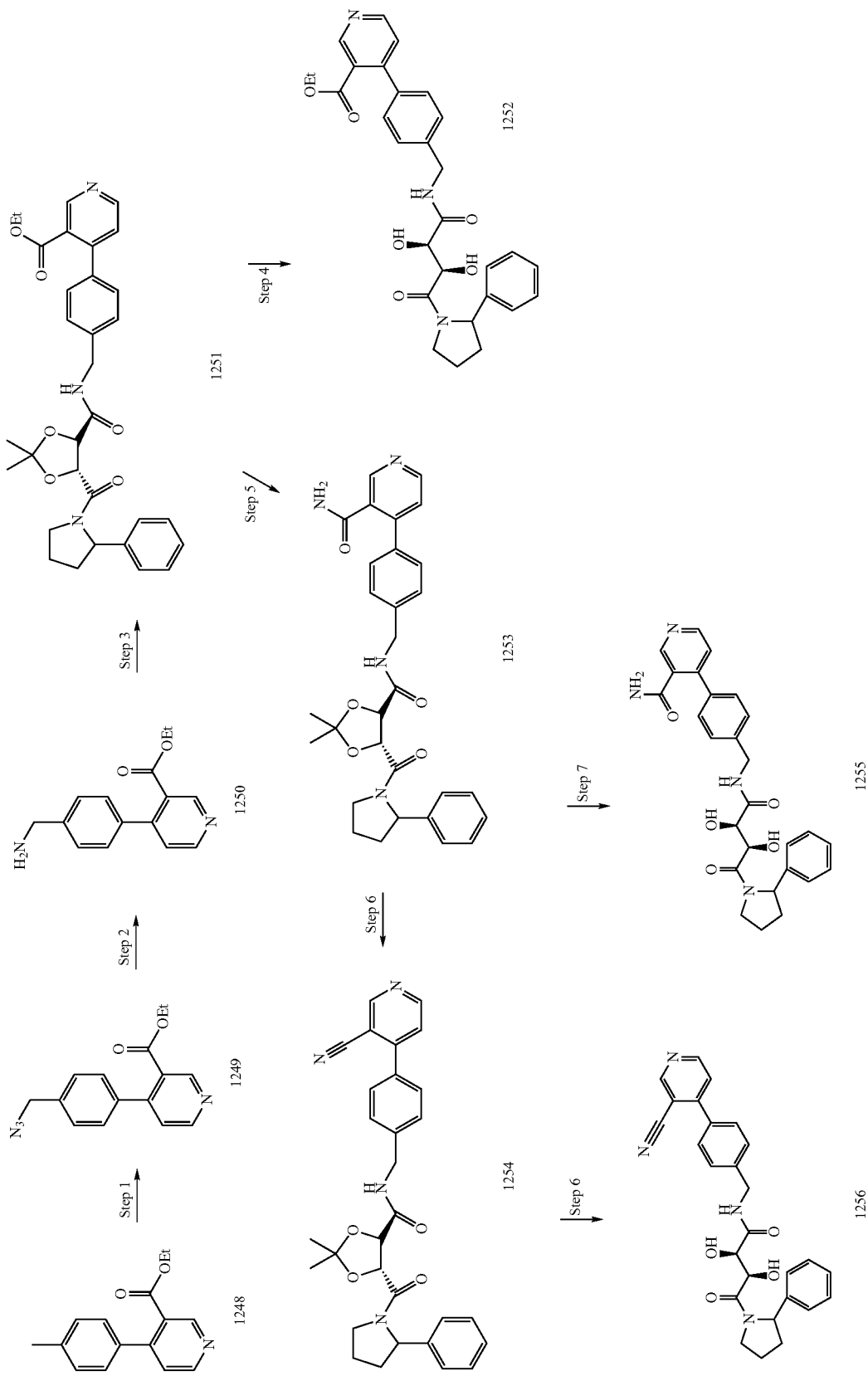

Step 1:
Compound 1248 was prepared according to the literature procedure: Shiao, M.-J.; Liu, K.-H.; Lin, P.-Y *Hetereocycles* 1993, 36, 3, 507.

A solution of 1248 (2.20 g, 9.10 mmol), NBS (1.81 g, 10.20 mmol), 1,1'-azobis(cyclohexanecarbonitrile) (0.113 g, 0.46 mmol) in $CCl_4$ (40 mL) was stirred at 75° C. for 24 hours. The reaction was cooled to room temperature, and the mixture was diluted with $CH_2Cl_2$ and sat. $Na_2CO_3$. The organic layer was removed, and the aqueous phase was extracted with $CH_2Cl_2$ (4×). The combined organics were dried ($Na_2SO_4$), filtered, and concentrated. The crude product mixture was used without further purification.

A solution of the crude product mixture prepared above and sodium azide (0.75 g, 11.5 mmol) in a MeOH (15 mL)/DMF (15 mL)/DMSO (15 mL) solvent mixture was stirred at room temperature for 24 hours. The reaction was diluted with $H_2O$ and EtOAc. The organic layer was removed, and the aqueous phase was extracted with EtOAc (1×). The combined organics were washed with $H_2O$ (3×), brine (1×), dried ($Na_2SO_4$), filtered, and concentrated.

The resulting brown oil was purified by silica gel chromatography to furnish 1249 (1.2 g, 4.25 mmol, 47% yield over 2 steps). MS m/e: 283.1 (M+H).

Step 2:
To a solution of 1249 (1.2 g, 4.2 mmol) in THF (20 mL) at room temperature was added $PPh_3$ (1.1 g, 4.2 mmol). The reaction was stirred at room temperature for 1 hour at which time $H_2O$ (2 mL) was added. The resulting mixture was stirred for 24 hours. After concentration, the mixture was taken up in $Et_2O$ and 0.25 N HCl. The organic phase was removed, and the aqueous phase was basicified with sat. $Na_2CO_3$ and extracted with EtOAc (4×). The combined organics were dried ($Na_2SO_4$), filtered, and concentrated. The compound was purified by silica gel chromatography to furnish 1250 (0.51 g, 47% yield). MS m/e: 257.1 (M+H).

Step 3:
Compound 1251 was prepared with 1250 in a similar manner as previously stated in Example 12B.

Step 4:
Compound 1252 was prepared in a similar fashion from 1251 as previously stated in Example 12B. MS m/e: 518.1 (M+H).

Step 5:
To a solution of 1251 (0.20 g, 0.36 mmol) in THF (2 mL)/MeOH (2 mL)/$H_2O$ (2 mL) was added LiOH (0.050 g, 1.2 mmol). The reaction was stirred at room temperature for 20 hours. The reaction was acidified to pH~4 with 1 N HCl and diluted with EtOAc. The organic layer was removed and the aqueous phase was extracted with EtOAc (3×). The combined organics were dried ($Na_2SO_4$), filtered, and concentrated. The compound was used without further purification.

To the crude product mixture prepared above in $CH_2Cl_2$ (2 mL) was added NMM (0.200 mL, 1.82 mmol), EDCI (0.100 g, 0.52 mmol), and HOBt (0.059 g, 0.38 mmol). This mixture was stirred for 10 minutes at which time $NH_4Cl$ (0.100 g, 1.86 mmol) was added. After 72 hours of stirring, the reaction was quenched with $H_2O$ and diluted with EtOAc. The organic layer was removed, and the aqueous phase was extracted with EtOAc (3×). The combined organics were dried ($Na_2SO_4$), filtered, and concentrated. The residue was purified by silica gel chromatography to yield 1253 (0.062 g, 61% yield over 2 steps). MS m/e: 529.1 (M+H).

Step 6:
To a solution of 1253 (0.050 g, 0.095 mmol) in $CH_2Cl_2$ (2 mL) cooled to 0° C. was added DIEA (0.050 mL, 0.28 mmol) followed by TFAA (0.030 mL, 0.22 mmol). The reaction was stirred at 0° C. for 3 hours and then quenched with 1 N NaOH. The organic layer was removed, and the aqueous phase was acidified with 1 N HCl to pH~4. The aqueous phase was then extracted with EtOAc (3×). The combined organics were dried ($Na_2SO_4$), filtered, and concentrated. The residue was purified by silica gel chromatography to furnish 1254 (0.042 g, 0.082 mmol, 88% yield). MS m/e: 511.1 (M+H).

Step 7:
Compound 1255 was prepared in a similar fashion from 1253 as previously stated in Example 12B. MS m/e: 489.1 (M+H).

Step 8:
Compound 1256 was prepared in a similar fashion from 1254 as previously stated in Example 12A. MS m/e: 471.1 (M+H).

Example 43B

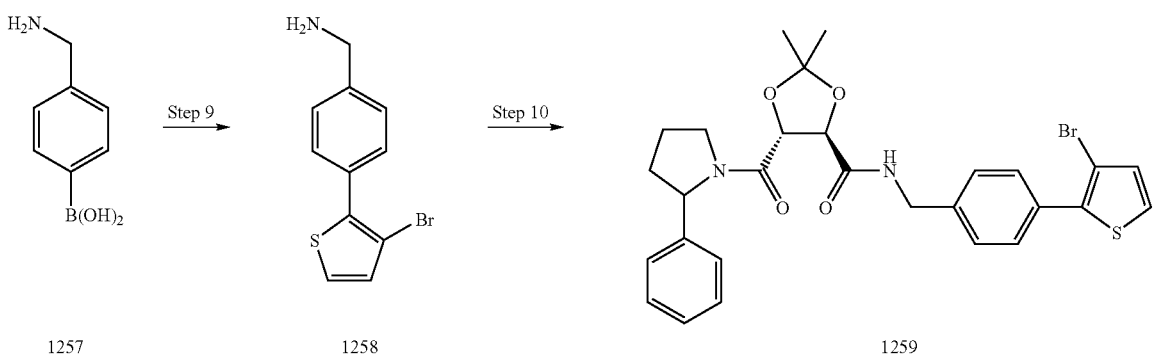

Step 11

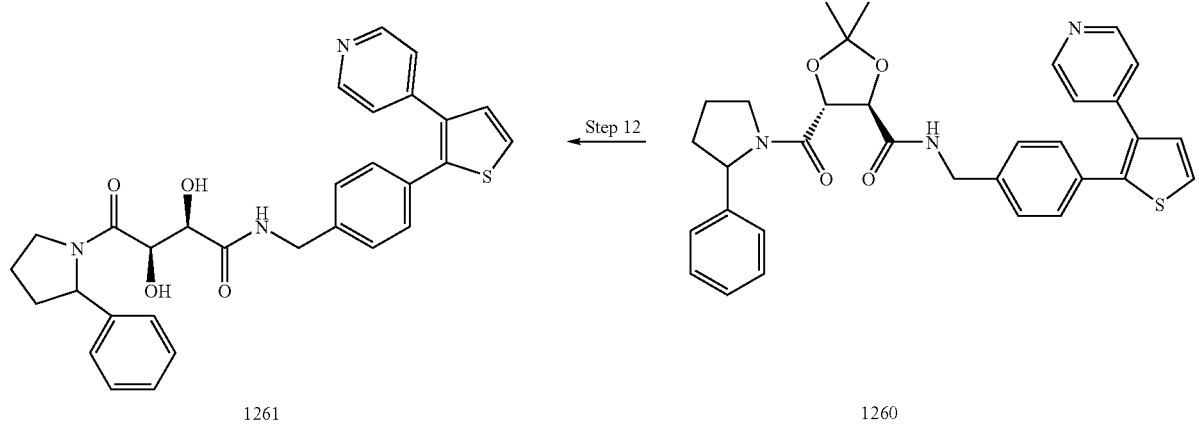

1261      1260

Step 9:

A solution of aminomethylphenyl boronic acid hydrochloride (1257) (2.0 g, 10.7 mmol), 2,3-dibromothiophene (2.7 g, 11.0 mmol), and Pd(dppf)Cl$_2$ (0.51 g, 0.69 mmol) in CH$_3$CN (40 mL)/1 M K$_2$CO$_3$ (40 mL) was stirred at 80° C. for 3 hours. The reaction was cooled to room temperature and diluted with EtOAc. The organic layer was removed, and the aqueous phase was extracted with EtOAc (3×). The combined organics were dried (Na$_2$SO$_4$), filtered, and concentrated. The brown oil was purified by silica gel chromatography to furnish 1258 (1.4 g, 5.3 mmol, 50% yield) as a brown oil. MS m/e: 268.1 (M+H).

Step 10:

Compound 1259 was prepared in a similar fashion from 1258 as previously stated in Example 12B. MS m/e: 569.1 (M+H).

Step 11:

A solution of 1259 (0.059 g, 0.10 mmol), pyridine-4-yl boronic acid (0.017 g, 0.14 mmol), and Pd(dppf)Cl$_2$ (0.010 g, 0.014 mmol) in CH$_3$CN (1 mL)/1 M K$_2$CO$_3$ (1 mL) was heated in SmithCreator microwave (2-5 mL vessel, 150° C. for 5 minutes). The liquid was concentrated, and the residue was purified by silica gel chromatography to furnish 1260 (0.057 g, 0.10 mmol, 99% yield). MS m/e: 568.1 (M+H).

Step 12:

Compound 1261 was prepared in a similar fashion from 1260 as previously stated in Example 12A MS m/e: 528.1 (M+H).

Example 44

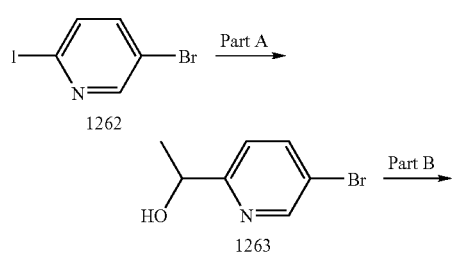

Part A:

Isopropylmagnesium chloride (2.0 M solution in THF, 5 mL, 10 mmol) was added dropwise to the solution of 2-iodo-5-bromopyridine (1262) in THF (20 mL) at −40° C. in an acetonitrile/dry ice bath. After stirring for 1 h at this temperature for 1 h, acetaldehyde (0.615 mL, 1 mmol) in 5 mL of THF was slowly added. The reaction mixture was allowed to stir at −40° C. for 0.5 h, then quenched with 1 N NH₄Cl (5 mL) solution, and concentrated under reduced pressure. The residue was dissolved in ethyl acetate and water. Organic layer was separated, washed with 1N NH₄Cl, brine, dried over Na₂SO₄, and concentrated, affording 1263 as a colorless oil (1.95 g, 97%). ¹H NMR (CDCl₃, 300 MHz), δ 8.58 (d, J=2.4 Hz, 1H), 7.80 (dd, J=8.6, 2.4 Hz, 1H), 7.21 (d, J=8.6 Hz, 1H), 4.87 (br q, J=6.2 Hz, 1H), 3.79 (br s, 1H), 1.50 (d, J=6.2 Hz, 3H). Mass calculated for formula $C_7H_8BrNO$ 200.98, observed LCMS m/z 202.0 (M+H).

Part B:

Diisopropyl azodicaboxylate (1.2 g, 6 mmol) in THF (5 mL) was added into a solution of 1263 (1.0 g, 5 mmol), phthalimide (0.88 g, 6 mmol) and triphenylphosphine (1.57 g, 6 mmol) in 20 mL of THF. After stirring overnight at room temperature, the reaction mixture was concentrated to dryness. It was then dissolved in 30 mL of ethanol, added with hydrazine monohydrate (5 mL), heated to reflux for 3 h. The reaction mixture was filtered and the filtrate was concentrated. The residue was dissolved with ethyl acetate and 1 N HCl. The aqueous phase was backed extracted with ethyl acetate. The organic extract was discarded. The aqueous phase was added with 1N NaOH to pH 12. It was extracted with EtOAc (30 mL×3). The ester extract was combined, washed with brine, dried over Na₂SO₄, and concentrated, resulting in 1264 (0.61 g, 61%). ¹H NMR (CDCl₃, 300 MHz), δ 8.58 (s, 1H), 7.75 (dd, J=8.1, 2.0 Hz, 1H), 7.23 (d, J=8.5 Hz, 1H), 4.15 (q, J=6.5 Hz, 1H), 1.43 (d, J=6.5 Hz, 3H). Mass calculated for formula $C_7H_9BrN_2$ 199.99, observed LCMS m/z 201.0 (M+H).

Part C:

To 1264 (400 mg, 2 mmol) in DMF (5 mL) was added 563 (707 mg, 2 mmol), and HATU (912 mg, 2.4 mmol). The reaction mixture was stirred overnight at room temperature, and diluted with ethyl acetate and water. The organic layer was washed with saturated NaHCO₃, and brine. It was dried over Na₂SO₄, and concentrated, resulting in 1265 (600 mg, 56%). Mass calculated for formula $C_{24}H_{27}BrClN_3O_4$ 535.09, observed LCMS m/z 534.1 (M+H).

Part D:

Step 1: To 1265 (120 mg, 0.22 mmol) in 1 mL of dioxane, was added with 2-cyanophenylboronic acid (49 mg, 0.33 mmol), potassium phosphate (142 mg, 0.66 mmol) and PdCl₂ (dppf) (7.2 mg, 0.0088 mmol, 4 mol %). The reaction mixture was stirred overnight at 80° C. under argon, then diluted with EtOAc and water, washed with saturated NaHCO₃, brine, dried over Na₂SO₄, and concentrated.

Step 2: The above residue was dissolved in 0.5 mL of TFA/H₂O (80:20) and stirred at room temperature for 2 h. The reaction mixture was quenched with ACN/H₂O (50:50) and concentrated in vacuo. Purification by reverse phase prep-LC afforded 1266 as a white solid. HPLC-MS $t_R$=4.04 min (UV₂₅₄ ₙₘ, 10 min), Mass calculated for formula $C_{28}H_{27}ClN_4O_4$ 518.17, observed LCMS m/z 519.1 (M+H).

| Compound # | Structure | Exact mass | MS m/e (M + H) |
|---|---|---|---|
| 1267 | 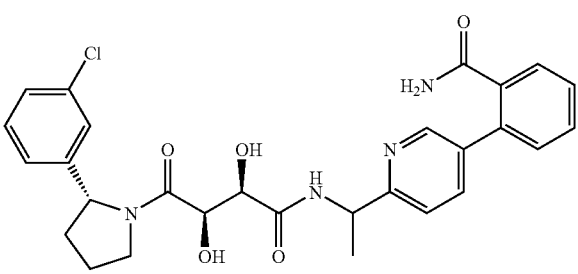 | 536.2 | 537.1 |
| 1268 | 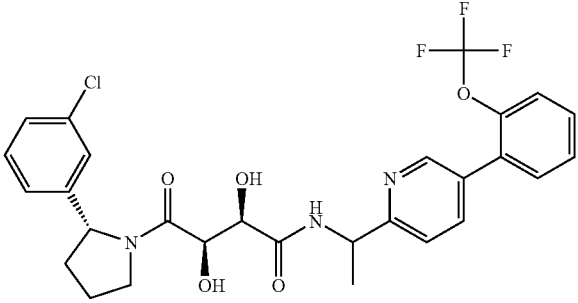 | 577.2 | 578.0 |

| Compound # | Structure | Exact mass | MS m/e (M + H) |
|---|---|---|---|
| 1269 | 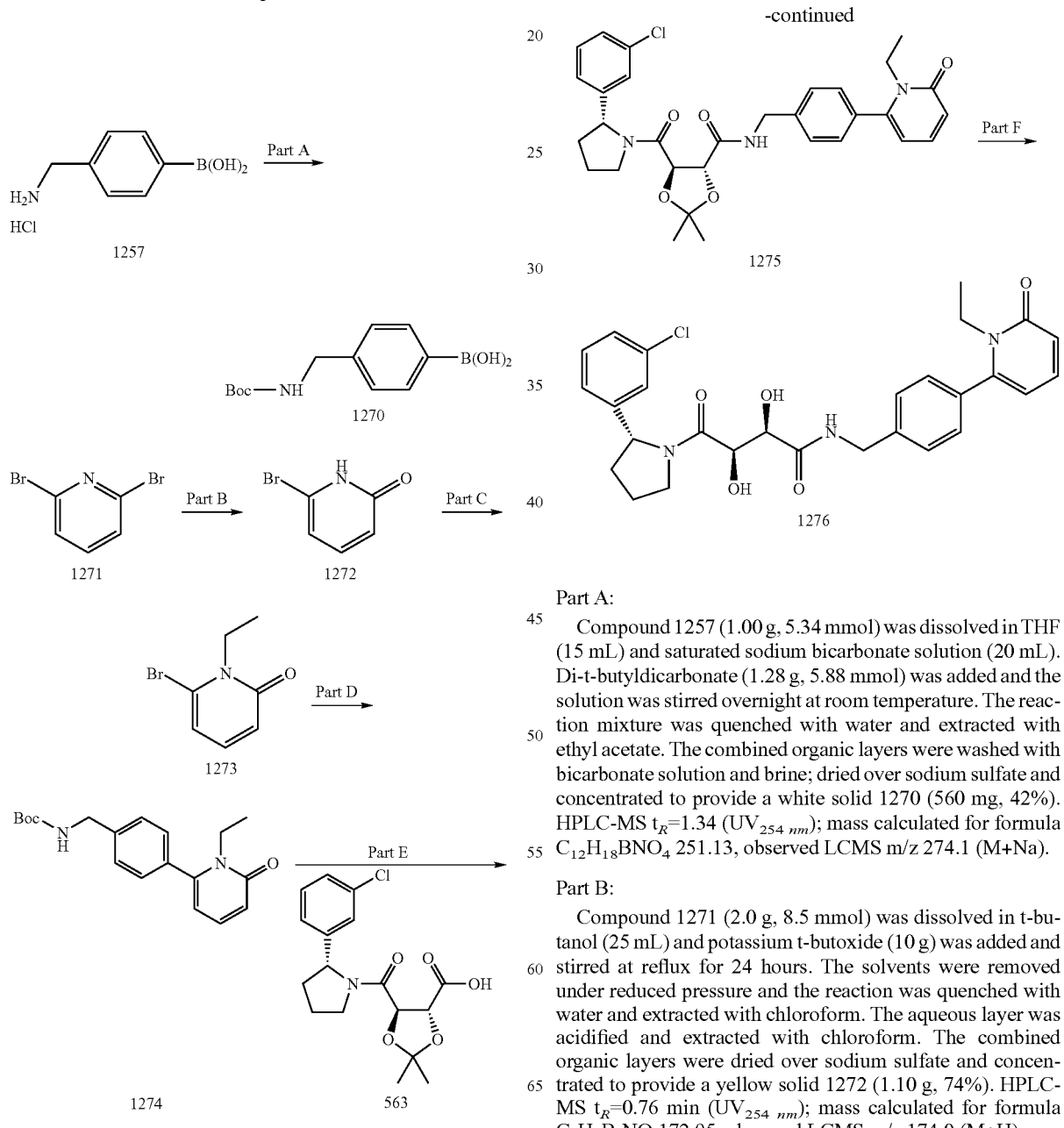 | 537.20 | 538.2 |

Example 45

Part A:

Compound 1257 (1.00 g, 5.34 mmol) was dissolved in THF (15 mL) and saturated sodium bicarbonate solution (20 mL). Di-t-butyldicarbonate (1.28 g, 5.88 mmol) was added and the solution was stirred overnight at room temperature. The reaction mixture was quenched with water and extracted with ethyl acetate. The combined organic layers were washed with bicarbonate solution and brine; dried over sodium sulfate and concentrated to provide a white solid 1270 (560 mg, 42%). HPLC-MS $t_R$=1.34 ($UV_{254\ nm}$); mass calculated for formula $C_{12}H_{18}BNO_4$ 251.13, observed LCMS m/z 274.1 (M+Na).

Part B:

Compound 1271 (2.0 g, 8.5 mmol) was dissolved in t-butanol (25 mL) and potassium t-butoxide (10 g) was added and stirred at reflux for 24 hours. The solvents were removed under reduced pressure and the reaction was quenched with water and extracted with chloroform. The aqueous layer was acidified and extracted with chloroform. The combined organic layers were dried over sodium sulfate and concentrated to provide a yellow solid 1272 (1.10 g, 74%). HPLC-MS $t_R$=0.76 min ($UV_{254\ nm}$); mass calculated for formula $C_5H_4BrNO$ 172.95, observed LCMS m/z 174.0 (M+H).

Part C:

Compound 1273 was prepared according to the procedure of Lui, H. et. al. (Tet. Lett. 1995, 36, 8917). Data for 1273: HPLC-MS $t_R$=1.12 (UV$_{254\ nm}$); mass calculated for formula $C_7H_8BrNO$ 200.98, observed LCMS m/z 202.0 (M+H).

Part D:

Compound 1273 (50 mg, 0.247 mmol) was dissolved in dioxane (5 mL) and compound 1270 (93 mg, 0.370 mmol), potassium phosphate (108 mg, 0.51 mmol), triphenylphosphine (10 mg), and Pd(dba)$_3$ (5 mg) were added and stirred at 90° C. overnight. The reaction was filtered through celite and purified by column chromatography (EtOAc) to provide the desired product 1274 as a white solid (60 mg, 75%). HPLC-MS $t_R$=1.64 (UV$_{254\ nm}$); mass calculated for formula $C_{19}H_{24}N_2O_3$ 328.18, observed LCMS m/z 329.2 (M+H).

Part E:

Compound 1274 (60 mg, 0.183 mmol) was dissolved in methylene chloride (4 mL) and TFA (1 mL) was added. The reaction mixture was stirred for 1 hour and then the solvent was removed under reduced pressure. The residue was dissolved in DMF (5 mL) and compound 563 (63.5 mg, 0.183 mmol), HATU (90.5 mg, 0.0.2379 mmol), and DIEA (0.5 mL) were added and stirred overnight. The reaction was quenched with water and extracted with ethyl acetate. The combined organic layers were washed with 1 N HCl solution, bicarbonate solution and brine; dried over sodium sulfate and concentrated. Purification of the residue by column chromatography (EtOAc) provided compound 1275 as a white solid (87 mg, 85%). HPLC-MS $t_R$=1.81 min (UV$_{254\ nm}$); mass calculated for formula $C_{31}H_{34}ClN_3O_5$ 563.22, observed LCMS m/z 564.1 (M+H).

Part F:

Compound 1276 was synthesized using procedures similar to Example 1, Part D. HPLC-MS $t_R$=1.48 min (UV$_{254\ nm}$); mass calculated for formula $C_{28}H_{30}ClN_3O_5$ 523.19, observed LCMS m/z 524.2 (M+H).

Example 46

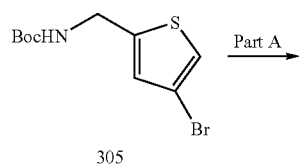

305

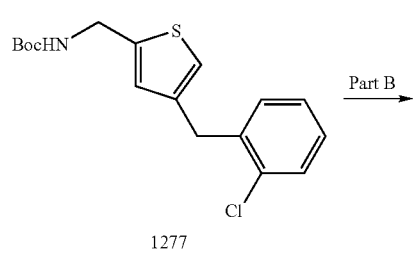

1277

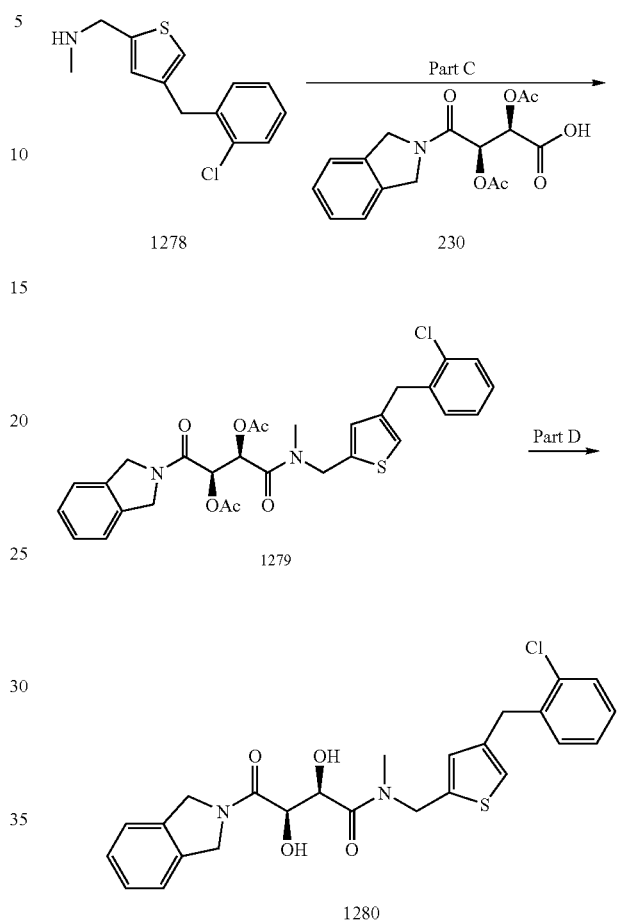

Part A:

Compound 1277 was prepared from 305 according to the procedures described in Example 4A Part A.

Part B:

To 1277 (150 mg, 0.44 mmol) in THF (5 mL) was added lithium hexamethyldisilazide (1.0 M, 0.66 mL, 0.66 mmol) at 0° C. The reaction mixture was stirred for 10 minutes. To the reaction mixture was added methyl iodide (0.034 mL, 0.53 mmol). The reaction mixture was stirred overnight at room temperature. The reaction mixture was diluted with ethyl acetate and washed with 1.0 N citric acid, satureated sodium bicarbonate solution and brine, dried over sodium sulfate and concentrated. The residue was dissolved in DCM (5 ml) and treated with 4N HCl in dioxane (2 mL). The reaction was stirred at room temperature and concentrated. Compound 1278 was used without further purification.

Part C and D:

Compound 1280 was obtained from 1278 and 230 using the procedures described in Example 4A Part D and E. Data for 1280: HPLC-MS $t_R$=5.05 min (UV$_{254\ nm}$ 10 min); mass calculated for formula $C_{25}H_{25}ClN_2O_4S$ 484.1, observed LCMS m/z 485.0 (M+H).

1191
Example 47

Heterocyclic Isoindolines

Example 47A

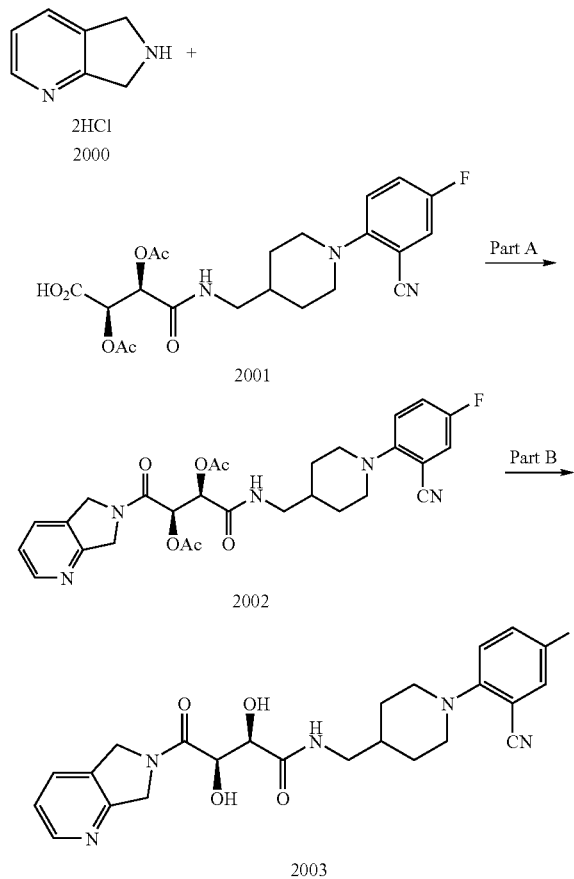

Compound 2000 was prepared according to the procedures in U.S. Pat. No. 5,371,090.

Compound 2001 was prepared using procedures described in Example 2 and 27. HPLC-MS $t_R$=min ($UV_{254\ nm}$); mass calculated for formula $C_{21}H_{24}FN_3O_7$ 449.2, observed LCMS m/z 450.1 (M+H).

Part A:

Compound 2002 was prepared using the coupling conditions described in Example 2. HPLC-MS $t_R$=1.60 min ($UV_{254\ nm}$); mass calculated for formula $C_{28}H_{30}FN_5O_6$ 551.2, observed LCMS m/z 552.1 (M+H).

Part B:

Compound 2002 (50 mg) was dissolved in methanol (2 mL). To this solution was added 7.0 M ammonia in methanol (2 mL). The reaction mixture was stirred for 1 hour at room temperature and concentrated. Purification by prep-LC and conversion to a hydrochloric salt afforded 2003 as an off-white solid (32 mg). HPLC-MS $t_R$=1.35 min ($UV_{254\ nm}$); mass calculated for formula $C_{24}H_{26}FN_5O_4$ 467.2, observed LCMS m/z 468.1 (M+H).

1192
Example 47B

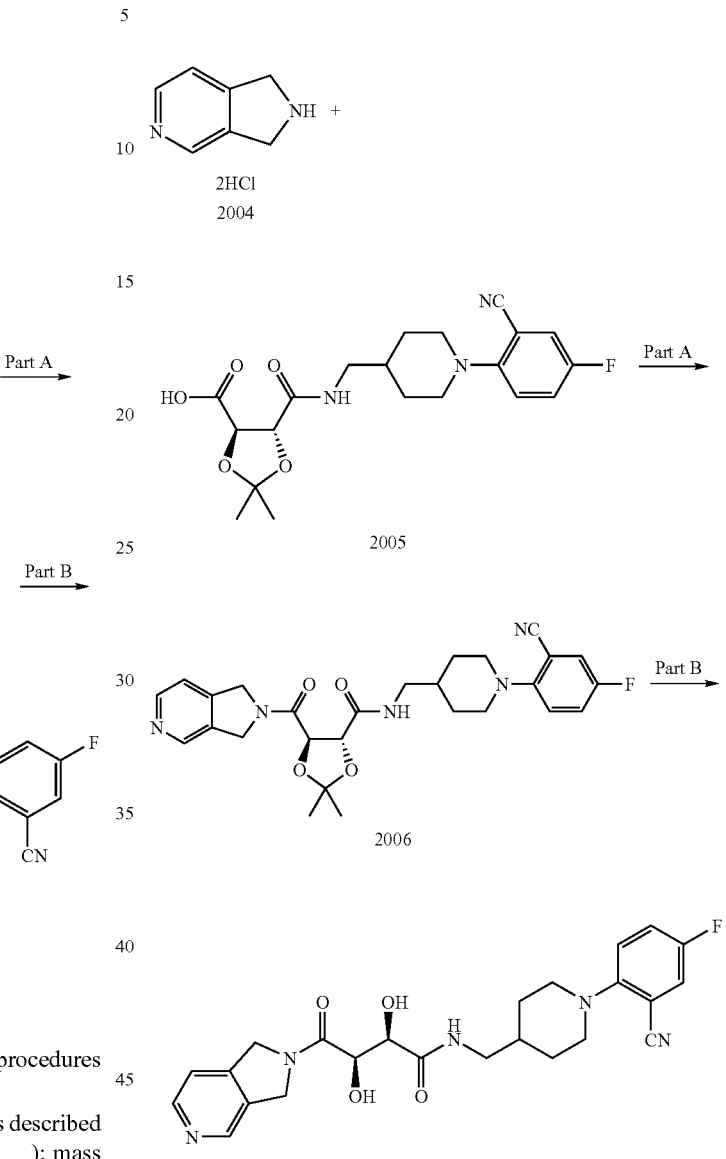

Compound 2004 was prepared according to the procedures in U.S. Pat. No. 5,371,090.

Compound 2005 was prepared using procedures described in Example 1 and 27.

Part A:

Compound 2006 was prepared using the coupling conditions described in Example 1. HPLC-MS $t_R$=1.40 min ($UV_{254\ nm}$); mass calculated for formula $C_{27}H_{30}FN_5O_4$ 507.2, observed LCMS m/z 508.1 (M+H).

Part B:

Compound 2006 (50 mg) was deprotected using procedures described in Example 1. Purification by prep-LC and conversion to a hydrochloric salt afforded 2007 as an off-white solid (32 mg). HPLC-MS $t_R$=1.09 min ($UV_{254\ nm}$); mass calculated for formula $C_{24}H_{26}FN_5O_4$ 467.2, observed LCMS m/z 468.1 (M+H).

Example 47C

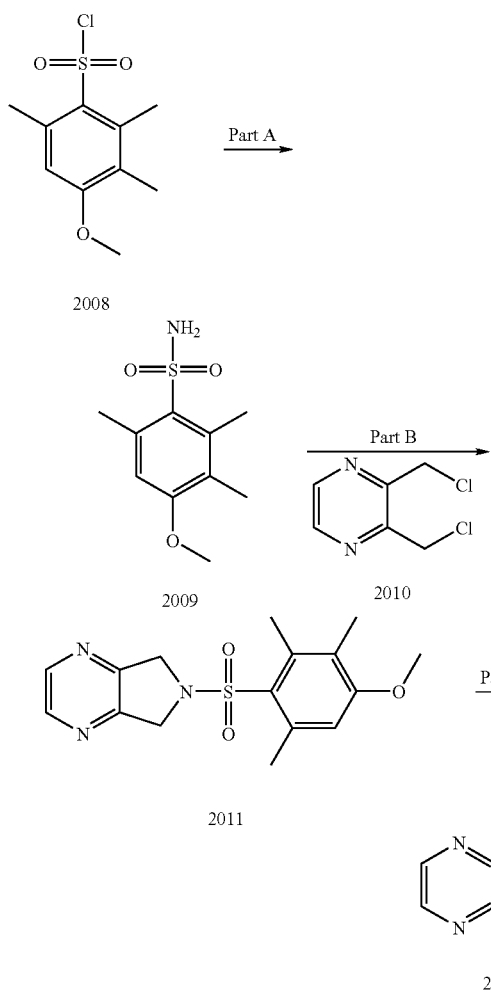

and concentrated. Purification by column chromatography (SiO$_2$, 30% ethyl acetate/hexanes) afforded recovered sulfonamide 2009 (218 mg) and 2011 (245 mg). HPLC-MS t$_R$=1.82 min (UV$_{254\ nm}$); mass calculated for formula C$_{16}$H$_{19}$N$_3$O$_3$S 333.1, observed LCMS m/z 334.1 (M+H).

Part C:

A mixture of sulfonamide 2011 (245 mg, 0.73 mmol), anhydrous methanesulfonic acid (3 mL) and 1:9 thioanisole:trifluoroacetic acid (3 mL) was stirred for 3 hours at room temperature. The reaction mixture was poured over ice and treated with 50% sodium hydroxide (10 mL). The aqueous layer was salted and extracted with chloroform. The combined organics were dried over sodium sulfate and concentrated. The residue was dissolved in 1.0 M HCl (5 mL) and extracted with ether. The aqueous layer was lyophilized to afford 2012 (105 mg) as a brown solid. $^1$H NMR (400 MHz, DMSO-d$_6$) δ 10.27 (s, NH), 8.58 (s, 2H), 4.59 (m, 4H).

Example 47D

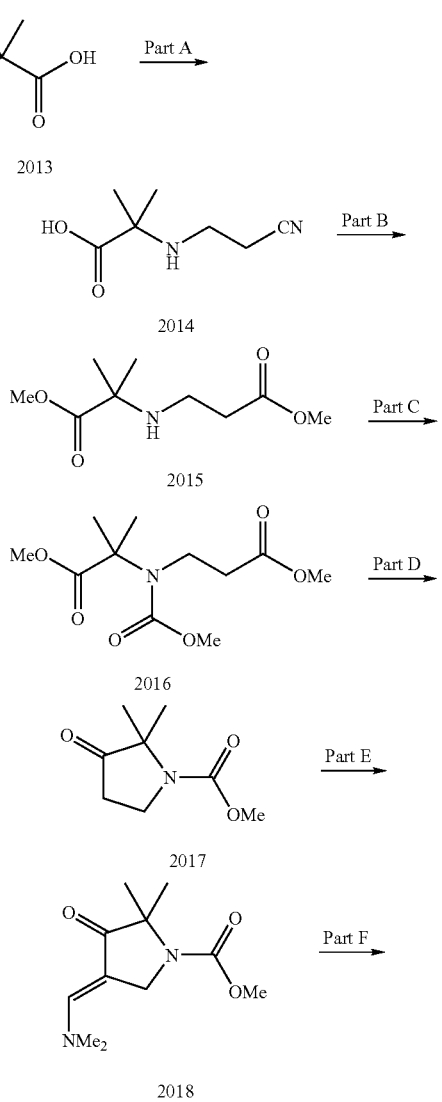

Part A:

Sulfonyl chloride 2008 (2.44 g, 9.8 mmol) was dissolved in dioxane (40 mL) and cooled in an ice bath. Ammonia gas was bubbled into the reaction mixture for 10 minutes. The reaction mixture was warmed to room temperature and filtered. The filtrate was concentrated. The crude product was recrystallized from ethyl acetate/hexanes to afford 2009 as an off-white solid (1.74 g). $^1$H NMR (400 MHz, DMSO-d$_6$) δ 7.09 (s, 2H), 6.74 (s, 1H), 3.80 (s, 3H), 2.57 (s, 3H), 2.48 (s, 3H), 2.08 (s, 3H); HPLC-MS t$_R$=1.43 min (UV$_{254\ nm}$); mass calculated for formula C10H15NO3S 229.1, observed LCMS m/z 230.1 (M+H).

Part B:

To sodium hydride (95%, 131 mg, 5.19 mmol) in DMF (10 mL) was added sulfonamide 2009 (596 mg, 2.6 mmol). The reaction mixture was heated to 70° C. and stirred for 45 minutes. To this mixture was added 2,3-bis(chloromethyl)pyrazine (2010) (Yoshiizumi, K. et. al. *Bioorg. Med. Chem.* 2003, 11, 433) (448 mg, 2.53 mmol) in DMF (3 mL). The reaction mixture was heated at 70° C. overnight. The reaction mixture was cooled and poured into water. The aqueous layer was salted and extracted with chloroform. The combined organics were washed with water, dried over sodium sulfate

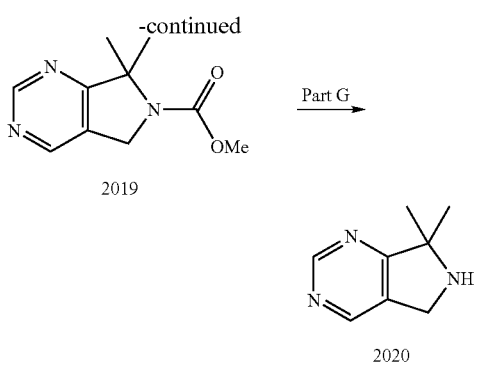

2019

2020

Part A:

Compound 2014 was prepared according to the procedure in *Helv. Chim. Acta.* 1986, 905-907.

Part B:

Acetyl chloride (20 mL) was added dropwise to methanol (130 mL) cooled in an ice bath. This solution was then added to compound 2014 (5.00 g, 31.8 mmol) and stirred overnight at reflux. The solvent was removed under reduced pressure and the residue was partitioned between ethyl acetate and 1N NaOH. The organic layer was washed with brine, dried over sodium sulfate, and concentrated to provide 2015 (5.0 g). $^1$H NMR (400 MHz, CDCl$_3$) δ 3.72 (s, 3H), 3.69 (s, 3H), 2.77 (t, 2H), 2.5 (t, 2H), 1.32 (s, 6H).

Part C:

Compound 2015 (5.00 g, 24 mmol) was dissolved in THF (60 mL) and saturated sodium bicarbonate (60 mL) and cooled in an ice bath. Methyl chloroformate (2.93 g, 31.2 mmol) was added dropwise and the reaction was stirred at room temperature overnight. The reaction mixture was partitioned between ethyl acetate and water. The organic layer was washed with 1 N HCl, saturated sodium bicarbonate, brine, dried over sodium sulfate and concentrated. Purification by column chromatography (SiO$_2$, 20% ethyl acetate/hexanes) afforded 2016 (5.5 g). $^1$H NMR (400 MHz, CDCl$_3$) δ 3.72-3.68 (m, 9H), 3.65-3.6 (t, 2H), 2.66 (t, 2H), 1.5 (s, 6H).

Part D:

Compound 2016 (1.66 g, 6.36 mmol) was dissolved in THF (20 mL) and cooled on an ice bath. Potassium hydride (35% in oil, 1.12 g, 9.54 mmol) was added in portions and stirring was continued for 2 hours at room temperature. The reaction was slowly quenched with water, acidified to pH 3, and extracted with ethyl acetate. The combined organic layers were dried over sodium sulfate and concentrated (1.5 g). A portion of the residue (350 mg) was dissolved in MeOH (5 mL) and 6N HCl (5 mL) and stirred at reflux for 3 hours and room temperature overnight. The solvent was evaporated under reduced pressure and partitioned between ethyl acetate and water. The organic layer was washed with water, dried over sodium sulfate, and concentrated to yield 2017 (150 mg). $^1$H NMR (400 MHz, CDCl$_3$) δ 3.72-3.55 (m, 5H), 2.5 (t, 2H), 1.4-1.25 (m, 6H).

Part E:

According to a modification of a procedure by Fukui, H. et al. (*Heterocycles* 2002, 56, 257-264) a mixture of ketone 2017 (200 mg, 1.17 mmol) and N,N-dimethylformamide dimethyl acetal (3 mL) was heated at 100° C. for 2 h, and then concentrated to give enamino-ketone 2018 (244 mg, 92%) as a yellow solid. $^1$H NMR (400 MHz, CDCl$_3$) δ 7.32-7.31 (m, 1H), 4.54-4.51 (d, 2H), 3.78-3.22 (d, 3H), 3.12 (s, 6H), 1.48 (s, 3H), 1.40 (s, 3H).

Part F:

According to a modification of a procedure by Fukui, H. et al. (*Heterocycles* 2002, 56, 257-264) a mixture of enamino-ketone 2018 (690 mg, 3.05 mmol) and formamidine acetate (3.17 g, 30.5 mmol) in ethanol (15 mL) was heated at reflux for 3 days, and then concentrated. The residue was partitioned between dichloromethane and water, and extracted with dichloromethane. The combined organic extracts were concentrated to give an oil which was chromatographed (SiO$_2$, 50%-80% ethyl acetate/hexane) to give pyrimidine 2019 (334 mg, 53%). $^1$H NMR (400 MHz, CDCl$_3$) δ 9.15 (s, 1H), 8.67 (s, 1H, broad), 4.76-4.71 (d, 2H), 3.84-3.77 (d, 3H), 1.75 (s, 3H), 1.67 (s, 3H).

Part G:

A mixture of compound 2019 (235 mg, 1.13 mmol), powder potassium hydroxide (900 mg, 16 mmol) and hydrazine monohydrate (1.36 mL, 28 mmol) in ethylene glycol (5 mL) was heated at 100° C. overnight. The reaction mixture was cooled to rt, poured into brine and extracted several times with dichloromethane. The combined organic extracts were washed with brine and concentrated to give compound 2020 (121 mg, 72%). $^1$H NMR (400 MHz, CDCl$_3$) δ 9.06 (s, 1H), 8.58 (s, 1H), 4.24 (s, 2H), 1.47 (s, 6H). HPLC-MS t$_R$=0.2 min (UV$_{254\ nm}$); mass calculated for formula C$_8$H$_{11}$N$_3$ 149.1, observed LCMS m/z 150.1 (M+H).

Example 47E

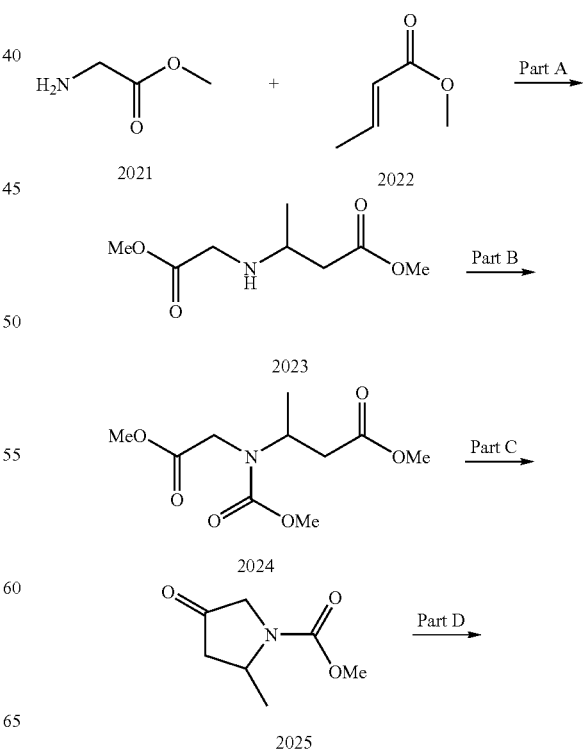

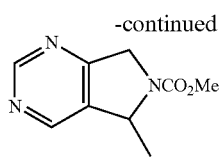

2026

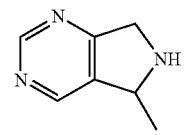

2027

Part A:

To a mixture of methyl crotonate (2022) (2.0 g, 20 mmol) and methyl glycine hydrochloride (2021) (5.5 g, 44 mmol) in methanol (27 mL) was added triethylamine (6.4 mL, 46 mmol). The mixture was stirred at room temperature for 2 days and filtered to remove the white precipitate. The filtrate was concentrated and the residue was dissolved in ethyl acetate, washed with sodium bicarbonate solution, water and brine, dried over sodium sulfate and concentrated to afford 2023 as a light yellow oil (2.4 g, 64%). $^1$H NMR (400 MHz, CDCl$_3$) δ 3.74 (s, 3H), 3.69 (s, 3H), 3.46 (d, J=3.2 Hz, 2H), 3.14 (m, 1H), 2.45 (m, 2H), 1.15 (d, J=7.2 Hz, 3H).

Part B:

Compound 2023 (2.42 g, 13 mmol) was dissolved in THF (20 mL) and saturated sodium bicarbonate (20 mL) and cooled in an ice bath. Methyl chloroformate (1.2 mL, 15 mmol) was added dropwise and the reaction was stirred at room temperature overnight. The reaction mixture was partitioned between ethyl acetate and water. The organic layer was washed with 1 N HCl, saturated sodium bicarbonate and brine, dried over sodium sulfate and concentrated to afford 2024 (2.9 g).

Part C:

Compound 2024 (1.30 g, 5.26 mmol) was dissolved in THF (20 mL) and cooled on an ice bath. Potassium hydride (35% in oil, 1.12 g, 9.54 mmol) was added in portions and the mixture was stirred at room temperature overnight. The reaction was slowly quenched with water, acidified to pH 3, and extracted with ethyl acetate. The combined organic layers were dried over sodium sulfate and concentrated. Purification by column chromatography (SiO$_2$, 25% ethyl acetate/hexane) afforded an oil (1.27 g). This oil (1.27 g) was dissolved in MeOH (5 mL) and 6N HCl (5 mL) and stirred at reflux overnight. The mixture was extracted with ethyl acetate and the combined organic layers were washed with sodium bicarbonate solution, water and brine, dried over sodium sulfate and concentrated to afford 2025 (663 mg). $^1$H NMR (400 MHz, CDCl$_3$) δ 4.5 (bs, 1H), 3.95 (m, 1H), 3.78 (s, 3H), 3.70 (m, 1H), 2.73 (m, 1H), 2.25 (m, 1H), 1.28 (m, 3H).

Part D:

Compound 2026 was prepared from the material from part C according to procedures described in Example 47D Part E and Part F. $^1$H NMR (400 MHz, CDCl$_3$) δ 9.13 (s, 1H), 8.61 (m, 1H), 5.24 (m, 1H), 4.88-4.64 (m, 2H), 3.82 (m, 3H), 1.59 (m, 3H).

Part E:

A mixture of compound 2026 (300 mg, 1.45 mmol), powder potassium hydroxide (600 mg, 10.7 mmol) and hydrazine monohydrate (1.0 mL, 21 mmol) in ethylene glycol (5 mL) was heated at 100° C. overnight. The reaction mixture was cooled to rt, poured into brine and extracted several times with dichloromethane. The combined organic extracts were washed with brine and concentrated to give compound 2027 (105 mg, 54%).

Example 47F

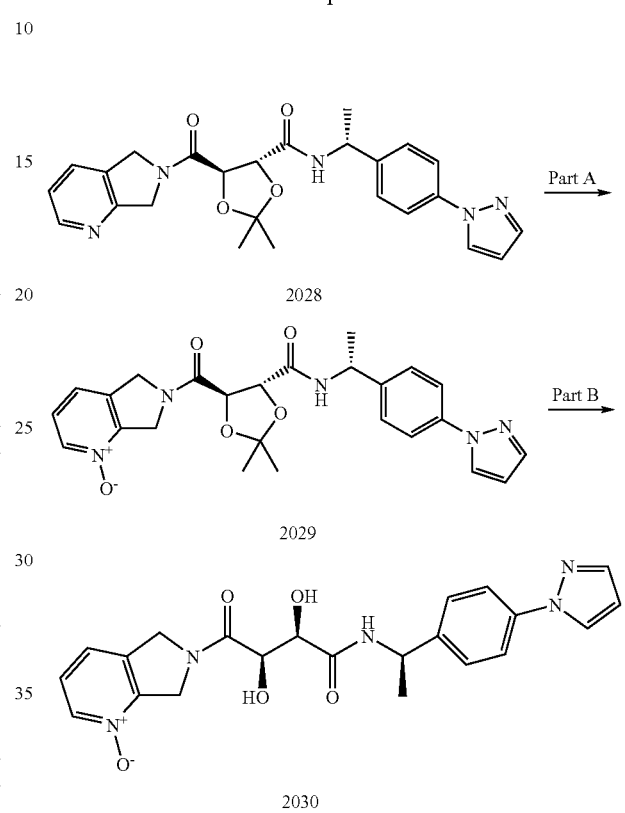

Part A:

To a solution of compound 2028 (0.29 g, 0.63 mmol) in CH$_2$Cl$_2$ at 0° C. was added 70% m-CPBA (0.31 g, 1.26 mmol) and the reaction mixture was warmed to room temperature and stirred for 1 hour. Diluted with CH$_2$Cl$_2$ (5 mL) and washed with a solution of water (6 mL) and concentrated NH$_4$OH (0.5 mL). Aqueous layer was extracted with CH$_2$Cl$_2$ (3×10 mL) and 5% MeOH/CH$_2$Cl$_2$ (2×5 mL). The organic layer was dried over MgSO$_4$, filtered and concentrated. Purification by column chromatography (SiO$_2$, 5% MeOH/CH$_2$Cl$_2$) afforded the desired product with some impurity. Dissolved the impure product in EtOAc (15 mL) and washed with 10% NH$_4$OH (5 mL).

The aqueous layer was extracted with CH$_2$Cl$_2$ (3×5 mL). The combined organic layers (EtOAc and CH$_2$Cl$_2$) were dried over MgSO$_4$, filtered and concentrated to give the desired compound 2029 (0.25 g, 92%).

Part B:

Compound 2030 was obtained from compound 2029 using the TFA deprotection procedure as described in Example 1.

The following compounds were prepared using previously described procedures.

| Compound # | Structure | Exact mass | MS m/z (M + H) |
|---|---|---|---|
| 2031 | 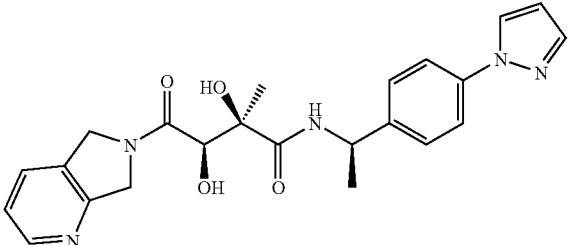 | 435.2 | 436.2 |
| 2003 | 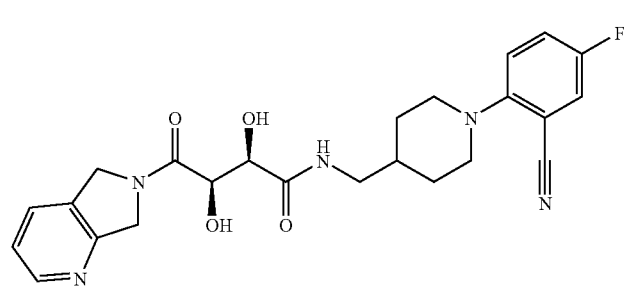 | 467.2 | 468.1 |
| 2032 | 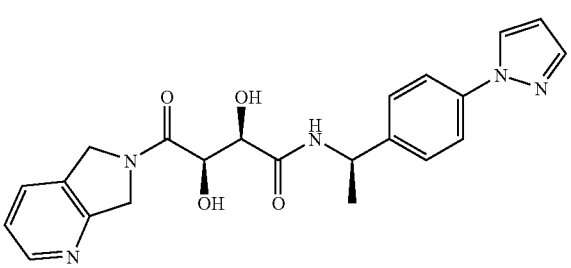 | 421.2 | 422.1 |
| 2030 | 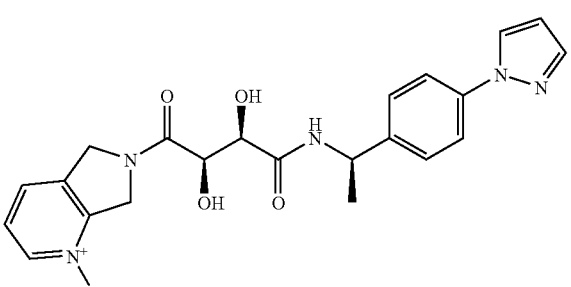 | 437.2 | 438.1 |
| 2033 | 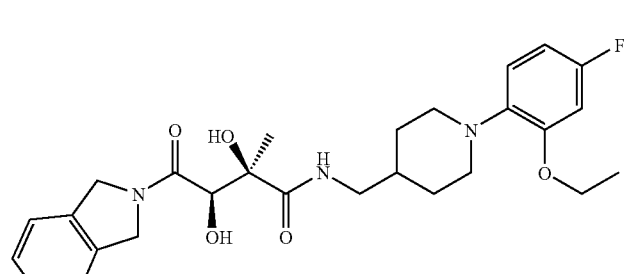 | 493.2 | 494.1 |

-continued

| Compound # | Structure | Exact mass | MS m/z (M + H) |
|---|---|---|---|
| 2034 | 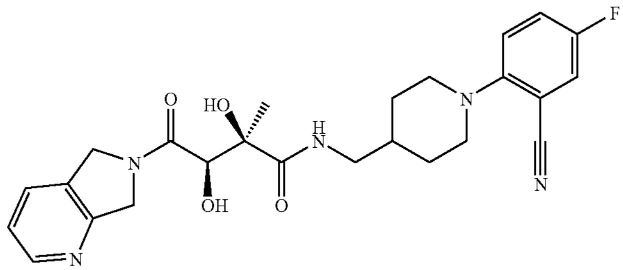 | 481.2 | 482.1 |
| 2035 | 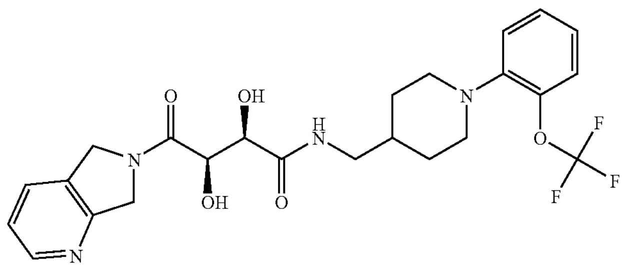 | 508.2 | 509.1 |
| 2036 | 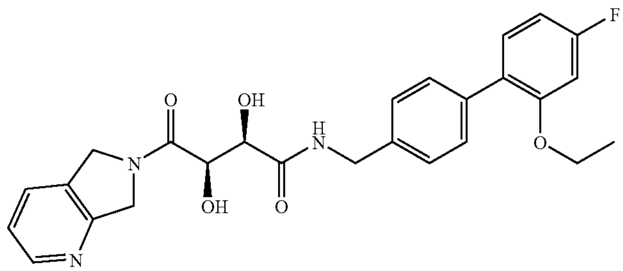 | 479.2 | 480.1 |
| 2037 | 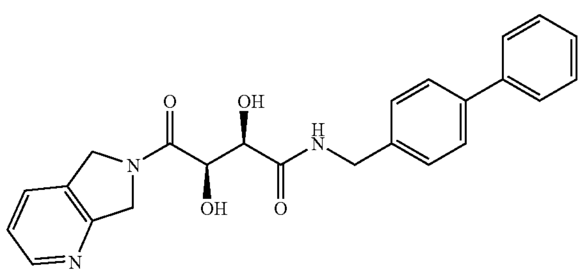 | 417.2 | 418.2 |
| 2038 | 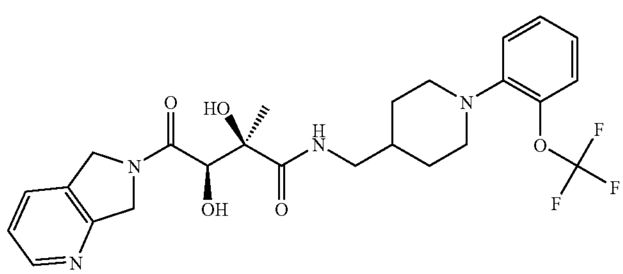 | 522.2 | 523.2 |

-continued

| Compound # | Structure | Exact mass | MS m/z (M + H) |
|---|---|---|---|
| 2039 | 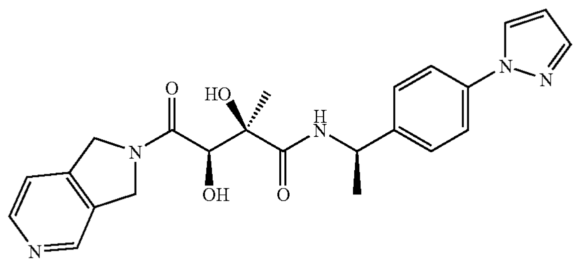 | 435.2 | 436.1 |
| 2040 | 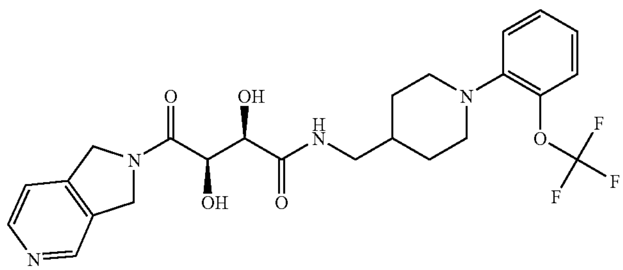 | 508.2 | 509.1 |
| 2041 | 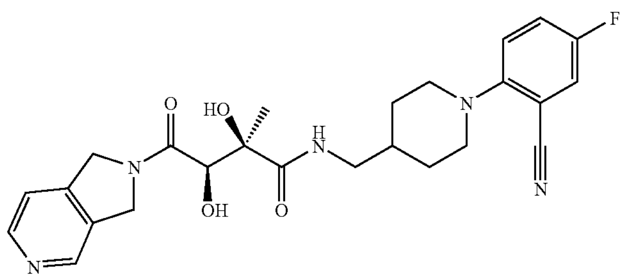 | 481.2 | 482.2 |
| 2007 | 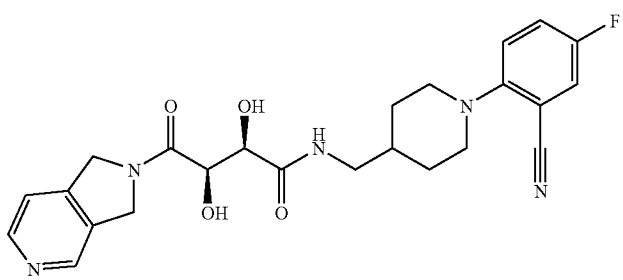 | 467.2 | 468.1 |
| 2042 | 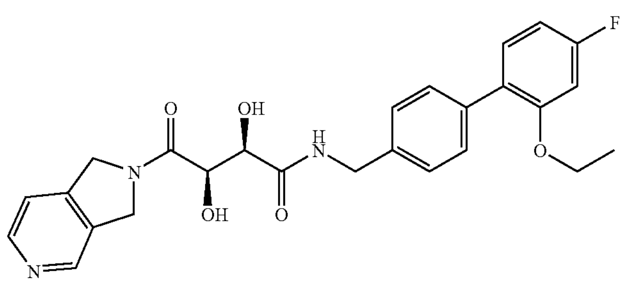 | 479.2 | 480.1 |

-continued

| Compound # | Structure | Exact mass | MS m/z (M + H) |
|---|---|---|---|
| 2043 | 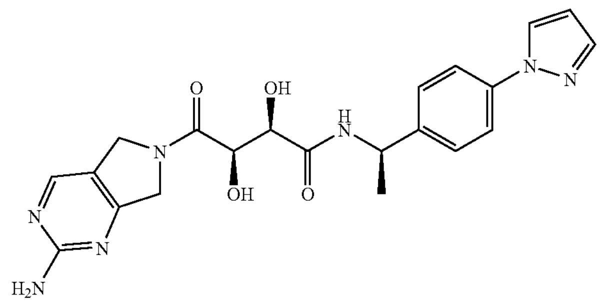 | 437.2 | 438.1 |
| 2044 | 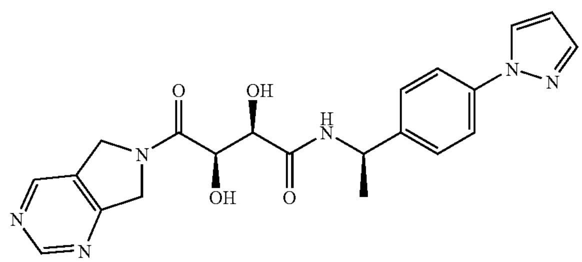 | 422.2 | 423.1 |
| 2045 | 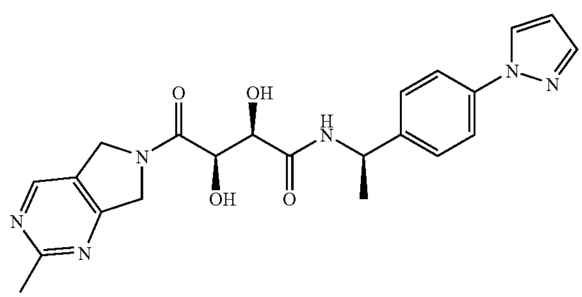 | 436.2 | 437.2 |
| 2046 | 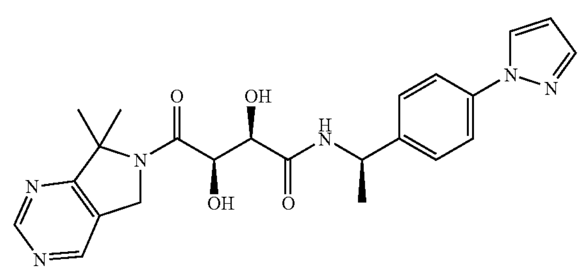 | 450.2 | 451.1 |
| 2047 | 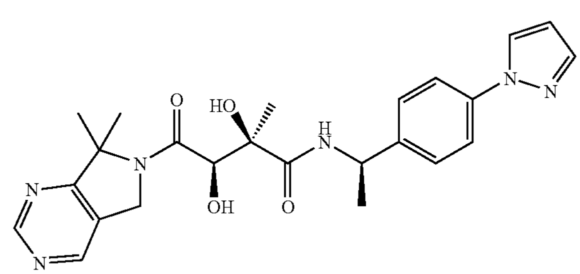 | 464.2 | 465.1 |

-continued

| Compound # | Structure | Exact mass | MS m/z (M + H) |
|---|---|---|---|
| 2048 | 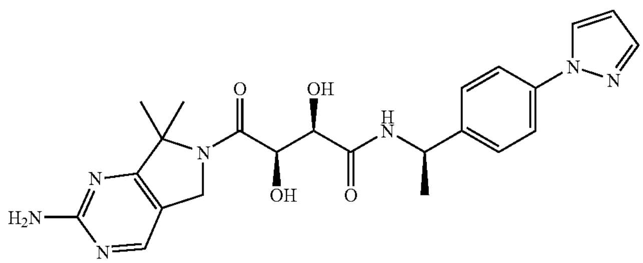 | 465.2 | 466.1 |
| 2049 | 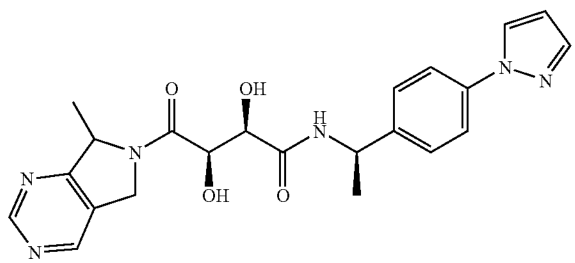 | 436.2 | 437.0 |
| 2050 | 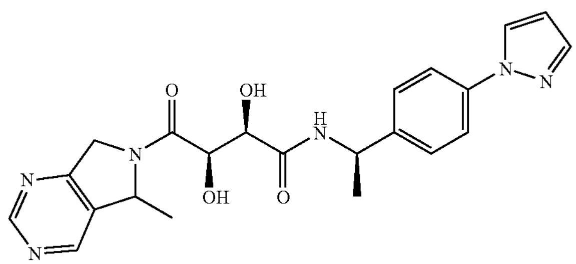 | 436.2 | 437.2 |
| 2051 | 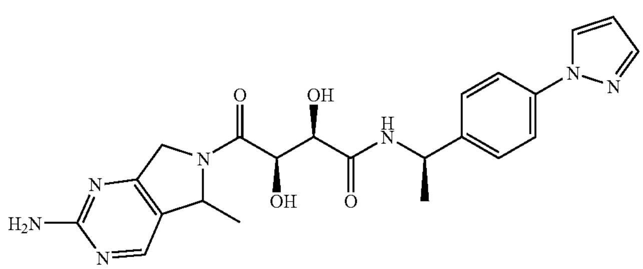 | 451.2 | 452.2 |
| 2052 | 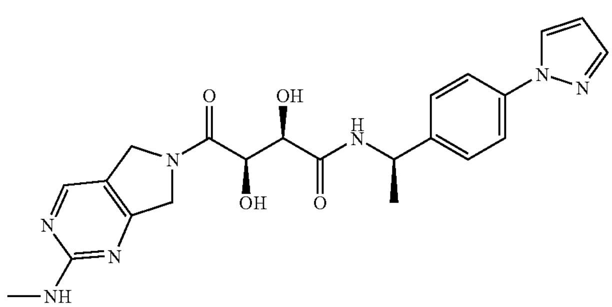 | 451.2 | 452.0 |

-continued

| Compound # | Structure | Exact mass | MS m/z (M + H) |
|---|---|---|---|
| 2053 | 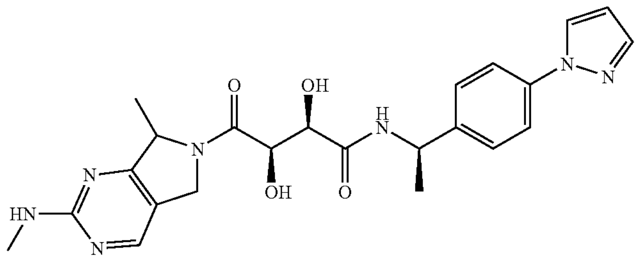 | 465.2 | 466.1 |
| 2054 | 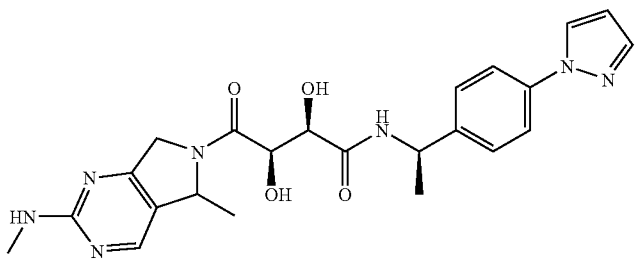 | 465.2 | 466.1 |
| 2055 | 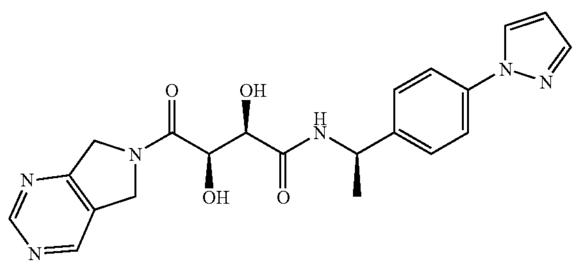 | 422.2 | 423.1 |
| 2056 | 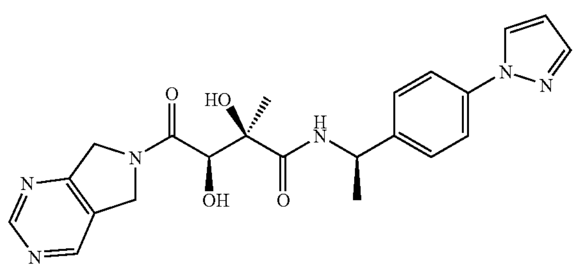 | 436.2 | 437.1 |
| 2057 | 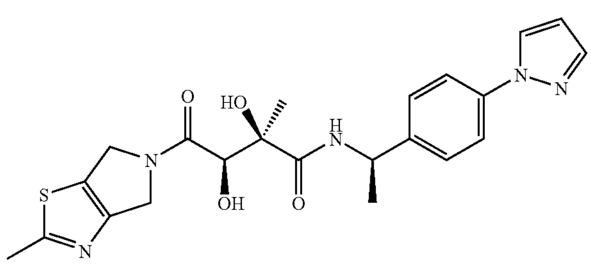 | 455.2 | 456.1 |

Example 48

Heterocyclic Tetrahydroisoquinoline Analogs

Example 48A

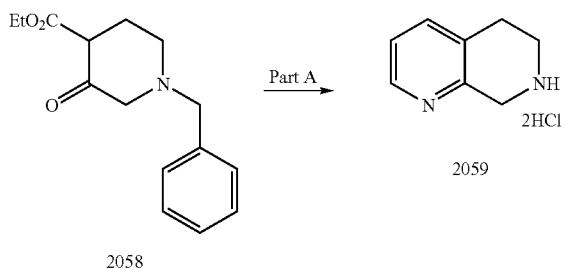

2058 → 2059 · 2HCl

Part A:

Compound 2059 was synthesized according to the literature procedures. (Dow, R. L.; Schneider, S. R. *J. Heterocyclic Chem.* 2001, 38, 535).

Example 48B

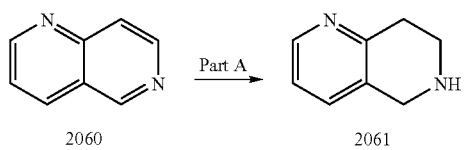

2060 → 2061

Part A:

Compound 2061 was synthesized according to the procedures of U.S. Pat. No. 5,037,834.

Example 48C

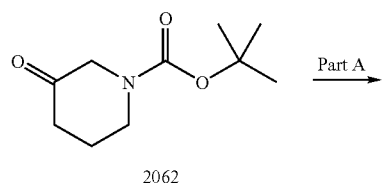

2062

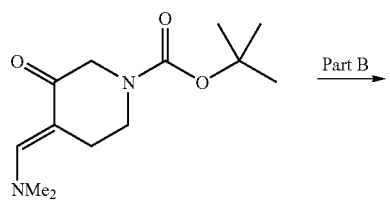

2063

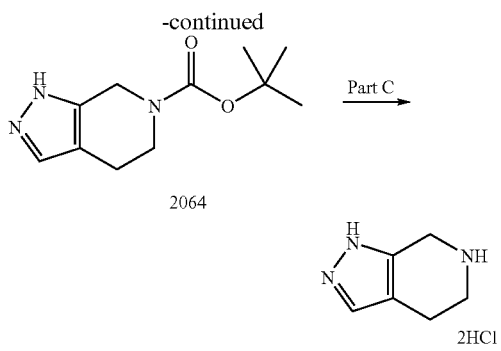

2064 → 2065 · 2HCl

Part A:

According to a modification of a procedure by Fukui, H. et al. (*Heterocycles* 2002, 56, 257-264) a mixture of ketone 2062 (2.5 g, 12.5 mmol) and N,N-dimethylformamide dimethyl acetal (21 mL) was heated at 100° C. for 2 h. The mixture was concentrated to a residue which was passed through a short silica gel column (9:1:90 methanol:triethylamine:dichloromethane) to give enamino-ketone 2063 (3.1, 97%) as a viscous brown oil. HPLC-MS $t_R$=1.34 min ($UV_{254\ nm}$); mass calculated for formula $C_{13}H_{22}N_2O_3$ 254.1, observed LCMS m/z 255.1 (M+H).

Part B:

According to a modification of a procedure by Fukui, H. et al. (*Heterocycles* 2002, 56, 257-264) a mixture of enamino-ketone 2063 (732 mg, 2.88 mmol) and hydrazine monohydrate (0.28 mL, 5.76 mmol) in ethanol (8 mL) was heated at reflux overnight, and then concentrated. The residue was partitioned between dichloromethane and water, and extracted with dichloromethane. The combined organic extracts were concentrated to give an oil which was chromatographed ($SiO_2$, 80% ethyl acetate/hexane) to give compound 2064 as an oil (major isomer, 300 mg, 46%). HPLC-MS $t_R$=1.39 min ($UV_{254\ nm}$); mass calculated for formula $C_{11}H_{17}N_3O_2$ 223.1, observed LCMS m/z 224.2 (M+H).

Part C:

Compound 2064 (300 mg, 1.34 mmol) was deprotected according to a procedure described by Fukui, H. et al. (*Heterocycles* 2002, 56, 257-264) to give compound 2065 (57 mg, 22%). $^1$H NMR (400 MHz, DMSO-$d_6$) δ 10.9 (s, 1H, broad), 9.4 (s, 1H, broad), 7.57 (s, 1H), 4.19 (t, 2H), 3.30-3.26 (m, 2H), 2.78 (t, 2H). HPLC-MS $t_R$=0.2 min ($UV_{254\ nm}$); mass calculated for formula $C_6H_9N_3$ 123.1, observed LCMS m/z 124.2 (M+H).

Example 48D

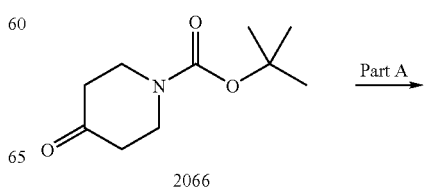

2066

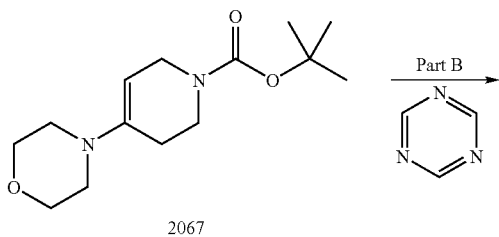

2067

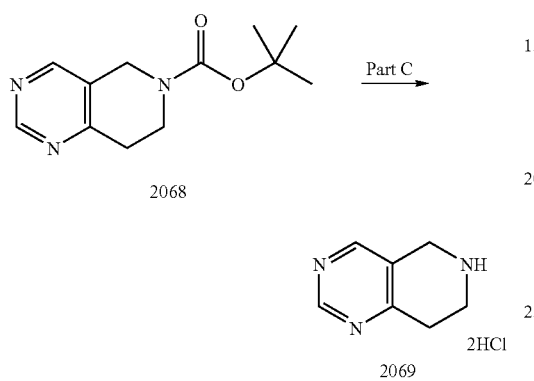

2068

2069 · 2HCl

Part A:

A mixture of ketone 2066 (4.0 g, 20 mmol), morpholine (7.5 mL, 85 mmol) and p-toluenesulfonic acid monohydrate (160 mg, 0.84 mmol) in benzene (30 mL) was heated at reflux for 3 days using a Dean-Stark trap. The mixture was then washed with saturated sodium bicarbonate solution and concentrated to give 2067 as a yellow oil (4.36 g, 65%). $^1$H NMR (400 MHz, CDCl$_3$) δ 4.58 (s, 1H, broad), 3.96-3.95 (m, 2H), 3.77-3.73 (m, 4H), 3.55 (t, 2H), 2.83-2.80 (m, 4H), 2.18 (t, 2H), 1.49 (s, 9H).

Part B:

According to a modification of a procedure by Güindisch, D. et. al. (*Bioorg. Med. Chem.* 2002, 10, 1-9) a mixture of enamine 2067 (2.27 g, 8.48 mmol) and 1,3,5-triazine (688 mg, 8.48 mmol) in 1,4-dioxane (10 mL) was heated at 100° C. in a sealed tube overnight. The reaction mixture was concentrated and chromatographed (SiO$_2$, 50-65% ethyl acetate/hexane) to give pyrimidine 2068 as a yellow oil (665 mg, 35%). $^1$H NMR (400 MHz, CDCl$_3$) δ 9.01 (s, 1H), 8.49 (s, 1H), 4.64 (s, 2H), 3.80 (t, 2H), 3.00 (t, 2H), 1.54 (s, 9H). HPLC-MS t$_R$=1.32 min (UV$_{254\ nm}$); mass calculated for formula C$_{12}$H$_{17}$N$_3$O$_2$ 235.1, observed LCMS m/z 236.1 (M+H).

Part C:

Compound 2068 (100 mg) was deprotected using procedures described in Example 48C to give amine 2069 as a yellow solid (68 mg, 78%). $^1$H NMR (400 MHz, DMSO-d$_6$) δ 9.67 (s, 2H, broad), 9.01 (s, 1H), 8.67 (s, 1H), 4.33 (t, 2H), 3.50-3.45 (m, 2H), 3.09 (t, 2H). HPLC-MS t$_R$=0.18 min (UV$_{254\ nm}$); mass calculated for formula C$_7$H$_9$N$_3$ 135.1, observed LCMS m/z 136.2 (M+H).

Example 48E

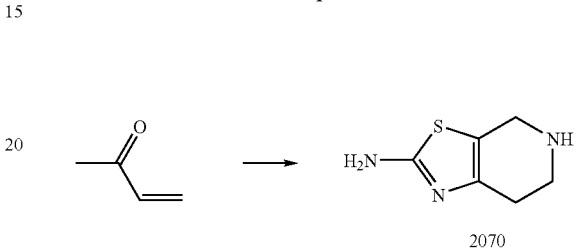

2070

Compound 2070 was prepared from methyl vinyl ketone in 6 steps following procedures described in U.S. Pat. No. 5,037, 834/1991.

Example 48F

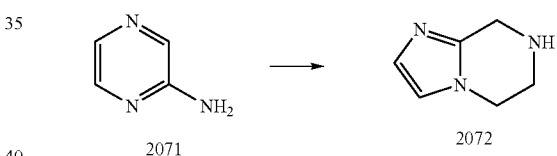

2071 · 2072

Compound 2072 was prepared from 2-aminopyrazine (2071) in 2 steps following procedures described by Sablay-rolles, C. et. al. (*J. Med. Chem.* 1984, 27, 206-212) and Bonnet, P. A. et. al. (*J. Chem. Res. Miniprint FR* 1984, 2, 0468-0480).

The following compounds were prepared using previously described procedures.

| Compound # | Structure | Exact mass | MS m/z (M + H) |
|---|---|---|---|
| 2073 | 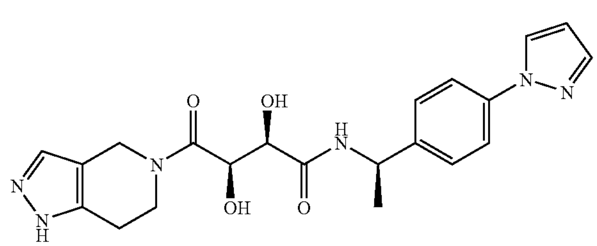 | 424.2 | 425.0 |

| Compound # | Structure | Exact mass | MS m/z (M + H) |
|---|---|---|---|
| 2074 | 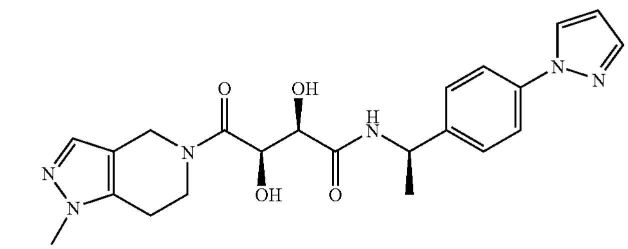 | 438.2 | 439.1 |
| 2075 | 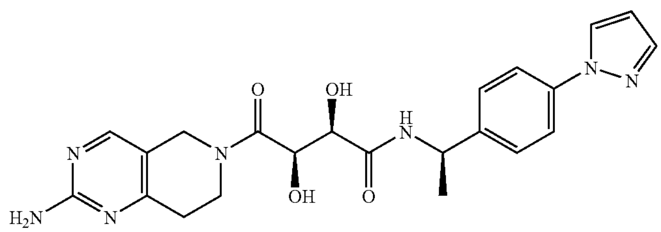 | 451.2 | 452.0 |
| 2076 | 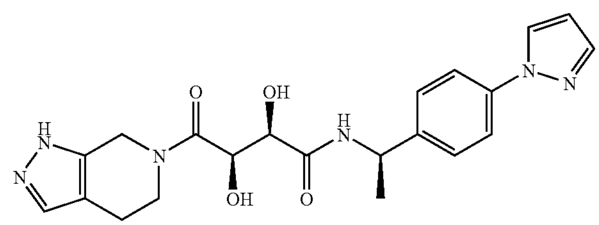 | 424.2 | 425.1 |
| 2077 | 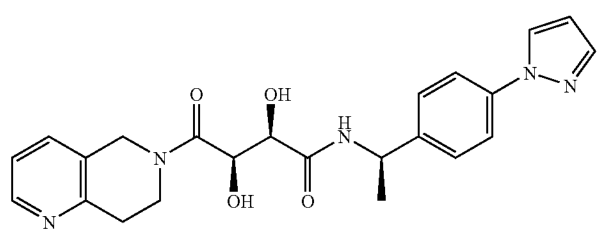 | 435.2 | 436.1 |
| 2078 | 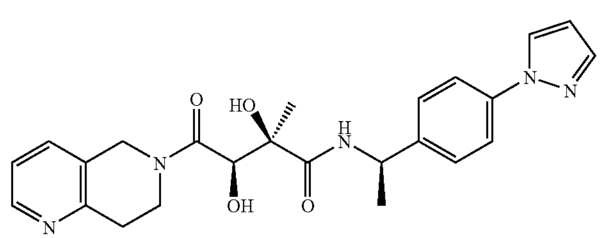 | 449.2 | 450.1 |
| 2079 | 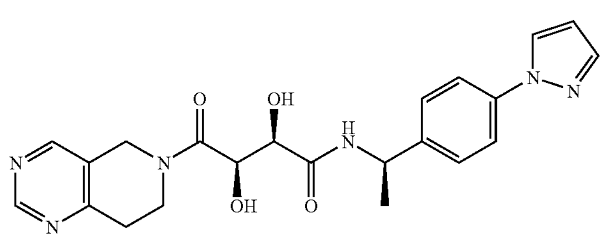 | 436.2 | 437.1 |

-continued

| Compound # | Structure | Exact mass | MS m/z (M + H) |
|---|---|---|---|
| 2080 | 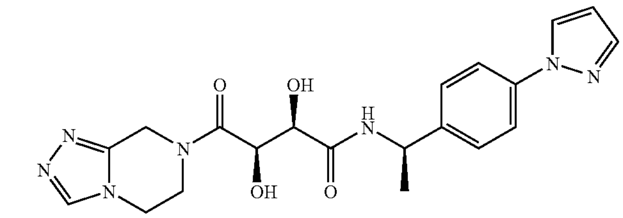 | 425.2 | 426.1 |
| 2081 | 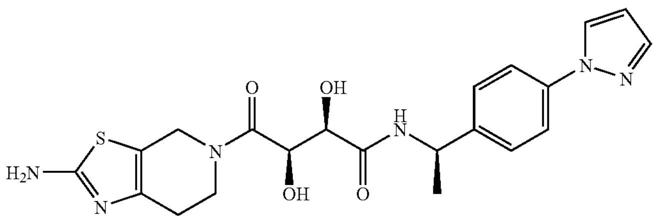 | 456.2 | 457.1 |
| 2082 | 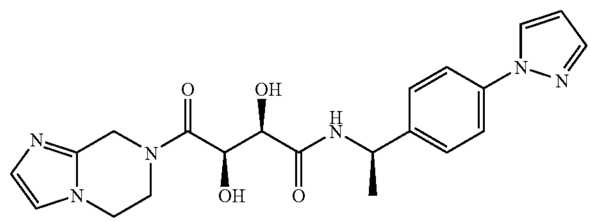 | 424.2 | 425.1 |
| 2083 | 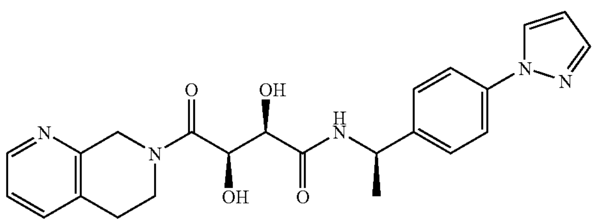 | 435.2 | 436.1 |
| 2084 | 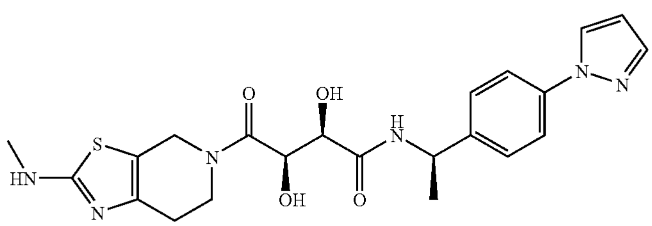 | 470.2 | 471.1 |

Example 49

Example 49A

Part A:
Compound 2086 was prepared according to the procedure in *Org. Lett.* 2002, 4, 24, 4353-4356.

Part B:

Compound 2087 was prepared according to the procedure in *Org. Lett.* 2002, 4, 24, 4353-4356. $^1$H NMR (400 MHz, CDCl$_3$) δ 7.05 (t, 2H), 5.1 (bs, 2H), 2.15 (m, 2H), 1.4 (s, 9H), 1.3 (m, 2H).

Part C:

Compound 2087 (80 mg, 0.30 mmol) was dissolved in 4 M HCl in dioxane (2 mL) and stirred at room temperature for 1 hr. The reaction was diluted with diethyl ether (5 mL) and the resulting solid was filtered to provide 2088 as an HCl salt (45 mg).

Example 49B

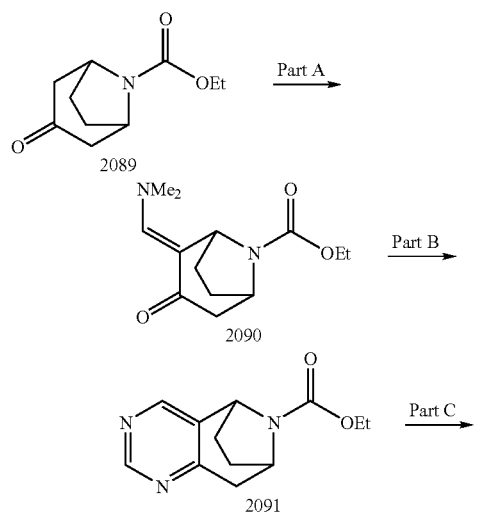

-continued

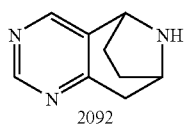

Part A:

Compound 2090 was prepared according to the procedure in *Bioorg. Med. Chem.* 2002, 10, 5, 1197-1206.

Part B:

Compound 2091 was prepared according to the procedure in *Bioorg. Med. Chem.* 2002, 10, 5, 1197-1206. $^1$H NMR (400 MHz, CDCl$_3$) δ 9.00 (s, 1H), 8.40 (s, 1H), 5.10 (bs, 1H), 4.70 (bs, 1H), 4.10 (m, 2H), 3.40 (bs, 1H), 2.50 (s, 1H), 2.40-2.30 (m, 2H), 1.80 (m, 2H), 1.75 (m, 2H), 1.25 (m, 3H).

Part C:

Compound 2091 (350 mg, 1.5 mmol) was dissolved in ethylene glycol (4 mL) and KOH (0.5 g) and hydrazine monohydrate (1 mL) were added and stirred at 100° C. for 12 hours. The reaction mixture was poured into brine and extracted with methylene chloride. The combined organic layers were washed with water, dried over sodium sulfate and concentrated to afford 2092 (150 mg). $^1$H NMR (400 MHz, CDCl$_3$) δ 9.00 (s, 1H), 8.40 (s, 1H), 4.30 (d, 1H), 4.00 (t, 1H), 3.20 (m, 1H), 2.80 (m, 1H), 2.20-2.10 (m, 2H), 2.00-1.90 (m, 2H), 1.80-1.60 (m, 2H).

The following compounds were prepared using previously described procedures.

| Compound # | Structure | Exact mass | MS m/z (M + H) |
|---|---|---|---|
| 2093 | 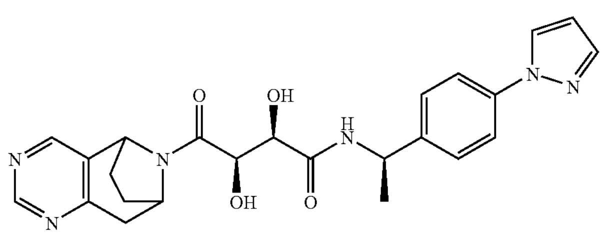 | 462.2 | 463.1 |
| 2094 | 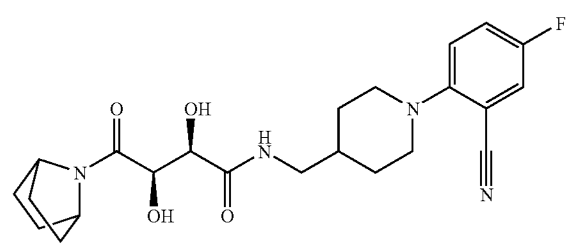 | 444.2 | 445.1 |

US 7,652,020 B2

-continued

| Compound # | Structure | Exact mass | MS m/z (M + H) |
|---|---|---|---|
| 2095 | 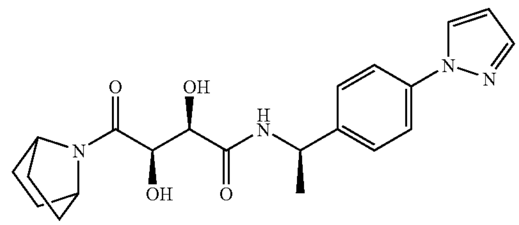 | 398.2 | 399.3 |
| 2096 | 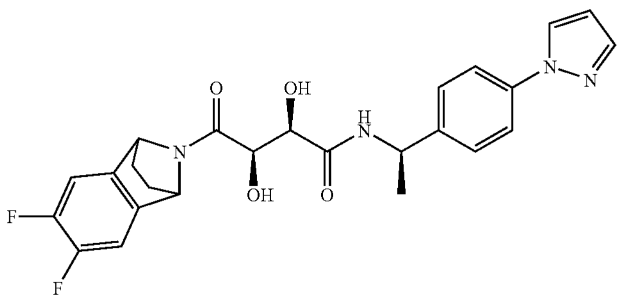 | 482.2 | 483.1 |
| 2097 | 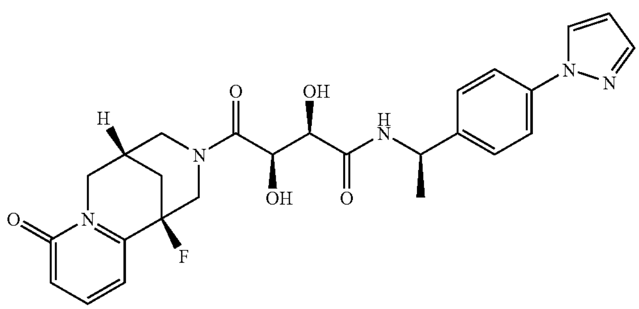 | 491.2 | 492.1 |
| 2098 | 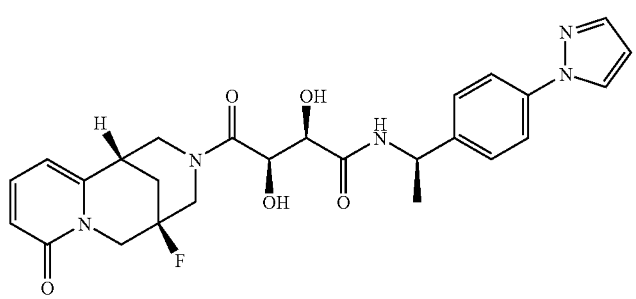 | 491.2 | 492.1 |
| 2099 | 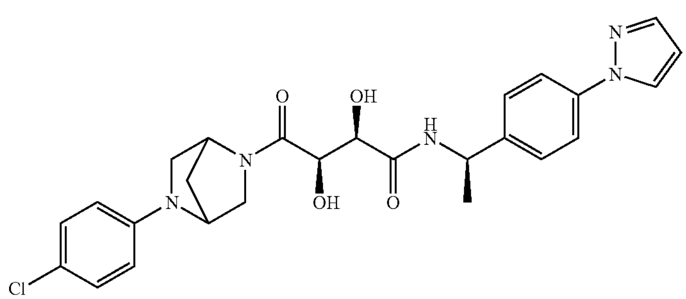 | 509.2 | 510.1 |

Example 50

Piperidine-Aryl Compounds

Example 50A

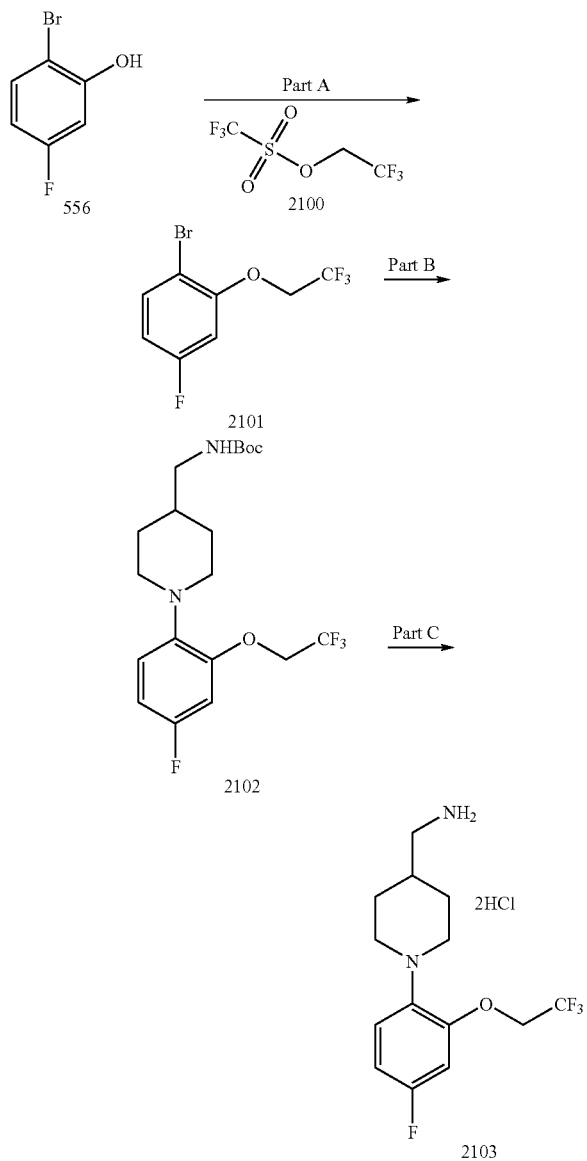

Part A:

A mixture of 2-bromo-5-fluorophenol (556) (0.111 mL, 1 mmol), 2,2,2-trifluoroethyl trifluoromethanesulfonate (2100) (279 mg, 1.2 mmol) and cesium carbonate (358 mg, 1.1 mmol) in NMP (5 mL) was stirred at room temperature overnight. The reaction mixture was poured into water and extracted with ethyl acetate. The combined organic layers were washed with water (2×) and brine, dried over sodium sulfate and concentrated. Purification by column chromatography (SiO$_2$, hexanes to 2% ethyl acetate/hexanes) afforded 2101 (232 mg) as an oil. $^1$H NMR (400 MHz, CDCl$_3$) δ 7.53 (m, 1H), 6.70 (m, 2H), 4.40 (q, 2H, J=8.0 Hz).

Part B:

Compound 2102 was prepared according to the procedures in Example 27B Part A. HPLC-MS t$_R$=2.10 min (UV$_{254\,nm}$); mass calculated for formula C19H26F4N2O3 406.2, observed LCMS m/z 407.2 (M+H).

Part C:

Compound 2102 (8 mg, 0.02 mmol) was dissolved in 3:1 DCM:TFA (4 mL) and stirred for 1 hour at room temperature. The solvent was removed in vacuo. The residue was dissolved in ether and treated with 1.0 M HCl in ether (1 mL). The solvents were concentrated to afford 2103 as a white solid (8 mg).

Example 50B

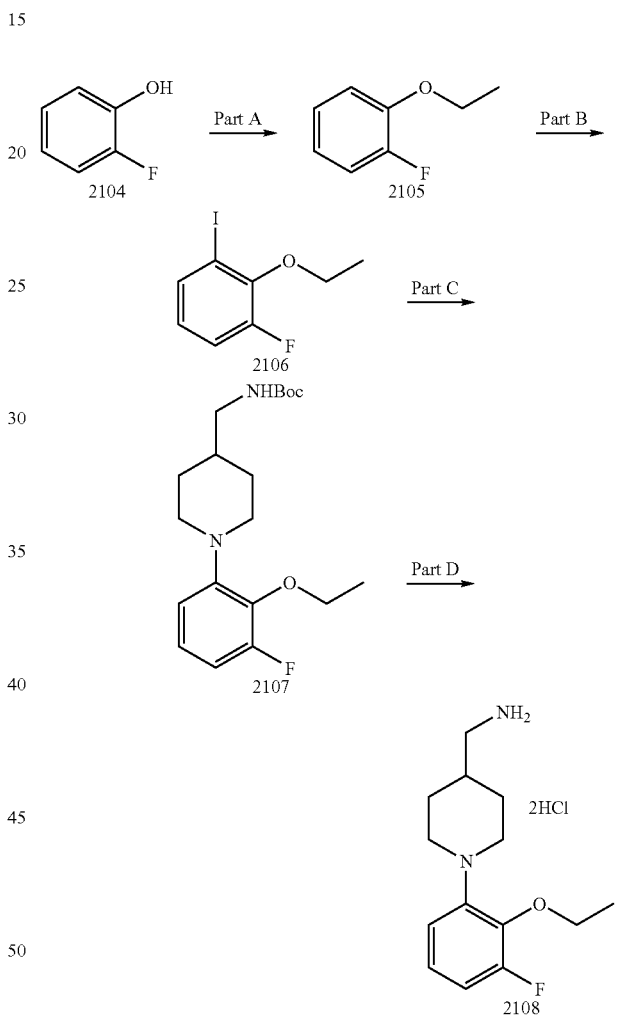

Part A:

A mixture of 2-fluorophenol (2104) (1.0 mL, 10.7 mmol), ethyl iodide (1.05 mL, 13 mmol) and potassium carbonate (1.66 g, 12 mmol) in acetone (20 mL) was stirred at room temperature overnight. Additional ethyl iodide (0.24 mL, 3 mmol) was added to the reaction and the mixture was stirred for 24 hours. The mixture was filtered and concentrated. The residue was partitioned between water and ethyl acetate. The layers were separated. The organic layer was washed with water and brine, dried over sodium sulfate and concentrated to afford 2105 (1.23 g) as an oil. $^1$H NMR (400 MHz, CDCl$_3$) δ 7.07 (m, 2H), 6.96 (m, 1H), 6.87 (m, 1H), 4.12 (q, 2H, J=7.1 Hz), 1.48 (t, 3H, J=7.1 Hz).

Part B:

To arene 2105 (1.23 g, 8.8 mmol) and TMEDA (1.32 mL, 8.8 mmol) in THF (20 mL) at −78° C. under argon was added s-BuLi (1.4 M, 6.3 mL, 8.8 mmol).

The reaction mixture was stirred for 2 hours at −78° C. To the reaction mixture was added iodine (2.23 g, 8.8 mmol) in THF (10 mL) at −78° C. The reaction was stirred for 10 minutes then warmed to 0° C. The reaction mixture was poured into water and extracted with diethyl ether. The combined organics were washed with water (2×), 5% sodium hydrogensulfite and brine, dried over sodium sulfate and concentrated. The crude product 2106 (1.70 g) was a mixture of 75:25 product:starting material by $^1$H NMR. It was used without further prurification. $^1$H NMR (400 MHz, CDCl$_3$) δ 7.28 (m, 1H), 6.94 (m, 1H), 6.81 (m, 1H), 4.11 (q, 2H, J=7.1 Hz), 1.47 (t, 3H, J=7.1 Hz).

Part C:

Compound 2107 was prepared according to the procedures in Example 27B Part A. HPLC-MS $t_R$=2.15 min (UV$_{254\ nm}$); mass calculated for formula $C_{19}H_{29}FN_2O_3$ 352.2, observed LCMS m/z 353.2 (M+H).

Part D:

Compound 2107 (276 mg, 0.78 mmol) was dissolved in 3:1 DCM:TFA (4 mL) and stirred for 1 hour at room temperature. The solvent was removed in vacuo. The residue was dissolved in ether and treated with 1.0 M HCl in ether (1 mL). The solvents were concentrated to afford 2108 as a white solid (241 mg). $^1$H NMR (400 MHz, DMSO-d$_6$) δ7.89 (bs, NH), 6.97 (m, 1H), 6.75 (m, 1H), 6.63 (m, 1H), 4.04 (q, 2H, J=6.9 Hz), 3.33 (m, 2H), 2.76 (m, 2H), 2.62 (m, 2H), 1.80 (m, 2H), 1.70 (m, 1H), 1.38 (m, 2H), 1.32 (t, 3H, J=7.1 Hz).

Example 50C

Compound 2109 was prepared using procedures described in Example 27. $^1$H NMR (400 MHz, CDCl$_3$) δ 7.00-6.80 (m, 4H), 4.64 (m, 1H), 3.55 (m, 2H), 3.09 (m, 2H), 2.65 (m, 2H), 1.82 (m, 2H), 1.60-1.50 (m, 2H), 1.49 (s, 9H), 1.42 (m, 1H).

Part A:

To compound 2109 (100 mg, 0.32 mmol) and pyridine (0.026 mL, 0.32 mmol) in DMF (2 mL) was added NBS (115 mg, 0.64 mmol). The mixture was stirred at room temperature for 2 hours and diluted with ethyl acetate. The mixture was washed with sodium carbonate solution, water and brine, dried over sodium sulfate and concentrated. Purification by column chromatography (SiO$_2$, 5% ethyl acetate/hexane) afforded 2110 as a white solid (88 mg). $^1$H NMR (400 MHz, CDCl$_3$) δ 7.3 (m, 1H), 7.0 (m, 2H), 4.65 (bs, 1H), 3.28 (m, 2H), 3.10 (m, 2H), 2.61 (m, 2H), 1.8 (m, 2H), 1.65-1.4 (m, 12H).

Part B:

To 2110 (21 mg, 0.055 mmol) in dichloromethane (2 mL) at 0° C. was added TFA (1 mL). The mixture was stirred at room temperature for 1 hour. The mixture was quenched with acetonitrile and concentrated. Compound 2111 was used without further purification.

Example 50D

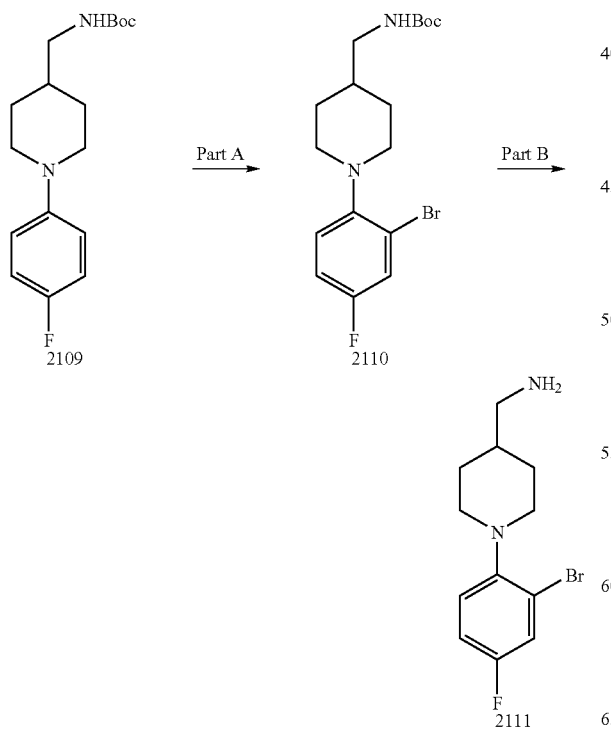

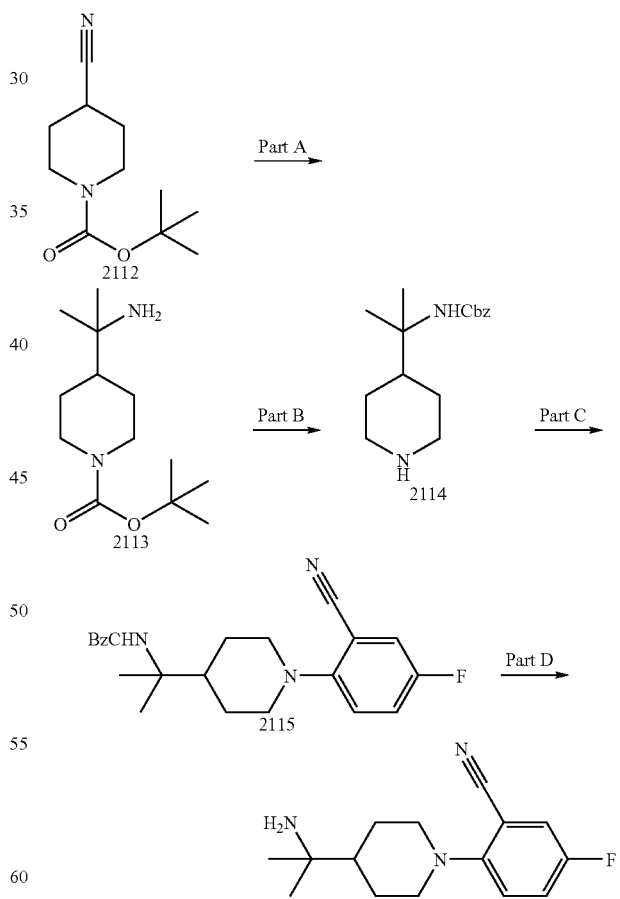

Part A:

Compound 2113 was prepared from 1-N-(t-butoxycarbonyl)-4-cyano-piperidine (2112) according to a procedure described in *J. Org. Chem.* 1992, 57, 4521-4527.

Part B:

Step 1: To 2113 (100 mg, 0.41 mmol) in THF (2 mL) were added benzyl chloroformate (0.089 mL, 0.619 mmol) and potassium carbonate (114 mg, 0.82 mmol). The mixture was stirred at room temperature overnight, diluted with ethyl acetate, washed with water, brine, dried over sodium sulfate and concentrated. The product was purified by column chromatography (SiO$_2$, 10% ethyl acetate/hexane to 25% ethyl acetate/hexane) to give a pale yellow oil (80 mg). HPLC-MS t$_R$=2.14 min (UV$_{254\ nm}$); Mass calculated for C$_{21}$H$_{32}$N$_2$O$_4$ 376.5, observed LSMS m/z 399.2 (M+Na).

Step 2: The material from step 1 (80 mg) was stirred in 4 N HCl in 1,4-dioxane (2 mL) for 1 hour. The solvent was removed in vacuum and 2114 was used without further purification.

Part C:

A mixture of 2114, 2,5-difluorobenzonitrile (32.5 mg, 0.234 mmol) and DIEA (0.113 mL, 0.637 mmol) in NMP (2 mL) under argon atmosphere was stirred overnight at 100° C. The reaction mixture was diluted with ethyl acetate, washed with water and brine, dried over sodium sulfate and concentrated. Purification by column chromatography (SiO$_2$, 25% ethyl acetate/hexane) afforded 2115 as a yellow oil (26 mg). $^1$H NMR (400 MHz, CDCl$_3$) δ 7.3-7.2 (m, 6H), 7.2 (m, 1H), 7.0 (m, 1H), 5.05 (s, 2H), 4.7 (m, 1H), 3.52 (m, 2H), 2.77 (m, 2H), 2.15 (m, 1H), 1.8 (m, 2H), 1.63 (m, 2H), 1.32 (s, 6H).

Part D:

A mixture of 2115 (26 mg) and 10% palladium on carbon (5 mg) in ethanol (4 mL) under hydrogen atmosphere was stirred for 3 hours. The mixture was filtered through a pad of celite and the filtrate was concentrated to give 2116 as a yellow residue (20 mg), which was used without further purification.

Example 50E

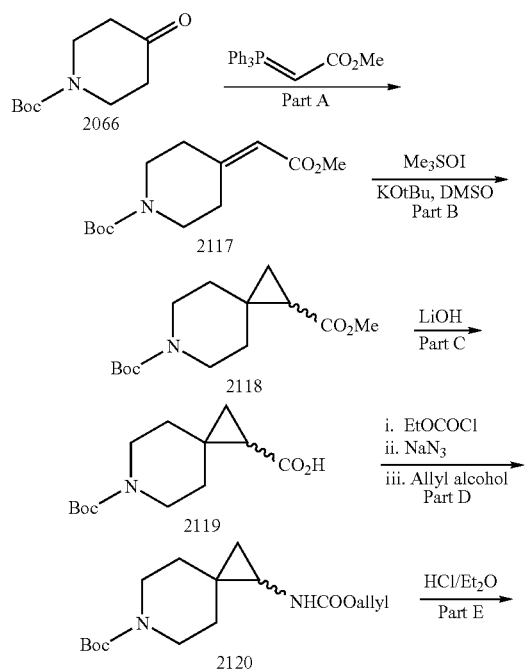

-continued

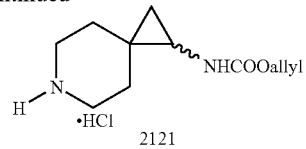

Part A:

Methyl (triphenylphosphoranylidene)acetate (104.5 g, 0.31 mmol) was added to a solution of N-Boc-piperidinone (2066) (49.79 g, 0.25 mol) in toluene (625 mL). The resulting reaction mixture was heated to reflux and stirred for 17 h. The reaction mixture was then cooled to room temperature and concentrated under vacuum. The resulting residue was then pre-adsorbed on silica gel and purified by eluting it through a plug of silica gel with 50% ethyl acetate/hexanes, to yield unsaturated ester 2117 (62.16 g, 0.243 mol) as a white solid.

Part B:

Potassium tert-butoxide (450 g, 0.41 mol) was added to a solution of trimethylsulfoxonium iodide (90.0 g, 0.41 mol) in DMSO (700 mL), in one portion. The mixture was stirred at room temperature for 3 h. The unsaturated ester 2117 (59.64 g, 0.23 mol) was dissolved in DMSO (0.26 L) and added to the reaction mixture. The reaction mixture was stirred for 20 h at room temperature and then added to brine (1 L). Saturated aqueous NH$_4$Cl was then added to the reaction mixture in order to adjust the pH to approximately 7. The reaction mixture was then extracted several times with ether, the ether extracts combined, washed with water and brine, dried with anhydrous MgSO$_4$, filtered, and concentrated under vacuum to yield ester 2118 (53.5 g, 0.20 mol) as an oil.

Part C:

An aqueous LiOH solution (2N, 200 mL) was added to a solution of the ester 2118 (53.5 g, 0.20 mol) in THF (200 mL). The mixture was then stirred at room temperature for 17 h, diluted with water (750 mL) and washed with ether. The ether phase was discarded, and the aqueous phase acidified to a pH of 3-4 with 6N HCl. The acidified aqueous phase was then extracted with ether several times. The ether washes were combined, washed with water and brine, dried with anhydrous MgSO$_4$, filtered, and concentrated under vacuum to provide carboxylic acid 2119 (49.25 g, 0.19 mol) as a white solid.

Part D:

Triethylamine (8.7 g, 0.086 mol) followed by ethyl chloroformate (9.4 g, 0.086 mol) was added to a solution of carboxylic acid 2119 (20.0 g, 0.078 mol) in acetone (78 mL) at 0° C. The resulting mixture was stirred at 0° C. for 40 minutes. Sodium azide (10.2 g, 0.15 mol) in water (50 mL) was then added to the mixture. The mixture was then allowed to warm to room temperature and stirred for 4 h. Water was then added, and then the mixture was extracted several times with CH$_2$Cl$_2$. The organic extracts were combined and washed with water and brine, dried over magnesium sulfate and concentrated under vacuum to provide an oil. The oil was taken up into toluene (200 mL), allyl alcohol (5.5 g, 0.094 mol) was added, and the mixture was heated to reflux and stirred at reflux for 17 h. The reaction mixture was then cooled to room temperature and EtOAc (250 mL) was added. Then, the mixture was washed with water and brine, dried over magnesium sulfate and concentrated under vacuum. The resulting residue was purified by silica gel chromatography (35% ethyl acetate/hexanes) to provide the carbamate 2120 (24.4 g, 0.061 mol).

Part E:

A solution of HCl/Et$_2$O (2 N, 50 mL) was added to a solution of the carbamate 2120 (24.4 g, 0.061 mol) in CH$_2$Cl$_2$ (100 mL). The reaction mixture was stirred overnight and then concentrated under vacuum to yield 2121 as a hygroscopic foam (17.4 g, 0.052 mol).

Example 50F

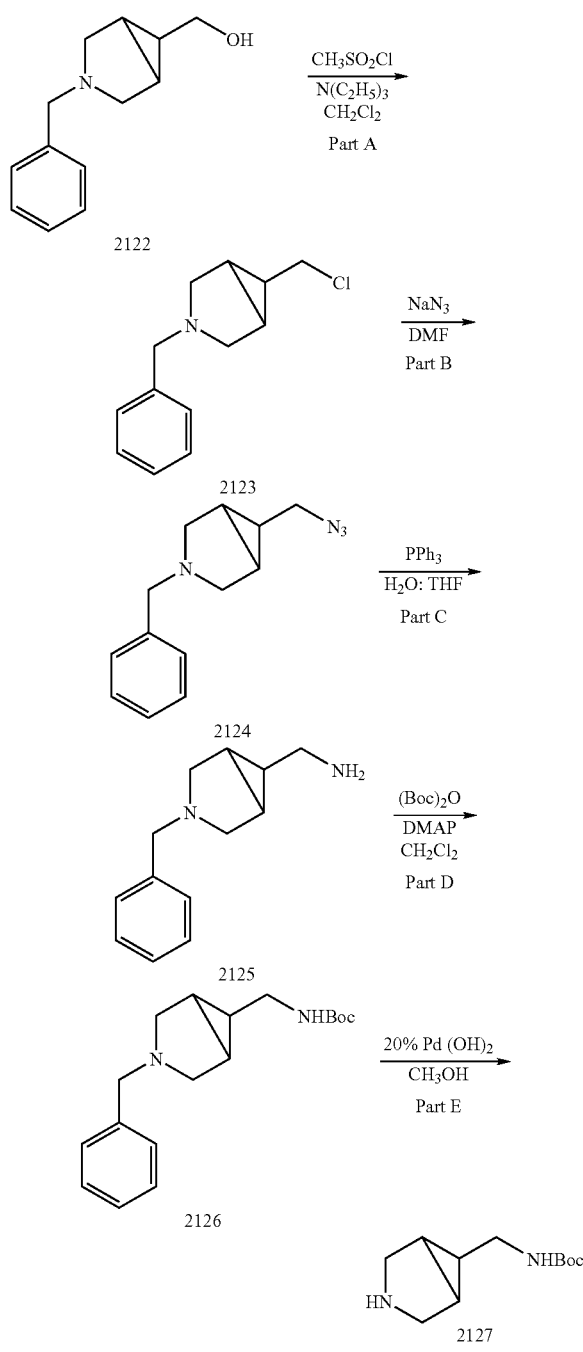

Starting alcohol (2122) (1α, 5α, 6α)-3-benzyl-6-hydroxymethyl-3-azabicyclo[3.1.0]hexane was prepared by known methods (i.e., Brighty, K. E; Castaldi, M. *J Synlett*, 1996, 1097).

Part A:

Alcohol 2122 (11 g, 54 mmol) and triethylamine (38 mL, 27 mmol) were dissolved in CH$_2$Cl$_2$ (200 mL) and cooled to 0° C. The cooled solution was stirred, and CH$_3$SO$_2$Cl (as a CH$_2$Cl$_2$ solution; 6 mL, 78 mmol, 25 mL CH$_2$Cl$_2$) was added dropwise, and the stirring was continued for 3-4 h. The reaction mixture was then washed two times with 100 mL of water and two times with 100 ml of brine. The organic and aqueous phases were separated, and the organic phase was dried, and concentrated to provide a crude product. The crude product was purified by silica gel chromatography (eluted with 1:6 ethyl acetate:hexane). The appropriate fractions were collected from the chromatography column and concentrated to provide pure chloro compound 2123 as an oil (7 g, 59%).

Part B:

The chloro compound 2123 was dissolved in DMF (100 mL) and treated with NaN$_3$ (10.3 g, 157 mmol), and the mixture was stirred vigorously for 36-48 h. The reaction mixture was then diluted with 100 mL water and extracted with ethyl acetate (2×100 mL). The organic extracts were combined, dried, and concentrated to yield pure azide 2124 (6.2 g, 87%).

Part C:

The azide 2124 (6.2 g, 27 mmol) and triphenylphosphine (15 g, 57 mmol) were dissolved in 100 mL of THF, and then water (6 mL, 333 mmol) was added. The resulting mixture was stirred vigorously for 16-24 h. The solvent was removed and the crude amine 2125 was obtained without further purification.

Part D:

The crude amine 2125 and N,N-dimethylaminopyridine (0.66 g, 5.4 mmol) were dissolved in CH$_2$Cl$_2$ (100 mL). To this solution was added di-tert-butyldicarbonate (7 g, 33 mmol), in portions, and the reaction mixture was stirred for 16 h. The reaction mixture was then washed two times (50 mL) with water and once with brine (50 mL). The organic phase was isolated and dried, and the solvent was removed under reduced pressure. The crude product was subjected to silica gel chromatography using 1:3 ethyl acetate:hexane as the eluting solvent. The eluted fractions were combined and concentrated to yield 6.9 g of pure carbamate 2126 (84%).

Part E:

The carbamate 2126 (1.9 g, 6.3 mmol) was dissolved in methanol (100 mL) and mixed with palladium hydroxide (20%, 0.4 g). The mixture was transferred to a Parr bottle, which was then charged with hydrogen (20 psi). The Parr bottle was shaken for 10 h. The remaining hydrogen was removed from the Parr bottle under vacuum, and the reaction was filtered through Celite. The filtrate was then concentrated to provide pure amine 2127 (1.4 g).

Example 50G

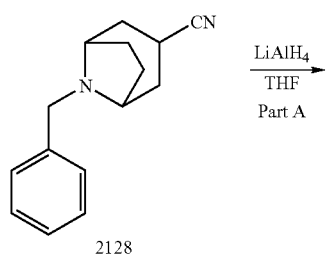

2128

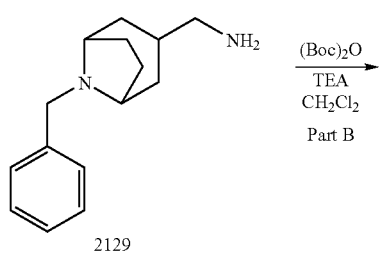

2129

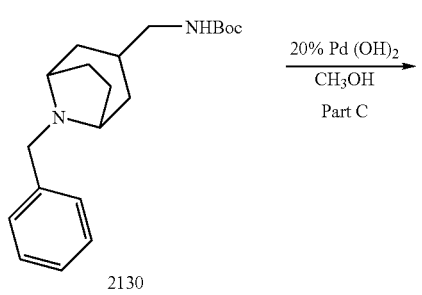

2130

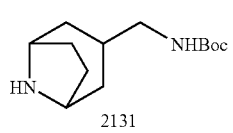

2131

N-Benzyltropinanecarbonitrile 2128 was prepared using known procedures (see, for example: Montzka, T. A.; Matiskella, J. D.; Partyka, R. A. *Tetrahedron Letters* 1974, 14, 1325; Lowe, J. A.; Drozda, S. E.; McLean, S.; Bryce, D. K.; Crawford, R. T.; Snider, R. M.; Tsuchiya, M. *J. Med. Chem.* 1994, 37, 2831).

Part A:

LiAlH$_4$ was added to dry THF (40 mL) and the mixture was then cooled to 0° C. Then carbonitrile 2128 (0.9 g, 3.8 mmol, in a 10 mL THF solution) was added to the mixture dropwise. The reaction mixture was allowed to warm to ambient temperature and stirred for 48 h, then cooled to back to 0° C. and quenched by the sequential addition of 1 mL of water, 2 mL of 0.5 N aq. NaOH, and 1 mL of water. The resulting mixture was stirred vigorously for 2 h and then filtered through Celite. The filtrate was concentrated to yield pure 2129 as an oil (0.9 g, 100%).

Part B:

The crude product 2129 and triethylamine (TEA) (0.6 mL, 4.3 mmol) were dissolved in CH$_2$Cl$_2$ (50 mL). Di-tert-butyidicarbonate (0.85 g, 3.9 mmol) was added to this solution in portions, and the reaction mixture was stirred for 16 h. The reaction mixture was then washed two times with 50 mL of water and once with 50 mL of brine. The organic phase was dried and the solvent was removed under reduced pressure. The crude product was subjected to silica gel chromatography using 2.5% ammonia saturated methanol in CH$_2$Cl$_2$ as the eluting solvent. The eluted fractions were combined and concentrated to yield 0.78 g of pure carbamate product 2130 (61%).

Part C:

The carbamate 2130 (0.8 g, 2.3 mmol) was dissolved in methanol (60 mL) and treated with palladium hydroxide (20%, 0.08 g). The mixture was transferred to a Parr bottle, which was then charged with hydrogen (20 psi). The Parr bottle was shaken for 10 h. The hydrogen was removed from the Parr bottle under vacuum, and the reaction mixture was filtered through Celite. The filtrate was then concentrated to provide pure amine 2131 (0.6 g).

Example 50H

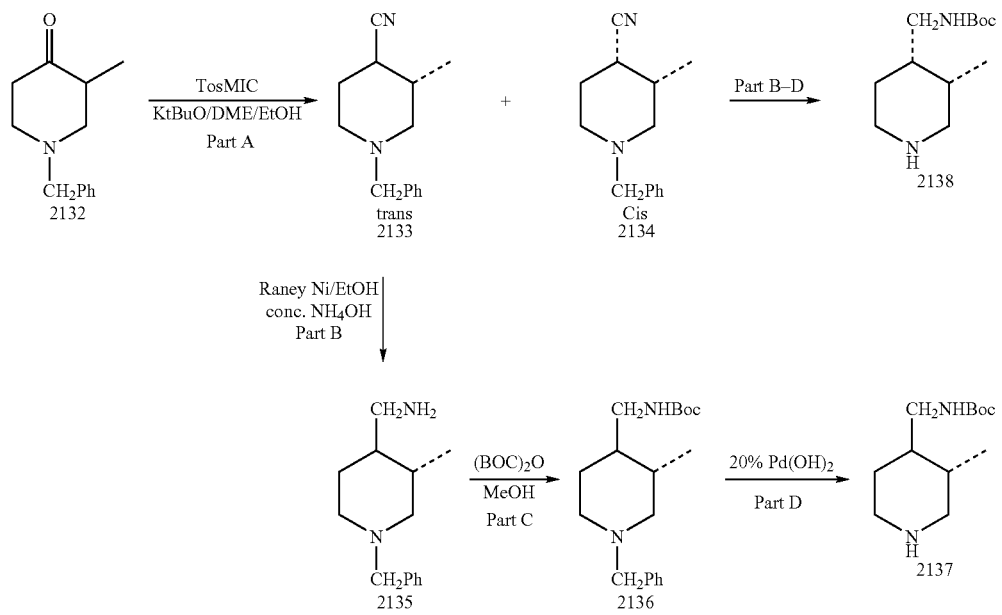

Part A:

Tosylmethyl isocyanide (TosMIC) (7.2 g, 37 mmol) was added to 3-methyl-N-benzyl piperidone (2132) (4.25 g, 20.93 mmol) in DME (150 mL) and cooled to 0° C. Ethyl alcohol (2.9 mL) and potassium tert-butoxide (7 g, 62.4 mmol) were added to the reaction mixture and stirred at room temperature for 4 hours. The reaction mixture was poured into ice and extracted with ethyl acetate (2×50 mL). The organic layer was washed with brine, dried over anhydrous MgSO$_4$ and concentrated under vacuum. The resulting residue was purified by silica gel chromatography (20% ethyl acetate/hexane) to give first 2133 (trans isomer, 1.85 g, 41%), and second 2134 (cis isomer, 1.05 g, 22%).

Part B:

The trans intermediate 2133 (2.0 g, 9.34 mmol) was dissolved in ethyl alcohol (50 mL) and Raney Nickel (wet, 5.0 g) was added under N$_2$, followed by addition of conc. ammonium hydroxide (1.0 mL). The mixture was subjected to H$_2$ atmosphere at 50 p.s.i. for 16 hours with vigorous shaking. The reaction was filtered through celite under N$_2$ and the filtrate was concentrated under vacuum to provide 1.8 g (88%) of intermediate 2135.

Part C:

Intermediate 2135 (1.0 g, 4.6 mmol) was dissolved in methyl alcohol (35 mL). A solution of BOC-anhydride (1.2 g, 5.5 mmol) in methyl alcohol (15 mL) was added dropwise at 0° C. The resulting mixture was stirred at 0° C. for one hour, then at ambient temperature for an additional hour. The solvent was removed under vacuum to provide a crude product that was purified by silica-gel column chromatography using ethyl acetate as the eluting solvent. The relevant fractions were collected and concentrated under reduced pressure to yield 1.1 g (76%) of intermediate 2136.

Part D:

Intermediate 2136 (0.5 g, 1.57 mmol) was dissolved in methyl alcohol (25 mL).

Palladium hydroxide (20 wt % Pd, 0.1 g) was added under N$_2$. The resulting mixture was exposed to H$_2$ atmosphere at 20 p.s.i. for 16 hours with vigorous shaking. The reaction mixture was filtered through celite and washed with methyl alcohol (1×25 mL). The filtrate was concentrated under vacuum to provide intermediate 2137 (0.38 g) as an oil which was used in the next step without further purification.

Intermediate 2138 was prepared using methods similar to those used in Part B-D. The following compounds were prepared using previously described procedures.

| Compound # | Structure | Exact mass | MS m/z (M + H) |
|---|---|---|---|
| 2139 | 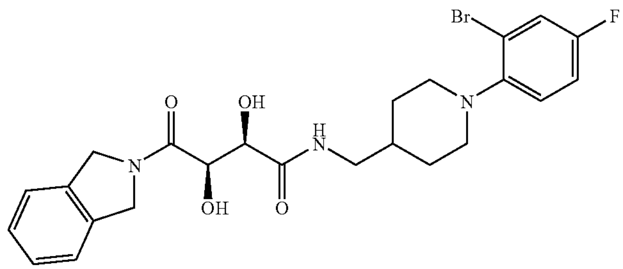 | 519.1 | 520.1 |
| 2140 | 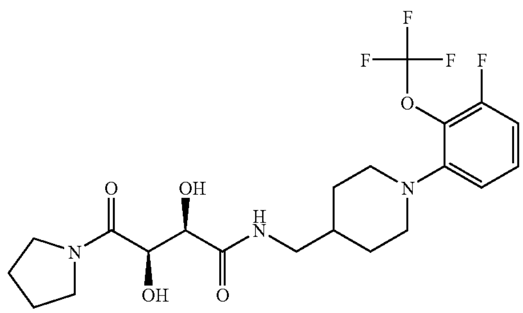 | 477.2 | 478.1 |
| 2141 | 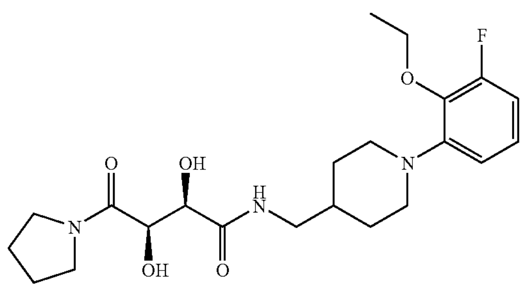 | 437.2 | 438.1 |
| 2142 | 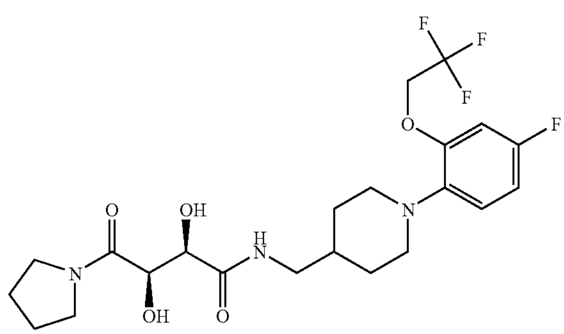 | 491.2 | 492.1 |
| 2143 | 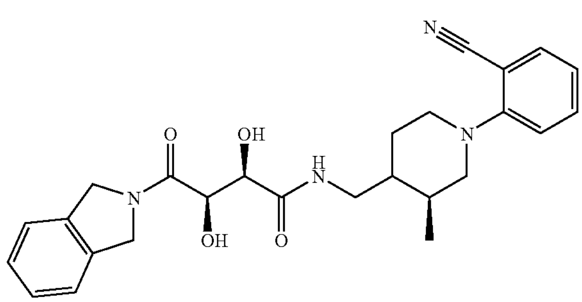 | 462.2 | 463.1 |

| Compound # | Structure | Exact mass | MS m/z (M + H) |
|---|---|---|---|
| 2144 | 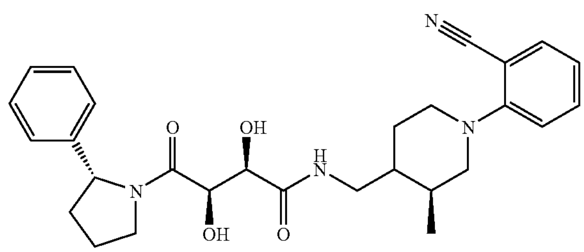 | 490.3 | 491.1 |
| 2145 | 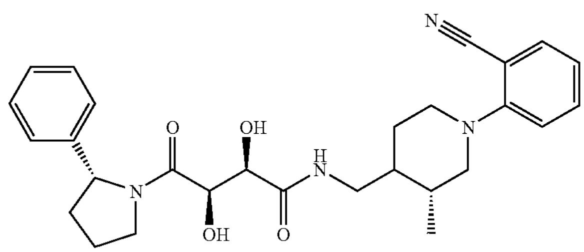 | 490.3 | 491.3 |
| 2146 | 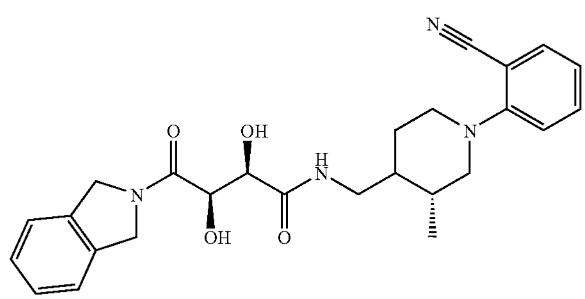 | 462.2 | 463.3 |
| 2147 | 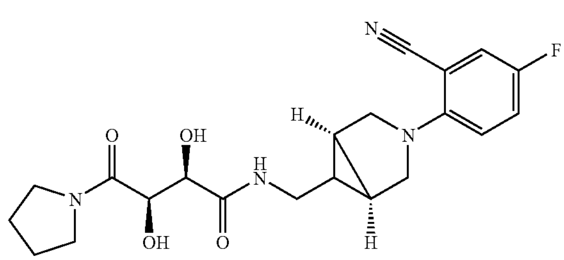 | 416.2 | 417.2 |
| 2148 | 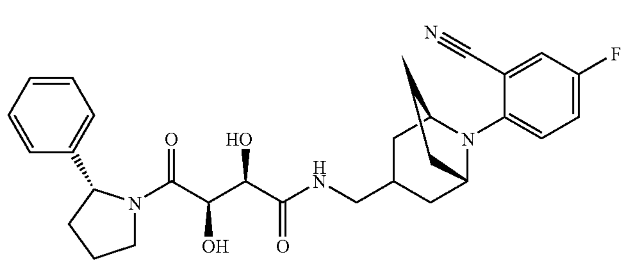 | 520.2 | 521.1 |

-continued

| Compound # | Structure | Exact mass | MS m/z (M + H) |
|---|---|---|---|
| 2149 | 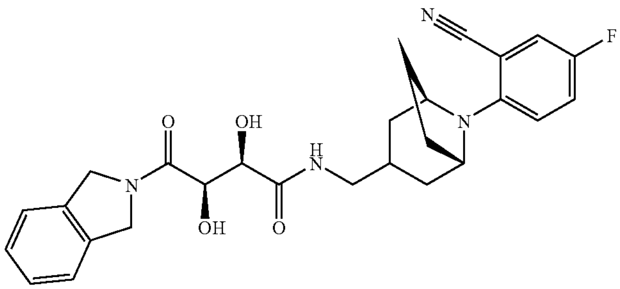 | 492.2 | 493.3 |
| 2150 | 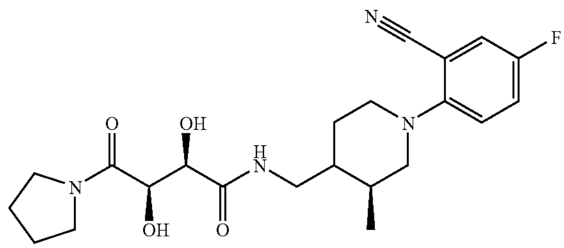 | 432.2 | 433.2 |
| 2151 | 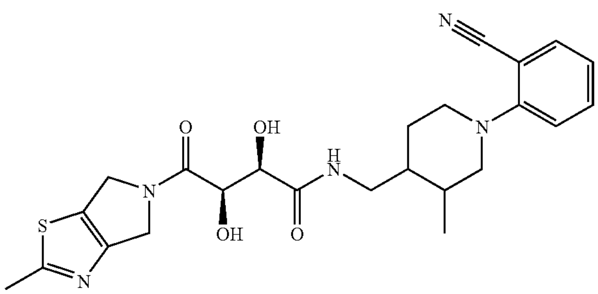 | 483.2 | 484.1 |
| 2152 | 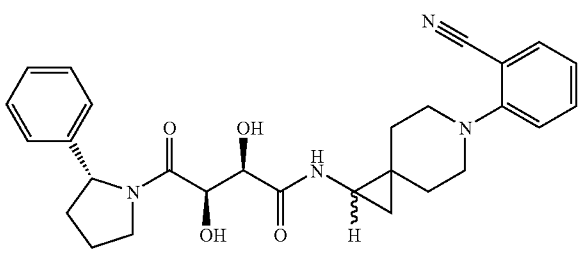 | 488.2 | 489.1 |
| 2153 | 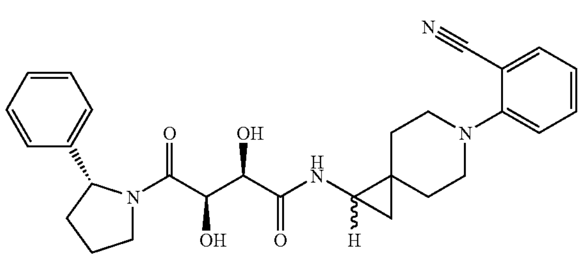 | 488.2 | 489.1 |

-continued

| Compound # | Structure | Exact mass | MS m/z (M + H) |
|---|---|---|---|
| 2154 | 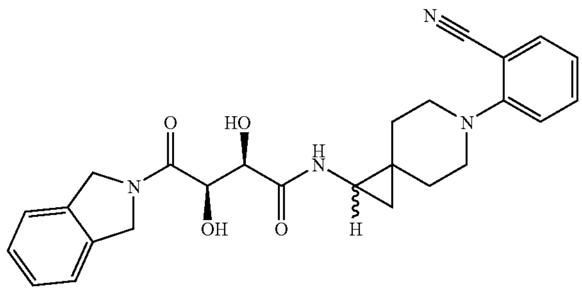 | 460.2 | 461.1 |
| 2155 | 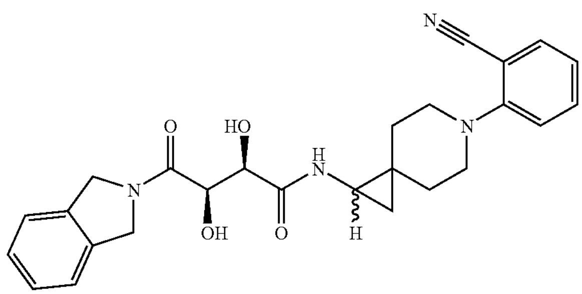 | 460.2 | 461.3 |
| 2156 | 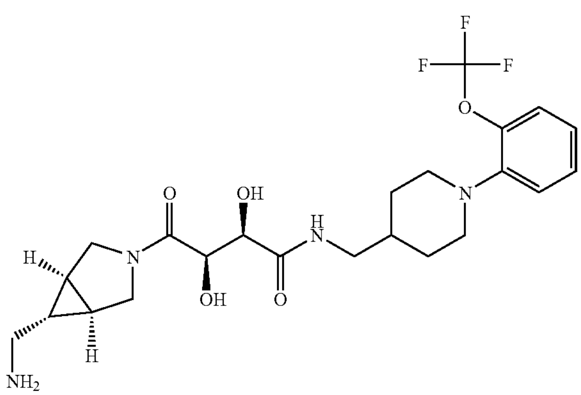 | 500.2 | 500.1 |
| 2157 | 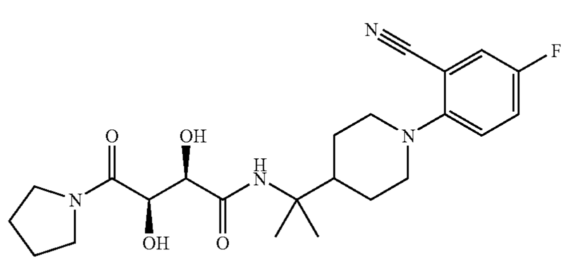 | 446.2 | 447.3 |

-continued
| Compound # | Structure | Exact mass | MS m/z (M + H) |
|---|---|---|---|
| 2158 | 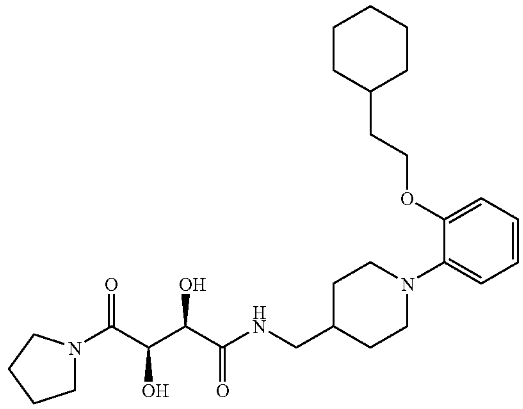 | 501.3 | 502.3 |
| 2159 | 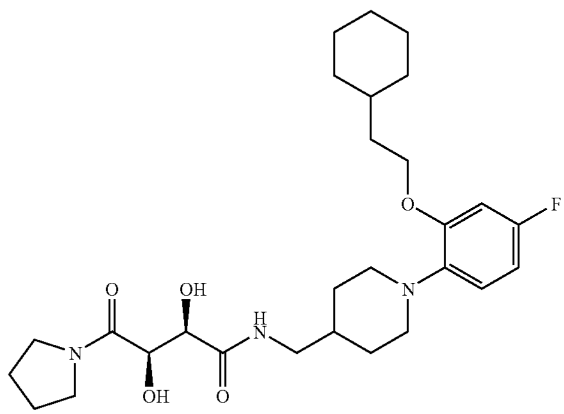 | 519.3 | 520.3 |
Example 51
Example 51A

Part A:
Compound 2161 was synthesized according to the procedures of WO02060894A2. $^1$H NMR (400 MHz, DMSO-$d_6$) δ 9.58 (bs, NH), 8.89 (m, 2H), 7.57 (m, 1H), 4.88 (m, 1H), 3.80 (m, 2H), 2.06 (m, 4H).
Example 51B -continued


2166

Part A:
Compound 2163 was synthesized from Compound 2162 (made according to the procedures of WO2004/052850) according to the procedures of Hanessian et. al. (*Bioorg. Med. Chem Lett.* 1998, 8, 2123 and the references therein.) HPLC-MS $t_R$=1.90 min ($UV_{254\ nm}$); mass calculated for formula C13H21NO4 255.2, observed LCMS m/z 278.2 (M+Na).

Part B:
Compound 2164 was synthesized according to the procedures of Example 10B Part A. HPLC-MS $t_R$=1.79 min ($UV_{254\ nm}$); mass calculated for formula C12H18ClNO3 259.1, observed LCMS m/z 282.1 (M+Na).

Part C:
Compound 2164 (190 mg) was cyclized with N-methylthiourea in DMF (2 mL) to afford 2165 (81 mg) according to the procedures of Example 10B Part B. HPLC-MS $t_R$=1.27 min ($UV_{254\ nm}$); mass calculated for formula C14H21N3O2S 295.1, observed LCMS m/z 296.2 (M+H).

Part D:
To compound 2165 (81 mg) in methanol (2 mL) was added 4.0 M HCl/dioxane (1 mL) with ice bath cooling. The reaction mixture was stirred for 1.5 hours and concentrated. The residue was suspended in DCM (5 mL) and concentrated to afford impure 2166. The material was used without purification.

Example 51C

-continued

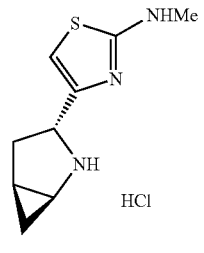

2170

Part A:
Compound 2167 was synthesized from Compound 2162 (made according to the procedures of WO2004/052850) according to the procedures of Hanessian et. al. *Bioorg. Med. Chem Lett.* 1998, 8, 2123 and the references therein. HPLC-MS $t_R$=1.83 min (MS); mass calculated for formula C13H21NO4 255.2, observed LCMS m/z 278.2 (M+Na).

Part B:
Compound 2168 was synthesized according to the procedures of Example 10B Part A. HPLC-MS $t_R$=1.78 min (MS); mass calculated for formula C12H18ClNO3 259.1, observed LCMS m/z 282.1 (M+Na).

Part C:
Compound 2168 (117 mg) was cyclized with N-methylthiourea in DMF (2 mL) to afford 2169 (35 mg) according to the procedures of Example 10B Part B. HPLC-MS $t_R$=1.16 min ($UV_{254\ nm}$); mass calculated for formula $C_{14}H_{21}N_3O_2S$ 295.1, observed LCMS m/z 296.2 (M+H).

Part D:
To compound 2169 (35 mg) in methanol (2 mL) was added 4.0 M HCl/dioxane (1 mL) with ice bath cooling. The reaction mixture was stirred for 1.5 hours and concentrated. The residue was suspended in DCM (5 mL) and concentrated to afford impure 2170. The material was used without purification.

Example 51D

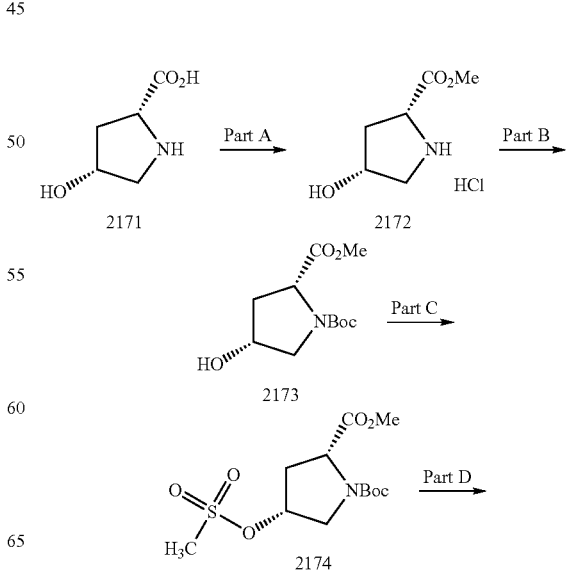

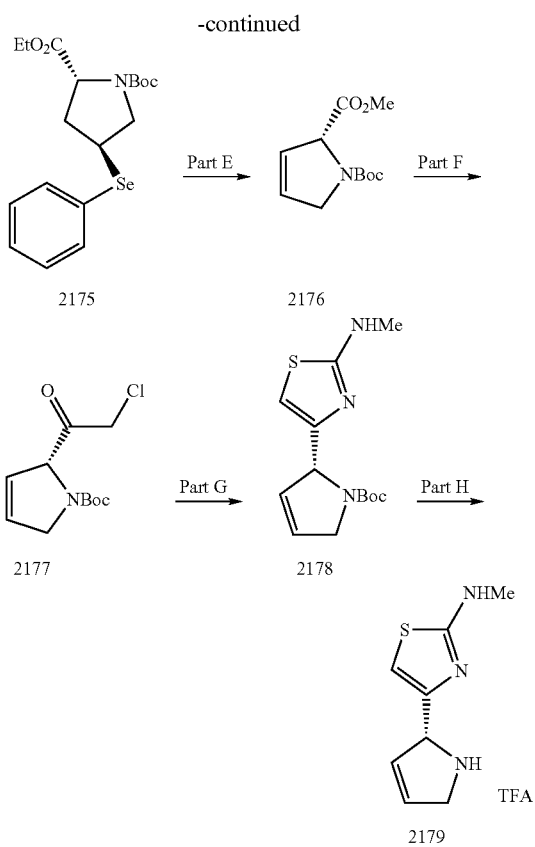

Part A:

To hydroxy proline 2171 (1.52 g, 11.6 mmol) in methanol (25 mL) in an ice bath was added thionyl chloride (0.95 mL, 13 mmol). The ice bath was removed and the reaction mixture was heated to reflux overnight. The reaction mixture was cooled and concentrated. The residue was dissolved in methanol and concentrated. The residue was dissolved in diethyl ether and concentrated to afford 2172 quantitatively. $^1$H NMR (400 MHz, DMSO-$d_8$) δ 10.25 (bs, 1H), 8.95 (bs, 1H), 4.50 (d, 1H, J=7.0 Hz), 4.36 (m, 1H), 3.75 (s, 3H), 3.16 (m, 2H), 2.31 (m, 1H), 2.13 (m, 1H).

Part B:

To compound 2172 (2.11 g, 11.6 mmol) in DCM (25 mL) was added DIEA (4.2 mL, 24 mmol) and a solution of BOC-anhydride (3.03 g, 13.9 mmol) in DCM (25 mL) with ice bath cooling. The reaction mixture was slowly warmed to room temperature and stirred overnight. The reaction mixture was washed with water, 0.1 N HCl, bicarbonate solution and brine, dried over sodium sulfate and concentrated. Purification by column chromatography (SiO$_2$, loaded with ethyl acetate and eluted with 30% ethyl acetate/hexane to ethyl acetate) afforded 2173 (2.66 g) as an oil. $^1$H NMR (400 MHz, CDCl$_3$) δ rotomers 4.40-4.29 (m, 2H), 3.81 and 3.80 (s, 3H), 3.75-3.64 (m, 1H), 3.57-3.50 (m, 1H), 2.35 (m, 1H), 2.11 (m, 1H), 1.48 and 1.44 (s, 9H).

Part C:

To compound 2173 (2.66 g, 10.8 mmol) in DCM (50 mL) in an ice bath was added triethyl amine (1.66 mL, 11.9 mmol) and methanesulfonyl chloride (1.09 mL, 14.1 mmol) dropwise. The reaction mixture was slowly warmed to room temperature and stirred overnight. The reaction mixture was quenched with ice water and the layers were separated. The aqueous layer was extracted with DCM. The combined organic layers were washed with 0.1 N HCl and brine, dried over sodium sulfate and concentrated. Purification by column chromatography (SiO$_2$, 50% ethyl acetate/hexanes) afforded 2174 (3.36 g) as an oil. HPLC-MS $t_R$=1.49 min (ELSD); mass calculated for formula C$_{12}$H$_{21}$N$O_7$S 323.1, observed LCMS m/z 346.1 (M+Na).

Part D:

To diphenylselenide (1.97 g, 6.3 mmol) in ethanol (20 mL) in an ice bath was added sodium borohydride (472 mg, 12.5 mmol) portion wise. The reaction mixture was stirred for 10 minutes after the bubbling had ceased. The above solution was added to compound 2174 (3.36 g, 10.4 mmol) in ethanol (10 mL). The reaction mixture was heated to reflux for 2 hours. The reaction was cooled and the solvents removed in vacuo. The residue was partitioned between water (50 mL) and ethyl acetate (50 mL). The layers were separated. The organic layer was washed with water and brine, dried over sodium sulfate and concentrated. Purification by column chromatography (SiO$_2$, 5% to 20% ethyl acetate/hexanes) afforded 2175 (2.91 g) as an oil. HPLC-MS $t_R$=2.32 min (UV$_{254\ nm}$); mass calculated for formula C18H25NO4Se 399.1, observed LCMS m/z 422.0 (M+Na).

Part E:

To 2175 (481 mg, 1.21 mmol) in DCM (5 mL) in an ice bath was added dropwise pyridine (0.162 mL, 2.0 mmol) and 50% hydrogen peroxide (0.161 mL, 2.63 mmol). The ice bath was removed and the reaction mixture was stirred at room temperature for 1.25 hours. The reaction mixture was diluted with ethyl acetate (50 mL), washed with 0.1 N HCl, bicarbonate solution and brine, dried over sodium sulfate and concentrated to afford 2176 (272 mg) as a yellow oil. HPLC-MS $t_R$=1.81 min (MS); mass calculated for formula C12H19NO4 241.1, observed LCMS m/z 264.1 (M+Na).

Part F:

Compound 2177 (123 mg) was prepared from 2176 (202 mg, 0.84 mmol) according to the procedure described in Example 10B Part B. HPLC-MS $t_R$=1.70 min (MS); mass calculated for formula C11H16ClNO3 245.1, observed LCMS m/z 264.1 (M+Na).

Part G:

Compound 2178 (48 mg) was prepared as described in Example 51B Part C from compound 2177 (123 mg, 0.5 mmol). HPLC-MS $t_R$=1.12 min (UV$_{254\ nm}$); mass calculated for formula C$_{13}$H$_{19}$N$_3$O$_2$S 281.1, observed LCMS m/z 282.1 (M+H).

Part H:

A mixture of compound 2178 (48 mg, 0.17 mmol), TFA (2 mL) and DCM (2 mL) were stirred at room temperature for 1 hour. The solvents were removed and the residue was dissolved in DCM (5 ml) and concentrated to afford 2179 (70 mg). $^1$H NMR (400 MHz, CDCl$_3$) δ 9.58 (bs, NH), 6.75 (s, 1H), 6.26 (d, 1H, J=6.3 Hz), 5.92 (d, 1H, J=7.5 Hz), 5.77 (m, 1H), 4.43 (d, 1H, J=17.2 Hz), 4.28 (d, 1H, J=17.2 Hz), 3.11 (s, 3H).

Example 51E

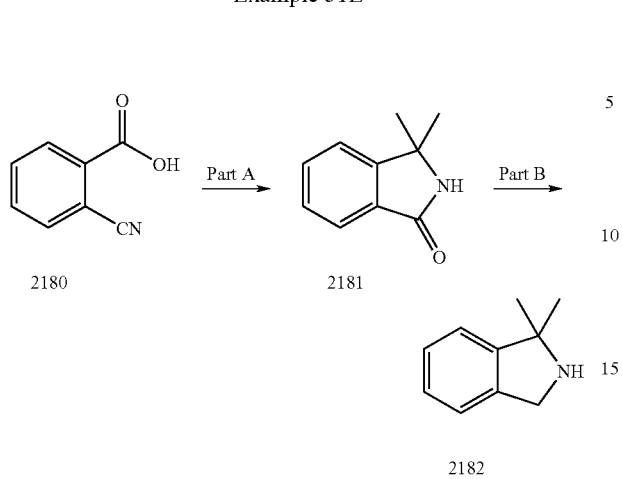

Part A:

Compound 2180 was prepared using a modification of the procedure in *J. Org. Chem.* 1998, 63, 8, 2451-2455. Compound 2180 (0.400 g, 2.72 mmol) was dissolved in THF (60 mL) and cooled in a dry ice/acetone bath. A solution of methyllithium (1.6 M in diethylether, 18 mL) was added dropwise and the solution was warmed to room temperature. The reaction was quenched with brine after 10 minutes. The reaction mixture was poured into water and extracted with ethyl acetate. The combined organics were washed with 1N HCl, saturated sodium bicarbonate and water, dried over sodium sulfate and concentrated. Purification by column chromatography (SiO$_2$, 50% ethyl acetate/hexanes) afforded 2181 (0.200 g). HPLC-MS t$_R$=1.126 min (UV$_{254\ nm}$); mass calculated for formula C$_{10}$H$_{11}$NO 161.1, observed LCMS m/z 162 (M+H).

Part B:

Compound 2181 (0.200 g, 1.24 mmol) was dissolved in THF (10 mL) and a solution of borane (2.5 M in THF, 3 mL) was added dropwise and the solution was stirred at reflux overnight. The reaction was quenched with a solution of 1 M sodium hydroxide (2 mL) and methanol (2 mL) and reflux was continued for 5 hours. The reaction mixture was poured into water and extracted with ethyl acetate. The combined organics were washed with saturated sodium bicarbonate, water, dried over sodium sulfate and concentrated to afford 2182 (65 mg). HPLC-MS t$_R$=0.595 min (UV$_{254\ nm}$); mass calculated for formula C$_{10}$H$_{11}$N 147.1, observed LCMS m/z 148 (M+H).

Example 51F

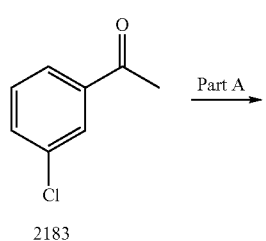

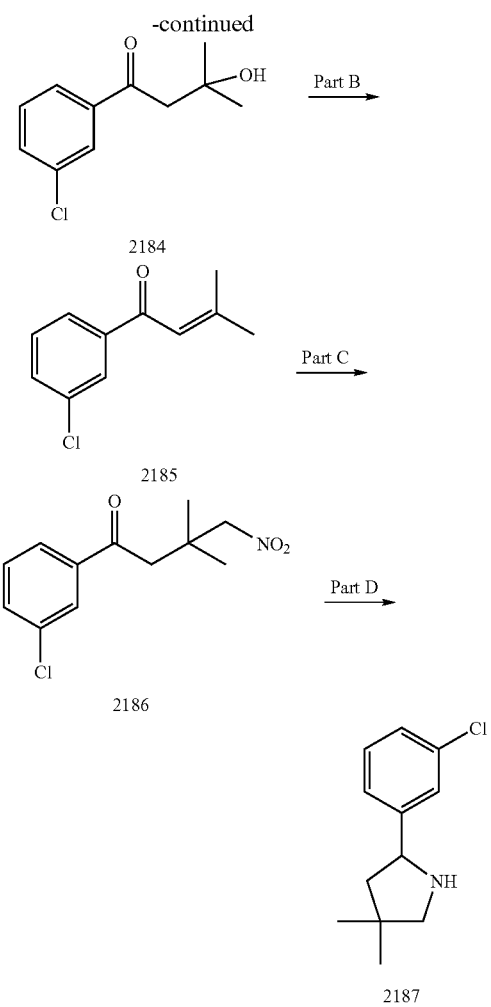

Part A:

Compound 2184 was prepared using a modification of the procedure in *J. Med. Chem.* 1994, 37, 23, 3878-3881. Compound 2183 (2.0 g, 12.9 mmol) was dissolved in methylene chloride and cooled in an ice bath. Triethylamine (3.61 mL, 26 mmol) was added followed by the dropwise addition of TMSOTf (2.81 mL, 15.5 mmol). The reaction was warmed to room temperature and stirred for 30 minutes. Saturated sodium bicarbonate was added slowly to quench the reaction and the aqueous layer was extracted with ethyl acetate. The combined organic layers were washed with brine, dried over sodium sulfate. In a separate flask TiCl$_4$ (1M in toluene, 20 mL) was added to methylene chloride (80 mL) at −78 0C. Acetone (1.2 g, 22 mmol) was added and stirred for 2 minutes. The silyl enol ether from the earlier was added and the reaction was stirred for 4 hours. After warming to room temperature, the reaction was quenched with saturated sodium bicarbonate and extracted with methylene chloride. The combined organic layers were dried over sodium sulfate and evaporated. Purification by column chromatography (SiO$_2$, 33% ethyl acetate/hexanes) afforded 2184 (600 mg). $^1$H NMR (400 MHz, CDCl$_3$) δ 7.90 (d, 1H), 7.80 (d, 1H), 7.55 (d, 1H), 7.40 (t, 1H), 3.15 (s, 2H), 1.40 (s, 6H).

Part B:

Compound 2184 (600 mg, 2.84 mmol) was dissolved in methylene chloride (2 mL) and pyridine (2 mL) and cooled in an ice bath. TFM (0.894 g, 4.26 mmol) was added dropwise and stirred 1 hour at room temperature. The reaction mixture was partitioned between ethyl acetate and water. The organic layers were washed with 1N HCl, saturated sodium bicarbonate, brine, dried over sodium sulfate, and concentrated. The residue was dissolved in methylene chloride (5 mL) and DBU (0.5 mL) was added and stirred for 1 hour at room temperature. The reaction mixture was partitioned between methylene chloride and water. The organic layers were washed with 1N HCl, saturated sodium bicarbonate, brine, dried over sodium sulfate, and concentrated. Purification by column chromatography (SiO$_2$, 10% ethyl acetate/hexanes) afforded 2185 (460 mg). $^1$H NMR (400 MHz, CDCl$_3$) δ 7.90 (d, 1H), 7.80 (d, 1H), 7.50 (d, 1H), 7.40 (t, 1H), 6.70 (m, 1H), 2.20 (d, 3H), 2.05 (d, 3H).

Part C:

Compound 2185 (460 mg, 2.38 mmol) was dissolved in nitromethane (295 mg, 4.76 mmol) and benzyltrimethylammonium hydroxide (40% weight in MeOH, 200 mg) and stirred for 2 hours at room temperature. The reaction was quenched with acetic acid (1 mL) and partitioned between diethyl ether and water. The organic layer was dried over sodium sulfate and concentrated to afford 2186 (550 mg). $^1$H NMR (400 MHz, CDCl$_3$) δ 7.90 (d, 1H), 7.80 (d, 1H), 7.58 (d, 1H), 7.40 (t, 1H), 4.70 (s, 2H), 3.10 (s, 2H), 1.30 (s, 6H).

Part D:

Compound 2187 was prepared according to the procedure in *Chem. Ber.* 1958, 91, 1978-1980. $^1$H NMR (400 MHz, CDCl$_3$) δ 7.38 (m, 1H), 7.22 (m, 2H), 7.18 (m, 1H), 4.30 (m, 1H), 2.90-2.80 (dd, 2H), 2.00 (m, 1H), 1.50 (m, 1H), 1.15 (d, 6H).

Example 51G

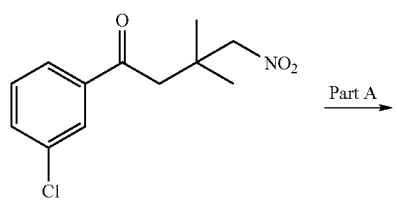

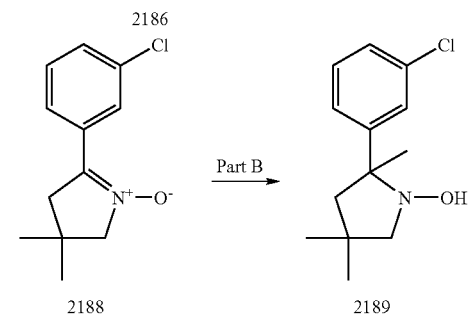

Part A:

Compound 2186 (500 mg, 1.96 mmol) and ammonium chloride (104 mg, 1.96 mmol) were dissolved in THF (5 mL) and water (5 mL) and cooled in an ice bath. Zn dust (637 mg, 9.8 mmol) was added in portions and stirred overnight. The reaction mixture was partitioned between ethyl acetate and water. The organic layers were washed with saturated sodium bicarbonate, brine, dried over sodium sulfate, and concentrated. The residue was dissolved in methylene chloride (10 mL) and m-CPBA (510 mg, 2.94 mmol) was added and stirred for 2 hours. The reaction mixture was partitioned between methylene chloride and water. The organic layers were washed with saturated sodium bicarbonate, brine, dried over sodium sulfate, and concentrated to yield 2188 (300 mg). $^1$H NMR (400 MHz, CDCl$_3$) δ 7.80 (m, 1H), 7.65 (m, 2H), 7.40-7.30 (m, 2H), 3.80 (t, 2H), 2.80 (t, 2H), 1.20 (s, 6H).

Part B:

Compound 2188 (300 mg, 1.35 mmol) was dissolved in THF (10 mL) and MeMgBr (3M in THF, 5 mL) was added dropwise. After stirring for 30 minutes at room temperature the reaction mixture was partitioned between ethyl acetate and water. The organic layers were washed with saturated sodium bicarbonate, brine, dried over sodium sulfate, and concentrated to afford 2189 (280 mg). $^1$H NMR (400 MHz, CDCl$_3$) δ 7.53 (t, 1H), 7.42 (m, 1H), 7.30-7.20 (m, 2H), 3.20 (m, 2H), 2.00 (m, 2H), 1.55 (s, 3H), 1.20 (s, 3H), 1.15 (s, 3H).

Part C:

Compound 2189 (280 mg, 1.26 mmol) was dissolved in 1N HCl (10 mL) and Zn dust (0.5 g) was added. The reaction mixture was stirred at 60° C. for 12 hours. The reaction mixture was partitioned between ethyl acetate and water. The organic layers were washed with saturated sodium bicarbonate, brine, dried over sodium sulfate, and concentrated to afford 2190 (110 mg). $^1$H NMR (400 MHz, CDCl$_3$) δ 7.53 (bs, 1H), 7.38 (m, 1H), 7.30-7.20 (m, 2H), 2.85 (m, 1H), 2.75 (m, 1H), 2.05 (m, 1H), 1.85 (m, 1H), 1.50 (s, 3H), 1.20 (s, 3H), 0.95 (s, 3H).

Example 51H

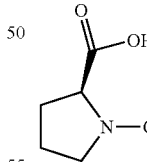
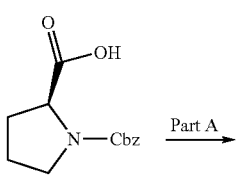

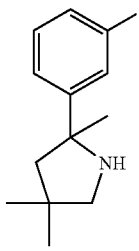

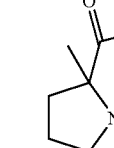
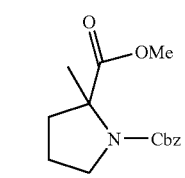

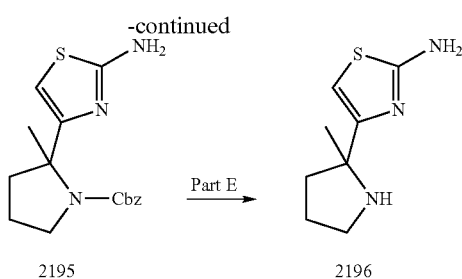

Part A:

Compound 2191 (2.8 g, 11.2 mmol) was dissolved in toluene (10 mL) and MeOH (10 mL) and cooled in an ice bath. A solution of TMS diazomethane in hexanes (2M, 8.4 mL) was added dropwise until yellow color persisted. The reaction was quenched with acetic acid until color became clear and the solvent was removed under reduced pressure. The residue was partitioned between ethyl acetate and water. The organic layer was washed with 1N HCl, saturated sodium bicarbonate, brine, dried over sodium sulfate and concentrated to afford 2192 (3.1 g). The product was used without purification.

Part B:

Diisopropylamine (3.9 mL, 28 mmol) was dissolved in THF (20 mL) and cooled to −40° C. A solution of n-BuLi (2.5M in hexanes, 8.9 mL) was added dropwise and the reaction was stirred for 30 minutes. Compound 2192 (3.1 g, 11.2 mmol) dissolved in THF (10 mL) was added dropwise at −78° C. and stirred for another 30 minutes. Iodomethane (3.1 g, 22.4 mmol) was added dropwise and the reaction was stirred for one additional hour. The reaction was warmed to room temperature and quenched with brine and extracted with ethyl acetate. The combined organic layers were washed with water, brine, dried over sodium sulfate and concentrated to provide 2193 (2.5 g). $^1$H NMR (400 MHz, CDCl$_3$) δ 7.40-7.20 (m, 5H), 5.20-5.00 (m, 2H), 3.70-3.40 (d, 3H), 3.70-3.60 (m, 2H), 2.20 (m, 1H), 1.90 (m, 3H), 1.60 (d, 3H).

Part C:

Diisopropylamine (1.24 mL, 8.85 mmol) was dissolved in THF (10 mL) and cooled to −40° C. A solution of n-BuLi (2.5M in hexanes, 3.5 mL) was added dropwise and the reaction was stirred for 30 minutes. This solution was added dropwise to a solution of compound 2193 (450 mg, 1.61 mmol) and chloroiodomethane (1.12 g, 6.44 mmol) in THF (10 mL) at −780C. The reaction was stirred for 30 minutes and then quenched by the dropwise addition of acetic acid (1 mL) in THF (5 mL). After 10 minutes of stirring the reaction mixture was partitioned between ethyl acetate and water. The organic layers were washed with saturated sodium bicarbonate, brine, dried over sodium sulfate and concentrated. Purification by column chromatography (SiO$_2$, 25% ethyl acetate/hexanes) afforded 2194 (330 mg). $^1$H NMR (400 MHz, CDCl$_3$) δ 7.40-7.20 (m, 5H), 5.20-5.00 (m, 2H), 4.40-4.00 (m, 2H), 3.80-3.60 (m, 2H), 2.20 (m, 1H), 2.00-1.8 (m, 3H), 1.60-1.40 (m, 3H).

Part D:

Compound 2194 (175 mg, 0.59 mmol) was dissolved in DMF (5 mL) and thiourea (91 mg, 1.2 mmol) was added and stirred at room temperature overnight. The reaction mixture was partitioned between ethyl acetate and water. The organic layers were washed with saturated sodium bicarbonate, brine, dried over sodium sulfate and concentrated. Purification by column chromatography (SiO$_2$, 50% ethyl acetate/hexanes) afforded 2195 (115 mg). HPLC-MS $t_R$=1.17 min (UV$_{254\,nm}$); mass calculated for formula C$_{16}$H$_{19}$N$_3$O$_2$S 317.1, observed LCMS m/z 318.1 (M+H).

Part E:

Compound 2195 (115 mg, 0.36 mmol) was dissolved in 30% HBr/AcOH (2 mL) and stirred for 2 hours. The solvent was removed under reduced pressure and the residue was dissolved in water and washed with diethyl ether. The aqueous layer was lyophilized to provide 2196 as a di-HBr salt (100 mg).

Example 51I

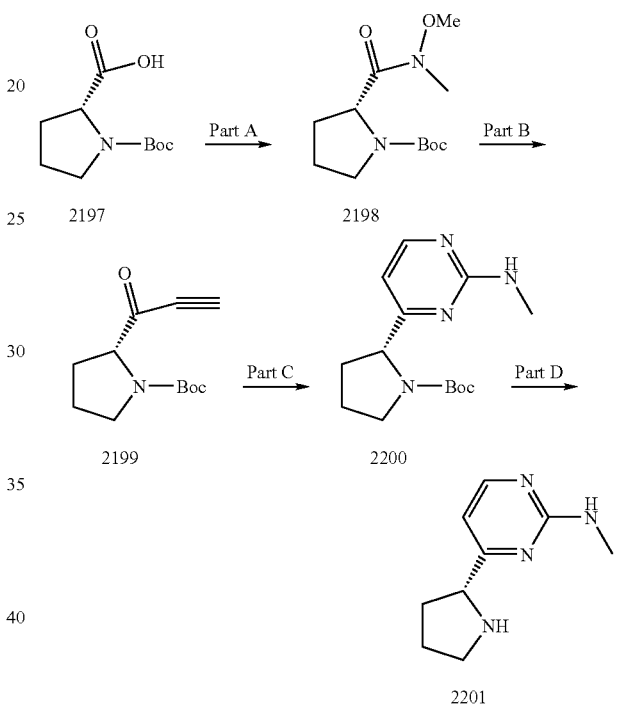

Part A:

Compound 2197 (2.3 g, 10.6 mmol), 4-chloro-2,6-dimethoxytriazine (2.4 g, 13.9 mmol) and NMM (7.3 mL, 53 mmol) were dissolved in THF (50 mL) and stirred for 1 hour. N,O-dimethylhydroxylamine hydrochloride (2.05 g, 21.2 mmol) was added and the reaction mixture was stirred overnight at room temperature. The reaction mixture was partitioned between ethyl acetate and water. The organic layers were washed with 1N HCl, saturated sodium bicarbonate, brine, dried over sodium sulfate and concentrated. Purification by column chromatography (SiO$_2$, 50% ethyl acetate/hexanes) afforded 2198 (2.0 g). $^1$H NMR (400 MHz, CDCl$_3$) δ 4.70-4.60 (m, 1H), 3.75 (m, 3H), 3.60-3.40 (m, 2H), 3.20 (s, 3H), 2.20 (m, 1H), 2.00-1.80 (m, 3H), 1.50-1.40 (m, 9H).

Part B:

Compound 2198 (550 mg, 2.13 mmol) was dissolved in THF (10 mL) and a solution of lithium (trimethylsilyl)acetylide (0.5 M in THF, 12 mL) was added dropwise and stirred overnight. The reaction mixture was partitioned between ethyl acetate and 1N HCl. The organic layer was washed with 1N HCl, saturated sodium bicarbonate, brine, dried over sodium sulfate and concentrated. Purification by column chromatography (SiO$_2$, 20% ethyl acetate/hexanes) afforded 2199 (370 mg). HPLC-MS t$_R$=1.69 min (UV$_{254\ nm}$); mass calculated for formula C$_{12}$H$_{17}$NO$_3$ 223.1, observed LCMS m/z 168.1 (M-(t-butyl)).

Part C:

Compound 2199 (350 mg, 1.56 mmol) and diethylamine (228 mg, 3.13 mmol) were dissolved in EtOH (1.5 mL) and water (1.5 mL) and stirred for 3 hours. The reaction mixture was partitioned between ethyl acetate and water. The organic layers were washed with saturated sodium bicarbonate, brine, dried over sodium sulfate and concentrated. The residue was combined with methyl guanidine hydrochloride (756 mg, 7.8 mmol) and sodium carbonate (826 mg, 7.8 mmol) in EtOH (6 mL) and refluxed for 48 hours. The reaction mixture was partitioned between ethyl acetate and water. The organic layer was washed with saturated sodium bicarbonate, brine, dried over sodium sulfate and concentrated. Purification by column chromatography (SiO$_2$, 80% ethyl acetate/hexanes) afforded 2200 (210 mg). HPLC-MS t$_R$=1.26 min (UV$_{254\ nm}$); mass calculated for formula C$_{14}$H$_{22}$N$_4$O$_2$ 278.1, observed LCMS m/z 279.1 (M+H).

Part D:

Compound 2200 (105 mg, 0.377 mmol) was dissolved in 4 M HCl in dioxane (2 mL) and methanol (0.5 mL) and stirred at room temperature for 1 hr. The reaction mixture was concentrated and triturated with diethyl ether to afford 2201 (74 mg) as an HCl salt. $^1$H NMR (400 MHz, DMSO-d$_6$) δ 10.00 (bs, 1H), 8.70 (bs, 1H), 8.30 (s, 1H), 6.70 (d, 1H), 4.60 (bs, 1H), 3.40 (m, 2H), 2.75 (s, 3H), 2.40 (m, 1H), 2.00-1.80 (m, 3H).

Example 51J

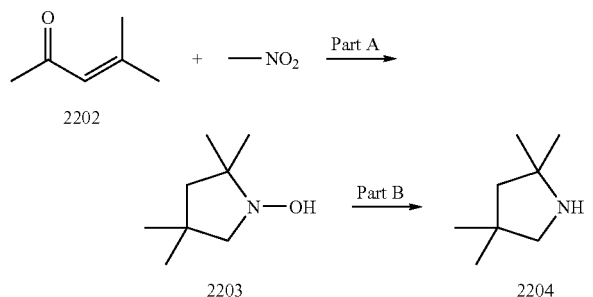

Part A:

Compound 2203 was prepared according to a procedure described in *J. Org. Chem.* 1991, 57, 7034-7038.

Part B:

A mixture of 2203 (200 mg, 1.42 mmol) and zinc dust (278 mg, 4.25 mmol) in concentrated hydrochloric acid (1.4 mL) and water (5.8 mL) was stirred at reflux overnight. The mixture was made basic with potassium hydroxide pellets, decanted and the aqueous solution extracted with ethyl acetate. The combined organic layers were washed with brine, dried over sodium sulfate and concentrated to give 2204 as a yellow sticky solid (95 mg). $^1$H NMR (400 MHz, CDCl$_3$) δ 3.35 (m, 2H), 1.88 (s, 2H), 1.66 (s, 6H), 1.30 (s, 6H).

Example 51K

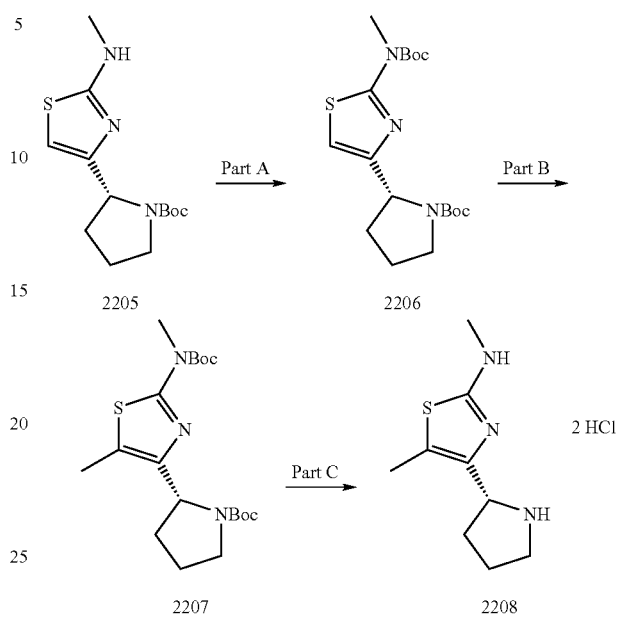

Compound 2205 was prepared using procedures described in Example 10B.

Part A:

To the solution of 2-methylaminothiazole 2205 (100 mg, 0.35 mmol) and DMAP (135 mg, 1.0 mmol) in THF (5 mL), Boc$_2$O (218 mg, 1.0 mmol) was added at room temperature. The resulting mixture was stirred overnight and then diluted with ethyl acetate (30 mL). The organics was washed with water, Brine and dried over sodium sulfate and concentrated. The residue which was purified by column chromatography (SiO$_2$, 20% ethyl acetate/hexanes) afforded the protected product 2206 (130 mg) as semi-oil. HPLC-MS t$_R$=2.42 min (UV$_{254\ nm}$); mass calculated for formula C18H29N3O4S 383.2, observed LCMS m/z 384.1 (M+H).

Part B:

The solution of thiazole 2206 (150 mg, 0.39 mmol) in THF (5 mL) was cooled to −78° C., and n-BuLi (2.5 M in hexane, 0.19 mL, 0.47 mmol) was added slowly. The resulting mixture was stirred at −78° C. for 30 min, and then iodomethane (0.1 mL, 1.55 mmol) was added. The mixture was stirred for another 30 min followed by the addition of saturated NH$_4$Cl solution (15 mL). The aqueous layer was extracted with ethyl acetate. The combined organics were washed with water, brine, dried over sodium sulfate and concentrated. Purification by column chromatography (SiO$_2$, 10% ethyl acetate/hexanes) afforded recovered thiazole 2206 (36 mg) and 2207 (100 mg). HPLC-MS t$_R$=2.51 min (UV$_{254\ nm}$); mass calculated for formula C19H31N3O4S 397.2, observed LCMS m/z 398.2 (M+H).

Part C:

To a solution of 5-methylthiazole 2207 (100 mg, 0.25 mmol) in dioxane (2 mL) was added HCl (4N in dioxane, 4 mL) followed by water (0.5 mL). The mixture was stirred at room temperature for 1 hour and concentrated. The resulting residue 2208 (72 mg) was dried under vacuum and used in the next step without further purification.

Example 51L

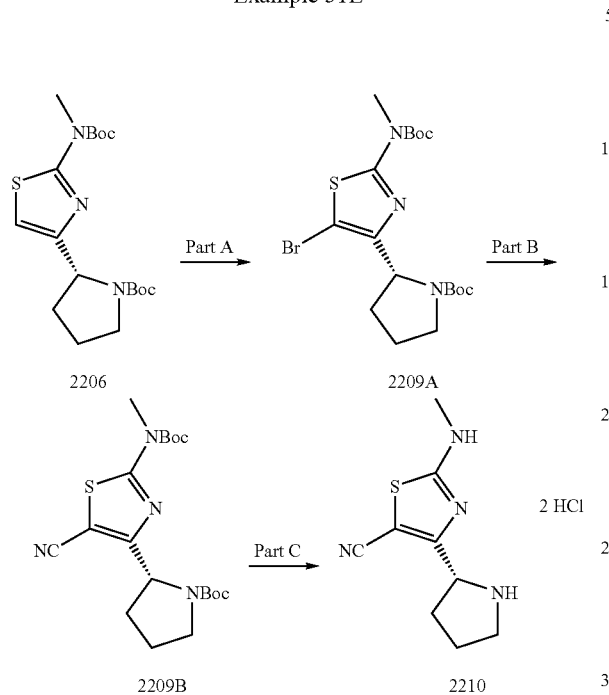

Part A:

To the solution of thiazole 2206 (190 mg, 0.5 mmol) in chloroform (5 mL), NBS (107 mg, 0.6 mmol) was added. The mixture was heated to 50° C. and stirred for 1 hour. After cooling to room temperature, the mixture was concentrated and purified by column chromatography (SiO$_2$, 10% ethyl acetate/hexanes) to afford 5-bromothiazole 2209A (221 mg). HPLC-MS $t_R$=2.65 min (UV$_{254\,nm}$); mass calculated for formula C18H28BrN3O4S 461.1, observed LCMS m/z 462.1 (M+H).

Part B:

A mixture of 5-bromothiazole 2209A (221 mg, 0.48 mmol), Zn(CN)$_2$ (117 mg, 1.0 mmol), Pd$_2$(dba)$_3$ (45 mg, 0.05 mmol) and DPPF (55 mg, 0.1 mmol) in a 25-ml round bottom flask was flushed with argon for 3 min. Under the argon, DMA (3 mL) was added and the flask was sealed under the argon atmosphere. The mixture was heated to 85° C. and stirred overnight. After cooling to room temperature, ethyl acetate (30 mL) was added to dilute the reaction mixture and the solution was filtered through celite. The filtrate was concentrated and purified by column chromatography (SiO$_2$, 10% ethyl acetate/hexanes) to afford 5-cyanothiazole 2209B (167 mg) as oil. HPLC-MS $t_R$=2.39 min (UV$_{254\,nm}$); mass calculated for formula C19H28N4O4S 408.2, observed LCMS m/z 409.2 (M+H).

Part C:

Compound 2210 (110 mg) was prepared from 2209B (167 mg, 0.41 mmol) according to the procedure described in Example 51K Part C. HPLC-MS $t_R$=0.62 min (UV$_{254\,nm}$); mass calculated for formula C9H12N4S 208.1, observed LCMS m/z 209.1 (M+H).

Example 51M

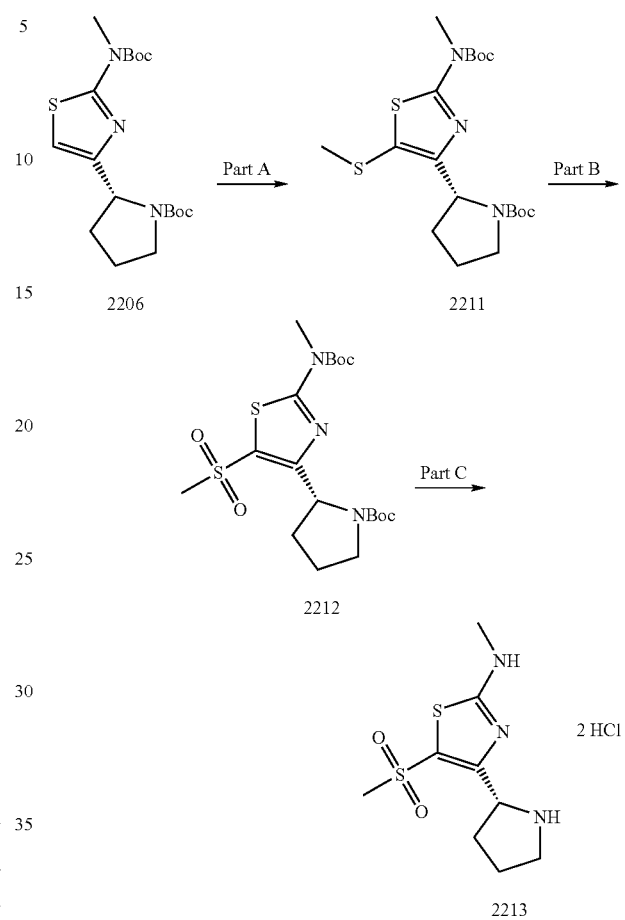

Part A:

A solution of n-BuLi (2.5 M in hexane, 0.24 mL, 0.6 mmol) was added slowly to a solution of thiazole 2206 (190 mg, 0.5 mmol) in THF (5 mL) at −78° C. The resulting mixture was stirred at −78° C. for 1 hour, and then methyl disulfide (94 mg, 1.0 mmol) was added. The mixture was stirred for another one hour, and then warmed to room temperature slowly. Then saturated NH$_4$Cl solution was added to quench the reaction. The mixture was extracted with ethyl acetate (30 mL×3). The combined organics were dried over sodium sulfate, concentrated and purified by column chromatography (SiO$_2$, 10% ethyl acetate/hexanes) to afford 5-methylsulfidethiazole 2211 (137 mg) and recovered thiazole 2206 (38 mg). HPLC-MS $t_R$=2.62 min (UV$_{254\,nm}$); mass calculated for formula C19H31N3O4S2 429.2, observed LCMS m/z 430.1 (M+H).

Part B:

A mixture of sulfide 2211 (137 mg, 0.32 mmol) and m-CPBA (~77%, 230 mg, 1.0 mmol) in dichloromethane (10 mL) was stirred at room temperature overnight. Ethyl acetate (80 mL) was added to dilute the mixture and the organics were washed with saturated sodium bicarbonate solution twice followed by brine, dried over sodium sulfate, concentrated. The residue was purified by column chromatography (SiO$_2$, 20% ethyl acetate/hexanes) afforded 5-methylsulfonethiazole 2212 (141 mg). HPLC-MS $t_R$=2.62 min (UV$_{254\,nm}$); mass calculated for formula C19H31N3O6S2 461.2, observed LCMS m/z 406.1 (M+H−t−Bu).

Part C:

Compound 2213 (110 mg) was prepared from 2212 (141 mg, 0.30 mmol) according to the procedure described in Example 51K Part C. HPLC-MS $t_R$=0.63 min (UV$_{254\,nm}$);

mass calculated for formula C9H15N3O2S2 261.1, observed LCMS m/z 262.0 (M+H).

Example 51N

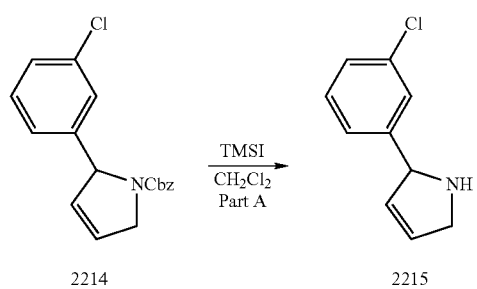

Starting pyrroline derivative 2214 was prepared by known methods (Billet, M; Schoenfelder, A; Klotz, P.; Mann, A. *Tetrahedron Letters*, 2002, 1453).

Part A:

Trimethylsilyl iodide (0.44 g, 2.24 mmol) was added dropwise to a solution of 2214 (0.47 g, 1.5 mmol; 20 mL CH$_2$Cl$_2$) at room temperature and stirred for 3 hours. The mixture was cooled to 0° C. before quenching with methanol (5 mL). The solvent was removed under reduced pressure to provide crude amine 2215, which was used without further purification.

Example 51O

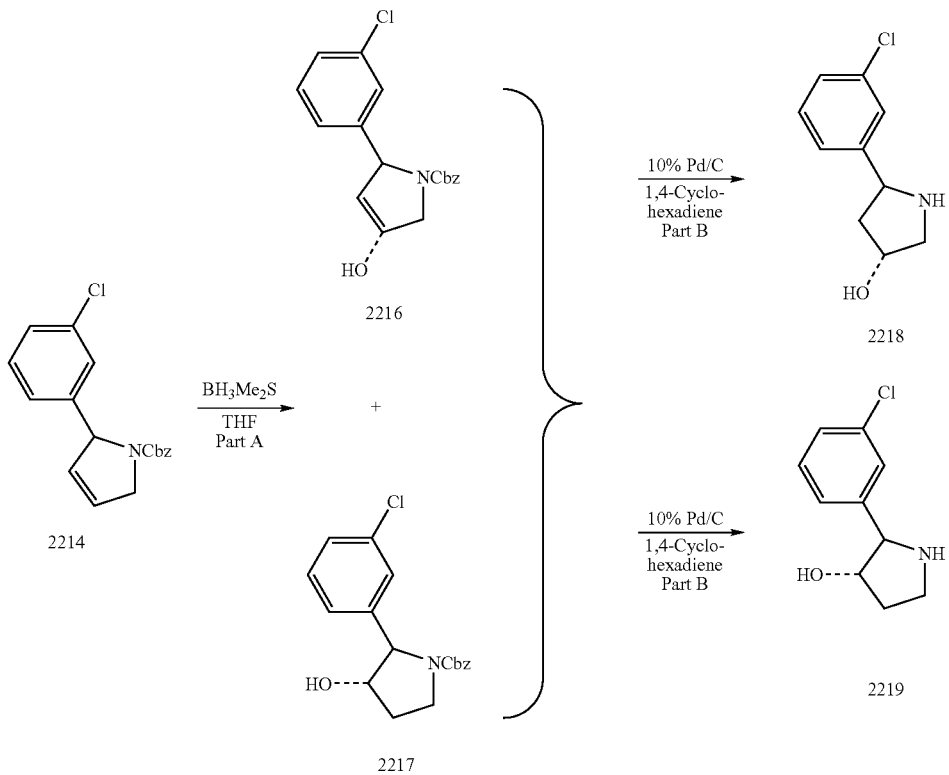

Part A:

Borane dimethyl sulfide (2.0 M solution in toluene, 1.45 mL, 2.9 mmol) was added dropwise to a solution of intermediate 2214 (0.65 g, 2 mmol) in THF (10 mL) at 0° C. After addition, the mixture was stirred at room temperature for 3 hours. The reaction mixture was quenched with dropwise addition of water (1.0 mL) and 3N NaOH (3.0 mL). The resulting mixture was stirred for 5 minutes and then cooled to 0° C. before adding 30% H$_2$O$_2$ (6.0 mL) dropwise. The mixture was stirred at ambient temperature for 2 hours and then treated with 5% Na$_2$S$_2$O$_3$ (25 mL) and stirred additional half hour. The reaction mixture was diluted with ethyl acetate (100 mL), and the organics were washed with brine, dried (Na$_2$SO$_4$), filtered, and concentrated under vacuum to provide a crude residue which was purified by silica-gel column chromatography (1:3 to 1:2 ethyl acetate/hexane) to give first intermediate 2217 (0.3 g, 44%) followed by intermediate 2216 (0.2 g, 29%).

Part B:

Intermediate 2216 (0.075 g, 0.22 mmol) was dissolved in ethyl alcohol (1.5 mL). Then 1,4-cyclohexadiene (0.21 mL, 2.24 mmol) was added, followed by addition of 10% Pd/C under N$_2$. The reaction mixture was stirred at r.t. for 2 hours, filtered through celite and concentrated under vacuum to give intermediate 2218 (0.035 g, 80%).

Compound 2219 was prepared by using methods similar to those described in Parts A-B for intermediate 2218.

Example 51P

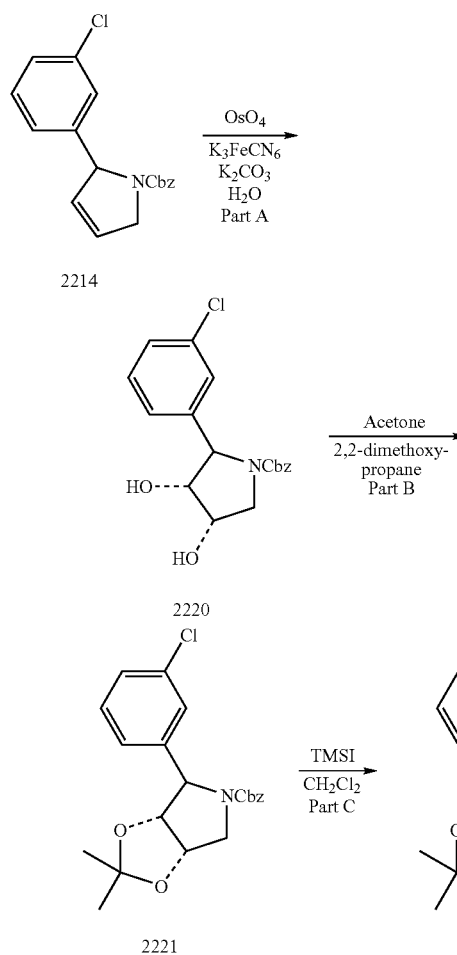

Part C:

Intermediate 2221 (0.06 g, 0.15 mmol) was dissolved in CH$_2$Cl$_2$ (0.5 mL), followed by addition of trimethylsilyl iodide (0.034 mL, 0.24 mmol) at 0° C. The mixture was stirred at r.t. for 2 hours. The reaction was quenched with methanol (5 mL) and stirred for another 2 hours. The reaction mixture was concentrated to provide the crude amine 2222, which was used without additional purification.

Example 51Q

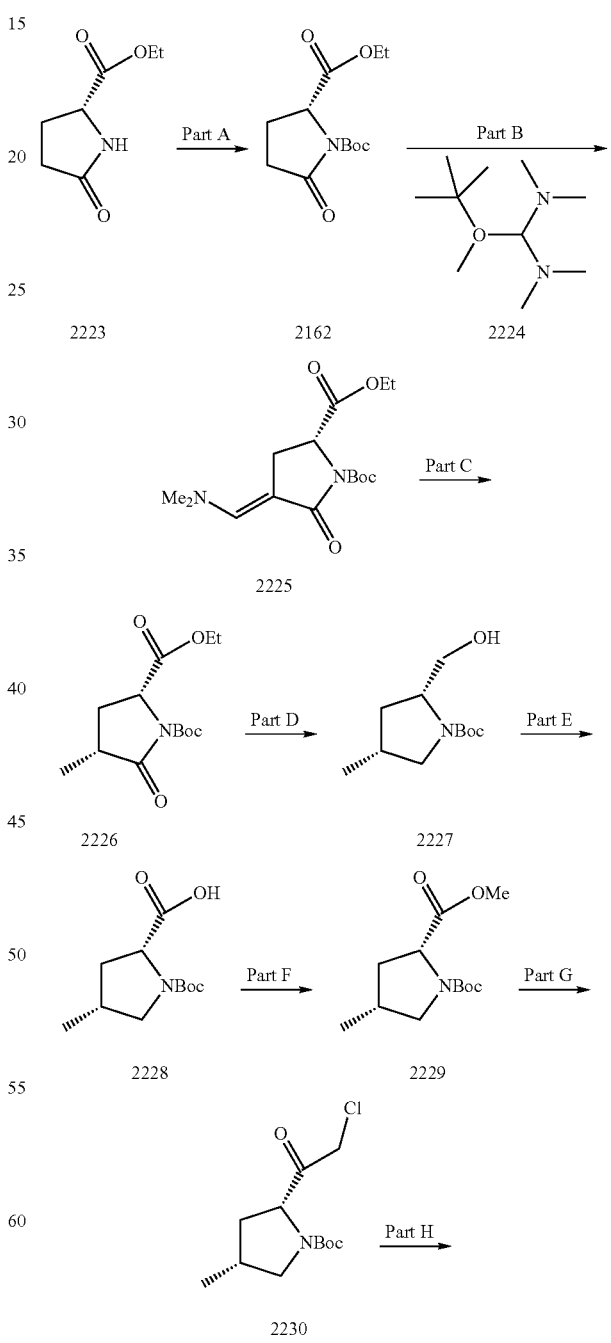

Part A:

Intermediate 2214 (0.1 g, 0.3 mmol) was dissolved in t-butanol (3 mL) and water (3 mL). Potassium hexacyanoferrate (0.31 g, 0.94 mmol) and potassium carbonate (0.13 g, 0.94 mmol) were added and stirred for 15 minutes. To this mixture osmium tetraoxide (0.005 g, 0.02 mmol) was added and stirred for 16 h. The reaction was diluted with ethyl acetate (50 mL) and the organics were washed once with brine (10 mL), dried (Na$_2$SO$_4$), filtered and concentrated under reduced pressure to provide intermediate 2220 (0.1 g, 91%).

Part B:

Diol 2220 (0.1 g, 0.28 mmol) was dissolved in acetone (5 mL) and 2,2-dimethoxypropane (0.045 g, 0.43 mmol) was added, followed by addition of catalytic amount of p-toluenesulfonic acid (0.06 g, 0.03 mmol). The reaction mixture was stirred at room temperature for 14 h. The solvent was removed under vacuum to provide a crude product which was purified by silica-gel preparative chromatography using ethyl acetate/hexane (⅓) as the eluting solvent to yield 2221 (0.075 g, 68%).

-continued

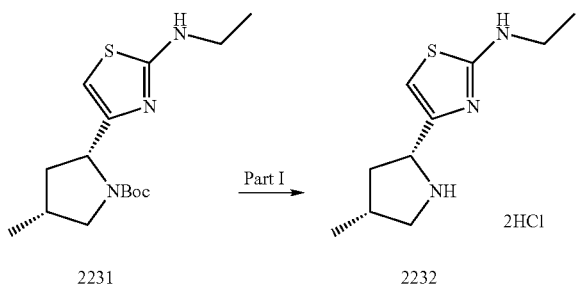

Part A:

Compound 2223 (2.2 g, 13.9 mmol) was dissolved in methylene chloride (25 mL) and triethylamine (3.9 mL, 27.8 mmol), DMAP (100 mg), and di-t-butyidicarbonate (3.33 g, 15.3 mmol) were added. The reaction mixture was stirred for 5 hours at room temperature and then diluted with water and methylene chloride. The organic layers were washed with 1N HCl, saturated sodium bicarbonate, water, brine, dried over sodium sulfate and concentrated. Purification by column chromatography (SiO$_2$, 33% ethyl acetate/hexanes) afforded the desired product (3.0 g). $^1$H NMR (400 MHz, CDCl$_3$) δ 4.60 (m, 1H), 4.20 (q, 2H), 2.70-2.60 (m, 1H), 2.50 (m, 1H), 2.40-2.30 (m, 1H), 2.05 (m, 1H), 1.50 (s, 9H), 1.20 (t, 3H).

Part B:

Compound 2162 (630 mg, 2.44 mmol) was added to t-butoxy-bis(dimethylamino)methane (2224) (0.705 mL, 3.42 mmol) and stirred at 80° C. overnight. The excess reagent was removed under reduced pressure to provide 2225 that was used without purification (750 mg). $^1$H NMR (400 MHz, CDCl$_3$) δ 7.10 (m, 1H), 4.50 (m, 1H), 4.30-4.20 (m, 2H), 3.30 (m, 1H), 3.00 (s, 6H), 2.80 (m, 1H), 1.50 (s, 9H), 1.30 (m, 3H).

Part C:

Compound 2225 (750 mg, 2.4 mmol) was dissolved in ethyl acetate (12 mL) and 10% Pd—C (200 mg) was added under an argon atmosphere. The reaction mixture was placed under a hydrogen atmosphere and stirred for 96 hours at room temperature. The reaction was filtered and the solvent was evaporated. Purification by column chromatography (SiO$_2$, 33% ethyl acetate/hexanes) afforded the desired product (350 mg). $^1$H NMR (400 MHz, CDCl$_3$) δ 4.50 (m, 1H), 4.25 (q, 2H), 2.60 (m, 2H), 1.65 (m, 1H), 1.50 (s, 9H), 1.32 (t, 3H), 1.28 (d, 3H).

Part D:

Compound 2226 (200 mg, 0.73 mmol) was dissolved in THF (2 mL) and borane dimethyl sulfide (2M in THF, 1.5 mL) was added. The reaction mixture was stirred for 40 hours and then cooled in an ice bath and quenched slowly with methanol. The solvent was evaporated and the residue was purified by column chromatography (SiO$_2$, 33% ethyl acetate/hexanes) to afford the desired product (80 mg). $^1$H NMR (400 MHz, CDCl$_3$) δ 3.95 (m, 1H), 3.75-3.50 (m, 3H), 2.75 (t, 1H), 2.25 (m, 2H), 1.50 (s, 9H), 1.20 (m, 1H), 1.00 (d, 3H).

Part E:

Compound 2227 (70 mg, 0.32 mmol) was dissolved in acetone (3 mL) and Jones Reagent (1 mL) was added dropwise. The reaction mixture was stirred overnight and then quenched with methanol. The mixture was then filtered and concentrated. The residue was dissolved in saturated sodium bicarbonate and washed with diethyl ether. The aqueous layer was acidified to pH 2 and then extracted with ethyl acetate. The ethyl acetate layers were dried over sodium sulfate and concentrated to provide the desired product (55 mg). $^1$H NMR (400 MHz, CDCl$_3$) δ 4.30-4.20 (m, 1H), 3.80-3.70 (m, 1H), 2.95 (m, 1H), 2.50-2.30 (m, 1H), 2.25 (m, 1H), 1.80-1.60 (m, 1H), 1.50 (d, 9H), 1.05 (m, 3H).

Part F:

Compound 2228 (370 mg, 1.62 mmol) was dissolved in toluene (2 mL) and methanol (2 mL) and cooled in an ice bath. A solution of trimethylsilyl diazomethane (2M in hexanes, 1.5 mL) was added dropwise. The solution was stirred for 1 hour and then concentrated. The residue was dissolved in ethyl acetate and water. The organic layer was washed with 1N HCl, saturated sodium bicarbonate, brine, dried over sodium sulfate, and concentrated to provide the methyl ester 2229 (310 mg).

Part G:

In a separate flask diisopropylamine (1.0 mL) was dissolved in THF (10 mL) and cooled to −78° C. A solution of n-butyl lithium (2.5 M in hexanes, 2.55 mL) was added dropwise and stirred for 30 minutes. This solution was added dropwise to a solution of the methyl ester 2229 (310 mg, 1.27 mmol) and chloroiodomethane (0.9 g, 5.08 mmol) in THF (5 mL) at −78° C. After thirty minutes the reaction was quenched dropwise with acetic acid (1 mL) in THF (5 mL). The reaction mixture was warmed to room temperature and diluted with water and ethyl acetate. The organic layer was dried over sodium sulfate and concentrated. Purification by column chromatography (SiO$_2$, 25% ethyl acetate/hexanes) afforded the desired alpha-chloro ketone 2230 (150 mg).

Part H:

The alpha-chloro ketone 2230 (150 mg, 0.575 mmol) was dissolved in DMF (5 mL) and ethyl thiourea (134 mg, 1.15 mmol) was added and stirred at 80° C. overnight. The reaction mixture was partitioned between ethyl acetate and water. The organic layer was washed with brine, dried over sodium sulfate and concentrated. Purification by column chromatography (SiO$_2$, ethyl acetate) afforded the desired product 2231 (85 mg). HPLC-MS $t_R$=1.35 min (UV$_{254\,nm}$); mass calculated for formula C$_{15}$H$_{25}$N$_3$O$_2$S 311.1, observed LCMS m/z 312.1 (M+H).

Part I:

Compound 2231 (85 mg, 0.30 mmol) was dissolved in 4M HCl in dioxane (2 mL) and methanol (0.5 mL) and stirred for 30 minutes. The solvents were removed to provide 2232 as a di-HCl salt (65 mg). $^1$H NMR (400 MHz, DMSO-d$_6$) δ 9.50 (bs, 1H), 8.70 (bs, 1H), 7.80 (bs, 1H), 6.70 (s, 1H), 4.50 (m, 1H), 3.30-3.20 (m, 2H), 2.75-2.65 (m, 2H), 2.40 (m, 2H), 1.70 (m, 1H), 1.15 (t, 3H), 1.10 (d, 3H).

The following compounds were prepared using previously described procedures.

| Compound # | Structure | Exact mass | MS m/z (M + H) |
|---|---|---|---|
| 2233 | 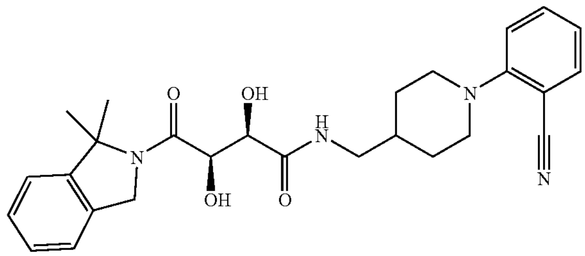 | 494.2 | 495.2 |
| 2234 | 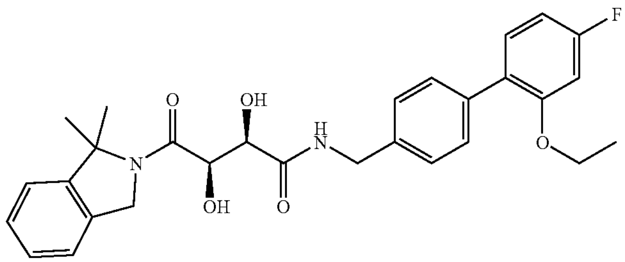 | 506.2 | 507.1 |
| 2235 | 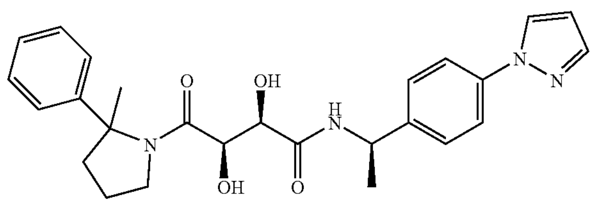 | 462.2 | 463.1 |
| 2236 | 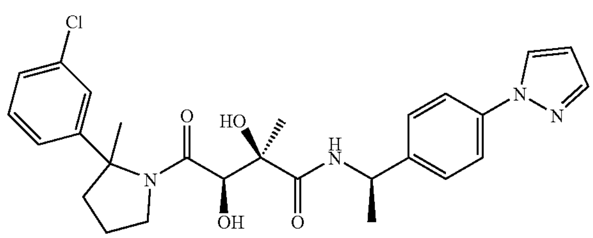 | 510.2 | 511.1 |
| 2237 | 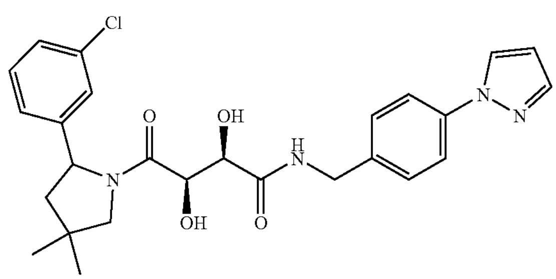 | 510.2 | 511.1 |
| 2238 | 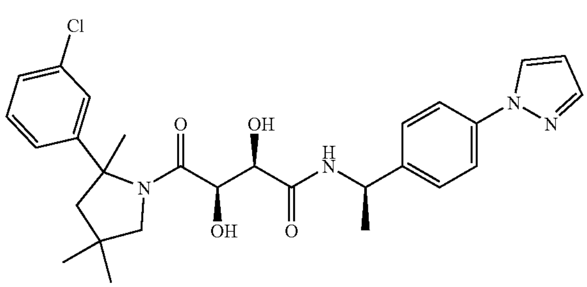 | 524.2 | 525.1 |

| Compound # | Structure | Exact mass | MS m/z (M + H) |
|---|---|---|---|
| 2239 | 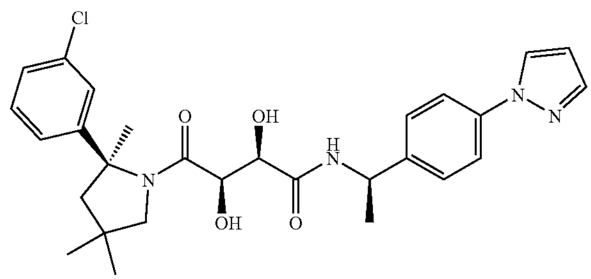 | 524.2 | 525.1 |
| 2240 | 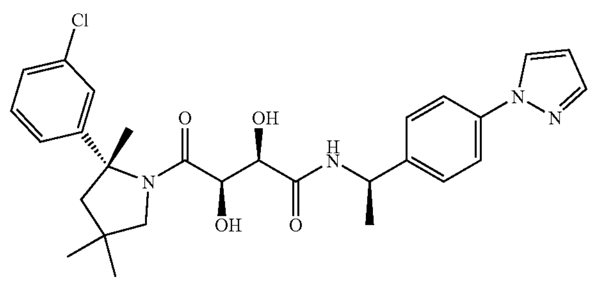 | 524.2 | 525.1 |
| 2241 | 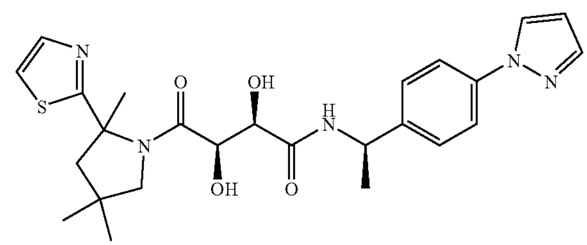 | 497.2 | 498.1 |
| 2242 | 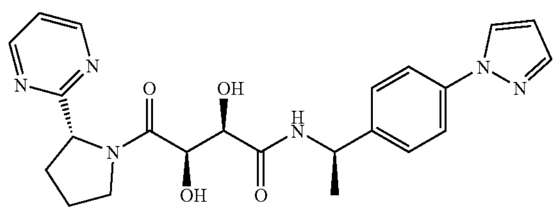 | 450.2 | 451.1 |
| 2243 | 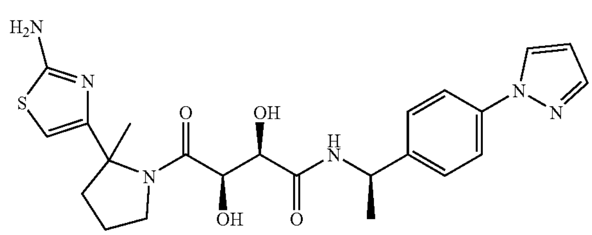 | 484.1 | 485.0 |
| 2244 | 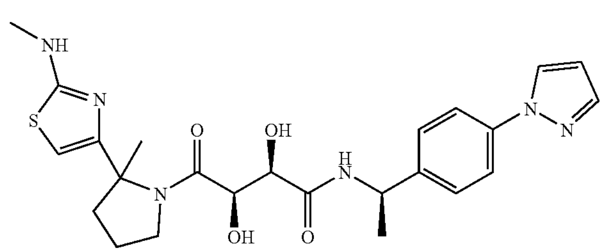 | 498.2 | 499.1 |

-continued

| Compound # | Structure | Exact mass | MS m/z (M + H) |
|---|---|---|---|
| 2245 | 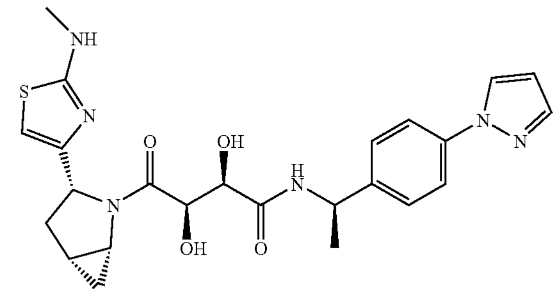 | 496.2 | 497.1 |
| 2246 | 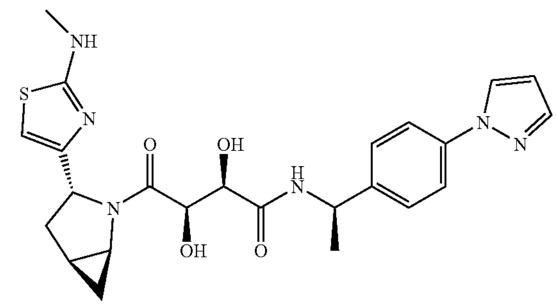 | 496.2 | 497.1 |
| 2247 | 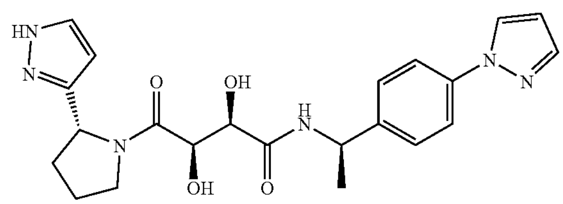 | 438.2 | 439.1 |
| 2248 | 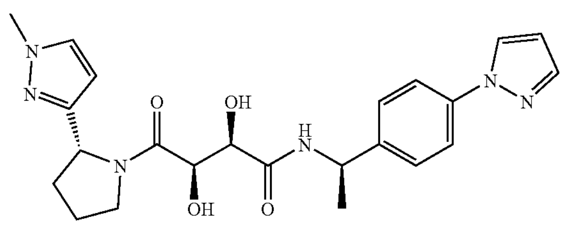 | 452.2 | 453.1 |
| 2249 | 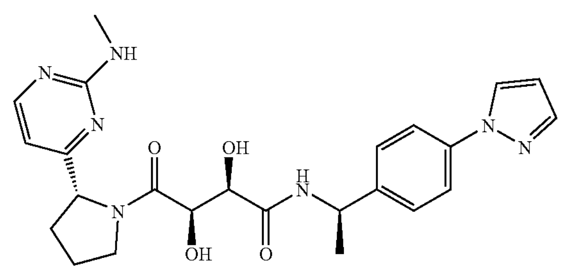 | 479.2 | 480.1 |

-continued

| Compound # | Structure | Exact mass | MS m/z (M + H) |
|---|---|---|---|
| 2250 | 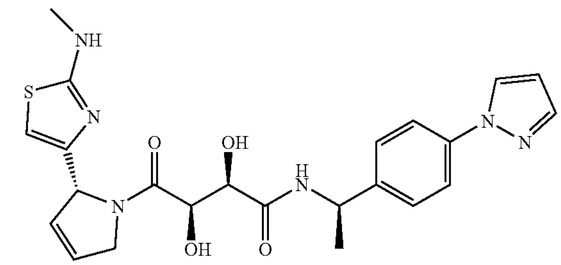 | 482.2 | 483.1 |
| 2251 | 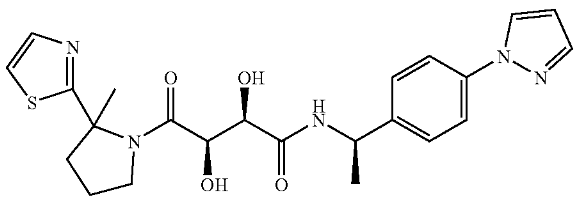 | 469.2 | 470.0 |
| 2252 | 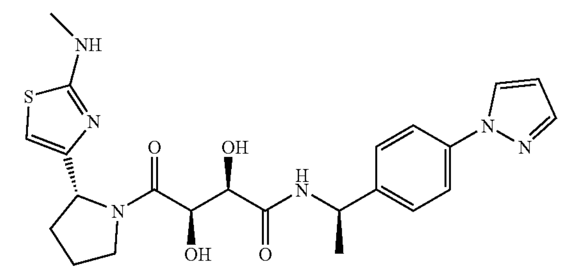 | 484.2 | 485.1 |
| 2253 | 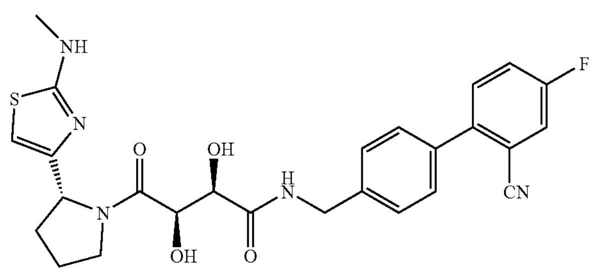 | 530.2 | 531.1 |
| 2254 | 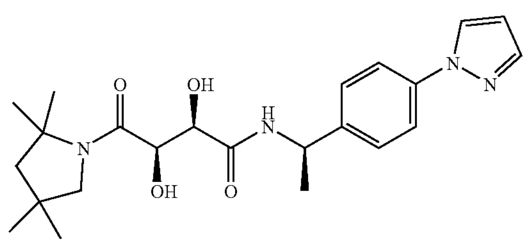 | 428.2 | 429.2 |
| 2255 | 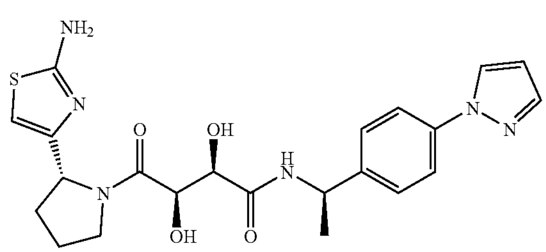 | 470.2 | 471.1 |

-continued

| Compound # | Structure | Exact mass | MS m/z (M + H) |
|---|---|---|---|
| 2256 | 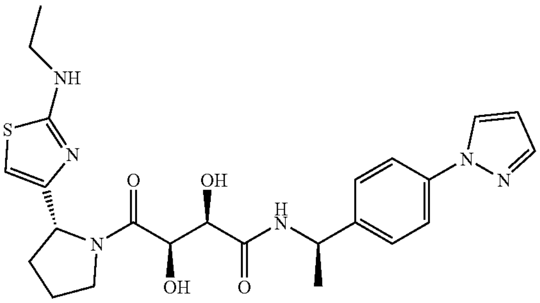 | 498.2 | 499.1 |
| 2257 | 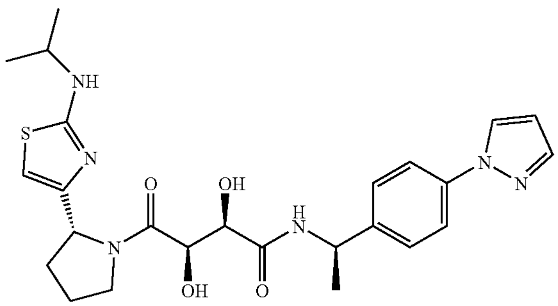 | 512.2 | 513.1 |
| 2258 | 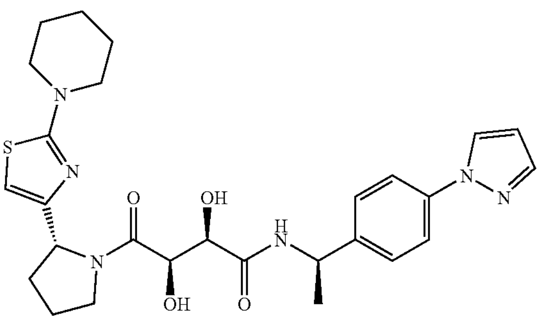 | 538.2 | 539.2 |
| 2259 | 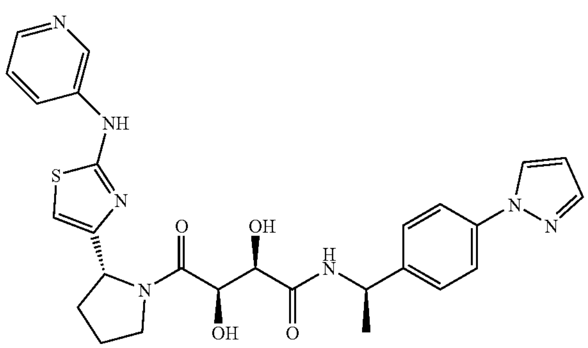 | 547.2 | 548.2 |
| 2260 | 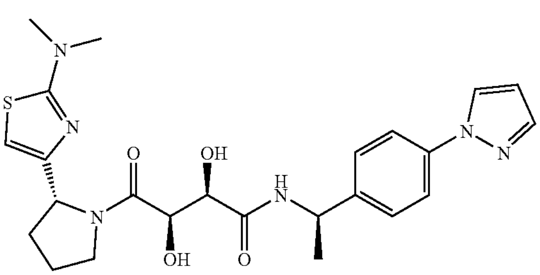 | 498.2 | 499.1 |

-continued

| Compound # | Structure | Exact mass | MS m/z (M + H) |
|---|---|---|---|
| 2261 | 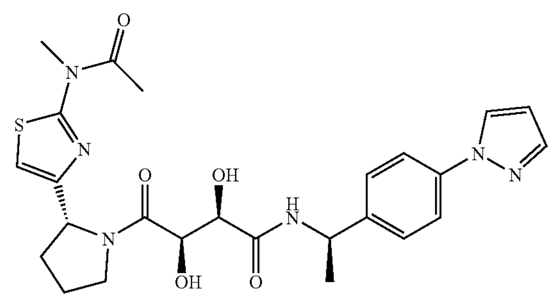 | 526.2 | 527.1 |
| 2262 | 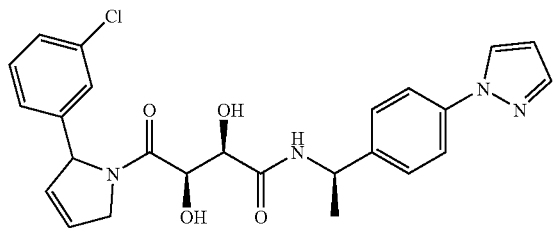 | 480.2 | 481.1 |
| 2263 | 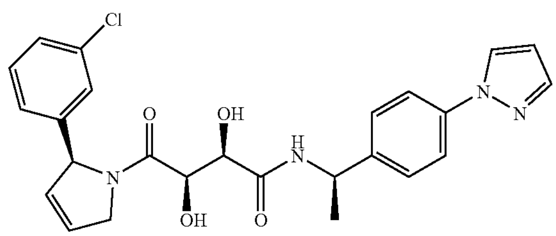 | 480.2 | 481.1 |
| 2264 | 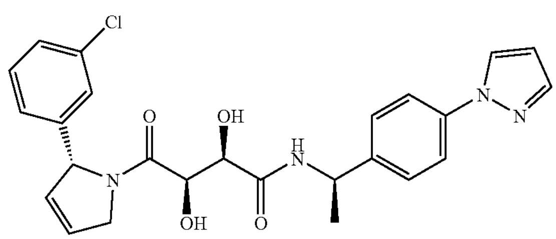 | 480.2 | 481.3 |
| 2265 | 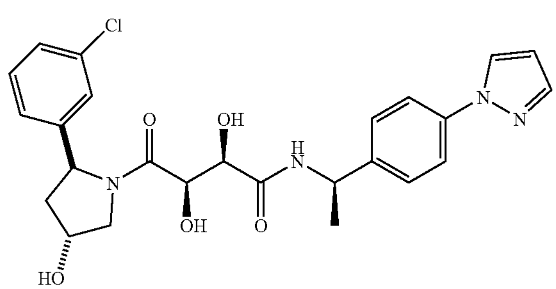 | 498.2 | 499.1 |
| 2266 | 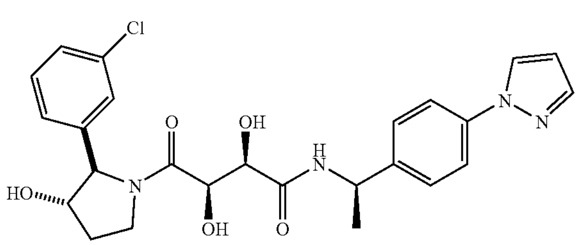 | 498.2 | 499.1 |

-continued

| Compound # | Structure | Exact mass | MS m/z (M + H) |
|---|---|---|---|
| 2267 | 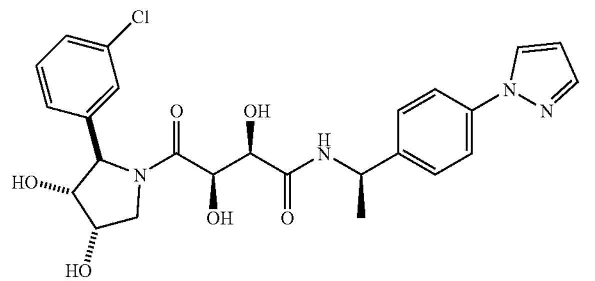 | 514.2 | 515.1 |
| 2268 | 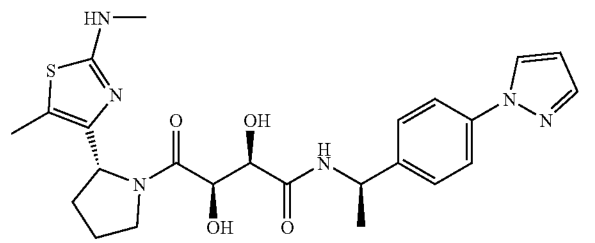 | 498.2 | 499.1 |
| 2269 | 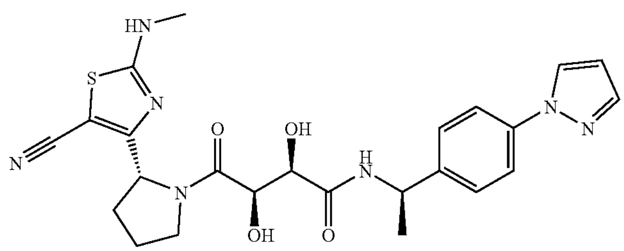 | 509.2 | 510.1 |
| 2270 | 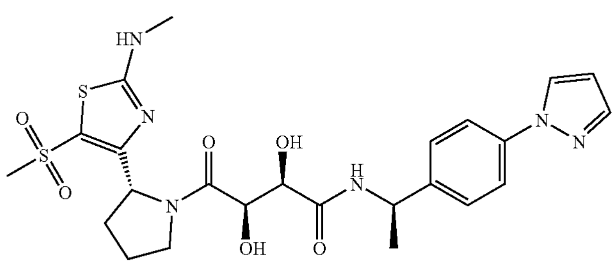 | 562.2 | 563.0 |
| 2271 | 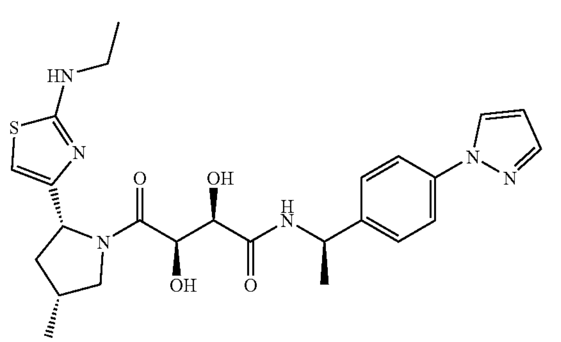 | 512.2 | 513.1 |

Example 52

Example 52A

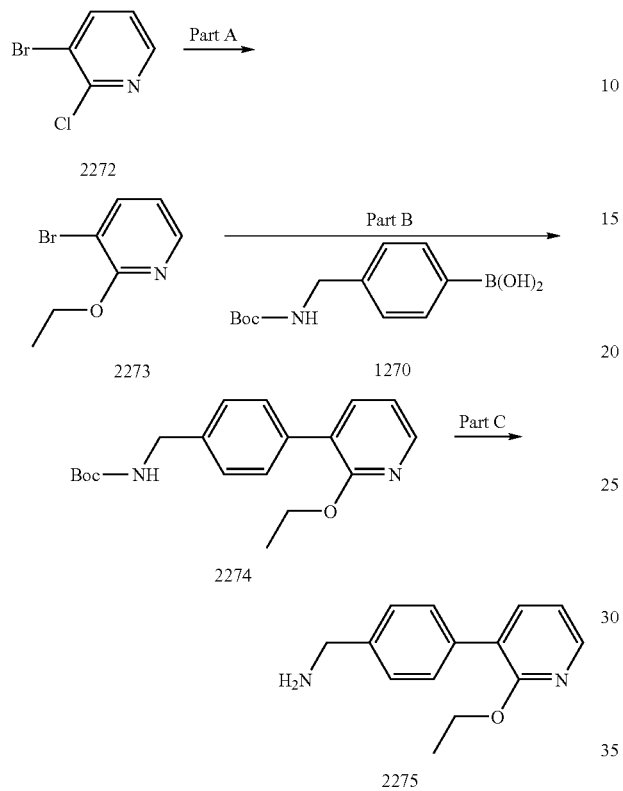

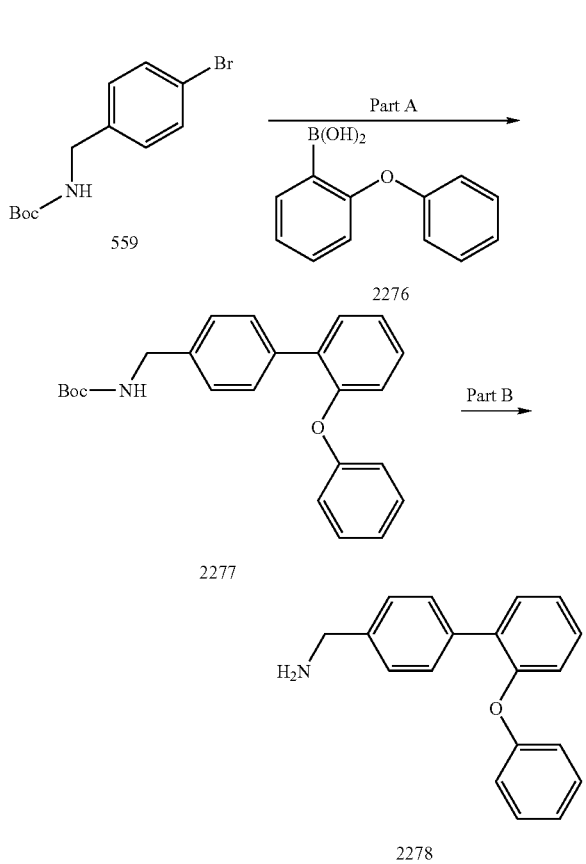

Part A:

Sodium pellets (1.0 g, 43 mmol) were dissolved in ethanol (35 mL). Compound 2272 (1.4 g, 7.2 mmol) was added to the solution and the reaction was refluxed overnight. The solvent was removed under reduced pressure and the residue was partitioned between ethyl acetate and water. The combined organic layers were washed with brine, dried over sodium sulfate and concentrated to afford 2273 (1.3 g). The product was used without further purification. HPLC-MS $t_R$=1.92 min ($UV_{254\ nm}$); mass calculated for formula $C_7H_8NOBr$ 201.0, observed LCMS m/z 202.1 (M+H).

Part B:

Compound 2273 (171 mg, 0.8592 mmol) was dissolved in toluene (10 mL). The boronic acid 1270 (409 mg, 1.69 mmol), $Pd_2(dba)_3$ (38 mg, 0.0423 mmol), S-PHOS (34 mg, 0.084 mmol), potassium phosphate (358 mg, 1.69 mmol) were added to the solution and stirred at reflux overnight. The reaction mixture was cooled to room temperature and filtered, and the toluene was removed under reduced pressure. The residue was partitioned between ethyl acetate and water. The combined organic layers were dried over sodium sulfate and concentrated to afford 2274 (190 mg). The material was used without further purification. HPLC-MS $t_R$=2.21 min ($UV_{254\ nm}$); mass calculated for formula $C_{19}H_{24}N_2O_3$ 328.2, observed LCMS m/z 329.2 (M+H).

Part C:

Compound 2274 (190 mg, 0.584 mmol) was dissolved in methylene chloride (4 mL) and TFA (1 mL) and stirred for 30 minutes. The solvents were removed to provide 2275 as the TFA salt (190 mg).

Example 52B

Part A:

Compound 559 (100 mg, 0.35 mmol) was dissolved in dioxane (5 mL). Then boronic acid 2276 (113 mg, 0.52 mmol), $Pd_2(dba)_3$ (27 mg, 0.03 mmol), triphenylphosphine (13.7 mg, 0.052 mmol), potassium phosphate (148 mg, 0.70 mmol) were added to the solution and stirred at reflux overnight. The reaction mixture was cooled to room temperature and filtered, and the toluene was removed under reduced pressure. The residue was partitioned between ethyl acetate and water. The combined organic layers were dried over sodium sulfate and concentrated. Purification by column chromatography ($SiO_2$, 25% ethyl acetate/hexanes) afforded 2277 (80 mg). $^1$H NMR (400 MHz, $CDCl_3$) δ 7.50 (d, 1H), 7.45 (m, 2H), 7.30-7.15 (m, 5H), 7.20-7.10 (m, 2H), 7.00-6.90 (m, 3H), 4.30 (d, 2H), 1.45 (s, 9H).

Part B:

Compound 2277 (80 mg, 0.21 mmol) was dissolved in 4 M HCl in dioxane (2 mL) and stirred at room temperature for 1 hr. The reaction was diluted with diethyl ether (5 mL) and 2278 (60 mg) was collected by filtration.

Example 52C

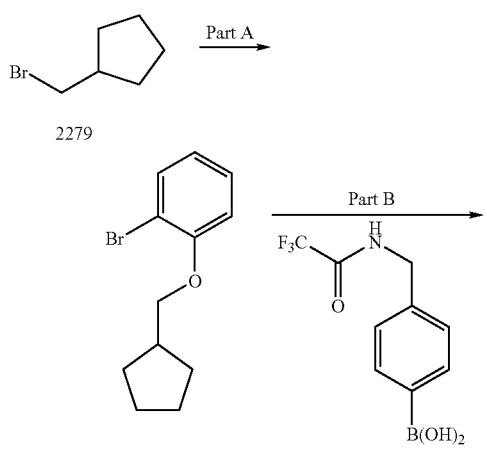

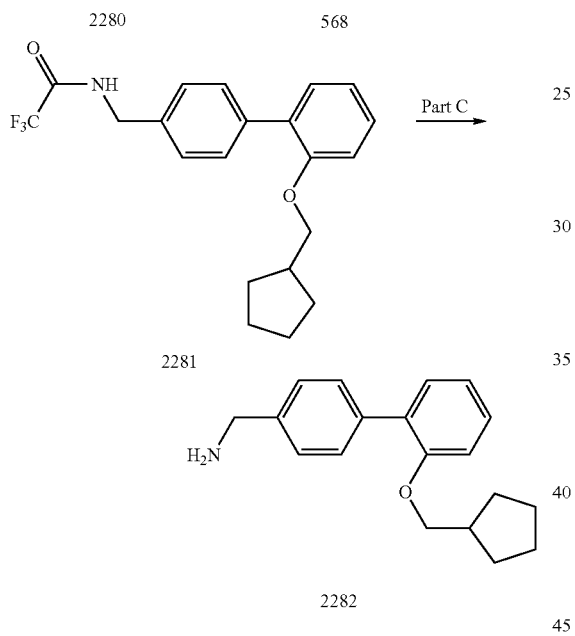

Part A:
Compound 2279 (500 mg, 3.08 mmol), cesium carbonate (3.0 g, 9.25 mmol), and 2-bromophenol (527 mg, 3.08 mmol) were dissolved in DMF (15 mL) and stirred at 60° C. for 2 hours. The reaction mixture was partitioned between ethyl acetate and water. The organic layers were washed with saturated sodium bicarbonate, brine, dried over sodium sulfate, and concentrated. Purification by column chromatography (SiO$_2$, 10% ethyl acetate/hexanes) afforded 2280 (400 mg). $^1$H NMR (400 MHz, CDCl$_3$) δ 7.50 (m, 1H), 7.20 (m, 1H), 6.85 (d, 1H), 6.80 (t, 1H), 3.90 (d, 2H), 2.40 (m, 1H), 1.85 (m, 2H), 1.60-1.45 (m, 4H), 1.40 (m, 2H).

Part B:
Compound 2280 (157 mg, 0.50 mmol), compound 568 (250 mg, 1.02 mmol), Pd$_2$(dba)$_3$ (9.1 mg, 0.01 mmol), S-PHOS (8.3 mg, 0.02 mmol), potassium fluoride (350 mg, 3.0 mmol) were dissolved in dioxane (8 mL) and stirred at reflux overnight. The reaction mixture was cooled to room temperature and filtered, and the toluene was removed under reduced pressure. The residue was partitioned between ethyl acetate and water. The combined organic layers were dried over sodium sulfate and concentrated. Purification by column chromatography (SiO$_2$, 10% ethyl acetate/hexanes) afforded 2281 (200 mg). $^1$H NMR (400 MHz, CDCl$_3$) δ 7.60 (m, 2H), 7.40 (m, 2H), 7.30 (m, 2H), 7.00 (m, 2H), 4.60 (d, 2H), 3.85 (d, 2H), 2.35 (m, 1H), 1.80 (m, 2H), 1.60 (m, 4H), 1.30 (m, 2H).

Part C:
Compound 2281 (100 mg, 0.317 mmol) was dissolved in MeOH (5 mL) and a saturated solution of potassium carbonate (1 mL) was added and the reaction was stirred for 3 hours. The reaction mixture was partitioned between ethyl acetate and water. The organic layers were washed with saturated sodium bicarbonate, brine, dried over sodium sulfate, and concentrated to afford 2282 (40 mg). $^1$H NMR (400 MHz, CDCl$_3$) δ 7.55 (d, 2H), 7.40 (m, 4H), 7.00 (m, 2H), 4.60 (d, 2H), 3.85 (d, 2H), 2.35 (m, 1H), 1.80 (m, 2H), 1.60 (m, 4H), 1.35 (m, 2H).

Example 52D

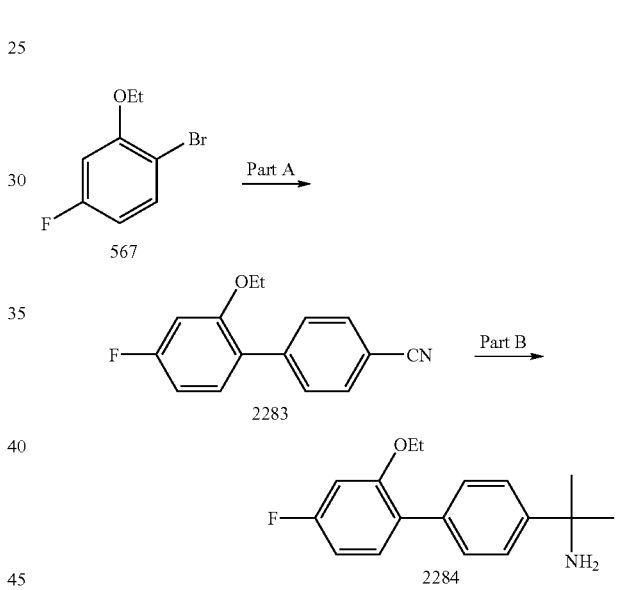

Part A:
Compound 567 (500 mg, 2.29 mmol), 4-cyanophenylboronic acid (483 mg, 3.43 mmol), Pd$_2$(dba)$_3$ (70 mg, 0.08 mmol), triphenylphosphine (70 mg, 0.26 mmol), potassium phosphate (970 mg, 4.58 mmol) were dissolved in dioxane (15 mL) and stirred at reflux overnight. The reaction mixture was cooled to room temperature and filtered and the dioxane was removed under reduced pressure. The residue was partitioned between ethyl acetate and water. The combined organic layers were dried over sodium sulfate and concentrated. Purification by column chromatography (SiO$_2$, 5% ethyl acetate/hexanes) afforded 2283 (240 mg). $^1$H NMR (400 MHz, CDCl$_3$) δ 7.70-7.58 (m, 4H), 7.27-7.23 (m, 1H), 6.75-6.70 (m, 2H), 4.05 (q, 2H), 1.38 (t, 3H).

Part B:
Compound 2284 was prepared according to the procedure in J. Org. Chem. 1992, 57, 4521-4527.

Example 52E

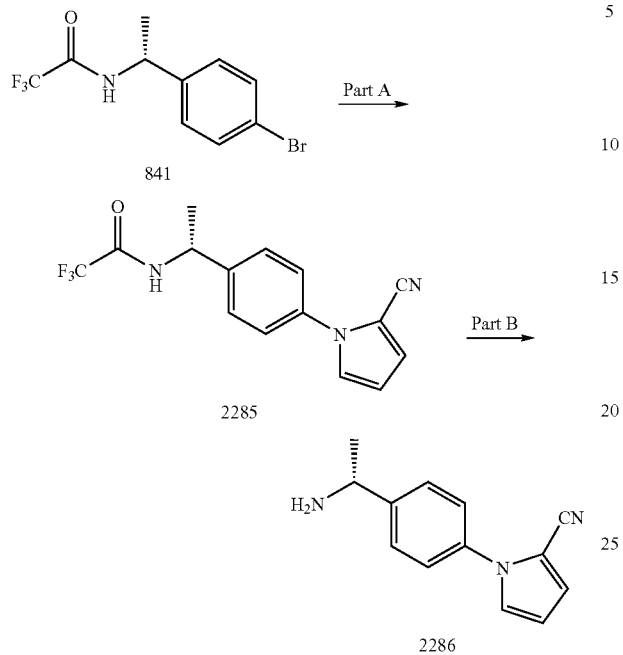

Part A:

To a mixture of compound 841 (2.96 g, 10 mmol), pyrrole-2-carbonitrile (1.1 g, 12 mmol) and 1,10-phenanthroline (1.17 g, 6.5 mmol) in DMA (10 mL) was added cesium carbonate (6.52 g, 20 mmol) and CuI (0.42 g, 2.2 mmol) and the mixture was heated at 150° C. for 18 hours. The mixture was filtered and rinsed with EtOAc (100 mL). The filtrate was washed with water (2×10 mL) and brine (10 mL), dried over MgSO$_4$ and concentrated. Purification by column chromatography (SiO$_2$, 10% EtOAc/hexane followed by 20% EtOAc/hexane) afforded compound 2285 as an oil (0.17 g, 5.7%).

Part B:

A mixture of compound 2285 (0.17 g, 0.57 mmol) and aq. 1M LiOH (1 mL, 1 mmol) in dioxane (3 mL) was stirred at room temperature for 18 hours. The reaction mixture was concentrated and added water (2 mL) and extracted with CH$_2$Cl$_2$ (2×10 mL). The organic layer was dried over MgSO$_4$, filtered and concentrated. Purification by column chromatography (SiO$_2$, 1% MeOH/CH$_2$Cl$_2$ followed by 5% MeOH/CH$_2$Cl$_2$) afforded compound 2286 as an oil (0.085 g, 71%).

Example 52F

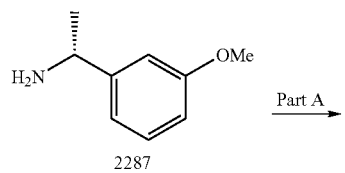

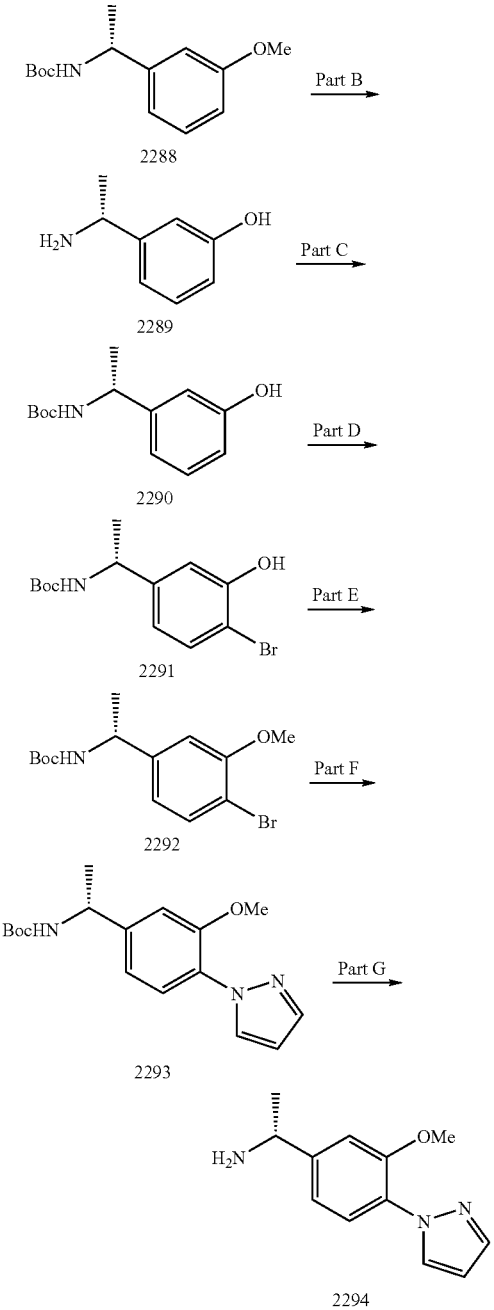

Part A:

To a solution of compound 2287 (20.6 g, 136.4 mmol) in CH$_2$Cl$_2$ (200 mL) was added triethylamine (27.5 g, 272.8 mmol) and the reaction mixture was cooled to 0° C., and (Boc)$_2$O (32.7 g, 150 mmol) was added. The mixture was stirred at 0° C. for 10 minutes and then warmed to room temperature and stirred for 4 hours. The reaction mixture was washed with aq. sat. NH$_4$Cl (100 mL) and dried over MgSO$_4$, filtered and concentrated. Purification by column chromatography (SiO$_2$, 10% EtOAc/hexane followed by 15% EtOAc/hexane) afforded the compound 2288 as white solid (32.7 g, 95%).

Part B:

To a solution of compound 2288 (3.95 g, 15.7 mmol) in CH$_2$Cl$_2$ (200 mL) at −78° C. was added a solution of 1M BBr3/CH$_2$Cl$_2$ (37 mL) dropwise via a dropping funnel over 15 minutes. The reaction mixture was stirred at −78° C. for 2 hours, then poured carefully into MeOH (100 mL) and concentrated to a brown tar (3.6 g). Trituration with ether (3×20 mL) and concentrated afforded compound 2289 as brown tar which was used in next reaction without further purification.

Part C:

The crude compound 2289 was suspended in CH$_2$Cl$_2$ (100 mL) and triethylamine (8.8 mL, 63 mmol) was added. The reaction mixture was cooled to 0° C. and (Boc)$_2$O (3.77 g, 17.3 mmol) was added. The mixture was stirred at room temperature for 1 hour. The reaction mixture was then washed with water (100 mL), sat. NaHCO$_3$ (25 mL) and brine (10 mL). The organic layer was dried over MgSO$_4$, filtered and concentrated. Purification by column chromatography (SiO$_2$, 10% EtOAc/hexane followed by 15% EtOAc/hexane and 20% EtOAc/hexane) afforded compound 2290 as an oil (1.85 g, 62% over two steps).

Part D:

To a solution of compound 2290 (0.45 g, 1.9 mmol) in CH$_2$Cl$_2$ (10 mL) was added a solution of NBS (0.34 g, 1.9 mmol) in CH$_2$Cl$_2$ (10 mL) via a dropping funnel. Stirred at room temperature for 3.5 hours and then washed with aq. 10% H$_2$SO$_4$ (10 mL). The organic layer was dried over MgSO$_4$, filtered and concentrated. Purification by column chromatography (SiO$_2$, 100% CH$_2$Cl$_2$ followed by 1% EtOAc/CH$_2$Cl$_2$) afforded compound 2291 (0.13 g, 21%).

Part E:

To a solution of compound 2291 (0.22 g, 0.7 mmol) in acetone (6 mL) was added K$_2$CO$_3$ (0.288 g, 2.1 mmol) followed by a solution of methyl iodide (0.065 mL, 1.05 mmol) and the reaction mixture was stirred at room temperature for 18 hours. The mixture was filtered and concentrated to dryness. The residue was dissolved in EtOAc (20 mL) and washed with water (2 mL) followed by brine (2 mL). The organic layer was dried over MgSO$_4$, filtered and concentrated to afford the compound 2292 (0.2 g, 86%).

Part F:

Compound 2293 was prepared following the procedure described in Example 52E, Part A.

Part G:

Compound 2294 was prepared from compound 2293 via TFA deprotection as described in Example 1.

Example 52G

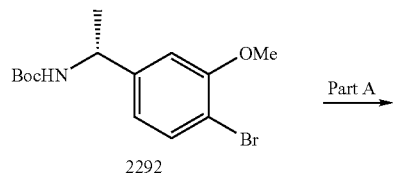

2292

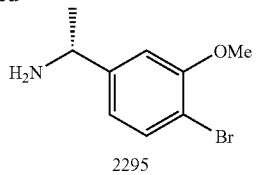

2295

Part A:

Compound 2295 was prepared from compound 2292 2293 via TFA as described in Example 1.

Examples 52H

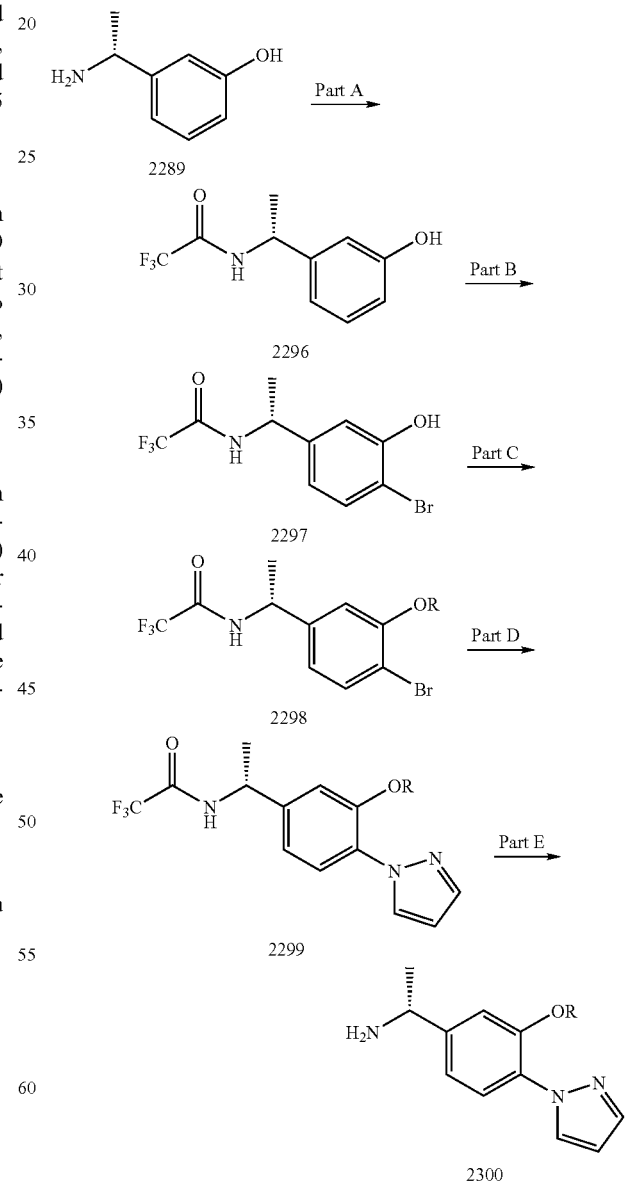

R = Bn, H$_2$C—◁

Part A:

Compound 2289 was converted to compound 2296 via the procedure described in Example 52F Part C and using trifluoroacetic anhydride in place of Boc$_2$O.

Part B, C, D:

Compounds 2297, 2298 and 2299 were prepared following the procedures described in Example 52F, Part D, E and F using benzyl bromide and cyclopropyl bromide in place of methyl iodide.

Part E:

Compound 2300 were prepared from compound 2299 following the procedures described in Example 52E, Part B.

Example 52I

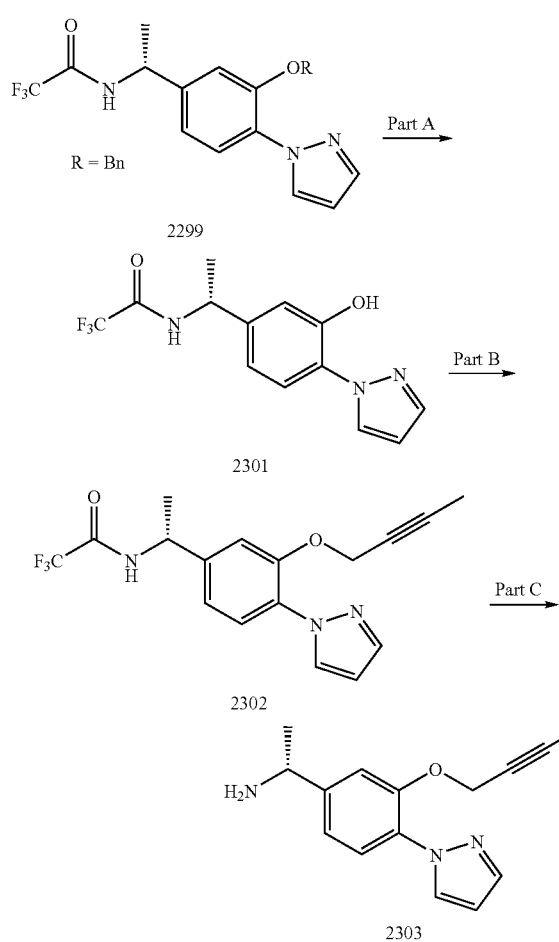

Part A:

A mixture of compound 2299 (0.27 g, 0.69 mmol), 10% Pd—C (0.18 g) and EtOH (25 mL) was stirred under hydrogen atmosphere at 55 psi for 18 hours. Filtered through celite and rinsed with CH$_2$Cl$_2$ and concentrated to afford the desired compound 2301 (0.21 g, 100%).

Part B, C:

Compounds 2302 and 2303 were prepared following the procedures described in Example 52H, Part C and E and using 1-bromo-2-butyne as the alkylating reagent.

Example 52J

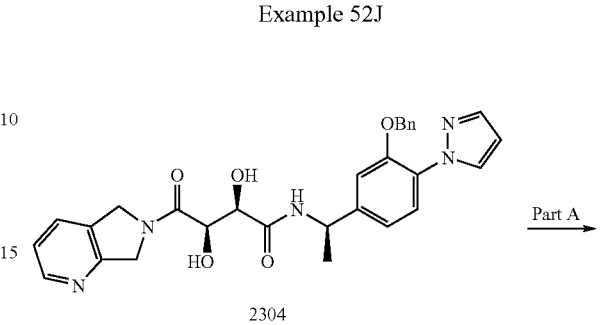

Part A:

A mixture of compound 2304 (60 mg), 10% Pd—C (30 mg) and MeOH (10 mL) was stirred at room temperature under hydrogen atmosphere for 18 hours. Filtered and rinsed with CH$_2$Cl$_2$ and concentrated to afford the desired product 2305 (50 mg).

Example 52K

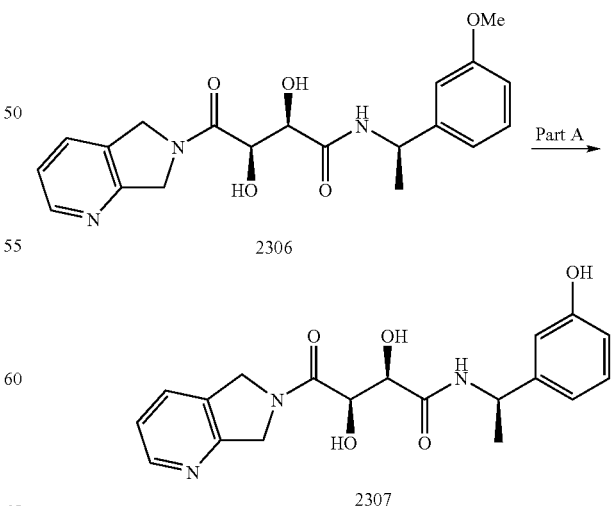

Part A:

Compound 2307 was prepared from compound 2306 following the procedure described in Example 52F, Part B.

Example 52L

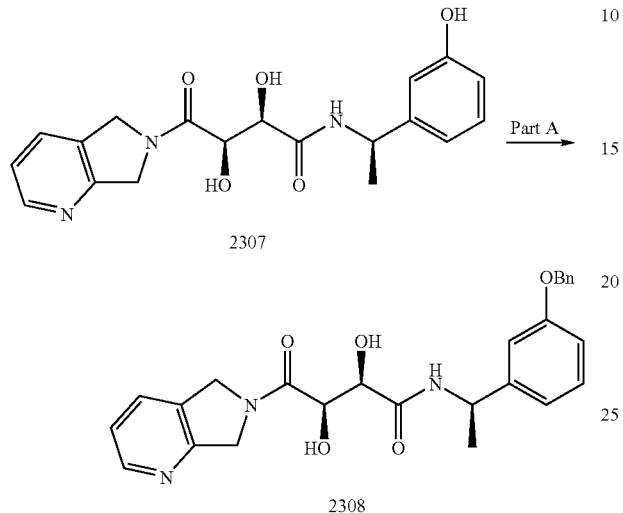

Part A:

To a mixture of 2307 (0.065 g, 0.18 mmol) in acetone (10 mL) was added K$_2$CO$_3$ (0.082 g, 0.59 mmol) followed by benzyl bromide (0.022 mL, 0.19 mmol) and the reaction mixture was refluxed for 18 hours. DMF (0.5 mL) was added to the reaction mixture and heated at 70° C. for 18 hours. The reaction mixture was cooled to room temperature and EtOAc (5 mL) was added, then was washed with water (2×1 mL) followed by brine (1 mL). The organic layer was dried over MgSO$_4$, filtered and concentrated. Purification by column chromatography (SiO$_2$, 5% MeOH(NH$_3$)/CH$_2$Cl$_2$) afforded 2308 (0.019 g, 23%).

Example 52M

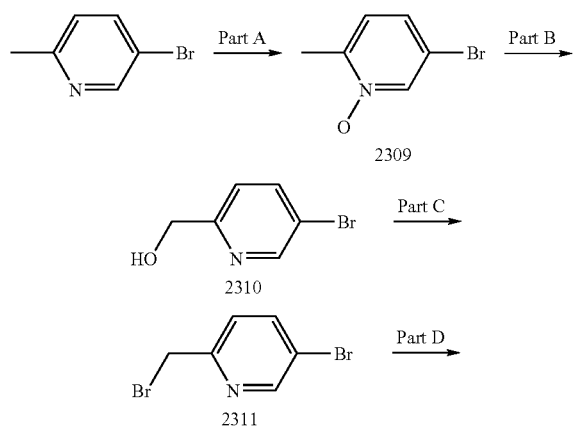

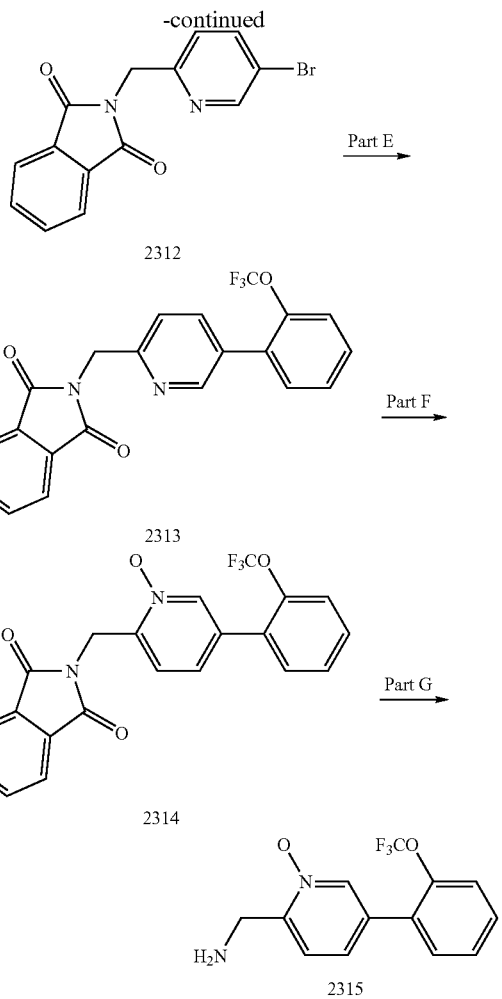

Part A:

To a solution of 5-bromopicoline (20 g, 116 mmol) in chloroform (100 mL) at 0° C. was added portionwise 77% mCPBA (28.7 g, 128 mmol) over 20 min. The reaction mixture was allowed to stir at room temperature overnight, after which time the solid was filtered off, the filtrate was washed with saturated Na$_2$CO$_3$, dried over Na$_2$SO$_4$, and concentrated to afford 2309 (17.83 g, 82%) as a white solid. $^1$H NMR (400 MHz, CDCl$_3$) δ 8.39 (s, 1H), 7.29 (d, J=8.0 Hz, 1H), 7.12 (d, J=8.3 Hz, 1H), 2.47 (s, 3H).

Part B:

Compound 2309 (15 g, 80 mmol) was cooled to 0° C., and trifluoroacetic anhydride (35 mL, 250 mmol) was slowly added under argon. The mixture was allowed to stir at room temperature for 30 min, then at 55° C. for 30 min after which it was cooled to 0° C. in an ice bath. NaHCO$_3$ aqueous solution (10%, 150 mL) was slowly added with caution. After the completion of addition, the mixture was allowed to stir at room temperature for 6 h. The solution was extracted with dichloromethane, dried over Na$_2$SO$_4$, and concentrated. The residue was purified by flash column chromatography on silica gel (EtOAc/hexane 50:50), affording product 2310 as a white solid (9.2 g, 61%). $^1$H NMR (400 MHz, CDCl$_3$) δ 8.61 (d, J=1.9 Hz, 1H), 7.80 (dd, J=7.9, 2.4 Hz, 1H), 7.19 (dd, J=8.3, 0.9 Hz, 1H), 4.73 (s, 2H), 3.37 (br s, 1H).

Part C:

To a solution of 2310 (9.0 g, 47.86 mmol) in toluene (40 mL) was added PBr$_3$ (5 mL, 52.6 mmol) dropwise. After the completion of addition, the mixture was stirred at 100° C. for 2 h. It was cooled to room temperature; the solid was collected by filtration to afford 2311 as a yellow solid (HBr salt, 14.83 g, 93%). $^1$H NMR (400 MHz, DMSO-d$_6$) δ 9.74 (br, 1H), 8.66 (d, J=1.8 Hz, 1H), 8.06 (dd, J=8.4, 1.4 Hz, 1H), 7.19 (dd, J=8.3, 0.9 Hz, 1H), 4.67 (s, 2H).

Part D:

To a solution of 2311 (14.83 g, 44.7 mmol) in DMF at 0° C. was slowly added Cs$_2$CO$_3$ (29.1 g, 89.4 mmol) and potassium phthalimde (9.1 g, 49.2 mmol). The reaction mixture was allowed to stir at room temperature for 6 h after which the solvent was evaporated to dryness. The resulting solid was washed with H$_2$O. The solid cake was recrystallized in hot EtOH, affording compound 2312 (7.64 g, 54%) as a white solid. $^1$H NMR (400 MHz, DMSO-d$_6$) δ 8.54 (d, J=1.9 Hz, 1H), 8.00 (dd, J=8.4, 2.3 Hz, 1H), 7.90-7.83 (m, 4H), 7.41 (d, J=7.8 Hz, 1H), 4.88 (s, 2H).

Part E:

A mixture of Pd(OAc)$_2$ (45 mg, 0.2 mmol), 2-bis(tert-butyl)phosphino-biphenyl (120 mg, 0.4 mmol), compound 2312 (3.17 g, 10 mmol), 2-trifluoromethoxyphenyl boronic acid (2.47 g, 12 mmol) and KF (2.1 g, 36 mmol) was charged into a 250-mL round bottom flask. Then THF (30 mL) was added under argon, and the reaction mixture was allowed to stir at 50° C. overnight, after which it was cooled to room temperature, filtered through celite and concentrated. Flash column chromatography on silica gel (EtOAc/hexane (5:95) provided compound 2313 (3.27 g, 82%) as a white solid. $^1$H NMR (400 MHz, CDCl$_3$) δ 8.59 (d, J=1.5 Hz, 1H), 7.91-7.89 (m, 2H), 7.77-7.73 (m, 3H), 7.44-7.34 (m, 5H), 5.08 (s, 2H).

Part F:

Compound 2314 was prepared according to the same procedure as in Example 52M Part A. HPLC-MS t$_R$=1.74 min (UV$_{254\ nm}$); mass calculated for formula C$_{21}$H$_{13}$F$_3$N$_2$O$_4$ 414.1, observed LCMS m/z 415.0 (M+H).

Part G:

To a solution of compound 2314 (210 mg, 0.51 mmol) in EtOH (10 mL) was added with hydrazine (0.5 mL). The solution was refluxed for 3 h, then cooled to room temperature. After removing the precipitate by filtration, the solution was concentrated. The resulting residue was extracted with Et$_2$O and concentrated, affording compound 2315 as a pale yellow oil (160 mg, 91%). HPLC-MS t$_R$=1.74 min (UV$_{254\ nm}$); mass calculated for formula C$_{13}$H$_{11}$F$_3$N$_2$O$_2$ 284.1, observed LCMS m/z 285.1 (M+H).

Example 52N

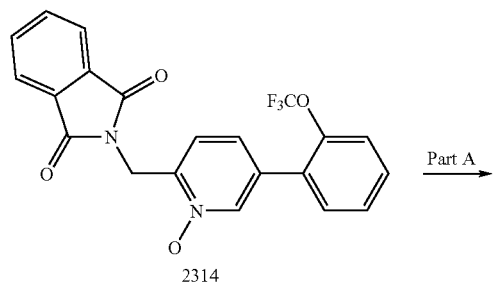

-continued

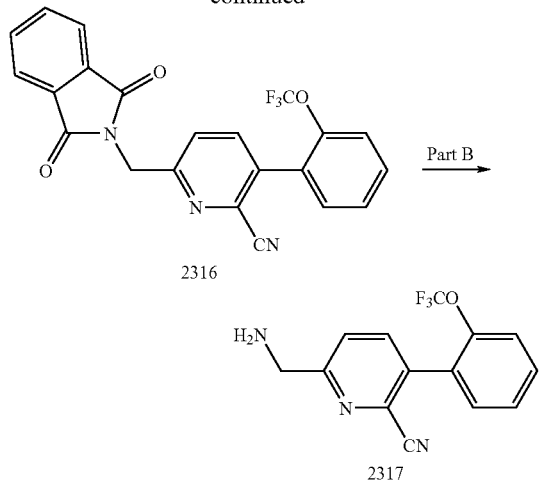

Part A:

To compound 2314 (200 mg, 0.48 mmol) in acetonitrile (1 mL) was added Et$_3$N (0.094 mL, 0.672 mmol) and Me$_3$SiCN (0.225 mL, 1.69 mmol) subsequently under argon. The reaction mixture was stirred at 80° C. for 48 h, after which it was cooled to room temperature and concentrated in vacuo. The residue was dissolved in EtOAc, washed with saturated NaHCO$_3$, brine, dried (Na$_2$SO$_4$), and concentrated. Flash column chromatography (EtOAc/hexane 40:60) afforded compound 2316 (130 mg, 64%). HPLC-MS t$_R$=2.06 min (UV$_{254\ nm}$); mass calculated for formula C$_{22}$H$_{12}$F$_3$N$_3$O$_3$ 423.1, observed LCMS m/z 424.0 (M+H).

Part B:

Compound 2317 was prepared using the procedure described in Example 52M Part G. $^1$H NMR (400 MHz, CDCl$_3$) δ 7.77 (d, J=8.1 Hz, 1H), 7.60 (d, J=8.0 Hz, 1H), 7.47-7.42 (m, 4H), 4.12 (s, 2H). 1.98 (br s, 2H).

Example 52O

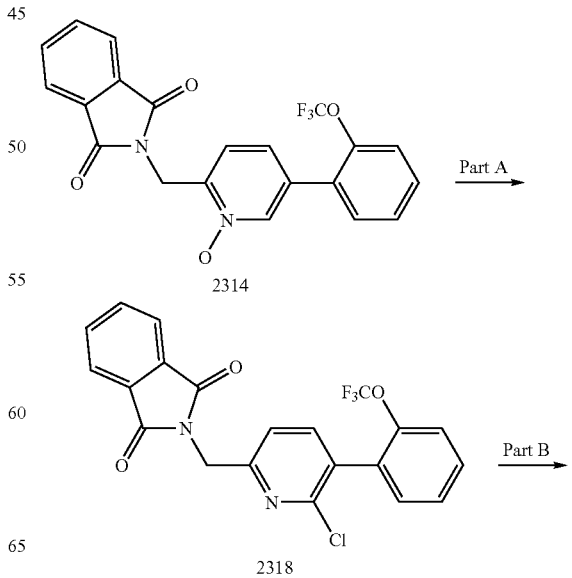

-continued

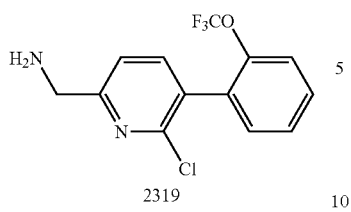

2319

Part A:

Phosphorous trichloride (0.330 mL, 3.62 mmol) was added to a solution of 2314 (300 mg, 0.72 mmol) in CHCl$_3$ (1 mL). The reaction mixture was stirred at 60° C. overnight, after which it was cooled to room temperature and concentrated in vacuo. The residue was dissolved in EtOAc, washed with saturated NaHCO$_3$, brine, dried (Na$_2$SO$_4$), and concentrated. Flash column chromatography (EtOAc/hexane 30:70) afforded 2318 (180 mg, 58%). HPLC-MS $t_R$=2.33 min (UV$_{254\ nm}$); mass calculated for formula C$_{21}$H$_{12}$ClF$_3$N$_2$O$_3$ 432.1, observed LCMS m/z 433.0 (M+H).

Part B:

Compound 2319 was prepared using the procedure described in Example 52M Part G. HPLC-MS $t_R$=1.26 min (UV$_{254\ nm}$); mass calculated for formula C$_{13}$H$_{10}$ClF$_3$N$_2$O 302.0, observed LCMS m/z 303.0 (M+H).

Example 52P

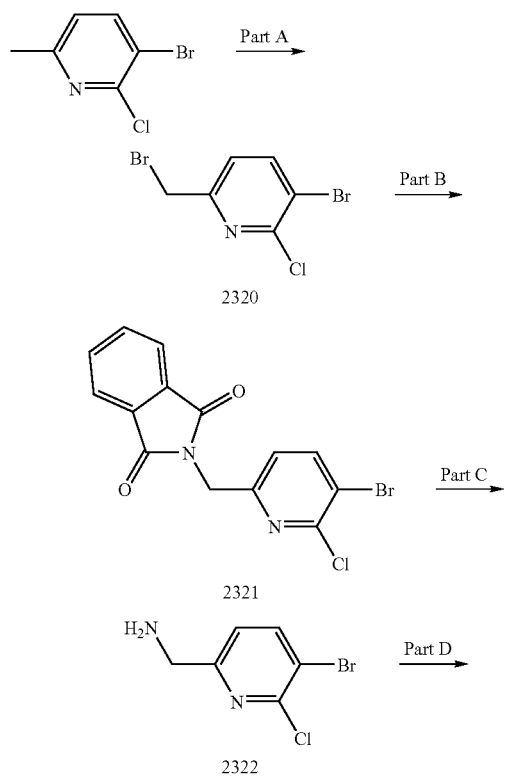

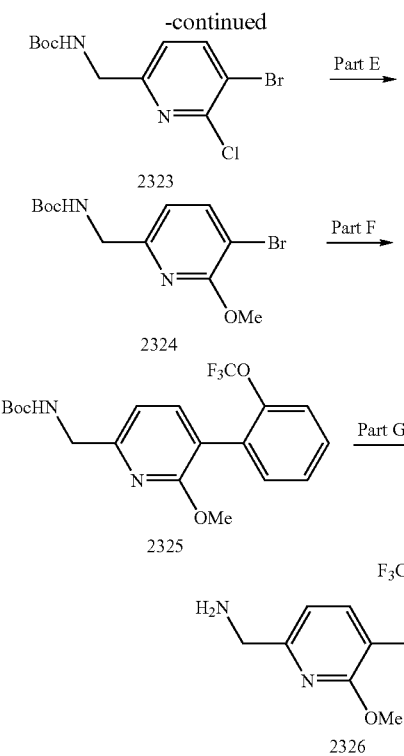

Part A:

3-Bromo-2-chloro-6-picoline (1.0 g, 4.84 mmol) and NBS (1.20 g, 6.78 mmol) were dissolved in CCl$_4$ (20 mL). The solution was briefly flushed with argon, then AIBN (16 mg, 0.097 mmol) was added. The mixture was stirred at room temperature overnight, after which the solvent was evaporated in vacuo. The residue was purified by flash column chromatography (EtOAc/hexane 5:95) providing compound 2320 as a white solid (1.28 g, 92%). $^1$H NMR (400 MHz, CDCl$_3$) δ 8.01 (d, J=8.2 Hz, 1H), 7.65 (d, J=8.2 Hz, 1H), 4.19 (s, 2H).

Part B:

Compound 2321 was prepared according to the procedure described in Example 52M, Part D. $^1$H NMR (400 MHz, DMSO-d$_6$) δ 8.19 (d, J=8.0 Hz, 1H), 7.92-7.84 (m, 4H), 7.41 (d, J=8.0 Hz, 1H), 4.86 (s, 2H).

Part C:

Compound 2322 was prepared according to the procedure described in Example 52M, Part G. $^1$H NMR (400 MHz, CDCl$_3$) δ 7.87 (d, J=8.0 Hz, 1H), 7.41 (d, J=8.1 Hz, 1H), 3.93 (s, 2H), 1.78 (br s, 2H).

Part D:

Compound 2322 (370 mg, 1.67 mmol) in THF (10 mL) was added dropwise into the solution of Boc$_2$O (437 mg, 2.0 mmol) in THF (10 mL), followed by DIEA (300 mL). The mixture was stirred at room temperature overnight and concentrated. Column chromatography on silica gel (EtOAc/hexane 20:80) provided compound 2323 (450 mg, 84%) as a white solid. $^1$H NMR (400 MHz, CDCl$_3$) δ 7.89 (d, J=7.5 Hz, 1H), 7.12 (d, J=8.2 Hz, 1H), 5.35 (br s, 1H), 4.37 (d, J=5.9 Hz, 2H), 1.47 (s, 9H).

Part E:

Sodium (4 pellets) was dissolved in MeOH (15 mL). The mixture was stirred at room temperature for 10 min until all the sodium had reacted. To this solution was added compound 2323 (450 mg, 1.4 mmol) in MeOH (5 mL) via syringe. The reaction mixture was stirred at 60° C. for 48 h and concentrated. The residue was dissolved with EtOAc and 1 N NH$_4$Cl solution, washed with brine, dried over Na$_2$SO$_4$, and concentrated. Column chromatography (SiO$_2$, EtOAc/hexane 20:80) afforded compound 2324 as a white solid (350 mg, 79%). $^1$H NMR (400 MHz, CDCl$_3$) δ 7.43 (d, J=7.3 Hz, 1H), 6.73 (d, J=7.5 Hz, 1H), 5.26 (br s, 1H), 4.32 (d, J=5.1 Hz, 2H), 4.02 (s, 3H), 1.48 (s, 9H).

Part F:

Compound 2325 was prepared according to the same procedure as in Example 52M Part E for the Suzuki coupling. HPLC-MS $t_R$=2.35 min (UV$_{254\ nm}$); mass calculated for formula C$_{19}$H$_{21}$F$_3$N$_2$O$_4$ 398.2, observed LCMS m/z 399.1 (M+H).

Part G:

Compound 2325 was deprotected with TFA in CH$_2$Cl$_2$. HPLC-MS $t_R$=1.12 min (UV$_{254\ nm}$); mass calculated for formula C$_{14}$H$_{13}$F$_3$N$_2$O$_2$ 298.1, observed LCMS m/z 299.0 (M+H).

Example 52Q reaction mixture was diluted with ethyl acetate (200 mL) and washed in sequence with water (2×100 mL) and brine (1×100 mL). The organics were dried and concentrated to yield a crude which was subjected to silica-gel column chromatography (10% ethyl acetate/hexane) to yield pure 2328 (0.2 g, 0.6 mmol).

Part B:

LiAlH$_4$ was added to dry THF (40 mL) and the mixture was then cooled to 0° C. Then ester 2328 (0.2 g, 0.6 mmol) in THF (5 mL) was added to the mixture dropwise. The reaction mixture was allowed to warm to ambient temperature and stirred for 48 h, then cooled back to 0° C. and quenched by the sequential addition of 1 mL of water, 2 mL of 0.5 N NaOH, and 1 mL of water. The resulting mixture was stirred vigorously for 2 h and then filtered through Celite. The filtrate was concentrated to yield pure 2329 as an oil (0.2 g, 0.6 mmol).

Part C:

Alcohol 2329 (0.2 g, 0.6 mmol) and triethylamine (0.18 g, 1.8 mmol) were dissolved in CH$_2$Cl$_2$ (200 mL) and cooled to 0° C. The cooled solution was stirred, and CH$_3$SO$_2$Cl (as a CH$_2$Cl$_2$ solution; 0.2 g, 1.8 mmol, 5 mL CH$_2$Cl$_2$) was added dropwise, and the stirring was continued for 24 h. The reaction mixture was then washed two times with 50 mL of water and two times with 50 mL of brine. The organic and aqueous phases were separated, and the organic phase was dried, and concentrated to provide pure product 2330 as an oil (0.21 g).

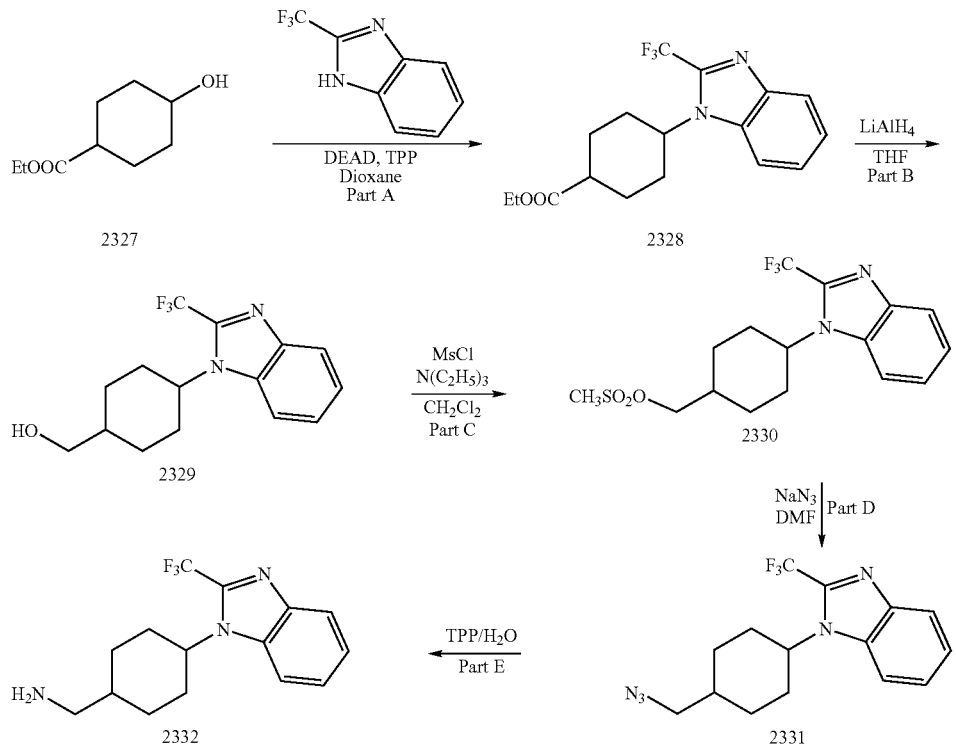

Part A:

Ethyl-4-hydroxycyclohexylcarboxylate (2327) (cis/trans mixture) (4.3 g, 25 mmol), 2-trifluoromethylbenzimidazole (4.65 g, 25 mmol), and triphenylphosphine (9.8 g, 37.5 mmol) were dissolved in dioxane (60 mL). The resulting solution was treated with diethyldiazodicarboxylate (6.5 g, 37.5 mmol), dropwise, over a period of 1 h and stirred for 16 h. The Part D:

The mesylate 2330 was dissolved in DMF (10 mL) and treated with NaN$_3$ (0.23 g, 1.8 mmol), and the mixture was stirred vigorously for 36-72 h. The reaction mixture was then diluted with 100 mL water and extracted with ethyl acetate (2×100 mL). The organic phases were combined, dried, and concentrated to yield pure azide 2331 (0.19 g, 87%).

Part E:

The azide 2331 (0.19 g, 0.6 mmol)) and triphenylphosphine (0.15 g, 0.6 mmol) were dissolved in 5 mL of THF, and then water (0.6 mL, 33.3 mmol) was added. The resulting mixture was stirred vigorously for 16-24 h. The solvent was removed and the crude amine 2332 was taken to the next step without further purification.

The following compounds were prepared using previously described procedures.

| Compound # | Structure | Exact mass | MS m/z (M + H) |
| --- | --- | --- | --- |
| 2333 | 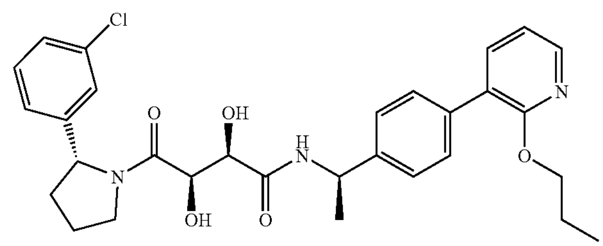 | 537.2 | 538.1 |
| 2334 | 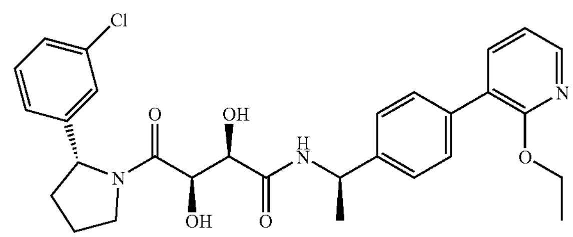 | 523.2 | 524.1 |
| 2335 | 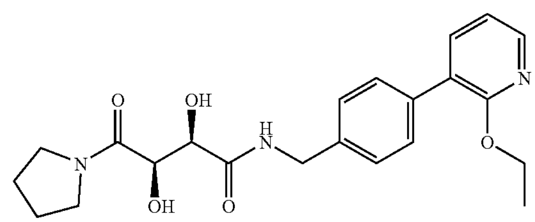 | 413.2 | 414.2 |
| 2336 | 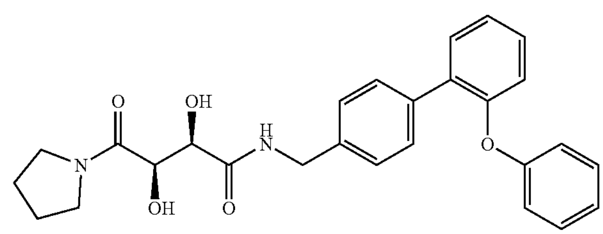 | 460.2 | 461.0 |
| 2337 | 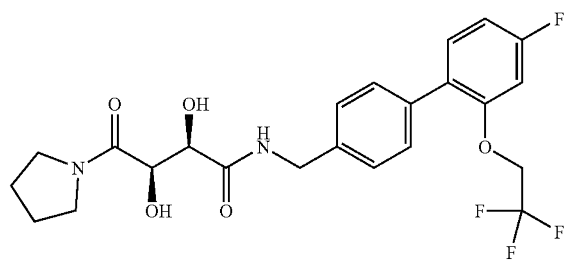 | 484.2 | 485.2 |

-continued

| Compound # | Structure | Exact mass | MS m/z (M + H) |
|---|---|---|---|
| 2338 | 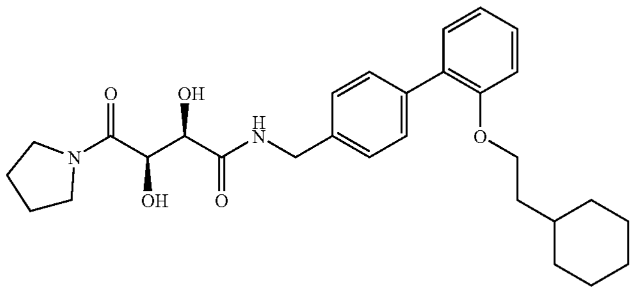 | 494.3 | 495.2 |
| 2339 | 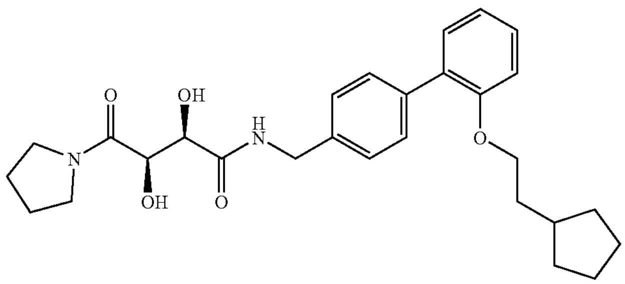 | 480.3 | 481.1 |
| 2340 | 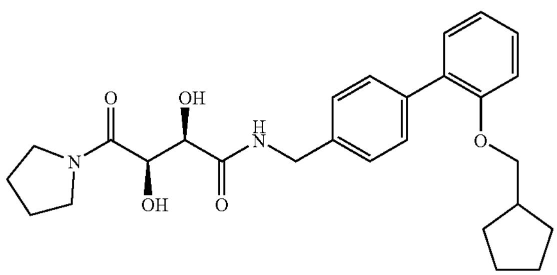 | 466.3 | 467.2 |
| 2341 | 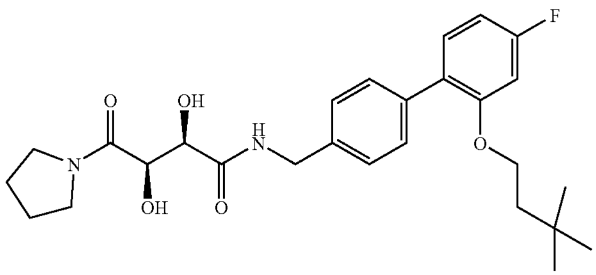 | 486.3 | 487.2 |
| 2342 | 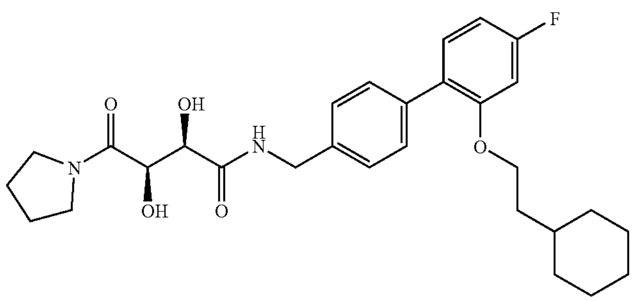 | 512.3 | 513.2 |

-continued
| Compound # | Structure | Exact mass | MS m/z (M + H) |
|---|---|---|---|
| 2343 | 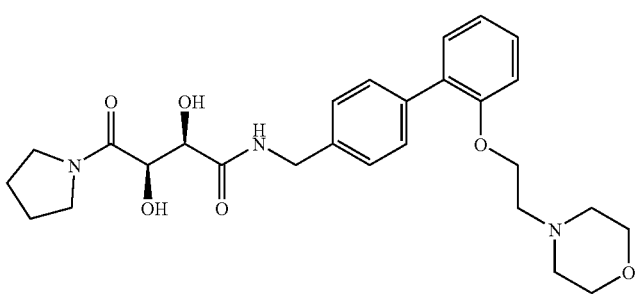 | 497.3 | 498.2 |
| 2344 | 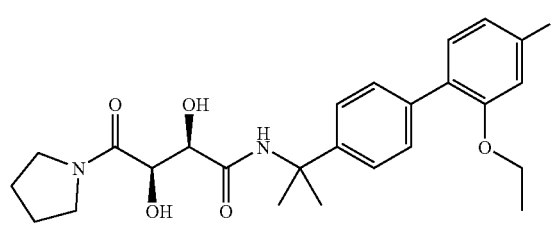 | 458.2 | 459.2 |
| 2345 | 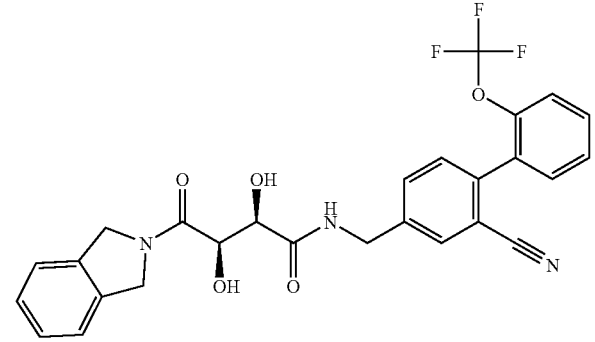 | 526.2 | 527.0 |
| 2346 | 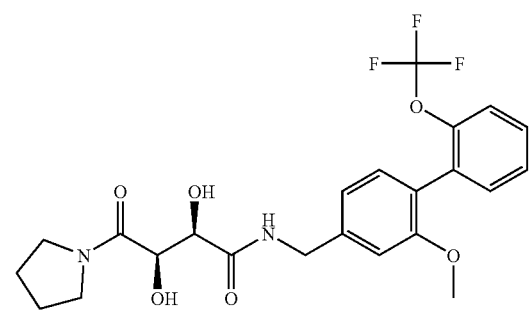 | 483.2 | 484.0 |
| 2347 | 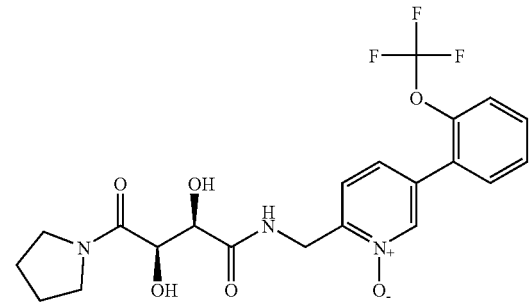 | 469.2 | 470.0 |

-continued

| Compound # | Structure | Exact mass | MS m/z (M + H) |
|---|---|---|---|
| 2348 | 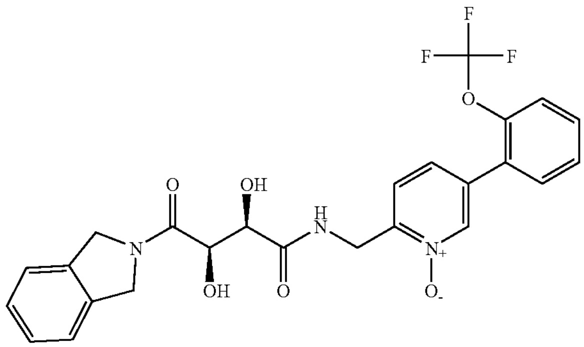 | 517.2 | 518.0 |
| 2349 | 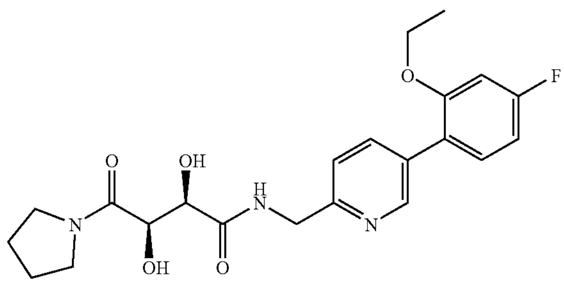 | 431.2 | 432.1 |
| 2350 | 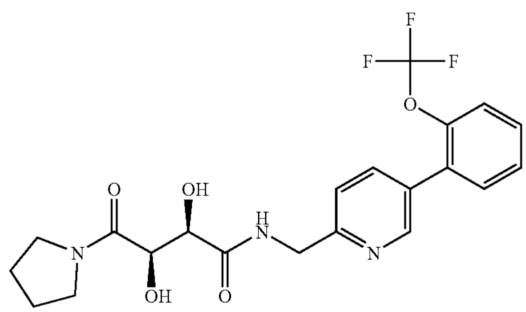 | 453.2 | 454.1 |
| 2351 | 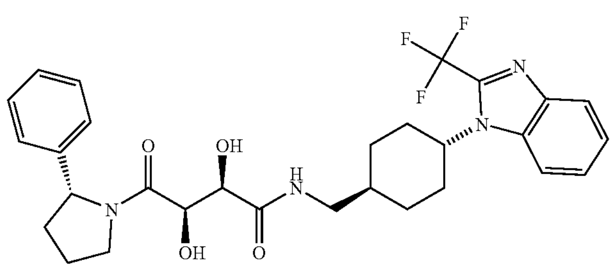 | 558.2 | 559.1 |
| 2352 | 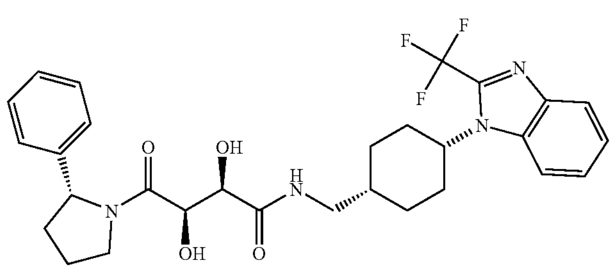 | 558.2 | 559.1 |

-continued

| Compound # | Structure | Exact mass | MS m/z (M + H) |
|---|---|---|---|
| 2306 | 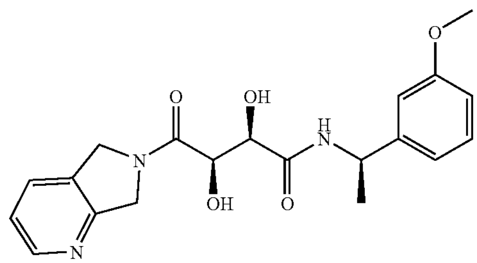 | 385.2 | 386.1 |
| 2307 | 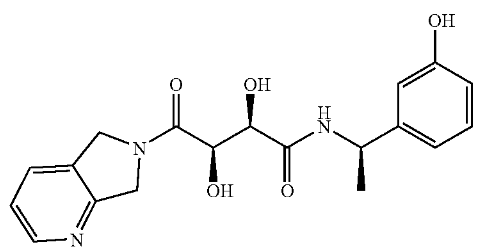 | 371.2 | 372.1 |
| 2308 | 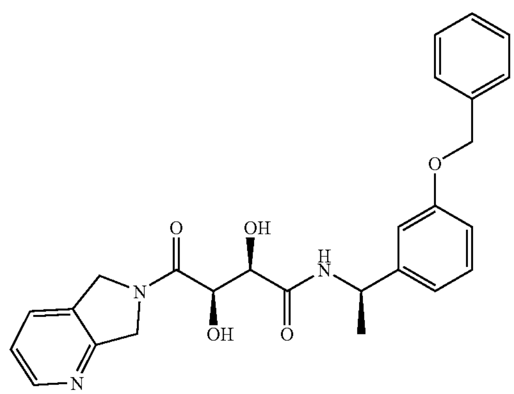 | 461.2 | 462.1 |
| 2353A | 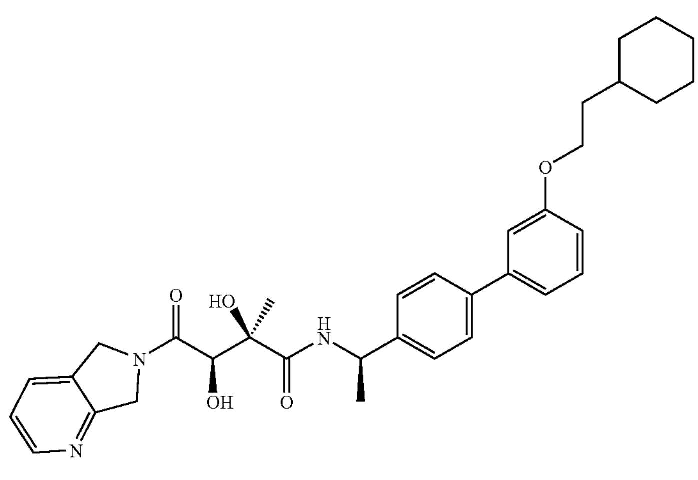 | 571.3 | 572.3 |

-continued

| Compound # | Structure | Exact mass | MS m/z (M + H) |
|---|---|---|---|
| 2353B | 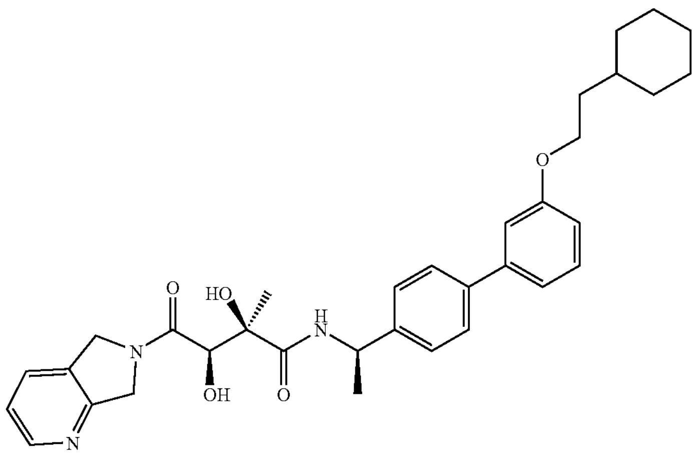 | 557.3 | 558.1 |
| 2354 | 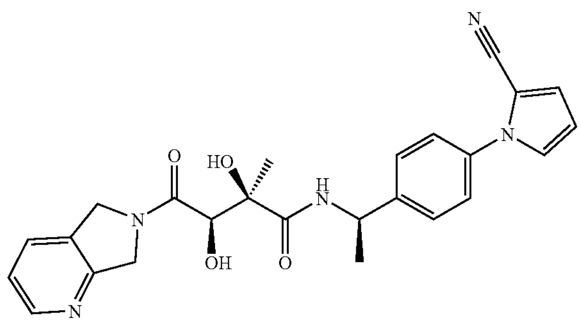 | 459.2 | 460.1 |
| 2355 | 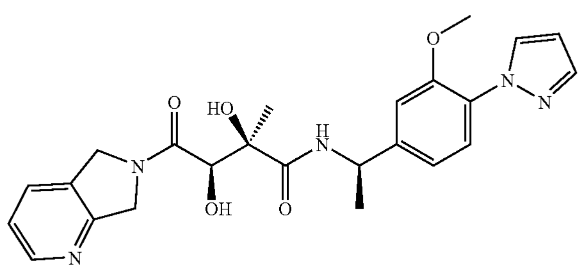 | 465.2 | 466.3 |
| 2356 | 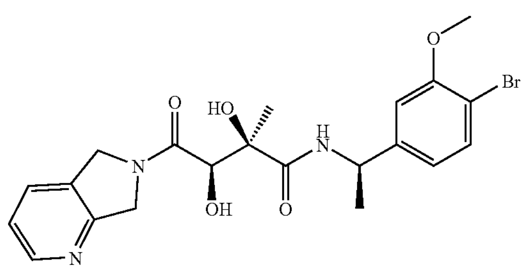 | 477.1 | 478.3 |

-continued

| Compound # | Structure | Exact mass | MS m/z (M + H) |
|---|---|---|---|
| 2357 | 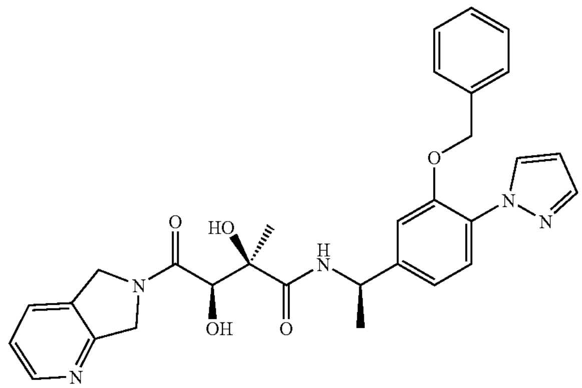 | 541.2 | 542.3 |
| 2358 | 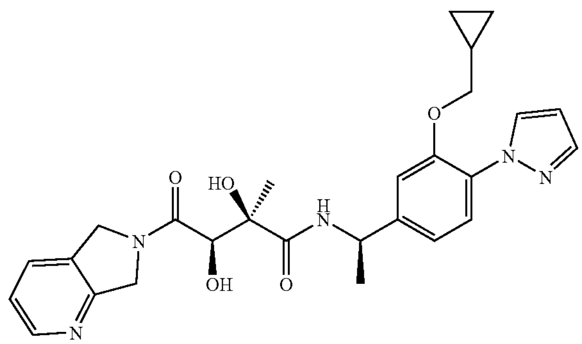 | 505.2 | 506.3 |
| 2304 | 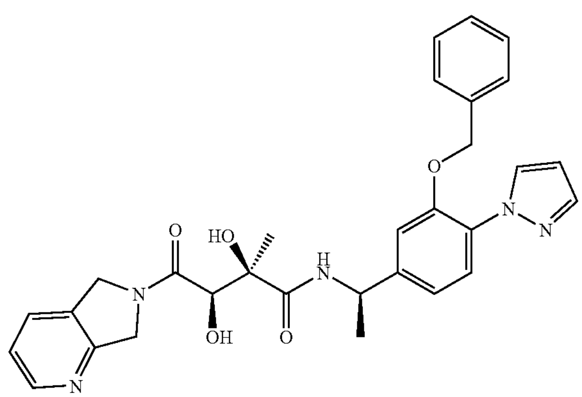 | 527.2 | 528.3 |
| 2359 | 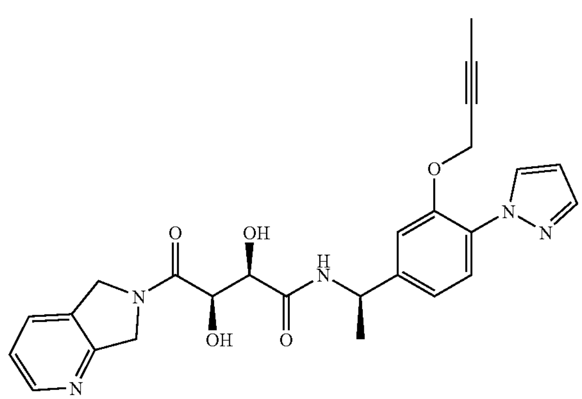 | 489.2 | 490.3 |

-continued
| Compound # | Structure | Exact mass | MS m/z (M + H) |
|---|---|---|---|
| 2360 | 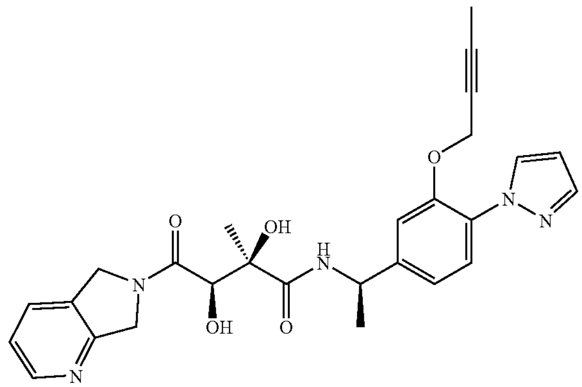 | 503.2 | 504.3 |
| 2305 | 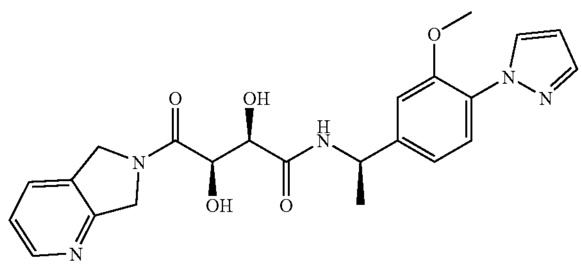 | 437.2 | 438.1 |
Example 53
Example 53A
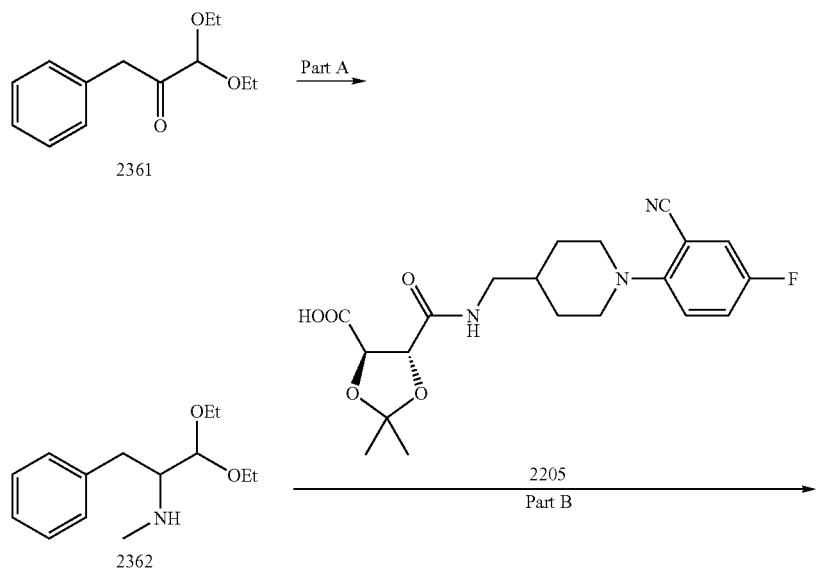

-continued

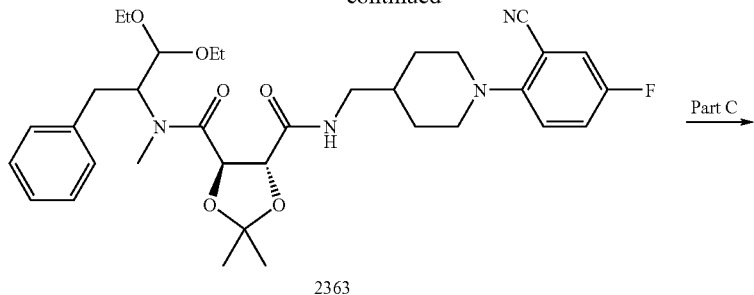

2363

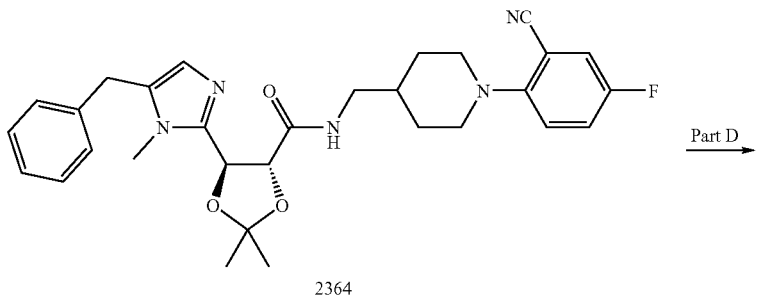

2364

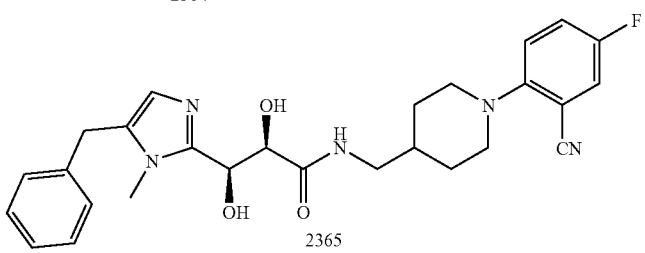

2365

Part A:

Compound 2361 was prepared using procedures described in Adamczyk, M. et al. *Synth. Commun.* 2002, 32, 3199-3205.

According to a modification of a procedure by Neidigh, K. A. et al. (*J. Chem. Soc. Perkin Trans.* 1 1998, 2527-2531) a mixture of ketone 2361 (1.56 g, 7 mmol), titanium (IV) isopropoxide (4.1 mL, 14 mmol), methylamine hydrochloride (0.94 g, 14 mmol) and triethylamine (1.95 mL, 14 mmol) in ethanol (15 mL) was stirred at rt overnight. Then sodium borohydride (0.4 g, 10.5 mmol) was added and the resulting mixture was stirred at rt for 8 h. The reaction mixture was then poured into aqueous ammonium hydroxide (40 mL), the resulting white inorganic precipitate was filtered off, and washed several times with dichloromethane. The organic layer was separated, and the aqueous phase was extracted with dichloromethane. Combined dichloromethane extracts were washed with brine, concentrated and chromatographed (SiO$_2$, 5% methanol/dichloromethane) to give 2362 (1.03 g, 62%). $^1$H NMR (400 Mhz, CDCl$_3$) δ 7.30-7.17 (m, 5H), 4.31-4.30 (d, 1H), 3.78-3.62 (m, 2H), 3.57-3.47 (m, 2H), 2.97-2.70 (m, 3H), 2.43 (s, 3H), 1.27-1.20 (m, 6H).

Part B:

Compound 2005 was prepared using procedures described in Example 27. Compound 2363 was prepared using the coupling conditions described in Example 1. HPLC-MS $t_R$=2.42 min (UV$_{254\ nm}$); mass calculated for formula C$_{34}$H$_{45}$FN$_4$O$_6$ 624.3, observed LCMS m/z 625.2 (M+H).

Part C:

Compound 2364 was prepared using the cyclization conditions described in Example 29. HPLC-MS $t_R$=1.66 min (UV$_{254\ nm}$); mass calculated for formula C$_{30}$H$_{34}$FN$_5$O$_3$ 531.3, observed LCMS m/z 532.2 (M+H).

Part D:

Compound 2364 was deprotected using procedures described in Example 29. Purification by prep-LC and conversion to a hydrochloric salt afforded 2365 as an off-white solid. HPLC-MS $t_R$=3.54 min (10 min; UV$_{254\ nm}$); mass calculated for formula C$_{27}$H$_{30}$FN$_5$O$_3$ 491.2, observed LCMS m/z 492.1 (M+H).

Example 53B

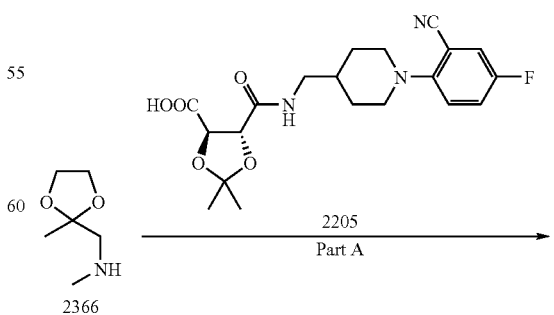

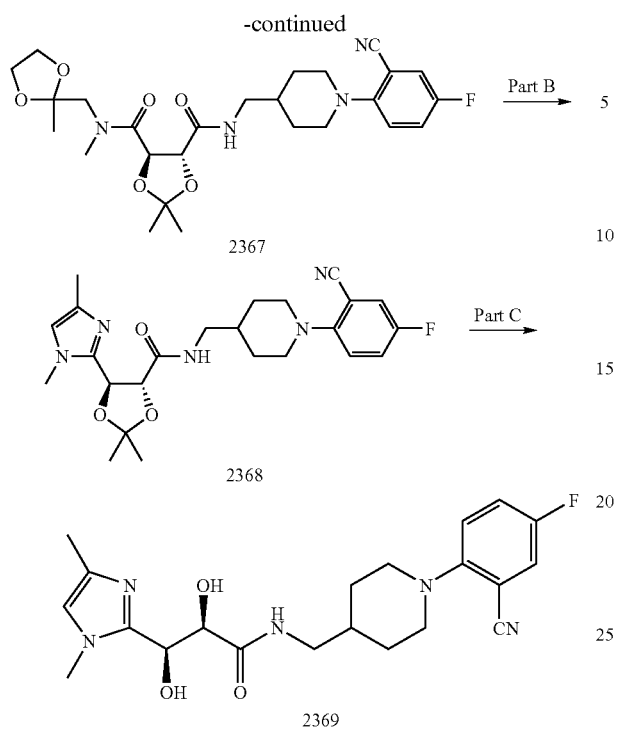

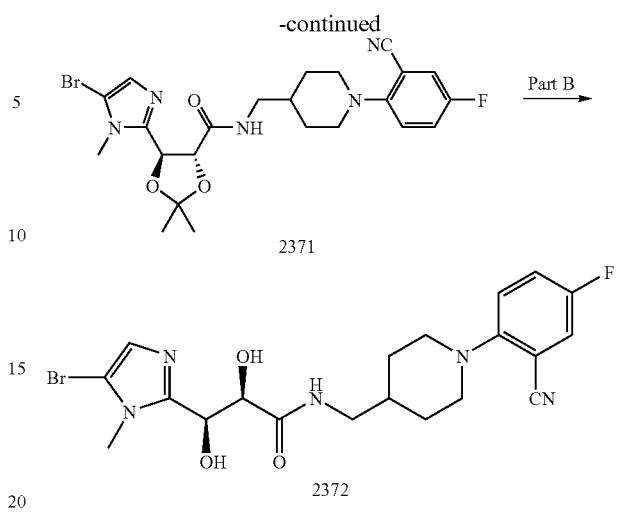

Part A:

Compound 2366 was prepared using procedures described in Waldvogel, E. et al. *Helv. Chim. Acta.* 1997, 80, 2084-2099.

Compound 2367 was prepared using the coupling conditions described in Example 1. HPLC-MS $t_R$=1.88 min (UV$_{254\ nm}$); mass calculated for formula C26H35FN4O6 518.2, observed LCMS m/z 519.2 (M+H).

Part B:

Compound 2368 was prepared using the cyclization conditions described in Example 29. HPLC-MS $t_R$=1.40 min (UV$_{254\ nm}$); mass calculated for formula C24H30FN5O3 455.2, observed LCMS m/z 456.1 (M+H).

Part C:

Compound 2368 was deprotected using procedures described in Example 29. Purification by prep-LC and conversion to a hydrochloric salt afforded 2369 as an off-white solid. HPLC-MS $t_R$=2.99 min (10 min; UV$_{254\ nm}$); mass calculated for formula C$_{21}$H$_{26}$FN$_5$O$_3$ 415.2, observed LCMS m/z 416.2 (M+H).

Example 53C

Part A:

Compound 2370 was prepared using previously described procedures in Example 29. HPLC-MS $t_R$=1.30 min (UV$_{254\ nm}$); mass calculated for formula C23H28FN5O3 441.2, observed LCMS m/z 442.1 (M+H).

According to a modification of a procedure by Miller, R. D. et al. (*Chem. Mater.* 1994, 6, 1023-1032) to an ice cold solution of compound 2370 (104 mg, 0.23 mmol) and pyridine (0.039 mL, 0.48 mmol) in dichloromethane (3 mL) was added dropwise a solution of bromine (0.016 mL, 0.31 mmol) in dichloromethane (1 mL) and the resulting solution was stirred at 0° C. for 20 min. The reaction mixture was quenched with 10% sodium thiosulfate solution, and extracted with dichloromethane. Combined organic extracts were dried, concentrated and chromatographed (SiO$_2$, gradient elution 50% to 80% ethyl acetate/hexane, ethyl acetate followed by 5% methanol/ethyl acetate) to give 2371 as a white solid (35 mg, 37% based on reacted starting material). HPLC-MS $t_R$=1.94 min (UV$_{254\ nm}$); mass calculated for formula C23H27BrFN5O3 519.1, observed LCMS m/z 520.0 (M+H).

Part B:

Compound 2371 was deprotected using procedures described in Example 29. Purification by prep-LC and conversion to a hydrochloric salt afforded 2372 as a white solid. HPLC-MS $t_R$=3.1 min (10 min; UV$_{254\ nm}$); mass calculated for formula C20H23BrFN5O3 479.1, observed LCMS m/z 480.0 (M+H).

Example 53D

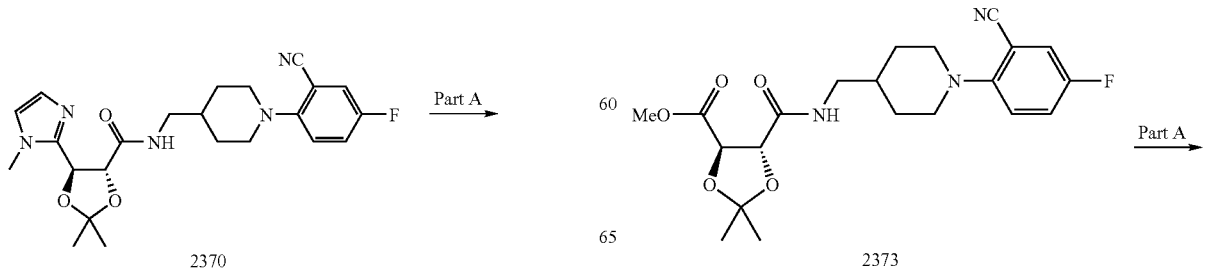

-continued

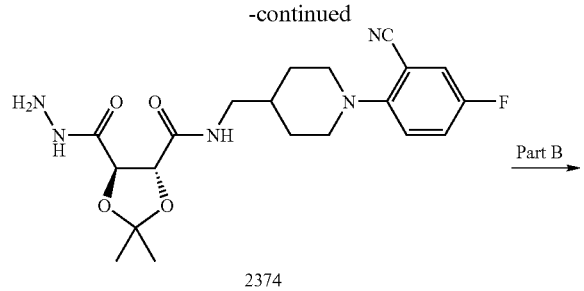

2374

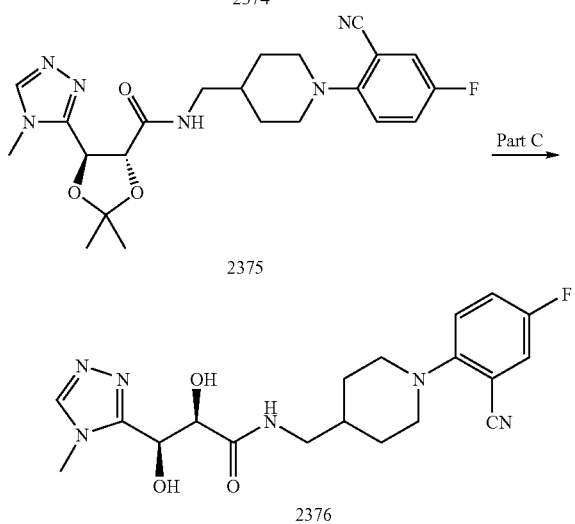

2375

2376

Part A:

Compound 2373 was prepared using previously described procedures in Examples 1 and 27.

To a solution of 2373 (300 mg, 0.71 mmol) in methanol (7 mL) was added hydrazine monohydrate (0.35 mL, 7.1 mmol) and the resulting mixture was heated at 70° C. in a sealed tube overnight. The mixture was then cooled to rt, concentrated, diluted with ethyl acetate, washed with water, brine and concentrated to give 2374 (220 mg, 73%).

$^1$H NMR (400 MHz, CDCl$_3$) δ 7.27-7.24 (m, 1H), 7.22-7.17 (m, 1H), 7.00 (t, 1H, NH), 6.99-6.96 (m, 2H), 4.62-4.57 (dd, 2H), 3.51-3.48 (d, 2H), 3.38-3.24 (m, 2H), 2.80-2.74 (m, 2H), 1.88-1.84 (d, 2H), 1.79-1.69 (m, 1H), 1.61-1.50 (m, 2H), 1.53 (s, 3H), 1.52 (s, 3H). HPLC-MS t$_R$=1.49 min (UV$_{254\,nm}$); mass calculated for formula C$_{20}$H$_{26}$FN$_5$O$_4$ 419.2 observed LCMS m/z 420.1 (M+H).

Part B:

According to a modification of a procedure by Stocks, M. J. et al. (*Org. Lett.* 2004, 17, 2969-2971) to a solution of hydrazide 2374 (110 mg, 0.26 mmol) in acetonitrile (1 mL) was added N,N-dimethylformamide dimethyl acetal (0.035 mL, 0.26 mmol) and the mixture was heated at 50° C. for 50 min. Then methylamine (0.18 mL of 2 M solution in THF, 0.36 mmol) was added, followed by acetic acid (1 mL) and the resulting mixture was heated at 80° C. overnight. The reaction mixture was then concentrated and chromatographed (SiO$_2$, 9:1:90 methanol:triethylamine:dichloromethane) to give 2375. $^1$H NMR (400 MHz, CDCl$_3$) δ 8.42 (s, 1H), 7.27-7.24 (m, 1H), 7.21-7.18 (m, 1H), 7.02-6.97 (m, 1H), 6.92 (t, 1H, NH), 5.48-5.37 (dd, 2H), 3.51-3.47 (m, 2H), 3.36-3.23 (m, 2H), 2.80-2.74 (m, 2H), 1.88-1.81 (m, 2H), 1.76-1.70 (m, 1H), 1.58-1.54 (m, 2H), 1.58 (s, 3H), 1.43 (s, 3H). HPLC-MS t$_R$=1.58 min (UV$_{254\,nm}$); mass calculated for formula C$_{22}$H$_{27}$FN$_6$O$_3$ 442.2 observed LCMS m/z 443.2 (M+H).

Part C:

Compound 2375 was deprotected with 4 M HCl in dioxane (3 mL) and water (0.3 mL) at 55° C. for 1 hour. Purification by prep-LC and conversion to a hydrochloric salt afforded 2376 as an off-white solid (20 mg). HPLC-MS t$_R$=1.23 min (UV$_{254\,nm}$); mass calculated for formula C$_{19}$H$_{23}$FN$_6$O$_3$ 402.2, observed LCMS m/z 403.1 (M+H).

Example 53E

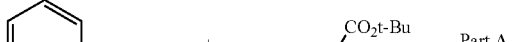

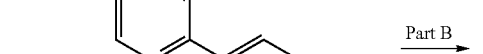
2377

2378

2379

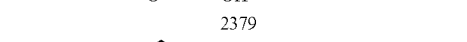
2380

2381

2382

Part A:

(tert-Butoxycarbonylmethylene)triphenylphosphorane (15.1 g, 40 mmol) was added portionwise to a solution of 2-pyridinecarboxaldehyde (4.28 g, 40 mmol) in THF (60 mL)

at 0° C. over a period of 5 min. The reaction mixture was allowed to stir at room temperature overnight. The solution was concentrated, extracted with hexane (120 mL). After filtration to remove the solid, the filtrate was concentrated to give a yellow oil. Purification by flash chromatography on silica gel (EtOAc/hexane 15:85) yielded the desired product 2377 (4.5 g, 55%) as slightly yellow liquid. $^1$H NMR (400 MHz, CDCl$_3$) δ 8.62 (d, J=4.9 Hz, 1H), 7.69 (td, J=6.6, 1.7 Hz, 1H), 7.58 (d, J=15.5 Hz, 1H), 7.41 (dd, J=7.8, 0.6 Hz, 1H), 7.23 (m, 1H), 6.82 (d, J=16.1 Hz, 1H), 1.54 (s, 9H).

Part B:

Compound 2377 (4.5 g, 21.92 mmol) was dissolved in dry DCM (40 mL) and cooled to 0° C., then 77% m-CPBA (5.41 g, 24.12 mmol) was added in three portions over 5 min. The reaction mixture was allowed to stir overnight at room temperature. It was poured into saturated aqueous NaHCO$_3$ (100 mL) and the product was extracted into DCM. The organic layer was washed with water and brine and dried (Na$_2$SO$_4$). Flash chromatography on silica gel (MeOH/DCM 5:95) afforded compound 2378 as a pale yellow solid (3.2 g, 66%). $^1$H NMR (400 MHz, CDCl$_3$) δ 8.24 (m, 1H), 7.96 (d, J=16.0 Hz, 1H), 7.51 (m, 1H), 7.22 (m, 1H), 6.85 (d, J=16.0 Hz, 1H), 1.55 (s, 1H).

Part C:

A 250-mL round bottom flask filled with H$_2$O (30 mL) was cooled to 0° C. in an ice bath. Reagents K$_3$[Fe(CN)$_6$] (9.88 g, 30 mmol), K$_2$CO$_3$ (6.91 g, 50 mmol), and MeSO$_2$NH$_2$ (0.95 g, 10 mmol) were subsequently added, followed by K$_2$[OsO$_2$(OH)$_4$] (14.7 mg, 0.04 mmol), (DHQ)PHAL (233.7 mg, 0.3 mmol), compound 2378 (2.21 g, 10 mmol) and t-BuOH (20 mL). The reaction mixture was stirred at 0° C. for 24 h. The solid was filtered off and washed with excess EtOAc. The organic layer was separated. The aqueous solution was concentrated to dryness, and the resulting solid was extracted with CH$_2$Cl$_2$. The above EtOAc and CH$_2$Cl$_2$ solutions were combined and concentrated. Flash chromatography on silica gel (MeOH/CH$_2$Cl$_2$ 10:90) provided compound 2379 as a white solid (2.2 g, 86%). Recrystallization from EtOAc afforded analytically pure material (1.51 g, 52% yield). $^1$H NMR (400 MHz, CDCl$_3$), δ 8.24 (d, J=6.5 Hz, 1H), 7.54 (dd, J=7.7, 2.0 Hz, 1H), 7.39 (t, J=7.5 Hz, 1H), 7.30 (m, 1H), 5.41 (d, J=2.6 Hz, 1H), 4.69 (d, J=2.7 Hz, 1H), 1.54 (s, 9H).

Part D:

Compound 2379 (1.0 g, 3.9 mmol) in CH$_2$Cl$_2$ (10 mL) was treated with TFA (4 mL). The solution was allowed to stir at room temperature for 2 h, and then concentrated to afford compound 2380 as a white solid (750 mg, 96%). $^1$H NMR (400 MHz, DMSO-d$_6$) δ 8.20 (dd, J=6.3, 1.2 Hz, 1H), 7.54 (dd, J=6.4, 2.2 Hz, 1H), 7.37-7.32 (m, 2H), 5.38 (d, J=2.1 Hz, 1H), 4.62 (d, J=2.3 Hz, 1H).

Part E:

Compound 2381 was prepared using the coupling conditions described in Example 1. Purification by prep-LC afforded 2381 as a white solid (63 mg). HPLC-MS t$_R$=1.30 min (UV$_{254\,nm}$); mass calculated for formula C$_{21}$H$_{23}$FN$_4$O$_4$, 414.2, observed LCMS m/z 415.1 (M+H).

Part F:

To compound 2381 (25 mg, 0.06 mmol) in EtOH (5 mL) was added with saturated NH$_4$Cl aqueous solution (5 mL) and indium (16.6 mg, 0.072 mmol). The reaction mixture was allowed to reflux for 24 h. After cooling to room temperature, it was concentrated and extracted with DCM. The DCM extract was filtered and concentrated. Purification by column chromatography on silica gel (Et$_3$N/MeOH/EtOAc 5:5:95) afforded compound 2382 as a white solid (8.5 mg, 35%). HPLC-MS t$_R$=1.16 min (UV$_{254\,nm}$); mass calculated for formula C$_{21}$H$_{23}$FN$_4$O$_3$, 398.2, observed LCMS m/z 399.1 (M+H).

Example 53F

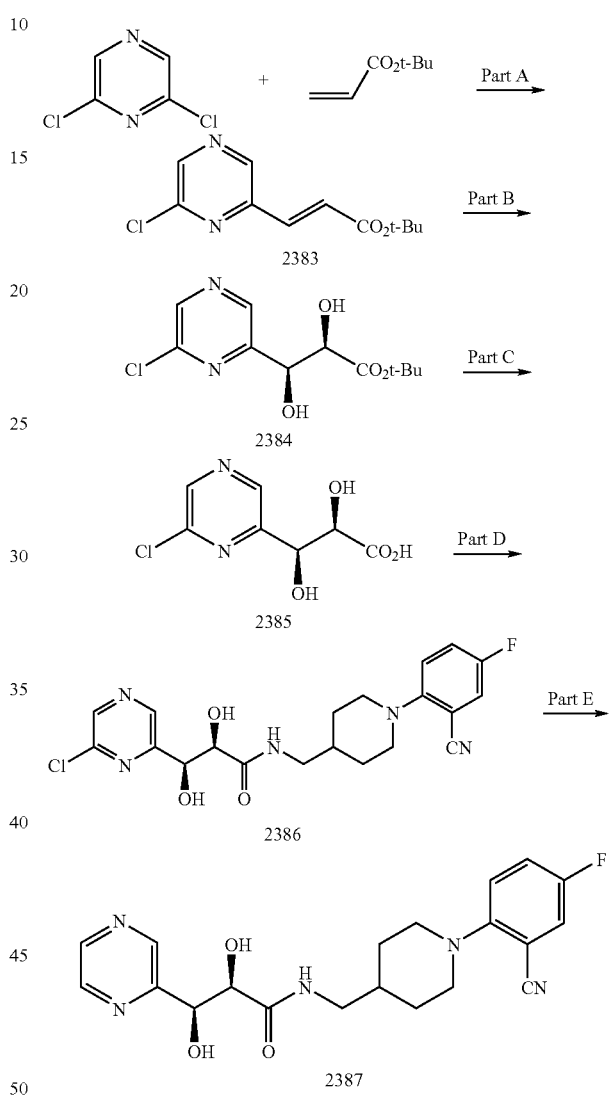

Part A:

Under argon, to a mixture of Pd$_2$(dba)$_3$ (384 mg, 0.42 mmol), tri(t-butyl)phosphinium tetrafluoroborate (243 mg, 0.84 mmol), and 2,6-dichloropyrizine (5.0 g, 33.56 mmol) were added sequentially NMP (10 mL), t-butyl acrylate (2.46 mL, 16.78 mmol) and Et$_3$N (3.51 mL, 25.17 mmol). The reaction mixture was allowed to stir at 50° C. for 12 h. After cooling to room temperature, the mixture was diluted with EtOAc and water, filtered through a pad of celite, washed with water, brine, dried (Na$_2$SO$_4$), and concentrated. Flash column chromatography on silica gel (EtOAc/hexane 15:85) afforded compound 2383 as a pale yellow solid (2.32 g, 57%). $^1$H NMR (400 MHz, acetone-d$_6$) δ 8.84 (s, 1H), 8.68 (s, 1H), 7.61 (d, J=15.7 Hz, 1H), 6.92 (d, J=15.5 Hz, 1H), 1.55 (s, 9H).

Part B:

A 50-mL round bottom flask filled with $H_2O$ (9 mL) was cooled to 0° C. in an ice bath. Reagents $K_3[Fe(CN)_6]$ (1.29 g, 3.93 mmol), $K_2CO_3$ (905 mg, 6.55 mmol), and $MeSO_2NH_2$ (124.6 mg, 1.31 mmol) were subsequently added, followed by $K_2[OsO_2(OH)_4]$ (2.0 mg, 0.005 mmol), (DHQ)PHAL (31.0 mg, 0.04 mmol), compound 2383 (315 mg, 1 mmol) and t-BuOH (6 mL). The reaction mixture was stirred at 0° C. for 36 h. Then EtOAc and $H_2O$ were added to dissolve the solid. The organic layer was separated and the aqueous layer was back extracted with EtOAc. The EtOAc extracts were combined, washed with water and brine, dried ($Na_2SO_4$), and concentrated. Flash chromatography on silica gel (EtOAc/hexane 40:60) provided compound 2384 as a white solid (285 mg, 79%). $^1$H NMR (400 MHz, $CDCl_3$) δ 8.68 (s, 1H), 8.54 (s, 1H), 5.13 (d, J=2.3 Hz, 1H), 4.55 (d, J=2.9 Hz, 1H), 1.55 (s, 9H). HPLC-MS $t_R$=1.73 min ($UV_{254\,nm}$); mass calculated for formula $C_{11}H_{15}ClN_2O_4$, 274.1, observed LCMS m/z 275.0 (M+H).

Part C:

Compound 2384 (285 mg, 1.04 mmol) in dioxane (5 mL) was treated with 4N HCl in dioxane (5 mL). After stirring at room temperature for 2 h, the solution was concentrated to afford compound 2385 (200 mg, 88%). $^1$H NMR (400 MHz, $CDCl_3$) δ 8.70 (s, 1H), 8.66 (s, 1H), 5.00 (d, J=2.6 Hz, 1H), 4.31 (d, J=2.2 Hz, 1H), 1.55 (s, 9H).

Part D:

Compound 2386 was prepared using the coupling conditions described in Example 1. Purification by prep-LC afforded 2386 as a white solid (42 mg). HPLC-MS $t_R$=1.55 min ($UV_{254\,nm}$); mass calculated for formula $C_{20}H_{21}ClFN_5O_3$, 433.1, observed LCMS m/z 434.0

Part E:

Compound 2386 (20 mg, 0.046 mmol) along with 10% Pd/C (20 mg) in EtOAc (10 mL) was stirred at room temperature for 12 h under hydrogen atmosphere (1 atm). The solution was filtered through celite and concentrated. Purification by prep-LC afforded 2387 as a white solid (15 mg, 81%). HPLC-MS $t_R$=1.35 min ($UV_{254\,nm}$); mass calculated for formula $C_{20}H_{22}FN_5O_3$, 399.2, observed LCMS m/z 400.1

Example 53G

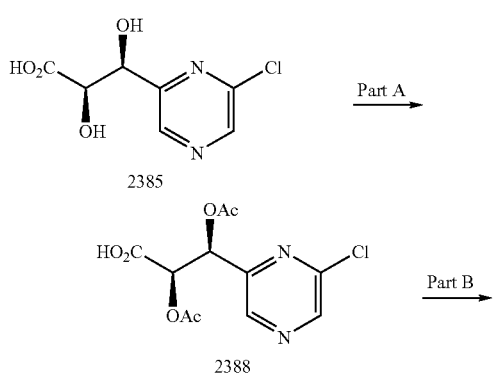

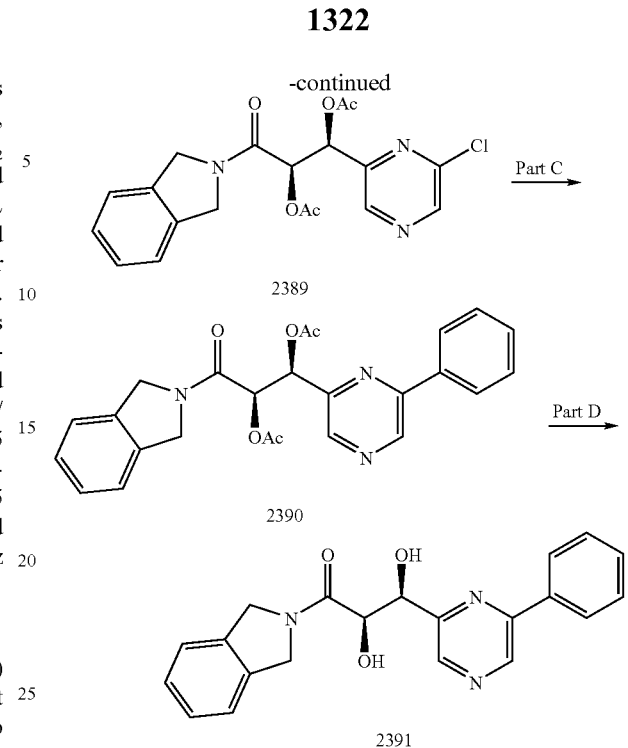

Part A:

To compound 2385 (150 mg, 0.69 mmol) in acetic acid (2 mL) was added acetic anhydride (0.5 mL). The reaction mixture was stirred at room temperature for 2 h, and then concentrated. The residue was dissolved in EtOAc, washed with $H_2O$, brine, dried over $Na_2SO_4$, and concentrated, giving rise to compound 2388 as oily solid (180 mg, 86%). HPLC-MS $t_R$=1.10 min ($UV_{254\,nm}$); mass calculated for formula $C_{11}H_{11}ClN_2O_6$ 302.0, observed LCMS m/z 303.0 (M+H).

Part B:

To compound 2388 (180 mg, 0.59 mmol) and HATU (269 mg, 0.71 mmol) in DMF (4 mL) was added isoindoline (84 mg, 0.71 mmol). The reaction mixture was stirred at room temperature for 12 h, and concentrated. The residue was dissolved with EtOAc and water, washed with saturated bicarbonate solution, and brine, dried over $Na_2SO_4$, and concentrated. Purification by column chromatography on silica gel (EtOAc/hexane 60:40) afforded the desired product 2389 as a pale yellow solid (150 mg, 63%). $^1$H NMR (400 MHz, CDCl3) δ 8.67 (s, 1H), 8.51 (s, 1H), 7.29 (m, 4H), 6.39 (d, J=7.1 Hz, 1H), 5.93 (d, J=6.7 Hz, 1H), 5.21 (d, J=5.4 Hz, 1H), 5.05 (d, J=4.1 Hz, 1H), 4.78 (d, J=5.6 Hz, 1H), 4.52 (d, J=4.7 Hz, 1H), 2.18 (s, 3H), 2.16 (s, 3H). HPLC-MS $t_R$=1.70 min ($UV_{254\,nm}$); mass calculated for formula $C_{19}H_{18}ClN_3O_5$ 403.1, observed LCMS m/z 404.0 (M+H).

Part C:

A 4-mL vial was charged with $Pd_2(dba)_3$ (2.3 mg, 0.0025 mmol), tri(t-butyl)phosphonium tetrafluoroborate (1.5 mg, 0.0025 mmol), compound 2389 (20 mg, 0.05 mmol), phenylboronic acid (9.1 mg, 0.075 mmol) and potassium fluoride (13 mg, 0.225 mmol). Under argon, dioxane (1 mL) was added via syringe. The vial was sealed with a Teflon coated screw cap and placed into an oil bath preheated to 80° C. The reaction mixture was allowed to stir at 80° C. for 12 h. LC-MS indicated the reaction was completed. After cooling to room temperature, the reaction mixture was filtered through celite with the aid of EtOAc. The filtrate was washed with saturated NaHCO3, brine, dried over Na2SO4, and concentrated. The resulting solid (21 mg) was used for next step without purification. HPLC-MS $t_R$=1.89 min (UV$_{254\,nm}$); mass calculated for formula $C_{25}H_{23}N_3O_5$ 445.1, observed LCMS m/z 446.0 (M+H).

Part D:

Compound 2390 (21 mg) was deprotected using procedures described in Example 2. Purification by prep-LC afforded 2391 as an off-white solid (8.3 mg). HPLC-MS $t_R$=4.02 min (10 min method) (UV$_{254\,nm}$); mass calculated for formula $C_{21}H_{19}N_3O_5$ 361.1, observed LCMS m/z 362.0 (M+H).

Example 53H

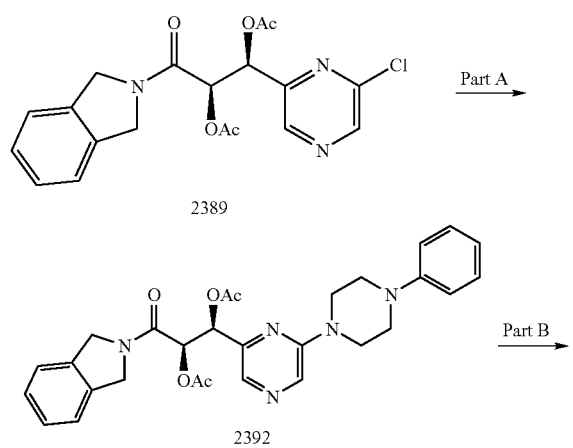

2389

2392

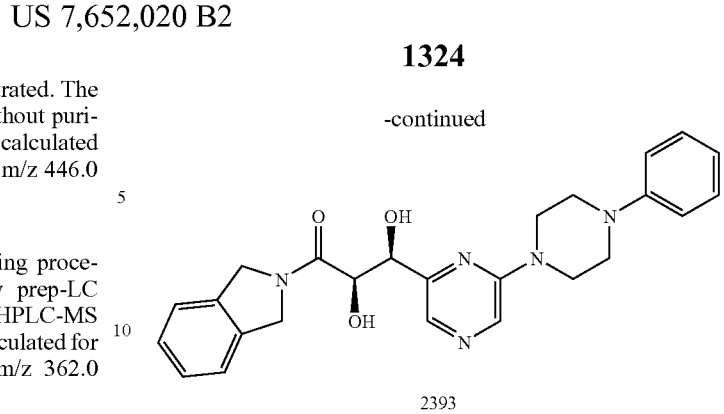

2393

Part A:

To compound 2389 (50 mg, 0.12 mmol) in NMP (1 mL) was added 4-N-phenylpipyzine (29 mg, 0.18 mmol) and DIEA (0.032 mL, 0.18 mmol). The reaction mixture was allowed to stir at 80° C. for 16 h. After cooling to room temperature, the solution was diluted with EtOAc, washed with water and brine, dried over Na2SO4, and concentrated. The resulting oily solid (52 mg) was utilized for next step without further purification. HPLC-MS $t_R$=1.96 min (UV$_{254\,nm}$); mass calculated for formula $C_{29}H_{31}N_5O_5$ 529.2, observed LCMS m/z 530.2 (M+H).

Part B:

Compound 2392 (52 mg) was deprotected using procedures described in Example 2. Purification by prep-LC afforded 2393 as an off-white solid (15 mg). HPLC-MS $t_R$=1.60 min (UV$_{254\,nm}$); mass calculated for formula $C_{25}H_{27}N_5O_3$ 445.2, observed LCMS m/z 446.1 (M+H).

The following compounds were prepared using previously described procedures.

| Compound # | Structure | Exact mass | MS m/z (M + H) |
|---|---|---|---|
| 2394 | 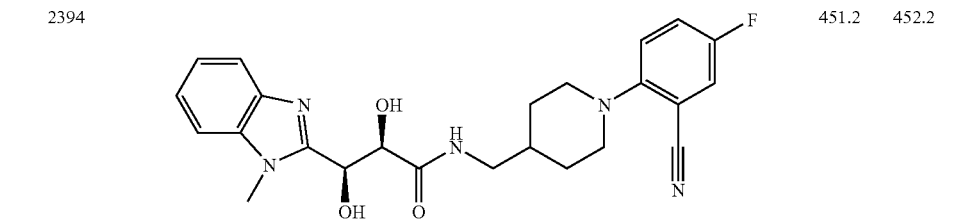 | 451.2 | 452.2 |
| 2395 | 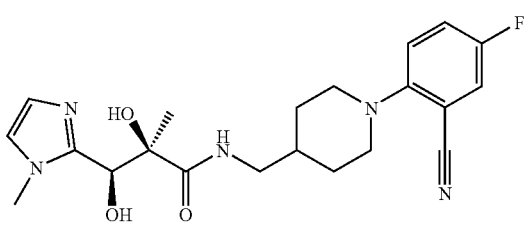 | 415.2 | 416.2 |

-continued

| Compound # | Structure | Exact mass | MS m/z (M + H) |
|---|---|---|---|
| 2382 | 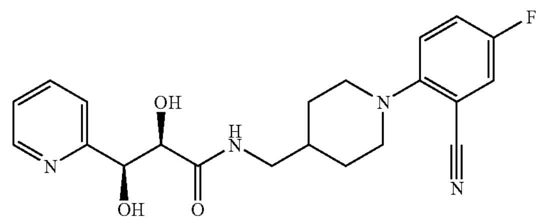 | 398.2 | 399.1 |
| 2396 | 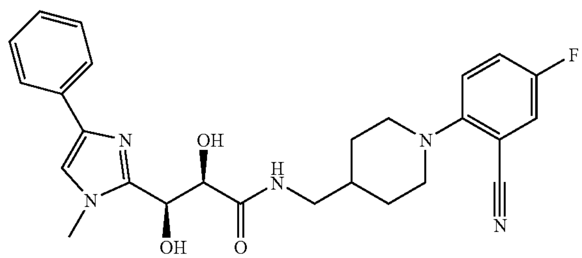 | 477.2 | 478.2 |
| 2397 | 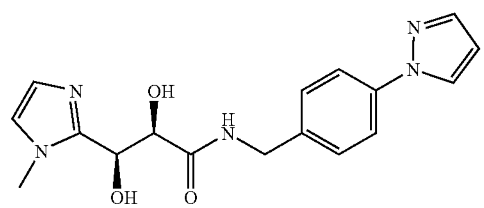 | 341.2 | 342.1 |
| 2398 | 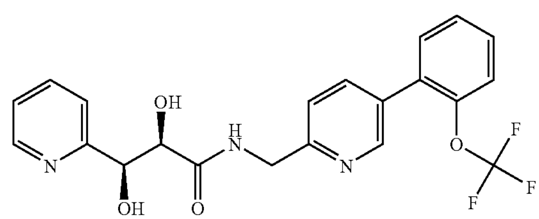 | 433.1 | 434.0 |
| 2376 | 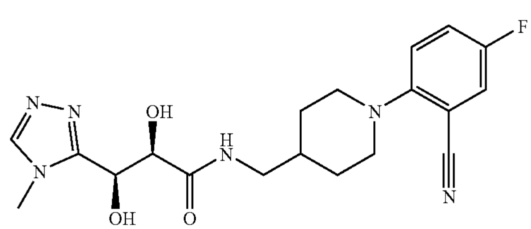 | 402.2 | 403.1 |
| 2399 | 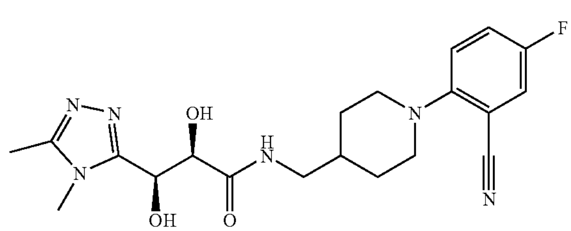 | 416.2 | 417.1 |

-continued

| Compound # | Structure | Exact mass | MS m/z (M + H) |
|---|---|---|---|
| 2400 | 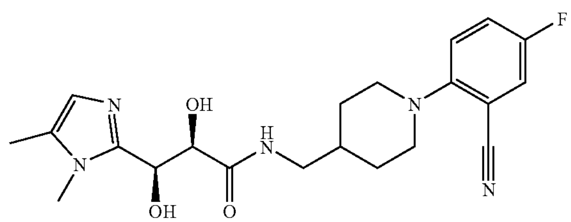 | 415.2 | 416.2 |
| 2369 | 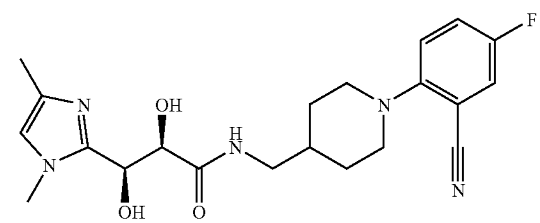 | 415.2 | 416.2 |
| 2401 | 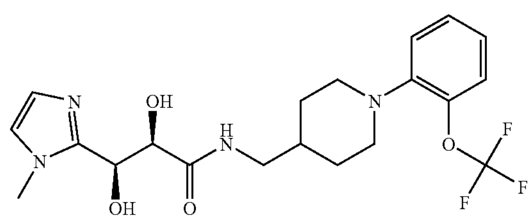 | 442.2 | 443.2 |
| 2372 | 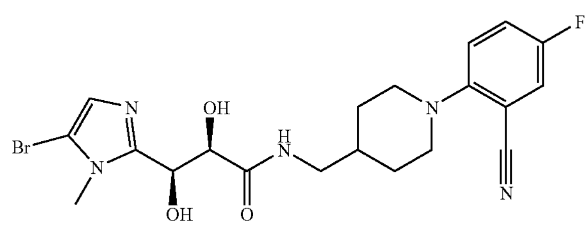 | 479.1 | 480.0 |
| 2402 | 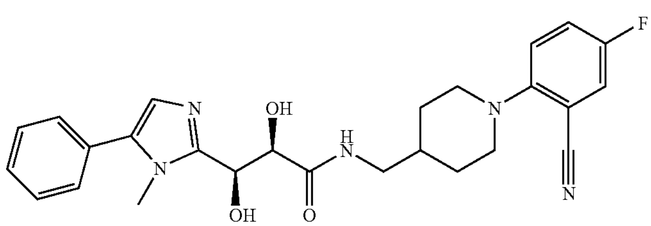 | 477.2 | 478.1 |
| 2365 | 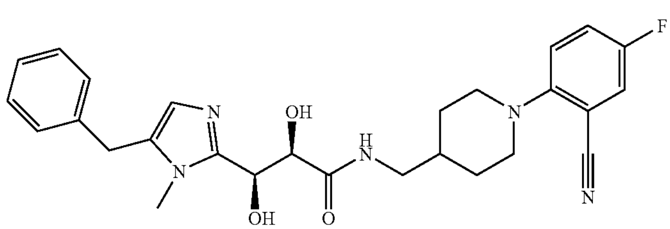 | 491.2 | 492.1 |

-continued

| Compound # | Structure | Exact mass | MS m/z (M + H) |
|---|---|---|---|
| 2387 | 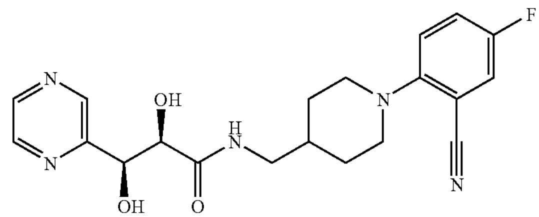 | 399.2 | 400.1 |
| 2403 | 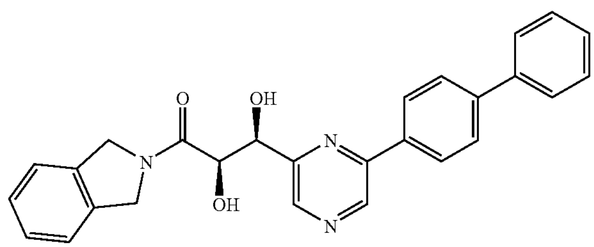 | 437.2 | 438.0 |
| 2393 | 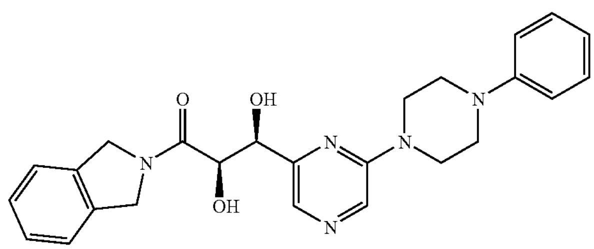 | 445.2 | 446.1 |
| 2391 | 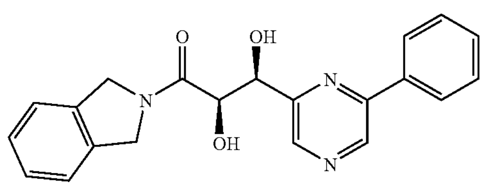 | 361.1 | 362.0 |
| 2408 | 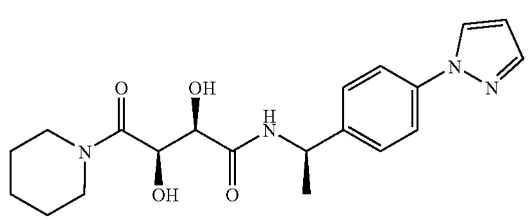 | 386.2 | 387.1 |
| 2409 | 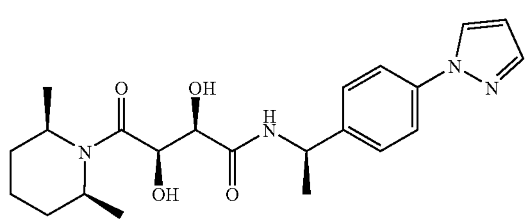 | 414.2 | 415.1 |

-continued

| Compound # | Structure | Exact mass | MS m/z (M + H) |
|---|---|---|---|
| 2410 | 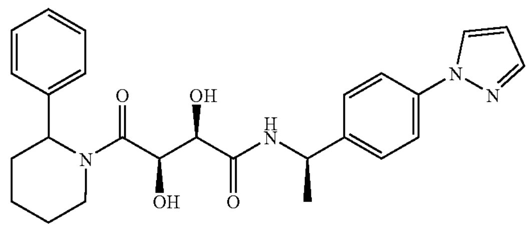 | 462.2 | 463.1 |
| 2411 | 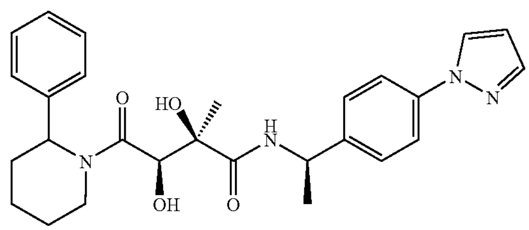 | 476.2 | 477.1 |
| 2412 | 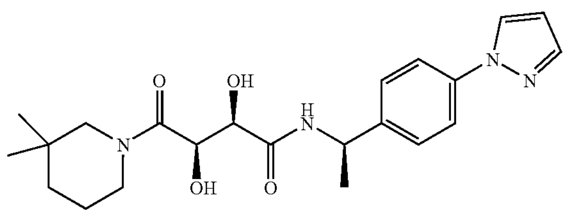 | 414.2 | 415.1 |
| 2413 | 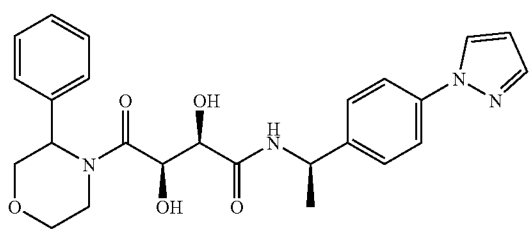 | 464.2 | 465.1 |
| 2414 | 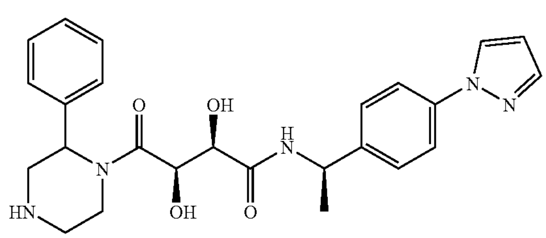 | 463.2 | 464.2 |
| 2415 | 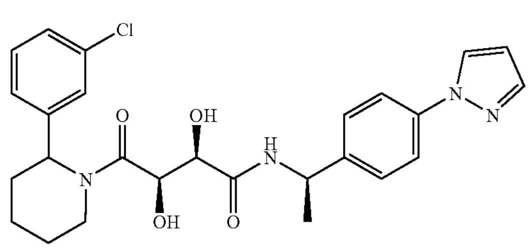 | 496.2 | 497.0 |

-continued

| Compound # | Structure | Exact mass | MS m/z (M + H) |
|---|---|---|---|
| 2416 | 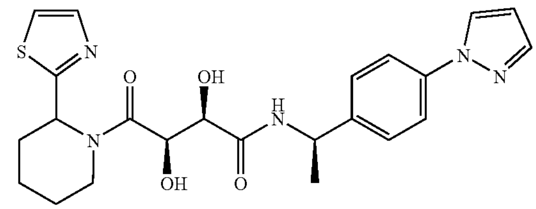 | 469.2 | 470.0 |
| 2417 | 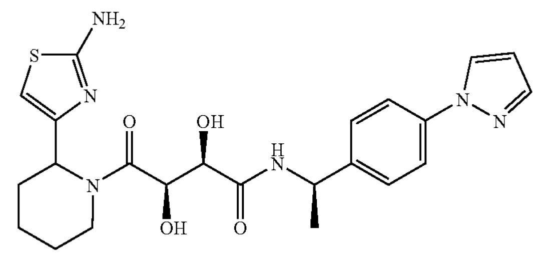 | 484.2 | 485.0 |
| 2418 | 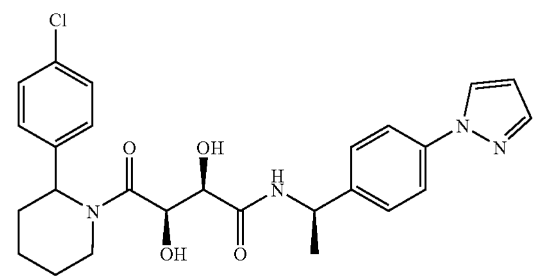 | 496.2 | 497.0 |
| 2419 | 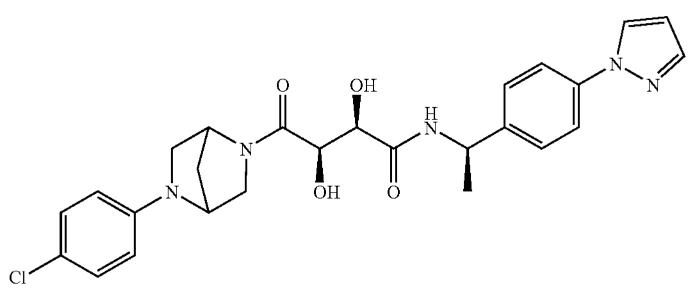 | 509.2 | 510.1 |
| 2420 | 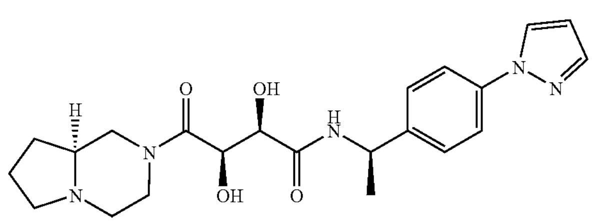 | 427.2 | 428.2 |
| 2421 | 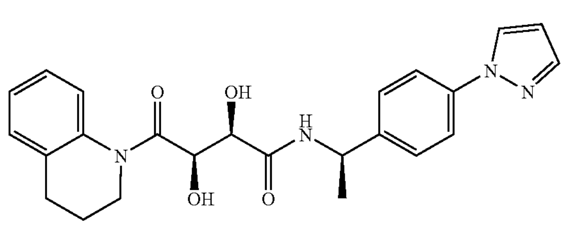 | 434.2 | 435.1 |

-continued
| Compound # | Structure | Exact mass | MS m/z (M + H) |
|---|---|---|---|
| 2422 | 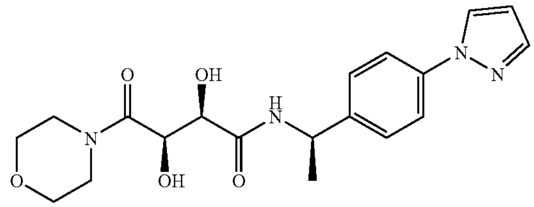 | 388.2 | 389.1 |
| 2423 | 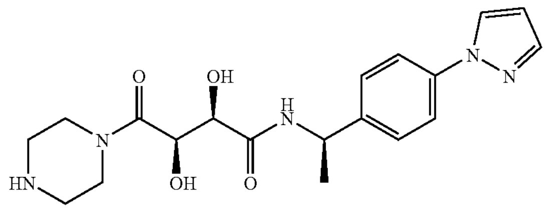 | 387.2 | 388.1 |
| 2424 | 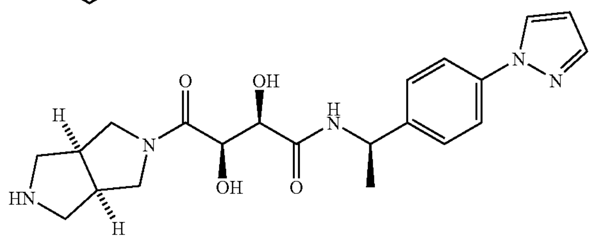 | 413.2 | 414.1 |
| 2425 | 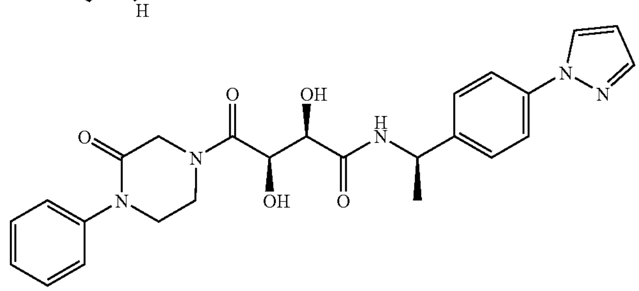 | 477.2 | 478.1 |
Example 54
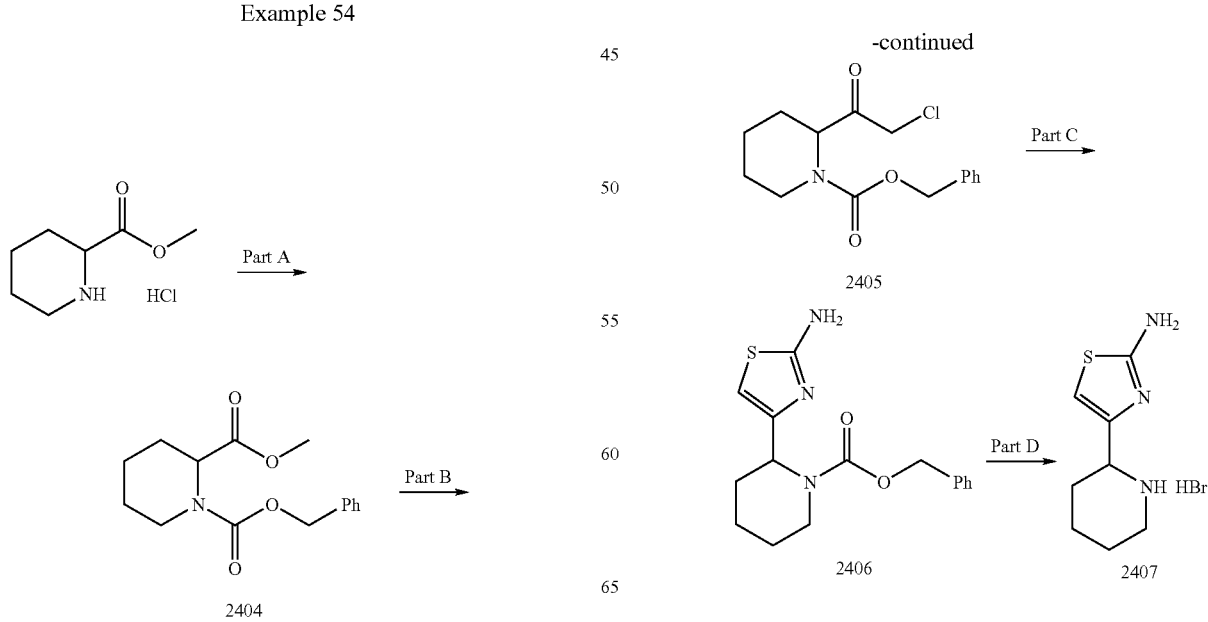

Part A:

Methyl pipecolinate hydrochloride (2.0 g, 11 mmol) was dissolved in THF (20 mL) and saturated sodium bicarbonate (20 mL) and cooled in an ice bath. Benzyl chloroformate (1.5 mL, 11 mmol) was added dropwise and the reaction was stirred at room temperature overnight. The reaction mixture was partitioned between ethyl acetate and water. The organic layer was washed with 1 N HCl, saturated sodium bicarbonate, water and brine, dried over sodium sulfate and concentrated. Purification by column chromatography (SiO$_2$, 10% ethyl acetate/hexane to 15% ethyl acetate/hexane) afforded 2404 as a clear oil (2.9 g, 93%).

Part B and C:

Compounds 2405 and 2406 were prepared following the procedures described in Example 10B part A and part B. Compound 2406: $^1$H NMR (400 MHz, CDCl$_3$) δ 7.40-7.30 (m, 5H), 6.11 (s, 1H), 5.36 (m, 1H), 5.18 (s, 2H), 3.72 (m, 1H), 3.00 (m, 1H), 2.33 (m, 1H), 1.90-1.40 (m, 7H). HPLC-MS t$_R$=1.34 min (UV$_{254\,nm}$); Mass calculated for C16H19N3O2S 317.4, observed LSMS m/z 318.1 (M+H).

Part D:

Compound 2406 (75 mg, 0.24 mmol) was stirred in 30% HBr in acetic acid (2 mL) for 1 hour at room temperature. The solvent was evaporated and the residue was dissolved in water and lyophilized to afford 2407 (66 mg) as a red solid.

The following compounds were prepared using previously described procedures.

| Compound # | Structure | Exact mass | MS m/z (M + H) |
|---|---|---|---|
| 2408 | 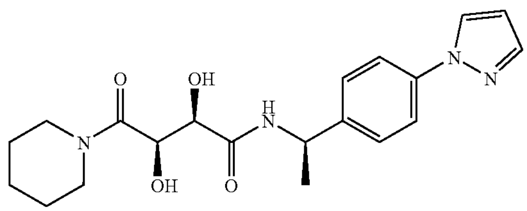 | 386.2 | 387.1 |
| 2409 | 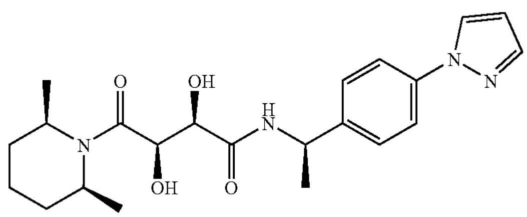 | 414.2 | 415.1 |
| 2410 | 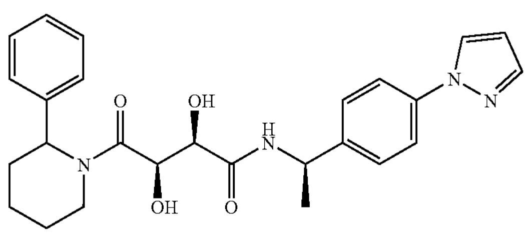 | 462.2 | 463.1 |
| 2411 | 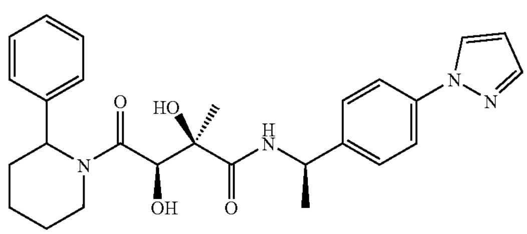 | 476.2 | 477.1 |
| 2412 | 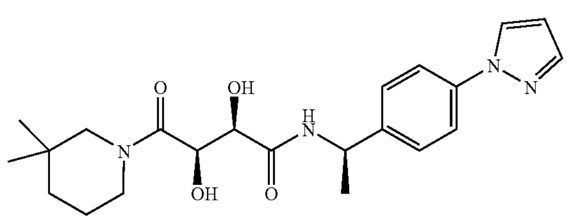 | 414.2 | 415.1 |

-continued

| Compound # | Structure | Exact mass | MS m/z (M + H) |
|---|---|---|---|
| 2413 | 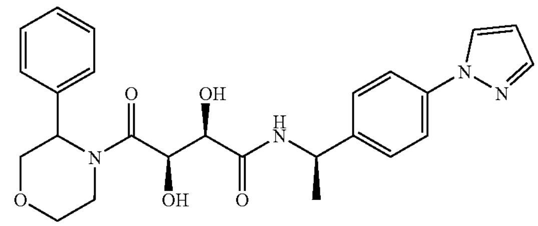 | 464.2 | 465.1 |
| 2414 | 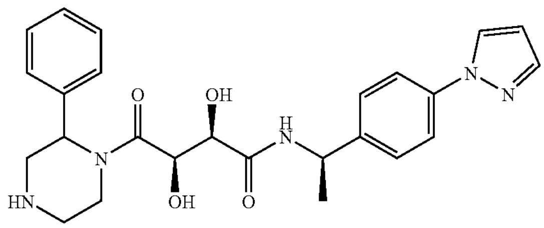 | 463.2 | 464.2 |
| 2415 | 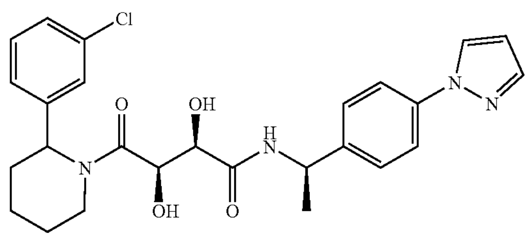 | 496.2 | 497.0 |
| 2416 | 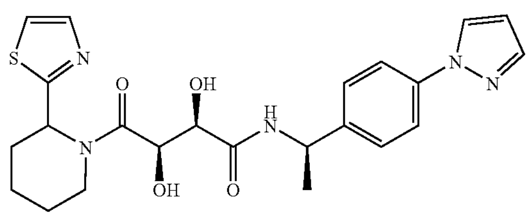 | 469.2 | 470.0 |
| 2417 | 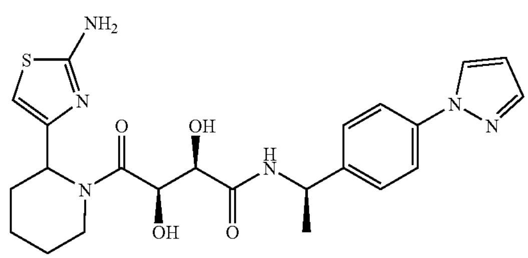 | 484.2 | 485.0 |
| 2418 | 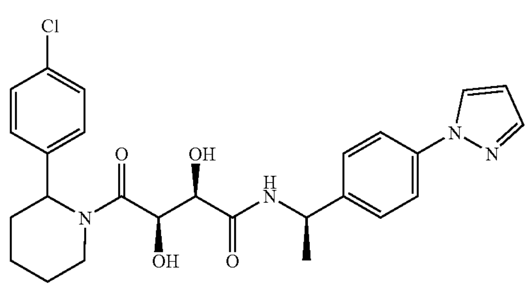 | 496.2 | 497.0 |

-continued

| Compound # | Structure | Exact mass | MS m/z (M + H) |
|---|---|---|---|
| 2419 | 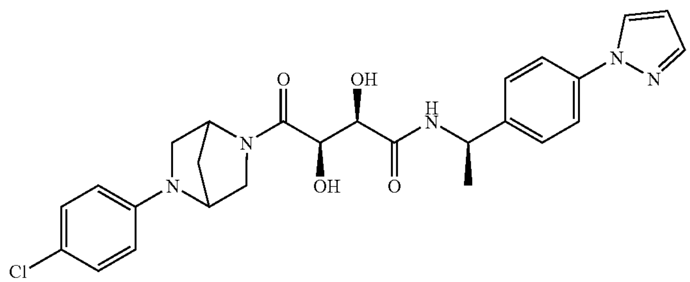 | 509.2 | 510.1 |
| 2420 | 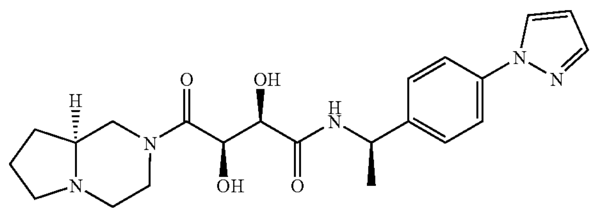 | 427.2 | 428.2 |
| 2421 | 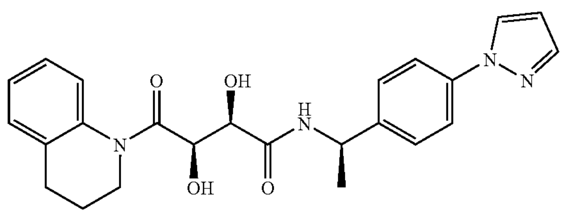 | 434.2 | 435.1 |
| 2422 | 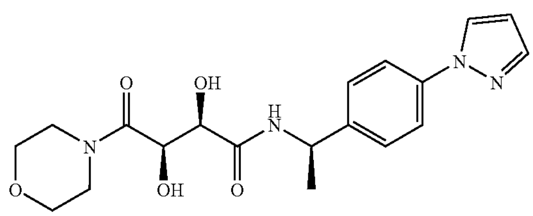 | 388.2 | 389.1 |
| 2423 | 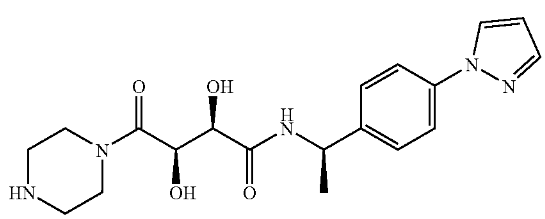 | 387.2 | 388.1 |
| 2424 | 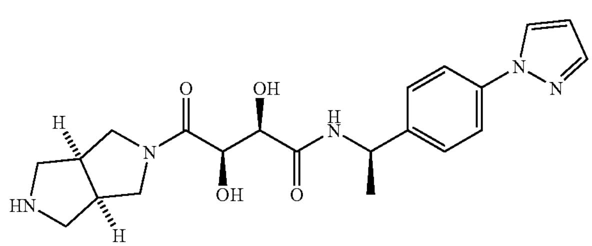 | 413.2 | 414.1 |

| Compound # | Structure | Exact mass | MS m/z (M + H) |
|---|---|---|---|
| 2425 | 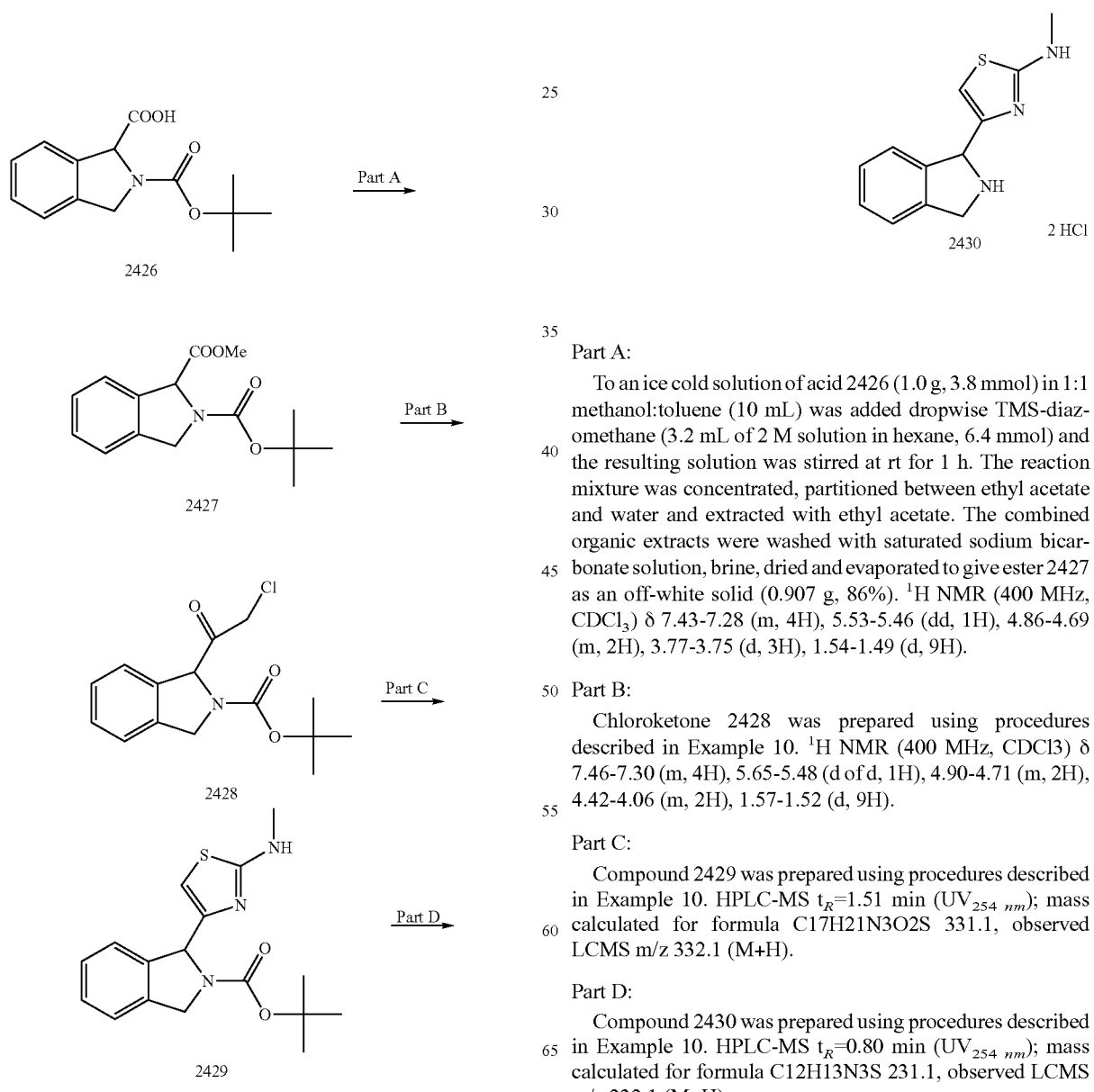 | 477.2 | 478.1 |

Example 55

Example 55A

Part A:

To an ice cold solution of acid 2426 (1.0 g, 3.8 mmol) in 1:1 methanol:toluene (10 mL) was added dropwise TMS-diazomethane (3.2 mL of 2 M solution in hexane, 6.4 mmol) and the resulting solution was stirred at rt for 1 h. The reaction mixture was concentrated, partitioned between ethyl acetate and water and extracted with ethyl acetate. The combined organic extracts were washed with saturated sodium bicarbonate solution, brine, dried and evaporated to give ester 2427 as an off-white solid (0.907 g, 86%). $^1$H NMR (400 MHz, CDCl$_3$) δ 7.43-7.28 (m, 4H), 5.53-5.46 (dd, 1H), 4.86-4.69 (m, 2H), 3.77-3.75 (d, 3H), 1.54-1.49 (d, 9H).

Part B:

Chloroketone 2428 was prepared using procedures described in Example 10. $^1$H NMR (400 MHz, CDCl3) δ 7.46-7.30 (m, 4H), 5.65-5.48 (d of d, 1H), 4.90-4.71 (m, 2H), 4.42-4.06 (m, 2H), 1.57-1.52 (d, 9H).

Part C:

Compound 2429 was prepared using procedures described in Example 10. HPLC-MS $t_R$=1.51 min (UV$_{254\ nm}$); mass calculated for formula C17H21N3O2S 331.1, observed LCMS m/z 332.1 (M+H).

Part D:

Compound 2430 was prepared using procedures described in Example 10. HPLC-MS $t_R$=0.80 min (UV$_{254\ nm}$); mass calculated for formula C12H13N3S 231.1, observed LCMS m/z 232.1 (M+H).

1345

Example 55B

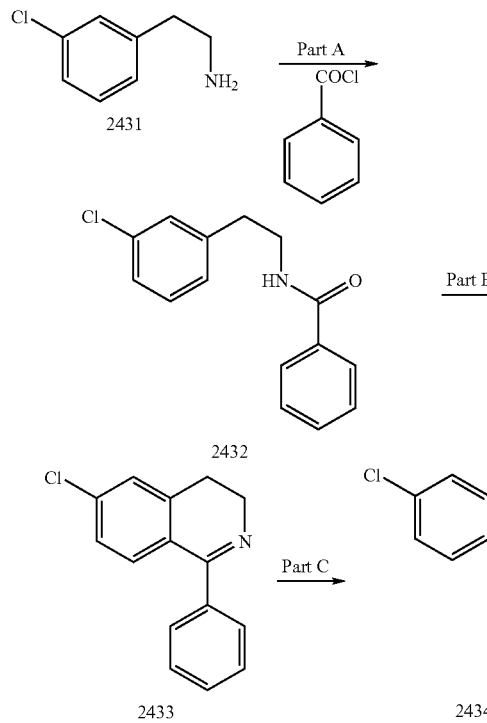

Part A:

According to a modification of a procedure by Mach, U. R. et al. (*ChemBioChem* 2004, 5, 508-518) to a mixture of 3-chlorophenethylamine 2431 (3.89 g, 25 mmol) and 2 M potassium hydroxide solution (35 mL) was added dropwise benzoyl chloride (3.48 mL, 30 mmol). Within minutes a white precipitate formed, it was filtered and washed thoroughly with water, dried (air) and recrystallized (ethanol) to give amide 2432 as a white solid (4.22 g, 65%). $^1$H NMR (400 MHz, DMSO-d$_6$) δ 8.53 (t, 1H, NH), 7.78-7.76 (d, 2H), 7.50-7.17 (m, 7H), 3.50-3.46 (m, 2H), 2.85 (t, 2H). HPLC-MS t$_R$=1.81 min (UV$_{254\ nm}$); mass calculated for formula C15H14ClNO 259.1, observed LCMS m/z 260.0 (M+H).

Part B:

According to a modification of a procedure by Mach, U. R. et al. (*ChemBioChem* 2004, 5, 508-518) to a mixture of amide 2432 (1.79 g, 6.9 mmol) and powder zinc chloride (3.29 g, 24.1 mmol) in toluene (30 mL) was added dropwise phosphorus oxychloride (4.4 mL, 48.3 mmol) and the mixture was heated at reflux for 2 h, during which time a polymer-like residue formed. The reaction mixture was cooled in an ice bath, quenched by the addition of 2 M sodium hydroxide solution, extracted and sonicated with dichloromethane (the residue dissolved). The combined dichloromethane extracts were concentrated to a solid residue, which was then triturated with THF. The resulting white solid was filtered and dried to give compound 2433 (1.23 g, 74%). $^1$H NMR (400 MHz, DMSO-d$_6$) δ 7.82-7.67 (m, 6H), 7.58-7.55 (dd, 1H), 7.41-7.39 (d, 1H), 3.98 (t, 2H), 3.23 (t, 2H). HPLC-MS t$_R$=0.96 min (UV$_{254\ nm}$); mass calculated for formula C15H12ClN 241.1, observed LCMS m/z 242.1 (M+H).

1346

Part C:

According to a modification of a procedure by Mach, U. R. et al. (*ChemBioChem* 2004, 5, 508-518) to a solution of imine 2433 (760 mg, 3.14 mmol) in ethanol (50 mL) was added portionwise sodium borohydride (300 mg, 7.86 mmol) and the resulting mixture was heated at reflux overnight. The reaction mixture was cooled, quenched with water, concentrated, partitioned between ethyl acetate and water, and extracted with ethyl acetate. The combined organic extracts were dried and concentrated to give amine 2434 (418 mg, 55%). $^1$H NMR (400 MHz, DMSO-d$_6$) δ 7.33-7.04 (m, 7H), 6.62-6.60 (d, 1H), 5.00 (s, 1H), 3.36-3.26 (m, 1H), 3.11-3.06 (m, 1H), 2.98-2.73 (m, 2H). HPLC-MS t$_R$=1.14 min (UV$_{254\ nm}$); mass calculated for formula C15H14ClN 243.1, observed LCMS m/z 244.1 (M+H).

Example 55C

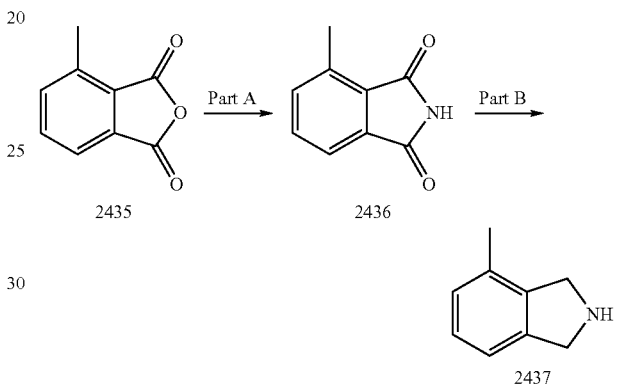

Part A:

A mixture of compound 2435 (6 g, 36.5 mmol) and urea (1.95 g, 32.5 mmol) was heated over a sand bath at 350° C. for 30 minutes. The resulting black tar was cooled down to 100° C. and water (25 mL) was carefully added. This mixture was stirred for 1 hour. The solid was collected by filtration, dissolved in DMF (40 mL) and stirred with Darco (1 g) for 1 hour. The mixture was filtered and water (100 mL) was added to the filtrate to precipitate out a brown solid. The solid was collected by filtration and air dried. The the solid was dissolved in boiling MeOH (120 mL) with Darco (1 g). The mixture was filtered and the filtrate was concentrated to dryness. The residue was suspended in EtOAc and filtered to afford the desired compound 2436 as brown solid (2.5 g, 43%).

Part B:

Compound 2436 (1 g, 6.2 mmol) was added to a solution of 1M borane/THF (21 mL, 21 mmol) at 0° C. and the mixture was warmed to room temperature and then refluxed for 18 hours. The reaction mixture was cooled to room temperature and 6N HCl (50 mL) was added dropwise. The reaction mixture was concentrated to remove THF and then cooled to 0° C. and sodium hydroxide pellets (13 g) were added carefully to the reaction mixture. The reaction mixture was extracted with CH$_2$Cl$_2$ (1×50 mL, 1×20 mL). The organic layer was dried over MgSO$_4$, filtered and concentrated. Purification by column chromatography (SiO$_2$, 3% MeOH(NH$_3$)/CH$_2$Cl$_2$, followed by 5% MeOH(NH$_3$)/CH$_2$Cl$_2$) afforded the desired compound 2437 as tan solid (64 mg, 7.7%).

The following compounds were prepared using previously described procedures.

| Compound # | Structure | Exact mass | MS m/z (M + H) |
|---|---|---|---|
| 2438 | 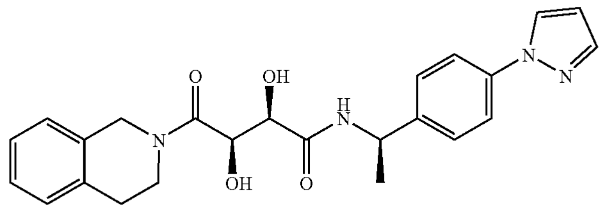 | 434.2 | 435.1 |
| 2439 | 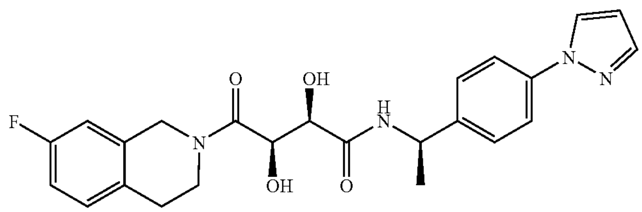 | 452.2 | 453.1 |
| 2440 | 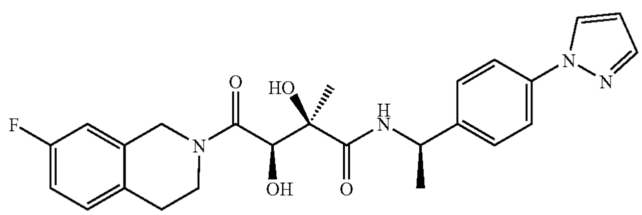 | 466.2 | 467.0 |
| 2441 | 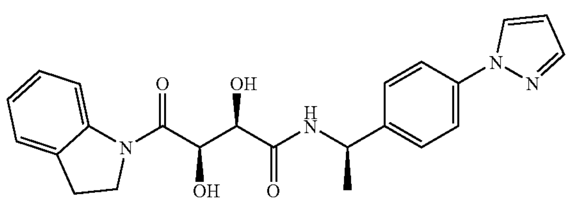 | 420.2 | 421.1 |
| 2442 | 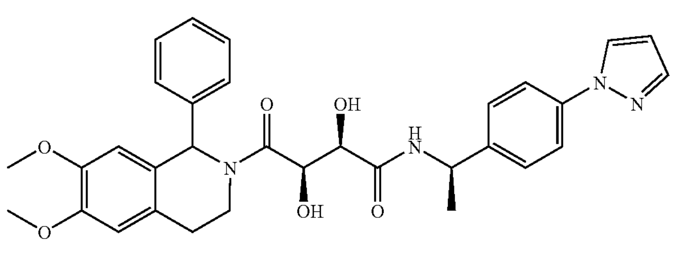 | 570.2 | 571.1 |
| 2443 | 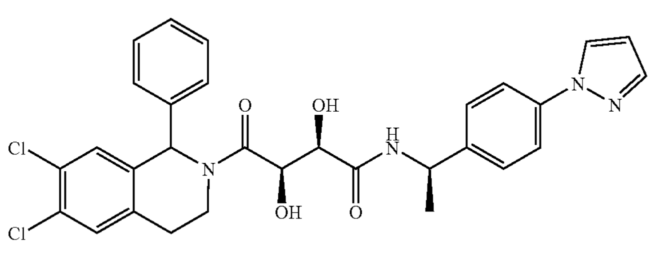 | 578.2 | 579.1 |

-continued
| Compound # | Structure | Exact mass | MS m/z (M + H) |
|---|---|---|---|
| 2444 | 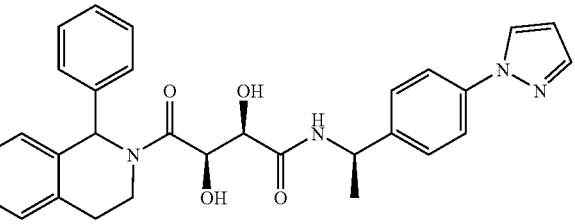 | 544.2 | 545.0 |
| 2445 | 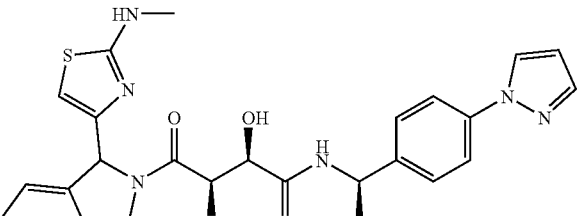 | 532.2 | 533.0 |
| 2446 | 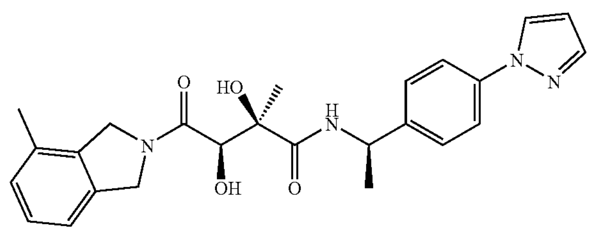 | 448.2 | 449.1 |
Example 56
Example 56A
2447
2448
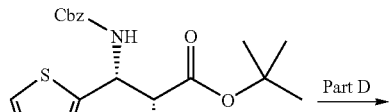
2449
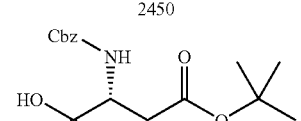
2450
2451
2452
2453
3000

-continued

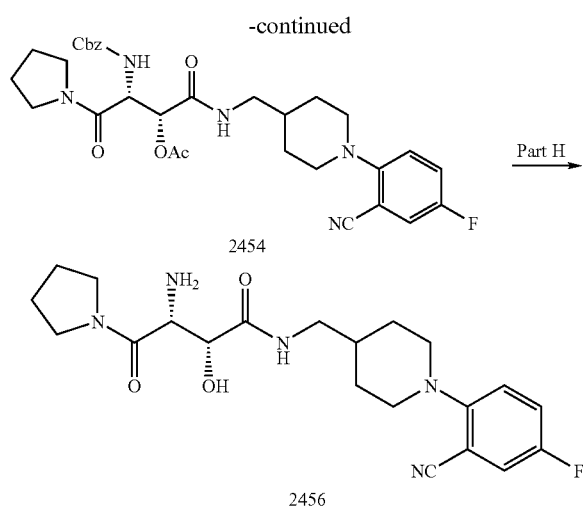

Parts A-D:

Compounds 2448-2451 were prepared according to the procedures in *Syn. Lett.* 1999, 12, 1907-1910.

Part E:

Compound 2451 (200 mg, 0.52 mmol), HATU (260 mg, 0.68 mmol), pyrrolidine (0.052 mL, 0.624 mmol), and DIEA (0.1 mL) were dissolved in DMF (5 mL). The reaction mixture was stirred overnight at room temperature and then partitioned between ethyl acetate and water. The organic layers were washed with 1 M HCl, saturated sodium bicarbonate, brine, dried over sodium sulfate, and concentrated. Purification by column chromatography (SiO$_2$, 50% ethyl acetate/hexanes) afforded the desired product (200 mg). HPLC-MS $t_R$=1.91 min (UV$_{254\ nm}$); mass calculated for formula C$_{22}$H$_{30}$N$_2$O$_7$ 434.21, observed LCMS m/z 435.1 (M+H).

Part F:

Compound 2452 (200 mg, 0.46 mmol) was dissolved in methylene chloride (4 mL) and trifluoroacetic acid (1 mL). The reaction mixture was stirred at room temperature for 4 hours. The solvent was evaporated and the material was used without further purification (160 mg). HPLC-MS $t_R$=1.31 min (UV$_{254\ nm}$); mass calculated for formula C$_{18}$H$_{22}$N$_2$O$_7$ 434.21, observed LCMS m/z 379.1 (M+H).

Part G:

Compound 2453 (160 mg, 0.423 mmol), compound 3000 (prepared as described in Example 27A) (122 mg, 0.423 mmol), HATU (210 mg, 0.55 mmol), and DIEA (0.5 mL) were dissolved in DMF (10 mL). The reaction mixture was stirred overnight at room temperature and then partitioned between ethyl acetate and water. The organic layers were washed with 1 M HCl, saturated sodium bicarbonate, brine, dried over sodium sulfate, and concentrated. Purification by column chromatography (SiO$_2$, 25% ethyl acetate/hexanes to 100% ethyl acetate) afforded the desired product (175 mg). HPLC-MS $t_R$=1.94 min (UV$_{254\ nm}$); mass calculated for formula C$_{31}$H$_{36}$FN$_5$O$_6$ 593.2, observed LCMS m/z 594.2 (M+H).

Part H:

Compound 2454 (50 mg, 0.084 mmol) was dissolved in 7 M ammonia in MeOH (0.5 mL) and MeOH (2 mL) and stirred for 30 minutes. The solvent was removed under reduced pressure. The residue was dissolved in MeOH (5 mL) and acetic acid (0.3 mL) and Pd—C (100 mg) was added under an argon atmosphere. The reaction was stirred under a hydrogen atmosphere for 3 hours and then filtered through a pad of celite. The solvent was evaporated and the residue was partitioned between ethyl acetate and water. The combined organic layers were washed with saturated sodium bicarbonate, brine, dried over sodium sulfate and concentrated. The residue was dissolved in ethyl acetate (2 mL) and treated with 4 M HCl in dioxane (0.1 mL). The solids were filtered and washed several times with ethyl acetate to obtain the desired product as an HCl salt (23 mg). HPLC-MS $t_R$=1.15 min (UV$_{254\ nm}$); mass calculated for formula C$_{21}$H$_{28}$FN$_5$O$_3$ 417.2, observed LCMS m/z 418.1 (M+H).

Example 56B

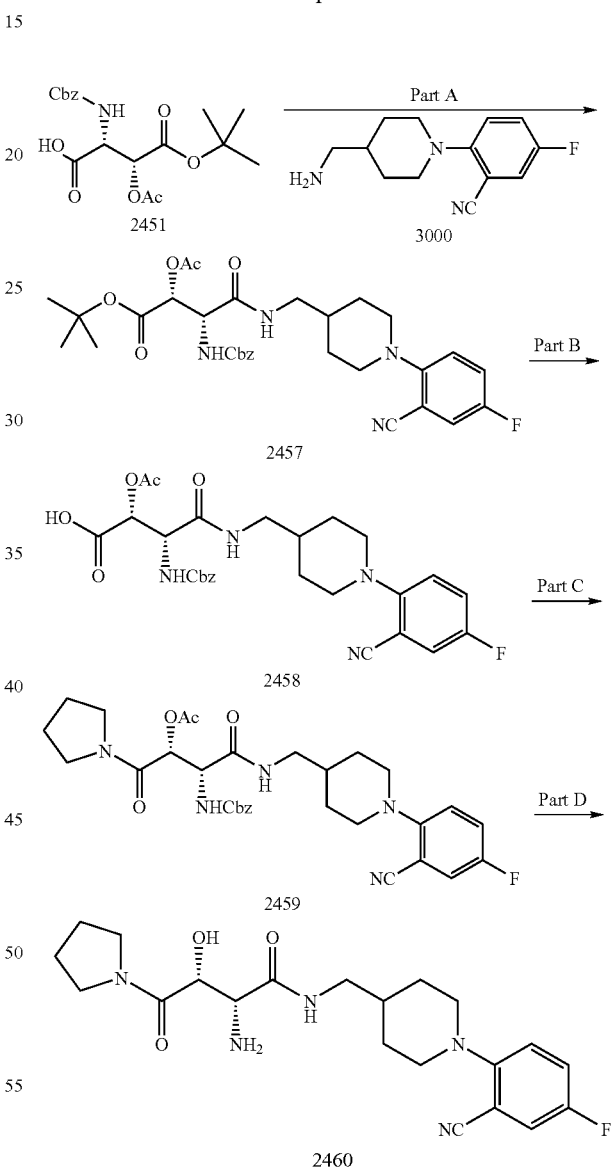

Part A:

Compound 2451 (200 mg, 0.52 mmol), compound 3000 (194 mg, 0.68 mmol), HATU (260 mg, 0.68 mmol), and DIEA (0.5 mL) were dissolved in DMF (5 mL). The reaction mixture was stirred overnight at room temperature and then partitioned between ethyl acetate and water. The organic layers were washed with 1 M HCl, saturated sodium bicarbonate, brine, dried over sodium sulfate, and concentrated. Purification by column chromatography (SiO$_2$, 33% ethyl acetate/hexanes to 100% ethyl acetate) afforded the desired product (230 mg). HPLC-MS t$_R$=2.20 min (UV$_{254\ nm}$); mass calculated for formula C$_{31}$H$_{37}$FN$_4$O$_7$ 596.2, observed LCMS m/z 597.2 (M+H).

Part B:

Compound 2457 (230 mg, 0.386 mmol) was dissolved in methylene chloride (4 mL) and trifluoroacetic acid (1 mL). The reaction mixture was stirred at room temperature for 4 hours. The solvent was evaporated and 2458 (190 mg) was used without further purification. HPLC-MS t$_R$=1.77 min (UV$_{254\ nm}$); mass calculated for formula C$_{27}$H$_{29}$FN$_4$O$_7$ 540.2, observed LCMS m/z 541.2 (M+H).

Part C:

Compound 2458 (190 mg, 0.32 mmol), HATU (160 mg, 0.416 mmol), pyrrolidine (0.035 mL, 0.416 mmol), and DIEA (0.5 mL) were dissolved in DMF (5 mL). The reaction mixture was stirred overnight at room temperature and then partitioned between ethyl acetate and water. The organic layers were washed with 1 M HCl, saturated sodium bicarbonate, brine, dried over sodium sulfate, and concentrated. Purification by column chromatography (SiO$_2$, 25% ethyl acetate/hexanes to 100% ethyl acetate) afforded the desired product (200 mg). HPLC-MS t$_R$=1.92 min (UV$_{254\ nm}$); mass calculated for formula C$_{31}$H$_{36}$FN$_5$O$_6$ 593.2, observed LCMS m/z 594.2 (M+H).

Part D:

Compound 2459 (55 mg, 0.092 mmol) was dissolved in 7 M ammonia in MeOH (0.5 mL) and MeOH (2 mL) and stirred for 30 minutes. The solvent was removed under reduced pressure. The residue was dissolved in MeOH (5 mL) and acetic acid (0.3 mL) and Pd—C (100 mg) was added under an argon atmosphere. The reaction was stirred under a hydrogen atmosphere for 3 hours and then filtered over a bed of celite. The solvent was evaporated and the residue was partitioned between ethyl acetate and water. The combined organic layers were washed with saturated sodium bicarbonate, brine, dried over sodium sulfate and concentrated. The residue was dissolved in ethyl acetate (2 mL) and treated with 4 M HCl in dioxane (0.1 mL). The solids were filtered and washed several times with ethyl acetate to obtain 2460 as an HCl salt (29 mg). HPLC-MS t$_R$=1.15 min (UV$_{254\ nm}$); mass calculated for formula C$_{21}$H$_{28}$FN$_5$O$_3$ 417.2, observed LCMS m/z 418.1 (M+H).

Example 56C

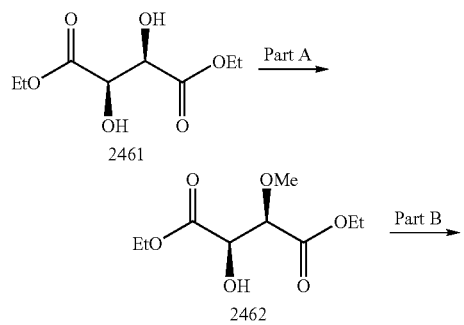

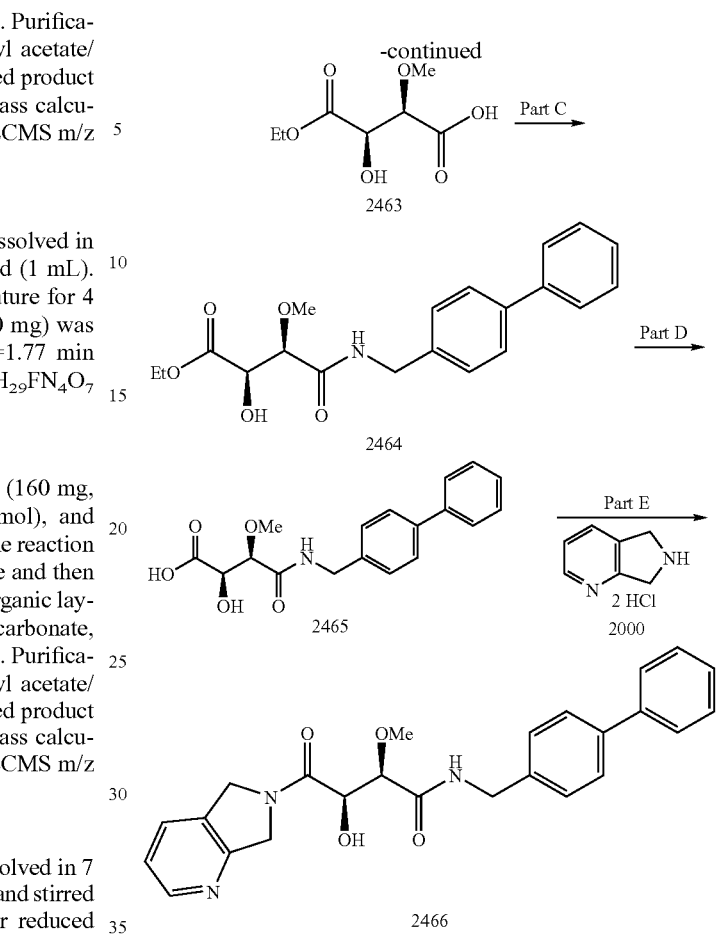

Part A:

Compound 2462 was prepared using a modification of the procedure in *Chem. Pharm. Bull.* 1991, 39, 8, 1972-1982. Compound 2461 (1.06 g, 5.14 mmol) and Bu$_2$SnO (1.28 g, 5.14 mmol) were dissolved in toluene (20 mL) and stirred at reflux for 1.5 hours using a Dean-Stark trap to azeotrope the water formed in the reaction. The solvent was evaporated under reduced pressure and placed under vacuum for 1 hr. Cesium fluoride (1.08 g, 6.68 mmol) was added to the residue and placed under vacuum for an additional 2 hours. The mixture was then dissolved in DMF (20 mL) and iodomethane (2.99 g, 22.1 mmol) and stirred overnight at room temperature. The reaction mixture was partitioned between ethyl acetate and water. The organic layers were washed with 1 N HCl, saturated sodium bicarbonate, brine, dried over sodium sulfate, and concentrated. Purification by column chromatography (SiO$_2$, 33% ethyl acetate/hexanes) afforded the desired product (800 mg). $^1$H NMR (400 MHz, CDCl$_3$) δ 4.60 (d, 1H), 4.30 (m, 4H), 4.15 (d, 1H), 3.50 (s, 3H), 1.35 (t, 6H).

Part B:

Compound 2463 was prepared using a modification to a procedure found in Tetrahedron 1993, 49, 37, 8381-8396. The diester 2462 (0.837 g, 3.6 mmol) was suspended in pH 8 phosphate buffer (75 mL) and pH was monitored at 8.33. Pig liver esterase (20 mg) was added to the suspension and the reaction mixture was stirred at room temperature. The pH of the reaction was maintained between 7.9-8.2 by the dropwise addition of 1 M NaOH (3.27 mL, 3.24 mmol) over 1.5 hours.

The reaction mixture was partitioned between diethyl ether and water. The aqueous layer was acidified to pH 2 and extracted with ethyl acetate. The combined ethyl acetate layers were dried over sodium sulfate and evaporated to provide the desired product as a 4.5:1 mixture of inseparable acids (275 mg). $^1$H NMR (400 MHz, CDCl$_3$) δ 4.60 (d, 1H), 4.40 (m, 2H), 4.25 (d, 1H), 3.50 (s, 3H), 1.35 (t, 3H).

Part C:

Compound 2463 (130 mg, 0.65 mmol), HATU (322 mg, 0.845 mmol), 4-phenylbenrzylamine (153 mg, 0.845 mmol), and DIEA (0.2 mL) were dissolved in DMF (6 mL). The reaction mixture was stirred overnight at room temperature and then partitioned between ethyl acetate and water. The organic layers were washed with 1 M HCl, saturated sodium bicarbonate, brine, dried over sodium sulfate, and concentrated. Recrystallization from ethyl acetate provided pure product (50 mg) and slightly impure product (150 mg). HPLC-MS $t_R$=1.70 min (UV$_{254\,nm}$); mass calculated for formula C$_{20}$H$_{23}$NO$_5$ 357.1, observed LCMS m/z 358.1 (M+H).

Part D:

Compound 2464 (50 mg, 0.140 mmol) was dissolved in 1 M LiOH (0.151 mL, 0.151 mmol) and THF (5 mL) and stirred for 1 hour. The reaction mixture was partitioned between ethyl acetate and water and the aqueous layer was acidified to pH 2 using 1N HCl. The organic layers were dried over sodium sulfate and concentrated to provide the desired product (46 mg). HPLC-MS $t_R$=1.43 min (UV$_{254\,nm}$); mass calculated for formula C$_{18}$H$_{19}$NO$_5$ 329.1, observed LCMS m/z 330.1 (M+H).

Part E:

Compound 2465 (46 mg, 0.140 mmol), HATU (70 mg, 0.182 mmol), compound 2000 (35 mg, 0.182 mmol), and DIEA (0.12 mL) were dissolved in DMF (6 mL). The reaction mixture was stirred overnight at room temperature and then partitioned between ethyl acetate and water. The organic layers were washed with saturated sodium bicarbonate, brine, dried over sodium sulfate, and concentrated. Recrystallization from ethyl acetate provided pure product (30 mg). HPLC-MS (10 min) $t_R$=3.51 min (UV$_{254\,nm}$); mass calculated for formula C$_{25}$H$_{25}$N$_3$O$_4$ 431.2, observed LCMS m/z 432.1 (M+H).

Example 56D

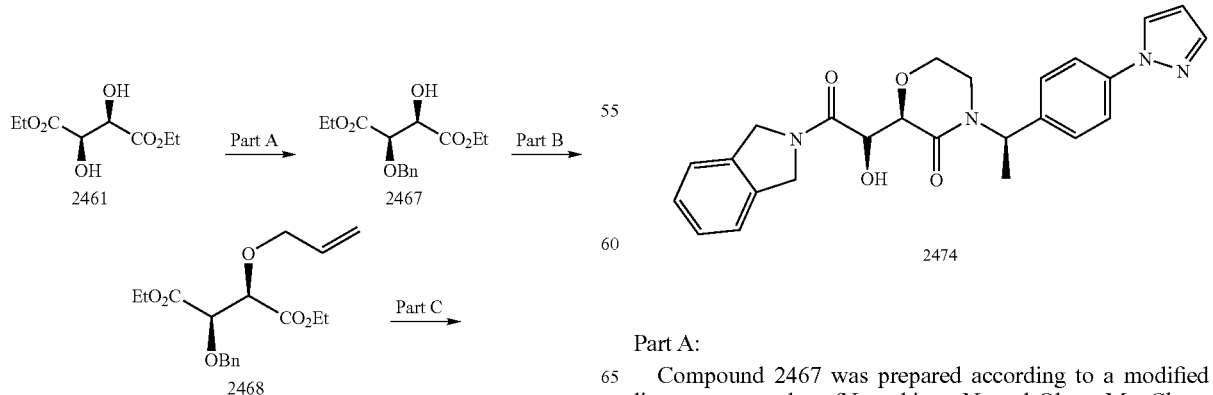

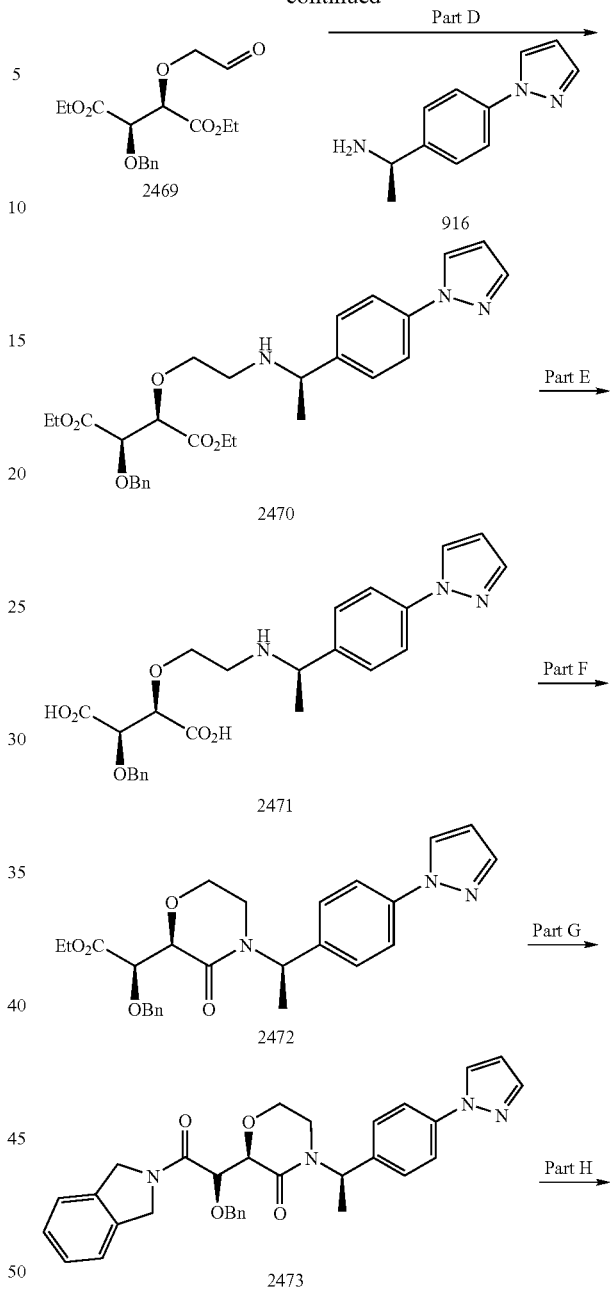

Part A:

Compound 2467 was prepared according to a modified literature procedure (Nagashima, N. and Ohno, M., *Chem. Pharm. Bull.*, 1991, 39, 1972-1982.)

L-Diethyl tartrate (2461) (6.18 g, 30 mmol) and dibutyltin oxide (7.47 g, 30 mmol) in toluene (100 mL) was heated under reflux for 1 h, removing water formed as the azotropic mixture. The solution was evaporated to complete dryness in vacuo to afford a white solid. To this solid was added dry CsF (8.66 g, 59 mmol) and DMF (60 mL). The resulting mixture was cooled to 0° C., and benzyl bromide (6 mL, 51 mmol) was added dropwise via a syringe. After the completion of addition, the reaction mixture was allowed to stir rigorously at room temperature for 12 h. The solvent was removed under vacuum and the obtained residue was dissolved in EtOAc and $H_2O$. The organic layer was washed with $NaHCO_3$ aqueous solution, brine, dried over $Na_2SO_4$, and concentrated. Purification by flask column chromatography on silica gel (EtOAc/hexane 30:70) afforded compound 2467 as colorless liquid (8.10 g, 91%). $^1$H NMR (400 MHz, $CDCl_3$) δ 7.37-7.25 (m, 5H), 4.87 (d, J=12.0 Hz, 1H), 4.58 (br s, 1H), 4.02 (d, J=12.0 Hz, 1H), 4.34-4.25 (m, 3H), 4.23-4.21 (m, 1H), 4.08-4.03 (m, 1H), 3.12 (br s, 1H), 1.35 (t, J=7.0 Hz, 3H), 1.19 (t, J=6.9 Hz, 3H).

Part B:

To compound 2467 (2.96 g, 10 mmol) in toluene (10 mL) was added with $Ag_2O$ (4.63 g, 20 mmol) and allyl bromide (1.31 mL, 15 mmol). The reaction mixture was allowed to stir at 110° C. for 16 h and cooled to room temperature. After filtering through a pad of celite, the solution was concentrated. Flash column chromatography on silica gel (EtOAc/hexane 20:80) afforded the desired product 2468 (2.65 g, 79%). $^1$H NMR (400 MHz, $CDCl_3$) δ 7.33-7.25 (m, 5H), 4.87 (d, J=12.0 Hz, 1H), 5.89-5.79 (m, 1H), 5.26-5.15 (m, 2H), 4.87 (d, J=11.4 Hz, 1H), 4.46 (d, J=11.7 Hz, 1H), 4.41-4.38 (m, 2H), 4.34-3.92 (m, 6H), 1.32 (t, J=7.2 Hz, 3H), 1.19 (t, J=7.2 Hz, 3H).

Part C:

To an ice-cold mixture of compound 2468 (1.0 g, 3 mmol) and N-methylmorpholine monohydrate (703 mg, 6 mmol) in $THF/H_2O$ 3:1 (20 mL) was added $OsO_4$ (2.5 wt % in t-BuOH, 610 mg, 0.06 mmol). After stirring for 30 min, the ice bath was removed and the reaction mixture was stirred at room temperature overnight. Solid $NaHSO_3$ (750 mg, 7.2 mmol) was added, and the mixture was stirred for an additional 30 min. The mixture was filtered through a pad of silica and the solution was concentrated in vacuo giving rise to an oil. This material was dissolved in $THF/H_2O$ 3:1 (20 mL) and $NaIO_4$ (1.28 g, 6 mmol) was added. The mixture was allowed to stir at room temperature for 1 h. It was filtered through silica, and the solvent was evaporated. Flash column chromatography on silica gel (EtOAc/hexane 50:50) provided the aldehyde 2469 (760 mg, 75%) as a colorless oil). $^1$H NMR (400 MHz, $CDCl_3$) δ 9.72 (s, 1H), 7.35-7.26 (m, 5H), 4.89 (d, J=11.8 Hz, 1H), 4.52-4.48 (m, 2H), 4.45-4.04 (m, 7H), 1.34 (t, J=7.7 Hz, 3H), 1.19 (t, J=7.4 Hz, 3H).

Part D:

Compound 2469 (340 mg, 1 mmol) and amine 916 (187 mg, 1 mmol) in 1,2-dichloroethane (5 mL) were stirred at room temperature for 5 min, after which sodium tri(acetoxyl)borohydride (254 mg, 1.2 mmol) was added slowly. The reaction mixture was allowed to stir at room temperature overnight. The solution was concentrated, the crude residue was purified by flash column chromatography on silica gel (MeOH/EtOAc 10:90), affording desired product 2470 (350 mg, 69%) as a colorless oil. HPLC-MS $t_R$=1.49 min ($UV_{254\,nm}$); mass calculated for formula $C_{28}H_{35}N_3O_6$ 509.2, observed LCMS m/z 510.1 (M+H).

Part E:

To a solution of compound 2470 (170 mg, 0.33 mmol) in dioxane/water 1:1 (10 mL) was added LiOH (1 M, 1.32 mL, 1.32 mmol) dropwise. The mixture was stirred at room temperature for 2 h after which it was neutralized with 1 M HCl and concentrated. The residue was utilized for the following step without further purification. HPLC-MS $t_R$=1.12 min ($UV_{254\,nm}$); mass calculated for formula $C_{24}H_{27}N_3O_6$ 453.2, observed LCMS m/z 454.1 (M+H).

Part F:

The crude compound 2471 was dissolved in DMF (10 mL) and cooled to 0° C. in an ice bath, HATU (304 mg, 0.8 mmol) was added slowly and the reaction mixture was stirred at 0° C. for 2 h. LC-MS indicated the disappearance of diacid and the formation of the cyclized product 2472. HPLC-MS $t_R$=1.65 min ($UV_{254\,nm}$); mass calculated for formula $C_{24}H_{25}N_3O_5$ 435.2, observed LCMS m/z 436.1 (M+H).

Part G:

To the above solution at 0° C. was added isoindoline (48 mg, 0.4 mmol) and the reaction mixture was stirred at room temperature overnight. The DMF was evaporated, the residue was dissolved inn EtOAc and water, washed with 1N HCl, saturated NaHCO3 and brine, dried over Na2SO4 and concentrated to afford 2437 as an oily solid (85 mg, 47% yield over three steps). HPLC-MS $t_R$=2.00 min ($UV_{254\,nm}$); mass calculated for formula $C_{32}H_{32}N_4O_4$ 536.1, observed LCMS m/z 537.1 (M+H).

Part H:

Crude compound 2473 was dissolved in EtOH (20 mL), and palladium on carbon (10%, 40 mg) was added. The mixture was hydrogenated (atmospheric pressure) at room temperature overnight. The suspension was filtered through celite and concentrated. The resulting residue was purified by preparative LC affording 2474 as a white solid (9.4 mg). HPLC-MS $t_R$=3.57 min (10 min method, $UV_{254\,nm}$); mass calculated for formula $C_{25}H_{26}N_4O_4$ 446.2, observed LCMS m/z 447.1 (M+H).

The following compounds were prepared using previously described procedures.

| Compound # | Structure | Exact mass | MS m/z (M + H) |
|---|---|---|---|
| 2475 | 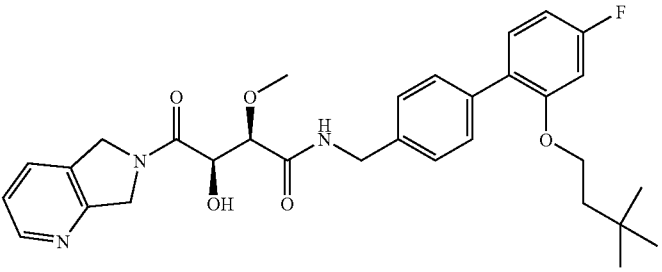 | 549.3 | 550.2 |
| 2476 | 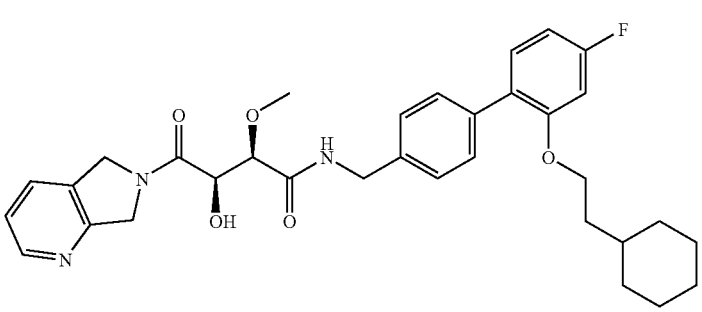 | 575.3 | 576.1 |
| 2477 | 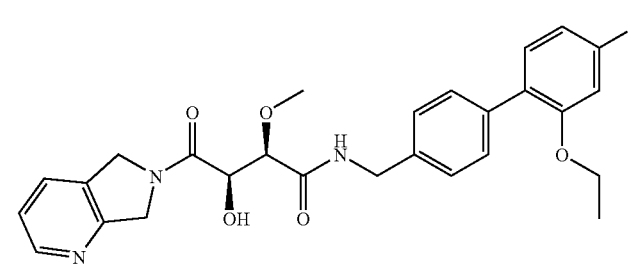 | 493.2 | 494.2 |
| 2478 | 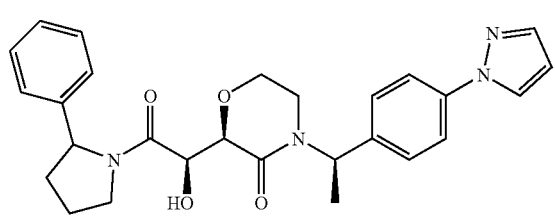 | 474.2 | 475.1 |
| 2474 | 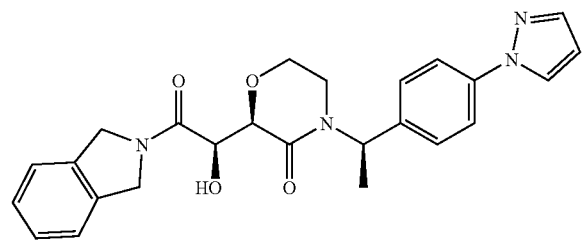 | 446.2 | 447.1 |

Example 57

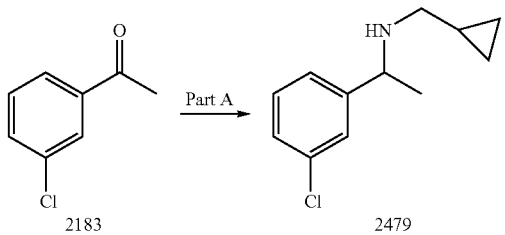

Part A:

Compound 2183 (200 mg, 1.3 mmol) and cyclopropylmethyl amine (0.16 mL) were dissolved in MeOH (5 mL) and stirred at 50° C. overnight. Then sodium borohydride (42 mg, 1.3 mmol) was added and the mixture was stirred for 2 hours. The solvent was removed under reduced pressure and the residue was partitioned between diethyl ether and 1 N HCl. The aqueous layer was made basic and extracted with ethyl acetate. The combined ethyl acetate layers were dried over sodium sulfate and concentrated to provide the desired product 2479 (130 mg). $^1$H NMR (400 MHz, CDCl$_3$) δ 7.32 (m, 1H), 7.28-7.18 (m, 3H), 3.79 (m, 1H), 2.50-2.25 (m, 2H), 1.38 (d, 3H), 1.00-0.90 (m, 1H), 0.50-0.45 (m, 2H), 0.10-0.00 (m, 2H).

The following compounds were prepared using previously described procedures.

| Compound # | Structure | Exact mass | MS m/z (M + H) |
|---|---|---|---|
| 2480 | 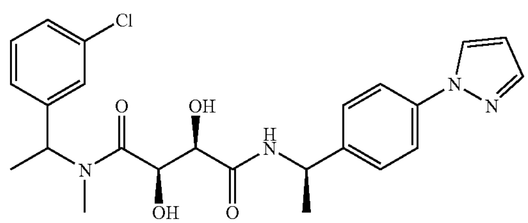 | 470.2 | 471.1 |
| 2481 | 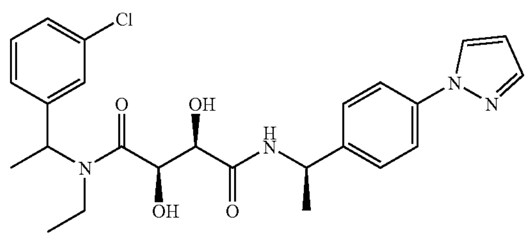 | 484.2 | 485.0 |
| 2482 | 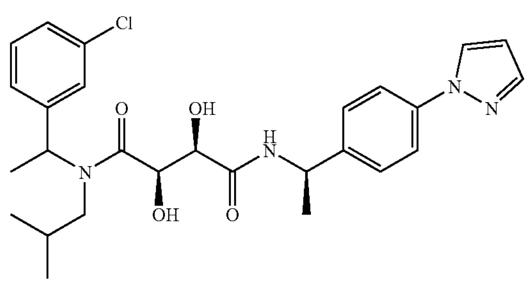 | 512.2 | 513.1 |
| 2483 | 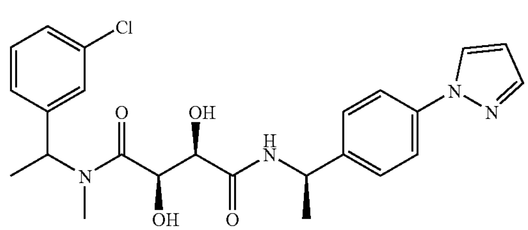 | 496.2 | 497.0 |

-continued
| Compound # | Structure | Exact mass | MS m/z (M + H) |
|---|---|---|---|
| 2485 | 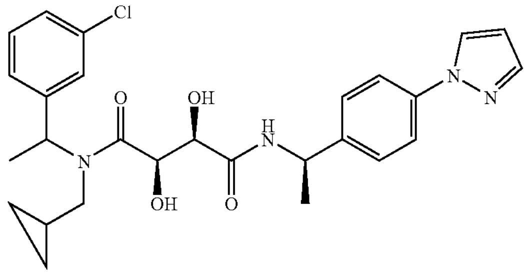 | 510.2 | 511.1 |
| 2486 | 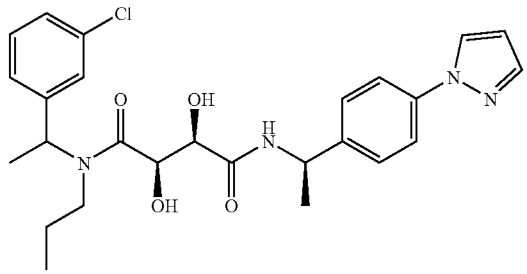 | 498.2 | 499.1 |
| 2487 | 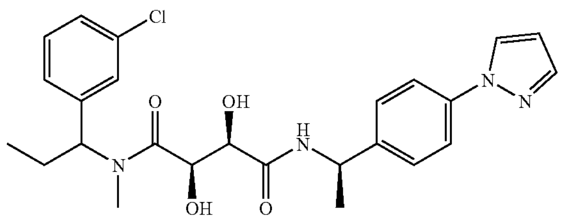 | 484.2 | 485.0 |
| 2489 | 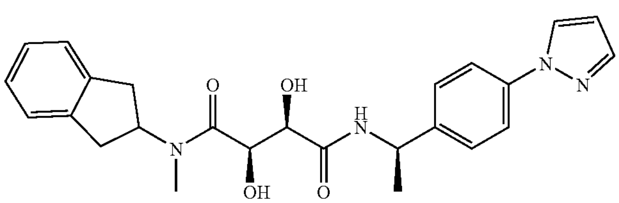 | 448.2 | 449.1 |
Example 58
Example 58A
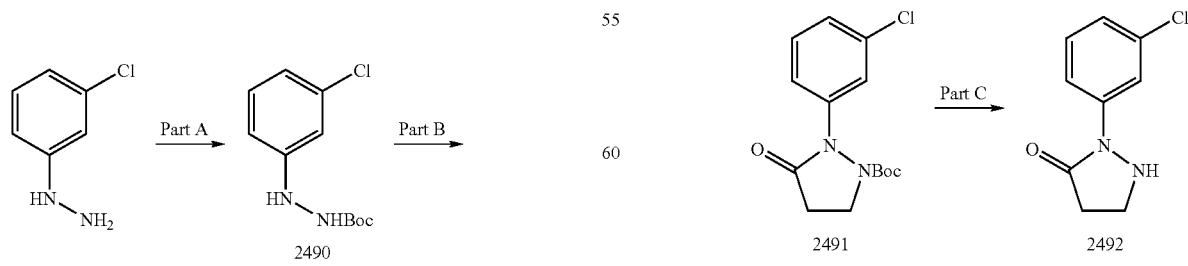
-continued Part A:

To a solution of Boc$_2$O (6.1 g, 28 mmol) and Et$_3$N (7.8 mL, 56 mmol) in DMF (20 mL) at 0° C. was added portionwise 3-chlorophenylhyrazine hydrocloride (5.0 g, 28 mmol) in DMF (20 mL). The reaction mixture was allowed to stir at room temperature for 2 h and concentrated. The residue was dissolved in EtOAc and H$_2$O, washed with 1N citric acid and saturated NaHCO$_3$, dried over Na$_2$SO$_4$ and concentrated, affording 2490 (17.83 g, 97%) as a off-white solid. $^1$H NMR (400 MHz, CDCl$_3$) δ 7.13 (t, J=8.3 Hz, 1H), 6.86-6.81 (m, 2H), 6.70-6.66 (m, 1H), 6.36 (br s, 1H), 1.48 (s, 10H).

Part B:

3-Chloropropionyl chloride (0.400 mL, 4.12 mmol) was added dropwise into a solution of compound 2490 (1.0 g, 4.12 mmol) and K$_2$CO$_3$ (1.14 g, 8.24 mmol) in DMF (10 mL) at 0° C. The reaction mixture was allowed to stir at 80° C. overnight and concentrated. The residue was dissolved in EtOAc and H$_2$O, washed with 1N citric acid and saturated NaHCO$_3$, dried over Na$_2$SO$_4$, and concentrated. Column chromatography (EtOAc/hexane 25:75) provided compound 2491 (600 mg, 49%) as an off-white solid. $^1$H NMR (400 MHz, CDCl$_3$) δ 7.57 (t, J=2.3 Hz, 1H), 7.51-7.48 (m, 1H), 7.27 (t, J=8.3 Hz, 1H), 7.12-7.09 (m, 1H), 4.16 (t, J=7.2 Hz, 2H), 2.77 (t, J=7.3 Hz, 2H), 1.34 (s, 9H).

Part C:
Compound 2491 was deprotected with TFA in CH$_2$Cl$_2$. The material was used without further purification.

Example 58B

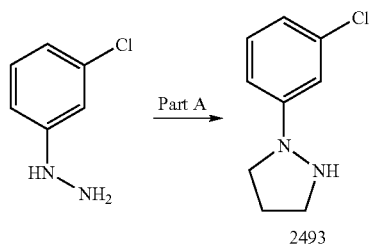

Part A:
To a suspension of NaH (60% in mineral oil, 1.56 g, 39 mmol) in benzene (40 mL) at 0° C. was added with 3-chlorophenylhyrazine (2.13 g, 15 mmol). The mixture was stirred at 80° C. for 1 h, after which 1,3-dibromopropane (2.0 g, 10 mmol) was added slowly via syringe. It was stirred at 80° C. overnight and quenched by adding water (20 mL). The organic layer was separated, washed with water and brine, dried over Na$_2$SO$_4$, and concentrated. Column chromatography (DCM) provided compound 2493 (850 mg, 47%) as pale yellow oil. $^1$H NMR (400 MHz, CDCl$_3$) δ 7.12 (t, J=8.2 Hz, 1H), 7.04 (t, J=2.3 Hz, 1H), 6.84-6.81 (m, 1H), 6.74-6.71 (m, 1H), 3.75 (bs, 1H), 3.35 (t, J=7.5 Hz, 2H), 3.00 (t, J=6.7 Hz, 2H), 2.16-2.11 (m, 2H).

The following compounds were prepared using previously described procedures.

| Compound # | Structure | Exact mass | MS m/z (M + H) |
|---|---|---|---|
| 2494 | (structure shown) | 497.2 | 498.1 |
| 2495 | (structure shown) | 483.2 | 484.1 |

-continued

| Compound # | Structure | Exact mass | MS m/z (M + H) |
|---|---|---|---|
| 2496 | 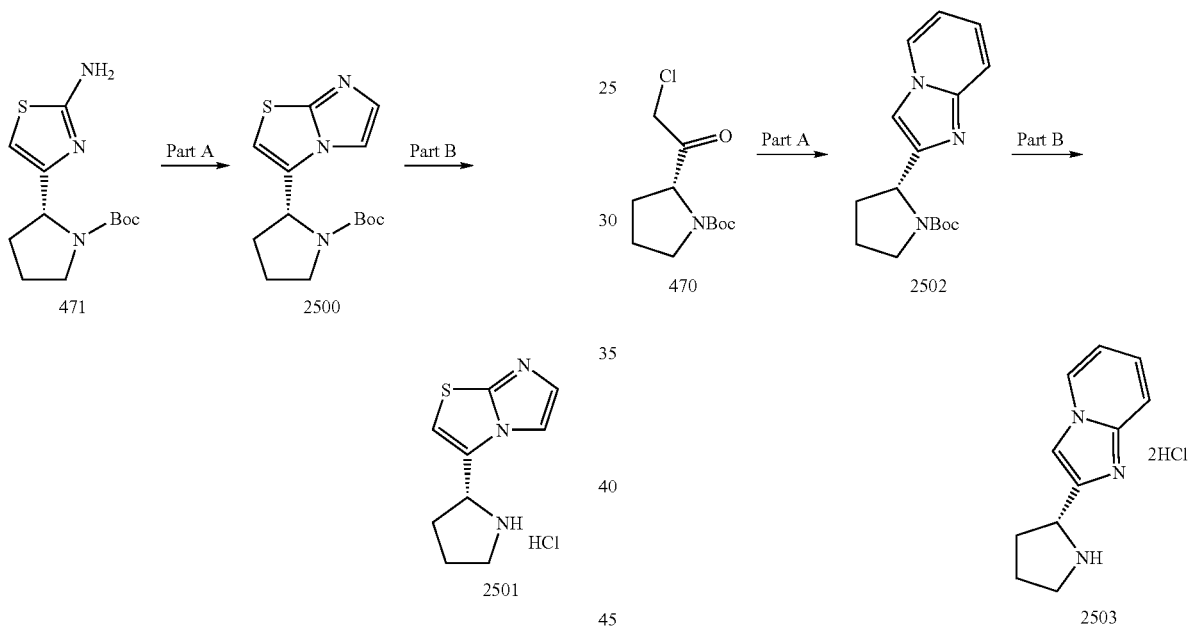 | 449.2 | 450.1 |

Example 59

Example 59A

Example 59B

Part A:

To compound 471 (100 mg, 0.37 mmol) in EtOH (2 mL) was added chloroacetaldehyde (50 wt. % in water, 233 mg, 1.48 mmol). The reaction mixture was allowed to stir at 90° C. overnight and concentrated. The residue was dissolved in EtOAc, washed with water and brine, dried (Na$_2$SO$_4$) and concentrated. The crude product 2500 (90 mg, 82%) was used without further purification. HPLC-MS $t_R$=1.10 min; Mass calculated for formula C$_{14}$H$_{19}$N$_3$O$_2$S 293.1, observed m/z 294.1 (M+H).

Part B:

Compound 2500 (90 mg) was dissolved in 2 mL of 4 N HCL in dioxane/H$_2$O (1:1). After stirring at room temperature for 1 h, the solution was concentrated, affording a brown solid (80 mg, 90%). HPLC-MS $t_R$=0.22 min; Mass calculated for formula C$_9$H$_{11}$N$_3$S 193.1, observed m/z 194.1 (M+H).

Part A:

A mixture of chloroketone 470 (200 mg, 0.81 mmol) and 2-aminopyridine (77 mg, 0.82 mmol) in ethanol (5 ml) was heated to reflux and stirred overnight. The reaction mixture was concentrated and purified by prep-HPLC to afford 2502 (103 mg). HPLC-MS $t_R$=1.00 min (UV$_{254\ nm}$); mass calculated for formula C$_{16}$H$_{21}$N$_3$O$_2$ 287.2, observed LCMS m/z 288.3 (M+H).

Part B:

To a solution of imidazopyridine 2502 (103 mg, 0.56 mmol) in dioxane (2 mL) was added HCl (4N in dioxane, 4 mL) and water (0.5 mL). The mixture was stirred at room temperature for 1 hour and concentrated. The resulting residue 2503 (81 mg) was dried under vacuum and used in the next step without further purification. HPLC-MS $t_R$=0.19 min (UV$_{254\ nm}$); mass calculated for formula C11H13N3 187.1, observed LCMS m/z 188.1 (M+H).

Example 59C

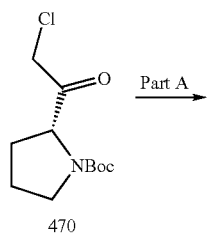

470

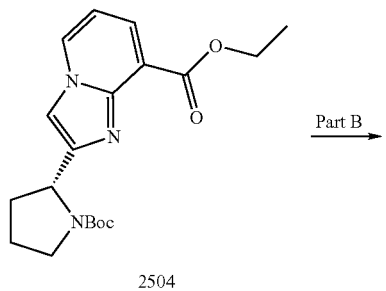

2504

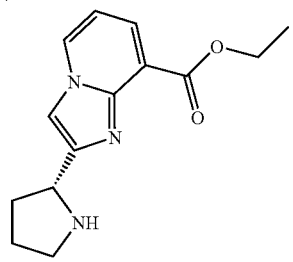

2505

Part A:

A mixture of chloroketone 471 (200 mg, 0.81 mmol) and 2-aminopyridine (140 mg, 0.81 mmol) in ethanol (5 ml) was heated up to reflux and stirred overnight. The reaction mixture was concentrated and purified by prep-HPLC to afford 2504 (119 mg). HPLC-MS $t_R$=1.22 min ($UV_{254\ nm}$); mass calculated for formula $C_{19}H_{25}N_3O_4$ 359.2, observed LCMS m/z 360.1 (M+H).

Part B:

To a solution of imidazopyridine 2504 (119 mg, 0.33 mmol) in dioxane (2 mL) was added HCl (4N in dioxane, 4 mL) and water (0.5 mL). The mixture was stirred at room temperature for 1 hour and concentrated. The resulting residue 2505 (83 mg) was dried under vacuum and used in the next step without further purification. HPLC-MS $t_R$=0.70 min ($UV_{254\ nm}$); mass calculated for formula $C_{14}H_{17}N_3O_2$ 259.1, observed LCMS m/z 260.1 (M+H).

The following compounds were prepared using previously described procedures.

| Compound # | Structure | Exact mass | MS m/z (M + H) |
|---|---|---|---|
| 2506 | 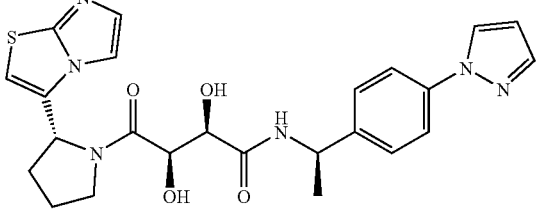 | 494.2 | 495.1 |
| 2507 | 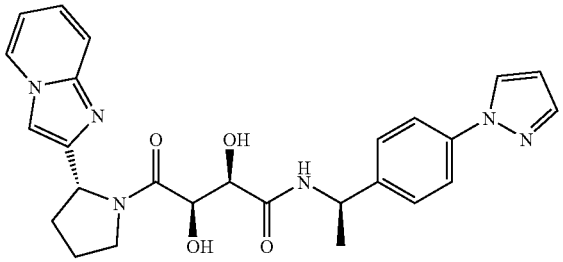 | 488.2 | 489.1 |

| Compound # | Structure | Exact mass | MS m/z (M + H) |
|---|---|---|---|
| 2508 | 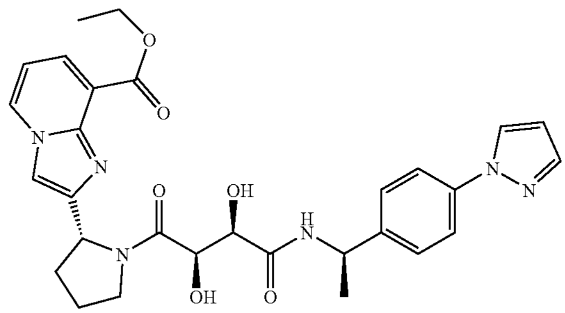 | 560.2 | 561.2 |

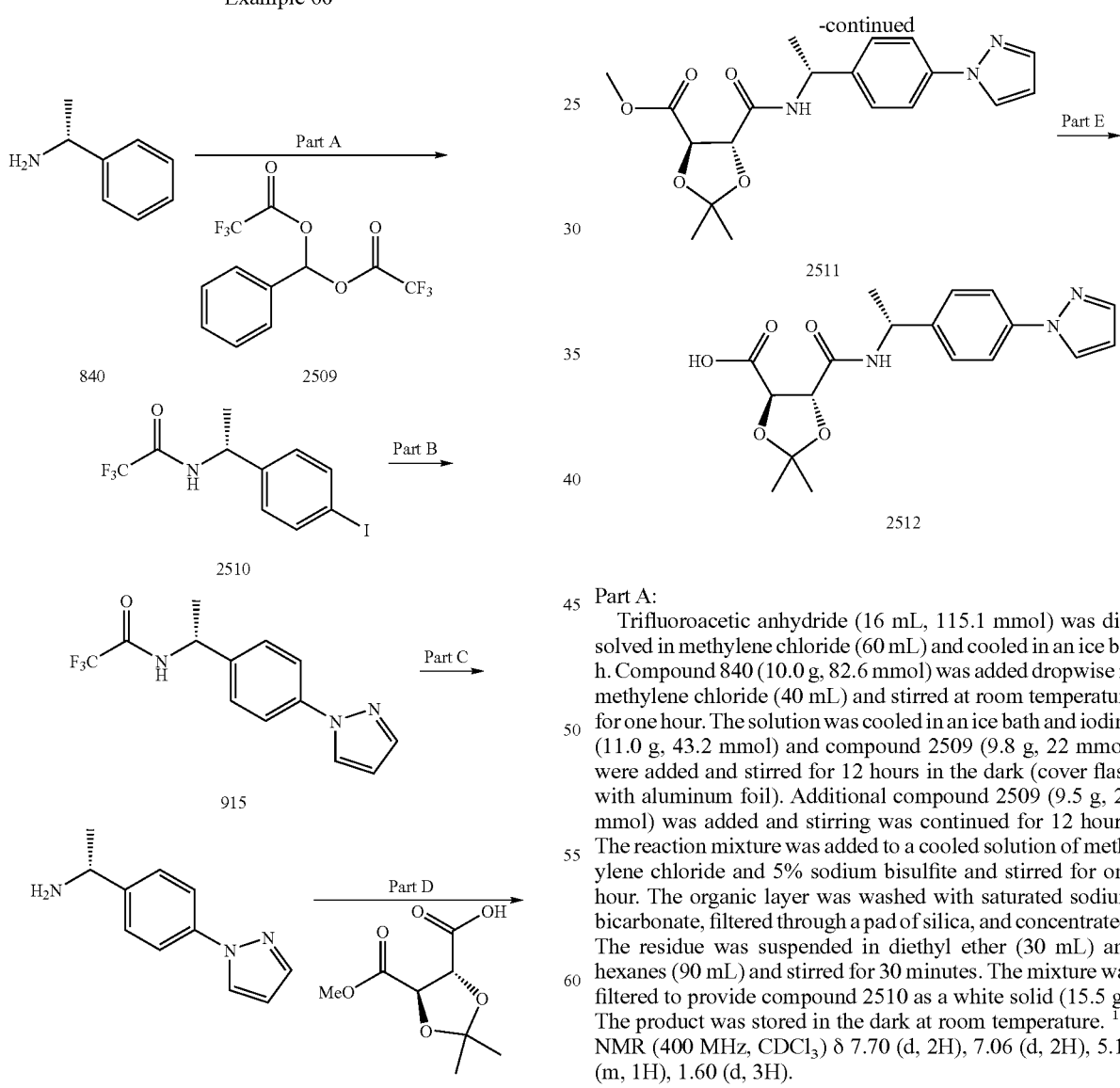

Example 60

Part A:

Trifluoroacetic anhydride (16 mL, 115.1 mmol) was dissolved in methylene chloride (60 mL) and cooled in an ice bath. Compound 840 (10.0 g, 82.6 mmol) was added dropwise in methylene chloride (40 mL) and stirred at room temperature for one hour. The solution was cooled in an ice bath and iodine (11.0 g, 43.2 mmol) and compound 2509 (9.8 g, 22 mmol) were added and stirred for 12 hours in the dark (cover flask with aluminum foil). Additional compound 2509 (9.5 g, 20 mmol) was added and stirring was continued for 12 hours. The reaction mixture was added to a cooled solution of methylene chloride and 5% sodium bisulfite and stirred for one hour. The organic layer was washed with saturated sodium bicarbonate, filtered through a pad of silica, and concentrated. The residue was suspended in diethyl ether (30 mL) and hexanes (90 mL) and stirred for 30 minutes. The mixture was filtered to provide compound 2510 as a white solid (15.5 g). The product was stored in the dark at room temperature. $^1$H NMR (400 MHz, CDCl$_3$) δ 7.70 (d, 2H), 7.06 (d, 2H), 5.10 (m, 1H), 1.60 (d, 3H).

Part B:

Compound 2510 (4.0 g, 11.66 mmol), pyrazole (0.953 g, 14 mmol), copper (I) iodide (444 mg, 2.33 mmol), cesium carbonate (7.6 g, 23.3 mmol), 1,10 phenanthroline (844 mg, 4.66 mmol) and dimethylacetamide (40 mL) were combined in a 80 mL screw-capped vial and stirred in the dark at 120° C. for 12 hours. The reaction mixture was poured into ethyl acetate (200 mL) and filtered. The organic layer was washed with water several times followed by 1N citric acid solution. The organic layer was dried over sodium sulfate and concentrated. The residue was recrystallized from ethyl acetate and hexanes to provide 2.45 g of compound 915. $^1$H NMR (400 MHz, CDCl$_3$) δ 7.92 (m, 1H), 7.70 (m, 2H), 7.40 (d, 1H), 6.45 (t, 1H), 5.20 (m, 1H), 1.65 (d, 3H).

Part C:

Compound 915 (2.43 g, 9.13 mmol) was dissolved in methanol (20 mL) and 1N lithium hydroxide (20 mL) and stirred for 6 hours. The reaction mixture was poured into ethyl acetate and water. The aqueous layer was extracted with ethyl acetate. The combined organic layers were washed with brine, dried over sodium sulfate, and concentrated to provide compound 916 (1.45 g). $^1$H NMR (400 MHz, CDCl) δ 7.90 (d, 1H), 7.70 (d, 1H), 7.64 (d, 2H), 7.43 (d, 2H), 6.46 (t, 1H), 1.44 (d, 3H).

Part D:

Compound 916 (1.45 g, 7.7 mmol), compound 1 (1.5 g, 7.35 mmol), HATU (3.63 g, 9.55 mmol), and diisopropylethylamine (1.28 mL, 7.35 mmol) were dissolved in DMF (20 mL) at 0° C. The reaction mixture was stirred for 12 hours and then diluted with water and extracted with ethyl acetate. The combined organic layers were washed with 1N HCl, saturated sodium bicarbonate, brine and water, dried over sodium sulfate and concentrated. The residue was purified by column chromatography (2:1 hexanes/ethyl acetate) to provide compound 2511 (2.15 g). $^1$H NMR (400 MHz, CDCl$_3$) δ 7.90 (d, 1H), 7.72 (m, 1H), 7.66 (d, 2H), 7.40 (d, 2H), 6.75 (d, 1H), 6.49 (d, 1H), 5.20 (m, 1H), 4.82-4.75 (dd, 2H), 3.83 (s, 3H), 1.57 (d, 3H), 1.54 (s, 3H), 1.50 (s, 3H).

Part E:

Compound 2511 (2.15 g, 5.76 mmol) was dissolved in THF (20 mL) and 1N lithium hydroxide and stirred for 2 hours. Diethyl ether was added and the aqueous layer was acidified to pH 2 with 1 N HCl and extracted with ethyl acetate. The combined ethyl acetate layers were dried over sodium sulfate and concentrated to provide compound 2512 as a white solid (1.95 g). 1H NMP (400 MHz CDCl$_3$) δ 7.9 (d, 1H), 7.74 (m, 1H), 7.70 (d, 2H), 7.42 (d, 2H), 6.96 (d, 1H), 6.49 (t, 1H), 5.2 (m, 1H), 4.60-4.50 (dd, 2H), 1.64 (d, 3H), 1.54 (d, 3H).

Example 61

Example 61A

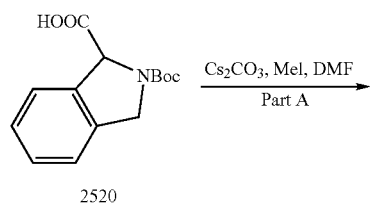

2520

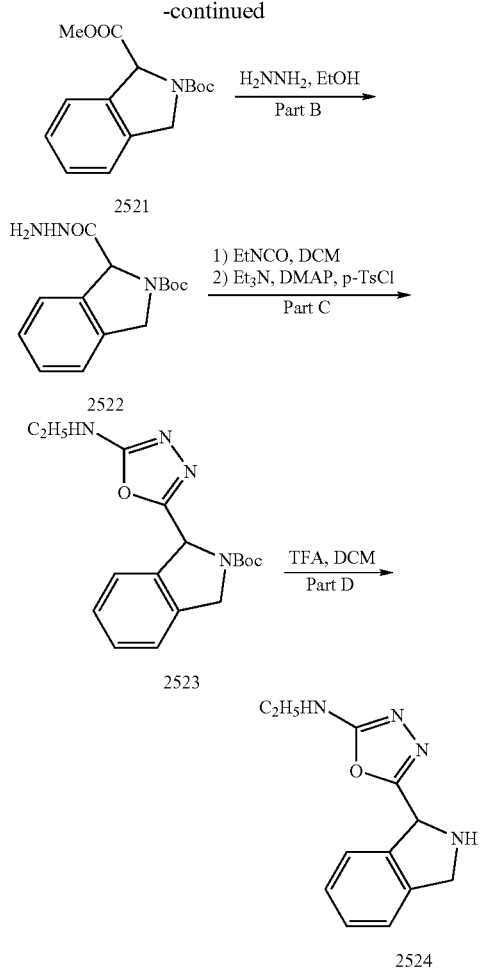

Part A:

(R,S)-BOC-1,3-Dihydro-2H-Isoindole carboxylic acid 2520 (3.0 g, 11.39 mmol) and cesium carbonate (4.05 g, 12.43 mmol) were stirred together in DMF (25 mL) at r.t. for one hour. Iodomethane (1.05 mL, 16.86 mmol) was added and the reaction mixture was stirred at ambient temperature overnight. The reaction mixture was diluted with ethyl acetate then washed several times with water, brine (1×50 mL), dried over Na$_2$SO$_4$ and concentrated to give light yellow oil. Purification by column chromatography (SiO2, 25% ethyl acetate/hexane) afforded 2521 (2.66 g, 84%) as white solid.

Part B:

A mixture of 2521 (0.2 g, 0.72 mmol) and hydrazine (0.22 mL, 7.0 mmol) in ethanol (20 mL) was heated at 70° C. for 5 hours. The solvent was removed under reduced pressure and the resulting residue was dissolved in ethyl acetate, washed with water (2×30 mL), brine (1×20 mL), dried over Na$_2$SO$_4$ and concentrated to provide 2522 (0.18 g, 86%) as an yellow oil, which was used in the next step without further purification.

Part C:

A mixture of 2522 (0.2 g, 0.72 mmol) and ethyl isocyanate (0.077 g, 1.083 mmol) in DCM (5 mL) was stirred at r.t. for 16 hours. Additional ethyl isocyanate (0.077 g, 1.083 mmol) was added and reaction was stirred for another two hours. The solvent was removed under reduced pressure to provide the crude product as a white gum. It was dissolved in DCM (20 mL) and treated triethyl amine (0.5 mL, 3.6 mmol), DMAP (0.017 g, 0.139 mmol) and p-toluene sulphonyl chloride (0.16 g, 0.83 mmol). The mixture was stirred at room temperature for 64 hours and the solvent was removed. The residue was purified by preparative chromatography using 5% MeOH/CH$_2$Cl$_2$, to provide the product which was again purified using ethyl acetate/Hexane (3/1) to yield intermediate 2523 (0.1 g, 44%) as a light brown solid.

Part D:

Intermediate 2523 (0.05 g, 0.15 mmol) was dissolved in DCM (10 mL) then trifluoroacetic acid (0.06 mL, 0.77 mmol) was added. Reaction was stirred at ambient temperature for 3 hours and then concentrated. The residue was dissolved in DCM and washed with saturated sodium bicarbonate solution (1×0.8 mL), saline (1×0.8 mL), dried over sodium sulfate and concentrated under vacuum to provide amine 2524 (0.03 g, 86%) as a brown oil. It was used in the next step without additional purification.

Example 61B

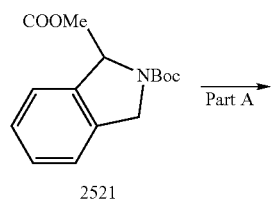

2521

-continued

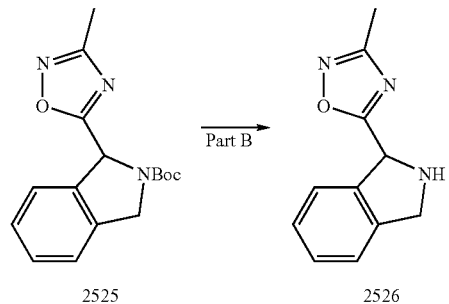

2525    2526

Part A:

Intermediate 2525 was prepared by known methods (Showell, G. A.; Gibbons, T. L.; Kneen, C. O.; Macleod, A. M.; Merchant, K.; Saunders, J.; Freedman, S. B.; Patel, S; Baker, R. *J Med. Chem.* 1991, 34 (3), 1086-1094).

Part B:

Intermediate 2526 was prepared using the method described in Example 61A Part D.

The following compounds were prepared using previously described procedures.

| Compound # | SCH | Structure | Exact mass | MS m/z (M + H) |
|---|---|---|---|---|
| 2527 | 786656 | 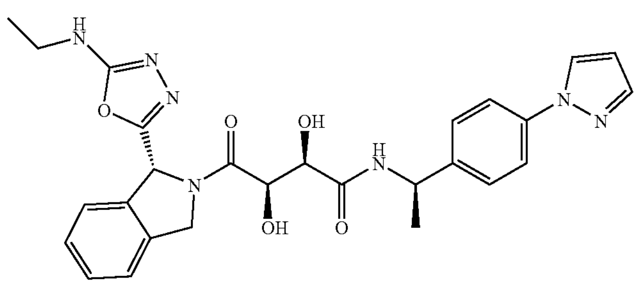 | 531.2 | 532.2 |
| 2528 | 7867566 | 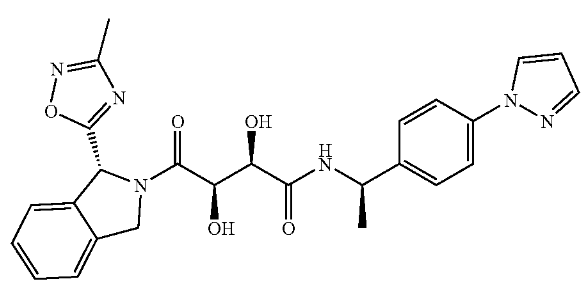 | 502.2 | 503.2 |

Example 62

Example 62A

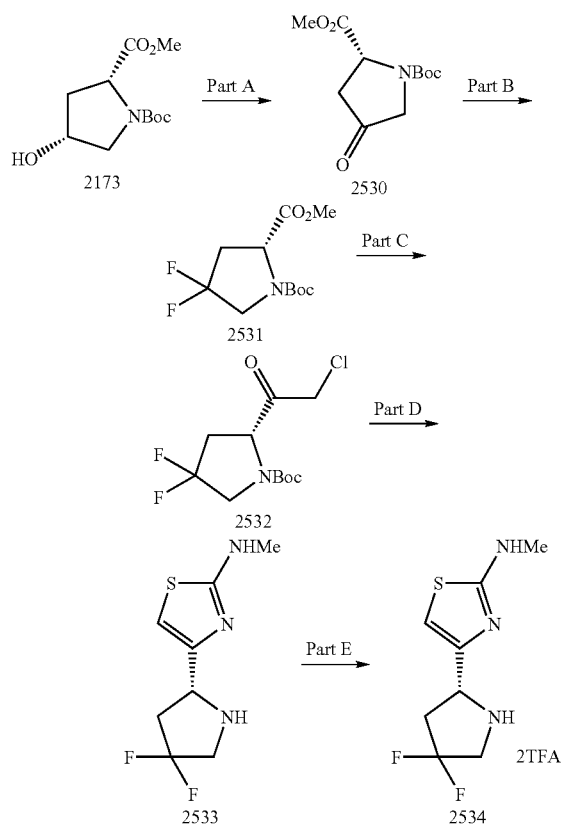

Part A:

A mixture of 2173 (1.54 g, 6.28 mmol) and Dess-Martin periodinane (2.72 g, 6.41 mmol) in DCM (30 ml) was stirred at room temperature overnight. To the reaction mixture was add saturated sodium bicarbonate solution and the mixture was stirred for 2 hours. The solids were removed by filtration. The filtrate was separated and the organic layer was washed with brine, dried over sodium sulfate and concentrated. Purification by column chromatography (SiO$_2$, 30% ethyl acetate/hexane) afforded 2530 (939 mg, 61%) as an oil. HPLC-MS $t_R$=1.10 min (MS); Mass calculated for formula C11H17NO5 243.1, observed m/z 266.1 (M+Na).

Part B:

To ketone 2530 (939 mg, 3.86 mmol) in DCM (30 mL) at −78° C. under argon was added (diethylamino)sulfur trifluoride (2.53 mL, 19.3 mmol). The bath was slowly warmed to room temperature while the mixture was stirred overnight. The reaction mixture was poured into saturated sodium bicarbonate and the layers were separated. The organic layer was washed with brine, dried over sodium sulfate and concentrated. Purification by column chromatography (SiO$_2$, 10% to 30% ethyl acetate/hexane) afforded 2531 (751 mg, 74%) as an oil. HPLC-MS $t_R$=4.72 min (10 min, MS); Mass calculated for formula C1H17F2NO4 265.1, observed m/z 288.1 (M+Na).

Part C:

Compound 2531 (751 mg, 2.83 mmol) was converted to 2532 (418 mg, 52%) using the procedures described in Example 10 Part A. HPLC-MS $t_R$=1.85 min (MS); Mass calculated for formula C11H16ClF2NO3 283.1, observed m/z 228.1 (M-55).

Part D:

Compound 2532 (418 mg, 1.47 mmol) was cyclized with N-methylthiourea according to the procedures described in Example 51B Part C to afford 2533 (200 mg, 42%). HPLC-MS $t_R$=1.38 min (UV 254 nm); Mass calculated for formula C8H11F2N3S 319.1, observed m/z 320.1 (M+H).

Part E:

Compound 2534 was synthesized in quantitative yield using the procedure described in Example 51D Part H. $^1$H NMR (400 MHz, CDCl$_3$) δ 6.89 (s, 1H), 4.98 (dd, 1H, J=7.2, 11.7 Hz), 3.89 (m, 1H), 3.72 (m, 1H), 3.13 (s, 3H), 3.09-2.85 (m, 2H).

Example 62B

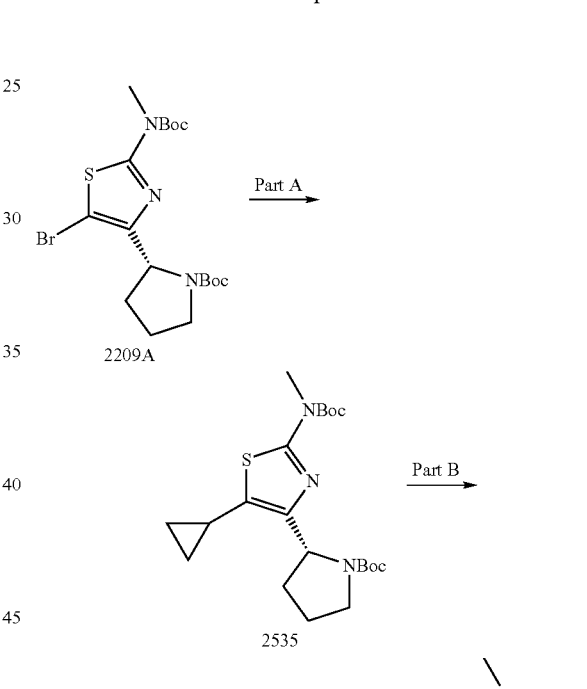

Part A:

The mixture of 5-bromothiazole 2209A (210 mg, 0.45 mmol), cyclopropylboronic acid (80 mg, 1.0 mmol), Pd(dppf)Cl$_2$ (41 mg, 0.05 mmol) and K$_3$PO$_4$ (424 mg, 2.0 mmol) in 20-ml vial was flushed with argon for 3 min. Under the argon, dioxane (5 mL) was added and the vial was sealed under the argon atmosphere. The mixture was heated to 80° C. and stirred overnight. After cooling to room temperature, ethyl acetate (30 mL) was added to the reaction mixture and the solution was filtered through celite. The filtrate was concentrated and purified by column chromatography (SiO$_2$, 10% ethyl acetate/hexanes) to afford 5-cyclopropylthiazole 2535 (166 mg) as oil. HPLC-MS $t_R$=2.65 min (UV$_{254\ nm}$); mass calculated for formula C21H33N3O4S 423.2, observed LCMS m/z 424.1 (M+H).

Part B:

To the solution of 5-cyclopropylthiazole 2535 (166 mg, 0.39 mmol) in dioxane (2 mL), HCl (4N in dioxane, 4 mL) was added followed by the addition of water (0.5 mL). The mixture was stirred at room temperature for 1 hour and concentrated. The resulting residue 2536 (111 mg) was dried under vacuum and used in the next step without further purification. HPLC-MS $t_R$=0.86 min (UV$_{254\ nm}$); mass calculated for formula C11H17N3S 223.1, observed LCMS m/z 224.1 (M+H).

Example 62C

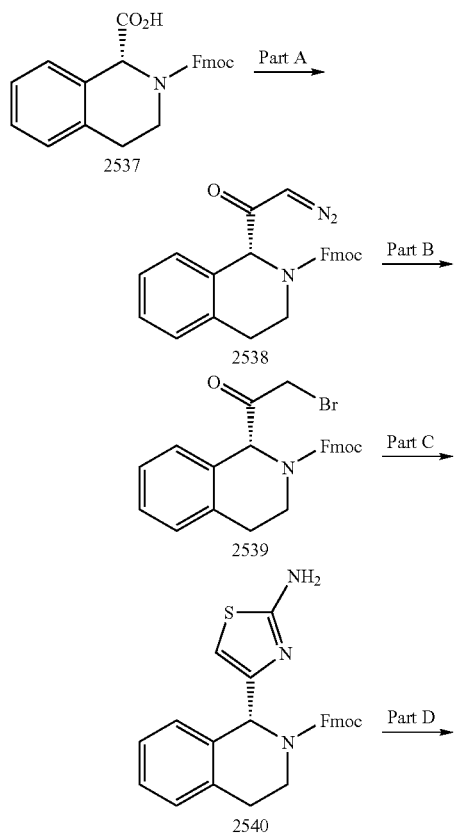

Part A:

To Fmoc-D-Tiq-OH (2537) (1.0 g, 2.5 mmol) in dichloromethane (20 mL) at 0° C. was added (COCl)$_2$ (0.262 mL, 3.0 mmol) and DMF (2 drops, catalytic) under argon. The reaction mixture was stirred at 0° C. for 2 hr and concentrated to dryness in vacuo. The resulting syrup was dissolved in dry THF (20 mL) and cooled to 0° C. Trimethylsilyidiazomethane (2.0 M in Et2O, 5 mL, 10 mmol) was added dropwise under argon during a period of 30 min. After the completion of addition, the solution was stirred at 0° C. for 3 hr and concentrated under reduced pressure. Flash column chromatography on silica (EtOAc/hexane 25:75) afforded 2538 (630 mg, 60%) as a yellow oily solid. HPLC-MS $t_R$=2.23 min (UV$_{254\ nm}$); mass calculated for formula C$_{26}$H$_{21}$N$_3$O$_3$ 423.2, observed LCMS m/z 446.2 (M+Na).

Part B:

Compound 2538 (630 mg, 1.49 mmol) in Et$_2$O (20 mL) was cooled to 0° C. To this solution was added 2.15 M hydrobromide acid in Et$_2$O (830 □L, 1.79 mmol) dropwise. The reaction mixture was stirred for 20 min at 0° C. and concentrated. The residue was dissolved in EtOAc, the solution was than washed with saturated bicarbonate solution, brine, dried (Na$_2$SO$_4$) and concentrated in vacuo to afford 2539 (630 mg, 89%) as an off white solid. HPLC-MS $t_R$=2.40 min (UV$_{254\ nm}$); mass calculated for formula C$_{26}$H$_{22}$BrNO$_3$ 475.1, observed LCMS m/z 476.0 (M+H).

Part C:

Compound 2539 (150 mg, 0.31 mmol) and thiourea (36 mg, 0.47 mmol) in DMF (2 mL) was allowed to stir at room temperature for 3 hr. The solution was concentrated and the residue was dissolved with EtOAc and saturated NaHCO$_3$ solution. The organic phase was washed with H$_2$O, brine, dried over Na$_2$SO$_4$, and concentrated. Flash column chromatography on silica (EtOAc/hexane 60:40) afforded 2540 (120 mg, 84%) as a white solid. HPLC-MS $t_R$=1.96 min (UV$_{254\ nm}$); mass calculated for formula C$_{27}$H$_{23}$N$_3$O$_2$S 453.2, observed LCMS m/z 454.1 (M+H).

Part D:

Compound 2540 (150 mg, 0.26 mmol) was treated with 20% piperidine in DMF (10 mL). The solution was stirred at room temperature for 2 hr and concentrated. LC-MS indicated the clean deprotection of the Fmoc group. HPLC-MS $t_R$=0.72 min (UV$_{254\ nm}$); mass calculated for formula C$_{12}$H$_{13}$N$_3$S 231.1, observed LCMS m/z 232.1 (M+H).

Example 62D

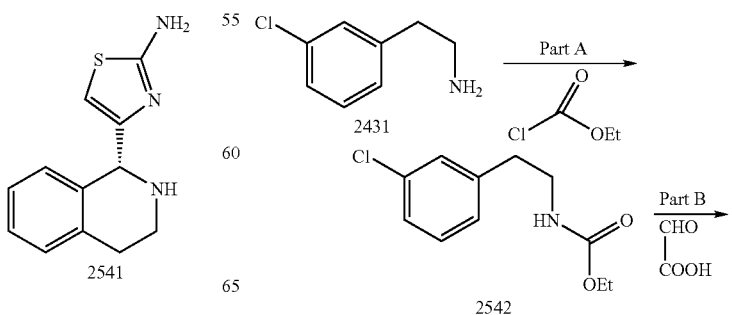

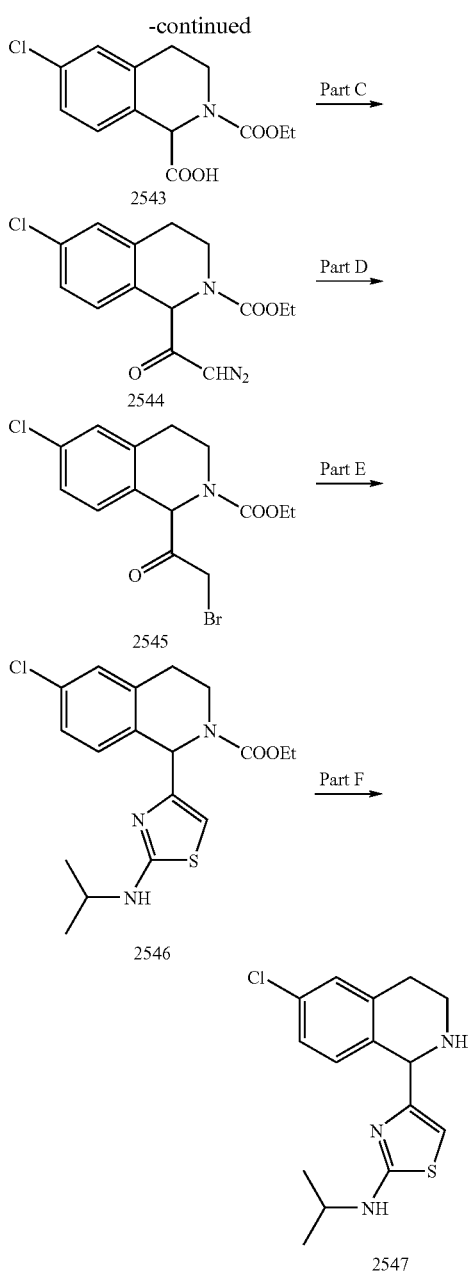

Part A:

According to a modification of a procedure by Ortwine, D. F. et al. (*J. Med. Chem.* 1992, 35, 1345-1370) to an ice-cold solution of 3-chlorophenethylamine 2431 (10 g, 64.6 mmol) and triethylamine (6.46 mL, 67.8 mmol) in DCM (200 mL) was added dropwise ethyl chloroformate (9.45 mL, 67.8 mmol), and the resulting solution was stirred at 0° C. for 1 h, and then at rt for 1.5 h. The reaction mixture was washed with saturated sodium bicarbonate solution, brine, dried and concentrated to give ethyl carbamate 2542 as a colorless oil (14.36 g, 98%). $^1$H NMR (400 MHz, CDCl$_3$) δ 7.24-7.19 (m, 3H), 7.09-7.07 (d, 1H), 4.66 (s, broad, NH), 4.12 (q, 2H), 3.44 (q, 2H), 2.81 (t, 2H), 1.25 (t, 3H).

Part B:

According to a modification of a procedure by Ortwine, D. F. et al. (*J. Med. Chem.* 1992, 35, 1345-1370) to an ice-cold mixture of carbamate 2542 (6.81 g, 29.9 mmol) and 3:1 glacial acetic acid:sulfuric acid (64 mL) was added (in two portions) glyoxylic acid monohydrate (3.03 g, 32.9 mmol) and the mixture was stirred at rt overnight. The reaction mixture was poured in ice, and extracted with dichloromethane (5 times). The combined dichloromethane extracts were dried and concentrated to an oily residue, which was then taken in toluene and concentrated (3 times) and dried under vacuum overnight to give compound 2543 (7.91 g, 93%). $^1$H NMR (400 MHz, DMSO-d$_6$). 12.9 (s, broad, COOH), 7.50-7.12 (m, 3H), 5.42 (s, 1H), 4.12-4.03 (m, 2H), 3.77-3.50 (m, 2H), 2.89-2.79 (m, 2H), 1.24-1.16 (m, 3H). HPLC-MS $t_R$=1.68 min (UV$_{254\,nm}$); mass calculated for formula C13H$_{14}$ClNO4 283.1, observed LCMS m/z 284.0 (M+H).

Part C:

Diazoketone 2544 was prepared using procedures described in Example 62C Part A. $^1$H NMR (400 MHz, CDCl$_3$) δ 7.23-7.18 (m, 3H), 5.60-5.41 (m, 2H), 4.26-4.22 (m, 2H), 3.90-3.65 (m, 2H), 2.97-2.82 (m, 2H), 1.36-1.32 (m, 3H). HPLC-MS $t_R$=1.8 min (UV$_{254\,nm}$); mass calculated for formula C14H14ClN3O3 307.1, observed LCMS m/z 280.1 (M−N2+H), and 330.1 (M+Na).

Part D:

Bromoketone 2545 was prepared using procedures described in Example 62C Part B. $^1$H NMR (400 MHz, CDCl3) δ 7.31-7.20 (m, 3H), 5.87-5.81 (m, 1H), 4.25-4.04 (m, 4H), 3.90-3.82 (m, 1H), 3.60-3.51 (m, 1H), 2.98-2.79 (m, 2H), 1.34-1.31 (m, 3H). HPLC-MS $t_R$=2.07 min (UV$_{254\,nm}$); mass calculated for formula C14H15BrClNO3 359.0, observed LCMS m/z 360.0 (M+H).

Part E:

Thiazole 2546 was prepared using procedures described in Example 10. HPLC-MS $t_R$=2.05 min (UV$_{254\,nm}$); mass calculated for formula C18H22ClN3O2S 379.1, observed LCMS m/z 380.1 (M+H).

Part F:

To a solution of thiazole 2546 (117 mg, 0.31 mmol) in chloroform (1.5 mL) was added iodotrimethylsilane (0.32 mL, 2.24 mmol) and the resulting mixture was heated at 50° C. for 2 h. The reaction mixture was diluted with dichloromethane, washed with saturated sodium bicarbonate, brine and concentrated to give amine 2547 as a dark yellow solid (93 mg, 97%). $^1$H NMR (400 MHz, CDCl3) δ 7.12-6.97 (m, 3H), 6.01 (s, 1H), 5.26 (s, broad, 1H), 5.15 (s, 1H), 3.60-3.53 (m, 1H), 3.18-2.80 (m, 4H), 1.28-1.26 (d of d, 6H). HPLC-MS $t_R$=1.24 min (UV$_{254\,nm}$); mass calculated for formula C$_{15}$H$_{18}$ClN$_3$S 307.1, observed LCMS m/z 308.2 (M+H).

Example 62E

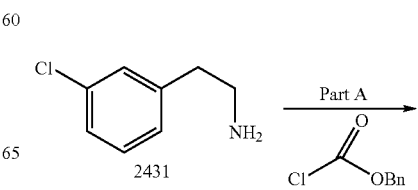

-continued

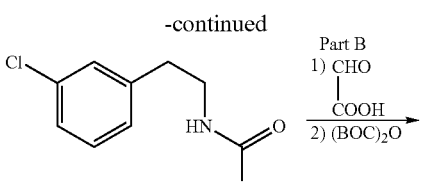
2548

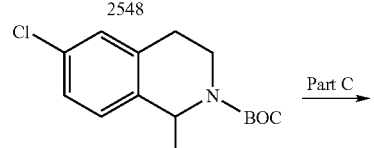
2549

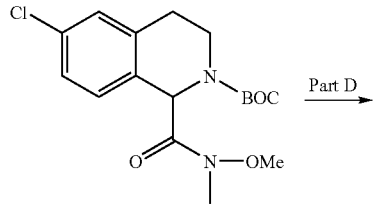
2550

2551

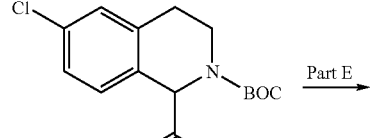
2552

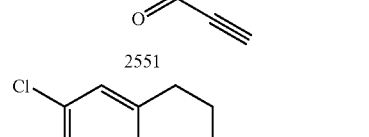
2553

Part A:

According to a modification of a procedure by Ortwine, D. F. et al. (*J. Med. Chem.* 1992, 35, 1345-1370) to an ice-cold solution of 3-chlorophenethylamine 2431 (11.6 g, 75 mmol) and triethylamine (10.9 mL, 78.7 mmol) in DCM (300 mL) was added dropwise benzyl chloroformate (11.1 mL, 78.1 mmol), and the resulting solution was stirred at 0° C. for 30 min, and then at rt overnight. The reaction mixture was washed with saturated sodium bicarbonate solution, brine, dried and concentrated to give benzyl carbamate 2548 as a colorless oil (21.4 g, 99%). $^1$H NMR (400 MHz, CDCl$_3$) δ 7.38-7.30 (m, 5H), 7.23-7.05 (m, 4H), 5.1 (s, 2H), 4.75 (s, broad, NH), 3.46 (q, 2H), 2.82 (t, 2H).

Part B:

According to a modification of a procedure by Ortwine, D. F. et al. (*J. Med. Chem.* 1992, 35, 1345-1370) to an ice-cold mixture of benzyl carbamate 2548 (8.6 g, 31.4 mmol) and 3:1 glacial acetic acid:sulfuric acid (64 mL) was added (in two portions) glyoxylic acid monohydrate (3.0 g, 32.6 mmol) and the mixture was stirred at rt overnight. The reaction mixture was poured in ice, and washed with dichloromethane (4 times). The aqueous phase was concentrated, diluted with tetrahydrofuran (200 mL), and treated with 6M NaOH solution (130 mL) to pH 12-13, followed by di-tert-butyl dicarbonate (7.94 g, 36.4 mmol), and then stirred at rt overnight. The reaction mixture was concentrated, diluted with water, acidified with 2 M HCl solution to pH 2, and extracted with ethyl acetate. The combined organic extracts were concentrated and chromatographed (SiO$_2$, 5% methanol/dichloromethane) to give compound 2549 (0.95 g, 15% based on reacted starting material). $^1$H NMR (400 MHz, CDCl$_3$) δ 7.54-7.27 (m, 3H), 5.67-5.50 (d, 1H), 3.87-3.79 (m, 2H), 3.01-2.88 (m, 2H), 1.61-1.57 (9H).

Part C:

Weinreb amide 2550 was prepared using procedures described in Example 51I, Part A. $^1$H NMR (400 MHz, CDCl3) δ 7.37-7.14 (m, 3H), 6.1-5.88 (d, 1H), 4.0 (s, 3H), 3.84-3.67 (m, 2H), 3.21 (s, 3H), 3.17-3.09 (m, 1H), 2.79-2.72 (m, 1H), 1.5 (s, 9H). HPLC-MS $t_R$=2.15 min (UV$_{254\ nm}$); mass calculated for formula C$_{17}$H$_{23}$ClN$_2$O$_4$ 354.1, observed LCMS m/z 255.1 (M-BOC+H).

Part D:

Acetylene 2551 was prepared using procedures described in Example 51I, Part B. HPLC-MS $t_R$=2.22 min (UV$_{254\ nm}$); mass calculated for formula C17H18ClNO3 319.1, observed LCMS m/z 264.0 (M-(t-butyl)).

Part E:

Pyrazole 2552 was prepared using procedures described in Example 62G Part A. HPLC-MS $t_R$=1.97 min (UV$_{254\ nm}$); mass calculated for formula C$_{17}$H$_{20}$ClN$_3$O$_2$ 333.1, observed LCMS m/z 234 (M–BOC+H).

Part F:

Amine 2553 was prepared using a procedure similar to that described in Example 51I, Part D. HPLC-MS $t_R$=0.89 min (UV$_{254\ nm}$); mass calculated for formula C12H12ClN3 233.1, observed LCMS m/z 234.1 (M+H).

Example 62F

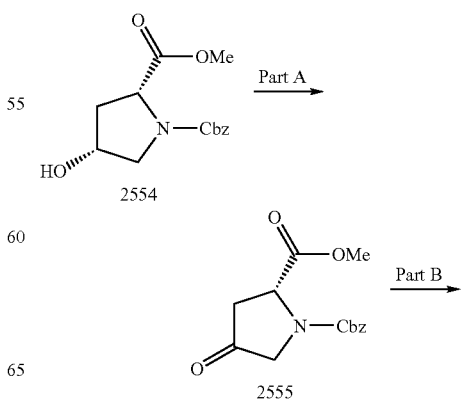

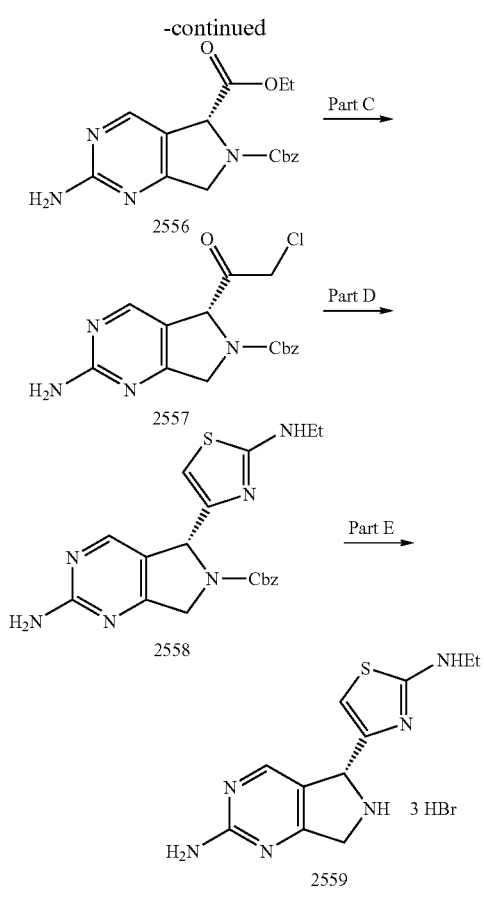

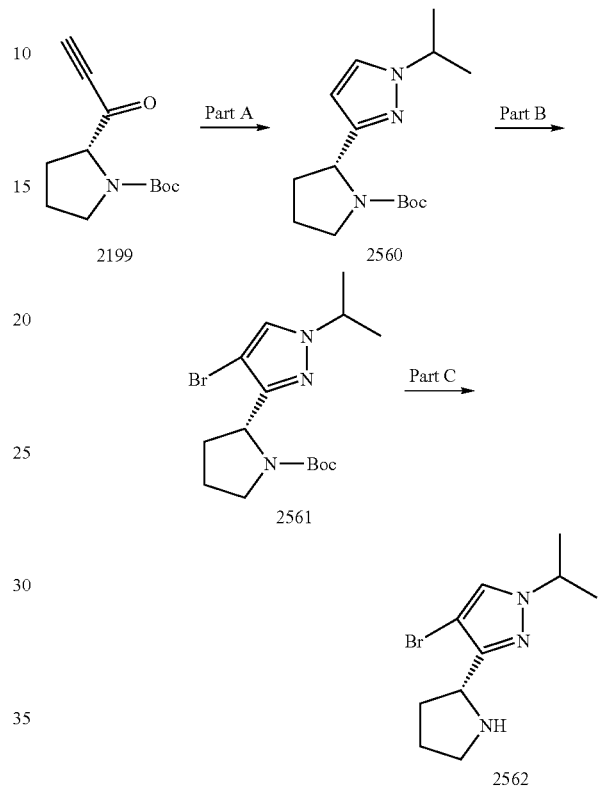

solvent was removed and the residue was dissolved in water and washed with ethyl acetate. The aqueous layer was lyophilized to provide 2559 as a red solid (100 mg). HPLC-MS $t_R=0.414$ min ($UV_{254\ nm}$); mass calculated for formula $C_{11}H_{14}N_6S$ 262.1, observed LCMS m/z 263.1 (M+H).

Example 62G

Part A:
Compound 2554 (3.7 g, 13.4 mmol) was dissolved in methylene chloride (35 mL) and Dess-Martin periodinane (8.55 g, 20.18 mmol) was added and stirred at room temperature overnight. The reaction was quenched with saturated sodium bicarbonate and stirred for 1 hour. The reaction mixture was filtered through celite. The aqueous layer was extracted with methylene chloride. The combined organic layers were dried over sodium sulfate and concentrated. Purification by column chromatography (SiO$_2$, 50% ethyl acetate/hexanes) afforded 2555 (1.75 g). $^1$H NMR (400 MHz, CDCl$_3$) δ 7.40-7.30 (m, 5H), 5.25-5.20 (m, 2H), 4.90-4.80 (m, 1H), 4.00-3.80 (m, 2H), 3.80-3.60 (m, 3H), 3.00 (m, 1H), 2.60 (m, 1H).

Part B:
Compound 2556 was prepared according to the procedure in *Bioorg. Med. Chem.* 2002, 10, 5, 1197-1206. $^1$H NMR (400 MHz, CDCl$_3$) δ 8.25 (s, 1H), 7.4-7.3 (m, 5H), 5.3-5.15 (m, 3H), 4.74.55 (m, 2H), 4.34.2 (m, 2H), 1.3 (t, 3H).

Part C:
Compound 2557 was prepared from compound 2556 according to the procedure described in Example 10B Part B. $^1$H NMR (400 MHz, CDCl$_3$) δ 8.00 (m, 1H), 7.60-7.40 (m, 5H), 5.30-5.20 (m, 2H), 5.10 (m, 2H), 4.80-4.60 (m, 1H).

Part D:
Compound 2558 was prepared as described in Example 51B Part C from compound 2557. $^1$H NMR (400 MHz, CDCl$_3$) δ 8.00 (s, 1H), 7.40-7.20 (m, 5H), 6.20 (s, 1H), 5.30-5.00 (m, 3H), 4.70 (m, 2H), 3.25 (m, 2H), 1.30 (m, 3H).

Part E:
Compound 2558 (80 mg, 0.202 mmol) was dissolved in 30% HBr in acetic acid (3 mL) and stirred for 2 hours. The Part A:
Compound 2199 (1.11 g, 3.7 mmol), isopropyl hydrazine hydrochloride (616 mg, 5.55 mmol), and sodium carbonate (980 mg, 9.25 mmol) were dissolved in ethanol (12 mL) and stirred at 80° C. for 5 hours. The reaction mixture was cooled to room temperature and diluted with ethyl acetate and water. The aqueous layer was extracted with ethyl acetate. The combined organic layers were washed with water, brine, dried over sodium sulfate and concentrated. Purification by column chromatography (SiO$_2$, 33% ethyl acetate/hexanes) afforded 2560 (750 mg). $^1$H NMR (400 MHz, CDCl$_3$) δ 7.35 (d, 1H), 6.00 (d, 1H), 5.10-4.90 (m, 1H), 4.50 (m, 1H), 3.60-3.40 (m, 2H), 2.30-2.10 (m, 1H), 2.10-1.80 (m, 3H), 1.50 (m, 9H), 1.30 (s, 6H).

Part B:
Compound 2560 (541 mg, 1.93 mmol) was dissolved in chloroform (10 mL) and N-bromosuccinimide (412 mg, 2.31 mmol) was added and stirred at room temperature overnight. The reaction was diluted with methylene chloride and water. The organic layer was washed with 1N NaOH, brine, dried over sodium sulfate, and concentrated. Purification by column chromatography (SiO$_2$, 15% ethyl acetate/hexanes) afforded 2561 (350 mg). $^1$H NMR (400 MHz, CDCl$_3$) δ 7.35 (s, 1H), 5.00-4.80 (m, 1H), 4.40 (m, 1H), 3.60-3.40 (m, 2H), 2.30-2.20 (m, 1H), 2.10-2.00 (m, 1H), 2.00-1.80 (m, 2H), 1.40 (m, 9H), 1.20 (s, 6H).

Part C:
Compound 2561 (86 mg, 0.238 mmol) was dissolved in 4M HCl in dioxane (2.0 mL) and stirred for 1 hour. The solvent was removed to provide 2562 as a white solid (82 mg). 
$^1$H NMR (400 MHz, DMSO-$d_6$) δ 9.60 (bs, 1H), 8.80 (bs, 1H), 8.18 (s, 1H), 4.60 (m, 1H), 4.50 (m, 1H), 3.25 (m, 2H), 2.35 (m, 1H), 2.10-1.90 (m, 3H), 1.40 (d, 6H).

Example 62H

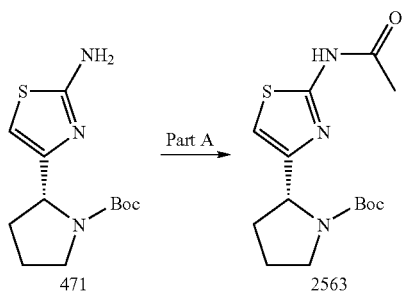

Part A:

To 471 (81 mg, 0.30 mmol) and DIEA (0.156 mL, 0.90 mmol) in dichloromethane (5 mL) was added slowly acetyl chloride (0.052 mL, 0.72 mmol) at 0° C. The reaction mixture was allowed to stir at room temperature for 2 hr and concentrated. The residue was then dissolved in EtOAc and H$_2$O, washed with 1N citric acid, NaHCO$_3$, brine, dried over Na$_2$SO$_4$, and concentrated. The resulting sticky solid was dissolved in methanol (5 mL) and stirred with solid K$_2$CO$_3$ (100 mg) for 2 hr. After removing the solvent, the residue was dissolved in EtOAc and H$_2$O, washed with H$_2$O, brine, dried (Na$_2$SO$_4$) and concentrated to afford 2563 (82 mg, 87%) as an oily solid. HPLC-MS $t_R$=1.60 min (UV$_{254\ nm}$); mass calculated for formula C$_{14}$H$_{21}$N$_3$O$_4$S 311.1, observed LCMS m/z 312.1 (M+H).

Example 62I

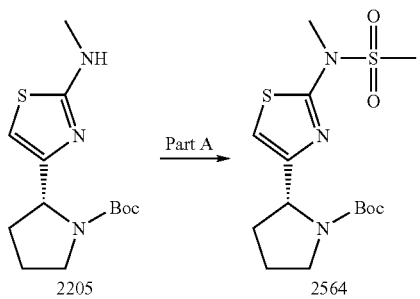

Part A:

To compound 2205 (100 mg, 0.35 mmol) and DIEA (0.092 mL, 0.53 mmol) in dichloromethane (5 mL) was slowly added methylsulfonic chloride (0.033 mL, 0.42 mmol) at 0° C. The reaction mixture was allowed to stir at room temperature for 2 hr and concentrated. The residue was dissolved in EtOAc, washed with water, 1N citric acid, NaHCO$_3$, and brine, dried over Na$_2$SO$_4$ and concentrated to afford 2564 (120 mg, 94%) as an oily solid. HPLC-MS $t_R$=1.96 min (UV$_{254\ nm}$); mass calculated for formula C$_{14}$H$_{23}$N$_3$O$_4$S$_2$ 361.1, observed LCMS m/z 362.0 (M+H).

Example 62J

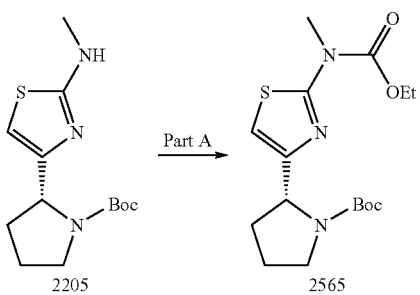

Part A:

To compound 2205 (80 mg, 0.28 mmol) and DIEA (0.098 mL, 0.56 mmol) in dichloromethane (5 mL) was added slowly ethyl chloroformate (0.054 mL, 0.56 mmol) at 0° C. The reaction mixture was allowed to stir at room temperature for 2 hr and concentrated. The residue was dissolved in EtOAc, washed with water, 1N citric acid, NaHCO$_3$ and brine, dried over Na$_2$SO$_4$ and concentrated to afford 2565 (88 mg, 88%) as an oily solid. HPLC-MS $t_R$=2.23 min (UV$_{254\ nm}$); mass calculated for formula C$_{11}$H$_{25}$N$_3$O$_4$S 355.2, observed LCMS m/z 356.2 (M+H).

The following compounds were prepared using previously described procedures.

| Compound # | Structure | Exact Mass | MS m/z (M + H) |
|---|---|---|---|
| 2567 | 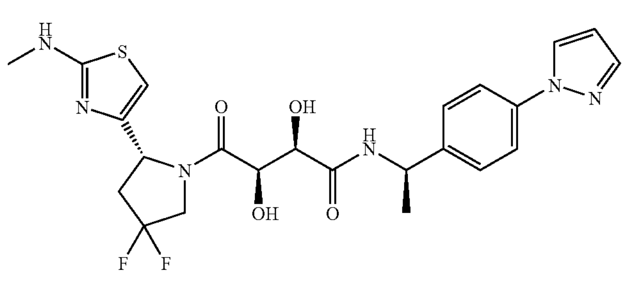 | 520.17 | 521.0 |

| Compound # | Structure | Exact Mass | MS m/z (M + H) |
|---|---|---|---|
| 2568 | 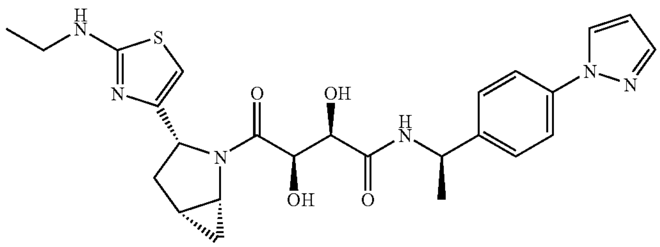 | 510.2 | 511.1 |
| 2569 | 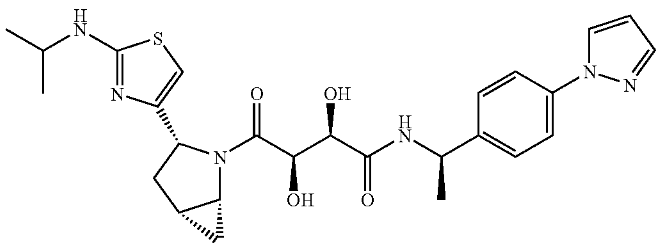 | 524.2 | 525.3 |
| 2570 | 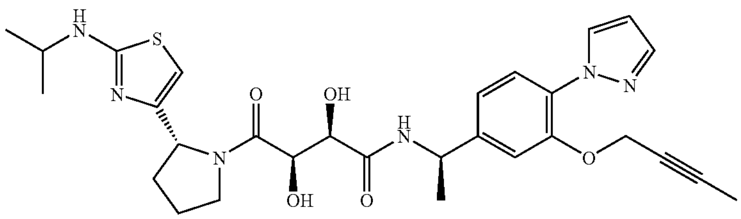 | 580.2 | 581.2 |
| 2571 | 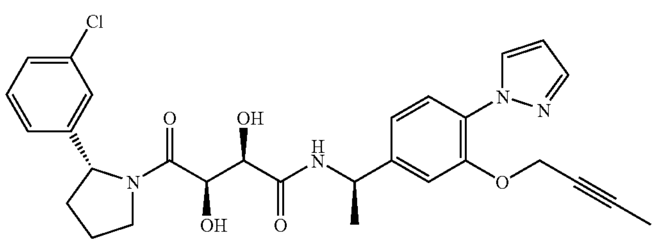 | 550.2 | 551.0 |
| 2572 | 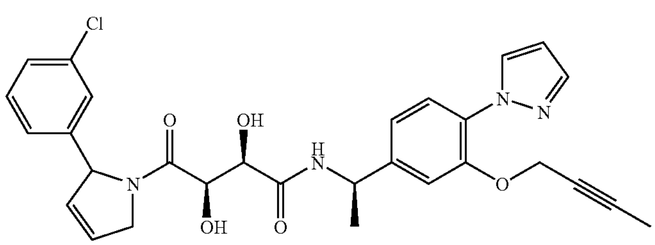 | 548.2 | 549.2 |
| 2573 | 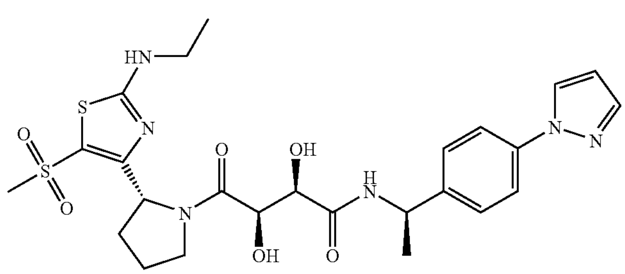 | 576.2 | 577.3 |

-continued

| Compound # | Structure | Exact Mass | MS m/z (M + H) |
|---|---|---|---|
| 2574 | 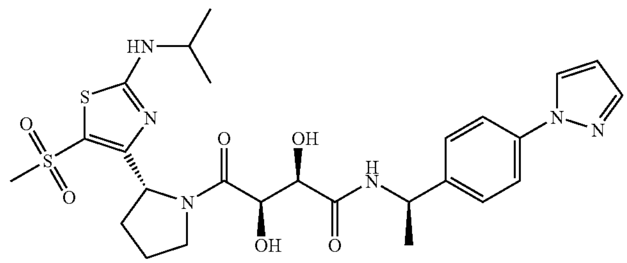 | 590.2 | 591.3 |
| 2575 | 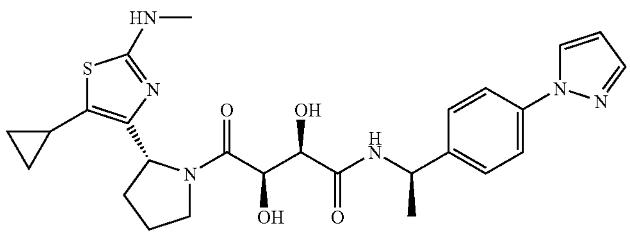 | 524.2 | 525.2 |
| 2576 | 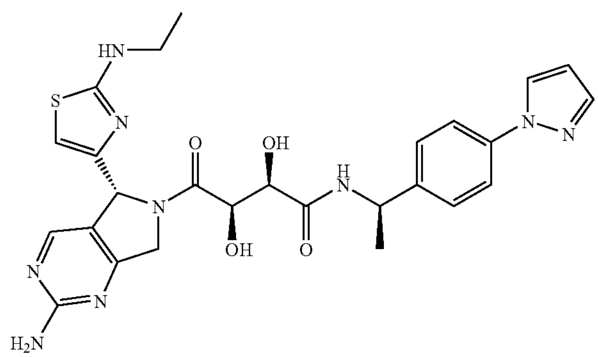 | 563.2 | 564.2 |
| 2577 | 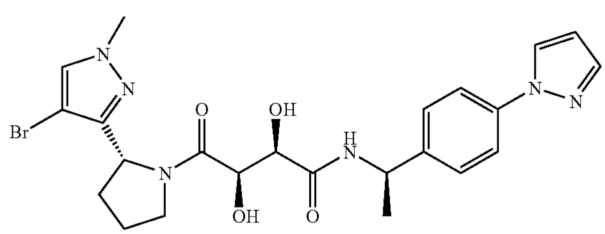 | 530.1 | 531.1 |
| 2578 | 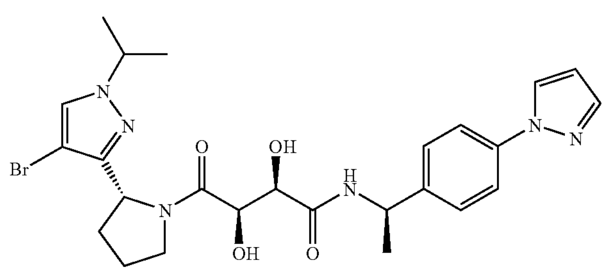 | 558.2 | 559.2 |

| Compound # | Structure | Exact Mass | MS m/z (M + H) |
| --- | --- | --- | --- |
| 2579 | 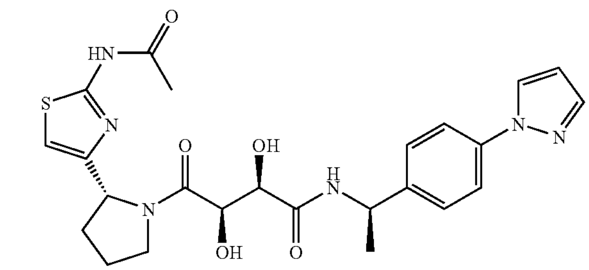 | 512.2 | 513.2 |
| 2580 | 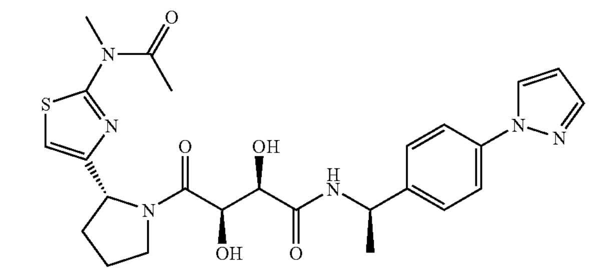 | 526.2 | 527.2 |
| 2581 | 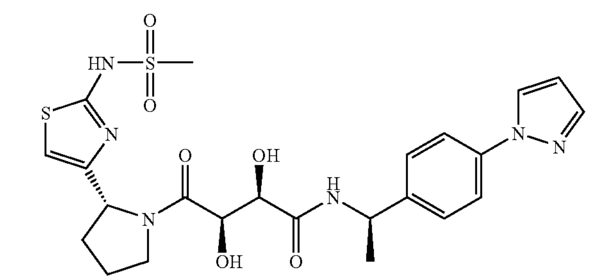 | 548.2 | 549.2 |
| 2582 | 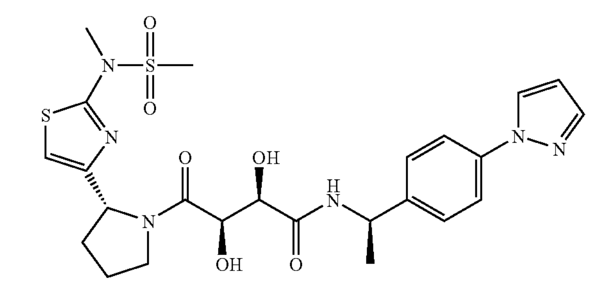 | 562.2 | 563.2 |
| 2583 | 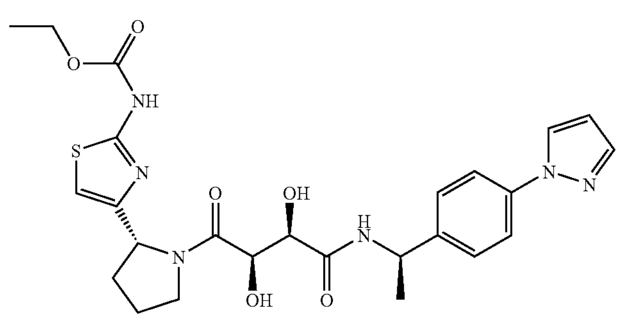 | 542.2 | 543.2 |

-continued

| Compound # | Structure | Exact Mass | MS m/z (M + H) |
|---|---|---|---|
| 2584 | 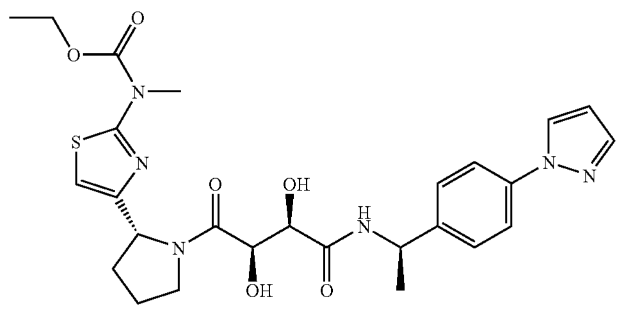 | 556.2 | 557.2 |
| 2585 | 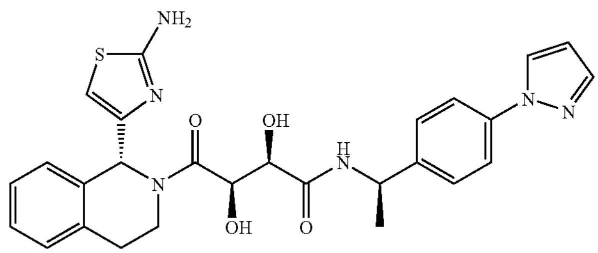 | 532.2 | 533.2 |
| 2586 | 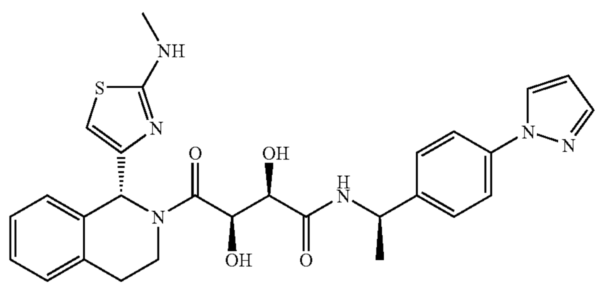 | 546.2 | 547.2 |
| 2587 | 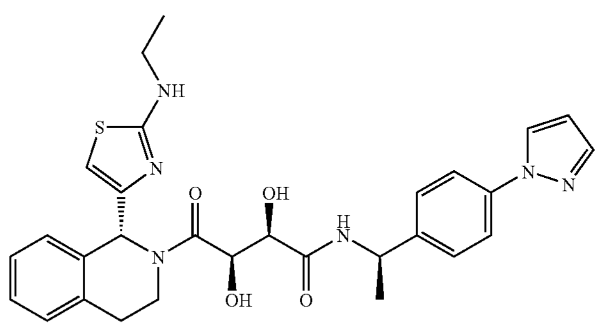 | 560.2 | 561.1 |
| 2588 | 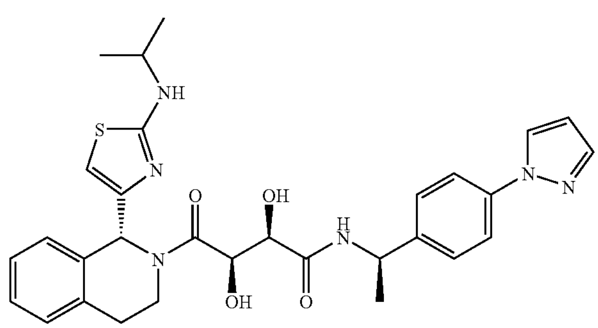 | 574.2 | 575.2 |

-continued

| Compound # | Structure | Exact Mass | MS m/z (M + H) |
|---|---|---|---|
| 2589 | 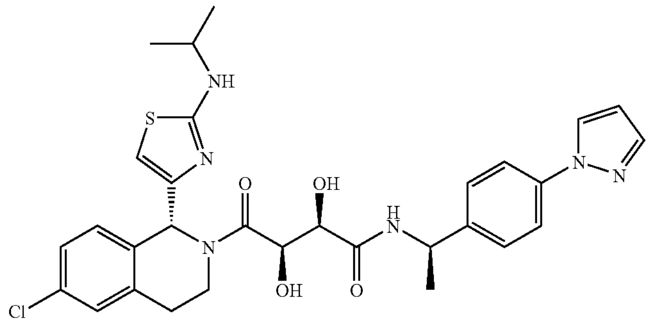 | 608.2 | 609.2 |
| 2590 | 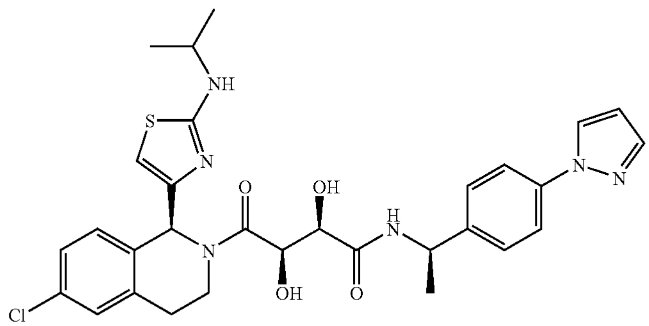 | 608.2 | 609.2 |
| 2591 | 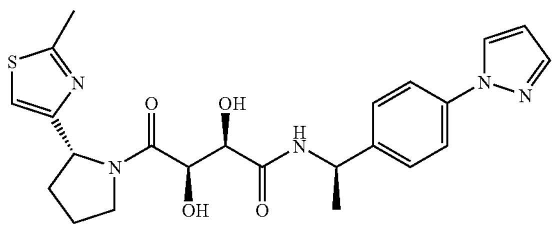 | 469.2 | 470.2 |
| 2592 | 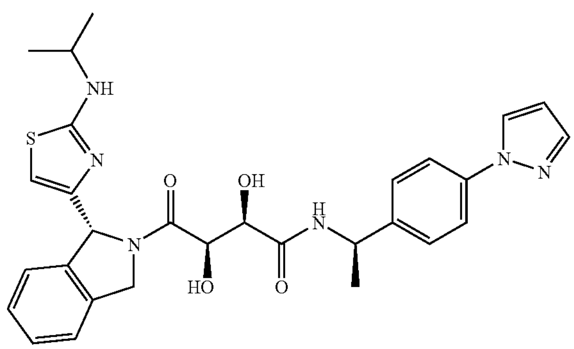 | 560.2 | 561.1 |
| 2593 | 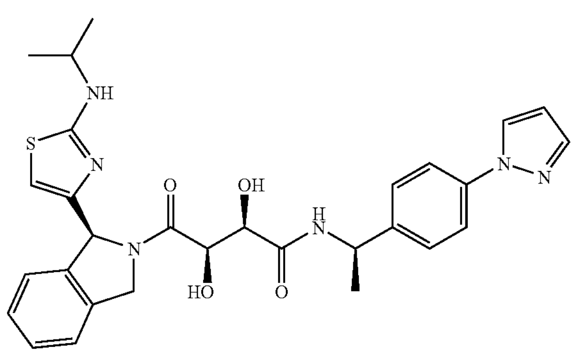 | 560.2 | 561.1 |

-continued

| Compound # | Structure | Exact Mass | MS m/z (M + H) |
|---|---|---|---|
| 2594 | 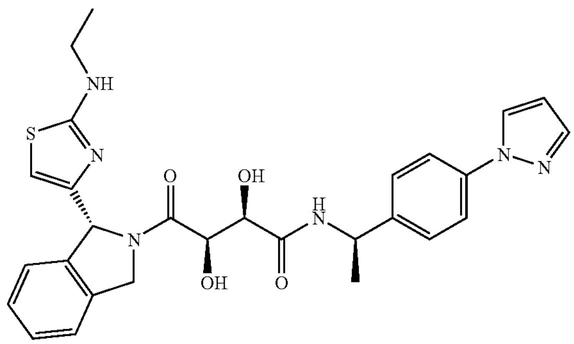 | 546.2 | 547.2 |
| 2595 | 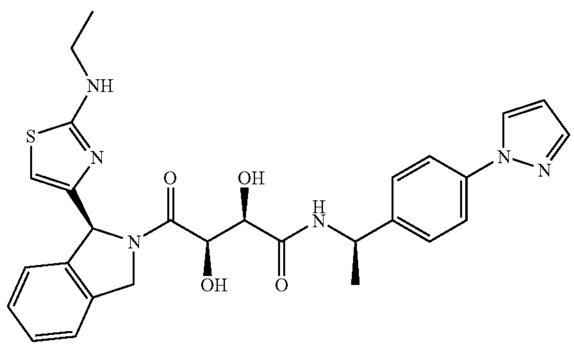 | 546.2 | 547.2 |
| 2596 | 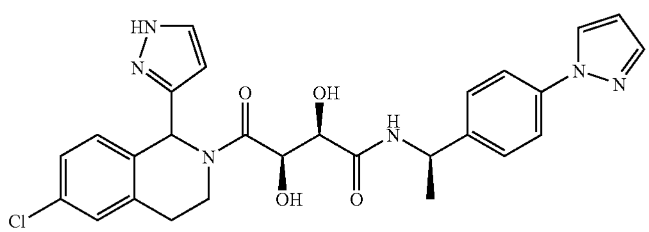 | 534.2 | 535.2 |
| 2597 | 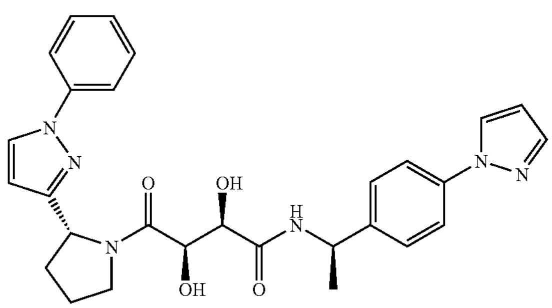 | 514.2 | 515.2 |
| 2598 | 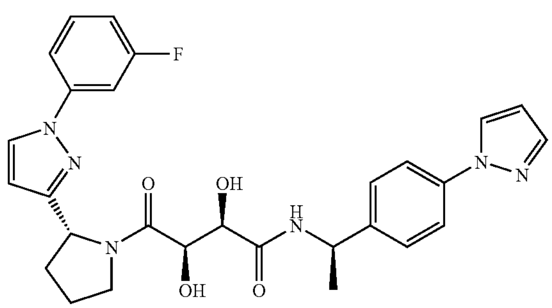 | 532.2 | 533.2 |

-continued

| Compound # | Structure | Exact Mass | MS m/z (M + H) |
|---|---|---|---|
| 2599 | 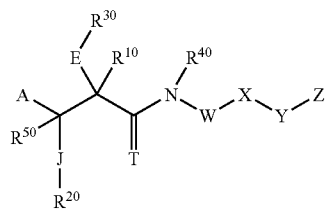 | 532.2 | 533.2 |
| 2600 | 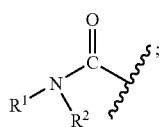 | 455.2 | 456.2 |

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A compound of formula (I):

formula (I)

or a pharmaceutically acceptable salt or solution-phase solvate thereof, wherein:

A is:

J is O;
E is O;
T is O;
$R^1$ and $R^2$, taken together with the N to which $R^1$ and $R^2$ are shown attached, represent a 4-8 membered heterocyclic ring having 1-3 heteroatoms including said N, said heterocyclic ring being optionally fused with aryl, heteroaryl, cycloalkyl, or heterocyclyl, wherein said 4-8 membered heterocyclic ring optionally with said fused aryl, heteroaryl, cycloalkyl or heterocyclyl is substituted with one or more moieties which can be the same or different, each moiety being independently selected from the group consisting of alkenyl, alkynyl, cycloalkyl, cycloalkenyl, heterocyclyl, aryl, arylalkyl, heteroaryl, heteroarylalkyl, halo, —CN, —CF$_3$, —OCF$_3$, —OR$^{15}$, —C(O)R$^{15}$, —C(O)OR$^{15}$, —C(O)N(R$^{15}$)(R$^{16}$), —SR$^{15}$, —S(O)$_q$N(R$^{15}$)(R$^{16}$) wherein q is 1 it 2, —C(=NOR$^{15}$)R$^{16}$, —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{17}$)S(O)$_2$N(R$^{16}$)(R$^{15}$), —N(R$^{17}$)S(O)N(R$^{16}$)(R$^{15}$), —N(R$^{17}$)C(O)N(R$^{16}$)(R$^{15}$), —CH$_2$—N(R$^{17}$)C(O)N(R$^{16}$)(R$^{15}$), —N(R$^{15}$)C(O)OR$^{16}$, —CH$_2$—N(R$^{15}$)C(O)OR$^{16}$, and —S(O)$_q$R$^{15}$ wherein q is 1 to 2; and wherein each of the cycloalkyl, heterocyclyl, aryl, arylalkyl, heteroaryl, heteroarylalkyl, alkenyl and alkynyl are independently unsubstituted or substituted by 1 to 5 groups independently selected from the group consisting of alkyl, cycloalkyl, heterocyclyl, aryl, heteroaryl, halo, —CF$_3$, —CN, —OR$^{15}$, —N(R$^{15}$)(R$^{16}$), —C(O)OR$^{15}$, —C(O)N(R$^{15}$)(R$^{16}$), and —N(R$^{15}$)S(O)R$^{16}$;

$R^{10}$ is H;
$R^{20}$ is H;
$R^{30}$ is H;
$R^{40}$ is H;
$R^{50}$ is H;
W is —(CR$^{13}_2$)$_n$—, wherein n is 1;
X is absent or present, and if present X is aryl, wherein said aryl is phenyl, which can be unsubstituted or optionally substituted with one or more moieties which can be the same or different, each moiety being independently selected from the group of R$^{70}$ moieties below;
Y is absent;
Z is selected from the group consisting of H, alkyl, alkenyl, alkynyl, cycloalkyl, heterocyclyl, aryl, and heteroaryl, said cycloalkyl, heterocyclyl, aryl, and heteroaryl being optionally fused with aryl, heterocyclyl, heteroaryl or cycloalkyl; wherein each of said alkyl, alkenyl, alkynyl, cycloalkyl, heterocyclyl, aryl, and heteroaryl, optionally with said fused aryl, heterocyclyl, heteroaryl or cycloalkyl, can be unsubstituted or optionally independently substituted with one or more moieties which can be the same or different, each moiety being independently selected from the group of $R^{70}$ moieties below;

$R^{13}$ is selected from the group consisting of hydrogen and alkyl;

each $R^{70}$ is a substituent for H where indicated and is the same or different and is independently selected from the group consisting of alkyl, alkenyl, alkynyl, cycloalkyl, cycloalkenyl, heterocyclyl, aryl, arylalkyl, heteroaryl, heteroarylalkyl, halo, —CN, —$CF_3$, —$OCF_3$, —$OR^{15}$, —C(O)$R^{15}$, —C(O)O$R^{15}$, —C(O)N($R^{15}$)($R^{16}$), —S$R^{15}$, —S(O)$_q$N($R^{15}$)($R^{16}$) wherein q is 1 to 2, —C(=NO$R^{15}$)$R^{16}$, —N($R^{15}$)($R^{16}$), -alkyl-N($R^{15}$)($R^{16}$), —N($R^{15}$)C(O)$R^{16}$, —$CH_2$—N($R^{15}$)C(O)$R^{16}$, —N($R^{15}$)S(O)$R^{16}$, —N($R^{15}$)S(O)$_2R^{16}$, —$CH_2$—N($R^{15}$) S(O)$_2R^{16}$, —N($R^{17}$)S(O)$_2$—N($R^{16}$)($R^{15}$), —N($R^{17}$)S(O)N($R^{16}$)($R^{15}$), —N($R^{17}$)C(O)N($R^{16}$)($R^{15}$), —$CH_2$—N($R^{17}$)C(O)N($R^{16}$)($R^{15}$), —N($R^{15}$)C(O)O$R^{16}$, —$CH_2$—N($R^{15}$)C(O)O$R^{16}$, and —S(O)$_qR^{15}$ wherein q is 1 to 2; and wherein each of the alkyl, cycloalkyl, heterocyclyl, aryl, arylalkyl, heteroaryl, heteroarylalkyl, alkenyl and alkynyl are independently unsubstituted or substituted by 1 to 5 groups independently selected from the group consisting of alkyl, cycloalkyl, heterocyclyl, aryl, heteroaryl, halo, —$CF_3$, —CN, —$OR^{15}$, —N($R^{15}$)($R^{16}$), —C(O)O$R^{15}$, —C(O)N($R^{15}$)($R^{16}$), and —N($R^{15}$)S(O)$R^{16}$;

each $R^{15}$, $R^{16}$ and $R^{17}$ are independently selected from the group consisting of H, alkyl, cycloalkyl, heterocyclyl, aryl, and heteroaryl, or alternatively $R^{15}$ and $R^{16}$ taken together with the N to which they are shown attached, are joined to form a 4-8 membered heterocylic ring, wherein said 4-8 membered cycloalkyl can be unsubstituted or optionally independently substituted with one or more moieties which can be the same or different, each moiety being independently selected from the group of $R^{75}$ moieties below;

each $R^{75}$ is independently selected from the group consisting of alkyl, cycloalkyl, heterocyclyl, aryl, arylalkyl, heteroaryl, heteroarylalkyl, alkenyl and alkynyl, and wherein each of the alkyl, cycloalkyl, heterocyclyl, aryl, arylalkyl, heteroaryl, heteroarylalkyl, alkenyl and alkynyl are independently unsubstituted or substituted by 1 to 5 groups independently selected from the group consisting of alkyl, cycloalkyl, heterocyclyl, aryl, heteroaryl, halo, —$CF_3$, —CN, —$OR^{19}$, —N($R^{19}$)$_2$, —C(O)O$R^{19}$, —C(O)N($R^{19}$)$_2$, and —N($R^{19}$)S(O)$R^{19}$; and each $R^{19}$ is independently selected from the group consisting of H, alkyl, cycloalkyl, heterocyclyl, aryl, and heteroaryl.

2. The compound of claim 1 wherein A is

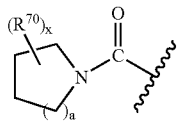

wherein
a is 0 to 4;
x is 1 to 4; and
$R^{70}$ is selected from the group consisting of alkenyl, alkynyl, cycloalkyl, cycloalkenyl, heterocyclyl, aryl, arylalkyl, heteroaryl, heteroarylalkyl, halo, —CN, —$CF_3$, —$OCF_3$, —$OR^{15}$, —C(O)$R^{15}$, —C(O)O$R^{15}$, —C(O)N($R^{15}$)($R^{16}$), —S$R^{15}$, —S(O)$_q$N($R^{15}$)($R^{16}$) wherein q is 1 it 2, —C(=NO$R^{15}$)$R^{16}$, —N($R^{15}$)($R^{16}$), -alkyl-N($R^{15}$)($R^{16}$), —N($R^{15}$)C(O)$R^{16}$, —$CH_2$—N($R^{15}$)C(O)$R^{16}$, —N($R^{15}$)S(O)$R^{16}$, —N($R^{15}$)S(O)$_2R^{16}$, —$CH_2$—N($R^{15}$)S(O)$_2R^{16}$, —N($R^{17}$)S(O)$_2$N($R^{16}$)($R^{15}$), —N($R^{17}$)S(O)N($R^{16}$)($R^{15}$), —N($R^{17}$)C(O)N($R^{16}$)($R^{15}$), —$CH_2$—N($R^{17}$)C(O)N($R^{16}$)($R^{15}$), —N($R^{15}$)C(O)O$R^{16}$, —$CH_2$—N($R^{15}$)C(O)O$R^{16}$, and S(O)$_qR^{15}$ wherein q is 1 it 2; and wherein each of the cycloalkyl, heterocyclyl, aryl, arylalkyl, heteroaryl, heteroarylalkyl, alkenyl and alkynyl are independently unsubstituted or substituted by 1 to 5 groups independently selected from the group consisting of alkyl, cycloalkyl, heterocyclyl, aryl, heteroaryl, halo, —$CF_3$, —CN, —$OR^{15}$, —N($R^{15}$)($R^{16}$), —C(O)O$R^{15}$, —O(O)N($R^{15}$)($R^{16}$), and —N($R^{15}$)S(O)$R^{16}$.

3. A compound of formula (I):

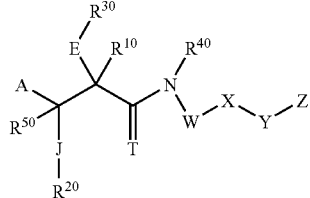

formula (I)

or a pharmaceutically acceptable salt or solution-phase solvate thereof, wherein A is

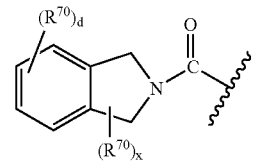

wherein
each x independently is 0 to 4;
J is O;
E is O;
T is O;
$R^{10}$ is H;
$R^{20}$ is H;
$R^{30}$ is H;
$R^{40}$ is H;
$R^{50}$ is H;
W is —(C$R^{13}_2$)$_n$—, wherein n is 1;
X is absent or present, and if present X is aryl, wherein said aryl is phenyl, which can be unsubstituted or optionally substituted with one or more moieties which can be the same or different, each moiety being independently selected from the group of $R^{70}$ moieties below;
Y is absent;
Z is selected from the group consisting of H, alkyl, alkenyl, alkynyl, cycloalkyl, heterocyclyl, aryl, and heteroaryl, said cycloalkyl, heterocyclyl, aryl, and heteroaryl being optionally fused with aryl, heterocyclyl, heteroaryl or cycloalkyl; wherein each of said alkyl, alkenyl, alkynyl, cycloalkyl, heterocyclyl, aryl, and heteroaryl, optionally with said fused aryl, heterocyclyl, heteroaryl or cycloalkyl, can be unsubstituted or optionally independently substituted with one or more moieties which can be the same or different, each moiety being independently selected from the group of $R^{70}$ moieties below;

$R^{13}$ is selected from the group consisting of hydrogen and alkyl;

each $R^{70}$ is a substituent for H where indicated and is the same or different and is independently selected from the group consisting of alkyl, alkenyl, alkynyl, cycloalkyl, cycloalkenyl, heterocyclyl, aryl, arylalkyl, heteroaryl, heteroarylalkyl, halo, —CN, —CF$_3$, —OCF$_3$, —OR$^{15}$, —C(O)R$^{15}$, —C(O)OR$^{15}$, C(O)N(R$^{15}$)(R$^{16}$), —SR$^{15}$, S(O)$_q$N(R$^{15}$)(R$^{16}$) wherein q is 1 to 2, —C(=NOR$^{15}$)R$^{16}$, —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{17}$)S(O)$_2$N(R$^{16}$)(R$^{15}$), —N(R$^{17}$)S(O)N(R$^{16}$)(R$^{15}$), —N(R$^{17}$)C(O)N(R$^{16}$)(R$^{15}$), —CH$_2$—N(R$^{17}$)C(O)N(R$^{16}$)(R$^{15}$), —N(R$^{15}$)C(O)OR$^{16}$, —CH$_2$—N(R$^{15}$)C(O)OR$^{16}$, and S(O)$_q$R$^{15}$ wherein q is 1 to 2; and wherein each of the alkyl, cycloalkyl, heterocyclyl, aryl, arylalkyl, heteroaryl, heteroarylalkyl, alkenyl and alkynyl are independently unsubstituted or substituted by 1 to 5 groups independently selected from the group consisting of alkyl, cycloalkyl, heterocyclyl, aryl, heteroaryl, halo, —CF$_3$, —CN, —OR$^{15}$, —N(R$^{15}$)(R$^{16}$), —C(O)OR$^{15}$, —C(O)N(R$^{15}$)(R$^{16}$), and —N(R$^{15}$)S(O)R$^{16}$; and each R$^{15}$, R$^{16}$ and R$^{17}$ are independently selected from the group consisting of H, alkyl, cycloalkyl, heterocyclyl, aryl, and heteroaryl, or alternatively R$^{15}$ and R$^{16}$ taken together with the N to which they are shown attached, are joined to form a 4-8 membered heterocyclic ring, wherein said 4-8 membered cycloalkyl can be unsubstituted or optionally independently substituted with one or more moieties which can be the same or different, each moiety being independently selected from the group of R$^{75}$ moieties below;

each R$^{75}$ is independently selected from the group consisting of alkyl, cycloalkyl, heterocyclyl, aryl, arylalkyl, heteroaryl, heteroarylalkyl, alkenyl and alkynyl, and wherein each of the alkyl, cycloalkyl, heterocyclyl, aryl, arylalkyl, heteroaryl, heteroarylalkyl, alkenyl and alkynyl are independently unsubstituted or substituted by 1 to 5 groups independently selected from the group consisting of alkyl, cycloalkyl, heterocyclyl, aryl, heteroaryl, halo, —CF$_3$, —CN, —OR$^{19}$, —N(R$^{19}$)$_2$, —C(O)OR$^{19}$, —C(O)N(R$^{19}$)$_2$, and —N(R$^{19}$)S(O)R$^{19}$ and each R$^{19}$ is independently selected from the group consisting of H, alkyl, cycloalkyl, heterocyclyl, aryl, and heteroaryl.

4. A compound of formula (I):

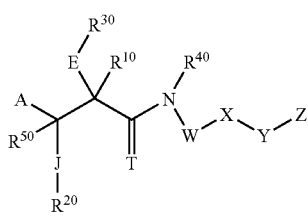

formula (I)

or a pharmaceutically acceptable salt or solution-phase solvate thereof, wherein:

A is:

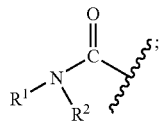

wherein said —NR$^1$R$^2$ is

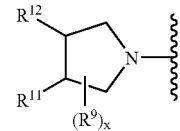

wherein each R$^9$ is a substituent for H where indicated and can be the same or different, each being independently selected from the group consisting of —OH, —OR$^{14}$, —CO(O)OR$^{15}$, —CO(O)N(R$^{15}$)(R$^{16}$), alkyl, aryl, heteroaryl, alkenyl, alkynyl, cycloalkyl and heterocyclyl, wherein said alkyl, aryl, heteroaryl, alkenyl, alkynyl, cycloalkyl and heterocyclyl can be unsubstituted or optionally independently substituted with one or more moieties which can be the same or different, each moiety being independently selected from the group of R$^{70}$ moieties;

R$^{11}$ and R$^{12}$ taken together with the carbon to which each R$^{11}$ and R$^{12}$ are shown attached are fused heteroaryl or fused cycloalkyl, wherein said fused heteroaryl and fused cycloalkyl can be unsubstituted or optionally independently substituted with one or more moieties which can be the same or different, each moiety being independently selected from the group of R$^{70}$ moieties; and x is 0 to 4, and when x is greater than 1, each R$^9$ moiety can be the same or different, each moiety being independently selected from the group of R$^9$ moieties;

J is O;
E is O;
T is O;
R$^{10}$ is H;
R$^{20}$ is H;
R$^{30}$ is H;
R$^{40}$ is H;
R$^{50}$ is H;
W is —(CR$^{13}$$_2$)$_2$—, wherein n is 1;
X is absent or present, and if present X is aryl, wherein said aryl is phenyl, which can be unsubstituted or optionally substituted with one or more moieties which can be the same or different, each moiety being independently selected from the group of R$^{70}$ moieties below;

Y is absent;

Z is selected from the group consisting of H, alkyl, alkenyl, alkynyl, cycloalkyl, heterocyclyl, aryl, and heteroaryl, said cycloalkyl, heterocyclyl, aryl, and heteroaryl being optionally fused with aryl, heterocyclyl, heteroaryl or cycloalkyl; wherein each of said alkyl, alkenyl, alkynyl, cycloalkyl, heterocyclyl, aryl, and heteroaryl, optionally with said fused aryl, heterocyclyl, heteroaryl or cycloalkyl, can be unsubstituted or optionally independently substituted with one or more moieties which can be the same or different, each moiety being independently selected from the group of R$^{70}$ moieties below;

R$^{13}$ is selected from the group consisting of hydrogen and alkyl;

each R$^{70}$ is a substituent for H where indicated and is the same or different and is independently selected from the group consisting of alkyl, alkenyl, alkynyl, cycloalkyl, cycloalkenyl, heterocyclyl, aryl, arylalkyl, heteroaryl, heteroarylalkyl, halo, —CN, —CF$_3$, —OCF$_3$, —OR$^{15}$, —C(O)R$^{15}$, —C(O)OR$^{15}$, —C(O)N(R$^{15}$)(R$^{16}$), —SR$^{15}$, —S(O)$_q$N(R$^{15}$)(R$^{16}$) wherein q is 1 to 2, —C(=NOR$^{15}$)R$^{16}$, —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{17}$)S(O)$_2$N(R$^{16}$)(R$^{15}$), —N(R$^{17}$)S(O)N(R$^{16}$)(R$^{15}$), —N(R$^{17}$)C(O)N(R$^{16}$)(R$^{15}$), —CH$_2$—N(R$^{17}$)C(O)N(R$^{16}$)(R$^{15}$), —N(R$^{15}$)C(O)

$OR^{16}$, —$CH_2$—$N(R^{15})C(O)OR^{16}$, and —$S(O)_qR^{15}$ wherein q is 1 to 2; and wherein each of the alkyl, cycloalkyl, heterocyclyl, aryl, arylalkyl, heteroaryl, heteroarylalkyl, alkenyl and alkynyl are independently unsubstituted or substituted by 1 to 5 groups independently selected from the group consisting of alkyl, cycloalkyl, heterocyclyl, aryl, heteroaryl, halo, —$CF_3$, —CN, —$OR^{15}$, —$N(R^{15})(R^{16})$, —$C(O)OR^{15}$, —$C(O)N(R^{15})(R^{16})$, and —$N(R^{15})S(O)R^{16}$; and each $R^{15}$, $R^{16}$ and $R^{17}$ are independently selected from the group consisting of H, alkyl, cycloalkyl, heterocyclyl, aryl, and heteroaryl, or alternatively $R^{15}$ and $R^{16}$ taken together with the N to which they are shown attached, are joined to form a 4-8 membered heterocyclic ring, wherein said 4-8 membered cycloalkyl can be unsubstituted or optionally independently substituted with one or more moieties which can be the same or different, each moiety being independently selected from the group of $R^{75}$ moieties below;

each $R^{75}$ is independently selected from the group consisting of alkyl, cycloalkyl, heterocyclyl, aryl, arylalkyl, heteroaryl, heteroarylalkyl, alkenyl and alkynyl, and wherein each of the alkyl, cycloalkyl, heterocyclyl, aryl, arylalkyl, heteroaryl, heteroarylalkyl, alkenyl and alkynyl are independently unsubstituted or substituted by 1 to 5 groups independently selected from the group consisting of alkyl, cycloalkyl, heterocyclyl, aryl, heteroaryl, halo, —$CF_3$, —CN, —$OR^{19}$, —$N(R^{19})_2$, —$C(O)OR^{19}$, —$C(O)N(R^{19})_2$, and —$N(R^{19})S(O)R^{19}$; and each $R^{19}$ is independently selected from the group consisting of H, alkyl, cycloalkyl, heterocyclyl, aryl, and heteroaryl.

5. A compound of formula (I):

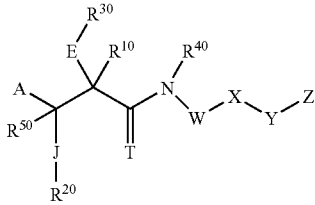

formula (I)

or a pharmaceutically acceptable salt or solution-phase solvate thereof, wherein:

A is:

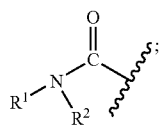

wherein said —$NR^1R^2$ is

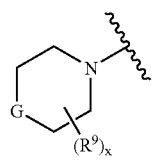

wherein each $R^9$ is a substituent for H where indicated and can be the same or different, each being independently selected from the group consisting of —OH, —$OR^{14}$, —$C(O)OR^{15}$, —$C(O)N(R^{15})(R^{16})$, alkyl, aryl, heteroaryl, alkenyl, alkynyl, cycloalkyl and heterocyclyl, wherein said alkyl, aryl, heteroaryl, alkenyl, alkynyl, cycloalkyl and heterocyclyl can be unsubstituted or optionally independently substituted with one or more moieties which can be the same or different, each moiety being independently selected from the group of $R^{70}$ moieties;

x is 0 to 4, and when x is greater than 1, each $R^9$ moiety can be the same or different, each moiety being independently selected from the group of $R^9$ moieties;

G is selected from the group consisting of $CH_2$, $NR^7$, O, S, or $SO_2$;

$R^7$ is selected from the group consisting of hydrogen, alkyl, aryl, cycloalkyl, heteroaryl, heterocyclyl, alkenyl, alkynyl, arylalkyl, alkylcarbonyl, and alkoxycarbonyl, wherein each of the aryl, heteroaryl and heterocyclyl can be unsubstituted or optionally independently substituted with one or more moieties which can be the same or different, each moiety being independently selected from the group of $R^{70}$ moieties;

J is O;

E is O;

T is O;

$R^{10}$ is H;

$R^{20}$ is H;

$R^{30}$ is H;

$R^{40}$ is H;

$R^{50}$ is H;

W is —$(CR^{13}_2)_n$—, wherein n is 1;

X is absent or present, and if present X is aryl, wherein said aryl is phenyl, which can be unsubstituted or optionally substituted with one or more moieties which can be the same or different, each moiety being independently selected from the group of $R^{70}$ moieties below;

Y is absent;

Z is selected from the group consisting of H, alkyl, alkenyl, alkynyl, cycloalkyl, heterocyclyl, aryl, and heteroaryl, said cycloalkyl, heterocyclyl, aryl, and heteroaryl being optionally fused with aryl, heterocyclyl, heteroaryl or cycloalkyl; wherein each of said alkyl, alkenyl, alkynyl, cycloalkyl, heterocyclyl, aryl, and heteroaryl, optionally with said fused aryl, heterocyclyl, heteroaryl or cycloalkyl, can be unsubstituted or optionally independently substituted with one or more moieties which can be the same or different, each moiety being independently selected from the group of $R^{70}$ moieties below;

$R^{13}$ is selected from the group consisting of hydrogen and alkyl;

each $R^{70}$ is a substituent for H where indicated and is the same or different and is independently selected from the group consisting of alkyl, alkenyl, alkynyl, cycloalkyl, cycloalkenyl, heterocyclyl, aryl, arylalkyl, heteroaryl, heteroarylalkyl, halo, —CN, —$CF_3$, —$OCF_3$, —$OR^{15}$, —$C(O)R^{15}$, —$C(O)OR^{15}$, —$C(O)N(R^{15})(R^{16})$, —$SR^{15}$, —$S(O)_qN(R^{15})(R^{16})$ wherein q is 1 to 2, —$C(=NOR^{15})R^{16}$, —$N(R^{15})(R^{16})$, -alkyl-$N(R^{15})(R^{16})$, —$N(R^{15})C(O)R^{16}$, —$CH_2$—$N(R^{15})C(O)R^{16}$, —$N(R^{15})S(O)R^{16}$, —$N(R^{15})S(O)_2R^{16}$, —$CH_2$—$N(R^{15})S(O)_2R^{16}$, —$N(R^{17})S(O)_2N(R^{16})(R^{15})$, —$N(R^{17})S(O)N(R^{16})(R^{15})$, —$N(R^{17})C(O)N(R^{16})(R^{15})$, —$CH_2$—$N(R^{17})C(O)N(R^{16})(R^{15})$, —$N(R^{15})C(O)OR^{16}$, —$CH_2$—$N(R^{15})C(O)OR^{16}$, and —$S(O)_qR^{15}$ wherein q is 1 to 2; and wherein each of the alkyl, cycloalkyl, heterocyclyl, aryl, arylalkyl, heteroaryl, heteroarylalkyl, alkenyl and alkynyl are independently unsubstituted or substituted by 1 to 5 groups independently selected from the group consisting of alkyl, cycloalkyl, heterocyclyl, aryl, heteroaryl, halo, —$CF_3$, —CN, —$OR^{15}$, —$N(R^{15})(R^{16})$, —$C(O)OR^{15}$, —$C(O)N(R^{15})(R^{16})$, and —$N(R^{15})S(O)R^{16}$; and each $R^{15}$, $R^{16}$ and $R^{17}$ are independently selected from the group consisting of H, alkyl, cycloalkyl, heterocyclyl, aryl, and heteroaryl, or alternatively $R^{15}$ and $R^{16}$ taken together with the N to which they are shown attached, are joined to form a 4-8 membered heterocyclic ring, wherein said 4-8 membered cycloalkyl can be unsubstituted or optionally independently substituted with one or more moieties which can be the same or different, each moiety being independently selected from the group of R[75] moieties below;

each R[75] is independently selected from the group consisting of alkyl, cycloalkyl, heterocyclyl, aryl, arylalkyl, heteroaryl, heteroarylalkyl, alkenyl and alkynyl, and wherein each of the alkyl, cycloalkyl, heterocyclyl, aryl, arylalkyl, heteroaryl, heteroarylalkyl, alkenyl and alkynyl are independently unsubstituted or substituted by 1 to 5 groups independently selected from the group consisting of alkyl, cycloalkyl, heterocyclyl, aryl, heteroaryl, halo, —CF$^3$, —CN, —OR$^{19}$, —N(R$^{19}$)$_2$, —C(O)OR$^{19}$, —C(O)N(R$^{19}$)$_2$, and —N(R$^{19}$)S(O)R$^{19}$; and each R$^{19}$ is independently selected from the group consisting of H, alkyl, cycloalkyl, heterocyclyl, aryl, and heteroaryl.

6. A compound of formula (I):

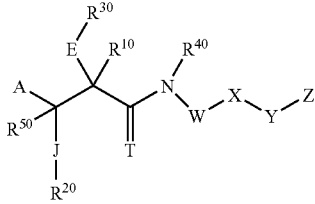

formula (I)

or a pharmaceutically acceptable salt or solution-phase solvate thereof, wherein:

A is:

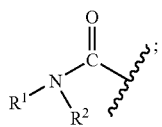

J is O;
E is O;
T is O;
—NR$^1$R$^2$ is selected from the group consisting of

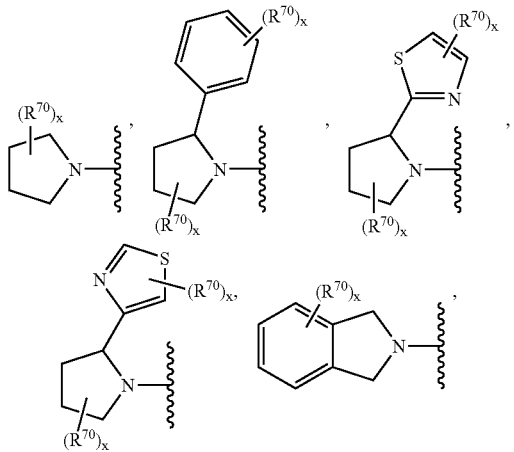

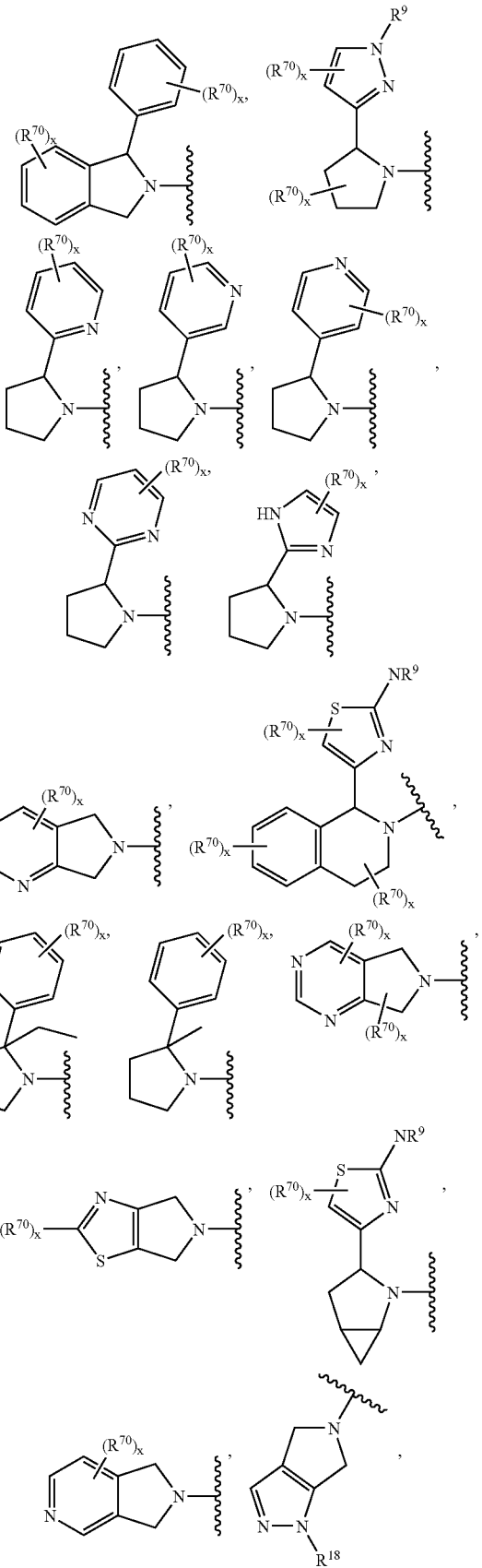

1411

-continued

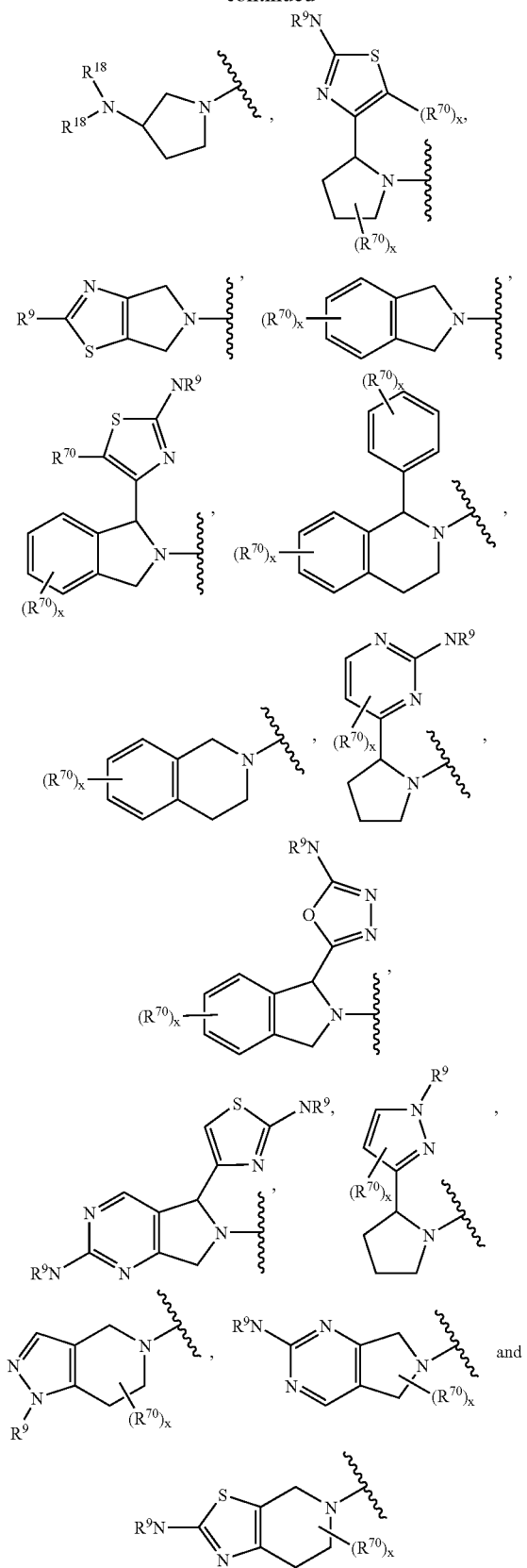

1412 wherein
x is 0 to 4, and when x is greater than 1, each $R^{70}$ moiety can be the same or different, each moiety being independently selected from the group of $R^{70}$ moieties;

each $R^9$ is a substituent for H where indicated and can be the same or different, each being independently selected from the group consisting of —OH, —$OR^{14}$, —C(O)$OR^{15}$, —C(O)N($R^{15}$)($R^{16}$), alkyl, aryl, heteroaryl, alkenyl, alkynyl, cycloalkyl and heterocyclyl, wherein said alkyl, aryl, heteroaryl, alkenyl, alkynyl, cycloalkyl and heterocyclyl can be unsubstituted or optionally independently substituted with one or more moieties which can be the same or different, each moiety being independently selected from the group of $R^{70}$ moieties;

$R^{14}$ is alkyl;

each $R^{18}$ is the same or different and is independently H or alkyl;

each $R^{70}$ is a substituent for H where indicated and is the same or different and is independently selected from the group consisting of alkyl, alkenyl, alkynyl, cycloalkyl, cycloalkenyl, heterocyclyl, aryl, arylalkyl, heteroaryl, heteroarylalkyl, halo, —CN, —$CF_3$, —$OCF_3$, —$OR^{15}$, —C(O)$R^{15}$, —C(O)$OR^{15}$, —C(O)N($R^{15}$)($R^{16}$), —$SR^{15}$, —S(O)$_q$N($R^{15}$)($R^{16}$) wherein q is 1 to 2, —C(=NO$R^{15}$)$R^{16}$, —N($R^{15}$)($R^{16}$), -alkyl-N($R^{15}$)($R^{16}$), —N($R^{15}$)C(O)$R^{16}$, —CH$_2$—N($R^{15}$)C(O)$R^{16}$, —N($R^{15}$)S(O)$R^{16}$, —N($R^{13}$)S(O)$_2R^{16}$, —CH$_2$—N($R^{15}$)S(O)$_2R^{16}$, —N($R^{17}$)S(O)$_2$N($R^{16}$)($R^{15}$), —N($R^{17}$)S(O)N($R^{16}$)($R^{15}$), —N($R^{17}$)C(O)N($R^{16}$)($R^{15}$), —CH$_2$—N($R^{17}$)C(O)N($R^{16}$)($R^{15}$), —N($R^{\cdot\cdot}$)C(O)$OR^{16}$, —CH$_2$—N($R^{15}$)C(O)$OR^{16}$, and —S(O)$_qR^{15}$ wherein q is 1 to 2; and wherein each of the alkyl, cycloalkyl, heterocyclyl, aryl, arylalkyl, heteroaryl, heteroarylalkyl, alkenyl and alkynyl are independently unsubstituted or substituted by 1 to 5 groups independently selected from the group consisting of alkyl, cycloalkyl, heterocyclyl, aryl, heteroaryl, halo, —$CF_3$, —CN, —$OR^{15}$, —N($R^{15}$)($R^{16}$), —C(O)$OR^{15}$, —C(O)N($R^{15}$)($R^{16}$), and —N($R^{15}$)S(O)$R^{16}$;

each $R^{15}$, $R^{16}$ and $R^{17}$ are independently selected from the group consisting of H, alkyl, cycloalkyl, heterocyclyl, aryl, and heteroaryl, or alternatively $R^{15}$ and $R^{16}$ taken together with the N to which they are shown attached, are joined to form a 4-8 membered heterocylic ring, wherein said 4-8 membered cycloalkyl can be unsubstituted or optionally independently substituted with one or more moieties which can be the same or different, each moiety being independently selected from the group of $R^{75}$ moieties below;

each $R^{75}$ is independently selected from the group consisting of alkyl, cycloalkyt, heterocyclyl, aryl, arylalkyl, heteroaryl, heteroarylalkyl, alkenyl and alkynyl, and wherein each of the alkyl, cycloalkyl, heterocyclyl, aryl, arylalkyl, heteroaryl, heteroarylalkyl, alkenyl and alkynyl are independently unsubstituted or substituted by 1 to 5 groups independently selected from the group consisting of alkyl, cycloalkyl, heterocyclyl, aryl, heteroaryl, halo, —$CF_3$, —CN, —$OR^{19}$, —N($R^{19}$)$_2$, —C(O)$OR^{19}$, —C(O)N($R^{19}$)$_2$, and —N($R^{19}$)S(O)$R^{19}$;

each $R^{19}$ is independently selected from the group consisting of H, alkyl, cycloalkyl, heterocyclyl, aryl, and heteroaryl;

$R^{10}$ is H;
$R^{20}$ is H;
$R^{30}$ is H;
$R^{40}$ is H;
$R^{50}$ is H;
W is —(CR$^{13}_2$)$_n$—, wherein n is 1;
X is absent or present, and if present X is aryl, wherein said aryl is phenyl, which can be unsubstituted or optionally substituted with one or more moieties which can be the same or different, each moiety being independently selected from the group of $R^{70}$ moieties below;

Y is absent;

Z is selected from the group consisting of H, alkyl, alkenyl, alkynyl, cycloalkyl, heterocyclyl, aryl, and heteroaryl, said cycloalkyl, heterocyclyl, aryl, and heteroaryl being optionally fused with aryl, heterocyclyl, heteroaryl or cycloalkyl; wherein each of said alkyl, alkenyl, alkynyl, cycloalkyl, heterocyclyl, aryl, and heteroaryl, optionally with said fused aryl, heterocyclyl, heteroaryl or cycloalkyl, can be unsubstituted or optionally independently substituted with one or more moieties which can be the same or different, each moiety being independently selected from the group of $R^{70}$ moieties below; and $R^{13}$ is selected from the group consisting of hydrogen and alkyl.

7. The compound of claim 5 wherein said —$NR^1R^2$ is selected from the group consisting of:

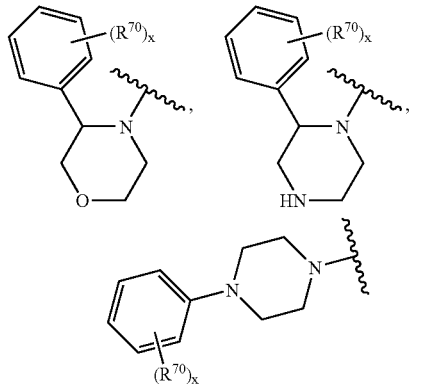

wherein x is 0 to 4, and when x is greater than 1, each $R^{70}$ moiety can be the same or different, each moiety being independently selected from the group of $R^{70}$ moieties.

8. A compound of formula (I):

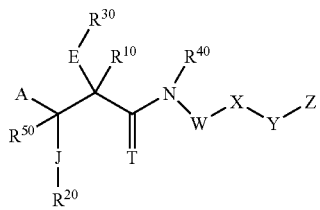

formula (I)

or a pharmaceutically acceptable salt or solution-phase solvate thereof, wherein:

A is:

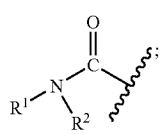

wherein said —$NR^1R^2$ is

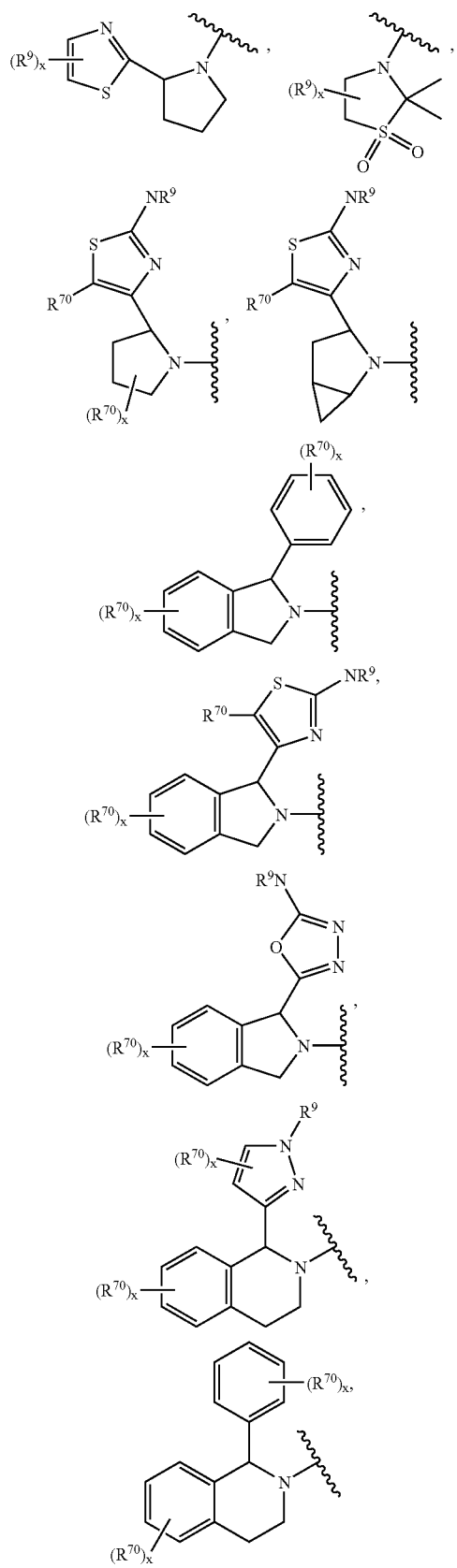

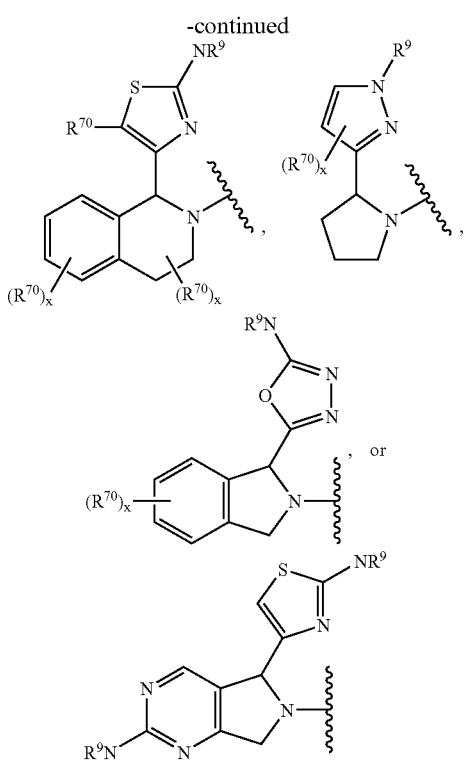

wherein
- each $R^9$ is a substituent for H where indicated and can be the same or different, each being independently selected from the group consisting of —OH, —OR$^{14}$, —C(O)OR$^{15}$, —C(O)N(R$^{15}$)(R$^{16}$), alkyl, aryl, heteroaryl, alkenyl, alkynyl, cycloalkyl and heterocyclyl, wherein said alkyl, aryl, heteroaryl, alkenyl, alkynyl, cycloalkyl and heterocyclyl can be unsubstituted or optionally independently substituted with one or more moieties which can be the same or different, each moiety being independently selected from the group of $R^{70}$ moieties;
- x is 0 to 4, and when x is greater than 1, each $R^{70}$ moiety can be the same or different, each moiety being independently selected from the group of $R^{70}$ moieties;
- J is O;
- E is O;
- T is O;
- $R^{10}$ is H;
- $R^{20}$ is H;
- $R^{30}$ is H;
- $R^{40}$ is H;
- $R^{50}$ is H;
- W is —(CR$^{13}{}_2$)$_n$—, wherein n is 1;
- X is absent or present, and if present X is aryl, wherein said aryl is phenyl, which can be unsubstituted or optionally substituted with one or more moieties which can be the same or different, each moiety being independently selected from the group of $R^{70}$ moieties below;
- Y is absent;
- Z is selected from the group consisting of H, alkyl, alkenyl, alkynyl, cycloalkyl, heterocyclyl, aryl, and heteroaryl, said cycloalkyl, heterocyclyl, aryl, and heteroaryl being optionally fused with aryl, heterocyclyl, heteroaryl or cycloalkyl; wherein each of said alkyl, alkenyl, alkynyl, cycloalkyl, heterocyclyl, aryl, and heteroaryl, optionally with said fused aryl, heterocyclyl, heteroaryl or cycloalkyl, can be unsubstituted or optionally independently substituted with one or more moieties which can be the same or different, each moiety being independently selected from the group of $R^{70}$ moieties below;
- $R^{13}$ is selected from the group consisting of hydrogen and alkyl;
- each $R^{70}$ is a substituent for H where indicated and is the same or different and is independently selected from the group consisting of alkyl, alkenyl, alkynyl, cycloalkyl, cycloalkenyl, heterocyclyl, aryl, arylalkyl, heteroaryl, heteroarylalkyl, halo, —CN, —CF$_3$, —OCF$_3$, —OR$^{15}$, —C(O)R$^{15}$, —C(O)OR$^{15}$, —C(O)N(R$^{15}$)(R$^{16}$), —SR$^{15}$, —S(O)$_q$N(R$^{15}$)(R$^{16}$) wherein q is 1 to 2, —C(=NOR$^{15}$)R$^{16}$, —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{17}$)S(O)$_2$N(R$^{16}$)(R$^{15}$), —N(R$^{17}$)S(O)N(R$^{16}$)(R$^{15}$), —N(R$^{17}$)C(O)N(R$^{16}$)(R$^{15}$), —CH$_2$—N(R$^{17}$)C(O)N(R$^{16}$)(R$^{15}$), —N(R$^{15}$)C(O)OR$^{16}$, —CH$_2$—N(R$^{15}$)C(O)OR$^{16}$, and —S(O)$_q$R$^{15}$ wherein q is 1 to 2; and wherein each of the alkyl, cycloalkyl, heterocyclyl, aryl, arylalkyl, heteroaryl, heteroarylalkyl, alkenyl and alkynyl are independently unsubstituted or substituted by 1 to 5 groups independently selected from the group consisting of alkyl, cycloalkyl, heterocyclyl, aryl, heteroaryl, halo, —CF$_3$, —CN, —OR$^{15}$, —N(R$^{15}$)(R$^{16}$), —C(O)OR$^{15}$, —C(O)N(R$^{15}$)(R$^{16}$), and —N(R$^{15}$)S(O)R$^{16}$; and
- each $R^{15}$, $R^{16}$ and $R^{17}$ are independently selected from the group consisting of H, alkyl, cycloalkyl, heterocyclyl, aryl, and heteroaryl, or alternatively $R^{15}$ and $R^{16}$ taken together with the N to which they are shown attached, are joined to form a 4-8 membered heterocylic ring, wherein said 4-8 membered cycloalkyl can be unsubstituted or optionally independently substituted with one or more moieties which can be the same or different, each moiety being independently selected from the group of $R^{75}$ moieties below;
- each $R^{75}$ is independently selected from the group consisting of alkyl, cycloalkyl, heterocyclyl, aryl, arylalkyl, heteroaryl, heteroarylalkyl, alkenyl and alkynyl, and wherein each of the alkyl, cycloalkyl, heterocyclyl, aryl, arylalkyl, heteroaryl, heteroarylalkyl, alkenyl and alkynyl are independently unsubstituted or substituted by 1 to 5 groups independently selected from the group consisting of alkyl, cycloalkyl, heterocyclyl, aryl, heteroaryl, halo, —CF$_3$, —CN, —OR$^{19}$, —N(R )$_2$, —C(O)OR$^{19}$, —C(O)N(R$^{19}$)$_2$, and —N(R$^{19}$)S(O)R$^{19}$; and
- each $R^{19}$ is independently selected from the group consisting of H, alkyl, cycloalkyl, heterocyclyl, aryl, and heteroaryl.

9. The compound of claim 1 wherein $R^1$ and $R^2$, taken together with the N to which $R^1$ and $R^2$ are shown attached, represent a 4-6 membered heterocyclic ring having 1-3 heteroatoms including said N, said heterocyclic ring being substituted with at least one aryl.

10. The compound of claim 1 wherein Z is selected from the group consisting of H, aryl and heteroaryl.

11. The compound of claim 10 wherein Z is selected from the group consisting of H, phenyl, indolyl, benzimidazolyl, pyrazolyl, thienyl, pyridinyl, thiazolyl, thiadiazolyl, imidazolyl, pyrrolidinyl, pyrazinyl, triazolyl, tetrazolyl and tetrazinyl, wherein said phenyl, indolyl, benzimidazolyl, pyrazolyl, thienyl, pyridinyl, thiazolyl, thiadiazolyl, imidazolyl, pyrrolidinyl, pyrazinyl, triazolyl, tetrazolyl and tetrazinyl can be unsubstituted or optionally independently substituted with one or more moieties which can be the same or different, each moiety being independently selected from the group consisting of $R^{70}$ moieties.

12. The compound of claim 11 wherein Z is selected from the group consisting of

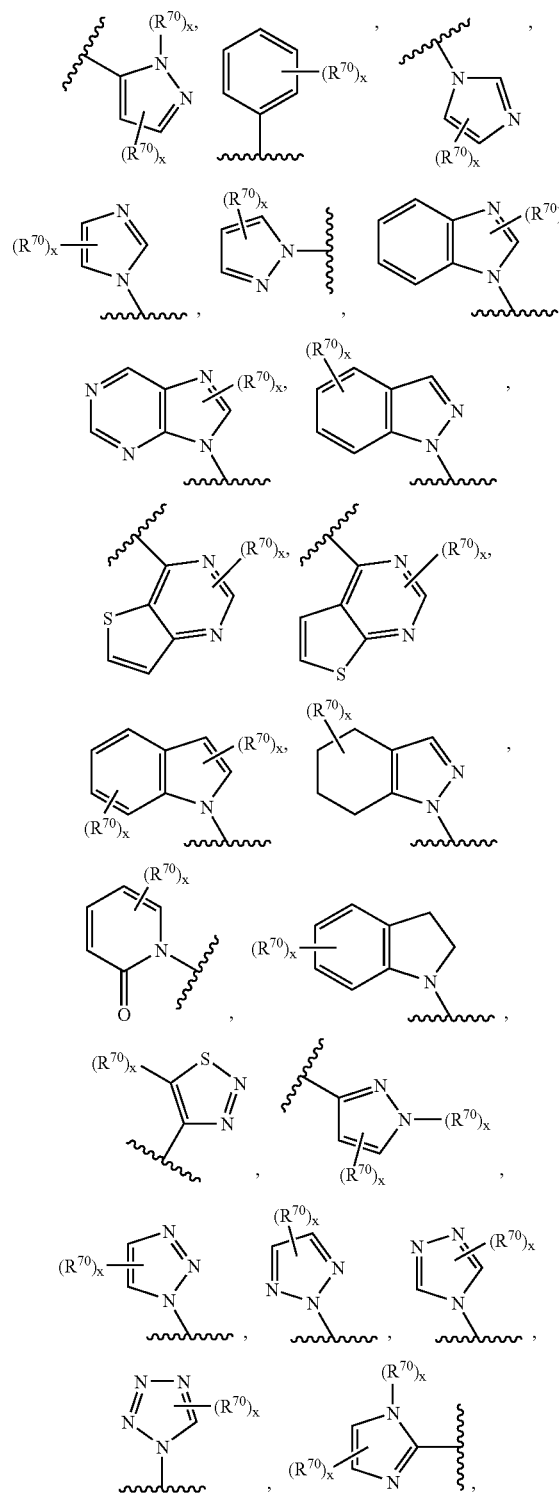

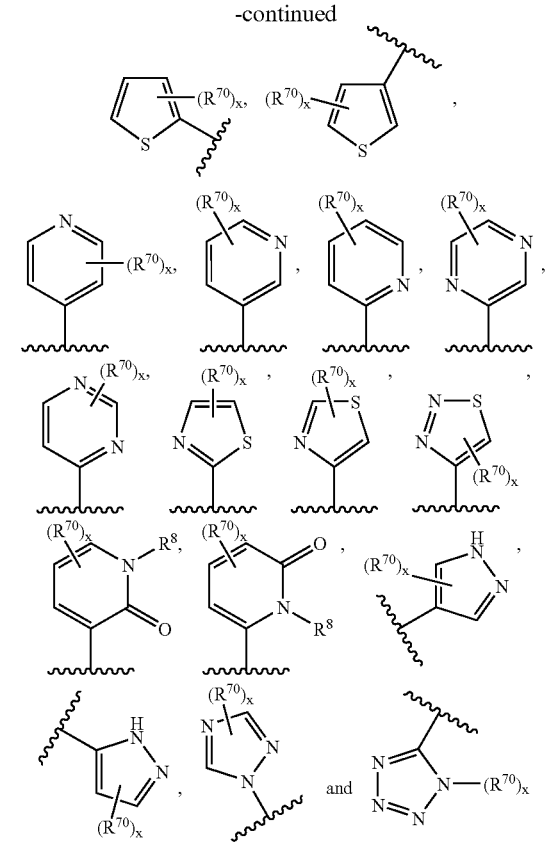

wherein
x is 0 to 4, and when x is greater than 1, each $R^{70}$ moiety can be the same or different, each moiety being independently selected from the group of $R^{70}$ moieties.

13. The compound of claim 11 wherein Z is phenyl.

14. The compound of claim 13 wherein said phenyl is substituted with at least one substituent selected from the group consisting of cyano, alkoxy, halogen, alkyl, haloalkyl, hydroxy, aryl, heteroaryl, aryloxy, amino and tetrazole.

15. The compound of claim 11 wherein Z is thienyl.

16. The compound of claim 15 wherein said thienyl is substituted with at least one substituent selected from the group consisting of cyano, alkoxy, halogen, alkyl, haloalkyl, hydroxy, aryl, heteroaryl, aryloxy, amino and tetrazole.

17. The compound of claim 11 wherein Z is pyrazolyl.

18. The compound of claim 17 wherein said pyrazolyl is substituted with at least one substituent selected from the group consisting of cyano, alkoxy, halogen, alkyl, haloalkyl, hydroxy, aryl, heteroaryl, aryloxy, amino and tetrazole.

19. The compound of claim 11 wherein Z is pyridinyl.

20. The compound of claim 19 wherein said pyridinyl is substituted with at least one substituent selected from the group consisting of cyano, alkoxy, halogen, alkyl, haloalkyl, hydroxy, aryl, heteroaryl, aryloxy, amino and tetrazole.

21. The compound of claim 11 wherein Z is imidazolyl.

22. The compound of claim 21 wherein said imidazolyl is substituted with at least one substituent selected from the group consisting of cyano, alkoxy, halogen, alkyl, haloalkyl, hydroxy, aryl, heteroaryl, aryloxy, amino and tetrazole.

23. A compound selected from the group consisting of:
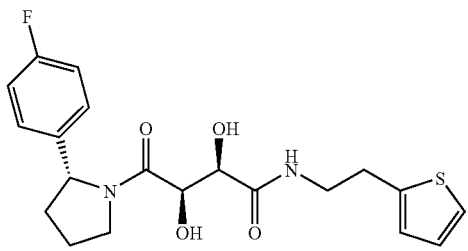
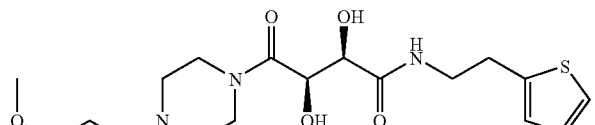
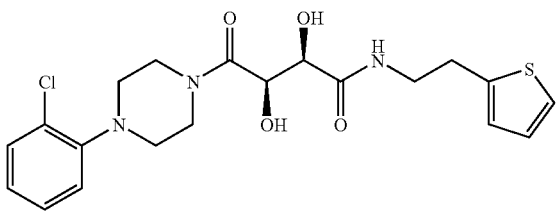
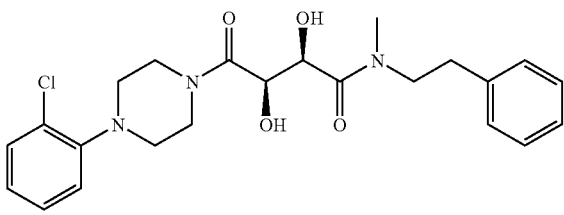
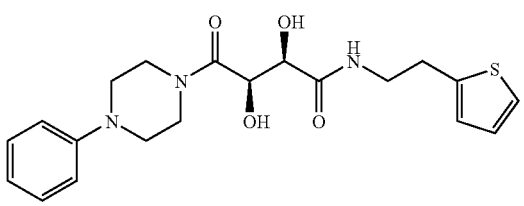
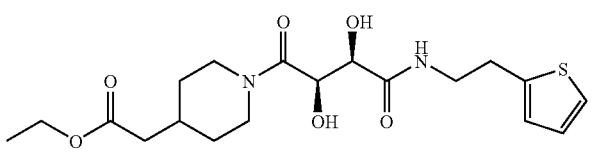
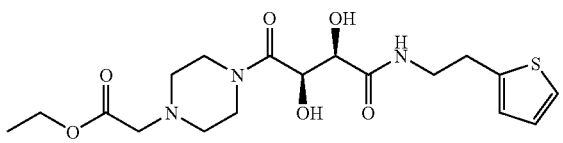
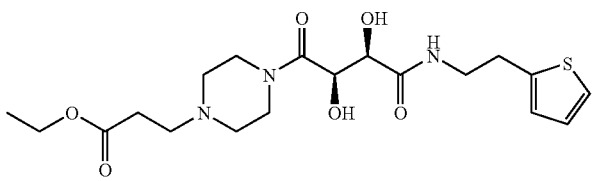
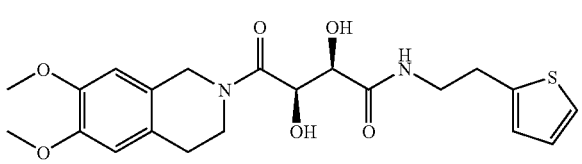
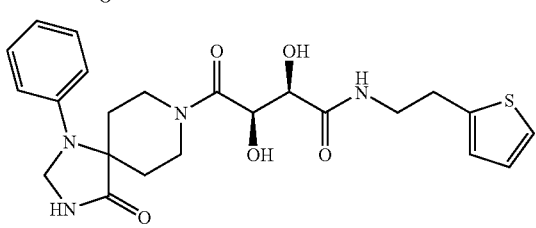
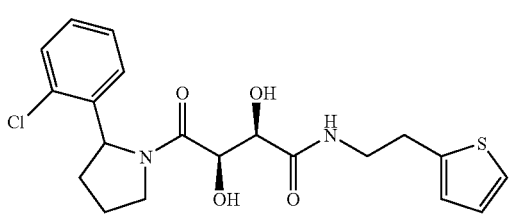
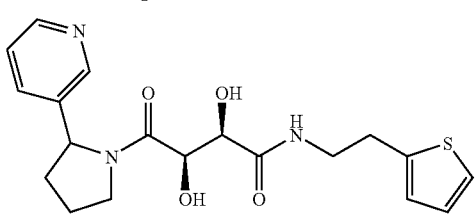
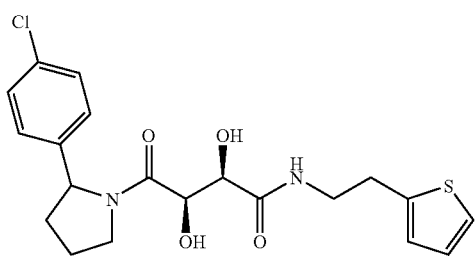
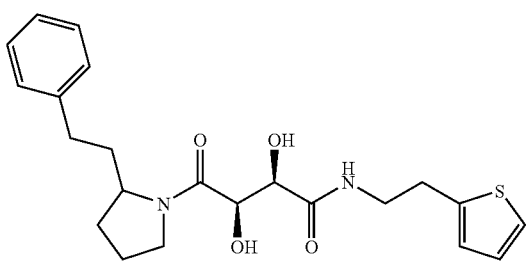

1421 1422
-continued
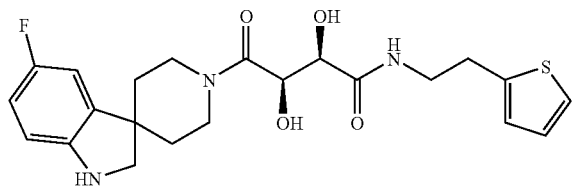
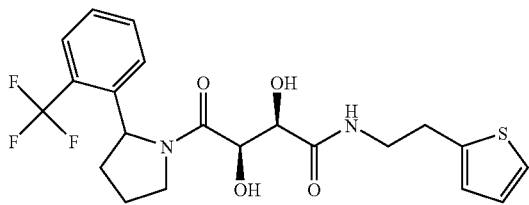
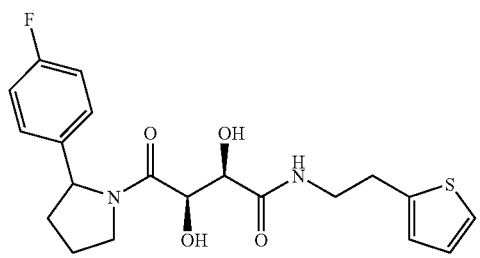
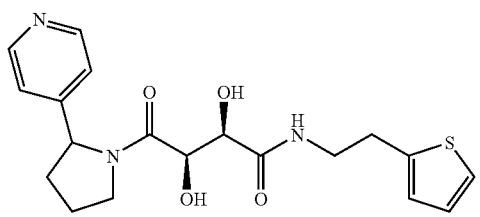
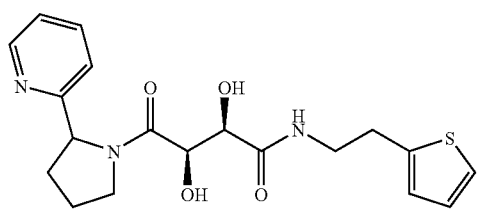
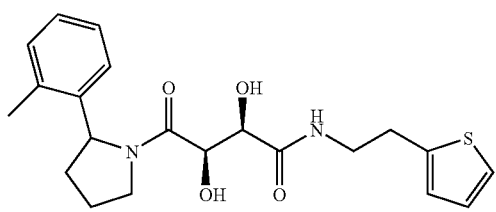
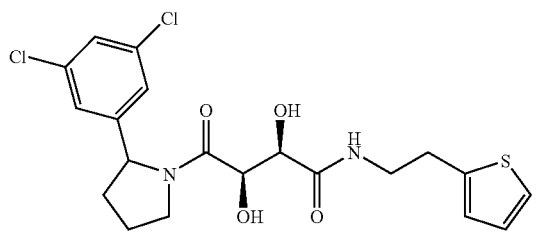
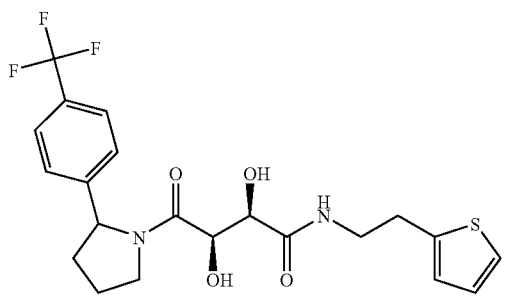
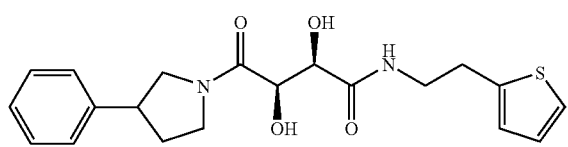
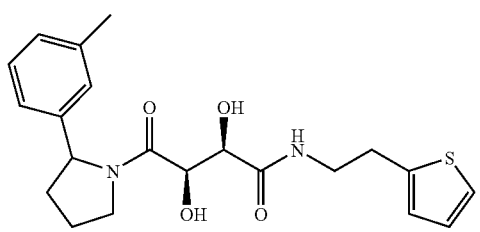
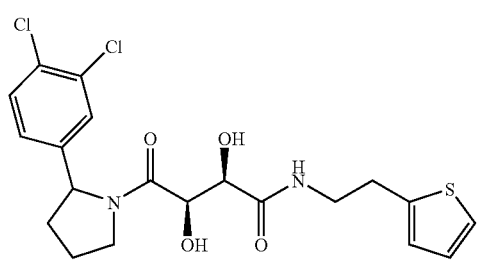
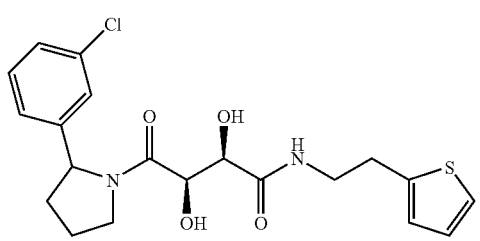
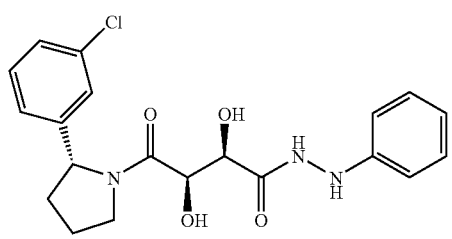
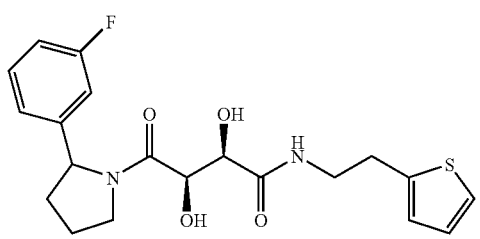

-continued
1423
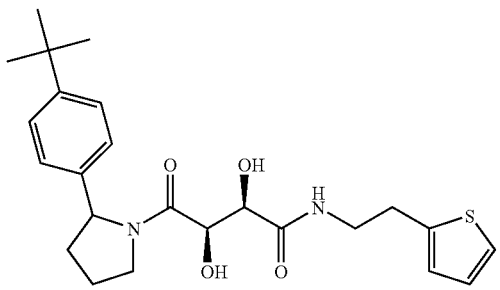
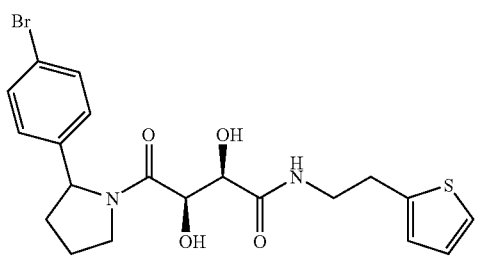
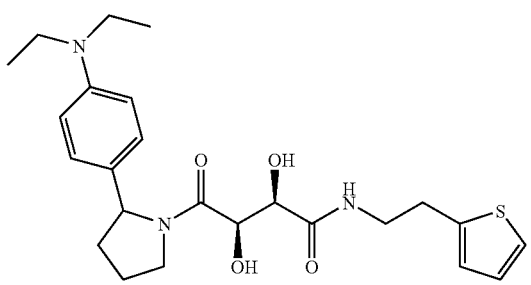
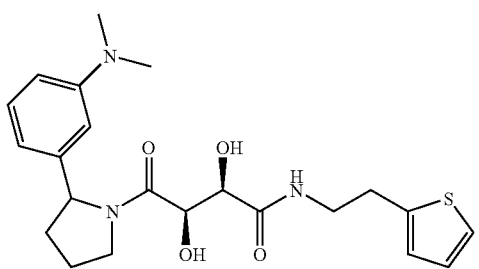
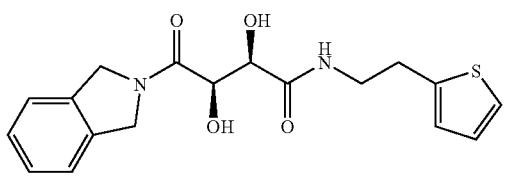
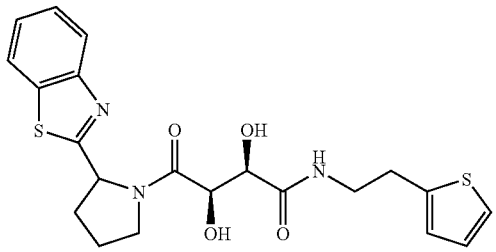
1424
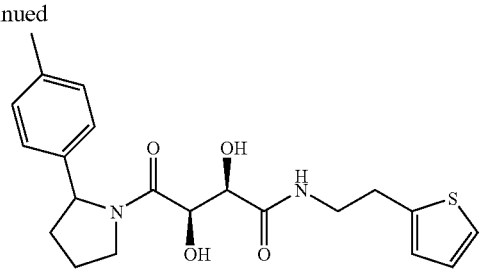
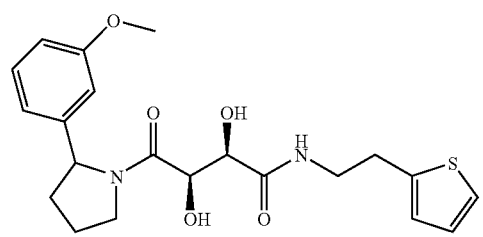
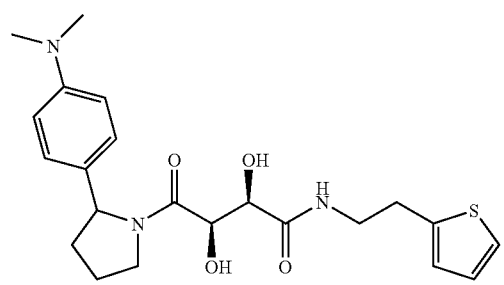
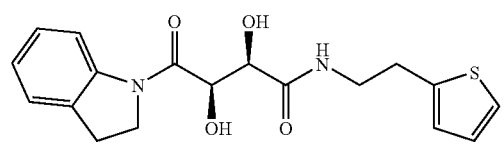
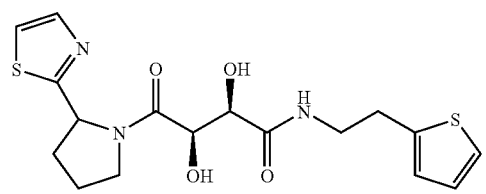
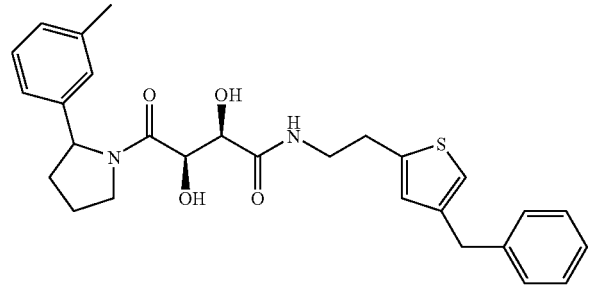

1425 1426
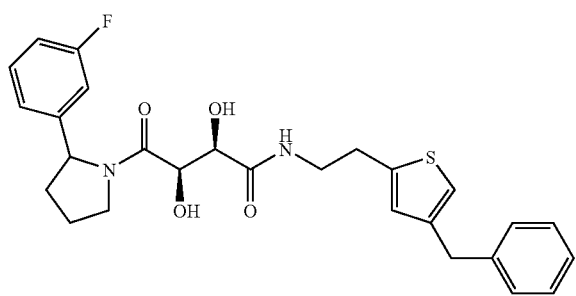
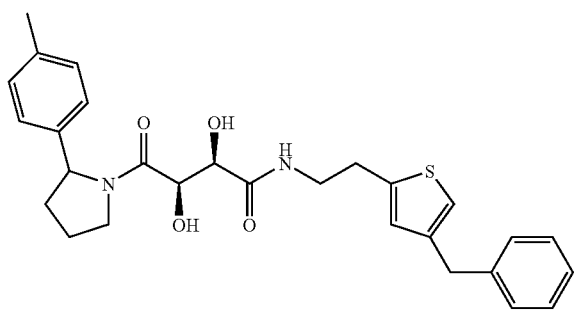
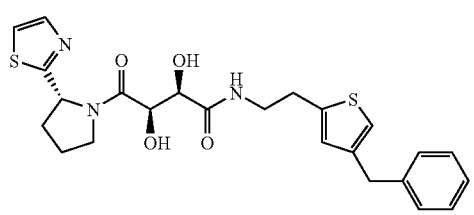
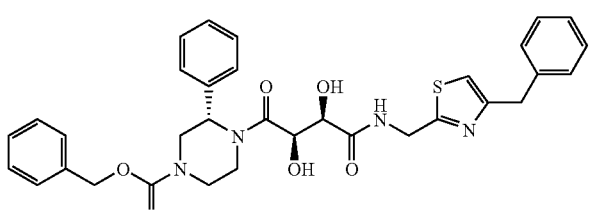
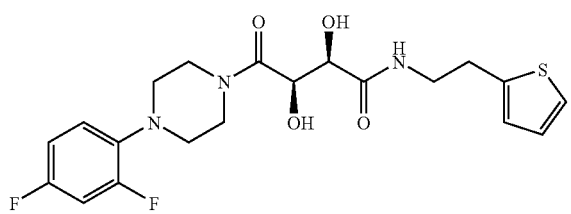
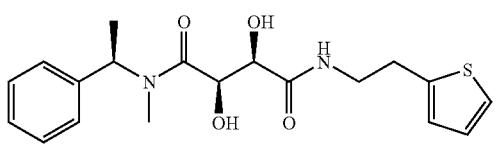
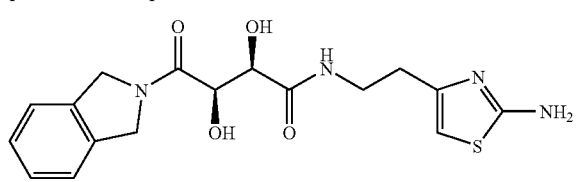
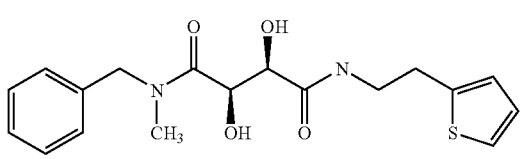
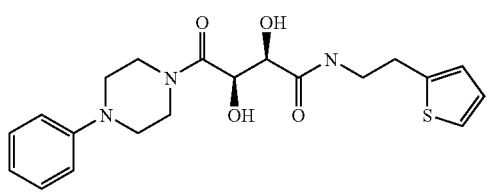
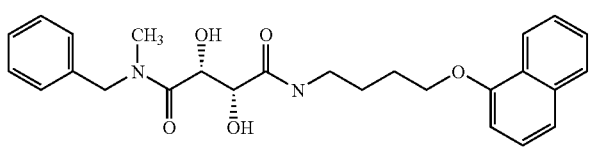
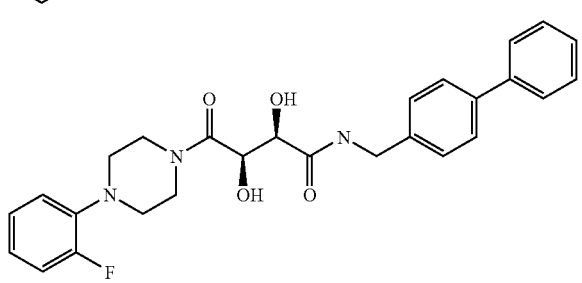
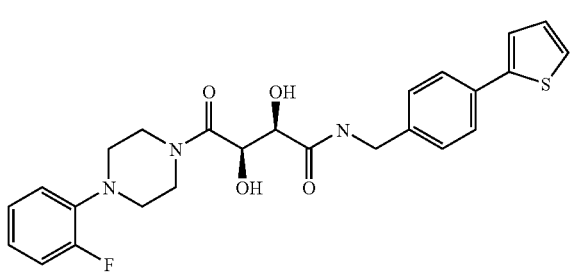
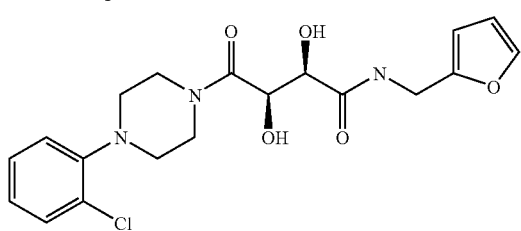
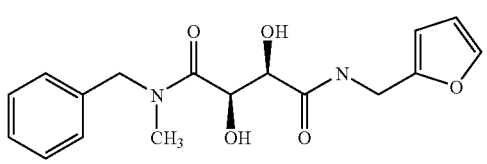

-continued
| 1427 | 1428 |
|---|---|
| 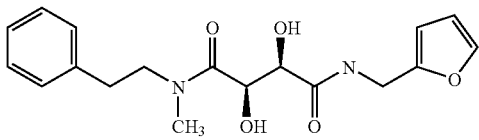 | 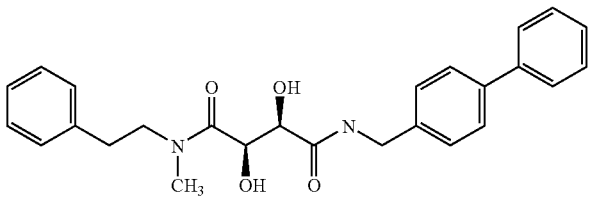 |
| 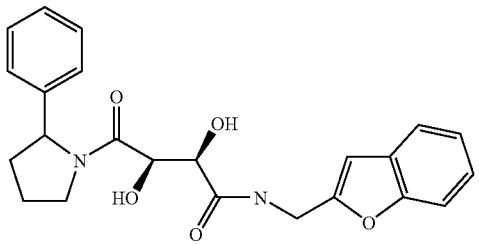 | 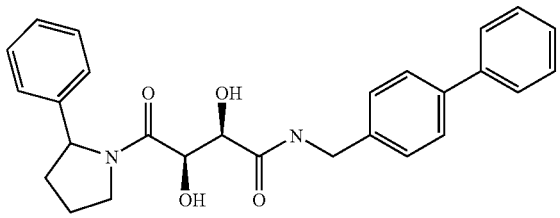 |
| 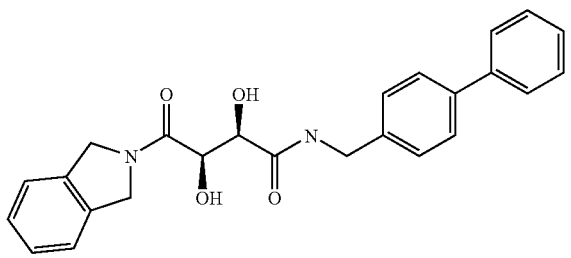 | 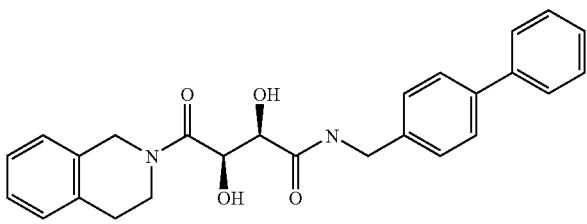 |
| 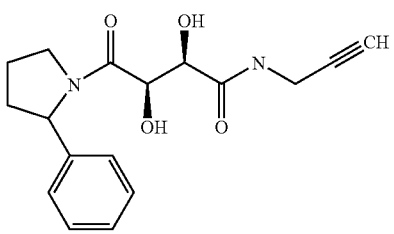 | 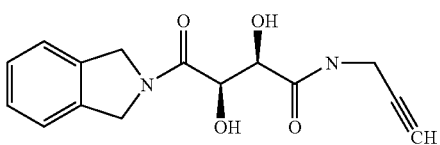 |
| 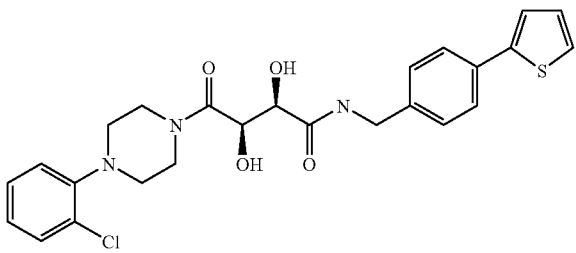 | 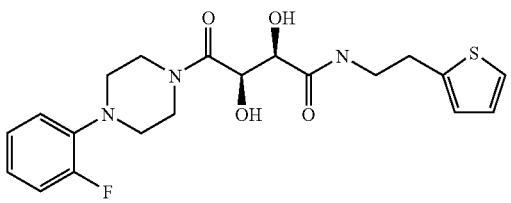 |
| 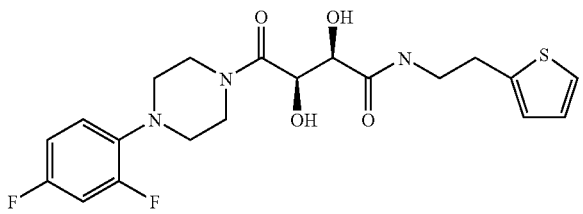 | 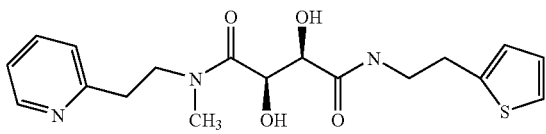 |
| 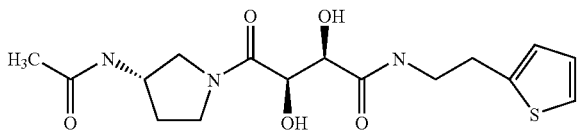 | 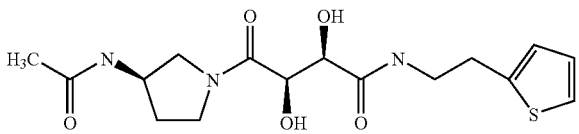 |
| 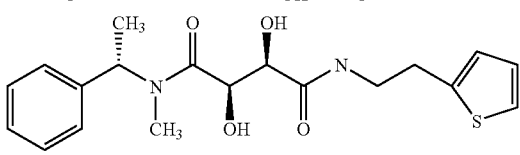 | 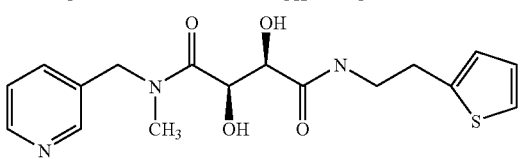 |

1429 1430
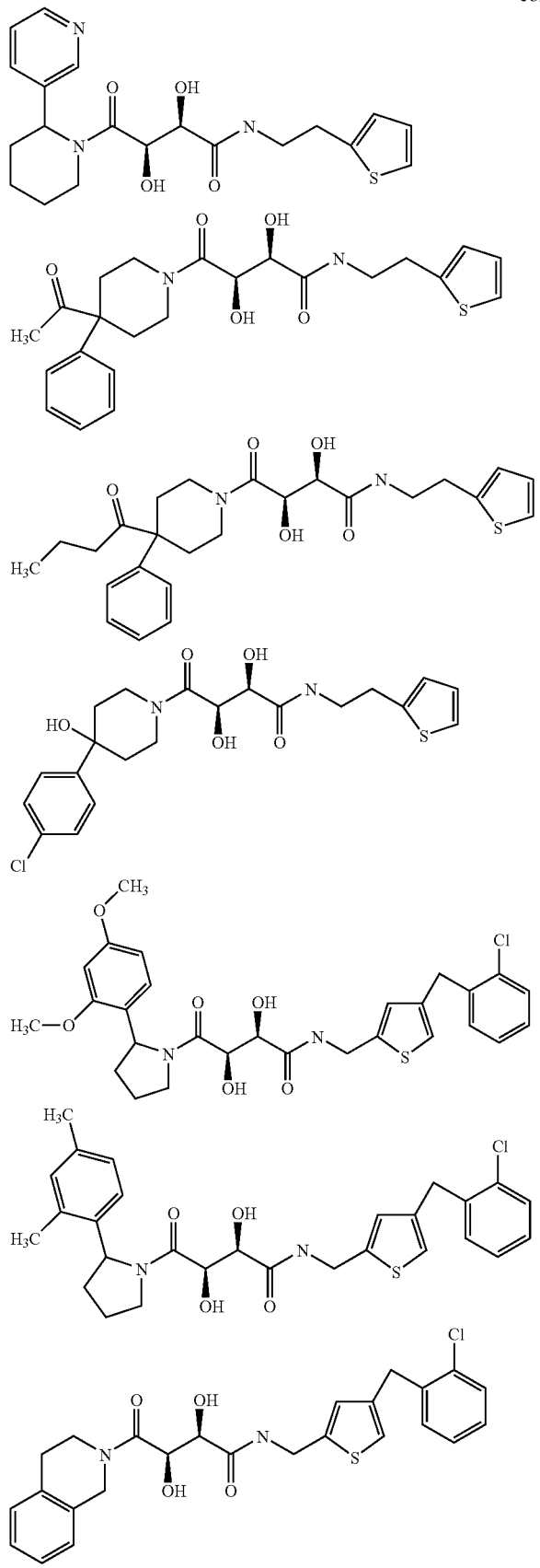
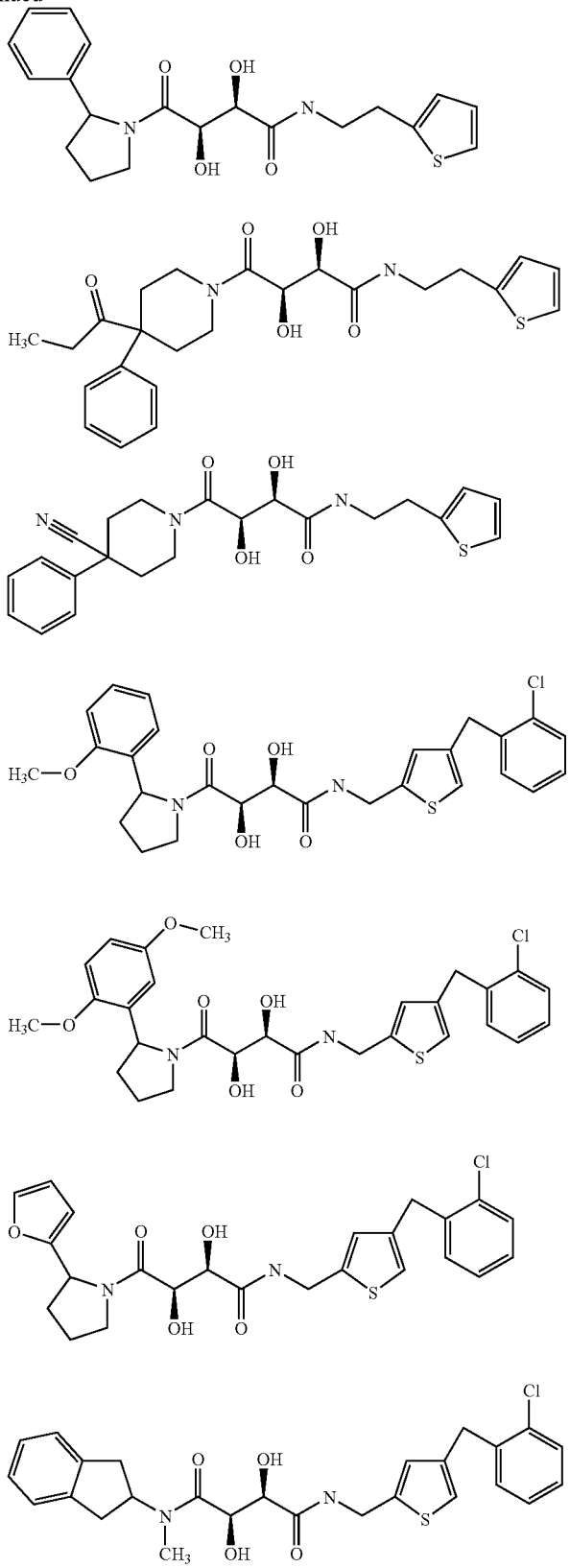
-continued

-continued
| 1431 | 1432 |
|---|---|
| 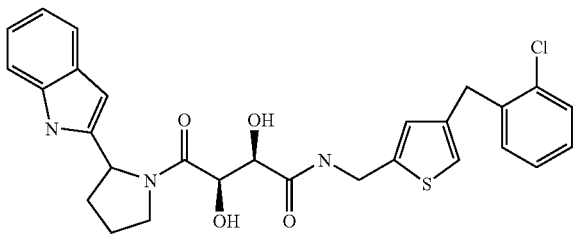 | 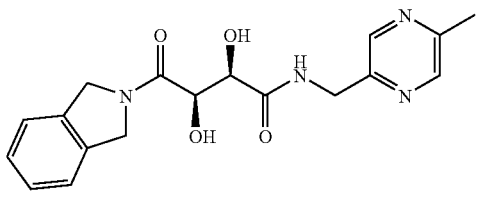 |
| 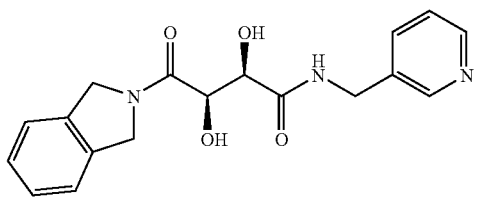 | 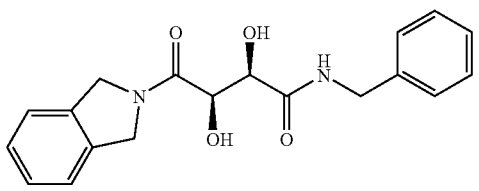 |
| 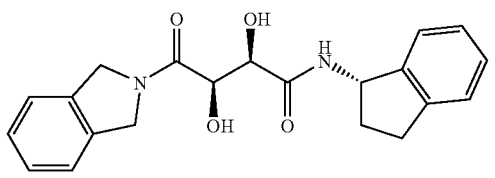 | 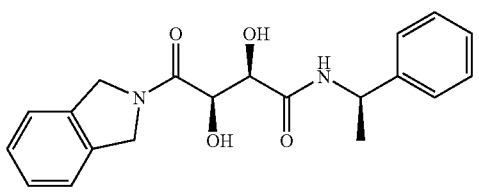 |
| 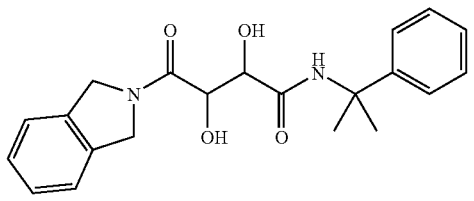 | 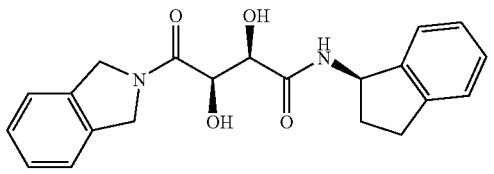 |
|  | 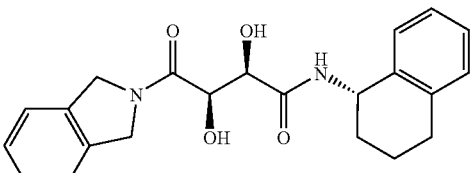 |
| 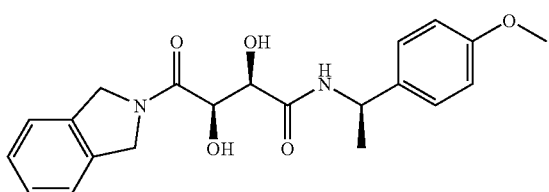 | 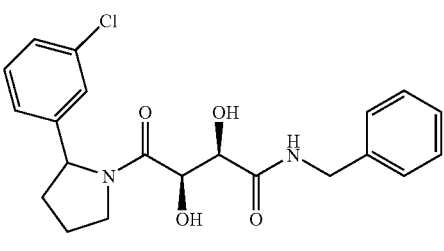 |
| 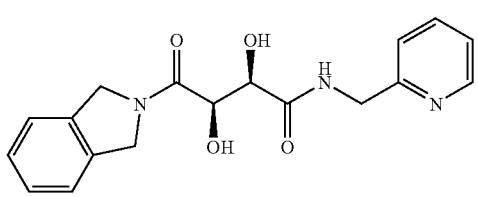 | 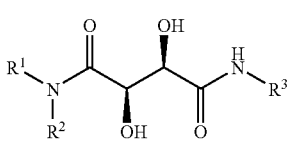<br>(R1 = R2 = CH$_2$Ph, R3 = CH$_2$CH$_2$(C$_4$H$_4$O)) |
| 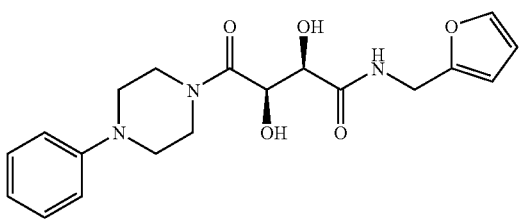 | 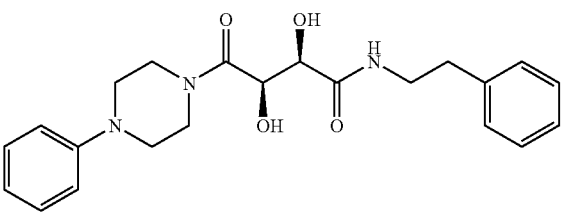 |

-continued
| 1433 | 1434 |
|---|---|
| 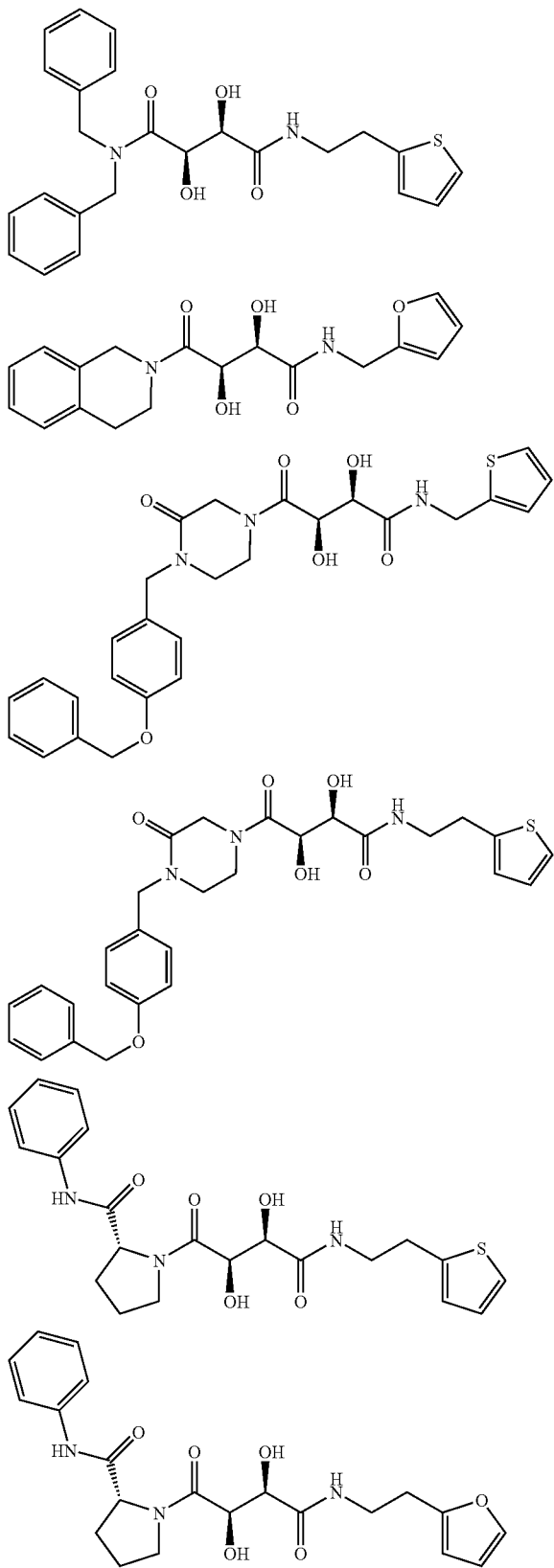 | 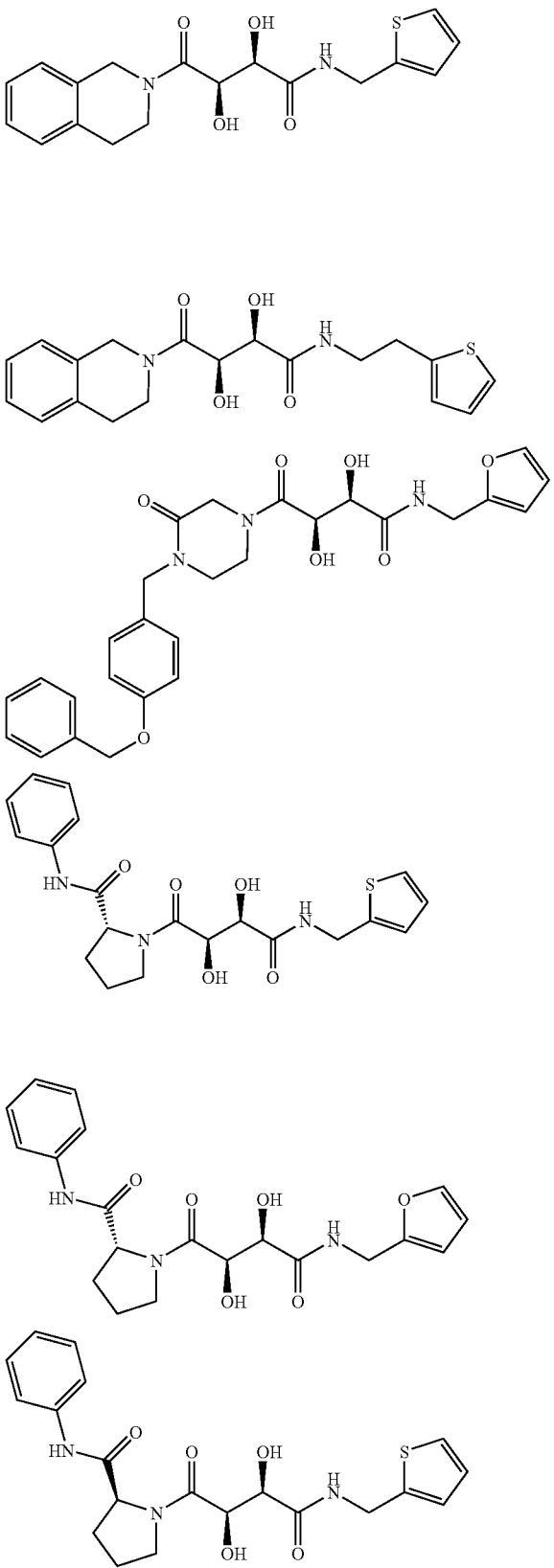 |

1435 1436
-continued
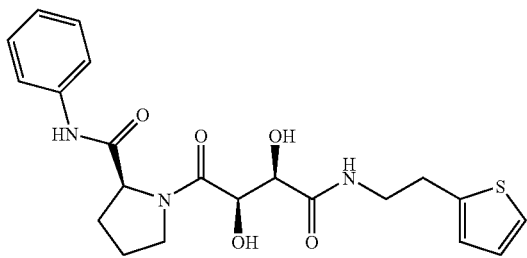
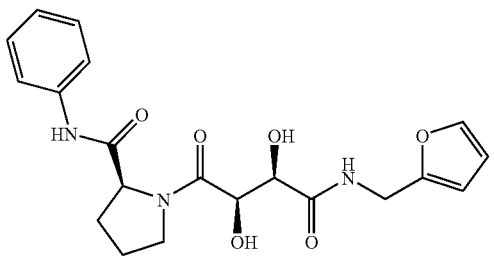
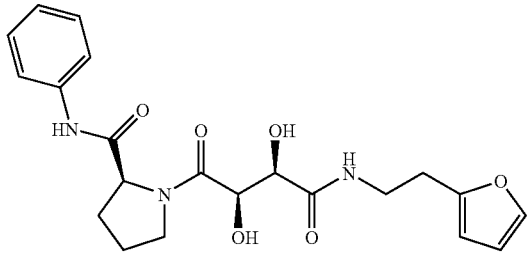
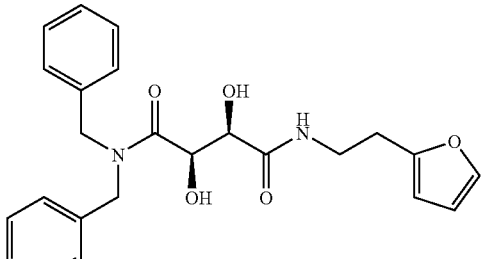
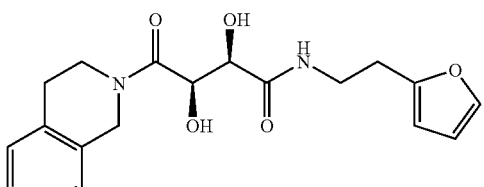
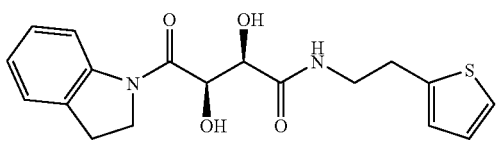
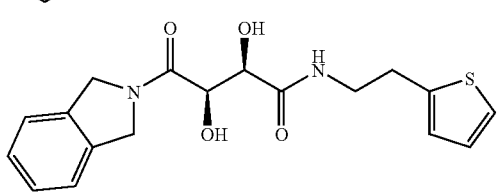
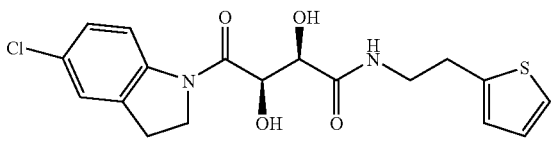
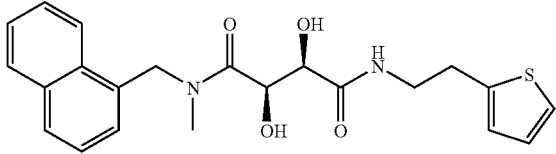
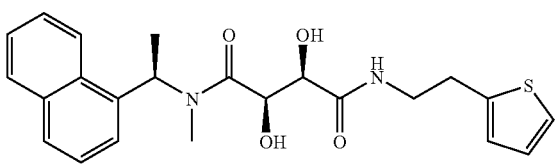
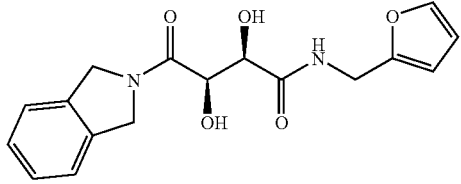
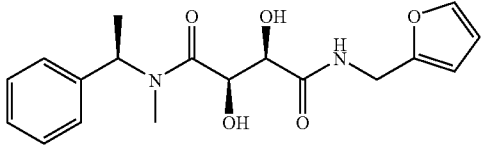
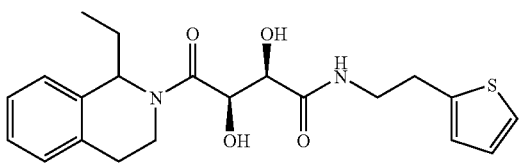
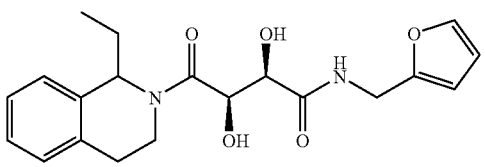
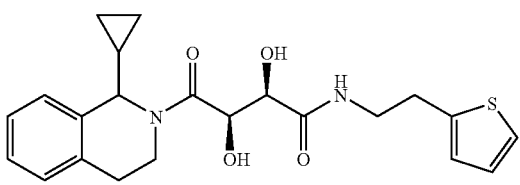
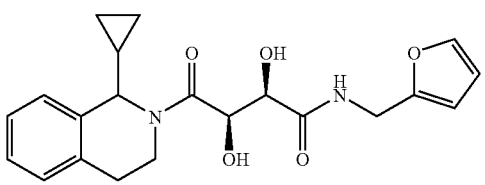

1437
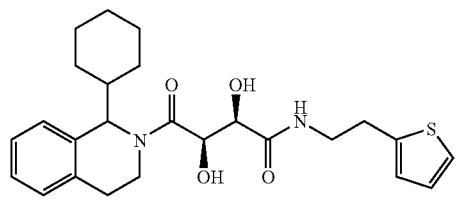
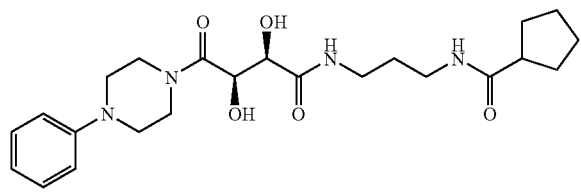
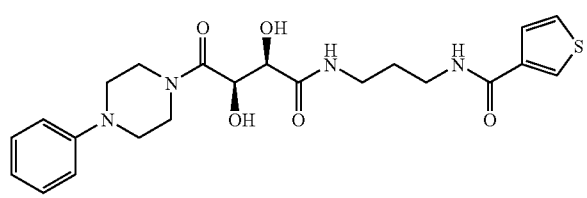
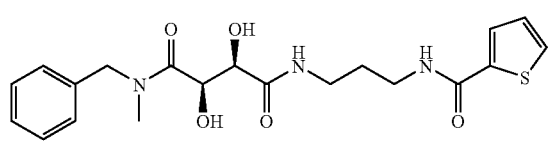
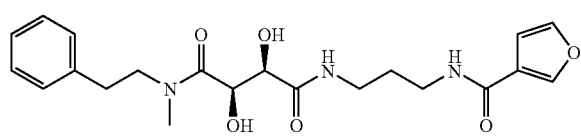
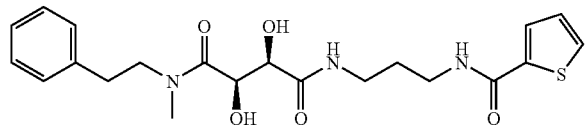
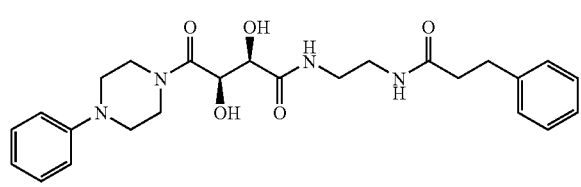
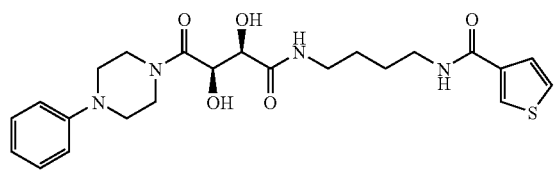
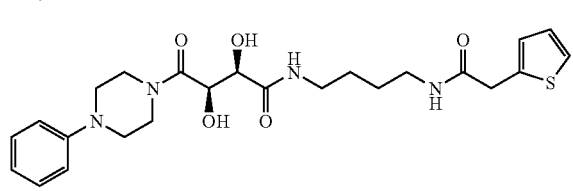
1438
-continued
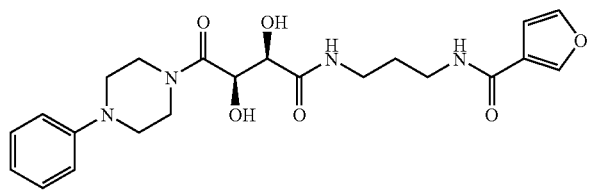
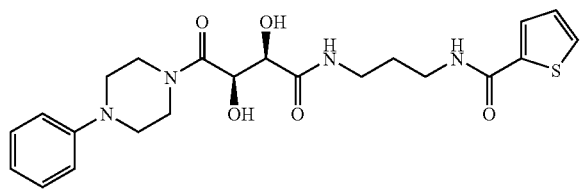
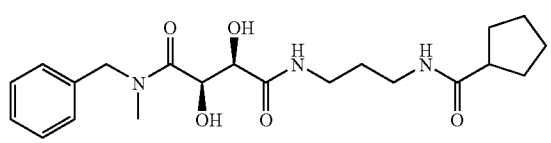
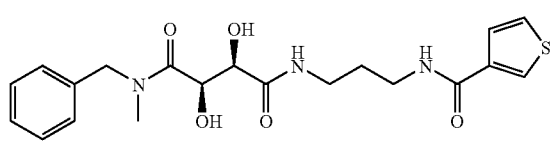
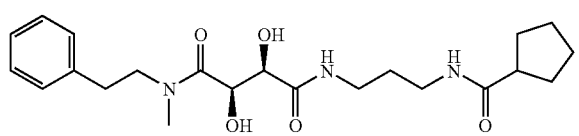
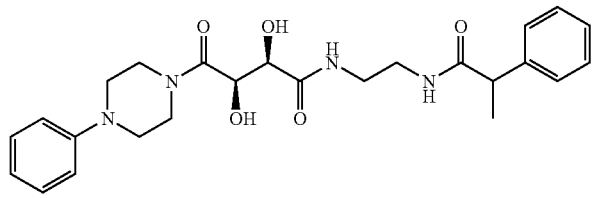
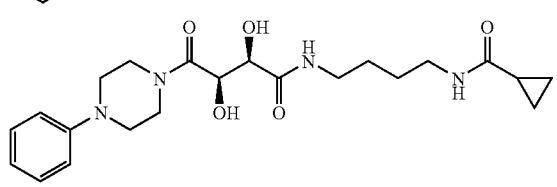
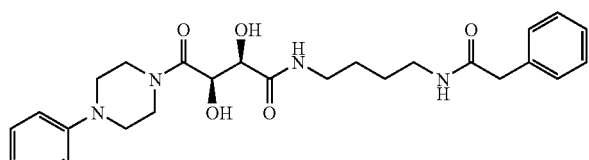
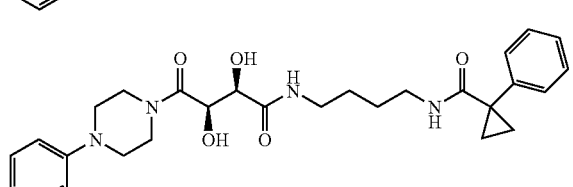

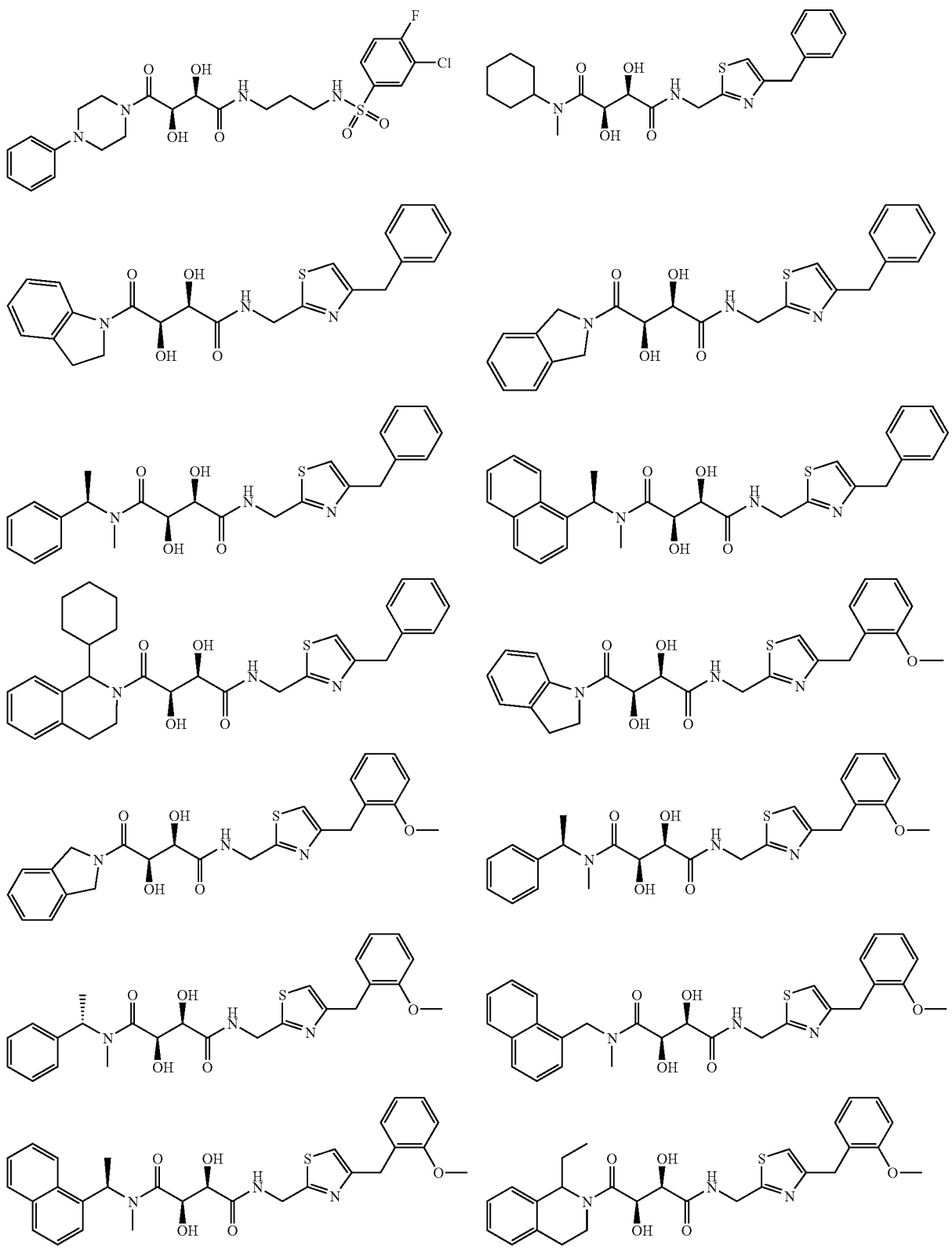

-continued
| 1441 | 1442 |
|---|---|
| 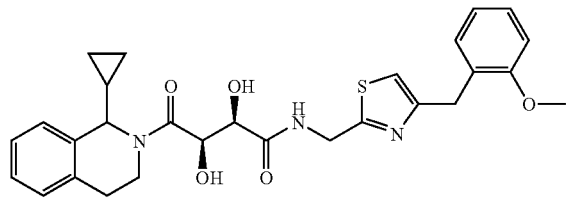 | 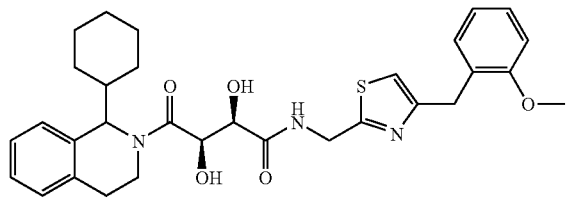 |
| 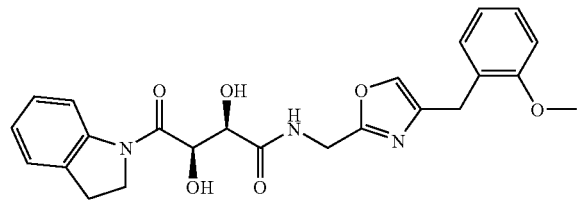 | 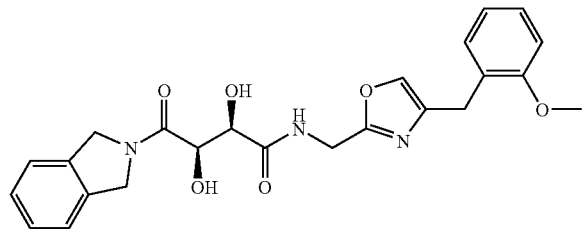 |
| 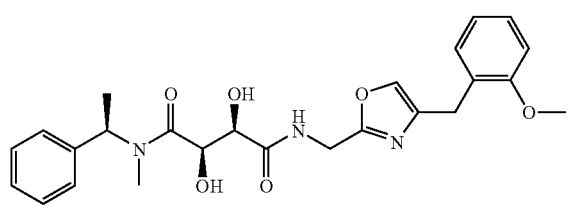 | 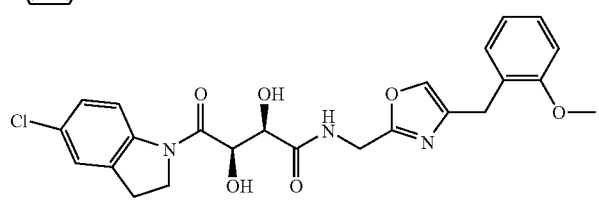 |
| 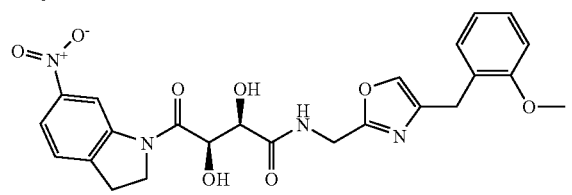 | 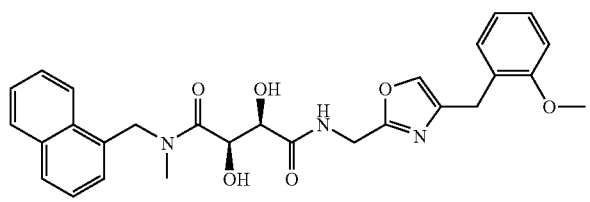 |
| 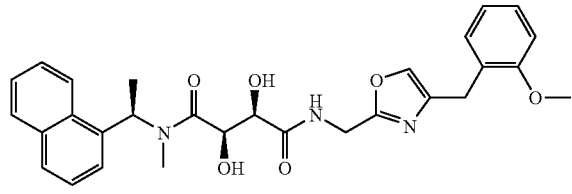 | 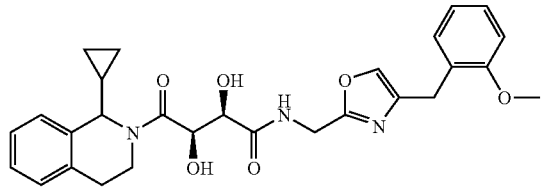 |
| 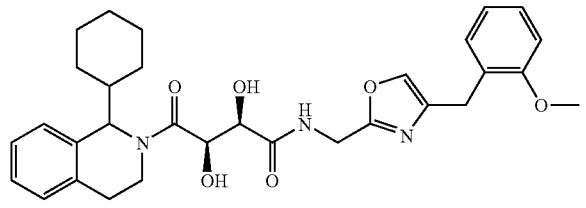 | 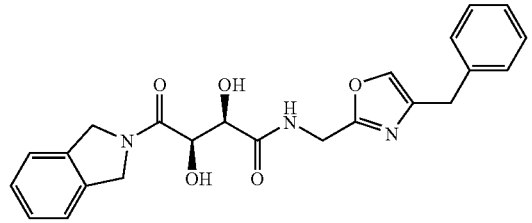 |
| 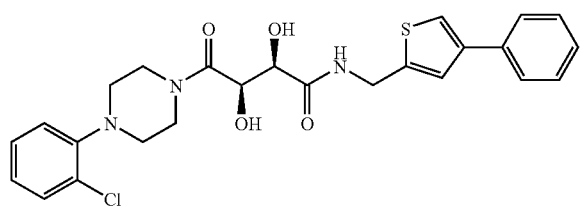 | 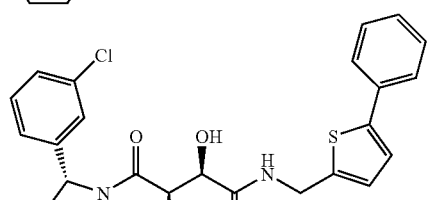 |
|  |  |

1443
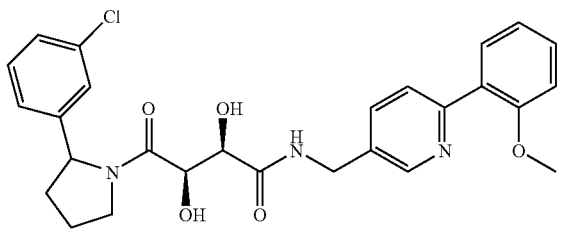
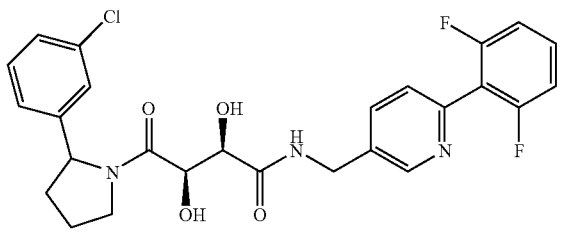
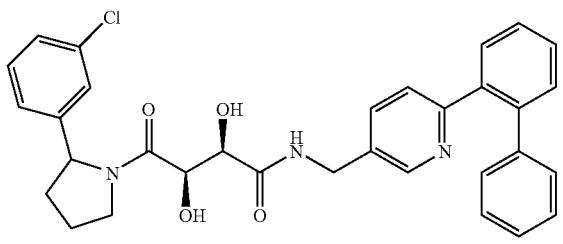
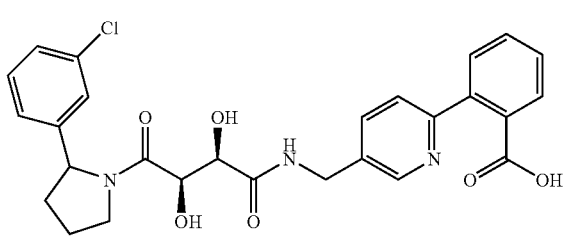
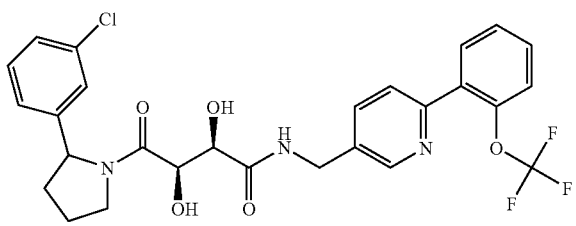
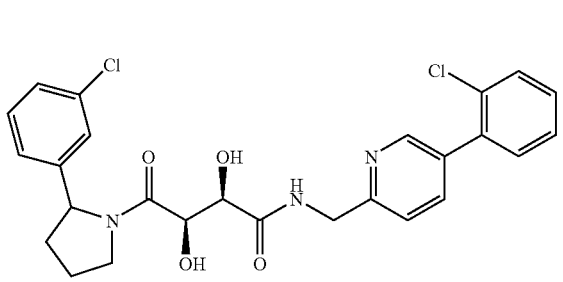
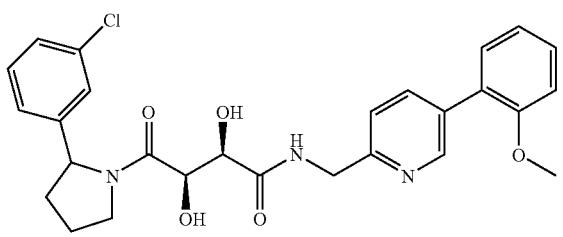
1444
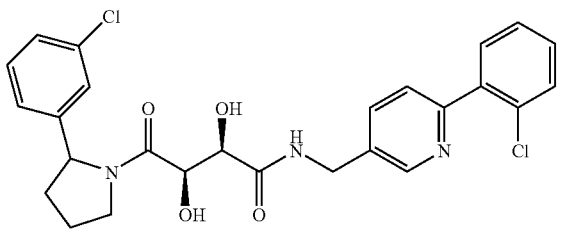
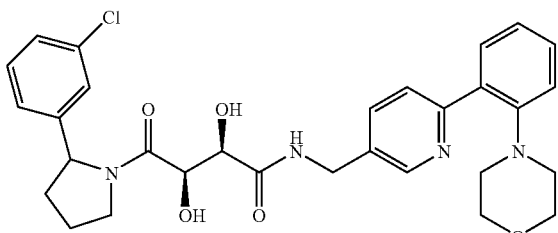
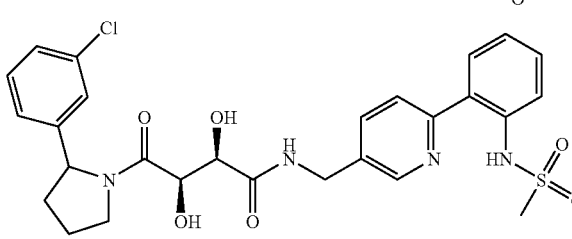
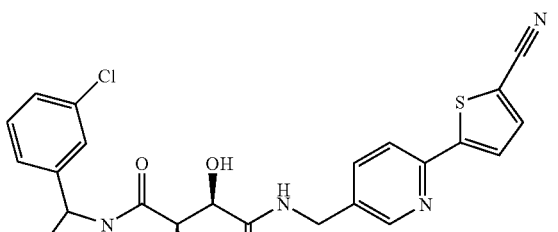
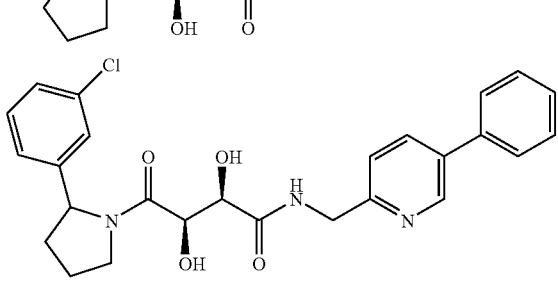
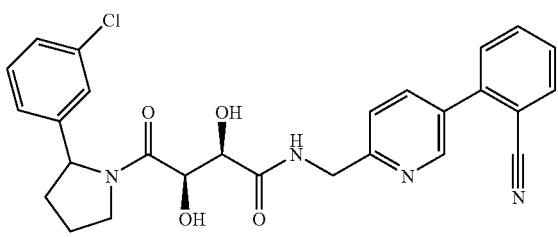

1445 1446
-continued
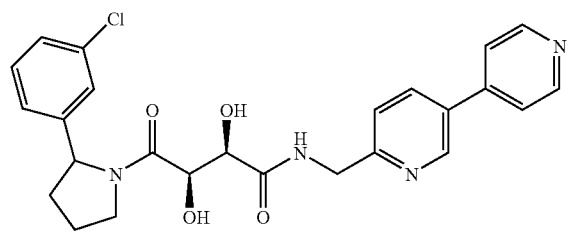
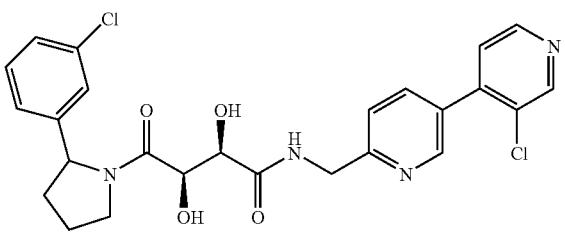
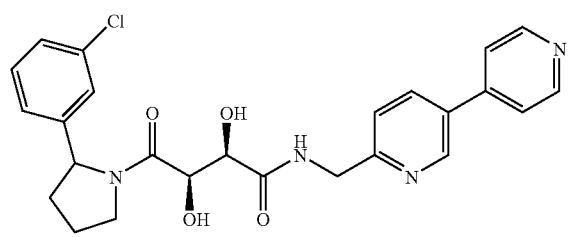
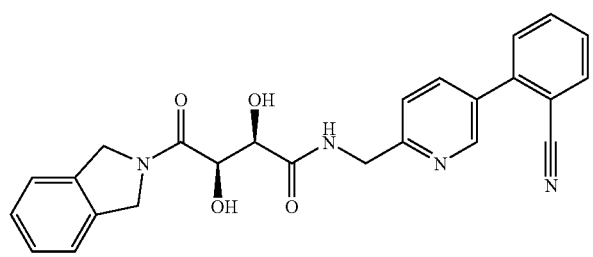
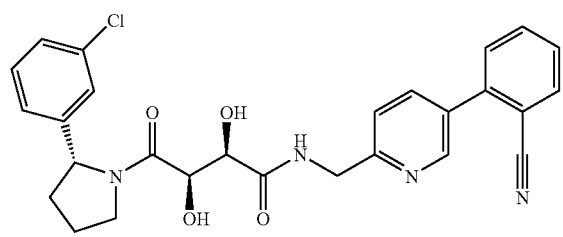
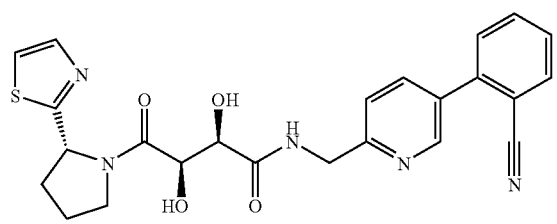
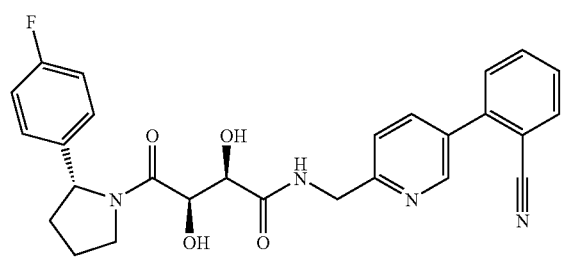
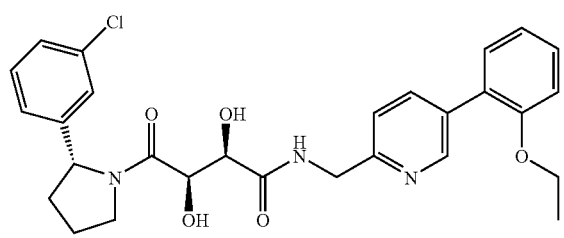
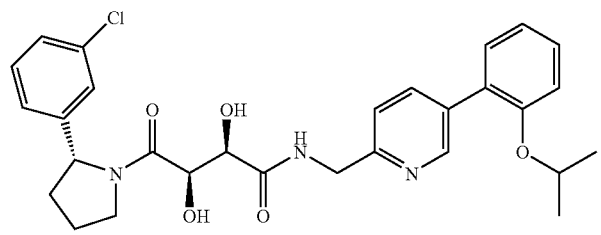
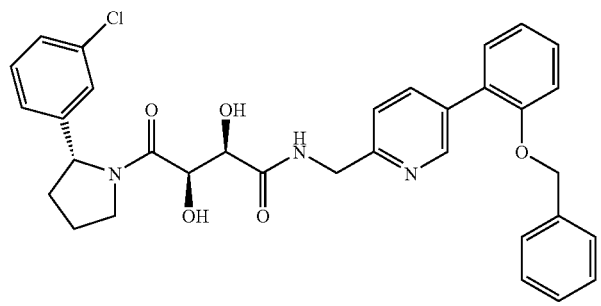
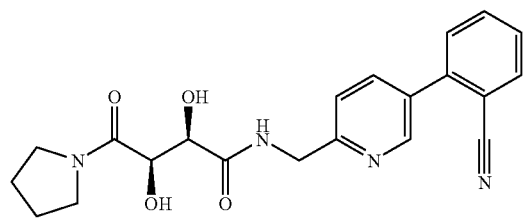

1447
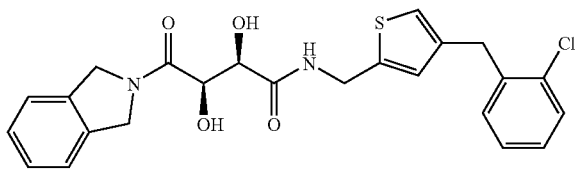
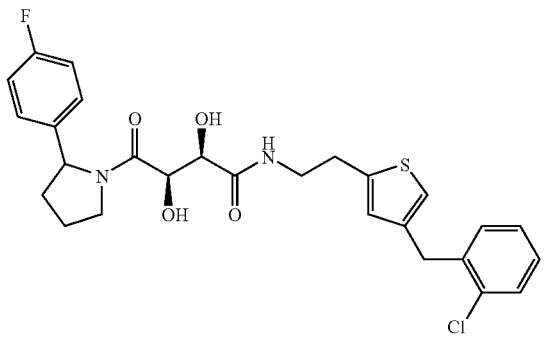
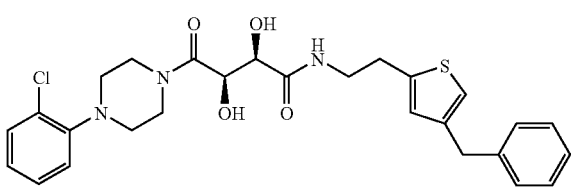
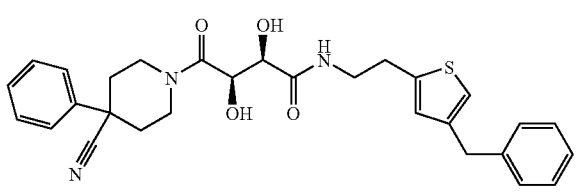
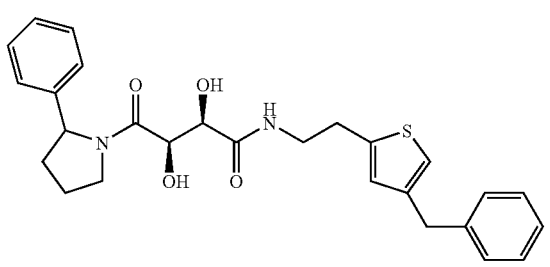
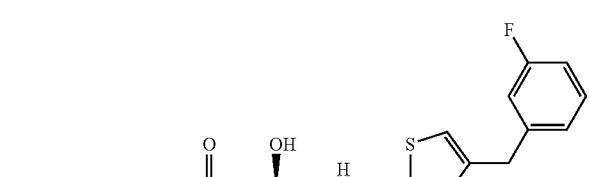
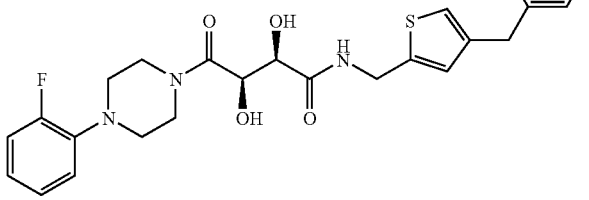
1448
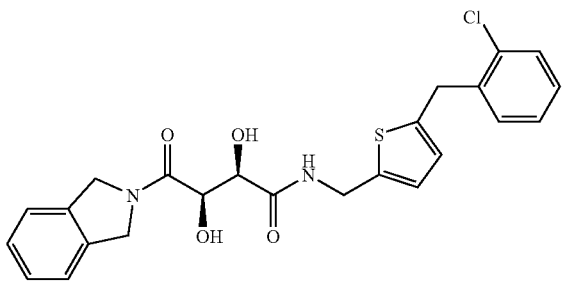
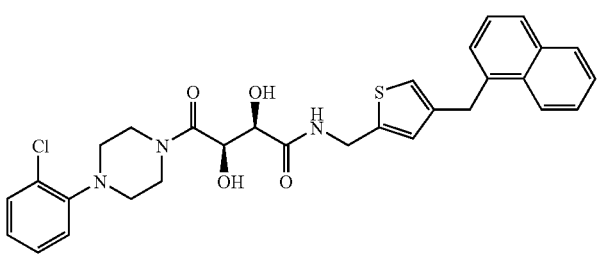
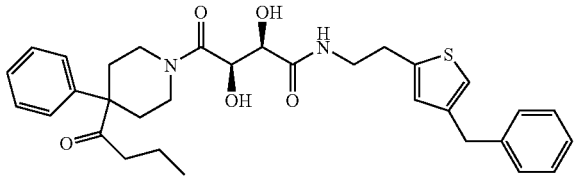
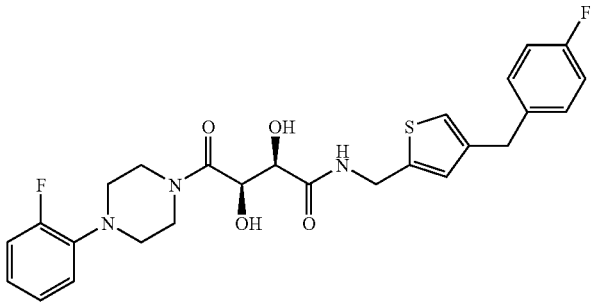
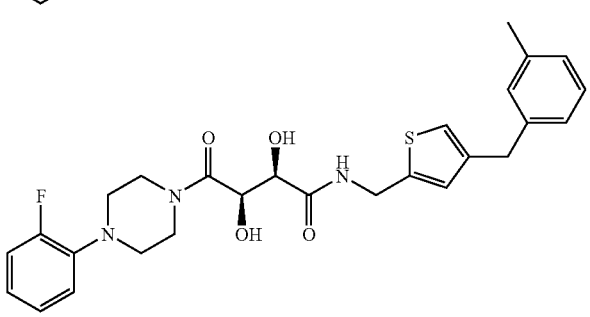

1449
1450
-continued
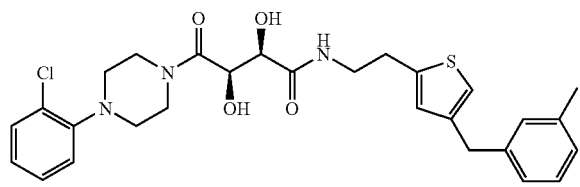
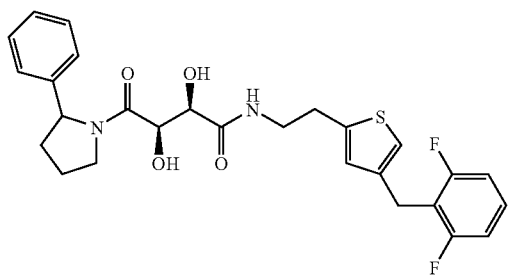
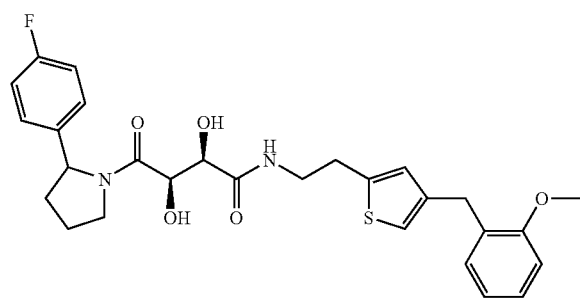
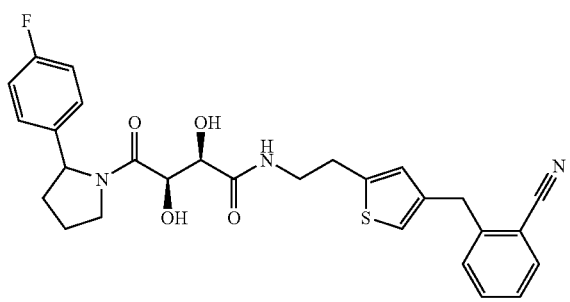
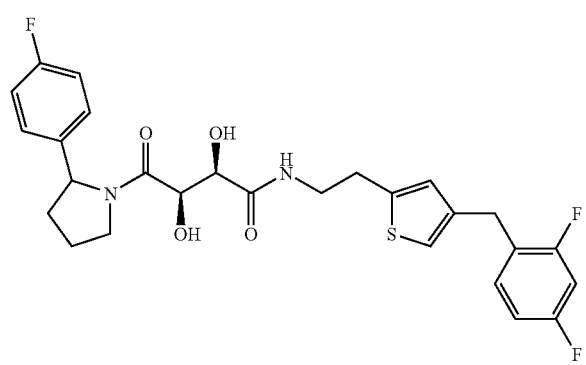
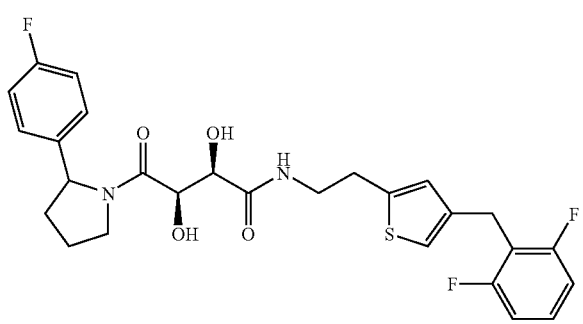
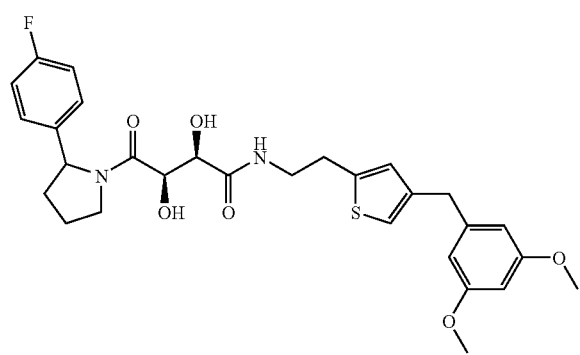
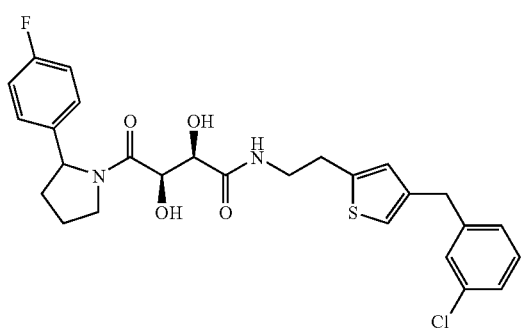
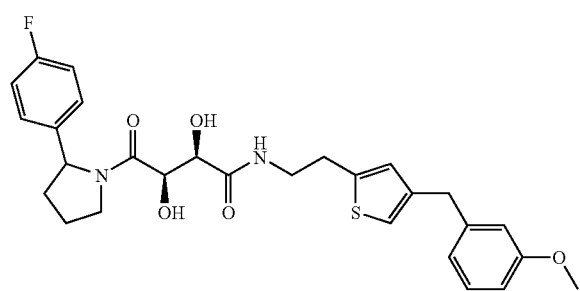
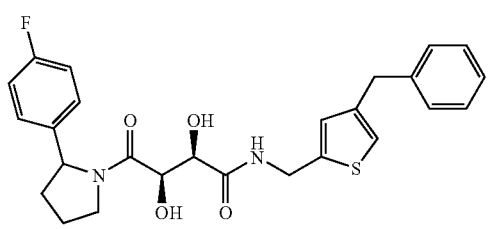

-continued
1451
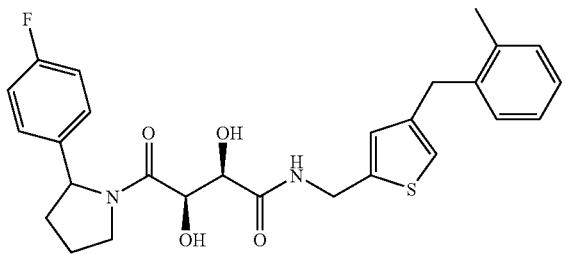
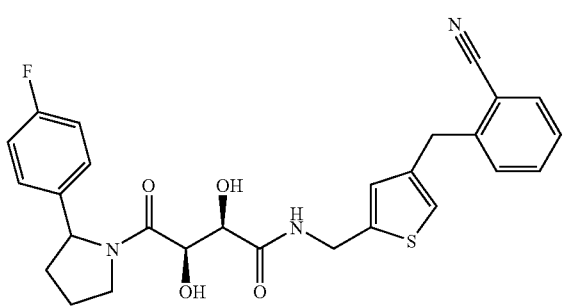
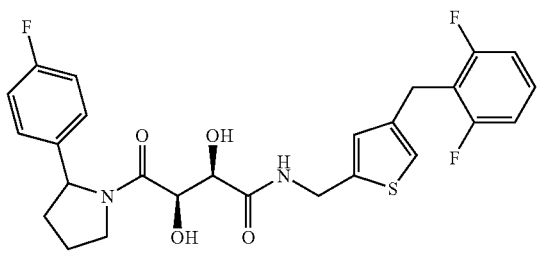
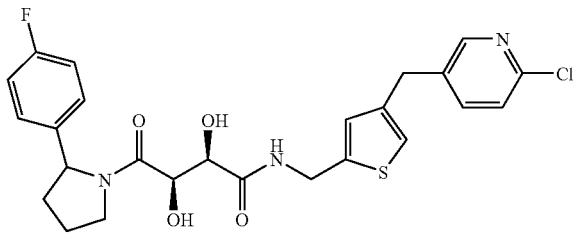
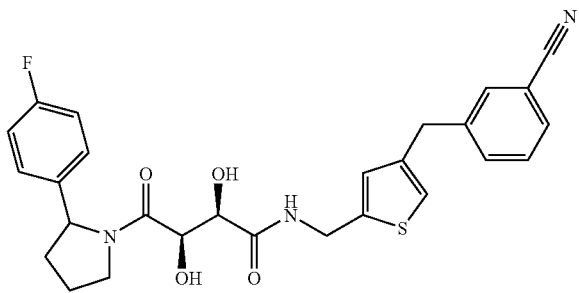
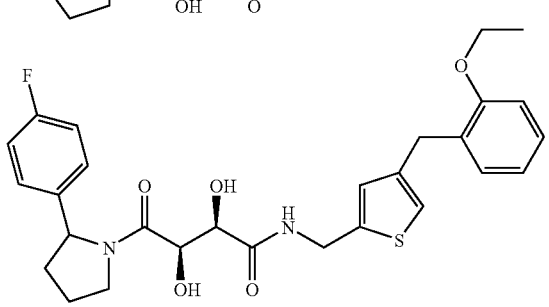
1452
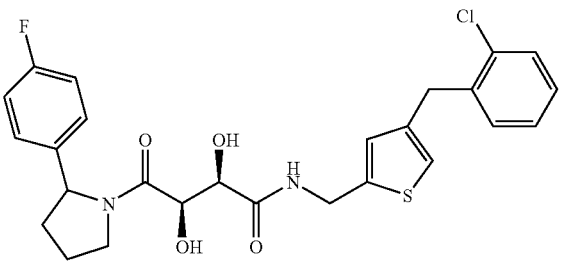
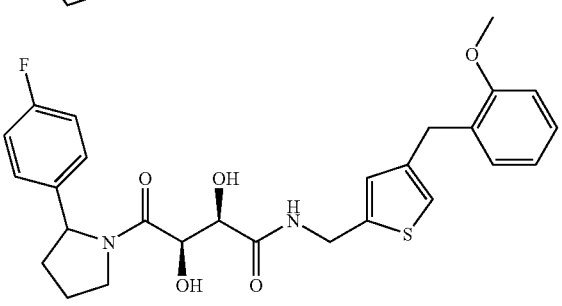
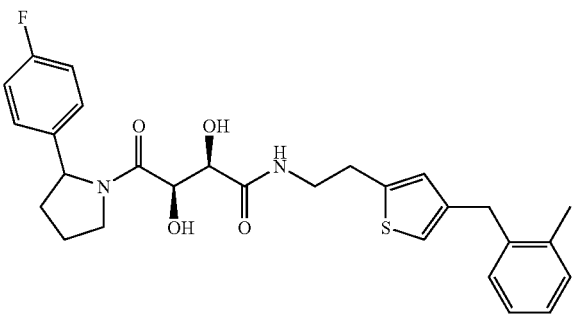
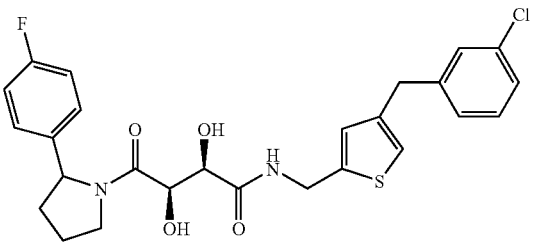
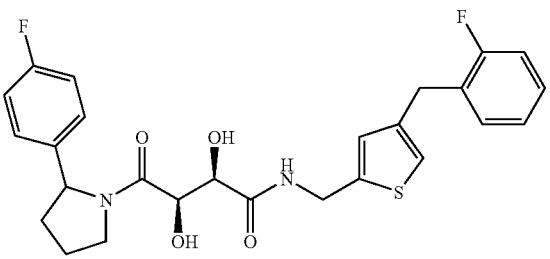
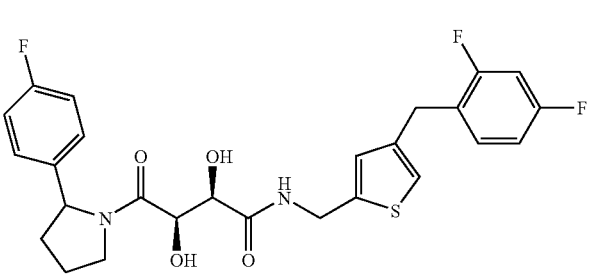

-continued
1453
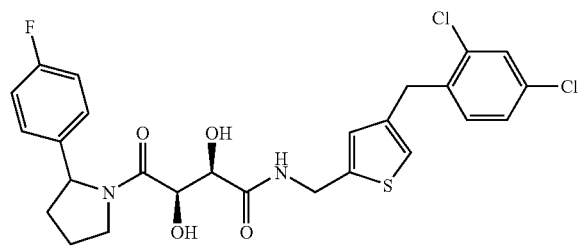
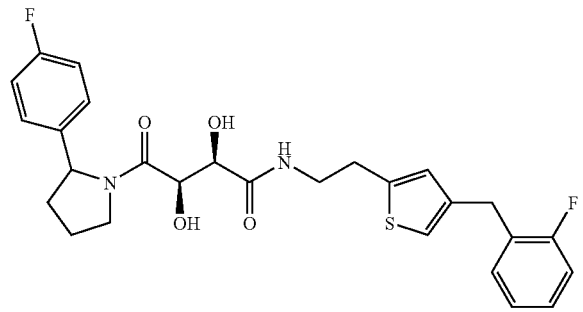
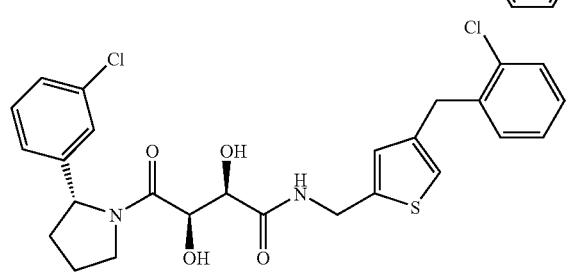
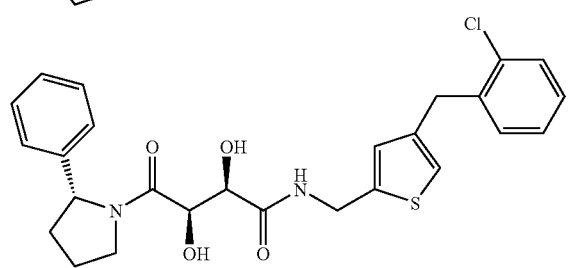
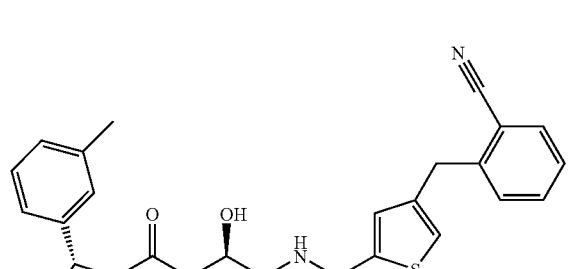
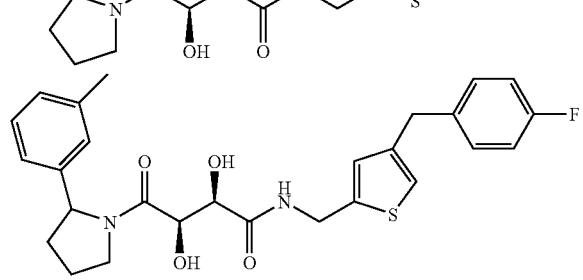
1454
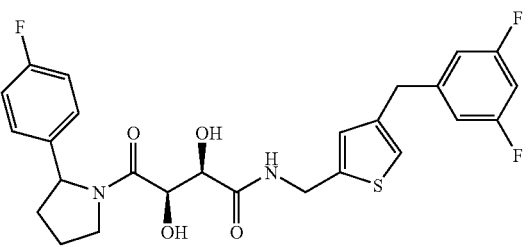
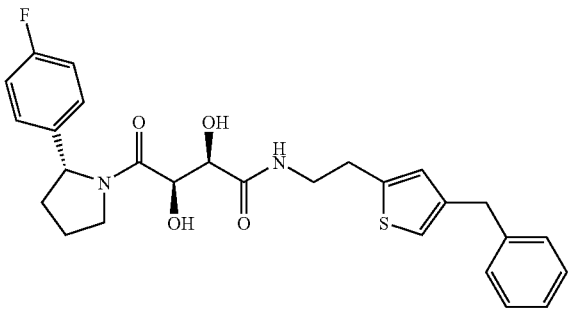
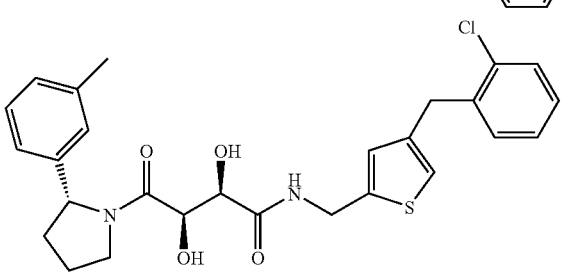
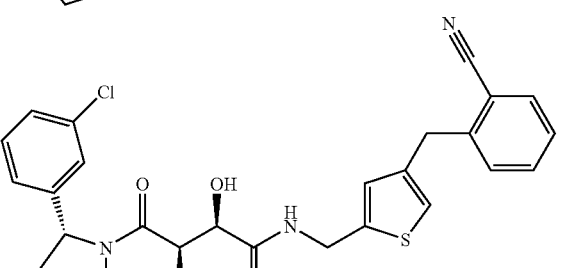
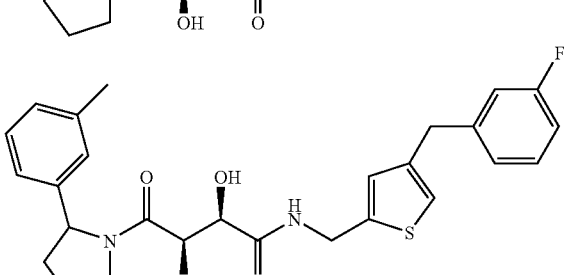
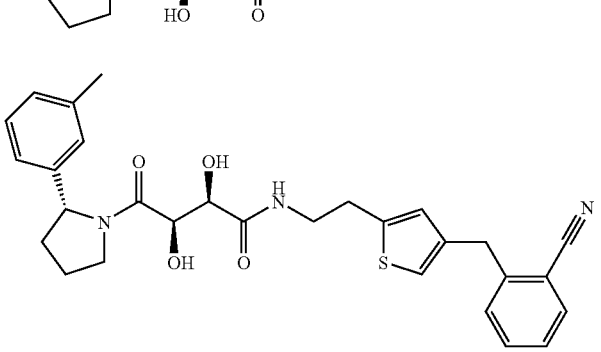

1455
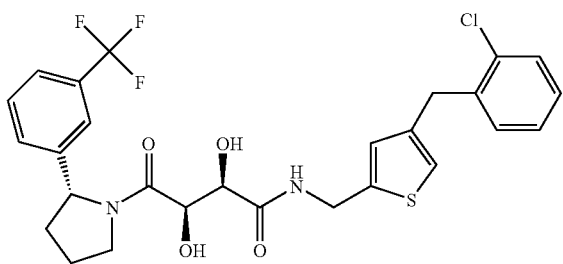
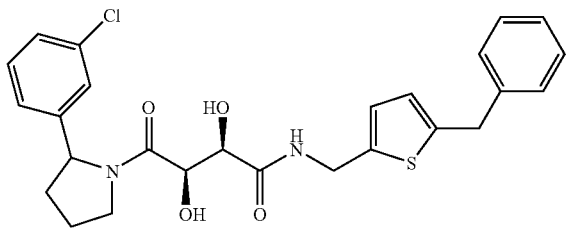
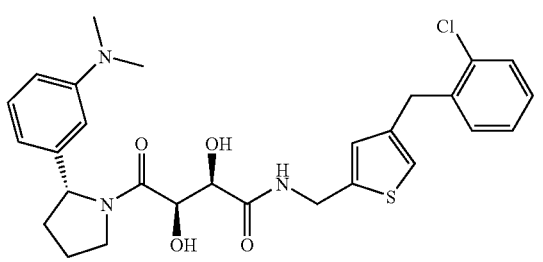
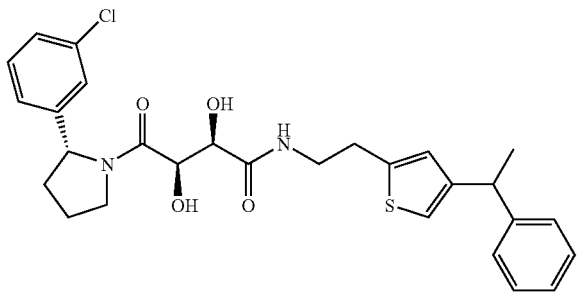
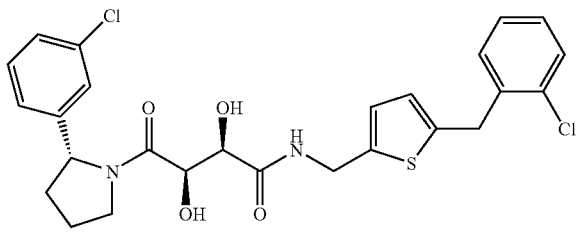
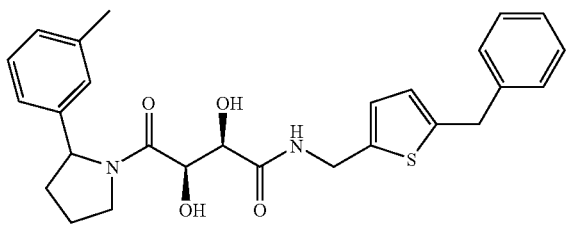
1456
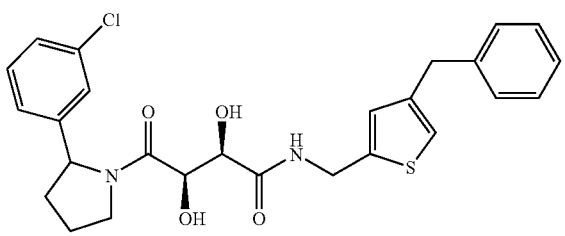
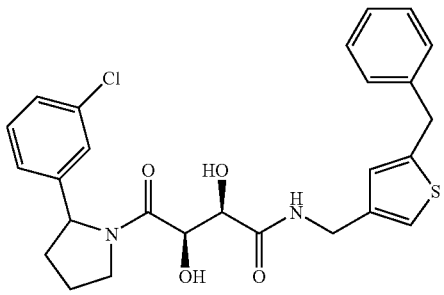
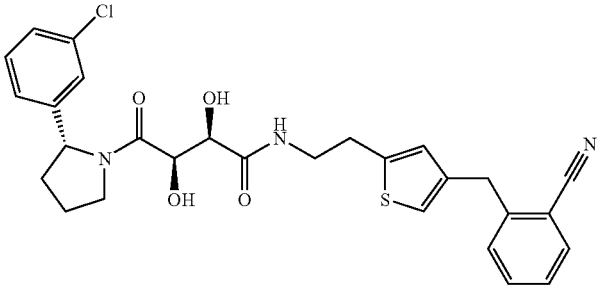
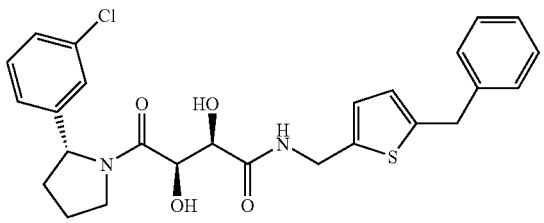
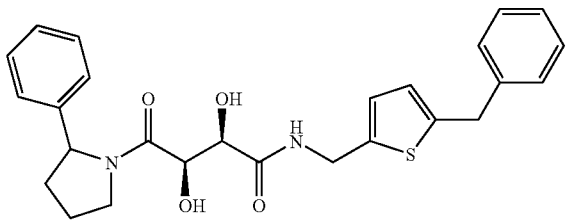
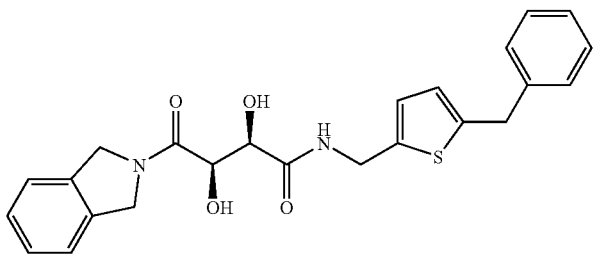

1457 1458
-continued
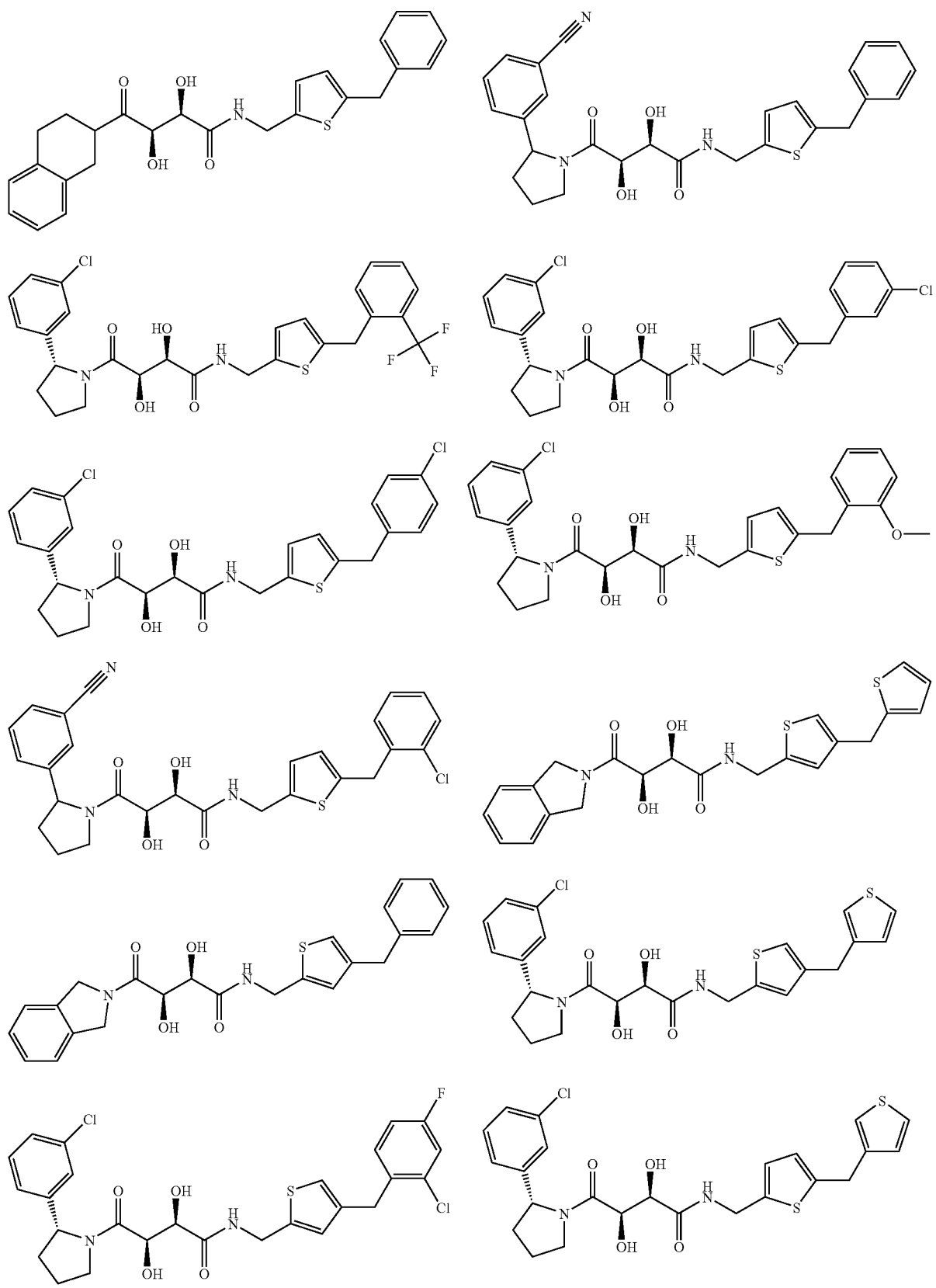

1459 1460
-continued
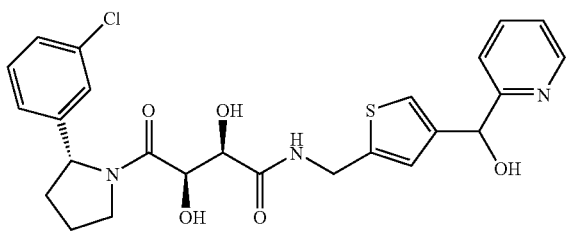
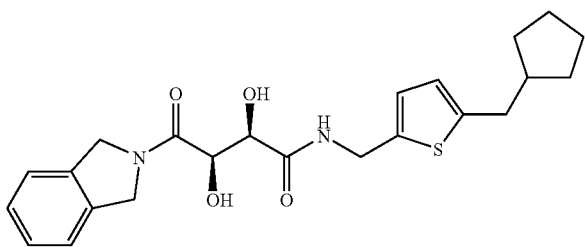
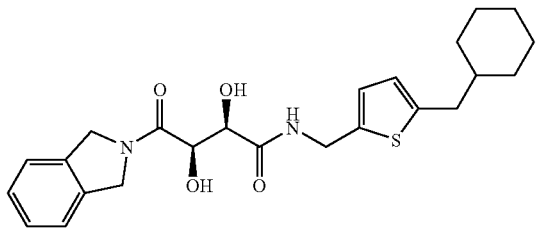
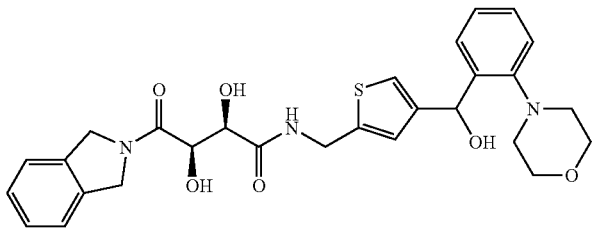
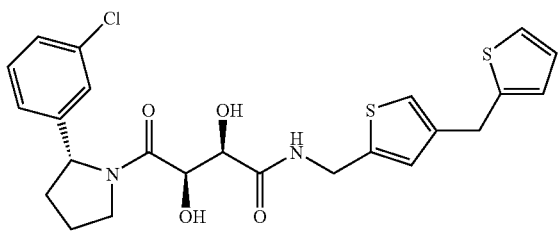
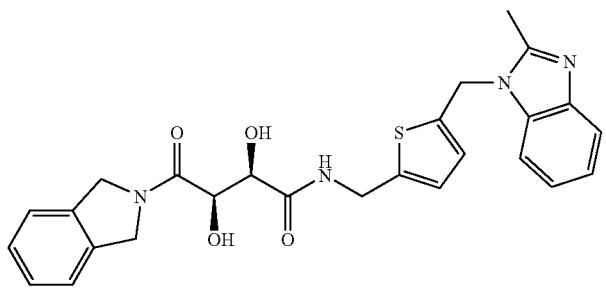
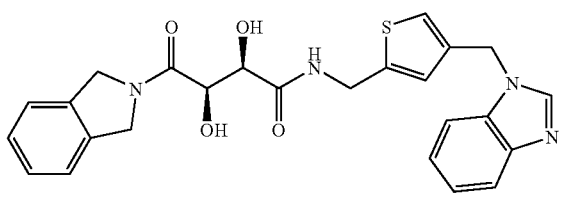
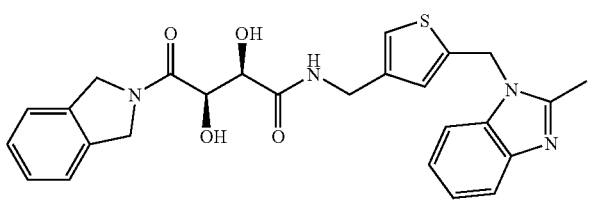
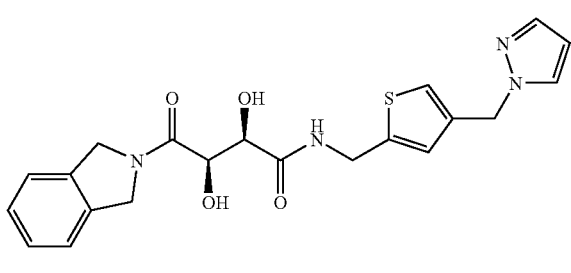
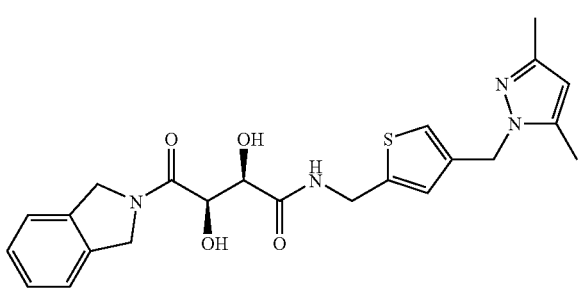
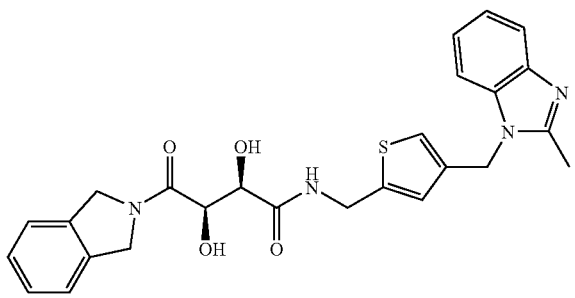
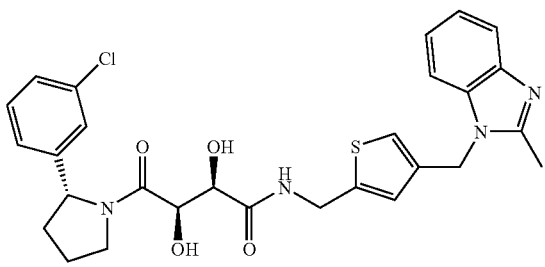

1461 1462
-continued
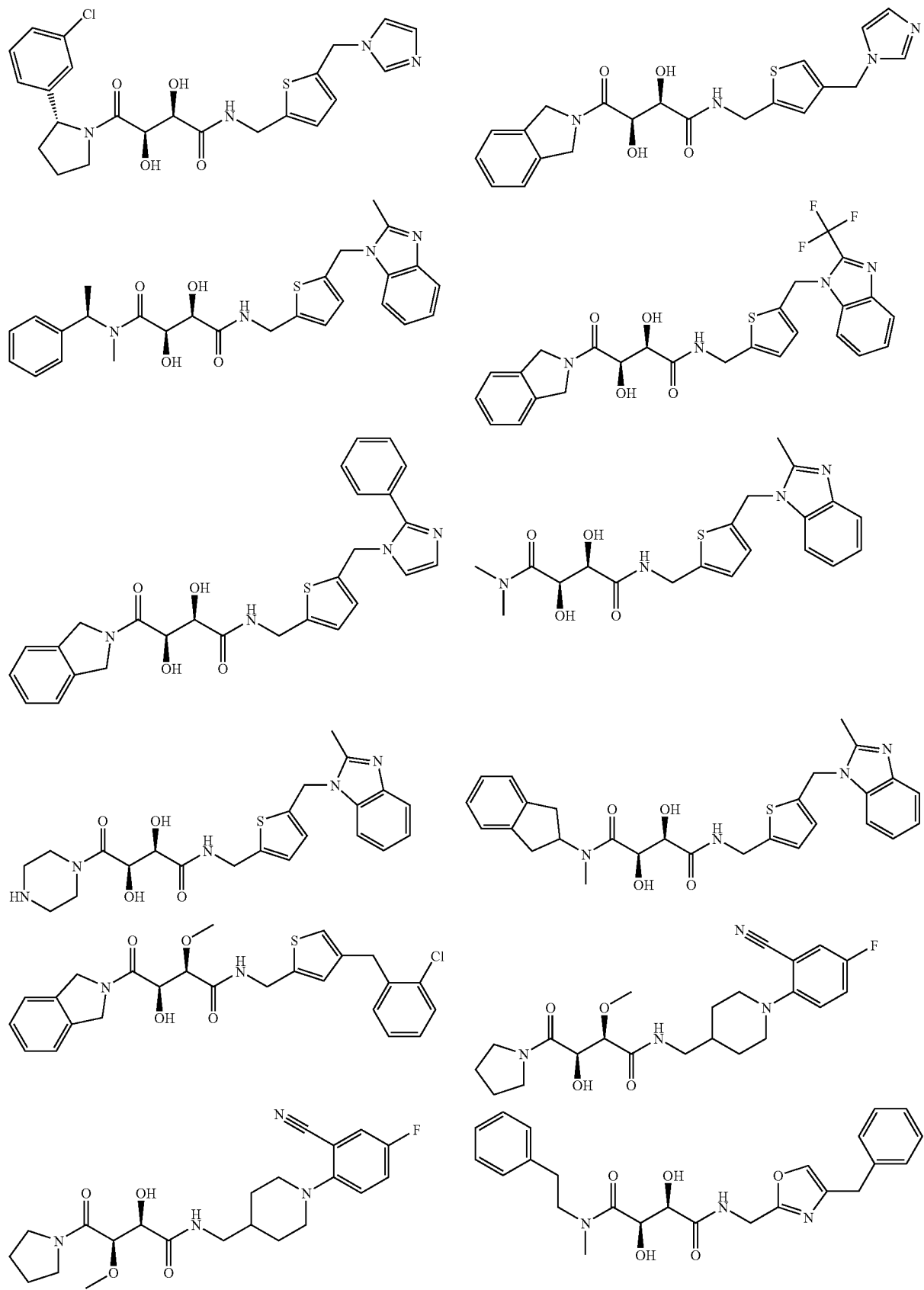

-continued
1463
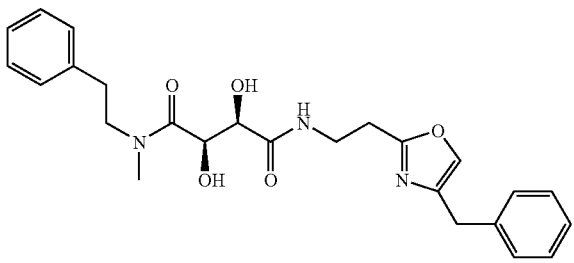
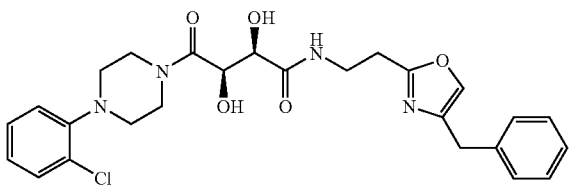
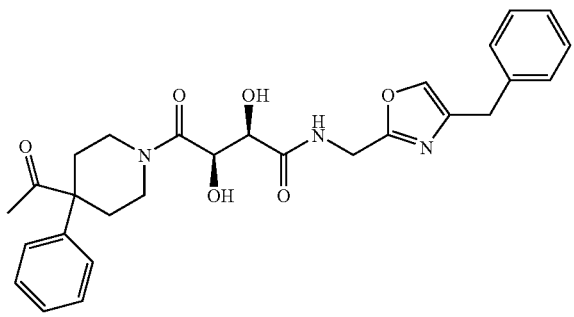
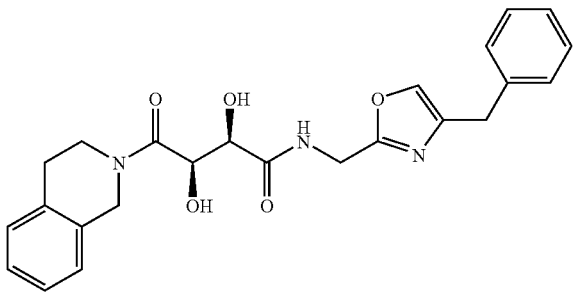
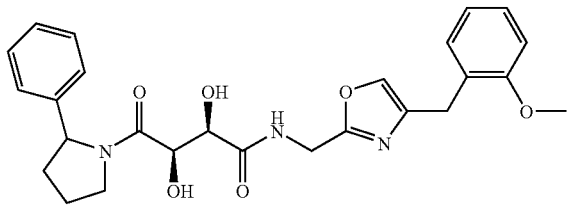
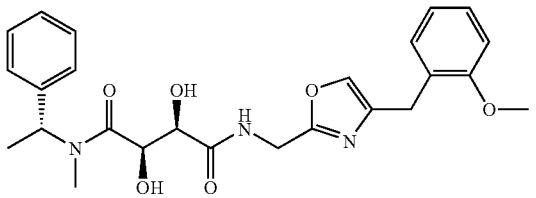
1464
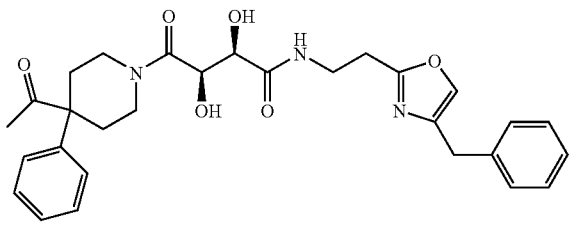
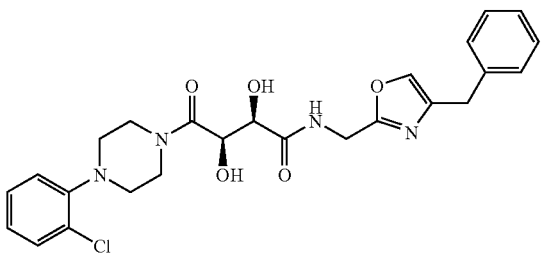
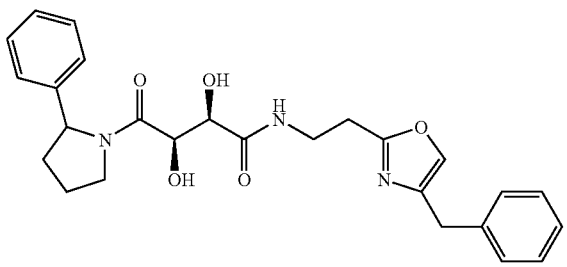
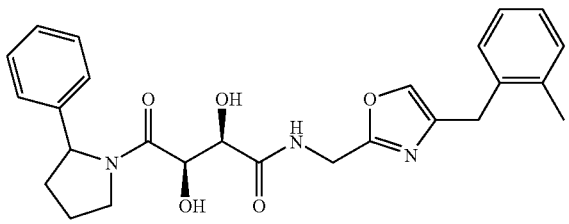
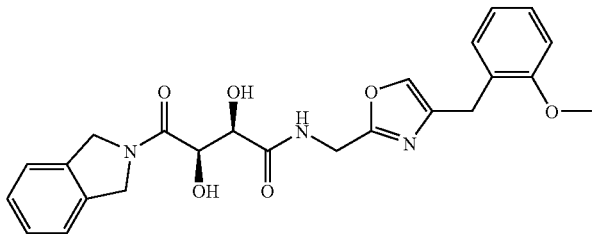
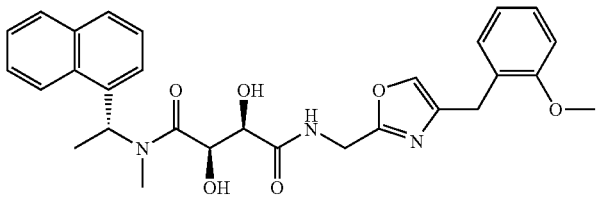

1465
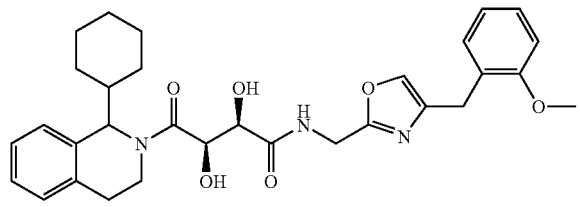
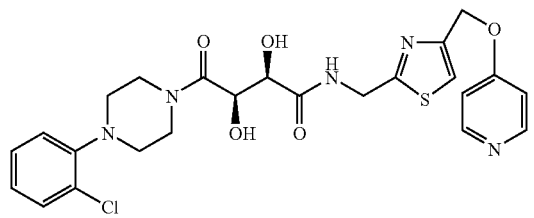
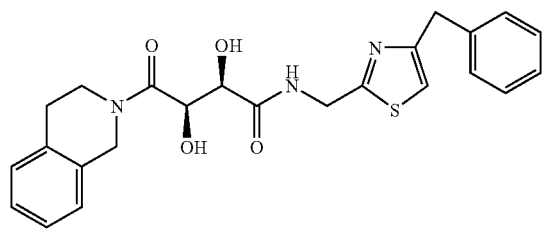
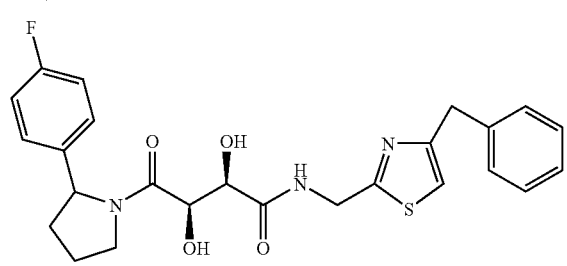
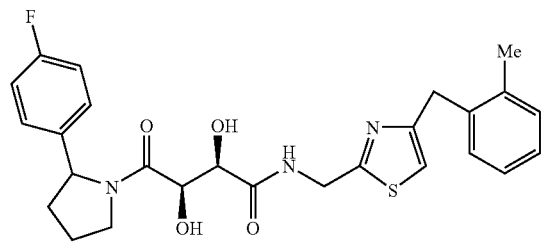
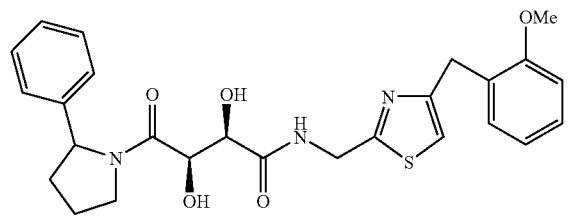
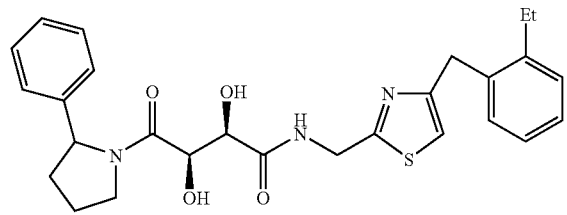
1466
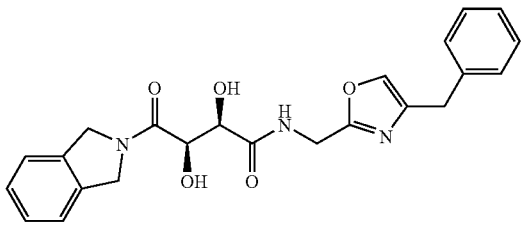
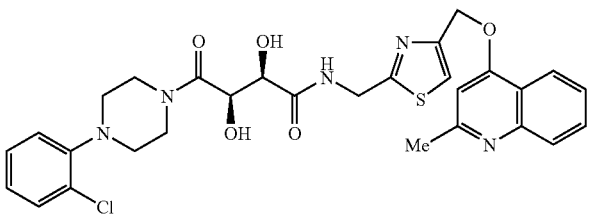
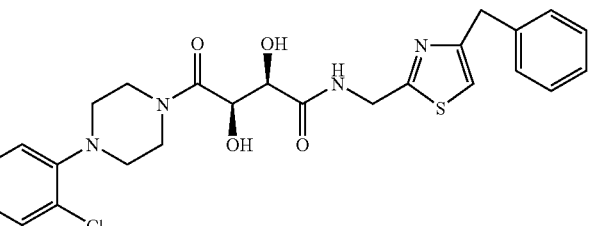
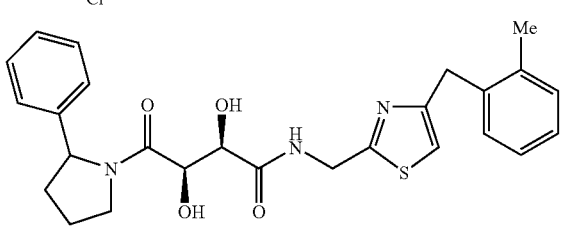
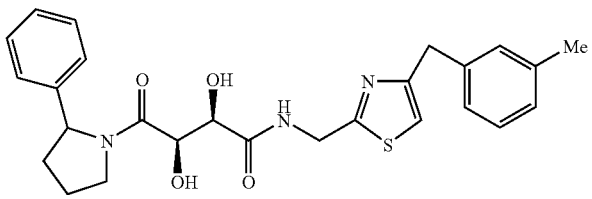
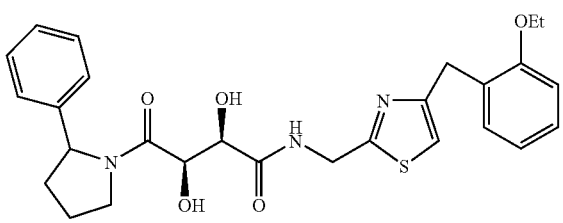
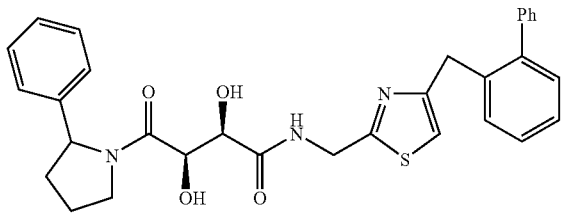

-continued
| 1467 | 1468 |
|---|---|
| 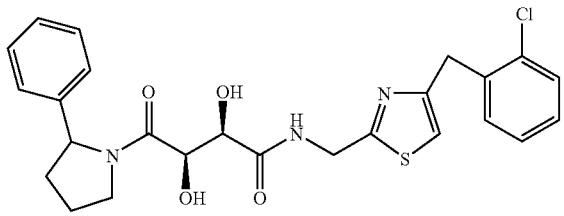 | 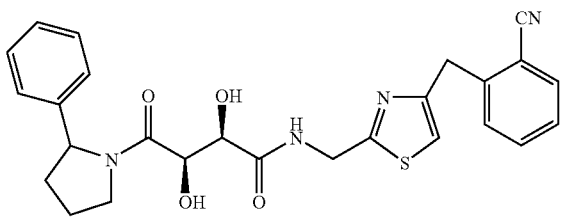 |
| 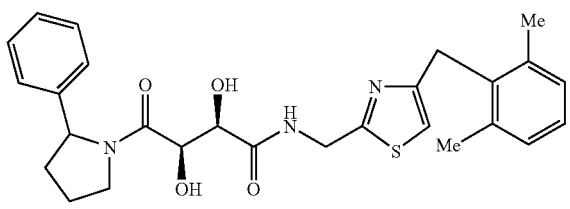 | 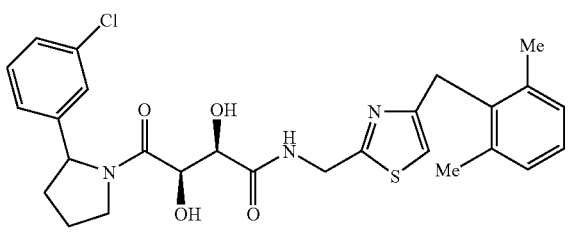 |
| 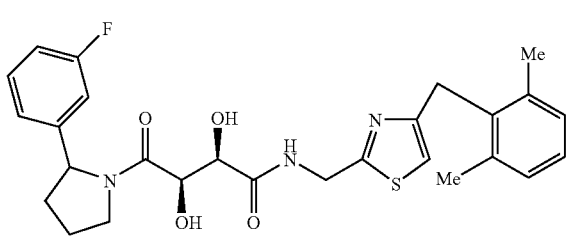 | 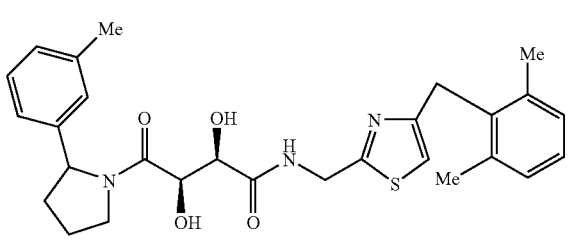 |
| 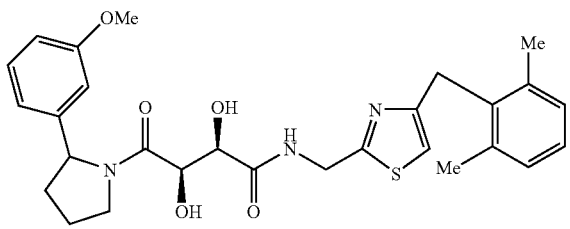 | 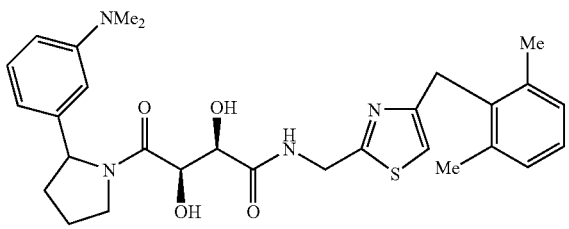 |
| 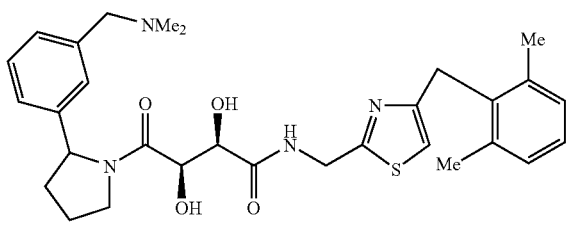 | 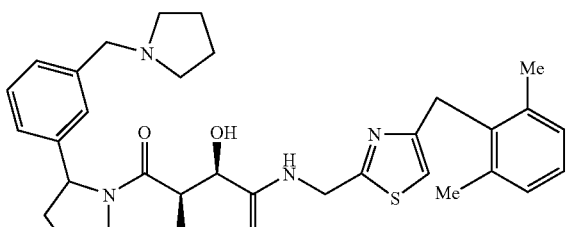 |
| 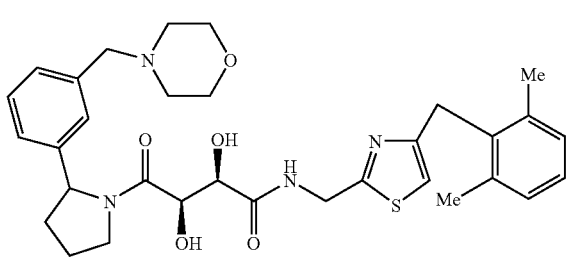 | 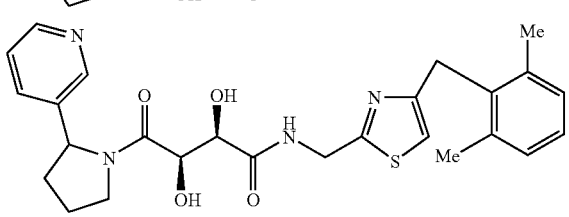 |
| 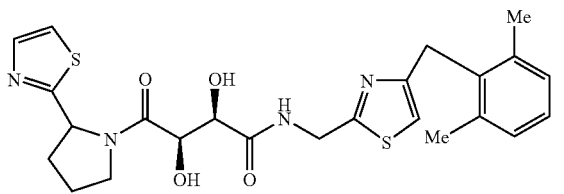 | 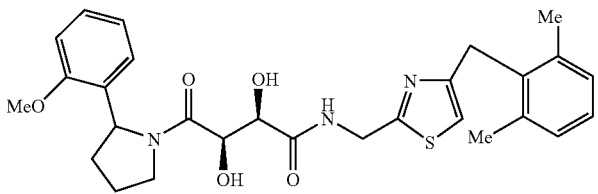 |

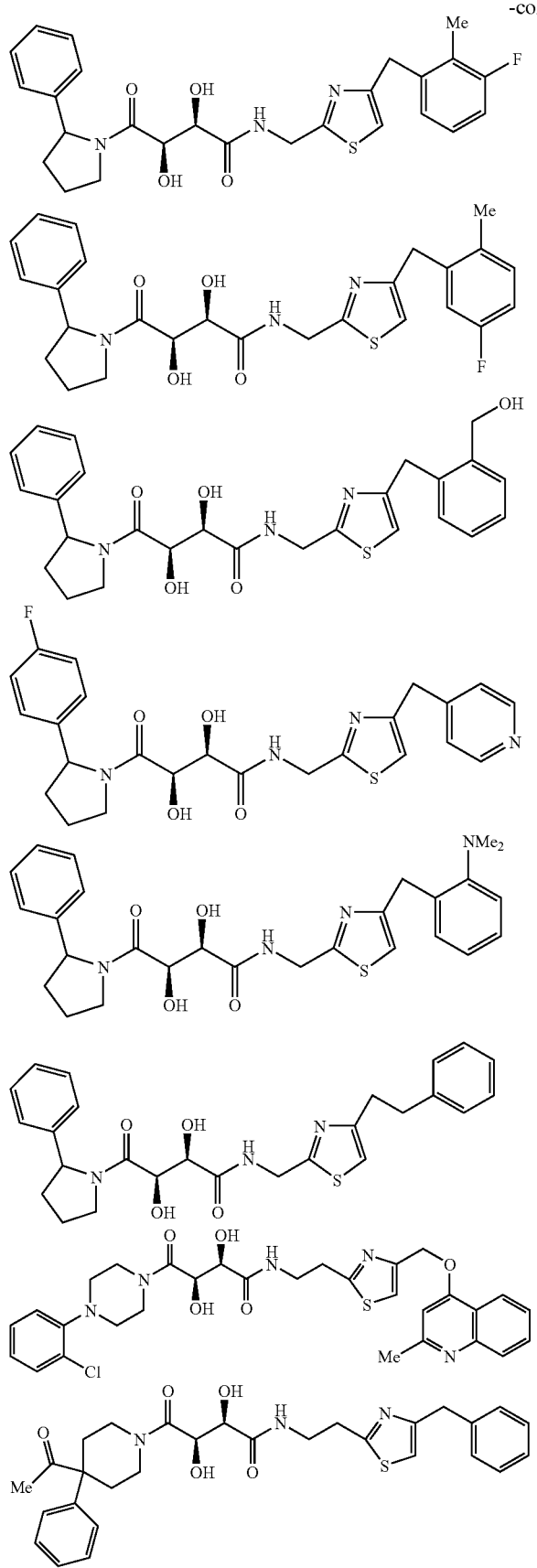

1471 1472
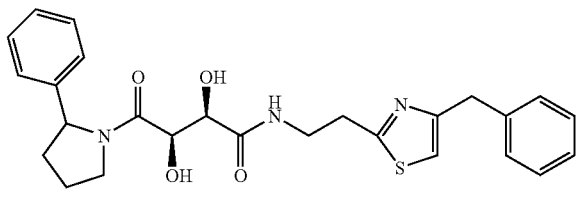
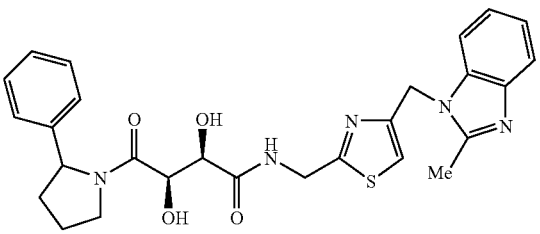
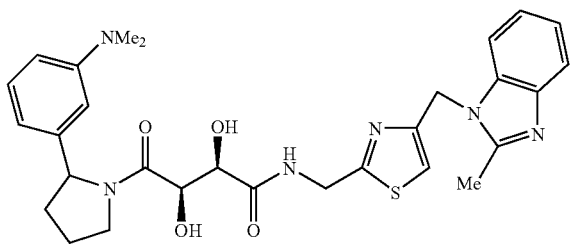
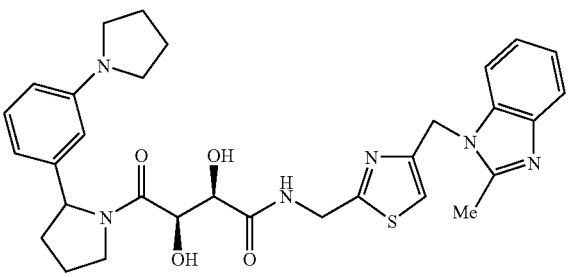
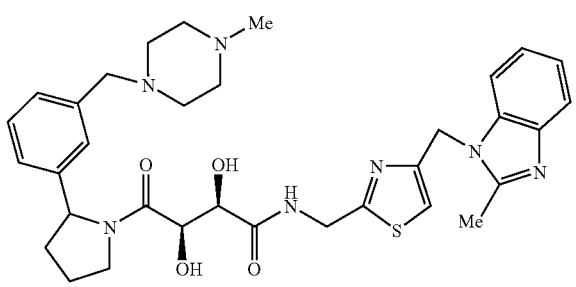
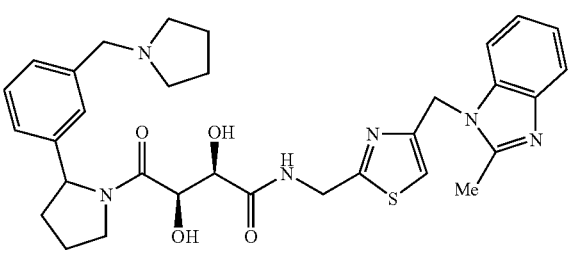
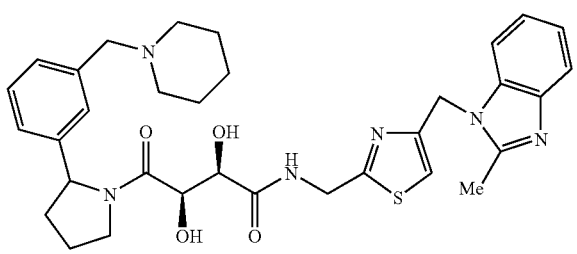
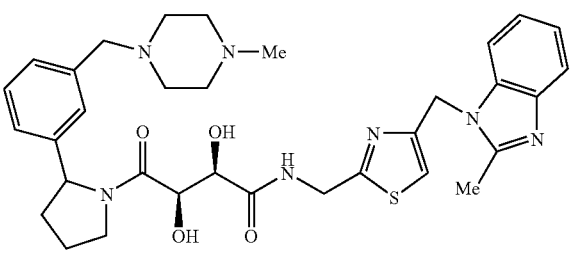
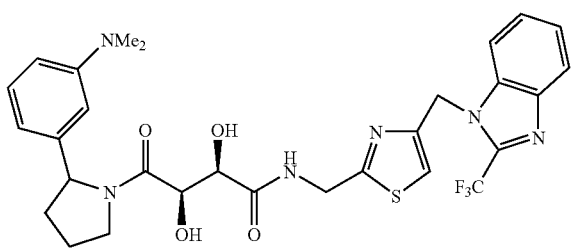
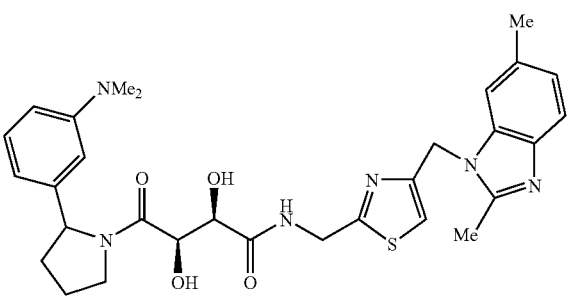
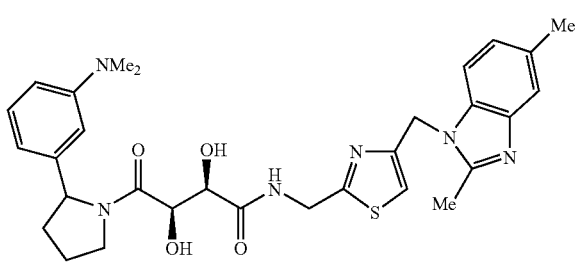
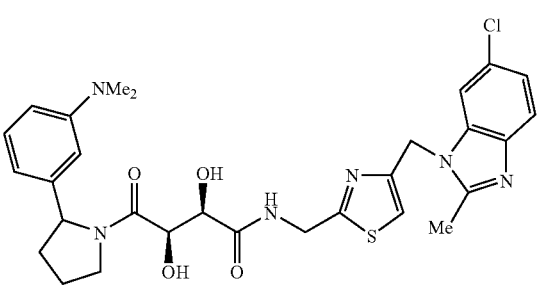

-continued
| 1473 | 1474 |
|---|---|
| 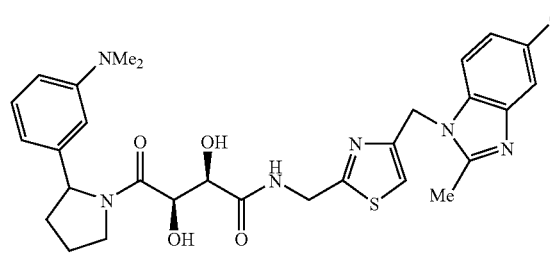 | 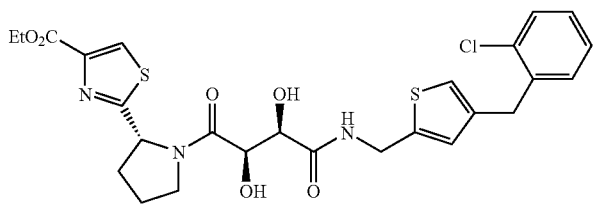 |
| 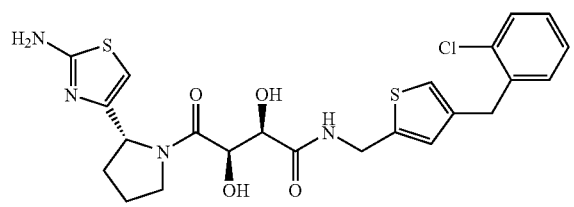 | 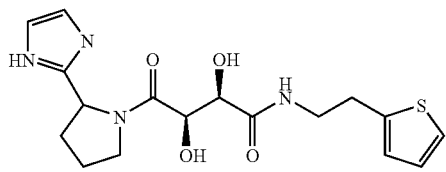 |
| 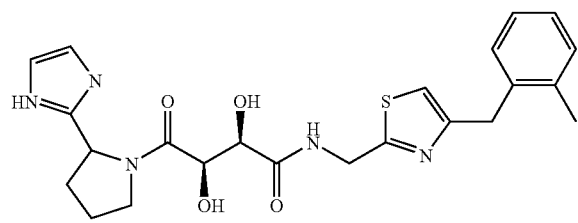 | 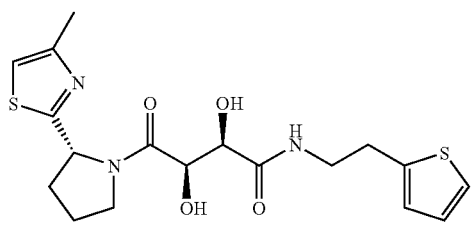 |
| 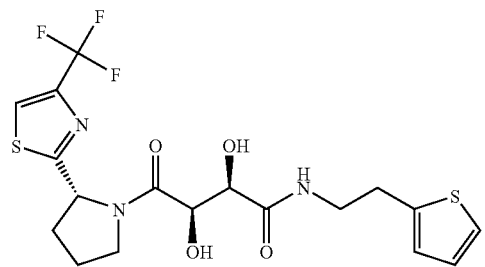 | 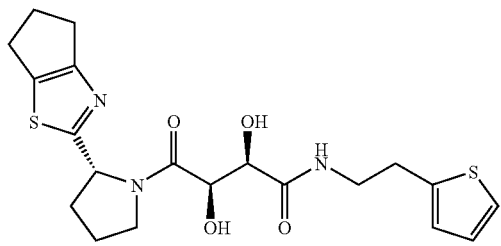 |
| 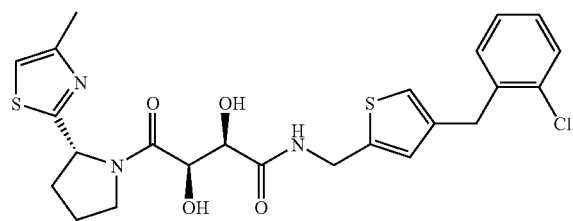 | 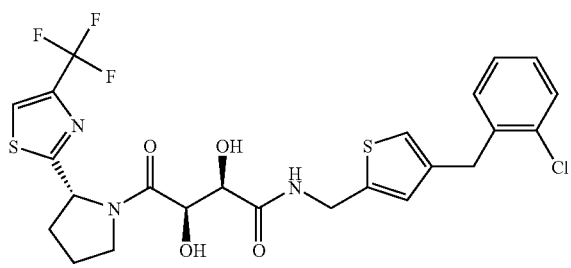 |
| 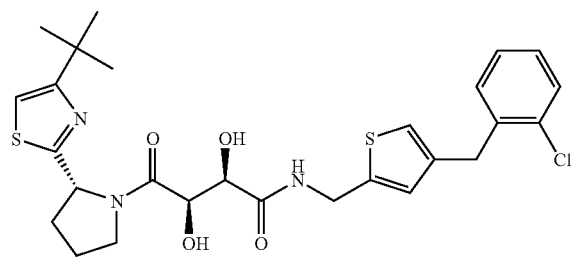 | 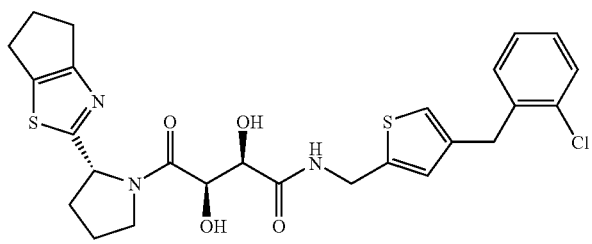 |

-continued
1475
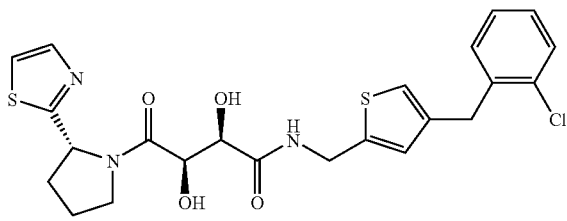
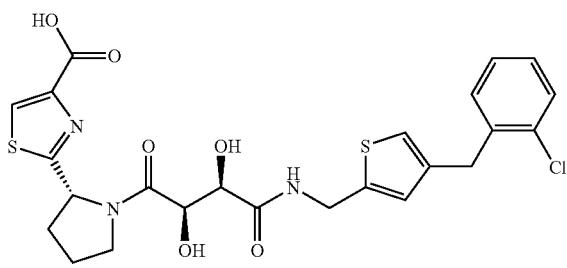
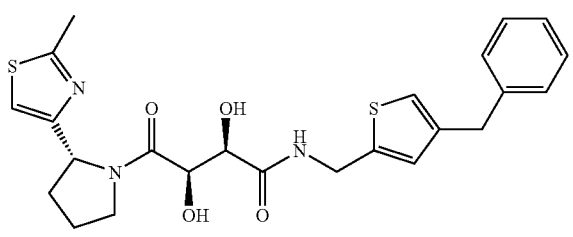
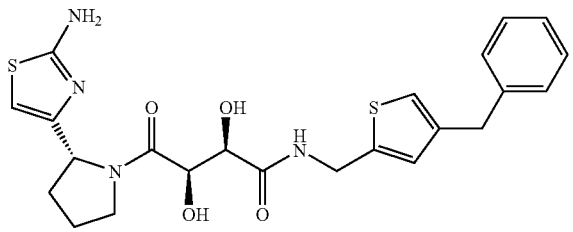
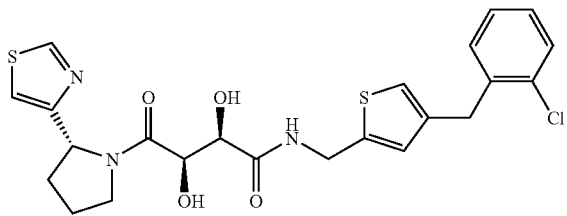
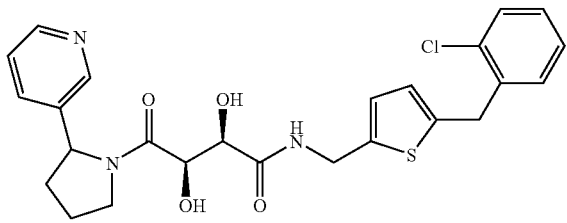
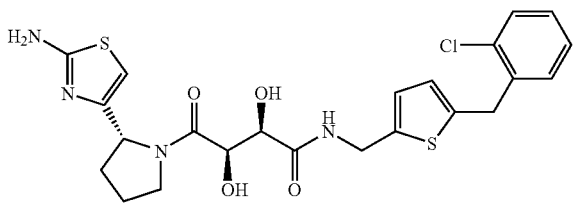
1476
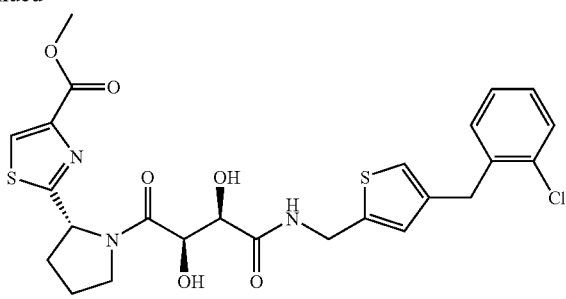
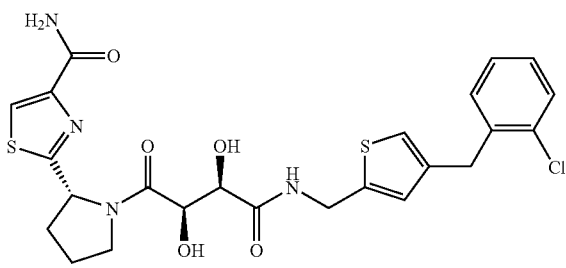
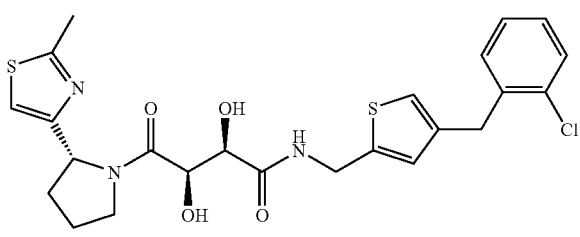
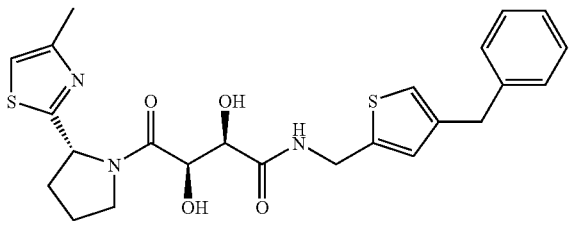
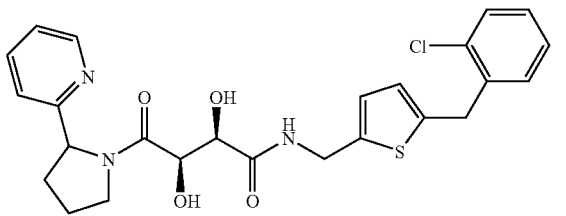
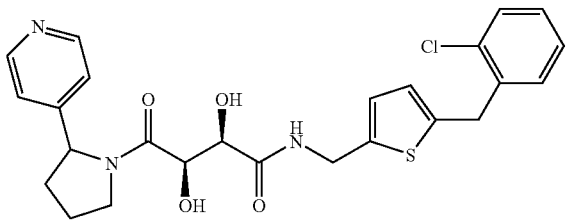
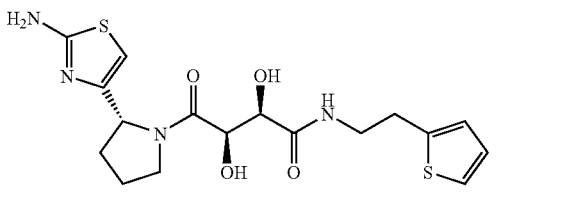

1477
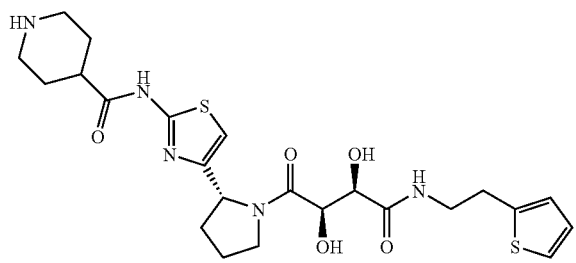
1478
-continued
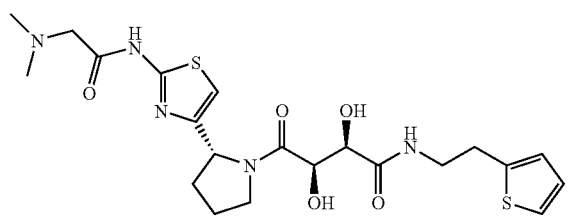
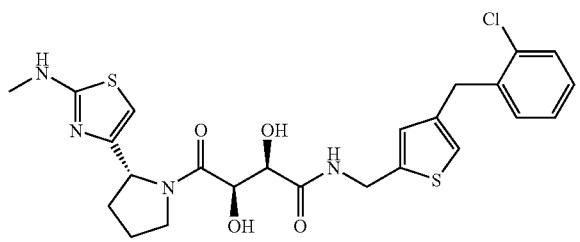
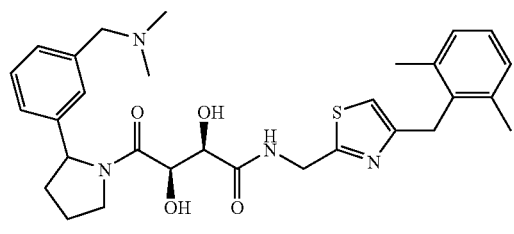
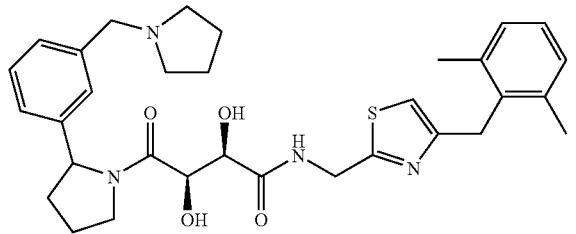
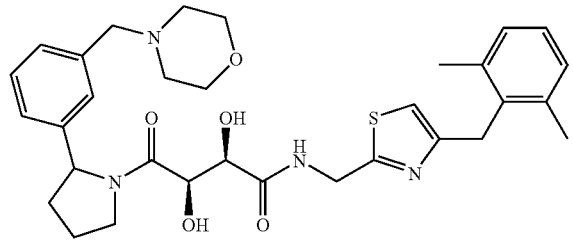
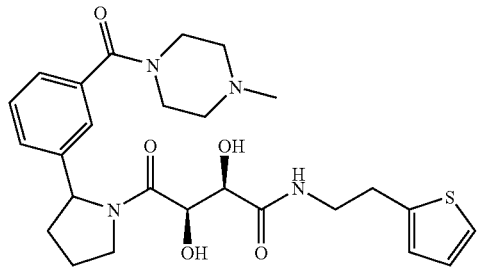
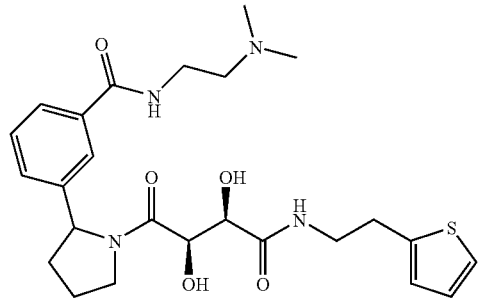
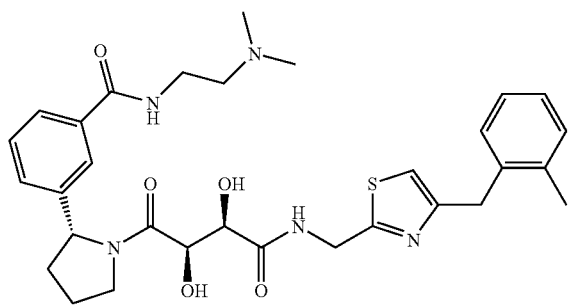
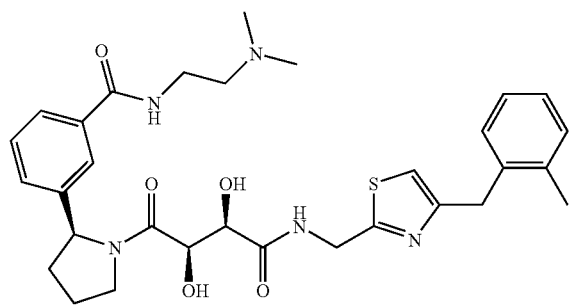
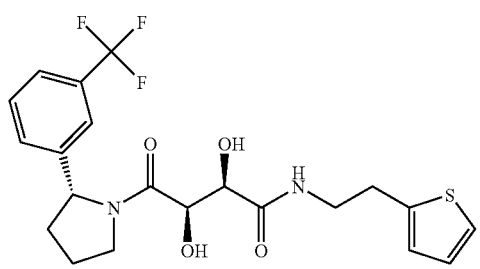
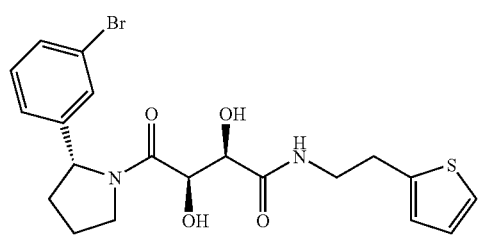

1479 1480
-continued
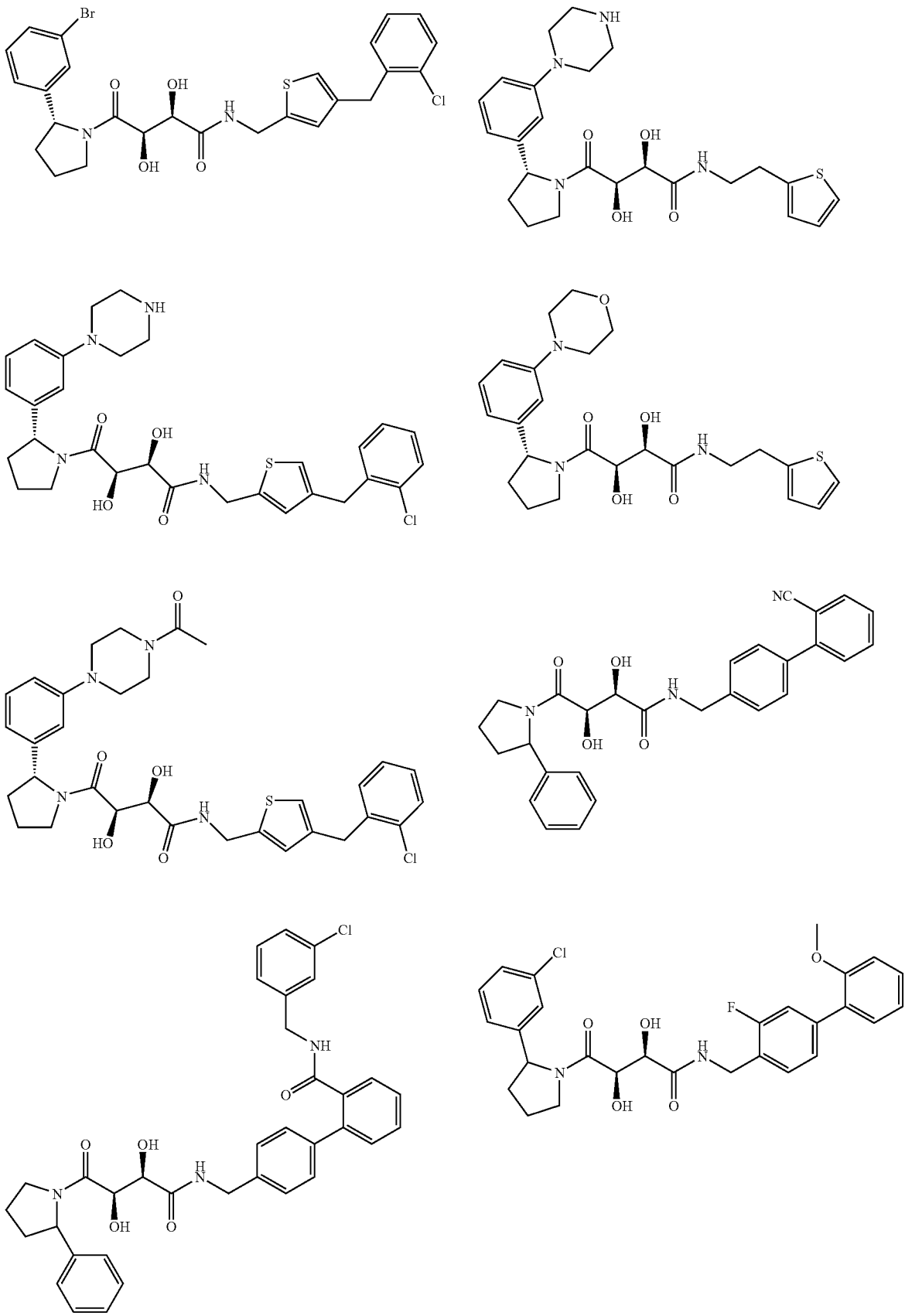

-continued
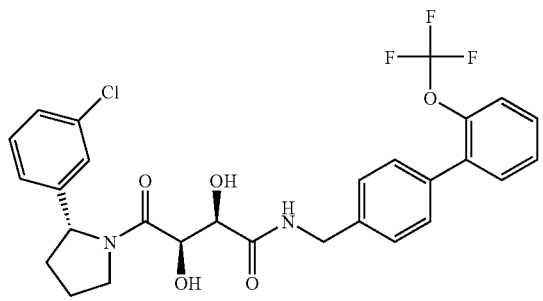
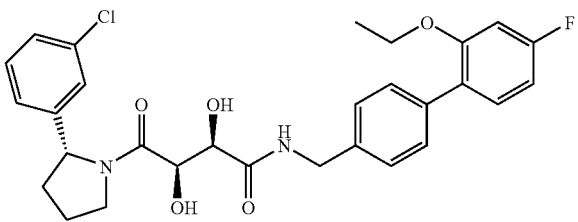
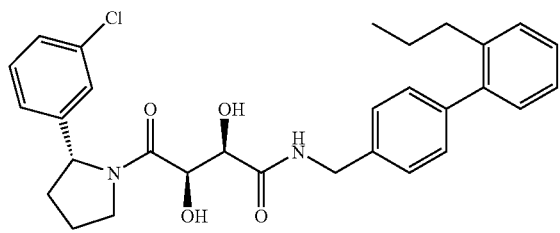
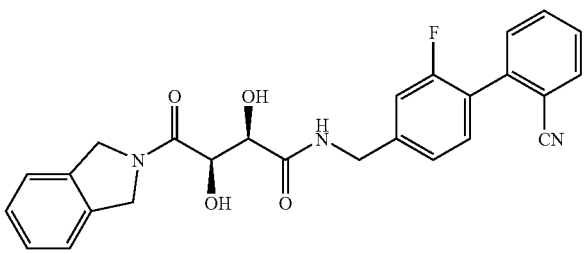
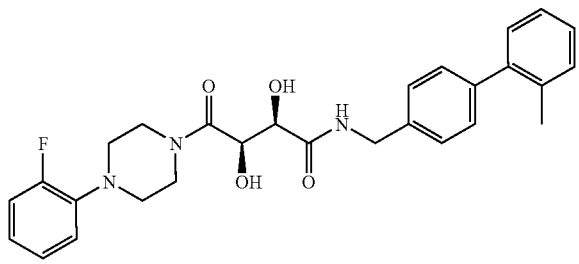
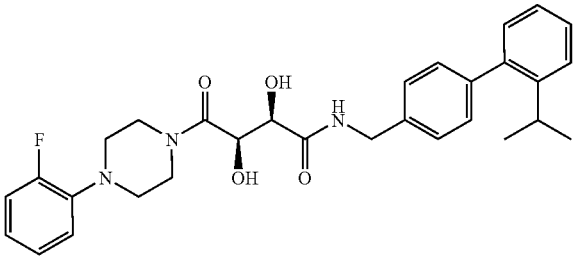
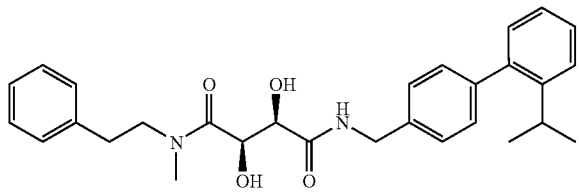
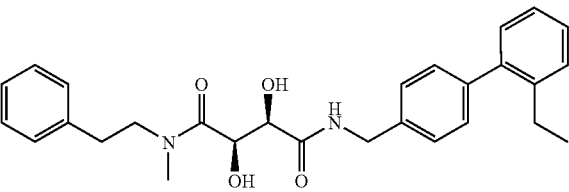
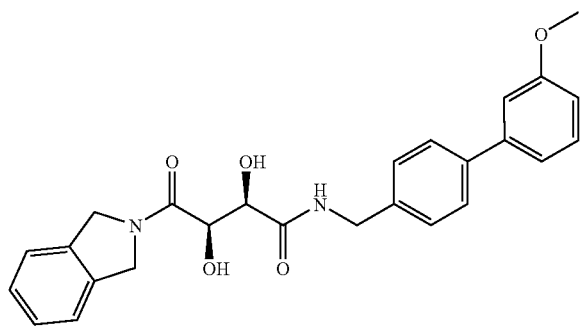
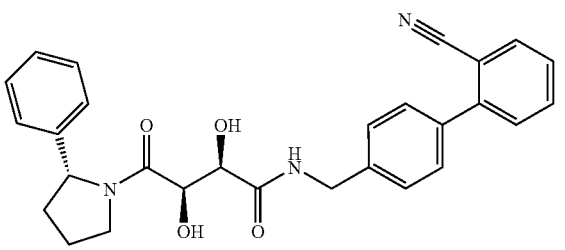
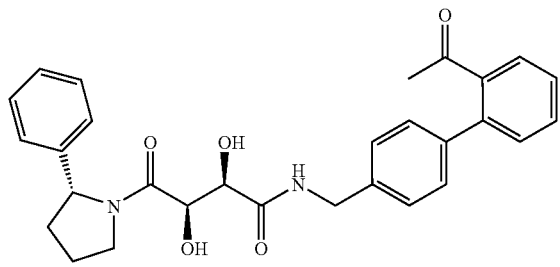
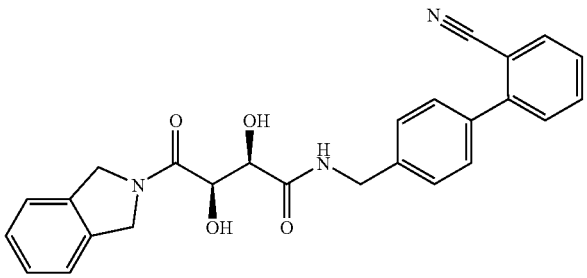

1483
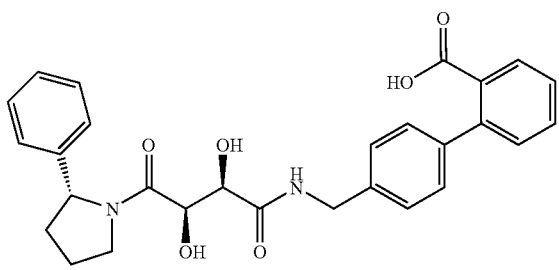
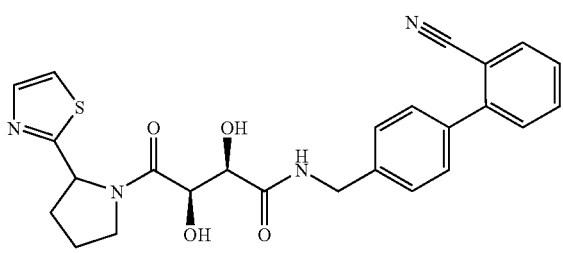
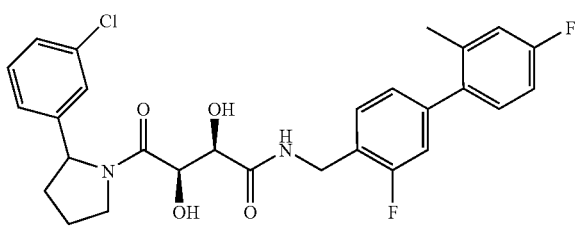
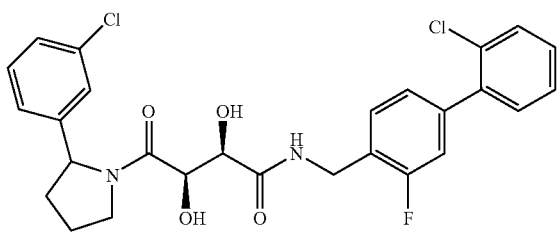
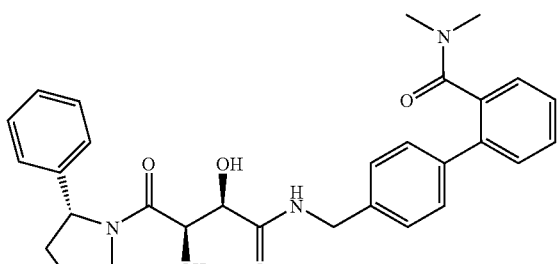
1484
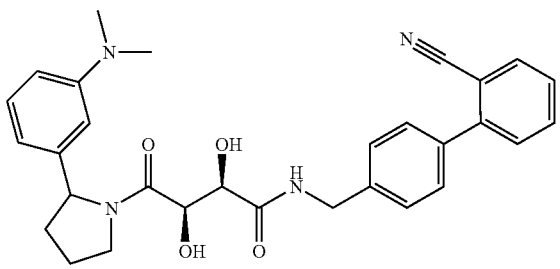
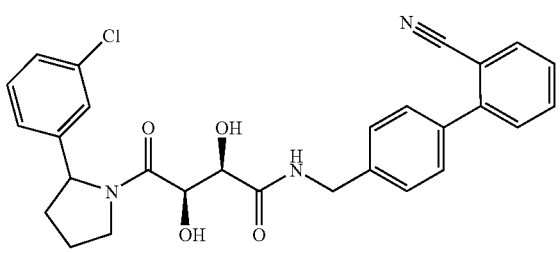
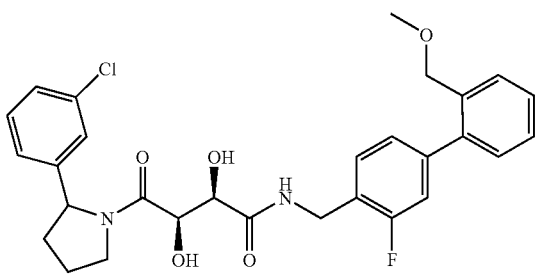
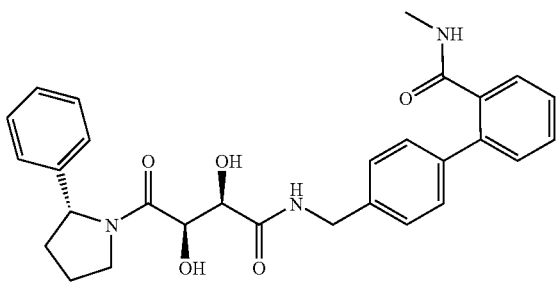
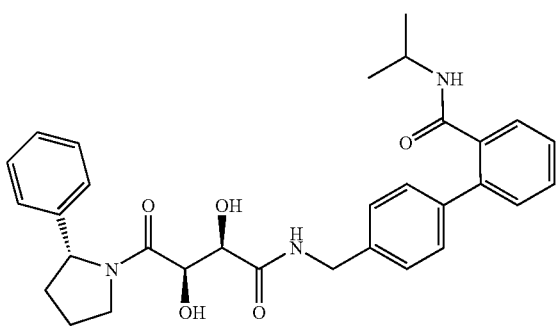

1485
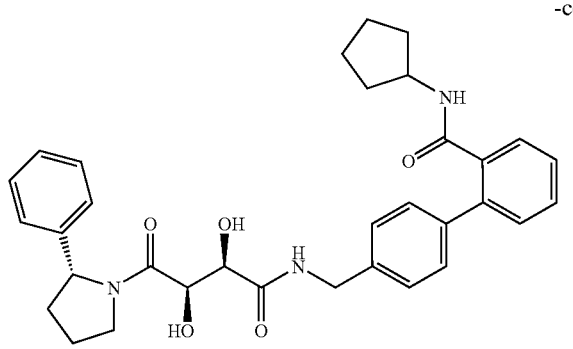
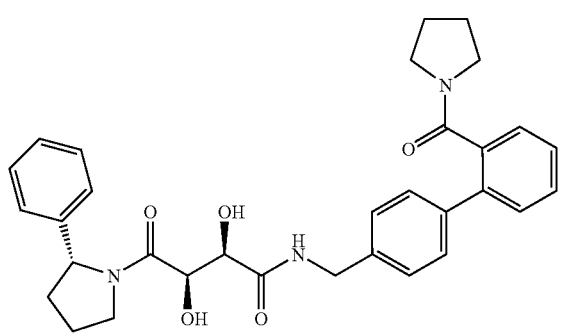
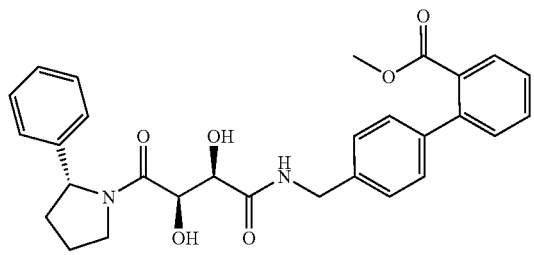
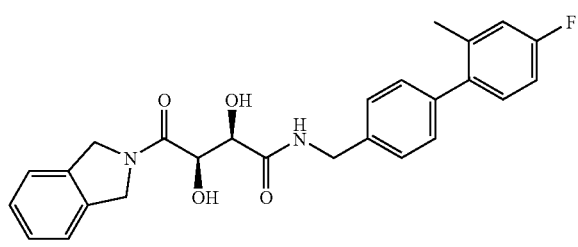
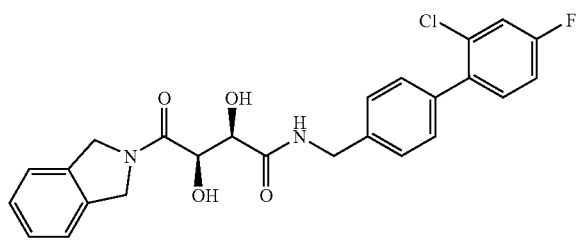
1486
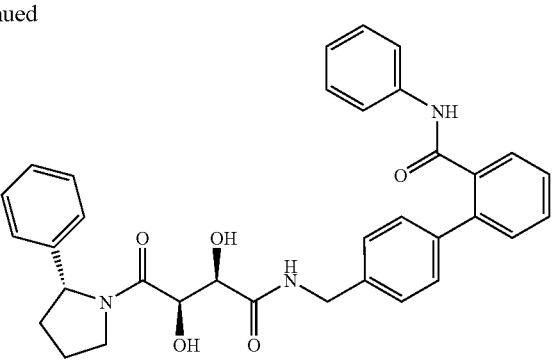
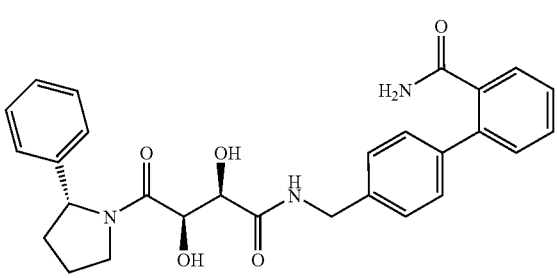
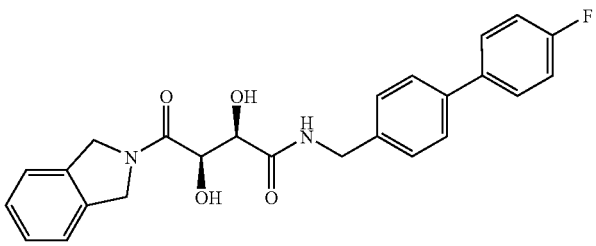
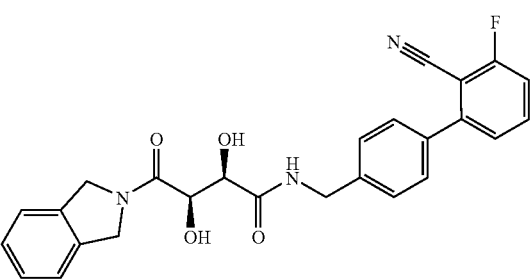
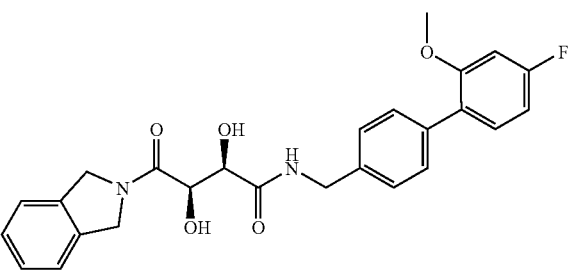

1487                                      1488
-continued
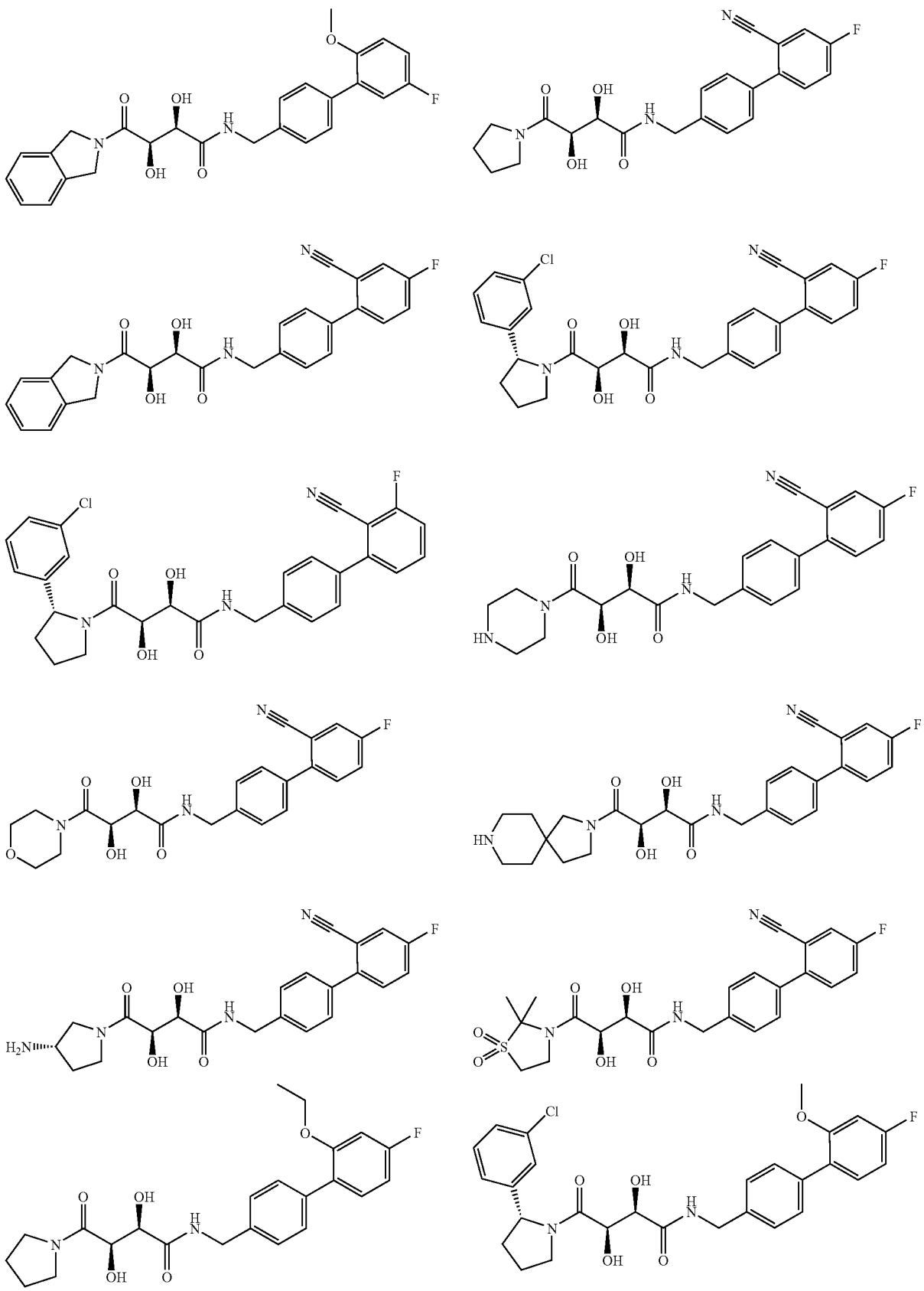

1489
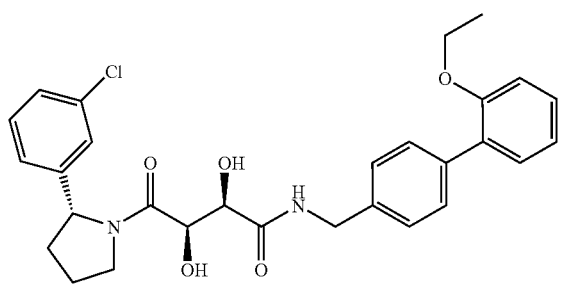
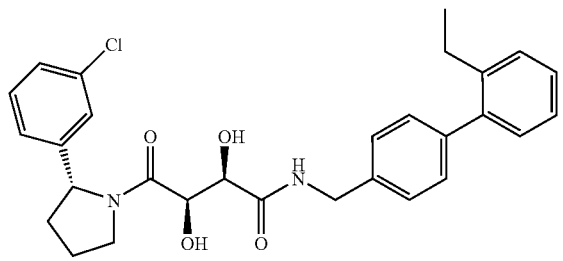
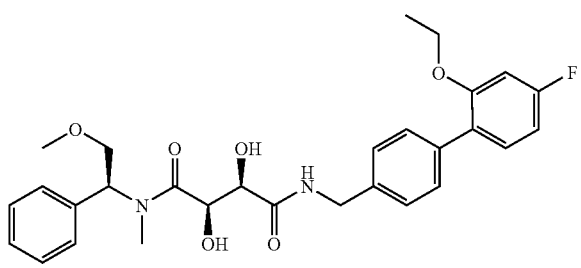
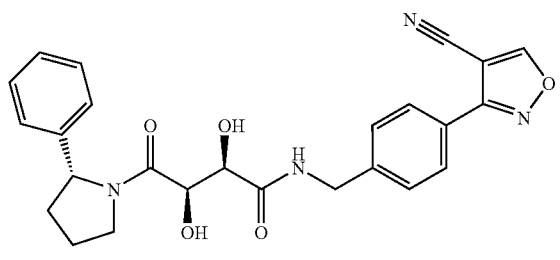
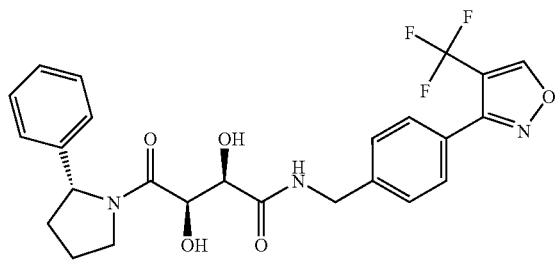
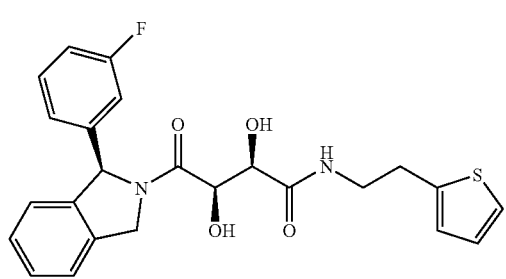
1490
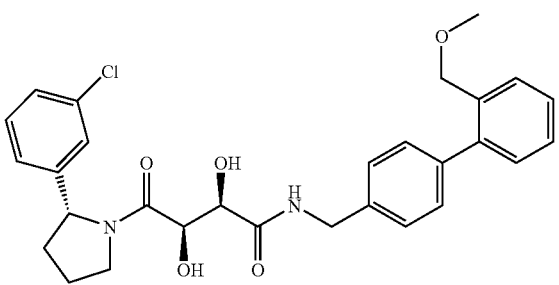
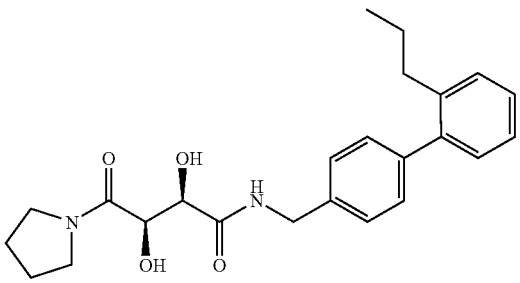
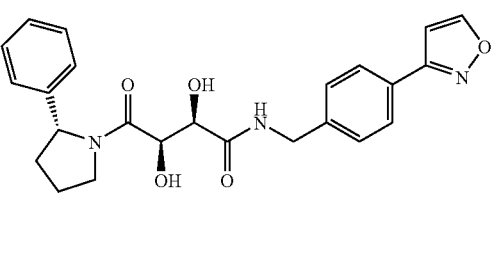
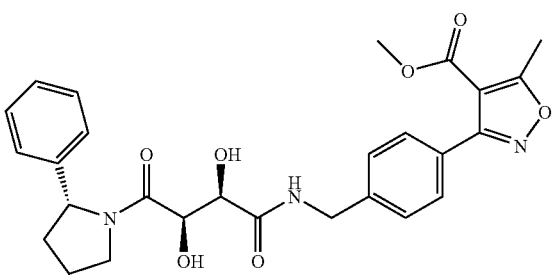
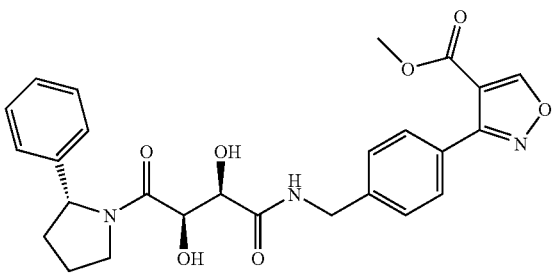
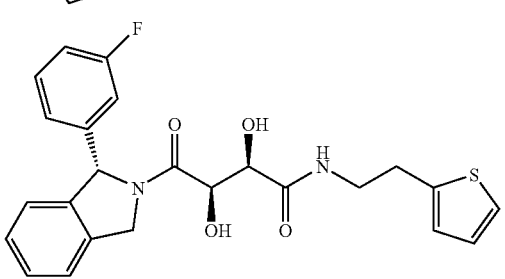

1491 1492
-continued
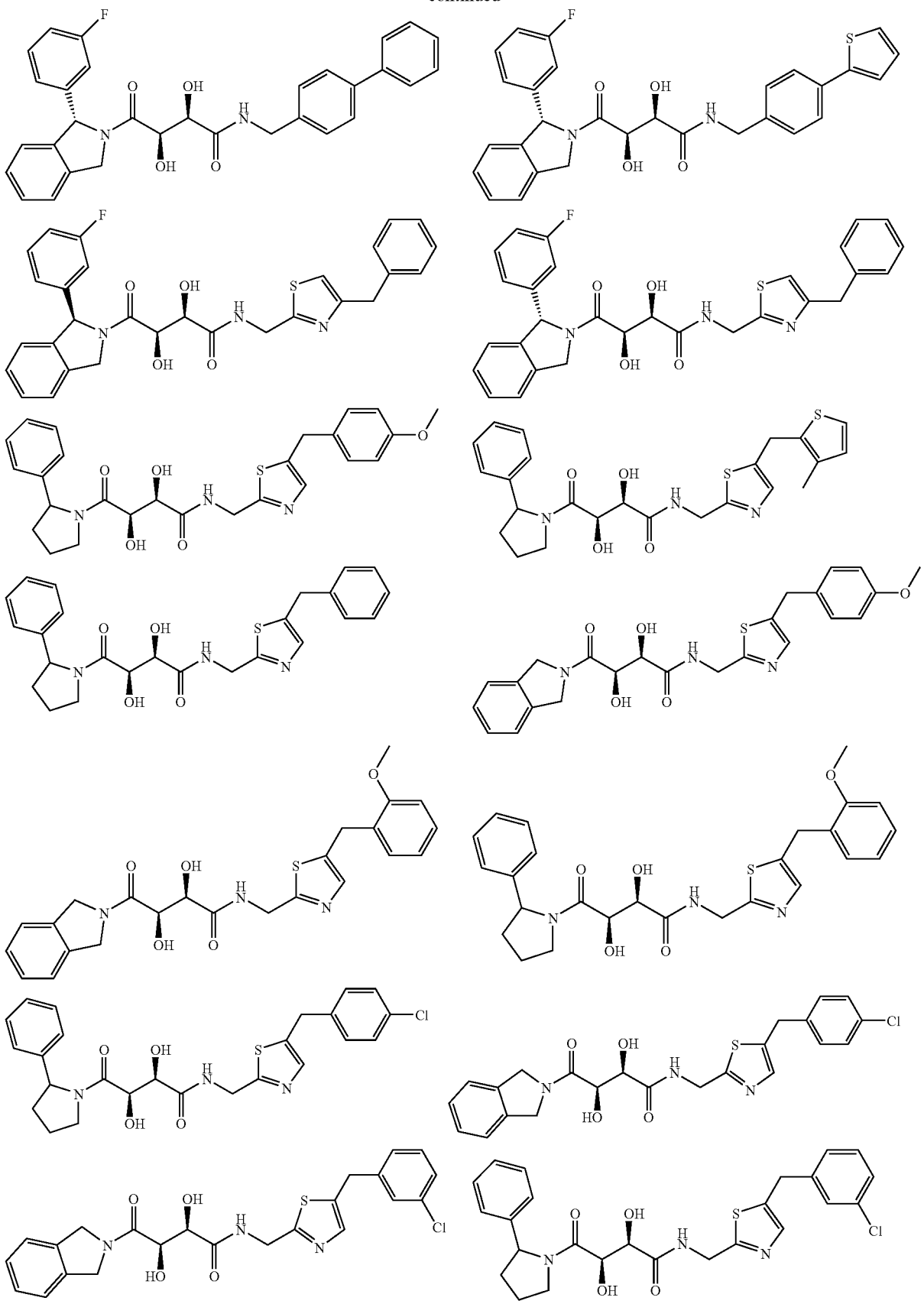

-continued
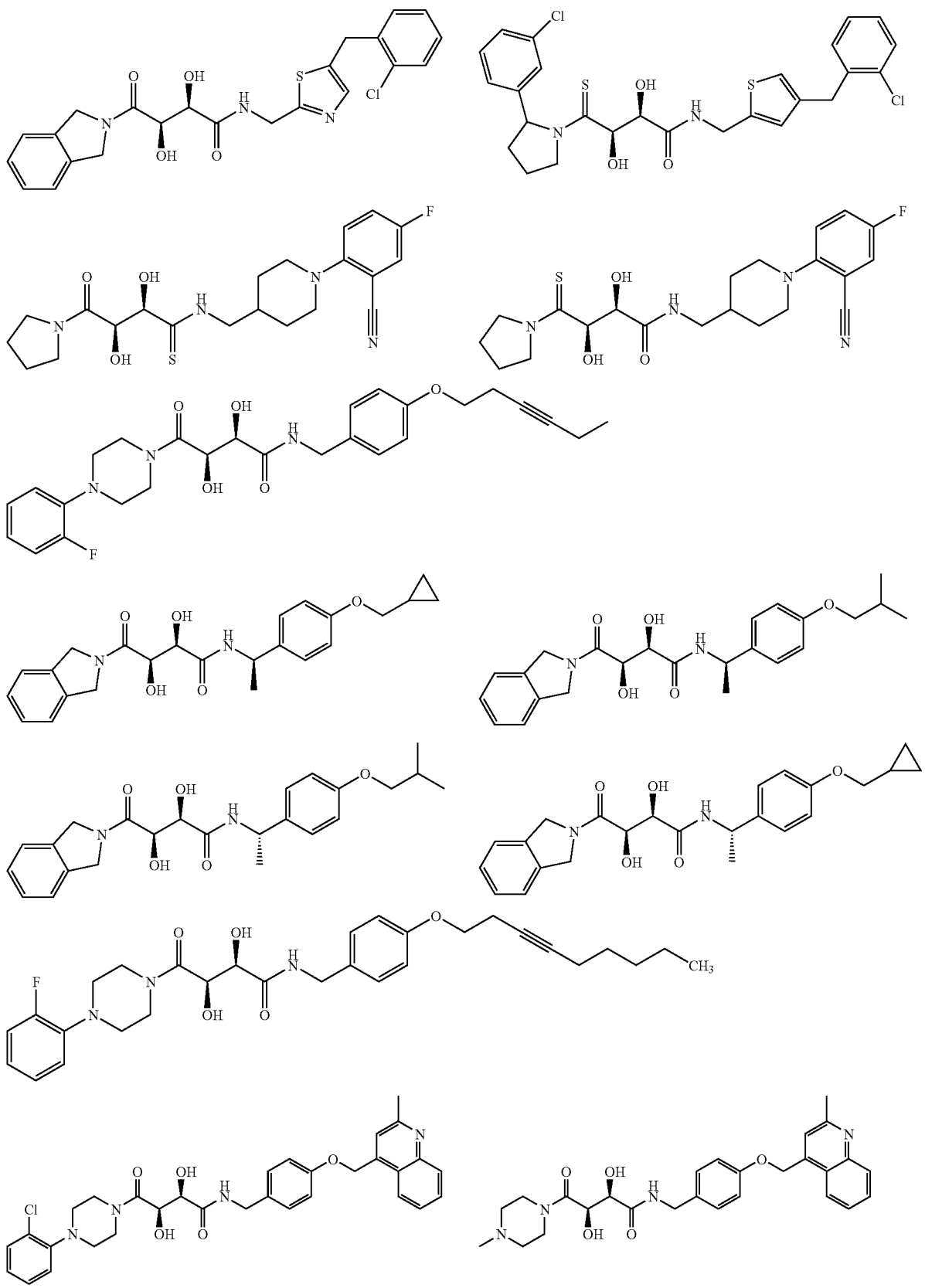

1495
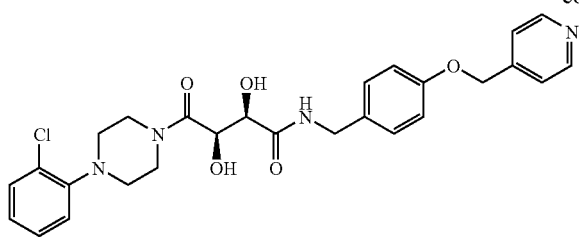
1496
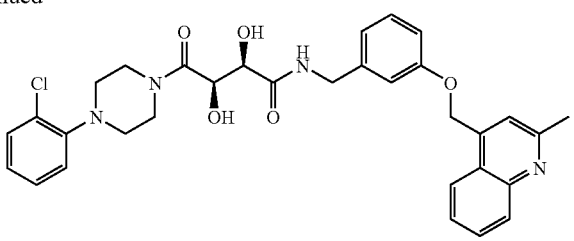
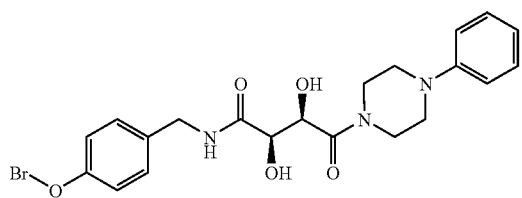
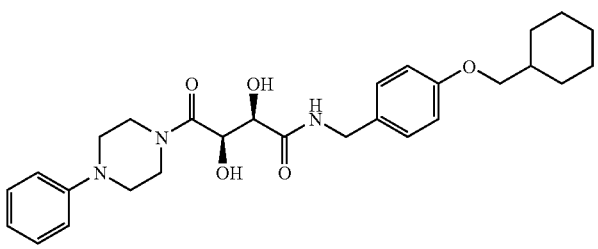
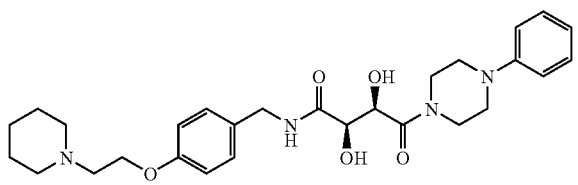
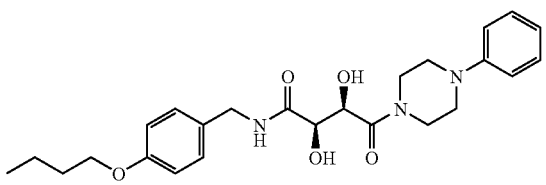
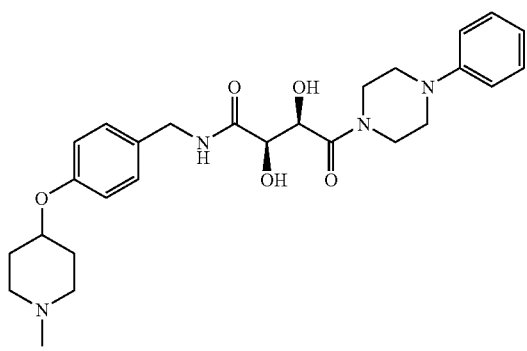
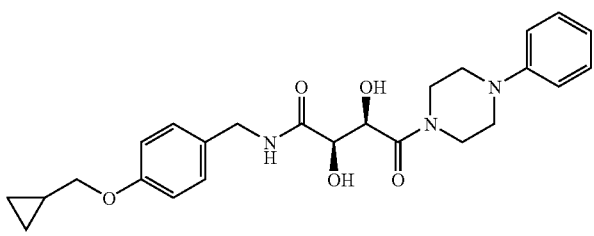
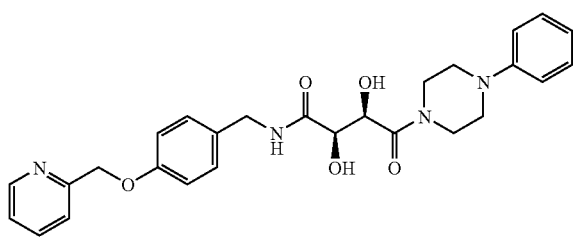
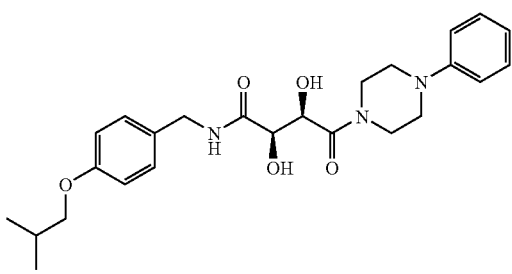
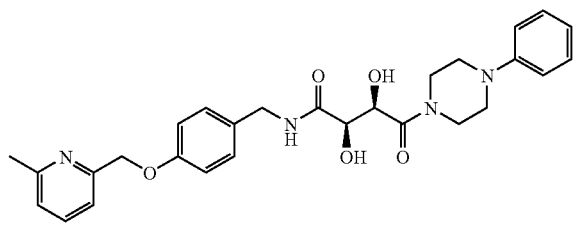
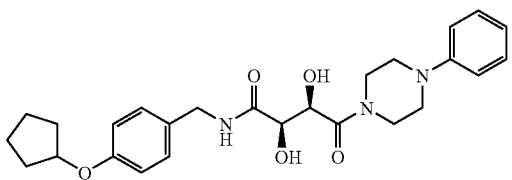

1497 1498
-continued
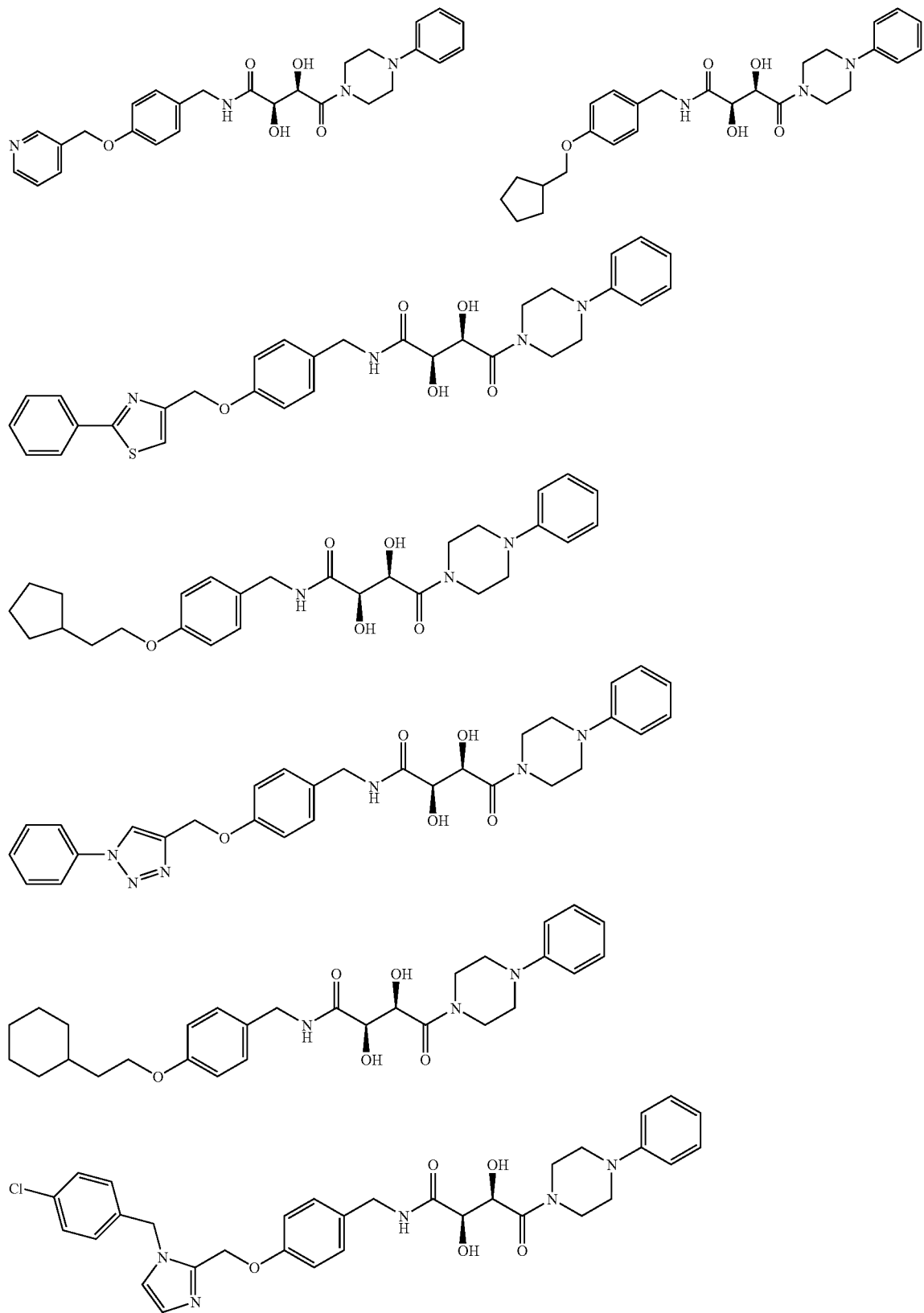

1499            1500
-continued
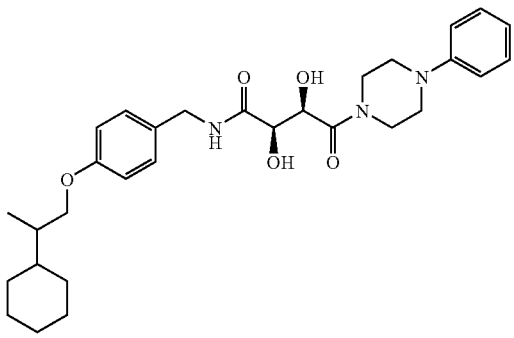
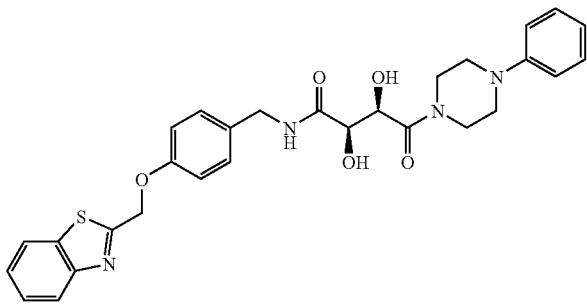
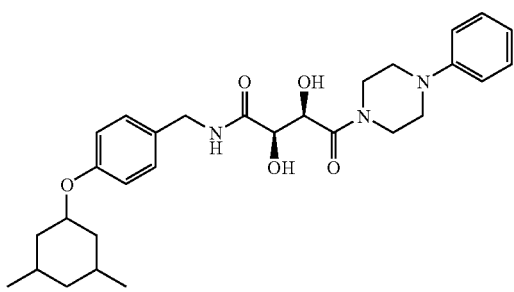
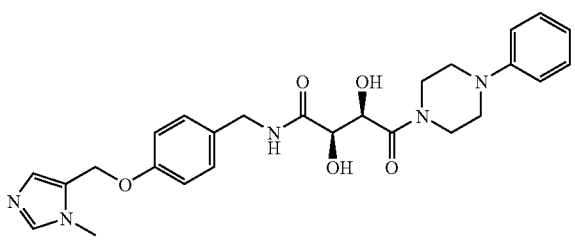
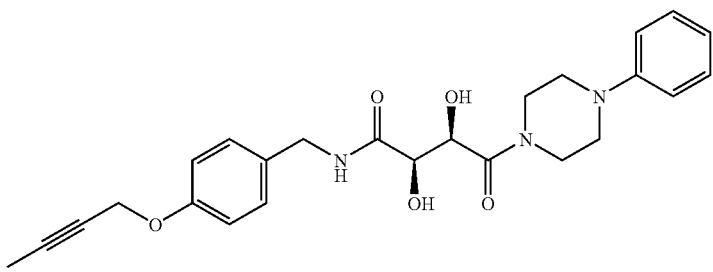
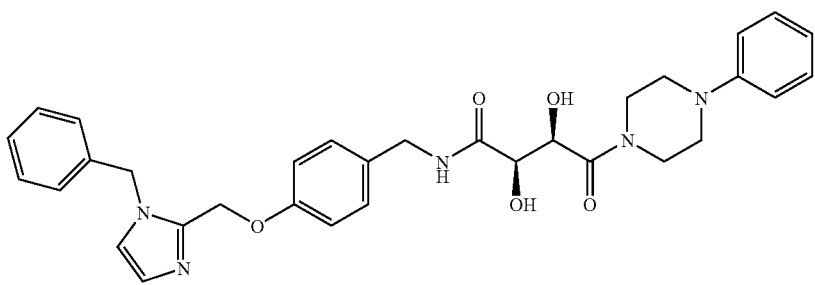
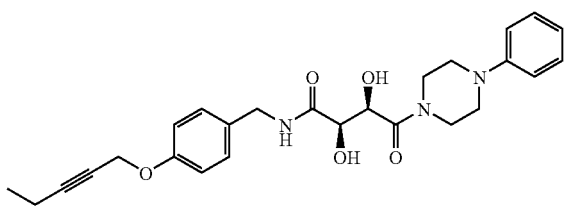
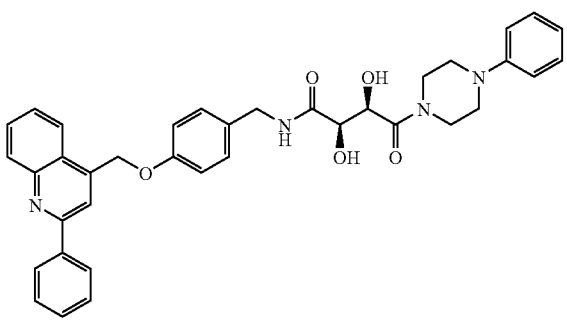
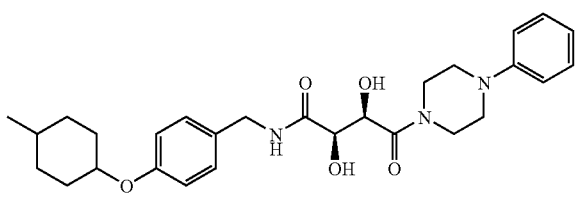
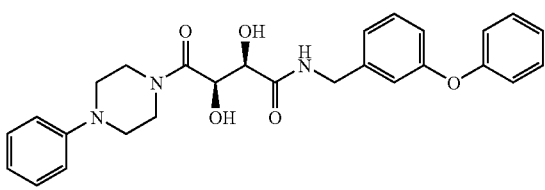

1501
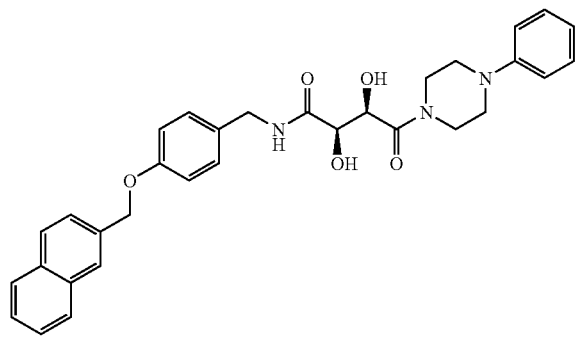
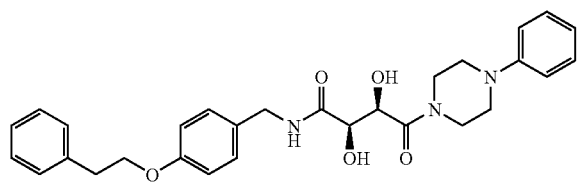
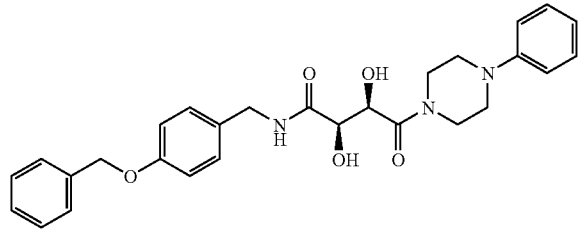
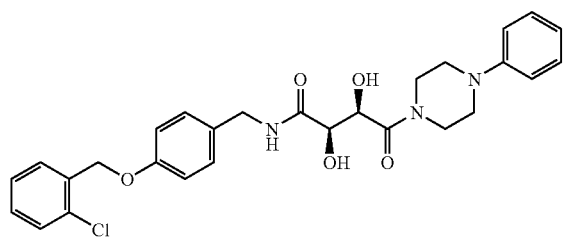
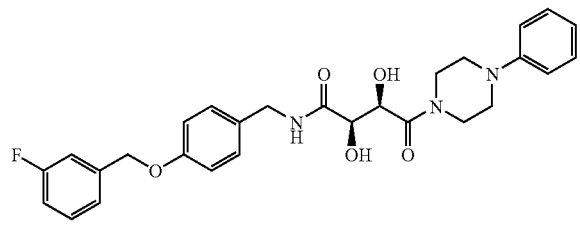
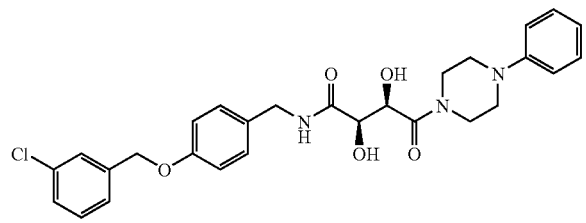
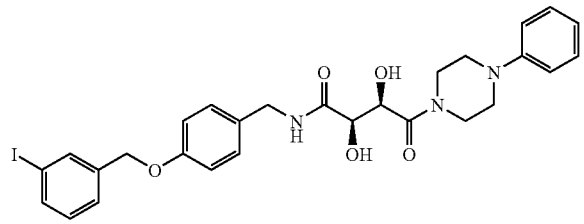
1502
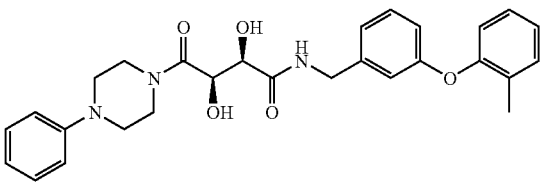
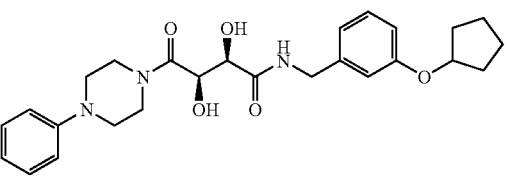
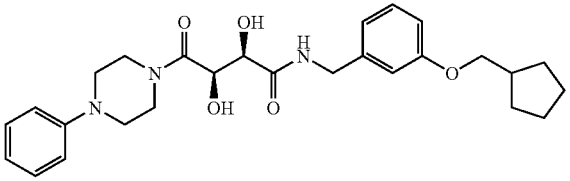
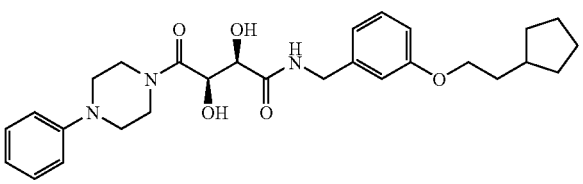
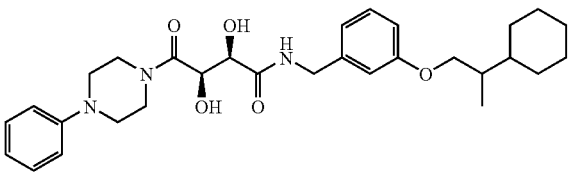
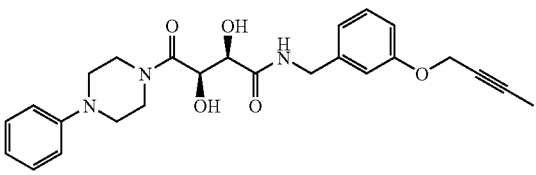
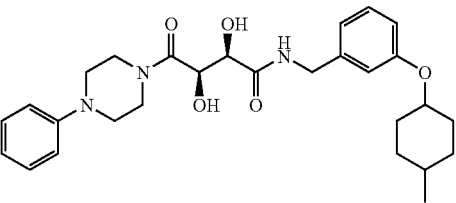

-continued
1503
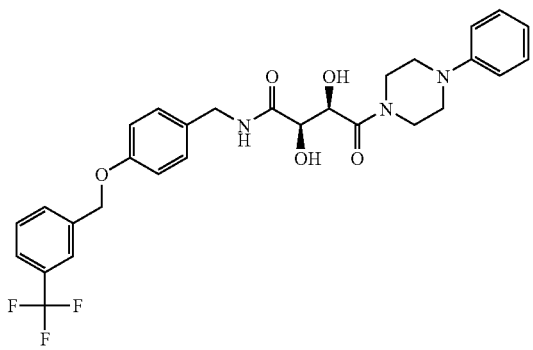
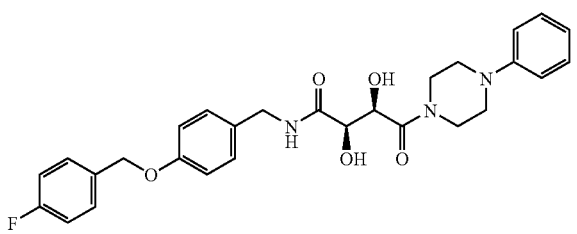
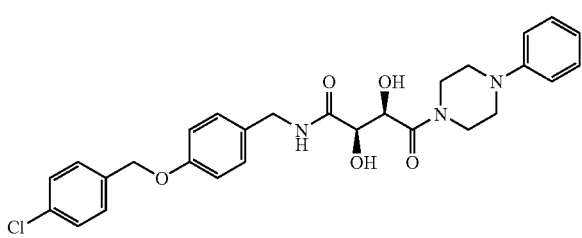
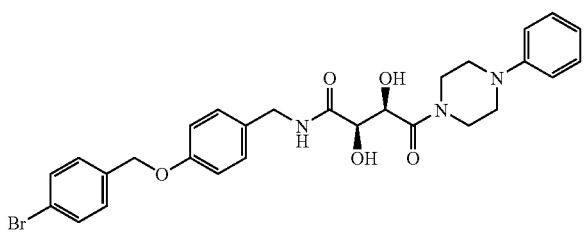
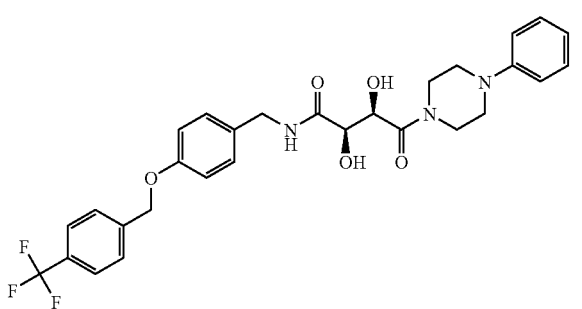
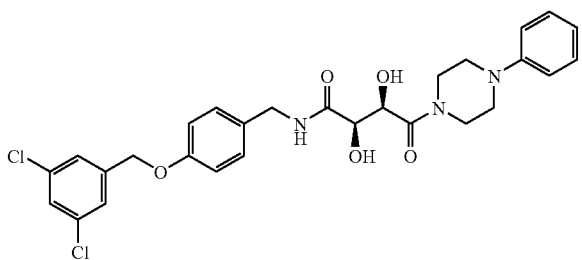
1504
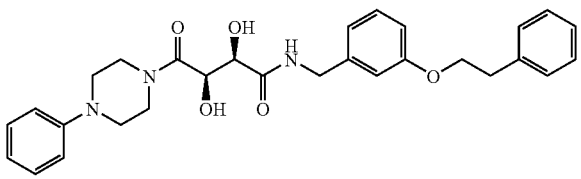
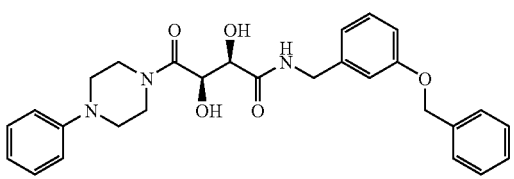
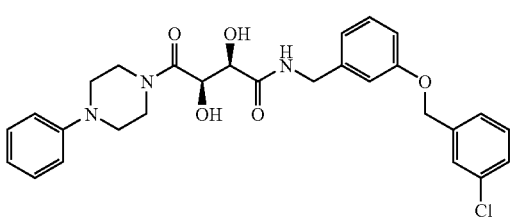
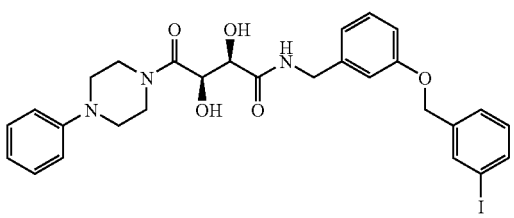
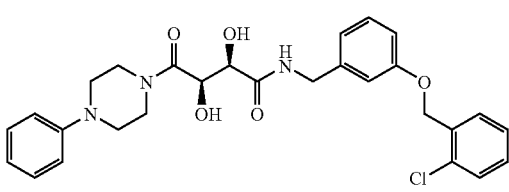
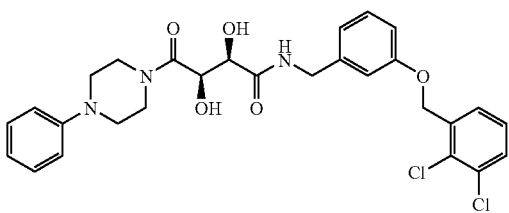

1505 1506
-continued
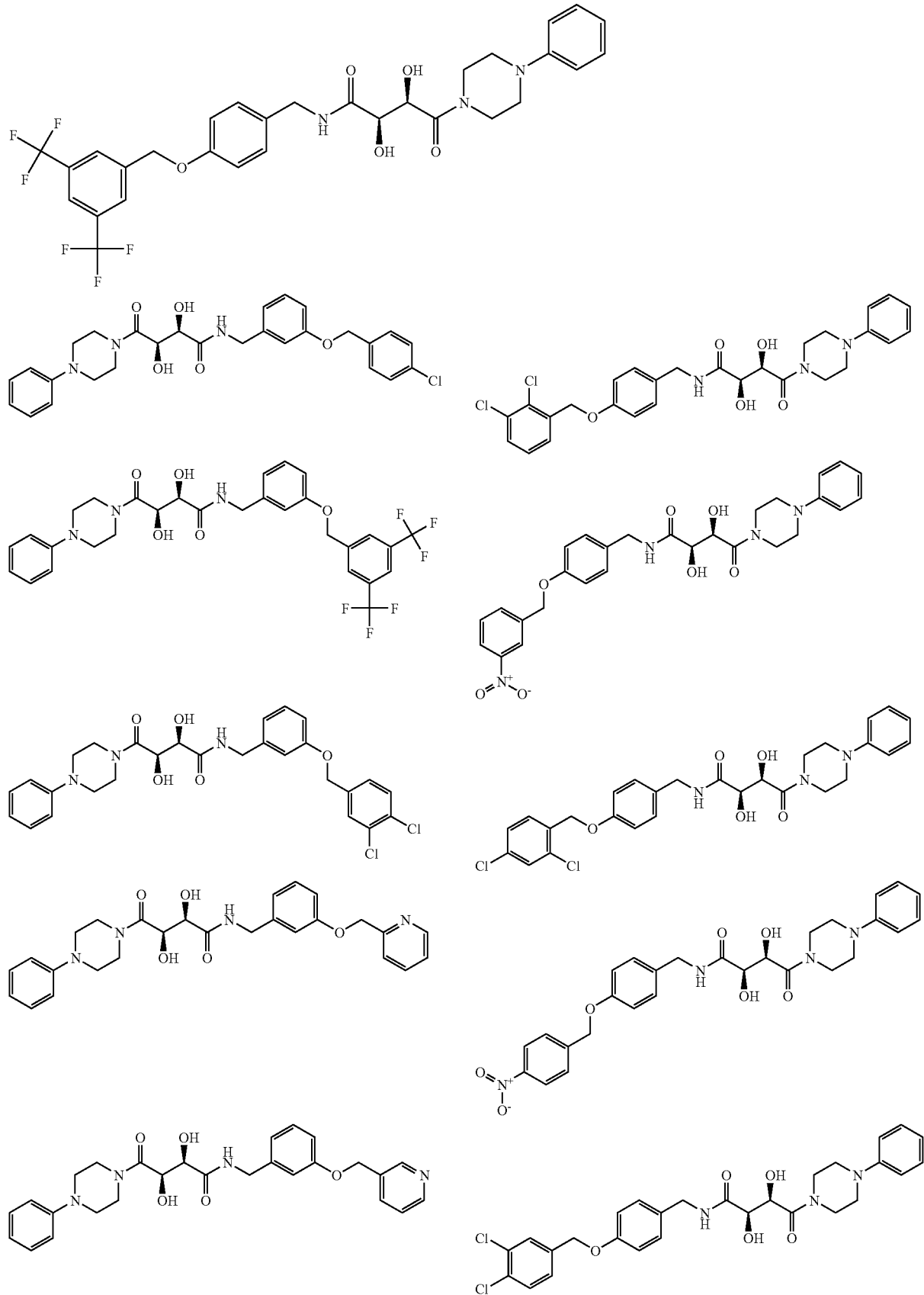

1507 1508
-continued
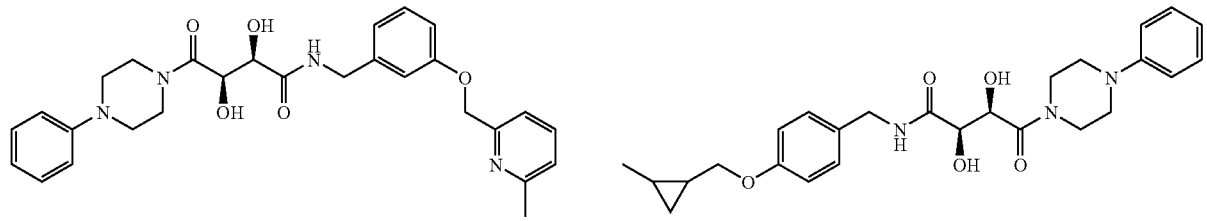
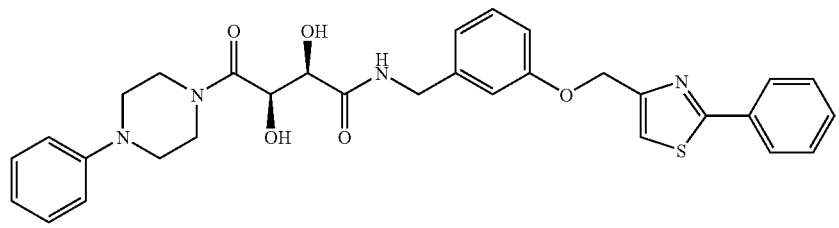
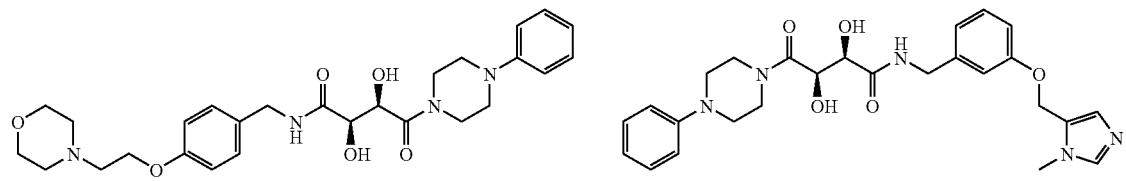
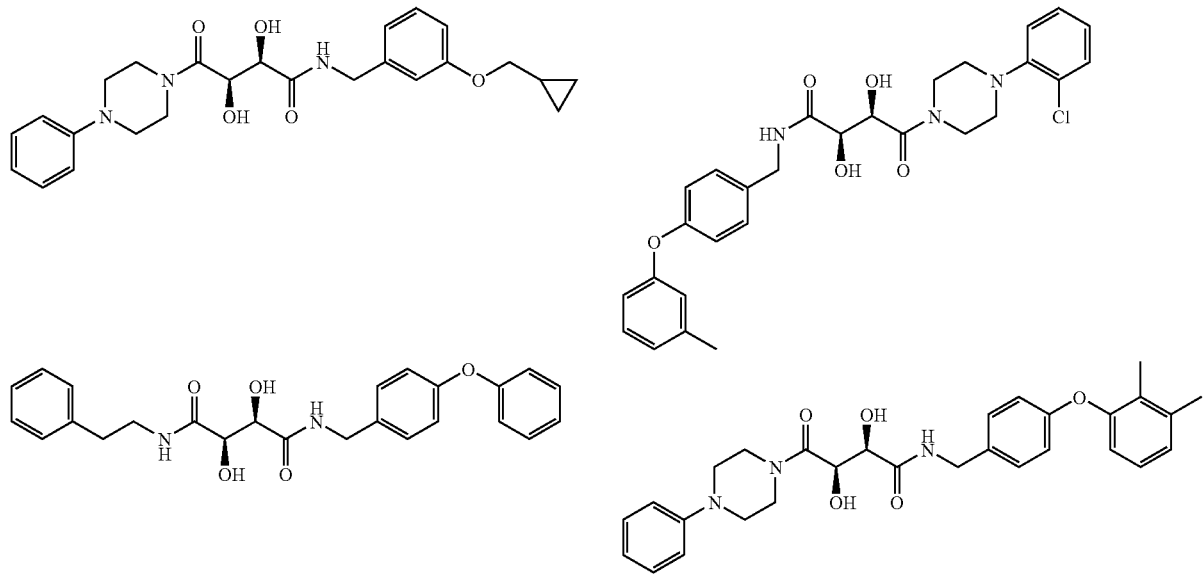
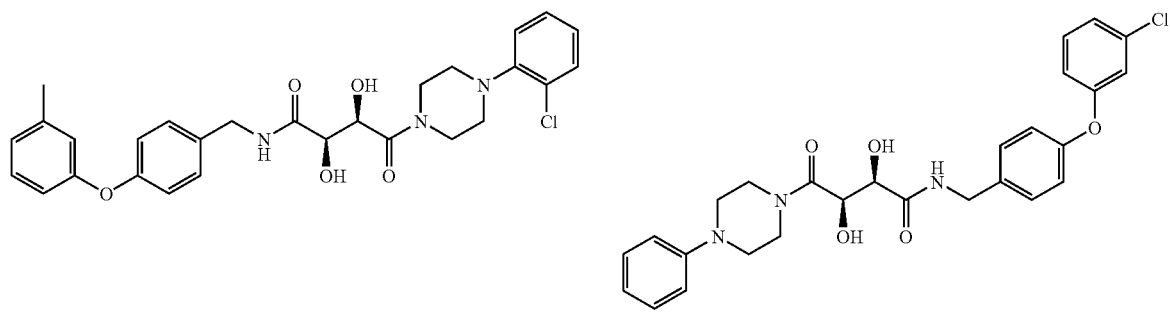

-continued
1509
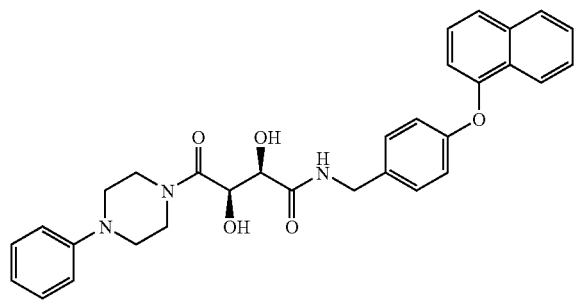
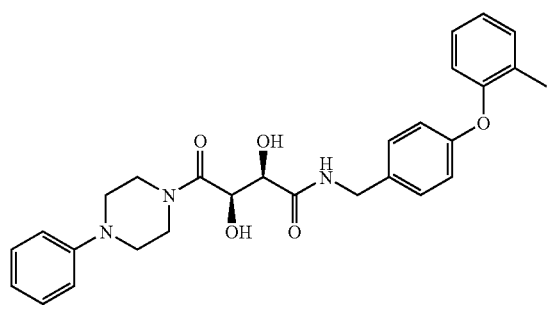
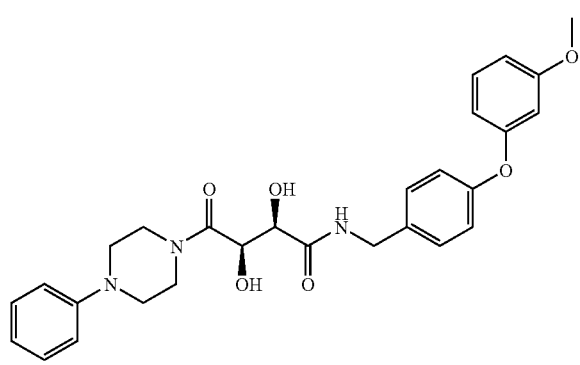
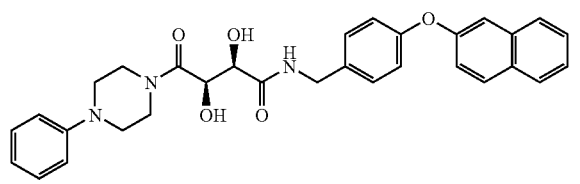
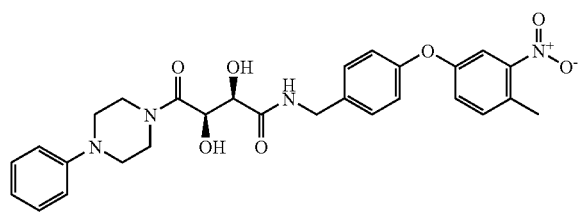
1510
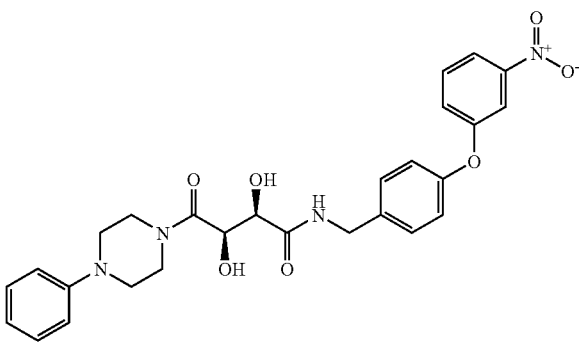
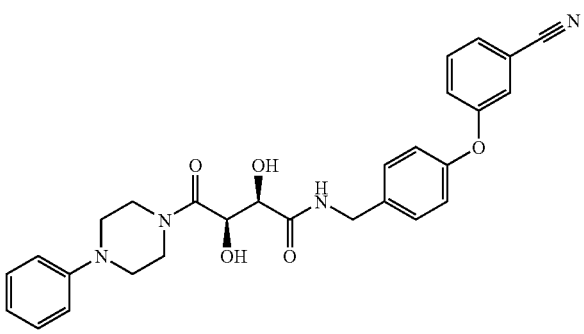
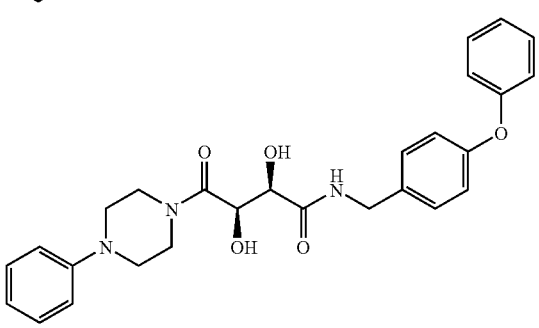
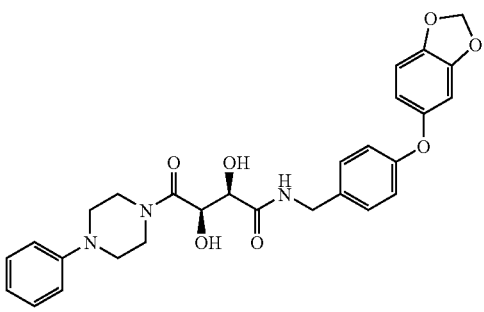
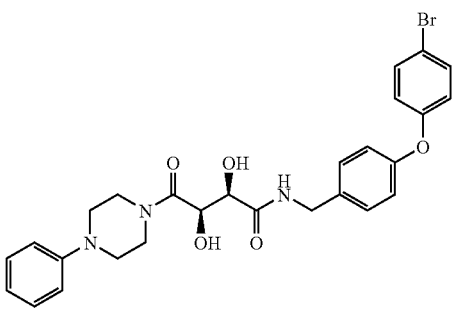

1511 1512
-continued
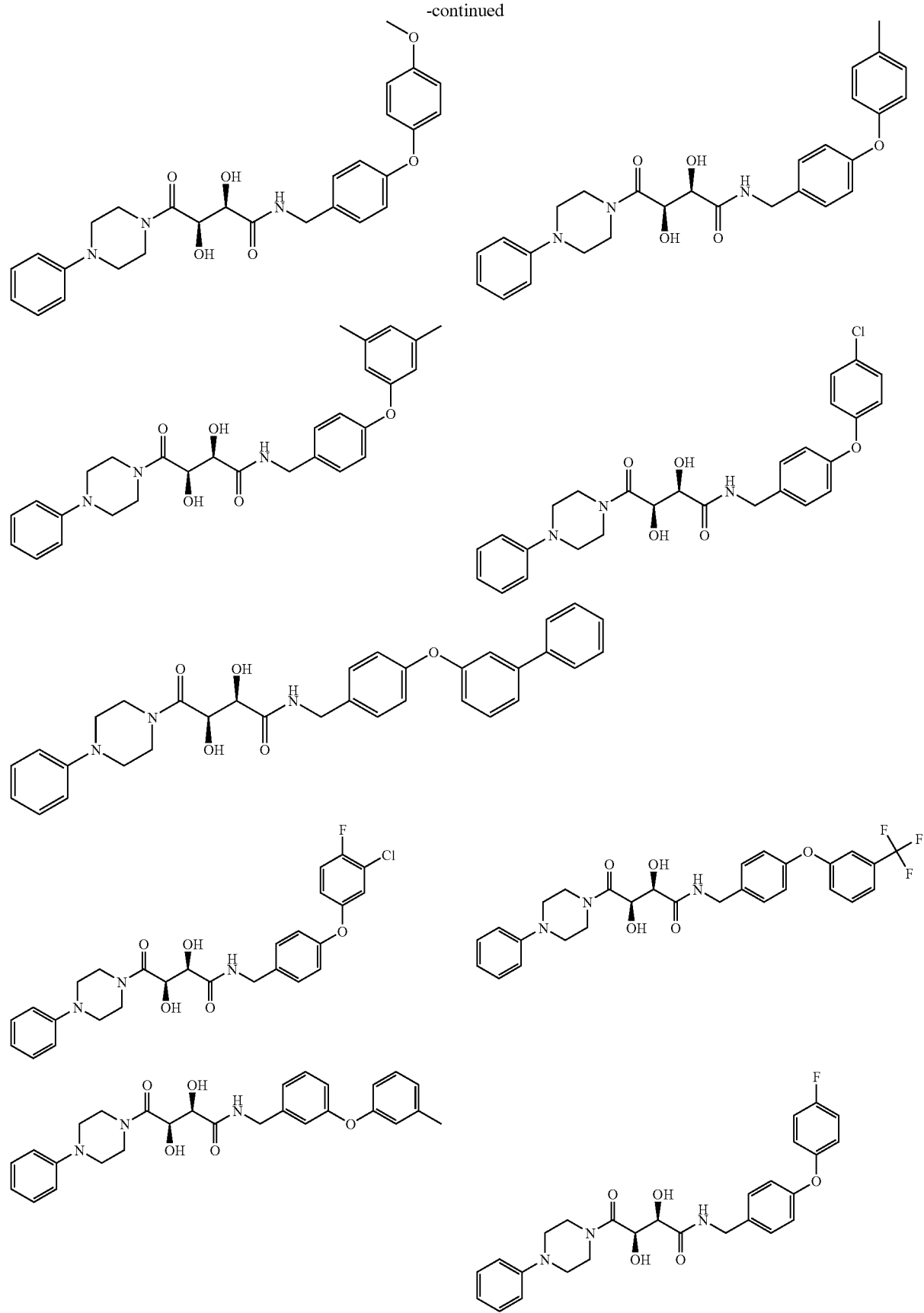

1513
-continued
1514
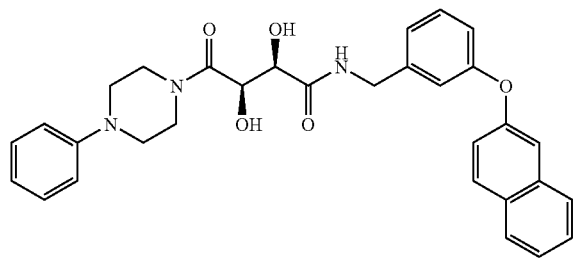
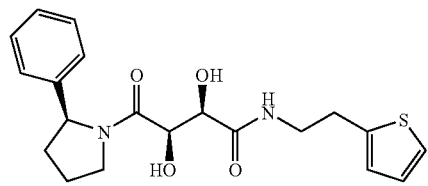
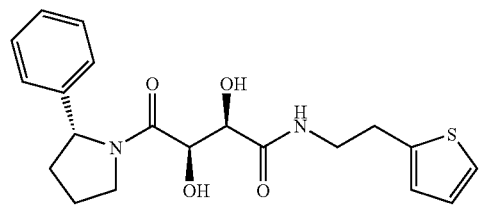
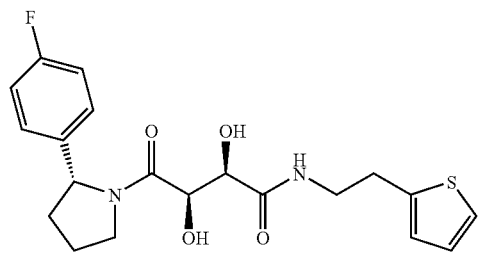
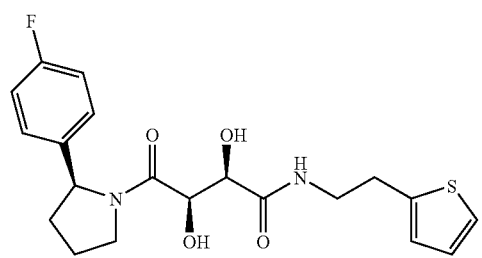
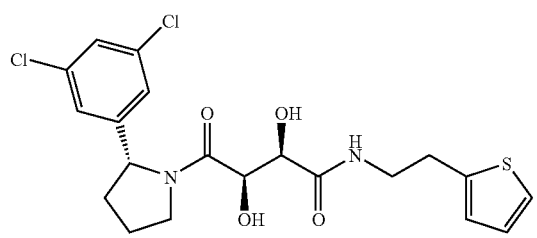
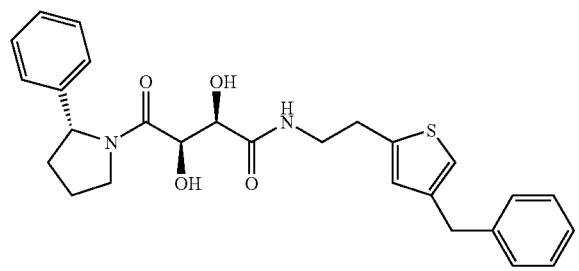
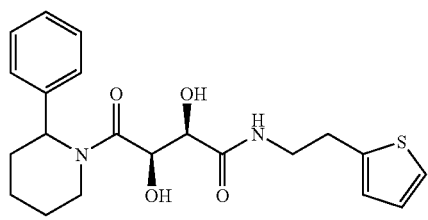
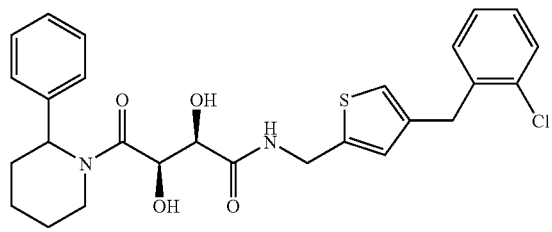
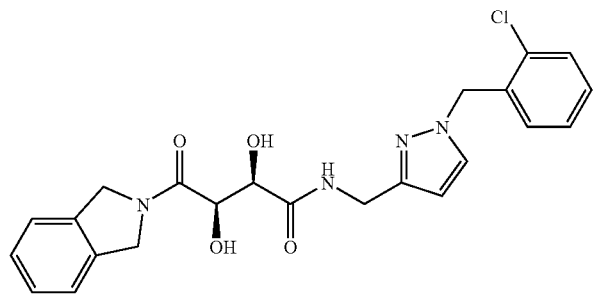
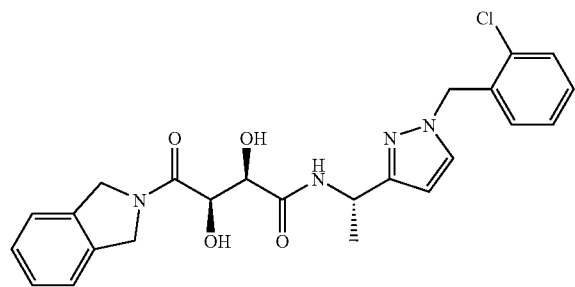
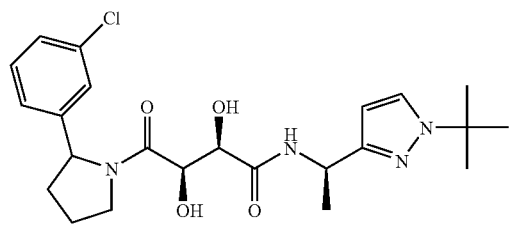

-continued
| 1515 | 1516 |
|---|---|
| 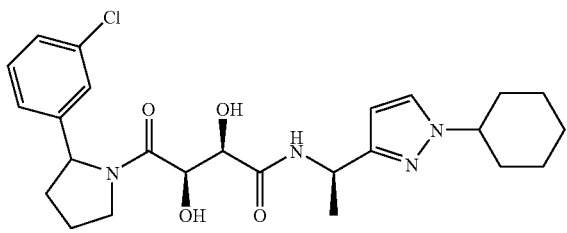 | 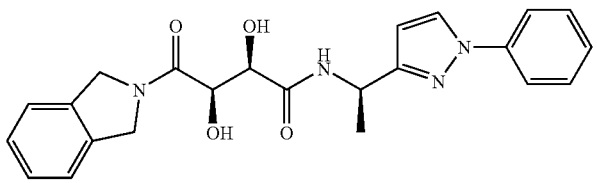 |
| 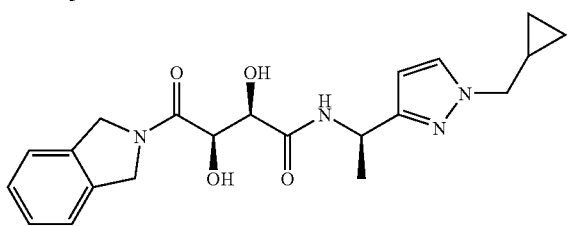 | 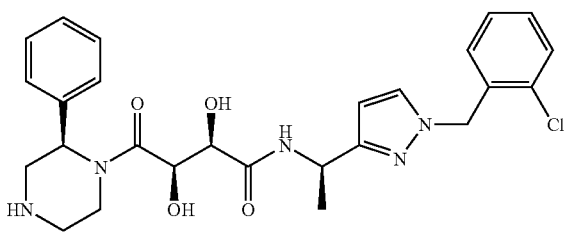 |
| 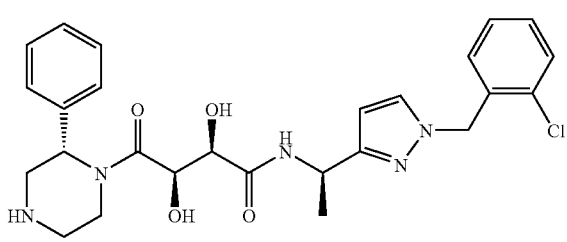 | 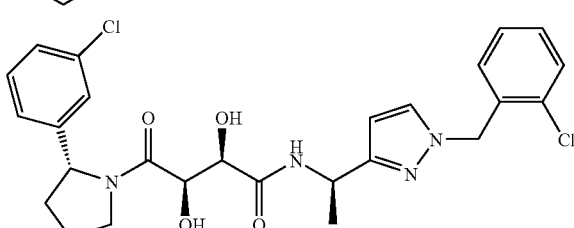 |
| 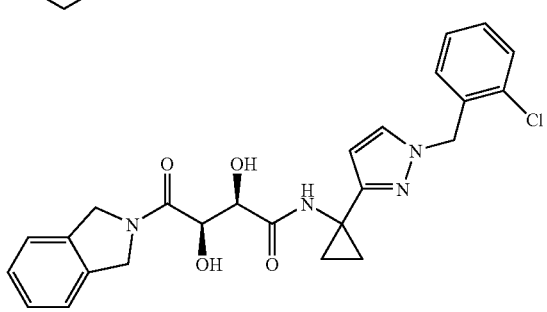 | 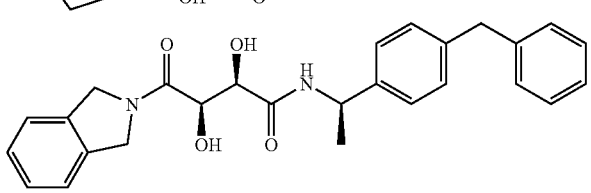 |
| 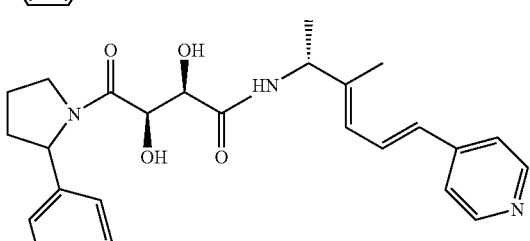 | 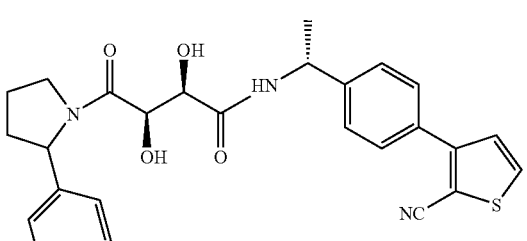 |
| 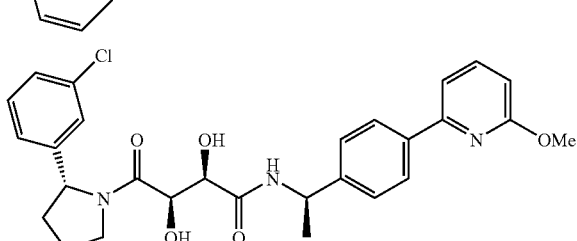 | 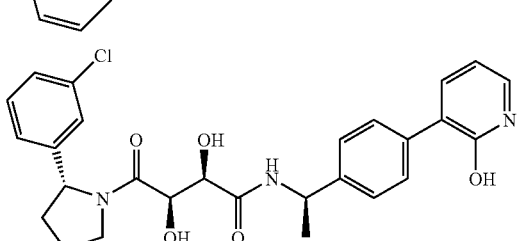 |
| 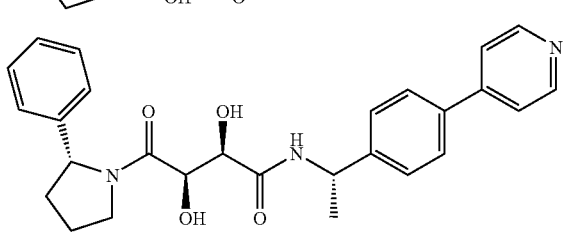 | 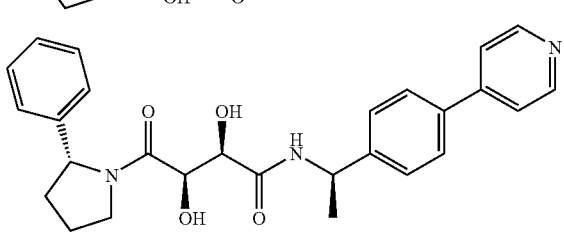 |

1517
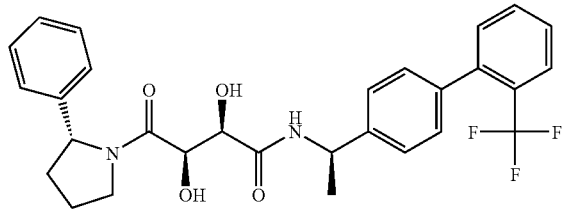
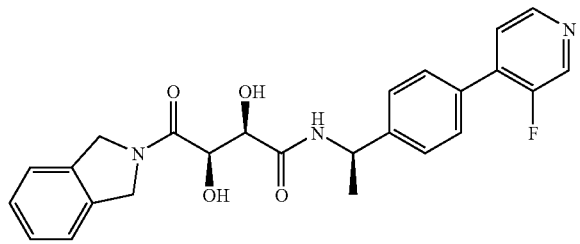
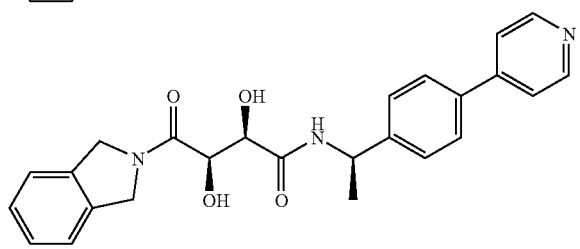
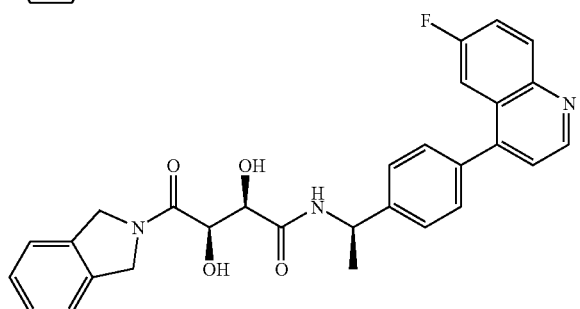
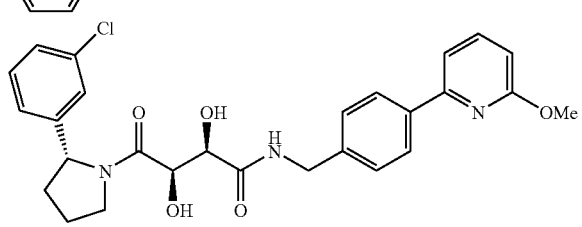
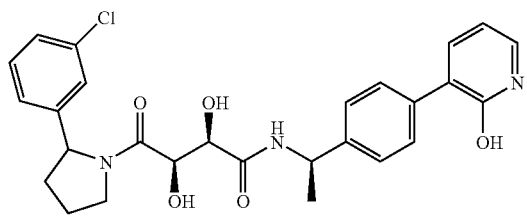
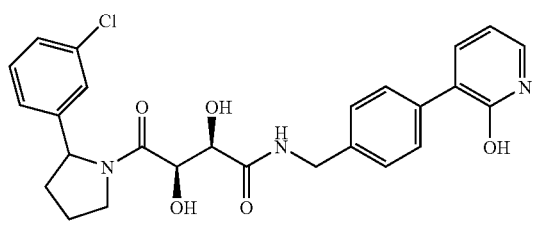
1518
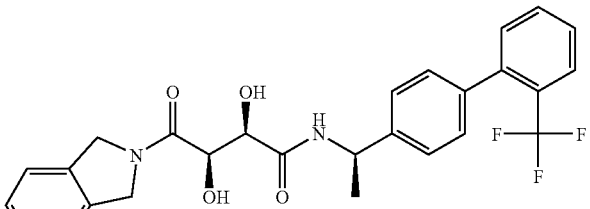
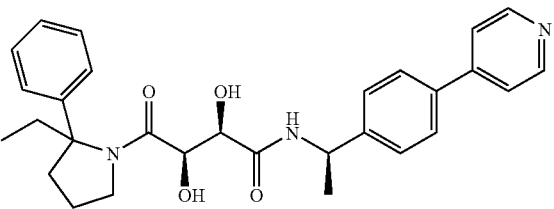
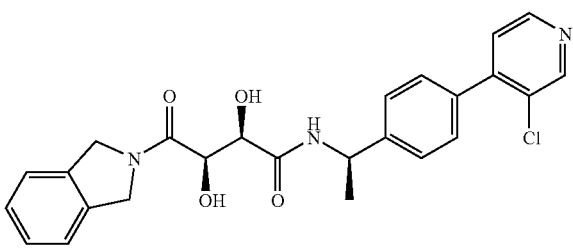
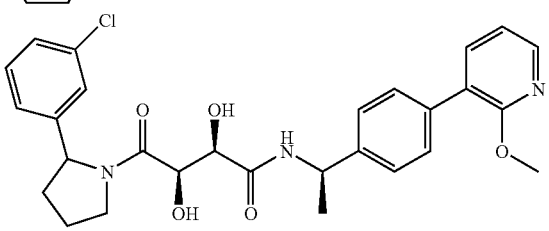
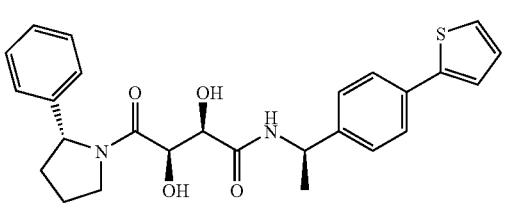
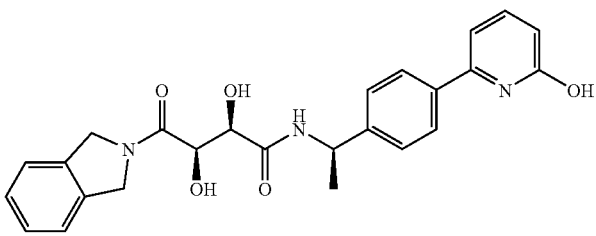
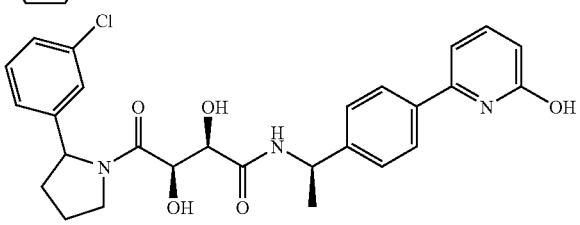

1519
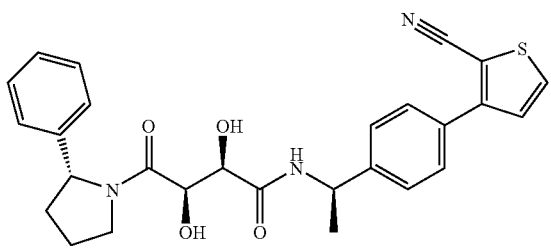
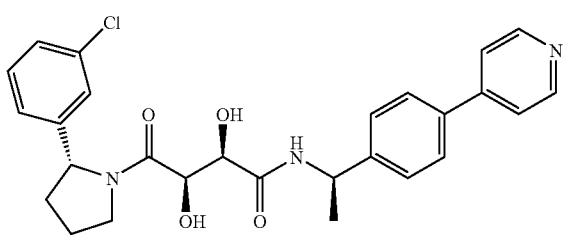
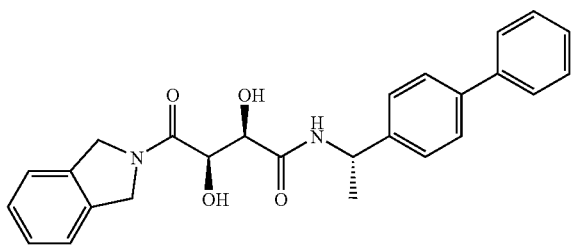
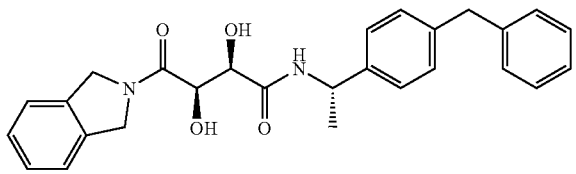
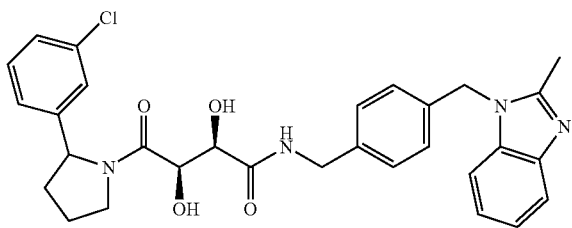
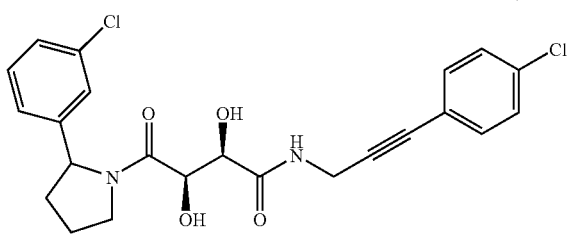
-continued
1520
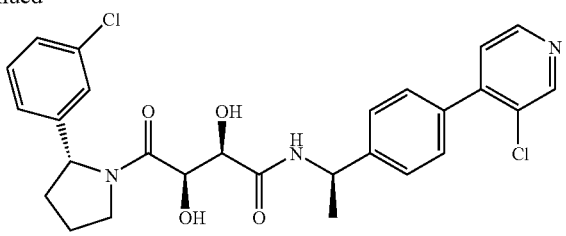
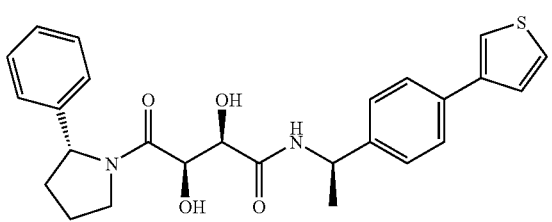
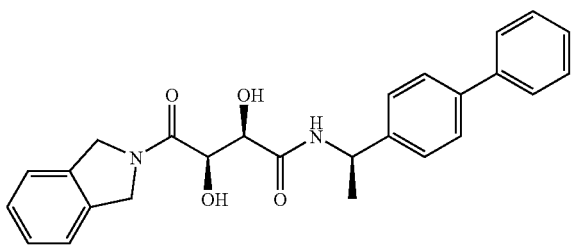
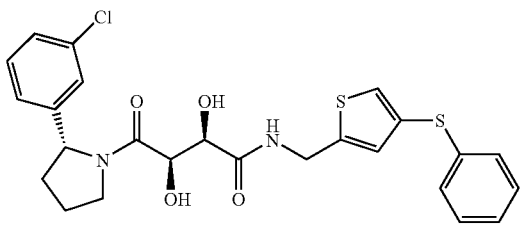
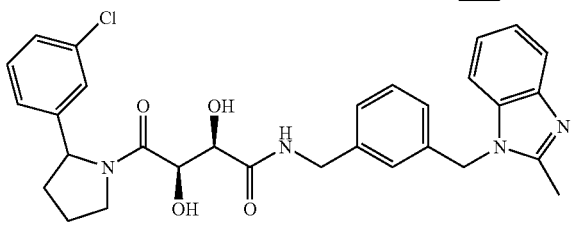
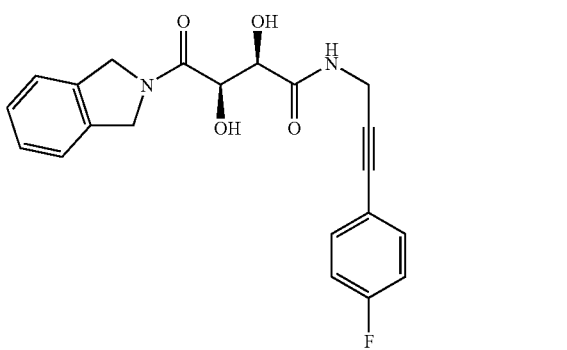

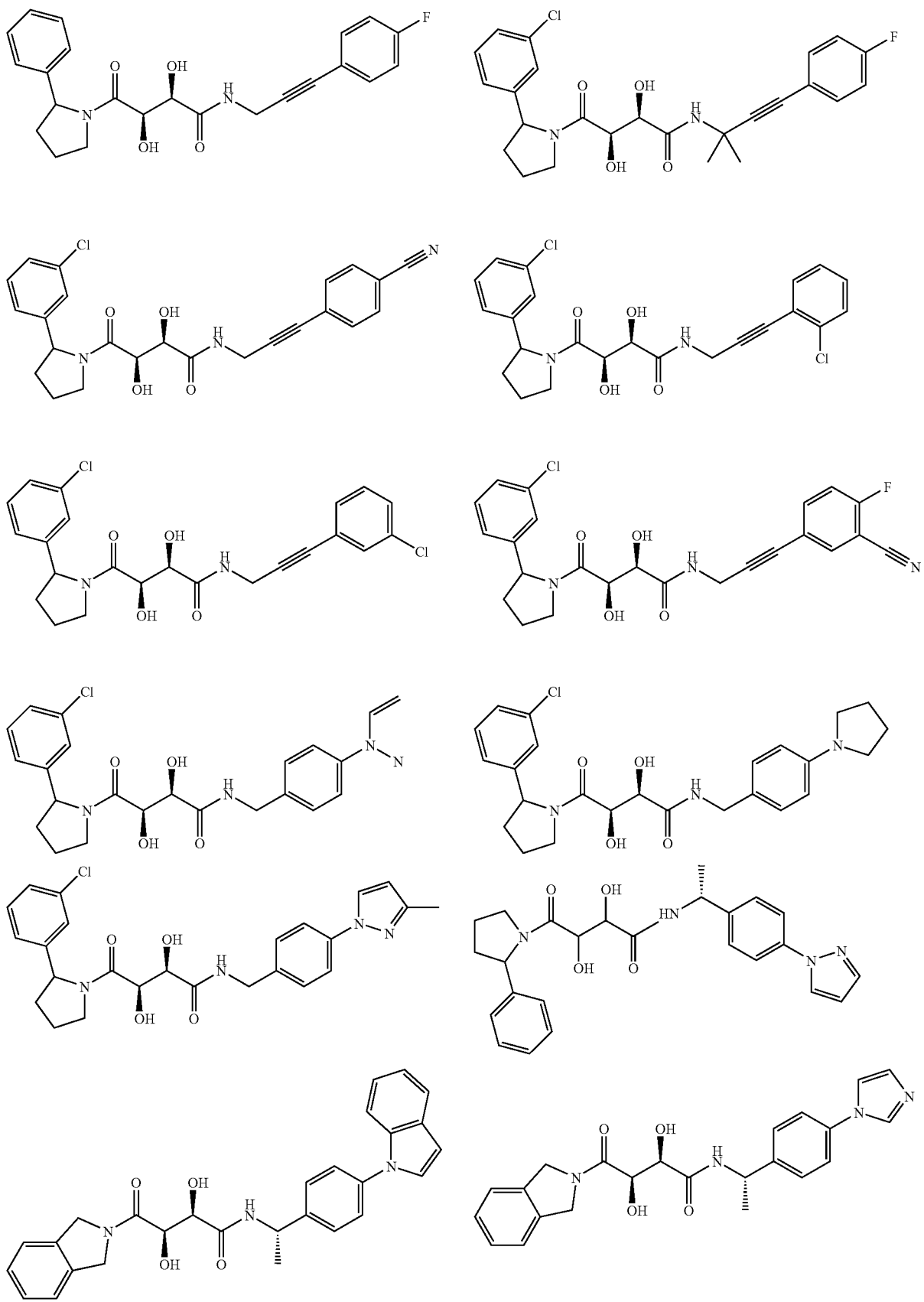

-continued
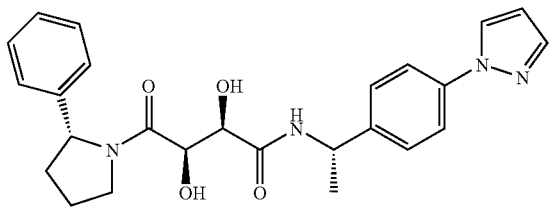
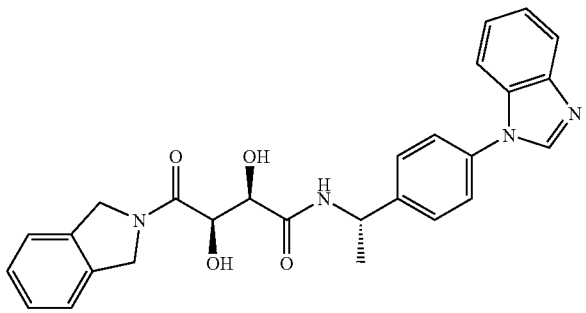
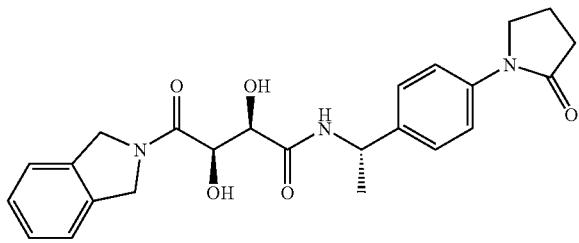
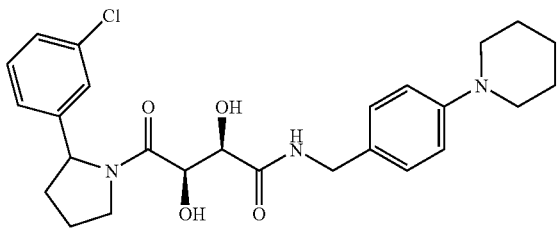
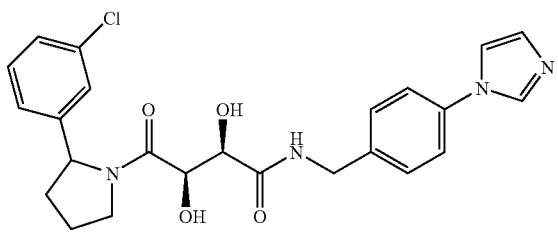
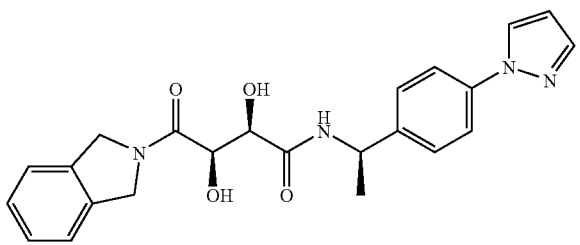
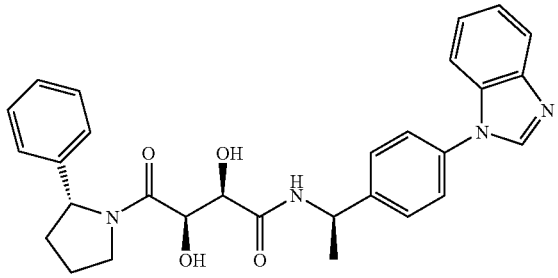
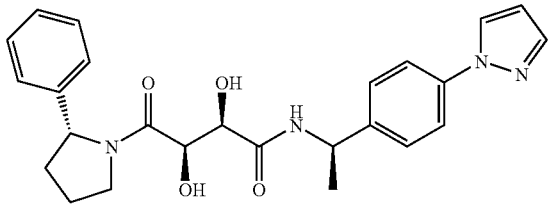
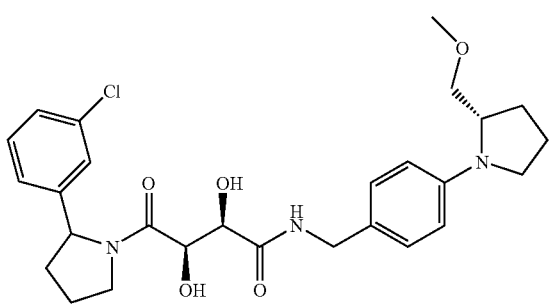
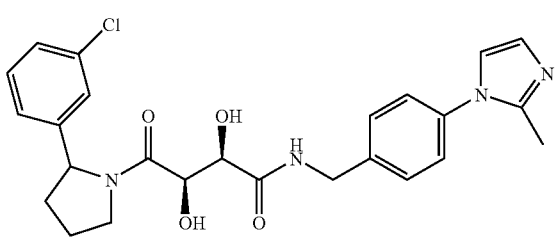
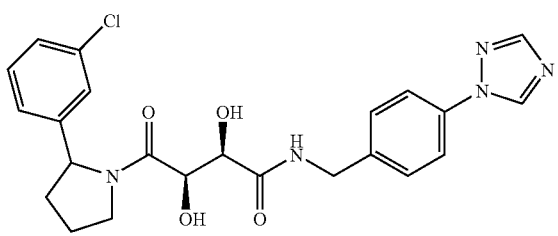
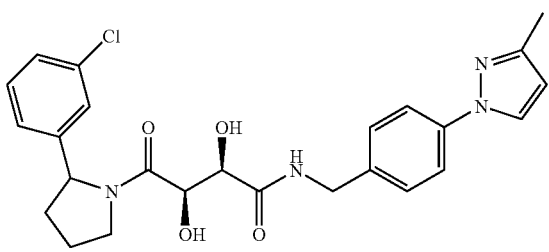

-continued
| 1525 | 1526 |
|---|---|
| 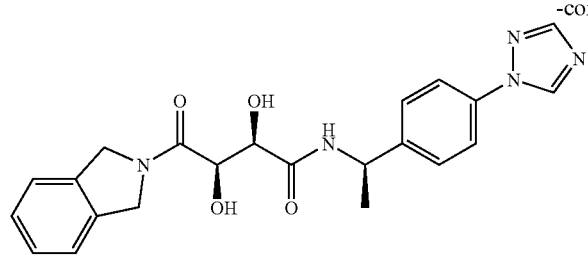 | 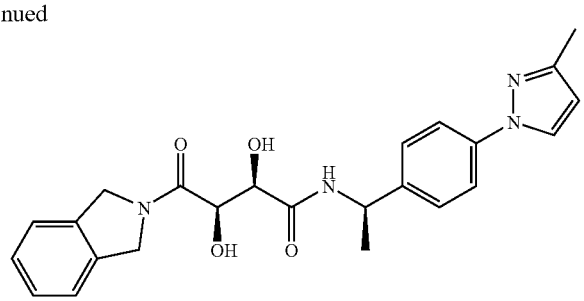 |
| 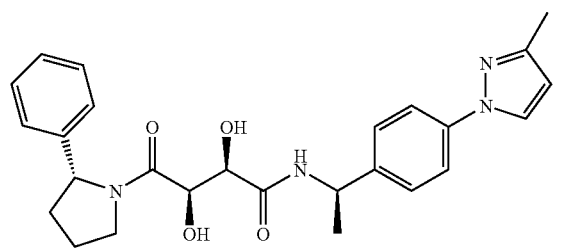 | 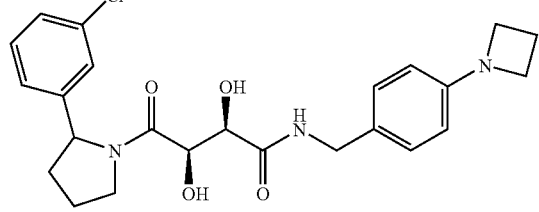 |
| 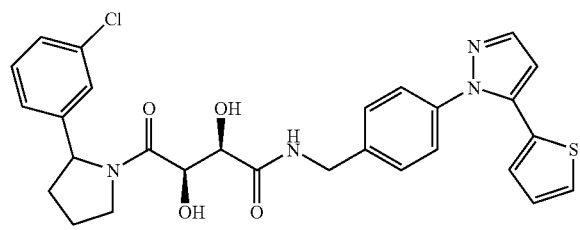 | 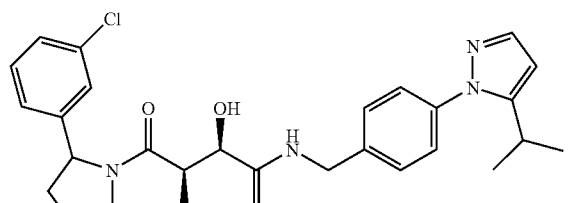 |
| 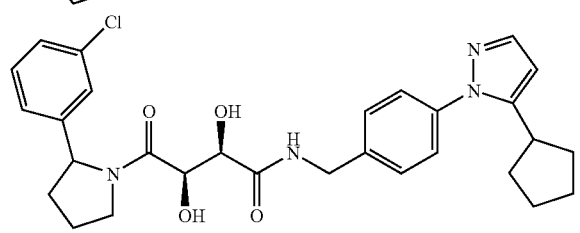 | 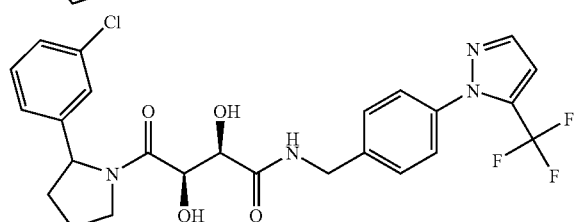 |
| 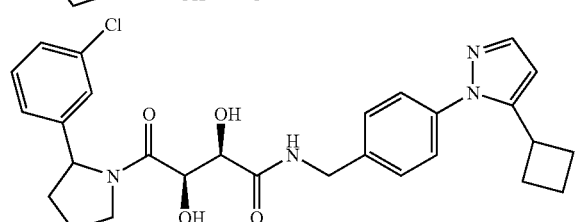 | 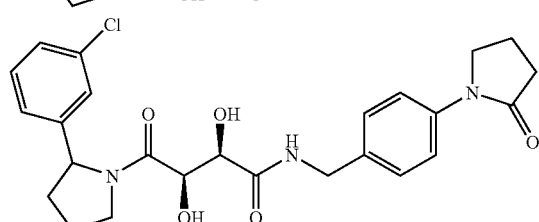 |
| 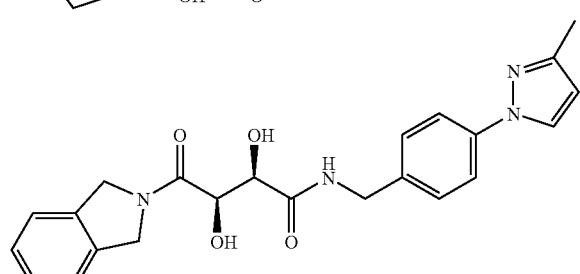 | 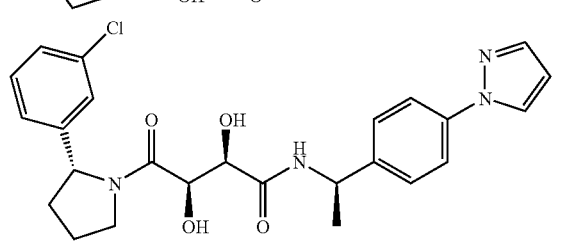 |
| 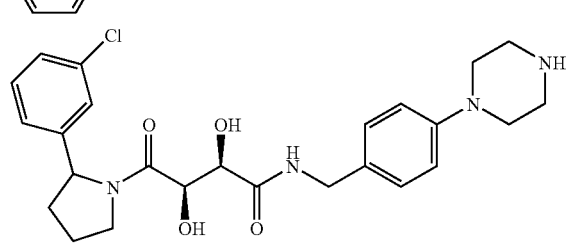 | 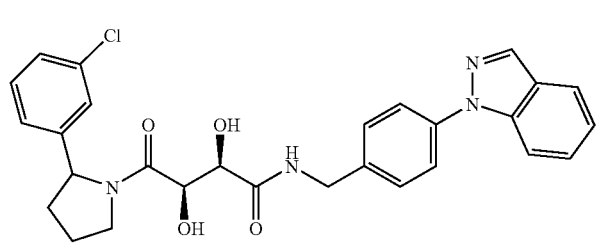 |

-continued
| 1527 | 1528 |
|---|---|
| 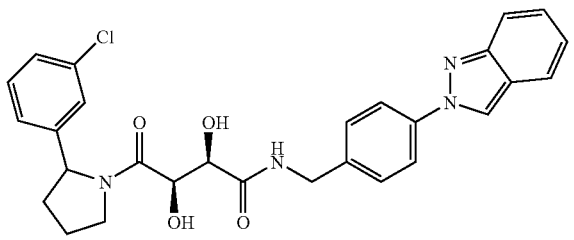 | 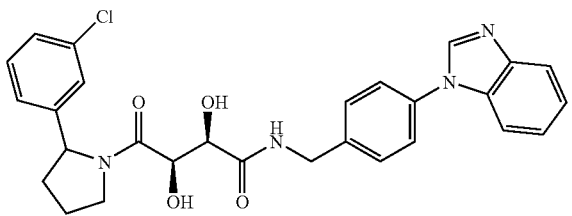 |
| 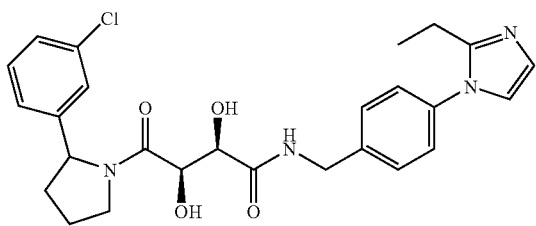 | 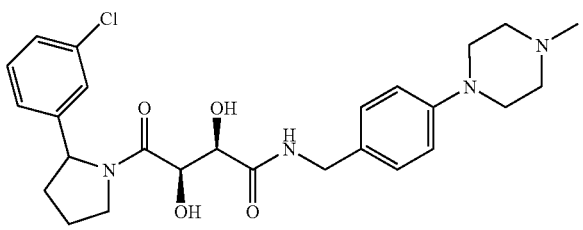 |
| 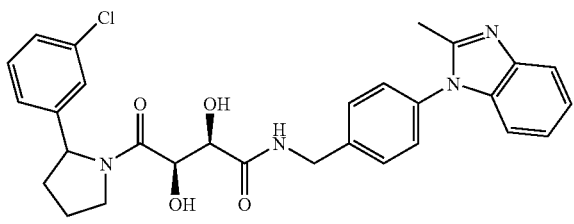 | 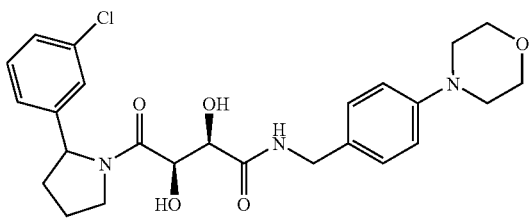 |
| 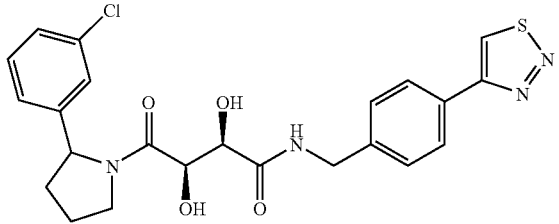 | 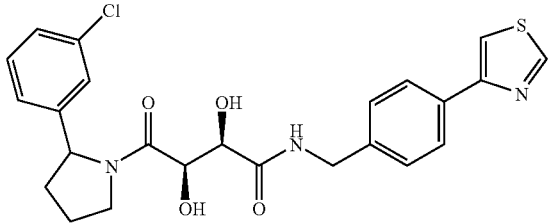 |
| 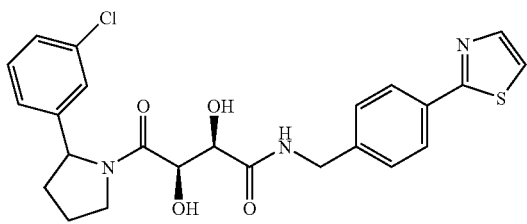 | 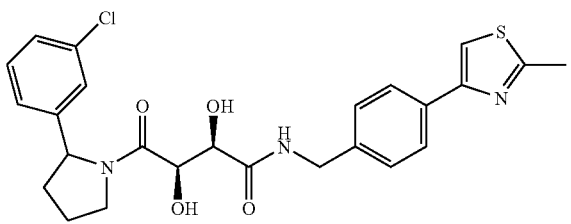 |
| 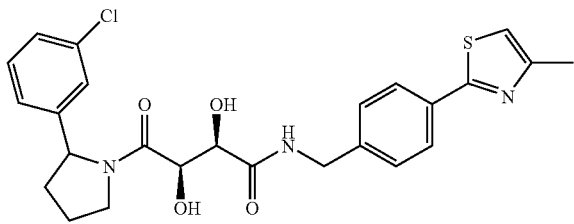 | 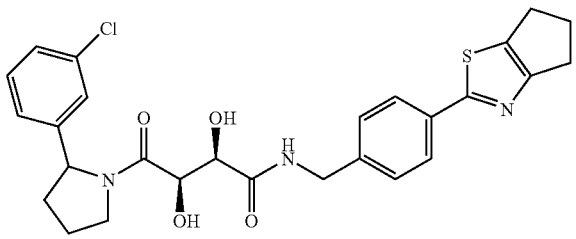 |
| 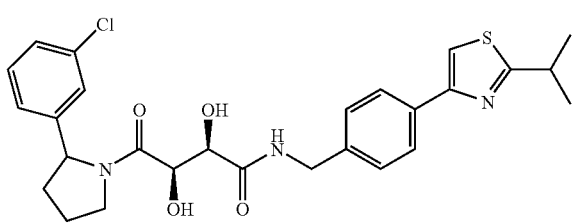 | 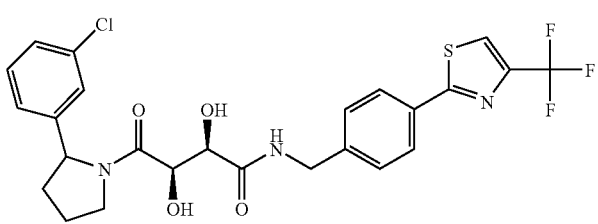 |

-continued
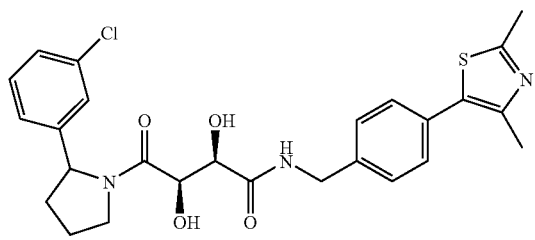
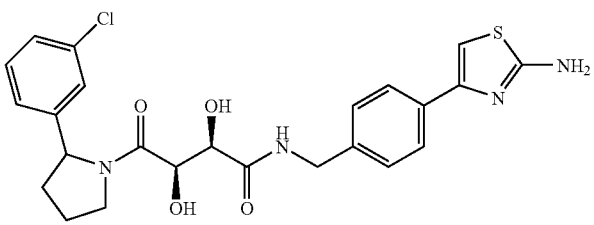
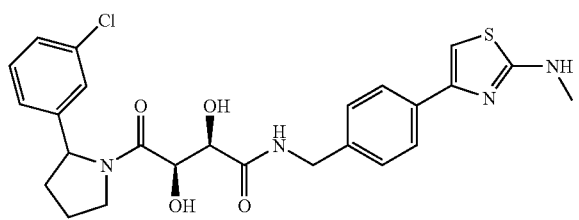
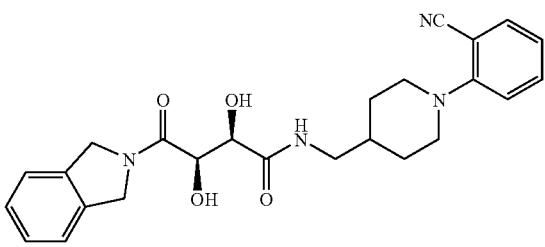
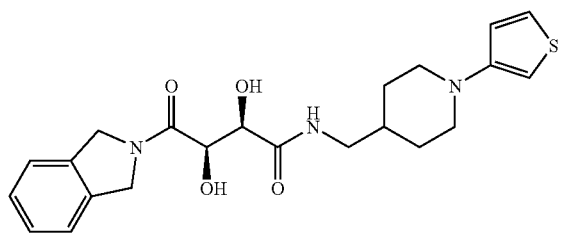
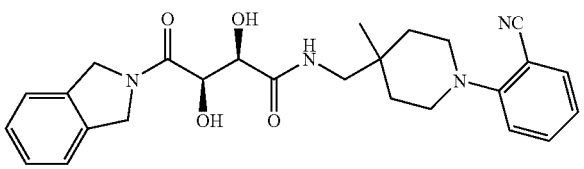
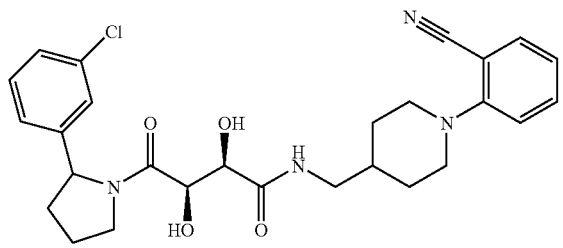
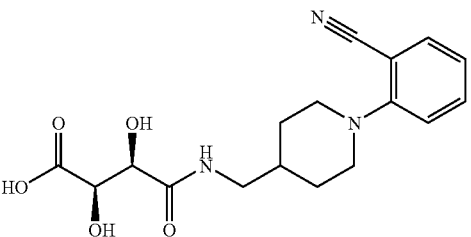
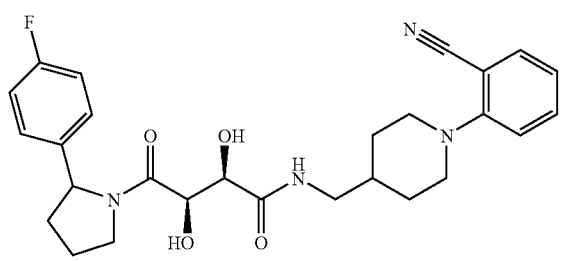
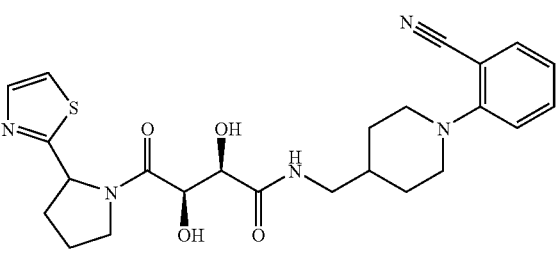
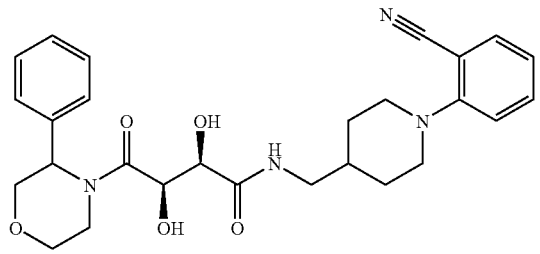
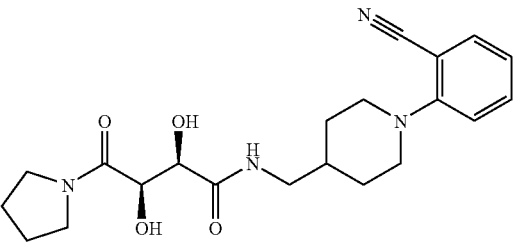

| 1531 | 1532 |
|---|---|
| 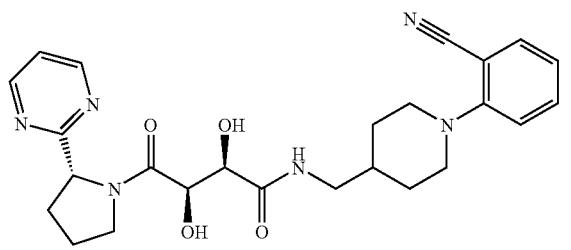 | 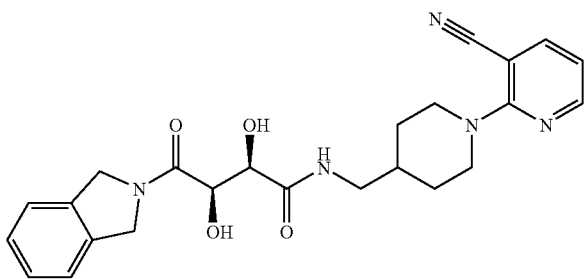 |
| 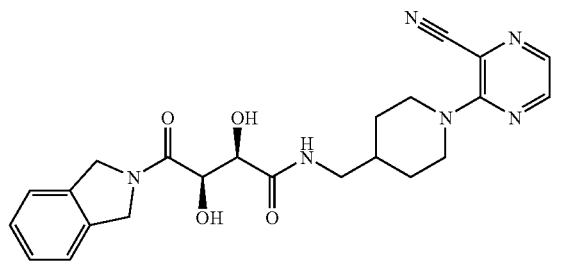 | 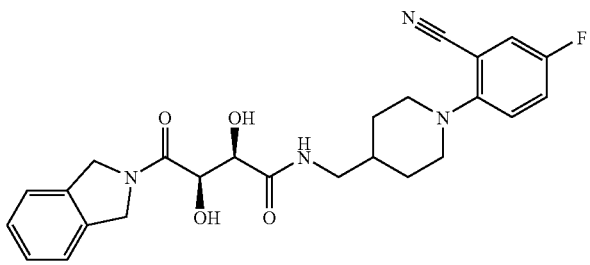 |
| 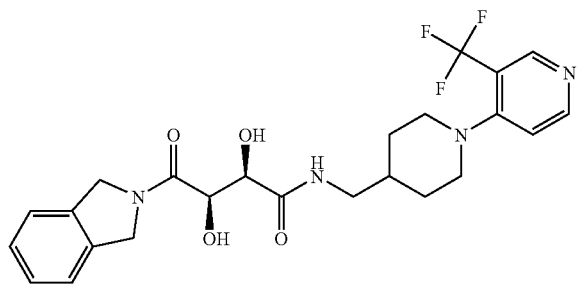 | 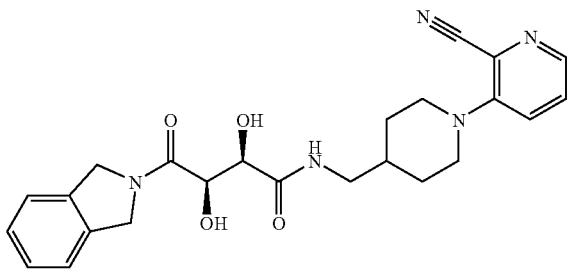 |
| 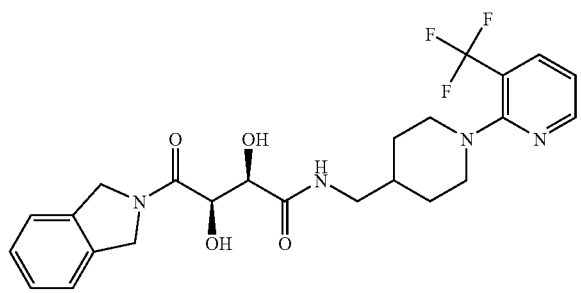 | 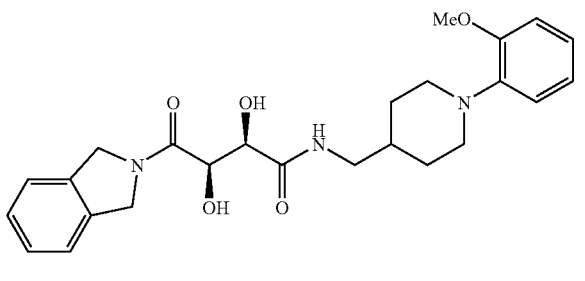 |
| 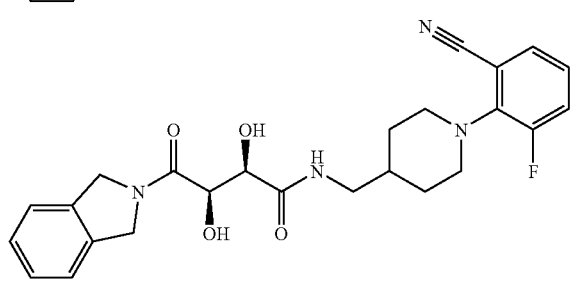 | 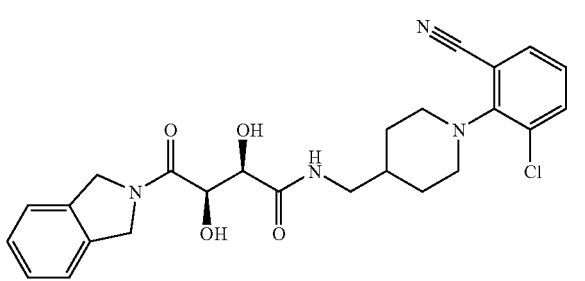 |
| 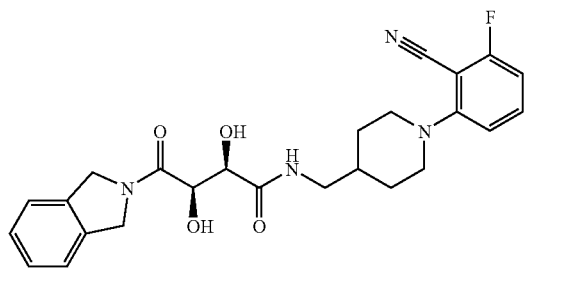 | 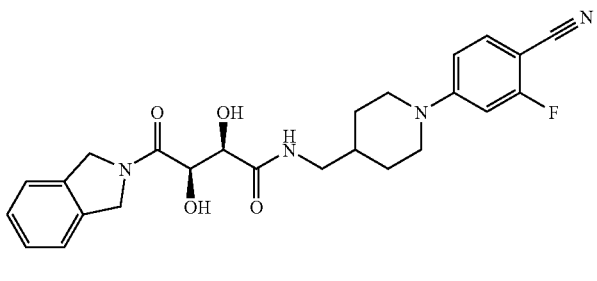 |

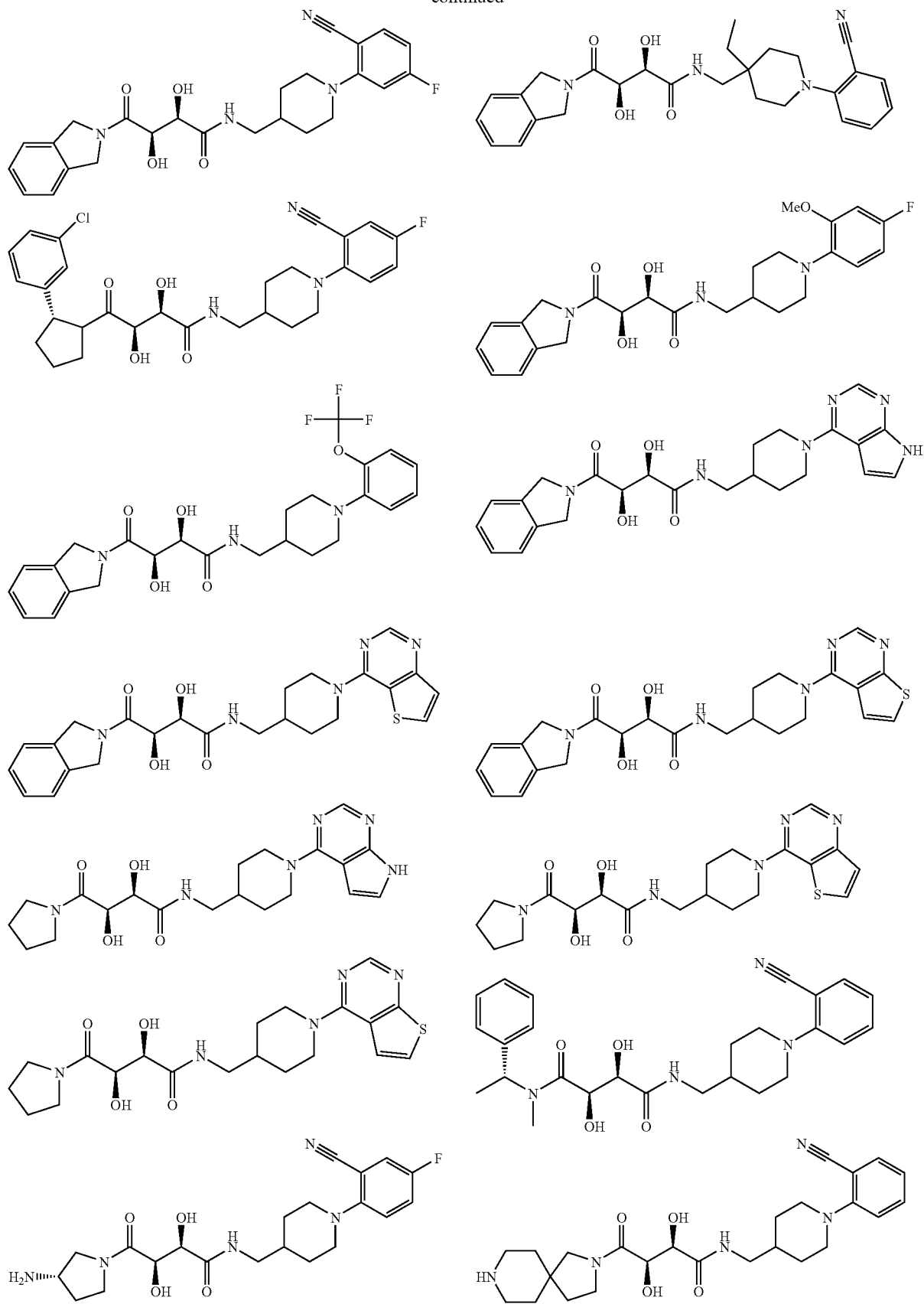

-continued
| 1535 | 1536 |
|---|---|
| 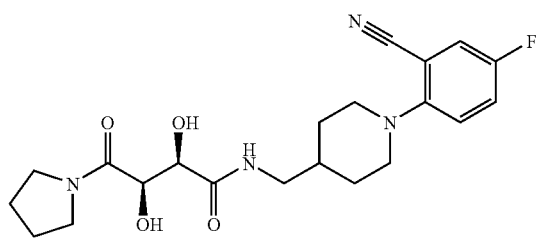 | 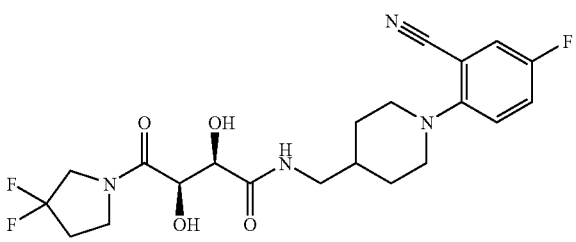 |
| 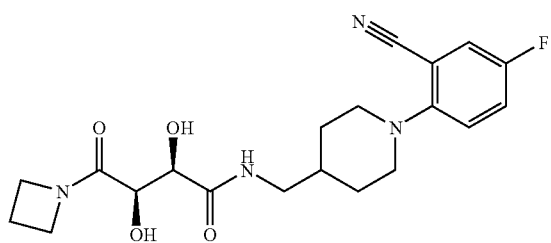 | 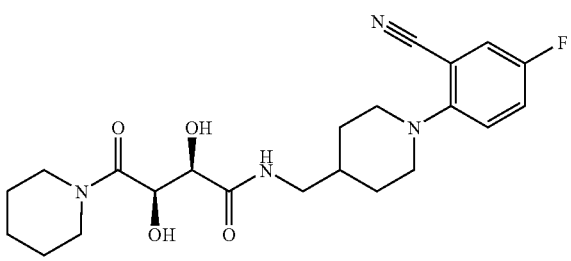 |
| 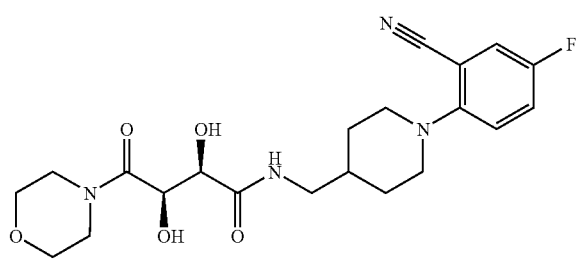 | 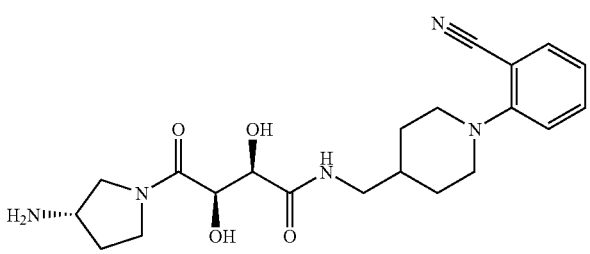 |
| 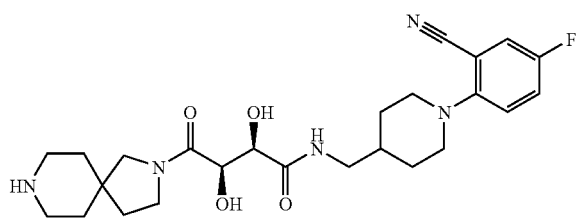 | 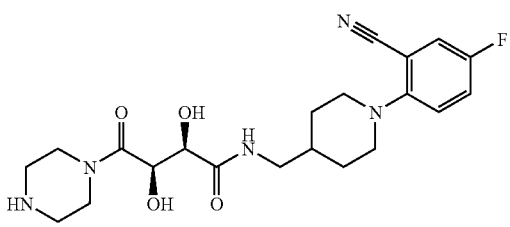 |
| 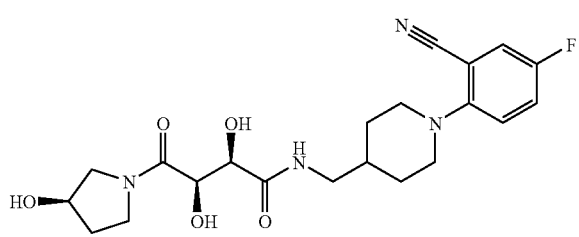 | 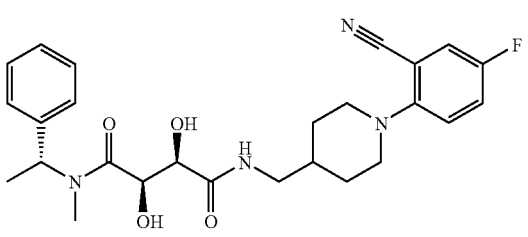 |
| 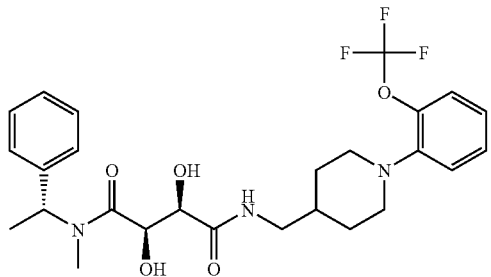 | 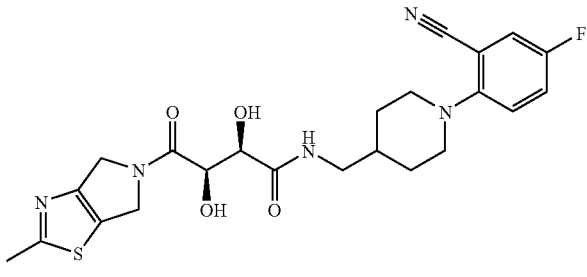 |

1537
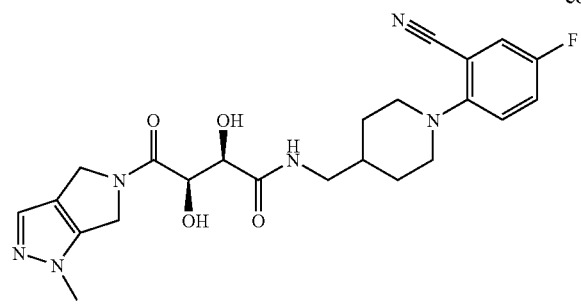
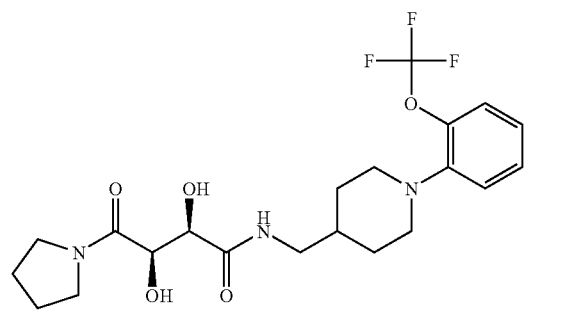
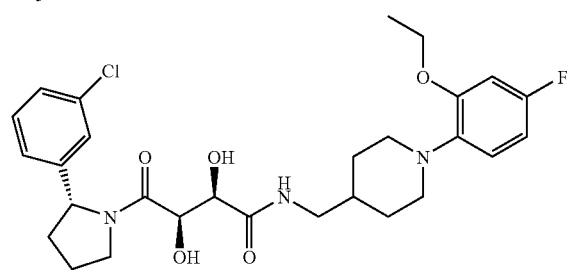
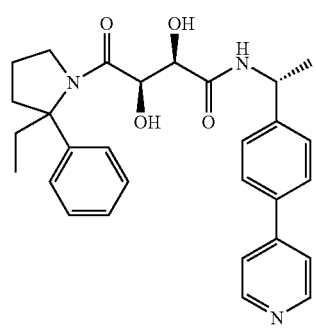
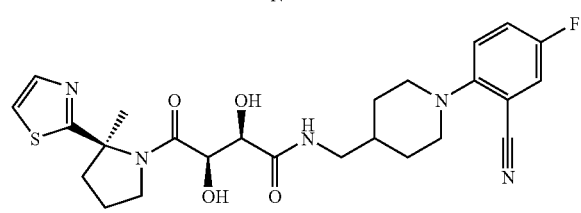
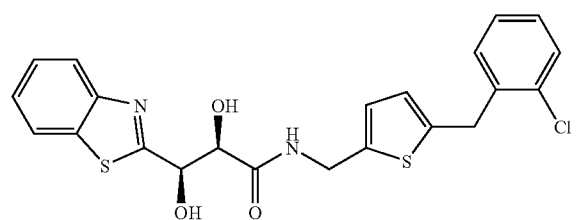
1538
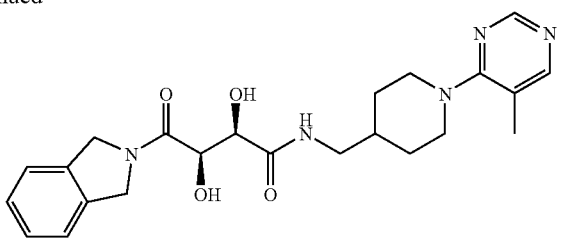
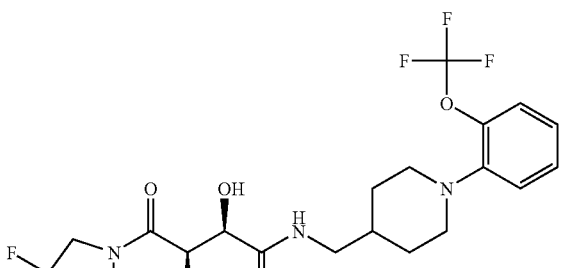
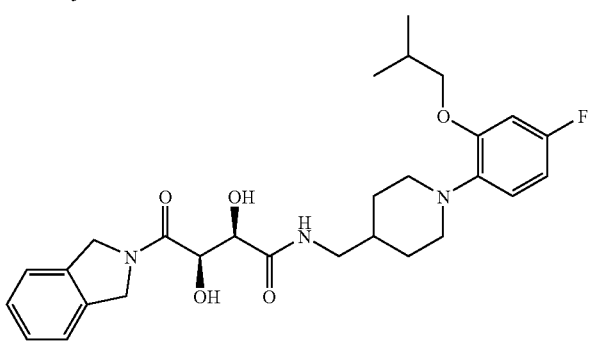
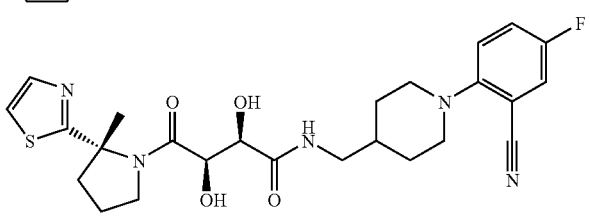
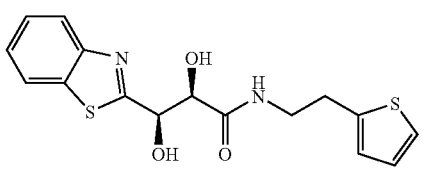
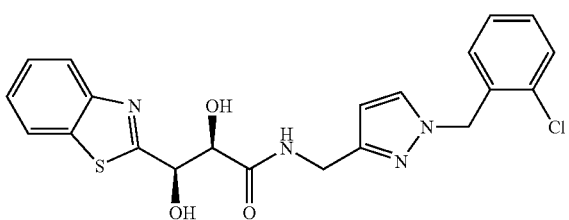

-continued
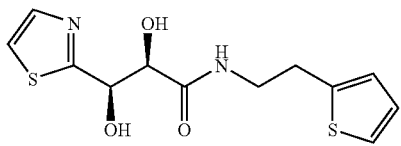
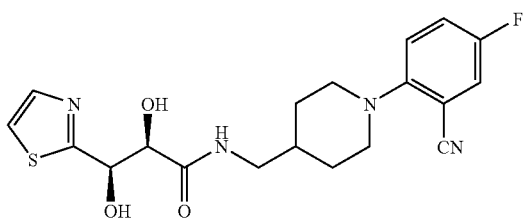
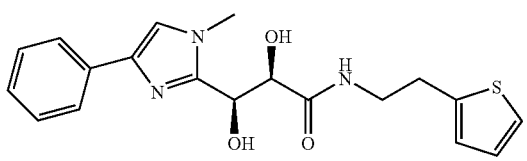
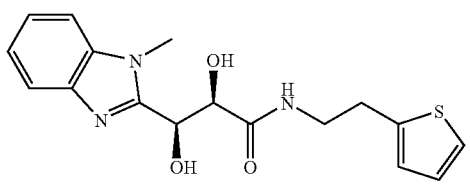
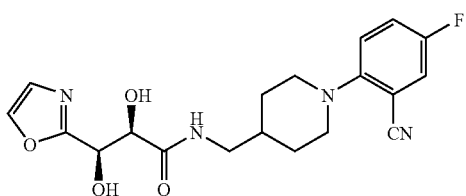
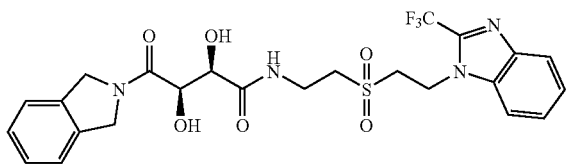
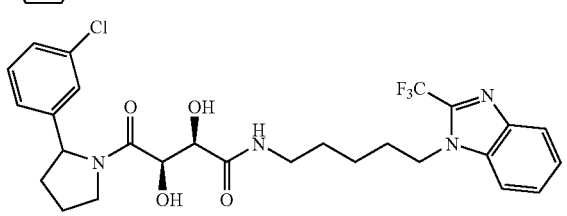
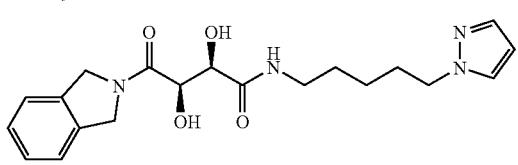
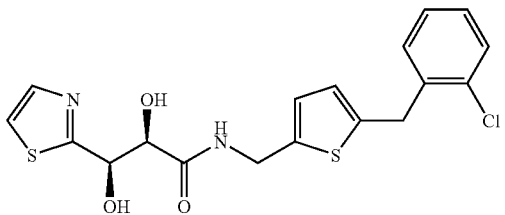
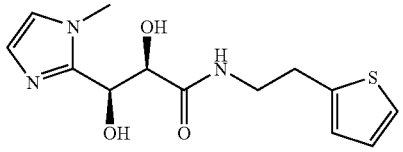
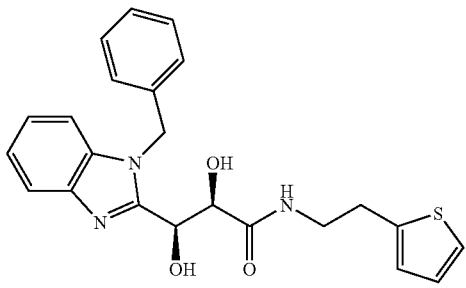
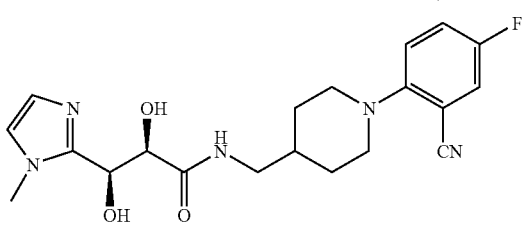
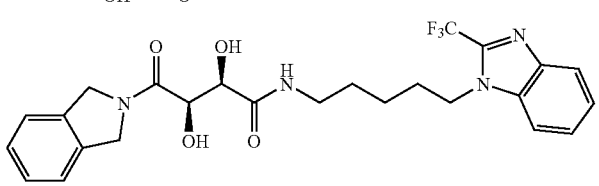
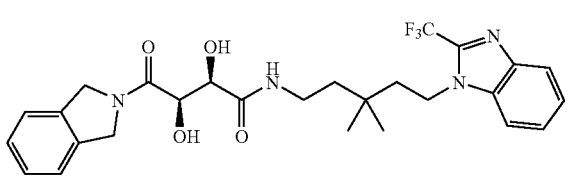
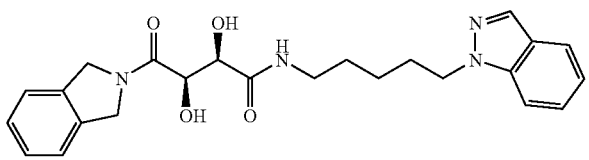
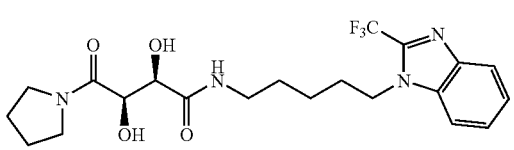

1541
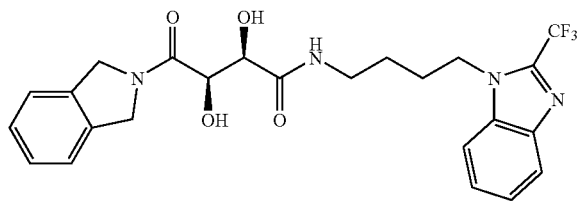
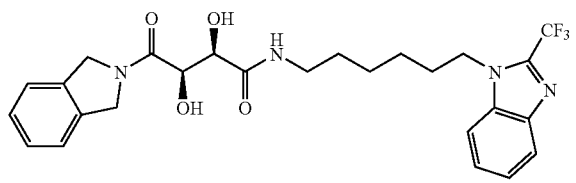
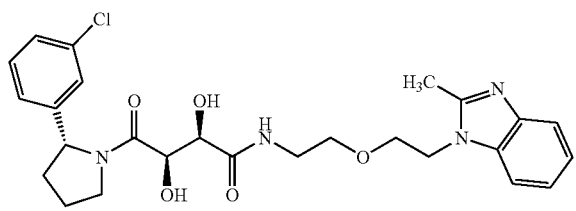
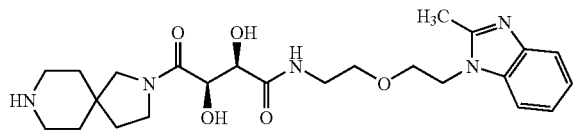
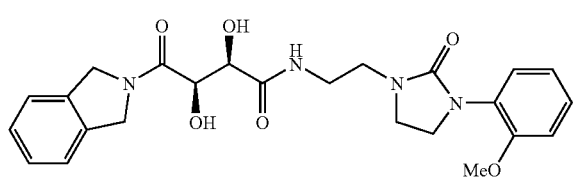
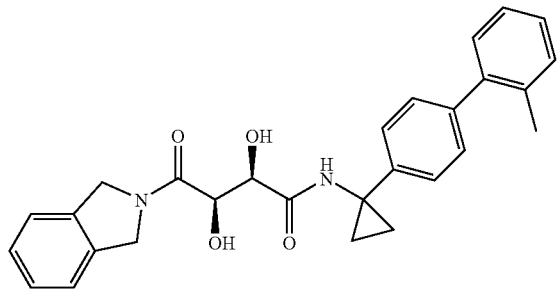
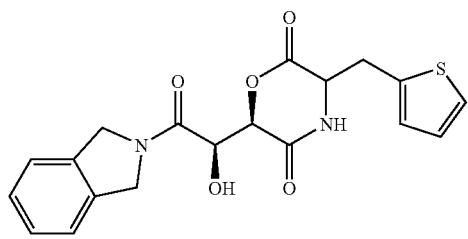
-continued
1542
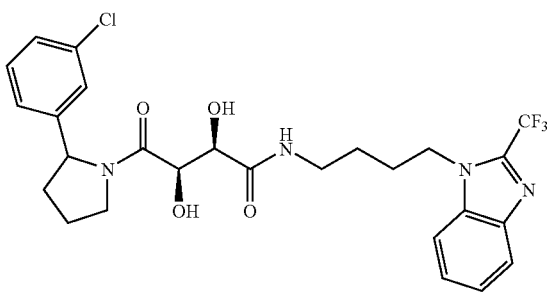
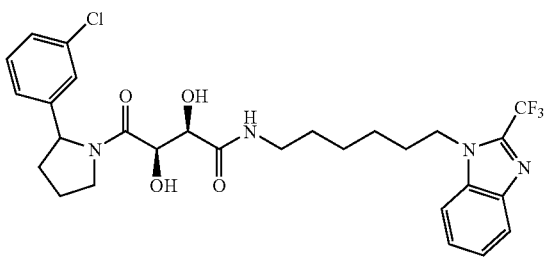
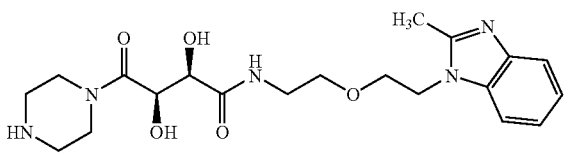
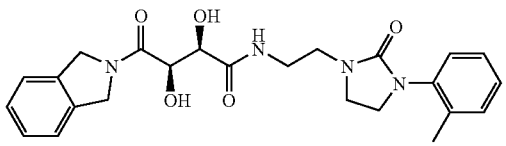
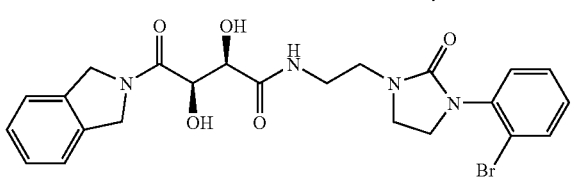
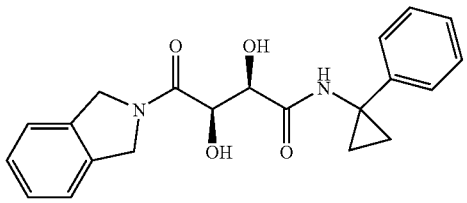
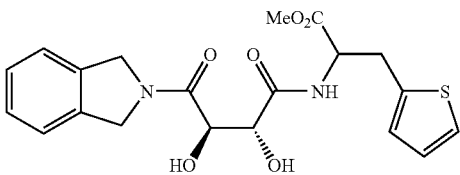

-continued
| 1543 | 1544 |
|---|---|
| 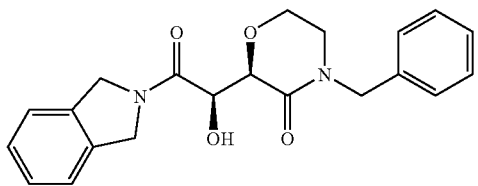 | 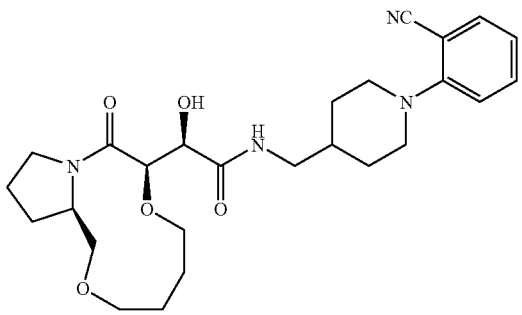 |
| 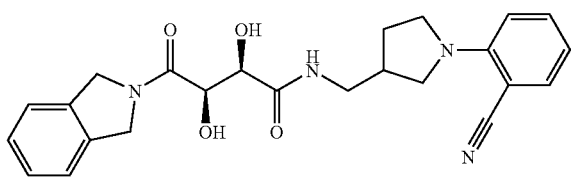 | 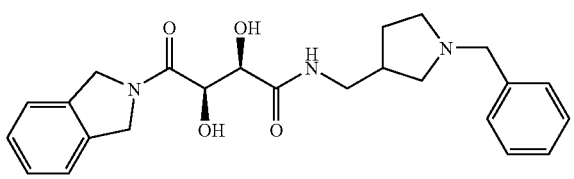 |
| 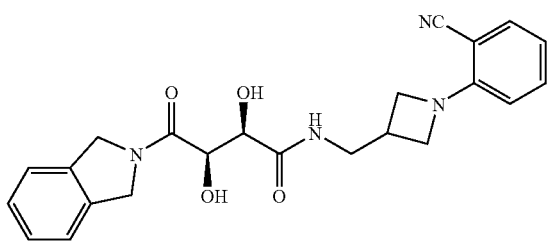 | 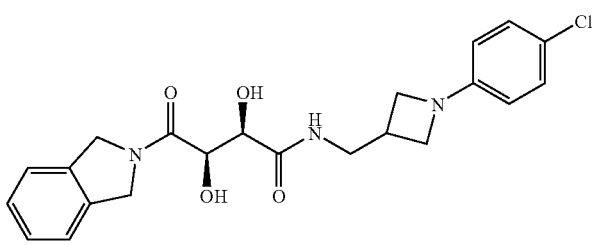 |
| 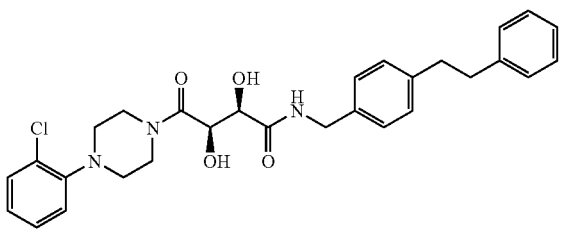 | 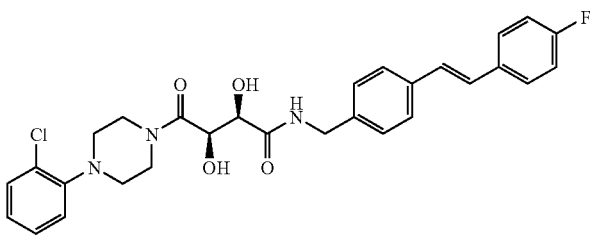 |
| 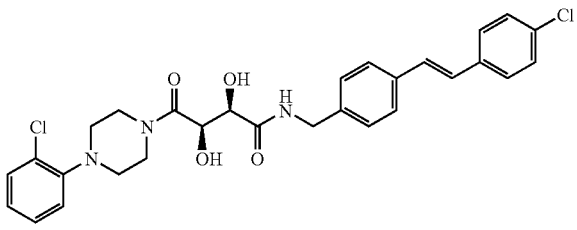 | 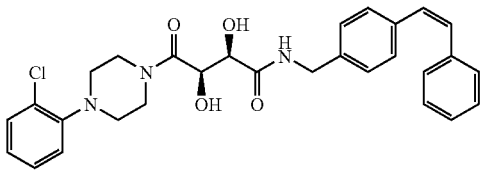 |
| 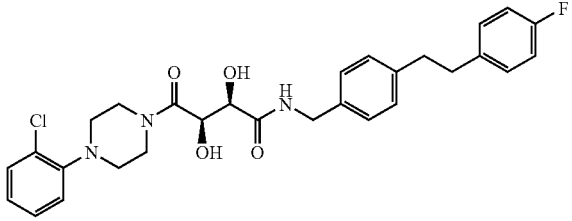 | 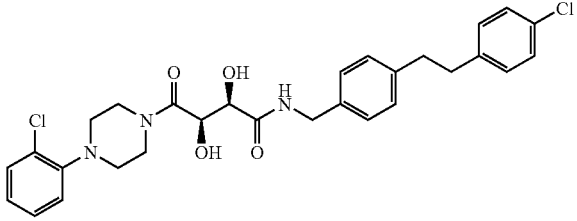 |
| 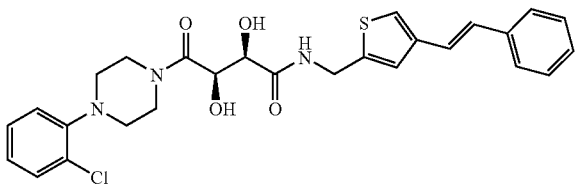 | 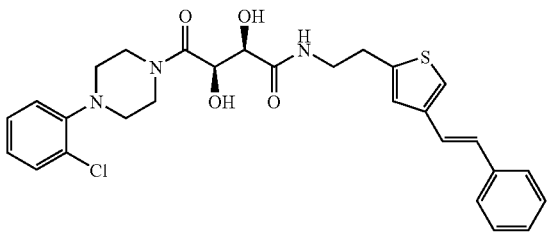 |

-continued
| 1545 | 1546 |
|---|---|
| 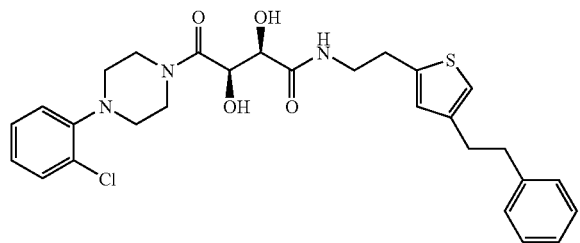 | 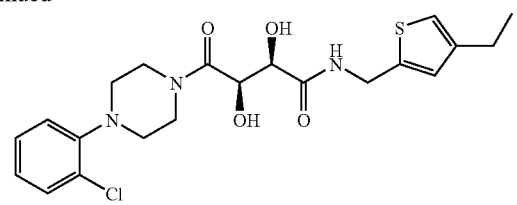 |
| 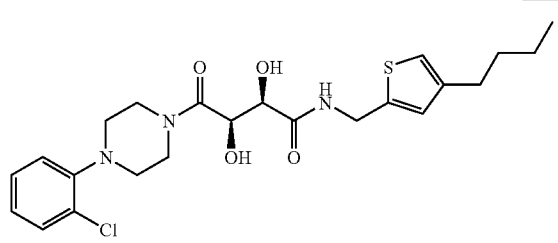 | 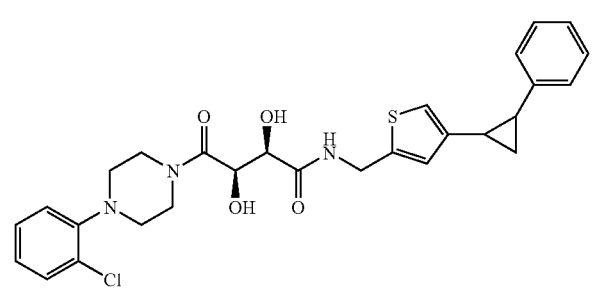 |
| 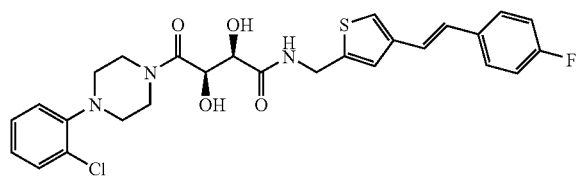 | 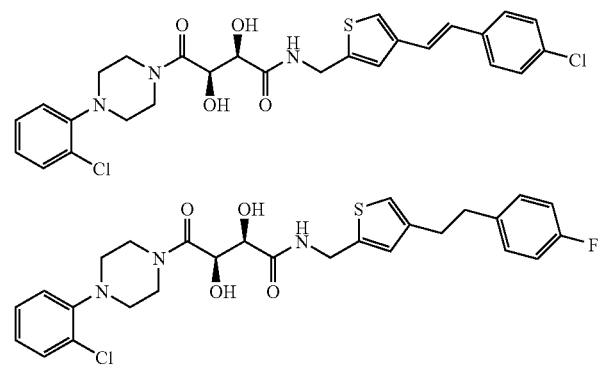 |
| 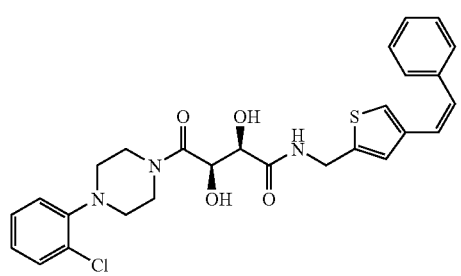 | |
| 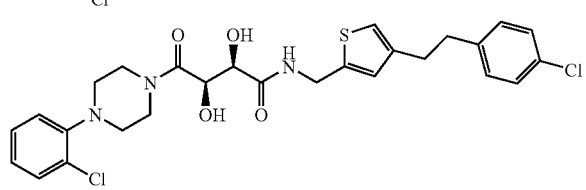 | 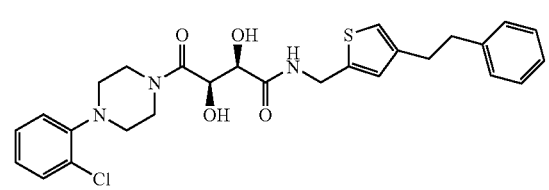 |
| 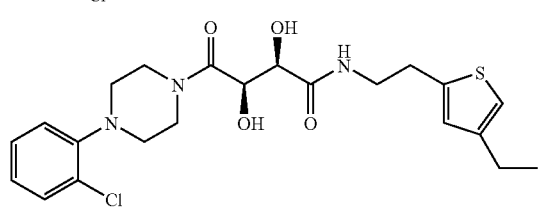 | 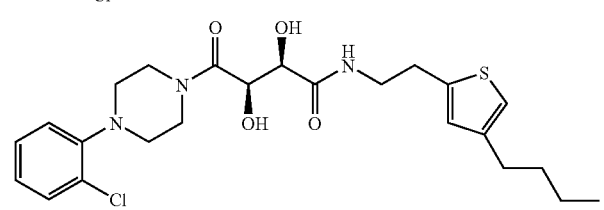 |
| 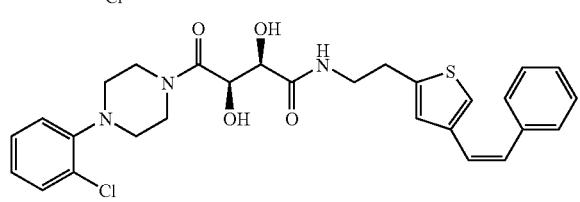 | 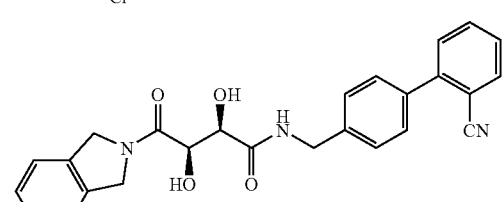 |

-continued
| 1547 | 1548 |
|---|---|
| 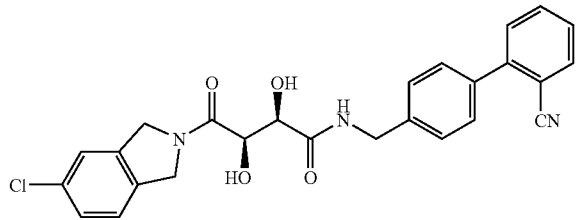 | 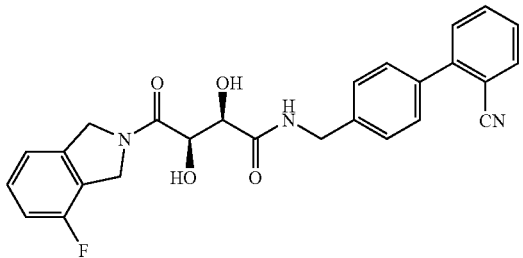 |
| 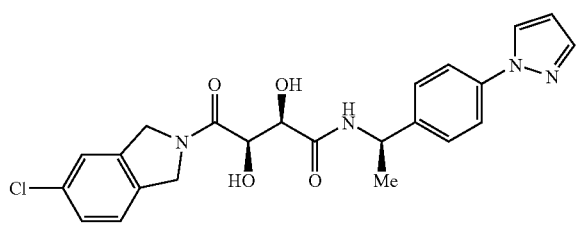 | 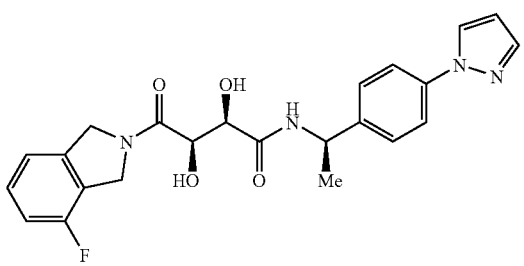 |
| 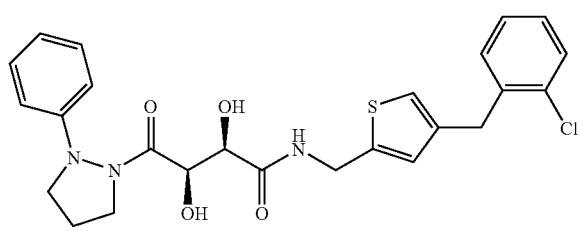 | 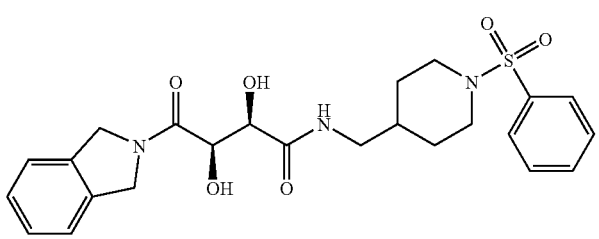 |
| 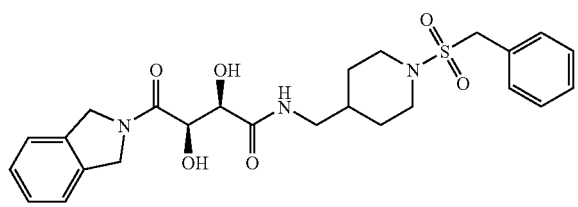 | 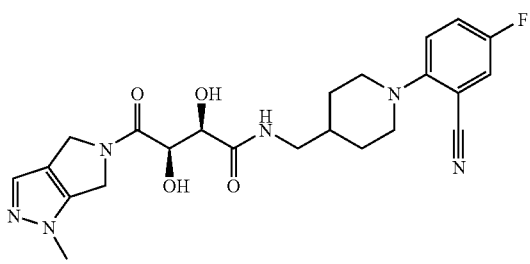 |
| 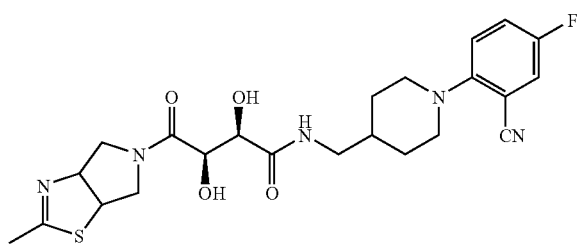 | 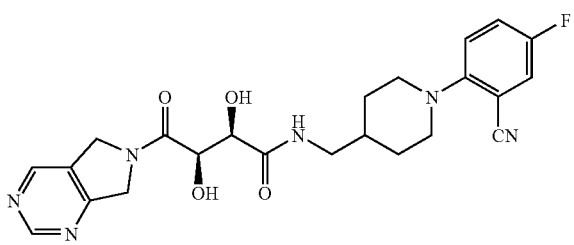 |
| 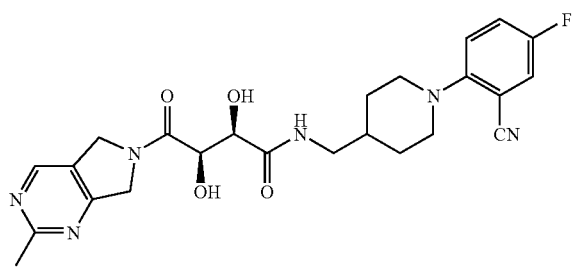 | 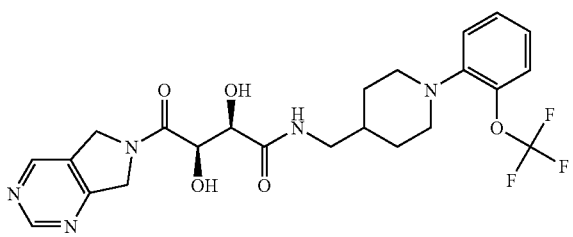 |

-continued
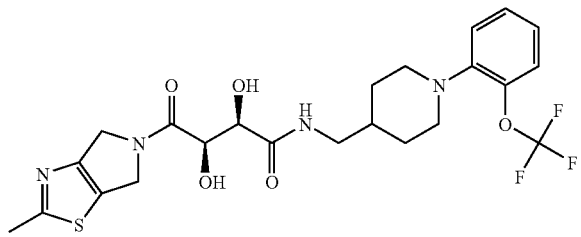
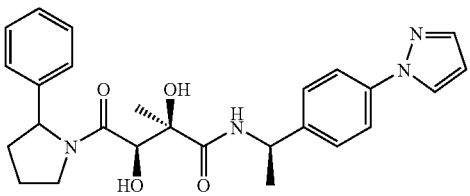
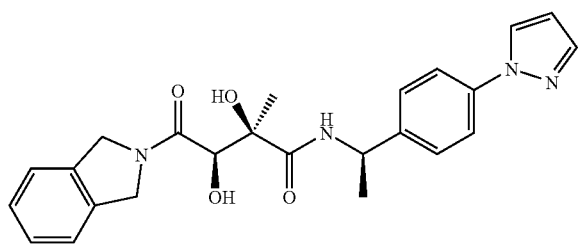
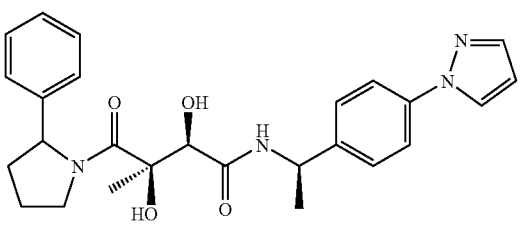
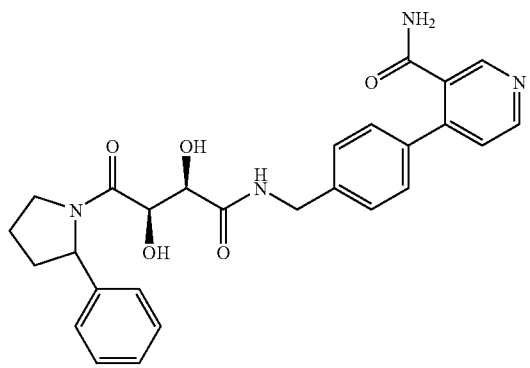
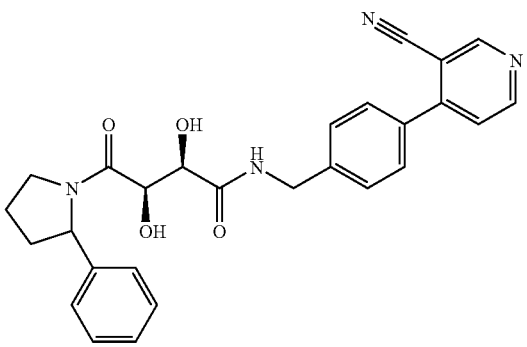
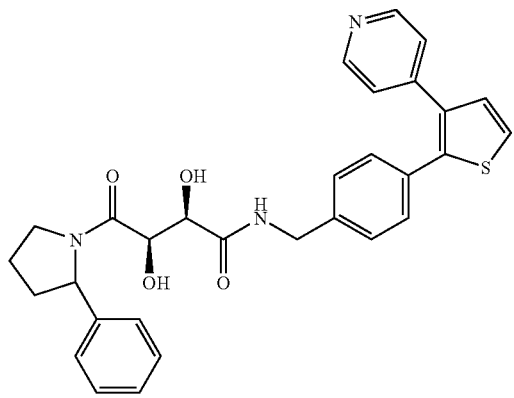
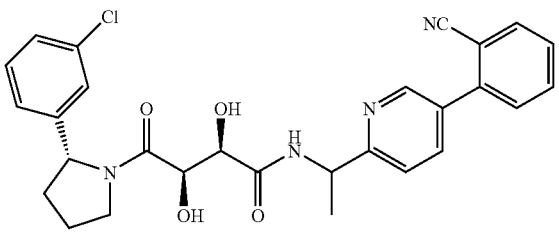
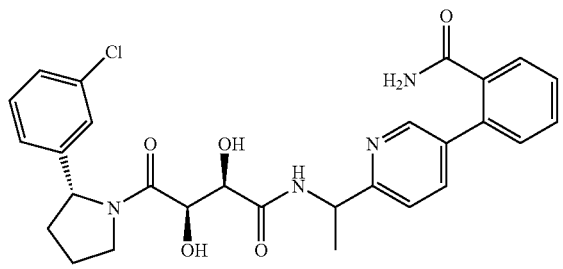
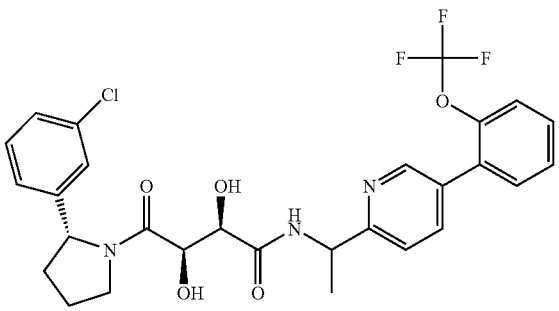

-continued
| 1551 | 1552 |
|---|---|
| 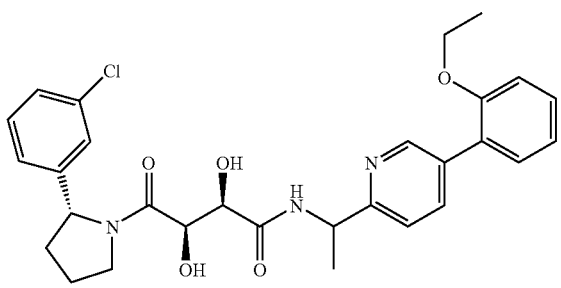 | 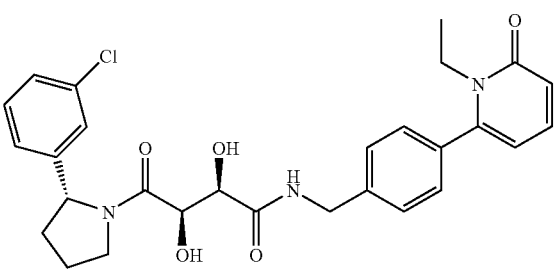 |
| 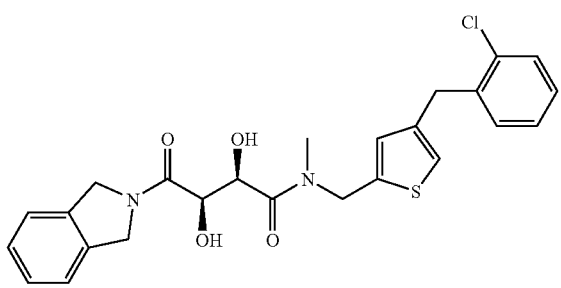 | 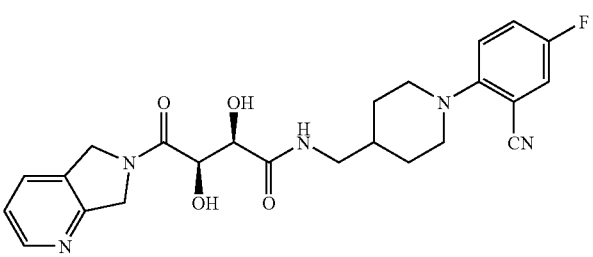 |
| 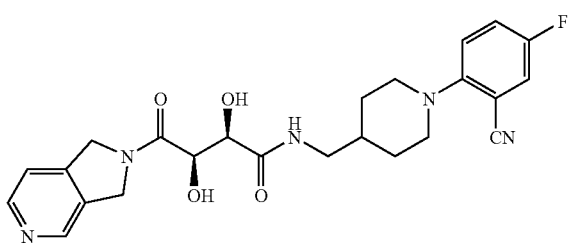 | 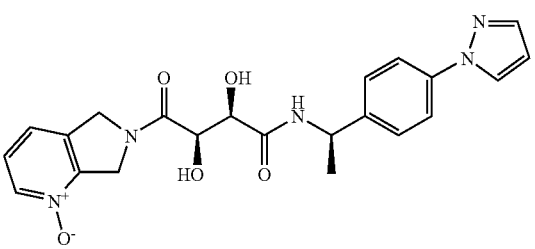 |
| 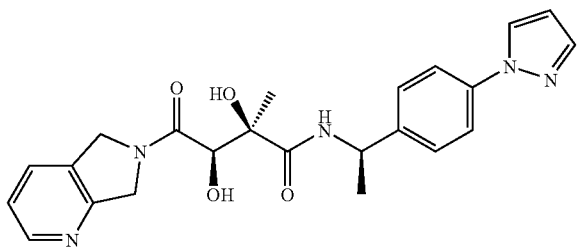 | 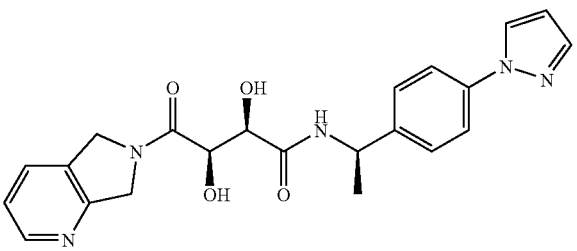 |
| 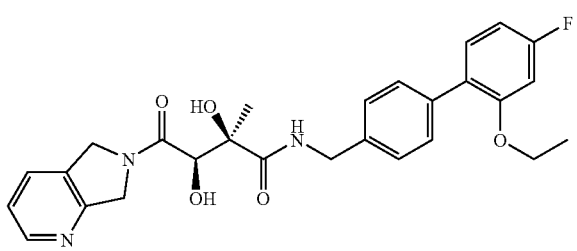 | 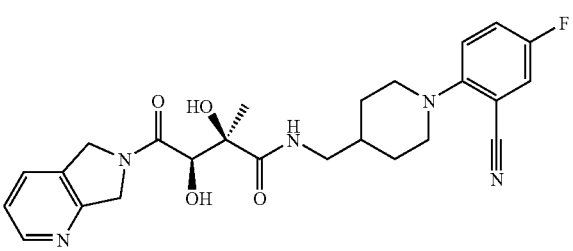 |
| 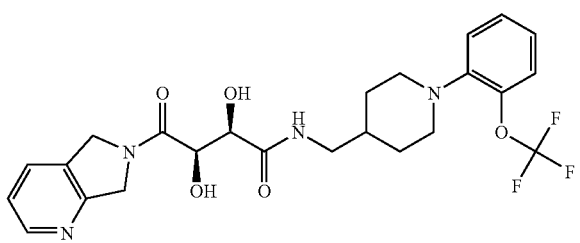 | 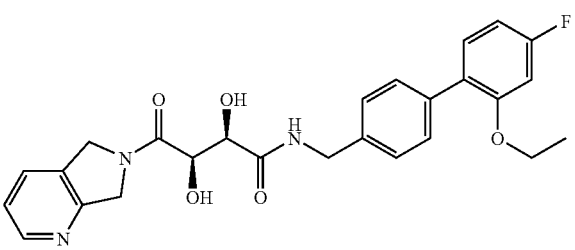 |

-continued
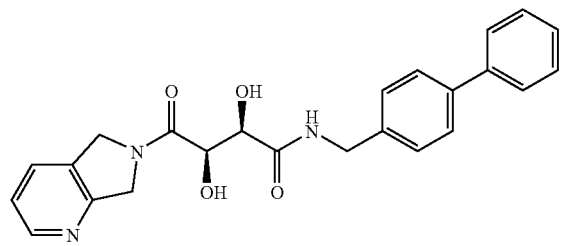
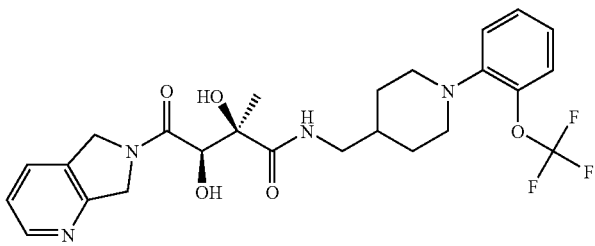
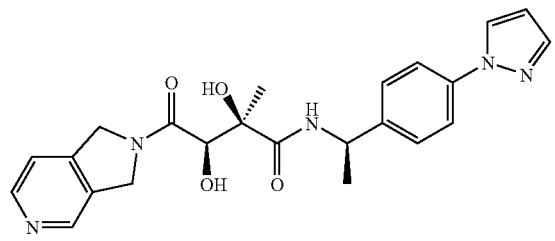
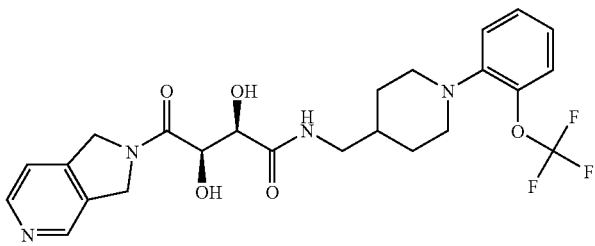
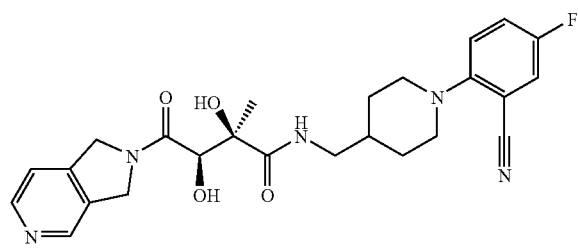
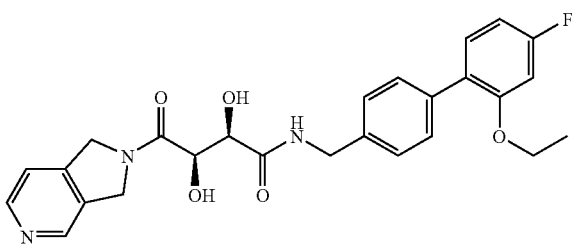
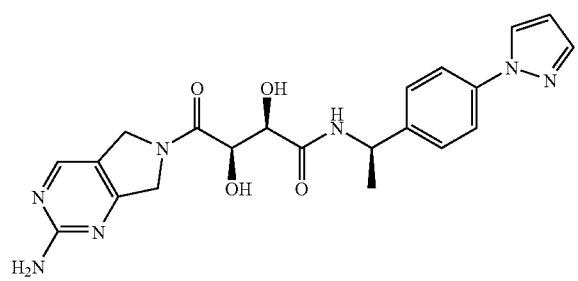
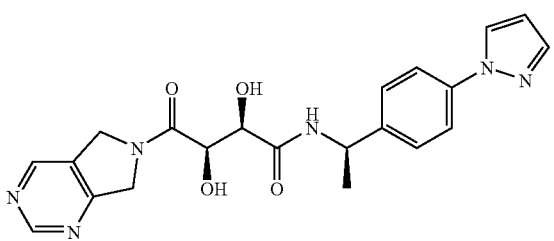
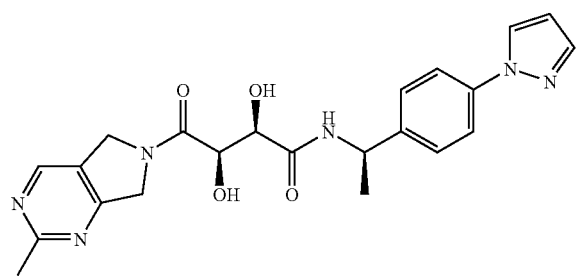
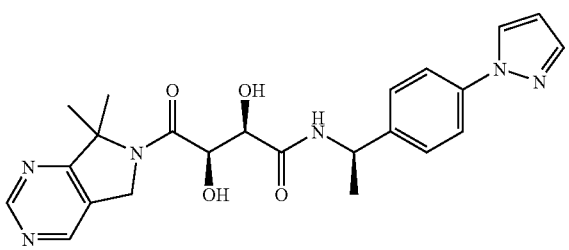
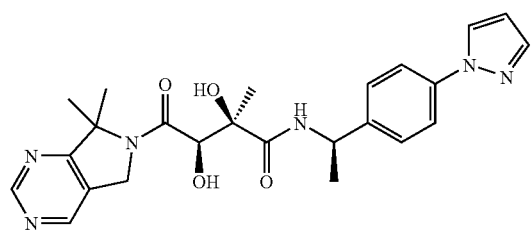
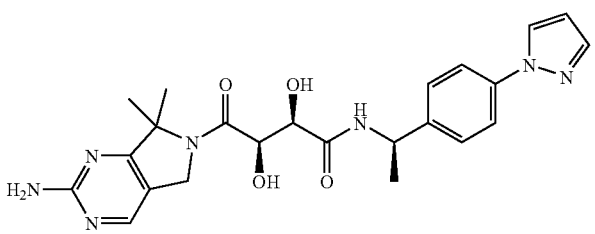

-continued
| 1555 | 1556 |
|---|---|
| 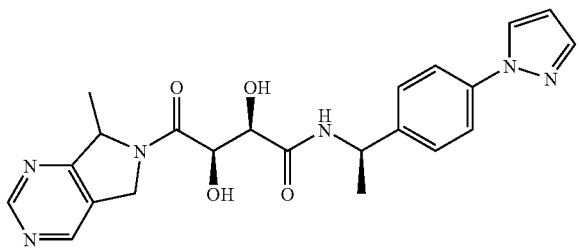 | 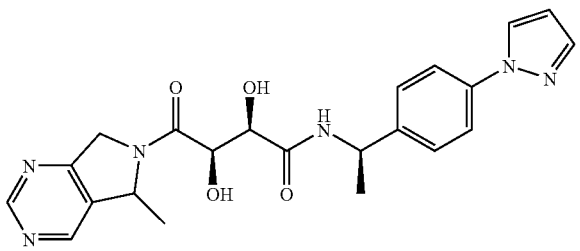 |
| 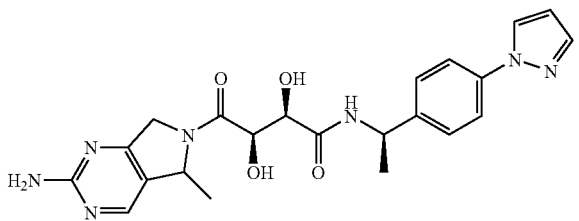 | 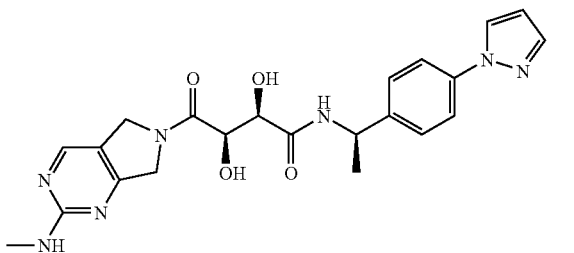 |
| 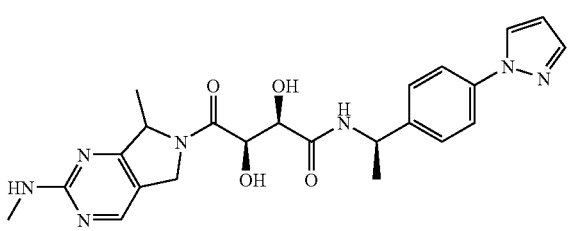 | 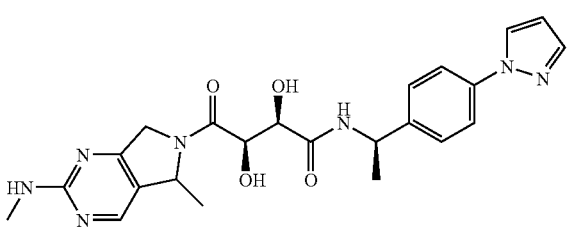 |
| 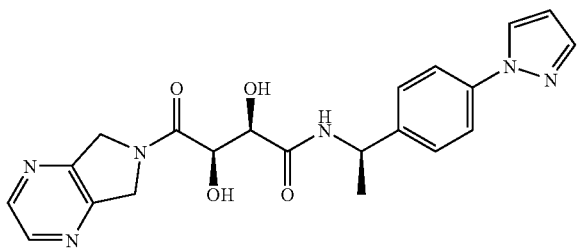 | 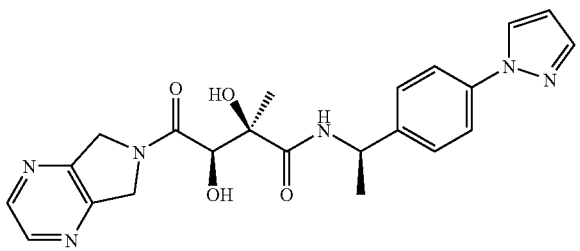 |
| 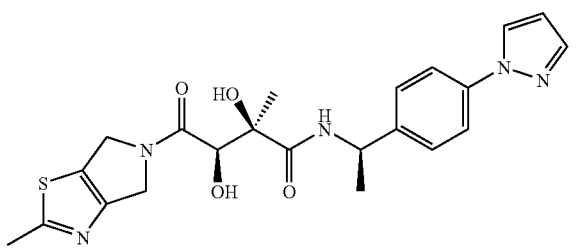 | 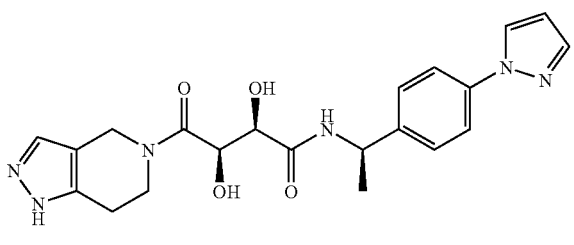 |
| 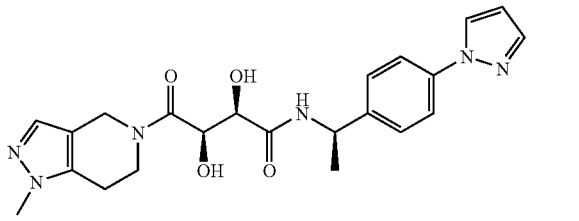 | 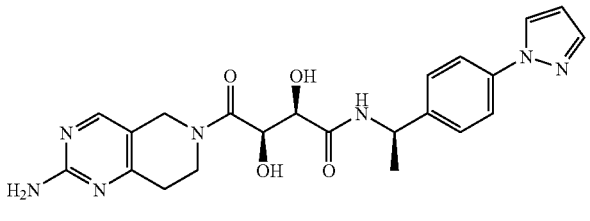 |
| 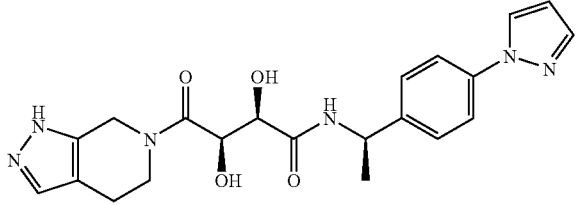 | 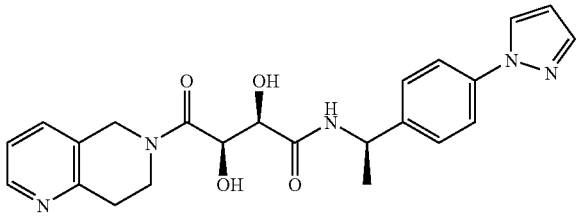 |

1557
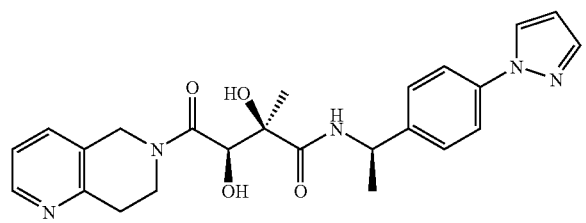
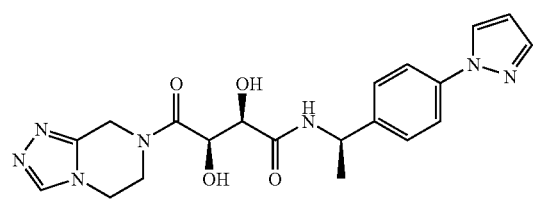
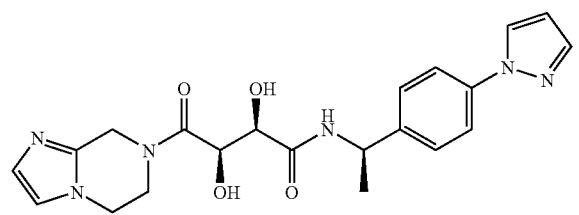
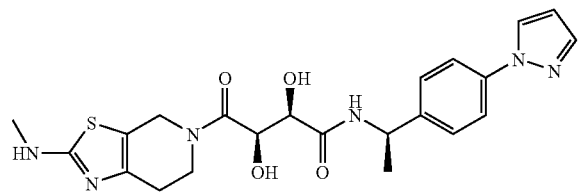
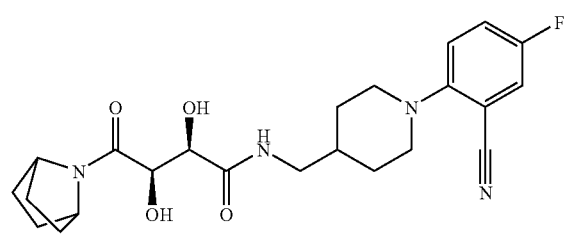
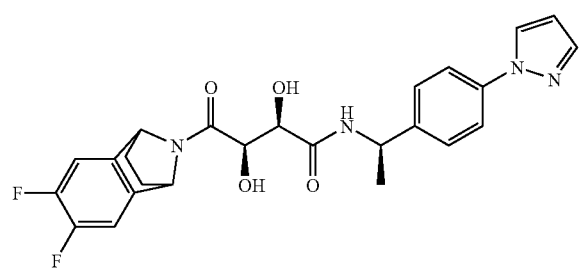
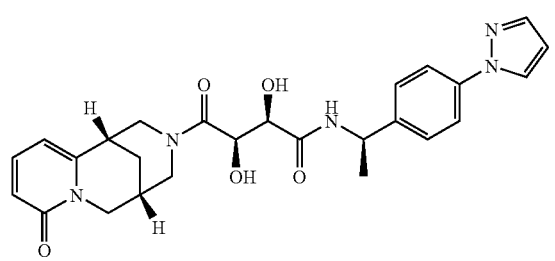
1558
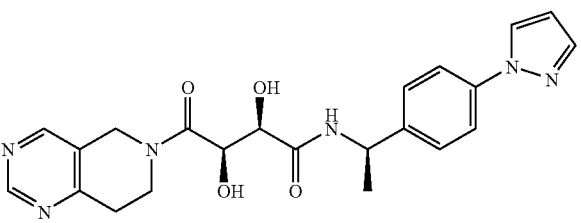
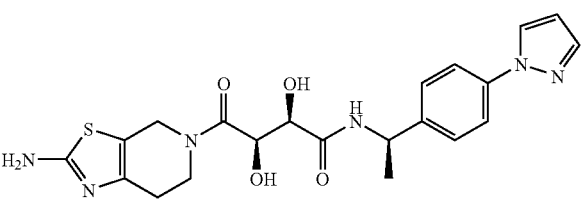
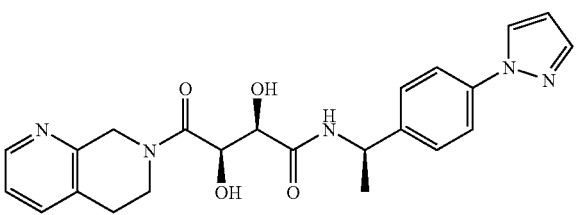
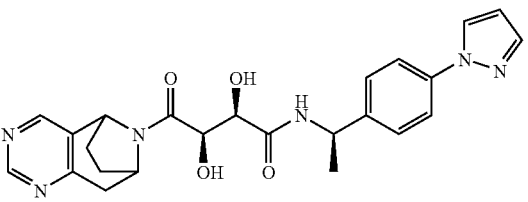
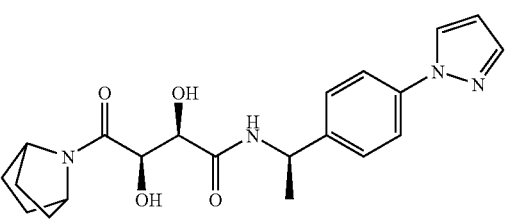
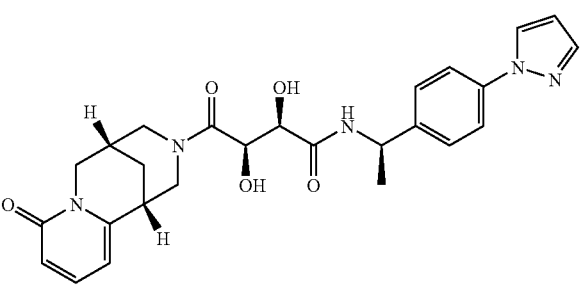
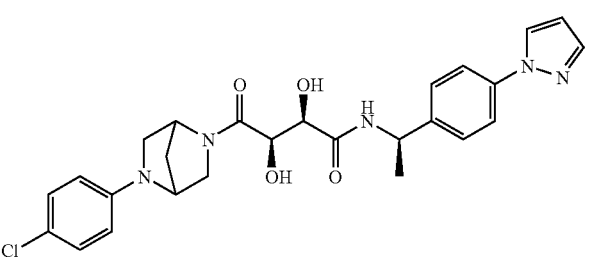

1559    -continued    1560
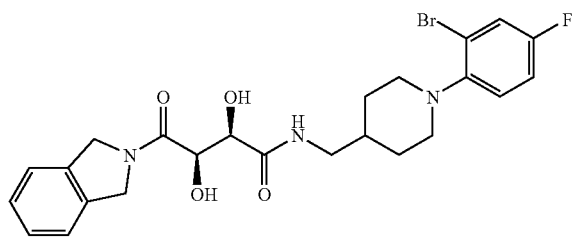
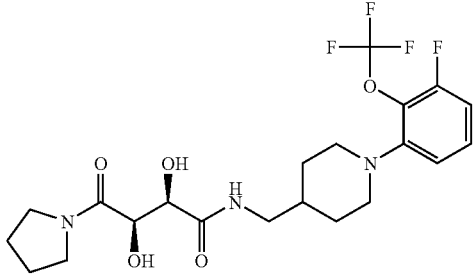
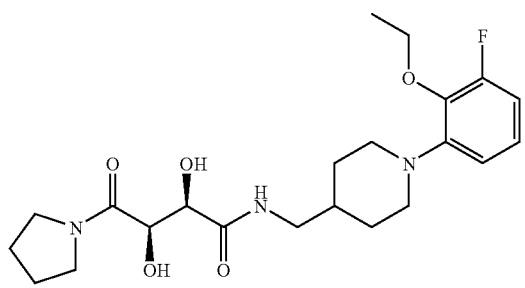
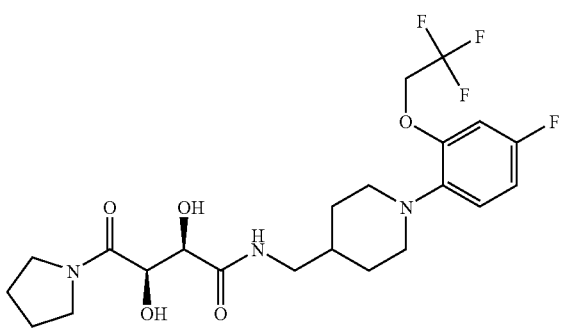
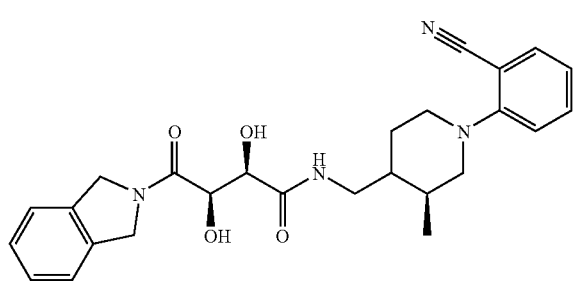
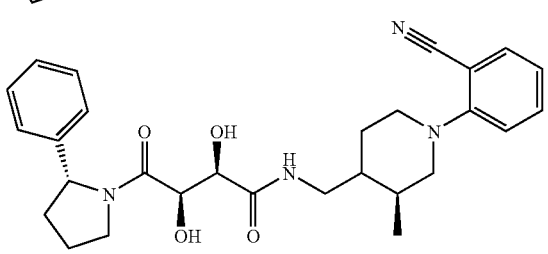
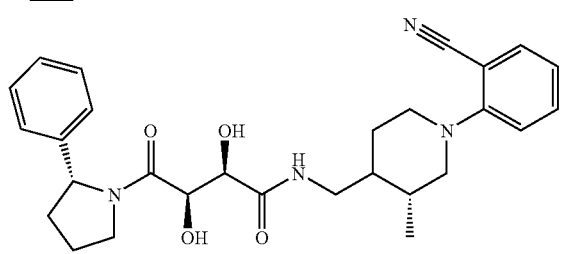
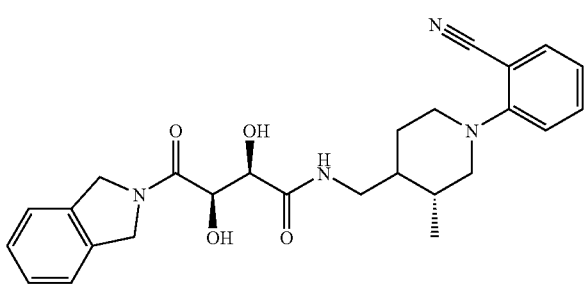
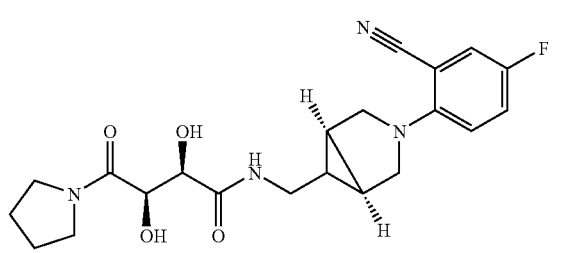
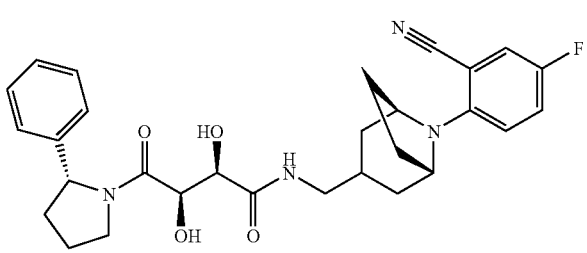
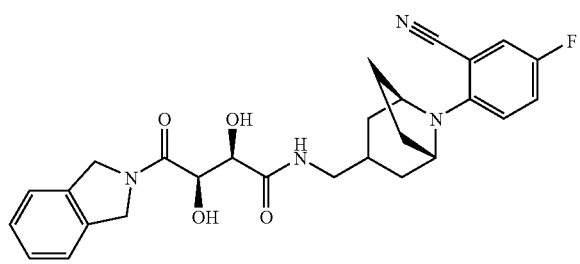
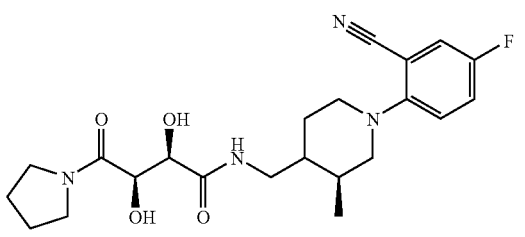

-continued
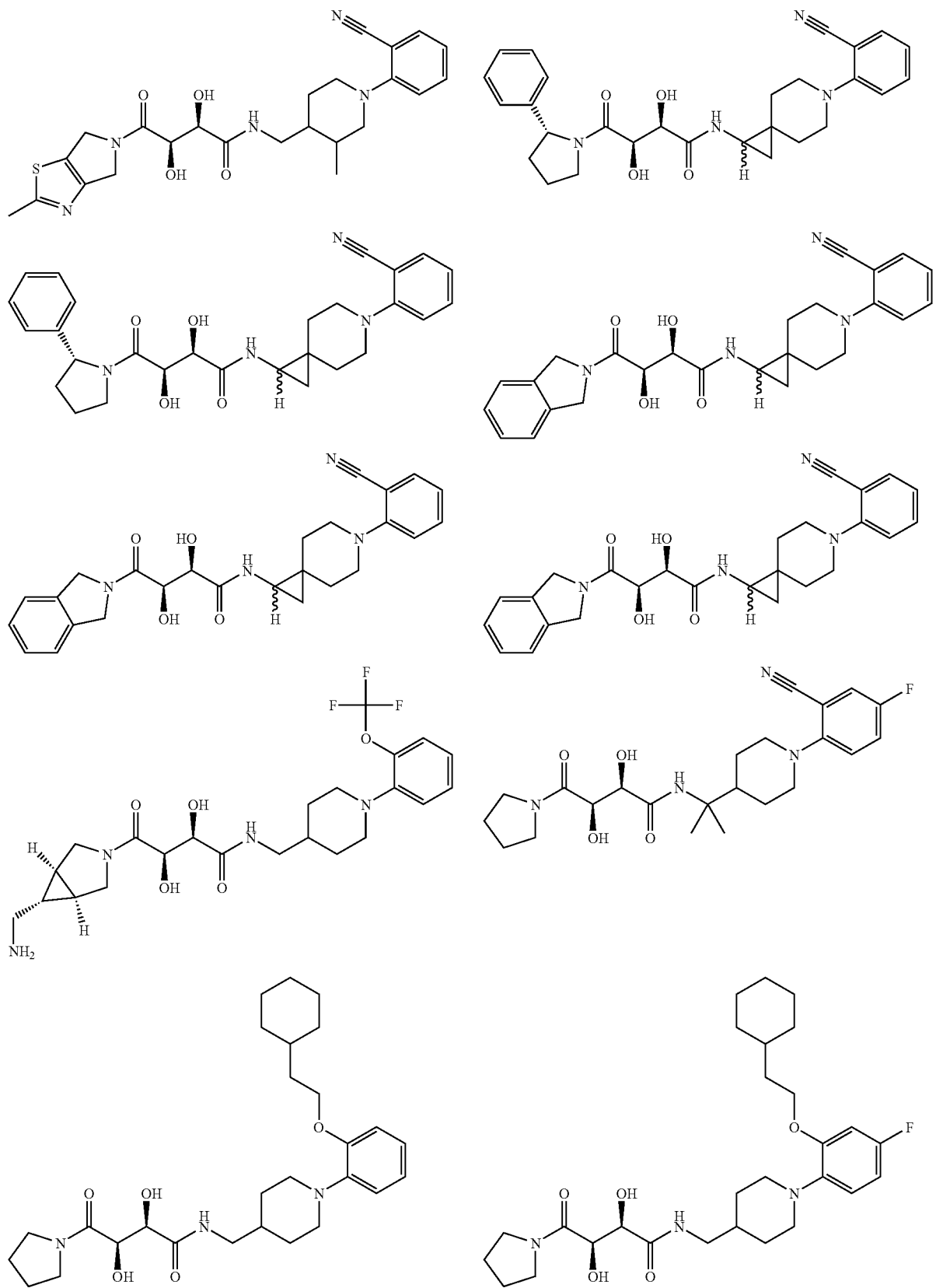

-continued
| 1563 | 1564 |
|---|---|
| 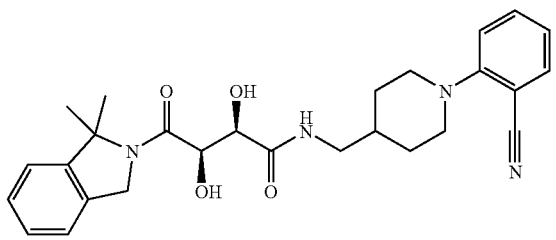 | 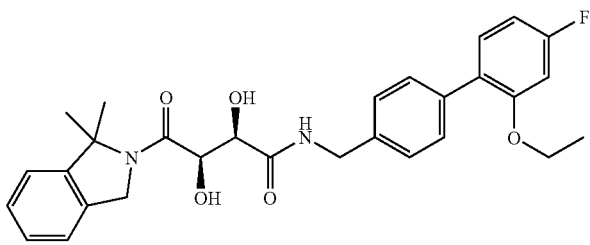 |
| 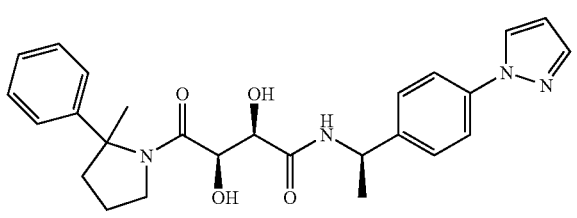 | 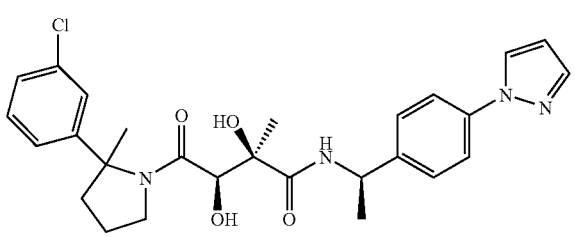 |
| 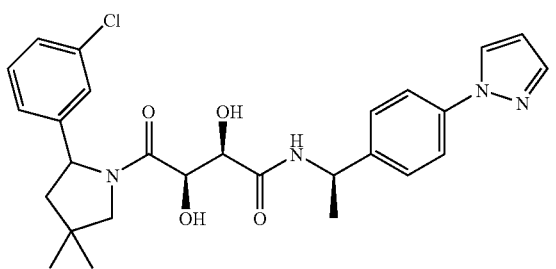 | 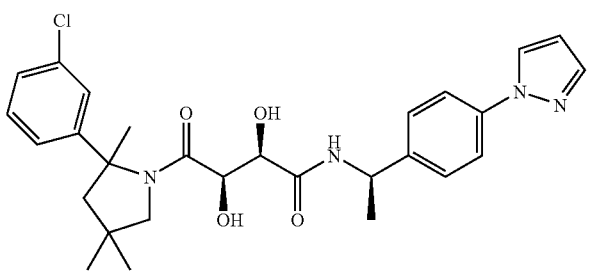 |
| 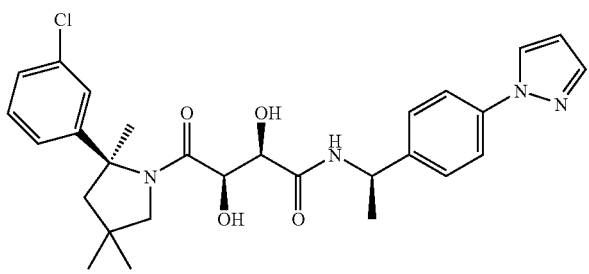 | 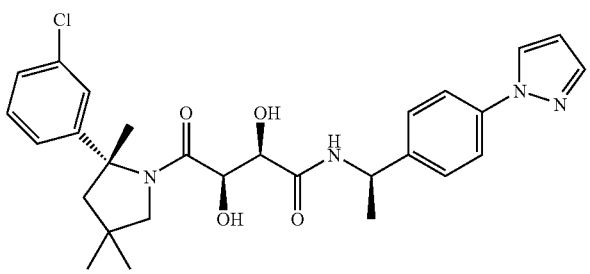 |
| 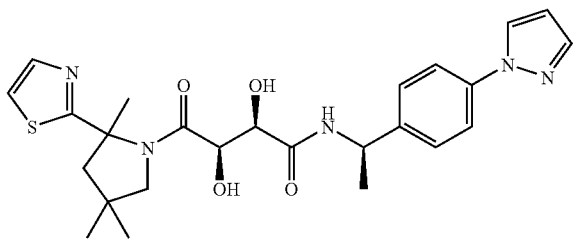 | 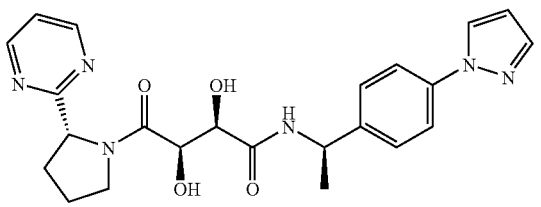 |
| 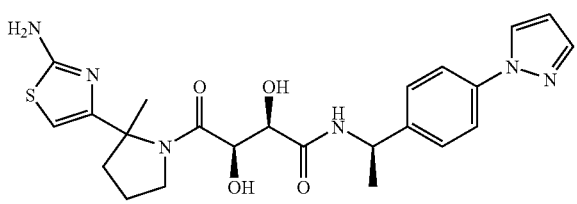 | 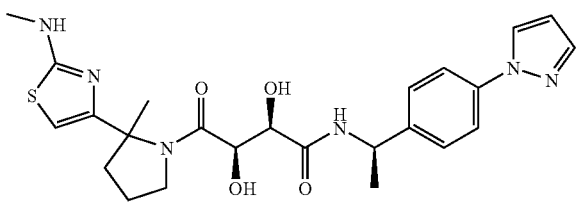 |

1565
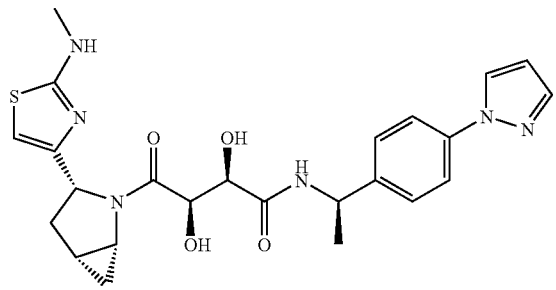
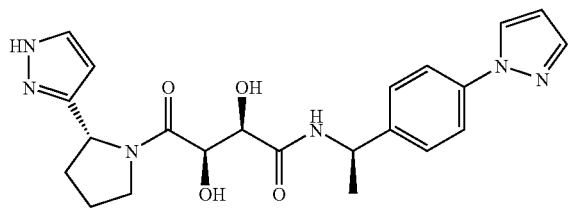
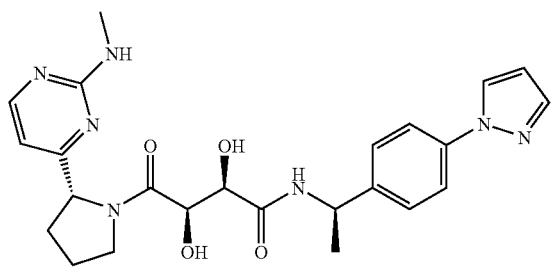
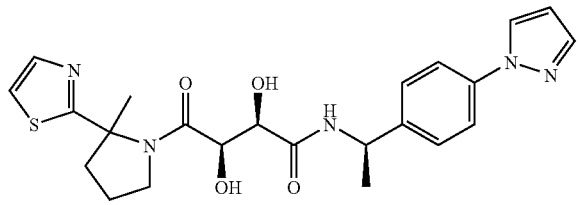
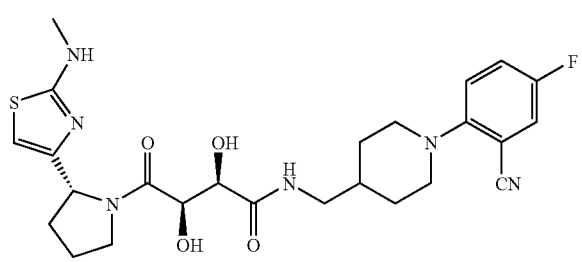
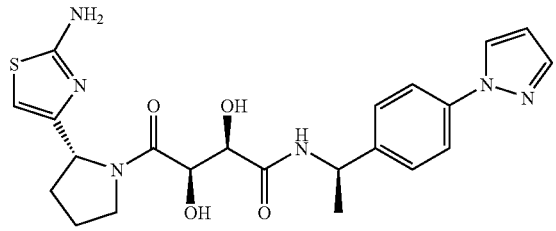
-continued
1566
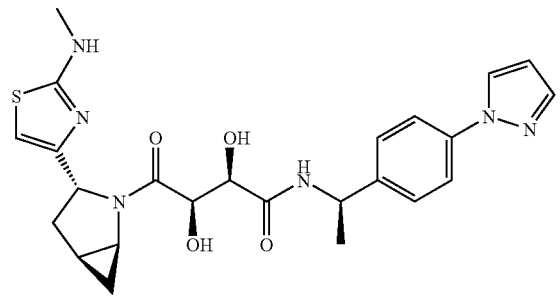
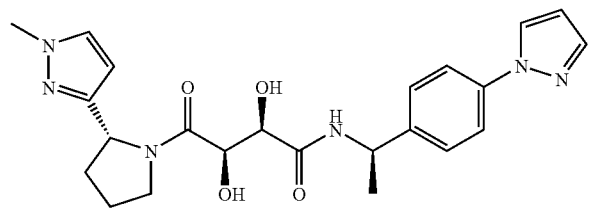
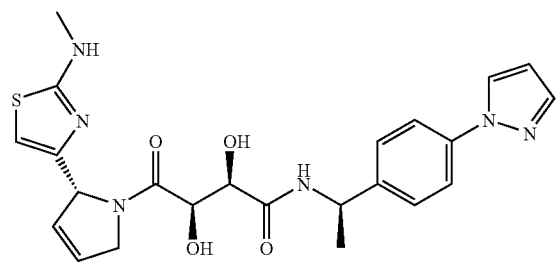
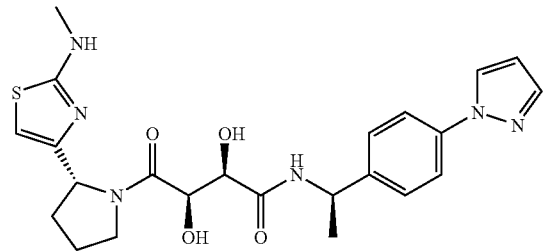
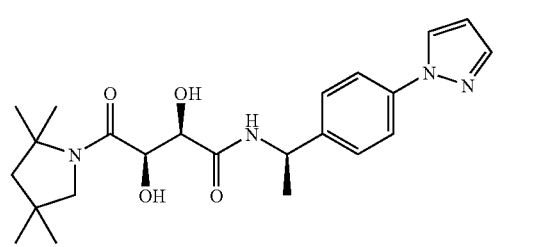
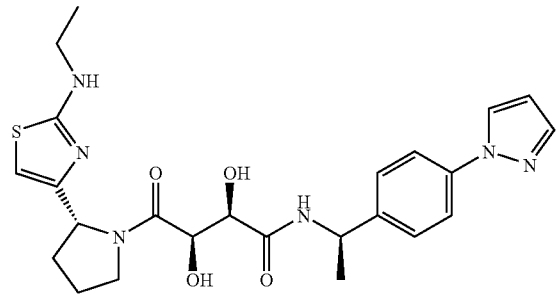

1567 1568
-continued
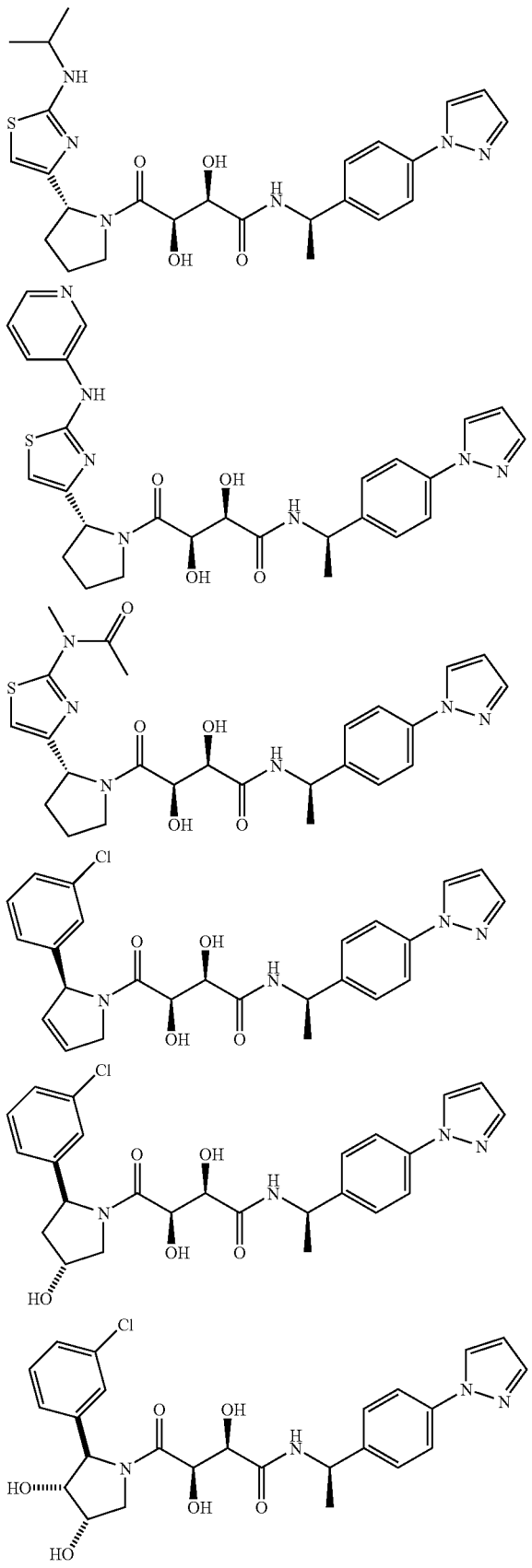
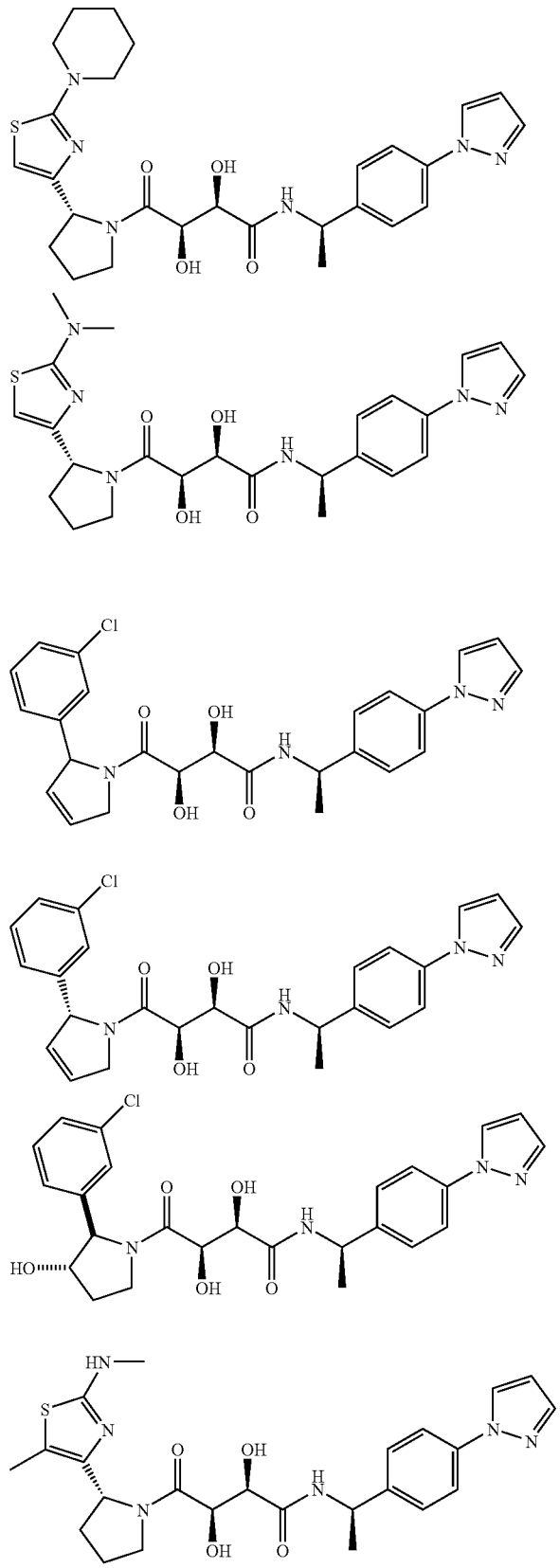

-continued
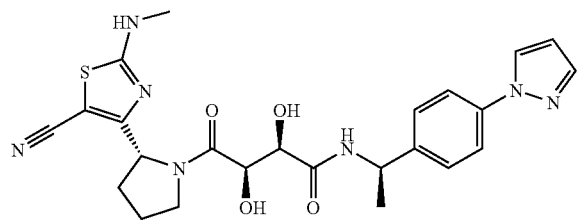
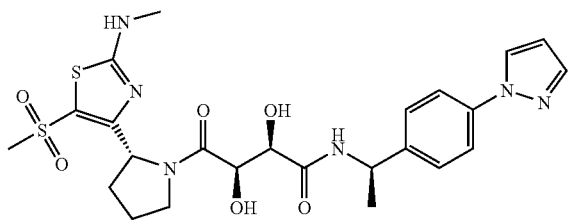
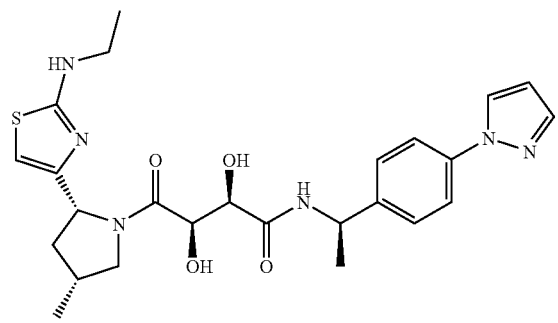
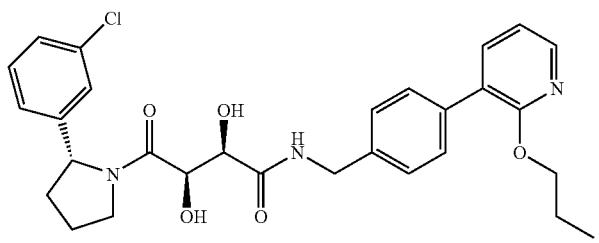
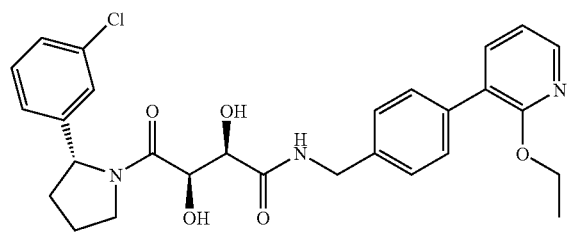
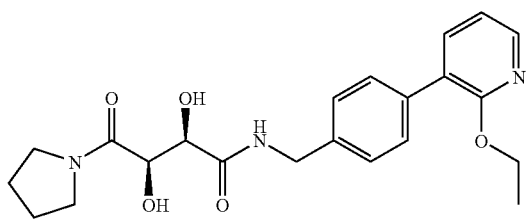
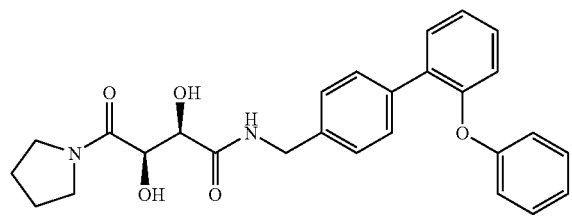
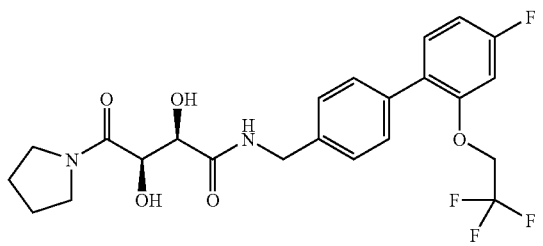
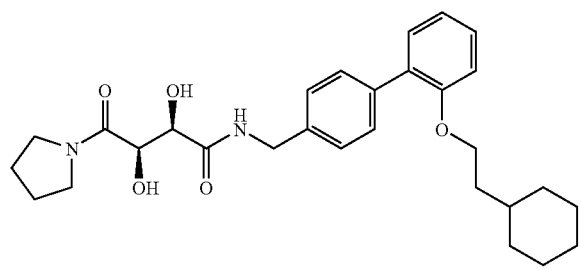
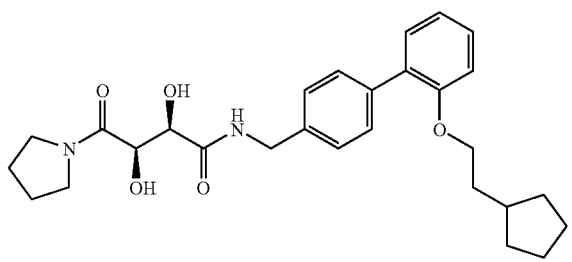
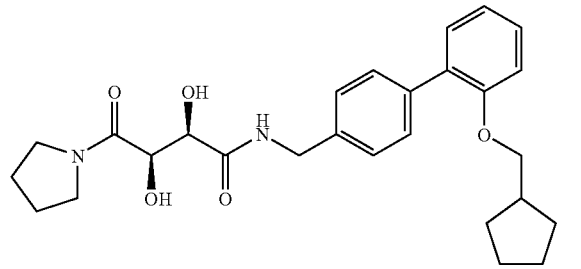
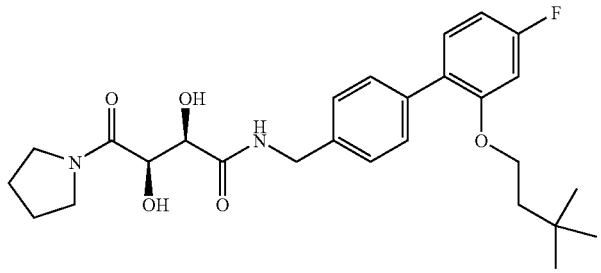

1571
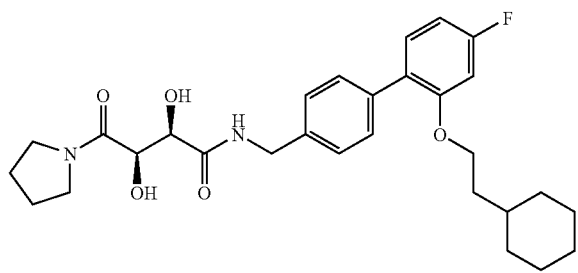
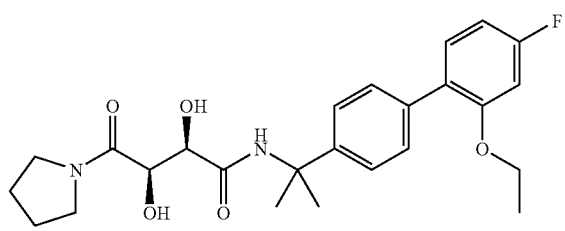
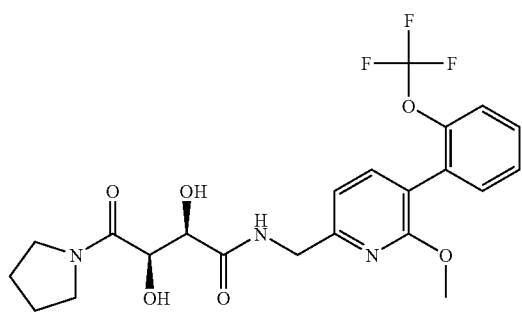
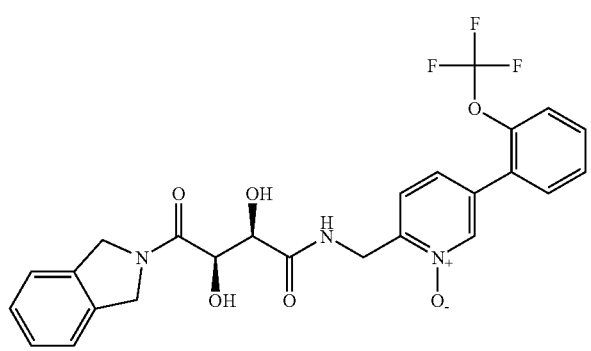
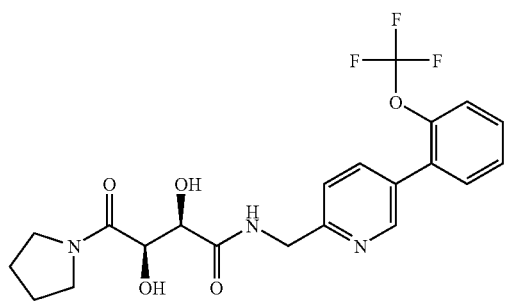
1572
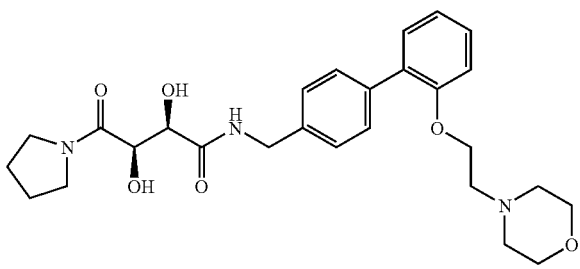
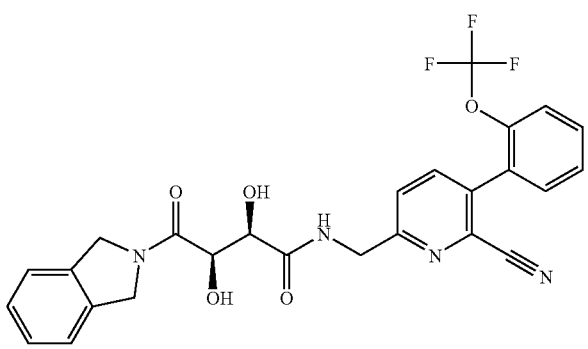
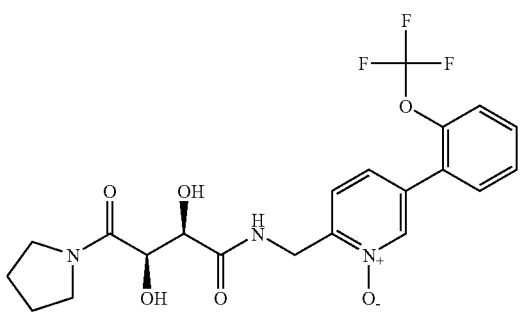
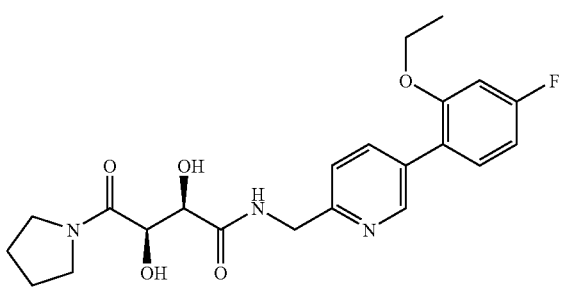
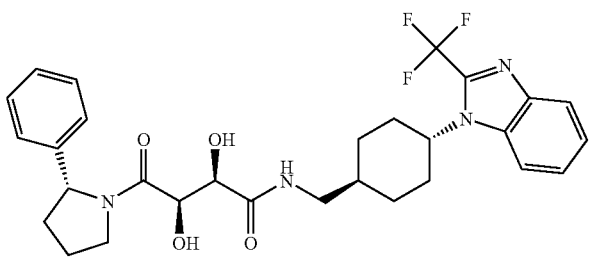

1573    1574
-continued
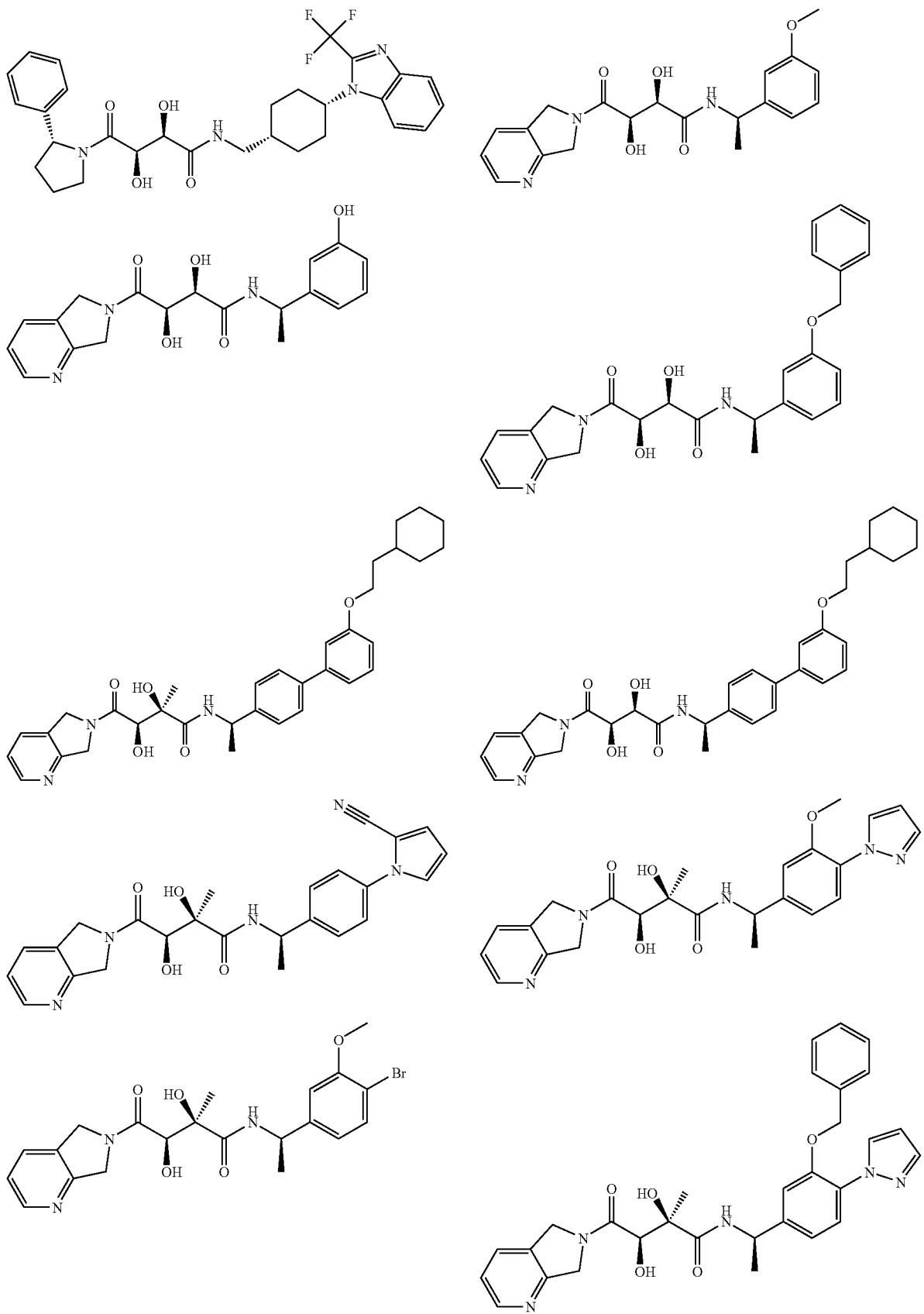

-continued
1575
1576
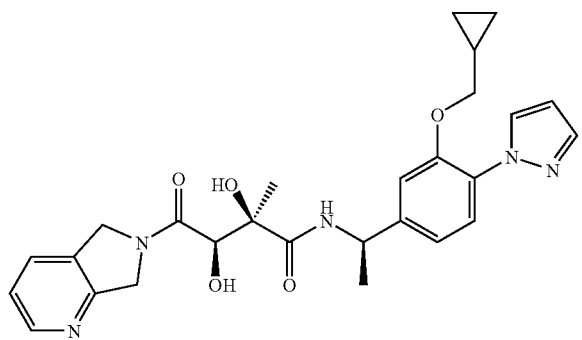
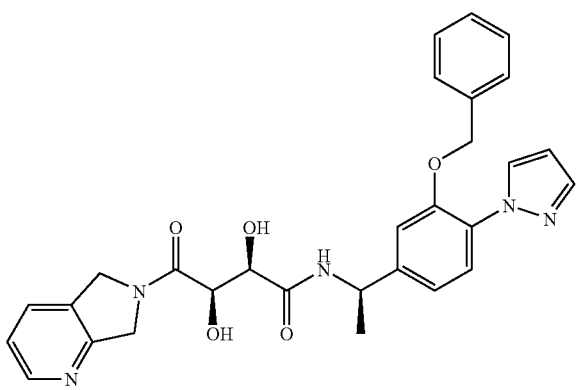
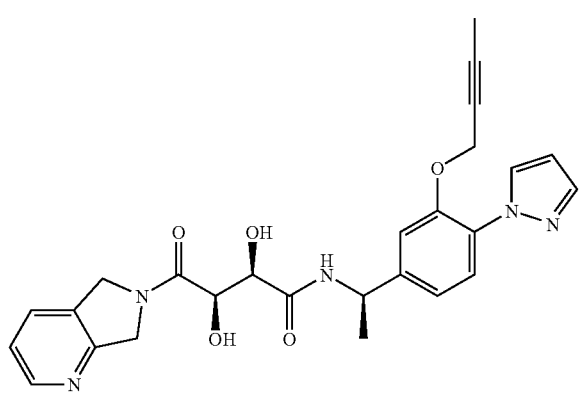
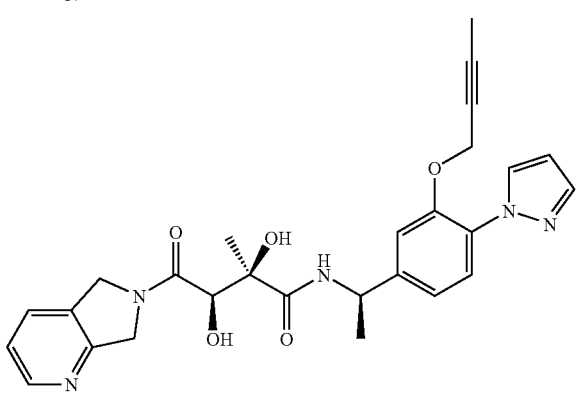
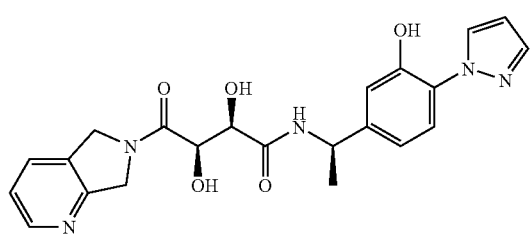
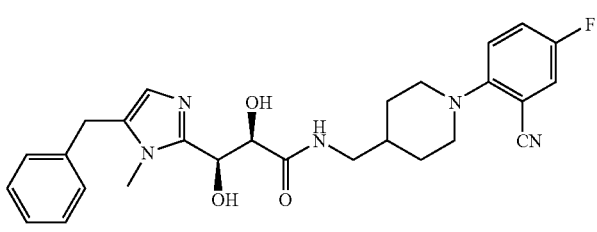
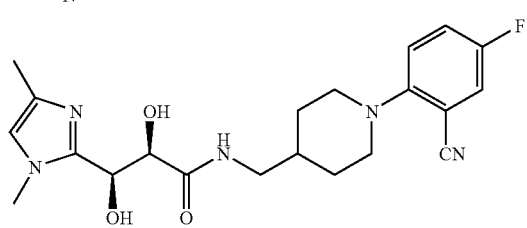
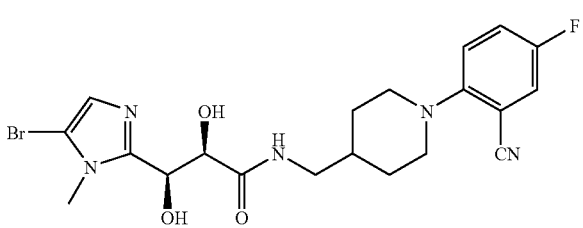
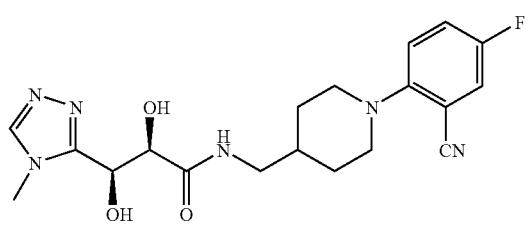
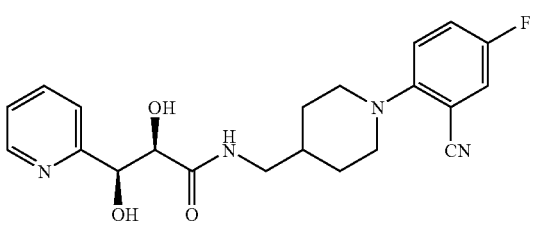
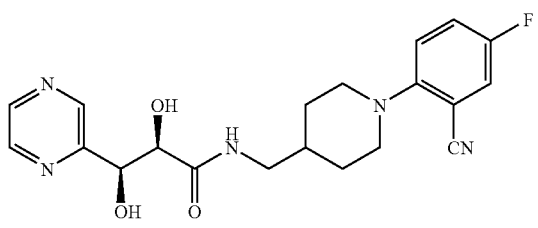
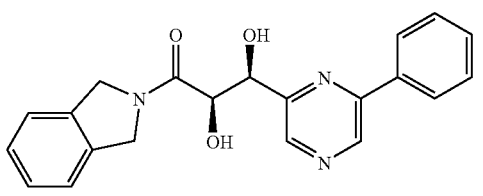

1577
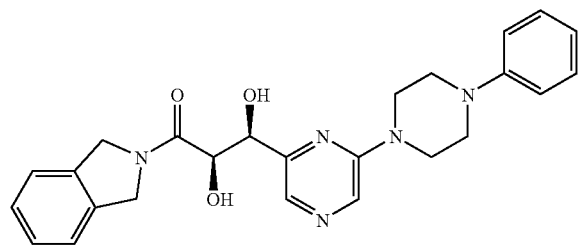
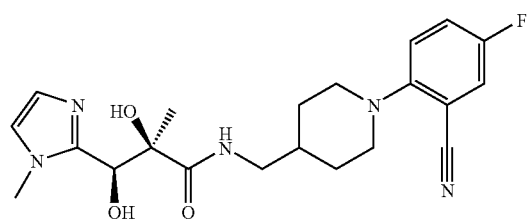
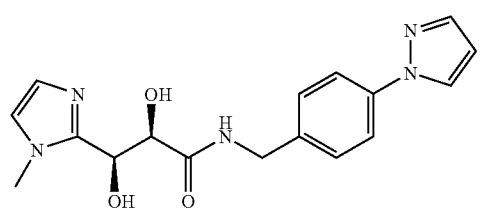
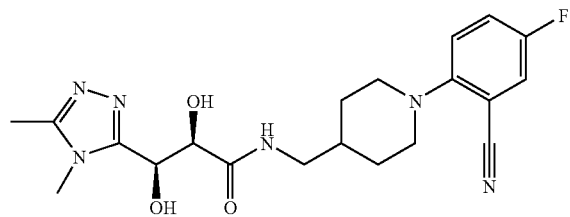
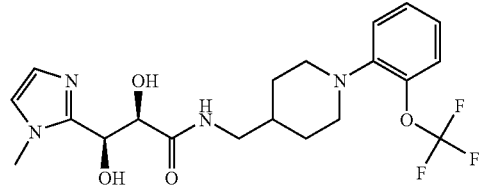
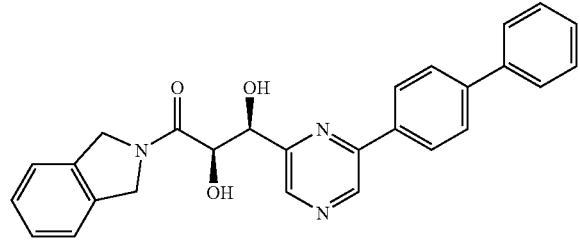
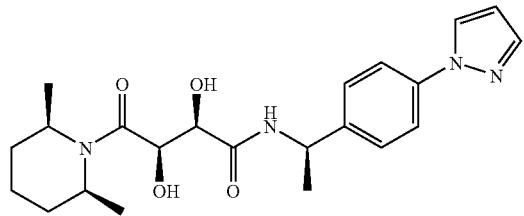
1578
-continued
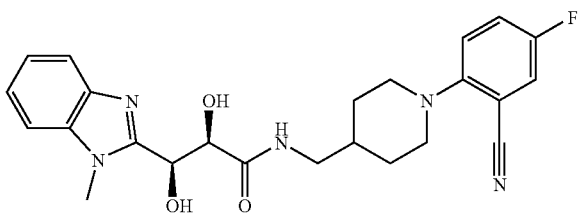
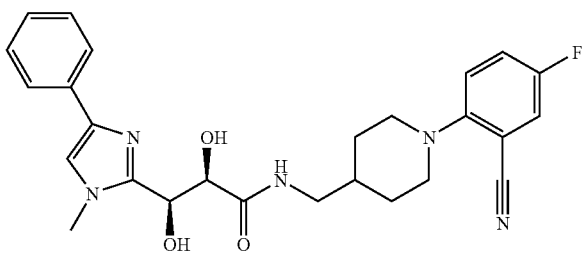
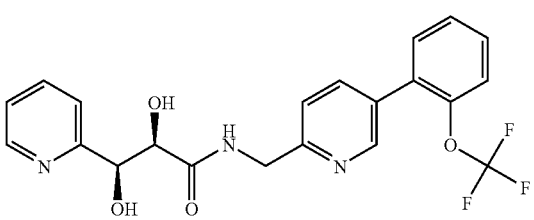
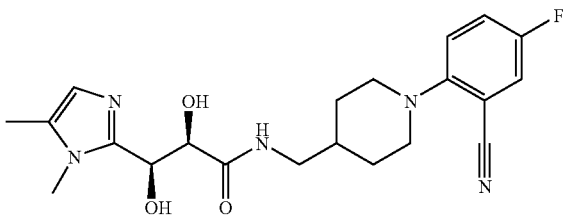
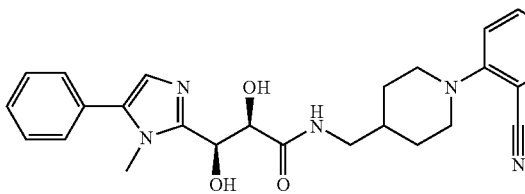
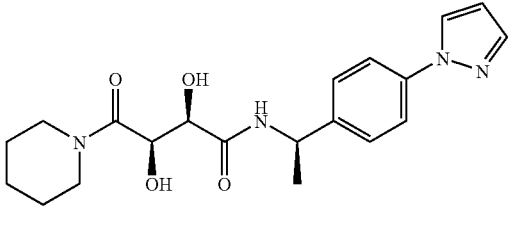
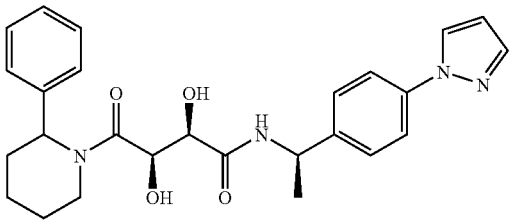

1579
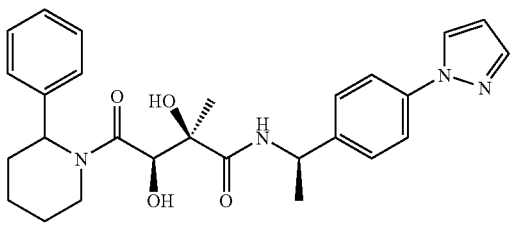
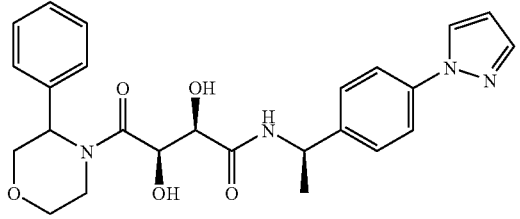
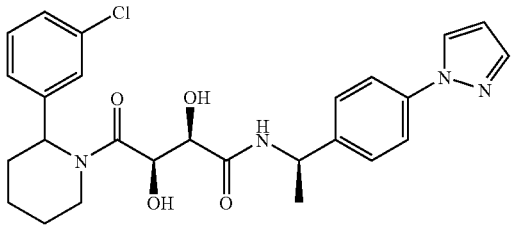
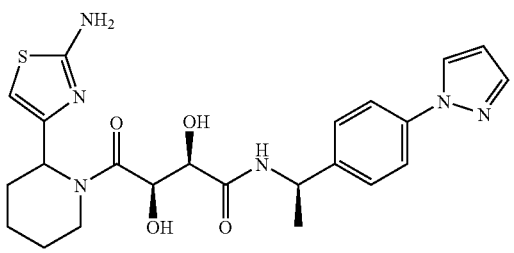
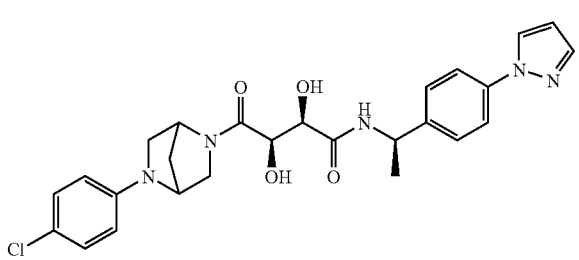
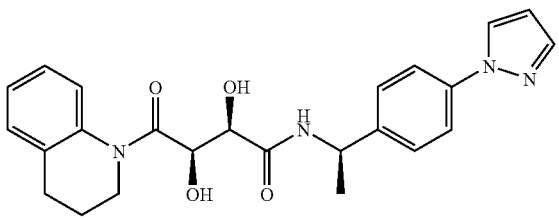
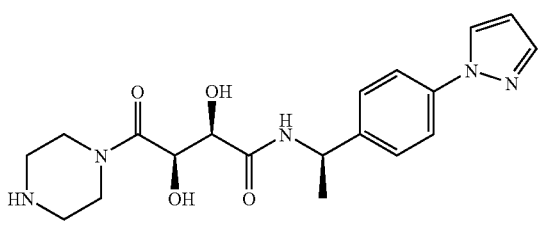
1580
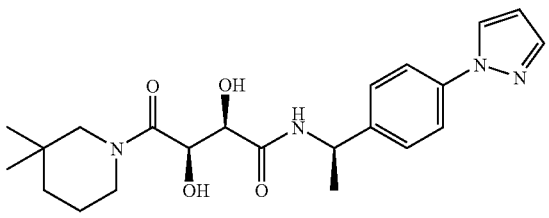
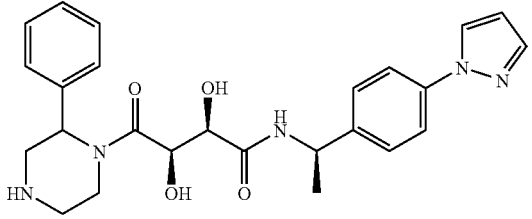
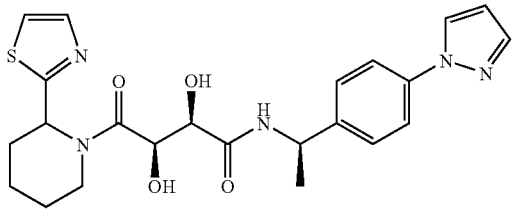
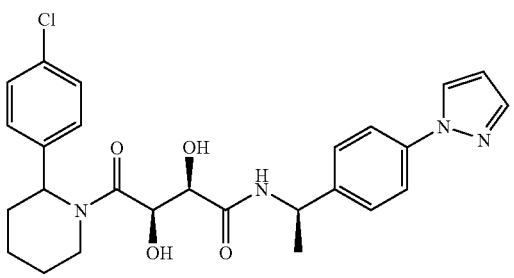
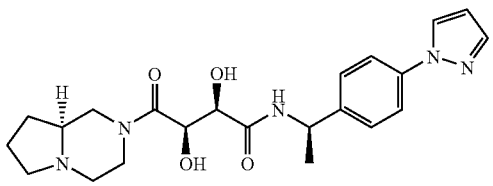
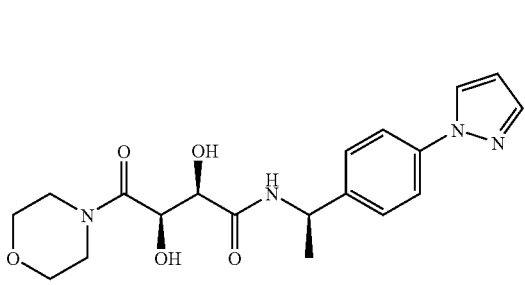
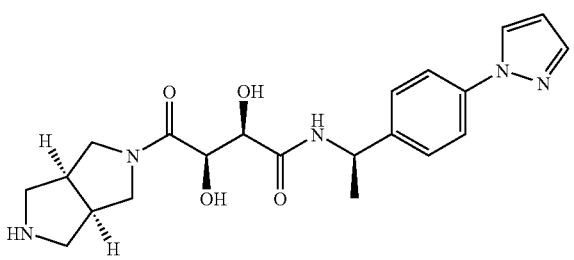

-continued
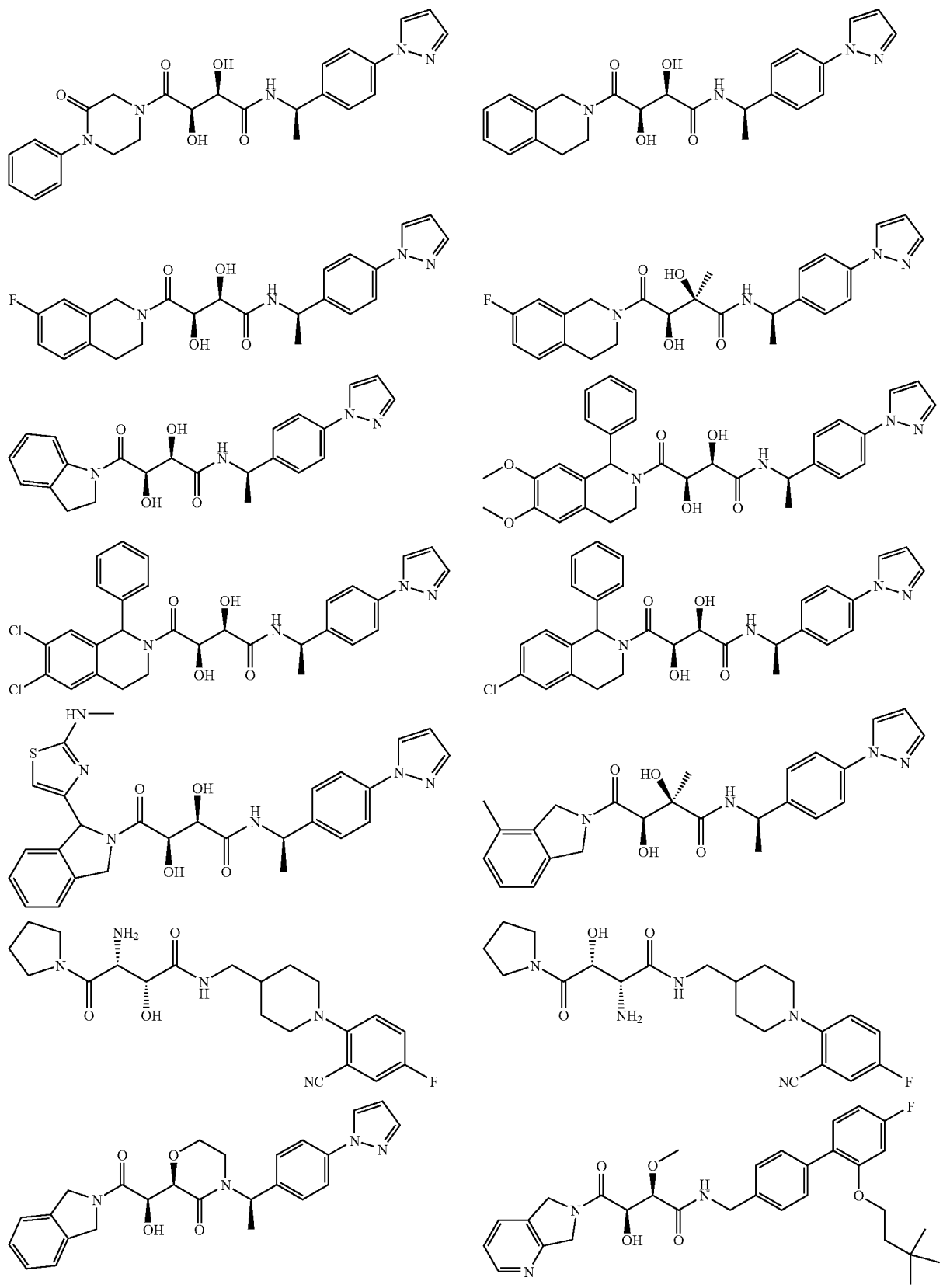

1583
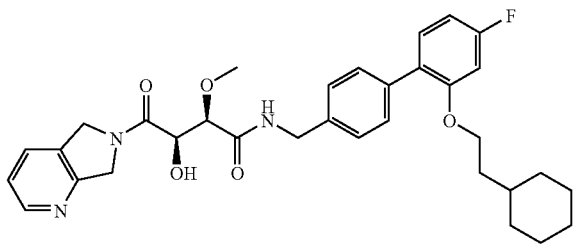
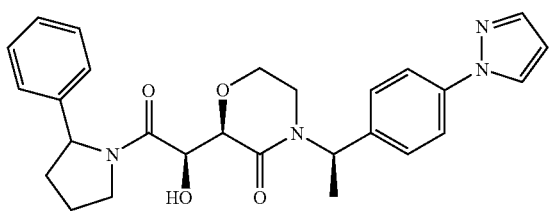
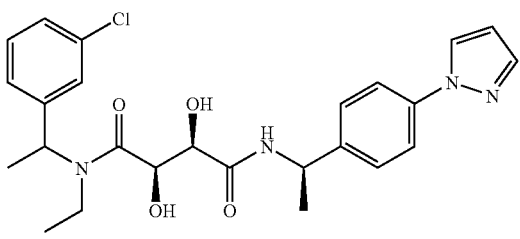
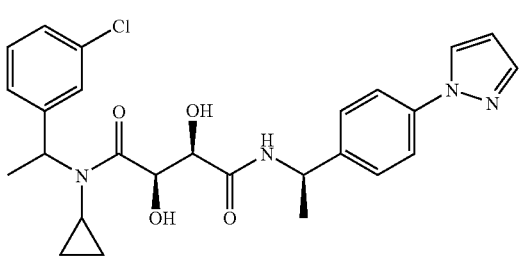
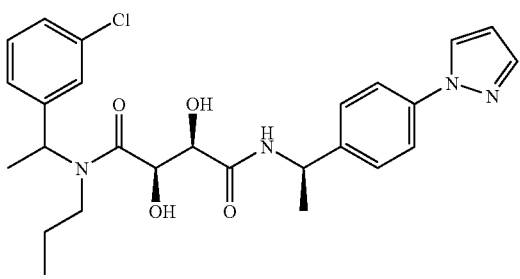
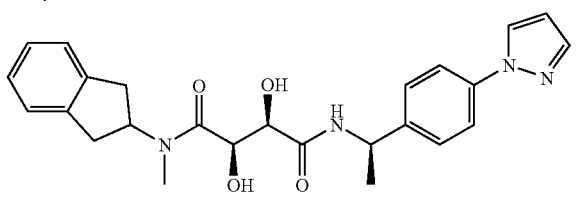
1584
-continued
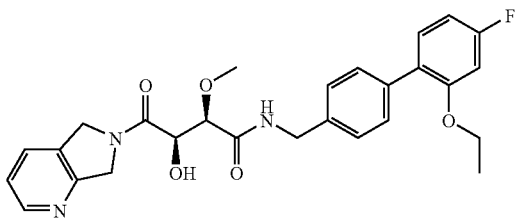
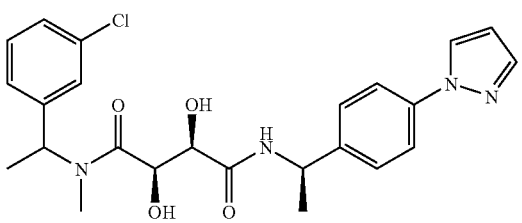
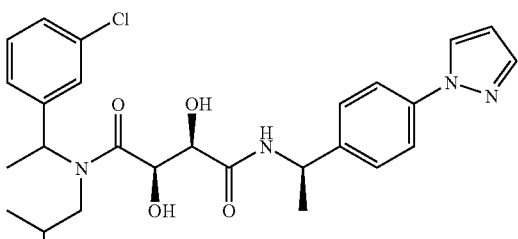
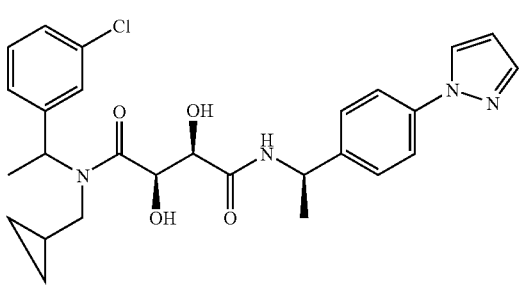
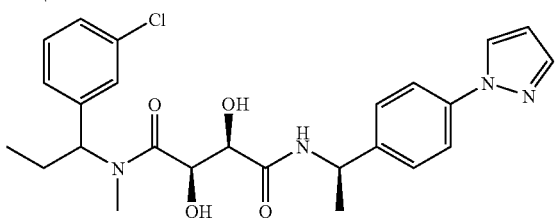
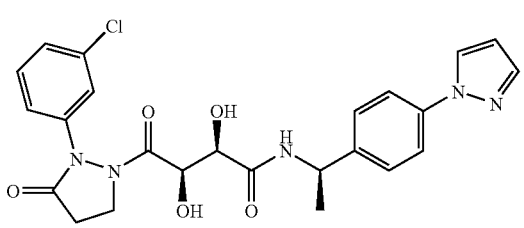

1585
1586
-continued
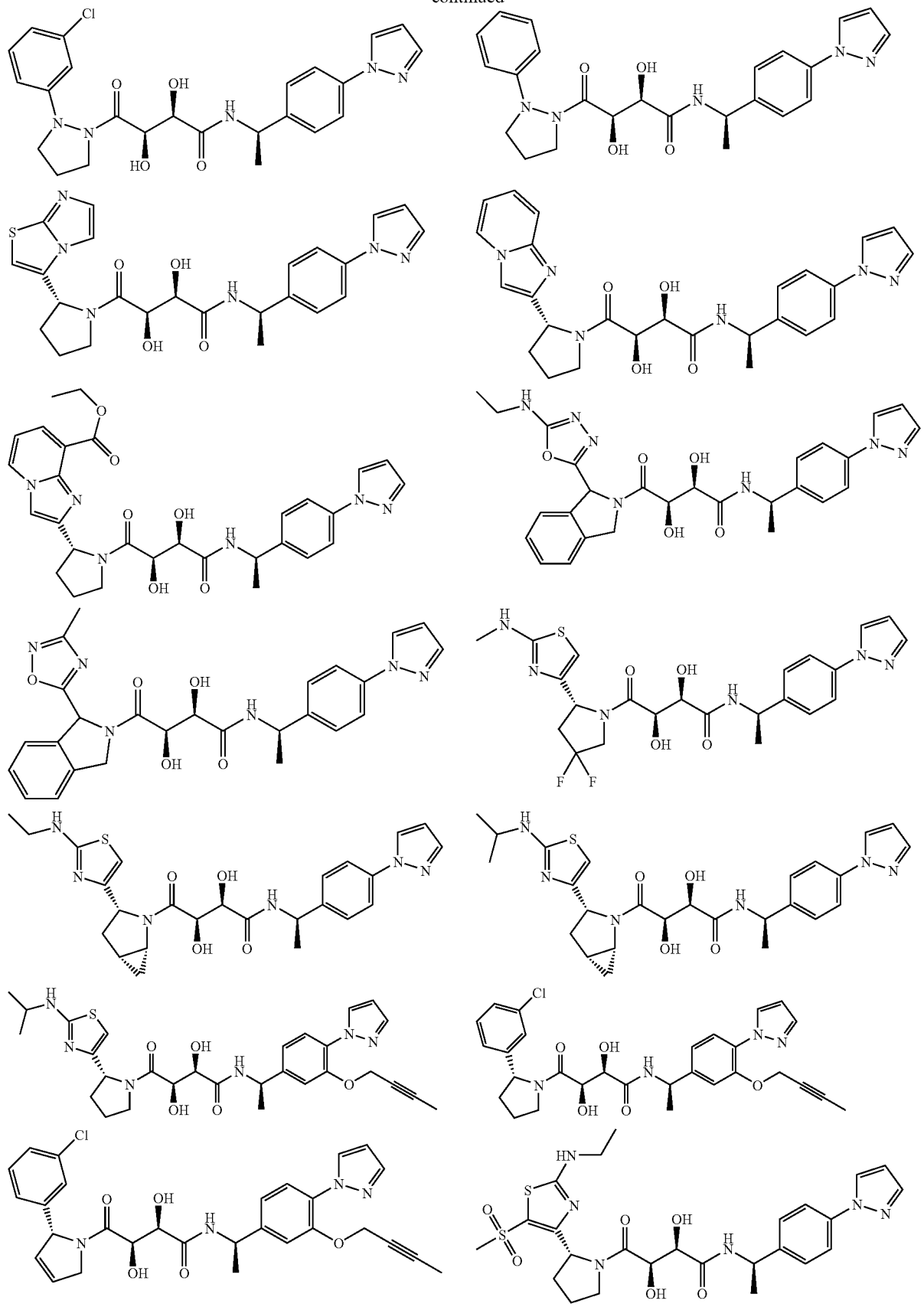

1587 | 1588
-continued
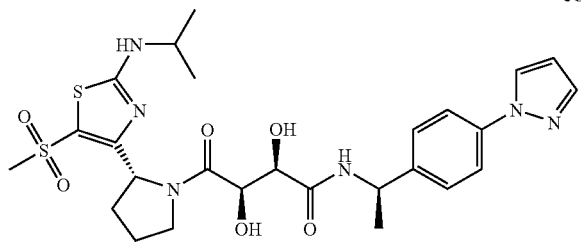
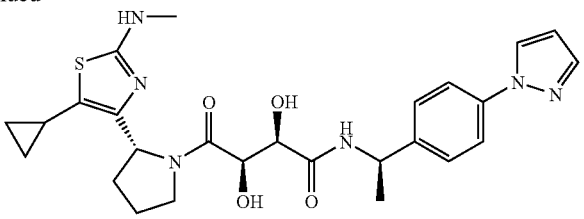
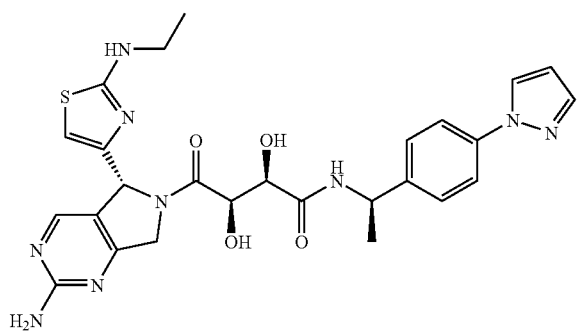
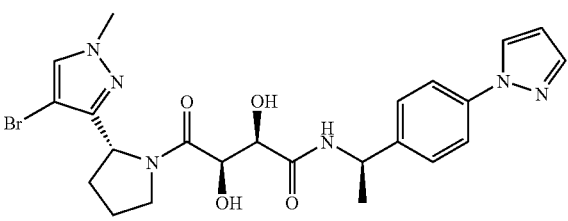
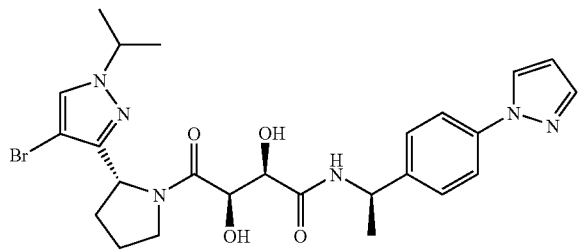
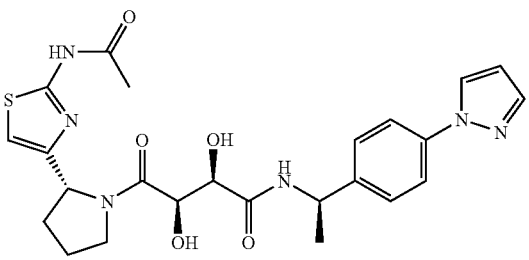
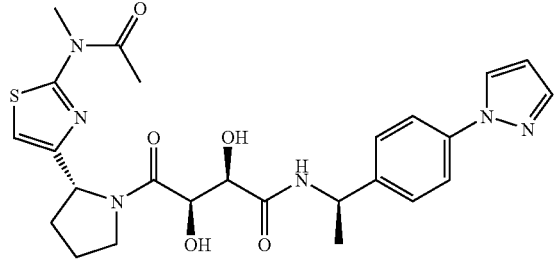
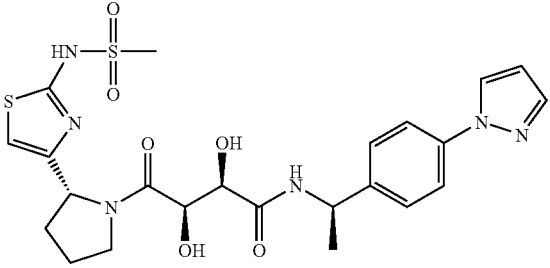
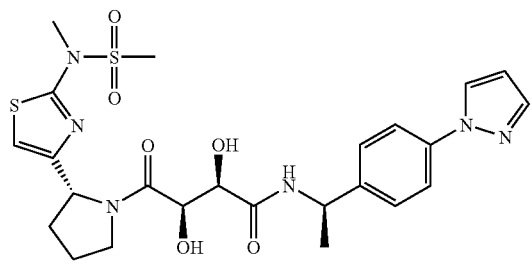
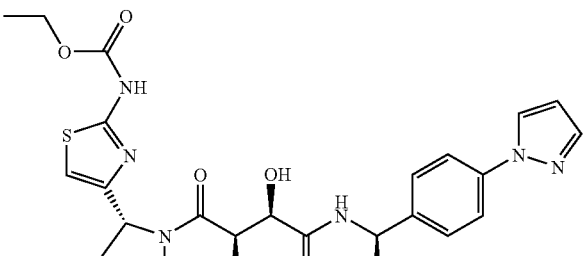
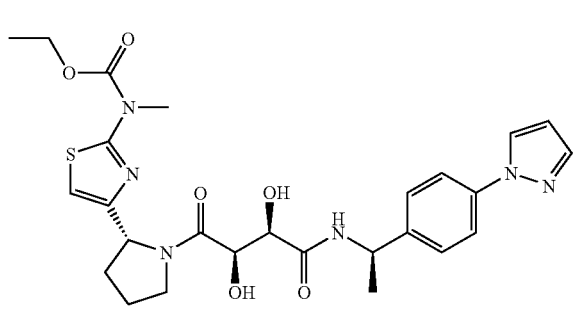
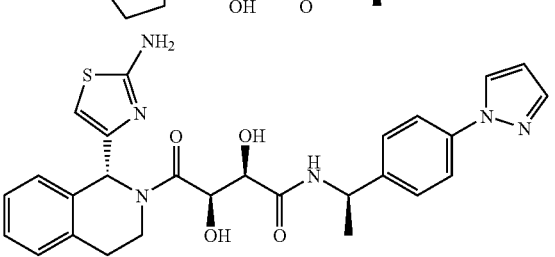

-continued
| 1589 | 1590 |
|---|---|
| 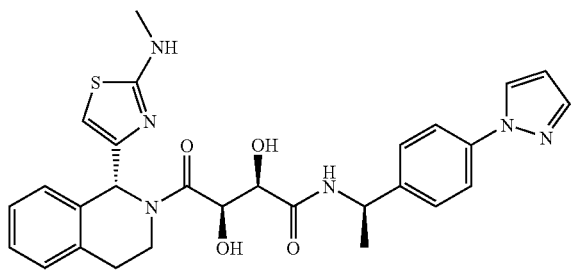 | 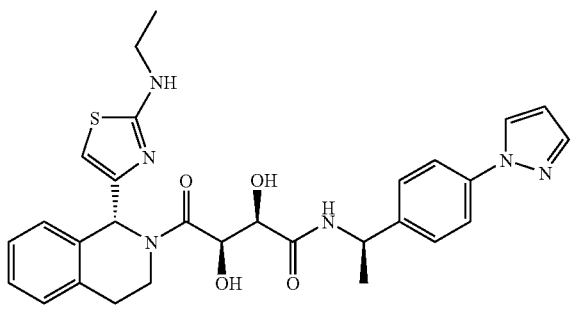 |
| 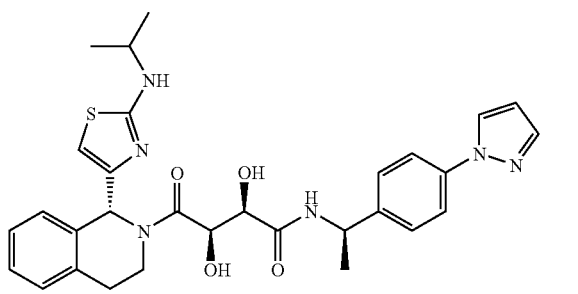 | 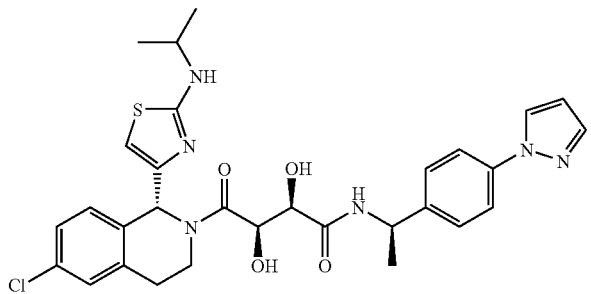 |
| 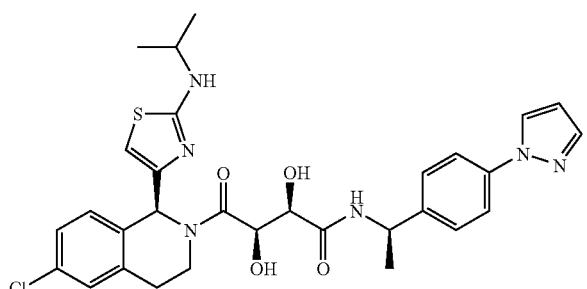 | 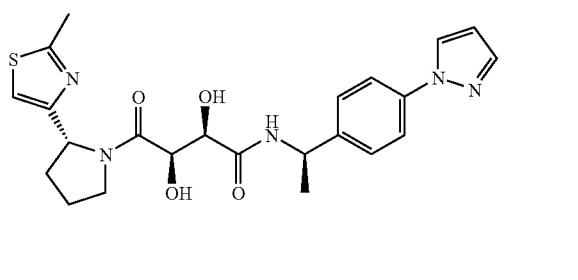 |
| 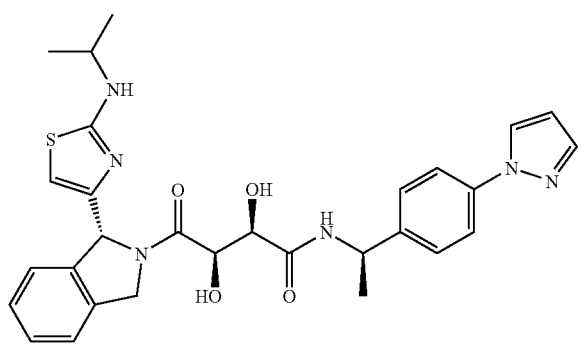 | 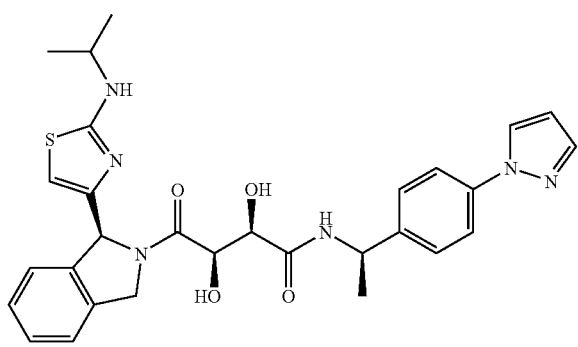 |
| 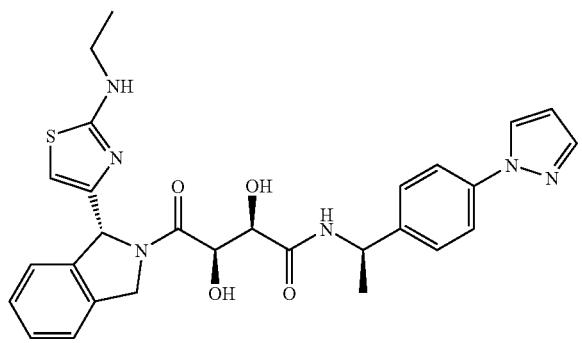 | 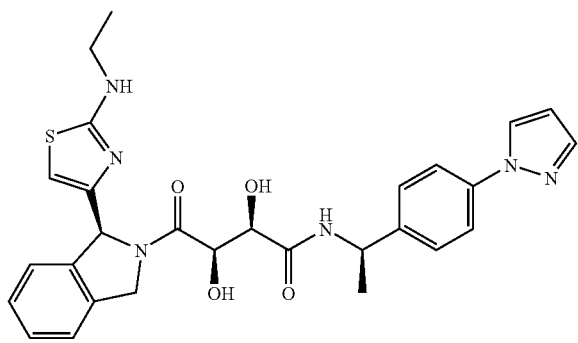 |

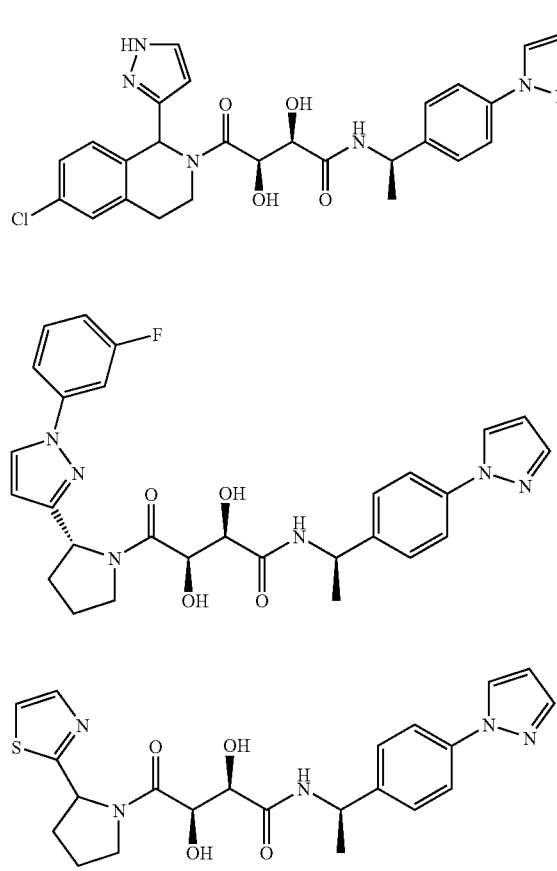
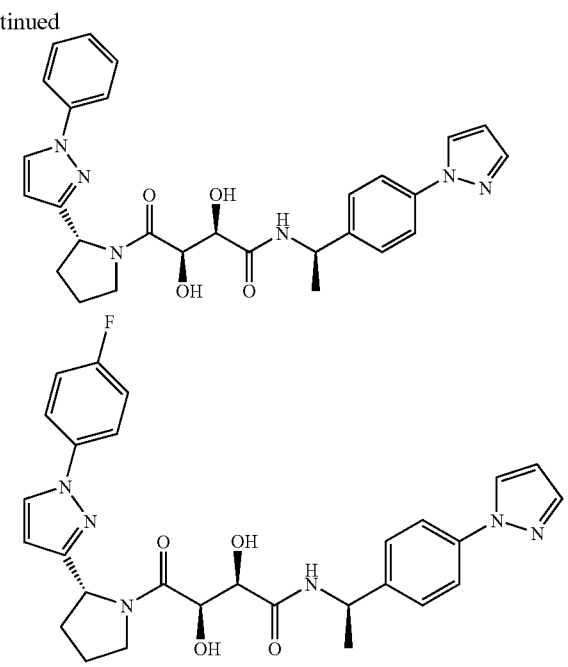
or a pharmaceutically acceptable salt or solution-phase solvate thereof.
24. The compound of claim 23 selected from the group consisting of:
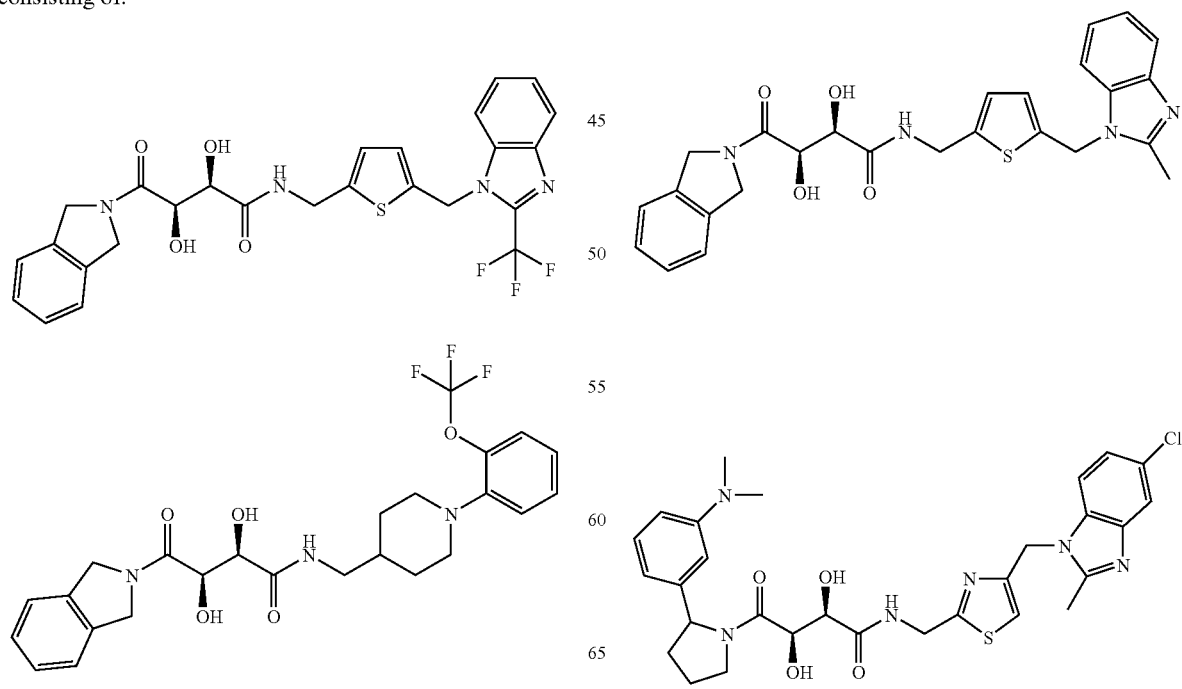

1593
-continued
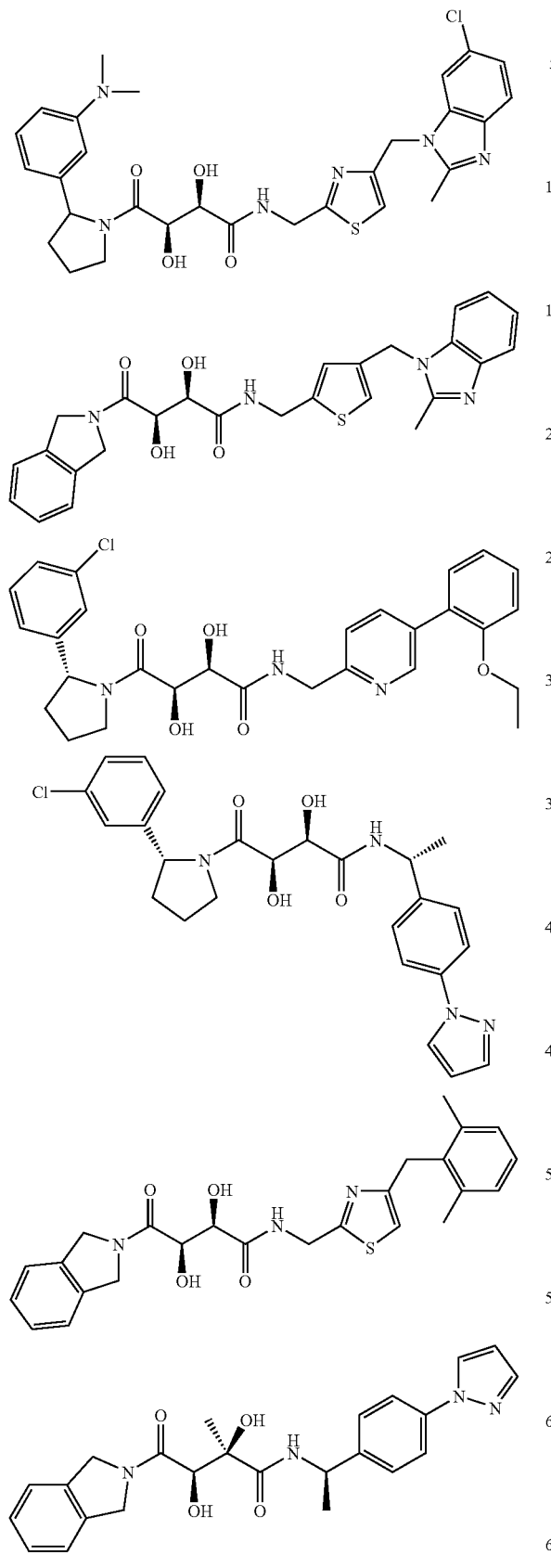
1594
-continued
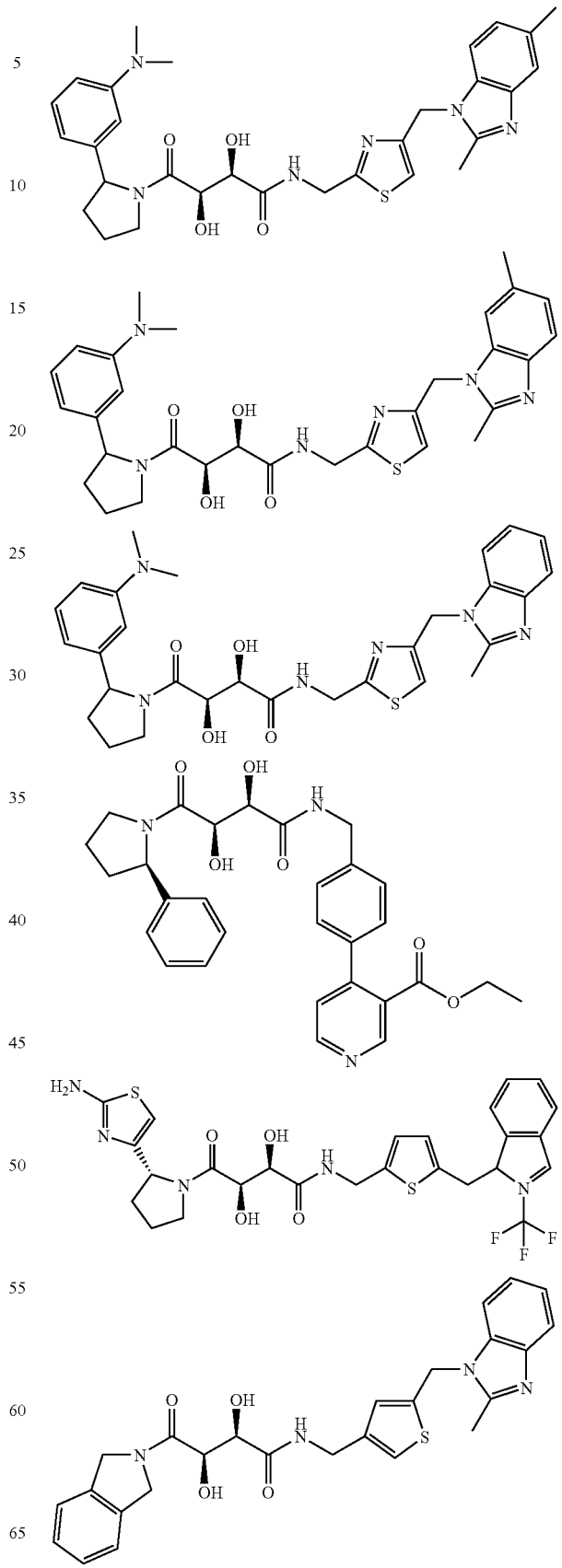

1595
-continued
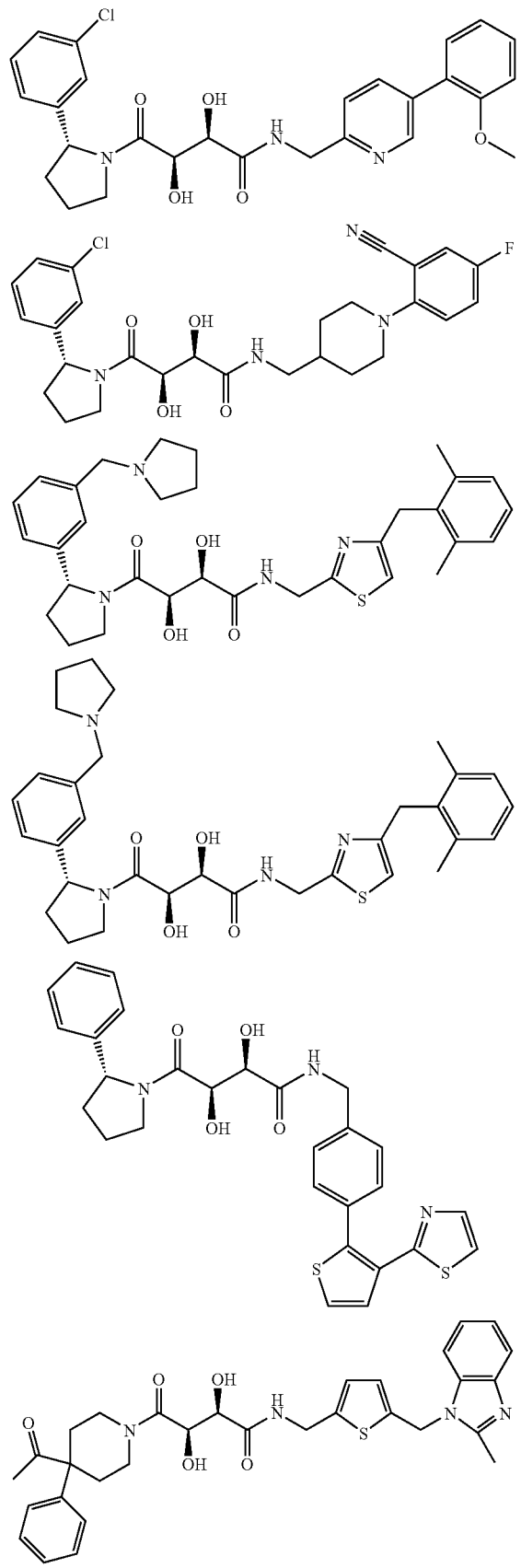
1596
-continued
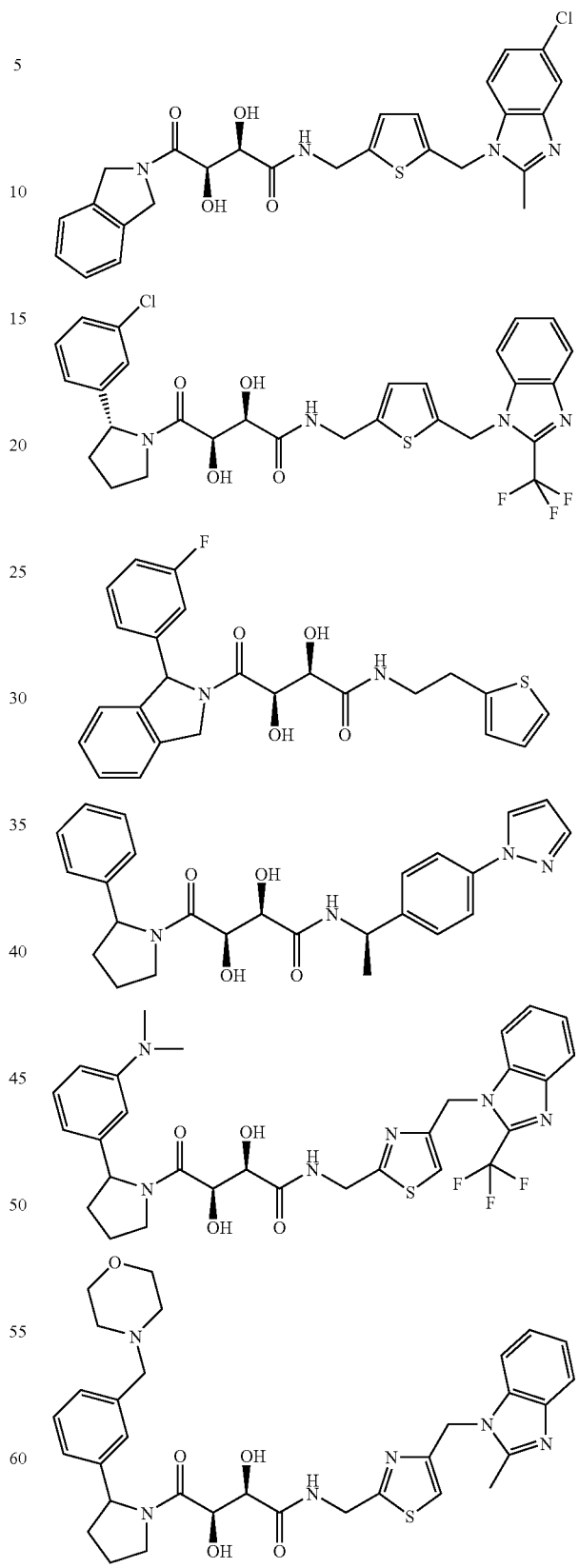

1597
-continued
1598
-continued
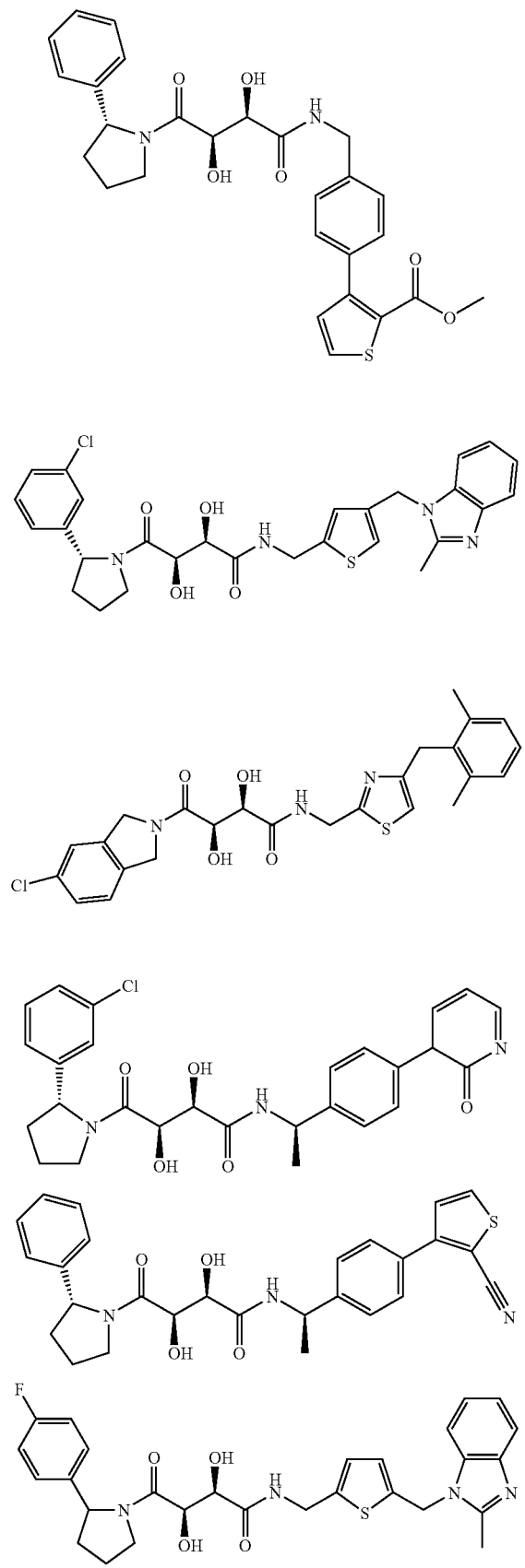
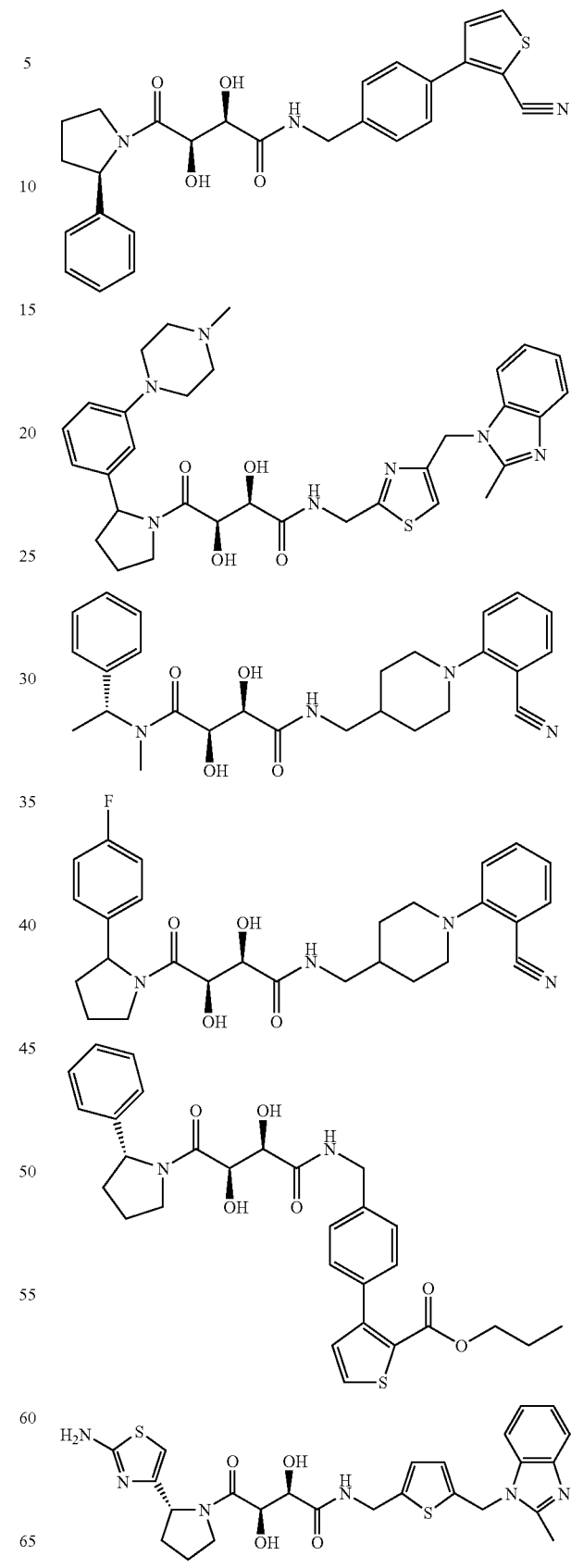

1599
-continued
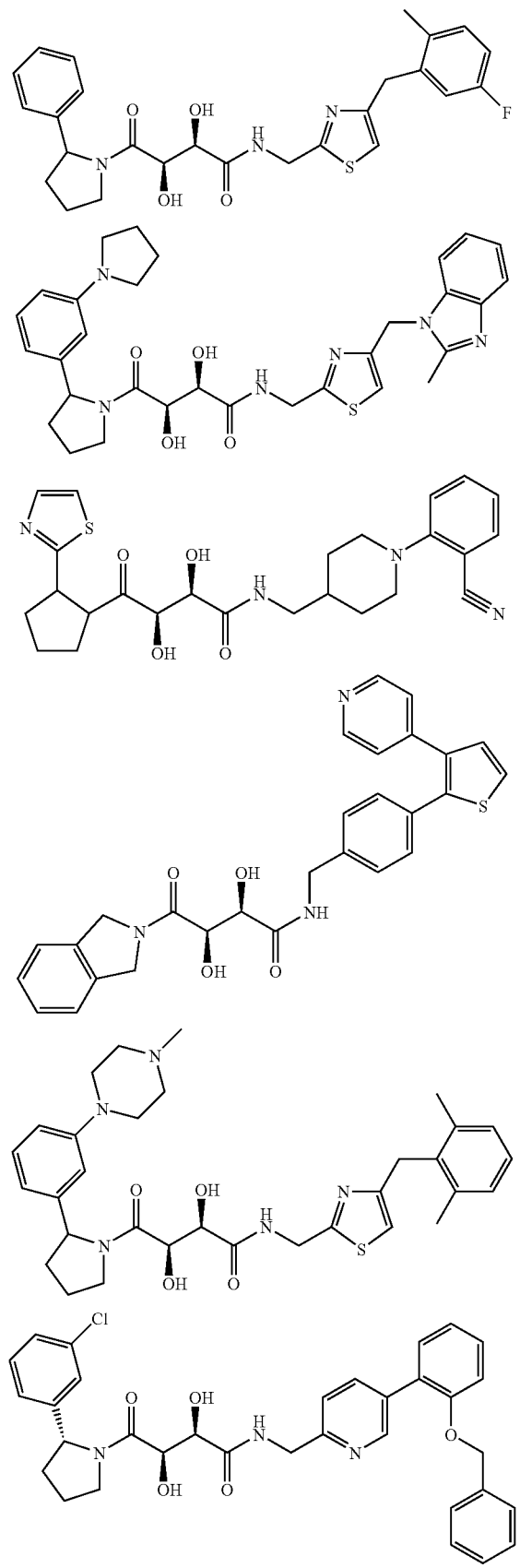
1600
-continued
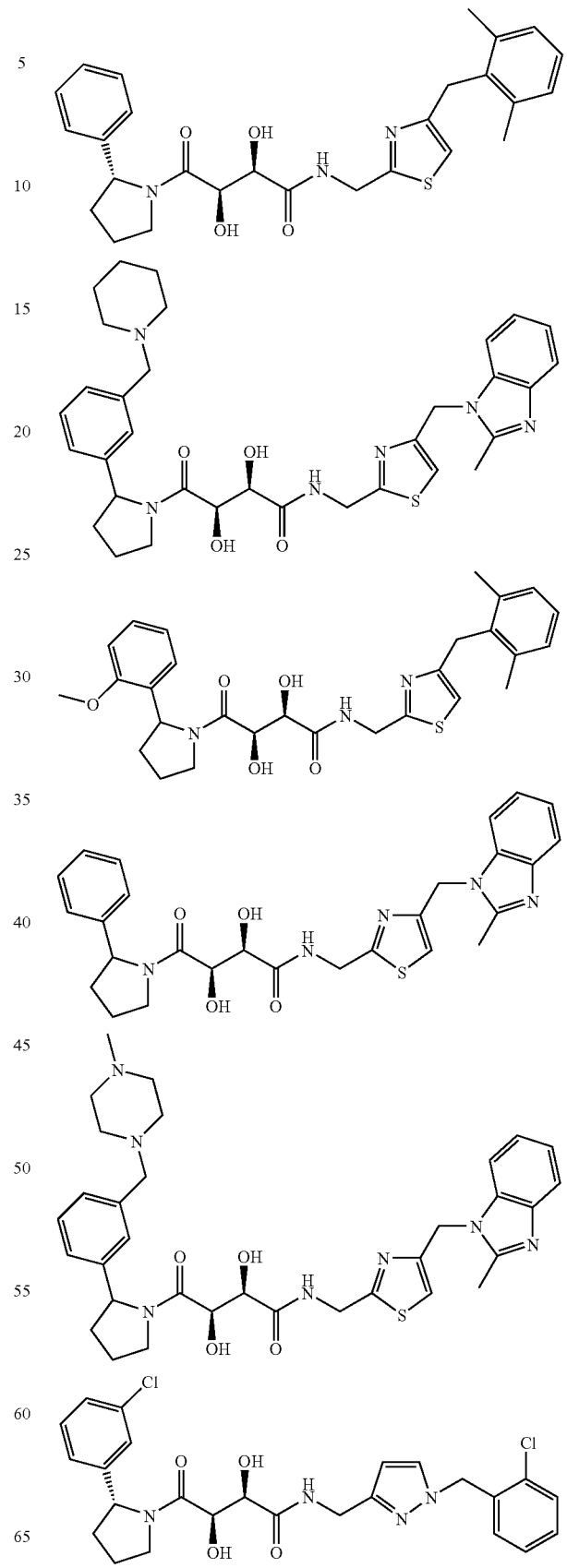

1601
-continued
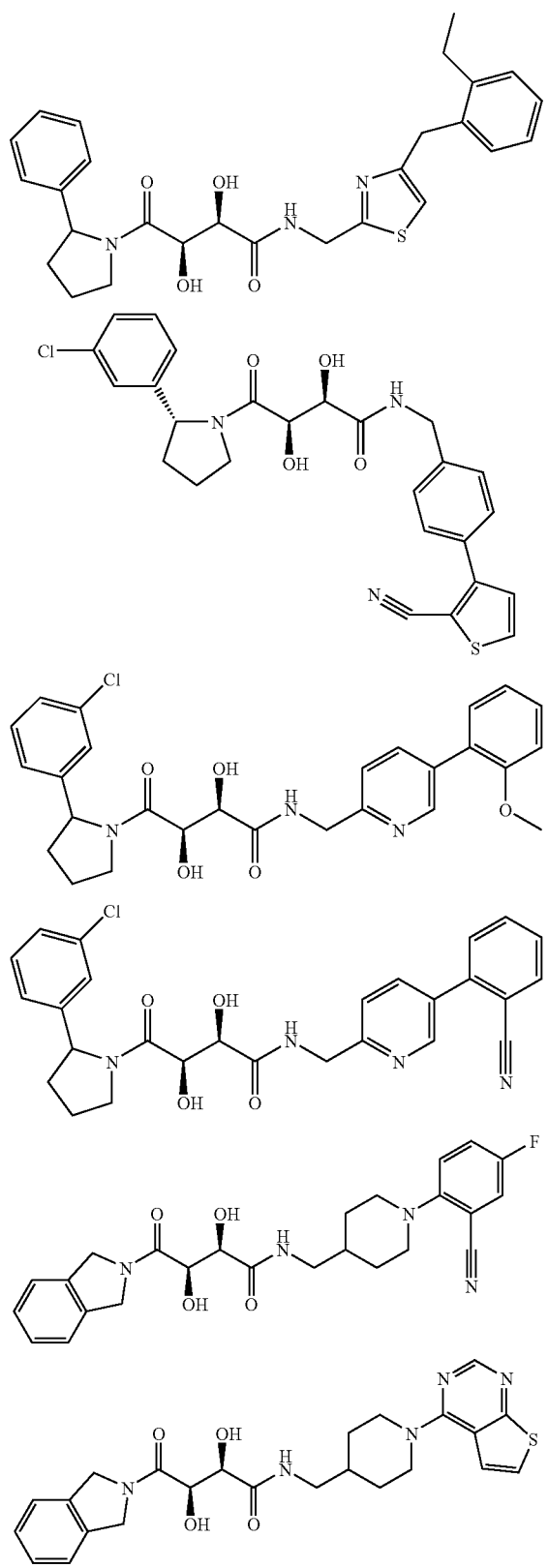
1602
-continued
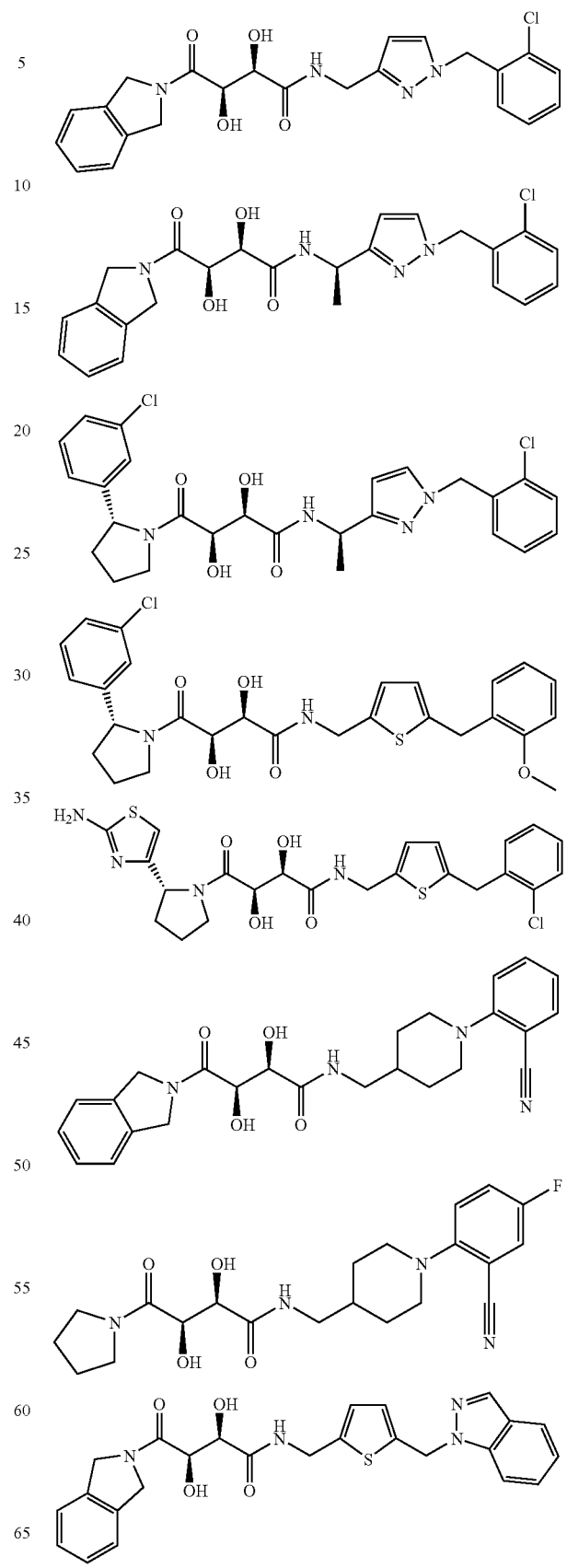

1603
-continued
1604
-continued
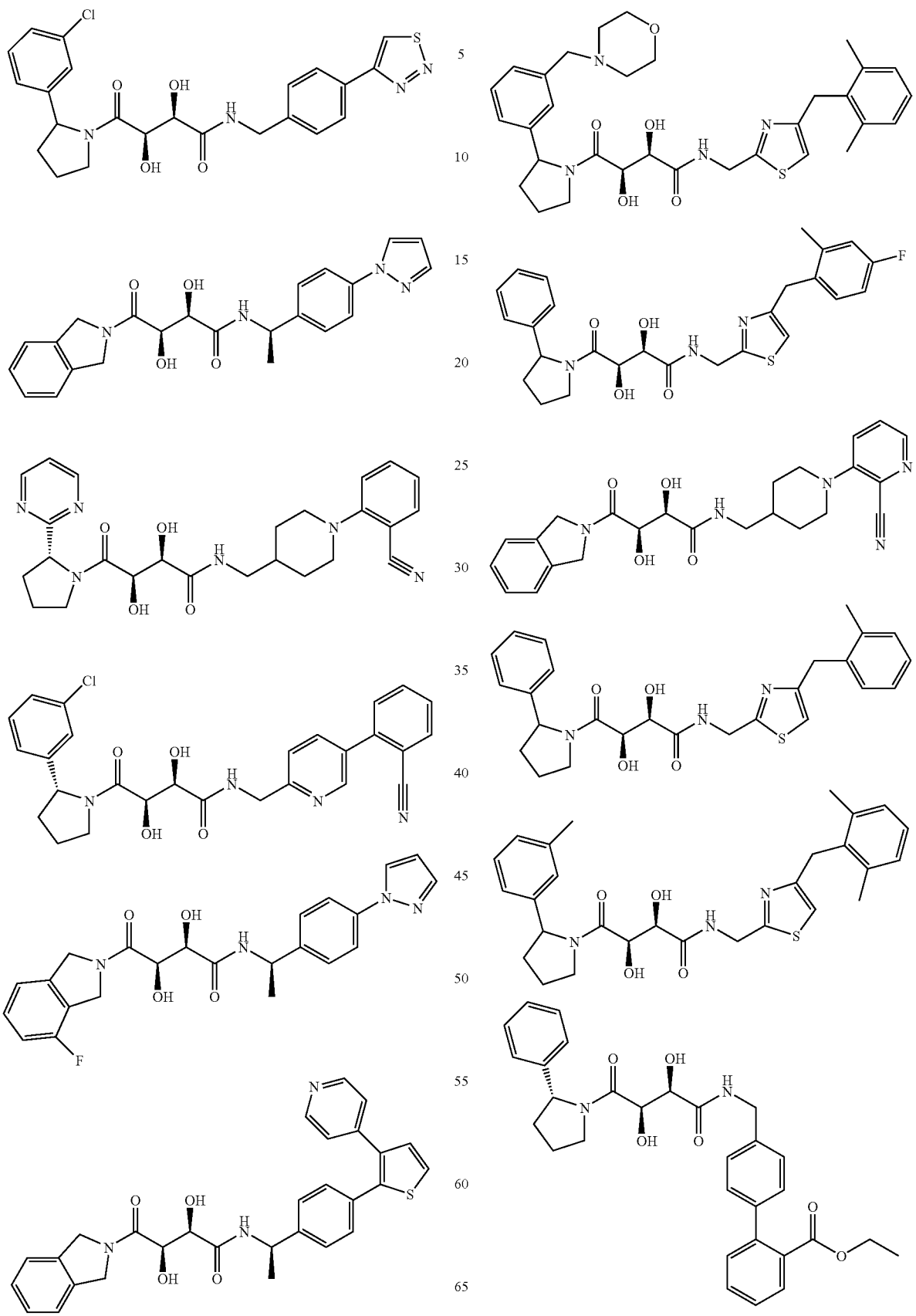

1605
-continued
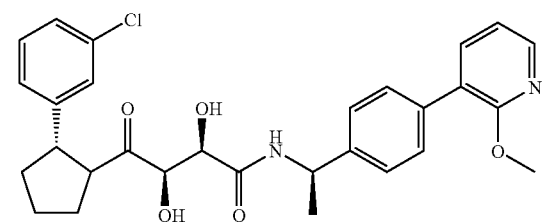
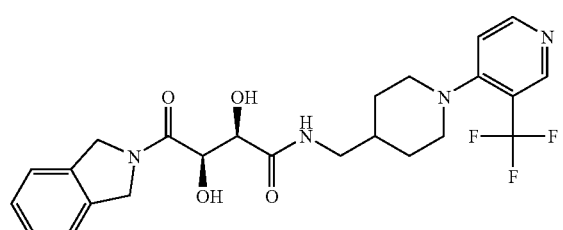
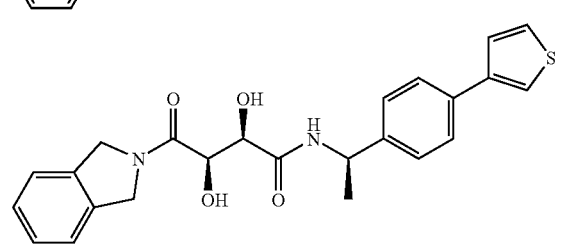
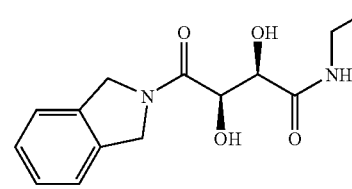
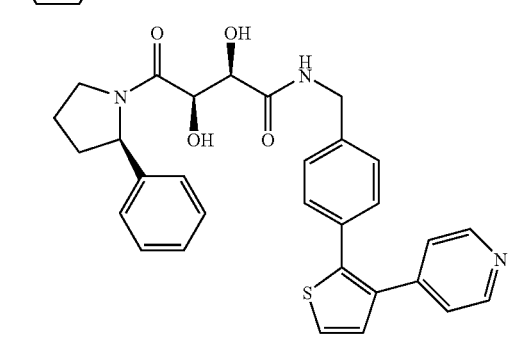
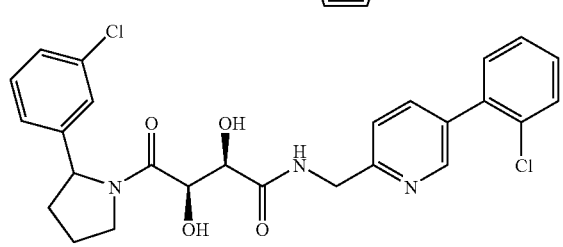
1606
-continued
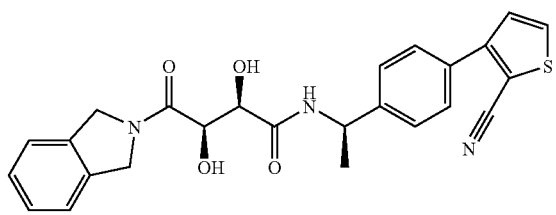
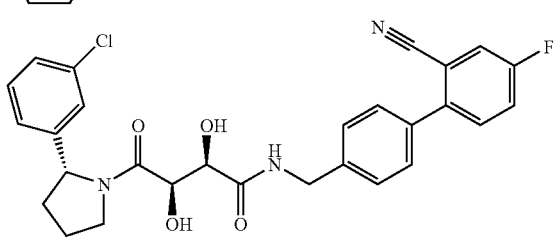
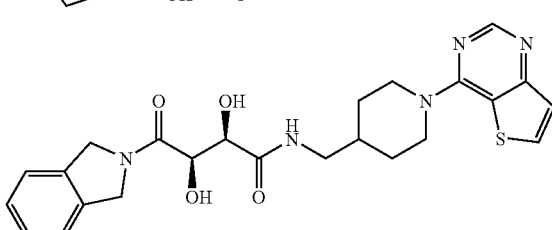
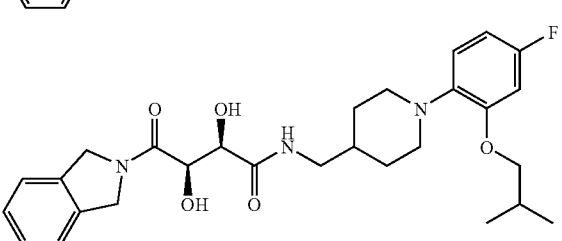
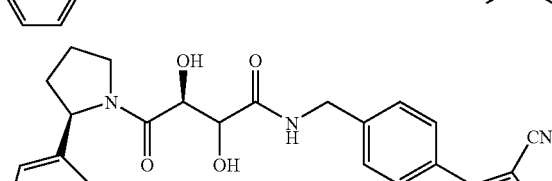
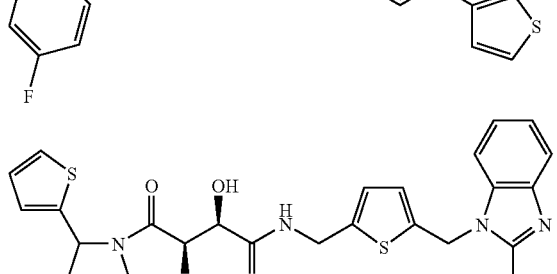
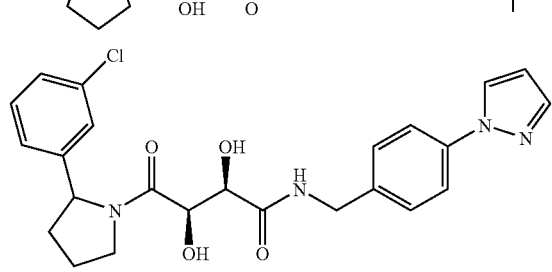

1607
-continued
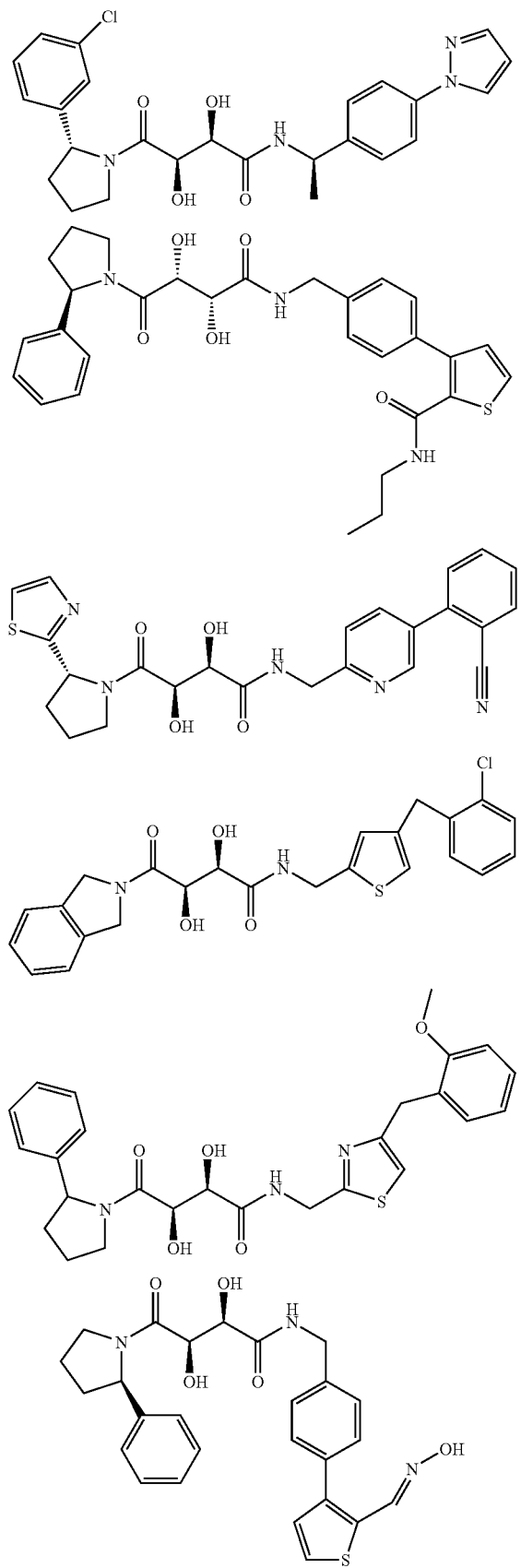
1608
-continued
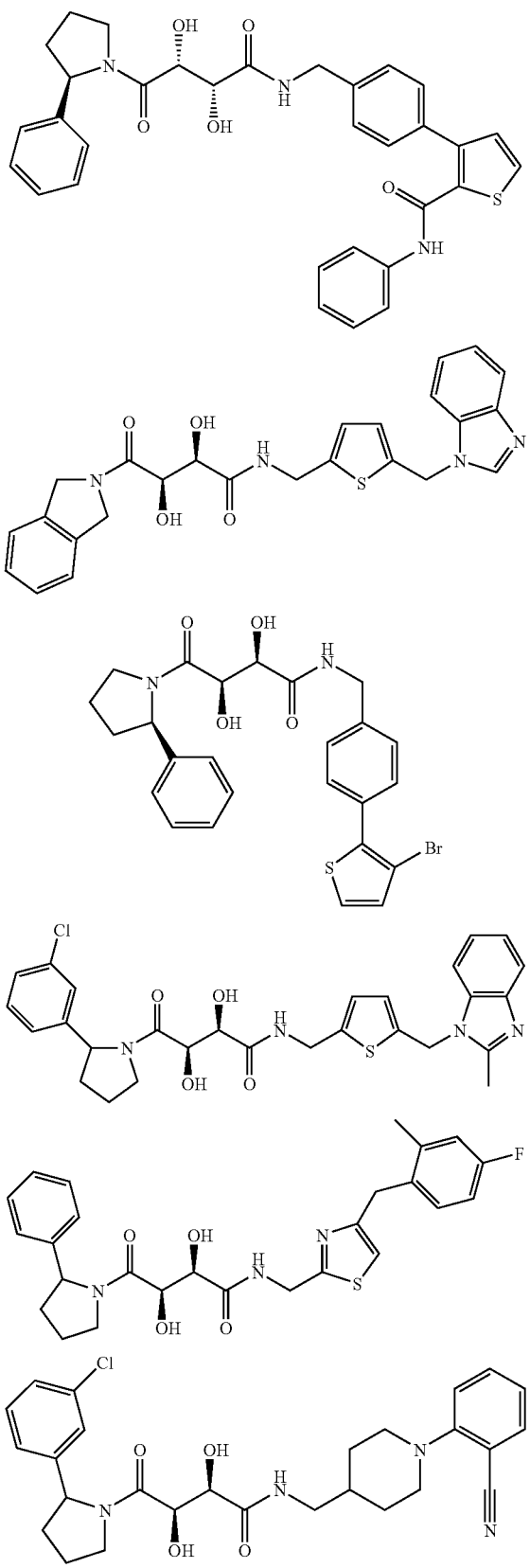

-continued
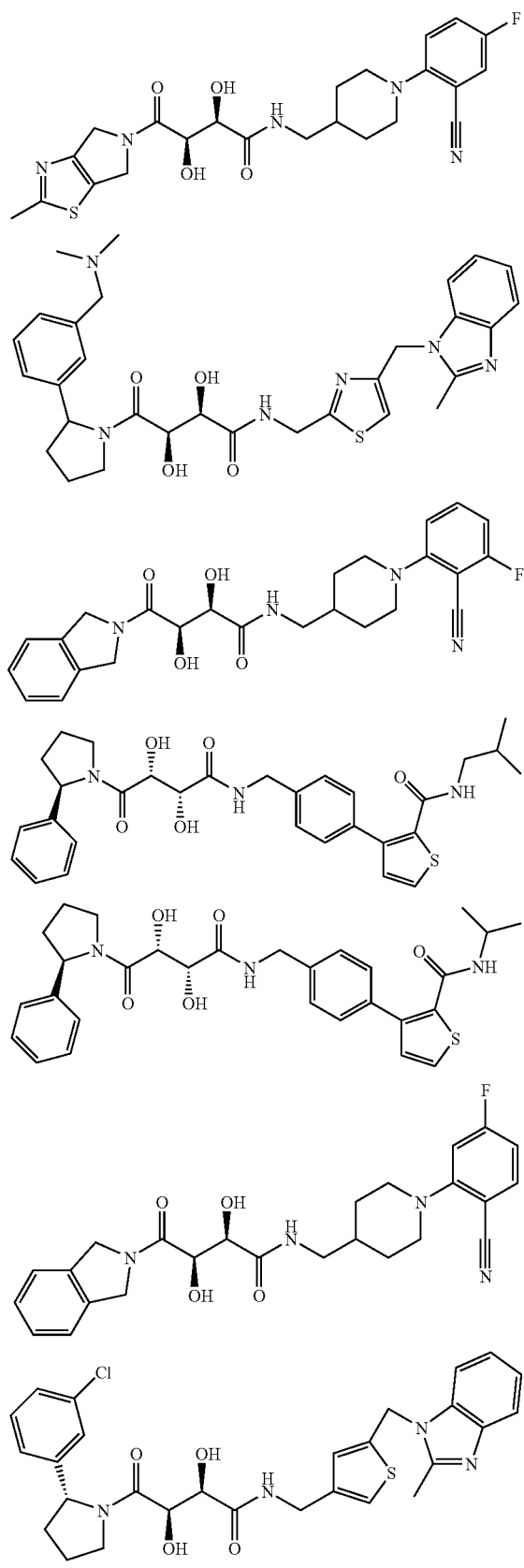
-continued
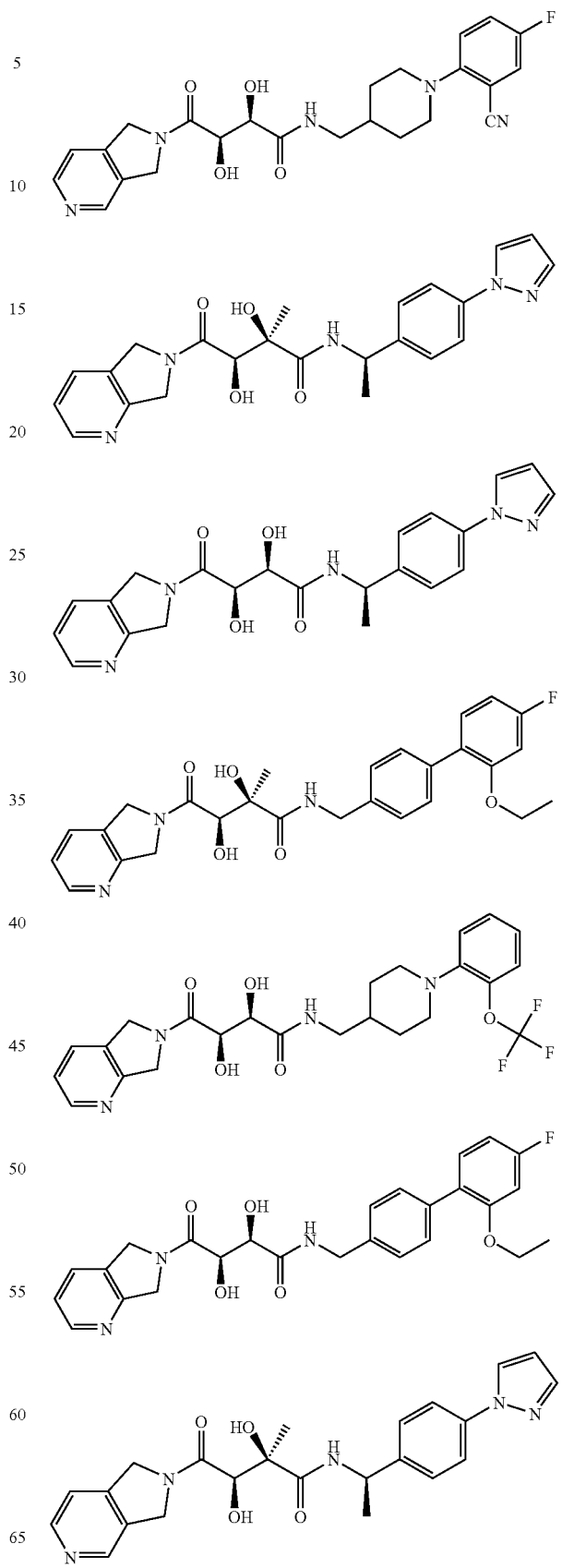

1611
-continued
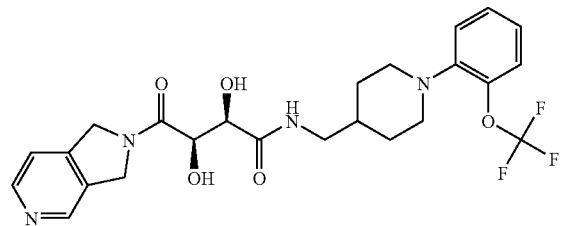
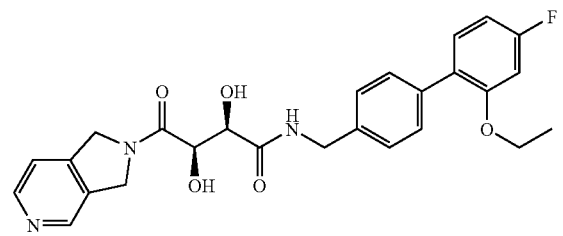
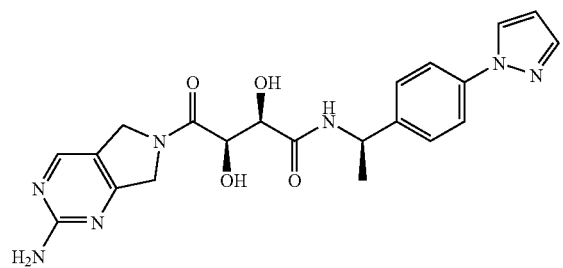
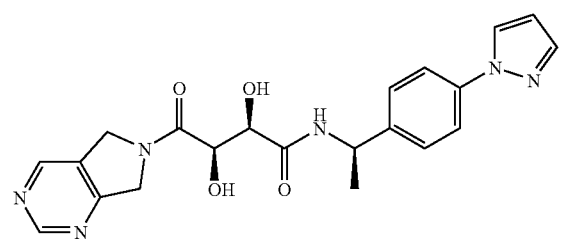
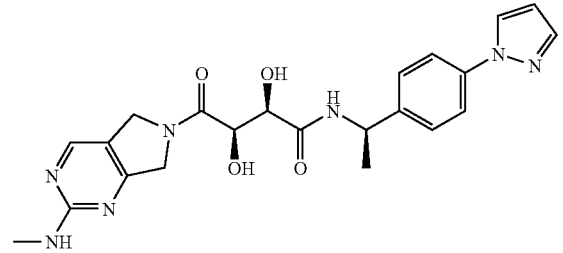
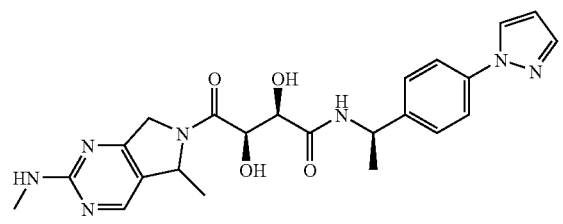
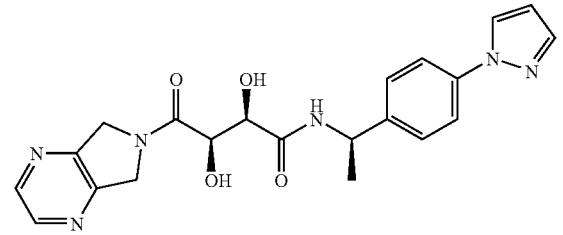
1612
-continued
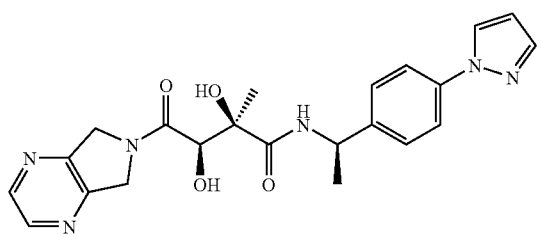
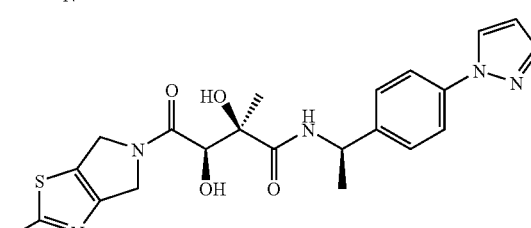
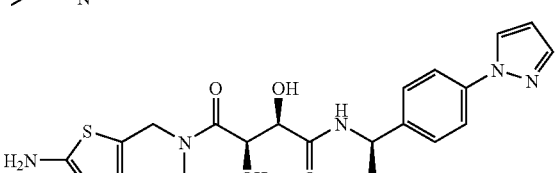
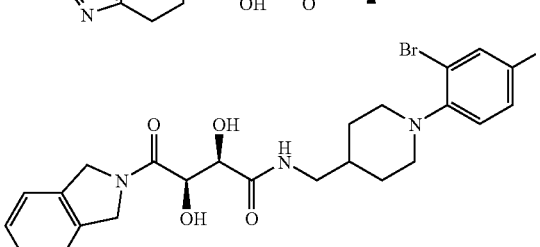
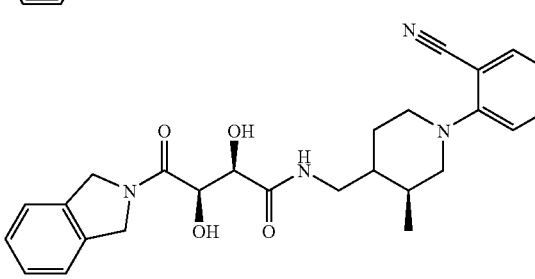
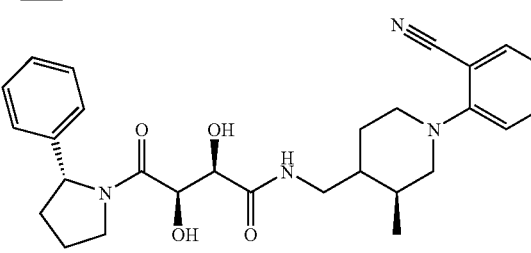
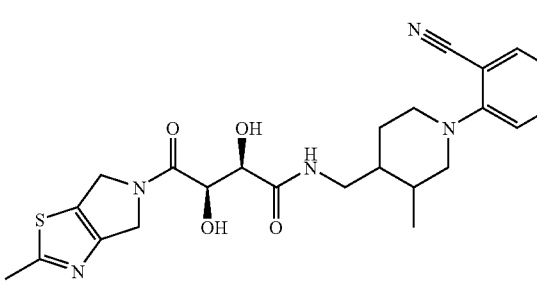

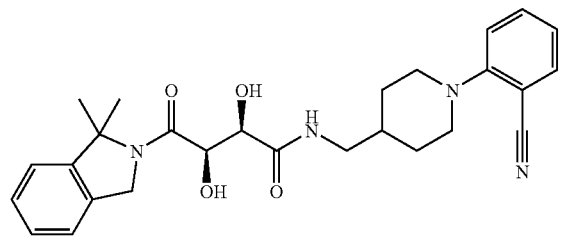
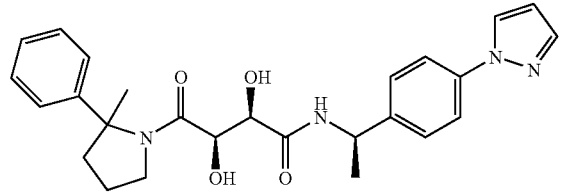
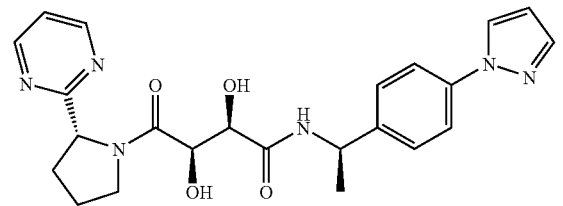
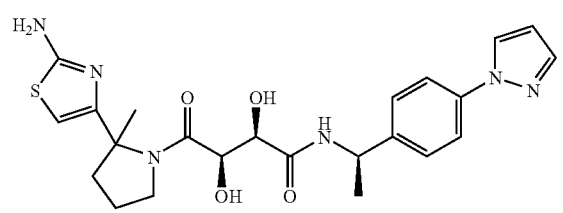
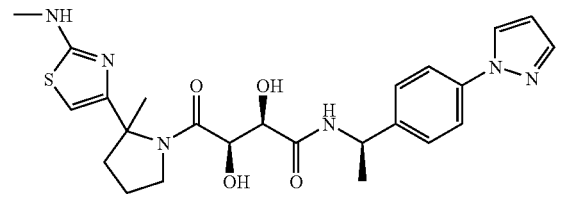
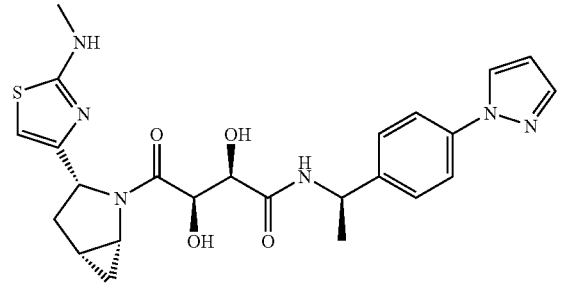
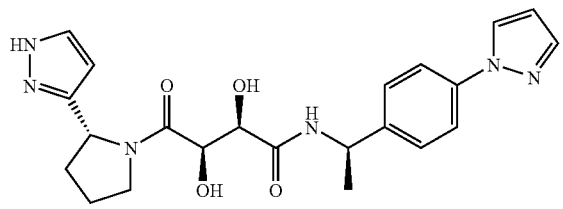
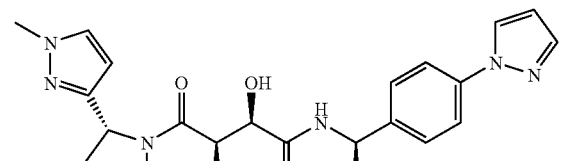
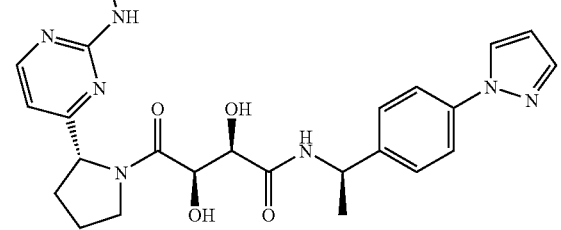
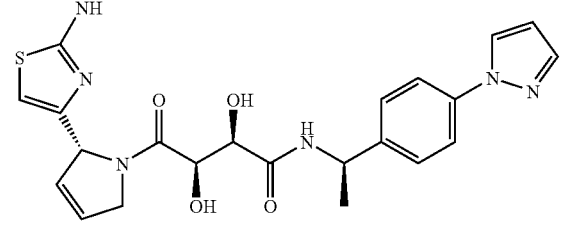
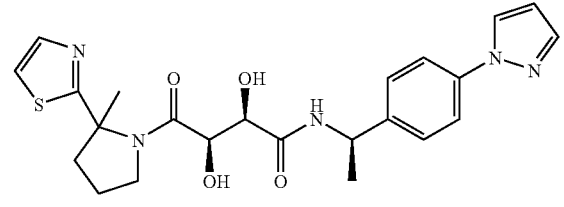
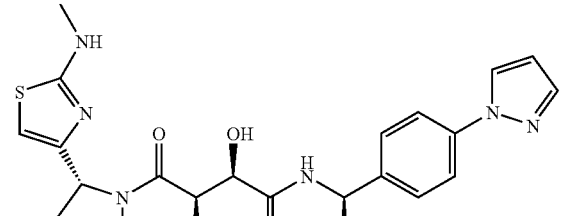
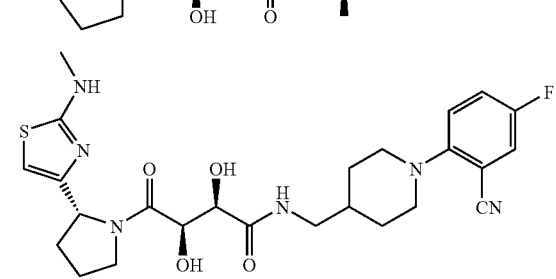
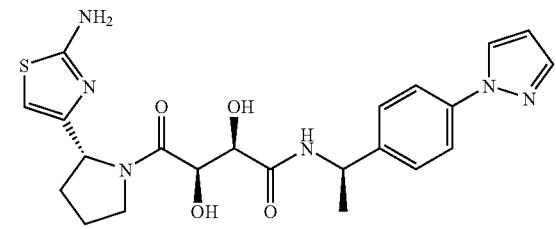

1615
-continued
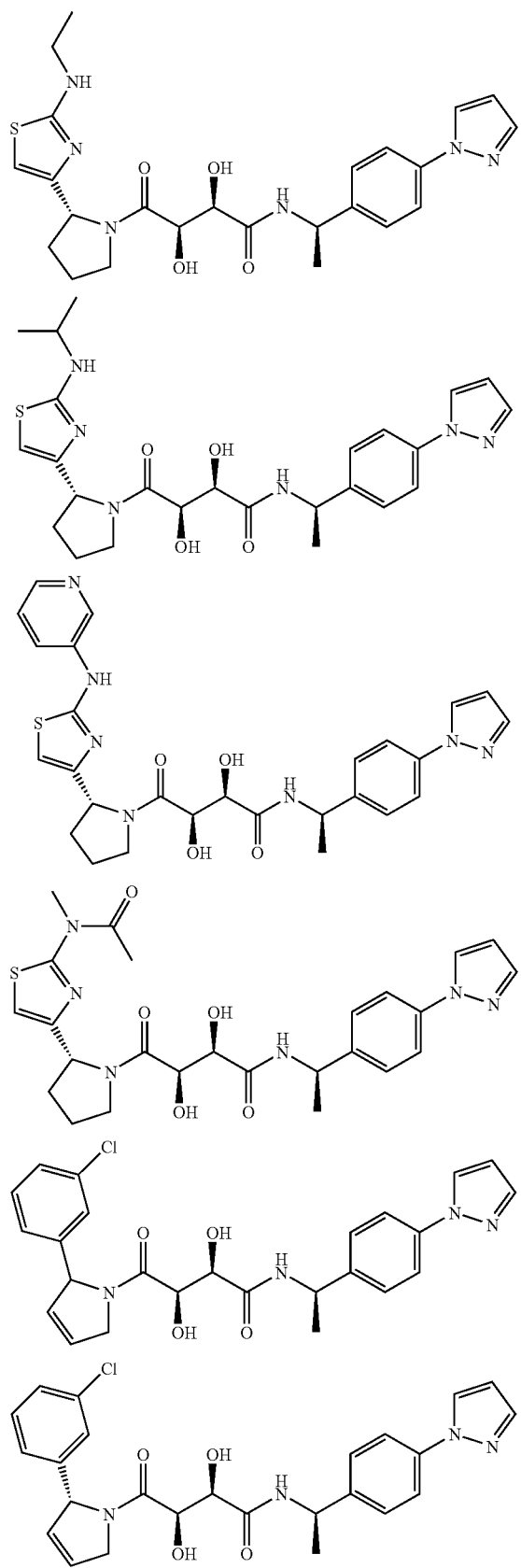
1616
-continued
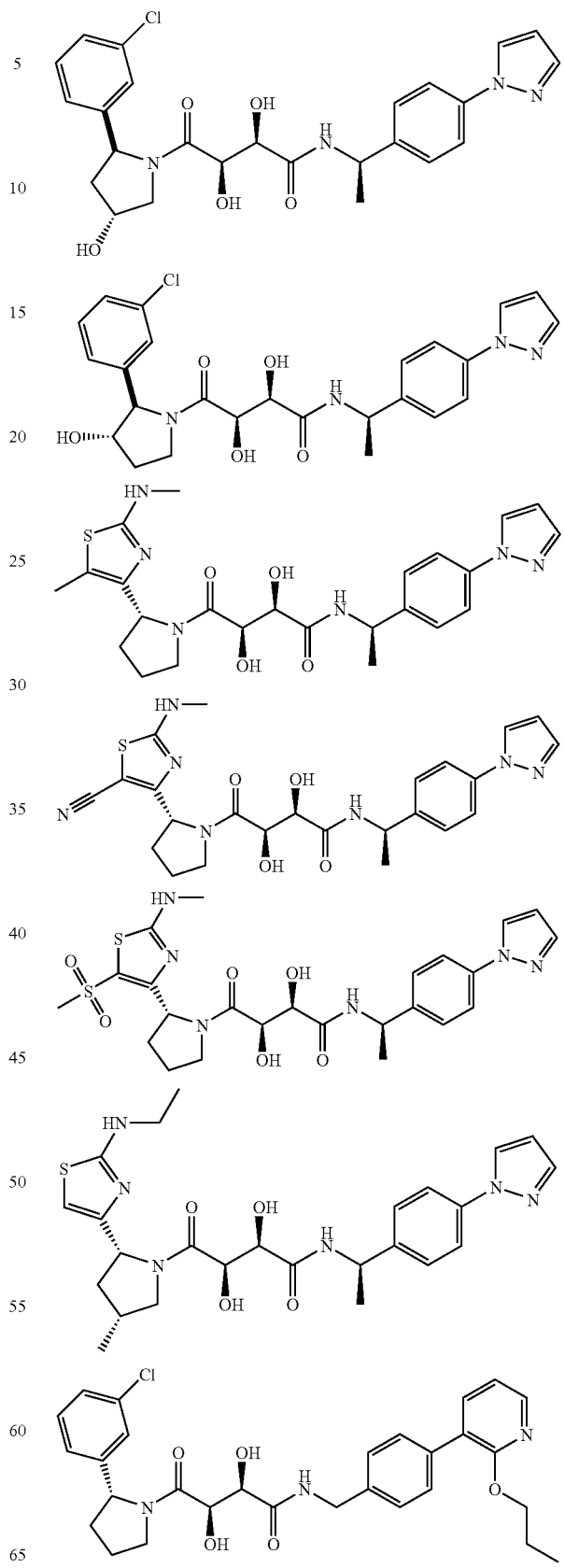

-continued
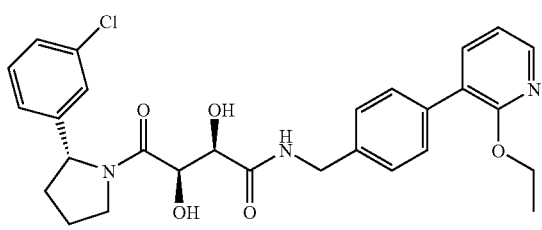
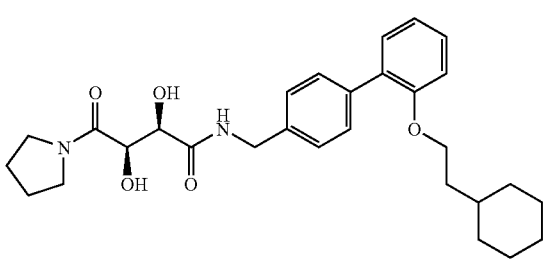
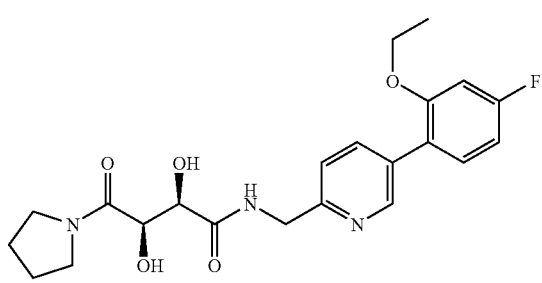
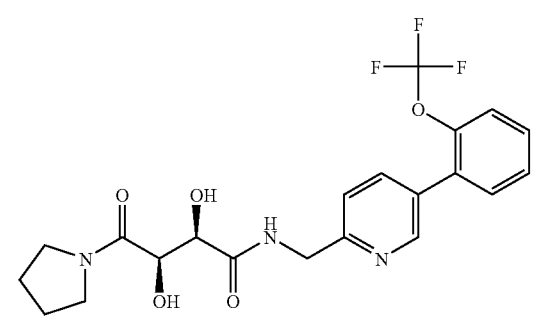
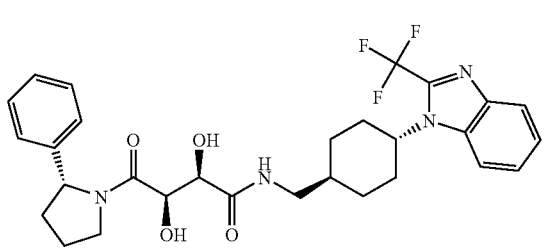
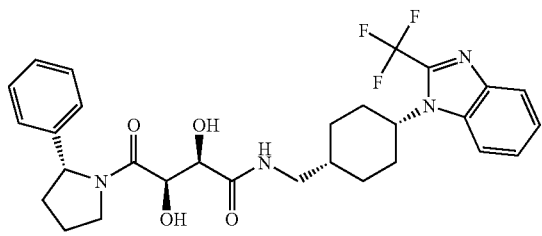
-continued
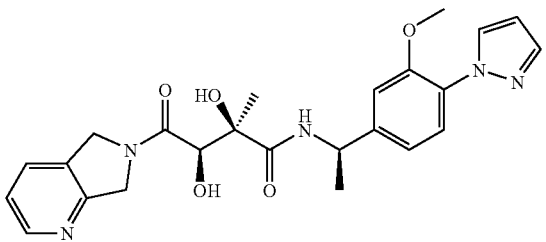
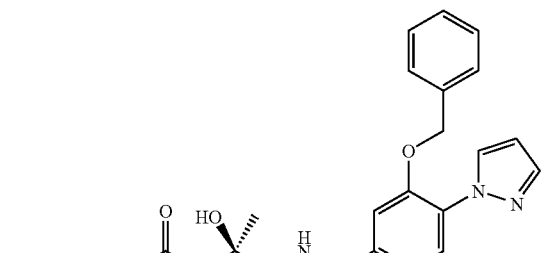
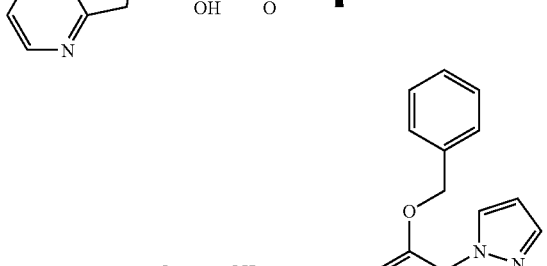
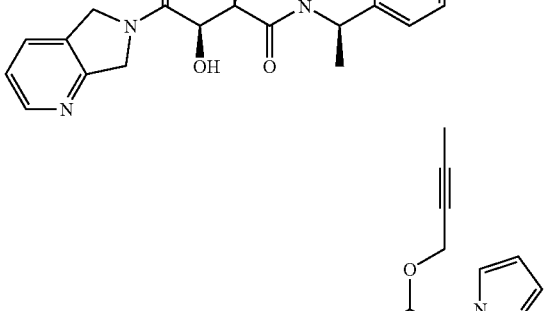
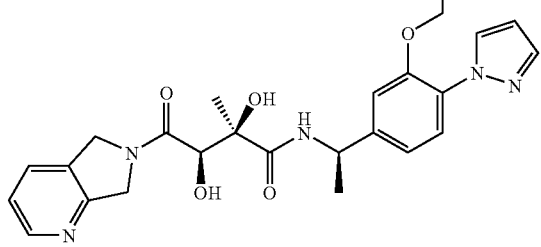

1619
-continued
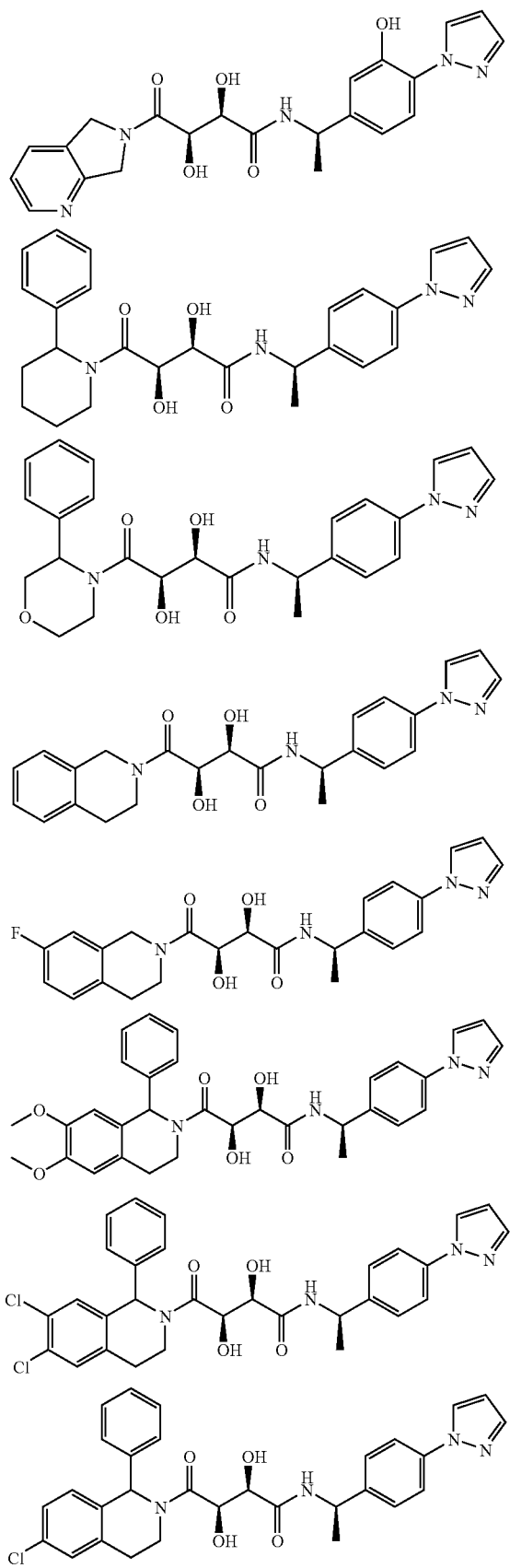
1620
-continued
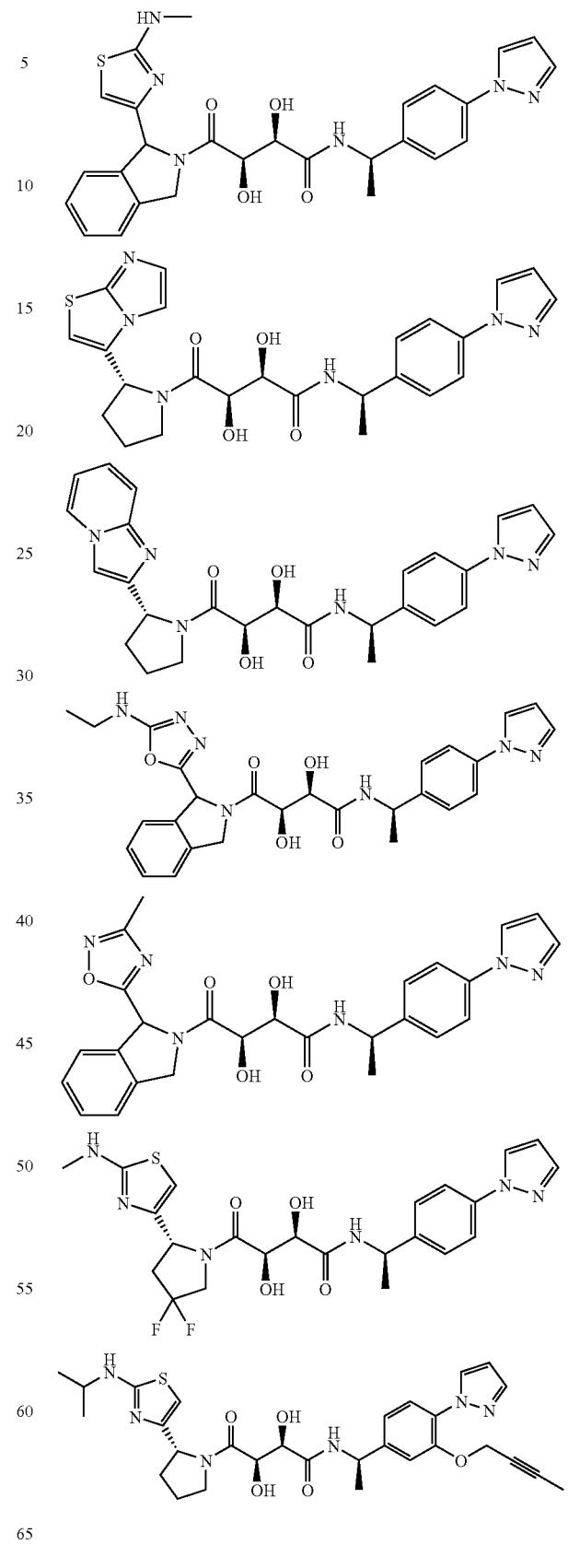

1621
-continued
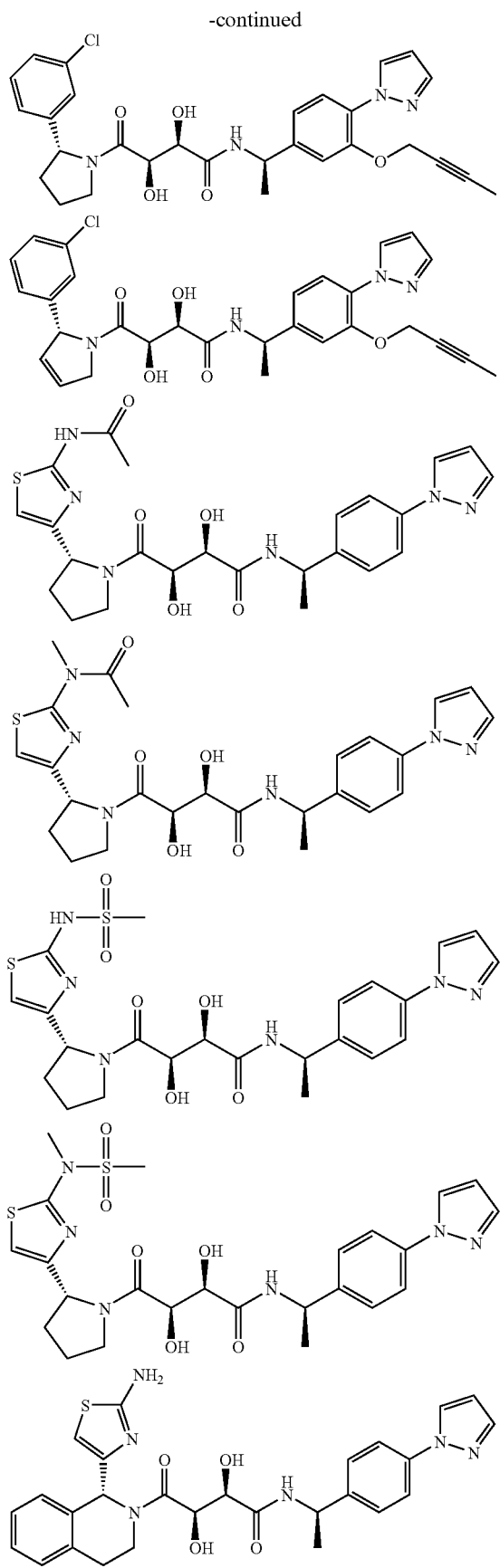
1622
-continued
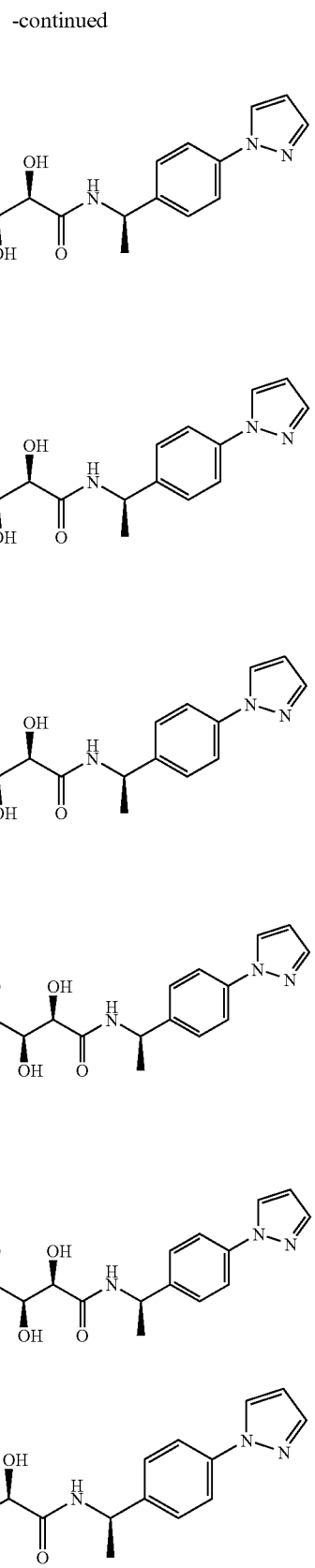

1623
-continued
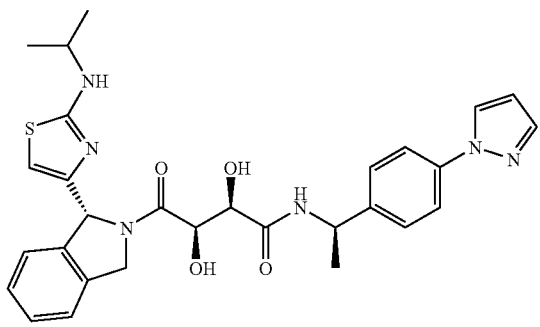
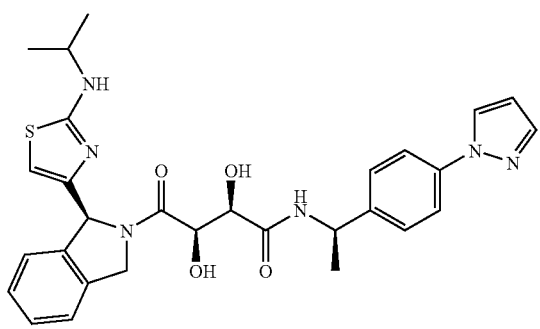
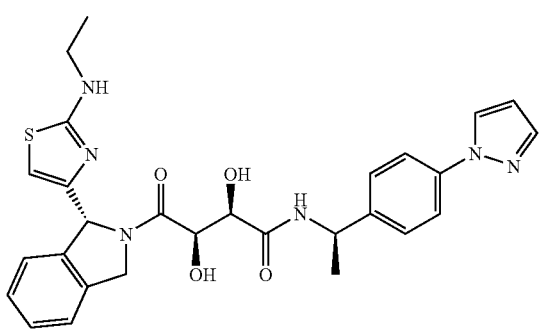
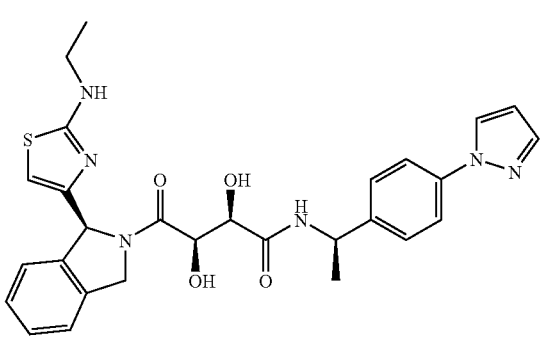
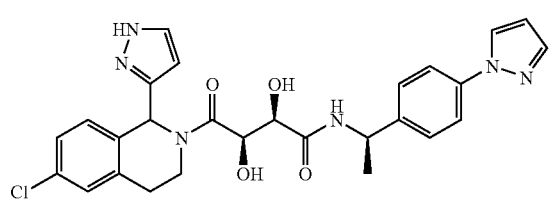
1624
-continued
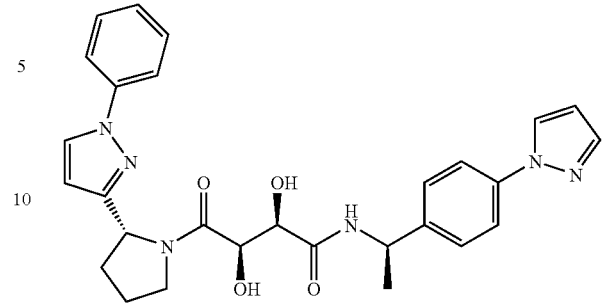
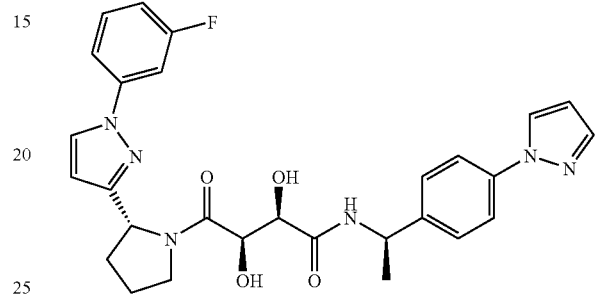
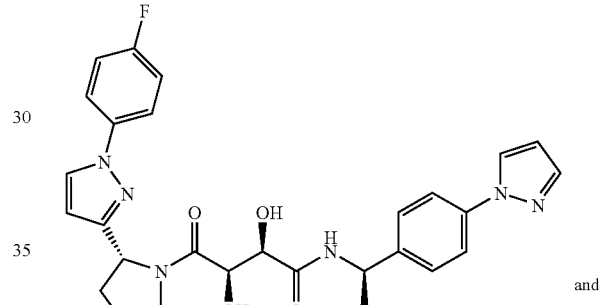
and
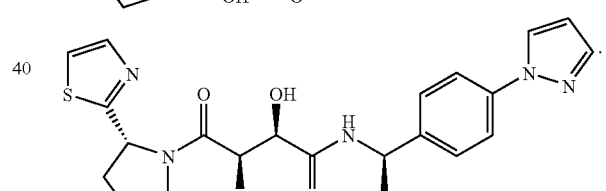
or a pharmaceutically acceptable salt, or solution-phase solvate thereof.
25. A compound selected from the group consisting of:
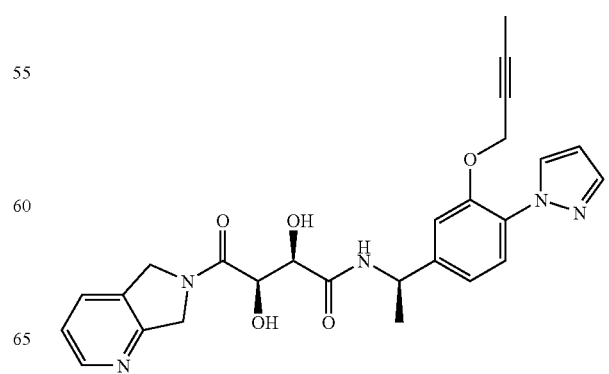

1625
-continued
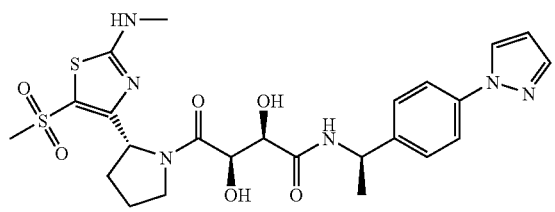
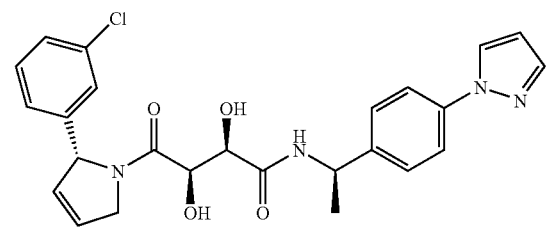
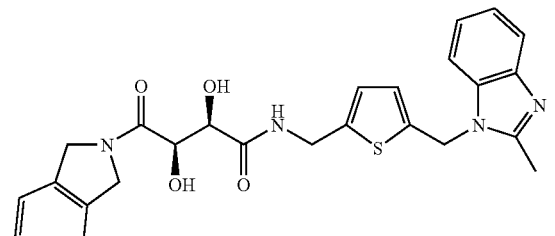
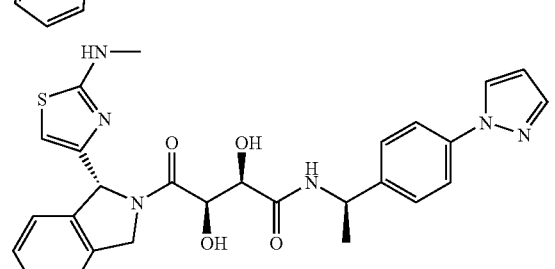
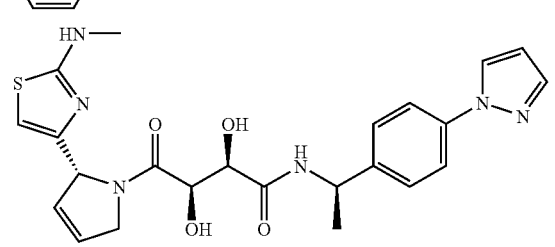
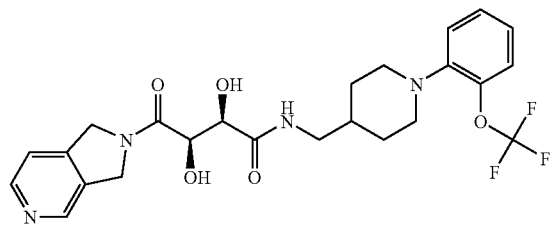
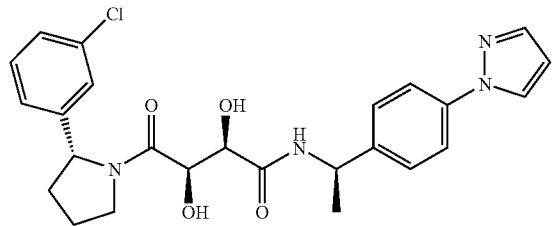
1626
-continued
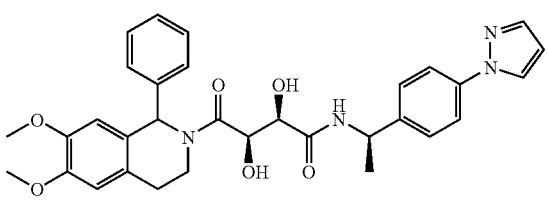
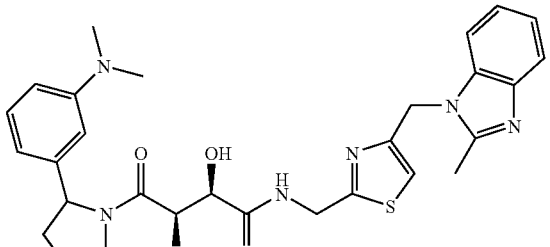
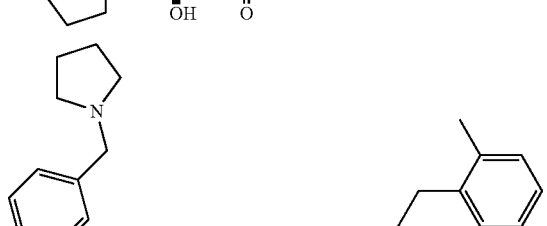
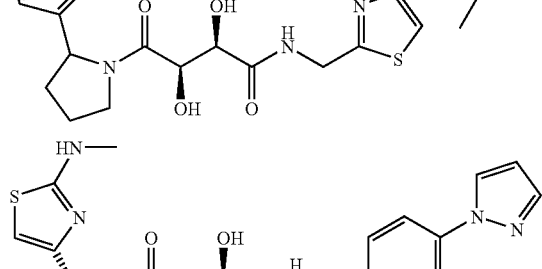
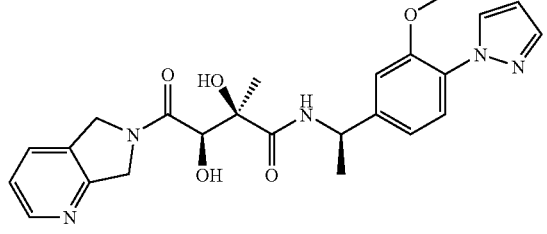
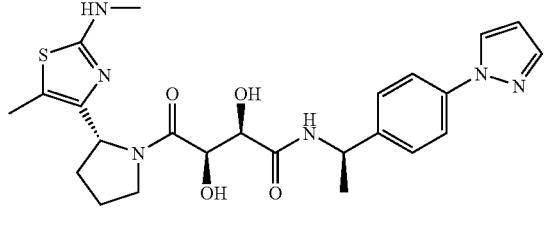

1627
-continued
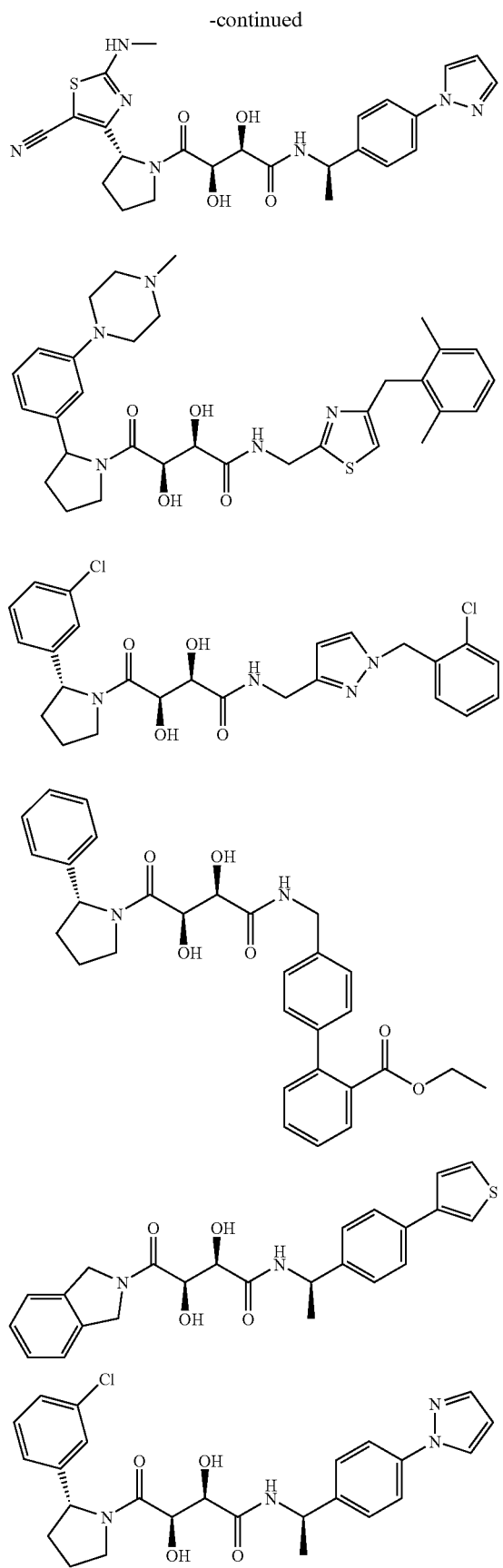
1628
-continued
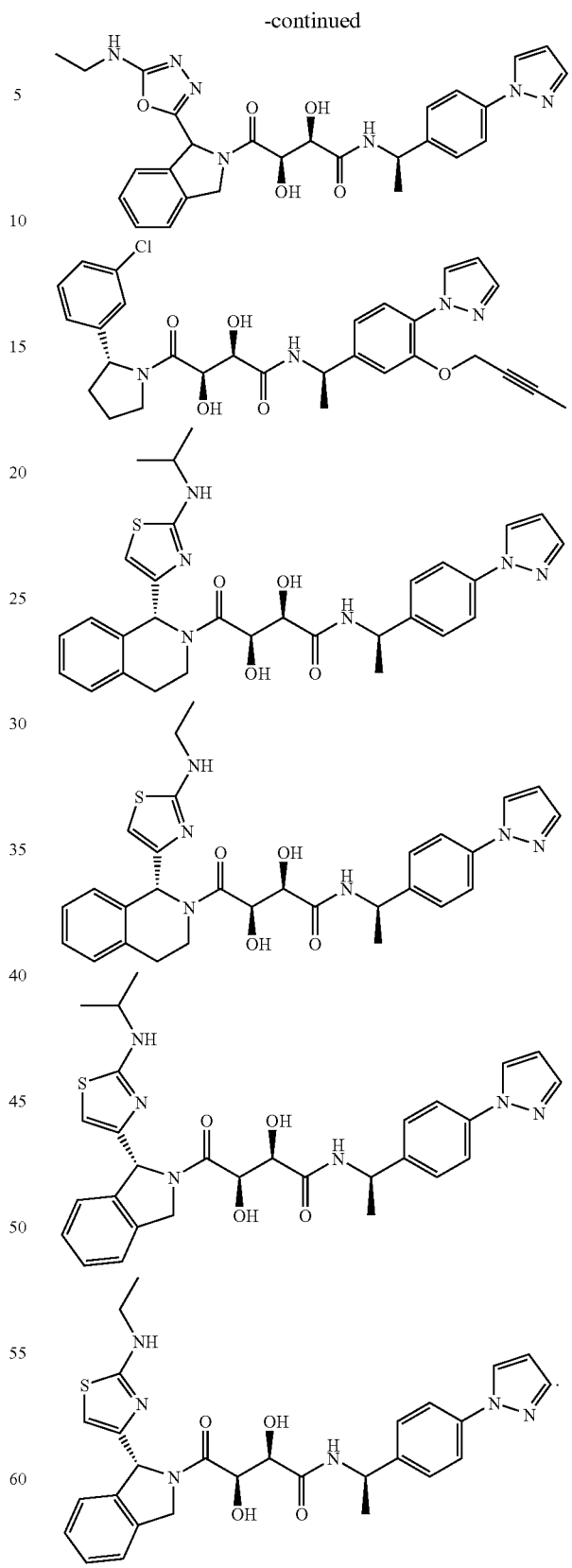
or a pharmaceutically acceptable salt or solution-phase solvate thereof.

26. A pharmaceutical composition comprising at least one compound of claim 1 or a pharmaceutically acceptable salt or solution-phase solvate thereof, and at least one pharmaceutically acceptable carrier.
27. A compound selected from the group consisting of:
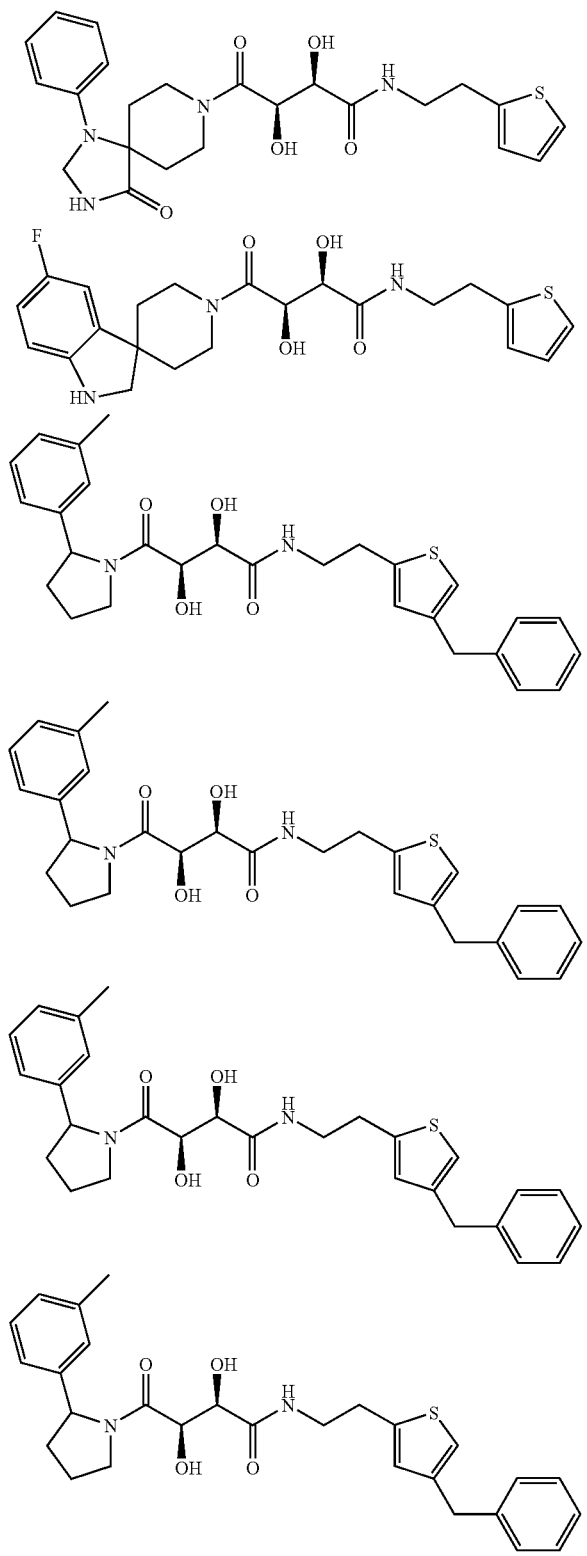
-continued
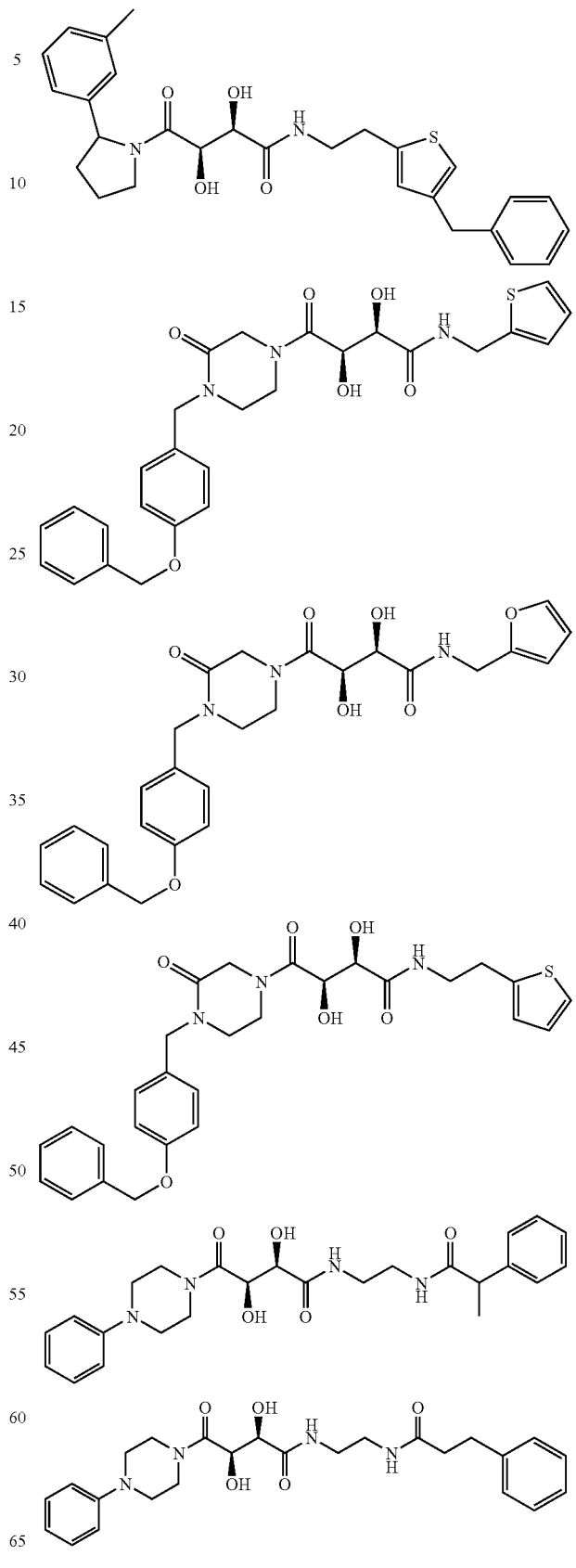

-continued
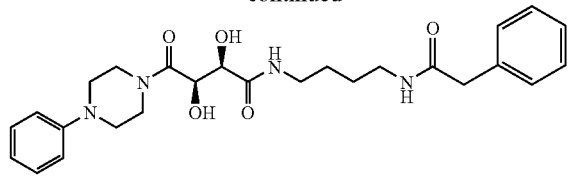
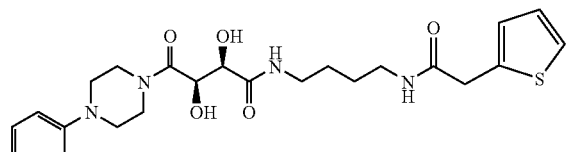
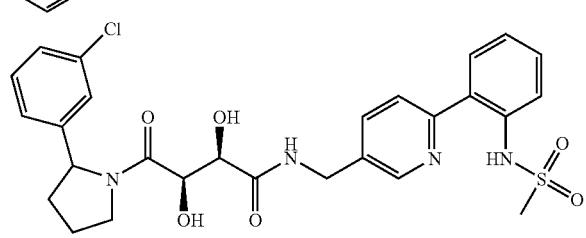
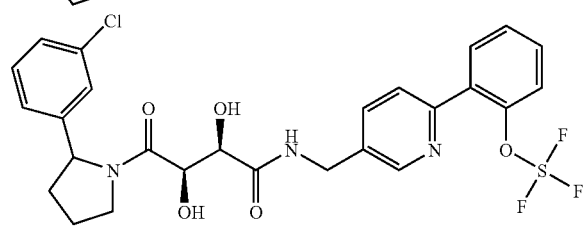
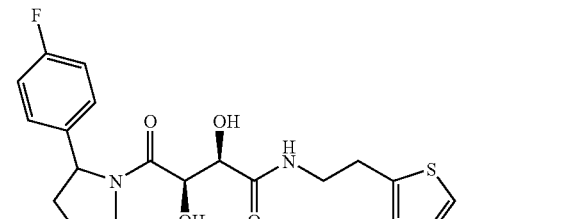
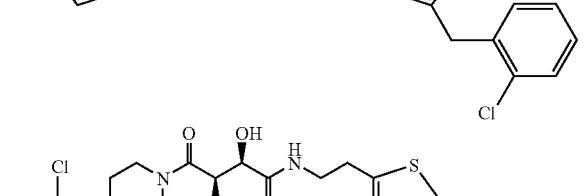
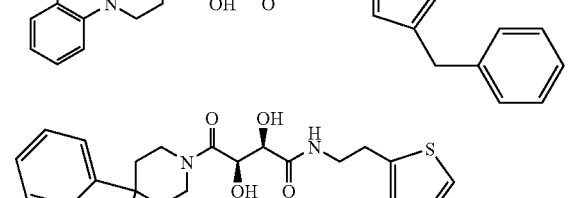
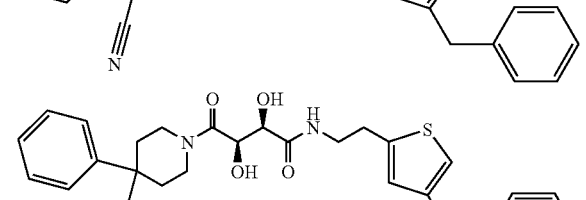
-continued
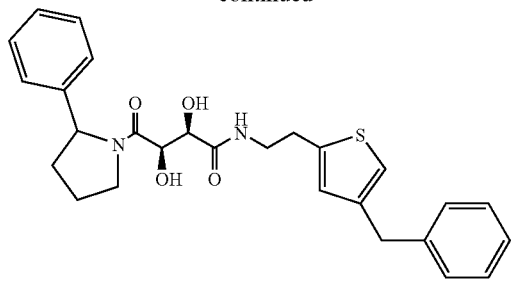
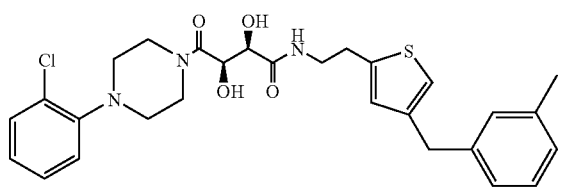
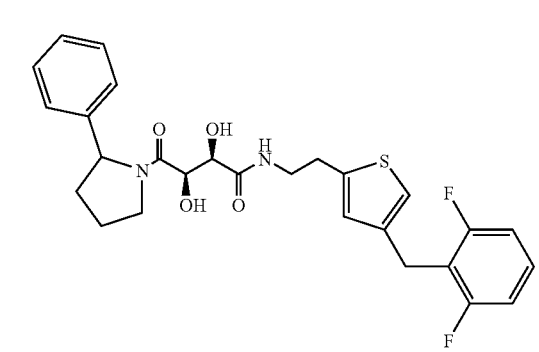
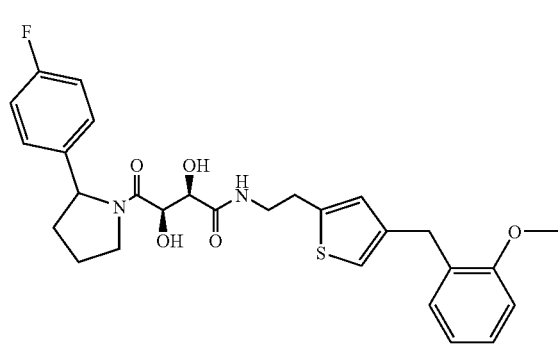
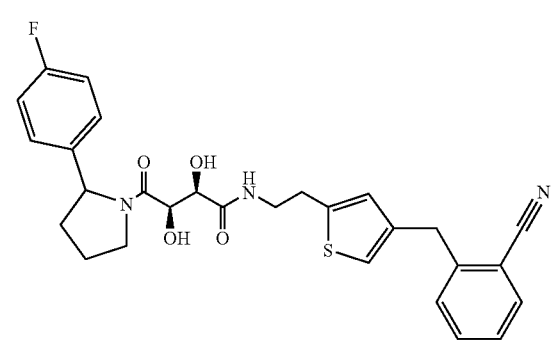

1633
-continued
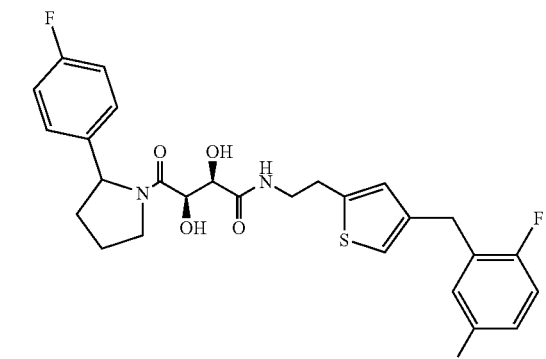
1634
-continued
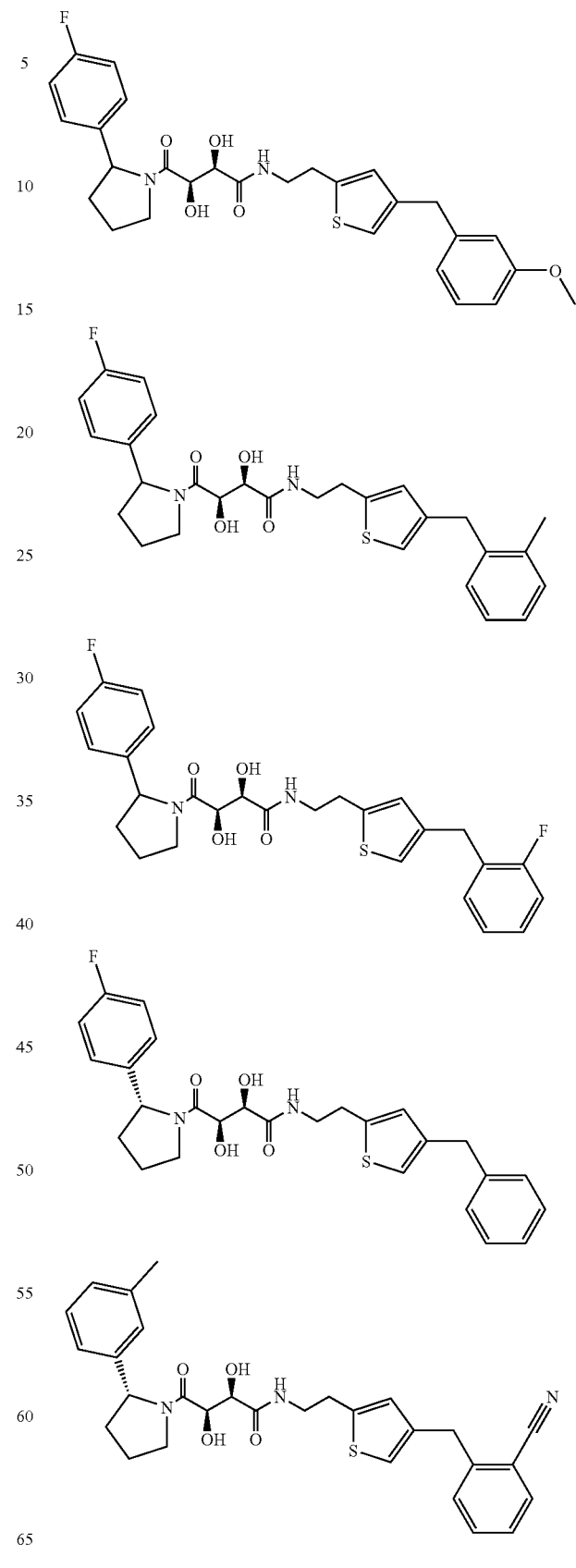

-continued
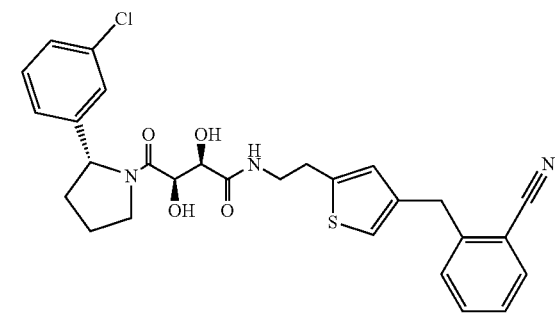
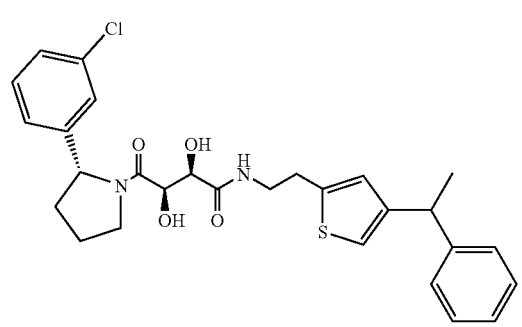
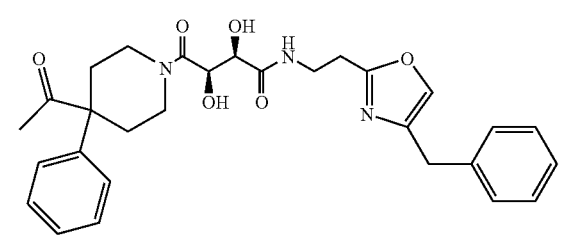
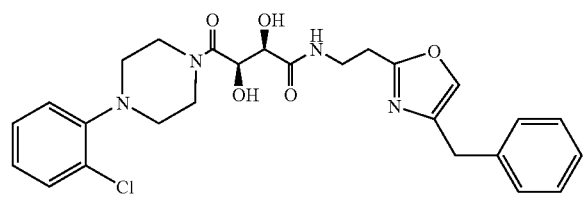
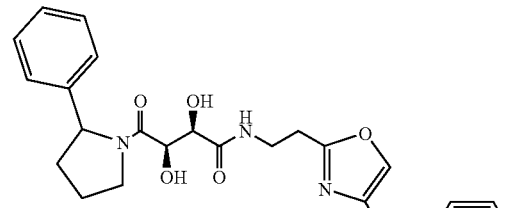
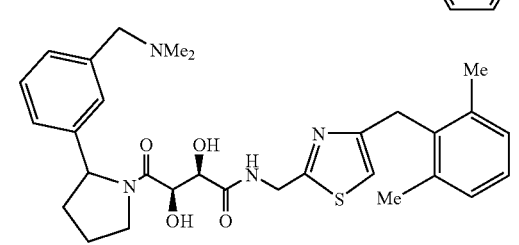
-continued
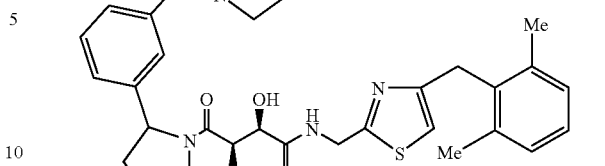
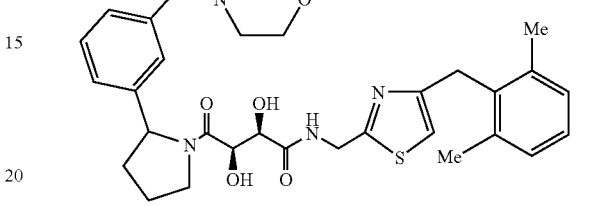
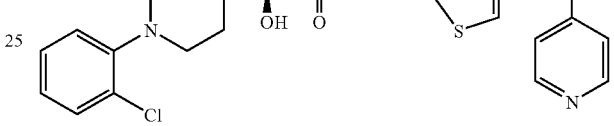
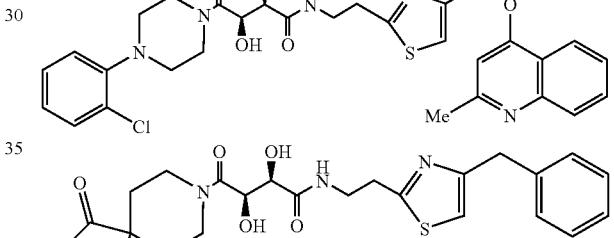
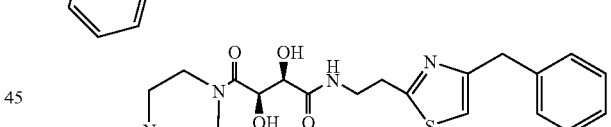
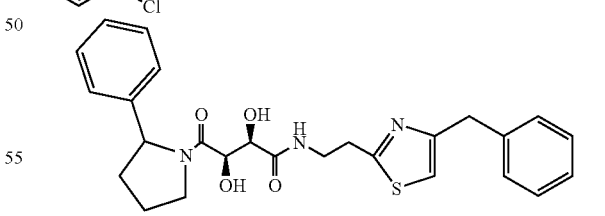
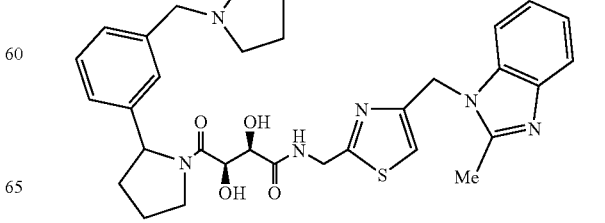

1637
-continued
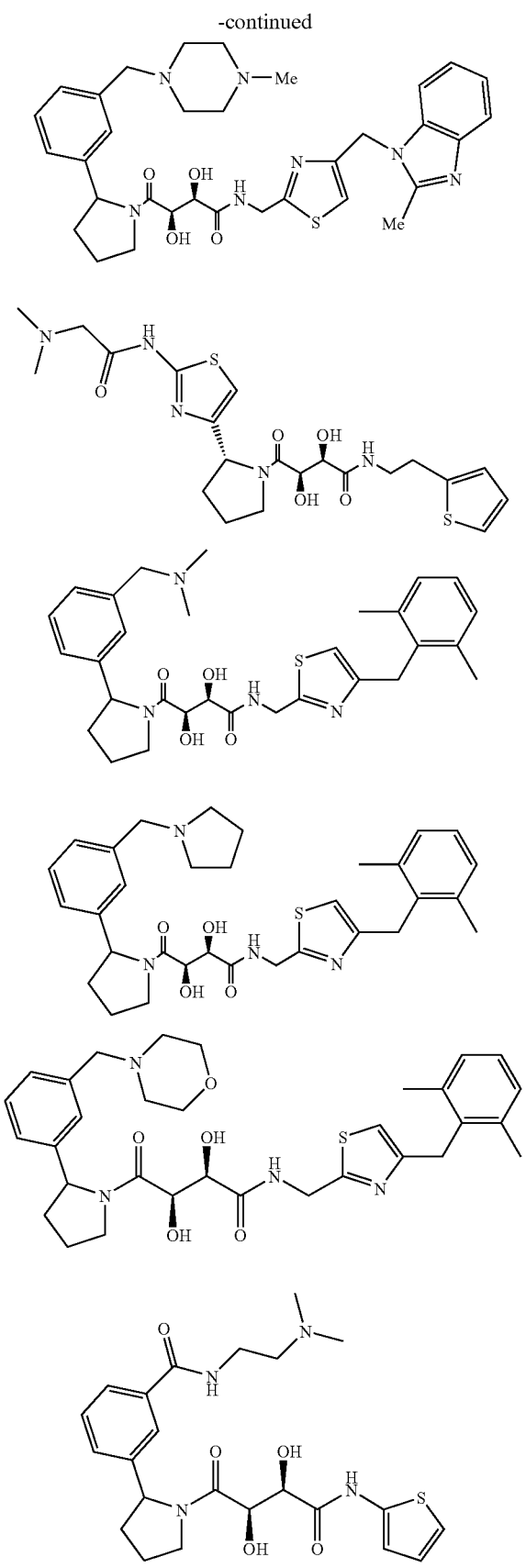
1638
-continued
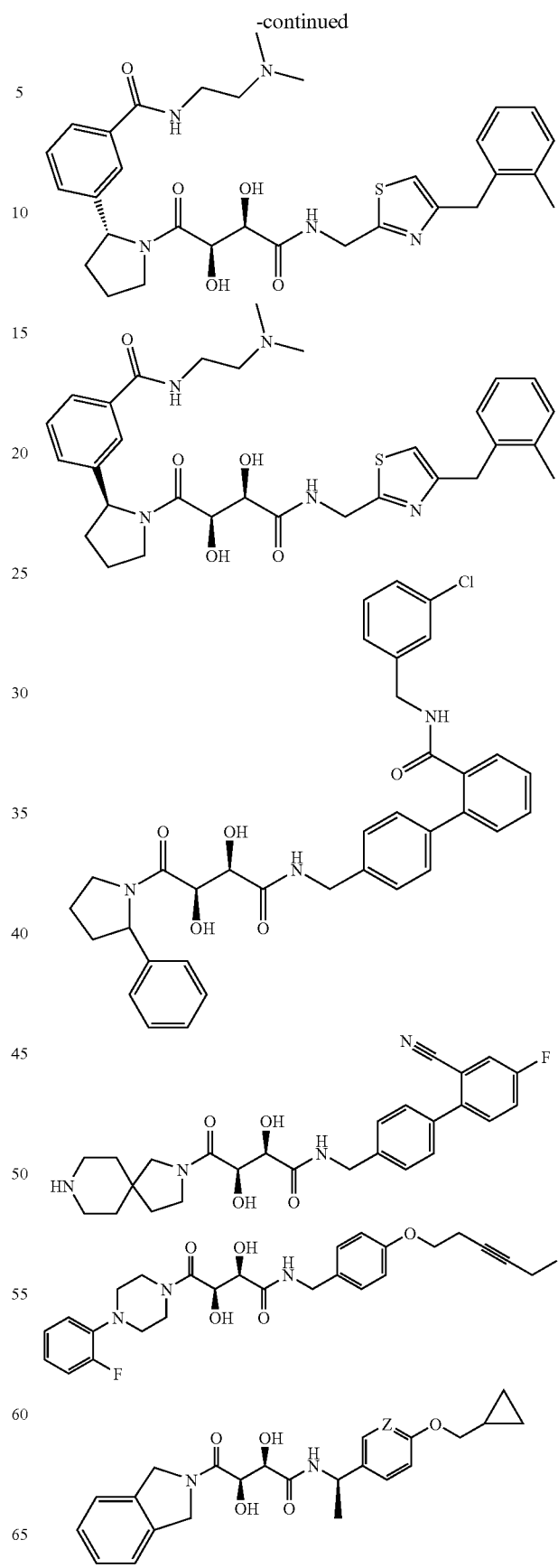

-continued
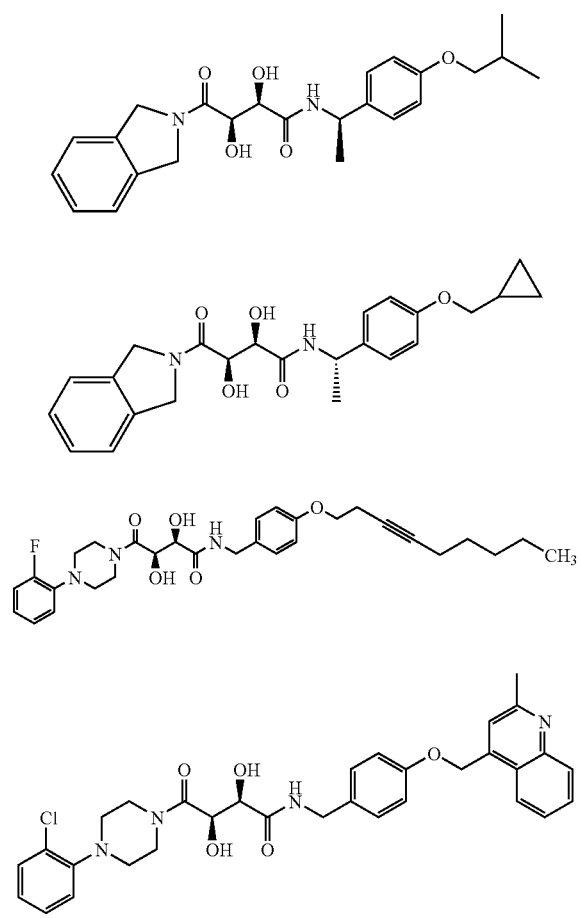
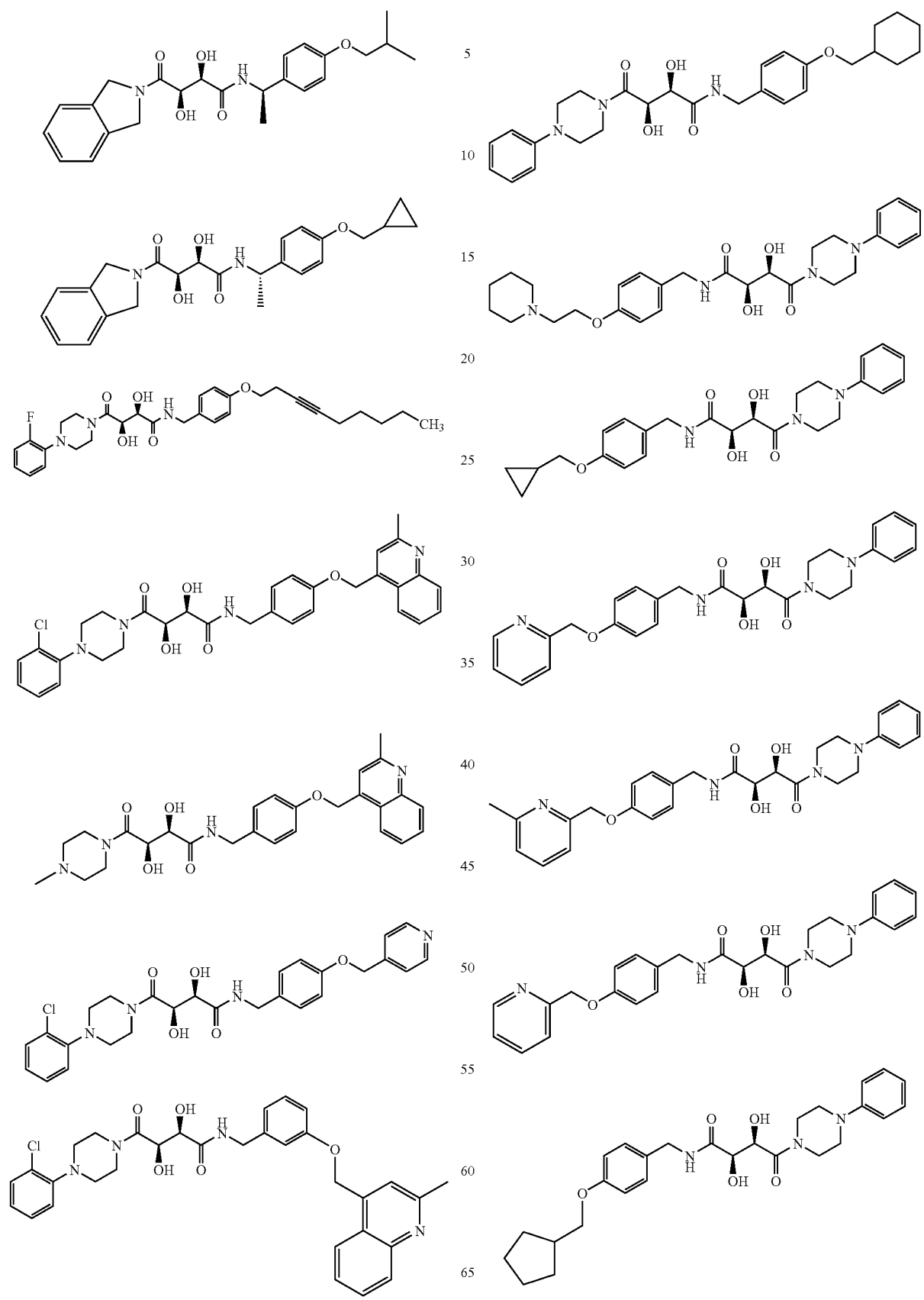

1641
-continued
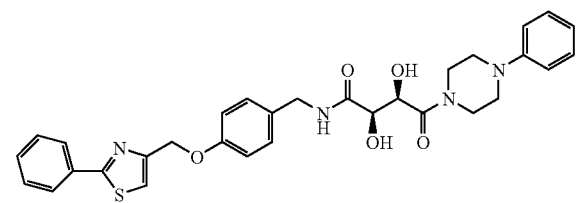
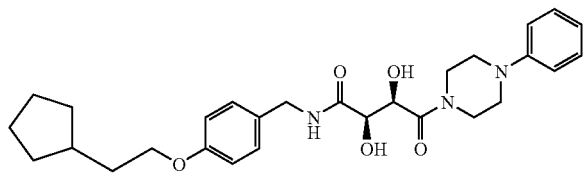
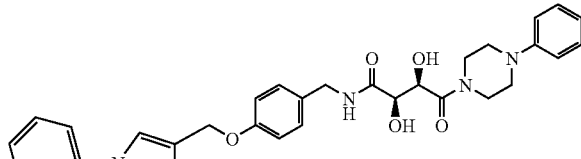
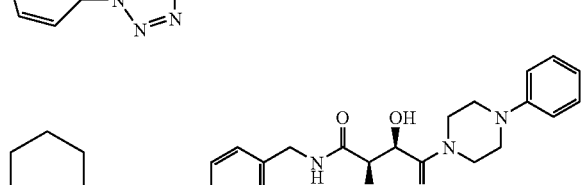
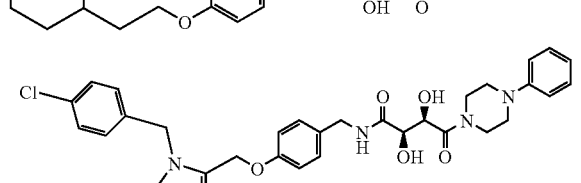
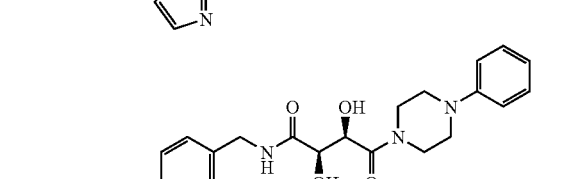
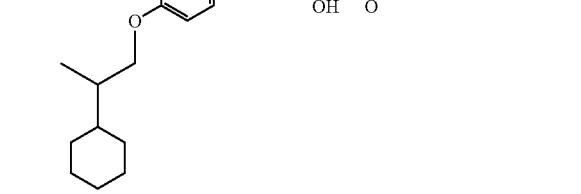
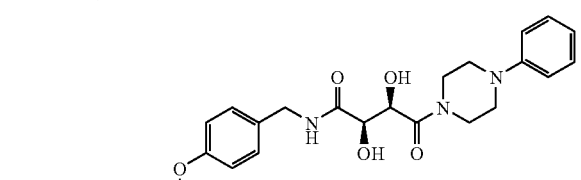
1642
-continued
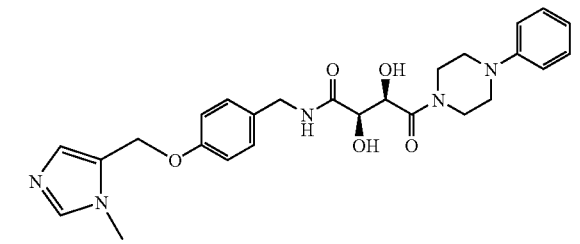
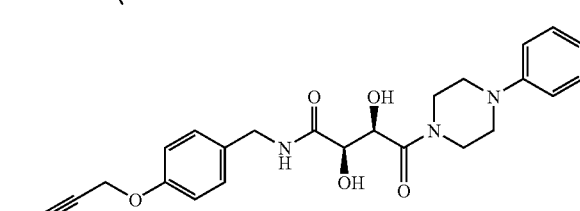
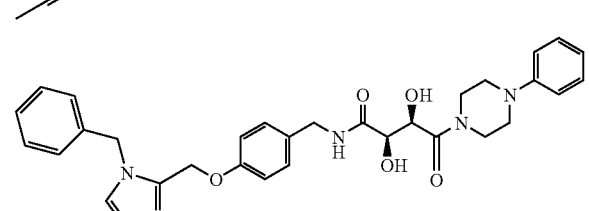
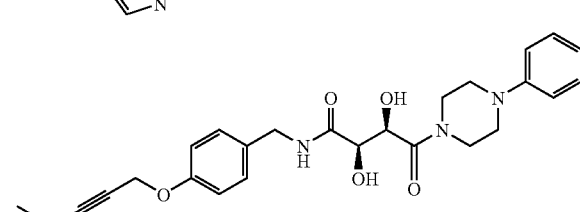
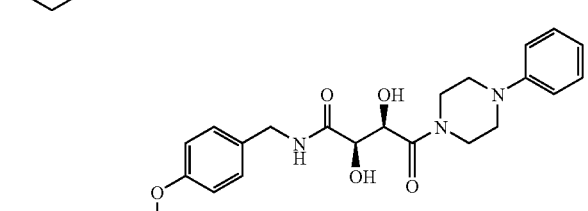
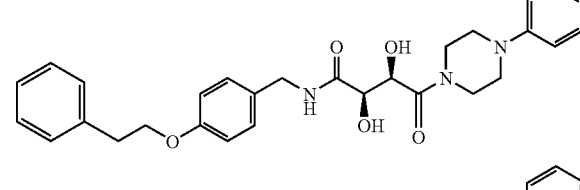
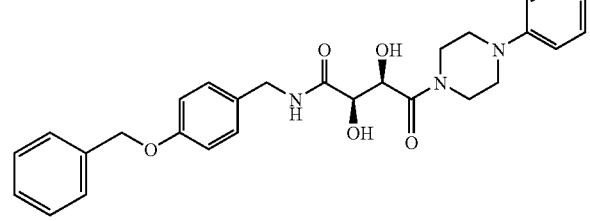

-continued
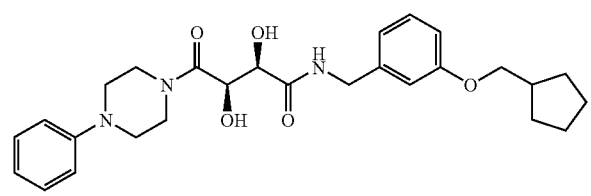
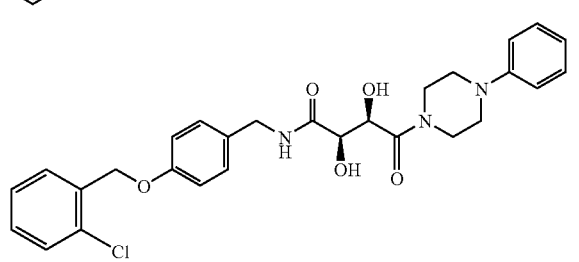
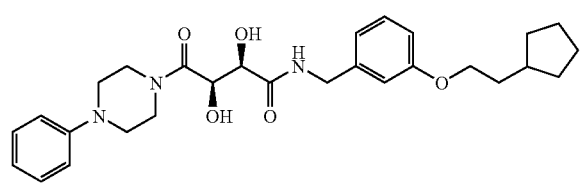
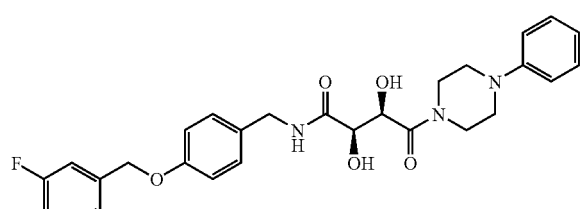
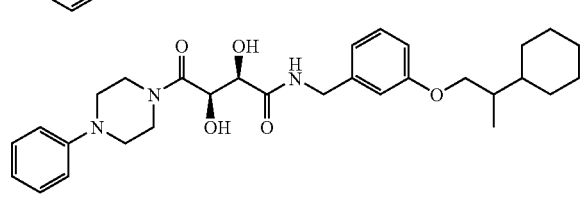
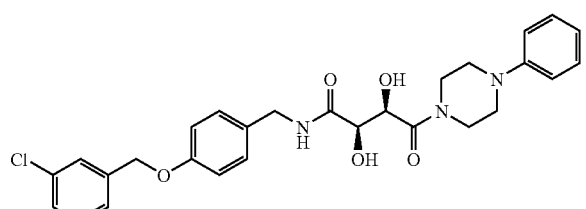
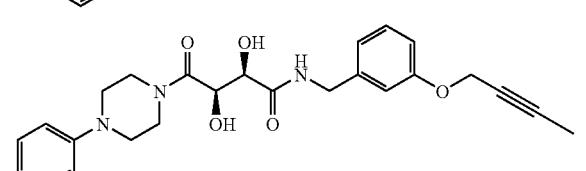
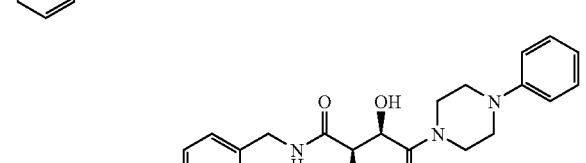
-continued
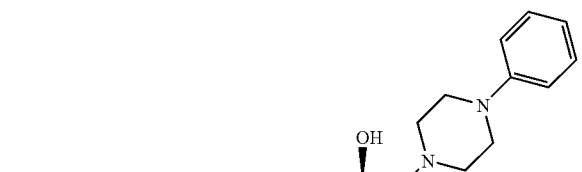
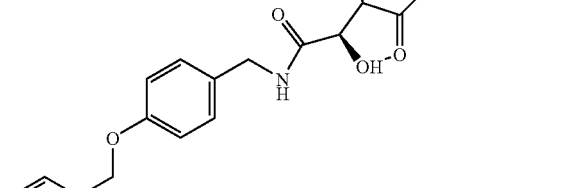
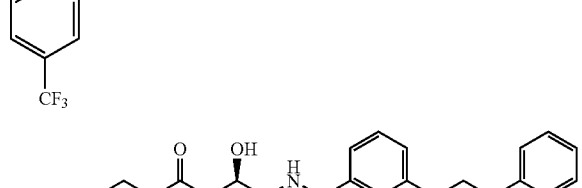
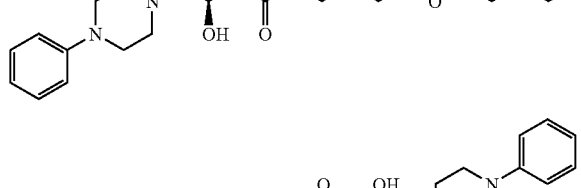
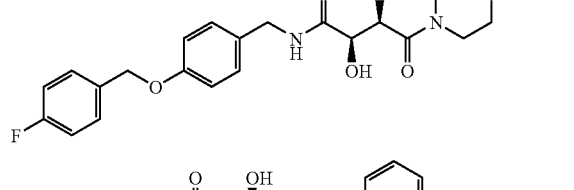
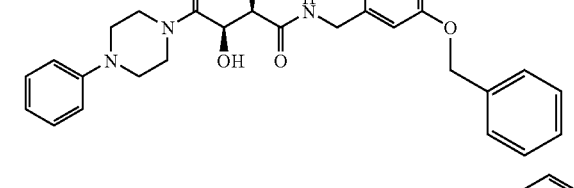
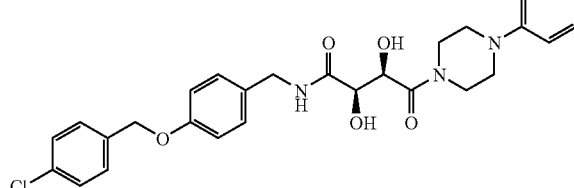
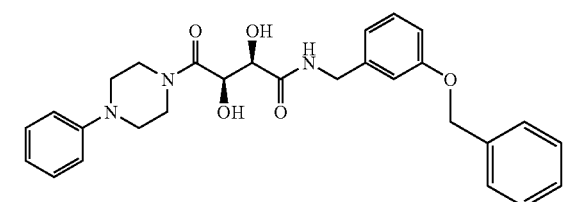

1645
-continued
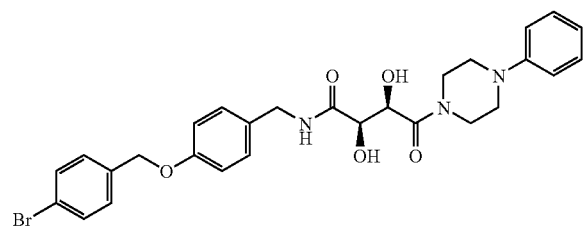
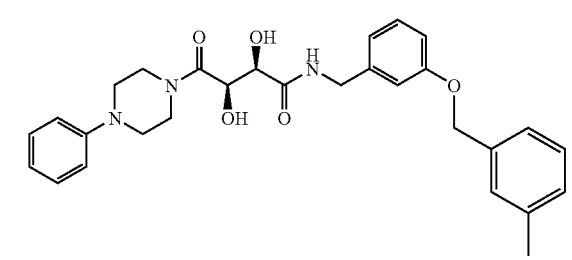
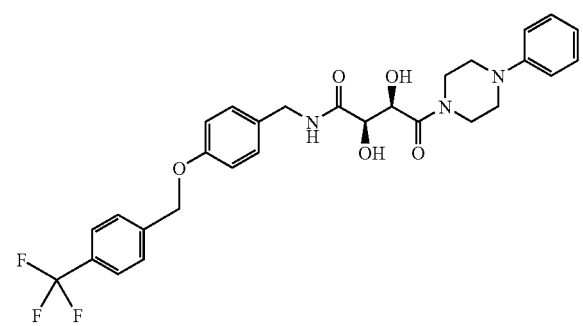
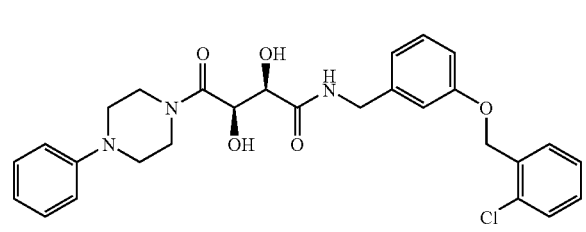
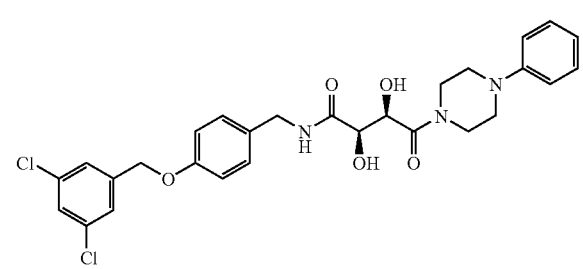
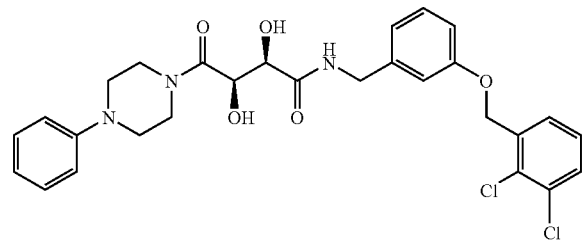
1646
-continued
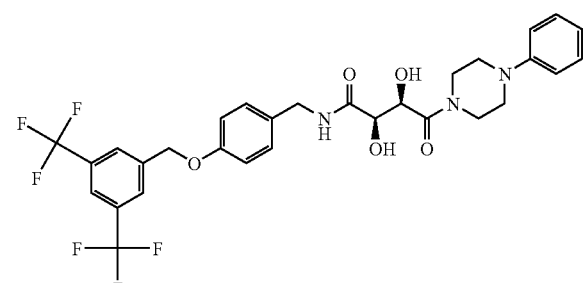
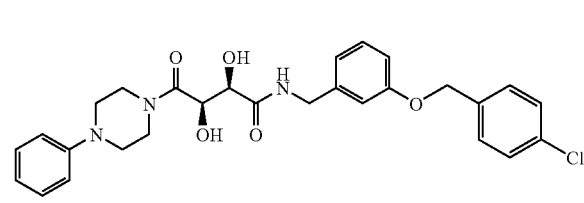
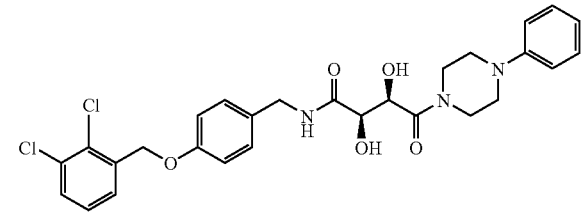
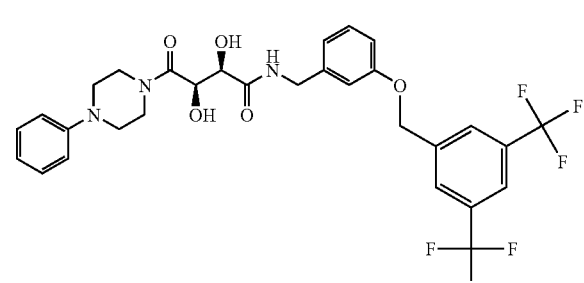

-continued
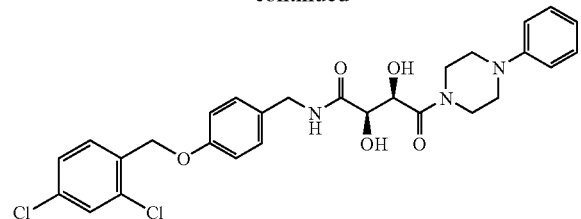
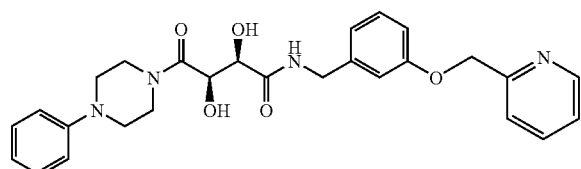
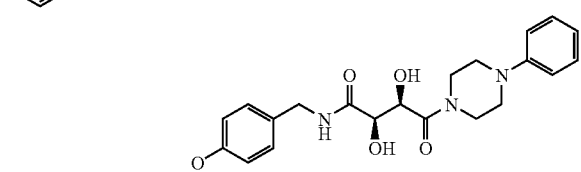
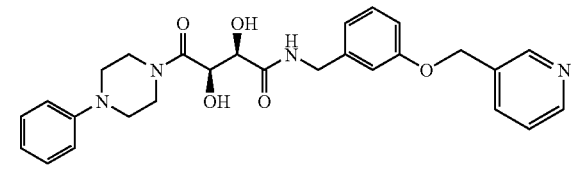
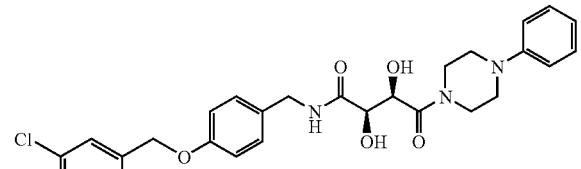
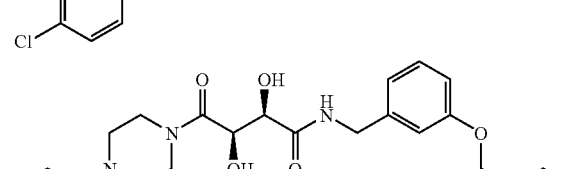
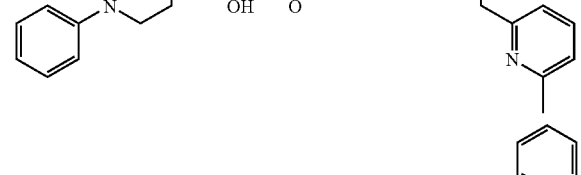
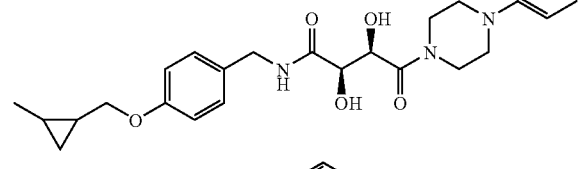
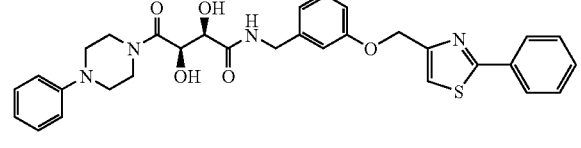
-continued
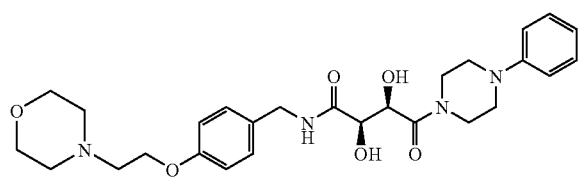
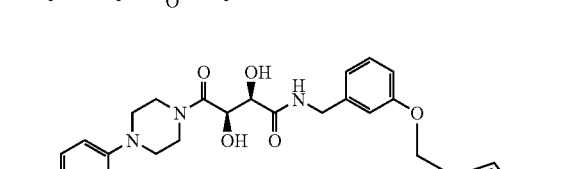
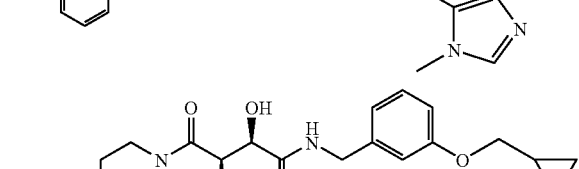
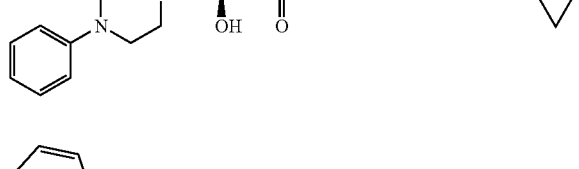
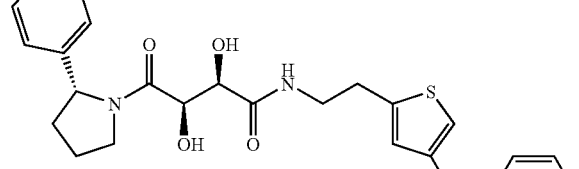
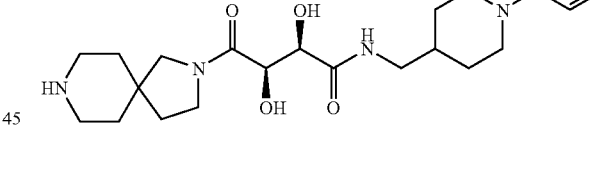
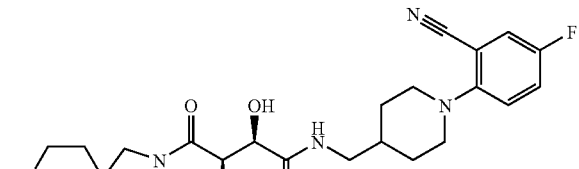
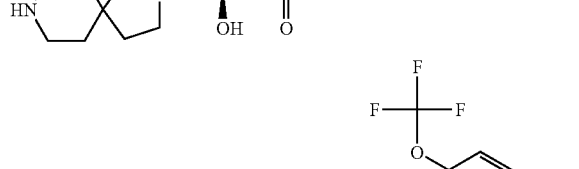
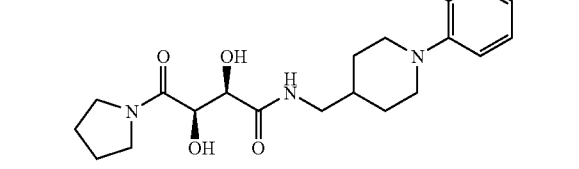

-continued
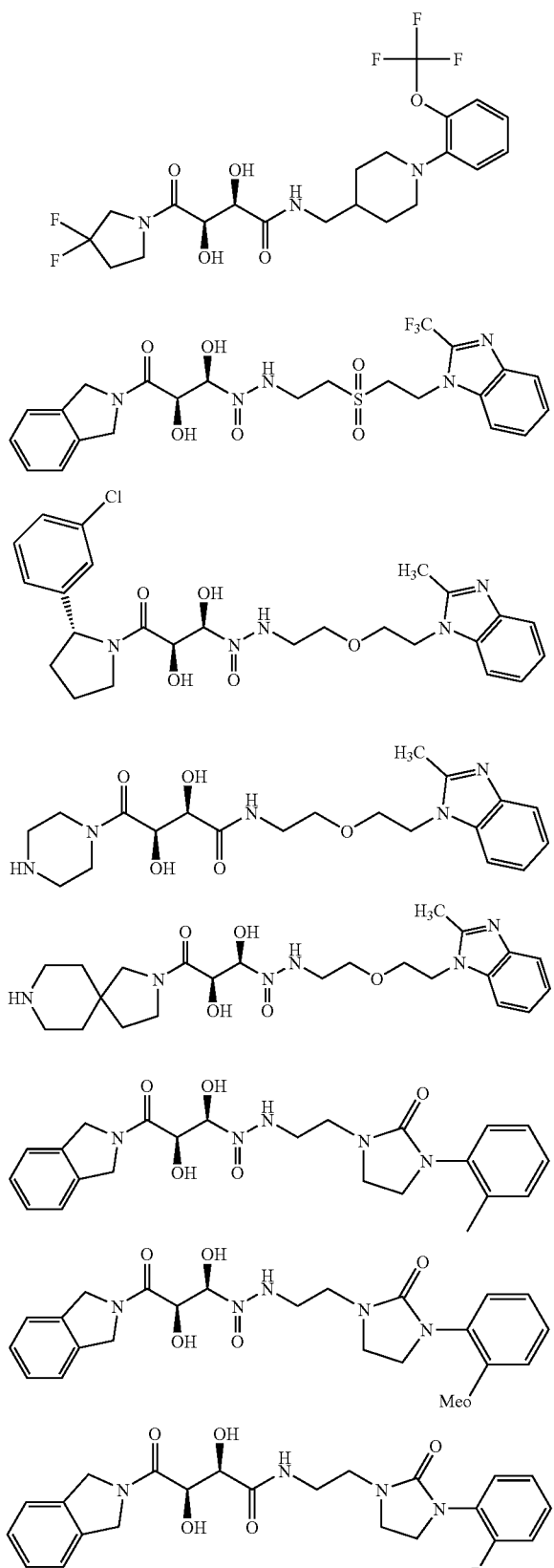
-continued
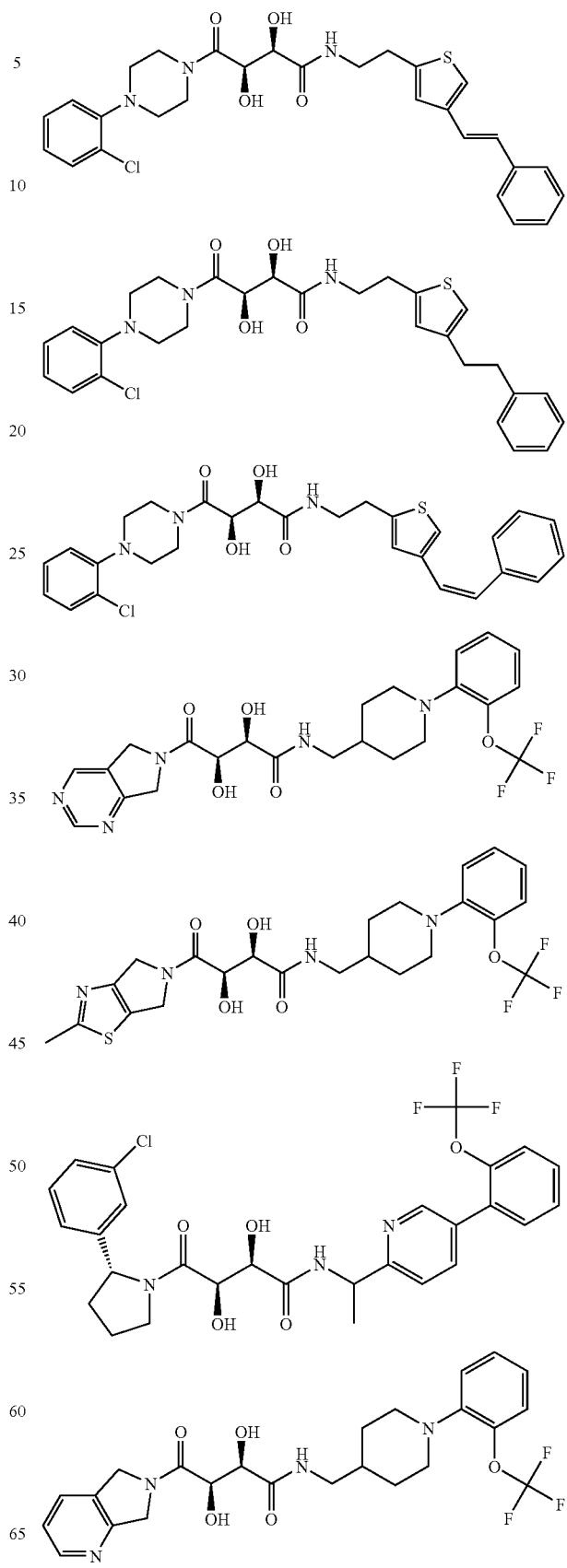

1651
-continued
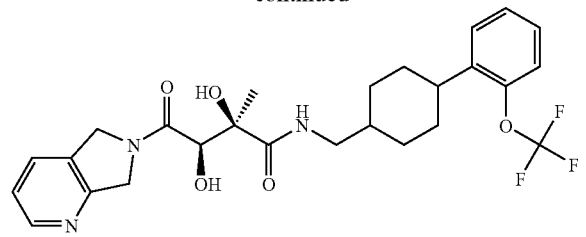
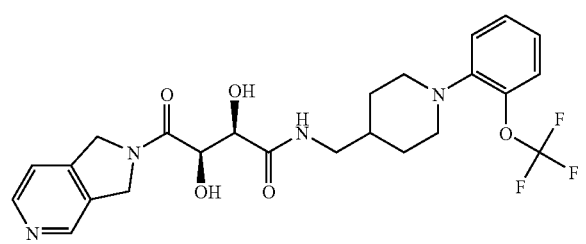
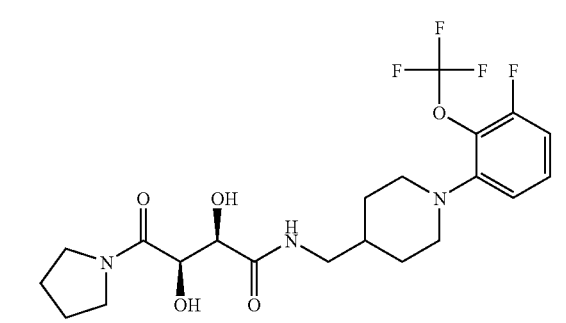
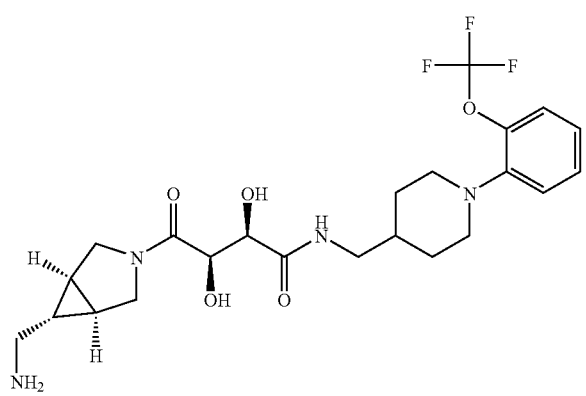
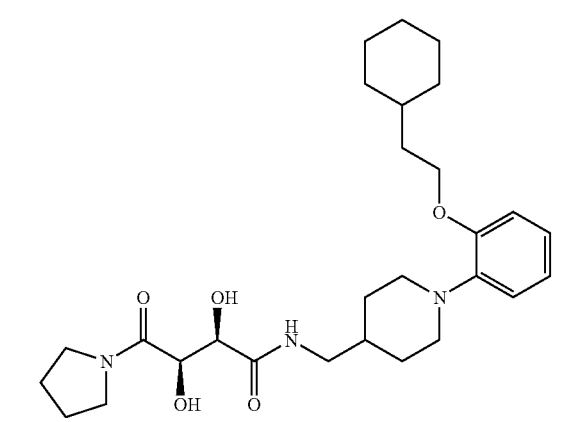
1652
-continued
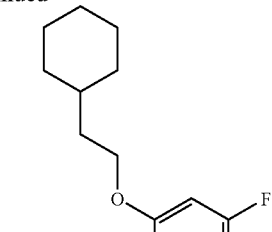
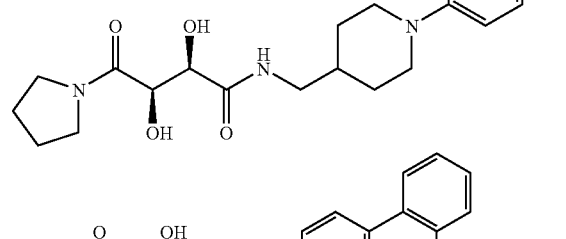
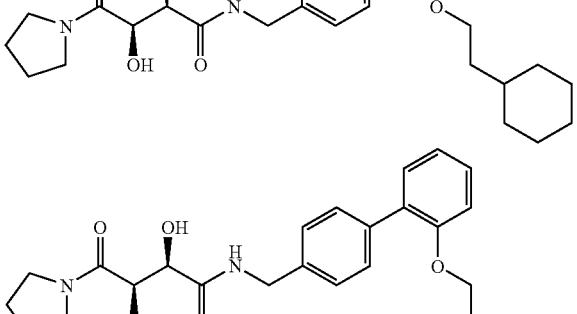
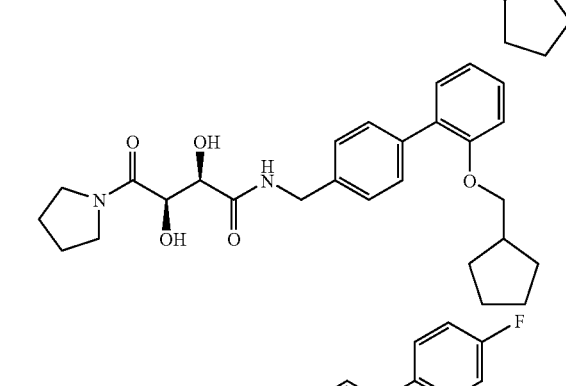
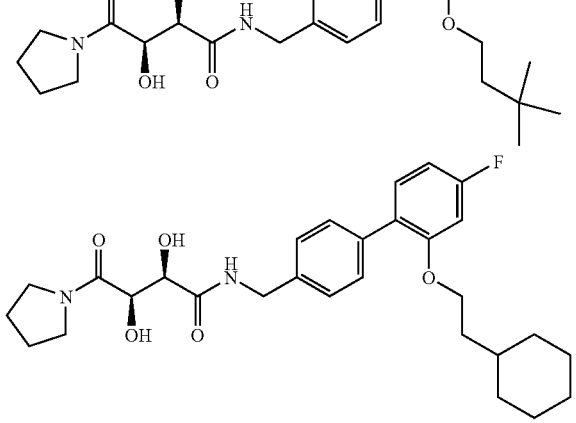

-continued
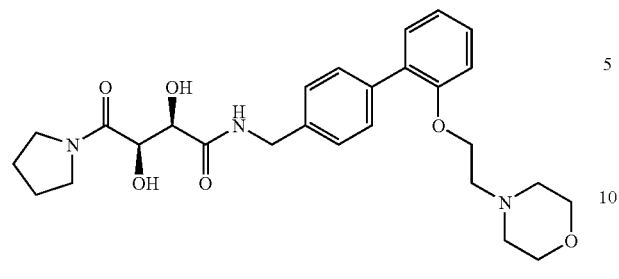
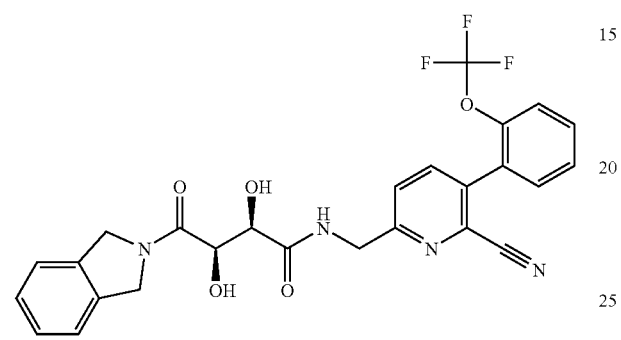
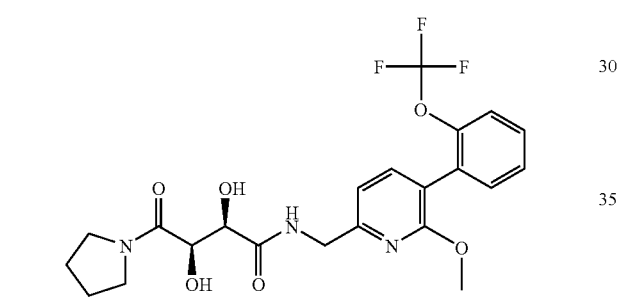
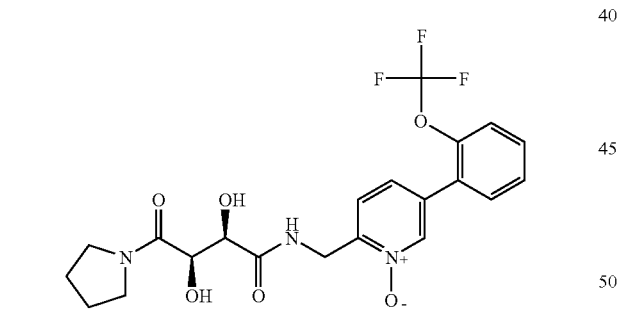
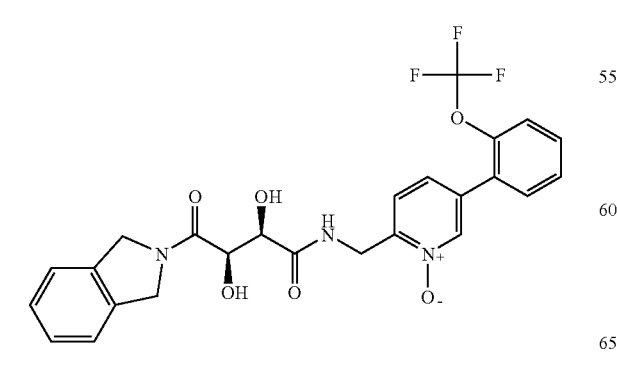
-continued
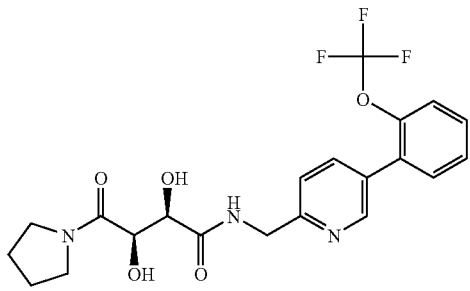
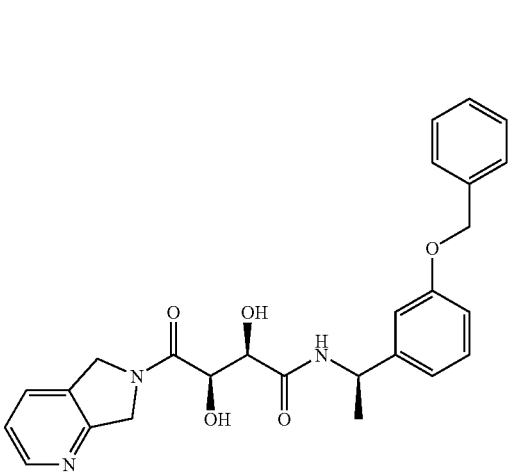
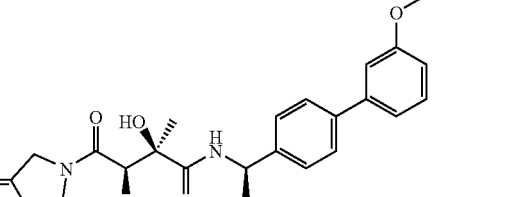

1655
-continued
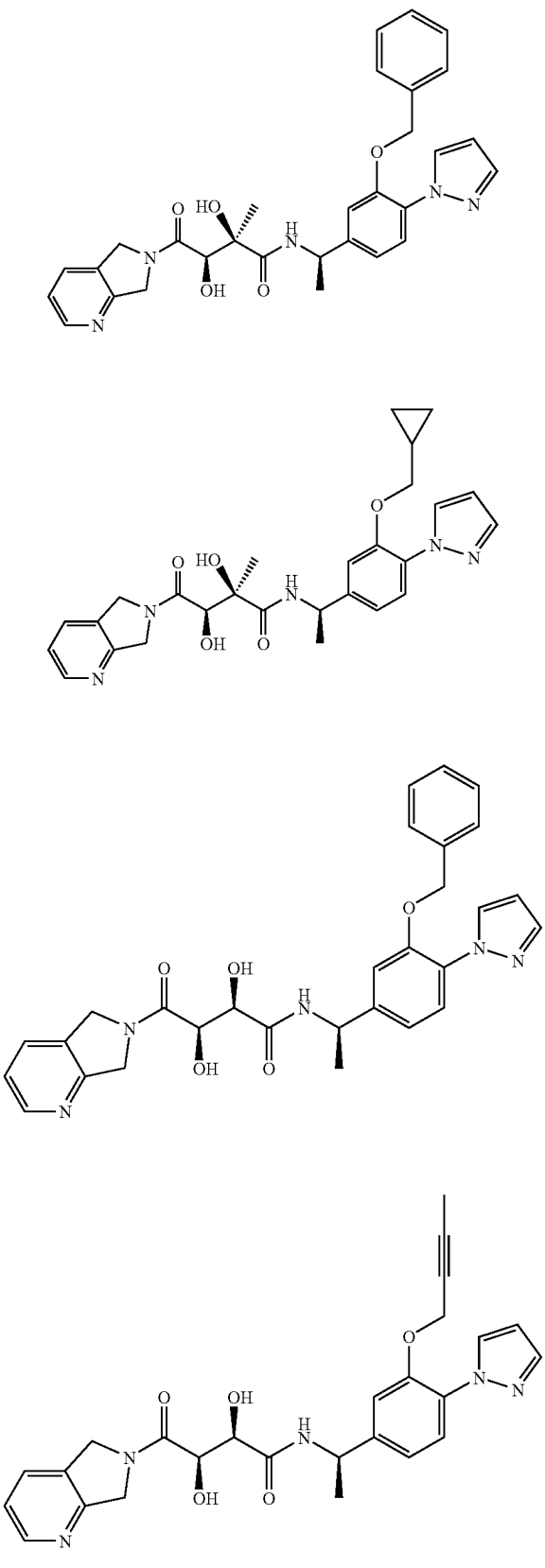
1656
-continued
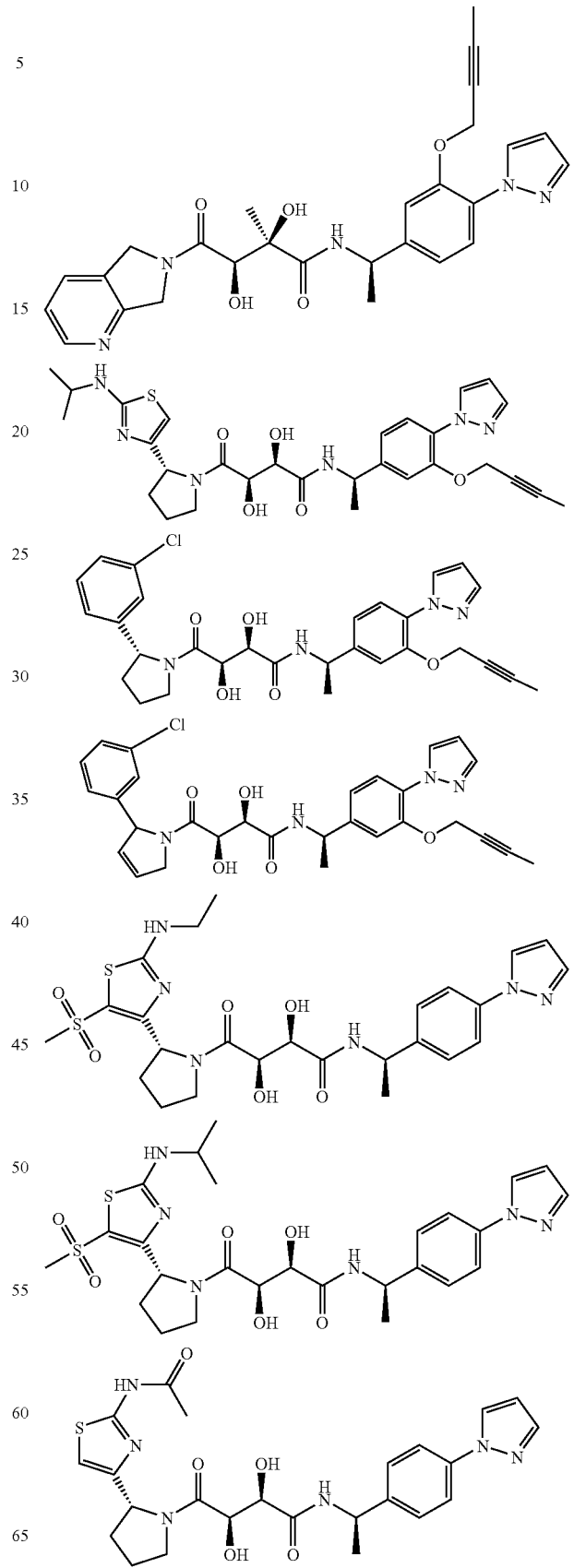

-continued

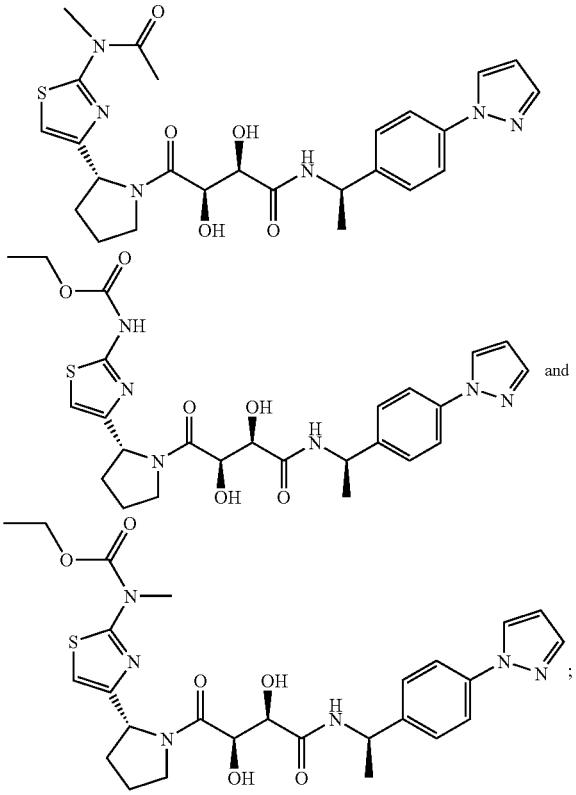

or a pharmaceutically acceptable salt or solution-phase solvate thereof.

28. A pharmaceutical composition comprising at least one compound of claim 27 or a pharmaceutically acceptable salt or solution-phase solvate thereof, and at least one pharmaceutically acceptable carrier.

29. A compound of formula (I):

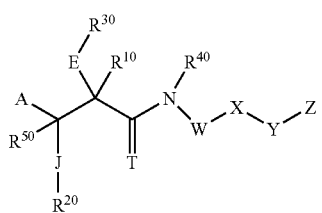

formula (I)

or a pharmaceutically acceptable salt or solution-phase solvate thereof, wherein:

A is:

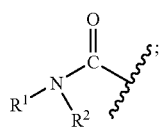

J is O;
E is O;
T is O;

—NR$^1$R$^2$ is selected from the group consisting of

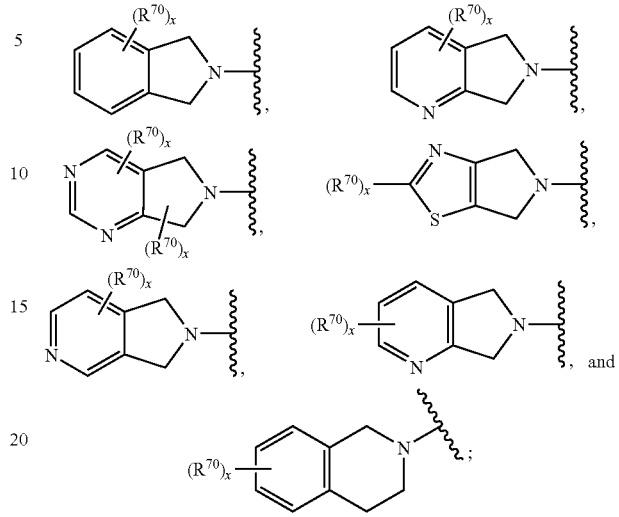

wherein x is 1 to 4;
R$^{10}$ is H;
R$^{20}$ is H;
R$^{30}$ is H;
R$^{40}$ is H;
R$^{50}$ is H;
W is —(CR$^{13}_2$)$_n$—, wherein n is 1;
X is absent or present, and if present X is aryl, wherein said aryl is phenyl, which can be unsubstituted or optionally substituted with one or more moieties which can be the same or different, each moiety being independently selected from the group of R$^{70}$ moieties below;
Y is absent;
Z is selected from the group consisting of H, alkyl, alkenyl, alkynyl, cycloalkyl, heterocyclyl, aryl, and heteroaryl, said cycloalkyl, heterocyclyl, aryl, and heteroaryl being optionally fused with aryl, heterocyclyl, heteroaryl or cycloalkyl; wherein each of said alkyl, alkenyl, alkynyl, cycloalkyl, heterocyclyl, aryl, and heteroaryl, optionally with said fused aryl, heterocyclyl, heteroaryl or cycloalkyl, can be unsubstituted or optionally independently substituted with one or more moieties which can be the same or different, each moiety being independently selected from the group of R$^{70}$ moieties below;
R$^{13}$ is selected from the group consisting of hydrogen and alkyl;
each R$^{70}$ is a substituent for H where indicated and is the same or different and is independently selected from the group consisting of alkyl, alkenyl, alkynyl, cycloalkyl, cycloalkenyl, heterocyclyl, aryl, arylalkyl, heteroaryl, heteroarylalkyl, halo, —CN, —CF$_3$, —OCF$_3$, —OR$^{15}$, —C(O)R$^{15}$, —C(O)OR$^{15}$, —C(O)N(R$^{15}$)(R$^{16}$), —SR$^{15}$, —S(O)$_q$N(R$^{15}$)(R$^{16}$) wherein q is 1 to 2, —C(=NOR$^{15}$)R$^{16}$, —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{17}$)S(O)$_2$N(R$^{16}$)(R$^{15}$), —N(R$^{17}$)S(O)N(R$^{16}$)(R$^{15}$), —N(R$^{17}$)C(O)N(R$^{16}$)(R$^{15}$), —CH$_2$—N(R$^{17}$)C(O)N(R$^{16}$)(R$^{15}$), —N(R$^{15}$)C(O)OR$^{16}$, —CH$_2$—N(R$^{15}$)C(O)OR$^{16}$, and —S(O)$_q$R$^{15}$ wherein q is 1 to 2; and wherein each of the alkyl, cycloalkyl, heterocyclyl, aryl, arylalkyl, heteroaryl, heteroarylalkyl, alkenyl and alkynyl are independently unsubstituted or substituted by 1 to 5 groups independently selected from the group consisting of alkyl, cycloalkyl, heterocyclyl, aryl, heteroaryl, halo, —CF$_3$, —CN, —OR$^{15}$, —N(R$^{15}$)(R$^{16}$), —C(O)OR$^{15}$, —C(O)N(R$^{15}$)(R$^{16}$), and —N(R$^{15}$)S(O)R$^{16}$;

each R$^{15}$, R$^{16}$ and R$^{17}$ are independently selected from the group consisting of H, alkyl, cycloalkyl, heterocyclyl, aryl, and heteroaryl, or alternatively R$^{15}$ and R$^{16}$ taken together with the N to which they are shown attached, are joined to form a 4-8 membered heterocyclic ring, wherein said 4-8 membered cycloalkyl can be unsubstituted or optionally independently substituted with one or more moieties which can be the same or different, each moiety being independently selected from the group of R$^{75}$ moieties below;

each R$^{75}$ is independently selected from the group consisting of alkyl, cycloalkyl, heterocyclyl, aryl, arylalkyl, heteroaryl, heteroarylalkyl, alkenyl and alkynyl, and wherein each of the alkyl, cycloalkyl, heterocyclyl, aryl, arylalkyl, heteroaryl, heteroarylalkyl, alkenyl and alkynyl are independently unsubstituted or substituted by 1 to 5 groups independently selected from the group consisting of alkyl, cycloalkyl, heterocyclyl, aryl, heteroaryl, halo, —CF$_3$, —CN, —OR$^{19}$, —N(R$^{19}$)$_2$, —C(O)OR$^{19}$, —C(O)N(R$^{19}$)$_2$, and —N(R$^{19}$)S(O)R$^{19}$; and each R$^{19}$ is independently selected from the group consisting of H, alkyl, cycloalkyl, heterocyclyl, aryl, and heteroaryl.

30. A compound of formula (I):

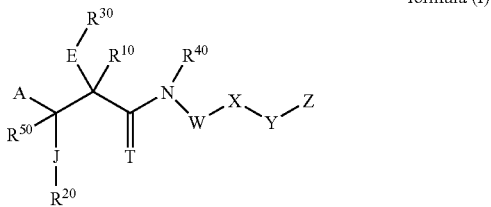

formula (I)

or a pharmaceutically acceptable salt or solution-phase solvate thereof, wherein:

A is:

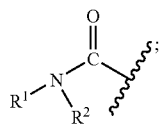

J is O;
E is O;
T is O;
R$^1$ and R$^2$, taken together with the N to which R$^1$ and R$^2$ are shown attached, represent a 4-8 membered heterocyclic ring having 1-3 heteroatoms including said N, said heterocyclic ring being fused with aryl, heteroaryl, cycloalkyl, or heterocyclyl, wherein said 4-8 membered heterocyclic ring with said fused aryl, heteroaryl, cycloalkyl or heterocyclyl is unsubstituted;
R$^{10}$ is H;
R$^{20}$ is H;
R$^{30}$ is H;
R$^{40}$ is H;
R$^{50}$ is H;
W is —(CR$^{13}$$_2$)$_n$—, wherein n is 1;
X is absent or present, and if present X is aryl, wherein said aryl is phenyl, which can be unsubstituted or optionally substituted with one or more moieties which can be the same or different, each moiety being independently selected from the group of R$^{70}$ moieties below;
Y is absent;
Z is selected from the group consisting of H, alkyl, alkenyl, alkynyl, cycloalkyl, heterocyclyl, aryl, and heteroaryl, said cycloalkyl, heterocyclyl, aryl, and heteroaryl being optionally fused with aryl, heterocyclyl, heteroaryl or cycloalkyl; wherein each of said alkyl, alkenyl, alkynyl, cycloalkyl, heterocyclyl, aryl, and heteroaryl, optionally with said fused aryl, heterocyclyl, heteroaryl or cycloalkyl, can be unsubstituted or optionally independently substituted with one or more moieties which can be the same or different, each moiety being independently selected from the group of R$^{70}$ moieties below;
R$^{13}$ is selected from the group consisting of hydrogen and alkyl;
each R$^{70}$ is a substituent for H where indicated and is the same or different and is independently selected from the group consisting of alkyl, alkenyl, alkynyl, cycloalkyl, cycloalkenyl, heterocyclyl, aryl, arylalkyl, heteroaryl, heteroarylalkyl, halo, —CN, —CF$_3$, —OCF$_3$, —OR$^{15}$, —C(O)R$^{15}$, —C(O)OR$^{15}$, —C(O)N(R$^{15}$)(R$^{16}$), —SR$^{15}$, —S(O)$_q$N(R$^{15}$)(R$^{16}$) wherein q is 1 to 2, —C(=NOR$^{15}$)R$^{16}$, —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —N(R$^{15}$)S(O)R$^{16}$, —N(R$^{15}$)S(O)$_2$R$^{16}$, —$^{CH}$$_2$—N(R$^{15}$)S(O)$_2$R$^{16}$, —N(R$^{17}$)S(O)$_2$N(R$^{16}$)(R$^{15}$), —N(R$^{17}$)S(O)N(R$^{16}$)(R$^{15}$), —N(R$^{17}$)C(O)N(R$^{16}$)(R$^{15}$), —CH$_2$—N(R$^{17}$)C(O)N(R$_{16}$)(R$^{15}$), —N(R$^{15}$)C(O)OR$^{16}$, —CH$_2$—N(R$^{15}$)C(O)OR$^{16}$, and —S(O)$_q$R$^{15}$ wherein q is 1 to 2; and wherein each of the alkyl, cycloalkyl, heterocyclyl, aryl, arylalkyl, heteroaryl, heteroarylalkyl, alkenyl and alkynyl are independently unsubstituted or substituted by 1 to 5 groups independently selected from the group consisting of alkyl, cycloalkyl, heterocyclyl, aryl, heteroaryl, halo, —CF$_3$, —CN, —OR$^{15}$, —N(R$^{15}$)(R$^{16}$), —C(O)OR$^{15}$, —C(O)N(R$^{15}$)(R$^{16}$), and —N(R$^{15}$)S(O)R$^{16}$; and each R$^{15}$, R$^{16}$ and R$^{17}$ are independently selected from the group consisting of H, alkyl, cycloalkyl, heterocyclyl, aryl, and heteroaryl, or alternatively R$^{15}$ and R$^{16}$ taken together with the N to which they are shown attached, are joined to form a 4-8 membered heterocylic ring, wherein said 4-8 membered cycloalkyl can be unsubstituted or optionally independently substituted with one or more moieties which can be the same or different, each moiety being independently selected from the group of R$^{75}$ moieties below;

each R$^{75}$ is independently selected from the group consisting of alkyl, cycloalkyl, heterocyclyl, aryl, arylalkyl, heteroaryl, heteroarylalkyl, alkenyl and alkynyl, and wherein each of the alkyl, cycloalkyl, heterocyclyl, aryl, arylalkyl, heteroaryl, heteroarylalkyl, alkenyl and alkynyl are independently unsubstituted or substituted by 1 to 5 groups independently selected from the group consisting of alkyl, cycloalkyl, heterocyclyl, aryl, heteroaryl, halo, —CF$_3$, —CN, —OR$^{19}$, —N(R$^{19}$)$_2$, —C(O)OR$^{19}$, —C(O)N(R$^{19}$)$_2$, and —N(R$^{19}$)S(O)R$^{19}$; and each R$^{19}$ is independently selected from the group consisting of H, alkyl, cycloalkyl, heterocyclyl, aryl, and heteroaryl.

31. The compound of claim 30, wherein A is

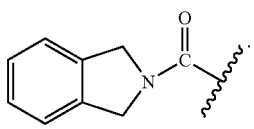

32. The compound of claim 30, wherein said —NR$^1$R$^2$ is

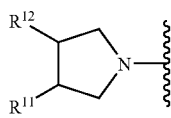

wherein
R$^{11}$ and R$^{12}$ taken together with the carbon to which each R$^{11}$ and R$^{12}$ are shown attached are fused heteroaryl or fused cycloalkyl, wherein said fused heteroaryl and fused cycloalkyl is unsubstituted.

33. The compound of claim 30, wherein said —NR$^1$R$^2$ is selected from the group consisting of

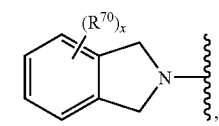 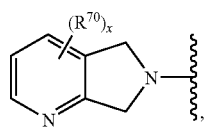

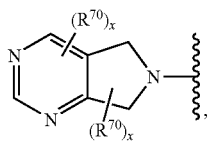 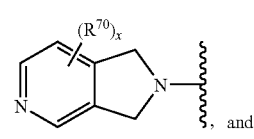, and

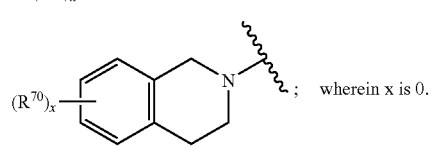; wherein x is 0.

34. A compound selected from the group consisting of:

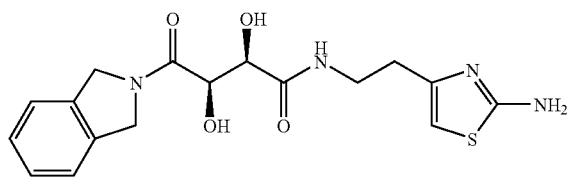

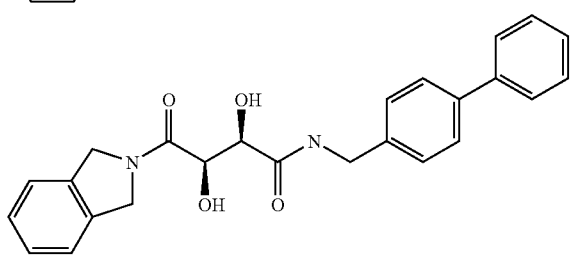

-continued

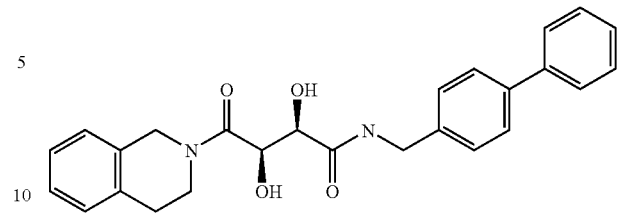

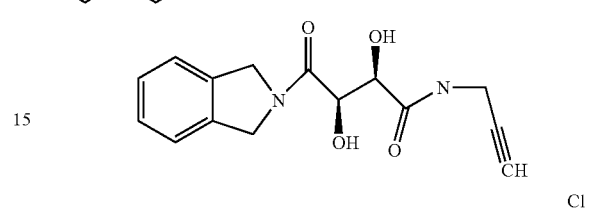

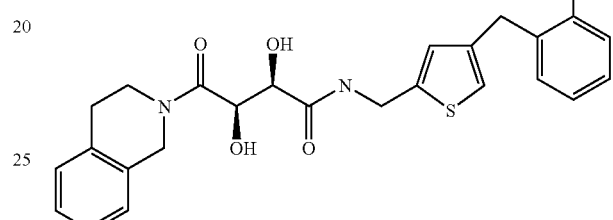

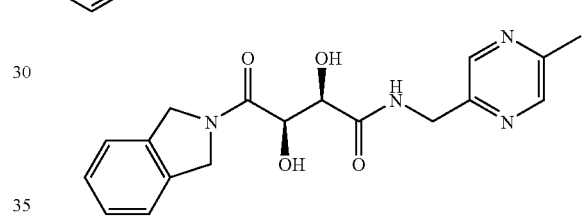

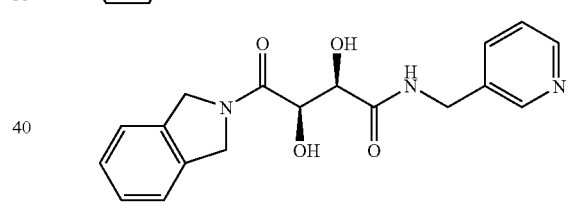

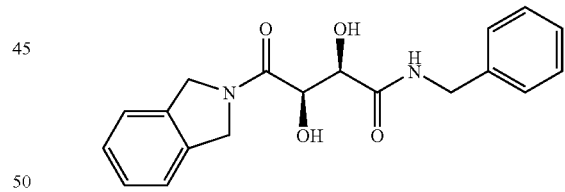

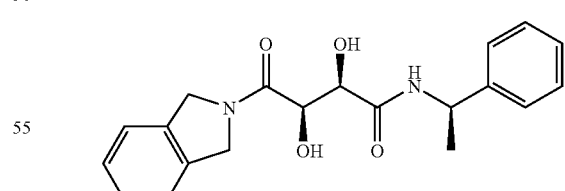

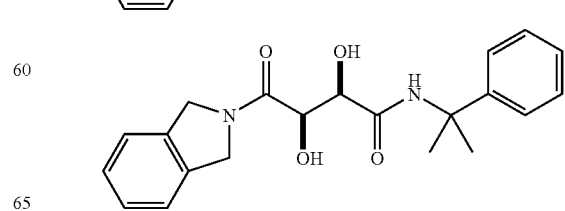

-continued
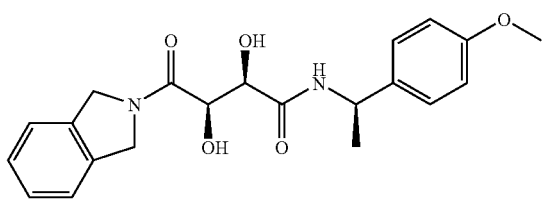
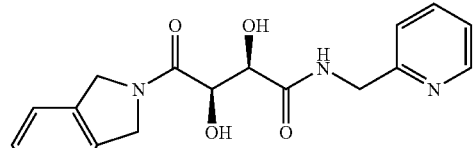
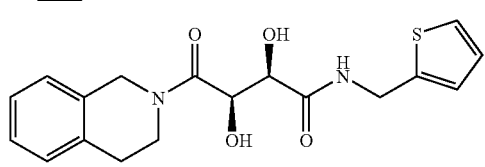
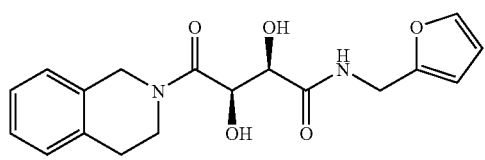
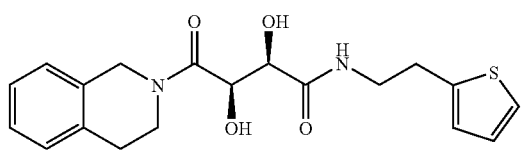
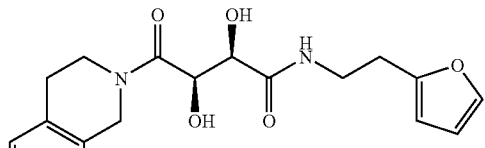
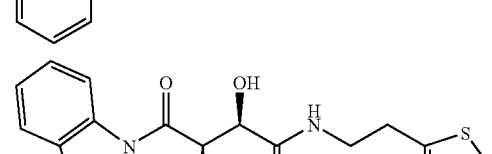
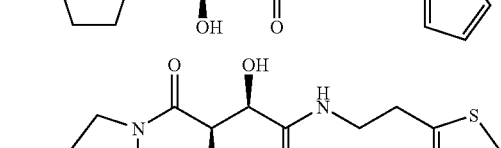
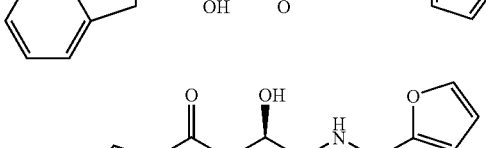
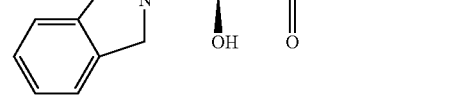
-continued
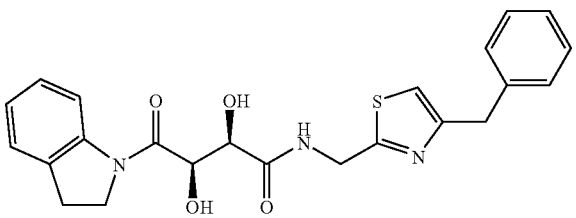
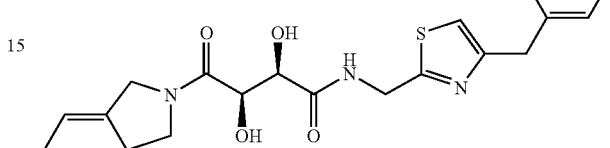
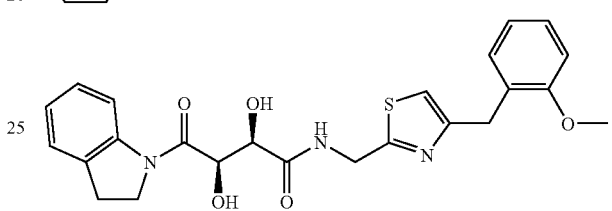
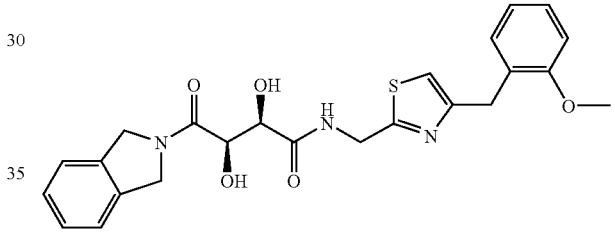
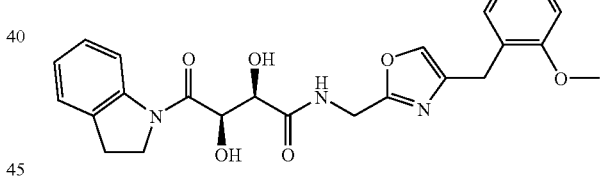
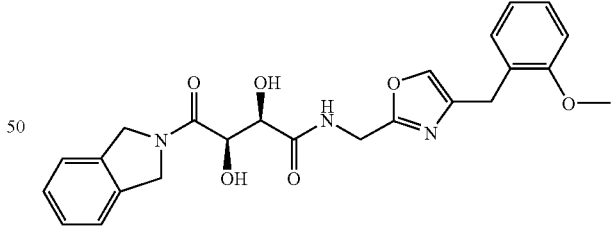
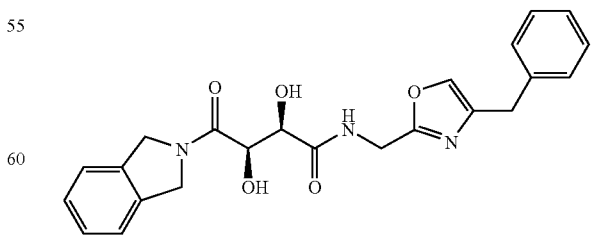

1665
-continued
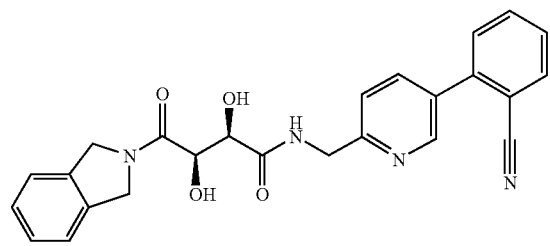
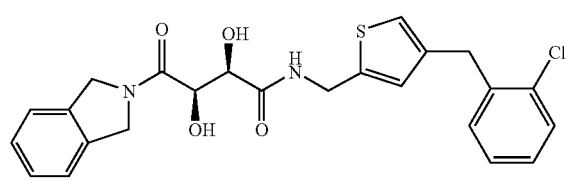
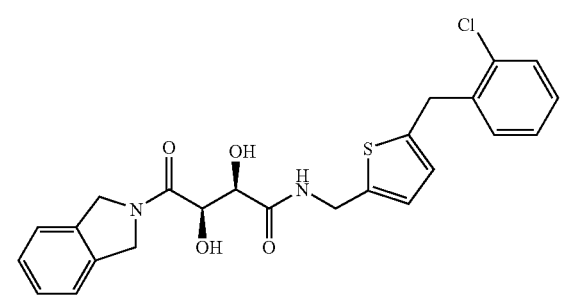
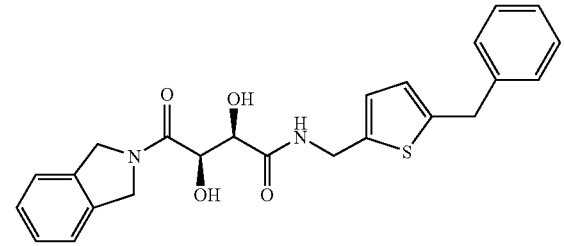
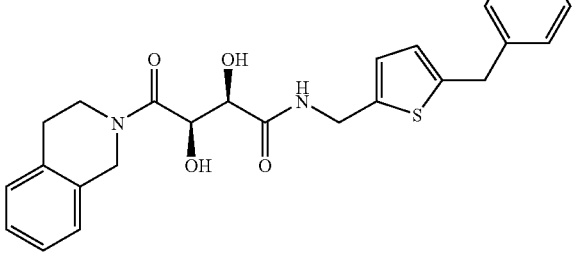
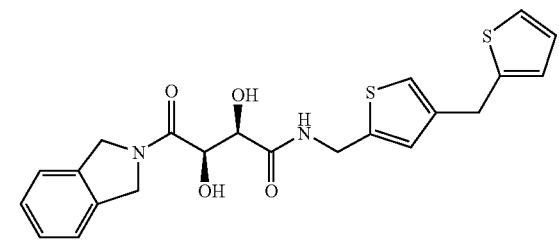
1666
-continued
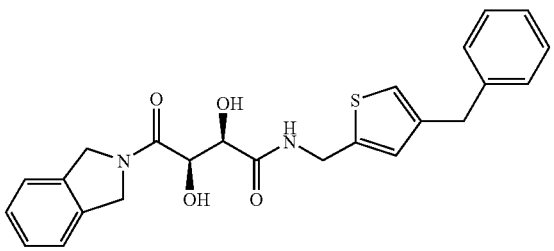
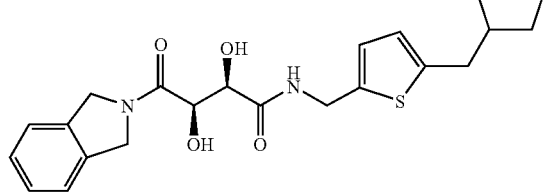
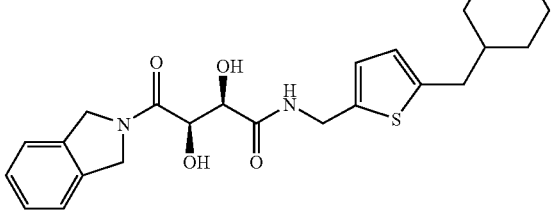
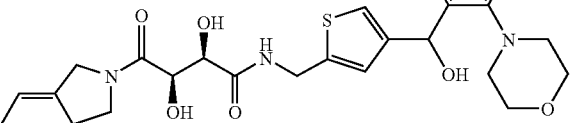
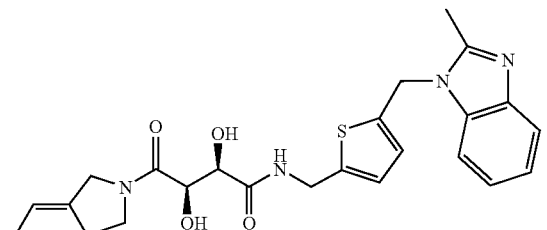
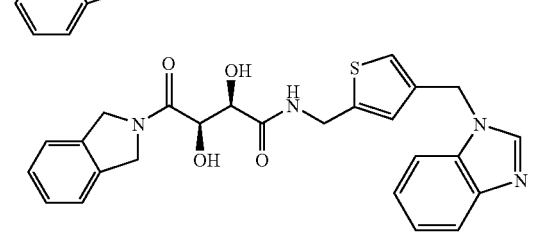
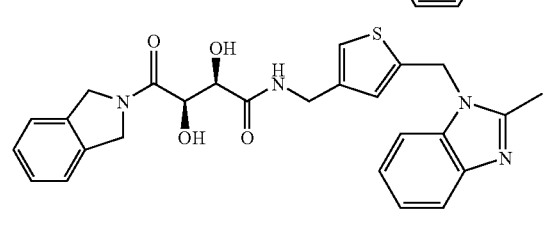

-continued
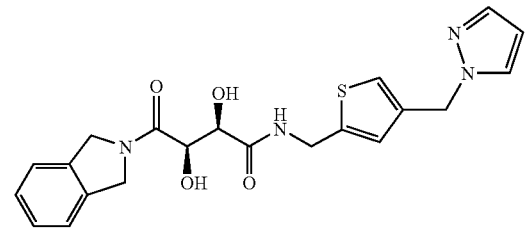
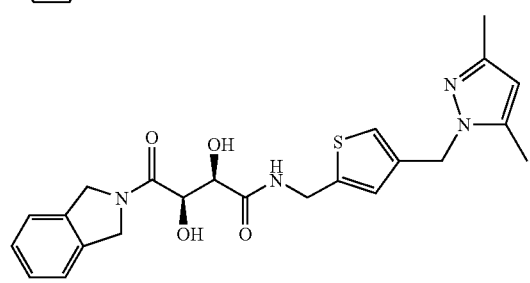
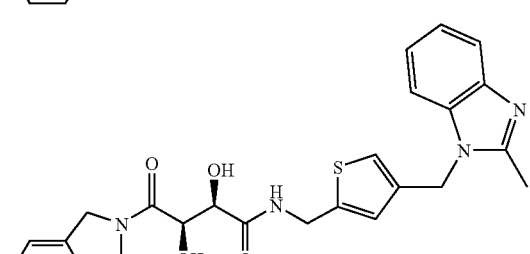
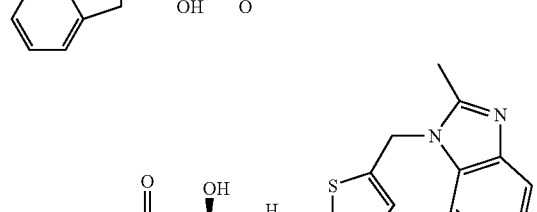
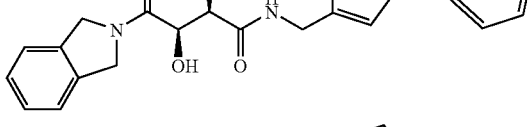
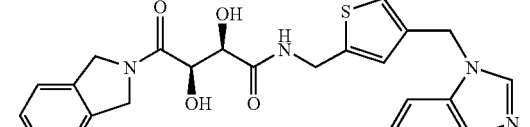
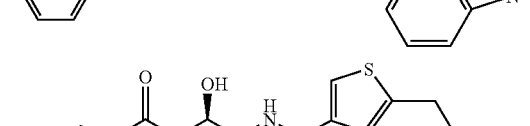
-continued
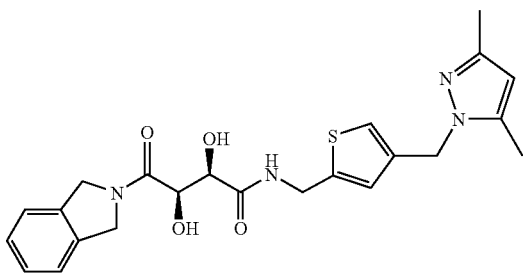
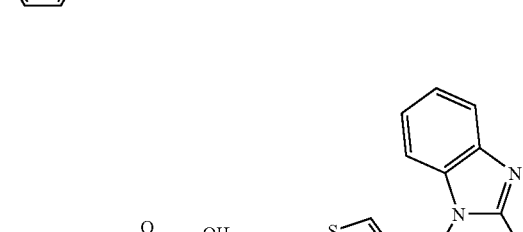
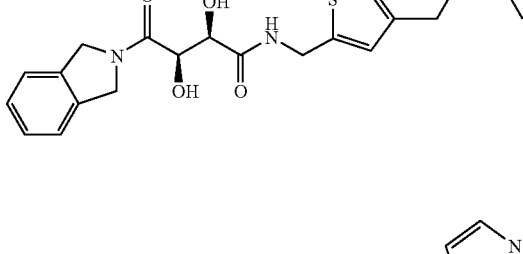
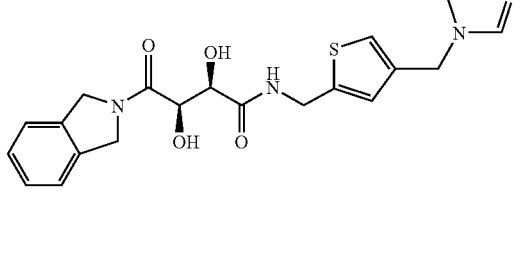
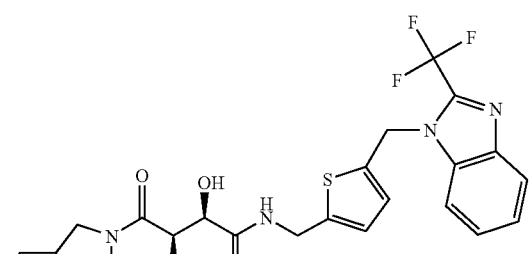
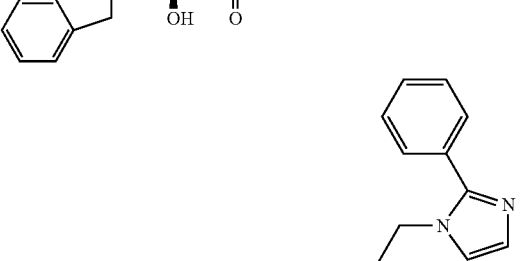
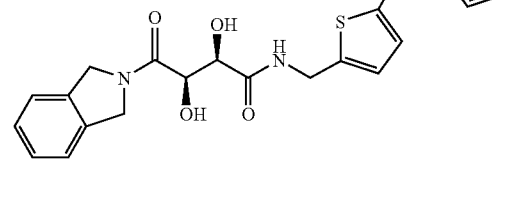

-continued
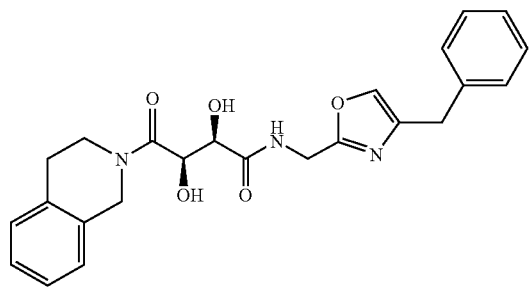
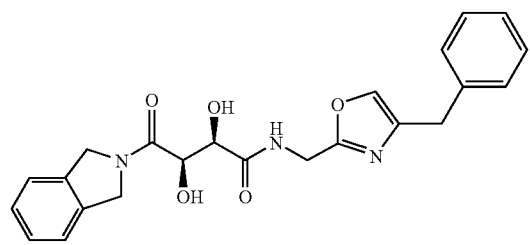
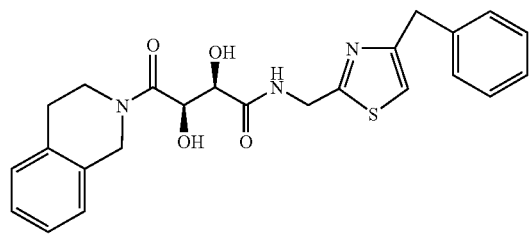
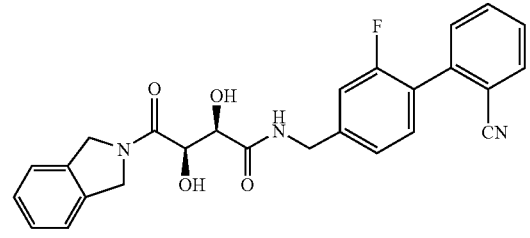
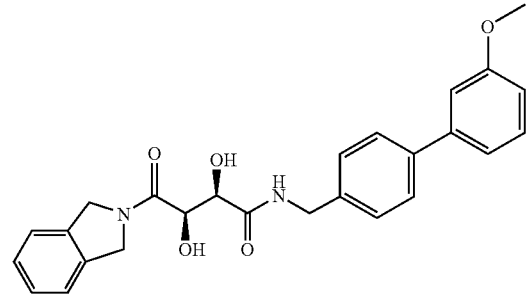
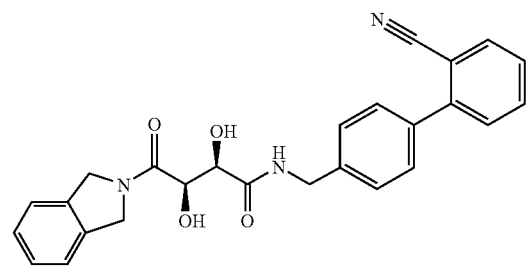
-continued
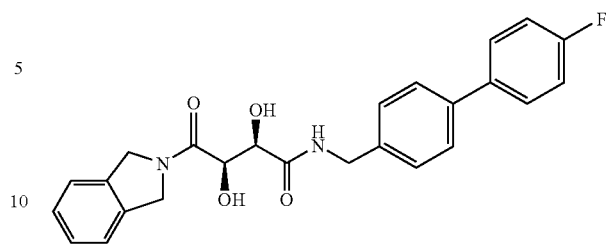
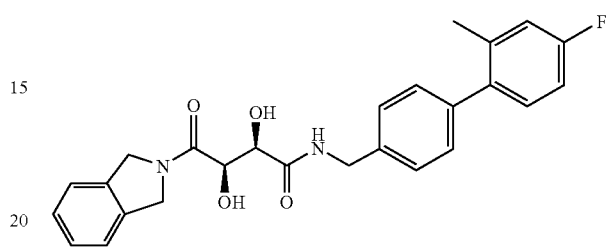
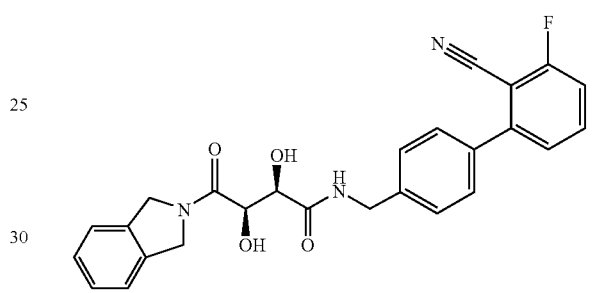
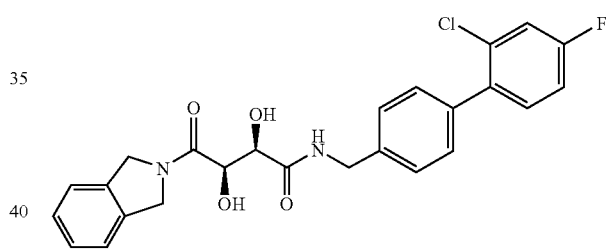
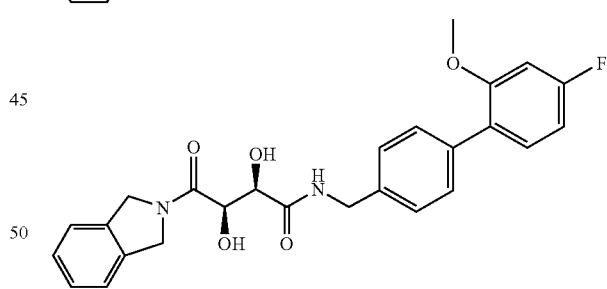
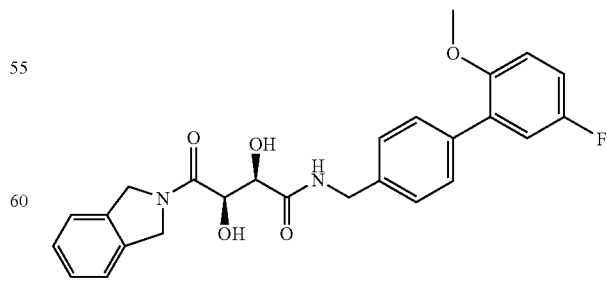

-continued
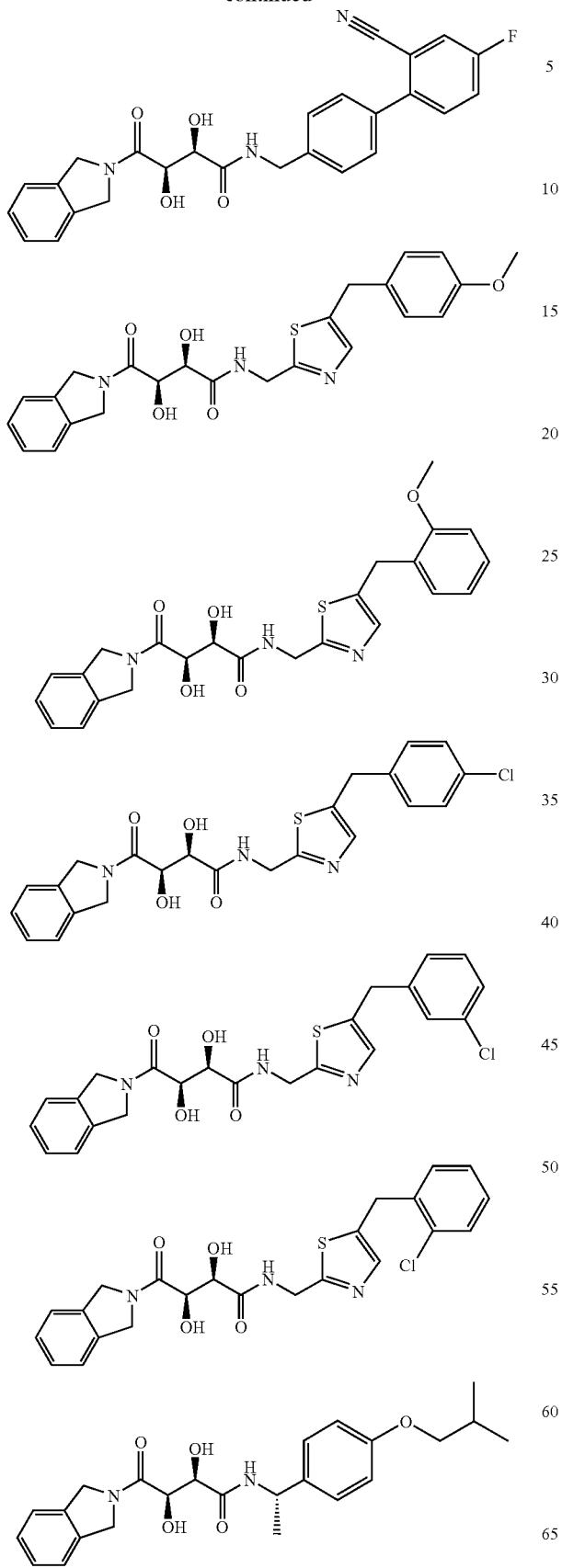
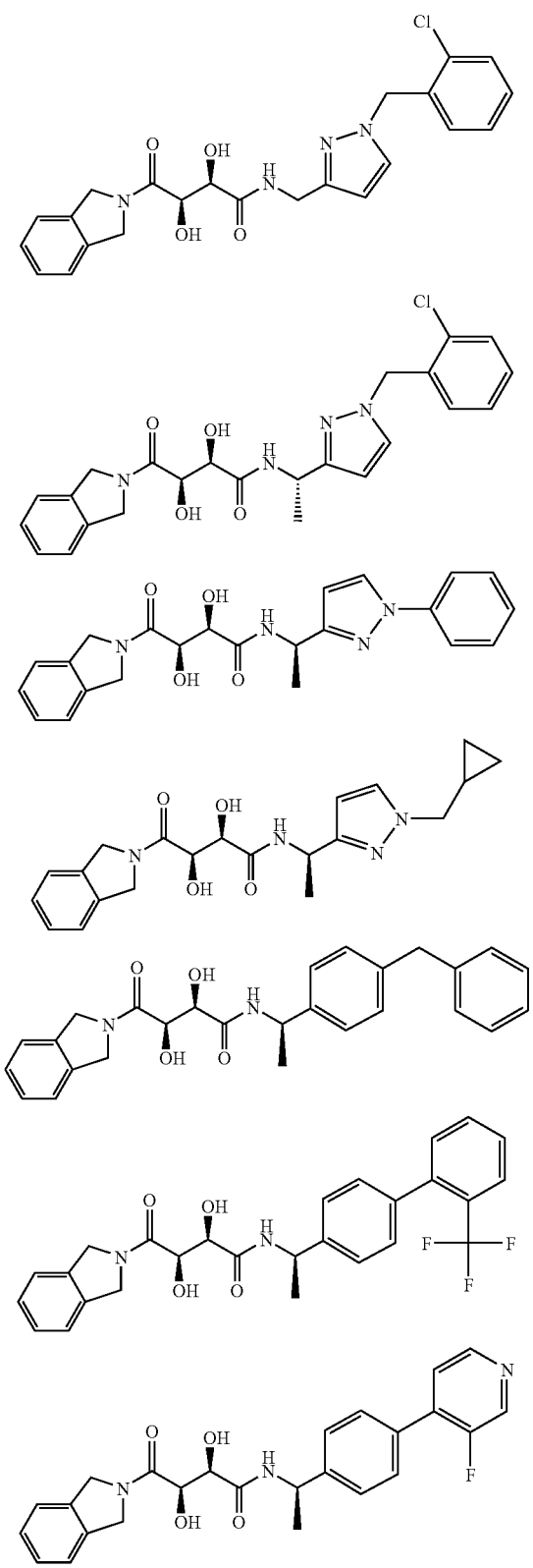

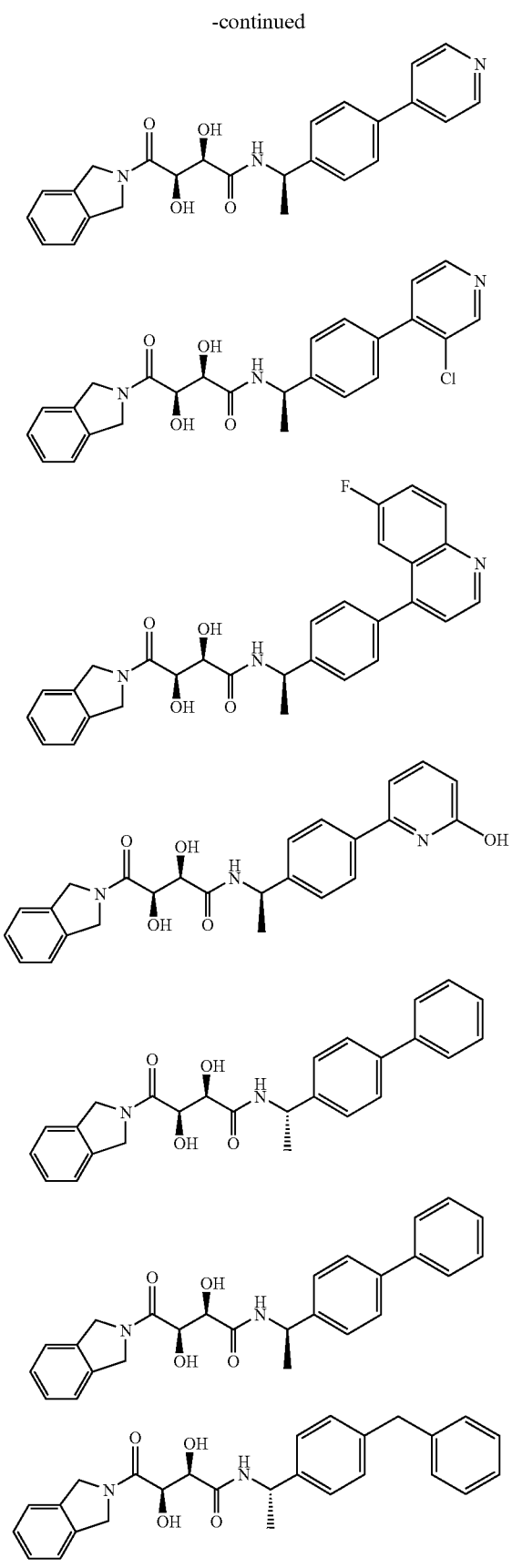
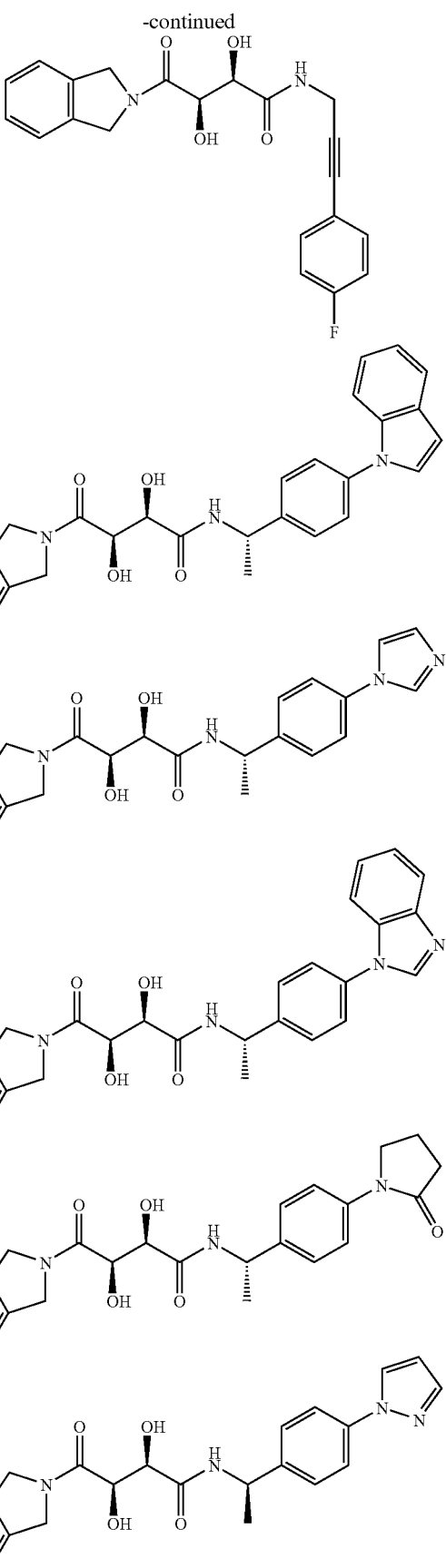

1675
-continued
1676
-continued
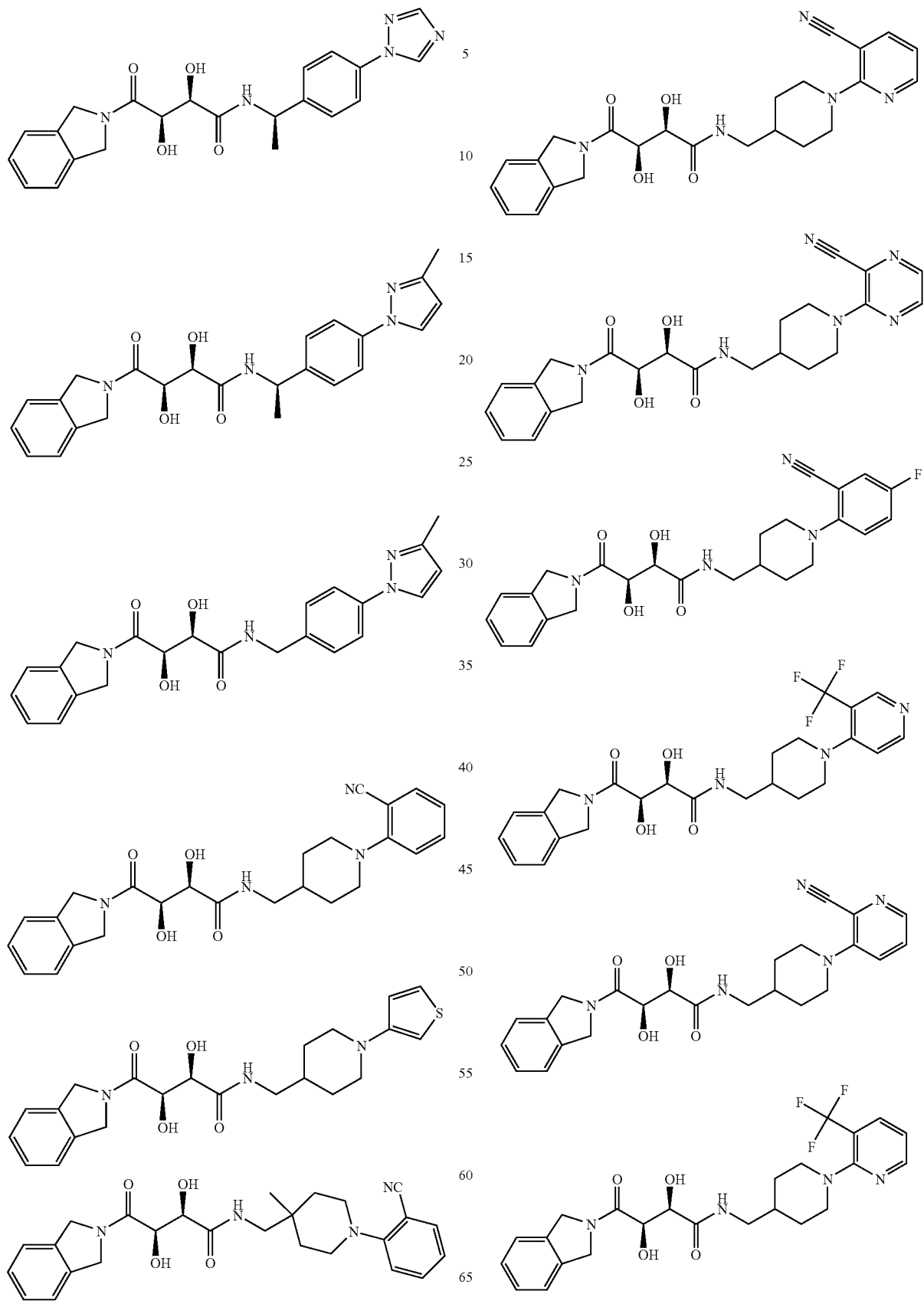

1677
-continued
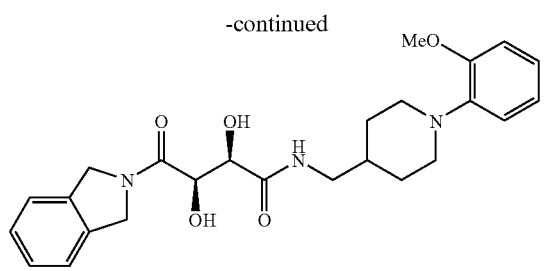
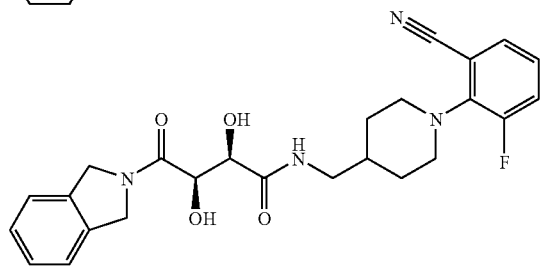
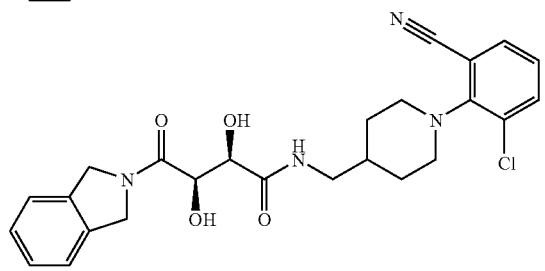
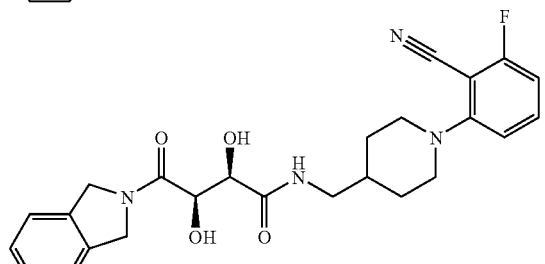
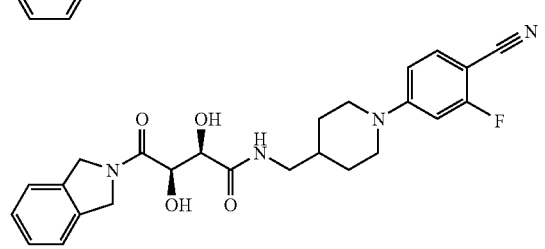
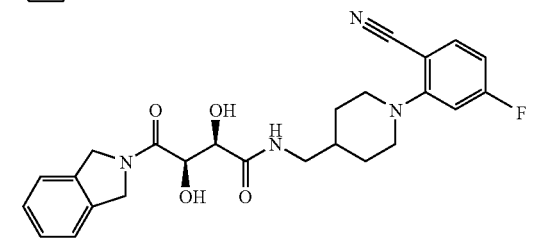
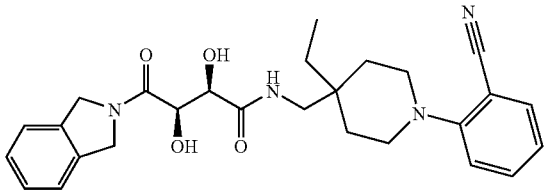
1678
-continued
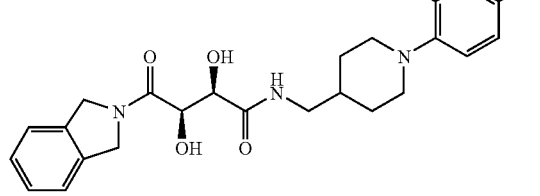
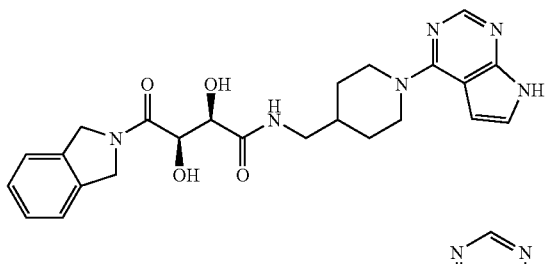
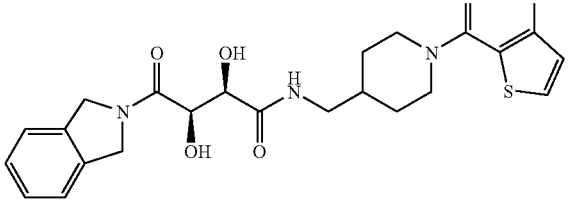
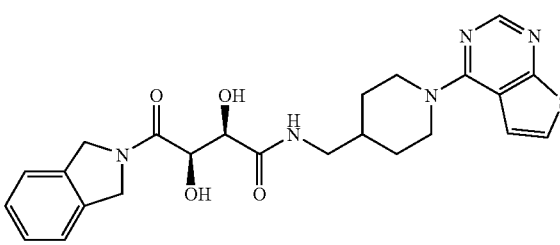
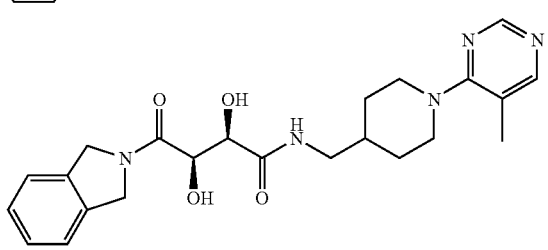
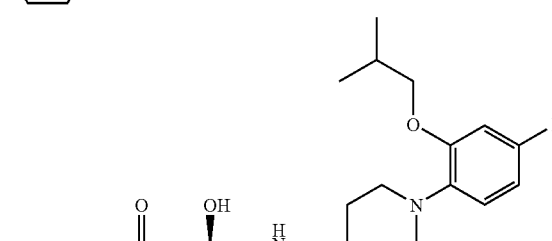
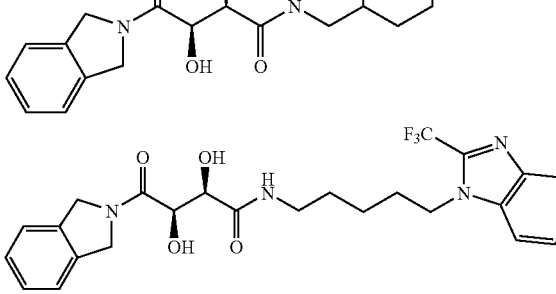

1679
-continued
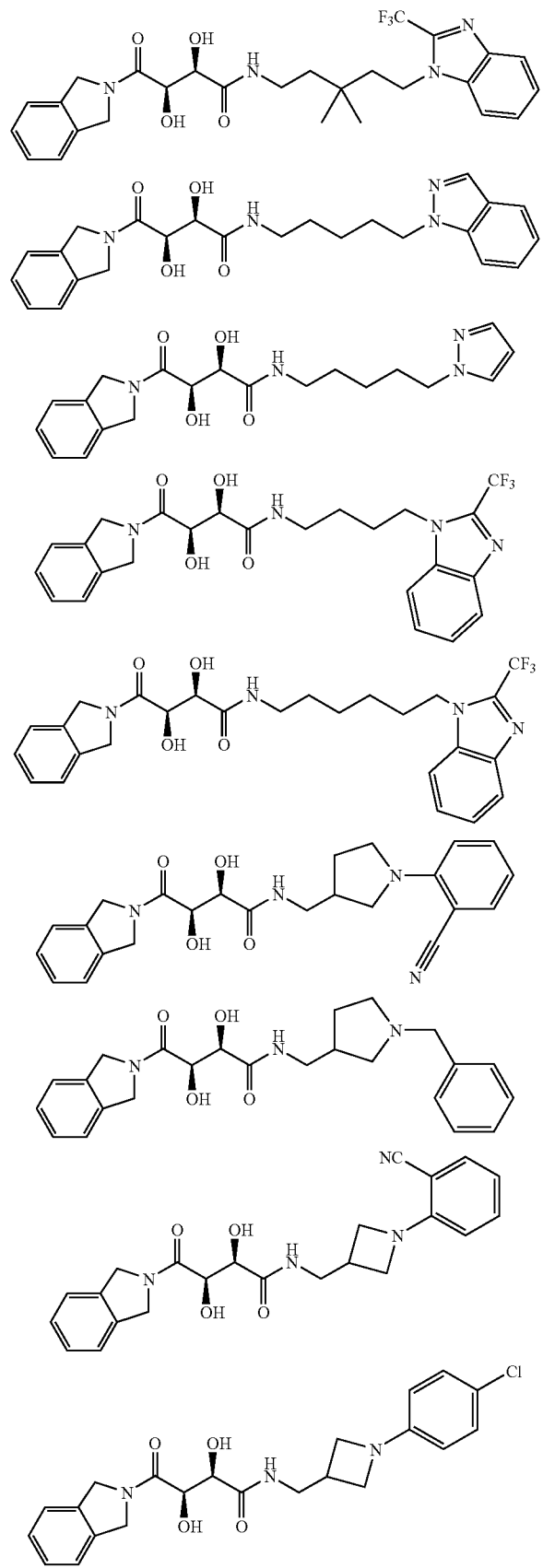
1680
-continued
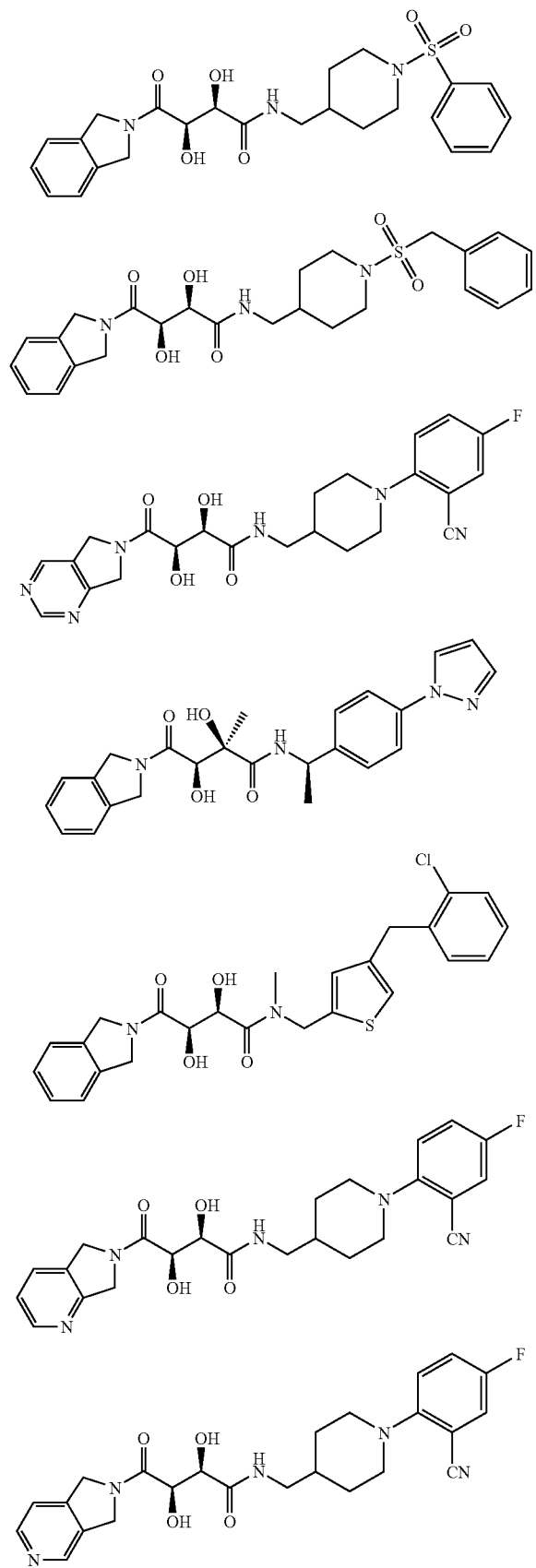

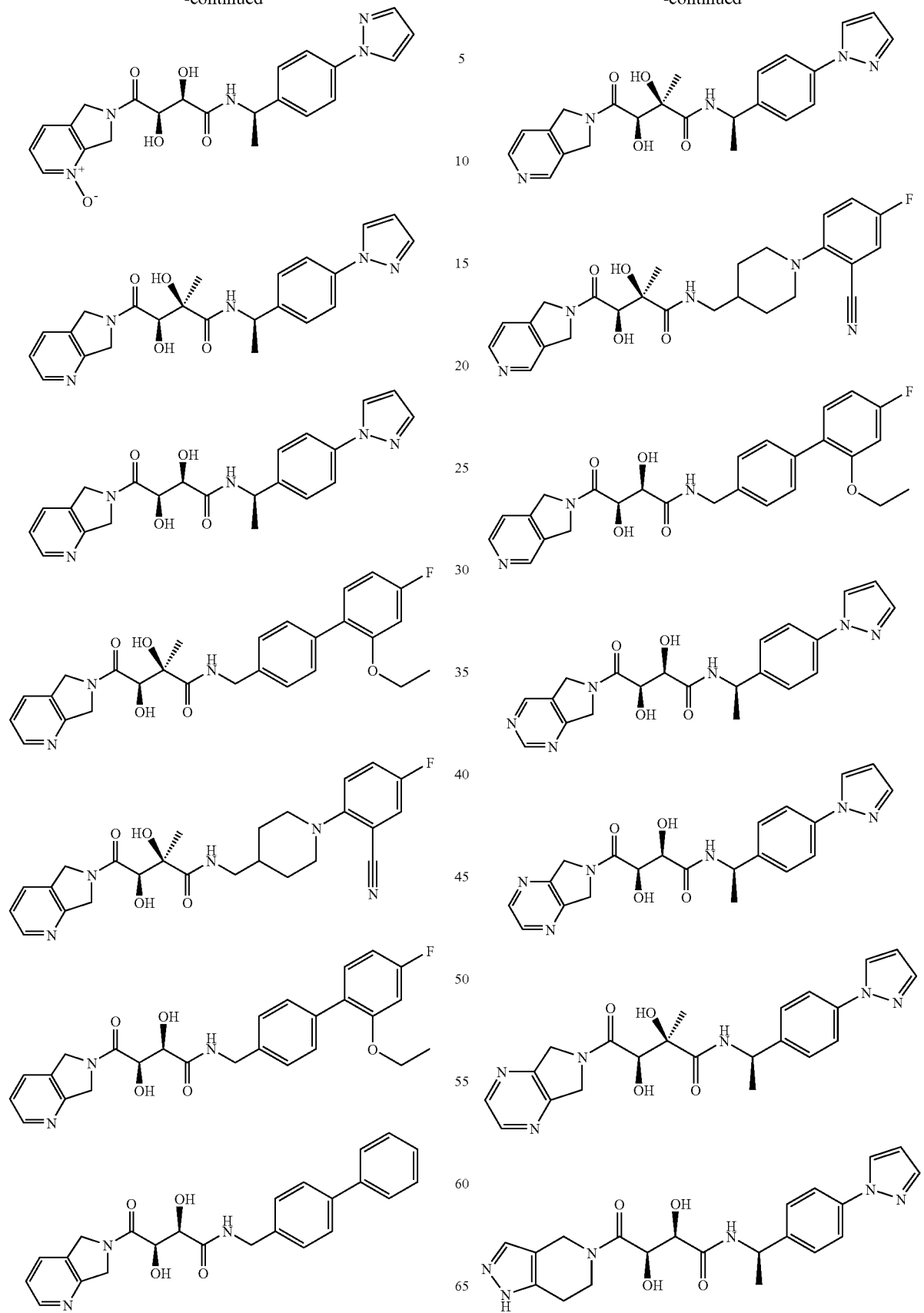

-continued
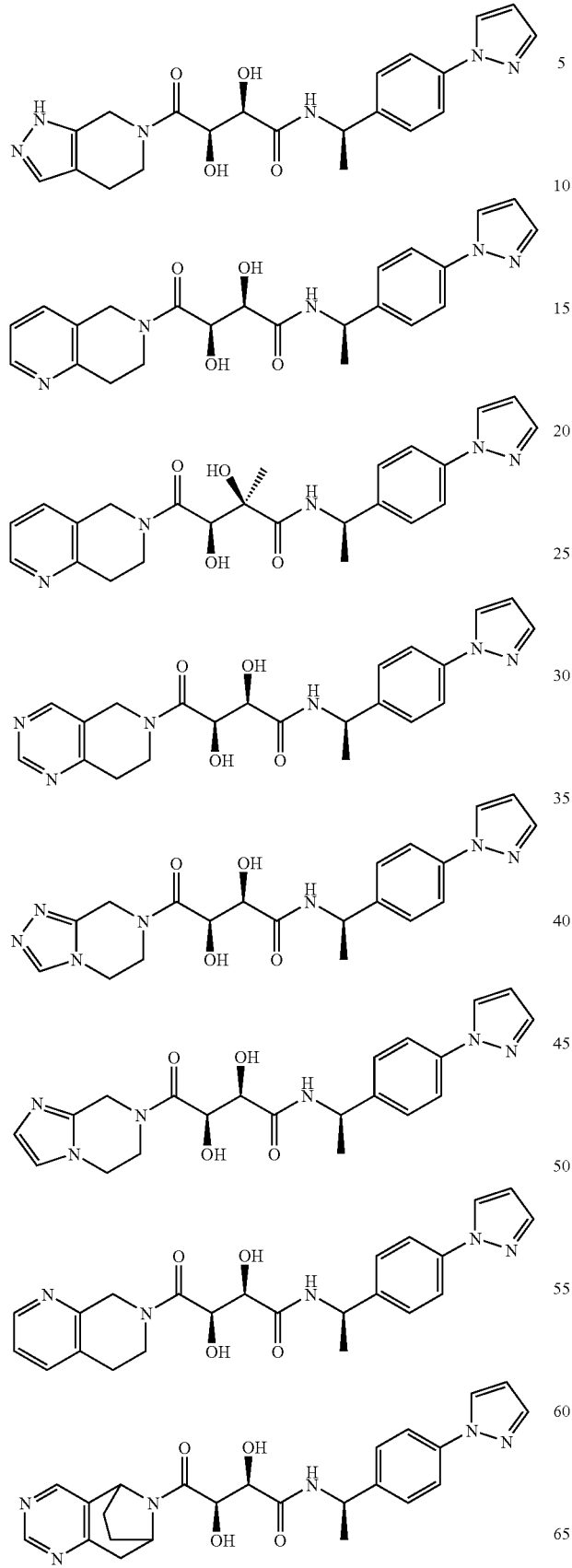
-continued
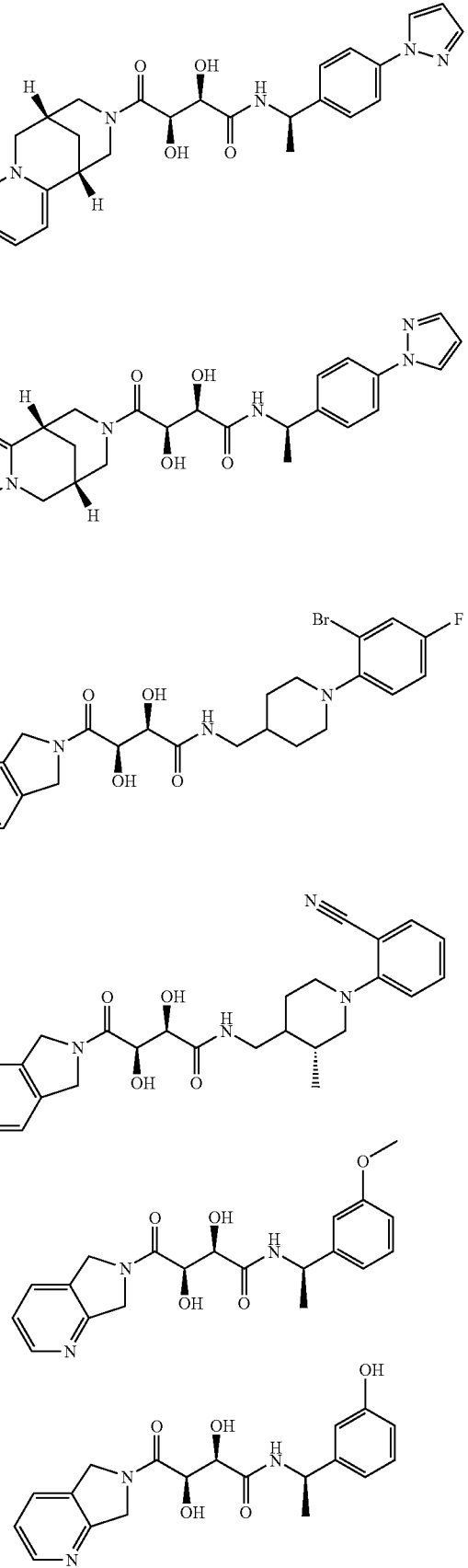

-continued

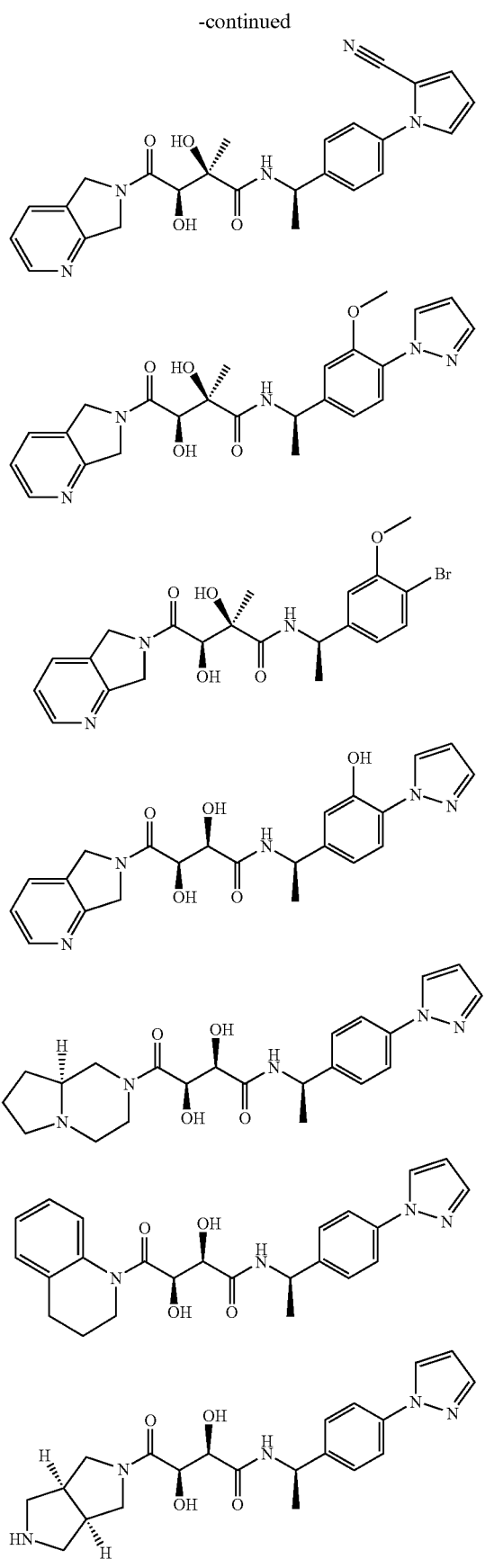

-continued

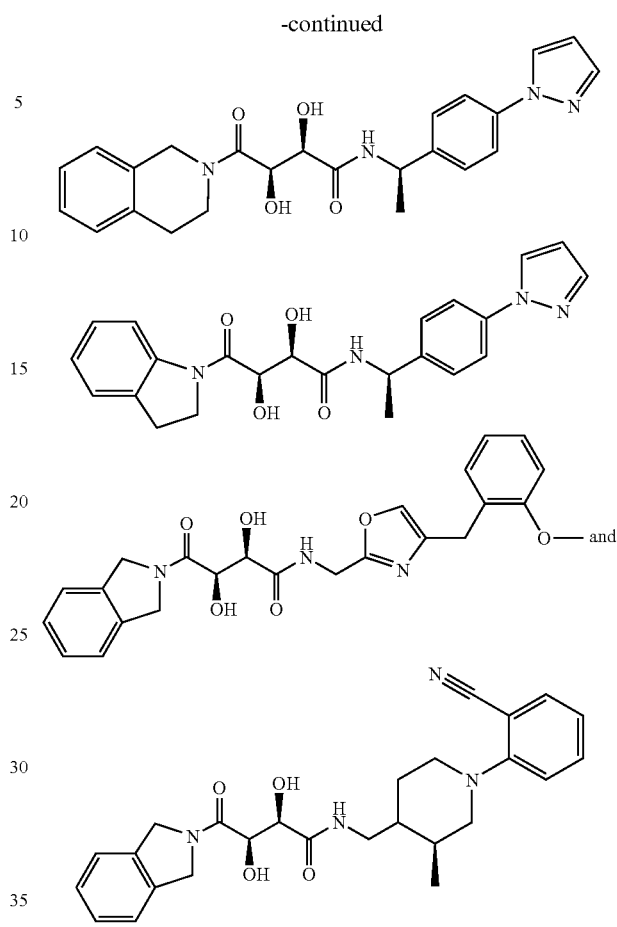

or a pharmaceutically acceptable salt or solution-phase solvate thereof.

35. A pharmaceutical composition comprising at least one compound of claim 30 or a pharmaceutically acceptable salt or solution-phase solvate thereof, and at least one pharmaceutically acceptable carrier.

36. A compound of formula (I):

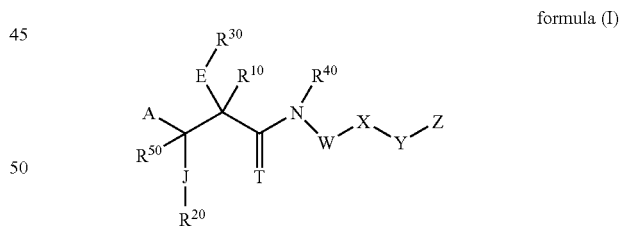

formula (I)

or a pharmaceutically acceptable salt or solution-phase solvate thereof, wherein:

A is selected from the group consisting of:

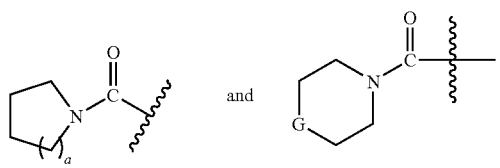

a is 1;
J is O;

E is O;
G is selected from the group consisting of CH$_2$, NH, O, S, or SO$_2$
T is O;
R$^{10}$ is H;
R$^{20}$ is H;
R$^{30}$ is H;
R$^{40}$ is H;
R$^{50}$ is H;
W is —(CR$^{13}$$_2$)$_n$—, wherein n is 1;
X is absent or present, and if present X is aryl, wherein said aryl is phenyl, which is substituted with one or more moieties which can be the same or different, each moiety being independently selected from the group of R$^{70}$ moieties below;
Y is absent;
Z is selected from the group consisting of heteroaryl and heterocyclyl, each of said heteroaryl and heterocyclyl being optionally fused with aryl, heterocyclyl, heteroaryl or cycloalkyl; wherein each of said Z heteroaryl, and heterocyclyl optionally with said fused aryl, heterocyclyl, heteroaryl or cycloalkyl, can be unsubstituted or optionally independently substituted with one or more moieties which can be the same or different, each moiety being independently selected from the group of R$^{70}$ moieties below;
R$^{13}$ is selected from the group consisting of hydrogen and alkyl;
each R$^{70}$ is a substituent for H where indicated and is the same or different and is independently selected from the group consisting of alkyl, alkenyl, alkynyl, cycloalkyl, cycloalkenyl, heterocyclyl, aryl, arylalkyl, heteroaryl, heteroarylalkyl, halo, —CN, —CF$_3$, —OCF$_3$, —OR$^{15}$, —C(O)R$^{15}$, —C(O)OR$^{15}$, —C(O)N(R$^{15}$)(R$^{16}$), —SR$^{15}$, —S(O)$_q$N(R$^{15}$)(R$^{16}$) wherein q is 1 to 2, —C(=NOR$^{15}$)R$^{16}$, —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{17}$)S(O)$_2$N(R$^{16}$)(R$^{15}$), —N(R$^{17}$)S(O)N(R$^{16}$)(R$^{15}$), —N(R$^{17}$)C(O)N(R$^{16}$)(R$^{15}$), —CH$_2$—N(R$^{17}$)C(O)N(R$^{16}$)(R$^{15}$), —N(R$^{15}$)C(O)OR$^{16}$, —CH$_2$—N(R$^{15}$)C(O)OR$^{16}$, and —S(O)$_q$R$^{15}$ wherein q is 1 to 2; and wherein each of the alkyl, cycloalkyl, heterocyclyl, aryl, arylalkyl, heteroaryl, heteroarylalkyl, alkenyl and alkynyl are independently unsubstituted or substituted by 1 to 5 groups independently selected from the group consisting of alkyl, cycloalkyl, heterocyclyl, aryl, heteroaryl, halo, —CF$_3$, —CN, —OR$^{15}$, —N(R$^{15}$)(R$^{16}$), —C(O)OR$^{15}$, —C(O)N(R$^{15}$)(R$^{16}$), and —N(R$^{15}$)S(O)R$^{16}$; and
each R$^{15}$, R$^{16}$ and R$^f$ are independently selected from the group consisting of H, alkyl, cycloalkyl, heterocyclyl, aryl, and heteroaryl, or alternatively R$^{15}$ and R$^{16}$ taken together with the N to which they are shown attached, are joined to form a 4-8 membered heterocyclic ring, wherein said 4-8 membered cycloalkyl can be unsubstituted or optionally independently substituted with one or more moieties which can be the same or different, each moiety being independently selected from the group of R$^{75}$ moieties below;
each R$^{75}$ is independently selected from the group consisting of alkyl, cycloalkyl, heterocyclyl, aryl, arylalkyl, heteroaryl, heteroarylalkyl, alkenyl and alkynyl, and wherein each of the alkyl, cycloalkyl, heterocyclyl, aryl, arylalkyl, heteroaryl, heteroarylalkyl, alkenyl and alkynyl are independently unsubstituted or substituted by 1 to 5 groups independently selected from the group consisting of alkyl, cycloalkyl, heterocyclyl, aryl, heteroaryl, halo, —CF$_3$, —CN, —OR$^{19}$, —N(R$^{19}$)$_2$, —C(O)OR$^{19}$, —C(O)N(R$^{19}$)$_2$, and —N(R$^{19}$)S(O)R$^{19}$; and
each R$^{19}$ is independently selected from the group consisting of H, alkyl, cycloalkyl, heterocyclyl, aryl, and heteroaryl.

37. A compound selected from the group consisting of:

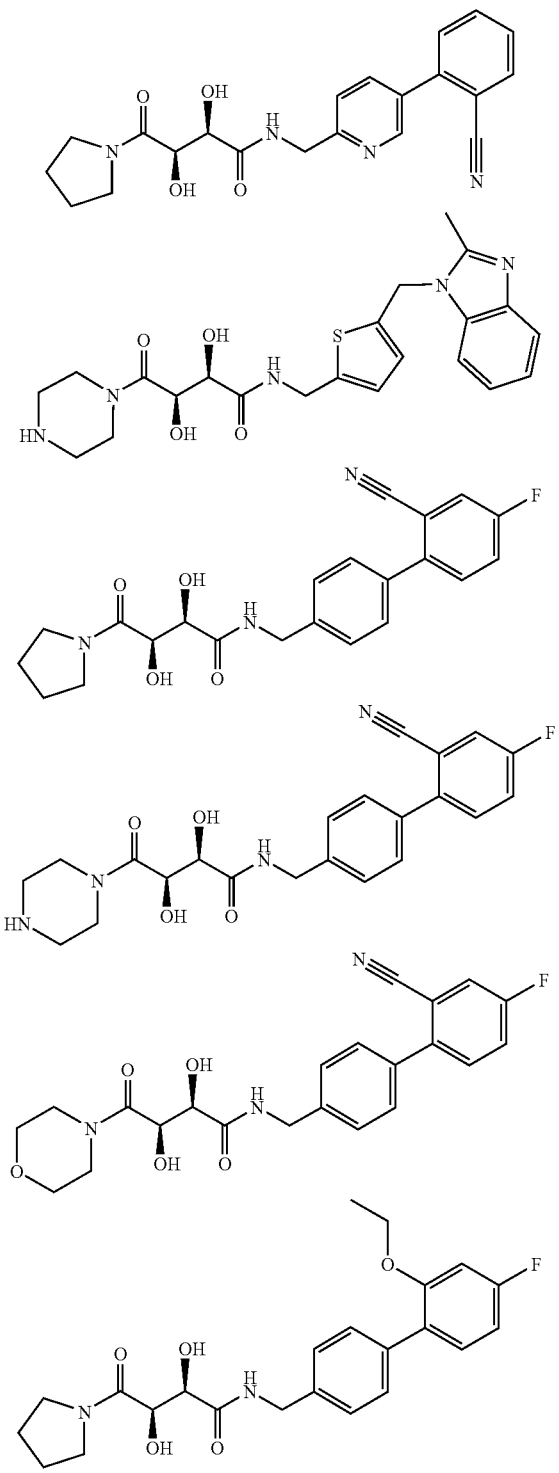

-continued
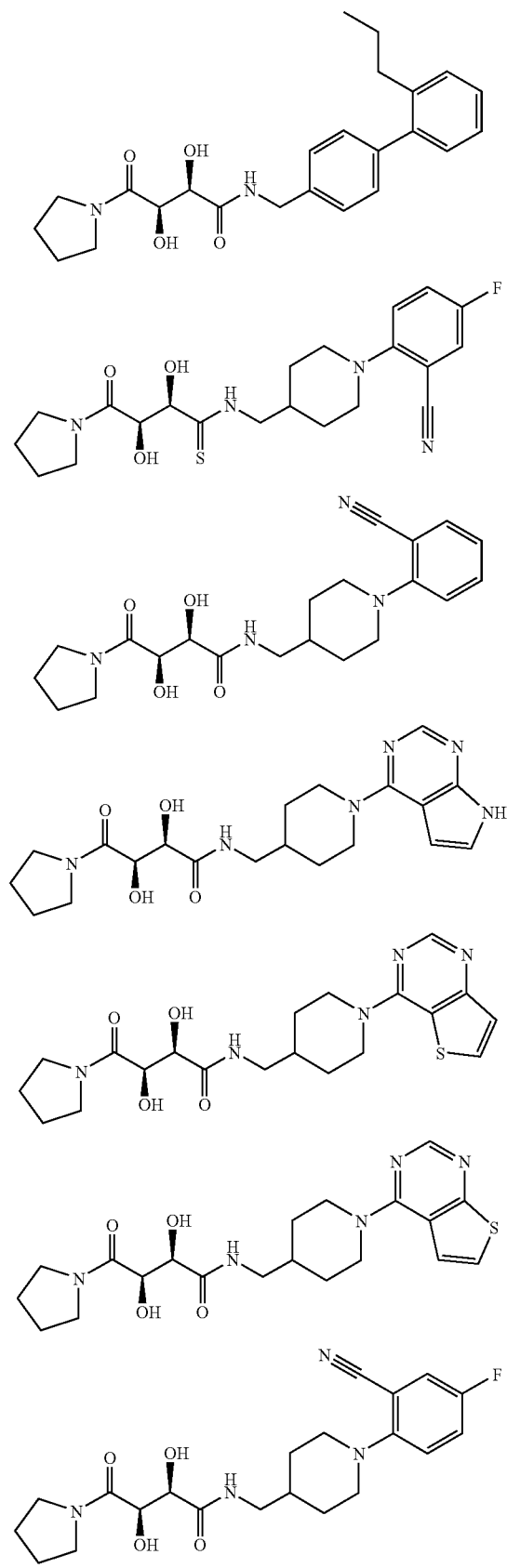
-continued
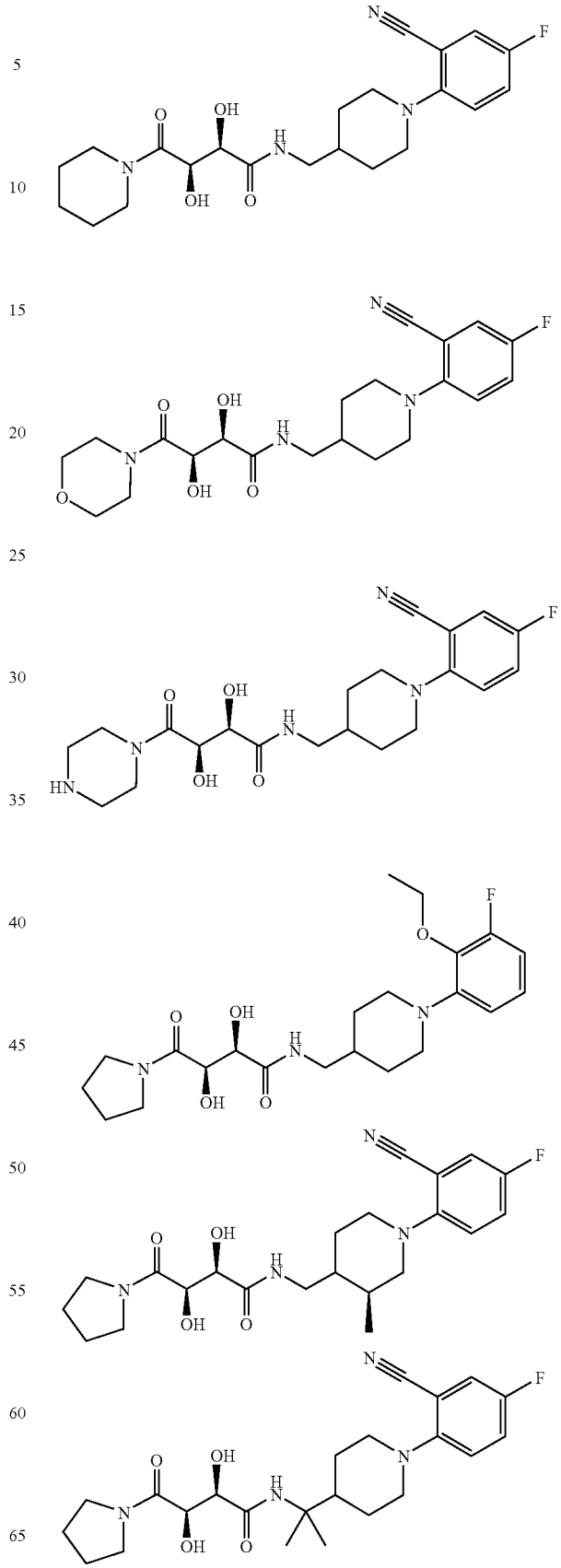

-continued

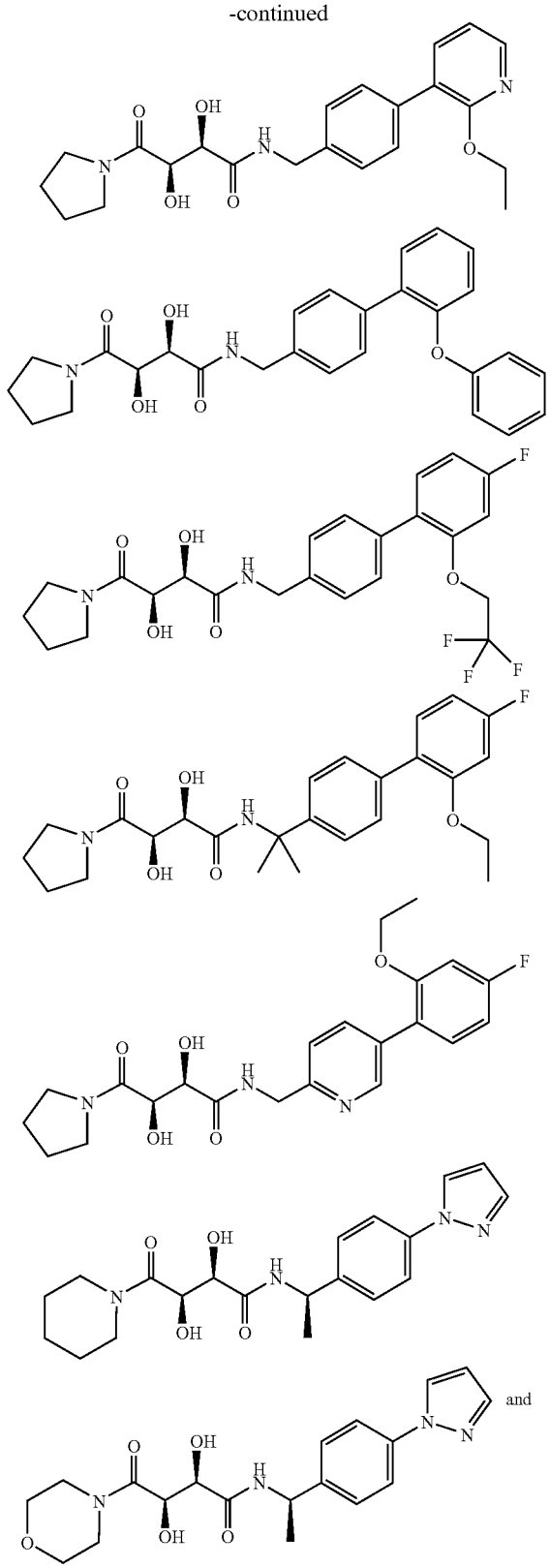

and

-continued

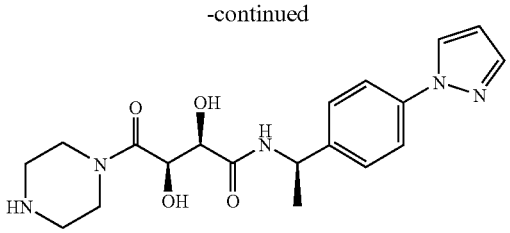

or a pharmaceutically acceptable salt or solution-phase solvate thereof.

38. A pharmaceutical composition comprising at least one compound of claim 36 or a pharmaceutically acceptable salt or solution-phase solvate thereof, and at least one pharmaceutically acceptable carrier.

39. A pharmaceutical composition comprising at least one compound of claim 3 or a pharmaceutically acceptable salt or solution-phase solvate thereof, and at least one pharmaceutically acceptable carrier.

40. A pharmaceutical composition comprising at least one compound of claim 4 or a pharmaceutically acceptable salt or solution-phase solvate thereof, and at least one pharmaceutically acceptable carrier.

41. A pharmaceutical composition comprising at least one compound of claim 5 or a pharmaceutically acceptable salt or solution-phase solvate thereof, and at least one pharmaceutically acceptable carrier.

42. A pharmaceutical composition comprising at least one compound of claim 8 or a pharmaceutically acceptable salt or solution-phase solvate thereof, and at least one pharmaceutically acceptable carrier.

43. A pharmaceutical composition comprising at least one compound of claim 23 or a pharmaceutically acceptable salt or solution-phase solvate thereof, and at least one pharmaceutically acceptable carrier.

44. A pharmaceutical composition comprising at least one compound of claim 25 or a pharmaceutically acceptable salt or solution-phase solvate thereof, and at least one pharmaceutically acceptable carrier.

45. A pharmaceutical composition comprising at least one compound of claim 6 or a pharmaceutically acceptable salt or solution-phase solvate thereof, and at least one pharmaceutically acceptable carrier.

46. A pharmaceutical composition comprising at least one compound of claim 29 or a pharmaceutically acceptable salt or solution-phase solvate thereof, and at least one pharmaceutically acceptable carrier.

47. A pharmaceutical composition comprising at least one compound of claim 34 or a pharmaceutically acceptable salt or solution-phase solvate thereof, and at least one pharmaceutically acceptable carrier.

48. A pharmaceutical composition comprising at least one compound of claim 37 or a pharmaceutically acceptable salt or solution-phase solvate thereof, and at least one pharmaceutically acceptable carrier.

* * * * *